United States Patent
Brnardic et al.

(10) Patent No.: US 11,976,057 B2
(45) Date of Patent: May 7, 2024

(54) MRGX2 ANTAGONISTS

(71) Applicant: GlaxoSmithKline Intellectual Property Development Limited, Stevenage (GB)

(72) Inventors: Edward Brnardic, Collegeville, PA (US); Michael Bury, Collegeville, PA (US); Rodolfo Cadilla, Durham, NC (US); Jon Collins, Durham, NC (US); Yu Guo, Collegeville, PA (US); Anthony Handlon, Collegeville, PA (US); Huijie Li, Collegeville, PA (US); Yue Li, Collegeville, PA (US); Daniel Paone, Collegeville, PA (US); Christie Schulte, Collegeville, PA (US); Barry Shearer, Collegeville, PA (US); Maben Ying, Collegeville, PA (US); Guosen Ye, Collegeville, PA (US); Huichang Zhang, Collegeville, PA (US); Millard Hurst Lambert, III, Collegeville, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 17/492,978

(22) Filed: Oct. 4, 2021

(65) Prior Publication Data

US 2022/0112174 A1 Apr. 14, 2022

Related U.S. Application Data

(60) Provisional application No. 63/087,997, filed on Oct. 6, 2020.

(51) Int. Cl.
| | |
|---|---|
| *C07D 401/14* | (2006.01) |
| *A61P 17/00* | (2006.01) |
| *C07D 409/14* | (2006.01) |
| *C07D 413/14* | (2006.01) |
| *C07D 417/14* | (2006.01) |
| *C07D 471/04* | (2006.01) |

(52) U.S. Cl.
CPC ............ *C07D 401/14* (2013.01); *A61P 17/00* (2018.01); *C07D 409/14* (2013.01); *C07D 413/14* (2013.01); *C07D 417/14* (2013.01); *C07D 471/04* (2013.01)

(58) Field of Classification Search
CPC .. C07D 401/14; C07D 409/14; C07D 413/14; C07D 417/14; C07D 471/04; A61P 17/00
See application file for complete search history.

(56) References Cited

U.S. PATENT DOCUMENTS 10,696,971 B2   6/2020   Dong et al.

OTHER PUBLICATIONS

Chen et al. Gastroenterology, 2021; 160(5): 1709-1724 (Year: 2021).*
Subramanian et al. J Allergy Clin Immunol. 2016, 138(3), 700-710 (Year: 2016).*
Database Registry, Database accession No. 2471825-28-0; Sep. 3, 2020, XP055869457, Anonymous: "1-Piperidineacetamide, N-(3-fluorophenyl)-3-(2-methyl-4-pyrimidinyl)-", retrieved from STN Database accession No. 2471825-28-0 abstract.
Database Registry, Database accession No. 2470703-46-7; Sep. 2, 2020, XP055869461, Anonymous: "1-Piperidineacetamide, N-(4-methylphenyl)-3-(2-methyl-4-pyrimidinyl)-", retrieved from STN Database accession No. 2470703-46-7.
Database Registry, Chemical Abstracts Service, Columbus, Ohio, US, Jun. 18, 2020 (Jun. 18, 2020), Anonymous: "1-Piperidineacetamide, N-phenyl-3-(4-pyridinyl)-", XP055869465, Database accession No. 2428505-72-8, abstract; further database accession Nos. 2428481-90-5, 2428365-57-3, 2428342-85-0, 2428246-04-0, 2427871-00-7, 2427793-72-2, 2427766-72-9.
Database Registry, Database accession Nos. 2427345-47-7 to 1311439-18-5; Jun. 17, 2020 to Jul. 6, 2011; 20 pages.
Ali, Adv. Immunol., 136, 123-162 (2017).
Okamura, Allerg. Intern., 26, S9-S20 (2017).
Mazi, Allergy, 54, 46-56 (1999).
Galli, Annu. Rev. Immunol., 38, 49-77 (2020).
Tatemoto, BBRC, 349, 1322-28 (2006).
Vena, Clinical and Molecular Allergy 16, 24 (2018).
Xuan, Frontiers in Cellular Neuroscience, 13, 1-11 (2019).
Voisin, Immunity, 50, 1163-1171 (2019).
Fujisawa, J. Allergy Clin. Immunol., 134, 622-633-2014.
Muto, J. Inv. Derm., 134, 2728 (2014).
Schwab, J. Invest. Dermatol., 15, 53-62, (2011).
Subramanian, J. Immunol., 191, 345-352 (2013).
Eklund, Immunol. Rev., 217, 38-52 (2007).
Dwyer, Nature Immunology, 17, 878-887 (2016).
Serhan, Nature Immunology, 20, 1435-1443 (2019).

(Continued)

*Primary Examiner* — Mark L Shibuya
*Assistant Examiner* — Luisalberto Gonzalez
(74) *Attorney, Agent, or Firm* — James K. Leonard

(57) ABSTRACT

This invention relates to novel compounds according to Formula (I) which are antagonists of MrgX2, to pharmaceutical compositions containing them, and to their use in therapy for the treatment of MrgX2-mediated diseases and disorders.

(I)

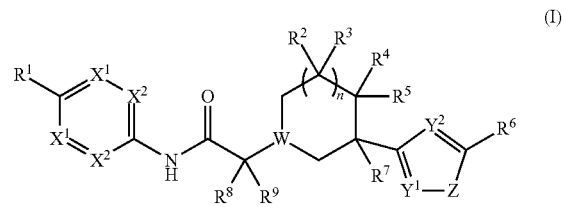

20 Claims, No Drawings

(56) References Cited

OTHER PUBLICATIONS

Galli, Nature Immunology, 6, 135-142 (2005).
McNeil, Nature, 519, 237-241 (2015).
Navratilova, Neuron, 101, 353-355, (2019).
Green, Neuron, 101, 412-420 (2019).
Rijnierse, Pharmacology and Therapeutics, 116, 207-235 (2007).
Manorak, Respiratory Research, 19, 1 (2018).
Ogasawara et al., "Novel MRGPRX2 antagonists inhibit IgE-independent activation of human umbilical cord blood-derived mast cells", Journal of Leukocyte Biology, Jul. 12, 2019, pp. 1-9.
International Search report for PCT/EP2021/077243 filed Oct. 4, 2021.

* cited by examiner

MRGX2 ANTAGONISTS

FIELD OF THE INVENTION

This invention relates to compounds which are antagonists of MrgX2 (Mas-related Gene X2) and thus are useful as therapeutic agents.

BACKGROUND OF THE INVENTION

Mature mammalian mast cells ordinarily reside: Near blood vessels or nerves; beneath or within epithelia; within airways, gastrointestinal, and genitourinary tracts; and near smooth muscle and mucus-producing glands. Classically, mast cells are activated by IgE antibodies, secreting a wide range of substances with local and systemic effects, including histamine, serotonin, proteases, chemokines, and cytokines. Indeed, mast cells are implicated in the progression and/or maintenance of many diseases (Nature Immunology, 6, 135-142 (2005)).

Recent work has emphasized the role of the Mas-related G protein-coupled receptor (MRGPR) family, specifically, Mrgprb2, in mast cell activation (Nature, 519, 237-241 (2015)). Mrgprb2 is the mouse receptor for several cationic molecules, collectively called basic secretagogues, and the ortholog of the human receptor MRGPRX2 (Adv. Immunol., 136, 123-62 (2017)). To date, Mrgprb2 and MRGPRX2 have been reported to be expressed only on certain populations of mast cells (Nature Immunology, 17, 878-887 (2016); Annu. Rev. Immunol., 38, 49-77 (2020)). This knowledge provides the opportunity to target mast cell degranulation in a very precise manner.

Natural endogenous ligands of Mrgprb2/MRGPRX2 have been reported and are mostly neuropeptides, including substance P (SP), vasoactive intestinal polypeptide (VIP), Cortistatin-14, and pituitary adenylate cyclase activating polypeptide (PACAP). Others include β-defensin, cathelicidin (LL-37), and proadrenomedullin N-terminal 20 peptide (PAMP9-20) (Journal of Allergy and Clinical Immunology, 138, 700-710 (2016); J. Immunol., 191, 345-352 (2013); BBRC, 349, 1322-28 (2006)). Given the close proximity between mast cells and sensory nerves in various pathological conditions, it follows that neuropeptide-activated MRGPRX2 could contribute to symptoms of neurogenic inflammation including pain, swelling and pruritus. Various observations using knock-out (KO) mice are consistent with the Mrgprb2/MRGPRX2 receptors playing a role in mast cell-mediated neurogenic inflammation. For instance, Mrgprb2/MRGPRX2 agonists induce various symptoms such as flushing, swelling and itch in wild type mice, but not in Mrgprb2-deficient mice (Nature, 519, 237-241 (2015); Immunity, 50, 1163-1171 (2019)). Mrgprb2-deficient mice have also demonstrated significant reductions in inflammation (leukocyte infiltration, including mast cells), swelling, pain and overall clinical score in various disease models (Neuron, 101, 412-420 (2019); Immunity, 50, 1163-1171 (2019); Nature Immunology, 20, 1435-1443 (2019)). An important and relevant observation was the demonstration that Substance P injection could stimulate the infiltration of leukocytes in wild type and NKR1 (canonical Substance P receptor) KO mice whereas the response was substantially blunted in Mrgprb2 null mice (Neuron, 101, 412-420 (2019)). This observation extends the role of Mrgprb2/MRGPRX2 as a key receptor in mediating Substance P-induced inflammatory responses, including pain (Neuron, 101, 353-355, (2019)). Indeed, a Substance P/Mrgprb2 sensory cluster was demonstrated to be critical in driving the clinical score of a severe preclinical model of atopic dermatitis (Nature Immunology, 20, 1435-1443 (2019)).

In addition to the various reports using Mrgprb2-deficient mice, further evidence suggests a role for various ligands of MRGPRX2 in human disease. For example, in addition to the number of MRGPRX2-expressing mast cells being significantly increased in severe chronic urticaria (Clinical and Molecular Allergy 16, 24 (2018)), PACAP nerve fibers were demonstrated to be in close proximity to tryptase-positive mast cells, providing the morphological basis for increased mast cell—sensory interactions (J. Allergy Clin. Immunol., 134, 622-633 (2014)). In support of this, patients with urticaria exhibit enhanced wheal reactions vs healthy individuals to MRGPRX2 agonists (e.g., Substance P) when injected intradermally (Allergy, 54, 46-56 (1999)). In addition, PACAP and the antimicrobial peptide, LL-37, which is implicated in cutaneous inflammation, were both demonstrated to be upregulated in rosacea (J. Invest. Dermatol., 15, 53-62, (2011)). Indeed, mast cell-deficient mice do not develop inflammation/flushing following LL-37 injection (J. Inv. Derm., 134, 2728 (2014)) thus inferring a role for Mrgprb2.

In addition to skin disorders, mast cell involvement has been highlighted for inflammatory bowel disease (IBD) and arthritis (Immunol. Rev., 217, 38-52 (2007); Pharmacology and Therapeutics, 116, 207-235 (2007)) as well as asthma (Respiratory Research, 19, 1 (2018)) and migraine. In patients with rheumatoid arthritis (RA), the number of degranulated mast cells is increased in synovial tissue and is correlated with disease activity, as it is for patients with IBD. A positive correlation between serum Substance P levels and chronic pain intensity has been noted in both osteoarthritic and RA patients (PLOS ONE, 10, e0139206 ((2015)) and a recent article suggested that the SP-MRGPRX2 axis may play a role in the pathogenesis of RA, especially in the regulation of inflammation and pain (Allerg. Intern., 26, S9-S20 (2017)). Finally, there is a growing body of evidence for a role of PACAP in migraine pathogenesis and that it is mediated via activation of mast cells (Frontiers in Cellular Neuroscience, 13, 1-11 (2019)).

In summary, a potent, selective antagonist of MRGPRX2 that blocks IgE-independent mast cell de-granulation is expected to provide therapeutic benefit in mast-cell driven pathologies including skin disorders such as urticaria, atopic dermatitis and rosacea as well as additional indications like inflammatory bowel disease, arthritis and migraine.

SUMMARY OF THE INVENTION

The present invention relates to compounds according to Formula (I) or pharmaceutically acceptable salts thereof:

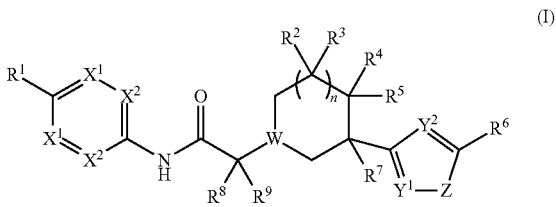

wherein:
W is N or CH;
each $X^1$ is independently N or $CR^{10}$;
each $X^2$ is independently N or $CR^{11}$;
Y is N or $CR^{12}$;
$Y^2$ is N or $CR^{12}$;

Z is

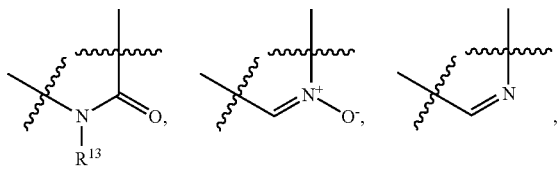

n is 0 or 1;

$R^1$ is hydrogen, halogen, $(C_1-C_6)$alkyl, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —$(C_1-C_6)$alkyl-$(C_3-C_8)$cycloalkyl, —$(C_1-C_6)$alkyl-aryl, 5- or 6-membered heteroaryl $(C_1-C_4)$alkyl-, $(C_3-C_8)$cycloalkyl, $(C_2-C_6)$alkenyl, —$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-aryl, —O—$(C_1-C_6)$alkyl-5-6 membered heteroaryl, —O—$(C_2-C_6)$alkenyl, —O—$(C_3-C_8)$cycloalkyl, —O-aryl, —O-heteroaryl, —C(O)-aryl, —$CO_2H$, —$CO_2(C_1-C_6)$alkyl, —$CO_2(C_3-C_8)$cycloalkyl, —$O_2C(C_1-C_6)$alkyl, —$O_2C(C_3-C_8)$cycloalkyl, —$NH_2$, —NH$(C_1-C_6)$alkyl, —N$((C_1-C_6)$alkyl$)((C_1-C_6)$alkyl$)$, aryl, or 5-6 membered heteroaryl, wherein any said $(C_1-C_6)$alkyl, —$(C_1-C_6)$alkyl-$(C_3-C_8)$cycloalkyl, —$(C_1-C_6)$alkyl-aryl, $(C_1-C_4)$alkoxy, —O—$(C_1-C_6)$alkyl-$(C_3-C_8)$cycloalkyl, —O—$(C_3-C_8)$cycloalkyl, —O-aryl, —O-5-6-membered heteroaryl, —C(O)-aryl, aryl, or 5-6 membered heteroaryl is optionally substituted one, two, or three times by $R^{14}$;

$R^2$ is hydrogen, halogen, $(C_1-C_6)$alkyl, or —OH, wherein any said $(C_1-C_6)$alkyl is optionally substituted one, two, or three times by halogen;

$R^3$ is hydrogen, halogen, $(C_1-C_6)$alkyl, or —OH, wherein any said $(C_1-C_6)$alkyl is optionally substituted one, two, or three times by halogen;

$R^4$ is hydrogen, halogen, or $(C_1-C_6)$alkyl;

$R^5$ is hydrogen, halogen, or $(C_1-C_6)$alkyl;

$R^6$ is hydrogen, halogen, $(C_1-C_6)$alkyl, $(C_3-C_8)$cycloalkyl, $(C_1-C_4)$alkoxy, —$(C_1-C_6)$alkyl-OH, —$(C_1-C_6)$alkyl-O—$(C_1-C_6)$alkyl, —$(C_1-C_6)$alkyl-$NH_2$, —$(C_1-C_6)$alkyl-NH$((C_1-C_6)$alkyl$)$, —$(C_1-C_6)$alkyl-N—$((C_1-C_6)$alkyl$)((C_1-C_6)$alkyl$)$, —$(C_1-C_6)$alkyl-NH$((C_1-C_6)$alkyl$)$-OH, —$(C_1-C_6)$alkyl-NH$(((C_1-C_6)$alkyl$)$-O—$(C_1-C_6)$alkyl$)$, —$(C_1-C_6)$alkyl-N—$((C_1-C_6)$alkyl$)((C_1-C_6)$alkyl$)$-OH, —$(C_1-C_6)$alkyl-N—$((C_1-C_6)$alkyl$)((C_1-C_6)$alkyl$)$-O—$(C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, —$(C_1-C_6)$alkyl-4- to 6-membered heterocycloalkyl, —$(C_1-C_6)$alkyl-NHC(O)—$((C_1-C_6)$alkyl$)$, —$(C_1-C_6)$alkyl-$SO_2$—$(C_1-C_6)$alkyl, —$(C_1-C_6)$alkyl-$SO_2$—NH—$(C_1-C_6)$alkyl, —CN, —C(O)$NH_2$, —C(O)NH$(C_1-C_6)$alkyl$)$, —C(O)N$(C_1-C_6)$alkyl$)$ $(C_1-C_6)$alkyl$)$, —$NH_2$, —NH$(C_1-C_6)$alkyl, —N$((C_1-C_6)$alkyl$)((C_1-C_6)$alkyl$)$, —$SO_2((C_1-C_6)$alkyl$)$, —$SO_2$—NH$((C_1-C_5)$alkyl$)$, or aryl, wherein any said $(C_1-C_6)$alkyl, $(C_3-C_8)$cycloalkyl, —$(C_1-C_6)$alkyl-OH, —$(C_1-C_6)$alkyl-$NH_2$, —$(C_1-C_6)$alkyl-NH$((C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, or —$(C_1-C_6)$alkyl-4- to 6-membered heterocycloalkyl is optionally substituted one, two, or three times by halogen;

$R^7$ is hydrogen, $(C_1-C_6)$alkyl, or —OH;

$R^8$ is hydrogen, $(C_1-C_6)$alkyl, or $(C_1-C_4)$alkoxy;

$R^9$ is hydrogen, $(C_1-C_6)$alkyl, or $(C_1-C_4)$alkoxy;

each $R^{10}$ is independently hydrogen, halogen, $(C_1-C_6)$alkyl, $(C_2-C_6)$alkenyl, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, $(C_2-C_6)$alkenyl, —O—$(C_1-C_6)$alkyl, —$NH_2$, —NH$((C_1-C_6)$alkyl$)$, —N$((C_1-C_6)$alkyl$)((C_1-C_6)$alkyl$)$, —$NCH_2$, or —CHNH;

or $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, $(C_1-C_6)$alkyl, —$(C_1-C_6)$alkyl-$(C_3-C_8)$cycloalkyl, halo$(C_1-C_6)$alkyl, and $(C_3-C_8)$cycloalkyl;

each $R^{11}$ is independently hydrogen, halogen, $(C_1-C_6)$alkyl, or $(C_2-C_6)$alkenyl;

or any $R^{10}$ and any $R^{11}$ taken together with the atoms to which they are attached, form a 5-, 6-, or 7-membered ring optionally containing one, two, or three heteroatoms independently selected from oxygen, nitrogen, and sulfur; wherein said ring is optionally substituted by one or two substituents independently selected from halogen, $(C_1-C_6)$alkyl, halo$(C_1-C_6)$alkyl, and $(C_3-C_8)$cycloalkyl;

$R^{12}$ is hydrogen, halogen, or $(C_1-C_6)$alkyl, wherein said $(C_1-C_6)$alkyl is optionally substituted one, two, or three times by halogen;

$R^{13}$ is hydrogen, $(C_1-C_6)$alkyl, —$(C_1-C_6)$alkyl-$SO_2$—$(C_1-C_6)$alkyl, —$(C_1-C_6)$alkyl-aryl, or —$(C_1-C_6)$alkyl-5-6-membered heteroaryl, wherein said $(C_1-C_6)$alkyl, —$(C_1-C_6)$alkyl-$SO_2$—$(C_1-C_6)$alkyl, —$(C_1-C_6)$alkyl-aryl, or —$(C_1-C_6)$alkyl-5-6-membered heteroaryl is optionally substituted one, two, or three times by halogen; and each $R^{14}$ is independently halogen, $(C_1-C_6)$alkyl, $(C_3-C_8)$cycloalkyl, —CN, —$(C_1-C_6)$—OH, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —OH, $(C_1-C_4)$alkoxy, —O—$(C_3-C_8)$cycloalkyl, -aryl, 5-6 membered heteroaryl, wherein $(C_1-C_6)$alkyl, $(C_3-C_8)$cycloalkyl, aryl, or 5-6 membered heteroaryl is further optionally substituted by one, two, or three substituents independently selected from halogen, $(C_1-C_6)$alkyl, —$(C_1-C_6)$alkyl-OH, —$(C_1-C_6)$alkyl-O—$(C_1-C_6)$alkyl, or $(C_1-C_4)$alkoxy.

This invention also relates to a pharmaceutical composition comprising a compound of Formula (I) or pharmaceutically acceptable salt thereof and a pharmaceutically acceptable excipient.

This invention relates to a method of treating MrgX2-mediated diseases or disorders in a human in need thereof comprising administering to the human a therapeutically effective amount of a compound of Formula (I) or pharmaceutically acceptable salt thereof, or a pharmaceutical composition comprising of a compound of Formula (I) or a pharmaceutically acceptable salt thereof.

Another aspect of this invention relates to a method of treating MrgX2-mediated diseases or disorders in a human in need thereof, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, migraine, chronic inducible urticaria, chronic pruritus, acute pruritus, prurigo nodularis, osteoarthritis, pseudo anaphalaxis, or contact urticaria comprising administering to the human a therapeutically effective amount of a compound of Formula (I) or a pharmaceutically acceptable salt thereof. Another aspect of this invention relates to a method of treating MrgX2-mediated diseases or disorders in a human in need thereof, wherein the disease or disorder is chronic spontaneous urticaria, atopic dermatitis, rosacea, Crohns disease, ulcerative colitis, irritable bowel syndrome, neuropathic pain, or inflammatory pain comprising administering to the human a therapeutically effective amount of a compound of Formula (I) or a pharmaceutically acceptable salt thereof. Another aspect of this invention relates to the method of treating chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, migraine, chronic inducible urticaria, chronic pruritus, acute pruritus, prurigo nodularis, osteoarthritis, pseudo anaphalaxis, or contact urticaria comprising administering to the human a therapeutically effective amount of a compound of Formula (I) or a pharmaceutically acceptable salt thereof. Another aspect of the invention relates to the method of treating chronic spontaneous urticaria, atopic dermatitis, rosacea, Crohns disease, ulcerative colitis, irritable bowel syndrome, neuropathic pain, or inflammatory pain comprising administering to the human a therapeutically effective amount of a compound of Formula (I) or a pharmaceutically acceptable salt thereof.

In another aspect, the invention provides a compound of Formula (I) or a pharmaceutically acceptable salt thereof for use in therapy.

In another aspect, there is provided a compound of Formula (I) or a pharmaceutically acceptable salt thereof for use in the treatment of an MrgX2-mediated disease or disorder.

In another aspect, there is provided a compound of Formula (I) or a pharmaceutically acceptable salt thereof for use in the treatment of an MrgX2-mediated disease or disorder, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, migraine, chronic inducible urticaria, chronic pruritus, acute pruritus, prurigo nodularis, osteoarthritis, pseudo anaphalaxis, or contact urticaria.

In another aspect, there is provided a compound of Formulae (I) or a pharmaceutically acceptable salt thereof for use in the treatment of an MrgX2-mediated disease or disorder, wherein the disease or disorder is chronic spontaneous urticaria, atopic dermatitis, rosacea, Crohns disease, ulcerative colitis, irritable bowel syndrome, neuropathic pain, or inflammatory pain.

In another aspect, there is provided a compound of Formula (I) or a pharmaceutically acceptable salt thereof for the use in the treatment of chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, migraine, chronic inducible urticaria, chronic pruritus, acute pruritus, prurigo nodularis, osteoarthritis, pseudo anaphalaxis, or contact urticaria. In another aspect, there is provided a compound of Formula (I) or pharmaceutically acceptable salt thereof for the use in the treatment of chronic spontaneous urticaria, atopic dermatitis, rosacea, Crohns disease, ulcerative colitis, irritable bowel syndrome, neuropathic pain, or inflammatory pain.

In another aspect, there is provided the use of a compound of Formula (I) or a pharmaceutically acceptable salt thereof, in the manufacture of a medicament for use in the treatment of an MrgX2-mediated disease or disorder.

In another aspect, there is provided the use of a compound of Formula (I) or a pharmaceutically acceptable salt thereof, in the manufacture of a medicament for use in the treatment of an MrgX2-mediated disease or disorder, wherein the disease or disorder is chronic spontaneous urticaria, atopic dermatitis, rosacea, Crohns disease, ulcerative colitis, irritable bowel syndrome, neuropathic pain, or inflammatory pain. In another aspect, there is provided the use of a compound of Formula (I) or a pharmaceutically acceptable salt thereof, in the manufacture of a medicament for use in the treatment of chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. In another aspect, there is provided the use of a compound of Formula (I) or a pharmaceutically acceptable salt thereof, in the manufacture of a medicament for use in the treatment of chronic spontaneous urticaria, atopic dermatitis, rosacea, Crohns disease, ulcerative colitis, irritable bowel syndrome, neuropathic pain, or inflammatory pain.

DETAILED DESCRIPTION OF THE INVENTION

This invention relates to compounds of the Formula (I) as defined above or pharmaceutically acceptable salts thereof. This invention further relates to compounds of the Formula (II) or pharmaceutically acceptable salts thereof

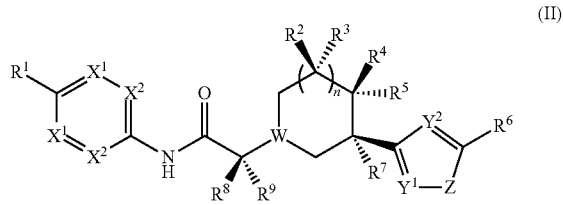

(II)

wherein:
W is N or CH;
each $X^1$ is independently N or $CR^{10}$;
each $X^2$ is independently N or $CR^{11}$;
$Y^1$ is N or $CR^{12}$;
$Y^2$ is N or $CR^{12}$;
Z is

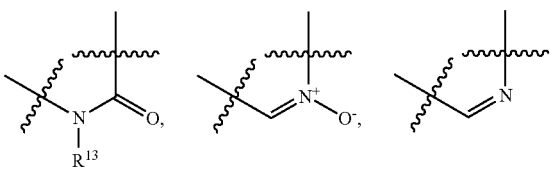

n is 0 or 1;
$R^1$ is hydrogen, halogen, $(C_1-C_6)$alkyl, —$(C_1-C_6)$alkyl-$NH_2$, —$(C_1-C_6)$alkyl-NH(($C_1-C_6$)alkyl), —$(C_1-C_6)$alkyl-N ((C$_1$-C$_6$)alkyl)((C$_1$-C$_6$)alkyl), —(C$_1$-C$_6$)alkyl-(C$_3$-C$_8$)cycloalkyl, —(C$_1$-C$_6$)alkyl-aryl, 5- or 6-membered heteroaryl (C$_1$-C$_4$)alkyl-, (C$_3$-C$_8$)cycloalkyl, (C$_2$-C$_6$)alkenyl, —(C$_2$-C$_6$)alkenyl-(C$_3$-C$_8$)cycloalkyl, —OH, (C$_1$-C$_4$)alkoxy, —O—(C$_1$-C$_6$)alkyl-(C$_3$-C$_8$)cycloalkyl, —O—(C$_1$-C$_6$)alkyl-aryl, —O—(C$_1$-C$_6$)alkyl-5-6 membered heteroaryl, —O—(C$_2$-C$_6$)alkenyl, —O—(C$_3$-C$_8$)cycloalkyl, —O-aryl, —O-heteroaryl, —C(O)-aryl, —CO$_2$H, —CO$_2$(C$_1$-C$_6$)alkyl, —CO$_2$(C$_3$-C$_8$)cycloalkyl, —O$_2$C(C$_1$-C$_6$)alkyl, —O$_2$C(C$_3$-C$_8$)cycloalkyl, —NH$_2$, —NH(C$_1$-C$_6$)alkyl, —N((C$_1$-C$_6$)alkyl)((C$_1$-C$_6$)alkyl), aryl, or 5-6 membered heteroaryl, wherein any said (C$_1$-C$_6$)alkyl, —(C$_1$-C$_6$)alkyl-(C$_3$-C$_8$)cycloalkyl, —(C$_1$-C$_6$)alkyl-aryl, (C$_1$-C$_4$)alkoxy, —O—(C$_1$-C$_6$)alkyl-(C$_3$-C$_8$)cycloalkyl, —O—(C$_3$-C$_8$)cycloalkyl, —O-aryl, —O-5-6-membered heteroaryl, —C(O)-aryl, aryl, or 5-6 membered heteroaryl is optionally substituted one, two, or three times by R$^{14}$;

R$^2$ is hydrogen, halogen, (C$_1$-C$_6$)alkyl, or —OH, wherein any said (C$_1$-C$_6$)alkyl is optionally substituted one, two, or three times by halogen;

R$^3$ is hydrogen, halogen, (C$_1$-C$_6$)alkyl, or —OH, wherein any said (C$_1$-C$_6$)alkyl is optionally substituted one, two, or three times by halogen;

R$^4$ is hydrogen, halogen, or (C$_1$-C$_6$)alkyl;

R$^5$ is hydrogen, halogen, or (C$_1$-C$_6$)alkyl;

R$^6$ is hydrogen, halogen, (C$_1$-C$_6$)alkyl, (C$_3$-C$_8$)cycloalkyl, (C$_1$-C$_4$)alkoxy, —(C$_1$-C$_6$)alkyl-OH, —(C$_1$-C$_6$)alkyl-O—(C$_1$-C$_6$)alkyl, —(C$_1$-C$_6$)alkyl-NH$_2$, —(C$_1$-C$_6$)alkyl-NH((C$_1$-C$_6$)alkyl), —(C$_1$-C$_6$)alkyl-N—((C$_1$-C$_6$)alkyl)((C$_1$-C$_6$)alkyl), —(C$_1$-C$_6$)alkyl-NH((C$_1$-C$_6$)alkyl)-OH, —(C$_1$-C$_6$)alkyl-NH(((C$_1$-C$_6$)alkyl)-O—(C$_1$-C$_6$)alkyl), —(C$_1$-C$_6$)alkyl-N—((C$_1$-C$_6$)alkyl)((C$_1$-C$_6$)alkyl)-OH, —(C$_1$-C$_6$)alkyl-N—((C$_1$-C$_6$)alkyl)((C$_1$-C$_6$)alkyl)-O—(C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, —(C$_1$-C$_6$)alkyl-4- to 6-membered heterocycloalkyl, —(C$_1$-C$_6$)alkyl-NHC(O)—((C$_1$-C$_6$)alkyl), —(C$_1$-C$_6$)alkyl-SO$_2$—(C$_1$-C$_6$)alkyl, —(C$_1$-C$_6$)alkyl-SO$_2$—NH—(C$_1$-C$_6$)alkyl, —CN, —C(O)NH$_2$, —C(O)NH(C$_1$-C$_6$)alkyl), —C(O)N(C$_1$-C$_6$)alkyl) (C$_1$-C$_6$)alkyl), —NH$_2$, —NH(C$_1$-C$_6$)alkyl, —N((C$_1$-C$_6$)alkyl)((C$_1$-C$_6$)alkyl), —SO$_2$((C$_1$-C$_6$)alkyl), —SO$_2$—NH((C$_1$-C$_6$)alkyl), or aryl, wherein any said (C$_1$-C$_6$)alkyl, (C$_3$-C$_8$)cycloalkyl, —(C$_1$-C$_6$)alkyl-OH, —(C$_1$-C$_6$)alkyl-NH$_2$, —(C$_1$-C$_6$)alkyl-NH((C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, or —(C$_1$-C$_6$)alkyl-4- to 6-membered heterocycloalkyl is optionally substituted one, two, or three times by halogen;

R$^7$ is hydrogen, (C$_1$-C$_6$)alkyl, or —OH;

R$^8$ is hydrogen, (C$_1$-C$_6$)alkyl, or (C$_1$-C$_4$)alkoxy;

R$^9$ is hydrogen, (C$_1$-C$_6$)alkyl, or (C$_1$-C$_4$)alkoxy;

each R$^{10}$ is independently hydrogen, halogen, (C$_1$-C$_6$)alkyl, (C$_2$-C$_6$)alkenyl, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), (C$_2$-C$_6$)alkenyl, —O—(C$_1$-C$_6$)alkyl, —NH$_2$, —NH((C$_1$-C$_6$)alkyl), —N((C$_1$-C$_6$)alkyl)((C$_1$-C$_6$)alkyl), —NCH$_2$, or —CHNH;

or R$^1$ and any R$^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, (C$_1$-C$_6$)alkyl, —(C$_1$-C$_6$)alkyl-(C$_3$-C$_8$)cycloalkyl, halo(C$_1$-C$_6$)alkyl, and (C$_3$-C$_8$)cycloalkyl;

each R$^{11}$ is independently hydrogen, halogen, (C$_1$-C$_6$)alkyl, or (C$_2$-C$_6$)alkenyl;

or any R$^{10}$ and any R$^{11}$ taken together with the atoms to which they are attached, form a 5-, 6-, or 7-membered ring optionally containing one, two, or three heteroatoms independently selected from oxygen, nitrogen, and sulfur; wherein said ring is optionally substituted by one or two substituents independently selected from halogen, (C$_1$-C$_6$)alkyl, halo(C$_1$-C$_6$)alkyl, and (C$_3$-C$_8$)cycloalkyl;

R$^{12}$ is hydrogen, halogen, or (C$_1$-C$_6$)alkyl, wherein said (C$_1$-C$_6$)alkyl is optionally substituted one, two, or three times by halogen;

R$^{13}$ is hydrogen, (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl, wherein said (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl is optionally substituted one, two, or three times by halogen; and each R$^{14}$ is independently halogen, (C$_1$-C$_6$)alkyl, (C$_3$-C$_8$)cycloalkyl, —CN, —(C$_1$-C$_6$)—OH, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), —OH, (C$_1$-C$_4$)alkoxy, —O—(C$_3$-C$_8$)cycloalkyl, -aryl, 5-6 membered heteroaryl, wherein (C$_1$-C$_6$)alkyl, (C$_3$-C$_8$)cycloalkyl, aryl, or 5-6 membered heteroaryl is further optionally substituted by one, two, or three substituents independently selected from halogen, (C$_1$-C$_6$)alkyl, —(C$_1$-C$_6$)alkyl-OH, —(C$_1$-C$_6$)alkyl-O—(C$_1$-C$_6$)alkyl, or (C$_1$-C$_4$)alkoxy.

In some embodiments, this invention relates to compounds of Formulae (I) and (II), wherein W is N. In some embodiments, W is CH.

In some embodiments, this invention relates to compounds of Formulae (I) and (II), wherein each X$^1$ is independently N. In some embodiments, this invention relates to compounds of Formulae (I) and (II), wherein each X$^1$ is independently CR$^{10}$. In some embodiments, this invention relates to compounds of Formulae (I) and (II), wherein each X$^1$ is independently CR$^{10}$, wherein each R$^{10}$ is independently hydrogen, halogen, (C$_1$-C$_6$)alkyl, (C$_2$-C$_6$)alkenyl, —NCH$_2$, or —CHNH.

In some embodiments, each X$^1$ is independently CR$^{10}$, wherein each R$^{10}$ is independently hydrogen, halogen, (C$_1$-C$_6$)alkyl, or (C$_2$-C$_6$)alkenyl. In some embodiments, this invention relates to compounds of Formulae (I) and (II), wherein each X$^1$ is independently CR$^{10}$, wherein each R$^{10}$ is independently hydrogen or halogen. In some embodiments, each X$^1$ is independently CR$^{10}$, wherein each R$^{10}$ is hydrogen.

In some embodiments, this invention relates to compounds of Formulae (I) and (II), wherein each X$^2$ is independently N. In some embodiments, this invention relates to compounds of Formulae (I) and (II), wherein each X$^2$ is independently CR$^{11}$, wherein each R$^{11}$ is independently hydrogen or halogen. In some embodiments, each X$^2$ is independently CR$^{11}$, wherein each R$^{11}$ is hydrogen. In some embodiments, each X$^2$ is independently CR$^{11}$, wherein each R$^{11}$ is halogen.

In some embodiments, this invention relates to compounds of Formulae (I) and (II), wherein Y$^1$ is N. In some embodiments, this invention relates to compounds of Formulae (I) and (II), wherein Y$^1$ is CR$^{12}$, wherein R$^{12}$ is hydrogen. In some embodiments, this invention relates to compounds of Formulae (I) and (II), wherein Y$^1$ is CR$^{12}$, wherein R$^{12}$ is (C$_1$-C$_6$)alkyl. In some embodiments, Y$^1$ is CR$^{12}$, wherein R$^{12}$ is (C$_1$-C$_6$)alkyl, wherein said (C$_1$-C$_6$)alkyl is optionally substituted one, two, or three times by halogen. In some embodiments, Y$^1$ is CR$^{12}$, wherein R$^{12}$ is ($C_1$-$C_6$)alkyl, wherein said ($C_1$-$C_6$)alkyl is substituted one time by fluorine. In some embodiments, $Y^1$ is $CR^{12}$, wherein $R^{12}$ is ($C_1$-$C_6$)alkyl, wherein said ($C_1$-$C_6$)alkyl is substituted two times by fluorine. In some embodiments, $Y^1$ is $CR^{12}$, wherein $R^{12}$ is ($C_1$-$C_6$)alkyl, wherein said ($C_1$-$C_6$)alkyl is substituted three times by fluorine. In some embodiments, $Y^1$ is —$CF_3$.

In some embodiments, this invention relates to compounds of Formulae (I) and (II), wherein $Y^2$ is N. In some embodiments, this invention relates to compounds of Formulae (I) and (II), wherein $Y^2$ is $CR^{12}$, wherein $R^{12}$ is hydrogen. In some embodiments, this invention relates to compounds of Formulae (I) and (II), wherein $Y^2$ is $CR^{12}$, wherein $R^{12}$ is ($C_1$-$C_6$)alkyl. In some embodiments, $Y^2$ is $CR^{12}$, wherein $R^{12}$ is ($C_1$-$C_6$)alkyl, wherein said ($C_1$-$C_6$)alkyl is optionally substituted one, two, or three times by halogen.

In some embodiments, $Y^2$ is $CR^{12}$, wherein $R^{12}$ is ($C_1$-$C_6$)alkyl, wherein said ($C_1$-$C_6$)alkyl is substituted one time by fluorine. In some embodiments, $Y^2$ is $CR^{12}$, wherein $R^{12}$ is ($C_1$-$C_6$)alkyl, wherein said ($C_1$-$C_6$)alkyl is substituted two times by fluorine.

In some embodiments, $Y^2$ is $CR^{12}$, wherein $R^{12}$ is ($C_1$-$C_6$)alkyl, wherein said ($C_1$-$C_6$)alkyl is substituted three times by fluorine. In some embodiments, $Y^2$ is —$CF_3$.

In some embodiments, this invention relates to compounds of Formulae (I) and (II), wherein Z is

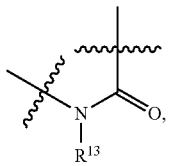

wherein $R^{13}$ is hydrogen, ($C_1$-$C_6$)alkyl, —($C_1$-$C_6$)alkyl-$SO_2$—($C_1$-$C_6$)alkyl, —($C_1$-$C_6$)alkyl-aryl, or —($C_1$-$C_6$)alkyl-5-6-membered heteroaryl, wherein said ($C_1$-$C_6$)alkyl is optionally substituted one, two, or three times by halogen. In some embodiments, $R^{13}$ is ($C_1$-$C_6$)alkyl. —($C_1$-$C_6$)alkyl-aryl, —($C_1$-$C_6$)alkyl-$SO_2$—($C_1$-$C_6$)alkyl, or —($C_1$-$C_6$)alkyl-5-6-membered heteroaryl. In some embodiments, $R^{13}$ is ($C_1$-$C_6$)alkyl, —($C_1$-$C_6$)alkyl-aryl, —($C_1$-$C_6$)alkyl-$SO_2$—($C_1$-$C_6$)alkyl, or —($C_1$-$C_6$)alkyl-5-6-membered heteroaryl, wherein said ($C_1$-$C_6$)alkyl is substituted three times by halogen. In some embodiments, this invention relates to compounds of Formulae (I) and (II), wherein $R^{13}$ is hydrogen. In some embodiments, $R^{13}$ is ($C_1$-$C_6$)alkyl is substituted one time by halogen. In some embodiments, $R^{13}$ is ($C_1$-$C_6$)alkyl is substituted two times by halogen. In some embodiments, $R^{13}$ is ($C_1$-$C_6$)alkyl is substituted three times by halogen. In some embodiments, $R^{13}$ is ($C_1$-$C_6$)alkyl is substituted three times by fluorine. In some embodiments, $R^{13}$ is —($C_1$-$C_6$)alkyl-aryl. In some embodiments, $R^{13}$ is —($C_1$-$C_6$)alkyl-$SO_2$—($C_1$-$C_6$)alkyl. In some embodiments, $R^{13}$ is —($C_1$-$C_6$)alkyl-5-6-membered heteroaryl. In some embodiments, $R^{13}$ is methyl, ethyl, isopropyl, —$CF_3$, —$CH_2CF_3$, benzyl, —$CH_2CH_2SO_2CH_3$, —$CH_2$-pyridine, or —$CH_2$-oxazole. In some embodiments, $R^{13}$ is methyl, ethyl, or isopropyl. In some embodiments, $R^{13}$ is —$CH_2CF_3$. In some embodiments, $R^{13}$ is benzyl. In some embodiments, $R^{13}$ is —$CH_2CH_2SO_2CH_3$. In some embodiments, $R^{13}$ is —$CH_2$-pyridine or —$CH_2$-oxazole.

In some embodiments, this invention relates to compounds of Formulae (I) and (II), wherein Z is

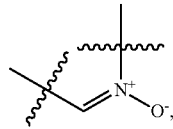

and $R^6$ is hydrogen, ($C_1$-$C_6$)alkyl, —($C_1$-$C_6$)alkyl-OH, —($C_1$-$C_6$)alkyl-NHC(O)—(($C_1$-$C_6$)alkyl), or —C(O)$NH_2$, wherein any said ($C_1$-$C_6$)alkyl or —($C_1$-$C_6$)alkyl-OH is optionally substituted one, two, or three times by halogen. In some embodiments, this invention relates to compounds of Formulae (I) and (II), wherein Z is In some embodiments, this invention relates to compounds of Formulae (I) and (II), wherein Z is

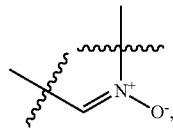

and $R^6$ is hydrogen, ($C_1$-$C_6$)alkyl, —($C_1$-$C_6$)alkyl-OH, —($C_1$-$C_6$)alkyl-NHC(O)—(($C_1$-$C_6$)alkyl), or —C(O)$NH_2$, wherein any said ($C_1$-$C_6$)alkyl or —($C_1$-$C_6$)alkyl-OH is optionally substituted three times by halogen. In some embodiments, this invention relates to compounds of Formulae (I) and (II), wherein Z is

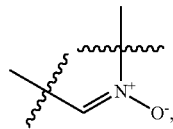

and $R^6$ is hydrogen, ($C_1$-$C_6$)alkyl, —($C_1$-$C_6$)alkyl-OH, —($C_1$-$C_6$)alkyl-NHC(O)—(($C_1$-$C_6$)alkyl), or —C(O)$NH_2$, wherein any said ($C_1$-$C_6$)alkyl or —($C_1$-$C_6$)alkyl-OH is optionally substituted three times by fluorine. In some embodiments, this invention relates to compounds of Formulae (I) and (II), wherein Z is

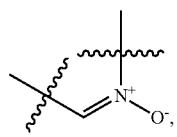

and $R^6$ is hydrogen, methyl, —$CH_2CF_3$, —$CH_2OH$, —CH(OH)$CF_3$, —C(O)$NH_2$, —$CH_2NHC(O)CH_3$. In some embodiments, this invention relates to compounds of Formulae (I) and (II), wherein Z is

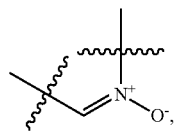

and R⁶ is hydrogen, methyl, —CH₂CF₃, —CH₂OH, —CH(OH)CF₃, —C(O)NH₂, —CH₂NHC(O)CH₃. In some embodiments, Z is

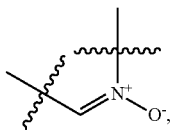

and R⁶ is hydrogen.

In some embodiments, this invention relates to compounds of Formulae (I) and (II), wherein Z is

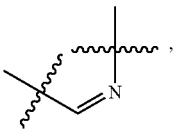 [SMILES: */C=N\*]

and R⁶ is hydrogen, —(C₁-C₆)alkyl-NH₂, —(C₁-C₆)alkyl-4- to 6-membered heterocycloalkyl, —C(O)NH₂, wherein any said —(C₁-C₆)alkyl-4- to 6-membered heterocycloalkyl is optionally substituted one, two, or three times by halogen. In some embodiments, this invention relates to compounds of Formulae (I) and (II), wherein Z is

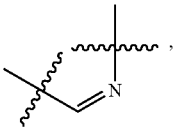 [SMILES: */C=N\*]

and R⁶ is hydrogen, —(C₁-C₆)alkyl-NH₂, —(C₁-C₆)alkyl-4- to 6-membered heterocycloalkyl, —C(O)NH₂, wherein any said —(C₁-C₆)alkyl-4- to 6-membered heterocycloalkyl is optionally substituted two or three times by fluorine.

In some embodiments, this invention relates to compounds of Formulae (I) and (II), wherein Z is

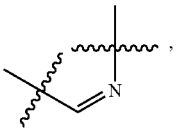

and R⁶ is hydrogen, —CH₂NH₂, —CH₂-azetidine, or —C(O)NH₂, wherein —CH₂-azetidine is substituted two times by fluorine. In some embodiments, this invention relates to compounds of Formulae (I) and (II), wherein Z is

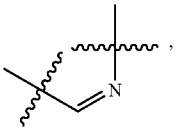 [SMILES: */C=N\*]

and R⁶ is hydrogen.

In some embodiments, this invention relates to compounds of Formulae (I) and (II), wherein n is 1. In some embodiments, this invention relates to compounds of Formulae (I) and (II), wherein n is 0.

In some embodiments, this invention relates to compounds of Formulae (I) and (II), wherein R¹ is halogen, (C₁-C₆)alkyl, —(C₁-C₆)alkyl-NH₂, —(C₁-C₆)alkyl-(C₃-C₈)cycloalkyl, —(C₁-C₆)alkyl-aryl, 5- or 6-membered heteroaryl(C₁-C₄)alkyl-, (C₃-C₈)cycloalkyl, (C₂-C₆)alkenyl, —(C₂-C₆)alkenyl-(C₃-C₈)cycloalkyl, —OH, (C₁-C₄)alkoxy, —O—(C₁-C₆)alkyl-(C₃-C₈)cycloalkyl, —O—(C₁-C₆)alkyl-5-6 membered heteroaryl, —O—(C₃-C₈)cycloalkyl, —O-aryl, —O-heteroaryl, —C(O)-aryl, —CO₂(C₃-C₈)cycloalkyl, —NH₂, aryl, or 5-6 membered heteroaryl, wherein any said (C₁-C₆)alkyl, —(C₁-C₆)alkyl-(C₃-C₈)cycloalkyl, —(C₁-C₆)alkyl-aryl, (C₁-C₄)alkoxy, —O—(C₁-C₆)alkyl-(C₃-C₈)cycloalkyl, —O—(C₃-C₈)cycloalkyl, —O-aryl, —O-5-6-membered heteroaryl, —C(O)-aryl, aryl, or 5-6 membered heteroaryl is optionally substituted one, two, or three times by R¹⁴;

and each R¹⁴ is independently halogen, (C₁-C₆)alkyl, (C₃-C₈)cycloalkyl, —CN, —(C₁-C₆)—OH, —(C₁-C₆)alkyl-N((C₁-C₆)alkyl)((C₁-C₆)alkyl), —OH, (C₁-C₄)alkoxy, 5-6 membered heteroaryl, wherein (C₁-C₆)alkyl, (C₃-C₈)cycloalkyl, aryl, or 5-6 membered heteroaryl is further optionally substituted by one, two, or three substituents independently selected from halogen, (C₁-C₆)alkyl, —(C₁-C₆)alkyl-OH, —(C₁-C₆)alkyl-O—(C₁-C₆)alkyl, or (C₁-C₄)alkoxy.

In some embodiments, this invention relates to compounds of Formulae (I) and (II), wherein R¹ is halogen, (C₁-C₆)alkyl, —(C₁-C₆)alkyl-NH₂, —(C₁-C₆)alkyl-(C₃-C₈)cycloalkyl, —(C₁-C₆)alkyl-aryl, 5- or 6-membered heteroaryl(C₁-C₄)alkyl-, (C₃-C₈)cycloalkyl, (C₂-C₆)alkenyl, —(C₂-C₆)alkenyl-(C₃-C₈)cycloalkyl, —OH, (C₁-C₄)alkoxy, —O—(C₁-C₆)alkyl-(C₃-C₈)cycloalkyl, —O—(C₁-C₆)alkyl-5-6 membered heteroaryl, —O—(C₃-C₈)cycloalkyl, —O-aryl, —O-heteroaryl, —C(O)-aryl, —CO₂(C₃-C₈)cycloalkyl, —NH₂, aryl, or 5-6 membered heteroaryl, wherein any said (C₁-C₆)alkyl, —(C₁-C₆)alkyl-(C₃-C₈)cycloalkyl, —(C₁-C₆)alkyl-aryl, (C₁-C₄)alkoxy, —O—(C₁-C₆)alkyl-(C₃-C₈)cycloalkyl, —O—(C₃-C₈)cycloalkyl, —O-aryl, —O-5-6-membered heteroaryl, —C(O)-aryl, aryl, or 5-6 membered heteroaryl is optionally substituted one, two, or three times by R¹⁴;

and each R¹⁴ is independently halogen, (C₁-C₆)alkyl, (C₃-C₈)cycloalkyl, —CN, —(C₁-C₆)—OH, —(C₁-C₆)alkyl-N((C₁-C₆)alkyl)((C₁-C₆)alkyl), —OH, (C₁-C₄)alkoxy, 5-6 membered heteroaryl, wherein (C₁-C₆)alkyl, (C₃-C₈)cycloalkyl, aryl, or 5-6 membered heteroaryl is further optionally substituted by one, two, or three substituents independently selected from halogen or (C₁-C₆)alkyl.

In some embodiments, this invention relates to compounds of Formulae (I) and (II), wherein R¹ is halogen, (C₁-C₆)alkyl, —(C₁-C₆)alkyl-(C₃-C₈)cycloalkyl, —(C₁-C₆)alkyl-aryl, 5- or 6-membered heteroaryl(C₁-C₄)alkyl-, (C₃-C₈)cycloalkyl, —(C₂-C₆)alkenyl-(C₃-C₈)cycloalkyl, (C₁-C₄)alkoxy, —O—(C₁-C₆)alkyl-(C₃-C₈)cycloalkyl, —O—(C₁-C₆)alkyl-5-6 membered heteroaryl, —O—(C₃-C₈)cycloalkyl, —O-aryl, —O-heteroaryl, —C(O)-aryl, —CO₂(C₃-C₈)cycloalkyl, aryl, or 5-6 membered heteroaryl, wherein any said (C₁-C₆)alkyl, —(C₁-C₆)alkyl-(C₃-C₈)cycloalkyl, —(C₁-C₆)alkyl-aryl, (C₁-C₄)alkoxy, —O—(C₁-C₆)alkyl-(C₃-C₈)cycloalkyl, —O—(C₃-C₈)cycloalkyl, —O-aryl, —O-5-6-membered heteroaryl, —C(O)-aryl, aryl, or 5-6 membered heteroaryl is optionally substituted one, two, or three times by R¹⁴;

and each R¹⁴ is independently halogen, (C₁-C₆)alkyl, (C₃-C₈)cycloalkyl, —CN, —(C₁-C₆)—OH, —(C₁-C₆)alkyl-N((C₁-C₆)alkyl)((C₁-C₆)alkyl), —OH, (C₁-C₄)alkoxy, 5-6 membered heteroaryl, wherein (C₁-C₆)alkyl, (C₃-C₈)cycloalkyl, aryl, or 5-6 membered heteroaryl is further optionally substituted by one, two, or three substituents independently selected from halogen or $(C_1-C_6)$alkyl.

In some embodiments, this invention relates to compounds of Formulae (I) and (II), wherein $R^1$ is halogen, $(C_1-C_6)$alkyl, —$(C_1-C_6)$alkyl-NH$_2$, —$(C_1-C_6)$alkyl-$(C_3-C_8)$cycloalkyl, —$(C_1-C_6)$alkyl-phenyl, 5- or 6-membered heteroaryl$(C_1-C_4)$alkyl-, $(C_3-C_8)$cycloalkyl, $(C_2-C_6)$alkenyl, —$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-5-6 membered heteroaryl, —O—$(C_3-C_8)$cycloalkyl, —O— phenyl, —O-heteroaryl, —C(O)-phenyl, —CO$_2$$(C_3-C_8)$cycloalkyl, —NH$_2$, aryl, or 5-6 membered heteroaryl, wherein 5-6 membered heteroaryl is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl; wherein any said $(C_1-C_6)$alkyl, —$(C_1-C_6)$alkyl-$(C_3-C_8)$cycloalkyl, —$(C_1-C_6)$alkyl-phenyl, $(C_1-C_4)$alkoxy, —O—$(C_1-C_6)$alkyl-$(C_3-C_8)$cycloalkyl, —O—$(C_3-C_8)$cycloalkyl, —O-phenyl, —O-5-6-membered heteroaryl, —C(O)— phenyl, phenyl, or 5-6 membered heteroaryl is optionally substituted one, two, or three times by $R^{14}$, wherein 5-6 membered heteroaryl is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl.

and each $R^{14}$ is independently halogen, $(C_1-C_6)$alkyl, $(C_3-C_8)$cycloalkyl, —CN, —$(C_1-C_6)$—OH, —$(C_1-C_6)$alkyl-N$((C_1-C_6)$alkyl$)((C_1-C_6)$alkyl$)$, —OH, $(C_1-C_4)$alkoxy, 5-6 membered heteroaryl, wherein $(C_1-C_6)$alkyl, $(C_3-C_8)$cycloalkyl, phenyl, or 5-6 membered heteroaryl is further optionally substituted by one, two, or three substituents independently selected from halogen or $(C_1-C_6)$alkyl.

In some embodiments, this invention relates to compounds of Formulae (I) and (II), wherein $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, $(C_1-C_6)$alkyl, —$(C_1-C_6)$alkyl-$(C_3-C_8)$cycloalkyl, halo$(C_1-C_6)$alkyl, and $(C_3-C_8)$cycloalkyl. In some embodiments, this invention relates to compounds of Formulae (I) and (II), wherein $R^1$ and any $R^{10}$ taken together with the atoms to which they are attached, form furanyl, thienyl, dihydropyrrolyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, triazinyl, or phenyl, wherein said ring is optionally substituted by one or two substituents independently selected from halogen, $(C_1-C_6)$alkyl, —$(C_1-C_6)$alkyl-$(C_3-C_8)$cycloalkyl, halo$(C_1-C_6)$alkyl, and $(C_3-C_8)$cycloalkyl. In some embodiments, this invention relates to compounds of Formulae (I) and (II), wherein $R^1$ and any $R^{10}$ taken together with the atoms to which they are attached, form dihydropyrrolyl, pyrrolyl, pyrazolyl, xazolyl, pyridinyl, or phenyl, wherein said ring is optionally substituted by one or two substituents independently selected from halogen, $(C_1-C_6)$alkyl, —$(C_1-C_6)$alkyl-$(C_3-C_8)$cycloalkyl, halo $(C_1-C_6)$alkyl, and $(C_3-C_8)$cycloalkyl.

In some embodiments, this invention relates to compounds of Formulae (I) and (II), wherein $R^2$ is hydrogen, halogen, or $(C_1-C_6)$alkyl. In some embodiments, $R^2$ is hydrogen or halogen. In some embodiments, $R^2$ is hydrogen, fluorine, or methyl. In some embodiments $R^2$ is hydrogen or fluorine.

In some embodiments, this invention relates to compounds of Formulae (I) and (II), wherein $R^3$ is hydrogen, halogen, or $(C_1-C_6)$alkyl. In some embodiments, $R^3$ is hydrogen or halogen. In some embodiments, $R^2$ is hydrogen, fluorine, or methyl. In some embodiments, $R^3$ is hydrogen or fluorine.

In some embodiments, this invention relates to compounds of Formulae (I) and (II), wherein $R^2$ and $R^3$ are hydrogen. In some embodiments, $R^2$ and $R^3$ are halogen. In some embodiments, this invention relates to compounds of Formulae (I) and (II), wherein $R^2$ is hydrogen and $R^3$ is $(C_1-C_6)$alkyl. In some embodiments, this invention relates to compounds of Formulae (I) and (II), wherein $R^2$ is $(C_1-C_6)$alkyl and $R^3$ is hydrogen. In some embodiments, $R^2$ and $R^3$ are fluorine. In some embodiments, $R^2$ is hydrogen and $R^3$ is methyl. In some embodiments, $R^2$ is methyl and $R^3$ is hydrogen.

In some embodiments, this invention relates to compounds of Formulae (I) and (II), wherein $R^4$ is hydrogen or halogen. In some embodiments, $R^4$ is hydrogen or fluorine.

In some embodiments, this invention relates to compounds of Formulae (I) and (II), wherein $R^5$ is hydrogen or halogen. In some embodiments, this invention relates to compounds of Formulae (I) and (II), wherein $R^5$ is hydrogen or fluorine.

In some embodiments, this invention relates to compounds of Formulae (I) and (II), wherein $R^1$ and $R^5$ are hydrogen. In some embodiments, this invention relates to compounds of Formulae (I) and (II), wherein $R^1$ and $R^5$ are halogen. In some embodiments, this invention relates to compounds of Formulae (I) and (II), wherein $R^4$ is hydrogen and $R^5$ is halogen. In some embodiments, this invention relates to compounds of Formulae (I) and (II), wherein $R^4$ is halogen and $R^5$ are hydrogen. In some embodiments, $R^4$ and $R^5$ are fluorine. In some embodiments, $R^4$ is hydrogen and $R^5$ is fluorine. In some embodiments, $R^4$ is fluorine and $R^5$ is hydrogen.

In some embodiments, this invention relates to compounds of Formulae (I) and (II), wherein $R^6$ is hydrogen, $(C_1-C_6)$alkyl, $(C_3-C_8)$cycloalkyl, —$(C_1-C_6)$alkyl-OH, —$(C_1-C_6)$alkyl-NH$_2$, —$(C_1-C_6)$alkyl-NH$((C_1-C_6)$alkyl$)$, —$(C_1-C_6)$alkyl-N—$((C_1-C_6)$alkyl$)((C_1-C_6)$alkyl$)$, —$(C_1-C_6)$alkyl-NH$((C_1-C_6)$alkyl$)$-OH, —$(C_1-C_6)$alkyl-NH$((C_1-C_6)$alkyl$)$-O—$(C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, —$(C_1-C_6)$alkyl-4- to 6-membered heterocycloalkyl, —$(C_1-C_6)$alkyl-NHC(O)—$((C_1-C_6)$alkyl$)$, —$(C_1-C_6)$alkyl-SO$_2$—$(C_1-C_6)$alkyl, —$(C_1-C_6)$alkyl-SO$_2$—NH—$(C_1-C_6)$alkyl, —CN, —C(O)NH$_2$, —NH$_2$, —SO$_2$$((C_1-C_6)$alkyl$)$, —SO$_2$—NH$((C_1-C_6)$alkyl$)$, or aryl, wherein any said $(C_1-C_6)$alkyl, —$(C_1-C_6)$alkyl-OH, —$(C_1-C_6)$alkyl-NH$_2$, —$(C_1-C_6)$alkyl-NH$((C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, or —$(C_1-C_6)$alkyl-4- to 6-membered heterocycloalkyl is optionally substituted one, two, or three times by halogen.

In some embodiments, this invention relates to compounds of Formulae (I) and (II), wherein $R^6$ is hydrogen, $(C_1-C_6)$alkyl, $(C_3-C_8)$cycloalkyl, —$(C_1-C_6)$alkyl-OH, —$(C_1-C_6)$alkyl-NH$_2$, —$(C_1-C_6)$alkyl-NH$((C_1-C_6)$alkyl$)$, —$(C_1-C_6)$alkyl-N—$((C_1-C_6)$alkyl$)((C_1-C_6)$alkyl$)$, —$(C_1-C_6)$alkyl-NH$((C_1-C_6)$alkyl$)$-OH, —$(C_1-C_6)$alkyl-NH$((C_1-C_6)$alkyl$)$-O—$(C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, —$(C_1-C_6)$alkyl-4- to 6-membered heterocycloalkyl, —$(C_1-C_6)$alkyl-NHC(O)—$((C_1-C_6)$alkyl$)$, —$(C_1-C_6)$alkyl-SO$_2$—$(C_1-C_6)$alkyl, —$(C_1-C_6)$alkyl-SO$_2$—

NH—($C_1$-$C_6$)alkyl, —CN, —C(O)NH$_2$, —NH$_2$, —SO$_2$(($C_1$-$C_6$)alkyl), —SO$_2$—NH(($C_1$-$C_6$)alkyl), or aryl, wherein any said ($C_1$-$C_6$)alkyl, —($C_1$-$C_6$)alkyl-OH, —($C_1$-$C_6$)alkyl-NH$_2$, —($C_1$-$C_6$)alkyl-NH(($C_1$-$C_6$)alkyl), —($C_1$-$C_6$)alkyl-NH—($C_3$-$C_8$)cycloalkyl, —($C_1$-$C_6$)alkyl-NH-4- to 6-membered heterocycloalkyl, or —($C_1$-$C_6$)alkyl-4- to 6-membered heterocycloalkyl is optionally substituted one, two, or three times by halogen, wherein aryl is phenyl and 4- to 6-membered heterocycloalkyl is azetidinyl, oxetanyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-oxathianyl, 1,4-oxathianyl, or 1,4-dithianyl.

In some embodiments, this invention relates to compounds of Formulae (I) and (II), wherein $R^6$ is hydrogen, ($C_1$-$C_6$)alkyl, ($C_3$-$C_8$)cycloalkyl, —($C_1$-$C_6$)alkyl-OH, —($C_1$-$C_6$)alkyl-NH$_2$, —($C_1$-$C_6$)alkyl-NH(($C_1$-$C_6$)alkyl), —($C_1$-$C_6$)alkyl-N—(($C_1$-$C_6$)alkyl)(($C_1$-$C_6$)alkyl), —($C_1$-$C_6$)alkyl-NH(($C_1$-$C_6$)alkyl)-OH, —($C_1$-$C_6$)alkyl-NH(($C_1$-$C_6$)alkyl)-O—($C_1$-$C_6$)alkyl), —($C_1$-$C_6$)alkyl-NH—($C_3$-$C_8$)cycloalkyl, —($C_1$-$C_6$)alkyl-NH-4- to 6-membered heterocycloalkyl, —($C_1$-$C_6$)alkyl-4- to 6-membered heterocycloalkyl, —($C_1$-$C_6$)alkyl-NHC(O)—(($C_1$-$C_6$)alkyl), —($C_1$-$C_6$)alkyl-SO$_2$—($C_1$-$C_6$)alkyl, —($C_1$-$C_6$)alkyl-SO$_2$—NH—($C_1$-$C_6$)alkyl, —CN, —C(O)NH$_2$, —NH$_2$, —SO$_2$(($C_1$-$C_6$)alkyl), —SO$_2$—NH(($C_1$-$C_6$)alkyl), or aryl, wherein any said ($C_1$-$C_6$)alkyl, —($C_1$-$C_6$)alkyl-OH, —($C_1$-$C_6$)alkyl-NH$_2$, —($C_1$-$C_6$)alkyl-NH(($C_1$-$C_6$)alkyl), —($C_1$-$C_6$)alkyl-NH—($C_3$-$C_8$)cycloalkyl, —($C_1$-$C_6$)alkyl-NH-4- to 6-membered heterocycloalkyl, or —($C_1$-$C_6$)alkyl-4- to 6-membered heterocycloalkyl is optionally substituted one, two, or three times by halogen.

In some embodiments, this invention relates to compounds of Formulae (I) and (II), wherein $R^6$ is hydrogen, ($C_1$-$C_6$)alkyl, cyclopropyl, —($C_1$-$C_6$)alkyl-OH, —($C_1$-$C_6$)alkyl-NH$_2$, —($C_1$-$C_6$)alkyl-NH(($C_1$-$C_6$)alkyl), —($C_1$-$C_6$)alkyl-N—(($C_1$-$C_6$)alkyl)(($C_1$-$C_6$)alkyl), —($C_1$-$C_6$)alkyl-NH(($C_1$-$C_6$)alkyl)-OH, —($C_1$-$C_6$)alkyl-NH(($C_1$-$C_6$)alkyl)-O—($C_1$-$C_6$)alkyl), —($C_1$-$C_6$)alkyl-NH-cyclobutyl, —($C_1$-$C_6$)alkyl-piperidinyl, —($C_1$-$C_6$)alkyl-morpholinyl, —($C_1$-$C_6$)alkyl-NHC(O)—(($C_1$-$C_6$)alkyl), —($C_1$-$C_6$)alkyl-SO$_2$—($C_1$-$C_6$)alkyl, —($C_1$-$C_6$)alkyl-SO$_2$—NH—($C_1$-$C_6$)alkyl, —CN, —C(O)NH$_2$, —NH$_2$, —SO$_2$(($C_1$-$C_6$)alkyl), —SO$_2$—NH(($C_1$-$C_6$)alkyl), or phenyl, wherein any said ($C_1$-$C_6$)alkyl, cyclopropyl, —($C_1$-$C_6$)alkyl-OH, —($C_1$-$C_6$)alkyl-NH$_2$, —($C_1$-$C_6$)alkyl-NH(($C_1$-$C_6$)alkyl), —($C_1$-$C_6$)alkyl-NH-cyclobutyl, or —($C_1$-$C_6$)alkyl-piperidinyl is optionally substituted one, two, or three times by halogen.

In some embodiments, this invention relates to compounds of Formulae (I) and (II), wherein $R^7$ is hydrogen. In some embodiments, this invention relates to compounds of Formulae (I) and (II), wherein $R^7$ is ($C_1$-$C_6$)alkyl. In some embodiments, this invention relates to compounds of Formulae (I) and (II), wherein $R^7$ is —OH. In some embodiments, $R^7$ is methyl.

In some embodiments, this invention relates to compounds of Formulae (I) and (II), wherein $R^8$ is hydrogen or ($C_1$-$C_6$)alkyl. In some embodiments, $R^8$ is hydrogen or methyl. In some embodiments, $R^8$ is hydrogen. In some embodiments, $R^8$ is methyl.

In some embodiments, this invention relates to compounds of Formulae (I) and (II), wherein $R^9$ is hydrogen or ($C_1$-$C_6$)alkyl. In some embodiments, $R^9$ is hydrogen or methyl.

In some embodiments, this invention relates to compounds of Formulae (I) and (II), wherein $R^8$ is hydrogen and $R^9$ is ($C_1$-$C_6$)alkyl. In some embodiments, $R^8$ is hydrogen and $R^9$ is methyl. In some embodiments, this invention relates to compounds of Formulae (I) and (II), wherein $R^8$ is ($C_1$-$C_6$)alkyl and $R^9$ is hydrogen. In some embodiments, $R^8$ is methyl and $R^9$ is hydrogen. In some embodiments, this invention relates to compounds of Formulae (I) and (II), wherein $R^8$ and $R^9$ are ($C_1$-$C_6$)alkyl. In some embodiments, $R^8$ and $R^9$ are methyl.

In some embodiments, this invention relates to compounds of Formula (I) and (II), wherein:
W is N or CH;
each $X^1$ is independently N or $CR^{10}$;
each $X^2$ is independently N or $CR^{11}$;
$Y^1$ is N or $CR^{12}$;
$Y^2$ is N or $CR^{12}$;
Z is

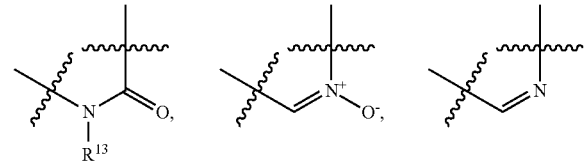

n is 0 or 1;
$R^1$ is hydrogen, halogen, ($C_1$-$C_6$)alkyl, —($C_1$-$C_6$)alkyl-NH$_2$, —($C_1$-$C_6$)alkyl-NH(($C_1$-$C_6$)alkyl), —($C_1$-$C_6$)alkyl-N(($C_1$-$C_6$)alkyl)(($C_1$-$C_6$)alkyl), —($C_1$-$C_6$)alkyl-($C_3$-$C_8$)cycloalkyl, —($C_1$-$C_6$)alkyl-aryl, 5- or 6-membered heteroaryl ($C_1$-$C_4$)alkyl-, ($C_3$-$C_8$)cycloalkyl, ($C_2$-$C_6$)alkenyl, —($C_2$-$C_6$)alkenyl-($C_3$-$C_8$)cycloalkyl, —OH, ($C_1$-$C_4$)alkoxy, —O—($C_1$-$C_6$)alkyl-($C_3$-$C_8$)cycloalkyl, —O—($C_1$-$C_6$)alkyl-aryl, —O—($C_1$-$C_6$)alkyl-5-6 membered heteroaryl, —O—($C_2$-$C_6$)alkenyl, —O—($C_3$-$C_8$)cycloalkyl, —O-aryl, —O-heteroaryl, —C(O)-aryl, —CO$_2$H, —CO$_2$($C_1$-$C_6$)alkyl, —CO$_2$($C_3$-$C_8$)cycloalkyl, —O$_2$C($C_1$-$C_6$)alkyl, —O$_2$C($C_3$-$C_8$)cycloalkyl, —NH$_2$, —NH($C_1$-$C_6$)alkyl, —N(($C_1$-$C_6$)alkyl)(($C_1$-$C_6$)alkyl), aryl, or 5-6 membered heteroaryl, wherein any said ($C_1$-$C_6$)alkyl, —($C_1$-$C_6$)alkyl-($C_3$-$C_8$)cycloalkyl, —($C_1$-$C_6$)alkyl-aryl, ($C_1$-$C_4$)alkoxy, —O—($C_1$-$C_6$)alkyl-($C_3$-$C_8$)cycloalkyl, —O—($C_3$-$C_8$)cycloalkyl, —O-aryl, —O-5-6-membered heteroaryl, —C(O)-aryl, aryl, or 5-6 membered heteroaryl is optionally substituted one, two, or three times by $R^{14}$;
$R^2$ is hydrogen, halogen, ($C_1$-$C_6$)alkyl, or —OH, wherein any said ($C_1$-$C_6$)alkyl is optionally substituted one, two, or three times by halogen;
$R^3$ is hydrogen, halogen, ($C_1$-$C_6$)alkyl, or —OH, wherein any said ($C_1$-$C_6$)alkyl is optionally substituted one, two, or three times by halogen;
$R^4$ is hydrogen, halogen, or ($C_1$-$C_6$)alkyl;
$R^5$ is hydrogen, halogen, or ($C_1$-$C_6$)alkyl;
$R^6$ is hydrogen, halogen, ($C_1$-$C_6$)alkyl, ($C_3$-$C_8$)cycloalkyl, ($C_1$-$C_4$)alkoxy, —($C_1$-$C_6$)alkyl-OH, —($C_1$-$C_6$)alkyl-O—($C_1$-$C_6$)alkyl, —($C_1$-$C_6$)alkyl-NH$_2$, —($C_1$-$C_6$)alkyl-NH(($C_1$-$C_6$)alkyl), —($C_1$-$C_6$)alkyl-N—(($C_1$-$C_6$)alkyl)(($C_1$-$C_6$)alkyl), —($C_1$-$C_6$)alkyl-NH(($C_1$-$C_6$)alkyl)-OH, —($C_1$-$C_6$)alkyl-NH(($C_1$-$C_6$)alkyl)-O—($C_1$-$C_6$)alkyl), —($C_1$-$C_6$)alkyl-N—(($C_1$-$C_6$)alkyl)(($C_1$-$C_6$)alkyl)-OH, —($C_1$-$C_6$)alkyl-N—(($C_1$-$C_6$)alkyl)(($C_1$-$C_6$)alkyl)-O—($C_1$-$C_6$)alkyl), —($C_1$-$C_6$)alkyl-NH—($C_3$-$C_8$)cycloalkyl, —($C_1$-$C_6$)alkyl-NH-4- to 6-membered heterocycloalkyl, —($C_1$-$C_6$)alkyl-4- to 6-membered heterocycloalkyl, —($C_1$-$C_6$)alkyl-NHC(O)—(($C_1$-$C_6$)

alkyl), —(C$_1$-C$_6$)alkyl-SO$_2$—(C$_1$-C$_6$)alkyl, —(C$_1$-C$_6$)alkyl-SO$_2$—NH—(C$_1$-C$_6$)alkyl), —CN, —C(O)NH$_2$, —C(O)NH(C$_1$-C$_6$)alkyl), —C(O)N(C$_1$-C$_6$)alkyl) (C$_1$-C$_6$)alkyl), —NH$_2$, —NH(C$_1$-C$_6$)alkyl, —N((C$_1$-C$_6$)alkyl)((C$_1$-C$_6$)alkyl), —SO$_2$((C$_1$-C$_6$)alkyl), —SO$_2$—NH((C$_1$-C$_6$)alkyl), or aryl, wherein any said (C$_1$-C$_6$)alkyl, (C$_3$-C$_8$)cycloalkyl, —(C$_1$-C$_6$)alkyl-OH, —(C$_1$-C$_6$)alkyl-NH$_2$, —(C$_1$-C$_6$)alkyl-NH((C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, or —(C$_1$-C$_6$)alkyl-4- to 6-membered heterocycloalkyl is optionally substituted one, two, or three times by halogen;

$R^7$ is hydrogen, (C$_1$-C$_6$)alkyl, or —OH;

$R^8$ is hydrogen, (C$_1$-C$_6$)alkyl, or (C$_1$-C$_4$)alkoxy;

$R^9$ is hydrogen, (C$_1$-C$_6$)alkyl, or (C$_1$-C$_4$)alkoxy;

each $R^{10}$ is independently hydrogen, halogen, (C$_1$-C$_6$)alkyl, (C$_2$-C$_6$)alkenyl, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), (C$_2$-C$_6$)alkenyl, —O—(C$_1$-C$_6$)alkyl, —NH$_2$, —NH((C$_1$-C$_6$)alkyl), —N((C$_1$-C$_6$)alkyl)((C$_1$-C$_6$)alkyl), —NCH$_2$, or —CHNH;

or $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, (C$_1$-C$_6$)alkyl, —(C$_1$-C$_6$)alkyl-(C$_3$-C$_8$)cycloalkyl, halo(C$_1$-C$_6$)alkyl, and (C$_3$-C$_8$)cycloalkyl;

each $R^{11}$ is independently hydrogen, halogen, (C$_1$-C$_6$)alkyl, or (C$_2$-C$_6$)alkenyl;

$R^{12}$ is hydrogen, halogen, or (C$_1$-C$_6$)alkyl, wherein said (C$_1$-C$_6$)alkyl is optionally substituted one, two, or three times by halogen;

$R^{13}$ is hydrogen, (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl, wherein said (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl is optionally substituted one, two, or three times by halogen; and each $R^{14}$ is independently halogen, (C$_1$-C$_6$)alkyl, (C$_3$-C$_8$)cycloalkyl, —CN, —(C$_1$-C$_6$)—OH, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), —OH, (C$_1$-C$_4$)alkoxy, —O—(C$_3$-C$_8$)cycloalkyl, -aryl, 5-6 membered heteroaryl, wherein (C$_1$-C$_6$)alkyl, (C$_3$-C$_8$)cycloalkyl, aryl, or 5-6 membered heteroaryl is further optionally substituted by one, two, or three substituents independently selected from halogen, (C$_1$-C$_6$)alkyl, —(C$_1$-C$_6$)alkyl-OH, —(C$_1$-C$_6$)alkyl-O—(C$_1$-C$_6$)alkyl, or (C$_1$-C$_4$)alkoxy.

In some embodiments, this invention relates to compounds of Formulae (I) and (II), wherein:

W is N or CH;

each $X^1$ is independently N or CR$^{10}$;

each $X^2$ is independently N or CR$^{11}$;

$Y^1$ is N or CR$^{12}$;

$Y^2$ is N or CR$^{12}$;

Z is

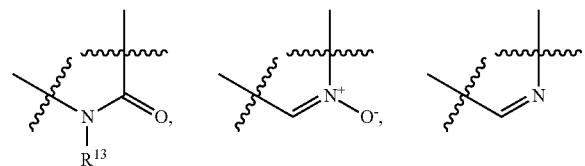

n is 0 or 1;

$R^1$ is halogen, (C$_1$-C$_6$)alkyl, —(C$_1$-C$_6$)alkyl-NH$_2$, —(C$_1$-C$_6$)alkyl-(C$_3$-C$_8$)cycloalkyl, —(C$_1$-C$_6$)alkyl-aryl, 5- or 6-membered heteroaryl(C$_1$-C$_4$)alkyl-, (C$_3$-C$_8$)cycloalkyl, (C$_2$-C$_6$)alkenyl, —(C$_2$-C$_6$)alkenyl-(C$_3$-C$_8$)cycloalkyl, —OH, (C$_1$-C$_4$)alkoxy, —O—(C$_1$-C$_6$)alkyl-(C$_3$-C$_8$)cycloalkyl, —O—(C$_1$-C$_6$)alkyl-5-6 membered heteroaryl, —O—(C$_3$-C$_8$)cycloalkyl, —O-aryl, —O-heteroaryl, —C(O)-aryl, —CO$_2$(C$_3$-C$_8$)cycloalkyl, —NH$_2$, aryl, or 5-6 membered heteroaryl, wherein any said (C$_1$-C$_6$)alkyl, —(C$_1$-C$_6$)alkyl-(C$_3$-C$_8$)cycloalkyl, —(C$_1$-C$_6$)alkyl-aryl, (C$_1$-C$_4$)alkoxy, —O—(C$_1$-C$_6$)alkyl-(C$_3$-C$_8$)cycloalkyl, —O—(C$_3$-C$_8$)cycloalkyl, —O-aryl, —O-5-6-membered heteroaryl, —C(O)-aryl, aryl, or 5-6 membered heteroaryl is optionally substituted one, two, or three times by $R^{14}$;

$R^2$ is hydrogen, halogen, or (C$_1$-C$_6$)alkyl wherein any said (C$_1$-C$_6$)alkyl is optionally substituted one, two, or three times by halogen;

$R^3$ is hydrogen, halogen, (C$_1$-C$_6$)alkyl, wherein any said (C$_1$-C$_6$)alkyl is optionally substituted one, two, or three times by halogen;

$R^4$ is hydrogen, halogen, or (C$_1$-C$_6$)alkyl;

$R^5$ is hydrogen, halogen, or (C$_1$-C$_6$)alkyl;

$R^6$ is hydrogen, (C$_1$-C$_6$)alkyl, (C$_3$-C$_8$)cycloalkyl, (C$_1$-C$_4$)alkoxy, —(C$_1$-C$_6$)alkyl-OH, —(C$_1$-C$_6$)alkyl-NH$_2$, —(C$_1$-C$_6$)alkyl-NH((C$_1$-C$_6$)alkyl), —(C$_1$-C$_6$)alkyl-N—((C$_1$-C$_6$)alkyl)((C$_1$-C$_6$)alkyl), —(C$_1$-C$_6$)alkyl-NH((C$_1$-C$_6$)alkyl)-OH, —(C$_1$-C$_6$)alkyl-NH((C$_1$-C$_6$)alkyl)-O—(C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, —(C$_1$-C$_6$)alkyl-4- to 6-membered heterocycloalkyl, —(C$_1$-C$_6$)alkyl-NHC(O)—((C$_1$-C$_6$)alkyl), —(C$_1$-C$_6$)alkyl-SO$_2$—(C$_1$-C$_6$)alkyl, —(C$_1$-C$_6$)alkyl-SO$_2$—NH—(C$_1$-C$_6$)alkyl), —CN, —C(O)NH$_2$, —NH$_2$, —SO$_2$((C$_1$-C$_6$)alkyl), —SO$_2$—NH((C$_1$-C$_6$)alkyl), or aryl, wherein any said (C$_1$-C$_6$)alkyl, (C$_3$-C$_8$)cycloalkyl, —(C$_1$-C$_6$)alkyl-OH, —(C$_1$-C$_6$)alkyl-NH$_2$, —(C$_1$-C$_6$)alkyl-NH((C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, or —(C$_1$-C$_6$)alkyl-4- to 6-membered heterocycloalkyl is optionally substituted one, two, or three times by halogen;

$R^7$ is hydrogen, (C$_1$-C$_6$)alkyl, or —OH;

$R^8$ is hydrogen, (C$_1$-C$_6$)alkyl, or (C$_1$-C$_4$)alkoxy;

$R^9$ is hydrogen, (C$_1$-C$_6$)alkyl, or (C$_1$-C$_4$)alkoxy;

each $R^{10}$ is independently hydrogen, halogen, (C$_1$-C$_6$)alkyl, (C$_2$-C$_6$)alkenyl, —NCH$_2$, or —CHNH;

or $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, (C$_1$-C$_6$)alkyl, —(C$_1$-C$_6$)alkyl-(C$_3$-C$_8$)cycloalkyl, halo(C$_1$-C$_6$)alkyl, and (C$_3$-C$_8$)cycloalkyl;

each $R^{11}$ is independently hydrogen or halogen;

$R^{12}$ is hydrogen or (C$_1$-C$_6$)alkyl, wherein said (C$_1$-C$_6$)alkyl is optionally substituted one, two, or three times by halogen;

$R^{13}$ is hydrogen, (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl, wherein said (C$_1$-C$_6$)alkyl is optionally substituted one, two, or three times by halogen; and each $R^{14}$ is independently halogen, (C$_1$-C$_6$)alkyl, (C$_3$-C$_8$)cycloalkyl, —CN, —(C$_1$-C$_6$)—OH, —(C$_1$-C$_6$)alkyl-N((C$_1$-C$_6$)alkyl)((C$_1$-C$_6$)alkyl), —OH, (C$_1$-C$_4$)alkoxy, 5-6 membered heteroaryl, wherein (C$_1$-C$_6$)alkyl, (C$_3$-C$_8$)cycloalkyl, aryl, or 5-6 membered heteroaryl is further optionally substituted by one, two, or three substituents independently selected from halogen, $(C_1-C_6)$alkyl, —$(C_1-C_6)$alkyl-OH, —$(C_1-C_6)$alkyl-O—$(C_1-C_6)$alkyl, or $(C_1-C_4)$alkoxy.

This invention further relates to compounds of the Formula (III) or pharmaceutically acceptable salts thereof:

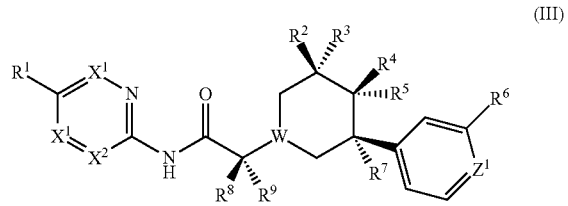

(III)

wherein:
W is N or CH;
each $X^1$ is independently N or $CR^{10}$;
$X^2$ is N or $CR^{11}$;
$Z^1$ is N or $N^+$—$O^-$
$R^1$ is hydrogen, halogen, $(C_1-C_6)$alkyl, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —$(C_1-C_6)$alkyl-$(C_3-C_8)$cycloalkyl, —$(C_1-C_6)$alkyl-aryl, 5- or 6-membered heteroaryl $(C_1-C_4)$alkyl-, $(C_3-C_8)$cycloalkyl, $(C_2-C_6)$alkenyl, —$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-aryl, —O—$(C_1-C_6)$alkyl-5-6 membered heteroaryl, —O—$(C_2-C_6)$alkenyl, —O—$(C_3-C_8)$cycloalkyl, —O-aryl, —O-heteroaryl, —C(O)-aryl, —$CO_2H$, —$CO_2(C_1-C_6)$alkyl, —$CO_2(C_3-C_8)$cycloalkyl, —$O_2C(C_1-C_6)$alkyl, —$O_2C(C_3-C_8)$cycloalkyl, —$NH_2$, —$NH(C_1-C_6)$alkyl, —N$((C_1-C_6)$alkyl$)((C_1-C_6)$alkyl$)$, aryl, or 5-6 membered heteroaryl, wherein any said $(C_1-C_6)$alkyl, —$(C_1-C_6)$alkyl-$(C_3-C_8)$cycloalkyl, —$(C_1-C_6)$alkyl-aryl, $(C_1-C_4)$alkoxy, —O—$(C_1-C_6)$alkyl-$(C_3-C_8)$cycloalkyl, —O—$(C_3-C_8)$cycloalkyl, —O-aryl, —O-5-6-membered heteroaryl, —C(O)-aryl, aryl, or 5-6 membered heteroaryl is optionally substituted one, two, or three times by $R^{14}$;
$R^2$ is hydrogen, halogen, $(C_1-C_6)$alkyl, or —OH, wherein any said $(C_1-C_6)$alkyl is optionally substituted one, two, or three times by halogen;
$R^3$ is hydrogen, halogen, $(C_1-C_6)$alkyl, or —OH, wherein any said $(C_1-C_6)$alkyl is optionally substituted one, two, or three times by halogen;
$R^4$ is hydrogen, halogen, or $(C_1-C_6)$alkyl;
$R^5$ is hydrogen, halogen, or $(C_1-C_6)$alkyl;
$R^6$ is hydrogen, halogen, $(C_1-C_6)$alkyl, $(C_3-C_8)$cycloalkyl, $(C_1-C_4)$alkoxy, —$(C_1-C_6)$alkyl-OH, —$(C_1-C_6)$alkyl-O—$(C_1-C_6)$alkyl, —$(C_1-C_6)$alkyl-$NH_2$, —$(C_1-C_6)$alkyl-NH$((C_1-C_6)$alkyl$)$, —$(C_1-C_6)$alkyl-N—$((C_1-C_6)$alkyl$)((C_1-C_6)$alkyl$)$, —$(C_1-C_6)$alkyl-NH$((C_1-C_6)$alkyl$)$-OH, —$(C_1-C_6)$alkyl-NH$((C_1-C_6)$alkyl$)$-O—$(C_1-C_6)$alkyl$)$, —$(C_1-C_6)$alkyl-N—$((C_1-C_6)$alkyl$)((C_1-C_6)$alkyl$)$-OH, —$(C_1-C_6)$alkyl-N—$((C_1-C_6)$alkyl$)((C_1-C_6)$alkyl$)$-O—$(C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, —$(C_1-C_6)$alkyl-4- to 6-membered heterocycloalkyl, —$(C_1-C_6)$alkyl-NHC(O)—$((C_1-C_6)$alkyl$)$, —$(C_1-C_6)$alkyl-$SO_2$—$(C_1-C_6)$alkyl, —$(C_1-C_6)$alkyl-$SO_2$—NH—$(C_1-C_6)$alkyl, —CN, —C(O)$NH_2$, —C(O)NH$(C_1-C_6)$alkyl, —C(O)N$(C_1-C_6)$alkyl$)$ $(C_1-C_6)$alkyl$)$, —$NH_2$, —NH$(C_1-C_6)$alkyl, —N$((C_1-C_6)$alkyl$)((C_1-C_6)$alkyl$)$, —$SO_2((C_1-C_6)$alkyl$)$, —$SO_2$—NH$((C_1-C_6)$alkyl$)$, or aryl, wherein any said $(C_1-C_6)$alkyl, $(C_3-C_8)$cycloalkyl, —$(C_1-C_6)$alkyl-OH, —$(C_1-C_6)$alkyl-$NH_2$, —$(C_1-C_6)$alkyl-NH$((C_1-C_6)$alkyl$)$, —$(C_1-C_6)$alkyl-NH—$(C_3-C_8)$cycloalkyl, —$(C_1-C_6)$alkyl-NH-4- to 6-membered heterocycloalkyl, or —$(C_1-C_6)$alkyl-4- to 6-membered heterocycloalkyl is optionally substituted one, two, or three times by halogen;
$R^7$ is hydrogen, $(C_1-C_6)$alkyl, or —OH;
$R^8$ is hydrogen, $(C_1-C_6)$alkyl, or $(C_1-C_4)$alkoxy;
$R^9$ is hydrogen, $(C_1-C_6)$alkyl, or $(C_1-C_4)$alkoxy;
each $R^{10}$ is independently hydrogen, halogen, $(C_1-C_6)$alkyl, $(C_2-C_6)$alkenyl, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, $(C_2-C_6)$alkenyl, —O—$(C_1-C_6)$alkyl, —$NH_2$, —NH$((C_1-C_6)$alkyl$)$, —N$((C_1-C_6)$alkyl$)((C_1-C_6)$alkyl$)$, —$NCH_2$, or —CHNH;
or $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, $(C_1-C_6)$alkyl, —$(C_1-C_6)$alkyl-$(C_3-C_8)$cycloalkyl, halo$(C_1-C_6)$alkyl, and $(C_3-C_8)$cycloalkyl;
$R^{11}$ is hydrogen, halogen, $(C_1-C_6)$alkyl, or $(C_2-C_6)$alkenyl;
or $R^{10}$ and $R^{11}$ taken together with the atoms to which they are attached, form a 5-, 6-, or 7-membered ring optionally containing one, two, or three heteroatoms independently selected from oxygen, nitrogen, and sulfur; wherein said ring is optionally substituted by one or two substituents independently selected from halogen, $(C_1-C_6)$alkyl, halo$(C_1-C_6)$alkyl, and $(C_3-C_8)$cycloalkyl; and
each $R^{14}$ is independently halogen, $(C_1-C_6)$alkyl, $(C_3-C_8)$cycloalkyl, —CN, —$(C_1-C_6)$—OH, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —OH, $(C_1-C_4)$alkoxy, —O—$(C_3-C_8)$cycloalkyl, -aryl, 5-6 membered heteroaryl, wherein $(C_1-C_6)$alkyl, $(C_3-C_8)$cycloalkyl, aryl, or 5-6 membered heteroaryl is further optionally substituted by one, two, or three substituents independently selected from halogen, $(C_1-C_6)$alkyl, —$(C_1-C_6)$alkyl-OH, —$(C_1-C_6)$alkyl-O—$(C_1-C_6)$alkyl, or $(C_1-C_4)$alkoxy.

This invention further relates to compounds of the Formula (IV) or pharmaceutically acceptable salts thereof:

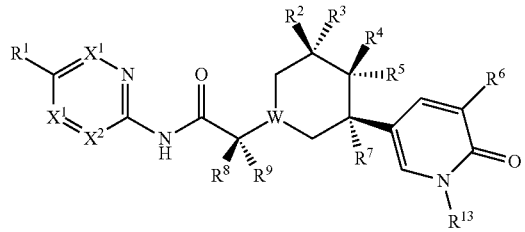

(IV)

wherein:
W is N or CH;
each $X^1$ is independently N or $CR^{10}$;
$X^2$ is N or $CR^{11}$;
$R^1$ is hydrogen, halogen, $(C_1-C_6)$alkyl, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —$(C_1-C_6)$alkyl-$(C_3-C_8)$cycloalkyl, —$(C_1-C_6)$alkyl-aryl, 5- or 6-membered heteroaryl $(C_1-C_4)$alkyl-, $(C_3-C_8)$cycloalkyl, $(C_2-C_6)$alkenyl, —$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-aryl, —O—(C$_1$-C$_6$)alkyl-5-6 membered heteroaryl, —O—(C$_2$-C$_6$)alkenyl, —O—(C$_3$-C$_8$)cycloalkyl, —O-aryl, —O-heteroaryl, —C(O)-aryl, —CO$_2$H, —CO$_2$(C$_1$-C$_6$)alkyl, —CO$_2$(C$_3$-C$_8$)cycloalkyl, —O$_2$C(C$_1$-C$_6$)alkyl, —O$_2$C(C$_3$-C$_8$)cycloalkyl, —NH$_2$, —NH(C$_1$-C$_6$)alkyl, —N((C$_1$-C$_6$)alkyl)((C$_1$-C$_6$)alkyl), aryl, or 5-6 membered heteroaryl, wherein any said (C$_1$-C$_6$)alkyl, —(C$_1$-C$_6$)alkyl-(C$_3$-C$_8$)cycloalkyl, —(C$_1$-C$_6$)alkyl-aryl, (C$_1$-C$_4$)alkoxy, —O—(C$_1$-C$_6$)alkyl-(C$_3$-C$_8$)cycloalkyl, —O—(C$_3$-C$_8$)cycloalkyl, —O-aryl, —O-5-6-membered heteroaryl, —C(O)-aryl, aryl, or 5-6 membered heteroaryl is optionally substituted one, two, or three times by R$^{14}$;

R$^2$ is hydrogen, halogen, (C$_1$-C$_6$)alkyl, or —OH, wherein any said (C$_1$-C$_6$)alkyl is optionally substituted one, two, or three times by halogen;

R$^3$ is hydrogen, halogen, (C$_1$-C$_6$)alkyl, or —OH, wherein any said (C$_1$-C$_6$)alkyl is optionally substituted one, two, or three times by halogen;

R$^4$ is hydrogen, halogen, or (C$_1$-C$_6$)alkyl;

R$^5$ is hydrogen, halogen, or (C$_1$-C$_6$)alkyl;

R$^6$ is hydrogen, halogen, (C$_1$-C$_6$)alkyl, (C$_3$-C$_8$)cycloalkyl, (C$_1$-C$_4$)alkoxy, —(C$_1$-C$_6$)alkyl-OH, —(C$_1$-C$_6$)alkyl-O—(C$_1$-C$_6$)alkyl, —(C$_1$-C$_6$)alkyl-NH$_2$, —(C$_1$-C$_6$)alkyl-NH((C$_1$-C$_6$)alkyl), —(C$_1$-C$_6$)alkyl-N—((C$_1$-C$_6$)alkyl)((C$_1$-C$_6$)alkyl), —(C$_1$-C$_6$)alkyl-NH((C$_1$-C$_6$)alkyl)-OH, —(C$_1$-C$_6$)alkyl-NH((C$_1$-C$_6$)alkyl)-O—(C$_1$-C$_6$)alkyl), —(C$_1$-C$_6$)alkyl-N—((C$_1$-C$_6$)alkyl)((C$_1$-C$_6$)alkyl)-OH, —(C$_1$-C$_6$)alkyl-N—((C$_1$-C$_6$)alkyl)((C$_1$-C$_6$)alkyl)-O—(C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, —(C$_1$-C$_6$)alkyl-4- to 6-membered heterocycloalkyl, —(C$_1$-C$_6$)alkyl-NHC(O)—((C$_1$-C$_6$)alkyl), —(C$_1$-C$_6$)alkyl-SO$_2$—(C$_1$-C$_6$)alkyl, —(C$_1$-C$_6$)alkyl-SO$_2$—NH—(C$_1$-C$_6$)alkyl, —CN, —C(O)NH$_2$, —C(O)NH(C$_1$-C$_6$)alkyl), —C(O)N(C$_1$-C$_6$)alkyl) (C$_1$-C$_6$)alkyl), —NH$_2$, —NH(C$_1$-C$_6$)alkyl, —N((C$_1$-C$_6$)alkyl)((C$_1$-C$_6$)alkyl), —SO$_2$((C$_1$-C$_6$)alkyl), —SO$_2$—NH((C$_1$-C$_6$)alkyl), or aryl, wherein any said (C$_1$-C$_6$)alkyl, (C$_3$-C$_8$)cycloalkyl, —(C$_1$-C$_6$)alkyl-OH, —(C$_1$-C$_6$)alkyl-NH$_2$, —(C$_1$-C$_6$)alkyl-NH((C$_1$-C$_6$)alkyl), —(C$_1$-C$_6$)alkyl-NH—(C$_3$-C$_8$)cycloalkyl, —(C$_1$-C$_6$)alkyl-NH-4- to 6-membered heterocycloalkyl, or —(C$_1$-C$_6$)alkyl-4- to 6-membered heterocycloalkyl is optionally substituted one, two, or three times by halogen;

R$^7$ is hydrogen, (C$_1$-C$_6$)alkyl, or —OH;

R$^8$ is hydrogen, (C$_1$-C$_6$)alkyl, or (C$_1$-C$_4$)alkoxy;

R$^9$ is hydrogen, (C$_1$-C$_6$)alkyl, or (C$_1$-C$_4$)alkoxy;

each R$^{10}$ is independently hydrogen, halogen, (C$_1$-C$_6$)alkyl, (C$_2$-C$_6$)alkenyl, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), (C$_2$-C$_6$)alkenyl, —O—(C$_1$-C$_6$)alkyl, —NH$_2$, —NH((C$_1$-C$_6$)alkyl), —N((C$_1$-C$_6$)alkyl)((C$_1$-C$_6$)alkyl), —NCH$_2$, or —CHNH;

or R$^1$ and any R$^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, (C$_1$-C$_6$)alkyl, —(C$_1$-C$_6$)alkyl-(C$_3$-C$_8$)cycloalkyl, halo(C$_1$-C$_6$)alkyl, and (C$_3$-C$_8$)cycloalkyl;

R$^{11}$ is hydrogen, halogen, (C$_1$-C$_6$)alkyl, or (C$_2$-C$_6$)alkenyl;

or R$^{10}$ and R$^{11}$ taken together with the atoms to which they are attached, form a 5-, 6-, or 7-membered ring optionally containing one, two, or three heteroatoms independently selected from oxygen, nitrogen, and sulfur; wherein said ring is optionally substituted by one or two substituents independently selected from halogen, (C$_1$-C$_6$)alkyl, halo(C$_1$-C$_6$)alkyl, and (C$_3$-C$_8$)cycloalkyl;

R$^{13}$ is hydrogen, (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl, wherein said (C$_1$-C$_6$)alkyl, —(C$_1$-C$_6$)alkyl-SO$_2$—(C$_1$-C$_6$)alkyl, —(C$_1$-C$_6$)alkyl-aryl, or —(C$_1$-C$_6$)alkyl-5-6-membered heteroaryl is optionally substituted one, two, or three times by halogen; and each R$^{14}$ is independently halogen, (C$_1$-C$_6$)alkyl, (C$_3$-C$_8$)cycloalkyl, —CN, —(C$_1$-C$_6$)—OH, —(C$_1$-C$_6$)alkyl-NH$_2$, —(C$_1$-C$_6$)alkyl-NH((C$_1$-C$_6$)alkyl), —(C$_1$-C$_6$)alkyl-N((C$_1$-C$_6$)alkyl)((C$_1$-C$_6$)alkyl), —OH, (C$_1$-C$_4$)alkoxy, —O—(C$_3$-C$_8$)cycloalkyl, -aryl, 5-6 membered heteroaryl, wherein (C$_1$-C$_6$)alkyl, (C$_3$-C$_8$)cycloalkyl, aryl, or 5-6 membered heteroaryl is further optionally substituted by one, two, or three substituents independently selected from halogen, (C$_1$-C$_6$)alkyl, —(C$_1$-C$_6$)alkyl-OH, —(C$_1$-C$_6$)alkyl-O—(C$_1$-C$_6$)alkyl, or (C$_1$-C$_4$)alkoxy.

In some embodiments, the invention relates to compounds of Formulae (I) to (V), wherein one X$^1$ is N and the other is CR$^{10}$, wherein R$^{10}$ is as defined above. In some embodiments, the invention relates to compounds of Formulae (I) to (V), wherein one X$^2$ is N and the other is CR$^{11}$ wherein R$^{11}$ is as defined above. In some embodiments, the invention relates to compounds of Formulae (I) to (V), wherein one X$^1$ is N and the other is CR$^{10}$, and one X$^2$ is N and the other is CR$^{11}$, wherein R$^{10}$ and R$^{11}$ are as defined above. For example, the group represented by

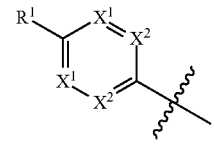

in Formula (I) may be selected from the group consisting of

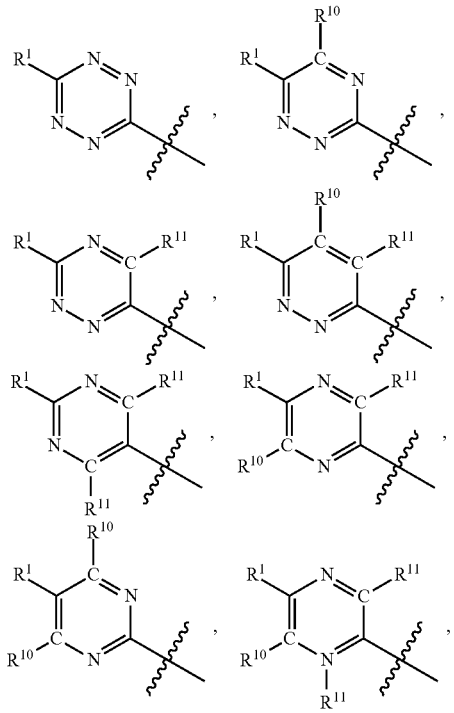

-continued

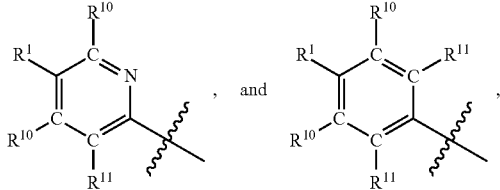

wherein R¹, R¹⁰ and R¹¹ are as defined above, and 〰 indicates a binding site to the adjacent nitrogen atom.

Specific compounds of this invention include:
- (S)—N-(6-(cyclopropylmethoxy)pyridazin-3-yl)-2-((S)-4,4-difluoro-3-(6-oxo-1-(2,2,2-trifluoroethyl)-1,6-dihydropyridin-3-yl)piperidin-1-yl)propanamide;
- (S)—N-(5-(cyclopropylmethoxy)pyridin-2-yl)-2-((S)-4,4-difluoro-3-(6-oxo-1-(2,2,2-trifluoroethyl)-1,6-dihydropyridin-3-yl)piperidin-1-yl)propanamide;
- (S)-2-((S)-4,4-difluoro-3-(6-oxo-1-(2,2,2-trifluoroethyl)-1,6-dihydropyridin-3-yl)piperidin-1-yl)-N-(5-fluoropyridin-2-yl)propanamide;
- (S)-2-((S)-4,4-difluoro-3-(6-oxo-1,6-dihydropyridin-3-yl)piperidin-1-yl)-N-(5-(2,4-difluorophenoxy)pyridin-2-yl)propanamide;
- (S)-2-((S)-4,4-difluoro-3-(6-oxo-1,6-dihydropyridin-3-yl)piperidin-1-yl)-N-(5-(4-fluorophenoxy)pyridin-2-yl)propanamide;
- (S)-2-((S)-4,4-difluoro-3-(6-oxo-1,6-dihydropyridin-3-yl)piperidin-1-yl)-N-(5-phenoxypyridin-2-yl)propanamide;
- (S)—N-(5-benzylpyridin-2-yl)-2-((S)-4,4-difluoro-3-(6-oxo-1,6-dihydropyridin-3-yl)piperidin-1-yl)propanamide;
- N-(6-(cyclopropylmethoxy)pyridazin-3-yl)-2-((S)-4,4-difluoro-3-(6-oxo-1,6-dihydropyridin-3-yl)piperidin-1-yl)propanamide;
- (S)—N-(5-(cyclopentyloxy)pyridin-2-yl)-2-((S)-4,4-difluoro-3-(6-oxo-1,6-dihydropyridin-3-yl)piperidin-1-yl)propanamide;
- (S)—N-(5-((E)-2-cyclopropylvinyl)pyridin-2-yl)-2-((S)-4,4-difluoro-3-(6-oxo-1,6-dihydropyridin-3-yl)piperidin-1-yl)propanamide;
- (S)—N-(6-benzylpyridazin-3-yl)-2-((S)-4,4-difluoro-3-(6-oxo-1,6-dihydropyridin-3-yl)piperidin-1-yl)propanamide;
- (S)-2-((S)-4,4-difluoro-3-(6-oxo-1,6-dihydropyridin-3-yl)piperidin-1-yl)-N-(5-(pyridin-4-ylmethyl)pyridin-2-yl)propanamide;
- (S)—N-(5-cyclopentylpyridin-2-yl)-2-((S)-4,4-difluoro-3-(6-oxo-1,6-dihydropyridin-3-yl)piperidin-1-yl)propanamide;
- (S)—N-(5-cyclopropylpyridin-2-yl)-2-((S)-4,4-difluoro-3-(6-oxo-1,6-dihydropyridin-3-yl)piperidin-1-yl)propanamide;
- (S)-2-((S)-4,4-difluoro-3-(6-oxo-1,6-dihydropyridin-3-yl)piperidin-1-yl)-N-(5-(m-tolyl)pyridin-2-yl)propanamide;
- (S)—N-(2-cyclopropyloxazolo[4,5-b]pyridin-5-yl)-2-((S)-4,4-difluoro-3-(6-oxo-1,6-dihydropyridin-3-yl)piperidin-1-yl)propanamide;
- (S)—N-(5-cyclobutylpyridin-2-yl)-2-((S)-4,4-difluoro-3-(6-oxo-1,6-dihydropyridin-3-yl)piperidin-1-yl)propanamide;
- 2-((S)-4,4-difluoro-3-(6-oxo-1,6-dihydropyridin-3-yl)piperidin-1-yl)-N-(6-phenoxypyridazin-3-yl)propanamide;
- (S)-2-((S)-4,4-difluoro-3-(6-oxo-1,6-dihydropyridin-3-yl)piperidin-1-yl)-N-(6-(o-tolyloxy)pyridazin-3-yl)propanamide;
- N-(5-(2-cyclopropylethyl)pyridin-2-yl)-2-((S)-4,4-difluoro-3-(6-oxo-1,6-dihydropyridin-3-yl)piperidin-1-yl)propanamide;
- (S)—N-(5-(benzyloxy)pyridin-2-yl)-2-((S)-4,4-difluoro-3-(6-oxo-1,6-dihydropyridin-3-yl)piperidin-1-yl)propanamide;
- (S)-2-((S)-4,4-difluoro-3-(6-oxo-1,6-dihydropyridin-3-yl)piperidin-1-yl)-N-(5-phenylpyridin-2-yl)propanamide;
- N-(5-(cyclohexyloxy)pyridin-2-yl)-2-((S)-4,4-difluoro-3-(6-oxo-1,6-dihydropyridin-3-yl)piperidin-1-yl)propanamide;
- (S)—N-(6-cyclopropylquinolin-2-yl)-2-((S)-4,4-difluoro-3-(6-oxo-1,6-dihydropyridin-3-yl)piperidin-1-yl)propanamide;
- 2-((S)-4,4-difluoro-3-(6-oxo-1,6-dihydropyridin-3-yl)piperidin-1-yl)-N-(5-isopropoxypyridin-2-yl)propanamide;
- N-(5-(cyclohexylmethyl)pyridin-2-yl)-2-((S)-4,4-difluoro-3-(6-oxo-1,6-dihydropyridin-3-yl)piperidin-1-yl)propanamide;
- (S)—N-(5-(cyclopropylmethoxy)-3-fluoropyridin-2-yl)-2-((S)-4,4-difluoro-3-(6-oxo-1,6-dihydropyridin-3-yl)piperidin-1-yl)propanamide;
- (S)—N-(5-(cyclopropylmethoxy)pyrazin-2-yl)-2-((S)-4,4-difluoro-3-(6-oxo-1,6-dihydropyridin-3-yl)piperidin-1-yl)propanamide;
- N-(5-(cyclobutylmethoxy)pyridin-2-yl)-2-((S)-4,4-difluoro-3-(6-oxo-1,6-dihydropyridin-3-yl)piperidin-1-yl)propanamide;
- N-(5-(1-cyclopropylethoxy)pyridin-2-yl)-2-((S)-4,4-difluoro-3-(6-oxo-1,6-dihydropyridin-3-yl)piperidin-1-yl)propanamide;
- (S)—N-(6-cyclopropyl-6,7-dihydro-5H-pyrrolo[3,4-b]pyridin-2-yl)-2-((S)-4,4-difluoro-3-(6-oxo-1,6-dihydropyridin-3-yl)piperidin-1-yl)propanamide;
- N-(5-(cyclopentylmethyl)pyridin-2-yl)-2-((S)-4,4-difluoro-3-(6-oxo-1,6-dihydropyridin-3-yl)piperidin-1-yl)propanamide;
- (S)-2-((S)-4,4-difluoro-3-(6-oxo-1,6-dihydropyridin-3-yl)piperidin-1-yl)-N-(isoquinolin-3-yl)propanamide;
- (S)—N-(5-(cyclopropylmethoxy)pyrimidin-2-yl)-2-((S)-4,4-difluoro-3-(6-oxo-1,6-dihydropyridin-3-yl)piperidin-1-yl)propanamide;
- 2-((S)-4,4-difluoro-3-(6-oxo-1,6-dihydropyridin-3-yl)piperidin-1-yl)-N-(5-((2,2-difluorocyclopropyl)methoxy)pyridin-2-yl)propanamide;
- cyclobutyl 6-((S)-2-((S)-4,4-difluoro-3-(6-oxo-1,6-dihydropyridin-3-yl)piperidin-1-yl)propanamido)nicotinate;
- (S)-2-((S)-4,4-difluoro-3-(6-oxo-1,6-dihydropyridin-3-yl)piperidin-1-yl)-N-(5-(oxazol-2-ylmethoxy)pyridin-2-yl)propanamide;
- 2-((S)-4,4-difluoro-3-(6-oxo-1,6-dihydropyridin-3-yl)piperidin-1-yl)-N-(4,5-difluoropyridin-2-yl)propanamide;
- N-(1-(cyclopropylmethyl)-1H-pyrazolo[3,4-c]pyridin-5-yl)-2-((S)-4,4-difluoro-3-(6-oxo-1,6-dihydropyridin-3-yl)piperidin-1-yl)propanamide;
- N-(5-(cyclopropylmethyl)pyridin-2-yl)-2-((S)-4,4-difluoro-3-(6-oxo-1,6-dihydropyridin-3-yl)piperidin-1-yl)propanamide;
- N-(5-cyclohexylpyridin-2-yl)-2-((S)-4,4-difluoro-3-(6-oxo-1,6-dihydropyridin-3-yl)piperidin-1-yl)propanamide;
- 2-((S)-4,4-difluoro-3-(6-oxo-1,6-dihydropyridin-3-yl)piperidin-1-yl)-N-(6-methoxypyridazin-3-yl)propanamide;
- 2-((S)-4,4-difluoro-3-(6-oxo-1,6-dihydropyridin-3-yl)piperidin-1-yl)-N-(5-methoxypyridin-2-yl)propanamide;

2-((S)-4,4-difluoro-3-(6-oxo-1,6-dihydropyridin-3-yl)piperidin-1-yl)-N-(5-(pyridin-3-ylmethyl)pyridin-2-yl)propanamide;
cyclopentyl 6-((S)-2-((S)-4,4-difluoro-3-(6-oxo-1,6-dihydropyridin-3-yl)piperidin-1-yl)propanamido)nicotinate;
N-(5-(cyclopentylmethoxy)pyridin-2-yl)-2-((S)-4,4-difluoro-3-(6-oxo-1,6-dihydropyridin-3-yl)piperidin-1-yl)propanamide;
N-(5-(cyclopropoxymethyl)pyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-(2,2-difluoroethoxy)pyridin-2-yl)propanamide;
2-((S)-4,4-difluoro-3-(6-oxo-1,6-dihydropyridin-3-yl)piperidin-1-yl)-N-(5-(thiophen-2-yl)pyridin-2-yl)propanamide;
N-(1-(cyclopropylmethyl)-1H-pyrrolo[2,3-c]pyridin-5-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-(thiazol-2-ylmethyl)pyridin-2-yl)propanamide;
2-((S)-4,4-difluoro-3-(6-oxo-1,6-dihydropyridin-3-yl)piperidin-1-yl)-N-(5-(oxazol-2-ylmethyl)pyridin-2-yl)propanamide;
(S)-2-((S)-4,4-difluoro-3-(6-oxo-1,6-dihydropyridin-3-yl)piperidin-1-yl)-N-(quinolin-2-yl)propanamide;
2-((S)-4,4-difluoro-3-(6-oxo-1,6-dihydropyridin-3-yl)piperidin-1-yl)-N-(5-(1-methyl-1H-pyrazol-3-yl)pyridin-2-yl)propanamide;
2-((S)-4,4-difluoro-3-(6-oxo-1,6-dihydropyridin-3-yl)piperidin-1-yl)-N-(5-(isoxazol-3-yl)pyridin-2-yl)propanamide;
2-((S)-4,4-difluoro-3-(6-oxo-1,6-dihydropyridin-3-yl)piperidin-1-yl)-N-(5-(pyridin-2-ylmethyl)pyridin-2-yl)propanamide hydrochloride;
(S)-2-((S)-4,4-difluoro-3-(6-oxo-1,6-dihydropyridin-3-yl)piperidin-1-yl)-N-(5-(pyridin-3-yloxy)pyridin-2-yl)propanamide;
(S)-2-((S)-4,4-difluoro-3-(6-oxo-1,6-dihydropyridin-3-yl)piperidin-1-yl)-N-(5-phenoxypyrazin-2-yl)propanamide;
(S)-2-((S)-4,4-difluoro-3-(6-oxo-1,6-dihydropyridin-3-yl)piperidin-1-yl)-N-(5-(pyridin-2-yloxy)pyridin-2-yl)propanamide;
N-(6-(2-cyanophenoxy)pyridazin-3-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(6-(4-fluorophenoxy)pyridazin-3-yl)propanamide;
2-((S)-4,4-difluoro-3-(6-oxo-1,6-dihydropyridin-3-yl)piperidin-1-yl)-N-(5-(pyridin-4-yloxy)pyridin-2-yl)propanamide;
(S)-2-((S)-4,4-difluoro-3-(6-oxo-1,6-dihydropyridin-3-yl)piperidin-1-yl)-N-(5-((3-fluoropyridin-2-yl)oxy)pyridin-2-yl)propanamide;
(S)-2-((S)-4,4-difluoro-3-(6-oxo-1,6-dihydropyridin-3-yl)piperidin-1-yl)-N-(5-((3,5-difluoropyridin-2-yl)oxy)pyridin-2-yl)propanamide;
2-((S)-4,4-difluoro-3-(6-oxo-1,6-dihydropyridin-3-yl)piperidin-1-yl)-N-(5-((5-fluoropyridin-3-yl)oxy)pyridin-2-yl)propanamide;
(S)-2-((S)-4,4-difluoro-3-(6-oxo-1,6-dihydropyridin-3-yl)piperidin-1-yl)-N-(5-(4-fluorophenoxy)pyrazin-2-yl)propanamide;
(S)-2-((S)-4,4-difluoro-3-(6-oxo-1,6-dihydropyridin-3-yl)piperidin-1-yl)-N-(5-((5-fluoropyridin-2-yl)oxy)pyridin-2-yl)propanamide;
(S)—N-(5-cyclopropylpyrazin-2-yl)-2-((S)-4,4-difluoro-3-(6-oxo-1,6-dihydropyridin-3-yl)piperidin-1-yl)propanamide;
(S)—N-(6-(cyclobutylmethoxy)pyridazin-3-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-((2-oxo-1,2-dihydropyridin-3-yl)oxy)pyridin-2-yl)propanamide;
2-((S)-4,4-difluoro-3-(6-oxo-1,6-dihydropyridin-3-yl)piperidin-1-yl)-N-(5-(spiro[3.3]heptan-2-yloxy)pyridin-2-yl)propanamide;
(S)-2-((S)-4,4-difluoro-3-(6-oxo-1,6-dihydropyridin-3-yl)piperidin-1-yl)-N-(5-(pyrimidin-4-yloxy)pyridin-2-yl)propanamide;
(S)—N-(5-(cyclopropylmethoxy)pyridin-2-yl)-2-((S)-4,4-difluoro-3-(6-oxo-1,6-dihydropyridin-3-yl)piperidin-1-yl)propanamide;
(S)—N-(5-(cyclopropylmethoxy)-4-fluoropyridin-2-yl)-2-((S)-4,4-difluoro-3-(6-oxo-1,6-dihydropyridin-3-yl)piperidin-1-yl)propanamide;
N-(6-cyclopropyl-1,8-naphthyridin-2-yl)-2-((S)-4,4-difluoro-3-(6-oxo-1,6-dihydropyridin-3-yl)piperidin-1-yl)propanamide;
N-(5-cyclobutoxypyridin-2-yl)-2-((S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(5-fluoropyridin-2-yl)propanamide;
(S)—N-(5-((Z)-2-cyclopropylvinyl)pyridin-2-yl)-2-((S)-4,4-difluoro-3-(6-oxo-1,6-dihydropyridin-3-yl)piperidin-1-yl)propanamide;
(S)—N-(5-chloropyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-isopropylpyridin-2-yl)propanamide;
cyclopropyl 6-(2-((S)-4,4-difluoro-3-(6-oxo-1,6-dihydropyridin-3-yl)piperidin-1-yl)propanamido)nicotinate;
(S)—N-(5-(cyclobutylmethyl)pyridin-2-yl)-2-((S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(5-(2,4-difluorophenoxy)pyrazin-2-yl)propanamide;
2-((S)-4,4-difluoro-3-(6-oxo-1,6-dihydropyridin-3-yl)piperidin-1-yl)-N-(3-fluoro-5-(4-fluorophenoxy)pyridin-2-yl)propanamide;
2-((S)-4,4-difluoro-3-(6-oxo-1,6-dihydropyridin-3-yl)piperidin-1-yl)-N-(5-(2,4-difluorophenoxy)-3-fluoropyridin-2-yl)propanamide;
(S)-2-((S)-4,4-difluoro-3-(6-oxo-1,6-dihydropyridin-3-yl)piperidin-1-yl)-N-(6-(neopentyloxy)pyridazin-3-yl)propanamide;
N-(5-((3-chloro-5-fluoropyridin-2-yl)oxy)pyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(3-fluoro-5-((5-fluoropyridin-2-yl)oxy)pyridin-2-yl)propanamide;
N-(5-((3-cyano-5-fluoropyridin-2-yl)oxy)pyridin-2-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(6-(spiro[3.3]heptan-2-yloxy)pyridazin-3-yl)propanamide;

N-(5-bromopyridin-2-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(5-((6-methoxypyridin-2-yl)oxy)pyridin-2-yl)propanamide;

(S)-2-((S)-4,4-difluoro-3-(6-oxo-1,6-dihydropyridin-3-yl)piperidin-1-yl)-N-(5-(2,4,6-trifluorophenoxy)pyridin-2-yl)propanamide;

(S)-2-((S)-4,4-difluoro-3-(6-oxo-1,6-dihydropyridin-3-yl)piperidin-1-yl)-N-(5-(2,4,5-trifluorophenoxy)pyridin-2-yl)propanamide;

(S)-2-((S)-4,4-difluoro-3-(6-oxo-1,6-dihydropyridin-3-yl)piperidin-1-yl)-N-(5-(2-((dimethylamino)methyl)-4-fluorophenoxy)pyridin-2-yl)propanamide;

(S)-2-((S)-4,4-difluoro-3-(6-oxo-1,6-dihydropyridin-3-yl)piperidin-1-yl)-N-(5-(2-fluoro-4-(2-methylthiazol-4-yl)phenoxy)pyridin-2-yl)propanamide;

(S)—N-(6-cyclobutoxypyridazin-3-yl)-2-((S)-4,4-difluoro-3-(6-oxo-1,6-dihydropyridin-3-yl)piperidin-1-yl)propanamide;

(S)—N-(6-(cyclopentyloxy)pyridazin-3-yl)-2-((S)-4,4-difluoro-3-(6-oxo-1,6-dihydropyridin-3-yl)piperidin-1-yl)propanamide;

(S)—N-(5-(difluoro(4-fluorophenyl)methyl)pyridin-2-yl)-2-((S)-4,4-difluoro-3-(6-oxo-1,6-dihydropyridin-3-yl)piperidin-1-yl)propanamide;

(S)-2-((R)-4,4-difluoro-3-(5-oxo-4-(2,2,2-trifluoroethyl)-4,5-dihydropyrazin-2-yl)piperidin-1-yl)-N-(5-fluoropyridin-2-yl)propanamide;

(S)-2-((R)-3-(6-amino-5-oxo-4,5-dihydropyrazin-2-yl)-4,4-difluoropiperidin-1-yl)-N-(6-(cyclopropylmethoxy)pyridazin-3-yl)propanamide;

(S)-2-((R)-3-(6-amino-5-oxo-4,5-dihydropyrazin-2-yl)-4,4-difluoropiperidin-1-yl)-N-(5-(cyclopropylmethoxy)pyridin-2-yl)propanamide;

(S)-2-((R)-3-(6-amino-5-oxo-4,5-dihydropyrazin-2-yl)-4,4-difluoropiperidin-1-yl)-N-(5-fluoropyridin-2-yl)propanamide;

(S)-2-((R)-3-(6-amino-5-oxo-4,5-dihydropyrazin-2-yl)-4,4-difluoropiperidin-1-yl)-N-(5-chloropyridin-2-yl)propanamide;

(S)-2-((R)-3-(6-amino-5-oxo-4,5-dihydropyrazin-2-yl)-4,4-difluoropiperidin-1-yl)-N-(5-(4-fluorophenoxy)pyridin-2-yl)propanamide;

4-((S)-1-((S)-1-((6-(cyclopropylmethoxy)pyridazin-3-yl)amino)-1-oxopropan-2-yl)-4,4-difluoropiperidin-3-yl)pyridine 1-oxide;

4-(4,4-difluoro-1-(1-oxo-1-((5-phenoxypyridin-2-yl)amino)propan-2-yl)piperidin-3-yl)pyridine 1-oxide;

4-((S)-1-((S)-1-((5-(cyclopropylmethoxy)pyridin-2-yl)amino)-1-oxopropan-2-yl)-4,4-difluoropiperidin-3-yl)pyridine 1-oxide;

4-((S)-1-((S)-1-((5-chloropyridin-2-yl)amino)-1-oxopropan-2-yl)-4,4-difluoropiperidin-3-yl)pyridine 1-oxide;

4-((S)-4,4-difluoro-1-((S)-1-((5-fluoropyridin-2-yl)amino)-1-oxopropan-2-yl)piperidin-3-yl)pyridine 1-oxide;

4-((S)-4,4-difluoro-1-((S)-1-((5-(4-fluorophenoxy)pyridin-2-yl)amino)-1-oxopropan-2-yl)piperidin-3-yl)pyridine 1-oxide;

4-((S)-4,4-difluoro-1-((S)-(1-((5-((5-fluoropyridin-2-yl)oxy)pyridin-2-yl)amino)-1-oxopropan-2-yl)piperidin-3-yl)pyridine 1-oxide;

4-((S)-1-((S)-(1-((5-((3,5-difluoropyridin-2-yl)oxy)pyridin-2-yl)amino)-1-oxopropan-2-yl)-4,4-difluoropiperidin-3-yl)pyridine 1-oxide;

4-((S)-1-((S)-1-((5-(2,4-difluorophenoxy)pyridin-2-yl)amino)-1-oxopropan-2-yl)-4,4-difluoropiperidin-3-yl)pyridine 1-oxide;

4-((S)-4,4-difluoro-1-((S)-1-((5-(4-fluorophenoxy)pyrazin-2-yl)amino)-1-oxopropan-2-yl)piperidin-3-yl)pyridine 1-oxide;

4-((S)-4,4-difluoro-1-((S)-1-oxo-1-((5-(2,4,6-trifluorophenoxy)pyrazin-2-yl)amino)propan-2-yl)piperidin-3-yl)pyridine 1-oxide;

4-((S)-4,4-difluoro-1-((S)-1-oxo-1-((5-(2,4,5-trifluorophenoxy)pyrazin-2-yl)amino)propan-2-yl)piperidin-3-yl)pyridine 1-oxide;

4-((S)-1-((S)-1-((5-(2,6-difluorophenoxy)pyrazin-2-yl)amino)-1-oxopropan-2-yl)-4,4-difluoropiperidin-3-yl)pyridine 1-oxide;

4-((S)-4,4-difluoro-1-((S)-1-oxo-1-((5-(2,3,4-trifluorophenoxy)pyrazin-2-yl)amino)propan-2-yl)piperidin-3-yl)pyridine 1-oxide;

4-((S)-4,4-difluoro-1-((S)-1-oxo-1-((5-(2,4,6-trifluorophenoxy)pyridin-2-yl)amino)propan-2-yl)piperidin-3-yl)pyridine 1-oxide;

4-((S)-4,4-difluoro-1-((S)-1-oxo-1-((5-(2,4,5-trifluorophenoxy)pyridin-2-yl)amino)propan-2-yl)piperidin-3-yl)pyridine 1-oxide;

4-((S)-4,4-difluoro-1-((S)-1-((5-((3-fluoropyridin-2-yl)oxy)pyridin-2-yl)amino)-1-oxopropan-2-yl)piperidin-3-yl)pyridine 1-oxide;

4-((S)-4,4-difluoro-1-((S)-1-oxo-1-((5-(pyridin-2-yloxy)pyridin-2-yl)amino)propan-2-yl)piperidin-3-yl)pyridine 1-oxide;

4-((S)-1-((S)-1-((5-(difluoro(4-fluorophenyl)methyl)pyridin-2-yl)amino)-1-oxopropan-2-yl)-4,4-difluoropiperidin-3-yl)pyridine 1-oxide;

4-((S)-4,4-difluoro-1-((S)-1-((5-(4-fluorobenzoyl)pyridin-2-yl)amino)-1-oxopropan-2-yl)piperidin-3-yl)pyridine 1-oxide;

4-((3S)-4,4-difluoro-1-(1-((5-((4-fluorophenyl)(hydroxy)methyl)pyridin-2-yl)amino)-1-oxopropan-2-yl)piperidin-3-yl)pyridine 1-oxide;

4-((S)-1-((S)-1-((5-(2,6-difluorophenoxy)pyridin-2-yl)amino)-1-oxopropan-2-yl)-4,4-difluoropiperidin-3-yl)pyridine 1-oxide;

4-((S)-4,4-difluoro-1-((S)-1-oxo-1-((5-(2,3,4-trifluorophenoxy)pyridin-2-yl)amino)propan-2-yl)piperidin-3-yl)pyridine 1-oxide;

4-((S)-1-((S)-1-((5-(2,4-difluorophenoxy)pyrazin-2-yl)amino)-1-oxopropan-2-yl)-4,4-difluoropiperidin-3-yl)pyridine 1-oxide;

(S)—N-(5-(cyclopropylmethoxy)pyridin-2-yl)-2-((R)-4,4-difluoro-3-(5-oxo-4,5-dihydropyrazin-2-yl)piperidin-1-yl)propanamide;

(S)—N-(6-(cyclopropylmethoxy)pyridazin-3-yl)-2-((R)-4,4-difluoro-3-(5-oxo-4,5-dihydropyrazin-2-yl)piperidin-1-yl)propanamide;

(S)-2-((R)-4,4-difluoro-3-(5-oxo-4,5-dihydropyrazin-2-yl)piperidin-1-yl)-N-(5-fluoropyridin-2-yl)propanamide;

(S)—N-(5-chloropyridin-2-yl)-2-((R)-4,4-difluoro-3-(5-oxo-4,5-dihydropyrazin-2-yl)piperidin-1-yl)propanamide;

(S)—N-(5-cyclopropylpyridin-2-yl)-2-((R)-4,4-difluoro-3-(5-oxo-4,5-dihydropyrazin-2-yl)piperidin-1-yl)propanamide;

(S)-2-((S)-3-(5-amino-6-oxo-1,6-dihydropyridin-3-yl)-4,4-difluoropiperidin-1-yl)-N-(5-(cyclopropylmethoxy)pyridin-2-yl)propanamide;

2-(3-(5-amino-6-oxo-1,6-dihydropyridin-3-yl)-4,4-difluoropiperidin-1-yl)-N-(5-phenoxypyridin-2-yl)propanamide;

(S)-2-((S)-3-(5-amino-6-oxo-1,6-dihydropyridin-3-yl)-4,4-difluoropiperidin-1-yl)-N-(6-(cyclopropylmethoxy)pyridazin-3-yl)propanamide;

(S)-2-((S)-3-(5-amino-6-oxo-1,6-dihydropyridin-3-yl)-4,4-difluoropiperidin-1-yl)-N-(5-chloropyridin-2-yl)propanamide;

(S)-2-((S)-3-(5-amino-6-oxo-1,6-dihydropyridin-3-yl)-4,4-difluoropiperidin-1-yl)-N-(5-fluoropyridin-2-yl)propanamide;

(S)-2-((R)-3-(5-amino-6-oxo-1,6-dihydropyridazin-3-yl)-4,4-difluoropiperidin-1-yl)-N-(5-fluoropyridin-2-yl)propanamide;

(S)-2-((R)-3-(5-amino-6-oxo-1,6-dihydropyridazin-3-yl)-4,4-difluoropiperidin-1-yl)-N-(6-(cyclopropylmethoxy)pyridazin-3-yl)propanamide;

(S)—N-(5-(cyclopropylmethoxy)pyridin-2-yl)-2-((R)-4,4-difluoro-3-(6-oxo-1,6-dihydropyridazin-3-yl)piperidin-1-yl)propanamide;

(S)—N-(6-(cyclopropylmethoxy)pyridazin-3-yl)-2-((R)-4,4-difluoro-3-(6-oxo-1,6-dihydropyridazin-3-yl)piperidin-1-yl)propanamide;

(S)—N-(5-cyclopropylpyridin-2-yl)-2-((R)-4,4-difluoro-3-(6-oxo-1,6-dihydropyridazin-3-yl)piperidin-1-yl)propanamide;

(S)-2-((R)-4,4-difluoro-3-(6-oxo-1,6-dihydropyridazin-3-yl)piperidin-1-yl)-N-(5-fluoropyridin-2-yl)propanamide;

(S)—N-(5-(cyclopropylmethoxy)pyridin-2-yl)-2-((S)-4,4-difluoro-3-(1-methyl-6-oxo-1,6-dihydropyridin-3-yl)piperidin-1-yl)propanamide;

(S)-2-((S)-4,4-difluoro-3-(6-oxo-5-(2,2,2-trifluoroethyl)-1,6-dihydropyridin-3-yl)piperidin-1-yl)-N-(5-fluoropyridin-2-yl)propanamide;

(S)—N-(5-(cyclopropylmethoxy)pyridin-2-yl)-2-((S)-4,4-difluoro-3-(5-(2-hydroxypropan-2-yl)-6-oxo-1,6-dihydropyridin-3-yl)piperidin-1-yl)propanamide;

(S)-2-((S)-4,4-difluoro-3-(5-(hydroxymethyl)-6-oxo-1,6-dihydropyridin-3-yl)piperidin-1-yl)-N-(5-fluoropyridin-2-yl)propanamide;

(S)—N-(6-(cyclopropylmethoxy)pyridazin-3-yl)-2-(4,4-difluoro-3-(5-(hydroxymethyl)-6-oxo-1,6-dihydropyridin-3-yl)piperidin-1-yl)propanamide;

N-(5-chloropyridin-2-yl)-2-(4,4-difluoro-3-(5-(hydroxymethyl)-6-oxo-1,6-dihydropyridin-3-yl)piperidin-1-yl)propanamide;

(S)-2-((S)-(4,4-difluoro-3-(5-(hydroxymethyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-(hydroxymethyl)-6-oxo-1,6-dihydropyridin-3-yl)piperidin-1-yl)-N-(5-((5-fluoropyridin-2-yl)oxy)pyridin-2-yl)propanamide;

(S)—N-(5-chloropyridin-2-yl)-2-((S)-3-(6-oxo-1,6-dihydropyridin-3-yl)piperidin-1-yl)propanamide;

(S)—N-(5-(cyclopropylmethoxy)pyridin-2-yl)-2-((S)-3-(6-oxo-1,6-dihydropyridin-3-yl)piperidin-1-yl)propanamide;

(S)—N-(5-(cyclopropylmethoxy)pyridin-2-yl)-2-((3S,4R)-(4-fluoro-3-(6-oxo-1,6-dihydropyridin-3-yl)piperidin-1-yl)propanamide;

(S)—N-(5-(cyclopropylmethoxy)pyridin-2-yl)-2-((3S,4S)-(4-fluoro-3-(6-oxo-1,6-dihydropyridin-3-yl)piperidin-1-yl)propanamide;

(S)-2-((3S,4R)-4-fluoro-3-(6-oxo-1,6-dihydropyridin-3-yl)piperidin-1-yl)-N-(5-fluoropyridin-2-yl)propanamide;

(S)-2-((3S,4S)-4-fluoro-3-(6-oxo-1,6-dihydropyridin-3-yl)piperidin-1-yl)-N-(5-fluoropyridin-2-yl)propanamide;

(S)—N-(5-fluoropyridin-2-yl)-2-((3S,5R)-3-methyl-5-(6-oxo-1,6-dihydropyridazin-3-yl)piperidin-1-yl)propanamide;

(S)—N-(5-(cyclopropylmethoxy)pyridin-2-yl)-2-((S)-4,4-difluoro-3-methyl-3-(6-oxo-1,6-dihydropyridin-3-yl)piperidin-1-yl)propanamide;

N-(5-(cyclopropylmethoxy)pyridin-2-yl)-2-(3,3-difluoro-4-(6-oxo-1,6-dihydropyridin-3-yl)pyrrolidin-1-yl)propanamide;

2-(3,3-difluoro-4-(6-oxo-1,6-dihydropyridin-3-yl)pyrrolidin-1-yl)-N-(5-fluoropyridin-2-yl)propanamide;

(S)—N-(5-chloropyridin-2-yl)-2-((R)-(3-(5-oxo-4,5-dihydropyrazin-2-yl)piperidin-1-yl)propanamide;

(S)—N-(5-chloropyridin-2-yl)-2-((S)-3-(6-oxo-1-(2,2,2-trifluoroethyl)-1,6-dihydropyridin-3-yl)piperidin-1-yl)propanamide;

(S)-2-((S)-3-(1-benzyl-6-oxo-1,6-dihydropyridin-3-yl)piperidin-1-yl)-N-(5-chloropyridin-2-yl)propanamide;

(S)—N-(5-(cyclopropylmethoxy)pyridin-2-yl)-2-((S)-3-(6-oxo-4-(trifluoromethyl)-1,6-dihydropyridin-3-yl)piperidin-1-yl)propanamide;

((S)-2-((S)-3-(5-amino-6-oxo-1,6-dihydropyridin-3-yl)piperidin-1-yl)-N-(5-chloropyridin-2-yl)propanamide;

(S)—N-(5-(cyclopropylmethoxy)pyridin-2-yl)-2-((R)-3-hydroxy-3-(6-oxo-1,6-dihydropyridin-3-yl)piperidin-1-yl)propanamide;

(S)—N-(5-chloropyridin-2-yl)-2-((3S,5S)-(3-methyl-5-(6-oxo-1,6-dihydropyridin-3-yl)piperidin-1-yl)propanamide;

(S)—N-(5-chloropyridin-2-yl)-2-((3R,5S)-(3-methyl-5-(6-oxo-1,6-dihydropyridin-3-yl)piperidin-1-yl)propanamide;

(S)-2-((R)-3-(6-amino-5-oxo-4,5-dihydropyrazin-2-yl)piperidin-1-yl)-N-(5-chloropyridin-2-yl)propanamide;

(S)-2-((S)-3-(5-(aminomethyl)-6-oxo-1,6-dihydropyridin-3-yl)piperidin-1-yl)-N-(5-chloropyridin-2-yl)propanamide;

(S)—N-(5-chloropyridin-2-yl)-2-((S)-3-(1-methyl-6-oxo-1,6-dihydropyridin-3-yl)piperidin-1-yl)propanamide;

(S)—N-(5-chloropyridin-2-yl)-2-((S)-3-(5-(hydroxymethyl)-6-oxo-1,6-dihydropyridin-3-yl)piperidin-1-yl)propanamide;

(S)—N-(5-chloropyridin-2-yl)-2-((S)-3-(6-oxo-5-phenyl-1,6-dihydropyridin-3-yl)piperidin-1-yl)propanamide;

(S)—N-(5-chloropyridin-2-yl)-2-((S)-3-(5-cyclopropyl-6-oxo-1,6-dihydropyridin-3-yl)piperidin-1-yl)propanamide;

4-((S)-1-((S)-1-((5-chloropyridin-2-yl)amino)-1-oxopropan-2-yl)piperidin-3-yl)pyridine 1-oxide;

4-((S)-1-((S)-1-((5-(2,4-difluorophenoxy)pyrazin-2-yl)amino)-1-oxopropan-2-yl)piperidin-3-yl)pyridine 1-oxide;

4-((S)-1-((S)-1-((5-(2,4-difluorophenoxy)pyridin-2-yl)amino)-1-oxopropan-2-yl)piperidin-3-yl)pyridine 1-oxide;

(S)—N-(5-(cyclopropylmethoxy)pyridin-2-yl)-2-(4,4-difluoro-3-(6-oxo-1,6-dihydropyridin-3-yl)piperidin-1-yl)-2-methylpropanamide;

(S)—N-(5-chloropyridin-2-yl)-2-((S)-3-(5-methyl-6-oxo-1,6-dihydropyridin-3-yl)piperidin-1-yl)propanamide;

(S)—N-(5-(cyclopropylmethoxy)pyridin-2-yl)-2-((R)-3-(6-oxo-1,6-dihydropyridazin-3-yl)piperidin-1-yl)propanamide;

(S)—N-(5-chloropyridin-2-yl)-2-((R)-3-(6-oxo-1,6-dihydropyridazin-3-yl)piperidin-1-yl)propanamide;

(2S)-2-(3-(5-amino-6-oxo-1-(2,2,2-trifluoroethyl)-1,6-dihydropyridin-3-yl)-4,4-difluoropiperidin-1-yl)-N-(5-fluoropyridin-2-yl)propanamide;

(2S)-2-(3-(1-ethyl-6-oxo-1,6-dihydropyridin-3-yl)-4,4-difluoropiperidin-1-yl)-N-(5-fluoropyridin-2-yl)propanamide;

(S)—N-(6-(cyclopropylmethoxy)pyridazin-3-yl)-2-((S)-(3-(1-ethyl-6-oxo-1,6-dihydropyridin-3-yl)-4,4-difluoropiperidin-1-yl)propanamide;

(2S)-2-(4,4-difluoro-3-(1-(2-(methylsulfonyl)ethyl)-6-oxo-1,6-dihydropyridin-3-yl)piperidin-1-yl)-N-(5-fluoropyridin-2-yl)propanamide;

(2S)—N-(6-(cyclopropylmethoxy)pyridazin-3-yl)-2-(4,4-difluoro-3-(1-(2-(methylsulfonyl)ethyl)-6-oxo-1,6-dihydropyridin-3-yl)piperidin-1-yl)propanamide;

2-(4,4-difluoro-3-(1-(2-(methylsulfonyl)ethyl)-6-oxo-1,6-dihydropyridin-3-yl)piperidin-1-yl)-N-(5-(4-fluorophenoxy)pyridin-2-yl)propanamide;

(S)-2-((S)-(3-(1-(2,2-difluoroethyl)-6-oxo-1,6-dihydropyridin-3-yl)-4,4-difluoropiperidin-1-yl)-N-(5-fluoropyridin-2-yl)propanamide;

(2S)-2-(4,4-difluoro-3-(1-isopropyl-6-oxo-1,6-dihydropyridin-3-yl)piperidin-1-yl)-N-(5-fluoropyridin-2-yl)propanamide;

(S)-2-((S)-(3-(1-benzyl-6-oxo-1,6-dihydropyridin-3-yl)-4,4-difluoropiperidin-1-yl)-N-(5-fluoropyridin-2-yl)propanamide;

2-(4,4-difluoro-3-(6-oxo-1-(pyridin-2-ylmethyl)-1,6-dihydropyridin-3-yl)piperidin-1-yl)-N-(5-fluoropyridin-2-yl)propanamide;

2-(4,4-difluoro-3-(6-oxo-1-(pyridin-4-ylmethyl)-1,6-dihydropyridin-3-yl)piperidin-1-yl)-N-(5-fluoropyridin-2-yl)propanamide;

2-(4,4-difluoro-3-(1-(oxazol-2-ylmethyl)-6-oxo-1,6-dihydropyridin-3-yl)piperidin-1-yl)-N-(5-fluoropyridin-2-yl)propanamide;

(2S)-2-(4,4-difluoro-3-(5-(hydroxymethyl)-6-oxo-1-(2,2,2-trifluoroethyl)-1,6-dihydropyridin-3-yl)piperidin-1-yl)-N-(5-fluoropyridin-2-yl)propanamide;

(2S)-2-(4,4-difluoro-3-(5-methyl-6-oxo-1-(2,2,2-trifluoroethyl)-1,6-dihydropyridin-3-yl)piperidin-1-yl)-N-(5-fluoropyridin-2-yl)propanamide;

(S)-2-((S)-3-(5-(aminomethyl)-6-oxo-1,6-dihydropyridin-3-yl)-4,4-difluoropiperidin-1-yl)-N-(5-fluoropyridin-2-yl)propanamide;

2-(3-(5-(aminomethyl)-6-oxo-1,6-dihydropyridin-3-yl)-4,4-difluoropiperidin-1-yl)-N-(5-phenoxypyridin-2-yl)propanamide;

(S)-2-((S)-3-(5-(aminomethyl)-6-oxo-1,6-dihydropyridin-3-yl)-4,4-difluoropiperidin-1-yl)-N-(6-(cyclopropylmethoxy)pyridazin-3-yl)propanamide;

(S)-2-((S)-3-(5-(aminomethyl)-6-oxo-1,6-dihydropyridin-3-yl)-4,4-difluoropiperidin-1-yl)-N-(5-(4-fluorophenoxy)pyridin-2-yl)propanamide;

(S)-2-((S)-3-(5-(aminomethyl)-6-oxo-1,6-dihydropyridin-3-yl)-4,4-difluoropiperidin-1-yl)-N-(5-(2,4-difluorophenoxy)pyridin-2-yl)propanamide;

(S)-2-((S)-3-(5-(aminomethyl)-6-oxo-1,6-dihydropyridin-3-yl)-4,4-difluoropiperidin-1-yl)-N-(5-(4-fluorophenoxy)pyrazin-2-yl)propanamide;

(S)-2-((S)-3-(5-(aminomethyl)-6-oxo-1,6-dihydropyridin-3-yl)-4,4-difluoropiperidin-1-yl)-N-(5-phenoxypyrazin-2-yl)propanamide;

(S)-2-((S)-3-(5-(aminomethyl)-6-oxo-1,6-dihydropyridin-3-yl)-4,4-difluoropiperidin-1-yl)-N-(5-((5-fluoropyridin-2-yl)oxy)pyridin-2-yl)propanamide;

(S)-2-((S)-4,4-difluoro-3-(6-oxo-5-((S)-2,2,2-trifluoro-1-hydroxyethyl)-1,6-dihydropyridin-3-yl)piperidin-1-yl)-N-(5-fluoropyridin-2-yl)propanamide;

(S)-2-((S)-4,4-difluoro-3-(6-oxo-5-((R)-2,2,2-trifluoro-1-hydroxyethyl)-1,6-dihydropyridin-3-yl)piperidin-1-yl)-N-(5-fluoropyridin-2-yl)propanamide;

(S)—N-(6-(cyclopropylmethoxy)pyridazin-3-yl)-2-((S)-4,4-difluoro-3-(6-oxo-5-((S)-2,2,2-trifluoro-1-hydroxyethyl)-1,6-dihydropyridin-3-yl)piperidin-1-yl)propanamide;

(S)—N-(6-(cyclopropylmethoxy)pyridazin-3-yl)-2-((S)-4,4-difluoro-3-(6-oxo-5-((R)-2,2,2-trifluoro-1-hydroxyethyl)-1,6-dihydropyridin-3-yl)piperidin-1-yl)propanamide;

(2S)-2-(4,4-difluoro-3-(6-oxo-5-(2,2,2-trifluoro-1-hydroxyethyl)-1,6-dihydropyridin-3-yl)piperidin-1-yl)-N-(5-(4-fluorophenoxy)pyridin-2-yl)propanamide;

(2S)-2-(4,4-difluoro-3-(6-oxo-5-(2,2,2-trifluoro-1-hydroxyethyl)-1,6-dihydropyridin-3-yl)piperidin-1-yl)-N-(5-(2,4-difluorophenoxy)pyridin-2-yl)propanamide;

2-(4,4-difluoro-3-(5-((methylsulfonyl)methyl)-6-oxo-1,6-dihydropyridin-3-yl)piperidin-1-yl)-N-(5-fluoropyridin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyrazin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(2,4-difluorophenoxy)pyridin-2-yl)propanamide;

4-(4,4-difluoro-1-((S)-1-((5-fluoropyridin-2-yl)amino)-1-oxopropan-2-yl)piperidin-3-yl)-2-methylpyridine 1-oxide;

4-((R)-4,4-difluoro-1-((R)-1-((5-(4-fluorophenoxy)pyridin-2-yl)amino)-1-oxopropan-2-yl)piperidin-3-yl)-2-methylpyridine 1-oxide;

4-((S)-4,4-difluoro-1-((S)-1-((5-(4-fluorophenoxy)pyridin-2-yl)amino)-1-oxopropan-2-yl)piperidin-3-yl)-2-methylpyridine 1-oxide;

4-((S)-4,4-difluoro-1-((S)-1-((5-fluoropyridin-2-yl)amino)-1-oxopropan-2-yl)piperidin-3-yl)-2-(2,2,2-trifluoroethyl)pyridine 1-oxide;

4-((S)-1-((S)-1-((6-(cyclopropylmethoxy)pyridazin-3-yl)amino)-1-oxopropan-2-yl)-4,4-difluoropiperidin-3-yl)-2-(2,2,2-trifluoroethyl)pyridine 1-oxide;

(2S)-2-(3-(5-bromo-6-oxo-1,6-dihydropyridin-3-yl)-4,4-difluoropiperidin-1-yl)-N-(6-(cyclopropylmethoxy)pyridazin-3-yl)propanamide;

(2S)-2-(3-(5-(1-aminoethyl)-6-oxo-1,6-dihydropyridin-3-yl)-4,4-difluoropiperidin-1-yl)-N-(6-(cyclopropylmethoxy)pyridazin-3-yl)propanamide;

(2S)-2-(3-(5-cyano-6-oxo-1,6-dihydropyridin-3-yl)-4,4-difluoropiperidin-1-yl)-N-(6-(cyclopropylmethoxy)pyridazin-3-yl)propanamide;

(2S)—N-(6-(cyclopropylmethoxy)pyridazin-3-yl)-2-(4,4-difluoro-3-(pyridin-4-yl)piperidin-1-yl)propanamide;

S)—N-(6-(cyclopropylmethoxy)pyridazin-3-yl)-2-((S)-4,4-difluoro-3-(5-(morpholinomethyl)-6-oxo-1,6-dihydropyridin-3-yl)piperidin-1-yl)propanamide;

2-(4,4-difluoro-3-(5-(morpholinomethyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-(2,4-difluorophenoxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-((3,5-difluoropyridin-2-yl)oxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-(2,4-difluorophenoxy)pyrazin-2-yl)propanamide;

2-(3-(5-((dimethylamino)methyl)-6-oxo-1,6-dihydropyridin-3-yl)-4,4-difluoropiperidin-1-yl)-N-(5-(4-fluorophenoxy)pyridin-2-yl)propanamide;

(S)—N-(6-(cyclopropylmethoxy)pyridazin-3-yl)-2-((S)-3-(5-((dimethylamino)methyl)-6-oxo-1,6-dihydropyridin-3-yl)-4,4-difluoropiperidin-1-yl)propanamide;

(2S)-2-(3-(5-(1-amino-2,2,2-trifluoroethyl)-6-oxo-1,6-dihydropyridin-3-yl)-4,4-difluoropiperidin-1-yl)-N-(5-fluoropyridin-2-yl)propanamide;

(S)-2-((S)-3-(5-((S)-1-amino-2,2,2-trifluoroethyl)-6-oxo-1,6-dihydropyridin-3-yl)-4,4-difluoropiperidin-1-yl)-N-(5-(4-fluorophenoxy)pyridin-2-yl)propanamide;

(S)-2-((S)-3-(5-((R)-1-amino-2,2,2-trifluoroethyl)-6-oxo-1,6-dihydropyridin-3-yl)-4,4-difluoropiperidin-1-yl)-N-(5-(4-fluorophenoxy)pyridin-2-yl)propanamide;

(S)-2-((S)-3-(5-((S)-1-amino-2,2,2-trifluoroethyl)-6-oxo-1,6-dihydropyridin-3-yl)-4,4-difluoropiperidin-1-yl)-N-(5-(2,4-difluorophenoxy)pyridin-2-yl)propanamide;

(S)-2-((S)-3-(5-((R)-1-amino-2,2,2-trifluoroethyl)-6-oxo-1,6-dihydropyridin-3-yl)-4,4-difluoropiperidin-1-yl)-N-(5-(2,4-difluorophenoxy)pyridin-2-yl)propanamide;

2-(4,4-difluoro-3-(5-((methylamino)methyl)-6-oxo-1,6-dihydropyridin-3-yl)piperidin-1-yl)-N-(5-(4-fluorophenoxy)pyridin-2-yl)propanamide;

2-(4,4-difluoro-3-(5-(((2-hydroxyethyl)amino)methyl)-6-oxo-1,6-dihydropyridin-3-yl)piperidin-1-yl)-N-(5-(4-fluorophenoxy)pyridin-2-yl)propanamide;

2-(4,4-difluoro-3-(5-(((2-methoxyethyl)amino)methyl)-6-oxo-1,6-dihydropyridin-3-yl)piperidin-1-yl)-N-(5-(4-fluorophenoxy)pyridin-2-yl)propanamide;

(S)—N-(5-(2,4-difluorophenoxy)pyridin-2-yl)-2-((S)-3-(5-((4,4-difluoropiperidin-1-yl)methyl)-6-oxo-1,6-dihydropyridin-3-yl)-4,4-difluoropiperidin-1-yl)propanamide;

(S)-2-((S)-3-(5-(((3,3-difluorocyclobutyl)amino)methyl)-6-oxo-1,6-dihydropyridin-3-yl)-4,4-difluoropiperidin-1-yl)-N-(5-(2,4-difluorophenoxy)pyridin-2-yl)propanamide;

(S)-2-((S)-4,4-difluoro-3-(6-oxo-5-(((2,2,2-trifluoroethyl)amino)methyl)-1,6-dihydropyridin-3-yl)piperidin-1-yl)-N-(5-(2,4-difluorophenoxy)pyridin-2-yl)propanamide;

(S)-2-((S)-4,4-difluoro-3-(5-((methylamino)methyl)-6-oxo-1,6-dihydropyridin-3-yl)piperidin-1-yl)-N-(5-(2,4-difluorophenoxy)pyridin-2-yl)propanamide;

S)-2-((S)-4,4-difluoro-3-(5-((methylamino)methyl)-6-oxo-1,6-dihydropyridin-3-yl)piperidin-1-yl)-N-(5-(2,4-difluorophenoxy)pyrazin-2-yl)propanamide;

(S)-2-((S)-3-(5-(acetamidomethyl)-6-oxo-1,6-dihydropyridin-3-yl)-4,4-difluoropiperidin-1-yl)-N-(5-(4-fluorophenoxy)pyridin-2-yl)propanamide;

(S)—N-(5-(4-fluorophenoxy)pyridin-2-yl)-2-((S)-3-(5-(methylsulfonyl)-6-oxo-1,6-dihydropyridin-3-yl)piperidin-1-yl)propanamide (R)—N-(5-(4-fluorophenoxy)pyridin-2-yl)-2-((R)-3-(5-(methylsulfonyl)-6-oxo-1,6-dihydropyridin-3-yl)piperidin-1-yl)propanamide;

(S)—N-(5-(4-fluorophenoxy)pyridin-2-yl)-2-((S)-3-(5-(N-methylsulfamoyl)-6-oxo-1,6-dihydropyridin-3-yl)piperidin-1-yl)propanamide;

(R)—N-(5-(4-fluorophenoxy)pyridin-2-yl)-2-((R)-3-(5-(N-methylsulfamoyl)-6-oxo-1,6-dihydropyridin-3-yl)piperidin-1-yl)propanamide;

(S)-2-((S)-3,3-difluoro-5-(6-oxo-1,6-dihydropyridin-3-yl)piperidin-1-yl)-N-(5-fluoropyridin-2-yl)propanamide;

(R)-2-((R)-3,3-difluoro-5-(6-oxo-1,6-dihydropyridin-3-yl)piperidin-1-yl)-N-(5-fluoropyridin-2-yl)propanamide;

2-(3-(5-cyano-6-oxo-1,6-dihydropyridin-3-yl)-4,4-difluoropiperidin-1-yl)-N-(5-fluoropyridin-2-yl)propanamide;

2-(3-(5-cyano-6-oxo-1,6-dihydropyridin-3-yl)-4,4-difluoropiperidin-1-yl)-N-(5-(4-fluorophenoxy)pyrazin-2-yl)propanamide;

(S)-2-((S)-3-(5-cyano-6-oxo-1,6-dihydropyridin-3-yl)-4,4-difluoropiperidin-1-yl)-N-(5-(4-fluorophenoxy)pyridin-2-yl)propanamide;

5-((S)-4,4-difluoro-1-((S)-1-((5-(4-fluorophenoxy)pyridin-2-yl)amino)-1-oxopropan-2-yl)piperidin-3-yl)-2-oxo-1,2-dihydropyridine-3-carboxamide;

5-(4,4-difluoro-1-(1-((5-fluoropyridin-2-yl)amino)-1-oxopropan-2-yl)piperidin-3-yl)-2-oxo-1,2-dihydropyridine-3-carboxamide;

4-((S)-4,4-difluoro-1-((S)-1-((5-(4-fluorophenoxy)pyridin-2-yl)amino)-1-oxopropan-2-yl)piperidin-3-yl)-2-(hydroxymethyl)pyridine 1-oxide;

4-((S)-1-((S)-1-((5-(2,4-difluorophenoxy)pyridin-2-yl)amino)-1-oxopropan-2-yl)-4,4-difluoropiperidin-3-yl)-2-(hydroxymethyl)pyridine 1-oxide;

4-(4,4-difluoro-1-(1-((5-fluoropyridin-2-yl)amino)-1-oxopropan-2-yl)piperidin-3-yl)-2-(2,2,2-trifluoro-1-hydroxyethyl)pyridine 1-oxide;

4-(4,4-difluoro-1-(1-((5-(4-fluorophenoxy)pyridin-2-yl)amino)-1-oxopropan-2-yl)piperidin-3-yl)-2-(2,2,2-trifluoro-1-hydroxyethyl)pyridine 1-oxide;

2-carbamoyl-4-((S)-1-((S)-1-((5-(2,4-difluorophenoxy)pyridin-2-yl)amino)-1-oxopropan-2-yl)-4,4-difluoropiperidin-3-yl)pyridine 1-oxide;

2-carbamoyl-4-((S)-4,4-difluoro-1-((S)-1-((5-fluoropyridin-2-yl)amino)-1-oxopropan-2-yl)piperidin-3-yl)pyridine 1-oxide;

2-carbamoyl-4-(1-(1-((5-(2,4-difluorophenoxy)pyrazin-2-yl)amino)-1-oxopropan-2-yl)-4,4-difluoropiperidin-3-yl)pyridine 1-oxide;

4-(1-((S)-1-((5-(2,4-difluorophenoxy)pyridin-2-yl)amino)-1-oxopropan-2-yl)-4,4-difluoropiperidin-3-yl)picolinamide;

2-(acetamidomethyl)-4-(1-(1-((5-(2,4-difluorophenoxy)pyridin-2-yl)amino)-1-oxopropan-2-yl)-4,4-difluoropiperidin-3-yl)pyridine 1-oxide;

2-(acetamidomethyl)-4-(4,4-difluoro-1-(1-((5-fluoropyridin-2-yl)amino)-1-oxopropan-2-yl)piperidin-3-yl)pyridine 1-oxide;

2-(3-(2-(aminomethyl)pyridin-4-yl)-4,4-difluoropiperidin-1-yl)-N-(5-(2,4-difluorophenoxy)pyridin-2-yl)propanamide;

(2S)-2-(4,4-difluoro-3-(5-(2,2,2-trifluoro-1-hydroxyethyl)pyridin-3-yl)piperidin-1-yl)-N-(5-(2,4-difluorophenoxy)pyridin-2-yl)propanamide;

3-(1-(1-((5-(2,4-difluorophenoxy)pyridin-2-yl)amino)-1-oxopropan-2-yl)-4,4-difluoropiperidin-3-yl)-5-(2,2,2-trifluoro-1-hydroxyethyl)pyridine 1-oxide;

2-((S)-4,4-difluoro-3-(6-oxo-1,6-dihydropyridin-3-yl)piperidin-1-yl)-N-(5-((6-oxo-1,6-dihydropyridin-2-yl)oxy)pyridin-2-yl)propanamide;

(S)-2-((S)-4,4-difluoro-3-(6-oxo-1,6-dihydropyridin-3-yl)piperidin-1-yl)-N-(5-(3,4-difluorophenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-methoxyphenoxy)pyridin-2-yl)propanamide;

(2S)-2-(3-(2-((3,3-difluoroazetidin-1-yl)methyl)pyridin-4-yl)-4,4-difluoropiperidin-1-yl)-N-(5-(2,4-difluorophenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-(hydroxymethyl)phenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-(hydroxymethyl)phenoxy)pyrazin-2-yl)propanamide;

4-((S)-4,4-difluoro-1-((S)-1-((5-(4-fluoro-2-(hydroxymethyl)phenoxy)pyridin-2-yl)amino)-1-oxopropan-2-yl)piperidin-3-yl)pyridine 1-oxide;

4-((3S)-4,4-difluoro-1-(1-((5-(4-fluoro-2-(hydroxymethyl)phenoxy)pyrazin-2-yl)amino)-1-oxopropan-2-yl)piperidin-3-yl)pyridine 1-oxide;

(R)—N-(5-(cyclopropylmethoxy)pyridin-2-yl)-2-((1S,3R)-4,4-difluoro-3-(6-oxo-1,6-dihydropyridin-3-yl)cyclohexyl)propanamide;

(R)—N-(6-(cyclopropylmethoxy)pyridazin-3-yl)-2-((1S,3R)-4,4-difluoro-3-(6-oxo-1,6-dihydropyridin-3-yl)cyclohexyl)propanamide;

(R)-2-((1S,3R)-4,4-difluoro-3-(6-oxo-1,6-dihydropyridin-3-yl)cyclohexyl)-N-(5-fluoropyridin-2-yl)propanamide;

2-(4,4-difluoro-3-(6-oxo-1,6-dihydropyridin-3-yl)cyclohexyl)-N-(5-(4-fluorophenoxy)pyridin-2-yl)propanamide;

(R)-2-((1S,3R)-4,4-difluoro-3-(6-oxo-1,6-dihydropyridin-3-yl)cyclohexyl)-N-(5-((5-fluoropyridin-2-yl)oxy)pyridin-2-yl)propanamide;

(R)-2-((1S,3R)-4,4-difluoro-3-(6-oxo-1,6-dihydropyridin-3-yl)cyclohexyl)-N-(5-(2,4-difluorophenoxy)pyridin-2-yl)propanamide;

(R)-2-((1S,3R)-4,4-difluoro-3-(6-oxo-1,6-dihydropyridin-3-yl)cyclohexyl)-N-(5-((3,5-difluoropyridin-2-yl)oxy)pyridin-2-yl)propanamide;

(R)—N-(5-(2,4-difluorophenoxy)pyridin-2-yl)-2-((1S,3R)-3-(6-oxo-1,6-dihydropyridin-3-yl)cyclohexyl)propanamide;

(R)—N-(5((5fluoropyridin-2yl)oxy)pyridin-2-yl)-2-((1S,3R)-3-(6-oxo-1,6-dihydropyridin-3yl)cyclohexyl)propanamide;

N-(5-(4-fluorophenoxy)pyrazin-2-yl)-2-((3R)-3-(6-oxo-1,6dihydropyridin-3-yl)cyclohexyl)propanamide;

(R)—N-(5-((3,5-difluoropyridin-2-yl)oxy)pyridin-2-yl)-2-((1S,3R)-3-(6-oxo-1,6-dihydropyridin-3-yl)cyclohexyl)propanamide;

(R)—N-(5-(2,4-difluorophenoxy)pyrazin-2-yl)-2-((1S,3R)-3-(6-oxo-1,6-dihydropyridin-3-yl)cyclohexyl)propanamide;

4-((1R,3S)-3-((R)-1-((5-((5-fluoropyridin-2-yl)oxy)pyridin-2-yl)amino)-1-oxopropan-2-yl)cyclohexyl)pyridine 1-oxide;

4-((1R,3S)-3-((R)-1-((5-((5-fluoropyridin-2-yl)oxy)pyridin-2-yl)amino)-1-oxopropan-2-yl)cyclohexyl)pyridine 1-oxide;

4-((1R,3S)-3-((R)-1-((5-(2,4-difluorophenoxy)pyridin-2-yl)amino)-1-oxopropan-2-yl)cyclohexyl)pyridine 1-oxide;

4-((1R,3S)-3-((S)-1-((5-((3,5-difluoropyridin-2-yl)oxy)pyridin-2-yl)amino)-1-oxopropan-2-yl)cyclohexyl)pyridine 1-oxide;

4-((1R,5S)-5-((R)-1-((5-(2,4-difluorophenoxy)pyridin-2-yl)amino)-1-oxopropan-2-yl)-2,2-difluorocyclohexyl)pyridine 1-oxide;

4-((1R,5S)-2,2-difluoro-5-((R)-1-((5-(4-fluorophenoxy)pyrazin-2-yl)amino)-1-oxopropan-2-yl)cyclohexyl)pyridine 1-oxide;

4-((1R,5S)-5-((R)-1-((5-((3,5-difluoropyridin-2-yl)oxy)pyridin-2-yl)amino)-1-oxopropan-2-yl)-2,2-difluorocyclohexyl)pyridine 1-oxide;

4-((1R,5S)-2,2-difluoro-5-((R)-1-((5-((5-fluoropyridin-2-yl)oxy)pyridin-2-yl)amino)-1-oxopropan-2-yl)cyclohexyl)pyridine 1-oxide; and 4-((1R,5S)-5-((R)-1-((5-(2,4-difluorophenoxy)pyrazin-2-yl)amino)-1-oxopropan-2-yl)-2,2-difluorocyclohexyl)pyridine 1-oxide;

or pharmaceutically acceptable salts thereof.

In one embodiment, the compound of the invention is (R)-2-((1S,3R)-4,4-difluoro-3-(6-oxo-1,6-dihydropyridin-3-yl)cyclohexyl)-N-(5-(2,4-difluorophenoxy)pyrazin-2-yl)propanamide;

(S)-2-((S)-4,4-difluoro-3-(pyridin-4-yl)piperidin-1-yl)-N-(5-(2,4-difluorophenoxy)pyrazin-2-yl)propanamide;

4-((S)-1-((S)-1-((5-(2,4-difluoro-6-(hydroxymethyl)phenoxy)pyrazin-2-yl)amino)-1-oxopropan-2-yl)-4,4-difluoropiperidin-3-yl)pyridine 1-oxide 4-((S)-1-((S)-1-((5-(2,4-difluoro-6-(hydroxymethyl)phenoxy)pyridin-2-yl)amino)-1-oxopropan-2-yl)-4,4-difluoropiperidin-3-yl)pyridine 1-oxide (S)-2-((S)-4,4-difluoro-3-(6-oxo-1,6-dihydropyridin-3-yl)piperidin-1-yl)-N-(5-(2,4-difluoro-6-(hydroxymethyl)phenoxy)pyrazin-2-yl)propanamide;

(S)-2-((S)-4,4-difluoro-3-(6-oxo-1,6-dihydropyridin-3-yl)piperidin-1-yl)-N-(5-(2,4-difluoro-6-(hydroxymethyl)phenoxy)pyridin-2-yl)propanamide;

or a pharmaceutically acceptable salt thereof.

In one embodiment, the compound of the invention is 4-((1R,5S)-5-((R)-1-((5-(2,4-difluorophenoxy)pyridin-2-yl)amino)-1-oxopropan-2-yl)-2,2-difluorocyclohexyl)pyridine 1-oxide or a pharmaceutically acceptable salt thereof.

In one embodiment, the compound of the invention is 4-((S)-1-((S)-1-((5-(2,4-difluorophenoxy)pyridin-2-yl)amino)-1-oxopropan-2-yl)-4,4-difluoropiperidin-3-yl)pyridine 1-oxide.

In one embodiment, the compound of the invention is 4-((S)-1-((S)-1-((5-(2,4-difluorophenoxy)pyrazin-2-yl)amino)-1-oxopropan-2-yl)-4,4-difluoropiperidin-3-yl)pyridine 1-oxide or a pharmaceutically acceptable salt thereof.

It is to be understood that the references herein are to a compound of Formulae (I)-(IV) or a pharmaceutically acceptable salt thereof. Thus, in one embodiment, the invention is directed to a compound of Formulae (I)-(IV). In another embodiment, the invention is directed to a pharmaceutically acceptable salt of a compound of Formulae (I)-(IV). In a further embodiment, the invention is directed to a compound of Formulae (I)-(IV) or a pharmaceutically acceptable salt thereof.

Another aspect of this invention relates to a pharmaceutical composition comprising a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide) or pharmaceutically acceptable salt thereof and a pharmaceutically acceptable excipient.

Another aspect of this invention relates to a method of treating an MrgX2-mediated disease or disorder in a human in need thereof, comprising administering to the human a therapeutically effective amount of a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or pharmaceutically acceptable salt thereof, or a pharmaceutical composition comprising of a compound of Formulae (I)-(IV), or a pharmaceutically acceptable salt thereof and a pharmaceutically acceptable excipient.

Another aspect of this invention relates to a method of treating an MrgX2-mediated disease in a human in need thereof, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine, chronic inducible urticaria, chronic pruritus, acute pruritus, prurigo nodularis, osteoarthritis, pseudo anaphalaxis, or contact urticaria. Another aspect of this invention relates to a method of treating an MrgX2-mediated disease in a human in need thereof, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. Another aspect of this invention relates to a method of treating an MrgX2-mediated disease or disorder in a human in need thereof, wherein the disease or disorder is chronic spontaneous urticaria, atopic dermatitis, rosacea, Crohns disease, ulcerative colitis, irritable bowel syndrome, neuropathic pain, or inflammatory pain.

Another aspect of this invention relates to the method of treating chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. Another aspect of the invention relates to the method of treating chronic spontaneous urticaria, atopic dermatitis, rosacea, Crohns disease, ulcerative colitis, irritable bowel syndrome, neuropathic pain, or inflammatory pain.

In another aspect, the invention provides a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof for use in therapy. In another aspect, there is provided a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof for use in the treatment of an MrgX2-mediated disease or disorder. In another aspect, there is provided a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof for use in the treatment of an MrgX2-mediated disease or disorder, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. In another aspect, there is provided a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof for use in the treatment of an MrgX2-mediated disease or disorder, wherein the disease or disorder is chronic spontaneous urticaria, atopic dermatitis, rosacea, Crohns disease, ulcerative colitis, irritable bowel syndrome, neuropathic pain, or inflammatory pain. In another aspect, there is provided a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or pharmaceutically acceptable salt thereof for the use in the treatment of chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. In another aspect, there is provided a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or pharmaceutically acceptable salt thereof for the use in the treatment of chronic spontaneous urticaria, atopic dermatitis, rosacea, Crohns disease, ulcerative colitis, irritable bowel syndrome, neuropathic pain, or inflammatory pain.

In another aspect, there is provided the use of a compound of Formulae (I)-(IV) ((e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof, in the manufacture of a medicament for use in the treatment of an MrgX2-mediated disease or disorder. In another aspect, there is provided the use of a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof, in the manufacture of a medicament for use in the treatment of an MrgX2-mediated disease or disorder, wherein the disease or disorder is chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. In another aspect, there is provided the use of a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide) or a pharmaceutically acceptable salt thereof, in the manufacture of a medicament for use in the treatment of an MrgX2-mediated disease or disorder, wherein the disease or disorder is chronic spontaneous urticaria, atopic dermatitis, rosacea, Crohns disease, ulcerative colitis, irritable bowel syndrome, neuropathic pain, or inflammatory pain.

In another aspect, there is provided the use of a compound of Formulae (I)-(IV) (e.g., 4-((S)-1-((S)-1-((5-(2,4-difluorophenoxy)pyrazin-2-yl)amino)-1-oxopropan-2-yl)-4,4-difluoropiperidin-3-yl)pyridine 1-oxide), or a pharmaceutically acceptable salt thereof, in the manufacture of a medicament for use in the treatment of chronic spontaneous urticaria, mastocytosis, cold urticaria, atopic dermatitis, rosacea, Crohns disease, ulcerative colitis, irritable bowel syndrome, rheumatoid arthritis, fibromyalgia, nasal polyps, neuropathic pain, inflammatory pain, chronic itch, drug-induced anaphlactoid reactions, metabolic syndrome, oesophagus reflux, asthma, cough, or migraine. In another aspect, there is provided the use of a compound of Formulae (I)-(IV) (e.g., 4-((S)-1-((S)-1-((5-(2,4-difluorophenoxy)pyrazin-2-yl)

amino)-1-oxopropan-2-yl)-4,4-difluoropiperidin-3-yl)pyridine 1-oxide), or a pharmaceutically acceptable salt thereof, in the manufacture of a medicament for use in the treatment of chronic spontaneous urticaria, atopic dermatitis, rosacea, Crohns disease, ulcerative colitis, irritable bowel syndrome, neuropathic pain, or inflammatory pain.

Because of its potential use in medicine, it will be appreciated that a salt of a compound of Formulae (I)-(IV) is ideally pharmaceutically acceptable.

Pharmaceutically acceptable salts include, amongst others, those described in Berge, J. Pharm. Sci., 66, 1-19, (1977) or those listed in P. H. Stahl and C. G. Wermuth, editors, *Handbook of Pharmaceutical Salts; Properties, Selection and Use, Second Edition* Stahl/Wermuth: Wiley-VCH/VHCA (2011) (see http://www.wiley.com/WileyCDA/WileyTitle/productCd-3906390519.html).

Suitable pharmaceutically acceptable salts can include acid or base addition salts. Such base addition salts can be formed by reaction of a compound of Formulae (I)-(IV) (which, for example, contains a 1H-tetrazole or other acidic functional group) with the appropriate base, optionally in a suitable solvent such as an organic solvent, to give the salt which can be isolated by a variety of methods, including crystallisation and filtration.

Such acid addition salts can be formed by reaction of a compound of Formulae (I)-(IV) (which, for example, contains a basic amine or other basic functional group) with the appropriate acid, optionally in a suitable solvent such as an organic solvent, to give the salt which can be isolated by a variety of methods, including crystallisation and filtration.

Salts may be prepared in situ during the final isolation and purification of a compound of Formulae (I)-(IV). If a basic compound of Formulae (I)-(IV) is isolated as a salt, the corresponding free base form of that compound may be prepared by any suitable method known to the art, including treatment of the salt with an inorganic or organic base. Similarly, if a compound of Formulae (I)-(IV) containing a carboxylic acid or other acidic functional group is isolated as a salt, the corresponding free acid form of that compound may be prepared by any suitable method known to the art, including treatment of the salt with an inorganic or organic acid.

It will be understood that if a compound of Formulae (I)-(IV) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of Formulae (I)-(IV) are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, tromethamine (tris(hydroxymethyl)aminomethane), and zinc.

In one aspect of the invention, there is provided a hydrochloride salt of 4-((S)-1-((S)-1-((5-(2,4-difluorophenoxy)pyrazin-2-yl)amino)-1-oxopropan-2-yl)-4,4-difluoropiperidin-3-yl)pyridine 1-oxide.

The compound of Formulae (I)-(IV) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formulae (I)-(IV) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures.

The subject invention also includes isotopically-labeled compounds, which are identical to those recited in Formulae (I)-(IV) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formulae (I)-(IV) and following of this invention can generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as pharmaceutical formulation) comprising a compound of Formulae (I)-(IV) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formulae (I)-(IV) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound of Formulae (I)-(IV) or salt thereof or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound of Formulae (I)-(IV) or salt thereof, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound of Formulae (I)-(IV) or salt thereof in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

It should be understood that in addition to the ingredients particularly mentioned above, the pharmaceutical compositions may include other agents conventional in the art having regard to the type of formulation in question, for example those suitable for oral administration may include flavoring agents.

Where appropriate, dosage unit formulations for oral administration can be microencapsulated. The formulation can also be prepared to prolong or sustain the release as, for example, by coating or embedding particulate material in polymers, wax, or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

In accordance with another aspect of the invention there is provided a process for the preparation of a pharmaceutical composition comprising mixing (or admixing) a compound of Formulae (I)-(IV) or salt thereof with at least one excipient.

The present invention also provides a method of treatment in a mammal, especially a human.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formulae (I)-(IV), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_6)$alkyl" refers to an alkyl moiety containing from 1 to 6 carbon atoms. Exemplary alkyls include, but are not limited to, methyl, ethyl, n-propyl, isopropyl, n-butyl, isobutyl, s-butyl, t-butyl, pentyl, and hexyl.

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include methoxy, ethoxy, n-propoxy, isopropoxy, n-butoxy, s-butoxy, isobutoxy, and t-butoxy.

When the term "alkyl" is used in combination with other substituent groups, such as "halo$(C_1-C_4)$alkyl", "aryl$(C_1-C_4)$alkyl-", or "$(C_1-C_4)$alkoxy$(C_1-C_4)$alkyl-", the term "alkyl" is intended to encompass a divalent straight or branched-chain hydrocarbon radical, wherein the point of attachment is through the alkyl moiety. The term "halo$(C_1-C_4)$alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo$(C_1-C_4)$alkyl" groups useful in the present invention include, but are not limited to, —$CF_3$ (trifluoromethyl), —$CCl_3$ (trichloromethyl), 1,1-difluoroethyl, 2-fluoro-2-methylpropyl, 2,2-difluoropropyl, 2,2,2-trifluoroethyl, and hexafluoroisopropyl. Examples of "aryl$(C_1-C_4)$alkyl" or "phenyl$(C_1-C_4)$alkyl" groups useful in the present invention include, but are not limited to, benzyl and phenethyl. Examples of "$(C_1-C_4)$alkoxy$(C_1-C_4)$alkyl-" groups useful in the present invention include, but are not limited to, methoxymethyl, methoxyethyl, methoxyisopropyl, ethoxymethyl, ethoxyethyl, ethoxyisopropyl, isopropoxymethyl, isopropoxyethyl, isopropoxyisopropyl, t-butoxymethyl, t-butoxyethyl, and t-butoxyisopropyl.

As used herein, the term "cycloalkyl" refers to a non-aromatic, saturated, cyclic hydrocarbon ring containing the specified number of carbon atoms. The term "$(C_3-C_8)$cycloalkyl" refers to a non-aromatic cyclic hydrocarbon ring having from three to eight ring carbon atoms. Exemplary "$(C_3-C_8)$cycloalkyl" groups useful in the present invention include cyclopropyl, cyclobutyl, cyclopentyl, cyclohexyl, cycloheptyl, and cyclooctyl.

As used herein, "4- to 6-membered heterocycloalkyl" represents a group or moiety comprising a non aromatic, monovalent monocyclic radical, which is saturated or partially unsaturated, containing 4, 5, or 6 ring atoms, which includes one or two heteroatoms selected independently from oxygen, sulfur, and nitrogen. Illustrative examples of 4- to 6-membered heterocycloalkyl groups useful in the present invention include, but are not limited to, azetidinyl, oxetanyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, and 1,4-dithianyl.

"Aryl" refers to optionally substituted monocyclic, fused bicyclic, or fused tricyclic groups having 6 to 14 carbon atoms and having at least one aromatic ring that complies with Hückel's Rule. Examples of "aryl" groups are phenyl, naphthyl, indenyl, dihydroindenyl, anthracenyl, phenanthrenyl, and the like.

"Heteroaryl" represents a group or moiety comprising an aromatic monovalent monocyclic or bicyclic radical, containing 5 to 10 ring atoms, including 1 to 4 heteroatoms independently selected from nitrogen, oxygen and sulfur. This term also encompasses bicyclic heterocyclic-aryl compounds containing an aryl ring moiety fused to a heterocycloalkyl ring moiety, containing 5 to 10 ring atoms, including 1 to 4 heteroatoms independently selected from nitrogen, oxygen and sulfur. Illustrative examples of heteroaryls useful in the present invention include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Examples of 5-membered "heteroaryl" groups include furanyl, thienyl, pyrrolyl, imidazolyl, pyrazolyl, triazolyl, tetrazolyl, thiazolyl, oxazolyl, isoxazolyl, oxadiazolyl, thiadiazolyl, and isothiazolyl. Examples of 6-membered "heteroaryl" groups include oxo-pyridyl, pyridinyl, pyridazinyl, pyrazinyl, and pyrimidinyl. Examples of 6,6-fused "heteroaryl" groups include quinolinyl, isoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Examples of 6,5-fused "heteroaryl" groups include benzofuranyl, benzothienyl, benzimidazolyl, benzthiazolyl, indolizinyl, indolyl, isoindolyl, and indazolyl.

As used herein, "5- or 6-membered heteroaryl" represents a group or moiety comprising an aromatic monovalent monocyclic radical, containing 5 or 6 ring atoms, including at least one carbon atom and 1 to 4 heteroatoms independently selected from nitrogen, oxygen, and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Illustrative examples of 5- or 6-membered heteroaryl groups useful in the present invention include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

The terms "halogen" and "halo" represent fluoro, chloro, bromo, or iodo substituents. "Hydroxy" or "hydroxyl" is intended to mean the radical —OH.

As used herein, the term "optionally" means that the subsequently described event(s) may or may not occur, and includes both event(s) that occur and event(s) that do not occur.

"Pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "treatment" refers to alleviating the specified condition, eliminating or reducing one or more symptoms of the condition, slowing or eliminating the progression of the condition, and delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formulae (I)-(IV), as well as salts thereof, may be administered as the raw chemical. Additionally, the active ingredient may be presented as a pharmaceutical composition.

Compound Preparation

Abbreviations

Ag$_2$CO$_3$ silver carbonate
AIBN azobisisobutyronitrile
aq aqueous
BH$_3$ THF borane tetrahydrofuran complex
BnBr benzyl bromide
BOC or t-BOC or Boc tert-butoxycarbonyl
BOC-anhydride or Boc-anhydride di-tert-butyl dicarbonate
CBZ—Cl or Cbz-Cl benzyl chloroformate
C18 column octadecylsilane column CDCl$_3$ or chloroform-d deuteriochloroform
CD$_3$OD or methanol-d$_4$ deuteriomethanol
CHCl$_3$ chloroform
CH$_2$Cl$_2$ dichloromethane
(C$_6$H$_{11}$)$_3$P tricyclohexylphosphine
CPME cyclopentyl methyl ether
Cs$_2$CO$_3$ cesium carbonate
CsF cesium fluoride
CuI copper(I) iodide
CyJohnPhos (2-biphenyl)dicyclohexylphosphine
DAST diethylaminosulfurtrifluoride
DBU 1,8-diazabicyclo[5.4.0]undec-7-ene
DCC N,N'-dicyclohexylcarbodiimide
DCM dichloromethane
DIAD diisopropyl azodicarboxylate
DIBAL-H or DIBAL diisobutylaluminum hydride
dichloromethane-d$_2$ deuterated dichloromethane
DMA dimethylacetamide
DME dimethoxyethane
DMF N,N-dimethylformamide
DIPEA or DIEA N,N-diisopropylethylamine
DMAP 4-dimethylaminopyridine
DMSO dimethylsulfoxide
DMSO-d$_6$ hexadeuteriodimethylsulfoxide
dppf 1,1'-bis(diphenylphosphino)ferrocene
eq equivalent(s)
EtOAc ethyl acetate
ES electrospray mass spectroscopy
Et$_3$N triethylamine
EtOH ethanol
Et$_2$O or ether diethyl ether
FA formic acid
Fe iron
h or hr hour(s)
hex hexane
H$_2$ hydrogen
HATU 1-[bis(dimethylamino)methylene]-1H-1,2,3-triazolo[4,5-b]pyridinium 3-oxid hexafluorophosphate
HBF$_4$PCy$_3$ tricyclohexylphosphonium tetrafluoroborate
HBr hydrobromic acid
HCl hydrochloric acid
H$_2$NBoc tert-butyl carbamate
$^1$H NMR proton nuclear magnetic resonance
H$_2$O water
HOAc acetic acid
HPLC high performance liquid chromatography
IPA isopropyl alcohol
K$_2$CO$_3$ potassium carbonate
KHCO$_3$ potassium bicarbonate
KI potassium iodide
K$_3$PO$_4$ potassium phosphate
LCMS or LC/MS liquid chromatography-mass spectroscopy
LDA lithium diisopropylamide
LHMDS lithium hexamethyldisilazide
LiAlH$_4$ lithium aluminum hydride
LiBH$_4$ lithium borohydride
LiCl lithium chloride
LiF lithium fluoride
LiOH lithium hydroxide
m-CPBA meta-chloroperbenzoic acid
MDAP mass-directed automated purification
MeCN or CH$_3$CN or ACN or AcCN acetonitrile
MeI or CH$_3$I methyl iodide
MeOH methanol
2-Me-THF 2-methyltetrahydrofuran
MgSO$_4$ magnesium sulfate
min minute(s)
MS mass spectrum
MTBE methyl tert-butyl ether
m/z mass-to-charge ratio
N$_2$ nitrogen
Na sodium
NaBH$_4$ sodium borohydride
NaBO$_3$ sodium perborate
Na$_2$CO$_3$ sodium carbonate
NaH sodium hydride
NaHCO$_3$ sodium bicarbonate
NaHSO$_3$ sodium bisulfite
NaI sodium iodide
NaN$_3$ sodium azide
NaOAc or AcONa sodium acetate
NaOH sodium hydroxide
NaOMe sodium methoxide
Na$_2$S$_2$O$_3$ sodium thiosulphate
Na$_2$SO$_4$ sodium sulfate
NBS N-bromosuccinimide
n-BuLi n-butyllithium
N$_2$H$_4$ hydrazine
NH$_3$ ammonia
NH$_4$Cl ammonium chloride
NH$_4$HCO$_3$ ammonium bicarbonate
NH$_4$OH ammonium hydroxide
NH$_2$OH—HCl or H$_2$NOH—HCl hydroxylamine hydrochloride
NiBr$_2$ nickel(II) bromide
NiCl$_2$(dme) nickel(II) chloride ethylene glycol dimethyl ether complex
Oxone potassium peroxymonosulfate
Pd/C or Pd—C palladium on carbon
Pd$_2$(dba)$_3$ tris(dibenzylideneacetone)dipalladium(0)
Pd$_2$(dba)$_3$CHCl$_3$ tris(dibenzylideneacetone)dipalladium(0) chloroform adduct
Pd$_2$(dba)$_3$CH$_2$Cl$_2$ tris(dibenzylideneacetone)dipalladium(0)-methylene chloride adduct
Pd(dppf)Cl$_2$ or PdCl$_2$(dppf) [1,1'-bis(diphenylphosphino)ferrocene]dichloro palladium(II)
Pd(dtbpf)Cl$_2$ or PdCl$_2$(dtbpf) [1,1'-bis(di-tert-butylphosphino)ferrocene]dichloropalladium(II)
Pd(OAc)$_2$ palladium acetate
Pd(OH)$_2$/C palladium hydroxide on carbon
Pd(PPh$_3$)$_4$ tetrakis(triphenylphosphine)palladium(0)
PE or pet ether petroleum ether
PPh$_3$ triphenylphosphine
POCl3 phosphorus oxychloride
ppm parts per million
prep preparative
PTFE polytetrafluoroethylene
Raney-Ni Raney nickel
rt room temperature or retention time
sat. or sat'd saturated
SFC supercritical fluid chromatography
TBAF tetra-n-butylammonium fluoride
TBS-Cl tert-butyldimethylsilyl chloride
TBSOTf tert-butyldimethylsilyl trifluoromethanesulfonate
TBTU (1H-benzotriazol-1-yloxy)(dimethylamino)-N,N-dimethylmethaniminium tetrafluoroborate
t-BuOK potassium tert-butoxide
t-BuONa sodium tert-butoxide
t-BuONO tert-butyl nitrite
(t-Bu)$_3$P tri-tert-butylphosphine
TEA triethylamine
TFA trifluoroacetic acid THF tetrahydrofuran
TLC thin layer chromatography
TMS-Cl trimethylsilyl chloride
TMS-CN trimethylsilyl cyanide
TMSI trimethylsilyl iodide
T3P propanephosphonic acid anhydride
UPLC ultra performance liquid chromatography
Xantphos 4,5-bis(diphenylphosphino)-9,9-dimethylxanthene
XantPhos Pd G3 [(4,5-bis(diphenylphosphino)-9,9-dimethylxanthene)-2-(2'-amino-1,1'-biphenyl)]palladium (II) methanesulfonate
XPhos or X-Phos 2-dicyclohexylphosphino-2',4',6'-triisopropylbiphenyl
XtalFluor-E (diethylamino)difluorosulfonium tetrafluoroborate
Zn zinc

EXPERIMENTALS

The following guidelines apply to all experimental procedures described herein. All reactions were conducted under a positive pressure of nitrogen, unless otherwise indicated. Temperatures designated are external (i.e. bath temperatures) and are approximate. Air and moisture-sensitive liquids were transferred via syringe. Reagents were used as received. Solvents utilized were those listed as "anhydrous" by vendors. Molarities listed for reagents in solutions are approximate and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage® Initiator 2.0 instrument with Biotage® microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO® CombiFlash Companion instrument with RediSep or ISCO® Gold silica gel cartridges (4 g-330 g), or an Analogix® IF280 instrument with SF25 silica gel cartridges (4 g-3-00 g), or a Biotage® SP1 instrument with HP® silica gel cartridges (10 g-100 g), unless otherwise indicated. Purification by reverse phase HPLC was conducted using a YMC-pack column (ODS-A 75×30 mm) as solid phase, unless otherwise noted. A mobile phase of 25 mL/min A ($CH_3CN$-0.1% TFA): B (water-0.1% TFA), 10-80% gradient A (10 min) was utilized with UV detection at 214 nM, unless otherwise noted.

PE Sciex® API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, MA, USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

$^1$H-NMR spectra were recorded at 250 MHz or 400 MHz using a Bruker® AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets, and br indicates a broad signal. J indicates the NMR coupling constant measured in Hertz.

LCMS Methods:

LC/MS Method 1: was conducted on a Shimadzu LCMS-2020 Xselect CSH C18 column (50 mm×3.0 mm i.d. 2.5 μm packing diameter) eluting with 0.1% formic acid in water (solvent A) and 0.1% formic acid in acetonitrile (solvent B), using the following elution gradient 0.01-3.60 min.: 30% to 70% B, 3.60-4.40 min to 95% B, 5.10-5.20 min. to 5% B, at a flow rate of 1.2 mL/min. at 45° C.

LC/MS Method 2: UPLC was conducted on an Acquity UPLC CSH C18 column (30 mm×2.1 mm i.d. 1.7 μm packing diameter) eluting with 0.1% formic acid in water (solvent A) and 0.1% formic acid in acetonitrile (solvent B), using the following elution gradient 0-1.85 min.: 1% to 100% B, 1.9 to 2.0 min. 100% B, at a flow rate of 1.3 mL/min. at 45° C. Mass spectrum was recorded on a Waters Acquity QDa mass detector using alternative-scan positive and negative mode electrospray ionisation, scan range of 100 to 1000 AMU, with targeted sample frequency of 8 Hz.

LC/MS Method 3: UPLC was conducted on an Acquity UPLC CSH C18 column (30 mm×2.1 mm i.d. 1.7 μm packing diameter) eluting with 10 mM ammonium bicarbonate in water adjusted to pH 10 with 25% ammonium hydroxide solution (solvent A) and acetonitrile (solvent B), using the following elution gradient 0-1.85 min.: 0% to 100% B, 1.9 to 2.0 min. 100% B, at a flow rate of 1.3 mL/min. at 45° C. Mass spectrum was recorded on a Waters Acquity QDa mass detector using alternative-scan positive and negative mode LC/MS Method 4: was conducted on a Shimadzu LCMS-2020 Ascentis CSH C18 column (50 mm×3.0 mm i.d. 2.7 μm packing diameter) eluting with 0.05% TFA in water (solvent A) and 0.05% TFA in acetonitrile (solvent B), using the following elution gradient 0.01-1.10 min.: 5% to 95% B, 1.80-1.90 to 5% B, at a flow rate of 1.5 mL/min. at 40° C.

LC/MS Method 5: UPLC was conducted on an Acquity UPLC CSH C18 column (30 mm×2.1 mm i.d. 1.7 μm packing diameter) eluting with 0.1% TFA in water (solvent A) and 0.1% TFA in acetonitrile (solvent B), using the following elution gradient 0-1.85 min.: 1% to 100% B, 1.9 to 2.0 min. 100% B, at a flow rate of 1.3 mL/min. at 45° C. Mass spectrum was recorded on a Waters Acquity QDa mass detector using alternative-scan positive and negative mode electrospray ionisation, scan range of 100 to 1000 AMU, with targeted sample frequency of 8 Hz.

LC/MS Method 6: was conducted on a Ascentis Express C18 column (50 mm×3.0 mm i.d. 2.7 μm packing diameter) eluting with water/0.05% TFA (solvent A) and acetonitrile/0.05% TFA (solvent B), using the following elution gradient: 0.01-2.00 min.: 5% to 100% B, 2.80-2.90 min. to 5% B, at a flow rate of 1.5 mL/min. at 40° C.

LC/MS Method 7: was conducted on a Kinetex 2.6 um EVO C18 100 A column (50 mm×3.0 mm i.d. 2.6 μm packing diameter) eluting with water/5 mM $NH_4HCO_3$ (solvent A) and acetonitrile (solvent B), using the following elution gradient: 0.01-3.40 min.: 25% to 65% B, to 4.00 min. to 95% B, 5.00-5.30 min. to 10% B at a flow rate of 1.2 mL/min. at 40° C.

LC/MS Method 8: was conducted on a Poroshell HPH-18 column (50 mm×3.0 mm i.d. 2.7 μm packing diameter) eluting with 6.5 mM $NH_4HCO_3+NH_3H_2O$ (solvent A) and acetonitrile (solvent B), using the following elution gradient: 0.01-2.00 min.: 10% to 95% B, 2.60-2.75 min. to 10% B at a flow rate of 1.2 mL/min. at 40° C.

LC/MS Method 9: was conducted on a Ascentis Express C18 column (50 mm×3.0 mm i.d. 2.7 µm packing diameter) eluting with water/0.05% TFA (solvent A) and acetonitrile/0.05% TFA (solvent B), using the following elution gradient: 0.01-2.00 min.: 5% to 95% B, 2.60-2.75 min. to 5% B, at a flow rate of 1.5 mL/min. at 40° C.

LC/MS Method 10: was conducted on a Kinetex 2.6 um EVO C18 100 A column (50 mm×3.0 mm i.d. 2.6 µm packing diameter) eluting with water/5 mM $NH_4HCO_3$ (solvent A) and acetonitrile (solvent B), using the following elution gradient: 0.01-2.10 min.: 10% to 95% B, 2.70-2.75 min. to 10% B at a flow rate of 1.2 mL/min. at 40° C.

LC/MS Method 11: column used was a Ascentis Express C18, 2.7 µm, 3.0×50 mm. A linear gradient was applied, starting at 95% A (A: water-0.05% TFA) and ending at 95% B (B: Acetonitrile-0.05% TFA) over 2.70 min with a total run time of 3.00 min. The column temperature was at 40° C. with the flow rate of 1.50 mL/min LC/MS Method 12: The column used was a Ascentis Express C18, 2.7 µm, 3.0×50 mm. A linear gradient was applied, starting at 95% A (A: Water/0.05% TFA) and ending at 95% B (B: Acetonitrile/0.05% TFA) over 2.60 min with a total run time of 3.00 min. The column temperature was at 40° C. with the flow rate of 1.50 mL/min.

LC/MS Method 13: The column used was a Ascentis Express C18, 2.7 µm, 3.0×50 mm. A linear gradient was applied, starting at 95% A (A: Water/0.05% TFA) and ending at 100% B (B: Acetonitrile/0.05% TFA) over 2.80 min with a total run time of 3.00 min. The column temperature was at 40° C. with the flow rate of 1.50 mL/min.

LC/MS Method 14 The column used was a Kinetex 2.6 µm, 3.0×50 mm. A linear gradient was applied, starting at 90% A (A: Water-5 mM $NH_4HCO_3$) and ending at 95% B (B: Acetonitrile) over 2.70 min with a total run time of 3.00 min. The column temperature was at 40° C. with the flow rate of 1.20 mL/min.

LC/MS Method 15 The column used was a Kinetex 2.6 um EVO C18 100 A, 2.6 µm, 3.0×50 mm. A linear gradient was applied, starting at 90% A (A: Water-5 mM $NH_4HCO_3$) and ending at 95% B (B: Acetonitrile) over 2.70 min with a total run time of 2.90 min. The column temperature was at 40° C. with the flow rate of 1.20 mL/min.

LC/MS Method 16 The column used was a Kinetex 2.6 um EVO C18 100 A, 2.6 µm, 3.0×50 mm. A linear gradient was applied, starting at 90% A (A: Water-5 mM $NH_4HCO_3$) and ending at 95% B (B: Acetonitrile) over 4.90 min with a total run time of 5.30 min. The column temperature was at 40° C. with the flow rate of 1.20 mL/min.

LC/MS Method 17: The column used was a Poroshell HPH-C18, 2.7 µm, 3.0×50 mm. A linear gradient was applied, starting at 90% A (A: 6.5 mM $NH_4HCO_3$+$NH_3H_2O$) and ending at 95% B (B: Acetonitrile) over 2.60 min with a total run time of 3.00 min. The column temperature was at 40° C. with the flow rate of 1.20 mL/min.

LC/MS Method 18: The column used was a Kinetex 2.6 um EVO C18 100 A, 2.6 µm, 3.0×50 mm. A linear gradient was applied, starting at 90% A (A: Water-5 mM $NH_4HCO_3$) and ending at 95% B (B: Acetonitrile) over 5.00 min with a total run time of 5.60 min. The column temperature was at 40° C. with the flow rate of 1.20 mL/min.

LC/MS Method 19 The column used was a CORTECS C18, 2.7 µm, 2.1×50 mm. A linear gradient was applied, starting at 95% A (A: water/0.05% TFA) and ending at 100% B (B: Acetonitrile/0.05% TFA) over 2.80 min with a total run time of 3.00 min. The column temperature was at 40° C. with the flow rate of 1.00 mL/min.

LC/MS Method 20: The column used was a Xselect CSH C18, 2.5 µm, 3.0×50 mm. A linear gradient was applied, starting at 95% A (A: Water/0.1% FA) and ending at 95% B (B: Acetonitrile/0.1% FA) over 2.70 min with a total run time of 3.00 min. The column temperature was at 40° C. with the flow rate of 1.20 mL/min.

LC/MS Method 21: The column used was a Poroshell HPH-C18, 2.7 µm, 3.0×50 mm. A linear gradient was applied, starting at 10% A (A: 6.5 mM $NH_4HCO_3$+$NH_3H_2O$) and ending at 95% B (B: Acetonitrile) over 2.00 min, followed by elution gradient at 2.60 to 2.75 min from 95 to 10% B with a total run time of 3.00 min. The column temperature was at 40° C. with the flow rate of 1.20 mL/min.

LC/MS Method 22: The column used was a Poroshell HPH-C18, 2.7 µm, 3.0×50 mm. A linear gradient was applied, starting at 90% A (A: 6.5 mM $NH_4HCO_3$+$NH_3H_2O$) and ending at 95% B (B: Acetonitrile) over 4.70 min with a total run time of 5.00 min. The column temperature was at 45° C. with the flow rate of 1.20 mL/min.

LC/MS Method 23: The column used was a Kinetex 2.6 um EVO C18 100 A, 2.6 µm, 3.0×50 mm. A linear gradient was applied, starting at 90% A (A: Water-5 mM $NH_4HCO_3$) and ending at 95% B (B: Acetonitrile) over 5.20 min with a total run time of 5.60 min. The column temperature was at 40° C. with the flow rate of 1.20 mL/min.

LC/MS Method 24: The column used was a Ascentis Express C18, 2.7 µm, 3.0×50 mm. A linear gradient was applied, starting at 95% A (A: Water/0.05% TFA) and ending at 95% B (B: Acetonitrile/0.05% TFA) over 5.00 min with a total run time of 5.30 min. The column temperature was at 40° C. with the flow rate of 1.50 mL/min.

LC/MS Method 25 The column used was a Poroshell HPH-C18, 2.7 µm, 3.0×50 mm. A linear gradient was applied, starting at 90% A (A: water-6.5 mM $NH_4HCO_3$+$NH_3H_2O$) and ending at 95% B (B: Acetonitrile) over 2.70 min with a total run time of 3.00 min. The column temperature was at 40° C. with the flow rate of 1.50 mL/min.)

LC/MS Method 26: The column used was a CORTECS C18, 2.7 µm, 2.1×50 mm. A linear gradient was applied, starting at 95% A (A: water/0.05% TFA) and ending at 100% B (B: Acetonitrile/0.05% TFA) over 4.40 min with a total run time of 5.00 min. The column temperature was at 40° C. with the flow rate of 1.00 mL/min.

LC/MS Method 27: The column used was a Xselect CSH C18, 2.5 µm, 3.0×50 mm. A linear gradient was applied, starting at 95% A (A: water/0.1% FA) and ending at 100% B (B: Acetonitrile/0.1% FA) over 2.70 min with a total run time of 3.00 min. The column temperature was at 40° C. with the flow rate of 1.20 mL/min.)

LC/MS Method 28: The column used was a Kinetex XB-C18, 2.6 µm, 3.0×50 mm. A linear gradient was applied, starting at 95% A (A: Water/0.1% FA) and ending at 100% B (B: Acetonitrile/0.1% FA) over 2.60 min with a total run time of 3.00 min. The column temperature was at 40° C. with the flow rate of 1.20 mL/min.

LC/MS Method 29: was conducted on a Kinetex 2.6 um EVO C18 100 A column (50 mm×3.0 mm i.d. 2.6 µm packing diameter) eluting with water/5 mM $NH_4HCO_3$ (solvent A) and acetonitrile (solvent B), using the following elution gradient: 0.01-1.10 min.: 10% to 95% B, 1.80-1.85 min. to 10% B at a flow rate of 1.2 mL/min. at 40° C.

LC/MS Method 30: was conducted on a Poroshell HPH-C18 column (50 mm×3.0 mm i.d. 2.7 µm packing diameter) eluting with 6.5 mM $NH_4HCO_3$+$NH_3H_2O$ (solvent A) and acetonitrile (solvent B), using the following elution gradient:

0.01-1.10 min.: 10% to 95% B, 1.80-1.90 min. to 10% B at a flow rate of 1.2 mL/min. at 40° C.

LC/MS Method 31: was conducted on a CORTECS C18 column (50 mm×2.1 mm i.d. 2.7 µm packing diameter) eluting with water/0.05% TFA (solvent A) and ACN/0.05% TFA (solvent B), using the following elution gradient: 0.01-1.10 min.: 5% to 100% B, 1.80-1.90 min. to 5% B at a flow rate of 1.0 mL min. at 40° C.

LC/MS Method 32: The column used was a Kinetex XB-C18, 2.6 µm, 3.0×50 mm. eluting with water/0.1% FA (solvent A) and ACN/0.1% FA (solvent B), using the following elution gradient: 0.01-1.10 min.: 5% to 100% B, 1.70-1.75 min. to 5% B at a flow rate of 1.0 mL/min. at 40° C.

LC/MS Method 33: was conducted on a Shimadzu LCMS-2020 Ascentis Express C18 column (50 mm×3.0 mm i.d. 2.7 µm packing diameter) eluting with 0.05% TFA in water (solvent A) and 0.05% TFA in acetonitrile (solvent B), using the following elution gradient 0.01-1.10 min.: 5% to 100% B, 1.80-1.90 to 5% B, at a flow rate of 1.5 mL/min. at 40° C.

LC/MS Method 34: was conducted on a Kinetex 2.6 um EVO C18 100 A column (50 mm×3.0 mm i.d. 2.6 µm packing diameter) eluting with water/5 mM NH$_4$HCO$_3$ (solvent A) and acetonitrile (solvent B), using the following elution gradient: 0.01-1.10 min.: 10% to 95% B, 1.80-1.85 min. to 10% B at a flow rate of 1.2 mL/min. at 40° C.

LC/MS Method 35: was conducted on a Kinetex 2.6 um EVO C18 100 A column (50 mm×3.0 mm i.d. 2.6 µm packing diameter) eluting with water/0.1% FA (solvent A) and acetonitrile/0.1% FA (solvent B), using the following elution gradient: 0.01-2.10 min.: 5% to 95% B, 2.70-2.75 min. to 5% B at a flow rate of 1.2 mL/min. at 40° C.

LC/MS Method 36: was conducted on a Xselect CSH C18 column (50 mm×3.0 mm i.d. 2.5 µm packing diameter) eluting with water/0.1% FA (solvent A) and acetonitrile/0.1% FA (solvent B), using the following elution gradient: 0.01-1.10 min.: 5% to 100% B, 1.70-1.75 min. to 5% B at a flow rate of 1.2 mL/min. at 40° C.

LC/MS Method 37 The column used was a Kinetex XB-C18, 1.7 µm, 2.1×30 mm. eluting with water/0.05% TFA (solvent A) and ACN/0.05% TFA (solvent B), using the following elution gradient: 0.01-0.60 min.: 5% to 95% B, 1.00-1.05 min. to 5% B at a flow rate of 1.0 mL/min. at 40° C.

LC/MS Method 38: was conducted on a Titank C18 column (50 mm×3.0 mm i.d. 3.0 µm packing diameter) eluting with water/5 mM NH$_4$HCO$_3$ (solvent A) and acetonitrile (solvent B), using the following elution gradient: 0.01-1.20 min.: 10% to 95% B, 1.70-1.75 min. to 10% B at a flow rate of 1.2 mL/min. at 40° C.

LC/MS Method 39: was conducted on a HALO 2.0 um C18 90 A column (30 mm×3.0 mm i.d. 2.0 µm packing diameter) eluting with water/0.1% FA (solvent A) and acetonitrile/0.1% FA (solvent B), using the following elution gradient: 0.01-0.45 min.: 5% to 95% B, 0.80-0.85 min. to 5% B at a flow rate of 1.5 mL/min. at 40° C.

Intermediates

Intermediate 1

2-bromo-N-(5-fluoropyridin-2-yl)propanamide

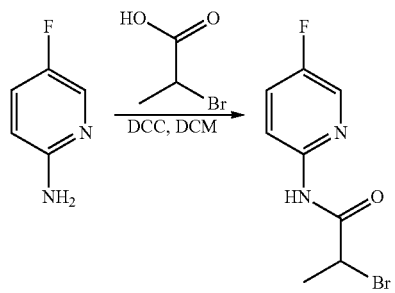

A mixture of 2-bromopropanoic acid (16.3 g, 107.2 mmol, 1.2 eq), DCM (200 mL), DCC (27.6 g, 134.0 mmol, 1.5 eq) and 5-fluoropyridin-2-amine (10.0 g, 89.3 mmol, 1.0 eq) was stirred for 2.0 h at 25° C., filtered, concentrated and dissolved in DCM (50 ml). Silica (100-200 mesh, 60.0 g) was added, and the mixture was concentrated and loaded onto a silica gel column (330 g, 100-200 mesh), eluting with ethyl acetate/petroleum ether (1/9) to give 2-bromo-N-(5-fluoropyridin-2-yl)propanamide (20.0 g, purity: 90%, yield: 90%) as yellow oil. LCMS: (ES, m/z): 247 [M+H]$^+$. $^1$H NMR: (400 MHz, CD$_3$OD) δ 8.22 (d, J=3.2 Hz, 1H), 8.18-8.15 (m, 1H), 7.64-7.59 (m, 1H), 4.76-4.69 (m, 1H), 1.84 (d, J=6.8 Hz, 3H). Intermediates 2-13 were synthesized in an analogous manner from commercially available aryl amines.

| Int. | Name | Structure | $^1$H NMR | LC: retention time (min); LC/MS Method of analysis | MS (M + H)$^+$ |
|---|---|---|---|---|---|
| 2 | 2-bromo-N-(5-cyclopropylpyridin-2-yl)propanamide | 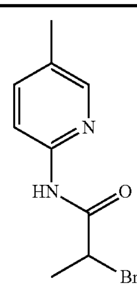 | $^1$H NMR (400 MHz, DMSO-d$_6$) δ ppm 10.76 (br, 1H), 8.18 (d, J = 2.4 Hz, 1H), 7.96 (d, J = 8.4 Hz, 1H), 7.48-7.45 (m, 1H), 4.88-4.84 (m, 1H), 1.96-1.89 (m, 1H), 1.73 (d, J = 6.8 Hz, 3H), 1.00-0.92 (m, 2H), 0.76-0.68 (m, 2H) | — | 269 |

-continued

| Int. | Name | Structure | ¹H NMR | LC: retention time (min); LC/MS Method of analysis | MS (M + H)⁺ |
|---|---|---|---|---|---|
| 3 | 2-bromo-N-(5-chloropyridin-2-yl)propanamide | 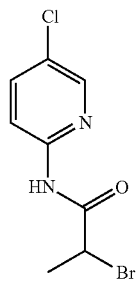 | — | 1.587; LC/MS Method 1 | 263 |
| 4 | 2-bromo-N-(5-bromopyridin-2-yl)propanamide | 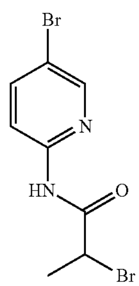 | ¹H NMR (400 MHz, CHLOROFORM-d) δ ppm 8.58 (br. s., 1 H) 8.38 (d, J = 1.96 Hz, 1 H) 8.15 (d, J = 9.05 Hz, 1 H) 7.86 (dd, J = 8.80, 2.45 Hz, 1 H) 4.62-4.46 (m, 1 H) 1.98 (d, J = 6.85 Hz, 3 H) | 0.86; LCMS Method 5 | 308 |
| 5 | 2-bromo-N-(5-isopropylpyridin-2-yl)propanamide | 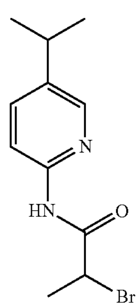 | ¹H NMR (300 MHz, CDCl₃) δ ppm 8.96 (s, 1H), 8.21-8.12 (m, 2H), 7.66-7.61 (m, 1H), 4.60-4.50 (m, 1H), 3.01-2.89 (m, 1H), 1.97 (d, J = 7.0 Hz, 3H), 1.29 (d, J = 6.9 Hz, 6H). | — | 271 |
| 6 | 2-bromo-N-(5-phenylpyridin-2-yl)propanamide | 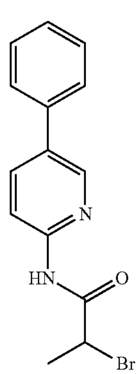 [SMILES: CC(Br)C(=O)Nc1ccc(-c2ccccc2)cn1] | ¹H NMR (300 MHz, DMSO-d₆) δ ppm 10.99 (s, 1H), 8.70-8.69 (m, 1H), 8.20-8.13 (m, 2H), 7.78-7.68 (m, 2H), 7.56-7.45 (m, 2H), 7.45-7.34 (m, 1H), 4.95-4.88 (m, 1H), 1.77 (d, J = 6.9 Hz, 3H) | — | 305 |

| Int. | Name | Structure | ¹H NMR | LC: retention time (min); LC/MS Method of analysis | MS (M + H)⁺ |
|---|---|---|---|---|---|
| 7 | 2-bromo-N-(isoquinolin-3-yl)propanamide | 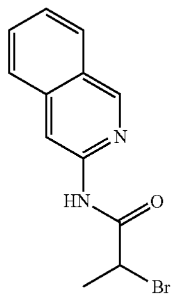 [SMILES: CC(Br)C(=O)Nc1cc2ccccc2cn1] | ¹H NMR (300 MHz, DMSO-$d_6$) δ ppm 11.01 (s, 1H), 9.18 (s, 1H), 8.49 (s, 1H), 8.08 (d, J = 8.1 Hz, 1H), 7.94 (d, J = 8.1 Hz, 1H), 7.77-7.71 (m, 1H), 7.63-7.51 (m, 1H), 4.99-4.92 (m, 1H), 1.79 (d, J = 6.9 Hz, 3H) | — | 279 |
| 8 | 2-bromo-N-(4,5-difluoropyridin-2-yl)propanamide | 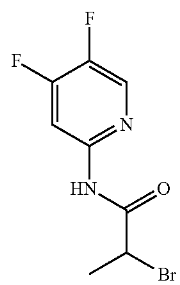 | ¹H NMR (400 MHz, CD₃OD) δ ppm 8.33 (dd, J = 2.1, 9.9 Hz, 1H), 8.14 (dd, J = 6.3, 12.9 Hz, 1H), 4.74-4.67 (m, 1H), 1.82 (d, J = 6.9 Hz, 3H). | — | 265 |
| 9 | 2-bromo-N-(6-methoxypyridazin-3-yl)propanamide | 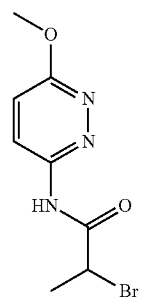 | ¹H NMR (300 MHz, CDCl₃) δppm 11.12 (s, 1H), 8.58 (d, J = 9.6 Hz, 1H), 7.12 (d, J = 9.6 Hz, 1H), 5.38-5.31 (m, 1H), 4.14 (s, 3H), 1.96 (d, J = 6.6 Hz, 3H). | — | 260 |
| 10 | 2-bromo-N-(5-methoxypyridin-2-yl)propanamide | 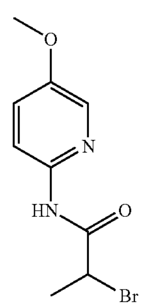 | ¹H NMR (300 MHz, CDCl₃) δ ppm 8.89 (br, 1H), 8.15 (d, J = 9.0 Hz, 1H), 8.03 (d, J = 2.7 Hz, 1H), 7.31 (dd, J = 3.0, 9.0 Hz, 1H), 4.58-4.51 (m, 1H), 3.87 (s, 3H), 1.96 (d, J = 6.9 Hz, 3H). | — | 259 |
| 11 | 2-bromo-N-(quinolin-2-yl)propanamide | 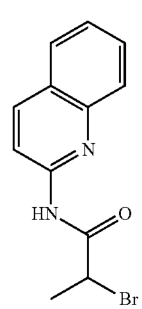 [SMILES: CC(Br)C(=O)Nc1ccc2ccccc2n1] | ¹H NMR (400 MHz, DMSO-$d_6$) δ ppm 11.21 (s, 1H), 8.91 (d, J = 9.2 Hz, 1H), 8.40 (d, J = 9.2 Hz, 1H), 8.12-8.03 (m, 1H), 7.97-7.91 (m, 1H), 7.87-7.66 (m, 2H), 4.95-4.93 (m, 1H), 1.81-1.74 (m, 3H). | — | 279 |

| Int. | Name | Structure | $^1$H NMR | LC: retention time (min); LC/MS Method of analysis | MS (M + H)$^+$ |
|---|---|---|---|---|---|
| 12 | 2-bromo-N-(5-(m-tolyl)pyridin-2-yl)propanamide | 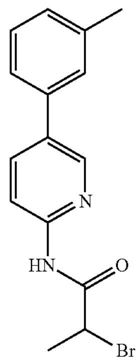 [SMILES: Cc1cccc(-c2ccc(NC(=O)C(C)Br)nc2)c1] | $^1$H NMR (400 MHz, DMSO-$d_6$) δ ppm 11.02 (s, 1H), 8.69-8.67 (m, 1H), 8.15 (d, J = 1.6 Hz, 2H), 7.58-7.48 (m, 2H), 7.38 (t, J = 7.6 Hz, 1H), 7.22 (d, J = 7.6 Hz, 1H), 4.94-4.85 (m, 1H), 2.39 (s, 3H), 1.77-1.60 (m, 3H). | — | 319 |
| 13 | 2-bromo-N-(5-cyclopropylpyrazin-2-yl)propanamide | 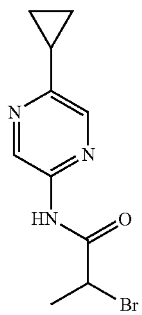 | $^1$H NMR (400 MHz, CDCl$_3$) δ ppm 9.37 (s, 1H), 8.89 (br. s., 1H), 8.16 (d, J = 1.47 Hz, 1H), 4.58 (q, J = 7.09 Hz, 1H), 2.08 (quin, J = 6.48 Hz, 1H), 1.98 (d, J = 7.09 Hz, 3H), 1.04-1.10 (m, 4H). | 0.80; LC/MS Method 3 | 270 |

Intermediate 14

2-bromo-N-(6-(cyclopropylmethoxy)pyridazin-3-yl)propanamide

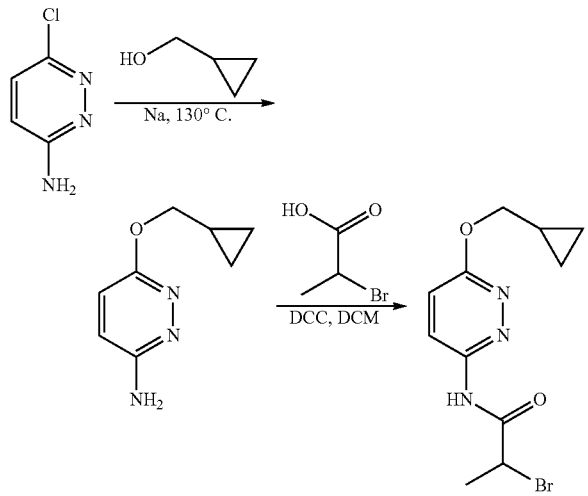

Step 1

Na (1.96 g, 85.22 mmol, 1.1 eq) was added to cyclopropylmethanol (78.14 g, 1.09 mol, 14.0 eq) in batches, and the mixture was stirred at rt. After 30 min, 6-chloropyridazin-3-amine (10.00 g, 77.52 mmol, 1.0 eq) was added. The reaction was flushed with nitrogen and stirred at 130° C. After 12 h, the mixture was poured into ice water (800 mL) and extracted with ethyl acetate (800 mL×3). The combined organic layers were washed with brine (1000 mL×2), dried over sodium sulfate, concentrated and purified by PRE-P_HPLC (column: C18 irregular 40-60 um 60 A 330 g), eluting with 5-40% AcCN in water (10 mmol/L, NH$_4$HCO$_3$) to give 6-(cyclopropylmethoxy)pyridazin-3-amine (10.5 g, yield: 82%, purity: 93%) as yellow solid. LCMS: (ES, m/z): 166 [M+H]$^+$. $^1$H NMR: (400 MHz, CDCl$_3$) δ 6.89-6.78 (m, 2H), 4.63 (s, 2H), 4.19 (d, J=7.2 Hz, 2H), 1.35-1.22 (m, 1H), 0.63-0.57 (m, 2H), 0.37-0.31 (m, 2H).

Step 2

To 6-(cyclopropylmethoxy)pyridazin-3-amine (5.00 g, 30.30 mmol, 1.0 eq) and 2-bromopropanoic acid (6.91 g, 45.46 mmol, 1.5 eq) in DCM (150 mL) were added DMAP (1.11 g, 9.09 mmol, 0.3 eq) and DCC (12.48 g, 60.60 mmol, 2.0 eq). After 16 h, the solids were filtered out, the filtrate was concentrated, and the residue was applied onto a silica gel column, eluting with 0-15% ethyl acetate in petroleum ether to give 2-bromo-N-(6-(cyclopropylmethoxy)pyridazin-3-yl)propanamide (4.8 g, yield: 53%, purity: 95%) as a yellow oil. LCMS: (ES, m/z): 300 [M+H]$^+$. $^1$H NMR: (400 MHz, CDCl$_3$) δ 11.55 (br, 1H), 8.60 (d, J=9.6 Hz, 1H), 7.13 (d, J=9.6 Hz, 1H), 5.48-5.41 (m, 1H), 4.31 (d, J=7.2 Hz, 2H), 1.92 (d, J=7.2 Hz, 3H), 1.75-1.67 (m, 1H), 0.71-0.68 (m, 2H), 0.42-0.37 (m, 2H).

Intermediates 15-21 were synthesized in an analogous manner, with 19 and 20 from the aryl bromide, and 16 using t-BuOK as base.

| Int. | Name | Structure | ¹H NMR | LC: retention time (min); LC/MS Method of analysis | MS (M + H)⁺ |
|---|---|---|---|---|---|
| 15 | 2-bromo-N-(5-(cyclopropylmethoxy)pyrazin-2-yl)propanamide | 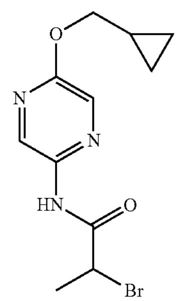 [SMILES: CC(Br)C(=O)Nc1cnc(OCC2CC2)cn1] | ¹H NMR: (400 MHz, DMSO-d₆) δ 10.94 (s, 1H), 8.84-8.83 (m, 1H), 8.14-8.13 (m, 1H), 4.88-4.83 (m, 1H), 4.12 (d, J = 7.2 Hz, 2H), 1.75 (d, J = 6.4 Hz, 3H), 1.27-1.23 (m, 1H), 0.60-0.53 (m, 2H), 0.41-0.35 (m, 2H). | — | 300 |
| 16 | 2-bromo-N-(6-(cyclobutylmethoxy)pyridazin-3-yl)propanamide | 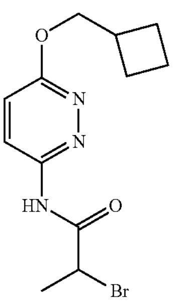 [SMILES: CC(Br)C(=O)Nc1ccc(OCC2CCC2)nn1] | ¹H NMR: (400 MHz, CDCl₃) δ 10.96 (br. s., 1H), 8.56 (d, J = 9.54 Hz, 1H), 7.12 (d, J = 9.78 Hz, 1H), 5.25 (q, J = 6.85 Hz, 1H), 4.47 (d, J = 6.85 Hz, 2H), 2.86 (quin, J = 7.46 Hz, 1H), 2.13-2.25 (m, 2H), 1.80-2.07 (m, 7H). | 1.02; LCMS Method 3 | 314 |
| 17 | 2-bromo-N-(6-(spiro[3.3]heptan-2-yloxy)pyridazin-3-yl)propanamide | 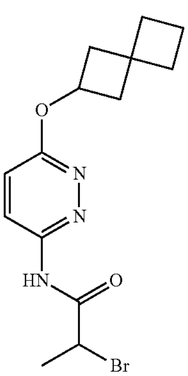 [SMILES: CC(Br)C(=O)Nc1ccc(OC2CC3(CCC3)C2)nn1] | ¹H NMR (400 MHz, CHLOROFORM-d) δ ppm 11.57 (br. s., 1 H) 8.59 (d, J = 9.54 Hz, 1 H) 7.07 (d, J = 9.54 Hz, 1 H) 5.41 (q, J = 6.68 Hz, 1 H) 5.27 (quin, J = 7.21 Hz, 1 H) 2.70-2.60 (m, 2 H) 2.21-2.08 (m, 4 H) 2.08-2.01 (m, 2 H) 2.01-1.55 (m, 12 H) 1.48-1.03 (m, 6 H). | 1.11; LCMS Method 5 | 340 |
| 18 | 2-bromo-N-(5-((6-methoxypyridin-2-yl)oxy)pyridin-2-yl)propanamide | 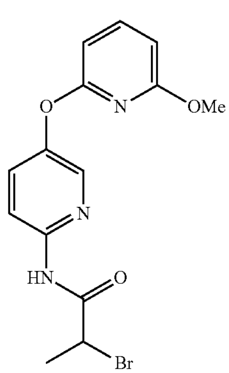 [SMILES: COc1cccc(Oc2ccc(NC(=O)C(C)Br)nc2)n1] | ¹H NMR (400 MHz, CHLOROFORM-d) δ ppm 8.97 (br. s., 1 H) 8.32-8.18 (m, 2 H) 7.68-7.55 (m, 2 H) 6.48 (dd, J = 7.70, 6.48 Hz, 2 H) 4.57 (q, J = 7.09 Hz, 1 H) 3.74 (s, 3 H) 1.98 (d, J = 6.85 Hz, 3 H). | 0.97; LCMS Method 5 | 353 |

| Int. | Name | Structure | ¹H NMR | LC: retention time (min); LC/MS Method of analysis | MS (M + H)⁺ |
|------|------|-----------|--------|---------|-----|
| 19 | 2-bromo-N-(6-cyclobutoxypyridazin-3-yl)propanamide | 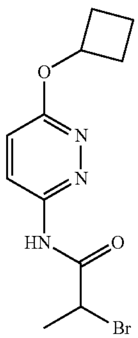 [SMILES: CC(Br)C(=O)Nc1ccc(OC2CCC2)nn1] | ¹H NMR (400 MHz, CHLOROFORM-d) δ ppm 11.13 (br. s., 1 H), 8.57 (d, J = 9.78 Hz, 1 H), 7.09 (d, J = 9.54 Hz, 1 H), 5.37 (quin, J = 7.15 Hz, 1 H), 5.27 (q, J = 6.85 Hz, 1 H), 2.49-2.62 (m, 2 H), 2.22 (dtdd, J = 12.56, 10.01, 10.01, 7.52, 2.93 Hz, 2 H), 1.97 (d, J = 6.85 Hz, 3 H), 1.85-1.95 (m, 1 H), 1.66-1.81 (m, 1 H). | 0.91; LCMS Method 3 | 300 |
| 20 | 2-bromo-N-(6-(cyclopentyloxy)pyridazin-3-yl)propanamide | 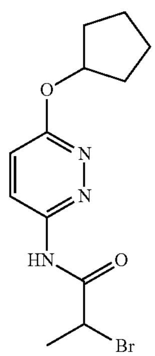 [SMILES: CC(Br)C(=O)Nc1ccc(OC2CCCC2)nn1] | ¹H NMR: NMR (400 MHz, CHLOROFORM-d) δ ppm 11.23 (br. s., 1 H), 8.56 (d, J = 9.54 Hz, 1 H), 7.08 (d, J = 9.54 Hz, 1 H), 5.58 (tt, J = 6.05, 2.87 Hz, 1 H), 5.29 (q, J = 6.85 Hz, 1 H), 2.00-2.13 (m, 2 H), 1.95 (d, J = 6.85 Hz, 3 H), 1.77-1.93 (m, 4 H), 1.62-1.76 (m, 2 H). | 1.02; LCMS Method 3 | 314 |
| 21 | 2-bromo-N-(6-(neopentyloxy)pyridazin-3-yl)propanamide | 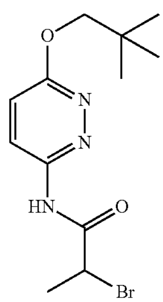 [SMILES: CC(Br)C(=O)Nc1ccc(OCC(C)(C)C)nn1] | ¹H NMR (400 MHz, DMSO-d₆) δ ppm 11.91-10.00 (m, 1H), 8.24 (d, J = 9.8 Hz, 1H), 7.29 (d, J = 9.3 Hz, 1H), 4.87 (q, J = 6.5 Hz, 1H), 4.07 (s, 2H), 1.75 (d, J = 6.8 Hz, 3H), 1.01 (s, 9H). | 1.04; LCMS Method 5 | 318 |

Intermediate 22

2-bromo-N-(5-(cyclopropylmethoxy)pyridin-2-yl)propanamide

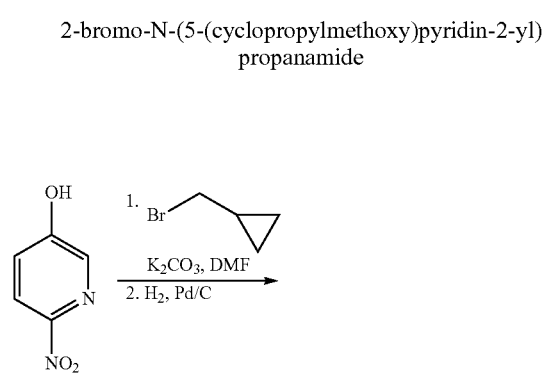

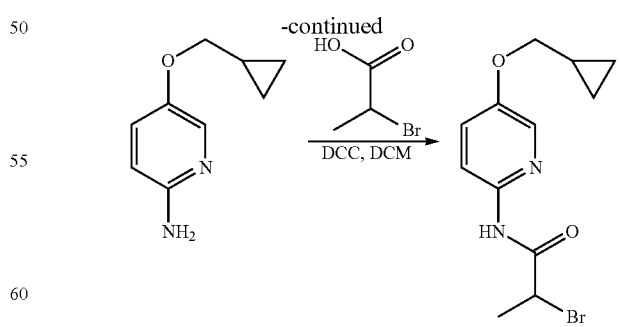

Step 1

To 6-nitropyridin-3-ol (1.00 g, 7.14 mmol) in DMF (15 mL) at 25° C. were added (bromomethyl)cyclopropane (1.156 g, 8.57 mmol) and K₂CO₃ (1.973 g, 14.28 mmol).

After 8 h, water (100 mL) was added, and the mixture was extracted with EtOAc (3×100 mL). The combined organic extracts were washed with brine (100 mL), dried over sodium sulfate, concentrated and purified over silica (80 g), eluting with 0-50% EtOAc in pet ether to give 5-(cyclopropylmethoxy)-2-nitropyridine (1.25 g, 5.79 mmol, purity: 90%, yield: 81%) as yellow solid. LCMS: (ES, m/z): 195 [M+H]+, RT=0.938 min, LC/MS Method 4. $^1$H NMR: (400 MHz, CDCl$_3$) δ 8.26-8.29 (m, 2H), 7.38-7.41 (m, 1H), 4.00 (d, J=8 Hz, 2H), 1.27-1.39 (m, 1H), 0.72-0.77 (m, 2H), 0.42-0.46 (m, 2H).

Step 2

A mixture of 5-(cyclopropylmethoxy)-2-nitropyridine (6.6 g, 34.0 mmol, 1.0 eq), MeOH (60.0 mL) and Pd/C (0.6 g, 10%) was evacuated and flushed three times with nitrogen, followed by flushing with hydrogen. The reaction was stirred 2 h at 25° C. under an atmosphere of hydrogen (balloon), filtered and concentrated to give crude 5-(cyclopropylmethoxy)pyridin-2-amine (5.8 g) as a yellow solid, which was used without purification. LCMS: (ES, m/z): 165 [M+H]+.

Step 3

To 5-(cyclopropylmethoxy)pyridin-2-amine (0.50 g, 3.05 mmol, 1.0 eq) and 2-bromopropanoic acid (0.7 g, 4.57 mmol, 1.5 eq) in DCM (10 mL) at 25° C. was added DCC (0.94 g, 4.57 mmol, 1.5 eq), in portions. After 2 h, the reaction was filtered, concentrated, and purified by prep-TLC with ethyl acetate:petroleum ether (1:10) to give 2-bromo-N-(5-(cyclopropylmethoxy)pyridin-2-yl)propanamide (0.9 g, yield: 53%, purity: 95%) as a white solid. LCMS: (ES, m/z): 299 [M+H]+. $^1$H NMR: (300 MHz, CD$_3$OD) δ 8.02-7.99 (m, 2H), 8.03-8.01 (m, 1H), 4.76-4.69 (m, 1H), 3.90 (d, J=6.9 Hz, 2H), 1.84 (d, J=6.9 Hz, 3H), 1.32-1.28 (m, 1H), 0.69-0.62 (m, 2H), 0.41-0.35 (m, 2H).

Intermediates 23-32 24-26, 28-29, 31-32 using cesium carbonate as base and iron/ammonium chloride as reducing agent; 31 using iron/ammonium chloride as reducing reagent) were synthesized in an analogous manner from alkyl halides.

| Int. | Name | Structure | $^1$H NMR | LC: retention time (min); LC/MS Method of analysis | MS (M + H)+ |
|---|---|---|---|---|---|
| 23 | 2-bromo-N-(5-(cyclopentyloxy)pyridin-2-yl)propanamide | 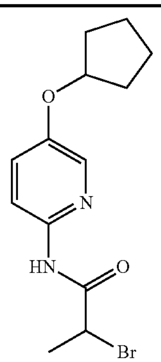 | $^1$H NMR: (300 MHz, DMSO-d$_6$) δ 10.70 (s, 1H), 8.04-7.95 (m, 2H), 7.45-7.42 (m, 1H), 4.92-4.79 (m, 2H), 3.68-3.54 (m, 2H), 1.96-1.85 (m, 2H), 1.85-1.69 (m, 4H), 1.68-1.57 (m, 1H), 1.30-1.21 (m, 2H). | — | 313 |
| 24 | 2-bromo-N-(5-(cyclobutylmethoxy)pyridin-2-yl)propanamide | 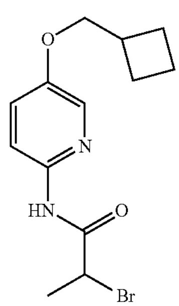 [SMILES: CC(Br)C(=O)Nc1ccc(OCC2CCC2)cn1] | $^1$H NMR: (300 MHz, DMSO-d$_6$) δ 10.73 (s, 1H), 8.05 (d, J = 2.8 Hz, 1H), 8.00 (d, J = 9.2 Hz, 1H), 7.45 (dd, J = 3.2, 9.2 Hz, 1H), 4.88-4.83 (m, 1H), 4.00 (d, J = 6.8 Hz, 2H), 2.75-2.68 (m, 1H), 2.10-2.03 (m, 2H), 1.93-1.80 (m, 4H), 1.73 (d, J = 6.8 Hz, 3H). | — | 313 |
| 25 | 2-bromo-N-(5-(oxazol-2-ylmethoxy)pyridin-2-yl)propanamide | 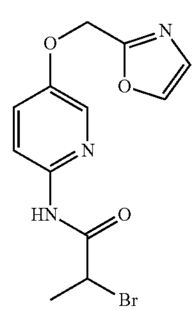 [SMILES: CC(Br)C(=O)Nc1ccc(OCc2ncco2)cn1] | $^1$H NMR: (400 MHz, CDCl$_3$) δ 10.29 (br, 1H), 8.34 (d, J = 9.2 Hz, 1H), 8.03 (d, J = 2.8 Hz, 1H), 7.74 (s, 1H), 7.38 (dd, J = 2.8, 9.2 Hz, 1H), 7.20 (s, 1H), 5.24 (s, 2H), 4.62-4.57 (m, 1H), 1.93 (d, J = 6.8 Hz, 3H). | — | 326 |

-continued

| Int. | Name | Structure | ¹H NMR | LC: retention time (min); LC/MS Method of analysis | MS (M + H)⁺ |
|---|---|---|---|---|---|
| 26 | N-(5-(benzyloxy)pyridin-2-yl)-2-bromopropanamide | 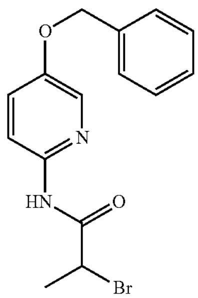 [SMILES: CC(Br)C(=O)Nc1ccc(OCc2ccccc2)cn1] | ¹H NMR: (400 MHz, CDCl₃) δ 8.79 (br, 1H), 8.16 (d, J = 8.8 Hz, 1H), 8.06 (d, J = 2.8 Hz, 1H), 7.46-7.37 (m, 6H), 5.13 (s, 2H), 4.57-4.52 (m, 1H), 1.97 (d, J = 6.8 Hz, 3H). | — | 335 |
| 27 | 2-bromo-N-(5-(cyclohexyloxy)pyridin-2-yl)propanamide | 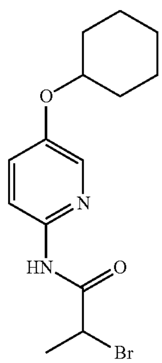 [SMILES: CC(Br)C(=O)Nc1ccc(OC2CCCCC2)cn1] | ¹H NMR: (300 MHz, DMSO-d₆) δ 8.70 (s, 1H), 8.12 (d, J = 9.0 Hz, 1H), 8.00 (d, J = 3.0 Hz, 1H), 7.31 (dd, J = 9.0, 3.0 Hz, 1H), 4.56-4.50 (m, 1H), 4.32-4.08 (m, 1H), 1.97 (d, J = 6.9 Hz, 3H), 1.85-1.80 (m, 2H), 1.64-1.48 (m, 4H), 1.43-1.23 (m, 4H). | — | 327 |
| 28 | 2-bromo-N-(5-isopropoxypyridin-2-yl)propanamide | 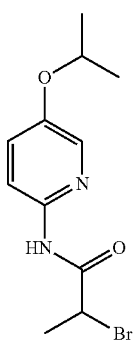 [SMILES: CC(C)Oc1ccc(NC(=O)C(C)Br)nc1] | ¹H NMR: (400 MHz, CDCl₃) δ 8.82 (s, 1H), 8.13 (d, J = 8.8 Hz, 1H), 7.99 (d, J = 2.8 Hz, 1H), 4.58-4.51 (m, 1H), 3.78-3.75 (m, 1H), 1.96 (d, J = 7.2 Hz, 3H), 1.32 (d, J = 6.4 Hz, 6H). | — | 287 |
| 29 | 2-bromo-N-(5-cyclobutoxypyridin-2-yl)propanamide | 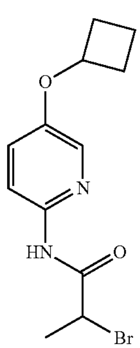 [SMILES: CC(Br)C(=O)Nc1ccc(OC2CCC2)cn1] | ¹H NMR: (300 MHz, DMSO-d₆) δ 10.71 (s, 1H), 8.04-7.93 (m, 2H), 7.38-7.34 (m, 1H), 4.92-4.60 (m, 1H), 2.48-2.36 (m, 2H), 2.10-1.98 (m, 2H), 1.77-1.56 (m, 4H), 1.49-1.23 (m, 2H). | — | 299 |

-continued

| Int. | Name | Structure | ¹H NMR | LC: retention time (min); LC/MS Method of analysis | MS (M + H)⁺ |
|---|---|---|---|---|---|
| 30 | 2-bromo-N-(5-((2,2-difluorocyclopropyl)methoxy)pyridin-2-yl)propanamide | 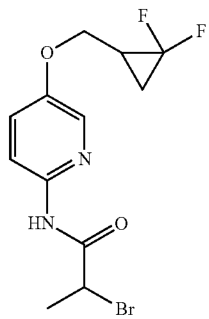 [SMILES: CC(Br)C(=O)Nc1ccc(OCC2CC2(F)F)cn1] | ¹H NMR: (400 MHz, CD₃OD) δ 8.06-8.03 (m, 2H), 7.45 (dd, J = 2.8, 8.8 Hz, 1H), 4.75-4.70 (m, 1H), 4.24-4.19 (m, 1H), 4.09-4.04 (m, 1H), 2.22-2.10 (m, 1H), 1.84 (d, J = 6.8 Hz, 3H), 1.67-1.62 (m, 1H), 1.42-1.34 (m, 1H). | — | 335 |
| 31 | 2-bromo-N-(5-(cyclopentylmethoxy)pyridin-2-yl)propanamide | 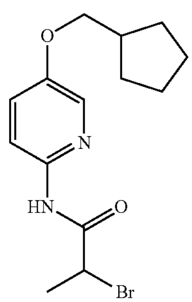 [SMILES: CC(Br)C(=O)Nc1ccc(OCC2CCCC2)cn1] | ¹H NMR: (400 MHz, CDCl₃) δ 8.74 (br, 1H), 8.14 (d, J = 9.2 Hz, 1H), 7.99 (d, J = 2.8 Hz, 1H), 7.32 (dd, J = 3.2, 9.2 Hz, 1H), 4.57-4.52 (m, 1H), 3.88 (d, J = 7.2 Hz, 2H), 2.42-2.35 (m, 1H), 1.97 (d, J = 6.8 Hz, 3H), 1.90-1.84 (m, 2H), 1.71-1.59 (m, 4H), 1.42-1.34 (m, 2H). | — | 327 |
| 32 | 2-bromo N-(5-(2,2-difluoroethoxy)pyridin-2-yl)propanamide | 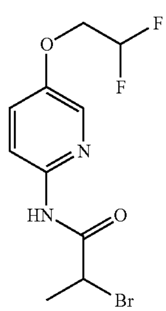 [SMILES: CC(Br)C(=O)Nc1ccc(OCC(F)F)cn1] | ¹H NMR: (400 MHz, DMSO-d₆) δ 10.79 (s, 1H), 8.14 (d, J = 2.8 Hz, 1H), 8.03 (d, J = 9.2 Hz, 1H), 7.55 (dd, J = 2.8, 9.2 Hz, 1H), 6.55-6.26 (m, 1H), 4.88-4.83 (m, 1H), 4.44-4.37 (m, 2H), 1.74 (d, J = 6.8 Hz, 3H). | — | 309 |

Intermediate 33

(E)-2-bromo-N-(5-(2-cyclopropylvinyl)pyridin-2-yl)propanamide

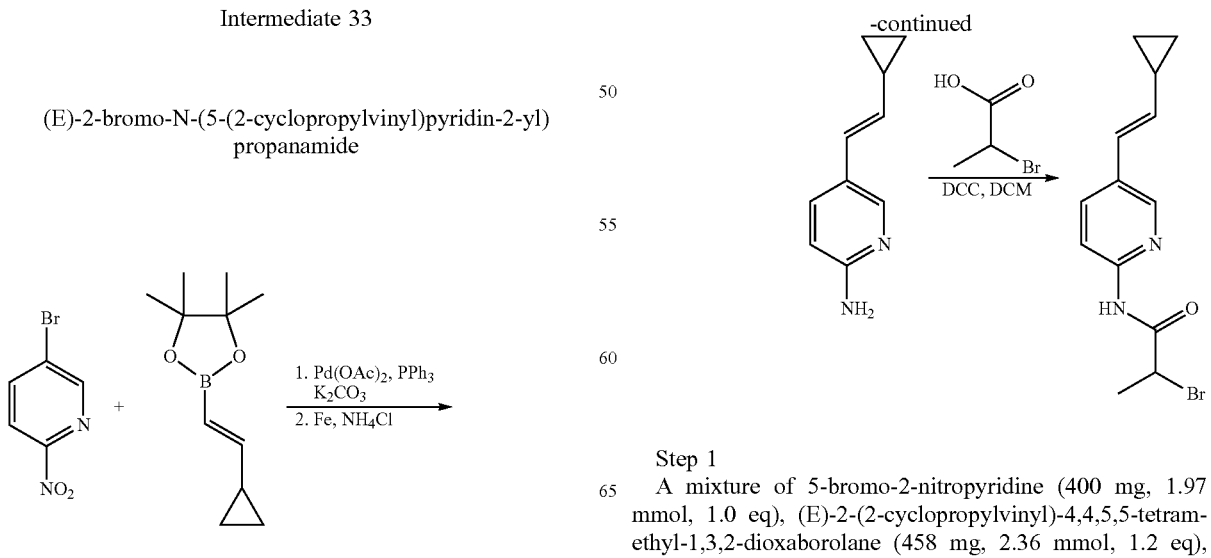

Step 1

A mixture of 5-bromo-2-nitropyridine (400 mg, 1.97 mmol, 1.0 eq), (E)-2-(2-cyclopropylvinyl)-4,4,5,5-tetramethyl-1,3,2-dioxaborolane (458 mg, 2.36 mmol, 1.2 eq), Pd(OAc)₂ (45 mg, 0.2 mmol, 0.1 eq), PPh₃ (516 mg, 1.97 mmol, 1.0 eq), K₂CO₃ (816 mg, 5.91 mmol, 3.0 eq) and DME/H₂O (8 mL, 1/1) was flushed three times with nitrogen and stirred at 85° C. After 12 h, the reaction was quenched with water (50 ML) and extracted with EtOAc (50 mL×3). The combined organic phases were dried over Na₂SO₄, concentrated and purified over silica gel, eluting with ethyl acetate:petroleum ether (1:3) to give (E)-5-(2-cyclopropylvinyl)-2-nitropyridine (280 mg, purity: 92%, yield: 69%) as a yellow oil. LCMS: (ES, m/z): 191 [M+H]⁺. ¹H NMR: (400 MHz, CDCl₃) δ 8.52 (d, J=2.3 Hz, 1H), 8.20 (d, J=8.5 Hz, 1H), 7.89 (dd, J=8.5, 2.3 Hz, 1H), 6.57 (d, J=15.8 Hz, 1H), 6.02 (dd, J=15.8, 9.3 Hz, 1H), 1.73-1.65 (m, 1H), 1.03-0.95 (m, 2H), 0.70-0.64 (m, 2H).

Step 2

To (E)-5-(2-cyclopropylvinyl)-2-nitropyridine (270 mg, 1.42 mmol, 1.0 eq) and NH₄Cl (753 mg, 14.2 mmol, 10.0 eq) in MeOH/H₂O (40 mL, 3/1) was added, in portions, Fe (795 mg, 14.2 mmol, 10.0 eq), and the mixture was stirred at 60° C. After 2 h, the reaction was filtered, concentrated and purified over silica gel, eluting with EtOAc:pet ether (1:1) to give (E)-5-(2-cyclopropylvinyl)pyridin-2-amine (200 mg) as a yellow oil. LCMS: (ES, m/z): 161 [M+H]⁺. ¹H NMR: (300 MHz, DMSO-d₆) δ 7.82 (d, J=2.4 Hz, 1H), 7.44 (dd, J=8.6, 2.4 Hz, 1H), 6.38 (d, J=8.6 Hz, 1H), 6.29 (dd, J=15.9, 8.8 Hz, 1H), 5.91 (s, 2H), 5.56 (dd, J=15.9, 8.8 Hz, 1H), 1.55-1.45 (m, 1H), 0.78-0.70 (m, 2H), 0.47-0.40 (m, 2H).

Step 3

A mixture of 2-bromopropanoic acid (133 mg, 0.875 mmol, 1.0 eq), DCC (217 mg, 1.05 mmol, 1.2 eq) and (E)-5-(2-cyclopropylvinyl)pyridin-2-amine (140 mg, 0.875 mmol, 1.0 eq) in DCM (5 mL) was stirred at 25° C. After 12 h, the mixture was quenched with water (20 mL) and extracted with DCM (20 mL×3). The combined organic phases were dried over Na₂SO₄, concentrated and purified over silica gel, eluting with ethyl acetate:petroleum ether (1:4) to give (E)-2-bromo-N-(5-(2-cyclopropylvinyl)pyridin-2-yl)propanamide (150 mg, yield: 58%, purity: 90%) as a yellow solid. LCMS: (ES, m/z): 295 [M+H]⁺. ¹H NMR: (400 MHz, DMSO-d₆) δ 10.85 (s, 1H), 8.30 (d, J=2.4 Hz, 1H), 8.00 (d, J=8.7 Hz, 1H), 7.83 (dd, J=8.6, 2.5 Hz, 1H), 6.45 (d, J=16.0 Hz, 1H), 5.91 (dd, J=15.9, 9.2 Hz, 1H), 4.92-4.81 (m, 1H), 1.74 (d, J=6.7 Hz, 3H), 1.63-1.55 (m, 1H), 0.88-0.75 (m, 2H), 0.58-0.47 (m, 2H).

Intermediate 34

2-bromo-N-(6-methyl-[2,3'-bipyridin]-6'-yl)propanamide

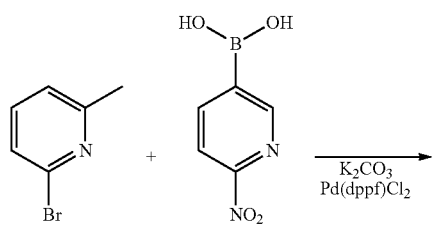

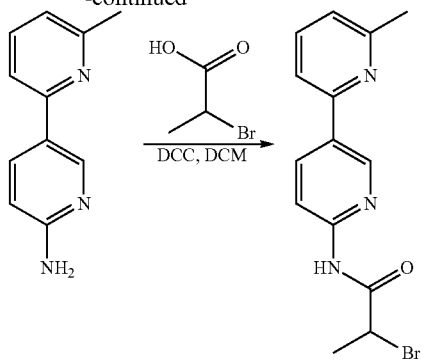

Step 1

A mixture of 2-bromo-6-methylpyridine (600 mg, 3.49 mmol, 1.0 eq), (6-aminopyridin-3-yl)boronic acid (626 mg, 4.53 mmol, 1.3 eq), Pd(dppf)Cl₂ (285 mg, 0.35 mmol, 0.1 eq) and K₂CO₃ (963 mg, 6.98 mmol, 2.0 eq) in DMF/H₂O (12 mL, 2/1), was flushed three times with nitrogen and stirred at 80° C. After 1 h, the reaction was quenched with water (50 mL) and extracted with EtOAc (50 mL×3). The combined organic phases were dried over Na₂SO₄, concentrated and purified over silica gel, eluting with MeOH in DCM (1-30%) to give 6-methyl-[2,3'-bipyridin]-6'-amine (620 mg, purity: 98%, yield: 96%) as a yellow solid. LCMS: (ES, m/z): 186 [M+H]⁺. ¹H NMR: (400 MHz, DMSO-d₆) δ 8.64 (d, J=2.4 Hz, 1H), 8.06 (dd, J=8.6, 2.5 Hz, 1H), 7.70-7.55 (m, 2H), 7.08 (d, J=7.4 Hz, 1H), 6.51 (d, J=8.7 Hz, 1H), 6.23 (s, 2H), 2.49 (s, 3H).

Step 2

To 2-bromopropanoic acid (263 mg, 1.72 mmol, 1.1 eq), DCC (484 mg, 2.35 mmol, 1.5 eq) and DMAP (19.0 mg, 0.15 mmol, 0.1 eq) in DCM (5 mL) was added 6-methyl-[2,3'-bipyridin]-6'-amine (290 mg, 1.56 mmol, 1.0 eq). After 2 h, water (100 mL) was added, and the mixture was extracted with EtOAc (100 mL×3). The combined organic phases were dried over Na₂SO₄, concentrated and purified over silica gel, eluting with ethyl acetate:petroleum ether (1:3) to give 2-bromo-N-(6-methyl-[2,3'-bipyridin]-6'-yl)propanamide (342 mg, yield: 68%, purity: 69%) as a yellow solid. LCMS: (ES, m/z): 320 [M+H]⁺. (400 MHz, DMSO-d₆) δ 11.07 (s, 1H), 9.05 (dd, J=2.5, 0.8 Hz, 1H), 8.48 (dd, J=8.7, 2.4 Hz, 1H), 8.19 (d, J=8.7 Hz, 1H), 7.85-7.75 (m, 2H), 7.25 (dd, J=7.1, 1.4 Hz, 1H), 4.96-4.87 (m, 1H), 2.55 (s, 3H), 1.77 (d, J=6.7 Hz, 3H).

Intermediates 35-39 (35 using cesium carbonate in THF; 36 with sodium bicarbonate and Pd(PPh₃)₄ in dioxane/water; 37 with K₃PO₄ and Pd(dtbpf)Cl₂ in THF/water; 38 with sodium carbonate and Pd(PPh₃)₄ in EtOH/water; 39 the boronate ester) were synthesized in an analogous manner from alkyl and aryl halides.

| Int. | Name | Structure | ¹H NMR | LC: retention time (min); LC/MS Method of analysis | MS (M + H)⁺ |
|---|---|---|---|---|---|
| 35 | 2-bromo-N-(5-(thiazol-2-ylmethyl)pyridin-2-yl)propanamide | 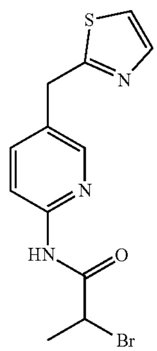 [SMILES: CC(Br)C(=O)Nc1ccc(Cc2nccs2)cn1] | ¹H NMR: (400 MHz DMSO-d₆) δ ppm 10.89 (s, 1H), 8.34 (d, J = 2.4 Hz, 1H), 8.05 (d, J = 8.5 Hz, 1H), 7.79 (dd, J = 8.5, 2.4 Hz, 1H), 7.74 (d, J = 3.3 Hz, 1H), 7.61 (d, J = 3.3 Hz, 1H), 4.92-4.83 (m, 1H), 4.36 (s, 2H), 1.74 (d, J = 6.6 Hz, 3H). | — | 326 |
| 36 | 2-bromo-N-(5-(1-methyl-1H-pyrazol-3-yl)pyridin-2-yl)propanamide | 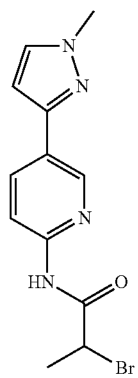 [SMILES: CC(Br)C(=O)Nc1ccc(-c2ccn(C)n2)cn1] | ¹H NMR: (300 MHz, CDCl₃) δ ppm 8.93 (s, 1H), 8.75-8.72 (m, 1H), 8.32-8.24 (m, 1H), 8.17-8.14 (m, 1H), 7.44-7.43 (m, 1H), 6.57-6.55 (m, 1H), 4.60-4.53 (m, 1H), 3.98 (s, 3H), 1.98 (d, J = 7.2 Hz, 3H). | 1.191; LCMS Method 8 | 309 |
| 37 | N-(5-benzylpyridin-2-yl)-2-bromopropanamide | 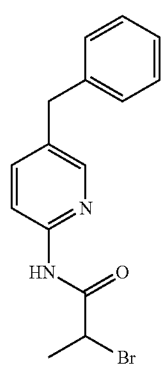 [SMILES: CC(Br)C(=O)Nc1ccc(Cc2ccccc2)cn1] | ¹H NMR: (300 MHz, CDCl₃) δ ppm 9.00 (s, 1H), 8.28-8.00 (m, 2H), 7.58 (dd, J = 8.6 Hz, J = 2.3 Hz, 1H), 7.43-7.06 (m, 5H), 4.58-4.47 (m, 1H), 3.98 (s, 2H), 1.95 (d, J = 7.0 Hz, 3H). | — | 319 |
| 38 | 2-bromo-N-(5-(pyridin-3-ylmethyl)pyridin-2-yl)propanamide | 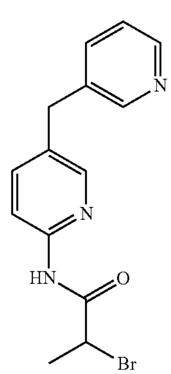 [SMILES: CC(Br)C(=O)Nc1ccc(Cc2cccnc2)cn1] | ¹H NMR: (300 MHz, CDCl₃) δ ppm 8.90 (br, 1H), 8.56-8.51 (m, 2H), 8.19-8.15 (m, 2H), 7.58-7.48 (m, 2H), 7.30-7.26 (m, 1H), 4.58-4.51 (m, 1H), 3.99 (s, 2H), 1.96 (d, J = 6.9 Hz, 3H). | 0.708; LCMS Method 36 | 320 |

| Int. | Name | Structure | ¹H NMR | LC: retention time (min); LC/MS Method of analysis | MS (M + H)⁺ |
|---|---|---|---|---|---|
| 39 | 2-bromo-N-(5-(thiophen-2-yl)pyridin-2-yl)propanamide | 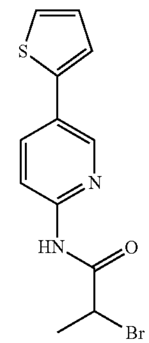 [SMILES: CC(Br)C(=O)Nc1ccc(-c2cccs2)cn1] | ¹H NMR: (300 MHz DMSO-d₆) δ ppm 10.99 (s, 1H), 8.66-8.65 (m, 1H), 8.13-8.06 (m, 2H), 7.59-7.56 (m, 2H), 7.16-7.13 (m, 1H), 4.91-4.84 (m, 1H), 1.73 (d, J = 8.8 Hz, 3H). | — | 311 |

Intermediate 40

2-bromo-N-(5-cyclopentylpyridin-2-yl)propanamide

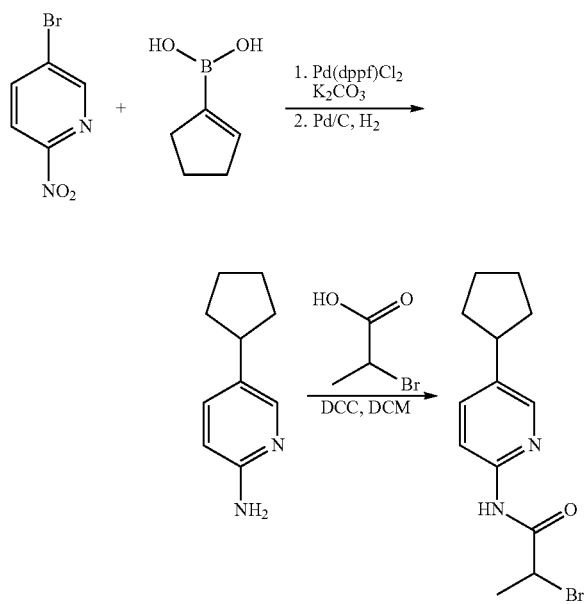

Step 1

A mixture of 5-bromopyridin-2-amine (2.0 g, 11.63 mmol, 1.0 eq), cyclopentenylboronic acid (1.7 g, 15.12 mmol, 1.3 eq), Pd(dppf)Cl₂ (900 mg, 1.2 mmol, 0.1 eq) and K₂CO₃ (3.3 g, 23.26 mmol, 2.0 eq) in DMF (20 mL) and H₂O (10 mL) was flushed three times with nitrogen and stirred at 80° C. After 1 h, the reaction was quenched with water (50 mL) and extracted with EtOAc (50 mL×3). The combined organic phases were dried over Na₂SO₄, concentrated and purified over silica gel, eluting with ethyl acetate: petroleum ether (2:5) to give 5-cyclopentenylpyridin-2-amine (1.7 g, purity: 99%, yield: 91%) as a yellow solid. LCMS: (ES, m/z): 161 [M+H]⁺. ¹H NMR: (400 MHz, DMSO-d₆) δ 7.94 (s, 1H), 7.51 (dd, J=8.7, 2.4 Hz, 1H), 6.40 (d, J=8.7 Hz, 1H), 5.99-5.93 (m, 3H), 2.60-2.52 (m, 2H), 2.44-2.36 (m, 2H), 1.96-1.94 (m, 2H).

Step 2

A mixture of 5-cyclopentenylpyridin-2-amine (1.70 g, 10.56 mmol, 1.0 eq), Pd/C (500 mg, 10%) and MeOH (40 mL) was evacuated and flushed three times with nitrogen, followed by flushing with hydrogen. The reaction was stirred 1 h at 25° C. under an atmosphere of hydrogen (balloon), filtered, concentrated and purified over silica gel, eluting with EtOAc:pet ether (1:1) to give 5-cyclopentylpyridin-2-amine (1.6 g, purity: 85%, yield: 93%) as a yellow solid. LCMS: (ES, m/z): 163 [M+H]⁺. ¹H NMR: (300 MHz, DMSO-d₆) δ 7.75 (d, J=2.4 Hz, 1H), 7.24 (dd, J=8.4, 2.4 Hz, 1H), 6.37 (d, J=8.7 Hz, 1H), 5.61 (s, 2H), 2.82-2.70 (m, 1H), 1.95-1.84 (m, 2H), 1.75-1.50 (m, 4H), 1.45-1.30 (m, 2H).

Step 3

A mixture of 5-cyclopentylpyridin-2-amine (300 m, g, 1.85 mmol, 1.0 eq), 2-bromopropanoic acid (282 mg, 1.85 mmol, 1.0 eq), DCC (458 mg, 2.22 mmol, 1.2 eq) and DMAP (23 mg, 0.2 mmol, 0.1 eq) in DCM (10 mL) was stirred at rt. After 2 h, the mixture was quenched with water (50 mL) and extracted with DCM (50 mL×3). The combined organic phases were dried over Na₂SO₄, concentrated and purified over silica gel, eluting with ethyl acetate:petroleum ether (1:10) to give 2-bromo-N-(5-cyclopentylpyridin-2-yl) propanamide (260 mg, yield: 47%, purity: 97%) as a yellow solid. LCMS: (ES, m/z): 297 [M+H]⁺. ¹H NMR: (300 MHz, DMSO-d₆) δ 10.75 (br, 1H), 8.24-8.19 (m, 1H), 8.00-7.92

(m, 1H), 7.72-7.62 (m, 1H), 4.90-4.80 (m, 1H), 3.02-2.90 (m, 1H), 2.10-1.90 (m, 2H), 1.85-1.40 (m, 9H).

Intermediate 41 was synthesized in an analogous manner.

| Int. | Name | Structure | $^1$H NMR | LC: retention time (min); LC/MS Method of analysis | MS $(M + H)^+$ |
|---|---|---|---|---|---|
| 41 | 2-bromo-N-(5-cyclohexylpyridin-2-yl)propanamide | 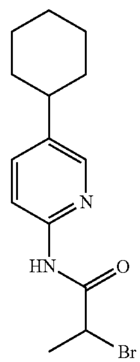 [SMILES: CC(Br)C(=O)Nc1ccc(C2CCCCC2)cn1] | $^1$H NMR: (400 MHz, DMSO-$d_6$) δ ppm 10.74 (s, 1H), 8.19 (d, J = 2.1 Hz, 1H), 7.94 (d, J = 8.4 Hz, 1H), 7.65 (dd, J = 2.4, 8.4 Hz, 1H), 4.88-4.81 (m, 1H), 2.58-2.52 (m, 1H), 1.78-1.66 (m, 8H), 1.45-1.18 (m, 5H). | — | 311 |

Intermediate 42

2-bromo-N-(5-(cyclopropylmethoxy)-3-fluoropyridin-2-1)propanamide

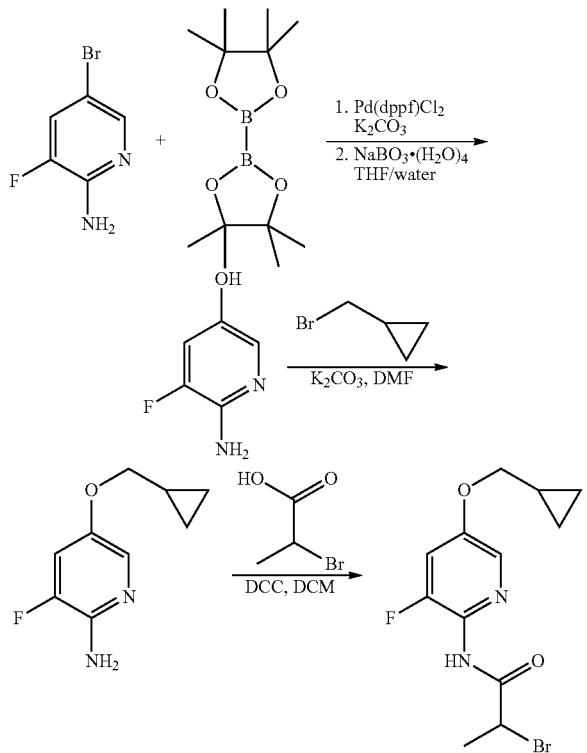

Step 1

To 5-bromo-3-fluoropyridin-2-amine (5.00 g, 26.3 mmol, 1.0 eq) in dixoane (60 mL) was added 4,4,4',4',5,5,5',5'-octamethyl-2,2'-bi(1,3,2-dioxaborolane) (10.0 g, 39.5 mmol, 1.5 eq), potassium carbonate (7.75 g, 78.9 mmol, 3.0 eq) and Pd(dppf)Cl$_2$ (1.95 g, 2.63 mmol, 0.1 eq). The reaction was flushed three times with nitrogen and stirred at 80° C. After 15 h, the reaction was directly purified by prep HPLC (column: C18, 330 g), eluting with 0-10% AcCN in water (0.05% TFA) to give (6-amino-5-fluoropyridin-3-yl)boronic acid (3.6 g, yield: 88%, purity: 70%) as a light yellow solid. LCMS: (ES, m/z): 157 [M+H]$^+$. $^1$H NMR: (300 MHz, DMSO-$d_6$) δ 7.71-7.66 (m, 1H), 7.57-7.47 (m, 1H), 6.45 (s, 2H), 3.59 (s, 2H).

Step 2

To (6-amino-5-fluoropyridin-3-yl)boronic acid (3.6 g, 23.1 mmol, 1.0 eq) in THF (40 mL) and water (40 mL) was added NaBO$_3$.4H$_2$O (10.7 g, 69.2 mmol, 3.0 eq). After 1 h, the reaction was directly purified by prep HPLC (column: C18, 330 g), eluting with 0-10% AcCN in water (with 0.05% NH$_4$HCO$_3$) to give 6-amino-5-fluoropyridin-3-ol (1.6 g, yield: 64%, purity: 80%) as a brown solid. LCMS: (ES, m/z): 129 [M+H]$^+$. $^1$H NMR: (300 MHz, CD$_3$OD) δ ppm 7.42 (d, J=2.4 Hz, 1H), 6.98-6.94 (m, 1H).

Step 3

To 6-amino-5-fluoropyridin-3-ol (1.35 g, 10.5 mmol, 1.0 eq) in DMF (20 mL) was added potassium carbonate (4.37 g, 31.6 mmol, 3.0 eq) and (bromomethyl)cyclopropane (1.41 g, 10.5 mmol, 1.0 eq), and the mixture was heated to 80° C. After 15 h, the reaction was quenched with water (100 mL) and extracted with EtOAc (3×100 mL). The combined organic layers were washed with brine (3×150 mL), dried over sodium sulfate, concentrated and purified over silica gel, eluting with MeOH:DCM (1:10) to give 5-(cyclopropylmethoxy)-3-fluoropyridin-2-amine (600 mg, yield: 31%, purity: 90%) as a brown solid. LCMS: (ES, m/z): 183 [M+H]$^+$. $^1$H NMR: (300 MHz, CD$_3$OD) δ ppm 7.51 (d, J=2.7 Hz, 1H), 7.16-7.11 (m, 1H), 3.79 (d, J=6.9 Hz, 2H), 1.28-1.15 (m, 1H), 0.64-0.56 (m, 2H), 0.36-0.29 (m, 2H).

Step 4

To 5-(cyclopropylmethoxy)-3-fluoropyridin-2-amine (600 mg, 3.30 mmol, 1.0 eq) in DCM (10 mL) were added DCC (1.02 g, 4.95 mmol, 1.5 eq) and 2-bromopropanoic acid (757 mg, 4.95 mmol, 1.5 eq). After 2 h, the reaction was filtered, concentrated and purified over silica gel, eluting with ethyl acetate:petroleum ether (1:3) to give 2-bromo-N-(5-(cyclopropylmethoxy)-3-fluoropyridin-2-yl)propanamide (830 mg, yield: 80%, purity: 90%) as a white solid. LCMS: (ES, m/z): 317 [M+H]$^+$. $^1$H NMR (300 MHz, DMSO-$d_6$) δ 10.38 (s, 1H), 8.00 (d, J=2.7 Hz, 1H), 7.53-

7.49 (m, 1H), 4.79-4.69 (m, 1H), 3.95-3.90 (m, 2H), 1.73 (d, J=6.9 Hz, 3H), 1.26-1.21 (m, 1H), 0.62-0.54 (m, 2H), 0.36-0.31 (m, 2H).

Intermediate 43 was synthesized in an analogous manner.

| Int. | Name | Structure | $^1$H NMR | LC: retention time (min); LC/MS Method of analysis | MS (M + H)$^+$ |
|---|---|---|---|---|---|
| 43 | 2-bromo-N-(5-(cyclopropylmethoxy)-4-fluoropyridin-2-yl)propanamide | 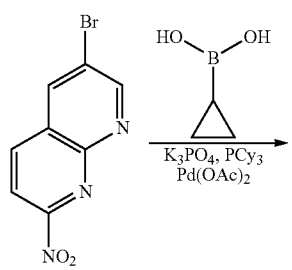 | — | — | 317 |

Intermediate 44

2-bromo-N-(6-cyclopropyl-1,8-naphthyridin-2-yl)propanamide

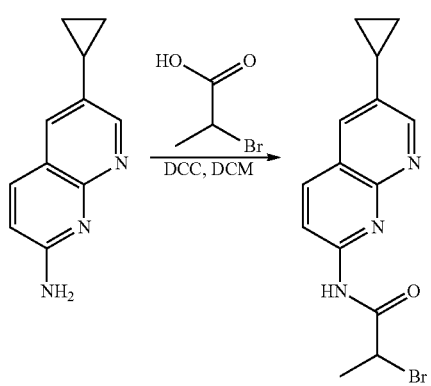

Step 1

A mixture of 6-bromo-1,8-naphthyridin-2-amine (840 mg, 3.77 mmol, 1.0 eq), cyclopropylboronic acid (650 mg, 7.54 mmol, 2.0 eq), palladium acetate (170 mg, 0.75 mmol, 0.2 eq), tricyclohexylphosphine (211 mg, 0.75 mmol, 0.2 eq, 10% in n-hexane), potassium phosphate (2.4 g, 11.31 mmol, 3 eq), water (1 mL) and toluene (20 mL) was flushed three times with nitrogen and stirred at 100° C. After 16 h, the reaction was quenched with water (100 mL) and extracted with EtOAc (100 mL×3). The combined organic phases were dried over Na$_2$SO$_4$, concentrated and purified over silica gel, eluting with MeOH:DCM (1:10) to give 6-cyclopropyl-1,8-naphthyridin-2-amine (200 mg, purity: 69%, yield: 28%) as a yellow solid. LCMS: (ES, m/z): 186 [M+H]$^+$. $^1$H NMR: (400 MHz, DMSO-d$_6$) δ 8.54 (d, J=2.4 Hz, 1H), 7.84 (d, J=8.7 Hz, 1H), 7.66 (d, J=2.4 Hz, 1H), 6.78 (d, J=8.7 Hz, 1H), 6.68 (s, 2H), 2.06-1.97 (m, 1H), 1.06-0.91 (m, 2H), 0.86-0.70 (m, 2H).

Step 2

A mixture of 2-bromopropanoic acid (166 mg, 1.08 mmol, 1 eq), dicyclohexylcarbodiimide (450 mg, 2.16 mmol, 2 eq), and 6-cyclopropyl-1,8-naphthyridin-2-amine (200 mg, 1.08 mmol, 1.0 eq) in dichloromethane (10 mL) was stirred at 25° C. for 2 h. The reaction was filtered, concentrated and purified over silica gel, eluting with DCM:MeOH (10:1) to give 2-bromo-N-(6-cyclopropyl-1,8-naphthyridin-2-yl)propanamide (300 mg, yield: 87%, purity: 69%) as a yellow oil. LCMS: (ES, m/z): 320 [M+H]$^+$. (400 MHz, DMSO-d$_6$) δ 11.42 (s, 1H), 8.87 (d, J=2.7 Hz, 1H), 8.54-8.25 (m, 2H), 8.02 (d, J=2.7 Hz, 1H), 4.94-4.92 (m, 1H), 2.16-2.13 (m, 1H), 1.80-1.60 (m, 5H), 1.34-1.14 (m, 2H). Intermediate 45 was synthesized in an analogous manner.

| Int. | Name | Structure | ¹H NMR | LC: retention time (min); LC/MS Method of analysis | MS (M + H)⁺ |
|---|---|---|---|---|---|
| 45 | 2-bromo-N-(6-cyclopropylquinolin-2-yl)propanamide | 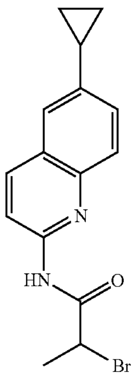 [SMILES: CC(Br)C(=O)Nc1ccc2cc(C3CC3)ccc2n1] | ¹H NMR: (400 MHz DMSO-$d_6$) δ ppm 11.12 (s, 1H), 8.33-8.32 (m, 2H), 7.72 (d, J = 8.8 Hz, 1H), 7.62 (d, J = 2.4 Hz, 1H), 7.46 (dd, J = 2.0, 8.4 Hz, 1H), 4.96-4.91 (m, 1H), 2.14-2.07 (m, 1H), 1.77 (d, J = 6.8 Hz, 3H), 1.06-1.02 (m, 2H), 0.82-0.78 (m, 2H). | — | 319 |

Intermediate 46

2-bromo-N-(5-cyclobutylpyridin-2-yl)propanamide

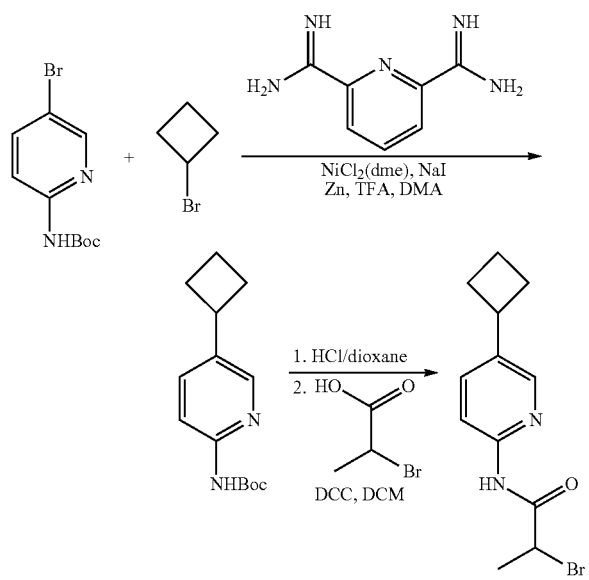

Step 1

A mixture of tert-butyl (5-bromopyridin-2-yl)carbamate (14 g, 51 mmol, 1.0 eq, pyridine-2,6-bis(carboximidamide) (660 mg, 4.1 mmol, 0.08 eq), NiCl$_2$(dme) (890 mg, 4.1 mmol, 0.08 eq), NaI (3 g, 20.2 mmol, 0.40 eq), bromocyclobutane (16.4 g, 121.4 mmol, 2.4 eq), Zn (10.2 g, 162 mmol, 3.2 eq) and TFA (923 mg, 8.1 mmol, 0.16 eq)) in DMA (120 mL) was flushed three times with nitrogen and stirred at 60° C. After 12 h, the reaction was quenched with water (500 mL) and extracted with EtOAc (500 mL×3). The combined organic phases were washed with brine (2×500 mL), dried over Na$_2$SO$_4$, concentrated and purified over silica gel, eluting with EtOAc:petroleum ether (1:1) to give tert-butyl (5-cyclobutylpyridin-2-yl)carbamate (4.3 g, yield: 34%) as a yellow solid. LCMS: (ES, m/z): 249 [M+H]⁺. ¹H NMR: (300 MHz, DMSO-$d_6$) δ 9.65 (s, 1H), 8.10 (d, J=2.4 Hz, 1H), 7.73 (d, J=8.4 Hz, 1H), 7.65 (dd, J=8.4, 2.4 Hz, 1H), 3.51-3.42 (m, 1H), 2.31-2.25 (m, 2H), 2.15-1.47 (m, 4H), 1.45 (s, 9H).

Step 2 tert-Butyl 5-cyclobutylpyridin-2-ylcarbamate (1.5 g, 6 mmol, 1.0 eq) in HCl (4M in dioxane, 10 mL) was stirred at 28° C. After 2 h, the reaction was concentrated, and 2-bromopropanoic acid (1.38 g, 9.0 mmol, 1.5 eq), DCC (2.48 g, 12.1 mmol, 2.0 eq), DMAP (147 mg, 1.2 mmol, 0.2 eq) and dichloromethane (20 mL) were added. After 2 h, the reaction was quenched with water (100 mL) and extracted with DCM (3×100 mL). The combined organic phases were dried over Na$_2$SO$_4$, concentrated and purified over silica gel, eluting with EtOAc:petroleum ether (1:1) to give 2-bromo-N-(5-cyclobutylpyridin-2-yl)propanamide (650 mg, yield: 45%) as a yellow solid. LCMS: (ES, m/z): 283 [M+H]⁺. (300 MHz, DMSO-$d_6$) δ 10.80 (s, 1H), 8.21 (d, J=2.4 Hz, 1H), 8.05 (d, J=8.4 Hz, 1H), 7.74 (dd, J=8.6, 2.5 Hz, 1H), 4.94-4.70 (m, 1H), 3.58-3.46 (m, 1H), 2.35-2.29 (m, 2H), 2.21-2.07 (m, 1H), 2.06-1.97 (m, 1H), 1.95-1.79 (m, 1H), 1.76-1.70 (m, 4H).

Intermediate 47

(Z)-2-bromo-N-(5-(2-cyclopropylvinyl)pyridin-2-yl)propanamide

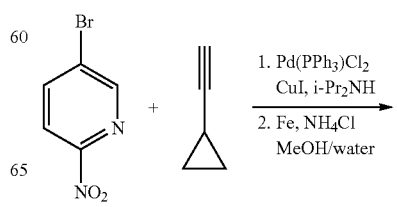

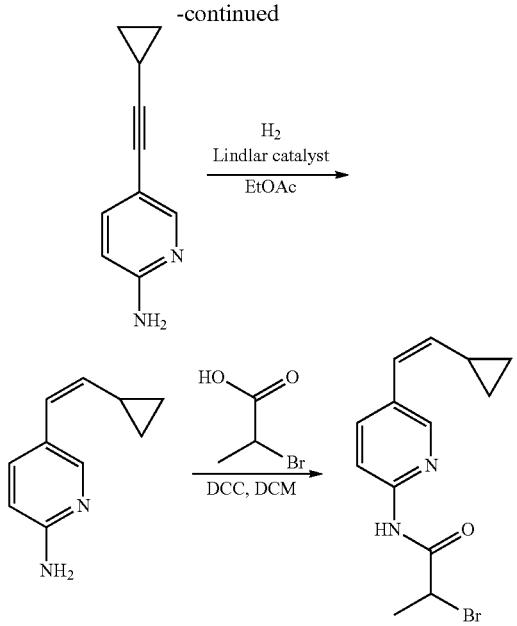

Step 1

To 5-bromo-2-nitropyridine (2.01 g, 10.00 mmol, 1.00 eq) in degassed DMF (20 mL) was added dichlorobis(triphenylphosphine)palladium (II) (420 mg, 0.60 mmol, 0.06 eq), copper (I) iodide (95 mg, 0.50 mmol, 0.05 eq), diisopropylamine (5.06 g, 50.00 mmol, 5.00 eq) and ethynylcyclopropane (0.99 g, 15.00 mmol, 1.50 eq). The mixture was stirred at 75° C. for 45 min, poured into water (200 mL) and extracted with ethyl acetate (200 mL×3). The combined organic extracts were washed with brine (400 mL), dried over sodium sulfate, concentrated and purified over silica gel, eluting with ethyl acetate in petroleum ether (0-10%, over 30 min) to give 5-(cyclopropylethynyl)-2-nitropyridine (1.3 g, yield: 69%, purity: 97%) as a yellow solid. LCMS: (ES, m/z): 189 [M+H]$^+$. $^1$H NMR: (300 MHz, CDCl$_3$) δ 8.58 (d, J=1.8 Hz, 1H), 8.20 (d, J=8.4 Hz, 1H), 7.94 (dd, J=2.1, 8.4 Hz, 1H), 1.59-1.50 (m, 1H), 1.03-0.91 (m, 4H).

Step 2

To 5-(cyclopropylethynyl)-2-nitropyridine (560 mg, 2.98 mmol, 1.0 eq) in methanol (8 mL) and water (2 mL) were added Fe (1.00 g, 17.85 mmol, 6.0 eq) and NH$_4$Cl (322 mg, 5.75 mmol, 2.0 eq) were added, and the reaction was stirred at 50° C. for 24 h. Solids were filtered out, and the filtrate was concentrated. The residue was applied onto a silica gel column, eluting with ethyl acetate:petroleum ether (0-35%, in 30 min) to give 5-(cyclopropylethynyl)pyridin-2-amine (220 mg, yield: 47%, purity: 96%) as a yellow solid. LCMS: (ES, m/z): 159 [M+H]$^+$. $^1$H NMR: (300 MHz, DMSO-d$_6$) δ ppm 7.91 (d, J=1.8 Hz, 1H), 7.32 (dd, J=2.4, 8.4 Hz, 1H), 6.35 (dd, J=0.6, 8.7 Hz, 1H), 6.22 (s, 2H), 1.53-1.44 (m, 1H), 0.87-0.80 (m, 2H), 0.69-0.64 (m, 2H).

Step 3

A mixture of 5-(cyclopropylethynyl)pyridin-2-amine (200 mg, 1.27 mmol, 1.0 eq) and Lindlar catalyst (100 mg) in ethyl acetate (5 mL) was evacuated and flushed three times with nitrogen, followed by flushing with hydrogen. The mixture was stirred 1.5 h under an atmosphere of hydrogen. The reaction was filtered, concentrated and purified over a silica gel column, eluting with ethyl acetate: petroleum ether (1:3) to give (Z)-5-(2-cyclopropylvinyl)pyridin-2-amine (120 mg, yield: 59%, purity: 76%) as a white solid. LCMS: (ES, m/z): 161 [M+H]$^+$. $^1$H NMR: (400 MHz, DMSO-d$_6$) δ ppm 7.96 (d, J=2.4 Hz, 1H), 7.51 (dd, J=2.4, 8.4 Hz, 1H), 6.43 (d, J=8.4 Hz, 1H), 6.10 (d, J=7.6 Hz, 1H), 5.96 (s, 2H), 4.94 (dd, J=8.8, 11.6 Hz, 1H), 1.79-1.69 (m, 1H), 0.83-0.78 (m, 2H), 0.42-0.36 (m, 2H).

Step 4

To (Z)-5-(2-cyclopropylvinyl)pyridin-2-amine (120 mg, 0.75 mmol, 1.0 eq) in dichloromethane (2 mL) were added 2-bromopropanoic acid (114 mg, 0.75 mmol, 1.0 eq) and DCC (230 mg, 1.13 mmol, 1.5 eq). The reaction was stirred for 24 h, poured into water (100 mL), filtered and extracted with ethyl acetate (100 mL×3). The organic layers were combined, dried over sodium sulfate, concentrated and purified by prep-TLC (ethyl acetate:petroleum ether, 1:5) to give (Z)-2-bromo-N-(5-(2-cyclopropylvinyl)pyridin-2-yl) propanamide (86 mg, yield: 39%, purity: 90%) as a yellow solid. LCMS: (ES, m/z): 295 [M+H]$^+$. $^1$H NMR: (300 MHz, CD$_3$OD) δ 8.38 (d, J=2.4 Hz, 1H), 8.08 (d, J=8.8 Hz, 1H), 7.89 (dd, J=2.4, 8.0 Hz, 1H), 6.30 (d, J=11.6 Hz, 1H), 5.23 (dd, J=10.0, 11.6 Hz, 1H), 4.78-4.71 (m, 1H), 2.26-2.15 (m, 1H), 1.85 (d, J=6.8 Hz, 3H), 0.83-0.78 (m, 2H), 0.42-0.36 (m, 2H).

Intermediate 48, using Pd/C as catalyst during hydrogenation, was synthesized in an analogous manner.

| Int. | Name | Structure | $^1$H NMR | LC: retention time (min); LC/MS Method of analysis | MS (M + H)$^+$ |
|---|---|---|---|---|---|
| 48 | 2-bromo-N-(5-(2-cyclopropylethyl)pyridin-2-yl)propanamide | 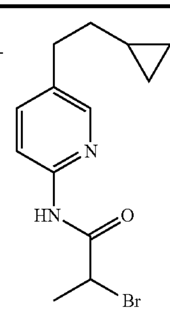 | $^1$H NMR: (400 MHz, DMSO-d$_6$) δ ppm 10.78 (s, 1H), 8.20 (d, J = 2.0 Hz, 1H), 7.98 (d, J = 8.4 Hz, 1H), 7.67 (dd, J = 2.4, 8.4 Hz, 1H), 4.90-4.85 (m, 1H), 2.67-2.63 (m, 2H), 1.73 (d, J = 6.8 Hz, 3H), 1.49-1.44 (m, 2H), 0.71-0.64 (m, 1H), 0.41-0.37 (m, 2H), 0.05-0.01 (m, 2H). | — | 297 |

Intermediate 49

2-bromo-N-(2-cyclopropyloxazolo[4,5-b]pyridin-5-yl)propanamide

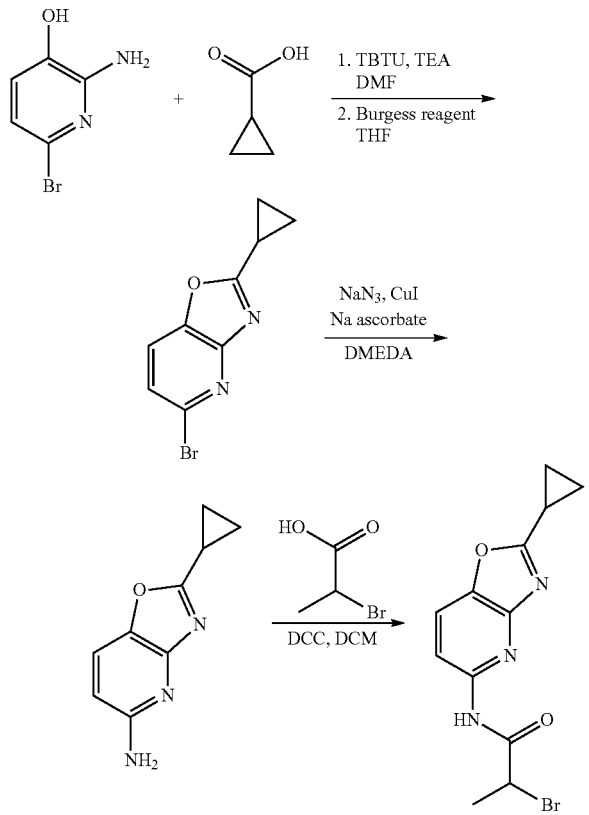

Step 1

To TBTU (0.308 g, 0.96 mmol, 1.2 eq) and TEA (0.23 g, 2.23 mmol, 2.8 eq) in DMF (5 mL) were added 2-amino-6-bromopyridin-3-ol (150 mg, 0.80 mmol, 1.0 eq) and cyclopropanecarboxylic acid (69 mg, 0.80 mmol, 1.0 eq). The mixture was stirred at 25° C. for 15 h, quenched with water (50 mL) and extracted with ethyl acetate (50 mL×2). The organic phases were combined, dried over $Na_2SO_4$, concentrated and purified over a silica gel column, eluting with ethyl acetate:petroleum ether (1:10) to give 2-amino-6-bromopyridin-3-yl cyclopropanecarboxylate (160 mg, purity: 87%, yield: 80%) as a light yellow oil. LCMS: (ES, m/z): 257 [M+H]$^+$. $^1$H NMR: (300 MHz, CD$_3$OD) δ 7.18 (d, J=8.1 Hz, 1H), 6.76 (d, J=8.1 Hz, 1H), 2.02-1.94 (m, 1H), 1.14-1.08 (m, 4H).

Step 2

In a sealed tube 2-amino-6-bromopyridin-3-yl cyclopropanecarboxylate (1.5 g, 5.88 mmol, 1.0 eq), THF (15 mL) and Burgess reagent (6.99 g, 29.4 mmol, 5.0 eq) were stirred for 1.0 h at 130° C. with microwaving. The reaction was quenched with water (100 mL) and extracted with ethyl acetate (100 mL×2). The organic phases were combined, dried over $Na_2SO_4$, concentrated and purified over a silica gel column, eluting with ethyl acetate:petroleum ether (1:20) to give 5-bromo-2-cyclopropyloxazolo[4,5-b]pyridine (0.24 g, purity: 80%, yield: 17%) as a light yellow solid. LCMS: (ES, m/z): 239 [M+H]$^+$. $^1$H NMR: (300 MHz, CD$_3$OD) δ ppm 7.89 (d, J=12.4 Hz, 1H), 7.53 (d, J=8.4 Hz, 1H), 2.35-2.30 (m, 1H), 1.35-1.31 (m, 4H).

Step 3

To 5-bromo-2-cyclopropyloxazolo[4,5-b]pyridine (280 mg, 1.18 mmol, 1.0 eq) in EtOH (7 mL) were added H$_2$O (3 mL), N,N-dimethylethylenediamine (31 mg, 0.35 mmol, 0.3 eq), sodium ascorbate (117 mg, 0.59 mmol, 0.5 eq), NaN$_3$ (85 mg, 1.30 mmol, 1.1 eq) and CuI (45 mg, 0.24 mmol, 0.2 eq). The mixture was stirred for 2 h at 25° C., quenched with water (50 mL) and extracted with ethyl acetate (50 mL×2). The organic phases were combined, dried over Na$_2$SO$_4$, concentrated and purified over a silica gel column, eluting with methanol:dichloromethane (1:20) to give 2-cyclopropyloxazolo[4,5-b]pyridin-5-amine (90 mg, purity: 80%) as a light yellow oil. LCMS: (ES, m/z): 176 [M+H]$^+$. $^1$H NMR: (400 MHz, CD$_3$OD) δ ppm 7.63 (d, J=8.7 Hz, 1H), 6.52-6.49 (m, 1H), 2.25-2.20 (m, 1H), 1.26-1.20 (m, 4H).

Step 4

To 2-cyclopropyloxazolo[4,5-b]pyridin-5-amine (100 mg, 0.57 mmol, 1.0 eq) in DCM (8 mL) were added 2-bromopropanoic acid (95 mg, 0.63 mmol, 1.1 eq), DCC (141 mg, 0.68 mmol, 1.2 eq) and DMAP (7.0 mg, 0.057 mmol, 0.1 eq). The mixture was stirred for 2 h, quenched with water (50 mL) and extracted with DCM (50 mL×2). The organic phases were combined, dried over Na$_2$SO$_4$, concentrated and purified over a silica gel column, eluting with ethyl acetate:petroleum ether (1:10) to give 2-bromo-N-(2-cyclopropyloxazolo[4,5-b]pyridin-5-yl)propanamide (170 mg, purity: 90%, yield: 96%) as a white solid. LCMS: (ES, m/z): 310 [M+H]$^+$. $^1$H NMR: (300 MHz, CD$_3$OD) δ 8.18-8.15 (m, 1H), 7.95 (d, J=9.2 Hz, 1H), 4.79-4.74 (m, 1H), 2.33-2.30 (m, 1H), 1.90-1.82 (m, 3H), 1.40-1.30 (m, 2H), 1.20-1.12 (m, 2H).

Intermediate 50

2-bromo-N-(5-(cyclohexylmethyl)pyridin-2-yl)propanamide

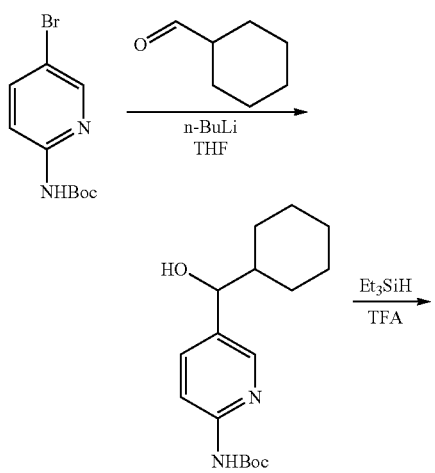

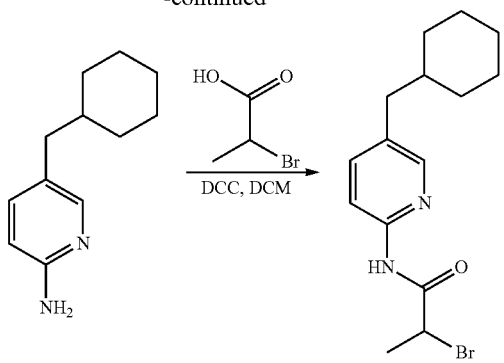

Step 1

To tert-butyl (5-bromopyridin-2-yl)carbamate (2 g, 7.32 mmol, 1.0 eq) in THF (50 mL) at −78° C. was added n-butyllithium (8.79 mL, 21.97 mmol, 3.0 eq, 2.5 M in hexanes), dropwise, over 15 min. After 30 min, cyclohexanecarbaldehyde (1.232 g, 10.98 mmol, 1.5 eq) was added dropwise, and the resulting mixture was allowed to warm to room temperature. After 2 h, the reaction was quenched with water (100 mL) and extracted with ethyl acetate (50 mL×3). The combined organic extracts were washed with brine (100 mL), dried over sodium sulfate, concentrated and purified over a silica gel column, eluting with ethyl acetate in petroleum ether (0-40%, in 15 min) to give tert-butyl (5-(cyclohexyl(hydroxy)methyl)pyridin-2-yl)carbamate (1.57 g, purity: 95%, yield: 67%) as a white solid. LCMS: (ES, m/z): 307 [M+H]$^+$, retention time 1.135 minutes, LCMS Method 36. $^1$H NMR: (400 MHz, DMSO-$d_6$) δ 9.69 (s, 1H), 8.10 (d, J=2.2 Hz, 1H), 7.73 (d, J=8.5 Hz, 1H), 7.63-7.57 (m, 1H), 5.12 (d, J=4.4 Hz, 1H), 4.27-4.18 (m, 1H), 1.89-1.79 (m, 1H), 1.73-1.54 (m, 3H), 1.47 (s, 9H), 1.45-1.27 (m, 2H), 1.21-1.01 (m, 3H), 0.99-0.81 (m, 2H).

Step 2

To tert-butyl (5-(cyclohexyl(hydroxy)methyl)pyridin-2-yl)carbamate (1.57 g, 5.12 mmol, 1.0 eq) in triethylsilane (7 mL, 43.8 mmol, 8.6 eq) was added 2,2,2-trifluoroacetic acid (7 mL, 94 mmol, 18.4 eq) at 0° C., and the resulting mixture was stirred at room temperature. After 15 h, the reaction was concentrated, and the residue was poured into ice water (100 mL) and extracted with ethyl acetate (80 mL×3). The organic phases were washed with saturated aqueous NaHCO$_3$ (100 mL×3), dried over anhydrous Na$_2$SO$_4$, filtered, concentrated and purified over a silica gel column, eluting with ethyl acetate in petroleum ether (0-55%, in 10 min) to give 5-(cyclohexylmethyl)pyridin-2-amine (360 mg, purity: 95%, yield: 35%) as a white solid. LCMS: (ES, m/z): 191 [M+H]$^+$, retention time 1.155 minutes, LCMS Method 30. (400 MHz, DMSO-$d_6$) δ 7.67 (d, J=2.4 Hz, 1H), 7.19-7.12 (m, 1H), 6.37 (d, J=8.4 Hz, 1H), 5.64 (s, 2H), 2.25 (d, J=7.0 Hz, 2H), 1.72-1.51 (m, 5H), 1.41-1.29 (m, 1H), 1.24-1.04 (m, 3H), 0.95-0.75 (m, 2H).

Step 3

To 5-(cyclohexylmethyl)pyridin-2-amine (200 mg, 1.05 mmol, 1.0 eq) in DCM (10 mL) were added 2-bromopropanoic acid (193 mg, 1.26 mmol, 1.2 eq), DCC (434 mg, 2.10 mmol, 2.0 eq) and DMAP (12.84 mg, 0.11 mmol, 0.1 eq). The reaction was stirred for 2 h, filtered, concentrated and purified over a silica gel column, eluting with ethyl acetate in petroleum ether (0-16%, in 10 min) to give 2-bromo-N-(5-(cyclohexylmethyl)pyridin-2-yl)propanamide (340 mg, purity: 93%, yield: 92%) as a white solid. LCMS: (ES, m/z): 325 [M+H]$^+$, retention time 1.385 minutes, LCMS Method 30. $^1$HNMR (400 MHz, DMSO-$d_6$) δ 10.79 (s, 1H), 8.13 (d, J=2.3 Hz, 1H), 7.99 (d, J=8.5 Hz, 1H), 7.65-7.58 (m, 1H), 4.91-4.81 (m, 1H), 2.44 (d, J=7.0 Hz, 2H), 1.74 (d, J=6.7 Hz, 3H), 1.69-1.54 (m, 5H), 1.54-1.42 (m, 1H), 1.20-1.08 (m, 3H), 0.99-0.81 (m, 2H).

Intermediates 51-53 were synthesized in an analogous manner.

| Int. | Name | Structure | $^1$H NMR | LC: retention time (min); LC/MS Method of analysis | MS (M + H)$^+$ |
|---|---|---|---|---|---|
| 51 | 2-bromo-N-(5-(cyclobutylmethyl)pyridin-2-yl)propanamide | 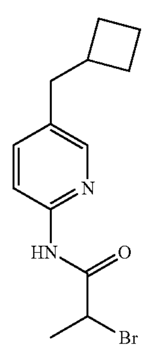 [SMILES: CC(Br)C(=O)Nc1ccc(CC2CCC2)cn1] | — | 1.196; LCMS Method 29 | 297 |

| Int. | Name | Structure | $^1$H NMR | LC: retention time (min); LC/MS Method of analysis | MS $(M + H)^+$ |
|---|---|---|---|---|---|
| 52 | 2-bromo-N-(5-(cyclopentylmethyl)pyridin-2-yl)propanamide | 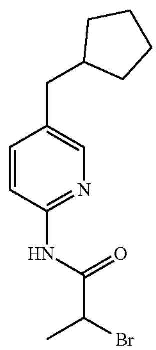 [SMILES: CC(Br)C(=O)Nc1ccc(CC2CCCC2)cn1] | $^1$H NMR: (400 MHz DMSO-$d_6$) δ ppm 10.78 (s, 1H), 8.17 (d, J = 2.4 Hz, 1H), 7.99 (d, J = 8.4 Hz, 1H), 7.70-7.59 (m, 1H), 4.92-4.81 (m, 1H), 2.55 (d, J = 7.5 Hz, 2H), 2.10-2.00 (m, 1H), 1.74 (d, J = 6.7 Hz, 3H), 1.67-1.54 (m, 4H), 1.53-1.41 (m, 2H), 1.15-1.09 (m, 2H). | 1.027; LCMS Method 31 | 311 |
| 53 | 2-bromo-N-(5-(cyclopropylmethyl)pyridin-2-yl)propanamide | 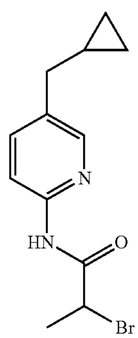 [SMILES: CC(Br)C(=O)Nc1ccc(CC2CC2)cn1] | $^1$H NMR: (400 MHz DMSO-$d_6$) δ ppm 10.79 (s, 1H), 8.23 (d, J = 2.4 Hz, 1H), 8.00 (d, J = 8.7 Hz, 1H), 7.73 (dd, J = 8.7, 2.4 Hz, 1H), 4.88 (m, 1H), 2.51-2.48 (m, 1H), 1.74 (d, J = 6.7 Hz, 4H), 1.12-0.83 (m, 1H), 0.54-0.42 (m, 2H), 0.33-0.15 (m, 2H). | — | 283 |

Intermediate 54

2-bromo-N-6-phenoxypyridazin-3-yl)propanamide

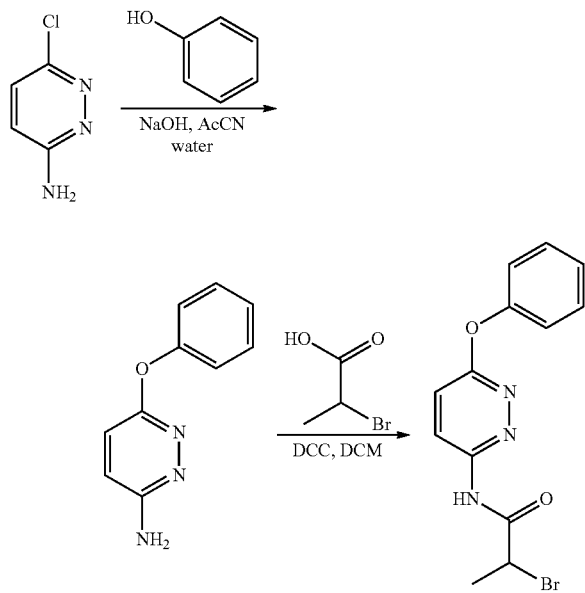

Step 1

To 6-chloropyridazin-3-amine (1.00 g, 7.75 mmol, 1.0 eq) in acetonitrile (10 mL) was added phenol (1.82 g, 19.38 mmol, 2.5 eq), followed by the addition of sodium hydroxide (0.93 g, 23.25 mmol, 3.0 eq) in water (5 mL). The resulting mixture was stirred 3 days at 120° C., poured into water (200 mL) and extracted with ethyl acetate (200 mL×3). The combined organic extracts were dried over sodium sulfate, concentrated and purified over a silica gel column, eluting with petroleum ether in ethyl acetate (0-50%, in 30 min) to give 6-phenoxypyridazin-3-amine (400 mg, yield: 28%, purity: 85%) as a yellow oil. LCMS: (ES, m/z): 188 [M+H]$^+$. $^1$H NMR: (300 MHz, CDCl$_3$) δ 7.42-7.36 (m, 2H), 7.25-7.14 (m, 3H), 7.06-6.95 (m, 2H), 4.94 (br, 2H).

Step 2

To 6-phenoxypyridazin-3-amine (400 mg, 2.14 mmol, 1.0 eq) and 2-bromopropanoic acid (389 mg, 2.56 mmol, 1.2 eq) DCM (10 mL) were added DCC (881 mg, 4.28 mmol, 2.0 eq) and DMAP (26 mg, 0.21 mmol, 0.1 eq). After 1 h the reaction was filtered, concentrated and purified over a silica gel column, eluting with ethyl acetate in petroleum ether (0-30%) to give 2-bromo-N-(6-phenoxypyridazin-3-yl)propanamide (300 mg, yield: 44%, purity: 95%) as a yellow solid. LCMS: (ES, m/z): 322 [M+H]$^+$. $^1$HNMR (400 MHz, DMSO-$d_6$) δ 11.51 (S, 1H), 8.71 (d, J=9.6 Hz, 1H), 7.51-7.45 (m, 2H), 7.36-7.30 (m, 2H), 7.24-7.21 (m, 2H), 4.99-4.93 (m, 1H), 1.61 (d, J=6.6 Hz, 3H).

Intermediates 55-64 were synthesized in an analogous manner, in some cases using cesium carbonate, CuI and dimethylglycine in dioxane in Step 1.

| Int. | Name | Structure | ¹H NMR | LC: retention time (min); LC/MS Method of analysis | MS (M + H)⁺ |
|---|---|---|---|---|---|
| 55 | 2-bromo-N-(6-(o-tolyloxy)pyridazin-3-yl)propanamide | 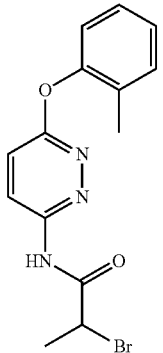 [SMILES: Cc1ccccc1Oc1ccc(NC(=O)C(C)Br)nn1] | ¹H NMR: (400 MHz DMSO-$d_6$) δ ppm 11.39 (s, 1H), 8.37 (d, 1 = 9.5 Hz, 1H), 7.51 (d, J = 9.5 Hz, 1H), 7.38-7.33 (m, 1H), 7.30-7.25 (m, 1H), 7.22-7.17 (m, 1H), 7.14-7.10 (m, 1H), 4.94-4.83 (m, 1H), 2.12 (s, 3H), 1.76 (d, J = 6.7 Hz, 3H). | 1.045; LC/MS Method 31 | 336 |
| 56 | 2-bromo-N-(5-phenoxypyrazin-2-yl)propanamide | 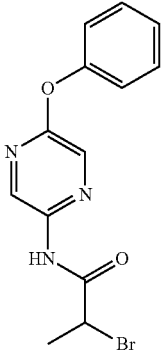 [SMILES: CC(Br)C(=O)Nc1cnc(Oc2ccccc2)cn1] | ¹H NMR: (400 MHz CDCl₃) δ ppm 9.08 (d, J = 0.98 Hz, 1H), 8.60 (br s, 1H), 8.14 (d, J = 1.47 Hz, 1H), 7.41-7.51 (m, 2H), 7.23-7.32 (m, 1H), 7.14-7.20 (m, 2H), 4.54-4.67 (m, 1H), 2.00 (d, J = 6.85 Hz, 4H). | 0.98; LC/MS Method 3 | 322 |
| 57 | 2-bromo-N-(6-(4-fluorophenoxy)pyridazin-3-yl)propanamide | 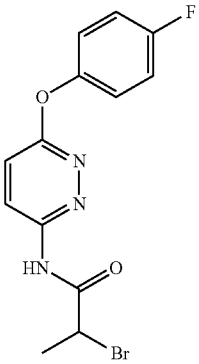 [SMILES: CC(Br)C(=O)Nc1ccc(Oc2ccc(F)cc2)nn1] | ¹H NMR: (400 MHz CD₃OD) δ ppm 8.47-8.51 (m, 2H), 7.77 (d, J = 10 Hz, 1H), 7.42 (d, J = 10 Hz, 1H), 7.17-7.21 (m, 2H), 4.44 (q, J = 8.0 Hz, 1H), 1.76 (d, J = 8.0 Hz, 3H). | 0.94; LC/MS Method 3 | 341 |
| 58 | 2-bromo-N-(5-(4-fluorophenoxy)pyrazin-2-yl)propanamide | 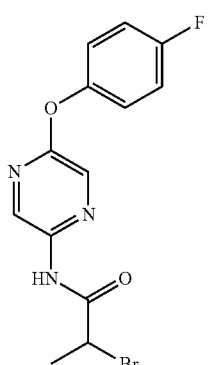 | ¹H NMR: (400 MHz CDCl₃) δ ppm 9.04 (d, J = 1.22 Hz, 1H), 8.51 (br. s., 1H), 8.14 (d, J = 1.47 Hz, 1H), 7.14-7.15 (m, 2H), 7.10-7.13 (m, 2H), 4.58 (q, J = 7.09 Hz, 1 H), 1.99 (d, J = 7.09 Hz, 3H). | 1.01; LC/MS Method 3 | 340 |

-continued

| Int. | Name | Structure | ¹H NMR | LC: retention time (min); LC/MS Method of analysis | MS (M + H)⁺ |
|---|---|---|---|---|---|
| 59 | 2-bromo-N-(5-(2,4-difluorophenoxy)-3-fluoropyridin-2-yl)propanamide | 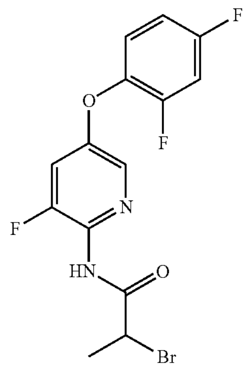 [SMILES: CC(Br)C(=O)Nc1ncc(Oc2ccc(F)cc2F)cc1F] | ¹H NMR (400 MHz, METHANOL-$d_4$) δ 8.02 (d, J = 2.4 Hz, 1H), 7.42-7.32 (m, 2H), 7.23 (ddd, J = 10.9, 8.2, 2.9 Hz, 1H), 7.13-7.04 (m, 1H), 4.72 (br d, J = 5.9 Hz, 1H), 1.86 (d, J = 6.8 Hz, 3H). | 0.99; LC/MS Method 3 | 375 |
| 60 | 2-bromo-N-(3-fluoro-5-(4-fluorophenoxy)pyridin-2-yl)propanamide | 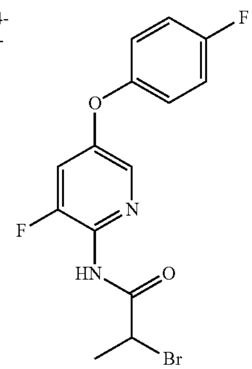 | ¹H NMR (400 MHz, METHANOL-$d_4$) δ 7.99 (d, J = 2.4 Hz, 1H), 7.34 (dd, J = 10.5, 2.7 Hz, 1H), 7.27-7.07 (m, 4H), 4.77-4.64 (m, 1H), 1.84 (d, J = 6.8 Hz, 3H). | 0.97; LC/MS Method 3 | 357 |
| 61 | 2-bromo-N-(5-(2,6-difluorophenoxy)pyrazin-2-yl)propanamide | 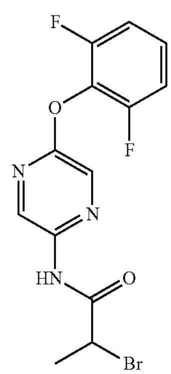 [SMILES: CC(Br)C(=O)Nc1cnc(Oc2c(F)cccc2F)cn1] | ¹H NMR (400 MHz, CHLOROFORM-d) δ ppm 9.00 (s, 1 H) 8.54 (br s, 1 H) 8.30 (s, 1 H) 7.17-7.27 (m, 1 H) 6.97-7.12 (m, 2 H) 4.58 (q, J = 6.85 Hz, 1 H) 1.99 (d, J = 6.85 Hz, 3 H). | 1.04; LC/MS Method 3 | 358 |
| 62 | 2-bromo-N-(5-(2,3,4-trifluorophenoxy)pyrazin-2-yl)propanamide | 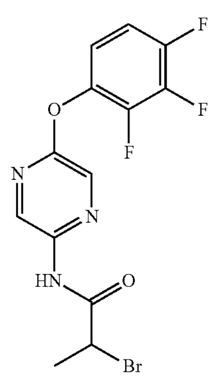 [SMILES: CC(Br)C(=O)Nc1cnc(Oc2ccc(F)c(F)c2F)cn1] | ¹H NMR (400 MHz, CHLOROFORM-d) δ ppm 9.00 (d, J = 1.47 Hz, 1 H) 8.55 (br s, 1 H) 8.24 (d, J = 1.47 Hz, 1 H) 6.96-7.09 (m, 2 H) 4.58 (q, J = 7.17 Hz, 1 H) 1.99 (d, J = 7.34 Hz, 3 H). | 1.10; LCMS Method 3 | 376 |

| Int. | Name | Structure | ¹H NMR | LC: retention time (min); LC/MS Method of analysis | MS (M + H)⁺ |
|---|---|---|---|---|---|
| 63 | 2-bromo-N-(5-(2,4,6-trifluorophenoxy)pyrazin-2-yl)propanamide | 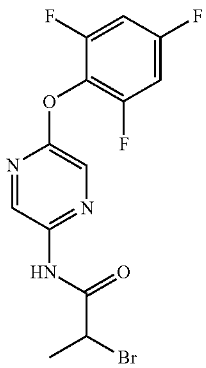 [SMILES: CC(Br)C(=O)Nc1cnc(Oc2c(F)cc(F)cc2F)cn1] | ¹H NMR (400 MHz, CHLOROFORM-d) δ ppm 8.99 (s, 1 H) 8.55 (br s, 1 H) 8.24-8.35 (m, 1 H) 6.83 (br t, J = 7.83 Hz, 2 H) 4.58 (q, J = 6.85 Hz, 1 H) 1.99 (d, J = 7.34 Hz, 3 H). | 1.10; LCMS Method 3 | 376 |
| 64 | 2-bromo-N-(5-(2,4,5-trifluorophenoxy)pyrazin-2-yl)propanamide | 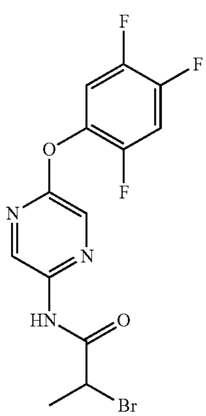 [SMILES: CC(Br)C(=O)Nc1cnc(Oc2cc(F)c(F)cc2F)cn1] | ¹H NMR (400 MHz, CHLOROFORM-d) δ ppm 9.02 (d, J = 0.98 Hz, 1 H) 8.64 (br s, 1 H) 8.22 (d, J = 1.47 Hz, 1 H) 7.05-7.21 (m, 2 H) 4.59 (q, J = 7.17 Hz, 1 H) 1.99 (d, J = 7.34 Hz, 3 H). | 1.09; LCMS Method 3 | 376 |

Intermediate 65

(R)-2-bromo-N-(5-(2,4-difluorophenoxy)pyrazin-2-yl)propanamide

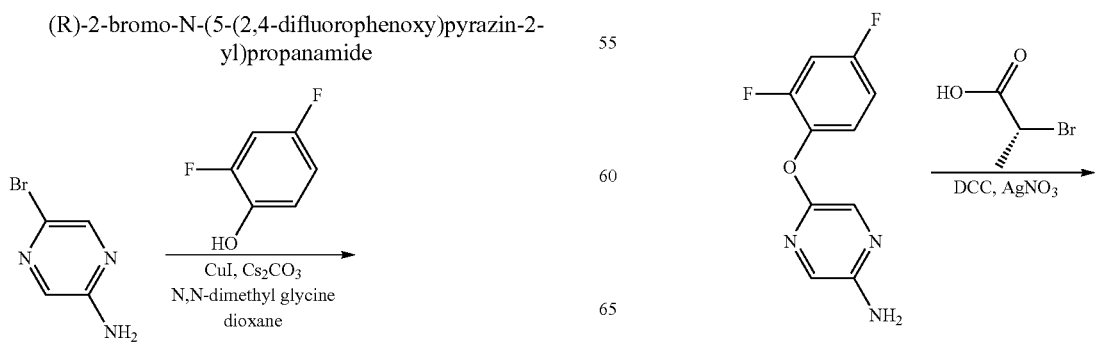

-continued

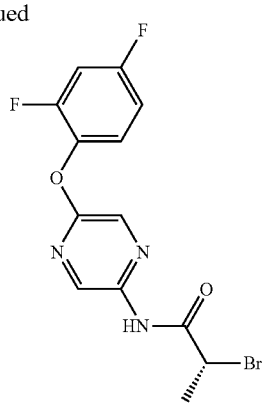

Step 1

A mixture of 5-bromopyrazin-2-amine (33.0 g, 190 mmol), 2,4-difluorophenol (29.6 g, 228 mmol), dimethylglycine (3.91 g, 37.9 mmol), cesium carbonate (93.0 g, 284 mmol) and copper(I) iodide (7.22 g, 37.9 mmol) in dioxane (600 mL) was heated at 110° C. After 2 h, the mixture was concentrated, diluted with EtOAc, washed with sat'd aq sodium carbonate solution (2×100 mL) and brine (1×100 mL), dried over magnesium sulfate, filtered and concentrated. The resulting residue was dissolved in MeCN (200 mL), water was added (500 mL), and the mixture was stirred at rt for 1 h. The resulting solid precipitate was collected by filtration, dissolved in EtOAc concentrated onto silica gel and purified by column chromatography, eluting with 0-100% ethyl acetate in heptane give 17.0 g (purity: 100%, yield: 40%) of 5-(2,4-difluorophenoxy)pyrazin-2-amine as a white solid. LCMS rt=0.72 min, Method 5, (ES, m/z) 224 [M+H]$^+$. $^1$H NMR: (400 MHz, DMSO-d$_6$) δ ppm 7.92 (d, J=1.5 Hz, 1H), 7.45-7.38 (m, 2H), 7.28 (td, J=9.2, 5.6 Hz, 1H), 7.13-7.05 (m, 1H), 6.16 (s, 2H).

Step 2

A mixture of 5-(2,4-difluorophenoxy)pyrazin-2-amine (40 g, 179 mmol), (R)-2-bromopropanoic acid (32.9 g, 215 mmol) and silver nitrate (4.57 g, 26.9 mmol) in DCM (700 mL) was treated portionwise with DCC (44.4 g, 215 mmol), maintaining a temperature between 15 and 20° C. using a cold water bath. The resulting mixture was stirred at rt overnight, filtered and loaded onto a silica gel column, eluting with 5-40% ethyl acetate in heptane to give a yellow solid which was triturated with heptane to give 43 g (purity: 97%, yield: 67%) (R)-2-bromo-N-(5-((5-chloropyridin-2-yl)oxy)pyridin-2-yl)propanamide as a pale yellow solid. LCMS (ES, m/z) 358 [M+H]$^+$, rt=1.03 min, Method 5. Analytical Chiral HPLC (Chiral IG 150×4.6 mm, 70:30 EtOH:Heptane): 3.43 min (desired product, major isomer) and 4.35 min (minor isomer), % ee=92%. $^1$H NMR: (400 MHz, DMSO-d$_6$) δ 11.16 (s, 1H), 8.80 (d, J=1.0 Hz, 1H), 8.47 (d, J=1.5 Hz, 1H), 7.58-7.36 (m, 2H), 7.28-7.06 (m, 1H), 4.86 (q, J=6.8 Hz, 1H), 1.75 (d, J=6.8 Hz, 3H).

Intermediate 66

Cyclopentyl 6-(2-bromopropanamido)nicotinate

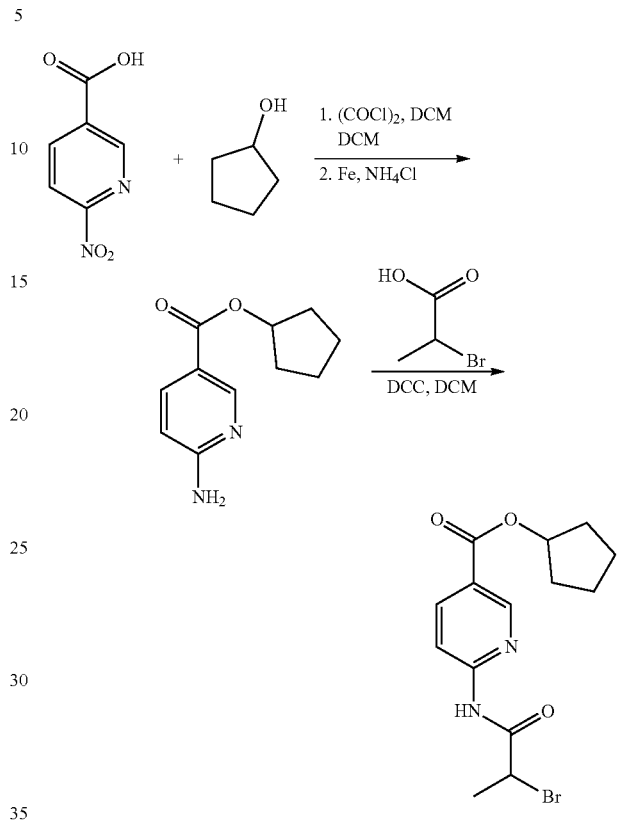

Step 1

To 6-nitronicotinic acid (1.00 g, 5.95 mmol, 1.0 eq) in DCM (30 mL) at 0° C. was added oxalyl chloride (1.50 g, 11.90 mmol, 2.0 eq) and DMF (5 drops), dropwise. The reaction was stirred at room temperature for 30 min and concentrated to give the 6-nitronicotinoyl chloride. Cyclopentanol (1.00 g, 11.62 mmol, 2.0 eq) and triethylamine (18.0 g, 17.85 mmol, 3.0 eq) in DCM (40 mL) were stirred at 0° C., and the 6-nitronicotinoyl chloride in dichloromethane (20 mL) was added dropwise. The reaction was stirred at room temperature for 2 h, poured into water (200 mL) and extracted with dichloromethane (200 mL×3). The combined organic extracts were washed with brine (500 mL), dried over sodium sulfate, concentrated and purified over a silica gel column, eluting with ethyl acetate in petroleum ether (0-30%) to give cyclopentyl 6-nitronicotinate (430 mg, yield: 28%, purity: 100%) as a white solid. $^1$H NMR: (400 MHz, CDCl$_3$) δ 9.20 (d, J=2.0 Hz, 1H), 8.62 (d, J=2.4, 8.4 Hz, 1H), 8.32 (d, J=8.4 Hz, 1H), 5.53-5.49 (m, 1H), 2.09-1.99 (m, 2H), 1.94-1.80 (m, 4H), 1.77-1.70 (m, 2H).

Step 2

To cyclopentyl 6-nitronicotinate (300 mg, 1.27 mmol, 1.0 eq) in EtOH (30 mL) and water (5 mL) were added Fe (356 mg, 6.36 mmol, 5.0 eq) and NH$_4$Cl (343 mg, 6.36 mmol, 5.0 eq). The reaction was stirred at 80° C. for 2 h, filtered and concentrated to give of cyclopentyl 6-aminonicotinate (250 mg, yield: 95%, purity: 98%) as a white solid, which was used without purification. LCMS: (ES, m/z): 207 [M+H]$^+$. $^1$H NMR: (300 MHz, CDCl$_3$) δ 8.50 (d, J=3.6 Hz, 1H), 7.95 (d, J=2.0, 8.8 Hz, 1H), 6.61 (d, J=8.8 Hz, 1H), 5.36-5.32 (m, 1H), 2.01-1.93 (m, 2H), 1.84-1.79 (m, 4H), 1.73-1.65 (m, 2H).

Step 3

To 2-bromopropanoic acid (369 mg, 2.42 mmol, 2.0 eq) in DCM (30 mL) were added DCC (500 mg, 2.42 mmol, 2.0 eq), DMAP (15 mg, 0.12 mmol, 0.1 eq) and cyclopentyl 6-aminonicotinate (250 mg, 1.21 mmol, 1.0 eq). After 16 h, the reaction was filtered, concentrated and purified by prep-TLC (ethyl acetate:petroleum ether=1:5) to give cyclopentyl 6-(2-bromopropanamido)nicotinate (290 mg, yield: 70%, purity: 97%) as a white solid. LCMS: (ES, m/z): 341 [M+H]$^+$. $^1$H NMR: (400 MHz, CD$_3$OD) δ 8.92-8.89 (m, 1H), 8.34-8.25 (m, 2H), 5.47-5.32 (m, 1H), 4.65-4.54 (m, 1H), 1.97 (d, J=6.9 Hz, 3H), 1.93-1.79 (m, 4H), 1.75-1.66 (m, 4H).

Intermediates 67-68 were synthesized in an analogous manner.

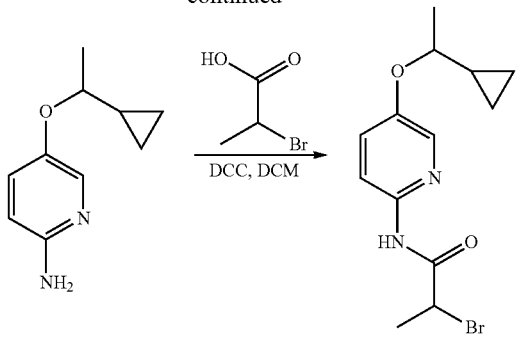

Step 1

To 5-fluoro-2-nitropyridine (500 mg, 3.52 mmol, 1.0 eq) and 1-cyclopropylethanol (546 mg, 6.34 mmol, 1.8 eq) in DMF (10 mL) was added cesium carbonate (2.29 g, 7.04 mmol, 2.0 eq), and the reaction was heated to 80° C. After

| Int. | Name | Structure | $^1$H NMR | LC: retention time (min); LC/MS Method of analysis | MS (M + H)$^+$ |
|------|------|-----------|-----------|---------------------------------------------------|----------------|
| 67 | cyclopropyl 6-(2-bromopropanamido)nicotinate | (structure) | — | — | 313 |
| 68 | cyclobutyl 6-(2-bromopropanamido)nicotinate | (structure) | $^1$H NMR: (400 MHz CDCl$_3$) δ ppm 8.95-8.94 (m, 1H), 8.86-8.85 (m, 1H), 8.36-8.33 (m, 1H), 8.29-8.26 (m, 1H), 5.29-5.21 (m, 1H), 4.59-4.52 (m, 1H), 2.52-2.45 (m, 2H), 2.29-2.19 (m, 2H), 1.98 (d, J = 7.2 Hz, 3H), 1.94-1.85 (m, 1H), 1.78-1.67 (m, 1H). | — | 327 |

Intermediate 69

2-bromo-N-(5-(1-cyclopropylethoxy)pyridin-2-yl)propanamide

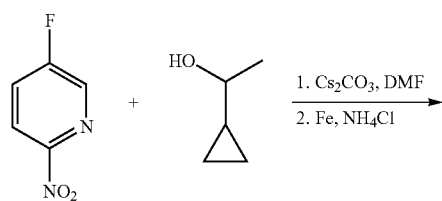

2 h, the mixture was quenched with water (100 mL) and extracted with ethyl acetate (100 mL×3). The combined extracts were dried over sodium sulfate, concentrated and purified over a silica gel column, eluting with ethyl acetate: petroleum ether (1:3) to give 5-(1-cyclopropylethoxy)-2-nitropyridine (400 mg, yield: 55%, purity: 84%) as a yellow oil. LCMS: (ES, m/z): 209 [M+H]$^+$. $^1$H NMR: (400 MHz, DMSO-d$_6$) δ 8.31-8.29 (m, 2H), 7.71 (d, J=2.8, 8.8 Hz, 1H), 4.33-4.26 (m, 1H), 1.36 (d, J=6.0 Hz, 3H), 1.21-1.14 (m, 1H), 0.57-0.52 (m, 2H), 0.43-0.32 (m, 2H).

Step 2

To 5-(1-cyclopropylethoxy)-2-nitropyridine (380 mg, 1.83 mmol, 1.0 eq) in methanol (8 mL) and water (2 mL) were added Fe (1.23 g, 21.92 mmol, 12.0 eq) and NH$_4$Cl (198 mg, 3.65 mmol, 2.0 eq), and the mixture was heated to 80° C. After 3 h, the reaction was filtered, concentrated and purified over a silica gel column, eluting with ethyl acetate: petroleum ether (1:1) to give 5-(1-cyclopropylethoxy)pyridin-2-amine (250 mg, yield: 78%, purity: 97%) as a yellow solid. LCMS: (ES, m/z): 179 [M+H]$^+$. $^1$H NMR: (300 MHz, DMSO-d$_6$) δ 7.59 (d, J=2.7 Hz, 1H), 7.06 (dd, J=2.7, 8.7 Hz, 1H), 6.36 (d, J=9.0 Hz, 1H), 5.45 (s, 2H), 3.59-3.50 (m, 1H), 1.20 (d, J=6.0 Hz, 3H), 0.98-0.90 (m, 1H), 0.44-0.41 (m, 2H), 0.26-0.18 (m, 2H).

Step 3

To 5-(1-cyclopropylethoxy)pyridin-2-amine (230 mg, 1.28 mmol, 1.0 eq) in DCM (5 mL) were added 2-bromopropanoic acid (200 mg, 1.3 mmol, 1.0 eq), DMAP (16.0 mg, 0.13 mmol, 0.1 eq) and DCC (320 mg, 1.55 mmol, 1.2 eq). After 2 h, the mixture was poured into water (100 mL) and extracted with ethyl acetate (100 mL×3). The combined organic extracts were dried over sodium sulfate, concentrated and purified over a silica gel column, eluting with ethyl acetate:petroleum (1:4) to give 2-bromo-N-(5-(1-cyclopropylethoxy)pyridin-2-yl)propanamide (280 mg, yield: 70%, purity: 86%) as a yellow solid. LCMS: (ES, m/z): 313 [M+H]$^+$. $^1$H NMR: (400 MHz, CD$_3$OD) δ 7.98-7.95 (m, 2H), 7.38 (dd, J=3.0, 9.3 Hz, 1H), 4.74-4.67 (m, 1H), 3.93-3.84 (m, 1H), 1.81 (d, J=6.6 Hz, 3H), 1.36 (d, J=6.0 Hz, 3H), 1.12-1.04 (m, 1H), 0.56-0.51 (m, 2H), 0.37-0.26 (m, 2H).

Intermediates 70-82, 70, 71, and 74-76 with nitro reduction by Pd/C-catalyzed hydrogenation) were synthesized in an analogous manner from 5-halo-2-nitropyridines.

| Int. | Name | Structure | $^1$H NMR | LC: retention time (min); LC/MS Method of analysis | MS (M + H)$^+$ |
|---|---|---|---|---|---|
| 70 | 2-bromo-N-(5-(4-fluorophenoxy)pyridin-2-yl)propanamide | 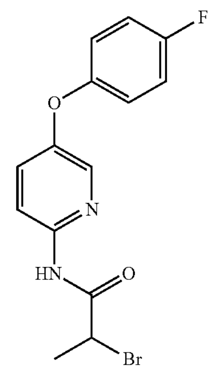 [SMILES: CC(Br)C(=O)Nc1ccc(Oc2ccc(F)cc2)cn1] | $^1$H NMR: (400 MHz DMSO-d$_6$) δ ppm 10.94 (s, 1H), 8.16 (d, J = 2.9 Hz, 1H), 8.11 (d, J = 9.1 Hz, 1H), 7.57-7.50 (m, 1H), 7.28-7.20 (m, 2H), 7.14-7.06 (m, 2H), 4.93-4.83 (m, 1H), 1.74 (d, J = 6.7 Hz, 3H). | 1.096; LC/MS Method 31 | 339 |
| 71 | 2-bromo-N-(5-(2,4-difluorophenoxy)pyridin-2-yl)propanamide | 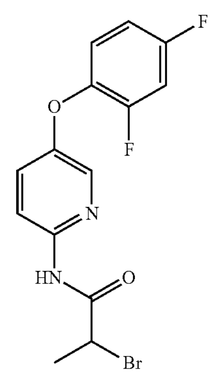 [SMILES: CC(Br)C(=O)Nc1ccc(Oc2ccc(F)cc2F)cn1] | $^1$H NMR: (400 MHz DMSO-d$_6$) δ ppm 10.94 (s, 1H), 8.18-8.17 (m, 1H), 8.09 (d, J = 8.0 Hz, 1H), 7.55-7.49 (m, 2H), 7.36-7.30 (m, 1H), 7.16-7.13 (m, 1H), 4.89-4.84 (m, 1H), 1.74 (d, J = 8.0 Hz, 3H). | 0.660; LCMS Method 39 | 357 |
| 72 | 2-bromo-N-(5-phenoxypyridin-2-yl)propanamide | 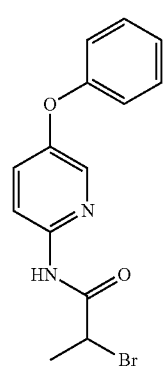 [SMILES: CC(Br)C(=O)Nc1ccc(Oc2ccccc2)cn1] | $^1$H NMR: (400 MHz DMSO-d$_6$) δ ppm 10.93 (s, 1H), 8.17 (d, J = 2.9 Hz, 1H), 8.12 (d, J = 9.0 Hz, 1H), 7.56 (dd, J = 9.0, 3.0 Hz, 1H), 7.45-7.36 (m, 2H), 7.19-7.12 (m, 1H), 7.08-7.01 (m, 2H), 4.91-4.86 (m, 1H), 1.75 (d, J = 6.7 Hz, 3H). | — | 321 |

-continued

| Int. | Name | Structure | $^1$H NMR | LC: retention time (min); LC/MS Method of analysis | MS (M + H)$^+$ |
|---|---|---|---|---|---|
| 73 | 2-bromo-N-(5-(4-cyanophenoxy)pyridin-2-yl)propanamide | 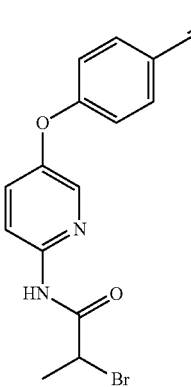 | $^1$H NMR: (400 MHz DMSO-d$_6$) δ ppm 10.99 (s, 1H), 8.27-8.29 (m, 1H), 8.18 (d, J = 10.4 Hz, 1H), 7.71-7.83 (m, 2H), 7.71 (dd, J = 10.4, 2.0 Hz, 1H), 7.14-7.18 (M, 2H), 4.89 (q, J = 9.6 Hz, 1H), 1.75 (d, 9.6 Hz, 3H). | 0.97; LC/MS Method 2 | 346 |
| 74 | 2-bromo-N-(5-(pyridin-3-yloxy)pyridin-2-yl)propanamide | 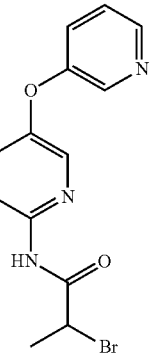 | $^1$H NMR: (400 MHz DMSO-d$_6$) δ ppm 11.00 (s, 1H), 8.42-8.44 (m, 1H), 8.37-8.39 (m, 1H), 8.23-8.25 (m, 1H), 8.13 (d, J = 8.8 Hz, 1H), 7.64 (dd, J = 8.8, 4.0 Hz, 1H), 7.45-7.49 (m, 1H), 7.40-7.44 (m, 1H), 4.87 (q, J = 7.6 Hz, 1H), 1.74 (d, J = 7.6 Hz, 3H). | 0.62; LC/MS Method 2 | 322 |
| 75 | 2-bromo-N-(5-((5-fluoropyridin-3-yl)oxy)pyridin-2-yl)propanamide | 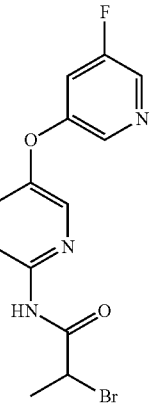 | $^1$H NMR: (400 MHz DMSO-d$_6$) δ ppm 11.00 (s, 1H), 8.41 (d, J = 2.4 Hz, 1H), 8.31 (dd, J = 13.8, 2.6 Hz, 1H), 8.15 (d, J = 9.2 Hz, 1H), 7.84 (td, J = 2.4, 9.9 Hz, 1H), 7.71 (dd, J = 9.2, 3.2 Hz, 1H), 7.56 (td, 3.5, 10.1 Hz, 1H), 4.88 (q, J = 6.7 Hz, 1H), 1.74 (d, J = 6.7 Hz, 3H). | 0.86; LC/MS Method 3 | 340 |

| Int. | Name | Structure | ¹H NMR | LC: retention time (min); LC/MS Method of analysis | MS (M + H)⁺ |
|---|---|---|---|---|---|
| 76 | 2-bromo-N-(5-((2-oxo-1,2-dihydropyridin-3-yl)oxy)pyridin-2-yl)propanamide | 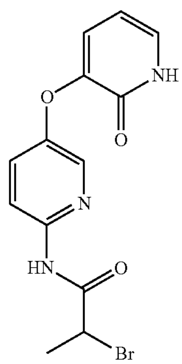 [SMILES: CC(Br)C(=O)Nc1ccc(Oc2ccc[nH]c2=O)cn1] | ¹H NMR: (400 MHz DMSO-$d_6$) δ ppm 12.00 (s, 1H), 10.85 (s, 1H), 8.03-8.05 (m, 1H), 8.02 (d, J = 9.2 Hz, 1H), 7.39 (dd, 2.6, 10.2 Hz, 1 H), 7.27-7.32 (m, 2H), 6.20 (t, J = 7.2 Hz, 1H), 4.79-4.87 (m, 1H), 1.73 (d, 6.4 Hz, 3H). | 0.54-0.56; LC/MS Method 5 | 340 |
| 77 | 2-bromo-N-(5-(2,4,6-trifluorophenoxy)pyridin-2-yl)propanamide | 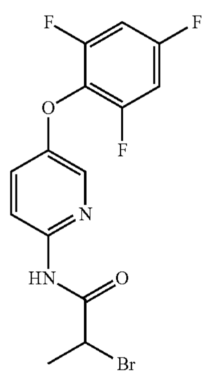 [SMILES: CC(Br)C(=O)Nc1ccc(Oc2c(F)cc(F)cc2F)cn1] | ¹H NMR (400 MHz, CHLOROFORM-d) δ ppm 8.74 (br. s., 1 H) 8.18 (d, J = 9.05 Hz, 1 H) 8.11 (d, J = 2.93 Hz, 1 H) 7.40-7.22 (m, 1 H) 6.93-6.76 (m, 2 H) 4.70-4.46 (m, 1 H) 2.01-1.91 (m, 3 H). | 1.05; LC/MS Method 5 | 375 |
| 78 | 2-bromo-N-(5-(2,4,5-trifluorophenoxy)pyridin-2-yl)propanamide | 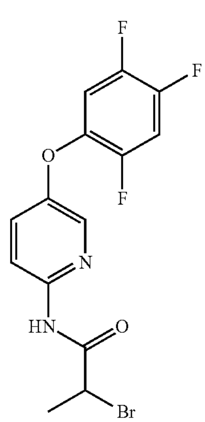 [SMILES: CC(Br)C(=O)Nc1ccc(Oc2cc(F)c(F)cc2F)cn1] | ¹H NMR (CHLOROFORM-d, 400 MHz) δ 8.93 (br s, 1H), 8.22 (d, 1H, J = 8.8 Hz), 8.11 (d, 1H, J = 2.9 Hz), 7.36 (dd, 1H, J = 3.2, 9.0 Hz), 7.11 (dt, 1H, J = 7.3, 10.0 Hz), 6.95 (td, 1H, J = 7.6, 10.3 Hz), 4.1-4.1 (m, 1H), 1.95 (d, 3H, J = 7.3 Hz). | 1.09; LCMS Method 5 | 375 |

-continued

| Int. | Name | Structure | ¹H NMR | LC: retention time (min); LC/MS Method of analysis | MS (M + H)⁺ |
|---|---|---|---|---|---|
| 79 | 2-bromo-N-(5-(2-((dimethylamino)methyl)-4-fluorophenoxy)pyridin-2-yl)propanamide | 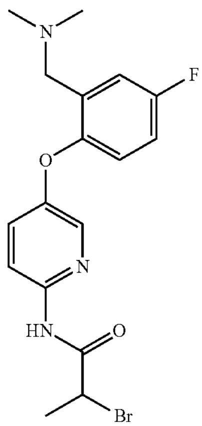 [SMILES: CC(Br)C(=O)Nc1ccc(Oc2ccc(F)cc2CN(C)C)cn1] | | 0.62; LCMS Method 5 | 396 |
| 80 | 2-bromo-N-(5-(2-fluoro-4-(2-methylthiazol-4-yl)phenoxy)pyridin-2-yl)propanamide | 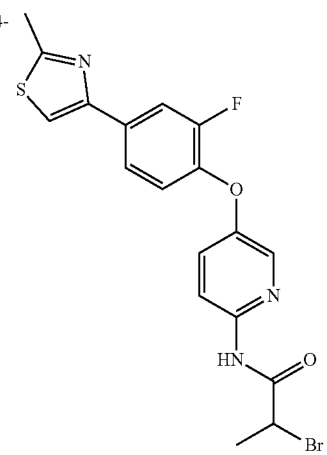 | | 1.14; LCMS Method 5 | 436 |
| 81 | 2-bromo-N-(5-(2,6-difluorophenoxy)pyridin-2-yl)propanamide | 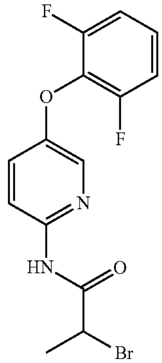 [SMILES: CC(Br)C(=O)Nc1ccc(Oc2c(F)cccc2F)cn1] | ¹H NMR (400 MHz, METHANOL-d₄) δ ppm 8.05-8.14 (m, 2 H) 7.37-7.42 (m, 1 H) 7.28-7.37 (m, 1 H) 7.13-7.22 (m, 2 H) 4.73 (q, J = 6.68 Hz, 1 H) 1.84 (d, J = 6.85 Hz, 3 H). | 1.05; LCMS Method 3 | 357 |

| Int. | Name | Structure | ¹H NMR | LC: retention time (min); LC/MS Method of analysis | MS (M + H)⁺ |
|---|---|---|---|---|---|
| 82 | 2-bromo-N-(5-(2,3,4-trifluorophenoxy)pyridin-2-yl)propanamide | 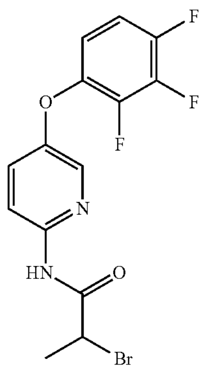 [SMILES: CC(Br)C(=O)Nc1ccc(Oc2ccc(F)c(F)c2F)cn1] | ¹H NMR (400 MHz, METHANOL-d₄) δ ppm 8.10-8.21 (m, 2 H) 7.45-7.55 (m, 1 H) 7.12-7.22 (m, 1 H) 6.94-7.05 (m, 1 H) 4.74 (q, J = 6.52 Hz, 1 H) 1.84 (d, J = 6.85 Hz, 3 H). | 1.11; LCMS Method 3 | 375 |

Intermediate 83

2-bromo-N-(6-cyclopropyl-6,7-dihydro-5H-pyrrolo[3,4-b]pyridin-2-yl)propanamide

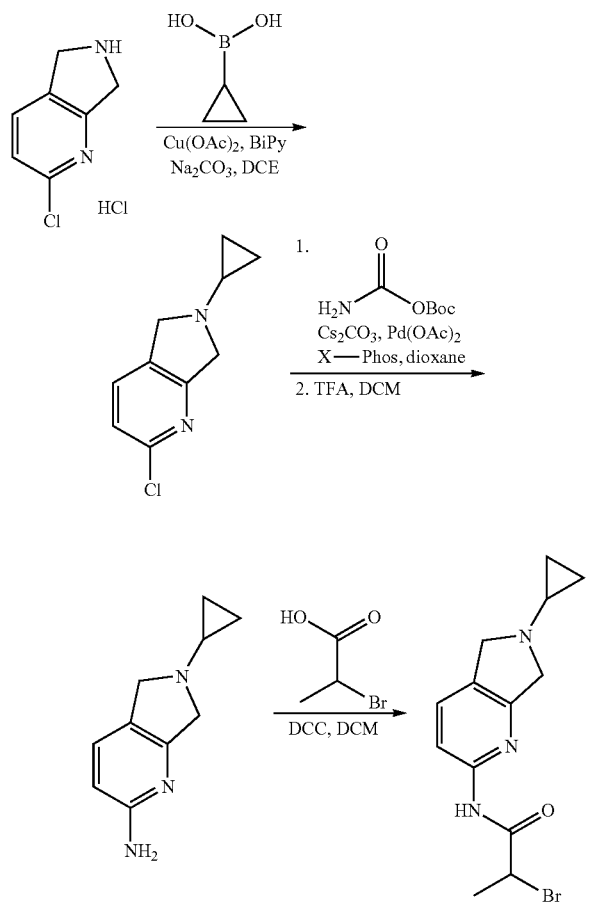

Step 1

A mixture of 2-chloro-6,7-dihydro-5H-pyrrolo[3,4-b]pyridine hydrochloride (200 mg, 1.047 mmol, 1.0 eq), cyclopropylboronic acid (180 mg, 2.094 mmol, 2.0 eq), 2,2'-bipyridine (164 mg, 1.047 mmol, 1.0 eq), diacetoxycopper (190 mg, 1.047 mmol, 1.0 eq) and Na₂CO₃ (333 mg, 3.14 mmol, 3.0 eq) in 1,2-dichloroethane (20 mL) was evacuated and flushed with nitrogen three times, then stirred at 70° C. After 2 h, the reaction was filtered and concentrated. The residue was diluted with 25% NH₃—H₂O (100 mL, aq.) and extracted with ethyl acetate (100 mL×2). The combined extracts were washed with water (100 mL), dried over sodium sulphate, concentrated and purified over a silica gel column, eluting with ethyl acetate:petroleum ether (1:1) to give 2-chloro-6-cyclopropyl-6,7-dihydro-5H-pyrrolo[3,4-b]pyridine (280 mg, purity: 90%) as a brown solid. LCMS: (ES, m/z): 195 [M+H]⁺, retention time 0.952 minutes, LCMS Method 34. ¹H NMR: (300 MHz, DMSO-d₆) δ 7.70 (d, J=8.1 Hz, 1H), 7.31 (d, J=8.1 Hz, 1H), 3.96 (d, J=8.7 Hz, 4H), 2.09-2.06 (m, 1H), 0.52-0.36 (m, 4H).

Step 2

A mixture of 2-chloro-6-cyclopropyl-6,7-dihydro-5H-pyrrolo[3,4-b]pyridine (800 mg, 4.11 mmol, 1.0 eq), X-phos (392 mg, 0.822 mmol, 0.2 eq), H₂NBoc (962 mg, 8.22 mmol, 2.0 eq), Cs₂CO₃ (2.68 g, 8.22 mmol, 2.0 eq) and Pd(OAc)₂ (92 mg, 0.411 mmol, 0.1 eq) in dioxane (10 mL) was evacuated and flushed three times with nitrogen, then stirred at 90° C. After 3 h, the reaction was filtered and concentrated. The residue was diluted with water (100 mL) and extracted with ethyl acetate (100 mL×3). The organic extracts were dried over sodium sulfate, concentrated and purified over a silica gel column, eluting with ethyl acetate:petroleum ether (1:3) to give tert-butyl (6-cyclopropyl-6,7-dihydro-5H-pyrrolo[3,4-b]pyridin-2-yl)carbamate 500 mg (purity: 90%, yield: 64%) as a yellow solid. LCMS: (ES, m/z): 276 [M+H]⁺. ¹H NMR: (300 MHz, DMSO-d₆) δ 9.65 (s, 1H), 7.61-7.53 (m, 2H), 3.92 (s, 2H), 3.84 (s, 2H), 2.08-2.03 (m, 1H), 1.44 (s, 9H), 0.51-0.34 (m, 4H).

Step 3

A mixture of tert-butyl (6-cyclopropyl-6,7-dihydro-5H-pyrrolo[3,4-b]pyridin-2-yl)carbamate (500 mg, 1.816 mmol 1.0 eq), dichloromethane (12 mL) and TFA (3 mL) was stirred at room temperature for 2 h and concentrated. The residue was diluted with water (100 mL) and washed with dichloromethane (100 mL). The aqueous phase was isolated and adjusted to pH 7-8 with saturated aqueous NaHCO$_3$ and extracted with methanol:dichloromethane (100 mL×3, 1:10). The combined organic phases were dried over Na$_2$SO$_4$ and concentrated to give 6-cyclopropyl-6,7-dihydro-5H-pyrrolo[3,4-b]pyridin-2-amine 260 mg (purity: 95%) as a brown solid, which was used without further purification. LCMS: (ES, m/z): 176 [M+H]$^+$, retention time 0.726 minutes, LCMS Method 30. $^1$H NMR: (400 MHz, DMSO-d$_6$) δ ppm 7.21 (d, J=8.0 Hz, 1H), 6.23 (d, J=8.0 Hz, 1H), 5.75 (s, 2H), 3.82 (s, 2H), 3.75 (s, 2H), 2.07-1.97 (m, 1H), 0.48-0.34 (m, 4H).

Step 4

A mixture of 6-cyclopropyl-6,7-dihydro-5H-pyrrolo[3,4-b]pyridin-2-amine (260 mg, 1.484 mmol, 1.0 eq), 2-bromopropanoic acid (340 mg, 2.226 mmol, 1.5 eq), DCC (459 mg, 2.226 mmol, 1.5 eq) and DMAP (18 mg, 0.148 mmol, 0.1 eq) in DCM (10 mL) was stirred for 2 h, filtered, and concentrated. The residue was dissolved in DMF (5 mL) and purified by reverse phase chromatography (C$_{18}$ spherical column, 100 A), eluting with 0-40% AcCN in water (10 mM NH$_4$HCO$_3$) to give 2-bromo-N-(6-cyclopropyl-6,7-dihydro-5H-pyrrolo[3,4-b]pyridin-2-yl)propanamide (310 mg, purity: 95%, yield: 66.7%) as a yellow oil. LCMS: (ES, m/z): 310 [M+H]$^+$, retention time 1.007 minutes, LCMS Method 34. $^1$H NMR: (300 MHz, DMSO-d$_6$) δ 10.88 (s, 1H), 7.93 (d, J=8.4 Hz, 1H), 7.67 (d, J=8.4 Hz, 1H), 4.88-4.81 (m, 1H), 4.10-3.96 (m, 4H), 2.20-2.16 (m, 1H), 1.74 (d, J=6.7 Hz, 3H), 0.54-0.43 (m, 4H).

Intermediate 84

2-bromo-N-(5-(cyclopropylmethoxy)pyrimidin-2-yl)propanamide with ethyl acetate in petroleum ether (0-25%, 30 min) to give 2-chloro-5-(cyclopropylmethoxy)pyrimidine (1.35 g, yield: 95%, purity: 97%) as a white solid. LCMS: (ES, m/z): 185 [M+H]$^+$. $^1$H NMR: (400 MHz, DMSO-d$_6$) δ 8.53 (s, 2H), 4.00 (d, J=7.2 Hz, 2H), 1.31-1.18 (m, 1H), 0.63-0.58 (m, 2H), 0.37-0.34 (m, 2H).

Step 2

In a sealed tube, 2-chloro-5-(cyclopropylmethoxy)pyrimidine (1.20 g, 6.53 mmol, 1.0 eq) and NH$_3$—H$_2$O (10 mL, 25%) were stirred 3 h at 150° C. The reaction was concentrated and purified over a silica gel column, eluting with methanol in dichloromethane (0-10%, 30 min) to give 5-(cyclopropylmethoxy)pyrimidin-2-amine (900 mg, yield: 94%, purity: 83.5%) as a white solid. LCMS: (ES, m/z): 166 [M+H]$^+$. $^1$H NMR: (400 MHz, DMSO-d$_6$) δ 8.03 (s, 2H), 6.17 (s, 2H), 3.77 (d, J=7.6 Hz, 2H), 1.20-1.12 (m, 1H), 0.57-0.53 (m, 2H), 0.30-0.26 (m, 2H).

Step 3

To 2-bromopropanoic acid (185 mg, 1.21 mmol, 1.0 eq) in dichloromethane (5 mL) was added DCC (300 mg, 1.45 mmol, 1.2 eq), followed by 5-(cyclopropylmethoxy)pyrimidin-2-amine (200 mg, 1.21 mmol, 1.0 eq). The resulting mixture was stirred 12 h, poured into water (50 mL) and extracted with dichloromethane (50 mL×3). The combined organic phases were dried over sodium sulfate, concentrated and purified by prep-TLC (ethyl acetate:petroleum ether=1:2) to give 2-bromo-N-(5-(cyclopropylmethoxy)pyrimidin-2-yl)propanamide (130 mg, yield: 36%, purity: 90%) as a yellow solid. LCMS: (ES, m/z): 300 [M+H]$^+$. $^1$H NMR: (400 MHz, DMSO-d$_6$) δ 10.81 (s, 1H), 8.45 (s, 2H), 4.95-4.89 (m, 1H), 3.96 (d, J=7.2 Hz, 2H), 1.72 (d, J=6.8 Hz, 3H), 1.65-1.58 (m, 1H), 0.61-0.57 (m, 2H), 0.37-0.34 (m, 2H).

Intermediate 85

2-bromo-N-(1-(cyclopropylmethyl)-1H-pyrazolo[3,4-c]pyridin-5-yl)propanamide

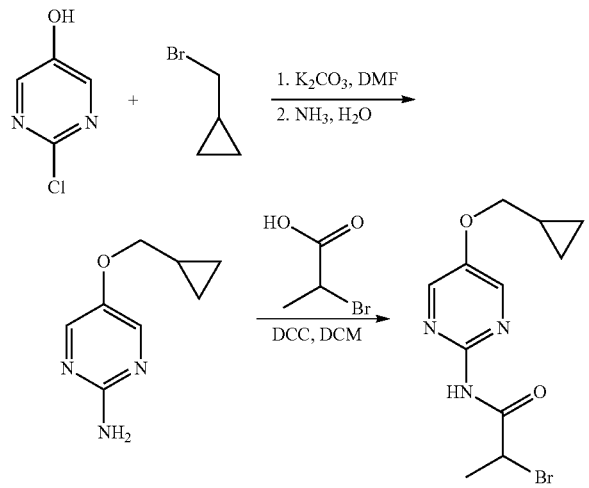

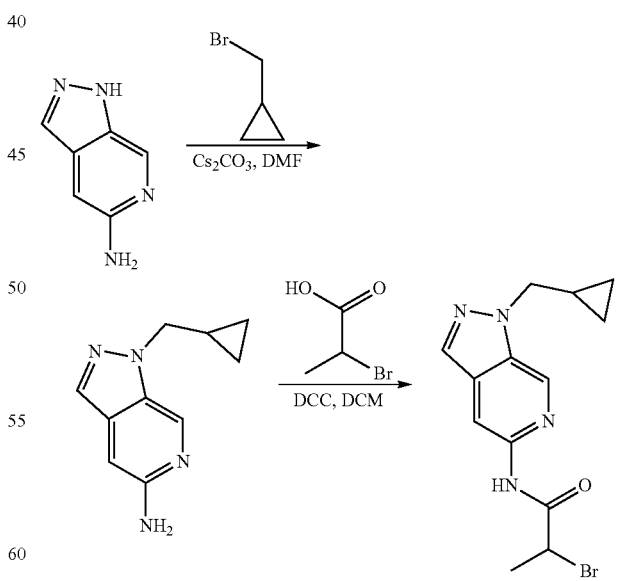

Step 1

To 2-chloropyrimidin-5-ol (1.00 g, 7.69 mmol, 1.0 eq) in DMF (10 mL) were added potassium carbonate (2.13 g, 15.38 mmol, 2.0 eq) and (bromomethyl)cyclopropane (2.06 g, 15.38 mmol, 2.0 eq), and the resulting mixture was stirred 2 h at 50° C. The reaction was quenched with water (100 mL) and extracted with ethyl acetate (100 mL×3). The combined organic phases were dried over sodium sulfate, concentrated and purified over a silica gel column, eluting Step 1

A mixture of 1H-pyrazolo[3,4-c]pyridin-5-amine (1 g, 7.46 mmol, 1.0 eq), (bromomethyl)cyclopropane (900 mg, 6.72 mmol, 0.9 eq) and Cs$_2$CO$_3$ (4.86 g, 14.9 mmol, 2.0 eq) in DMF (20 mL) was stirred 1 h at 28° C. The reaction was quenched with water (100 mL) and extracted with ethyl acetate (100 mL×3). The combined organic phases were dried over Na₂SO₄, concentrated and purified over a silica gel column, eluting with ethyl acetate:petroleum ether (1:4) to give 1-(cyclopropylmethyl)-1H-pyrazolo[3,4-c]pyridin-5-amine (250 mg, purity: 96%, yield: 17%) as a brown solid. LCMS: (ES, m/z): 189 [M+H]⁺. ¹H NMR: (300 MHz, DMSO-d₆) δ 8.65 (s, 1H), 7.79 (d, J=0.6 Hz, 1H), 6.58 (d, J=1.2 Hz, 1H), 5.41 (br, 2H), 4.24 (d, J=6.9 Hz, 2H), 1.32-1.11 (m, 1H), 0.52-0.38 (m, 2H), 0.36 (m, 2H).

Step 2

A mixture of 2-bromopropanoic acid (243 mg, 1.60 mmol, 1.5 eq), DCC (437 mg, 2.12 mmol, 2.0 eq), DMAP (26 mg, 0.21 mmol, 0.2 eq) and 1-(cyclopropylmethyl)-1H-pyrazolo[3,4-c]pyridin-5-amine (200 mg, 1.06 mmol, 1.0 eq) in dichloromethane (20 mL) was stirred 2 h at 28° C. The reaction was concentrated and purified over a silica gel column, eluting with ethyl acetate:petroleum ether (1:1) to give 2-bromo-N-(1-(cyclopropylmethyl)-1H-pyrazolo[3,4-c]pyridin-5-yl)propanamide (150 mg, purity: 87%, yield: 43%) as a yellow solid. LCMS: (ES, m/z): 323 [M+H]⁺. (400 MHz, DMSO-d₆) δ 10.71 (s, 1H), 8.53 (s, 1H), 8.31 (s, 1H), 7.96 (s, 1H), 4.96-4.91 (m, 1H), 4.36 (d, J=5.4 Hz, 2H), 1.76 (d, J=5.1 Hz, 3H), 1.32-1.11 (m, 1H), 0.64-0.55 (m, 2H), 0.50-0.46 (m, 2H).

Intermediate 86 was synthesized in an analogous manner.

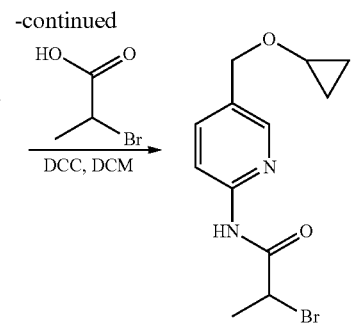

Step 1

To tert-butyl (5-(hydroxymethyl)pyridin-2-yl)carbamate (2.00 g, 8.93 mmol, 1.0 eq) in THF (50 mL) at 0° C., DIEA (6.91 g, 53.57 mmol, 6.0 eq) was added, followed by methanesulfonyl chloride (3.05 g, 26.79 mmol, 3.0 eq), dropwise. The resulting mixture was stirred 30 min at 0° C., then warmed to room temperature and stirred for 2 h. The reaction was poured into water (150 mL) and extracted with ethyl acetate (150 mL×3).

The combined extracts were dried over sodium sulfate, concentrated and purified by reversed phase column (C18 silica gel 80 g), eluting with 5-50% AcCN in water (10 mM NH₄HCO₃) to give tert-butyl (5-(chloromethyl)pyridin-2-yl)carbamate (1.58 g, yield: 73%, purity: 99.6%) as a yellow solid. LCMS: (ES, m/z): 243 [M+H]⁺. ¹H NMR: (400 MHz, CDCl₃) δ 8.37 (s, 1H), 8.31 (d, J=2.4 Hz, 1H), 8.01 (d, J=8.8 Hz, 1H), 7.73 (dd, J=2.4, 8.4 Hz, 1H), 4.57 (s, 2H), 1.57 (s, 9H).

| Int. | Name | Structure | ¹H NMR | LC: retention time (min); LC/MS Method of analysis | MS (M + H)⁺ |
|---|---|---|---|---|---|
| 86 | 2-bromo-N-(1-(cyclopropylmethyl)-1H-pyrrolo[2,3-c]pyridin-5-yl)propanamide | 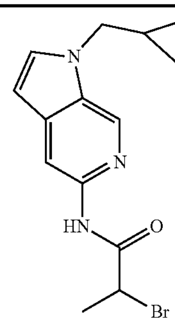 | ¹H NMR: (300 MHz CD₃OD) δ ppm 8.60 (s, 1H), 8.09-8.08 (m, 1H), 7.65 (d, J = 3.0 Hz, 1H), 6.56-6.54 (m, 1H), 4.79-4.72 (m, 1H), 4.15 (d, J = 6.9 Hz, 2H), 1.88-1.86 (m, 3H), 1.08-1.03 (m, 1H), 0.65-0.60 (m, 2H), 0.50-0.41 (m, 2H). | — | 322 |

Intermediate 87

2-bromo-N-(5-(cyclopropoxymethyl)pyridin-2-yl)propanamide

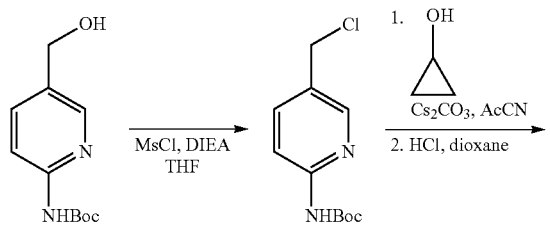

Step 2

To cyclopropanol (1.05 g, 18.10 mmol, 3.5 eq) in acetonitrile (60 mL) were added cesium carbonate (5.00 g, 15.34 mmol, 3.0 eq) and tert-butyl (5-(chloromethyl)pyridin-2-yl)carbamate (1.25 g, 5.16 mmol, 1.0 eq). The resulting mixture was stirred 2 h, concentrated and purified over a silica gel column, eluting with ethyl acetate in petroleum ether (0-50%, in 30 min) to give tert-butyl (5-(cyclopropoxymethyl)pyridin-2-yl)carbamate (168 mg, yield: 12%, purity: 99%) as a yellow solid. LCMS: (ES, m/z): 265 [M+H]⁺. ¹H NMR: (400 MHz, CDCl₃) δ 8.26 (d, J=2.0 Hz, 1H), 8.16 (s, 1H), 7.97 (d, J=8.4 Hz, 1H), 7.68 (dd, J=2.4, 8.8 Hz, 1H), 4.51 (s, 2H), 3.36-3.32 (m, 1H), 1.56 (s, 9H), 0.66-0.63 (m, 2H), 0.54-0.49 (m, 2H).

Step 3 tert-Butyl (5-(cyclopropoxymethyl)pyridin-2-yl)carbamate (168 mg, 0.64 mmol, 1.0 eq) was dissolved in HCl (10 mL, 4M in dioxane), and the resulting mixture was stirred 2 h at room temperature. The reaction was concentrated to give crude 5-(cyclopropoxymethyl)pyridin-2-amine (198 mg) as a yellow oil, which was used without purification. LCMS: (ES, m/z): 165 [M+H]$^+$.

Step 4 To 5-(cyclopropoxymethyl)pyridin-2-amine (198 mg, 1.21 mmol, 1.0 eq) and 2-bromopropanoic acid (367 mg, 2.41 mmol, 2.0 eq) in DCM (10 mL), DCC (748 mg, 3.63 mmol, 3.0 eq) and DMAP (15 mg, 0.12 mmol, 0.1 eq) were added. The resulting mixture was stirred 1 h, filtered, concentrated and purified over a silica gel column, eluting with ethyl acetate in petroleum ether (0-30%, in 15 min) to give 2-bromo-N-(5-(cyclopropoxymethyl)pyridin-2-yl)propanamide (66 mg, yield: 18%, purity: 96%) as a yellow oil. LCMS: (ES, m/z): 299 [M+H]$^+$. $^1$H NMR: (300 MHz, CD$_3$OD) δ 8.30 (s, 1H) 8.12-8.09 (m, 1H), 7.82-7.77 (m, 1H), 4.78-4.68 (m, 1H), 4.57 (s, 2H), 3.43-3.37 (m, 1H), 1.84 (d, J=6.6 Hz, 3H), 0.65-0.50 (m, 4H).

Intermediate 88

2-bromo-N-(5-(oxazol-2-ylmethyl)pyridin-2-yl)propanamide

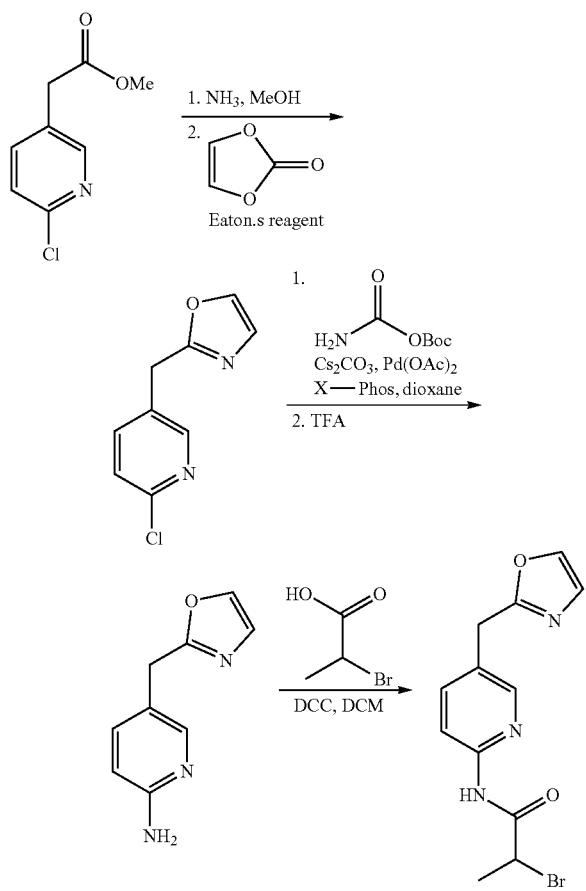

Step 1

A mixture of methyl 2-(6-chloropyridin-3-yl)acetate (5.1 g, 27.56 mmol, 1.0 eq) and NH$_3$ (7 M in methanol, 50 mL) was stirred for 16 h at 25° C., concentrated, diluted with water (100 mL), and extracted with ethyl acetate (100 mL×3). The combined organic extracts were dried over sodium sulfate and concentrated to give crude 2-(6-chloropyridin-3-yl)acetamide (4.6 g, purity: 93%, yield: 98%) as a yellow solid, which was used without purification. LCMS: (ES, m/z): 171 [M+H]$^+$. $^1$H NMR: (300 MHz, DMSO-d$_6$) δ 8.27 (d, J=2.4 Hz, 1H), 7.74 (dd, J=8.1, 2.4 Hz, 1H), 7.57 (s, 2H), 7.46 (d, J=8.1 Hz, 1H), 3.45 (s, 2H).

Step 2

A mixture of 2-(6-chloropyridin-3-yl)acetamide (1.6 g, 9.41 mmol, 1.0 eq), Eaton's reagent (14.4 g, 56.47 mmol, 6 eq) and 1,3-dioxol-2-one (1.61 g, 18.82 mmol, 2 eq) was evacuated and flushed three times with nitrogen, and the reaction was stirred at 100° C. After 16 h, the mixture was diluted with water (100 mL) and extracted with ethyl acetate (100 mL×3). The combined extracts were dried over sodium sulfate, concentrated and purified over a silica gel column, eluting with dichloromethane:methanol (10:1) to give 2-((6-chloropyridin-3-yl)methyl)oxazole (490 mg, purity: 88%, yield: 26%) as a yellow oil. LCMS: (ES, m/z): 195 [M+H]$^+$. $^1$H NMR: (400 MHz, DMSO-d$_6$) δ ppm 8.39 (d, J=2.4 Hz, 1H), 8.05 (d, J=0.9 Hz, 1H), 7.81 (dd, J=11.2, 3.6 Hz, 1H), 7.50 (d, J=11.2 Hz, 1H), 7.15 (d, J=0.9 Hz, 1H), 4.23 (s, 2H).

Step 3

To 2-((6-chloropyridin-3-yl)methyl)oxazole (480 mg, 2.47 mmol, 1 eq) and tert-butyl carbamate (348 mg, 2.97 mmol, 1.2 eq) in dioxane (5 ml), Cs$_2$CO$_3$ (2.01 g, 6.17 mmol, 2.5 eq), Pd(OAc)$_2$ (28 mg, 0.12 mmol, 0.05 eq) and X-Phos (118 mg, 0.247 mmol, 0.1 eq) were added. The flask was evacuated and flushed three times with nitrogen, and the mixture was stirred at 90° C. for 2 h. The solvent was removed under reduced pressure, and the residue was diluted with water (100 mL) and extracted with ethyl acetate (100 mL×3). The combined organic extracts were dried over sodium sulfate, concentrated and purified over a silica gel column, eluting with ethyl acetate:petroleum ether (1:1) to give tert-butyl (5-(oxazol-2-ylmethyl)pyridin-2-yl)carbamate (360 mg, purity: 80%, yield=53%) as a yellow solid. LCMS: (ES, m/z): 276 [M+H]$^+$. $^1$H NMR: (300 MHz, DMSO-d$_6$) δ ppm 9.77 (s, 1H), 8.18 (d, J=2.4 Hz, 1H), 8.03 (d, J=1.2 Hz, 1H), 7.76 (d, J=8.4 Hz, 1H), 7.65 (dd, J=8.4, 2.4 Hz, 1H), 7.14 (d, J=1.2 Hz, 1H), 4.11 (s, 2H), 1.47 (s, 9H).

Step 4

A mixture of tert-butyl (5-(oxazol-2-ylmethyl)pyridin-2-yl)carbamate (360 mg, 1.31 mmol, 1 eq) and trifluoroacetic acid (1 mL) in dichloromethane (5 mL) was stirred at 25° C. for 3 h. The mixture was concentrated and diluted with water (100 mL), and the pH value of the solution was adjusted to 7-8 with NaHCO$_3$. The solution was extracted with ethyl acetate (100 mL×3), and the extracts were dried over sodium sulfate, concentrated and purified over a silica gel column, eluting with dichloromethane:methanol (10:1) to give 5-(oxazol-2-ylmethyl)pyridin-2-amine (130 mg, purity: 80%, yield: 56%) as a yellow solid. LCMS: (ES, m/z): 176 [M+H]$^+$. $^1$H NMR: (300 MHz, DMSO-d$_6$) δ ppm 8.00 (d, J=0.9 Hz, 1H), 7.82 (d, J=2.4 Hz, 1H), 7.27 (dd, J=8.4, 2.4 Hz, 1H), 7.11 (d, J=0.9 Hz, 1H), 6.40 (d, J=8.4 Hz, 1H), 5.85 (s, 2H), 3.92 (s, 2H).

Step 5

A mixture of 2-bromopropanoic acid (108 mg, 0.71 mmol, 1 eq), DCC (368 mg, 1.78 mmol, 2.5 eq), DMAP (9 mg, 0.071 mmol, 0.1 eq) and 5-(oxazol-2-ylmethyl)pyridin-2-amine (125 mg, 0.71 mmol, 1 eq) in dichloromethane (2 mL) was stirred at 25° C. for 2 h, then filtered. The filtrate was concentrated and purified over a silica gel column, eluting with ethyl acetate:petroleum ether (1:1) to give 2-bromo-N-(5-(oxazol-2-ylmethyl)pyridin-2-yl)propanamide (170 mg, purity: 90%, yield: 77%) as a yellow solid. LCMS: (ES, m/z): 310 [M+H]$^+$. $^1$H NMR: (300 MHz, DMSO-d$_6$) δ ppm 10.90 (s, 1H), 8.30 (d, J=2.4 Hz, 1H), 8.09-8.00 (m, 2H), 7.75 (dd, J=8.4, 2.4 Hz, 1H), 7.15 (s, 1H), 4.90-4.84 (m, 1H), 4.17 (s, 2H), 1.78-1.66 (m, 3H).

Intermediate 89

2-bromo-N-(5-(isoxazol-3-yl)pyridin-2-yl)propanamide

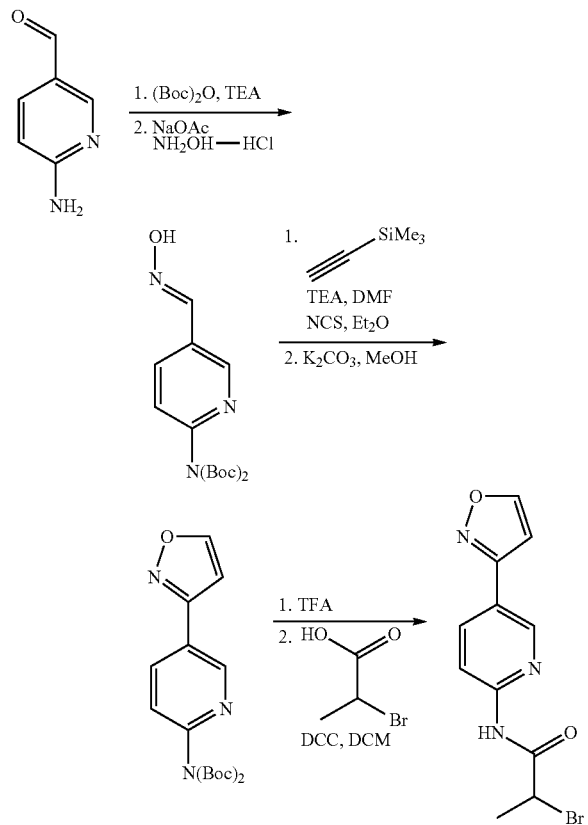

Step 1

To 6-aminonicotinaldehyde (2.5 g, 20.5 mmol, 1.0 eq) in THF (20 mL) was added di-tert-butyl dicarbonate (9.8 g, 45 mmol, 2.2 eq), triethylamine (6.2 g, 61.5 mmol, 3.0 eq) and 4-dimethylaminopyridine (0.25 g, 2 mmol, 0.1 eq). The resulting mixture was stirred for 16 h at room temperature, concentrated and partitioned between dichloromethane and water.

The aqueous layer was extracted again with dichloromethane (200 mL×2), and the combined extracts were dried over sodium sulfate, concentrated and purified over a silica gel column, eluting with ethyl acetate:petroleum (1:2) to give tert-butyl N-[(tert-butoxy)carbonyl]-N-(5-formylpyridin-2-yl)carbamate (2.7 g, purity: 90%, yield: 41%) as a yellow oil.

LCMS: (ES, m/z): 323 [M+H]$^+$. $^1$H NMR: (400 MHz, CDCl$_3$-d) δ ppm 10.08 (s, 1H), 8.88 (d, J=2.4 Hz, 1H), 8.22 (dd, J=8.8, 2.4 Hz, 1H), 7.68 (d, J=8.8 Hz, 1H), 1.53 (s, 18H).

Step 2

A mixture of tert-butyl N-[(tert-butoxy)carbonyl]-N-(5-formylpyridin-2-yl)carbamate (2.0 g, 6.2 mmol, 1.0 eq), AcONa (306 mg, 3.7 mmol, 0.6 eq) and H$_2$NOH—HCl (515 mg, 7.4 mmol, 1.2 eq) in methnol:water (10 mL, 1:1) was stirred for 1 h at 25° C. and poured into water (200 mL). The resulting solid was collected by filtration and dried to give tert-butyl N-[(tert-butoxy)carbonyl]-N-{5-[(1E)-(hydroxyimino)methyl]pyridin-2-yl}carbamate (1.7 g, purity: 95%, yield: 77%) as a white solid, which was used without further purification. LCMS: (ES, m/z): 195 [M+H]$^+$. $^1$H NMR: (400 MHz, DMSO-d$_6$) δ ppm 11.57 (s, 1H), 8.60 (d, J=2.4 Hz, 1H), 8.23 (dd, J=8.4, 2.4 Hz, 1H), 8.12-8.06 (m, 1H), 7.43 (d, J=8.4 Hz, 1H), 1.41 (s, 18H).

Step 3

To tert-butyl N-[(tert-butoxy)carbonyl]-N-{5-[(1E)-(hydroxyimino)methyl]pyridin-2-yl}carbamate (1.5 g, 4.45 mmol, 1.0 eq) in DMF (10 mL) was added N-chlorosuccinimide (710 mg, 5.34 mmol, 1.2 eq), and the reaction was stirred at 30° C. After 30 min, diethyl ether was added (90 mL), and the reaction was cooled to −5° C. Triethylamine (30 mL) was added, followed by ethynyltrimethylsilane (35 mL). After 1 h, the reaction was concentrated, diluted with water (100 mL) and extracted with ethyl acetate (100 mL×3).

The combined extracts were dried over sodium sulfate, concentrated and purified over a silica gel column, eluting with ethyl acetate:petroleum (1:1) to give tert-butyl N-[(tert-butoxy)carbonyl]-N-{5-[5-(trimethylsilyl)-1,2-oxazol-3-yl]pyridin-2-yl}carbamate (1.8 g, purity: 95%, yield: 91%) as a white solid.

LCMS: (ES, m/z): 434 [M+H]$^+$. $^1$H NMR: (300 MHz, CDCl$_3$) δ ppm 8.89 (d, J=2.4 Hz, 1H), 8.23 (dd, J=8.4, 2.4 Hz, 1H), 7.40 (dd, J=8.4, 0.9 Hz, 1H), 6.80 (s, 1H), 1.48 (s, 18H), 0.42 (s, 9H).

Step 4

A mixture of tert-butyl N-[(tert-butoxy)carbonyl]-N-{5-[5-(trimethylsilyl)-1,2-oxazol-3-yl]pyridin-2-yl}carbamate (1 g, 2.3 mmol, 1 eq), methanol (20 mL) and potassium carbonate (316 mg, 2.3 mmol, 1 eq) was stirred at 40° C. After 1 h, the reaction was concentrated, diluted with water (100 mL) and extracted with ethyl acetate (100 mL×3).

The combined extracts were dried over sodium sulfate, concentrated and purified over a silica gel column, eluting with ethyl acetate:petroleum (1:1) to give tert-butyl N-[(tert-butoxy)carbonyl]-N-[5-(1,2-oxazol-3-yl)pyridin-2-yl]carbamate (400 mg, purity: 80%, yield: 48%) as a white solid. LCMS: (ES, m/z): 362 [M+H]$^+$. $^1$H NMR: (300 MHz, CDCl$_3$) δ ppm 8.74 (s, 1H), 8.50 (d, J=1.8 Hz, 1H), 8.20 (s, 1H), 8.18-8.07 (m, 1H), 6.68 (d, J=1.8 Hz, 1H), 1.58 (s, 18H).

Step 5 tert-Butyl N-[(tert-butoxy)carbonyl]-N-[5-(1,2-oxazol-3-yl)pyridin-2-yl]carbamate (500 mg, 1.38 mmol, 1 eq) in dichloromethane (10 mL) and trifluoroacetic acid (2 mL) was stirred for 2 h, concentrated and diluted with water (100 mL). The pH value of the reaction was adjusted to 7-8 with saturated sodium bicarbonate aqueous solution, and the mixture was extracted with ethyl acetate (100 mL×3). The combined extracts were dried over sodium sulfate, concentrated and purified over a silica gel column, eluting with methanol:dichloromethane (1:5) to give 5-(isoxazol-3-yl)pyridin-2-amine (200 mg, purity: 97%, yield=89%) as a yellow solid. LCMS: (ES, m/z): 162 [M+H]$^+$. $^1$H NMR: (300 MHz, DMSO-d$_6$) δ ppm 8.90 (d, J=1.8 Hz, 1H), 8.44 (d, J=2.5 Hz, 1H), 7.85 (dd, J=8.6, 2.5 Hz, 1H), 7.03 (d, J=1.8 Hz, 1H), 6.58-6.46 (m, 1H), 6.42 (s, 2H).

Step 6

To a mixture of 5-(isoxazol-3-yl)pyridin-2-amine (200 mg, 1.24 mmol, 1 eq) and 2-bromopropanoic acid (190 mg, 1.24 mmol, 1.0 eq) in dichloromethane (4 mL), were added dicyclohexylcarbodiimide (512 mg, 2.48 mmol, 2 eq) and 4-dimethylaminopyridine (30 mg, 0.248 mmol, 0.1 eq). The reaction was stirred for 4 h, filtered through a Celite pad, filtered, concentrated and purified over a silica gel column, eluting with ethyl acetate:petroleum ether (1:1) to give 2-bromo-N-(5-(isoxazol-3-yl)pyridin-2-yl)propanamide (330 mg, purity: 90%, yield: 90%) as a yellow oil. LCMS: (ES, m/z): 296 [M+H]$^+$. $^1$H NMR: (300 MHz, DMSO-d$_6$) δ ppm 11.15 (s, 1H), 9.06 (d, J=1.8 Hz, 1H), 8.90-8.89 (m 1H), 8.34 (dd, J=8.7, 2.4 Hz, 1H), 8.23 (d, J=8.7 Hz, 1H), 7.24 (d, J=1.8 Hz, 1H), 4.91 (m, 1H), 1.77 (d, J=6.6 Hz, 3H).

Intermediate 90

N-(6-benzylpyridazin-3-yl)-2-bromopropanamide

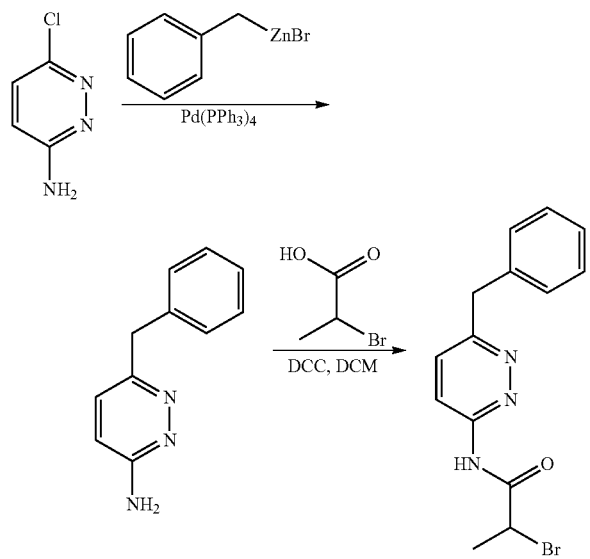

Step 1

To 6-chloropyridazin-3-amine (258 mg, 2.0 mmol, 1.0 eq) in dioxane (2 mL) were added benzylzinc(II) bromide (6.0 mL, 3.0 mmol, 1.5 eq) and Pd(PPh$_3$)$_4$ (230 mg, 0.2 mmol, 0.1 eq), and the flask was evacuated and flushed with nitrogen three times. The reaction was stirred for 1 h at 80° C. with microwave, filtered, concentrated and purified by prep-TLC (ethyl acetate:petroleum ether=1:2) to give 6-benzylpyridazin-3-amine (130 mg, purity: 98%) as a white solid. LCMS: (ES, m/z): 186 [M+H]$^+$. $^1$H NMR: (300 MHz, CDCl$_3$) δ 7.34-7.22 (m, 5H), 7.04 (d, J=9.0 Hz, 1H), 6.73 (d, J=9.3 Hz, 1H), 4.92 (br, 2H), 4.20 (s, 2H).

Step 2

A mixture of 6-benzylpyridazin-3-amine (100 mg, 0.54 mmol, 1.0 eq), 2-bromopropanoic acid (91 mg, 0.59 mmol, 1.1 eq), DCC (134 mg, 0.65 mmol, 1.2 eq) and DMAP (66.0 mg, 0.54 mmol, 0.1 eq) in DCM (3.0 mL) was stirred for 1 h, filtered, concentrated and purified by prep-TLC (ethyl acetate:petroleum ether=1:2) to give of N-(6-benzylpyridazin-3-yl)-2-bromopropanamide (140 mg, purity: 94%, yield: 77%) as a white solid. LCMS: (ES, m/z): 320 [M+H]$^+$. (400 MHz, DMSO-d$_6$) δ 11.46 (br, 1H), 8.23 (d, J=9.0 Hz, 1H), 7.60 (d, J=9.0 Hz, 1H), 7.34-7.22 (m, 5H), 4.93-4.87 (m, 1H), 4.25 (s, 2H), 1.75 (d, J=6.6 Hz, 3H).

Intermediate 91

2-bromo-N-(5-(pyridin-4-ylmethyl)pyridin-2-yl)propanamide

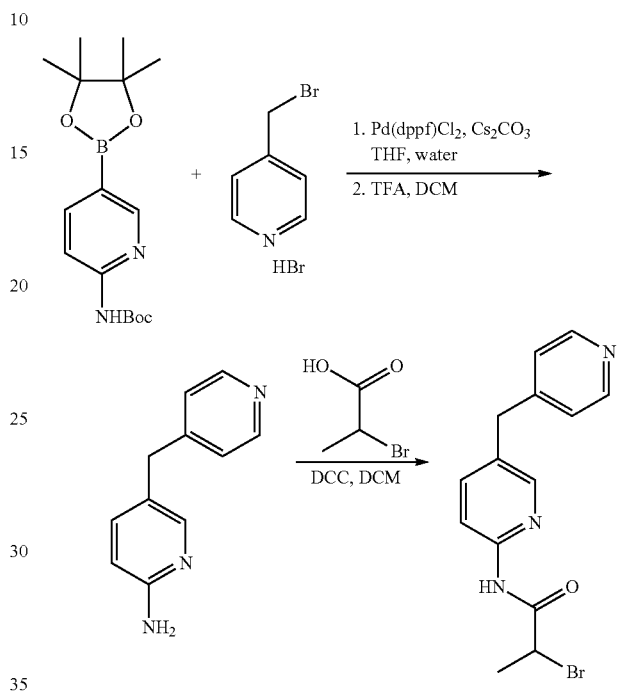

Step 1

A mixture of tert-butyl (5-(4,4,5,5-tetramethyl-1,3,2-dioxaborolan-2-yl)pyridin-2-yl)carbamate (1.00 g, 3.13 mmol, 1 eq), the HBr salt of 4-(bromomethyl)pyridine (791 mg, 3.13 mmol, 1 eq), Pd(dppf)Cl$_2$ (229 mg, 0.31 mmol, 0.1 eq) and Cs$_2$CO$_3$ (3.06, 9.38 mmol, 3 eq) in THF (10 mL) and water (5 mL) was evacuated and flushed three times with nitrogen, then stirred 6 h at 80° C., concentrated and purified by C18 (120 g) column chromatography, eluting with 0-80% AcCN in water (0.05%, TFA), to give tert-butyl (5-(pyridin-4-ylmethyl)pyridin-2-yl)carbamate (200 mg, yield: 24%, purity: 63%) as yellow oil. LCMS: (ES, m/z): 286 [M+H]$^+$. $^1$H NMR: (300 MHz, CDCl$_3$) δ 8.62-8.49 (m, 2H), 7.69-7.37 (m, 4H), 7.22-7.11 (m, 1H), 3.97 (s, 2H), 1.54 (s, 9H).

Step 2 tert-Butyl (5-(pyridin-4-ylmethyl)pyridin-2-yl)carbamate (200 mg, 0.70 mmol, 1 eq), DCM (10 mL) and TFA (3 mL) were stirred for 3 h, concentrated, purified by C$_{18}$ (120 g) column chromatography, eluting with 0-50% AcCN in water (10 mmol/L, NH$_4$HCO$_3$) to give 5-(pyridin-4-ylmethyl)pyridin-2-amine (110 mg, yield: 85%, purity: 100%) as red oil. LCMS: (ES, m/z): 186 [M+H]$^+$. $^1$H NMR: (300 MHz, CD$_3$OD) δ 8.90-8.75 (m, 2H), 8.15-7.80 (m, 4H), 7.14-6.95 (m, 1H), 4.34 (s, 2H).

Step 3

To 2-bromopropanoic acid (91 mg, 0.59 mmol, 1.0 eq) in DCM (10 mL) was added DCC (245 mg, 1.19 mmol, 2.0 eq), DMAP (14.51 mg, 0.12 mmol, 0.2 eq) and 5-(pyridin-4-ylmethyl)pyridin-2-amine (110 mg, 0.59 mmol, 1.0 eq). After 16 h, the reaction was adsorbed on silica and purified on a silica column (40 g), eluting with 0-100% ethyl acetate-petroleum ether to give 2-bromo-N-(5-(pyridin-4-ylmethyl)pyridin-2-yl)propanamide (120 mg, yield: 58.7%, purity: 93%) as a white solid. LCMS: (ES, m/z): 320 [M+H]+, retention time 0.669 minutes, LCMS Method 36. ¹H NMR: (400 MHz, CDCl₃) δ ppm 8.62 (s, 1H), 8.60-8.54 (m, 2H), 8.22-8.15 (m, 2H), 7.59-7.53 (m, 1H), 7.19 (d, J=5.7 Hz, 2H), 4.57-4.52 (m, 1H), 4.02 (s, 2H), 1.98 (d, J=6.8 Hz, 3H).

Intermediate 92

2-bromo-N-(5-(pyridin-2-ylmethyl)pyridin-2-yl)propanamide

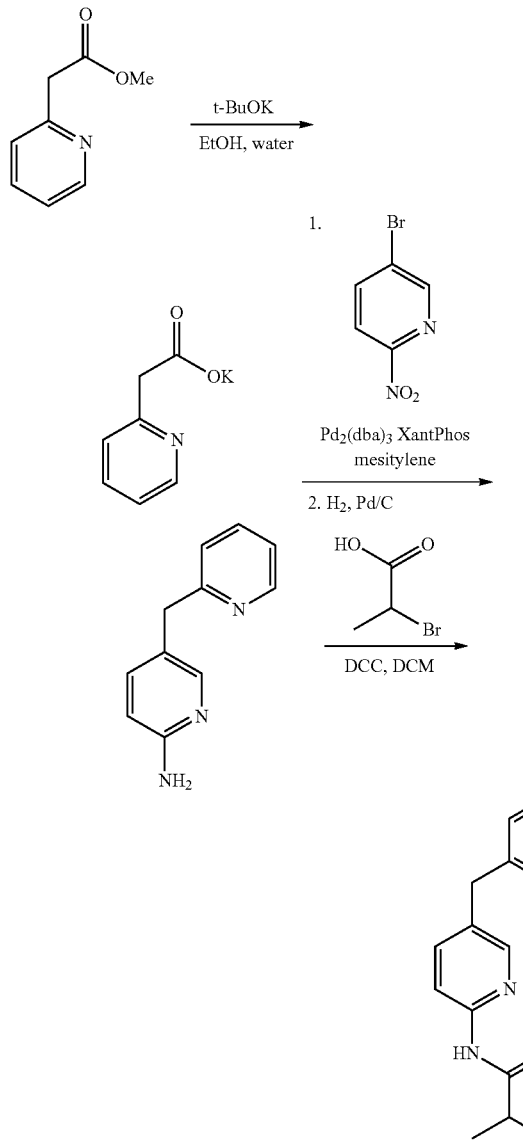

Step 1

To methyl 2-(pyridin-2-yl)acetate (1.51 g, 10.0 mmol, 1 eq) and H₂O (0.19 g, 10.5 mmol, 1.05 eq) at 60° C., t-BuOK (1.18 g, 10.5 mmol, 1.05 eq) in EtOH (10 mL) was added dropwise over 10 min. After 3 h, the reaction was concentrated under vacuum and ether (20 mL) was added. The resulting solid was collected by filtration to give potassium 2-(pyridin-2-yl)acetate (1.6 g, yield: 91%, purity: 100%) as white solid, which was used without purification. LCMS: (ES, m/z): 138 [M+H−39+H]+. ¹H NMR: (400 MHz, DMSO-d₆) δ 8.35-8.33 (m, 1H), 7.60-7.56 (m, 1H), 7.30-7.27 (m, 1H), 7.09-7.06 (m, 1H), 3.49 (s, 2H).

Step 2

To a 25 mL sealed tube was added potassium 2-(pyridin-2-yl)acetate (517 mg, 2.96 mmol, 1.2 eq) in mesitylene (10 mL), 5-bromo-2-nitropyridine (500 mg, 2.46 mmol, 1.0 eq), Pd₂(dba)₃ (113 mg, 0.12 mmol, 0.05 eq) and Xantphos (86 mg, 0.15 mmol, 0.06 eq), and the mixture was evacuated and flushed three times with nitrogen, then stirred overnight at 150° C. The reaction was cooled to rt, and MeOH (10 mL) was added. The mixture was filtered, concentrated and purified by C18 (120 g) column chromatography, eluting with AcCN in water (0.05%, TFA), to give 2-nitro-5-(pyridin-2-ylmethyl)pyridine (120 mg, yield: 23%, purity: 100%) as yellow oil. LCMS: (ES, m/z): 216 [M+H]+. ¹H NMR: (400 MHz, CDCl₃) δ ppm 8.67-8.60 (m, 1H), 8.56 (d, J=2.2 Hz, 1H), 8.21 (d, J=8.2 Hz, 1H), 8.01 (dd, J=8.3 Hz, 2.3 Hz, 1H), 7.88-7.86 (m, 1H), 7.43-7.37 (m, 1H), 7.35 (d, J=7.9 Hz, 1H), 4.40 (s, 2H).

Step 3

Through a mixture of 2-nitro-5-(pyridin-2-ylmethyl)pyridine (120 mg, 0.56 mmol, 1 eq), MeOH (5 mL) and Pd/C (10%, 24 mg), H₂ was bubbled over a period of 2 h at rt. The reaction was filtered and concentrated to give 5-(pyridin-2-ylmethyl)pyridin-2-amine (120 mg, yield:(crude), purity: 97%) as yellow oil, which was used without purification. LCMS: (ES, m/z): 186 [M+H]+. ¹H NMR: (400 MHz, CD₃OD) δ ppm 8.56 (d, J=5.1 Hz, 1H), 7.99-7.97 (m, 1H), 7.87 (dd, J=9.2 Hz, 2.2 Hz, 1H), 7.80-7.78 (m, 1H), 7.52 (d, J=7.9 Hz, 1H), 7.49-7.42 (m, 1H), 7.02-6.95 (m, 1H), 4.14 (s, 2H).

Step 4

A mixture of 2-bromopropanoic acid (119 mg, 0.78 mmol, 1.2 eq), DCC (267 mg, 1.30 mmol, 2 eq), DMAP (16 mg, 0.13 mmol, 0.2 eq) and 5-(pyridin-2-ylmethyl)pyridin-2-amine (120 mg, 0.65 mmol, 1 eq) in DCM (10 mL) was stirred at rt overnight, filtered, concentrated, and purified by prep-TLC with ethyl acetate:petroleum ether (1:3) to give 2-bromo-N-(5-(pyridin-2-ylmethyl)pyridin-2-yl)propanamide (50 mg, yield: 24%, purity: 74%) as a white solid. LCMS: (ES, m/z): 320 [M+H]+. ¹H NMR: (300 MHz, CD₃OD) δ ppm 8.00 (d, J=0.9 Hz, 1H), 7.82 (d, J=2.4 Hz, 1H), 7.27 (dd, J=8.4, 2.4 Hz, 1H), 7.11 (d, J=0.9 Hz, 1H), 6.40 (d, J=8.4 Hz, 1H), 5.85 (s, 2H), 3.92 (s, 2H).

Intermediate 93

2-bromo-N-(5-(pyridin-2-yloxy)pyridin-2-yl)propanamide

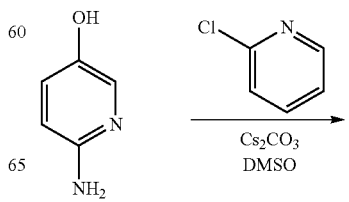

123
-continued

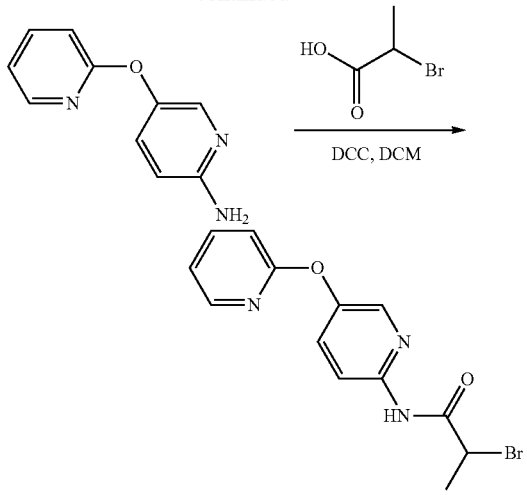

Step 1
2-Chloropyridine (0.644 mL, 6.81 mmol), 6-aminopyridin-3-ol (0.5 g, 4.54 mmol) and cesium carbonate (3.70 g, 11.35 mmol) were stirred in DMSO (6 mL) at 120° C. After 18 h, the mixture was slowly dripped into water (60 mL), stored in the refrigerator over the weekend, then extracted with EtOAc (4×100 mL). The combined organic layers were washed with brine (2×50 mL), dried over sodium sulfate, concentrated and purified by flash chromatography (silica 40 g Gold column), eluting with 0-20% MeOH in DCM to give 5-(pyridin-2-yloxy)pyridin-2-amine (460 mg, 2.334 mmol, purity: 95%, recovery: 51%) as an orange solid. LCMS (m/z) 188 (M+H)$^+$, retention time: 0.23 min, LC/MS Method 2. $^1$H NMR: (400 MHz, DMSO-d$_6$) δ 8.10 (dd, J=4.89, 1.47 Hz, 1H), 7.80 (ddd, J=8.31, 7.34, 1.96 Hz, 1H), 7.74 (d, J=2.45 Hz, 1H), 7.22 (dd, J=8.80, 2.93 Hz, 1H), 7.07 (ddd, J=7.34, 4.89, 0.98 Hz, 1H), 6.96 (d, J=8.31 Hz, 1H), 6.49 (d, J=8.80 Hz, 1H), 5.82 (s, 2H).

Step 2
To 5-(pyridin-2-yloxy)pyridin-2-amine (0.46 g, 2.457 mmol) and 2-bromopropanoic acid (0.243 mL, 2.70 mmol) in DCM (15 mL) at 0° C. was added DCC (0.608 g, 2.95 mmol), and the reaction was allowed to warm to rt. After 18 h, the reaction was filtered, concentrated and purified by column chromatography (24 g Gold), eluting with 0-100% EtOAc in heptane to provide 2-bromo-N-(5-(pyridin-2-yloxy)pyridin-2-yl)propanamide (790 mg, 2.33 mmol, purity: 95%, recovery: 95%) as a yellow solid. LCMS (m/z) 322 (M+H)$^+$, retention time: 0.82 min, LC/MS Method 2. $^1$H NMR: (400 MHz, DMSO-d$_6$) δ 10.91 (s, 1H) 8.19-8.30 (m, 1H), 8.09-8.18 (m, 2H), 7.88 (ddd, J=8.44, 6.72, 1.96 Hz, 1H), 7.67 (dd, J=8.80, 2.93 Hz, 1H), 7.07-7.21 (m, 2H), 4.89 (q, J=6.68 Hz, 1H) 1.76 (d, J=6.85 Hz, 3H).

Intermediates 94-96, with the addition of 0.2 eq CuI and dimethylglycine in dioxane in the chloride displacement, were synthesized in an analogous manner.

| Int. | Name | Structure | $^1$H NMR | LC: retention time (min); LC/MS Method of analysis | MS (M + H)$^+$ |
|---|---|---|---|---|---|
| 94 | 2-bromo-N-(5-(pyridin-4-yloxy)pyridin-2-yl)propanamide | 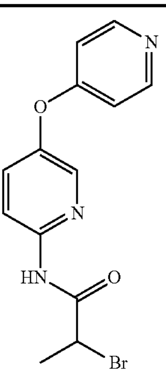 | $^1$H NMR: (400 MHz CD$_3$OD) δ ppm 8.44 (br d, J = 1.47 Hz, 2H), 8.16-8.30 (m, 2H), 7.65 (dd, J = 9.05, 2.69 Hz, 1H), 6.96-7.06 (m, 2H), 4.74 (q, J = 6.68 Hz, 1H), 1.83 (d, J = 6.85 Hz, 3H). | 0.77; LC/MS Method 3 | 324 |
| 95 | 2-bromo-N-((3-chloro-5-fluoropyridin-2-yl)oxy)pyridin-2-yl)propanamide | 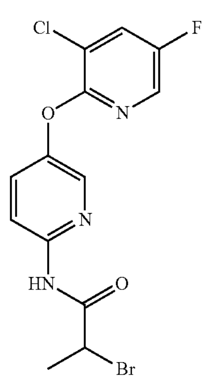 [SMILES: CC(Br)C(=O)Nc1ccc(Oc2ncc(F)cc2Cl)cn1] | $^1$H NMR (400 MHz, DMSO-d$_6$) δ ppm 11.08-10.81 (m, 1H), 8.32-8.22 (m, 2H), 8.14 (q, J = 3.1 Hz, 2H), 7.75-7.68 (m, 1H), 4.93-4.83 (m, 1H), 1.76 (s, 3H). | 1.03; LC/MS Method 5 | 374 |

| Int. | Name | Structure | ¹H NMR | LC: retention time (min); LC/MS Method of analysis | MS (M + H)⁺ |
|---|---|---|---|---|---|
| 96 | 2-bromo-N-(5-((3-cyano-5-fluoropyridin-2-yl)oxy)pyridin-2-yl)propanamide | 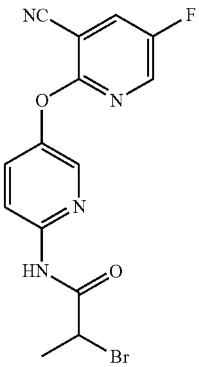 [SMILES: CC(Br)C(=O)Nc1ccc(Oc2ncc(F)cc2C#N)cn1] | ¹H NMR (400 MHz, DMSO-d₆) δ ppm 11.09-10.91 (m, 1H), 8.64-8.58 (m, 1H), 8.46 (d, J = 2.9 Hz, 1H), 8.36-8.33 (m, 1H), 8.20-8.11 (m, 1H), 7.80 (dd, J = 9.0, 2.7 Hz, 1H), 4.88 (q, J = 6.7 Hz, 1H), 1.80-1.70 (m, 3H). | 0.89; LC/MS Method 5 | 364 |

Intermediate 97

2-bromo-N-(6-(2-cyanophenoxy)pyridazin-3-yl)propanamide

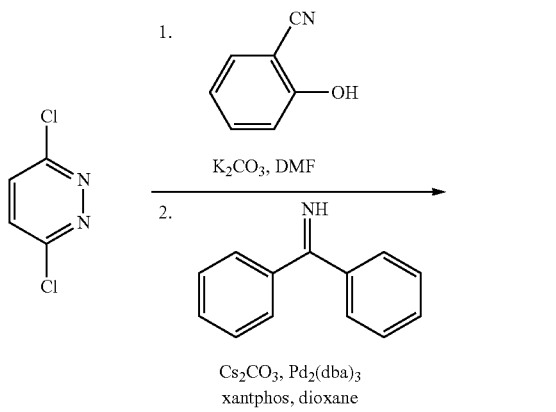

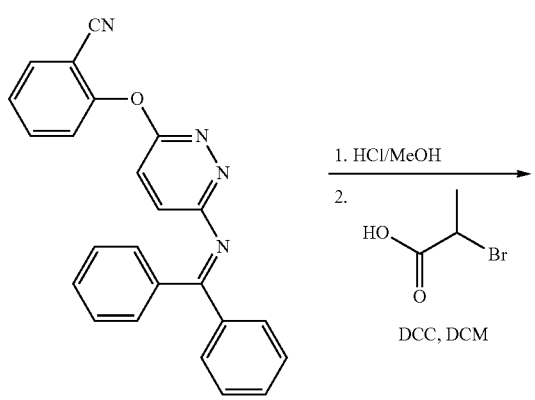

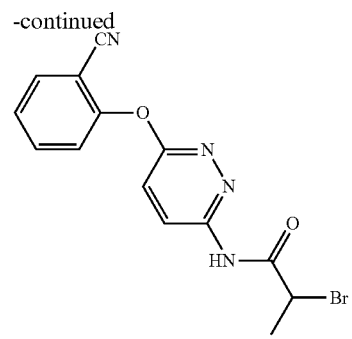

Step 1

3,6-Dichloropyridazine (5 g, 33.6 mmol), 2-hydroxybenzonitrile (4.40 g, 36.9 mmol) and potassium carbonate (6.96 g, 50.3 mmol) in DMF (35 mL) were stirred at 80° C. for 18 h. The reaction was partitioned between water and EtOAc, and the aqueous layer was extracted with EtOAc (2×100 mL). The combined organic layers were washed with water and brine, dried over sodium sulfate, concentrated and purified by column chromatography (ISCO 220 g Gold), eluting with 0-13% MeOH in DCM to provide 2-((6-chloropyridazin-3-yl)oxy)benzonitrile (7.348 g, 30.1 mmol, purity: 95%, recovery: 90%) as a white solid. LCMS (m/z) 232 (M+H)⁺, retention time: 0.73 min, LC/MS Method 2. ¹H NMR: (400 MHz, DMSO-d₆) δ 8.07 (d, J=9.29 Hz, 1H), 7.99 (dd, J=7.82, 1.47 Hz, 1H), 7.80-7.88 (m, 2H), 7.48-7.58 (m, 2H).

Step 2

To a nitrogen-purged microwave vial containing 2-((6-chloropyridazin-3-yl)oxy)benzonitrile (250 mg, 1.079 mmol), Pd₂(dba)₃ (49.4 mg, 0.054 mmol), Xantphos (31.2 mg, 0.054 mmol), and cesium carbonate (879 mg, 2.70 mmol) was added dioxane (5 mL), followed by diphenylmethanimine (0.181 mL, 1.079 mmol). The reaction was microwaved to 120° C. for 30 min, then to 150° C. for 16 h. The mixture was partitioned between water and EtOAc, and the aqueous layer was extracted with EtOAc (2×). The combined organic layers were washed with water and brine, dried over sodium sulfate, concentrated and purified by column chromatography (ISCO 24 g Gold), eluting with 0-100% EtOAc in heptane to provide 2-((6-((diphenylmethylene)amino)pyridazin-3-yl)oxy)benzonitrile (115 mg, 0.183 mmol, purity: 60%, recovery: 17%) as a tan-orange solid. LCMS (m/z) 377 (M+H)$^+$, retention time: 1.16 min, LC/MS Method 3. $^1$H NMR: (400 MHz, DMSO-d$_6$) δ 8.35-8.48 (m, 2H), 7.80 (d, J=2.93 Hz, 1H), 7.28 (dd, J=8.80, 2.93 Hz, 1H), 6.82-6.93 (m, 2H), 6.53 (d, J=8.80 Hz, 1H), 6.00 (s, 2H).

Step 3

To 2-((6-((diphenylmethylene)amino)pyridazin-3-yl)oxy)benzonitrile (115 mg, 0.306 mmol) in MeOH (3 mL) was added 1M aq HCl (3.00 mL). After several hours at rt, the reaction was extracted with DCM, and the aqueous layer was concentrated to provide crude 2-((6-((diphenylmethylene)amino)pyridazin-3-yl)oxy)benzonitrile (115 mg, 0.306 mmol, purity: 93%, recovery: 20%) as a pale yellow solid, which was used without purification. LCMS (m/z) 213 (M+H)$^+$, retention time: 0.56 min, LC/MS Method 3.

Step 4

2-((6-Aminopyridazin-3-yl)oxy)benzonitrile (16 mg, 0.075 mmol), 2-bromopropanoic acid (12.69 mg, 0.083 mmol), and DCC (18.67 mg, 0.090 mmol) in DCM (5 mL) were stirred over the weekend then purified directly by flash chromatography (ISCO 220 g Gold), eluting with 0-60% EtOAc in heptane to provide 2-bromo-N-(6-(2-cyanophenoxy)pyridazin-3-yl)propanamide (10 mg, 0.027 mmol, purity: 95%, recovery: 36%) as a white solid. LCMS (m/z) 348 (M+H)$^+$, retention time: 0.87 min, LC/MS Method 3. $^1$H NMR: (400 MHz, CD$_3$OD) δ 8.59 (d, J=9.3 Hz, 1H), 7.85 (dd, J=7.8, 1.5 Hz, 1H), 7.78 (td, J=7.9, 1.7 Hz, 1H), 7.61 (d, J=9.8 Hz, 1H), 7.40-7.50 (m, 2H), 4.77 (q, J=6.8 Hz, 1H), 1.84 (d, J=6.8 Hz, 3H).

Intermediate 98

2-bromo-N-(5-((3-fluoropyridin-2-yl)oxy)pyridin-2-yl)propanamide

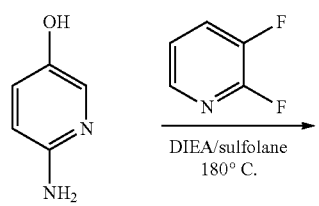

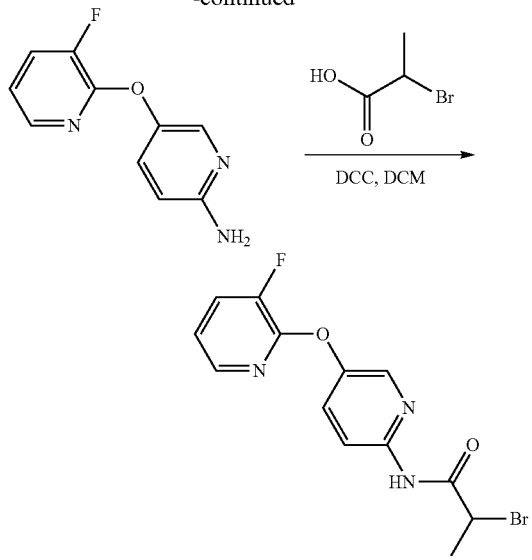

Step 1

To 6-aminopyridin-3-ol (124 mg, 1.130 mmol) in sulfolane (1.5 mL) in a microwave vial were added DIPEA (0.395 mL, 2.259 mmol) and 2,3-difluoropyridine (0.103 mL, 1.130 mmol). This mixture was irradiated at 180° C. for 12.5 h and purified to give 5-((3-fluoropyridin-2-yl)oxy)pyridin-2-amine (78 mg, 0.380 mmol, purity: 99%, recovery: 34%) as an off-white solid. LCMS (m/z) 206 (M+H)$^+$, retention time: 0.59 min, LC/MS Method 3. $^1$H NMR: (400 MHz, CDCl$_3$) δ 8.03 (d, J=2.69 Hz, 1H), 7.91 (dd, J=4.89, 1.71 Hz, 1H), 7.48 (ddd, J=9.84, 8.01, 1.47 Hz, 1H), 7.37 (dd, J=8.80, 2.69 Hz, 1H), 7.00 (ddd, J=7.89, 4.83, 3.18 Hz, 1H), 6.59 (d, J=9.05 Hz, 1H), 4.51 (br. s., 2H).

Step 2

To 5-((3-fluoropyridin-2-yl)oxy)pyridin-2-amine (78 mg, 0.380 mmol) and 2-bromopropanoic acid (0.041 mL, 0.456 mmol) in DCM (2 mL) were added DCC (118 mg, 0.570 mmol) and DMAP (4.64 mg, 0.038 mmol). After 2.5 h, the reaction was filtered, concentrated and purified by column chromatography (ISCO 12 g Gold), eluting with 0-30% EtOAc in heptane to provide 2-bromo-N-(5-((3-fluoropyridin-2-yl)oxy)pyridin-2-yl)propanamide (105 mg, 0.309 mmol, purity: 99%, recovery: 81%) as a white solid. LCMS (m/z) 340 (M+H)$^+$, retention time: 0.92 min, LC/MS Method 3. $^1$H NMR: (400 MHz, CDCl$_3$) δ 8.70 (br. s., 1H), 8.30 (d, J=9.05 Hz, 1H), 8.27 (d, J=2.69 Hz, 1H), 7.91 (dd, J=4.89, 1.47 Hz, 1H), 7.65 (dd, J=8.93, 2.81 Hz, 1H), 7.53 (ddd, J=9.84, 8.01, 1.47 Hz, 1H), 7.06 (ddd, J=7.89, 4.83, 3.18 Hz, 1H), 4.56 (q, J=6.93 Hz, 1H), 1.99 (d, J=7.09 Hz, 3H).

Intermediates 99-102 (102 using Cs$_2$CO$_3$ in AcCN at 60° C. for fluoride displacement) were synthesized in an analogous manner.

| Int. | Name | Structure | ¹H NMR | LC: retention time (min); LC/MS Method of analysis | MS (M + H)⁺ |
|---|---|---|---|---|---|
| 99 | 2-bromo-N-(5-((3,5-difluoropyridin-2-yl)oxy)pyridin-2-yl)propanamide | 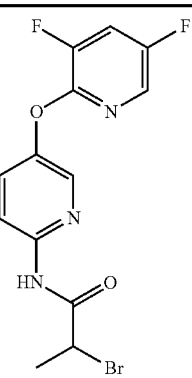 | ¹H NMR: (400 MHz CCl₃) δ ppm 9.08 (br. s., 1H), 8.33 (d, J = 9.05 Hz, 1H), 8.24 (d, J = 2.69 Hz, 1H), 7.83 (d, J = 2.45 Hz, 1H), 7.64 (dd, J = 9.05, 2.69 Hz, 1H), 7.35-7.43 (m, 1H), 4.58 (q, J = 6.85 Hz, 1H), 1.98 (d, J = 7.09 Hz, 3H). | 0.98; LC/MS Method 3 | 360 |
| 100 | 2-bromo-N-(5-((5-fluoropyridin-2-yl)oxy)pyridin-2-yl)propanamide | 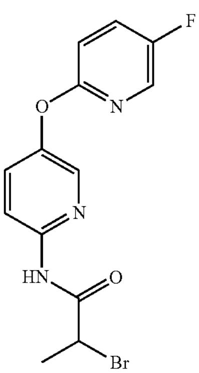 [SMILES: CC(Br)C(=O)Nc1ccc(Oc2ccc(F)cn2)cn1] | ¹H NMR: (400 MHz CCl₃) δ ppm 8.78 (br. s., 1 H) 8.29 (d, J = 9.05 Hz, 1H), 8.22 (d, J = 2.45 Hz, 1H), 8.00 (d, J = 2.93 Hz, 1H), 7.60 (dd, J = 8.93, 2.57 Hz, 1H), 7.44-7.54 (m, 1H), 7.01 (dd, J = 8.93, 3.55 Hz, 1H), 4.56 (q, J = 7.09 Hz, 1H), 1.99 (d, J = 7.09 Hz, 3H). | 0.92; LC/MS Method 3 | 340 |
| 101 | 2-bromo-N-(5-(pyrimidin-4-yloxy)pyridin-2-yl)propanamide | 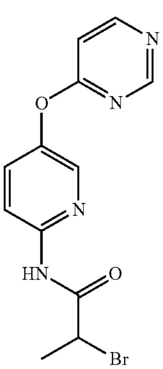 [SMILES: CC(Br)C(=O)Nc1ccc(Oc2ccncn2)cn1] | ¹H NMR: (400 MHz CD₃OD) δ ppm 8.71 (s, 1H), 8.65 (d, J = 5.87 Hz, 1H), 8.19-8.25 (m, 2H), 7.69 (dd, J = 8.80, 2.93 Hz, 1H), 7.18 (dd, J = 5.87, 0.98 Hz, 1H), 4.75 (q, J = 6.85 Hz, 1H), 1.84 (d, J = 6.85 Hz, 3H). | 0.92; LC/MS Method 3 | 324 |
| 102 | 2-bromo-N-(5-((5-chloropyridin-2-yl)oxy)pyridin-2-yl)propanamide | 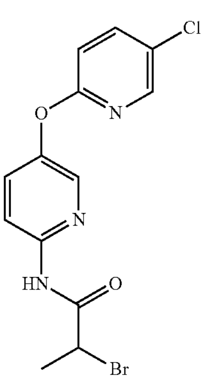 [SMILES: CC(Br)C(=O)Nc1ccc(Oc2ccc(Cl)cn2)cn1] | ¹H NMR: (400 MHz, DMSO-d₆) δ 10.97 (s, 1H), 8.26 (d, J = 2.9 Hz, 1H), 8.22-8.19 (m, 1H), 8.14 (d, J = 8.8 Hz, 1H), 8.00 (dd, J = 8.8, 2.9 Hz, 1H), 7.71 (dd, J = 8.8, 2.9 Hz, 1H), 7.20 (d, J = 8.8 Hz, 1H), 4.89 (q, J = 6.8 Hz, 1H), 1.76 (d, J = 6.8 Hz, 3H). | 1.00; LC/MS Method 5 | 356 |

Intermediate 103

2-bromo-N-(5-(spiro[3.3]heptan-2-yloxy)pyridin-2-yl)propanamide

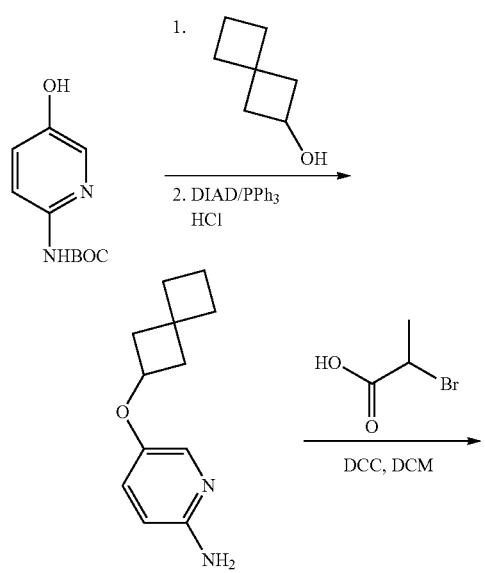

Step 1

To spiro[3.3]heptan-2-ol (500 mg, 4.46 mmol) and triphenylphosphine (780 mg, 2.97 mmol) in THF (10 mL) was added DIAD (0.578 mL, 2.97 mmol), followed after 15 min by tert-butyl (5-hydroxypyridin-2-yl)carbamate (625 mg, 2.97 mmol) in THF (10 mL). After 18 h, additional triphenylphosphine (780 mg, 2.97 mmol) and DIAD (0.578 mL, 2.97 mmol) were added, and the reaction was degassed and backfilled with nitrogen. After 4 h, the reaction was diluted with EtOAc and washed with water. The aqueous layer was extracted with EtOAc (2λ), and the combined organic layers were washed with brine (2×), dried over MgSO$_4$, concentrated, and purified by flash chromatography (silica 40 g Gold column), eluting with 20-70% EtOAc in heptanes to give to give tert-butyl (5-(spiro[3.3]heptan-2-yloxy)pyridin-2-yl)carbamate. The purified product was stirred in HCl (3M, 10 mL, 30.0 mmol) in CMPE for 18 h at rt and then 2 h at 50° C., and concentrated. The residue was taken up in EtOAc, neutralized with NaHCO$_3$, washed with water and brine, dried over MgSO$_4$ and concentrated to give 5-(spiro[3.3]heptan-2-yloxy)pyridin-2-amine (159 mg, 0.778 mmol, purity: 99%, recovery: 26%). LCMS (m/z) 205 (M+H)$^+$, retention time: 0.66 min, LC/MS Method 5. $^1$H NMR: (400 MHz, DMS)-d$_6$) δ 7.46-7.59 (m, 1H), 7.00 (dd, J=8.80, 2.93 Hz, 1H), 6.38 (d, J=8.80 Hz, 1H), 5.43 (s, 2H), 4.41 (quin, J=6.97 Hz, 1H), 2.46 (ddd, J=9.78, 6.85, 2.93 Hz, 2H), 2.00-2.04 (m, 1H), 1.90-1.97 (m, 4H), 1.75-1.84 (m, 2H).

Step 2

5-(Spiro[3.3]heptan-2-yloxy)pyridin-2-amine (160 mg, 0.783 mmol), 2-bromopropanoic acid (70 µL, 0.778 mmol) and DCC (162 mg, 0.783 mmol) in DMF (5.222 mL) were stirred for 18 h, poured into water, neutralized with sodium bicarbonate, and extracted with EtOAc. The combined organic layers were washed with brine, dried over MgSO$_4$, filtered, concentrated and purified by column chromatography (ISCO 40 g Gold), eluting with 0-80% EtOAc in heptanes to provide 2-bromo-N-(5-(spiro[3.3]heptan-2-yloxy)pyridin-2-yl)propanamide (80 mg, 0.236 mmol, purity: 96%, recovery: 30%) as a yellow oil. LCMS (m/z) 338 (M+H)$^+$, retention time: 1.09 min, LC/MS Method 5. $^1$H NMR: (400 MHz, DMS)-d$_6$) δ 10.49-10.90 (m, 1H), 7.88-8.04 (m, 2H), 7.35 (dd, J=9.05, 3.18 Hz, 1H), 4.85 (q, J=6.85 Hz, 1H), 4.63 (quin, J=6.85 Hz, 1H), 2.55-2.64 (m, 2H), 1.97-2.12 (m, 5H) 1.79-1.90 (m, 2H), 1.60-1.71 (m, 2H), 1.12-1.35 (m, 2H).

Intermediate 104

2-bromo-N-(5-(difluoro(4-fluorophenyl)methyl)pyridin-2-yl)propanamide

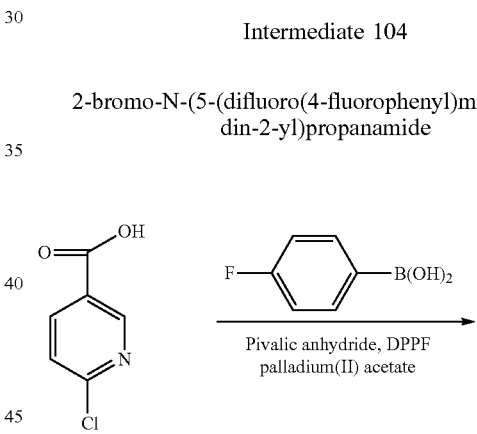

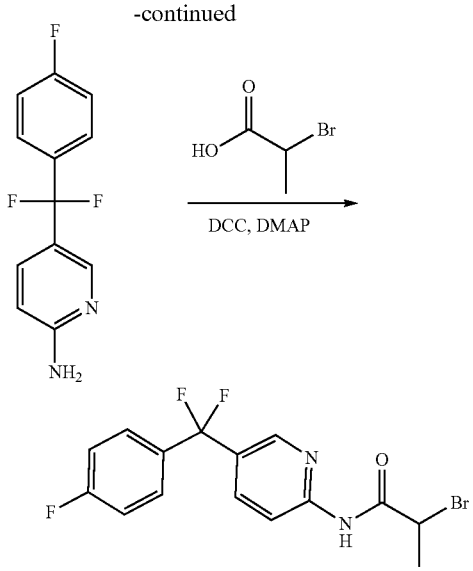

Step 1

To dppf (1.056 g, 1.904 mmol), palladium(II) acetate (0.342 g, 1.523 mmol) and 6-chloronicotinic acid (4 g, 25.4 mmol) in THF (40 ml) was added a slurry of pivalic anhydride (7.79 mL, 38.1 mmol), water (1.143 mL, 63.5 mmol) and (4-fluorophenyl)boronic acid (5.33 g, 38.1 mmol) in THF (30 ml). The reaction was purged with $N_2$, stirred at 60° C. overnight, cooled to rt, concentrated, taken up in DCM, concentrated with Isolute and loaded onto a silica column, eluting with 0-100% EtOAc in heptane to afford 690 mg (11.53% yield) (6-chloropyridin-3-yl)(4-fluorophenyl)methanone as a white solid. LCMS: (ES, m/s): 236 [M+H]$^+$. $^1$H NMR: NMR (400 MHz, CHLOROFORM-d) δ ppm 9.02 (d, J=1.71 Hz, 1H), 8.77 (d, J=2.45 Hz, 1H), 8.27 (dd, J=8.31, 2.45 Hz, 1H), 8.10 (dd, J=8.19, 2.32 Hz, 1H), 7.87 (dd, J=8.80, 5.38 Hz, 2H), 7.49-7.55 (m, 1H), 7.45 (d, J=8.31 Hz, 1H), 7.23 (t, J=8.56 Hz, 2H).

Step 2

To a fluoropolymer vial charged with (6-chloropyridin-3-yl)(4-fluorophenyl)methanone (500 mg, 2.122 mmol), DAST (280 μl, 2.122 mmol) was added. The resulting mixture was heated to 40° C. for 6 d, diluted with DCM, concentrated with Isolute then loaded onto a silica column, eluting with 0-50% EtOAc in heptane to afford 165 mg (0.640 mmol, 30.2% yield) 2-chloro-5-(difluoro(4-fluorophenyl)methyl)pyridine as a brown oil.

LCMS: (ES, m/s): 258 [M+H]$^+$. $^1$H NMR: NMR (400 MHz, CHLOROFORM-d) δ ppm 8.53 (d, J=1.71 Hz, 1H), 7.78 (dd, J=8.31, 2.45 Hz, 1H), 7.46-7.54 (m, 2H), 7.43 (d, J=7.82 Hz, 1H), 7.10-7.21 (m, 2H).

Step 3

To a microwave reaction vial was added $Pd_2(dba)_3$ (62.6 mg, 0.068 mmol) and CyJohnPhos (47.9 mg, 0.137 mmol), followed by 2-chloro-5-(difluoro(4-fluorophenyl)methyl)pyridine (176 mg, 0.683 mmol) in dioxane (2 mL) and LHMDS (2.049 mL, 2.049 mmol, 1 M THF solution). The reaction was degassed and purged with $N_2$, stirred at 60° C. for 24 h, and then at rt over the weekend. The mixture was concentrated, diluted with DCM, concentrated with Isolute then loaded onto a silica column, eluting with 0-40% EtOAc in heptane, followed by 20-100% 3:1 EtOAc: EtOH in heptane to afford 5-(difluoro(4-fluorophenyl)methyl)pyridin-2-amine (121 mg, 0.508 mmol, 74.4% yield) as a brownish solid. LCMS: (ES, m/s): 239 [M+H]. $^1$H NMR: (400 MHz, CHLOROFORM-d) δ ppm 8.12 (s, 1H), 7.47-7.58 (m, 3H), 7.14 (t, J=8.56 Hz, 2H), 6.54 (d, J=8.56 Hz, 1H), 4.77 (br. s., 2H).

Step 4

To DCC (146 mg, 0.705 mmol) in DCM (1.5 ml) was added 2-bromopropanoic acid (0.055 ml, 0.611 mmol). After 15 minutes, 5-(difluoro(4-fluorophenyl)methyl)pyridin-2-amine (112 mg, 0.470 mmol) in DCM (1.5 ml) was added dropwise, followed by a catalytic amount of DMAP. The mixture was stirred 2 h, diluted with DCM, washed with sat'd sodium bicarbonate solution, concentrated with Isolute and loaded onto a silica column (40 g), eluting with 0-50% EtOAc in heptane to afford 140 mg (0.375 mmol, 80% yield) 2-bromo-N-(5-(difluoro(4-fluorophenyl)methyl)pyridin-2-yl)propanamide as a colorless oil. LCMS (ES, m/s): 373 [M+H]$^+$, rt=1.17 min, Method 3. $^1$H NMR: NMR (400 MHz, CHLOROFORM-d) δ ppm 8.71 (br. s., 1H), 8.44 (d, J=1.22 Hz, 1H), 8.27 (d, J=8.56 Hz, 1H), 7.84 (dd, J=8.80, 2.20 Hz, 1H) 7.51 (dd, J=8.80, 5.14 Hz, 2H), 7.15 (t, J=8.68 Hz, 2H), 4.55 (q, J=6.93 Hz, 1H), 1.98 (d, J=7.09 Hz, 3H).

Intermediate 105

2-bromo-N-(5-(4-fluorobenzoyl)pyridin-2-yl)propanamide

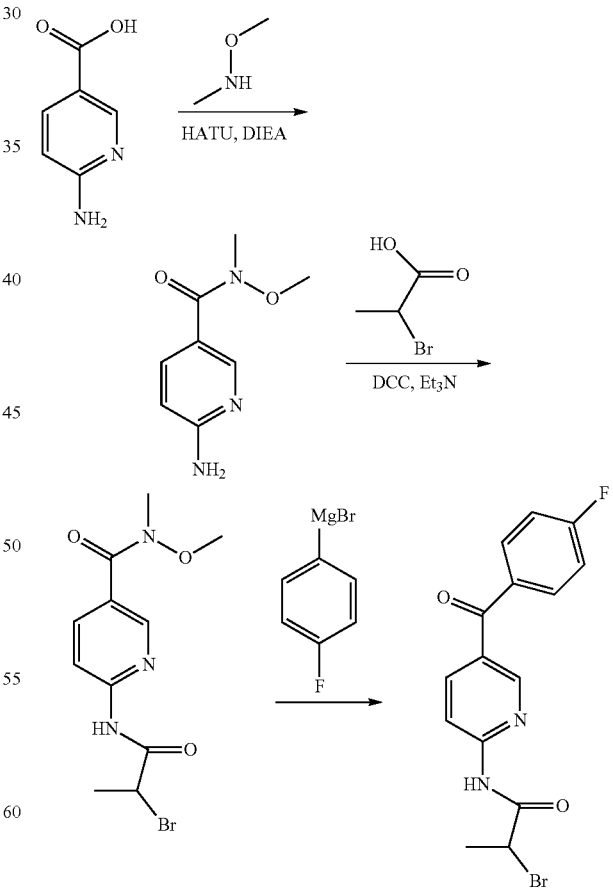

Step 1

To 6-aminonicotinic acid (1000 mg, 7.24 mmol), HATU (3303 mg, 8.69 mmol), and N,O-dimethylhydroxylamine hydrochloride (847 mg, 8.69 mmol) in DMF (15 mL) was added Hunig's base (2.53 mL, 14.48 mmol). The mixture was stirred overnight, then partitioned between water and EtOAc. The organic layer was washed with water (2×) and brine, dried over sodium sulfate, filtered, concentrated, then concentrated again with DCM and Isolute before loading onto a silica column, eluting with 0-100% 3:1 EtOAc: EtOH in heptane to afford 570 mg (3.15 mmol, 43.4% yield) 6-amino-N-methoxy-N-methylnicotinamide as a colorless oil. LCMS: (ES, m/s): 182 [M+H]+. 1H NMR (400 MHz, DMSO-d6) δ ppm 8.28 (d, J=2.45 Hz, 1H), 7.71 (dd, J=8.80, 2.45 Hz, 1H), 6.47 (dd, J=8.80, 0.98 Hz, 1H), 3.55 (s, 3H) 3.21 (s, 3H).

Step 2

To DCC (370 mg, 1.793 mmol) in DCM (1.5 ml) was added 2-bromopropanoic acid (0.140 ml, 1.556 mmol). After 15 min, 6-amino-N-methoxy-N-methylnicotinamide (260 mg, 1.435 mmol) in DCM (1.5 ml) was added dropwise, followed by a catalytic amount of DMAP. The reaction was stirred for 2 h, filtered through Celite and concentrated with Isolute before loading onto a silica column, eluting with 0-75% 3:1 EtOAc: EtOH in hepatane to afford 90 mg (0.285 mmol, 19.84% yield) 6-(2-bromopropanamido)-N-methoxy-N-methylnicotinamide as a clear oil. LCMS: (ES, m/s): 316, 318 [M+H]+. 1H NMR: (400 MHz, CHLOROFORM-d) δ 9.39 (br. s., 1H), 8.73 (d, J=1.71 Hz, 1H), 8.25-8.32 (m, 1H), 8.14-8.22 (m, 1H), 4.59 (q, J=7.01 Hz, 1H), 3.58 (s, 3H) 3.41 (s, 3H), 1.95 (d, J=7.09 Hz, 3H).

Step 3

To 6-(2-bromopropanamido)-N-methoxy-N-methylnicotinamide (84 mg, 0.266 mmol) in THF (2 mL) at 0° C. was added (4-fluorophenyl)magnesium bromide (0.664 mL, 0.664 mmol), dropwise, over 30 min. After 3 h, additional (4-fluorophenyl)magnesium bromide was added, and the mixture was warmed to rt overnight. The reaction was quenched with sat'd NH4Cl dropwise, and diluted with EtOAc. The layers were separated, and the aqueous was extracted with EtOAc. The combined organics were washed with brine, dried over sodium sulfate, filtered, concentrated, diluted with DCM, concentrated with Isolute, then loaded onto a silica column, eluting with 0-70% 3:1 EtOAc: EtOH in heptane to afford 41 mg (0.117 mmol, 43.9% yield) 2-bromo-N-(5-(4-fluorobenzoyl)pyridin-2-yl)propanamide as a white solid. LCMS (ES, m/s): 351 [M+H]+: rt=1.03 min, Method 3. 1H NMR: (400 MHz, CHLOROFORM-d) δ ppm 8.85 (br. s., 1H), 8.75 (d, J=1.71 Hz, 1H), 8.35 (d, J=8.56 Hz, 1H), 8.20 (dd, J=8.68, 2.32 Hz, 1H), 7.80-7.90 (m, 2H), 7.18-7.26 (m, 2H), 4.59 (q, J=7.09 Hz, 1H), 2.00 (d, J=7.09 Hz, 3H).

Intermediate 106

2-bromo-N-(5-((4-fluorophenyl)hydroxy)methyl) pyridin-2-yl)propanamide

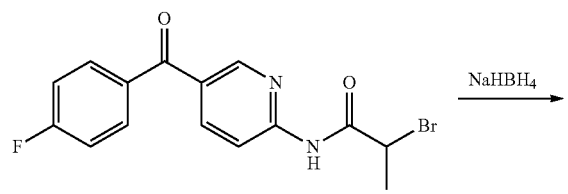

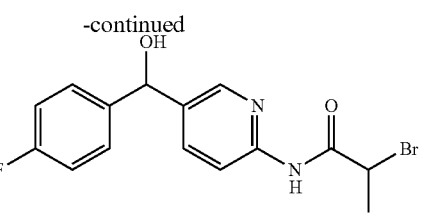

Step 1

To 2-bromo-N-(5-(4-fluorobenzoyl)pyridin-2-yl)propanamide (38 mg, 0.108 mmol) in methanol (2 mL) at 0° C., was added sodium borohydride (4.09 mg, 0.108 mmol). The reaction was stirred at rt for 30 minutes, concentrated, diluted with DCM and concentrated with Isolute before loading onto a silica column, eluting with 3:1 EtOAc: EtOH in heptane to afford (0.045 mmol, 41.9% yield) 2-bromo-N-(5-((4-fluorophenyl)(hydroxy)methyl)pyridin-2-yl)propanamide as a white solid. LCMS (ES, m/s): 351, 353 [M+H]+, rt=0.90 min., Method 3. 1H NMR (400 MHz, CHLOROFORM-d) δ ppm 8.81 (br. s., 1H), 8.32 (s, 1H), 8.17 (d, J=8.56 Hz, 1H), 7.72 (dt, J=8.56, 1.96 Hz, 1H), 7.31-7.39 (m, 2H), 7.07 (t, J=8.68 Hz, 2H), 4.52 (q, J=6.85 Hz, 1H), 1.95 (d, J=7.09 Hz, 3H).

Intermediate 107

2-bromo-N-(3-fluoro-5-((5-fluoropyridin-2-yl)oxy) pyridin-2-yl)propanamide

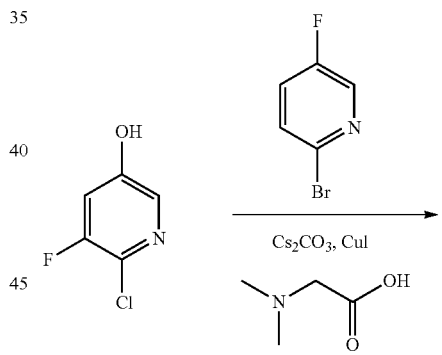

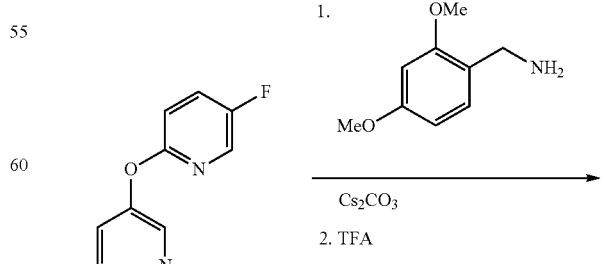

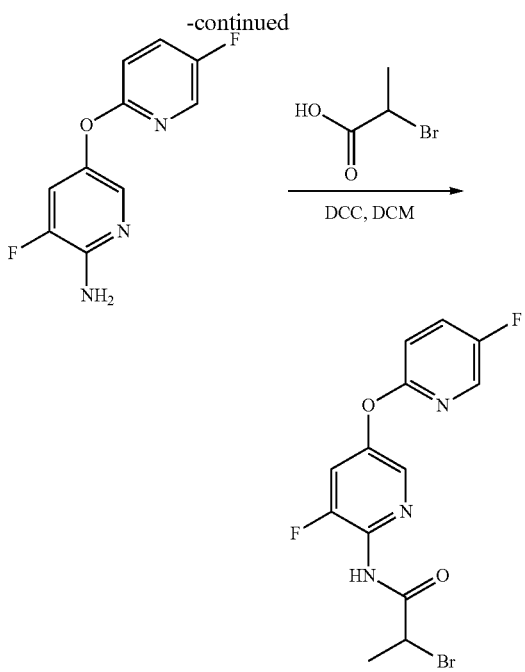

Step 1

A mixture of copper(I) iodide (0.258 g, 1.356 mmol), dimethylglycine (0.140 g, 1.356 mmol), cesium carbonate (3.31 g, 10.17 mmol), 6-chloro-5-fluoropyridin-3-ol (1 g, 6.78 mmol), and 2-bromo-5-fluoropyridine (1.431 g, 8.13 mmol) in dioxane (10 mL) was purged with nitrogen, evacuated (5×) and heated to 110° C. After 18 h, the reaction was cooled to rt, then partitioned between EtOAc and brine. The biphasic mixture was filtered through Celite, then separated. The aqueous layer was extracted with EtOAc (2×), and the combined organic layers were dried over sodium sulfate, concentrated and purified by flash chromatography, eluting with 0-80% ethyl acetate in heptane to afford 1.035 g (4.27 mmol, 62.9% yield) 2-chloro-3-fluoro-5-((5-fluoropyridin-2-yl)oxy)pyridine as a white solid. LCMS (ES, m/s): 243.0. $^1$H NMR (400 MHz, DMSO-d$_6$) δ 8.29 (d, J=2.4 Hz, 1H), 8.21 (d, J=3.4 Hz, 1H), 8.08 (dd, J=9.8, 2.4 Hz, 1H), 7.98-7.88 (m, 1H), 7.31 (dd, J=9.0, 3.7 Hz, 1H).

Step 2

A mixture of 2-chloro-3-fluoro-5-((5-fluoropyridin-2-yl)oxy)pyridine (400 mg, 1.649 mmol), cesium carbonate (1343 mg, 4.12 mmol) and (2,4-dimethoxyphenyl)methanamine (0.297 mL, 1.978 mmol) in dioxane (10 mL) was purged with N$_2$ for 10 min. XantPhos Pd G3 (156 mg, 0.165 mmol) was added, and the reaction was purged with N$_2$ for 1 min, heated at 80° C. for 19 h, stirred at rt over the weekend and poured into 1M HCl/ice and EtOAc, with stirring, for 15 min. The layers were separated, and the aqueous was back extracted with EtOAc. The combined organics were dried over magnesium sulfate, concentrated and purified via silica gel column, eluting with 5-50% 3:1 EtOAc: EtOH (+2% NH$_{40}$H) in heptane to a afford 538 mg (1.369 mmol, 83% yield) N-(2,4-dimethoxybenzyl)-3-fluoro-5-((5-fluoropyridin-2-yl)oxy)pyridin-2-amine as a yellow liquid. LCMS (ES, m/s): 374.3 [M+H]$^+$. $^1$H NMR (400 MHz, DMSO-d$_6$) δ 8.14-8.07 (m, 1H), 7.84-7.77 (m, 1H), 7.72-7.69 (m, 1H), 7.49-7.40 (m, 1H), 7.13-7.05 (m, 2H), 6.89-6.80 (m, 1H), 6.57-6.53 (m, 1H), 6.48-6.41 (m, 1H), 4.51-4.39 (m, 2H), 3.81 (s, 3H), 3.73 (s, 3H).

Step 3

N-(2,4-Dimethoxybenzyl)-3-fluoro-5-((5-fluoropyridin-2-yl)oxy)pyridin-2-amine (535 mg, 1.433 mmol) in TFA (5.52 ml, 71.6 mmol) was stirred for 30 min; diluted with CHCl$_3$ (about 50 ml); concentrated; azeotroped with CHCl$_3$; and stirred in CHCL$_3$ (30 ml), NaHCO$_3$ (sat) and water for 15 min. The layers were partitioned, and the aqueous was back extract with CHCl$_3$ (30 ml). The combined organics were dried over magnesium sulfate, filtered and concentrated to a afford 298 mg (1.202 mmol, 84% yield) 3-fluoro-5-((5-fluoropyridin-2-yl)oxy)pyridin-2-amine, which was used without further purification. LCMS (ES, m/s): 224.1 [M+H]$^+$. $^1$H NMR (400 MHz, DMSO-d$_6$) Shift 8.15-8.07 (m, 1H), 7.84-7.76 (m, 1H), 7.71-7.66 (m, 1H), 7.46-7.37 (m, 1H), 7.13-7.04 (m, 1H), 6.15 (s, 2H).

Step 4

To DCC (145 mg, 0.703 mmol) in DCM (5 ml) at 22° C. was added 2-bromopropanoic acid (0.063 ml, 0.703 mmol). After 10 min, 3-fluoro-5-((5-fluoropyridin-2-yl)oxy)pyridin-2-amine (112 mg, 0.502 mmol) was added, followed by a few crystals of DMAP. The reaction was stirred at rt overnight, and more 2-bromopropanoic acid (0.063 ml, 0.703 mmol) and DCC (105 mg) were added. The mixture was stirred overnight, diluted with DCM (15 ml), filtered, washed with NaHCO$_3$ (sat'd), dried over magnesium sulfate, filtered, concentrated and purified via silica gel column, eluting with 5-65% EtOAc in heptane to a afford 123 mg (0.275 mmol, 54.7% yield) 2-bromo-N-(3-fluoro-5-((5-fluoropyridin-2-yl)oxy)pyridin-2-yl)propanamide. LCMS (ES, m/s): 358.1 [M+H]$^+$. $^1$H NMR (400 MHz, DMSO-d$_6$) Shift 10.73-10.56 (m, 1H), 8.20 (dd, J=12.5, 2.7 Hz, 2H), 7.98-7.78 (m, 2H), 7.27 (dd, J=9.0, 3.7 Hz, 1H), 4.83-4.70 (m, 1H), 1.76 (d, J=6.8 Hz, 3H).

Intermediate 108

(R)-2-bromo-N-(5-(2-(((tert-butyldimethylsilyl)oxy)methyl)-4-fluorophenoxy)pyridin-2-yl)propanamide

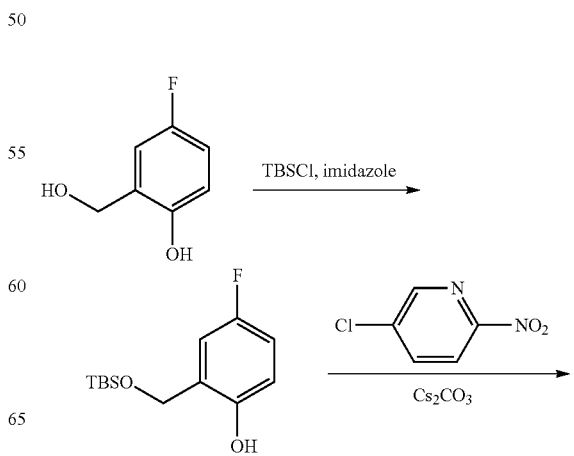

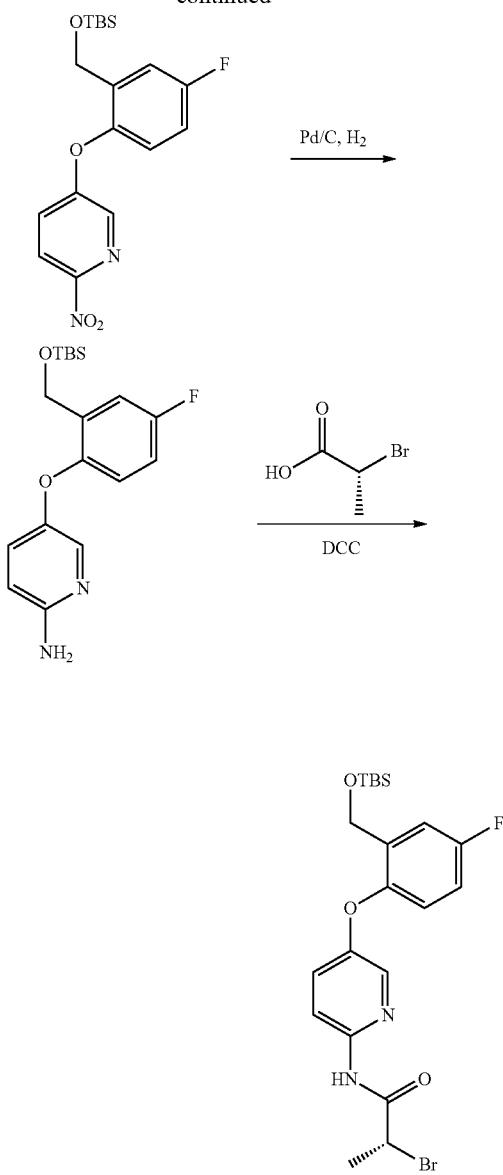

Step 1

To 4-fluoro-2-(hydroxymethyl)phenol (2 g, 14.07 mmol) and imidazole (1.437 g, 21.11 mmol) in DCM (35 mL) was added TBS-Cl (2.121 g, 14.07 mmol) in DCM (5.0 mL). After 2 h, the reaction was diluted with EtOAc (100 mL), washed with water (2×30 mL) and brine (30 mL), dried over Na$_2$SO$_4$, concentrated and purified via silica column (80 g), eluting with 0-20% EtOAc in heptane to give 2.95 g (11.51 mmol, 82% yield) 2-(((tert-butyldimethylsilyl)oxy)methyl)-4-fluorophenol as a clear oil. LCMS: (ES, m/z): 255.2 [M−H]+. $^1$H NMR (400 MHz, CHLOROFORM-d) δ ppm 7.83 (s, 1H) 6.85-6.91 (m, 1H) 6.78-6.83 (m, 1H) 6.69 (dd, J=8.56, 3.18 Hz, 1H) 4.86 (s, 2H) 0.92-0.96 (m, 9H) 0.12-0.18 (m, 6H).

Step 2

To 2-(((tert-butyldimethylsilyl)oxy)methyl)-4-fluorophenol (1 g, 3.90 mmol) and 5-chloro-2-nitropyridine (0.618 g, 3.90 mmol) in DMF (10 mL) was added cesium carbonate (1.271 g, 3.90 mmol). The reaction was stirred overnight, diluted with EtOAc (200 mL), washed with water (2×50 mL) and brine (50 mL), dried over Na$_2$SO$_4$, concentrated and purified over silica (80 g column), eluting with 0-20% EtOAc in heptane give 660 mg (1.744 mmol, 44.7% yield) 5-(2-(((tert-butyldimethylsilyl)oxy)methyl)-4-fluorophenoxy)-2-nitropyridine which contained significant impurity, and was used directly in next step. LCMS: (ES, m/z): 379.0 [M+H]+.

Step 3

A mixture of 5-(2-(((tert-butyldimethylsilyl)oxy)methyl)-4-fluorophenoxy)-2-nitropyridine (660 mg, 1.744 mmol) and Pd—C (93 mg, 0.087 mmol) in ethyl acetate (10 mL) was stirred under hydrogen for 3 h, filtered, concentrated and purified over silica (24 g column), eluting with 0-50% EtOAc in heptane to give 323 mg (0.927 mmol, 53.1% yield) 5-(2-(((tert-butyldimethylsilyl)oxy)methyl)-4-fluorophenoxy)pyridin-2-amine as yellow oil. LCMS: (ES, m/z): 349.2 [M+H]+. $^1$H NMR (400 MHz, CHLOROFORM-d) δ ppm 7.85 (d, J=2.93 Hz, 1H) 7.28-7.31 (m, 1H) 7.11 (dd, J=8.80, 2.93 Hz, 1H) 6.84 (td, J=8.44, 3.18 Hz, 1H) 6.66 (dd, J=9.05, 4.65 Hz, 1H) 6.51 (d, J=8.80 Hz, 1H) 4.81 (s, 2H) 4.34 (br s, 2H) 0.92-1.02 (m, 9H) 0.06-0.19 (m, 6H).

Step 4

To (R)-2-bromopropanoic acid (0.042 mL, 0.459 mmol) and 5-(2-(((tert-butyldimethylsilyl)oxy)methyl)-4-fluorophenoxy)pyridin-2-amine (160 mg, 0.459 mmol) in DCM (2 mL) was added DCC (123 mg, 0.597 mmol). The reaction was stirred overnight, filtered, concentrated and purified over silica (12 g column), eluting with 0-20% EtOAc in heptane to give 210 mg (0.434 mmol, 95% yield) (R)-2-bromo-N-(5-(2-(((tert-butyldimethylsilyl)oxy)methyl)-4-fluorophenoxy)pyridin-2-yl)propanamide. LCMS: (ES, m/z): 483.2 [M+H]+, rt=1.65 min; Method 3. $^1$H NMR (400 MHz, CHLOROFORM-d) δ ppm 8.58 (br s, 1H) 8.15 (d, J=9.29 Hz, 1H) 8.04 (d, J=2.45 Hz, 1H) 7.32 (dd, J=9.05, 3.18 Hz, 1H) 7.26-7.30 (m, 1H) 6.92 (td, J=8.31, 2.93 Hz, 1H) 6.79 (dd, J=9.05, 4.65 Hz, 1H) 4.75 (s, 2H) 4.53 (q, J=6.85 Hz, 1H) 1.97 (d, J=6.85 Hz, 3H) 0.91-0.98 (m, 9H) δ 0.07-0.15 (m, 6H).

Intermediate 109 (from 2-bromo-5-nitropyrazine) was synthesized in an analogous manner. Intermediates 110-111 were synthesized in an analagous manner to Intermediate 108, starting with the appropriate difluorophenyl diol.

| Int. | Name | Structure | ¹H NMR | LC: retention time (min); LC/MS Method of analysis | MS (M + H)⁺ |
|---|---|---|---|---|---|
| 109 | (R)-2-bromo-N-(5-(2-(((tert-butyldimethylsilyl)oxy)methyl)-4-fluorophenoxy)pyrazin-2-yl)propanamide | 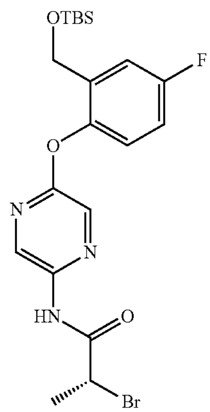 [SMILES: C[C@@H](Br)C(=O)Nc1cnc(Oc2ccc(F)cc2CO[Si](C)(C)C(C)(C)C)cn1] | ¹H NMR (400 MHz, CHLOROFORM-d) δ ppm 9.01 (d, J = 1.47 Hz, 1 H) 8.48 (s, 1 H) 8.11 (d, J = 1.47 Hz, 1 H) 7.31-7.35 (m, 1 H) 6.99 (d, J = 6.17 Hz, 2 H) 4.67 (d, J = 0.98 Hz, 2 H) 4.53-4.59 (m, 1 H) 1.97 (d, J = 7.34 Hz, 3 H) 0.91-0.93 (m, 9 H) 0.00-0.12 (m, 6 H). | 1.52; LCMS Method 3 | 486.3 |
| 110 | (R)-2-bromo-N-(5-(2-(((tert-butyldimethylsilyl)oxy)methyl)-4,6-difluorophenoxy)pyrazin-2-yl)propanamide | 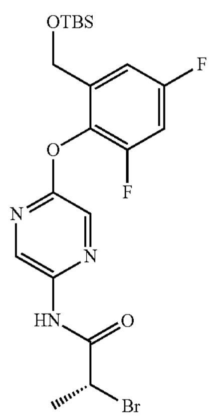 [SMILES: C[C@@H](Br)C(=O)Nc1cnc(Oc2c(F)cc(F)cc2CO[Si](C)(C)C(C)(C)C)cn1] | ¹H NMR: (400 MHz, DMSO-d₆) δ 11.17 (s, 1H), 8.77 (d, J = 1.5 Hz, 1H), 8.48 (d, J = 1.5 Hz, 1H), 7.48-7.32 (m, 1H), 7.21-7.11 (m, 1H), 4.86 (q, J = 6.7 Hz, 1H), 4.67 (s, 2H), 1.75 (d, J = 6.4 Hz, 3H), 0.86-0.78 (m, 9H), 0.05--0.04 (m, 6H | 1.55; LCMS Method 5 | 502 |
| 111 | (R)-2-bromo-N-(5-(2-(((tert-butyldimethylsilyl)oxy)methyl)-4,6-difluorophenoxy)pyridin-2-yl)propanamide | 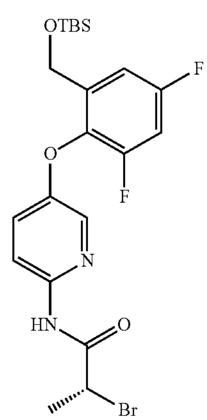 [SMILES: C[C@@H](Br)C(=O)Nc1ccc(Oc2c(F)cc(F)cc2CO[Si](C)(C)C(C)(C)C)cn1] | ¹H NMR: (400 MHz, DMSO-d₆) δ 10.89 (s, 1H), 8.11-7.96 (m, 2H), 7.45 (ddd, J = 11.1, 8.4, 2.9 Hz, 1H), 7.38 (dd, J = 9.0, 3.2 Hz, 1H), 7.20 (br dd, J = 9.0, 1.7 Hz, 1H), 4.86 (q, J = 6.8 Hz, 1H), 4.69 (s, 2H), 1.73 (d, J = 6.8 Hz, 3H), 0.91-0.77 (m, 9H), 0.08--0.11 (m, 6H). | 1.56; LCMS Method 5 | 501 |

EXAMPLES

Example 1

(S)—N-(6-(cyclopropylmethoxy)pyridazin-3-yl)-2-((S)-4,4-difluoro-3-(6-oxo-1-(2,2,2-trifluoroethyl)-1,6-dihydropyridin-3-yl)piperidin-1-yl)propanamide

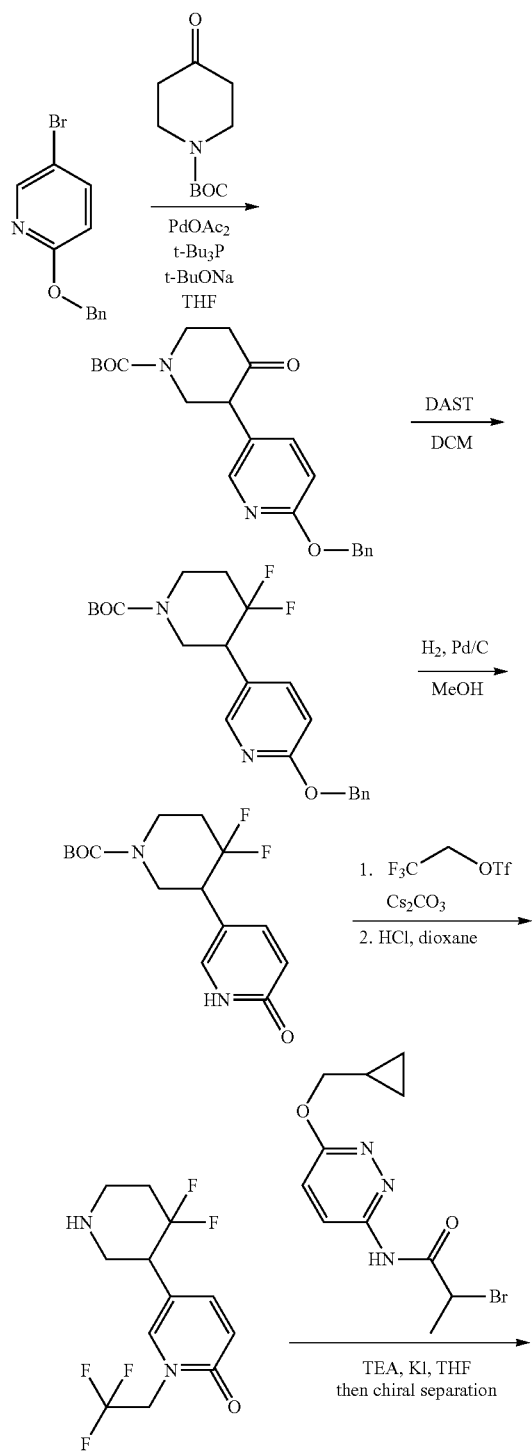

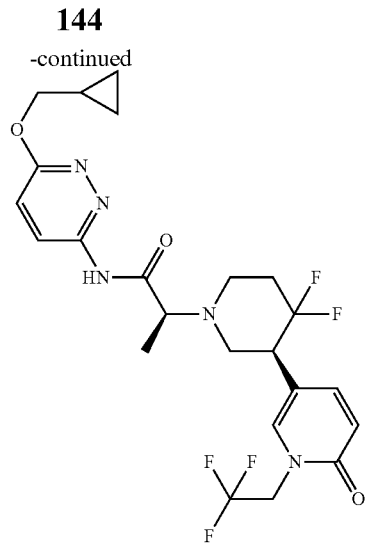

Step 1

A mixture of t-BuONa (6.66 g, 69.39 mmol, 2.5 eq) in THF (60 mL) was stirred at room temperature for 10 min followed by addition of Pd(OAc)$_2$ (622 mg, 2.78 mmol, 0.1 eq) and (t-Bu)$_3$P (5.61 g, 2.78 mmol, 0.1 eq, 10% in hexane). After 5 min, 2-(benzyloxy)-5-bromopyridine (7.30 g, 27.76 mmol, 1.0 eq) and tert-butyl 4-oxopiperidine-1-carboxylate (8.28 g, 41.63 mmol, 1.5 eq) were added, and the mixture was flushed with nitrogen and stirred for 18 h at 45° C. The reaction was quenched with water (300 mL) and extracted with ethyl acetate (300 mL×3). The combined organic extracts were washed with brine (600 mL), dried over sodium sulfate and concentrated to give the crude product as yellow oil. The residue was purified over a silica gel column, eluting with ethyl acetate in petroleum ether (0-30%, 30 min) to give tert-butyl 3-(6-(benzyloxy)pyridin-3-yl)-4-oxopiperidine-1-carboxylate 4.8 g (yield: 27%, purity: 59%) as yellow oil. LCMS: (ES, m/s) 383 [M+H]$^+$, retention time: 1.189 min, LC/MS Method 31. $^1$H NMR: (300 MHz, CDCl$_3$) δ ppm 8.00-7.99 (m, 1H), 7.49-7.31 (m, 6H), 6.85-6.82 (m, 1H), 5.39 (s, 2H), 4.33-4.28 (m, 2H), 3.76-3.67 (m, 1H), 3.48-3.18 (m, 2H), 2.70-2.43 (m, 2H), 1.52 (s, 9H).

Step 2

To tert-butyl 3-(6-(benzyloxy)pyridin-3-yl)-4-oxopiperidine-1-carboxylate (2.40 g, 6.28 mmol, 1.0 eq) in DCM (20 mL) at 0° C. was added DAST (2.02 g, 12.55 mmol, 2.0 eq), and the mixture was stirred overnight at room temperature, quenched with ice/water (50 mL) and extracted with DCM (50 mL×3). The combined organic phases were dried over Na$_2$SO$_4$, concentrated and purified over a silica gel column, eluting with ethyl acetate:petroleum ether (1:4) to give tert-butyl 3-(6-(benzyloxy)pyridin-3-yl)-4,4-difluoropiperidine-1-carboxylate 1.04 g (purity: 79%, yield: 39%) as a yellow oil. LCMS (ES, m/s): 405 [M+H]+

Step 3

A mixture of tert-butyl 3-(6-(benzyloxy)pyridin-3-yl)-4,4-difluoropiperidine-1-carboxylate (5 g, 12.4 mmol, 1.0 eq) and Pd/C (2.5 g, 10%) in methanol (100 mL) was evacuated and flushed three times with hydrogen. The mixture was stirred at room temperature for 2 h under an atmosphere of hydrogen, filtered, concentrated and purified by reverse column (330 g), eluting with 20-60% AcCN in water (10 mM NH$_4$HCO$_3$) to give of tert-butyl 4,4-difluoro-3-(6-oxo-1,6-dihydropyridin-3-yl)piperidine-1-carboxylate (2 g, purity: 95%) as a colorless oil. LCMS: (ES, m/s): 315[M+

H]+ ¹H NMR: (300 MHz, DMSO-d₆) δ ppm 13.14 (s, 1H), 7.46 (d, J=9.6 Hz, 1H), 7.36 (s, 1H), 6.60 (d, J=9.6 Hz, 1H), 4.27-4.15 (m, 2H), 3.15-3.05 (m, 2H), 2.90-2.81 (m, 1H), 2.20-1.93 (m, 2H), 1.49 (s, 9H).

Step 4

A mixture of tert-butyl 4,4-difluoro-3-(6-oxo-1,6-dihydropyridin-3-yl)piperidine-1-carboxylate (1.2 g, 3.82 mmol, 1.0 eq), 2,2,2-trifluoroethyl trifluoromethanesulfonate (2.21 g, 9.56 mmol, 2.5 eq) and Cs₂CO₃ (3.12 g, 9.56 mmol, 2.5 eq) in DMF (20 mL) was stirred for 6 h at 25° C., quenched with water (100 mL) and extracted with ethyl acetate (100 mL×3). The organic layers were dried over sodium sulfate, concentrated and purified over a silica gel column, eluting with ethyl acetate:petroleum ether (1:1) to give 0.69 g (purity: 90%, yield: 46%) of tert-butyl 4,4-difluoro-3-(6-oxo-1-(2,2,2-trifluoroethyl)-1,6-dihydropyridin-3-yl)piperidine-1-carboxylate as a white solid. LCMS: (ES, m/z): 397 [M+H]⁺. ¹H NMR (400 MHz, DMSO-d₆) δ 7.67-7.66 (m, 1H), 7.50-7.48 (m, 1H), 6.49 (d, J=9.6 Hz, 1H), 4.88-4.80 (m, 2H), 4.09-3.97 (m, 2H), 3.15-3.01 (m, 2H), 2.19-2.11 (m, 1H), 2.05-1.87 (m, 2H), 1.42 (s, 9H).

Step 5

A mixture of tert-butyl 4,4-difluoro-3-(6-oxo-1-(2,2,2-trifluoroethyl)-1,6-dihydropyridin-3-yl)piperidine-1-carboxylate (0.69 g, 1.74 mmol, 1.0 eq) and HCl (10 mL, 4 M in dioxane) was stirred for 2 h at rt. The reaction was concentrated to give 0.5 g (crude) 5-(4,4-difluoropiperidin-3-yl)-1-(2,2,2-trifluoroethyl)pyridin-2 (1H)-one as a white solid, the HCl salt, which was used without purification. LCMS (ES, m/z): 297 [M+H]⁺. ¹H NMR: (400 MHz, DMSO-d₆) δ 7.77-7.76 (m, 1H), 7.52-7.49 (m, 1H), 6.52 (d, J=9.6 Hz, 1H), 4.95-4.77 (m, 2H), 3.65-3.44 (m, 3H), 3.42-3.32 (m, 1H), 3.12-2.98 (m, 1H), 2.49-2.33 (m, 2H).

Step 6

A mixture of 5-(4,4-difluoropiperidin-3-yl)-1-(2,2,2-trifluoroethyl)pyridin-2 (1H)-one (as free base) (0.30 g, 1.0 mmol, 1.0 eq), 2-bromo-N-(6-(cyclopropylmethoxy)pyridazin-3-yl)propanamide (Intermediate 14) (0.30 g, 1.0 mmol, 1.0 eq), KI (0.17 g, 1.0 mmol, 1.0 eq) and TEA (1.01 g, 10.0 mmol, 10.0 eq) in THF (10 mL) was stirred 15 h at 60° C., poured into water (30 mL), and extracted with DCM (30 mL×3). The organic layers were dried over sodium sulfate, concentrated and purified over a silica gel column, eluting with methanol:dichloromethane (1:50) to give 0.3 g product as a white solid. The collected product (0.3 g) was chirally separated via two sets of conditions. The first chiral separation conditions: Column: CHIRAL ART Cellulose-SB, 2×25 cm, 5 μm; Mobile Phase A: Hex (8 mM NH₃.MeOH), Mobile Phase B: EtOH; Flow rate: 20 mL/min; Gradient: 1:1 A:B; giving peaks with retention times of RT1: 5.767; RT2-RT3: 8.621-8.846; and RT4: 10.993. The second peak (RT2-RT3: 8.621-8.846), was concentrated to give 130 mg product for the second chiral separation.

These second conditions were: Column: CHIRAL PAK IF, 2×25 cm, 5 μm; Mobile Phase A: Hex (8 mM NH₃.MeOH), Mobile Phase B: EtOH; Flow rate: 20 mL/min; 1:1 A:B; which gave products with retention times RT1: 7.107; and RT2: 9.310. The second peak (RT2: 9.310) was gave 35 mg (purity: 99.5%, yield: 7%) of (S)—N-(6-(cyclopropylmethoxy)pyridazin-3-yl)-2-((S)-4,4-difluoro-3-(6-oxo-1-(2,2,2-trifluoroethyl)-1,6-dihydropyridin-3-yl)piperidin-1-yl)propanamide, a white solid. LCMS (ES, m/s): 516 [M+H]+ ¹H NMR: (400 MHz, CD₃OD) δ 8.36 (d, J=9.6 Hz, 1H), 7.67-7.61 (m, 2H), 7.20 (d, J=9.6 Hz, 1H), 6.56 (d, J=9.6 Hz, 1H), 4.85-4.77 (m, 2H), 4.25 (d, J=7.2 Hz, 2H), 3.61-3.56 (m, 1H), 3.39-3.27 (m, 1H), 2.99-2.91 (m, 3H), 2.68-2.61 (m, 1H), 2.31-2.17 (m, 2H), 1.38-1.29 (m, 4H), 0.65-0.60 (m, 2H), 0.40-0.36 (m, 2H).

Examples 2 and 3 were synthesized in an analogous manner, using the designated Intermediate in Step 6.

| Ex | Name | Structure | ¹H NMR | Analytical LC/MS: (M + H)⁺; retention time (min); LC/MS Method of analysis | Int |
|---|---|---|---|---|---|
| 2 | (S)-N-(5-(cyclopropylmethoxy)pyridin-2-yl)-2-((S)-4,4-difluoro-3-(6-oxo-1-(2,2,2-trifluoroethyl)-1,6-dihydropyridin-3-yl)piperidin-1-yl)propanamide | 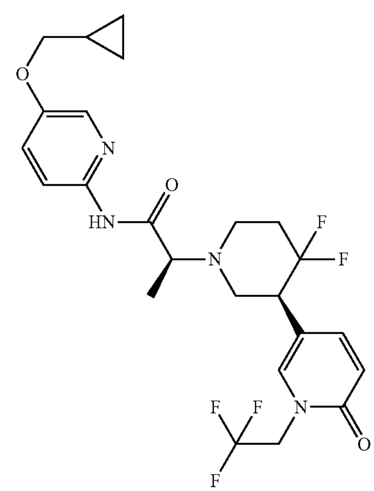 [SMILES: C[C@@H](C(=O)Nc1ccc(OCC2CC2)cn1)N1CCC(F)(F)[C@@H](c2ccc(=O)n(CC(F)(F)F)c2)C1] | Isomer 2: ¹H NMR: (400 MHz, CD₃OD) δ ppm 8.06 (d, J = 9.2 Hz, 1H), 7.99-7.98 (m, 1H), 7.67 (s, 1H), 7.62-7.60 (m, 1H), 7.43-7.40 (m, 1H), 6.56 (d, J = 9.2 Hz, 1H), 4.86-4.78 (m, 2H), 3.88 (d, J = 7.6 Hz, 2H), 3.55-3.49 (m, 1H), 3.37-3.31 (m, 1H), 2.98-2.95 (m, 2H), 2.92-2.89 (m, 1H), 2.66-2.59 (m, 1H), 2.21-2.17 (m, 2H), 1.34 (d, J = 7.2 Hz, 3H), 1.29-1.23 (m, 1H), 0.65-0.60 (m, 2H), 0.38-0.34 (m, 2H). | 515; rt 1.213. LC/MS Method 11 | 22 |

| Ex | Name | Structure | $^1$H NMR | Analytical LC/MS: (M + H)$^+$; retention time (min); LC/MS Method of analysis | Int |
|---|---|---|---|---|---|
| 3 | (S)-2-((S)-4,4-difluoro-3-(6-oxo-1-(2,2,2-trifluoroethyl)-1,6-dihydropyridin-3-yl)piperidin-1-yl)-N-(5-fluoropyridin-2-yl)propanamide | 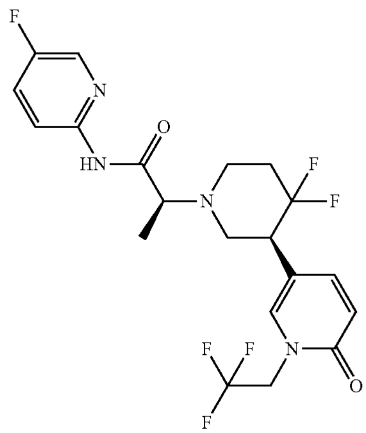 [SMILES: C[C@@H](C(=O)Nc1ccc(F)cn1)N1CCC(F)(F)[C@@H](c2ccc(=O)n(CC(F)(F)F)c2)C1] | $^1$H NMR: (400 MHz, CD$_3$OD) δ ppm 8.22-8.18 (m, 2H), 7.67-7.60 (m, 3H), 6.56 (d, J = 9.6 Hz, 1H), 4.85-4.74 (m, 2H), 3.58-3.53 (m, 1H), 3.38-3.33 (m, 1H), 3.02-2.89 (m, 3H), 2.67-2.61 (m, 1H), 2.29-2.14 (m, 2H), 1.36-1.34 (m, 3H). | 463; rt 1.082. LC/MS Method 12 | 1 |

Example 4

(S)-2-((S)-4,4-difluoro-3-(6-oxo-1,6-dihydropyridin-3-yl)piperidin-1-yl)-N-(5-(2,4-difluorophenoxy)pyridin-2-yl)propanamide

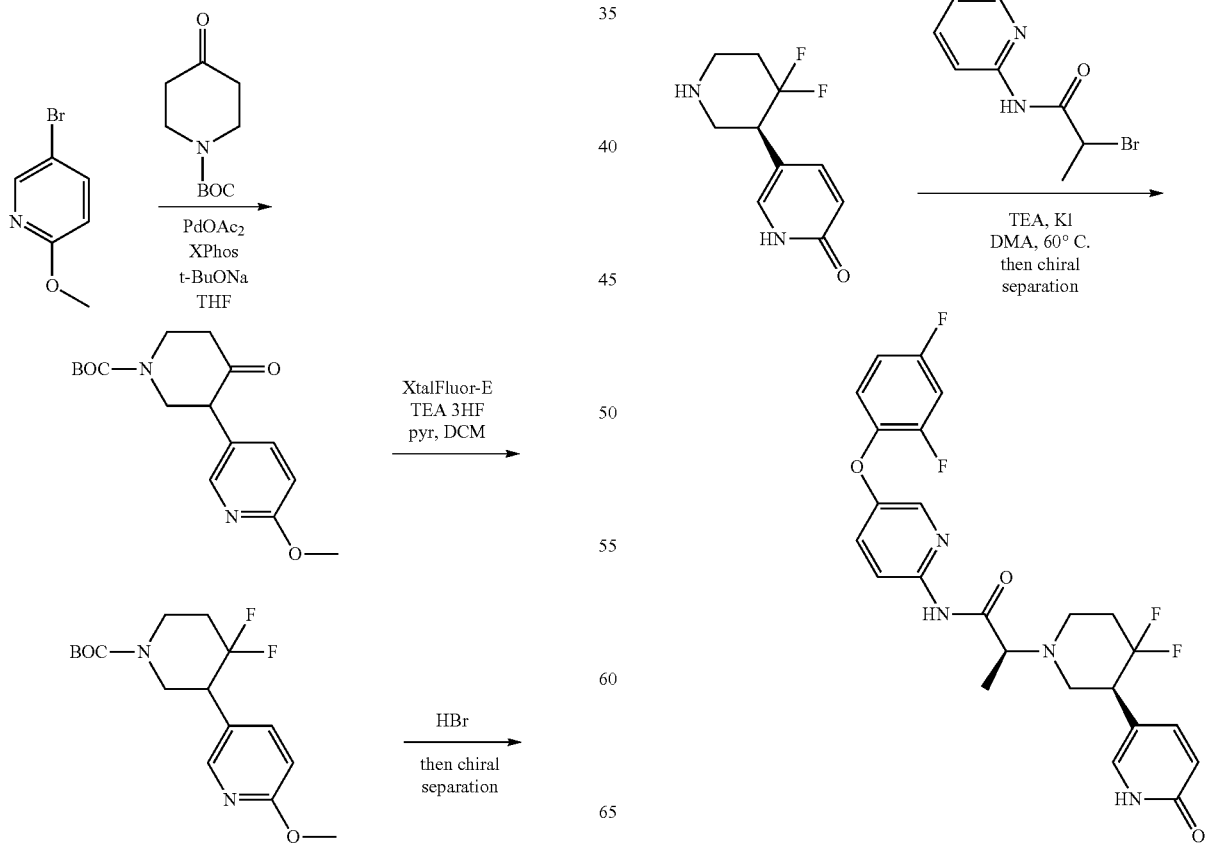

Step 1

To sodium tert-butoxide (278.1 g, 2894 mmol) in THF (2.15 L) were added tert-butyl 4-oxopiperidine-1-carboxylate (287.7 g, 1444 mmol) and 5-bromo-2-methoxypyridine (180.1 g, 958 mmol), using THF (250 mL) to rinse. The mixture was evacuated and back-filled with nitrogen (3×), then XPhos (45.7 g, 96 mmol) and palladium(II) acetate (10.75 g, 47.9 mmol) were added, using THF (0.35 L) to rinse. The reaction was heated to 45° C. for 22 h, cooled to 0° C., and quenched slowly with water (1.575 L) and brine (675 mL). EtOAc (2.3 L) was added, and the mixture was agitated for 10 min. The layers were separated, and the aqueous layer was extracted with EtOAc (2×1.35 L). The combined organics were washed with brine (900 mL), concentrated and purified by column chromatography, eluting with 15-75% EtOAc in heptane to provide tert-butyl 3-(6-methoxypyridin-3-yl)-4-oxopiperidine-1-carboxylate (210 g, 685 mmol, purity: 84%, recovery: 74%). LCMS (m/z) 307 (M+H)$^+$, retention time: 0.91 min, LC/MS Method 3. $^1$H NMR: (400 MHz, CDCl$_3$) δ ppm 7.99 (d, J=2.4 Hz, 1H), 7.41 (dd, J=8.8, 2.4 Hz, 1H), 6.77 (d, J=8.8 Hz, 1H), 4.24-4.39 (m, 2H), 3.95 (s, 3H), 3.69 (dd, J=10.5, 6.1 Hz, 1H), 3.43 (ddd, J=13.3, 10.1, 4.4 Hz, 2H), 2.53-2.65 (m, 2H), 1.53 (s, 9H).

Step 2

To XtalFluor-E (199 g, 868 mmol) in DCM (585 mL) at −1.1° C. was slowly added a solution of triethylamine trihydrofluoride (140 g, 868 mmol) and pyridine (34.3 g, 434 mmol) in DCM (414 mL), followed by a solution of tert-butyl 3-(6-methoxypyridin-3-yl)-4-oxopiperidine-1-carboxylate (133 g, 434 mmol) in DCM (794 mL). The reaction was warmed to 25° C. and after 3 h slowly poured into a stirred sat'd NaHCO$_3$ sol'n cooled to −5° C. The mixture was warmed to 25° C., the layers were separated, and the aqueous layer was extracted with DCM (2×1.3 L). The combined organics were dried over sodium sulfate, concentrated and purified by column chromatography, eluting with 5-45% EtOAc in heptane to provide tert-butyl 4,4-difluoro-3-(6-methoxypyridin-3-yl)piperidine-1-carboxylate (64.37 g, 196 mmol, purity: 90%, recovery: 45%). LCMS (m/z) 328 (M+H)$^+$, retention time: 1.02 min, LC/MS Method 5. $^1$H NMR: (400 MHz, CDCl$_3$) δ ppm 8.09 (d, J=2.45 Hz, 1H), 7.54 (br d, J=8.31 Hz, 1H), 6.74 (d, J=8.31 Hz, 1H), 4.19-4.38 (m, 3H), 3.94 (s, 3H), 2.85-3.19 (m, 2H), 1.87-2.09 (m, 2H), 1.42-1.55 (m, 9H).

Step 3

To a 48% aqueous solution of hydrobromic acid (40.9 mL, 361 mmol) was added a solution of tert-butyl 4,4-difluoro-3-(6-methoxypyridin-3-yl)piperidine-1-carboxylate (12.6 g, 38.4 mmol) in toluene (40 mL), dropwise. The reaction was stirred at 95° C. overnight, concentrated, taken up in 2-MeTHF (100 mL) and treated with a 3M solution of hydrochloric acid in cyclopentylmethyl ether (CPME) (130 mL). Dilution to approximately 250 mL total volume with 2-methyltetrahydrofuran, sonication of the gel-salt/organic mixture for approximately five minutes and subsequent stirring at room temperature for 30 minutes afforded a thick pale green suspension. The suspended solids were then collected by suction filtration and dried. In some cases this material was used as a racemic mixture and in other instances this material was subjected to chiral resolution, after neutralization with isopropylamine before injection, via Agilent semi-prep 1200 through an AD-H column (5 microns-20 mm×250 mm), eluting with 70:30 AcCN:MeOH at 45 ml/min. The enantiomers eluted at 3.981 min and 8.269 min. The first-eluting isomer (3.981 min) was stirred in AcCN (250 mL) at 60° C. with activated charcoal (3 g) for 90 min. The mixture was filtered through Celite, concentrated, and the residue was triturated with AcCN to provide (S)-5-(4,4-difluoropiperidin-3-yl)pyridin-2 (1H)-one (2.568 g, 11.87 mmol, recovery: 31%) as a light tan solid. LCMS (m/z) 215 (M+H)$^+$, retention time: 0.39 min, LC/MS Method 3. $^1$H NMR (400 MHz, MeOH-d4) S ppm 7.60 (ddd, J=9.54, 2.69, 0.98 Hz, 1H), 7.37 (d, J=2.45 Hz, 1H), 6.53 (d, J=8.80 Hz, 1H), 3.05-3.23 (m, 2H), 2.92-3.05 (m, 2H), 2.86 (td, J=13.21, 2.93 Hz, 1H), 1.84-2.21 (m, 2H).

Step 4

To 2-bromo-N-(5-(2,4-difluorophenoxy)pyridin-2-yl)propanamide (Intermediate 71) (92 mg, 0.257 mmol) in DMA (2 mL) were added (S)-5-(4,4-difluoropiperidin-3-yl)pyridin-2 (1H)-one (50 mg, 0.233 mmol), KI (42.6 mg, 0.257 mmol) and Et$_3$N (0.163 mL, 1.167 mmol). The resulting mixture was stirred at 60° C. for 3 h, cooled and purified by prep HPLC (SunFire C18 OBD Prep Column, 100 A), eluting with 40-41% AcCN in water (0.05% TFA), followed by repurification (XBridge Prep OBD C18 Column), eluting with 35-51% AcCN in water (10 mmol/L NH$_4$HCO$_3$) to give 39 mg of a white solid. In some cases this material was used as a racemic mixture, and in other cases was separated by chiral purification (Chiralpak IA, 2×25 cm, 5 um; Mobile Phase A: Hex [8 mM NH$_3$.MeOH], Mobile Phase B: EtOH; Flow rate: 35 mL/min; 1:1 A:B over 17 min) to give (S)-2-((S)-4,4-difluoro-3-(6-oxo-1,6-dihydropyridin-3-yl) piperidin-1-yl)-N-(5-(2,4-difluorophenoxy)pyridin-2-yl) propanamide (8.0 mg, 0.016 mmol, 26.5% yield), retention time 14.65 min, as a white solid. LCMS (m/z) 491 (M+H)+. $^1$H NMR: (400 MHz, CD$_3$OD) δ ppm 8.15 (d, J=9.2 Hz, 1H), 8.06 (d, J=3.2 Hz, 1H), 7.67-7.57 (m, 1H), 7.44-7.38 (m, 2H), 7.26-7.12 (m, 2H), 7.04-6.96 (m, 1H), 6.52 (d, J=9.6 Hz, 1H), 3.58-3.48 (m, 1H), 3.40-3.22 (m, 1H), 3.03-2.85 (m, 3H), 2.68-2.57 (m, 1H), 2.34-2.10 (m, 2H), 1.34 (d, J=6.8 Hz, 3H).

Examples 5-102 were synthesized in an analogous manner using the designated Intermediate in Step 4.

| Ex | Name | Structure | ¹H NMR | LC/MS: (M + H)⁺; retention time (min); LC/MS Method of analysis | Int |
|---|---|---|---|---|---|
| 5 | (S)-2-((S)-4,4-difluoro-3-(6-oxo-1,6-dihydropyridin-3-yl)piperidin-1-yl)-N-(5-(4-fluorophenoxy)pyridin-2-yl)propanamide | 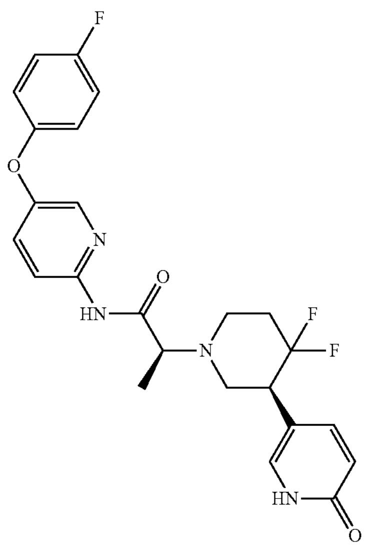 [SMILES: C[C@@H](C(=O)Nc1ccc(Oc2ccc(F)cc2)cn1)N1CCC(F)(F)[C@@H](c2ccc(=O)[nH]c2)C1] | ¹H NMR: (400 MHz, CD$_3$OD) δ ppm 8.18 (d, J = 9.0 Hz, 1H), 8.09 (d, J = 2.9 Hz, 1H), 7.67 (dd, J = 9.5, 2.2 Hz, 1H), 7.48 (dd, J = 9.0, 2.9 Hz, 1H), 7.45 (d, J = 2.4 Hz, 1H), 7.19-7.11 (m, 2H), 7.09-7.01 (m, 2H), 6.54 (d, J = 9.3 Hz, 1H), 3.61-3.48 (m, 1H), 3.43-3.37 (m, 1H), 3.01-2.91 (m, 3H), 2.69-2.61 (m, 1H), 2.24-2.14 (m, 2H), 1.37 (d, J = 6.8 Hz, 3H). | 473; rt 1.100. LC/MS Method 6 | 70 |
| 6 | (S)-2-((S)-4,4-difluoro-3-(6-oxo-1,6-dihydropyridin-3-yl)piperidin-1-yl)-N-(5-phenoxypyridin-2-yl)propanamide | 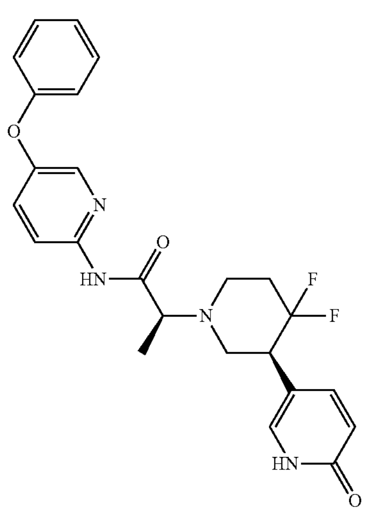 [SMILES: C[C@@H](C(=O)Nc1ccc(Oc2ccccc2)cn1)N1CCC(F)(F)[C@@H](c2ccc(=O)[nH]c2)C1] | ¹H NMR: (400 MHz, CD$_3$OD) δ ppm 8.18 (d, J = 9.0 Hz, 1H), 8.13-8.02 (m, 1H), 7.66 (t, J = 9.0 Hz, 1H), 7.49 (dd, J = 9.0, 2.9 Hz, 1H), 7.46-7.37 (m, 3H), 7.21-7.14 (m, 1H), 7.04 (d, J = 8.1 Hz, 2H), 6.54 (dd, J = 9.5, 4.9 Hz, 1H), 3.55 (dd, J = 9.3, 6.9 Hz, 1H), 3.38 (d, J = 10.5 Hz, 1H), 3.09-2.92 (m, 2H), 2.90-2.56 (m, 2H), 2.43-2.10 (m, 2H), 1.37 (d, J = 6.9 Hz, 3H). | 455; rt 2.139. LC/MS Method 7 | 72 |

-continued

| Ex | Name | Structure | ¹H NMR | LC/MS: (M + H)⁺; retention time (min); LC/MS Method of analysis | Int |
|----|------|-----------|--------|---------|-----|
| 7 | (S)-N-(5-benzylpyridin-2-yl)-2-((S)-4,4-difluoro-3-(6-oxo-1,6-dihydropyridin-3-yl)piperidin-1-yl)propanamide | 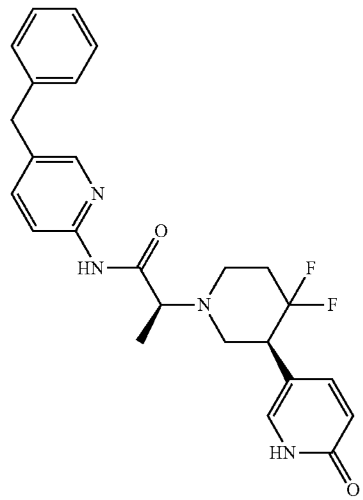 [SMILES: C[C@@H](C(=O)Nc1ccc(Cc2ccccc2)cn1)N1CCC(F)(F)[C@@H](c2ccc(=O)[nH]c2)C1] | ¹H NMR: (400 MHz, CDCl₃) δ ppm 12.30 (br, 1H), 9.58 (br, 1H), 8.18-8.14 (m, 2H), 7.55-7.53 (m, 1H), 7.46-7.44 (m, 1H), 7.32-7.16 (m, 6H), 6.57 (d, J = 9.6 Hz, 1H), 3.96 (s, 2H), 3.44-3.38 (m, 1H), 3.23-3.16 (m, 1H), 2.89-2.83 (m, 3H), 2.62-2.56 (m, 1H), 2.23-2.10 (m, 2H), 1.35 (d, J = 7.2 Hz, 3H). | 453; rt 1.139. LC/MS Method 13 | 37 |
| 8 | N-(6-(cyclopropylmethoxy)pyridazin-3-yl)-2-((S)-4,4-difluoro-3-(6-oxo-1,6-dihydropyridin-3-yl)piperidin-1-yl)propanamide | 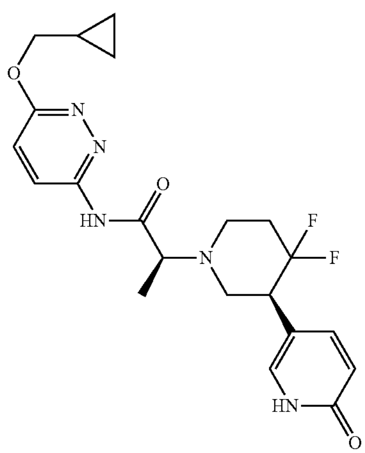 | ¹H NMR: (400 MHz, CD₃OD) δ ppm 8.36 (d, J = 9.6 Hz, 1H), 7.65 (dd, J = 2.0, 9.2 Hz, 1H), 7.43 (d, J = 2.4 Hz, 1H), 7.20 (d, J = 9.2 Hz, 1H), 6.52 (d, J = 9.6 Hz, 1H), 4.26-4.24 (m, 2H), 3.60-3.55 (m, 1H), 3.38-3.28 (m, 1H), 3.02-2.91 (m, 3H), 2.67-2.60 (m, 1H), 2.27-2.14 (m, 2H), 1.36-1.29 (m, 4H), 0.65-0.60 (m, 2H), 0.40-0.36 (m, 2H). | 434; rt 1.297. LC/MS Method 8 | 14 |
| 9 | (S)-N-(5-(cyclopentyloxy)pyridin-2-yl)-2-((S)-4,4-difluoro-3-(6-oxo-1,6-dihydropyridin-3-yl)piperidin-1-yl)propanamide | 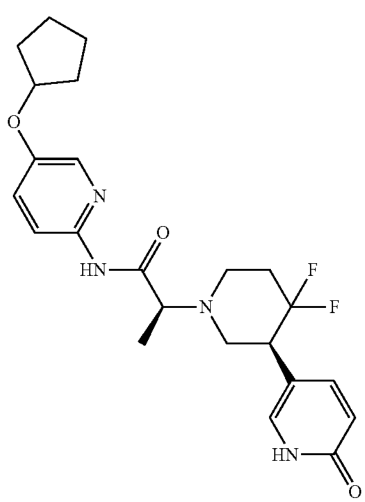 | ¹H NMR: (400 MHz, CD₃OD) δ ppm 8.07 (d, J = 9.1 Hz, 1H), 7.97 (d, J = 2.9 Hz, 1H), 7.71-7.63 (m, 1H), 7.47-7.34 (m, 2H), 6.54 (d, J = 9.4 Hz, 1H), 3.54 (q, J = 7.0 Hz, 1H), 3.41-3.30 m, 2H), 3.01-2.91 (m, 3H), 2.70-2.60 (m, 1H), 2.25-2.17 (m, 2H), 1.98 (tq, J = 11.0, 6.2 Hz, 2H), 1.88-1.78 (m, 4H), 1.73-1.63 (m, 2H), 1.37 (d, J = 7.0 Hz, 3H). | 473; rt 1.569. LC/MS Method 10 | 23 |

| Ex | Name | Structure | ¹H NMR | LC/MS: (M + H)⁺; retention time (min); LC/MS Method of analysis | Int |
|---|---|---|---|---|---|
| 10 | (S)-N-(5-((E-2-cyclopropylvinyl)pyridin-2-yl)-2-((S)-4,4-difluoro-3-(6-oxo-1,6-dihydropyridin-3-yl)piperidin-1-yl)propanamide | 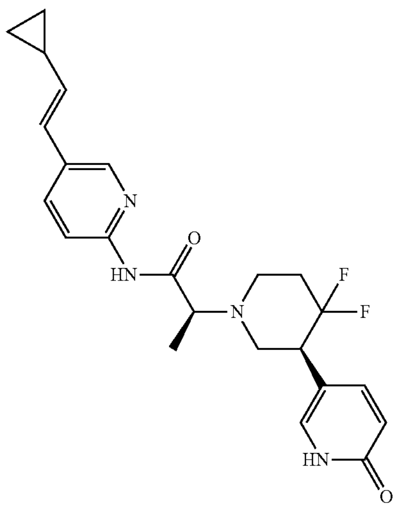 [SMILES: C[C@@H](C(=O)Nc1ccc(/C=C/C2CC2)cn1)N1CCC(F)(F)[C@@H](c2ccc(=O)[nH]c2)C1] | ¹H NMR: (400 MHz, CD$_3$OD) δ ppm 8.21 (d, J = 2.4 Hz, 1H), 8.08 (d, J = 8.8 Hz, 1H), 7.83-7.80 (m, 1H), 7.65-7.63 (m, 1H), 7.42 (d, J = 2.4 Hz, 1H), 6.49-6.47 (m, 2H), 5.89-5.82 (m, 1H), 3.56-3.35 (m, 2H), 3.01-2.83 (m, 3H), 2.65-2.59 (m, 1H), 2.33-2.13 (m, 2H), 1.64-1.55 (m, 1H), 1.34-1.29 (m, 3H), 0.87-0.81 (m, 2H), 0.55-0.51 (m, 2H). | 429; rt 1.134. LC/MS Method 13 | 33 |
| 11 | (S)-2-((S)-4,4-difluoro-3-(6-oxo-1,6-dihydropyridin-3-yl)piperidin-1-yl)-N-(6-methyl-[2,3'-bipyridin]-6'-yl)propanamide | 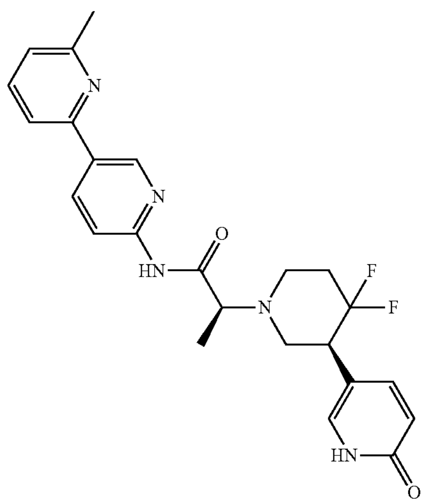 [SMILES: Cc1cccc(-c2ccc(NC(=O)[C@H](C)N3CCC(F)(F)[C@@H](c4ccc(=O)[nH]c4)C3)nc2)n1] | ¹H NMR: (400 MHz, CD$_3$OD) δ ppm 8.91 (d, J = 2.4 Hz, 1H), 8.40-8.39 (m, 1H), 8.30-8.28 (m, 1H), 7.80-7.76 (m, 1H), 7.67-7.65 (m, 2H), 7.46 (s, 1H), 7.25 (d, J = 7.2 Hz, 1H), 6.53 (d, J = 9.2 Hz, 1H), 3.72-3.60 (m, 1H), 3.47-3.40 (s, 1H), 3.00-2.94 (m, 2H), 2.92-2.83 (m, 1H), 2.66-2.63 (m, 1H), 2.62 (s, 3H), 2.33-2.18 (m, 2H), 1.36 (d, J = 6.8 Hz, 3H). | 454; rt 1.366. LC/MS Method 14 | 34 |
| 12 | (S)-N-(6-benzylpyridazin-3-yl)-2-((S)-4,4-difluoro-3-(6-oxo-1,6-dihydropyridin-3-yl)piperidin-1-yl)propanamide | 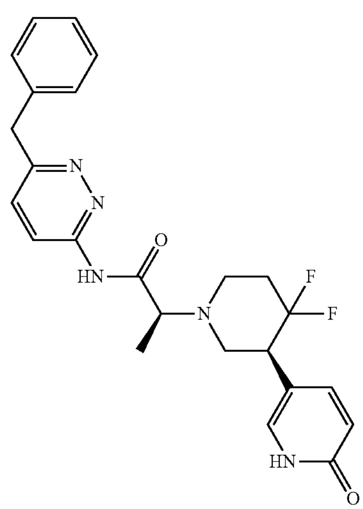 [SMILES: C[C@@H](C(=O)Nc1ccc(Cc2ccccc2)nn1)N1CCC(F)(F)[C@@H](c2ccc(=O)[nH]c2)C1] | ¹H NMR: (400 MHz, DMSO-d$_6$) δ ppm 11.58 (s, 1H), 10.82 (s, 1H), 8.25 (d, J = 9.2 Hz, 1H), 7.63-7.60 (m, 1H), 7.56 (d, J = 9.2 Hz, 1H), 7.42 (d, J = 2.7 Hz, 1H), 7.35-7.18 (m, 5H), 6.50 (d, J = 9.2 Hz, 1H), 4.26 (s, 2H), 3.63-3.55 (m, 1H), 3.08-2.95 (m, 1H), 2.95-2.68 (m, 2H), 2.55-2.51 (m, 1H), 2.38-2.12 (m, 2H), 1.21 (d, J = 6.8 Hz, 3H). | 454; rt 1.30. LC/MS Method 10 | 90 |

-continued

| Ex | Name | Structure | ¹H NMR | LC/MS: (M + H)⁺; retention time (min); LC/MS Method of analysis | Int |
|---|---|---|---|---|---|
| 13 | (S)-2-((S)-4,4-difluoro-3-(6-oxo-1,6-dihydropyridin-3-yl)piperidin-1-yl)-N-(5-(pyridin-4-ylmethyl)pyridin-2-yl)propanamide | 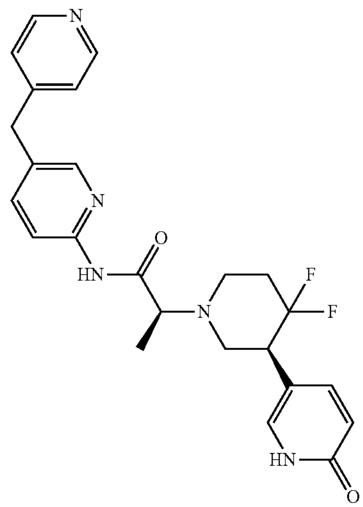 [SMILES: C[C@@H](C(=O)Nc1ccc(Cc2ccncc2)cn1)N1CCC(F)(F)[C@@H](c2ccc(=O)[nH]c2)C1] | ¹H NMR: (400 MHz, CD₃OD) δ ppm 8.48-8.43 (m, 2H), 8.26 (d, J = 2.0 Hz, 1H), 8.16 (d, J = 8.6 Hz, 1H), 7.71 (dd, J = 8.6, 2.4 Hz, 1H), 7.67 (dd, J = 9.4, 2.1 Hz, 1H), 7.44 (d, J = 2.4 Hz, 1H), 7.35-7.30 (m, 2H), 6.54 (d, J = 9.5 Hz, 1H), 4.07 (s, 2H), 3.56 (q, J = 6.8 Hz, 1H), 3.45-3.36 (m, 1H), 3.02-2.95 (m, 2H), 2.93-2.86 (m, 1H), 2.64 (td, J = 11.7, 3.2 Hz, 1H), 2.27-2.15 (m, 2H), 1.36 (d, J = 7.1 Hz, 3H). | 454; rt 1.13. LC/MS Method 10 | 91 |
| 14 | (S)-N-(5-cyclopentyl-pyridin-2-yl)-2-((S)-4,4-difluoro-3-(6-oxo-1,6-dihydropyridin-3-yl)piperidin-1-yl)propanamide | 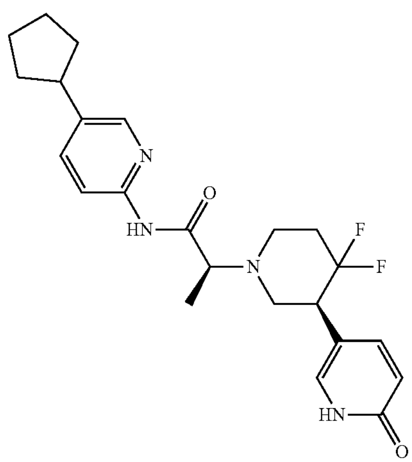 [SMILES: C[C@@H](C(=O)Nc1ccc(C2CCCC2)cn1)N1CCC(F)(F)[C@@H](c2ccc(=O)[nH]c2)C1] | ¹H NMR: (400 MHz, CD₃OD) δ ppm 8.18-8.16 (m, 1H), 8.09 (d, J = 8.8 Hz, 1H), 7.73-7.71 (m, 1H), 7.65-7.63 (m, 1H), 7.42 (d, J = 2.4 Hz, 1H), 6.52 (d, J = 9.2 Hz, 1H), 3.54-3.49 (m, 1H), 3.41-3.31 (m, 1H), 3.10-2.82 (m, 4H), 2.69-2.54 (m, 1H), 2.36-2.06 (m, 4H), 1.87-1.52 (m, 6H), 1.36-1.31 (m, 3H). | 431; rt 1.071. LC/MS Method 11 | 40 |
| 15 | (S)-N-(5-cyclopropyl-pyridin-2-yl)-2-((S)-4,4-difluoro-3-(6-oxo-1,6-dihydropyridin-3-yl)piperidin-1-yl)propanaraide | 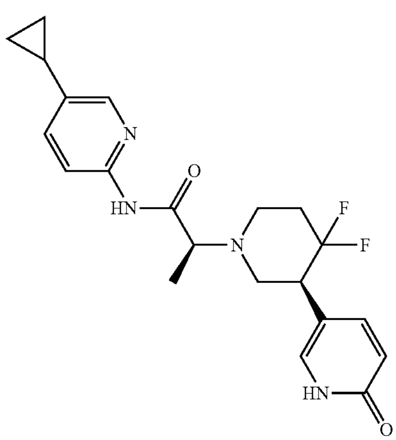 [SMILES: C[C@@H](C(=O)Nc1ccc(C2CC2)cn1)N1CCC(F)(F)[C@@H](c2ccc(=O)[nH]c2)C1] | ¹H NMR: (400 MHz, DMSO-d₆) δ ppm 11.57 (br, 1H), 10.13 (s, 1H), 8.15 (d, J = 2.4 Hz, 1H), 7.98 (d, J = 7.6 Hz, 1H), 7.44-7.42 (m, 2H), 7.32-7.30 (m, 1H), 6.29 (d, J = 9.6 Hz, 1H), 3.66-3.61 (m, 1H), 3.25-3.15 (m, 1H), 2.93-2.78 (m, 3H), 2.51-2.46 (m, 1H), 2.09-1.88 (m, 3H), 1.20 (d, J = 6.8 Hz, 3H), 0.97-0.93 (m, 2H), 0.70-0.66 (m, 2H). | 403; rt 0.890. LC/MS Method 12 | 2 |

-continued

| Ex | Name | Structure | ¹H NMR | LC/MS: (M + H)+; retention time (min); LC/MS Method of analysis | Int |
|----|------|-----------|--------|------|-----|
| 16 | (S)-2-((S)-4,4-difluoro-3-(6-oxo-1,6-dihydropyridin-3-yl)piperidin-1-yl)-N-(5-(m-tolyl)pyridin-2-yl)propanamide | 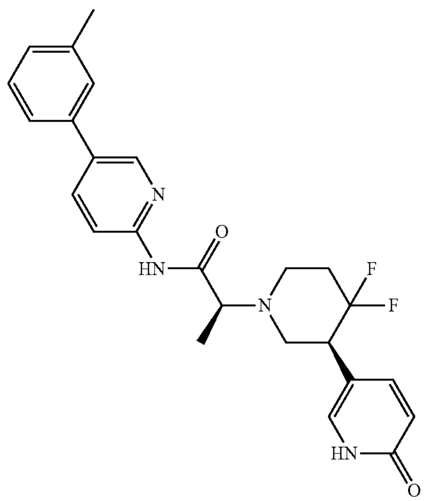 [SMILES: Cc1cccc(-c2ccc(NC(=O)[C@H](C)N3CCC(F)(F)[C@@H](c4ccc(=O)[nH]c4)C3)nc2)c1] | ¹H NMR: (400 MHz, CD₃OD) δ ppm 8.56-8.55 (m, 1H), 8.25 (d, J = 8.4 Hz, 1H), 8.08-8.05 (m, 1H), 7.67-7.64 (m, 1H), 7.46-7.41 (m, 3H), 7.37-7.33 (m, 1H), 7.22-7.20 (m, 1H), 6.53 (d, J = 9.6 Hz, 1H), 3.60-3.55 (m, 1H), 3.42-3.35 (m, 1H), 2.99-2.90 (m, 3H), 2.67-2.62 (m, 1H), 2.42 (s, 3H), 2.31-2.15 (m, 2H), 1.36 (d, J = 7.2 Hz, 3H). | 453; rt 0.890. LC/MS Method 15 | 12 |
| 17 | (S)-N-(2-cyclopropyl-oxazolo[4,5-b]pyridin-5-yl)-2-((S)-4,4-difluoro-3-(6-oxo-1,6-dihydropyridin-3-yl)piperidin-1-yl)propanamide | 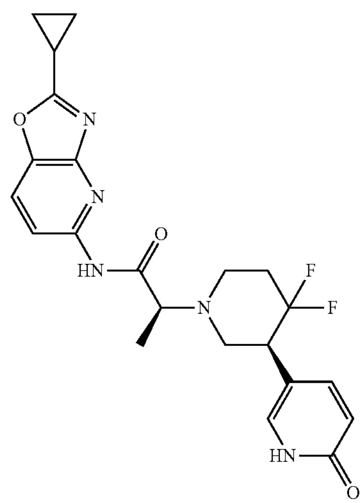 [SMILES: C[C@@H](C(=O)Nc1ccc2oc(C3CC3)nc2n1)N1CCC(F)(F)[C@@H](c2ccc(=O)[nH]c2)C1] | ¹H NMR: (400 MHz, CD₃OD) δ ppm 8.18 (d, J = 8.8 Hz, 1H), 7.93 (d, J = 8.8 Hz, 1H), 7.67-7.64 (m, 1H), 7.43 (d, J = 2.4 Hz, 1H), 6.52 (d, J = 9.2 Hz, 1H), 3.63-3.54 (m, 1H), 3.41-3.37 (m, 1H), 3.01-2.92 (m, 3H), 2.67-2.60 (m, 1H), 2.33-2.13 (m, 3H), 1.33 (d, J = 6.8 Hz, 3H), 1.31-1.30 (m, 4H). | 444; rt 1.274. LC/MS Method 14 | 49 |
| 18 | (S)-N-(5-cyclobutylpyridin-2-yl)-2-((S)-4,4-difluoro-3-(6-oxo-1,6-dihydropyridin-3-yl)piperidin-1-yl)propanamide | 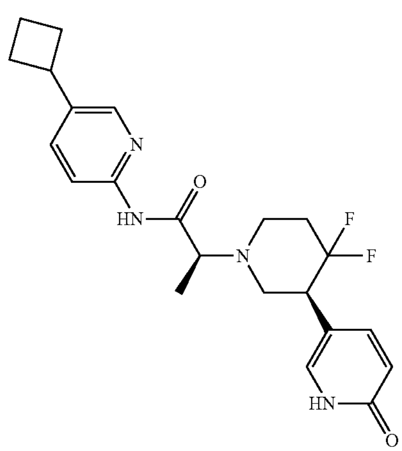 [SMILES: C[C@@H](C(=O)Nc1ccc(C2CCC2)cn1)N1CCC(F)(F)[C@@H](c2ccc(=O)[nH]c2)C1] | ¹H NMR: (300 MHz, DMSO-d₆) δ ppm 11.62 (s, 1H), 10.21 (s, 1H), 8.19 (d, J = 2.1 Hz, 1H), 8.05 (d, J = 9.3 Hz, 1H), 7.73 (dd, J = 2.4, 8.7 Hz, 1H), 7.45-7.33 (m, 2H), 6.31 (d, J = 9.1 Hz, 1H), 3.75-3.69 (m, 1H), 3.60-3.46 (m, 2H), 3.19-3.17 (m, 1H), 3.00-2.85 (m, 3H), 2.37-2.31 (m, 2H), 2.16-1.97 (m, 5H), 1.90-1.77 (m, 1H), 1.24 (d, J = 6.9 Hz, 3H). | 417; rt 0.979. LC/MS Method 11 | 46 |

-continued

| Ex | Name | Structure | ¹H NMR | LC/MS: (M + H)⁺; retention time (min); LC/MS Method of analysis | Int |
|---|---|---|---|---|---|
| 19 | 2-((S)-4,4-difluoro-3-(6-oxo-1,6-dihydropyridin-3-yl)piperidin-1-yl)-N-(6-phenoxy-pyridazin-3-yl)propanamide | 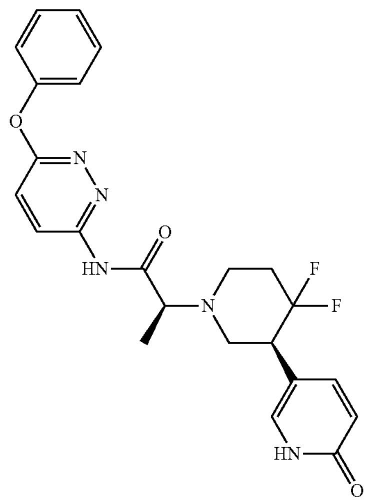 [SMILES: C[C@@H](C(=O)Nc1ccc(Oc2ccccc2)nn1)N1CCC(F)(F)[C@@H](c2ccc(=O)[nH]c2)C1] | ¹H NMR: (400 MHz, CD₃OD) δ ppm 8.52 (d, J = 9.6 Hz, 1H), 7.63 (d, J = 9.2 Hz, 1H), 7.39-7.46 (m, 4H), 7.23-7.27 (m, 1H), 7.17 (d, J = 7.6 Hz, 2H), 6.51 (d, J = 9.6 Hz, 1H), 3.57-3.62 (m, 1H), 3.31-3.39 (m, 1H), 2.92-2.99 (m, 3H), 2.62-2.64 (m, 1H), 2.14-2.28 (m, 2H), 1.28-1.36 (m, 3H). | 456; rt 1.325. LC/MS Method 10 | 54 |
| 20 | (S)-2-((S)-4,4-difluoro-3-(6-oxo-1,6-dihydropyridin-3-yl)piperidin-1-yl)-N-(o-tolyloxy)pyridazin-3-yl)propanamide | 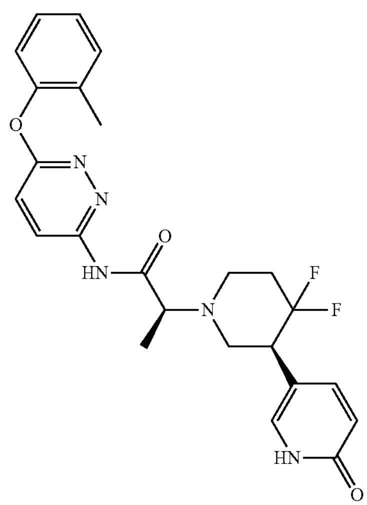 [SMILES: Cc1ccccc1Oc1ccc(NC(=O)[C@H](C)N2CCC(F)(F)[C@@H](c3ccc(=O)[nH]c3)C2)nn1] | ¹H NMR: (400 MHz, CD₃OD) δ ppm 8.52 (d, J = 9.6 Hz, 1H), 7.65-7.62 (m, 1H), 7.41-7.38 (m, 2H), 7.33-7.31 (m, 1H), 7.26-7.25 (m, 1H), 7.19-7.17 (m, 1H), 7.08-7.06 (m, 1H), 6.51 (d, J = 9.6 Hz, 1H), 3.60-3.55(m, 1H), 3.31-3.30 (m, 2H), 3.03-3.00 (m, 1H), 2.89-2.71 (m, 3H), 2.27-2.17 (m, 4H), 1.31 (d, J = 6.8 Hz, 3H). | 470; rt 1.053. LC/MS Method 6 | 55 |
| 21 | N-(5-(2-cyclopropylethyl)pyridin-2-yl)-2-((S)-4,4-difluoro-3-(6-oxo-1,6-dihydropyridin-3-yl)piperidin-1-yl)propanamide | 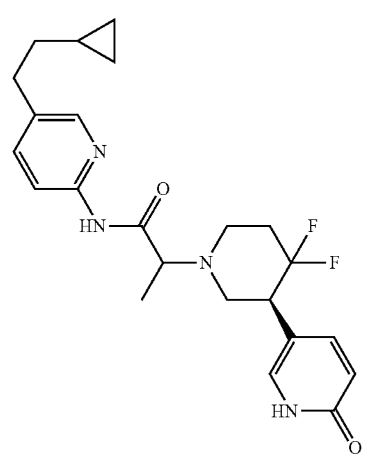 [SMILES: CC(C(=O)Nc1ccc(CCC2CC2)cn1)N1CCC(F)(F)[C@@H](c2ccc(=O)[nH]c2)C1] | ¹H NMR: (400 MHz, CD₃OD) δ ppm 8.18-8.10 (m, 2H), 7.72-7.63 (m, 2H), 7.45-7.44 (m, 1H), 6.56-6.52 (m, 1H), 3.57-3.53 (m, 1H), 3.35-3.32 (m, 1H), 3.02-2.72 (m, 6H), 2.21-2.19 (m, 2H), 1.56-1.51 (m, 2H), 1.36 (d, J = 7.2 Hz, 3H), 0.74-0.70 (m, 1H), 0.47-0.43 (m, 2H), 0.07-0.04 (m, 2H). | 431; rt 1.479 and 1.501. LC/MS Method 15 | 48 |

-continued

| Ex | Name | Structure | ¹H NMR | LC/MS: (M + H)⁺; retention time (min); LC/MS Method of analysis | Int |
|---|---|---|---|---|---|
| 22 | (S)-N-(5-(benzyloxy)pyridin-2-yl)-2-((S)-4,4-difluoro-3-(6-oxo-1,6-dihydropyridin-3-yl)piperidin-1-yl)propanamide | 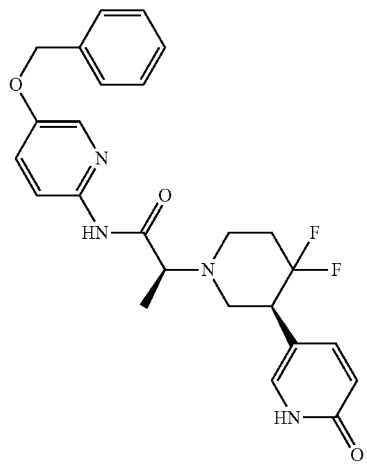 [SMILES: C[C@@H](C(=O)Nc1ccc(OCc2ccccc2)cn1)N1CCC(F)(F)[C@@H](c2ccc(=O)[nH]c2)C1] | ¹H NMR: (400 MHz, CD₃OD) δ ppm 8.07-8.05 (m, 2H), 7.66-7.63 (m, 1H), 7.51-7.29 (m, 7H), 6.52 (d, J = 9.6 Hz, 1H), 5.15 (s, 2H), 3.53-3.48 (m, 1H), 3.38-3.35 (m, 1H), 2.99-2.89 (m, 3H), 2.64-2.59 (m, 1H), 2.31-2.14 (m, 2H), 1.33 (d, J = 6.8 Hz, 3H). | 469; rt 1.494. LC/MS Method 15 | 26 |
| 23 | (S)-2-((S)-4,4-difluoro-3-(6-oxo-1,6-dihydropyridin-3-yl)piperidin-1-yl)-N-(5-phenylpyridin-2-yl)propanamide | 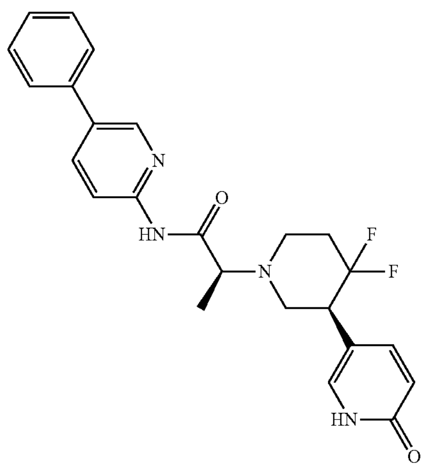 [SMILES: C[C@@H](C(=O)Nc1ccc(-c2ccccc2)cn1)N1CCC(F)(F)[C@@H](c2ccc(=O)[nH]c2)C1] | ¹H NMR: (400 MHz, DMSO-d₆) δ ppm 11.59 (br, 1H), 10.34 (s, 1H), 8.66-8.65 (m, 1H), 8.21-8.19 (m, 1H), 8.13-8.10 (m, 1H), 7.73-7.70 (m, 2H), 7.51-7.37 (m, 4H), 7.33-7.31 (m, 1H), 6.30 (d, J = 9.6 Hz, 1H), 3.71-3.68 (m, 1H), 3.30-3.15 (m, 1H), 2.96-2.81 (m, 3H), 2.57-2.50 (m, 1H), 2.19-1.93 (m, 2H), 1.23 (d, J = 6.8 Hz, 3H). | 439; rt 1.083. LC/MS Method 12 | 6 |
| 24 | N-(5-(cyclohexyloxy)pyridin-2-yl)-2-((S)-4,4-difluoro-3-(6-oxo-1,6-dihydropyridin-3-yl)piperidin-1-yl)propanamide | 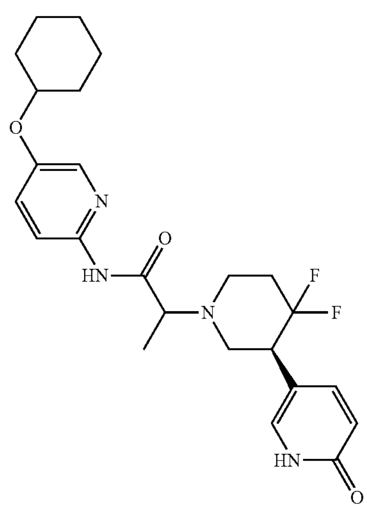 [SMILES: CC(C(=O)Nc1ccc(OC2CCCCC2)cn1)N1CCC(F)(F)[C@@H](c2ccc(=O)[nH]c2)C1] | ¹H NMR: (400 MHz, DMSO-d₆) δ ppm 11.65 (m, 1H), 10.08 (br, 1H), 8.02-7.99 (m, 2H), 7.46-7.38 (m, 2H), 7.31 (s, 1H), 6.30-6.26 (m, 1H), 4.36-4.31 (m, 1H), 3.64-3.54 (m, 1H), 3.31-3.12 (m, 1H), 2.98-2.79 (m, 3H), 2.66-2.61 (m, 1H), 2.10-1.97 (m, 2H), 1.92-1.88 (m, 2H), 1.72-1.71 (m, 2H), 1.54-1.51 (m, 1H), 1.46-1.30 (m, 4H), 1.27-1.22 (m, 1H), 1.20-1.19 (m, 3H). | 461; rt 1.152. LC/MS Method 11 | 27 |

| Ex | Name | Structure | ¹H NMR | LC/MS: (M + H)⁺; retention time (min); LC/MS Method of analysis | Int |
|---|---|---|---|---|---|
| 25 | (S)-N-(6-cyclopropylquinolin-2-yl)-2-((S)-4,4-difluoro-3-(6-oxo-1,6-dihydropyridin-3-yl)piperidin-1-yl)propanamide | 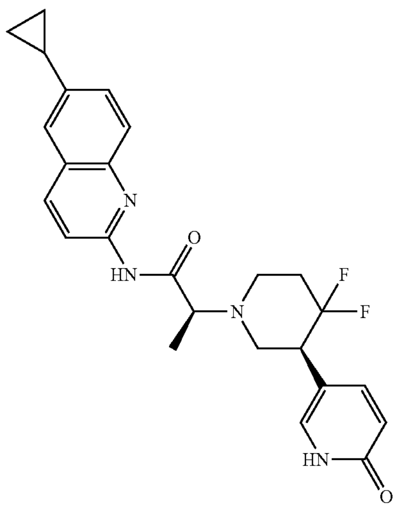 [SMILES: C[C@@H](C(=O)Nc1ccc2cc(C3CC3)ccc2n1)N1CCC(F)(F)[C@@H](c2ccc(=O)[nH]c2)C1] | ¹H NMR: (400 MHz, CD₃OD) δ ppm 8.34 (d, J = 8.8 Hz, 1H), 8.26 (d, J = 8.8 Hz, 1H), 7.76 (d, J = 8.8 Hz, 1H), 7.60 (d, J = 0.8 Hz, 1H), 7.51-7.45 (m, 3H), 6.55 (d, J = 9.2 Hz, 1H), 3.63-3.58 (m, 1H), 3.51-3.40 (m, 1H), 3.04-2.90 (m, 3H), 2.75-2.65 (m, 1H), 2.45-2.15 (m, 2H), 2.17-2.06 (m, 1H), 1.41-1.31 (m, 3H), 1.10-1.07 (m, 2H), 0.85-0.83 (m, 2H). | 453; rt 1.533. LC/MS Method 17 | 45 |
| 26 | 2-((S)-4,4-difluoro-3-(6-oxo-1,6-dihydropyridin-3-yl)piperidin-1-yl)-N-(5-isopropoxypyridin-2-yl)propanamide | 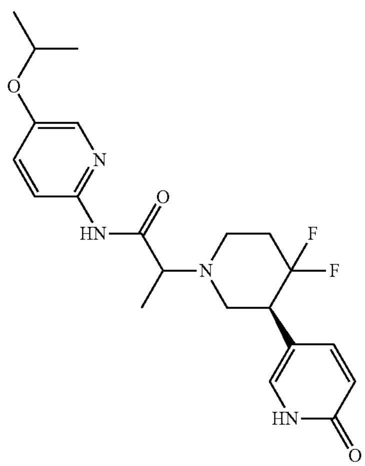 [SMILES: CC(C)Oc1ccc(NC(=O)C(C)N2CCC(F)(F)[C@@H](c3ccc(=O)[nH]c3)C2)nc1] | ¹H NMR: (400 MHz, CD₃OD) δ ppm 8.05 (d, J = 8.8 Hz, 1H), 7.96 (d, J = 3.2 Hz, 1H), 7.66-7.61 (m, 1H), 7.43-7.40 (m, 2H), 6.51 (dd, J = 5.6, 9.2 Hz, 1H), 4.65-4.58 (m, 1H), 3.52-3.46 (m, 1H), 3.39-3.35 (m, 1H), 3.02-2.61 (m, 4H), 2.31-2.16 (m, 2H), 1.34-1.31 (m, 9H). | 421; rt 2.478 and 2.535. LC/MS Method 18 | 28 |
| 27 | N-(5-(cyclohexylmethyl)pyridin-2-yl)-2-((S)-4,4-difluoro-3-(6-oxo-1,6-dihydropyridin-3-yl)piperidin-1-yl)propanamide | 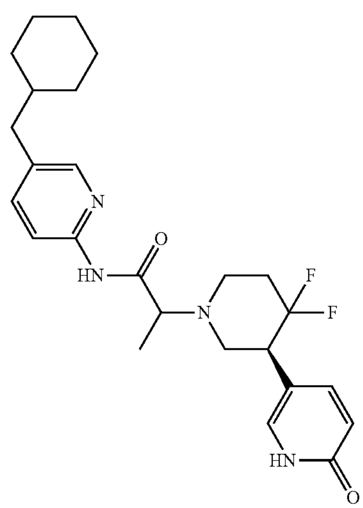 [SMILES: CC(C(=O)Nc1ccc(CC2CCCCC2)cn1)N1CCC(F)(F)[C@@H](c2ccc(=O)[nH]c2)C1] | ¹H NMR: (400 MHz, CD₃OD) δ ppm 8.13-8.04 (m, 2H), 7.68-7.56 (m, 2H), 7.45-7.39 (m, 1H), 6.55-6.46 (m, 1H), 3.58-3.47 (m, 1H), 3.44-3.32 (m, 1H), 3.07-2.55 (m, 4H), 2.49 (d, J = 6.8 Hz, 2H), 2.38-2.11 (m, 2H), 1.76-1.60 (m, 5H), 1.57-1.46 (m, 1H), 1.38-1.31 (m, 3H), 1.30-1.12 (m, 3H), 1.05-0.90 (m, 2H). | 459; rt 1.230. LC/MS Method 19 | 50 |

| Ex | Name | Structure | ¹H NMR | LC/MS: (M + H)⁺; retention time (min); LC/MS Method of analysis | Int |
|---|---|---|---|---|---|
| 28 | (S)-N-(5-(cyclopropyl-methoxy)-3-fluoropyridin-2-yl)-2-((S)-4,4-difluoro-3-(6-oxo-1,6-dihydropyridin-3-yl)piperidin-1-yl)propanamide | 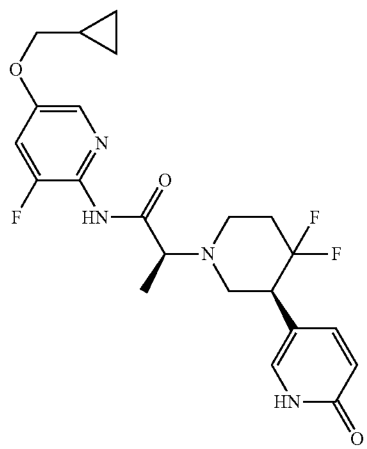 [SMILES: C[C@@H](C(=O)Nc1ncc(OCC2CC2)cc1F)N1CCC(F)(F)[C@@H](c2ccc(=O)[nH]c2)C1] | ¹H NMR: (300 MHz, CD₃OD) δ ppm 7.94 (d, J = 2.4 Hz, 1H), 7.66-7.62 (m, 1H), 7.43 (d, J = 2.4 Hz, 1H), 7.39-7.34 (m, 1H), 6.53 (d, J = 9.6 Hz, 1H), 3.94 (d, J = 6.9 Hz, 2H), 3.61-3.48 (m, 1H), 3.30-2.19 (m, 1H), 3.10-3.01 (m, 2H), 3.00-2.84 (m, 1H), 2.75-2.59 (m, 1H), 2.32-2.10 (m, 2H), 1.37 (d, J = 6.9 Hz, 3H), 1.31-1.20 (m, 1H), 0.67-0.64 (m, 2H), 0.41-0.38 (m, 2H). | 451; rt 1.303. LC/MS Method 20 | 42 |
| 29 | (S)-N-(5-(cyclopropyl-methoxy) pyrazin-2-yl)-2-((S)-4,4-difluoro-3-(6-oxo-1,6-dihydropyridin-3-yl)piperidin-1-yl)propanamide | 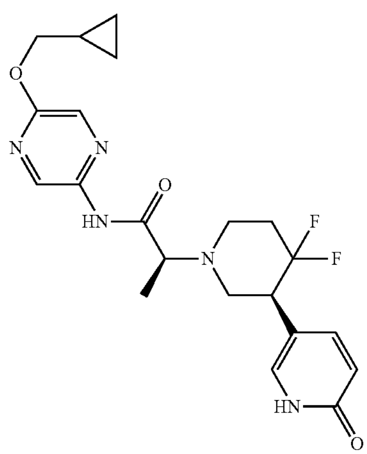 [SMILES: C[C@@H](C(=O)Nc1cnc(OCC2CC2)cn1)N1CCC(F)(F)[C@@H](c2ccc(=O)[nH]c2)C1] | ¹H NMR: (400 MHz, CD₃OD) δ ppm 8.86-8.85 (m, 1H), 7.98-7.97 (m, 1H), 7.66-7.63 (m, 1H), 7.42 (d, J = 2.0 Hz, 1H), 6.52 (d, J = 9.6 Hz, 1H), 4.16-4.14 (m, 2H), 3.58-3.52 (m, 1H), 3.31-3.22 (m, 1H), 2.95-2.85 (m, 3H), 2.66-2.59 (m, 1H), 2.25-2.14 (m, 2H), 1.35-1.23 (m, 4H), 0.63-0.54 (m, 2H), 0.38-0.31 (m, 2H). | 434; rt 1.445. LC/MS Method 20 | 15 |
| 30 | N-(5-(cyclobutyl-methoxy) pyridin-2-yl)-2-((S)-4,4-difluoro-3-(6-oxo-1,6-dihydropyridin-3-yl)piperidin-1-yl)propanamide | 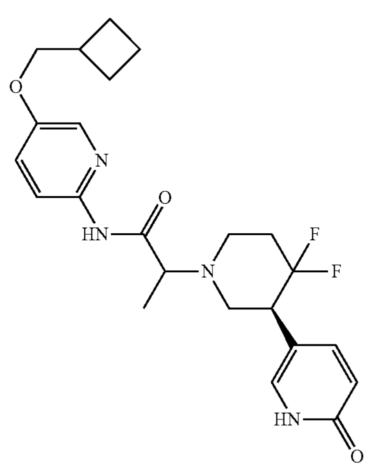 [SMILES: CC(C(=O)Nc1ccc(OCC2CCC2)cn1)N1CCC(F)(F)[C@@H](c2ccc(=O)[nH]c2)C1] | ¹H NMR: (400 MHz, CD₃OD) δ ppm 8.05 (d, J = 8.8 Hz, 1H), 8.00-7.98 (m, 1H), 7.66-7.60 (m, 1H), 7.44-7.40 (m, 2H), 6.54-6.49 (m, 1H), 4.01 (d, J = 6.8 Hz, 2H), 3.58-3.45 (m, 1H), 3.42-3.32 (m, 1H), 3.08-2.55 (m, 5H), 2.39-2.07 (m, 4H), 2.08-1.81 (m, 4H), 1.34 (d, J = 6.8 Hz, 3H). | 447; rt 1.086. LC/MS Method 19 | 24 |

| Ex | Name | Structure | ¹H NMR | LC/MS: (M + H)⁺; retention time (min); LC/MS Method of analysis | Int |
|---|---|---|---|---|---|
| 31 | N-(5-(1-cyclopropyl-ethoxy)pyridin-2-yl)-2-((S)-4,4-difluoro-3-(6-oxo-1,6-dihydropyridin-3-yl)piperidin-1-yl)propanamide | 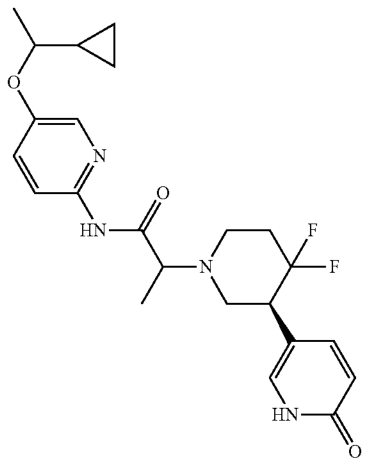 [SMILES: CC(Oc1ccc(NC(=O)C(C)N2CCC(F)(F)[C@@H](c3ccc(=O)[nH]c3)C2)nc1)C1CC1] | ¹H NMR: (400 MHz, CDCl₃) δ ppm 12.30 (br, 1H), 9.48 (br, 1H), 8.17-8.14 (m, 1H), 7.97-7.96 (m, 1H), 7.52-7.42 (m, 1H), 7.32-7.26 (m, 2H), 6.57-6.53 (m, 1H), 3.79-3.72 (m, 1H), 3.49-3.40 (m, 1H), 3.21-3.07 (m, 1H), 2.96-2.76 (m, 3H), 2.65-2.56 (m, 1H), 2.28-2.09 (m, 2H), 1.38-1.25 (m, 6H), 1.14-1.13 (m, 1H), 0.59-0.55 (m, 2H), 0.36-0.33 (m, 1H), 0.28-0.24 (m, 1H). | 447; rt 1.086. LC/MS Method 15 | 69 |
| 32 | (S)-N-(6-cyclopropyl-6,7-dihydro-5H-pyrrolo[3,4-b]pyridin-2-yl)-2-((S)-4,4-difluoro-3-(6-oxo-1,6-dihydropyridin-3-yl)piperidin-1-yl)propanamide | 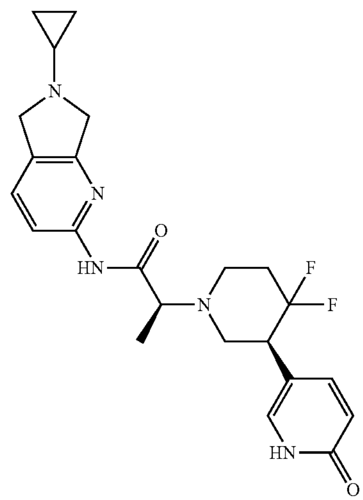 [SMILES: C[C@@H](C(=O)Nc1ccc2c(n1)CN(C1CC1)C2)N1CCC(F)(F)[C@@H](c2ccc(=O)[nH]c2)C1] | ¹H NMR: (400 MHz, CD₃OD) δ ppm 8.03 (d, J = 8.4 Hz, 1H), 7.62-7.68 (m, 2H), 7.42 (d, J = 2.0 Hz, 1H), 6.52 (d, J = 9.2 Hz, 1H), 4.09(s, 2H), 4.04(s, 2H), 3.54-3.57 (m, 1H), 3.34-3.41(m, 1H), 2.94-2.97(m, 2H), 2.87-2.91(m, 1H), 2.59-2.65(m, 1H), 2.17-2.29(m, 3H), 1.34 (d, J = 6.8 Hz, 3H), 0.57-0.61 (m, 2H), 0.51-0.55 (m, 2H). | 444; rt 1.212. LC/MS Method 21 | 83 |
| 33 | N-(5-(cyclopentyl-methyl)pyridin-2-yl)-2-((S)-4,4-difluoro-3-(6-oxo-1,6-dihydropyridin-3-yl)piperidin-1-yl)propanamide | 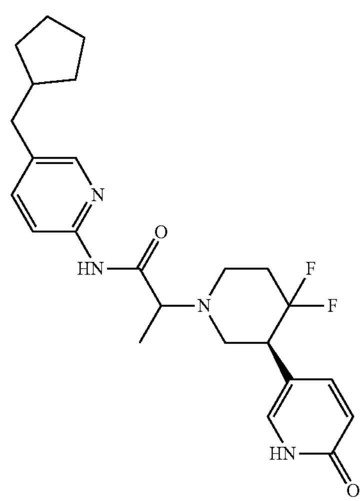 [SMILES: CC(C(=O)Nc1ccc(CC2CCCC2)cn1)N1CCC(F)(F)[C@@H](c2ccc(=O)[nH]c2)C1] | ¹H NMR: (400 MHz, DMSO-d₆) δ ppm 11.56 (s, 1H), 10.15 (d, J = 6.4 Hz, 1H), 8.14 (s, 1H), 8.02-8.00 (m, 1H), 7.64-7.61 (m, 1H), 7.44-7.38 (m, 1H), 7.32 (s, 1H), 6.30-6.26 (m, 1H), 3.65-3.57 (m, 1H), 3.33-3.12 (m, 1H), 2.99-2.80 (m, 3H), 2.67-2.51 (m, 3H), 2.10-1.97 (m, 3H), 1.64-1.60 (m, 4H), 1.56-1.47 (m, 2H), 1.23-1.11 (m, 5H). | 445; rt 1.610 and 1.643. LC/MS Method 20 | 52 |

-continued

| Ex | Name | Structure | ¹H NMR | LC/MS: (M + H)⁺; retention time (min); LC/MS Method of analysis | Int |
|---|---|---|---|---|---|
| 34 | (S)-2-((S)-4,4-difluoro-3-(6-oxo-1,6-dihydropyridin-3-yl)piperidin-1-yl)-N-(isoquinolin-3-yl)propanamide | 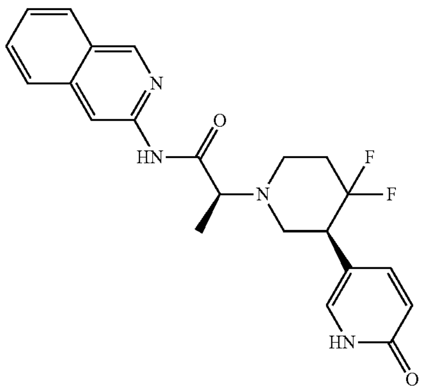 [SMILES: C[C@@H](C(=O)Nc1cc2ccccc2cn1)N1CCC(F)(F)[C@@H](c2ccc(=O)[nH]c2)C1] | ¹H NMR: (300 MHz, DMSO-d₆) δ ppm 11.51 (br, 1H), 10.39 (s, 1H), 9.15 (s, 1H), 8.50 (s, 1H), 8.06 (d, J = 8.1 Hz, 1H), 7.90 (d, J = 8.1 Hz, 1H), 7.74-7.69 (m, 1H), 7.56-7.51 (m, 1H), 7.42-7.39 (m, 1H), 7.32-7.30 (m, 1H), 6.28-6.25 (m, 1H), 3.71-3.65 (m, 1H), 3.29-3.13 (m, 1H), 3.04-2.92 (m, 2H), 2.73-2.64 (m, 2H), 2.12-2.09 (m, H), 1.27 (m, J = 6.9 Hz, 3H). | 413; rt 1.342. LC/MS Method 15 | 7 |
| 35 | (S)-N-(5-(cyclopropyl-methoxy)pyrimidin-2-yl)-2-((S)-4,4-difluoro-3-(6-oxo-1,6-dihydropyridin-3-yl)piperidin-1-yl)propanamide | 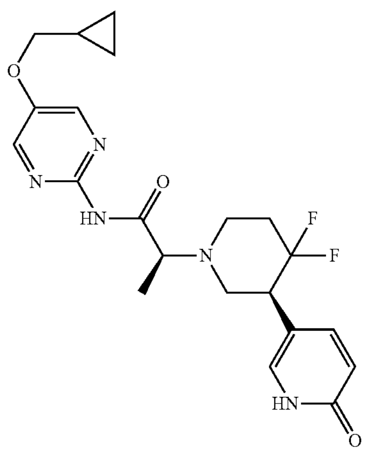 [SMILES: C[C@@H](C(=O)Nc1ncc(OCC2CC2)cn1)N1CCC(F)(F)[C@@H](c2ccc(=O)[nH]c2)C1] | ¹H NMR: (300 MHz, CD₃OD) δ ppm 8.36 (s, 2H), 7.67-7.62 (m, 1H), 7.43 (d, J = 2.4 Hz, 1H), 6.53 (d, J = 9.6 Hz, 1H), 3.97 (d, J = 7.2 Hz, 2H), 3.68-3.49 (m, 1H), 3.31-3.15 (m, 1H), 3.11-2.85 (m, 1H), 2.81-2.53 (m, 1H), 2.33-2.09 (m, 2H), 1.36 (d, J = 7.2 Hz, 3H), 1.33-1.19 (m, 1H), 0.66-0.61 (m, 2H), 0.41-0.36 (m, 2H). | 434; rt 1.139. LC/MS Method 20 | 84 |
| 36 | 2-((S)-4,4-difluoro-3-(6-oxo-1,6-dihydropyridin-3-yl)piperidin-1-yl)-N-(5-((2,2-difluorocyclopropyl)methoxy)pyridin-2-yl)propanamide | 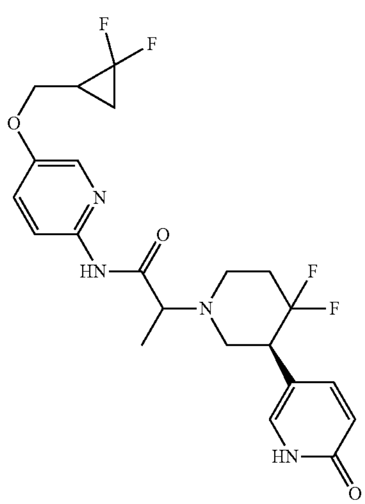 [SMILES: CC(C(=O)Nc1ccc(OCC2CC2(F)F)cn1)N1CCC(F)(F)[C@@H](c2ccc(=O)[nH]c2)C1] | ¹H NMR: (400 MHz, CD₃OD) δ ppm 8.09-8.02 (m, 2H), 7.66-7.61 (m, 1H), 7.47-7.42 (m, 2H), 6.53-6.49 (m, 1H), 4.23-4.18 (m, 1H), 4.07-4.02 (m, 1H), 3.53-3.48 (m, 1H), 3.39-3.30 (m, 1H), 2.99-2.61 (m, 4H), 2.20-2.10 (m, 3H), 1.68-1.59 (m, 1H), 1.40-1.33 (m, 4H). | 469; rt 2.586 and 2.634. LC/MS Method 22 | 30 |

-continued

| Ex | Name | Structure | ¹H NMR | LC/MS: (M + H)⁺; retention time (min); LC/MS Method of analysis | Int |
|---|---|---|---|---|---|
| 37 | cyclobutyl 6-((S)-2-((S)-4,4-difluoro-3-(6-oxo-1,6-dihydropyridin-3-yl)piperidin-1-yl)propanamido) nicotinate | 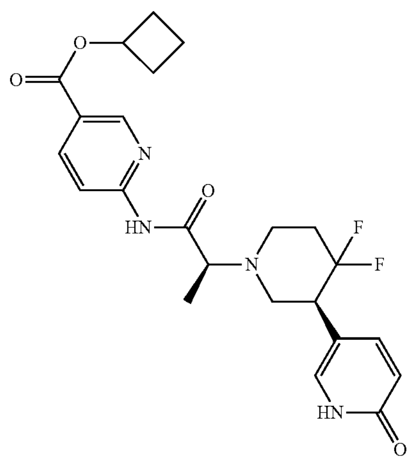 [SMILES: C[C@@H](C(=O)Nc1ccc(C(=O)OC2CCC2)cn1)N1CCC(F)(F)[C@@H](c2ccc(=O)[nH]c2)C1] | ¹H NMR: (400 MHz, CD₃OD) δ ppm 8.89-8.88 (m, 1H), 8.35-8.27 (m, 2H), 7.67-7.64 (m, 1H), 7.43 (d, J = 2.4 Hz, 1H), 6.52 (d, J = 9.6 Hz, 1H), 5.25-5.18 (m, 1H), 3.61-3.57 (m, 1H), 3.40-3.32 (m, 1H), 3.05-2.84 (m, 3H), 2.67-2.58 (m, 1H), 2.49-2.41 (m, 2H), 2.29-2.16 (m, 4H), 1.93-1.83 (m, 1H), 1.79-1.68 (m, 1H), 1.34 (d, J = 6.8 Hz, 3H). | 461; rt 1.476. LC/MS Method 15 | 68 |
| 38 | (S)-2-((S)-4,4-difluoro-3-(6-oxo-1,6-dihydropyridin-3-yl)piperidin-1-yl)-N-(5-(oxazol-2-ylmethoxy) pyridin-2-yl)propanamide | 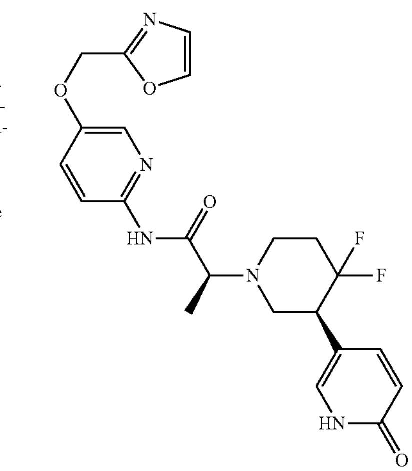 | ¹H NMR: (300 MHz, CD₃OD) δ ppm 8.13-8.10 (m, 2H), 7.99 (s, 1H), 7.66 (dd, J = 1.5, 9.0 Hz, 1H), 7.59-7.55 (m, 1H), 7.46-7.45 (m, 1H), 7.24 (s, 1H), 6.54 (d, J = 9.6 Hz, 1H), 5.28 (s, 2H), 3.65-3.58 (m, 1H), 3.44-3.40 (m, 1H), 3.08-3.05 (m, 3H), 2.77-2.70 (m, 1H), 2.35-2.19 (m, 2H), 1.30-1.41 (m, 3H). | 460; rt 1.129. LC/MS Method 14 | 25 |
| 39 | 2-((S)-4,4-difluoro-3-(6-oxo-1,6-dihydropyridin-3-yl)piperidin-1-yl)-N-(4,5-difluoropyridin-2-yl)propanamide | 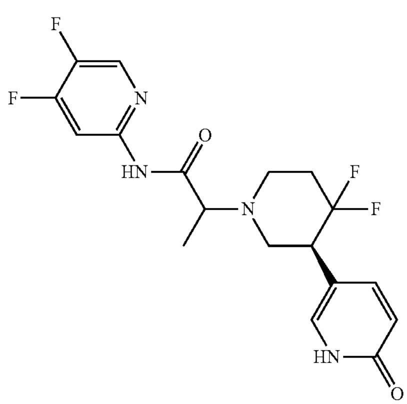 [SMILES: CC(C(=O)Nc1cc(F)c(F)cn1)N1CCC(F)(F)[C@@H](c2ccc(=O)[nH]c2)C1] | ¹H NMR: (400 MHz, CD₃OD) δ ppm 8.35-8.32 (m, 1H), 8.19-8.15 (m, 1H), 7.66-7.60 (m, 1H), 7.43-7.41 (m, 1H), 6.53-6.49 (m, 1H), 3.58-3.51 (m, 1H), 3.29-3.22 (m, 1H), 3.01-2.59 (m, 4H), 2.28-2.13 (m, 2H), 1.33 (d, J = 6.4 Hz, 3H). | 399; rt 0.914. LC/MS Method 13 | 8 |

-continued

| Ex | Name | Structure | ¹H NMR | LC/MS: (M + H)⁺; retention time (min); LC/MS Method of analysis | Int |
|---|---|---|---|---|---|
| 40 | N-(1-(cyclopropyl-methyl)-1H-pyrazolo[3,4-c]pyridin-5-yl)-2-((S)-4,4-difluoro-3-(6-oxo-1,6-dihydropyridin-3-yl)piperidin-1-yl)propanamide | 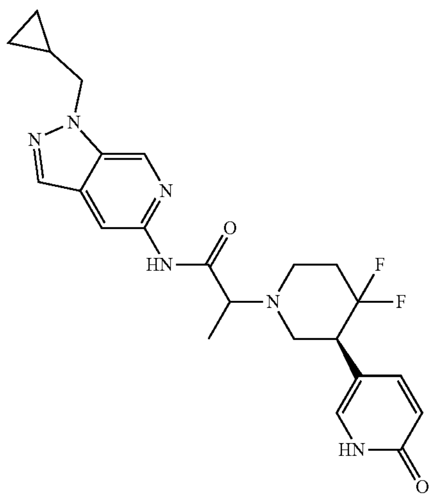 [SMILES: CC(C(=O)Nc1cc2cnn(CC3CC3)c2cn1)N1CCC(F)(F)[C@@H](c2ccc(=O)[nH]c2)C1] | ¹H NMR: (300 MHz, CD₃OD) δ ppm 8.95-8.94 (m, 1H), 8.48-8.33 (m, 2H), 7.68-7.62 (m, 1H), 7.44-7.42 (m, 1H), 6.54-6.49 (m, 1H), 4.37 (d, J = 7.2 Hz, 2H), 3.59-3.52 (m, 1H), 3.50-3.35 (m, 1H), 3.08-2.63 (m, 4H), 2.35-2.17 (m, 2H), 1.51-1.42 (m, 1H), 1.37 (d, J = 6.9 Hz, 3H), 0.81-0.64 (m, 2H), 0.54-0.48 (m, 2H). | 457; rt 1.222. LC/MS Method 15 | 85 |
| 41 | N-(5-(cyclopropyl-methyl)pyridin-2-yl)-2-((S)-4,4-difluoro-3-(6-oxo-1,6-dihydropyridin-3-yl)piperidin-1-yl)propanamide | 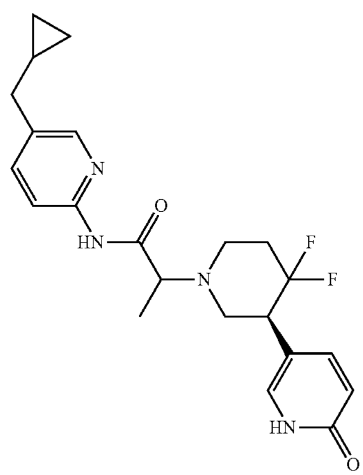 [SMILES: CC(C(=O)Nc1ccc(CC2CC2)cn1)N1CCC(F)(F)[C@@H](c2ccc(=O)[nH]c2)C1] | ¹H NMR: (400 MHz, CD₃OD) δ ppm 8.19 (d, J = 2.0 Hz, 1H), 8.09 (d, J = 8.4 Hz, 1H), 7.76-7.73 (m, 1H), 7.62-7.61 (m, 1H), 7.45-7.43 (m, 1H), 6.53-6.49 (m, 1H), 3.56-3.41 (m, 1H), 3.39-3.30 (m, 1H), 3.03-2.91 (m, 1H), 2.87-2.70 (m, 2H), 2.65-2.59 (m, 1H), 2.55-2.53 (m, 2H), 2.33-2.15 (m, 2H), 1.35-1.28 (m, 3H), 1.01-0.95 (m, 1H), 0.56-0.52 (m, 2H), 0.25-0.21 (m, 2H). | 417; rt 2.795 and 2.850. LC/MS Method 23 | 53 |
| 42 | N-(5-cyclohexyl-pyridin-2-yl)-2-((S)-4,4-difluoro-3-(6-oxo-1,6-dihydropyridin-3-yl)piperidin-1-yl)propanamide | 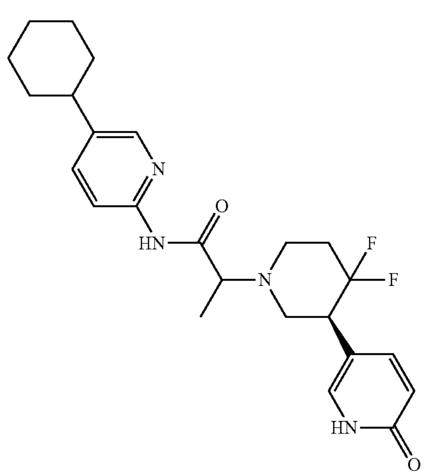 [SMILES: CC(C(=O)Nc1ccc(C2CCCCC2)cn1)N1CCC(F)(F)[C@@H](c2ccc(=O)[nH]c2)C1] | ¹H NMR: (400 MHz, CD₃OD) δ ppm 8.16 (d, J = 2.0 Hz, 1H), 8.08 (d, J = 8.4 Hz, 1H), 7.71-7.60 (m, 2H), 7.43-7.41 (m, 1H), 6.54-6.49 (m, 1H), 3.61-3.45 (m, 1H), 3.44-3.35 (m, 1H), 3.09-2.42 (m, 5H), 2.38-2.16 (m, 2H), 1.95-1.81 (m, 4H), 1.81-1.71 (m, 1H), 1.51-1.39 (m, 4H), 1.35-1.29 (m, 4H). | 445; rt 2.533. LC/MS Method 24 | 41 |

| Ex | Name | Structure | ¹H NMR | LC/MS: (M + H)⁺; retention time (min); LC/MS Method of analysis | Int |
|---|---|---|---|---|---|
| 43 | 2-((S)-4,4-difluoro-3-(6-oxo-1,6-dihydropyridin-3-yl)piperidin-1-yl)-N-(6-methoxy-pyridazin-3-yl)propanamide | 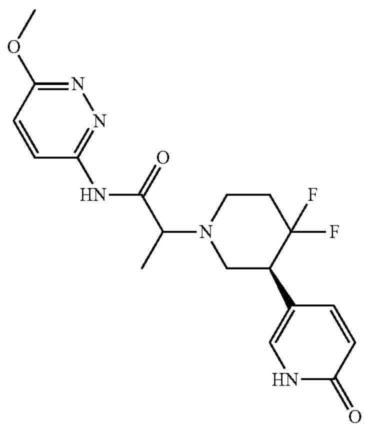 [SMILES: COc1ccc(NC(=O)C(C)N2CCC(F)(F)[C@@H](c3ccc(=O)[nH]c3)C2)nn1] | ¹H NMR: (400 MHz, CD₃OD) δ ppm 8.36 (dd, J = 2.8, 9.6 Hz, 1H), 7.66-7.61 (m, 1H), 7.43 (s, 1H), 7.2 (dd, J = 1.6, 9.6 Hz, 1H), 6.54-6.50 (m, 1H), 4.05 (s, 3H), 3.38-3.60 (m, 1H), 2.60-3.03 (m, 5H), 2.15-2.30 (m, 2H), 1.35 (m, 3H). | 394; rt 1.074. LC/MS Method 14 | 9 |
| 44 | 2-((S)-4,4-difluoro-3-(6-oxo-1,6-dihydropyridin-3-yl)piperidin-1-yl)-N-(5-methoxypyridin-2-yl)propanamide | 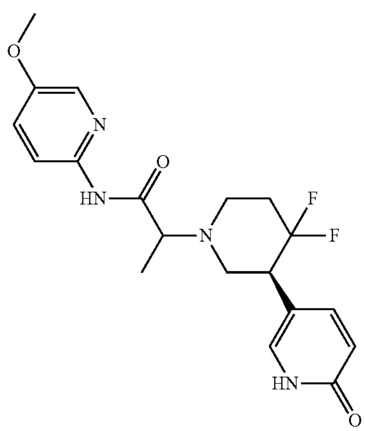 [SMILES: COc1ccc(NC(=O)C(C)N2CCC(F)(F)[C@@H](c3ccc(=O)[nH]c3)C2)nc1] | ¹H NMR: (400 MHz, CD₃OD) δ ppm 8.07 (d, J = 9.2 Hz, 1H), 8.00 (d, J = 3.2 Hz, 1H), 7.66-7.61 (m, 1H), 7.45-7.41 (m, 2H), 6.53-6.49 (m, 1H), 3.85 (s, 3H), 3.53-3.46 (m, 1H), 3.39-3.35 (m, 1H), 2.99-2.58 (m, 4H), 2.31-2.16 (m, 2H), 1.33 (d, J = 7.2 Hz, 3H). | 393; rt 1.977 and 2.020. LC/MS Method 18 | 10 |
| 45 | 2-((S)-4,4-difluoro-3-(6-oxo-1,6-dihydropyridin-3-yl)piperidin-1-yl)-N-(5-(pyridin-3-ylmethyl)pyridin-2-yl)propanamide | 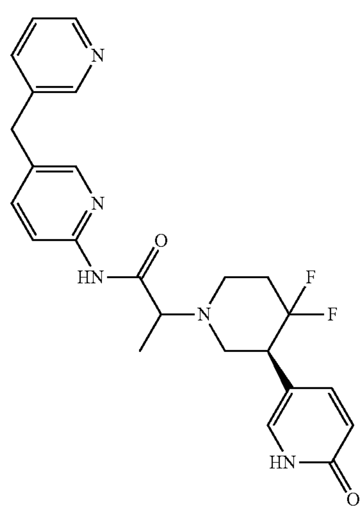 [SMILES: CC(C(=O)Nc1ccc(Cc2cccnc2)cn1)N1CCC(F)(F)[C@@H](c2ccc(=O)[nH]c2)C1] | ¹H NMR: (300 MHz, DMSO-d₆) δ ppm 11.54 (s, 1H), 10.26-10.21 (m, 1H) 8.54-8.53 (m, 1H), 8.44-8.42 (m, 1H), 8.28 (s, 1H), 8.04-8.02 (m, 1H), 7.70-7.63 (m, 2H), 7.41-7.30 (m, 3H), 6.31-6.26 (m, 1H), 4.00 (s, 2H), 3.66-3.59 (m, 1H), 3.93-3.80 (m, 1H), 2.95-2.82 (m, 3H), 2.67-2.60 (m, 1H), 2.10-1.97 (m, 2H), 1.22-1.19 (m, 3H). | 454; rt 1.130. LC/MS Method 25 | 92 |

| Ex | Name | Structure | ¹H NMR | LC/MS: (M + H)⁺; retention time (min); LC/MS Method of analysis | Int |
|---|---|---|---|---|---|
| 46 | cyclopentyl 6-((S)-2-((S)-4,4-difluoro-3-(6-oxo-1,6-dihydropyridin-3-yl)piperidin-1-yl)propanamido) nicotinate | 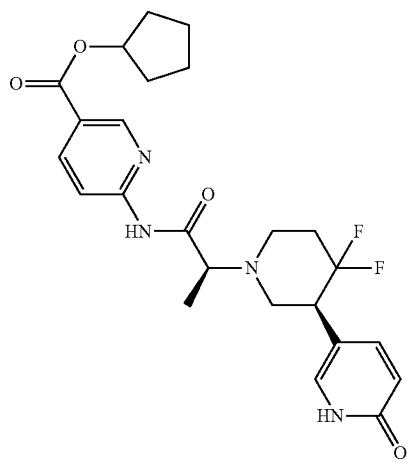 [SMILES: C[C@@H](C(=O)Nc1ccc(C(=O)OC2CCCC2)cn1)N1CCC(F)(F)[C@@H](c2ccc(=O)[nH]c2)C1] | ¹H NMR: (300 MHz, CD₃OD) δ ppm 8.88 (s, 1H), 8.36-8.29 (m, 2H), 7.69-7.66 (m, 1H), 7.46-7.44 (m, 1H), 6.56-6.53 (m, 1H), 5.42-5.39 (m, 1H), 3.65-3.56 (m, 1H), 3.42-3.39 (m, 1H), 3.01-2.89 (m, 3H), 2.69-2.62 (m, 1H), 2.34-2.17 (m, 2H), 2.05-1.98 (m, 2H), 1.95-1.83 (m, 4H), 1.79-1.65 (m, 2H), 1.36 (d, J = 6.9 Hz, 3H). | 475; rt 1.163. LC/MS Method 19 | 66 |
| 47 | N-(5-(cyclopentyl-methoxy)pyridin-2-yl)-2-((S)-4,4-difluoro-3-(6-oxo-1,6-dihydropyridin-3-yl)piperidin-1-yl)propanamide | 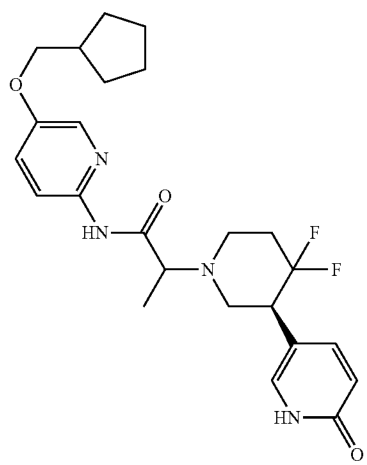 [SMILES: CC(C(=O)Nc1ccc(OCC2CCCC2)cn1)N1CCC(F)(F)[C@@H](c2ccc(=O)[nH]c2)C1] | ¹H NMR: (300 MHz, CD₃OD) δ ppm 8.03-7.95 (m, 2H), 7.67-7.63 (m, 1H), 7.54-7.50 (m, 2H), 6.60-6.58 (m, 1H), 4.15-4.12 (m, 1H), 3.93-3.91 (m, 2H), 3.68-3.42 (m, 4H), 3.41-3.21 (m, 1H), 2.48-2.31 (m, 3H), 1.89-1.83 (m, 2H), 1.70-1.54 (m, 7H), 1.43-1.35 (m, 2H). | 461; rt 1.576 and 1.603. LC/MS Method 25 | 31 |
| 48 | N-(5-(cyclopropoxy-methyl)pyridin-2-yl)-2-((S)-4,4-difluoro-3-(6-oxo-1,6-dihydropyridin-3-yl)piperidin-1-yl)propanamide | 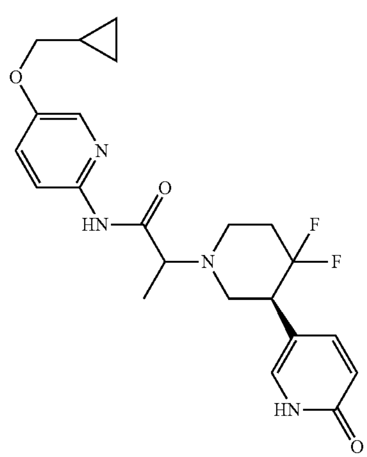 [SMILES: CC(C(=O)Nc1ccc(OCC2CC2)cn1)N1CCC(F)(F)[C@@H](c2ccc(=O)[nH]c2)C1] | ¹H NMR: (400 MHz, CD₃OD) δ ppm 8.29 (s, 1H), 8.11-8.09 (m, 1H), 7.87-7.85 (m, 1H), 7.65-7.62 (m, 1H), 7.46-7.44 (m, 1H), 6.54 (d, J = 9.6 Hz, 1H), 4.56 (s, 1H), 3.84-3.82 (m, 1H), 3.47-3.37 (m, 2H), 3.29-3.25 (m, 2H), 3.13-3.11 (m, 1H), 2.49-2.25 (m, 2H), 1.51-1.48 (m, 3H), 1.39-1.20 (m, 2H), 0.63-0.50 (m, 4H). | 433; rt 1.285 and 1.303. LC/MS Method 15 | 87 |

| Ex | Name | Structure | ¹H NMR | LC/MS: (M + H)⁺; retention time (min); LC/MS Method of analysis | Int |
|---|---|---|---|---|---|
| 49 | 2-((S)-4,4-difluoro-3-(6-oxo-1,6-dihydropyridin-3-yl)piperidin-1-yl)-N-(5-(2,2-difluoroethoxy)pyridin-2-yl)propanamide | 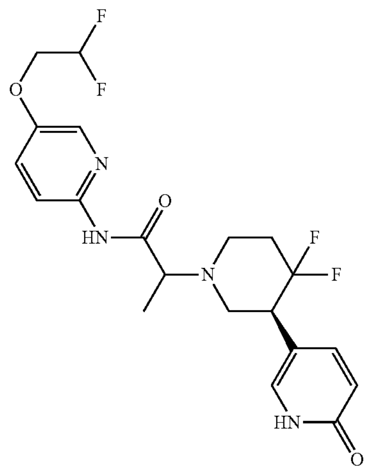 [SMILES: CC(C(=O)Nc1ccc(OCC(F)F)cn1)N1CCC(F)(F)[C@@H](c2ccc(=O)[nH]c2)C1] | ¹H NMR: (400 MHz, CD₃OD) δ ppm 8.12-8.07 (m, 2H), 7.65-7.61 (m, 1H), 7.52-7.48 (m, 1H), 7.43-7.41 (m, 1H), 6.53-6.49 (m, 1H), 6.30-6.01 (m, 1H), 4.34-4.26 (m, 2H), 3.53-3.49 (m, 1H), 3.35-3.28 (m, 1H), 3.02-2.73 (m, 4H), 2.33-2.09 (m, 2H), 1.34 (d, J = 6.8 Hz, 3H). | 443; rt 1.132. LC/MS Method 20 | 32 |
| 50 | 2-((S)-4,4-difluoro-3-(6-oxo-1,6-dihydropyridin-3-yl)piperidin-1-yl)-N-(5-(thiophen-2-yl)pyridin-2-yl)propanamide | 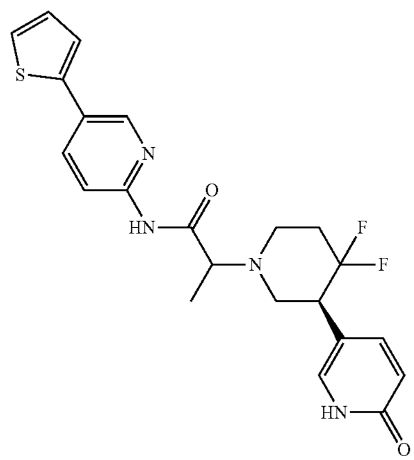 [SMILES: CC(C(=O)Nc1ccc(-c2cccs2)cn1)N1CCC(F)(F)[C@@H](c2ccc(=O)[nH]c2)C1] | ¹H NMR: (400 MHz, CD₃OD) δ ppm 8.56 (d, J = 2.4 Hz, 1H), 8.23-8.20 (m, 1H), 8.07-8.03 (m, 1H), 7.67-7.61 (m, 1H), 7.45-7.42 (m, 3H), 7.14-7.12 (m, 1H), 6.54-6.49 (m, 1H), 3.61-3.48 (m, 1H), 3.47-3.32 (m, 1H), 3.11-2.59 (m, 4H), 2.38-2.12 (m, 2H), 1.35 (d, J = 7.2 Hz, 3H). | 445; rt 1.068. LC/MS Method 12 | 39 |
| 51 | N-(1-(cyclopropyl-methyl)-1H-pyrrolo[2,3-c]pyridin-5-yl)-2-((S)-4,4-difluoro-3-(6-oxo-1,6-dihydropyridin-3-yl)piperidin-1-yl)propanamide | 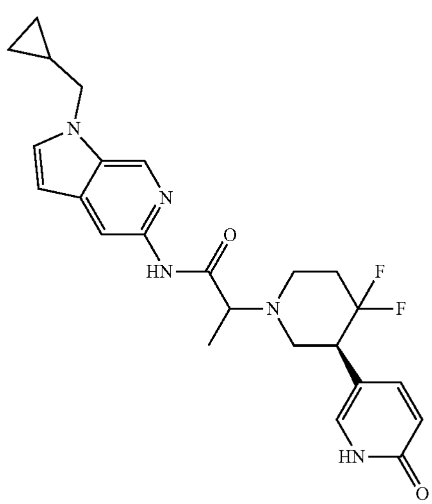 [SMILES: CC(C(=O)Nc1cc2ccn(CC3CC3)c2cn1)N1CCC(F)(F)[C@@H](c2ccc(=O)[nH]c2)C1] | ¹H NMR: (300 MHz, CD₃OD) δ ppm 8.89 (s, 1H), 8.22-8.21 (m, 1H), 7.88 (s, 1H), 7.66-7.60 (m, 1H), 7.45-7.42 (m, 1H), 6.86-6.85 (m, 1H), 6.54-6.49 (m, 1H), 4.27 (d, J = 7.2 Hz, 2H), 3.75-3.67 (m, 1H), 3.29-2.76 (m, 5H), 2.34-2.03 (m, 2H), 1.44 (d, J = 6.9 Hz, 3H), 1.39-1.32 (m, 1H), 0.72-0.66 (m, 2H), 0.51-0.46 (m, 2H). | 456; rt 1424 and 1.443. LC/MS Method 18 | 86 |

| Ex | Name | Structure | ¹H NMR | LC/MS: (M + H)⁺; retention time (min); LC/MS Method of analysis | Int |
|---|---|---|---|---|---|
| 52 | 2-((S)-4,4-difluoro-3-(6-oxo-1,6-dihydropyridin-3-yl)piperidin-1-yl)-N-(5-(thiazol-2-ylmethyl)pyridin-2-yl)propanamide | 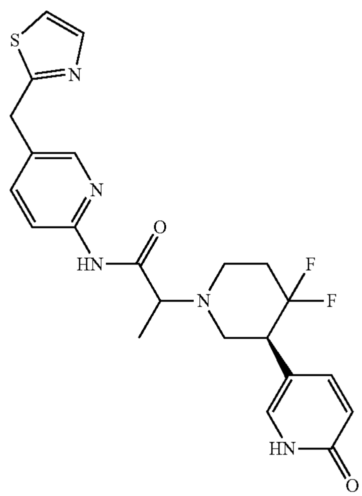 [SMILES: CC(C(=O)Nc1ccc(Cc2nccs2)cn1)N1CCC(F)(F)[C@@H](c2ccc(=O)[nH]c2)C1] | ¹H NMR: (300 MHz, CD₃OD) δ ppm 8.35-8.34 (m, 1H), 8.08-8.03 (m, 1H), 7.88 (d, J = 8.8 Hz, 1H), 7.76 (dd, J = 1.6, 3.6 Hz, 1H), 7.65-7.63 (m, 1H), 7.53-7.48 (m, 2H), 6.59-6.55 (m, 1H), 4.42 (s, 2H), 4.08 (s, 1H), 3.61-3.48 (m, 4H), 3.22-3.13 (m, 1H), 2.49-2.34 (m, 2H), 1.63 (d, J = 7.2 Hz, 3H). | 460; rt 2.171 and 2.209. LC/MS Method 18 | 35 |
| 53 | 2-((S)-4,4-difluoro-3-(6-oxo-1,6-dihydropyridin-3-yl)piperidin-1-yl)-N-(5-(oxazol-2-ylmethy)pyridin-2-yl)propanamide | 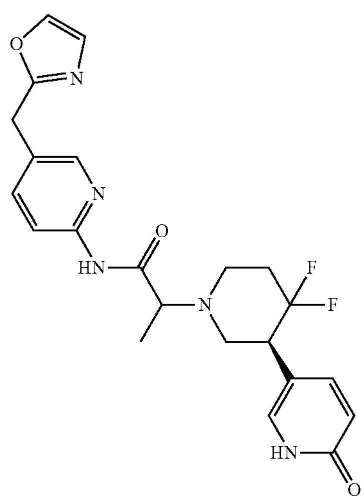 | ¹H NMR: (400 MHz, DMSO-d₆) δ ppm 11.55 (s, 1H), 10.25 (br, 1H), 8.27 (s, 1H), 8.08-8.05 (m, 2H), 7.72-7.70 (m, 1H), 7.44-7.38 (m, 1H), 7.31 (s, 1H), 7.13 (s, 1H), 6.30-6.25 (m, 1H), 4.14 (s, 2H), 3.68-3.58 (m, 1H), 3.32-3.11 (m, 1H), 2.98-2.77 (m, 3H), 2.67-2.61 (m, 1H), 2.09-1.97 (m, 2H), 1.22-1.19 (m, 3H). | 444; rt 0.785. LC/MS Method 11 | 88 |
| 54 | (S)-2-((S)-4,4-difluoro-3-(6-oxo-1,6-dihydropyridin-3-yl)piperidin-1-yl)-N-(quinolin-2-yl)propanamide | 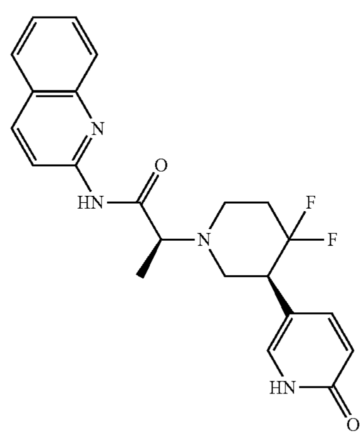 [SMILES: C[C@@H](C(=O)Nc1ccc2ccccc2n1)N1CCC(F)(F)[C@@H](c2ccc(=O)[nH]c2)C1] | ¹H NMR: (300 MHz, DMSO-d₆) δ ppm 11.57 (br, 1H), 10.57 (s, 1H), 8.40-8.32 (m, 2H), 7.94-7.92 (m, 1H), 7.84-7.82 (m, 1H), 7.75-7.70 (m, 1H), 7.53-7.44 (m, 2H), 7.35-7.33 (m, 1H), 6.30 (d, J = 9.6 Hz, 1H), 3.78-3.71 (m, 1H), 3.28-3.16 (m, 1H), 2.96-2.82 (m, 3H), 2.59-2.55 (m, 1H), 2.13-2.12 (m, 2H), 1.25 (d, J = 6.9 Hz, 3H). | 413; rt 0.962. LC/MS Method 12 | 11 |

| Ex | Name | Structure | ¹H NMR | LC/MS: (M + H)⁺; retention time (min); LC/MS Method of analysis | Int |
|---|---|---|---|---|---|
| 55 | 2-((S)-4,4-difluoro-3-(6-oxo-1,6-dihydropyridin-3-yl)piperidin-1-yl)-N-(5-(1-methyl-1H-pyrazol-3-yl)pyridin-2-yl)propanamide | 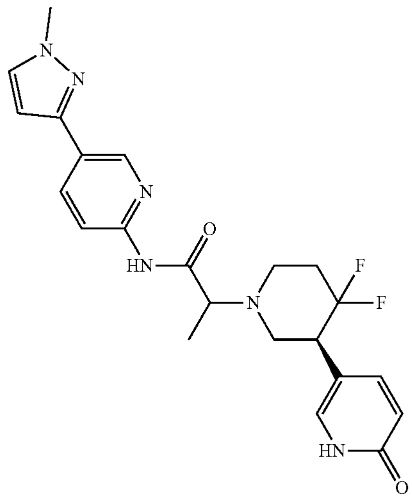 [SMILES: CC(C(=O)Nc1ccc(-c2ccn(C)n2)cn1)N1CCC(F)(F)[C@@H](c2ccc(=O)[nH]c2)C1] | ¹H NMR: (300 MHz, DMSO-d₆) δ ppm 11.57 (s, 1H), 10.34-10.31 (m, 1H), 8.75-8.74 (m, 1H), 8.16-8.15 (m, 2H), 7.77-7.76 (m, 1H), 7.46-7.39 (m, 1H), 7.33-7.32 (m, 1H), 6.76-6.75 (m, 1H), 6.32-6.26 (m, 1H), 3.90 (s, 3H), 3.72-3.60 (m, 1H), 3.36-3.13 (m, 1H), 3.01-2.81 (m, 3H), 2.70-2.63 (m, 1H), 2.12-1.98 (m, 2H), 1.25-1.22 (m, 3H). | 443; rt 1.688. LC/MS Method 26 | 36 |
| 56 | 2-((S)-4,4-difluoro-3-(6-oxo-1,6-dihydropyridin-3-yl)piperidin-1-yl)-N-(5-(isoxazol-3-yl)pyridin-2-yl)propanamide | 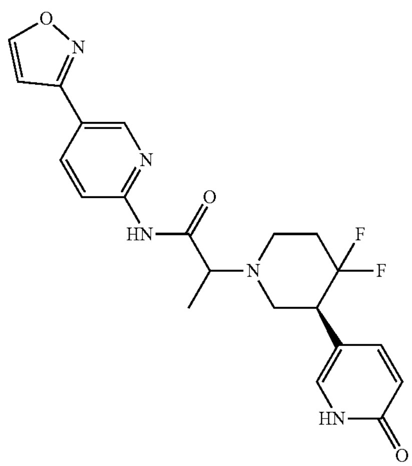 [SMILES: CC(C(=O)Nc1ccc(-c2ccon2)cn1)N1CCC(F)(F)[C@@H](c2ccc(=O)[nH]c2)C1] | ¹H NMR: (400 MHz, CD₃OD) δ ppm 8.81-8.75 (m, 2H), 8.33-8.26 (m, 2H), 7.67-7.61 (m, 1H), 7.44-7.42 (m, 1H), 6.98-6.96 (m, 1H), 6.53-6.49 (m, 1H), 3.62-3.53 (m, 1H), 3.47-3.29 (m, 1H), 3.12-3.00 (m, 1H), 2.99-2.80 (m, 2H), 2.78-2.61 (m, 1H), 2.35-2.13 (m, 2H), 1.36 (d, J = 6.8 Hz, 3H). | 430; rt 2.440 and 2.485. LC/MS Method 18 | 89 |
| 57 | 2-((S)-4,4-difluoro-3-(6-oxo-1,6-dihydropyridin-3-yl)piperidin-1-yl)-N-(5-(pyridin-2-ylmethyl)pyridin-2-yl)propanamide hydrochloride | 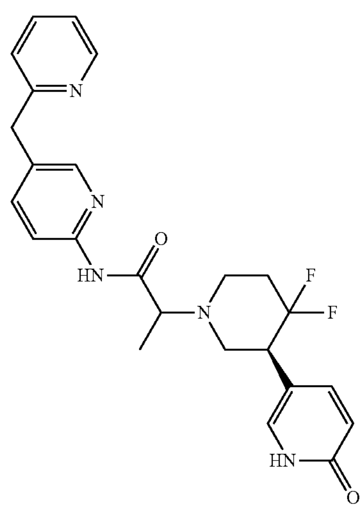 [SMILES: CC(C(=O)Nc1ccc(Cc2ccccn2)cn1)N1CCC(F)(F)[C@@H](c2ccc(=O)[nH]c2)C1] | ¹H NMR: (400 MHz, CD₃OD) δ ppm 8.84-8.83 (m, 1H), 8.61-8.57 (m, 2H), 8.34-8.18 (m, 3H), 8.04-7.92 (m, 3H), 7.24-7.14 (m, 1H), 4.69-4.65 (m, 2H), 4.59-4.57 (m, 1H), 4.18-3.89 (m, 4H), 3.71-3.47 (m, 1H), 2.84-2.59 (m, 2H), 1.84 (d, J = 6.8 Hz, 3H). | 454; rt 0.901. LC/MS Method 27 | 92 |

| Ex | Name | Structure | ¹H NMR | LC/MS: (M + H)⁺; retention time (min); LC/MS Method of analysis | Int |
|----|------|-----------|--------|---|-----|
| 58 | N-(5-(4-cyanophenoxy)pyridin-2-yl)-2-(4,4-difluoro-3-(6-oxo-1,6-dihydropyridin-3-yl)piperidin-1-yl)propanamide | 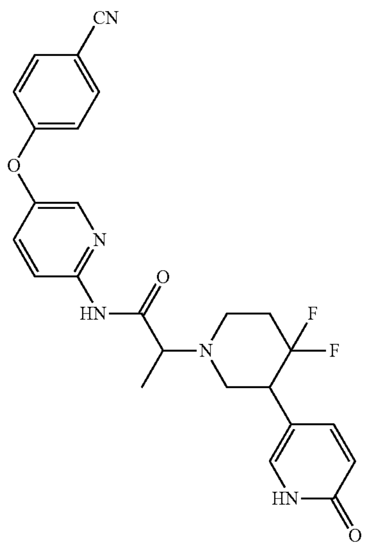 [SMILES: CC(C(=O)Nc1ccc(Oc2ccc(C#N)cc2)cn1)N1CCC(F)(F)C(c2ccc(=O)[nH]c2)C1] | ¹H NMR: (400 MHz, CD₃OD) δ ppm: 8.28 (d, J = 9.3 Hz, 1H), 8.20 (d, J = 2.9 Hz, 1H), 7.73-7.80 (m, 2H), 7.58-7.70 (m, 2H), 7.45 (t, J = 2.4 Hz, 1H), 7.09-7.18 (m, 2H), 6.54 (dd, J = 9.8, 4.4 Hz, 1H), 3.57 (dd, J = 10.5, 7.1 Hz, 1H), 3.37-3.44 (m, 1H), 2.58-3.09 (m, 4H), 2.12-2.33 (m, 2H), 1.38 (d, J = 6.8 Hz, 3H) | 480; rt 0.79-0.81. LC/MS Method 2 | 73 |
| 59 | (S)-2-((S)-4,4-difluoro-3-(6-oxo-1,6-dihydropyridin-3-yl)piperidin-1-yl)-N-(5-(pyridin-3-yloxy)pyridin-2-yl)propanamide | 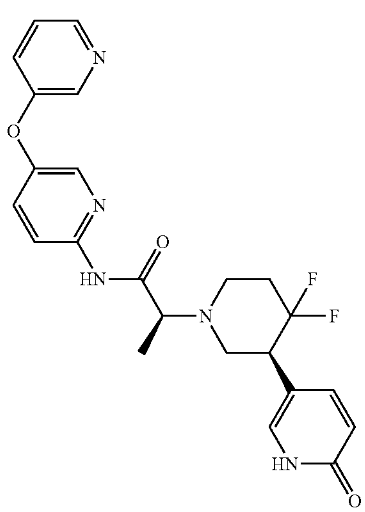 [SMILES: C[C@@H](C(=O)Nc1ccc(Oc2cccnc2)cn1)N1CCC(F)(F)[C@@H](c2ccc(=O)[nH]c2)C1] | ¹H NMR (400 MHz, DICHLOROMETHANE-d₂) δ ppm: 9.64 (s, 1H), 8.36-8.45 (m, 2H), 8.28 (d, J = 9.3 Hz, 1H), 8.14 (d, J = 2.9 Hz, 1H), 7.51 (dd, J = 9.3, 2.0 Hz, 1H), 7.46 (dd, J = 9.3, 2.9 Hz, 1H), 7.38 (d, J = 2.0 Hz, 1H), 7.28-7.35 (m, 2H), 6.55 (d, J = 9.3 Hz, 1H), 5.33-5.38 (m, 1H), 3.48 (q, J = 6.8 Hz, 1H), 3.17-3.32 (m, 1H), 2.84-3.02 (m, 3H), 2.61-2.70 (m, 1H), 2.25 (br d, J = 10.8 Hz, 2H), 1.37 (d, J = 6.8 Hz, 3H). | 456; rt 0.58. LC/MS Method 2 | 74 |

-continued

| Ex | Name | Structure | ¹H NMR | LC/MS: (M + H)⁺; retention time (min); LC/MS Method of analysis | Int |
|---|---|---|---|---|---|
| 60 | (S)-2-((S)-4,4-difluoro-3-(6-oxo-1,6-dihydropyridin-3-yl)piperidin-1-yl)-N-(5-phenoxypyrazin-2-yl)propanamide | 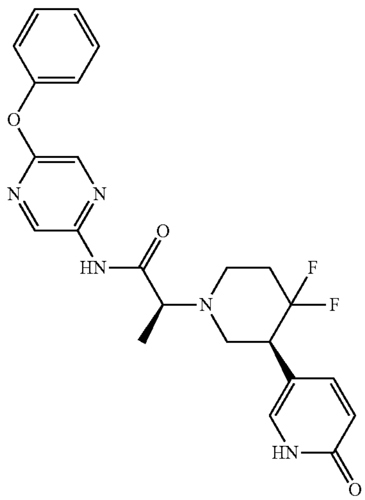 [SMILES: C[C@@H](C(=O)Nc1cnc(Oc2ccccc2)cn1)N1CCC(F)(F)[C@@H](c2ccc(=O)[nH]c2)C1] | ¹H NMR: (400 MHz, MeOH-d₄) δ ppm 8.94 (d, J = 1.5 Hz, 1H), 8.17 (d, J = 1.5 Hz, 1H), 7.66 (dd, J = 9.3, 2.4 Hz, 1H), 7.39-7.48 (m, 3H), 7.21-7.27 (m, 1H), 7.12-7.19 (m, 2H), 6.54 (d, J = 9.3 Hz, 1H), 3.55-3.68 (m, 1H), 3.24-3.31 (m, 1H), 2.90-3.06 (m, 3H), 2.61-2.71 (m, 1H), 2.13-2.25 (m, 2H), 1.37 (d, J = 7.3 Hz, 3H). | 456; rt 0.93. LC/MS Method 3 | 56 |
| 61 | (S)-2-((S)-4,4-difluoro-3-(6-oxo-1,6-dihydropyridin-3-yl)piperidin-1-yl)-N-(5-(pyridin-2-yloxy)pyridin-2-yl)propanamide | 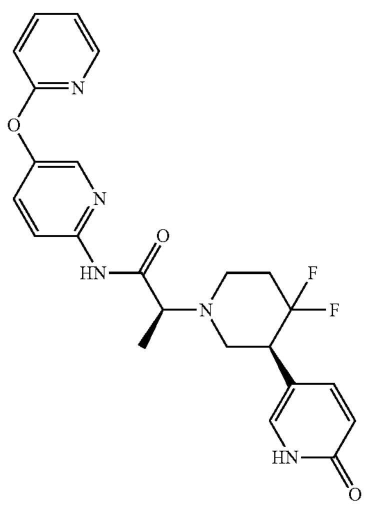 | ¹H NMR (400 MHz, MeOH-d₄) δ ppm 8.24 (d, J = 8.8 Hz, 1H), 8.19 (d, J = 2.4 Hz, 1H), 8.11 (dd, J = 5.1, 1.7 Hz, 1H), 7.79-7.89 (m, 1H), 7.58-7.73 (m, 2H), 7.45 (d, J = 2.0 Hz, 1H), 7.13 (dd, J = 6.8, 5.4 Hz, 1H), 7.06 (d, J = 8.3 Hz, 1H), 6.54 (d, J = 9.8 Hz, 1H), 3.57 (q, J = 6.8 Hz, 1H), 3.30-3.35 (m, 1H), 2.88-3.04 (m, 3H), 2.64 (td, J = 11.7, 2.9 Hz, 1H), 2.20 (br dd, J = 10.0, 3.2 Hz, 2H), 1.37 (d, J = 7.3 Hz, 3H) | 456; rt 0.70 LCMS Method 2 | 93 |
| 62 | N-(6-(2-cyanophenoxy)pyridazin-3-yl)-2-((S)-4,4-difluoro-3-(6-oxo-1,6-dihydropyridin-3-yl)piperidin-1-yl)propanamide | 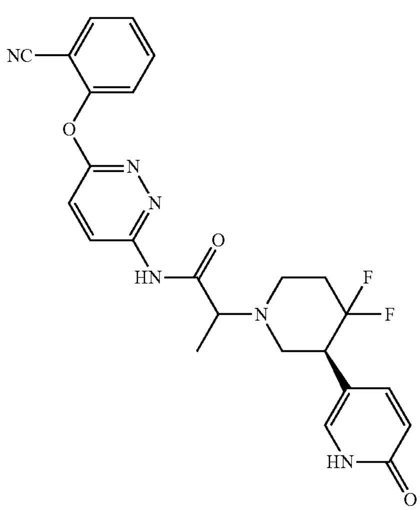 [SMILES: CC(C(=O)Nc1ccc(Oc2ccccc2C#N)nn1)N1CCC(F)(F)[C@@H](c2ccc(=O)[nH]c2)C1] | ¹H NMR (400 MHz, MeOH-d₄) δ ppm 8.63 (dd, J = 9.5, 2.7 Hz, 1H), 7.85 (dd, J = 7.8, 1.5 Hz, 1H), 7.74-7.81 (m, 1H), 7.59-7.69 (m, 2H), 7.39-7.50 (m, 3H), 6.53 (dd, J = 9.3, 7.8 Hz, 1H), 3.57-3.66 (m, 1H), 3.24-3.32 (m, 1H), 2.51-3.09 (m, 4H), 2.13-2.34 (m, 2H), 1.34-1.40 (m, 3H). | 481; rt 0.83-0.85 LCMS Method 3 | 97 |

| Ex | Name | Structure | ¹H NMR | LC/MS: (M + H)⁺; retention time (min); LC/MS Method of analysis | Int |
|---|---|---|---|---|---|
| 63 | 2-((S)-4,4-difluoro-3-(6-oxo-1,6-dihydropyridin-3-yl)piperidin-1-yl)-N-(6-(4-fluorophenoxy)pyridazin-3-yl)propanamide | 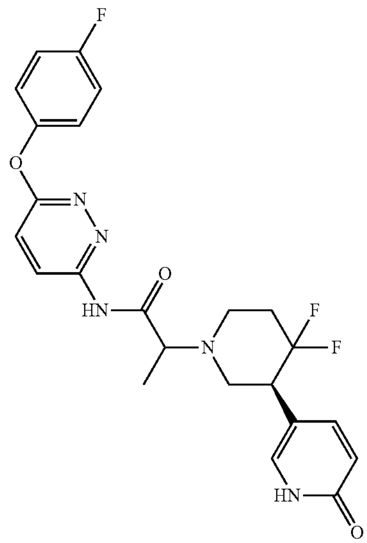 [SMILES: CC(C(=O)Nc1ccc(Oc2ccc(F)cc2)nn1)N1CCC(F)(F)[C@@H](c2ccc(=O)[nH]c2)C1] | ¹H NMR (400 MHz, MeOH-d₄) δ ppm 8.54 (dd, J = 9.5, 2.7 Hz, 1H), 7.65 (td, J = 9.8, 2.0 Hz, 1H), 7.41-7.47 (m, 2H), 7.15-7.26 (m, 4H), 6.53 (dd, J = 9.5, 6.6 Hz, 1H), 3.61 (qd, J = 6.9, 2.7 Hz, 1H), 2.49-3.10 (m, 5H), 2.13-2.34 (m, 2H), 1.37 (dd, J = 6.8, 1.0 Hz, 3H). | 474; rt 0.89-0.90 LCMS Method 3 | 57 |
| 64 | 2-((S)-4,4-difluoro-3-(6-oxo-1,6-dihydropyridin-3-yl)piperidin-1-yl)-N-(5-(pyridin-4-yloxy)pyridin-2-yl)propanamide | 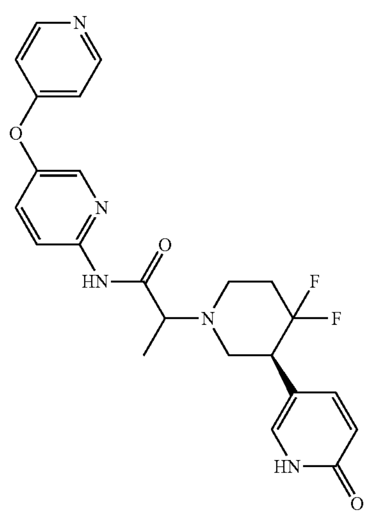 [SMILES: CC(C(=O)Nc1ccc(Oc2ccncc2)cn1)N1CCC(F)(F)[C@@H](c2ccc(=O)[nH]c2)C1] | ¹H NMR (400 MHz, MeOH-d₄) δ ppm 8.45 (d, J = 4.9 Hz, 2H), 8.32 (d, J = 9.3 Hz, 1H), 8.23 (d, J = 2.4 Hz, 1H), 7.62-7.71 (m, 2H), 7.46 (br s, 1H), 7.01 (dd, J = 6.4, 1.5 Hz, 2H), 6.54 (dd, J = 9.3, 5.4 Hz, 1H), 3.58 (dq, J = 9.8, 7.0 Hz, 1H), 3.30-3.35 (m, 1H), 2.69-3.11 (m, 4H), 2.11-2.37 (m, 2H), 1.37 (d, J = 7.3 Hz, 3H) | 456; rt 0.77 LCMS Method 3 | 94 |

-continued

| Ex | Name | Structure | ¹H NMR | LC/MS: (M + H)⁺; retention time (min); LC/MS Method of analysis | Int |
|---|---|---|---|---|---|
| 65 | (S)-2-((S)-4,4-difluoro-3-(6-oxo-1,6-dihydropyridin-3-yl)piperidin-1-yl)-N-(5-((3-fluoropyridin-2-yl)oxy)pyridin-2-yl)propanamide | 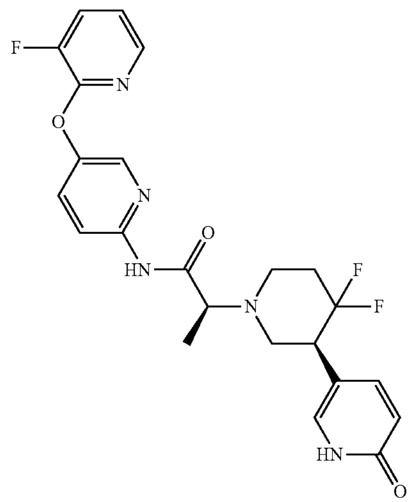 [SMILES: C[C@@H](C(=O)Nc1ccc(Oc2ncccc2F)cn1)N1CCC(F)(F)[C@@H](c2ccc(=O)[nH]c2)C1] | ¹H NMR (400 MHz, MeOH-d₄) δ ppm 8.23-8.30 (m, 2H), 7.88-7.92 (m, 1H), 7.69 (s, 3H), 7.44-7.48 (m, 1H), 7.14-7.20 (m, 1H), 6.53-6.58 (m, 1H), 3.56-3.63 (m, 1H), 3.35-3.45 (m, 1H), 2.91-3.07 (m, 3H), 2.62-2.71 (m, 1H), 2.16-2.36 (m, 2H), 1.38 (d, J = 6.85 Hz, 3H). | 474; rt 0.88. LC/MS Method 3 | 98 |
| 66 | (S)-2-((S)-4,4-difluoro-3-(6-oxo-1,6-dihydropyridin-3-yl)piperidin-1-yl)-N-(5-((3,5-difluoropyridin-2-yl)oxy)pyridin-2-yl)propanamide | 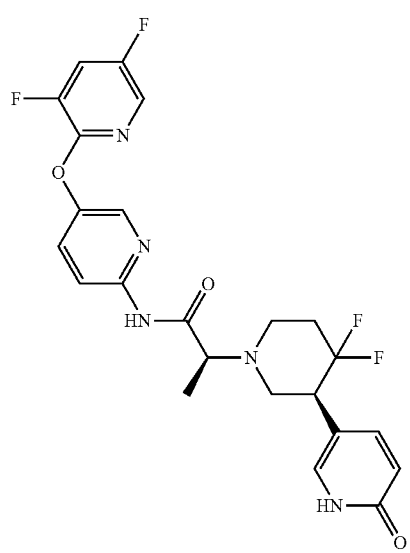 [SMILES: C[C@@H](C(=O)Nc1ccc(Oc2ncc(F)cc2F)cn1)N1CCC(F)(F)[C@@H](c2ccc(=O)[nH]c2)C1] | ¹H NMR (400 MHz, MeOH-d₄) δ ppm 8.23-8.29 (m, 2H), 7.88 (d, J = 2.45 Hz, 1H), 7.73-7.79 (m, 1H), 7.69 (s, 2H), 7.44-7.48 (m, 1H), 6.55 (d, J = 9.54 Hz, 1H), 3.55-3.63 (m, 1H) 3.35-3.45 (m, 1H), 2.90-3.07 (m, 3H), 2.62-2.71 (m, 1H), 2.16-2.36 (m, 2H), 1.38 (d, J = 6.85 Hz, 3H). | 492; rt 0.93. LC/MS Method 3 | 99 |

| Ex | Name | Structure | ¹H NMR | LC/MS: (M + H)⁺; retention time (min); LC/MS Method of analysis | Int |
|----|------|-----------|--------|-----------------------------------------------------------------|-----|
| 67 | 2-((S)-4,4-difluoro-3-(6-oxo-1,6-dihydropyridin-3-yl)piperidin-1-yl)-N-(5-((5-fluoropyridin-3-yl)oxy)pyridin-2-yl)propanamide | 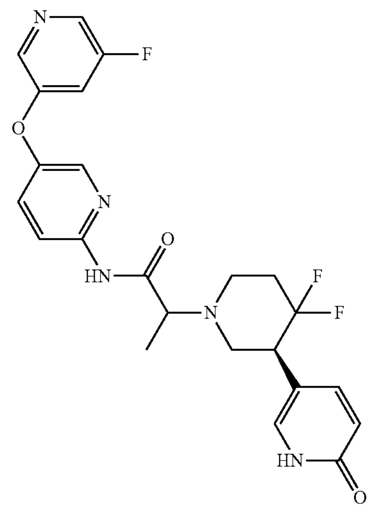 [SMILES: CC(C(=O)Nc1ccc(Oc2cncc(F)c2)cn1)N1CCC(F)(F)[C@@H](c2ccc(=O)[nH]c2)C1] | ¹H NMR (400 MHz, MeOH-d₄) δ ppm 8.19-8.33 (m, 4H), 7.62-7.69 (m, 2H), 7.45 (t, J = 2.4 Hz, 1H), 7.36 (dt, J = 9.8, 2.4 Hz, 1H), 6.54 (dd, J = 9.5, 5.1 Hz, 1H), 3.52-3.71 (m, 2H), 2.59-3.09 (m, 4H), 2.05-2.39 (m, 2H), 1.37 (d, J = 6.8 Hz, 3H). | 474; rt 0.82-0.83 LCMS Method 3 | 75 |
| 68 | (S)-2-((S)-4,4-difluoro-3-(6-oxo-1,6-dihydropyridin-3-yl)piperidin-1-yl)-N-(5-(4-fluorophenoxy)pyrazin-2-yl)propanamide | 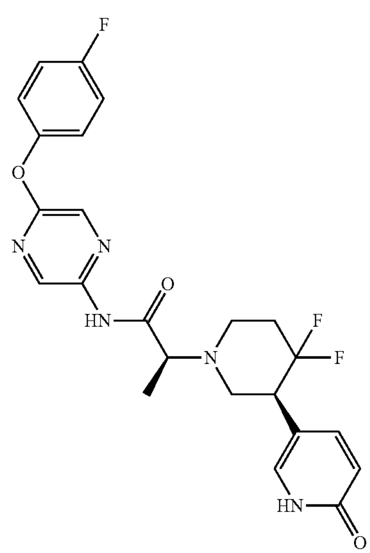 [SMILES: C[C@@H](C(=O)Nc1cnc(Oc2ccc(F)cc2)cn1)N1CCC(F)(F)[C@@H](c2ccc(=O)[nH]c2)C1] | ¹H NMR (400 MHz, MeOH-d₄) δ ppm 8.92 (d, J = 1.22 Hz, 1H), 8.20 (d, J = 1.47 Hz, 1H), 7.67 (dd, J = 9.54, 2.20 Hz, 1H), 7.45 (d, J = 2.20 Hz, 1H), 7.12-7.23 (m, 4H), 6.54 (d, J = 9.54 Hz, 1H), 3.60 (d, J = 7.09 Hz, 1H), 3.22-3.31 (m, 1H), 2.90-3.06 (m, 3H), 2.60-2.71 (m, 1H), 2.17 (m., 2H), 1.36 (d, J = 6.85 Hz, 3H). | 474; rt 0.95. LCMS Method 3 | 58 |

| Ex | Name | Structure | ¹H NMR | LC/MS: (M + H)⁺; retention time (min); LC/MS Method of analysis | Int |
|----|------|-----------|--------|-----|-----|
| 69 | (S)-2-((S)-4,4-difluoro-3-(6-oxo-1,6-dihydropyridin-3-yl)piperidin-1-yl)-N-(5-((5-fluoropyridin-2-yl)oxy)pyridin-2-yl)propanamide | 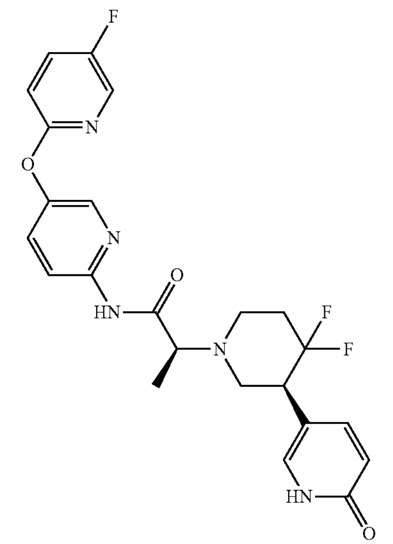 [SMILES: C[C@@H](C(=O)Nc1ccc(Oc2ccc(F)cn2)cn1)N1CCC(F)(F)[C@@H](c2ccc(=O)[nH]c2)C1] | ¹H NMR (400 MHz, MeOH-d₄) δ ppm 8.22-8.28 (m, 1H), 8.18-8.21 (m, 1H), 8.00-8.03 (m, 1H), 7.62-7.75 (m, 3H), 7.41-7.48 (m, 1H), 7.09-7.15 (m, 1H), 6.52-6.58 (m, 1H), 3.54-3.62 (m, 1H), 3.34-3.44 (m, 1H), 2.90-3.06 (m, 3H), 2.61-2.71 (m, 1H), 2.15-2.36 (m, 2H), 1.38 (d, J = 7.09 Hz, 3H). | 474; rt 0.89. LC/MS Method 3 | 100 |
| 70 | (S)-N-(5-cyclopropyl-pyrazin-2-yl)-2-((S)-4,4-difluoro-3-(6-oxo-1,6-dihydropyridin-3-yl)piperidin-1-yl)propanamide | 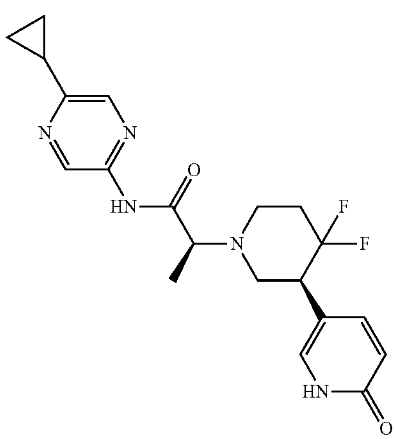 [SMILES: C[C@@H](C(=O)Nc1cnc(C2CC2)cn1)N1CCC(F)(F)[C@@H](c2ccc(=O)[nH]c2)C1] | ¹H NMR (400 MHz, MeOH-d₄) δ ppm 9.22 (d, J = 1.22 Hz, 1H), 8.30 (d, J = 1.47 Hz, 1H), 7.63-7.71 (m, 1H), 7.45 (s, 1H), 6.54 (d, J = 9.54 Hz, 1H), 3.56-3.64 (m, 1H), 3.23-3.32 (m, 1H), 2.87-3.08 (m, 3H), 2.59-2.71 (m, 1H), 2.07-2.31 (m, 3H), 1.36 (d, J = 7.09 Hz, 3H), 0.96-1.10 (m, 4H). | 404; rt 0.80. LC/MS Method 3 | 13 |
| 71 | (S)-N-(6-(cyclobutyl-methoxy)pyridazin-3-yl)-2-((S)-4,4-difluoro-3-(6-oxo-1,6-dihydropyridin-3-yl)piperidin-1-yl)propanamide | 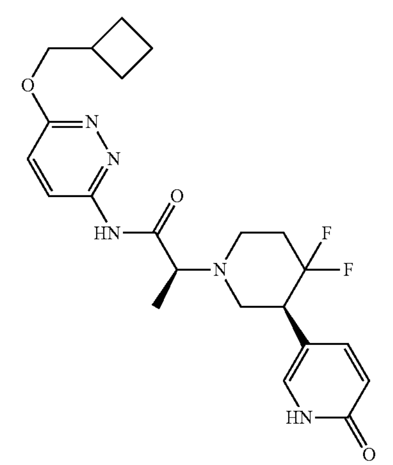 [SMILES: C[C@@H](C(=O)Nc1ccc(OCC2CCC2)nn1)N1CCC(F)(F)[C@@H](c2ccc(=O)[nH]c2)C1] | ¹H NMR (400 MHz, CDCl₃) δ ppm 11.74-12.97 (m, 1H), 10.06 (br. s., 1H), 8.42 (d, J = 9.54 Hz, 1H), 7.48 (dd, J = 9.54, 2.20 Hz, 1H), 7.35 (s, 1H), 7.06 (d, J = 9.29 Hz, 1H), 6.60 (d, J = 9.54 Hz, 1H), 4.45 (d, J = 6.85 Hz, 2H), 3.52 (br. s., 1H), 3.09-3.32 (m, 1H), 2.76-3.03 (m, 4H), 2.64 (br. s., 1H), 2.08-2.31 (m, 4H), 1.85-2.04 (m, 4H), 1.40 (d, J = 6.85 Hz, 3H). | 448; rt 0.96. LC/MS Method 3 | 16 |

| Ex | Name | Structure | ¹H NMR | LC/MS: (M + H)⁺; retention time (min); LC/MS Method of analysis | Int |
|---|---|---|---|---|---|
| 72 | 2-((S)-4,4-difluoro-3-(6-oxo-1,6-dihydropyridin-3-yl)piperidin-1-yl)-N-(5-((2-oxo-1,2-dihydropyridin-3-yl)oxy)pyridin-2-yl)propanamide | 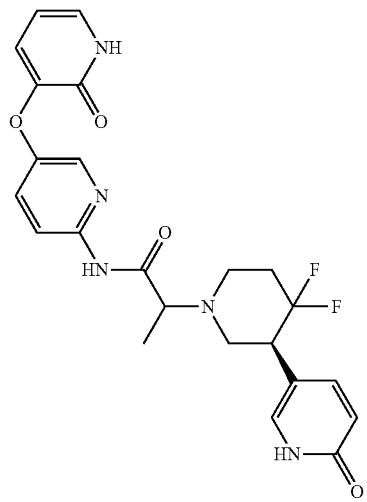 [SMILES: CC(C(=O)Nc1ccc(Oc2ccc[nH]c2=O)cn1)N1CCC(F)(F)[C@@H](c2ccc(=O)[nH]c2)C1] | ¹H NMR (400 MHz, CDCl₃) δ ppm 13.37 (br. s., 1H), 9.63 (br. s., 1H), 8.10-8.30 (m, 2H), 7.31-7.58 (m, 3H), 7.02-7.27 (m, 2H), 6.58 (dd, J = 9.41, 3.06 Hz, 1H), 6.21-6.34 (m, 1H), 2.16-3.61 (m, 8H), 1.34-1.43 (m, 3H). | 471; rt 0.42 LCMS Method 5 | 76 |
| 73 | 2-((S)-4,4-difluoro-3-(6-oxo-1,6-dihydropyridin-3-yl)piperidin-1-yl)-N-(5-(spiro[3.3]heptan-2-yloxy)pyridin-2-yl)propanamide | 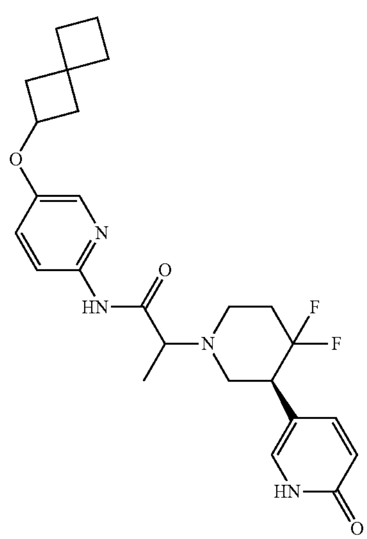 [SMILES: CC(C(=O)Nc1ccc(OC2CC3(CCC3)C2)cn1)N1CCC(F)(F)[C@@H](c2ccc(=O)[nH]c2)C1] | ¹H NMR (400 MHz, DMSO-d₆) δ ppm 11.59 (br. s., 1H), 10.09 (s, 1H), 7.81-8.11 (m, 2H), 7.08-7.55 (m, 3H), 6.30 (d, J = 9.54 Hz, 1H), 4.62 (quin, J = 6.91 Hz, 1H), 3.62 (q, J = 6.85 Hz, 1H), 3.08-3.29 (m, 1H), 2.76-3.02 (m, 3H), 2.53-2.63 (m, 2H), 1.93-2.20 (m, 9H), 1.72-1.88 (m, 2H), 1.20 (d, J = 6.85 Hz, 3H). | 473; rt 0.81 LCMS Method 2 | 103 |

-continued

| Ex | Name | Structure | ¹H NMR | LC/MS: (M + H)⁺; retention time (min); LC/MS Method of analysis | Int |
|---|---|---|---|---|---|
| 74 | (S)-2-((S)-4,4-difluoro-3-(6-oxo-1,6-dihydropyridin-3-yl)piperidin-1-yl)-N-(5-(pyrimidin-4-yloxy)pyridin-2-yl)propanamide | 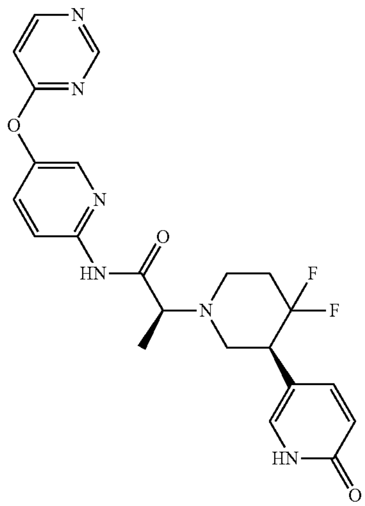 [SMILES: C[C@@H](C(=O)Nc1ccc(Oc2ccncn2)cn1)N1CCC(F)(F)[C@@H](c2ccc(=O)[nH]c2)C1] | ¹H NMR (400 MHz, CD₃OD) δ ppm 8.72 (s, 1H), 8.67 (d, J = 5.9 Hz, 1H), 8.29 (d, J = 9.3 Hz, 1H), 8.26 (d, J = 2.0 Hz, 1H), 7.70-7.77 (m, 1H), 7.67 (dd, J = 9.3, 2.0 Hz, 1H), 7.46 (d, J = 2.4 Hz, 1H), 7.20 (dd, J = 5.9, 1.5 Hz, 1H), 6.55 (d, J = 9.3 Hz, 1H), 3.55-3.61 (m, 1H), 3.35-3.48 (m, 1H), 2.90-3.08 (m, 3H), 2.58-2.72 (m, 1H), 2.13-2.32 (m, 2H), 1.38 (d, J = 7.3 Hz, 3H) | 457; rt 0.72. LC/MS Method 3 | 101 |
| 75 | (S)-N-(5-(cyclopropyl-methoxy)pyridin-2-yl)-2-((S)-4,4-difluoro-3-(6-oxo-1,6-dihydropyridin-3-yl)piperidin-1-yl)propanamide | 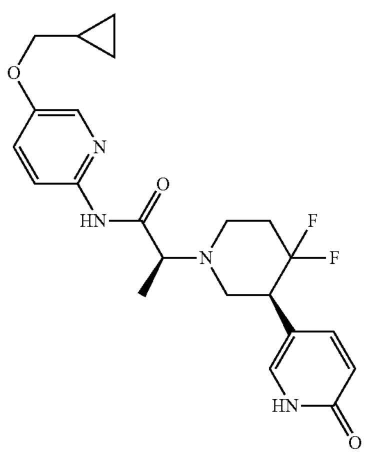 [SMILES: C[C@@H](C(=O)Nc1ccc(OCC2CC2)cn1)N1CCC(F)(F)[C@@H](c2ccc(=O)[nH]c2)C1] | ¹H NMR: (400 MHz, DMSO-d₆) δ ppm 11.59 (s, 1H), 10.10 (s, 1H), 8.03-8.00 (m, 2H), 7.44-7.41 (m, 2H), 7.31 (s, 1H), 6.29 (d, J = 9.6 Hz, 1H), 3.86 (d, J = 7.2 Hz, 2H), 3.65-3.60 (m, 1H), 3.34-3.16 (m, 1H), 2.93-2.79 (m, 3H), 2.51-2.47 (m, 1H), 2.12-1.97 (m, 2H), 1.25-1.03 (m, 4H), 0.59-0.55 (m, 2H), 0.34-0.31 (m, 2H). | 433; rt 0.972. LC/MS Method 11 | 22 |
| 76 | (S)-N-(5-(cyclopropyl-methoxy)-4-fluoropyridin-2-yl)-2-((S)-4,4-difluoro-3-(6-oxo-1,6-dihydropyridin-3-yl)piperidin-1-yl)propanamide | 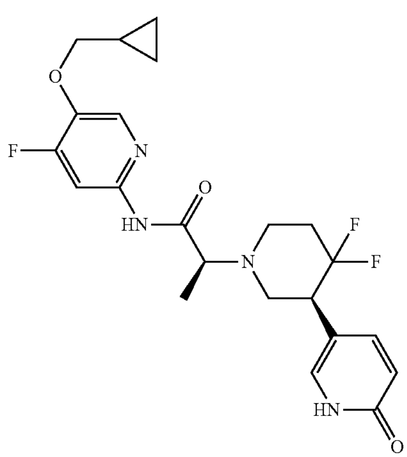 [SMILES: C[C@@H](C(=O)Nc1cc(F)c(OCC2CC2)cn1)N1CCC(F)(F)[C@@H](c2ccc(=O)[nH]c2)C1] | ¹H NMR: (400 MHz, CDCl₃) δ ppm 12.89 (br, 1H), 9.55 (br, 1H), 8.08 (d, J = 12.4 Hz, 1H), 7.99 (d, J = 10.0 Hz, 1H), 7.47-7.45 (m, 1H), 7.37 (d, J = 2.8 Hz, 1H), 6.57 (d, J = 9.2 Hz, 1H), 3.92 (d, J = 7.2 Hz, 2H), 3.44-3.43 (m, 1H), 3.21-3.15 (m, 1H), 2.91-2.86 (m, 3H), 2.64-2.58 (m, 1H), 2.23-2.09 (m, 2H), 1.36 (d, J = 7.2 Hz, 3H), 1.30-1.25 (m, 1H), 0.68-0.60 (m, 2H), 0.40-0.34 (m, 2H). | 451; rt 1.468. LC/MS Method 15 | 43 |

| Ex | Name | Structure | ¹H NMR | LC/MS: (M + H)⁺; retention time (min); LC/MS Method of analysis | Int |
|----|------|-----------|--------|-----|-----|
| 77 | N-(6-cyclopropyl-1,8-naphthyridin-2-yl)-2-((S)-4,4-difluoro-3-(6-oxo-1,6-dihydropyridin-3-yl)piperidin-1-yl)propanamide | 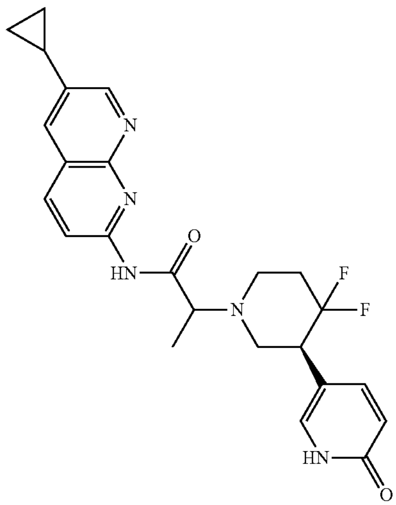 [SMILES: CC(C(=O)Nc1ccc2cc(C3CC3)cnc2n1)N1CCC(F)(F)[C@@H](c2ccc(=O)[nH]c2)C1] | ¹H NMR: (400 MHz, CD₃OD) δ ppm 8.84-8.83 (m, 1H), 8.49-8.45 (m, 1H), 8.32-8.29 (m, 1H), 7.97-7.96 (m, 1H), 7.67-7.61 (m, 1H), 7.47-7.45 (m, 1H), 6.53-6.48 (m, 1H), 3.63-3.58 (m, 1H), 3.44-3.30 (m, 1H), 3.02-2.66 (m, 4H), 2.35-2.13 (m, 3H), 1.38 (d, J = 6.8 Hz, 3H), 1.28-1.13 (m, 2H), 0.91-0.87 (m, 2H). | 454; rt 2.418 and 2.547. LC/MS Method 18 | 44 |
| 78 | N-(5-cyclobutoxy-pyridin-2-yl)-2-((S)-4,4-difluoro-3-(6-oxo-1,6-dihydropyridin-3-yl)piperidin-1-yl)propanamide | 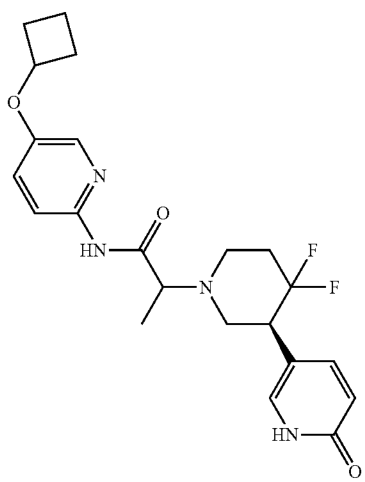 | ¹H NMR: (300 MHz, CD₃OD) δ ppm 8.06 (d, J = 9.0 Hz, 1H), 7.93-7.92 (m, 1H), 7.68-7.63 (m, 1H), 7.44 (s, 1H), 7.37-7.33 (m, 1H), 6.56-6.51 (m, 1H), 4.79-4.72 (m, 1H), 3.56-3.50 (m, 1H), 2.42-3.37 (m, 1H), 3.10-2.63 (m, 4H), 2.54-2.09 (m, 6H), 1.74-1.90 (m, 2H), 1.35 (d, J = 9.3 Hz, 3H). | 417; rt 1.002. LC/MS Method 11 | 29 |
| 79 | (S)-2-((S)-4,4-difluoro-3-(6-oxo-1,6-dihydropyridin-3-yl)piperidin-1-yl)-N-(5-fluoropyridin-2-yl)propanamide | 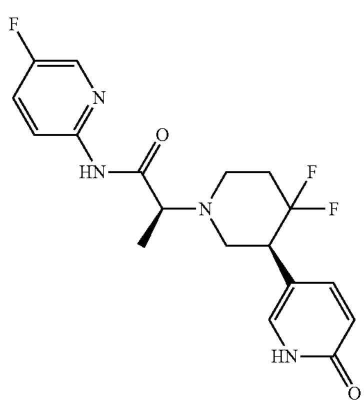 | ¹H NMR: (400 MHz, DMSO-d₆) δ ppm 11.60 (s, 1H), 10.37 (s, 1H), 8.35 (d, J = 3.2 Hz, 1H), 8.34-8.13 (m, 1H), 7.79-7.74 (m, 1H), 7.45-7.42 (m, 1H), 7.32-7.21 (m, 1H), 6.29 (d, J = 9.2 Hz, 1H), 3.66 (d, J = 6.8 Hz, 1H), 3.35-3.16 (m, 1H), 2.92-2.80 (m, 3H), 2.51-2.50 (m, 1H), 2.10-1.97 (m, 2H), 1.21 (d, J = 6.8 Hz, 3H). | 381; rt 2.090. LC/MS Method 18 | 1 |

| Ex | Name | Structure | ¹H NMR | LC/MS: (M + H)⁺; retention time (min); LC/MS Method of analysis | Int |
|---|---|---|---|---|---|
| 80 | (S)-N-(5-((Z)-2-cyclopropylvinyl)pyridin-2-yl)-2-((S)-4,4-difluoro-3-(6-oxo-1,6-dihydropyridin-3-yl)piperidin-1-yl)propanamide | 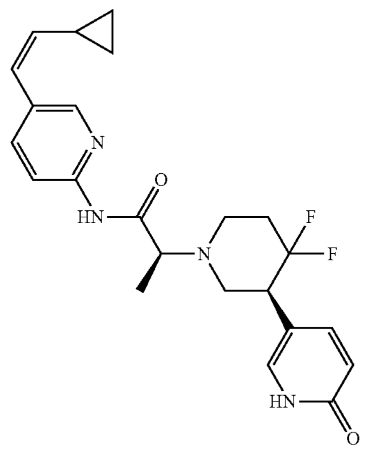 [SMILES: C[C@@H](C(=O)Nc1ccc(/C=C\C2CC2)cn1)N1CCC(F)(F)[C@@H](c2ccc(=O)[nH]c2)C1] | ¹H NMR: (400 MHz, CD₃OD) δ ppm 8.37 (d, J = 2.0 Hz, 1H), 8.17 (d, J = 8.4 Hz, 1H), 7.93 (dd, J = 2.0, 8.4 Hz, 1H), 7.67 (dd, J = 1.6, 9.2 Hz, 1H), 7.45 (d, J = 2.4 Hz, 1H), 6.55 (d, J = 9.6 Hz, 1H), 6.30 (d, J = 11.6 Hz, 1H), 5.24 (dd, J = 10, 11.2 Hz, 1H), 3.58-3.51 (m, 1H), 3.34-3.32 (m, 1H), 3.05-2.95 (m, 3H), 2.67-2.60 (m, 1H), 2.40-2.11 (m, 2H), 1.85-1.75 (m, 1H), 1.37 (d, J = 7.2 Hz, 3H), 0.92-0.88 (m, 2H), 0.52-0.50 (m, 2H). | 429; rt 1.482. LC/MS Method 17 | 47 |
| 81 | (S)-N-(5-chloropyridin-2-yl)-2-((S)-4,4-difluoro-3-(6-oxo-1,6-dihydropyridin-3-yl)piperidin-1-yl)propanamide | 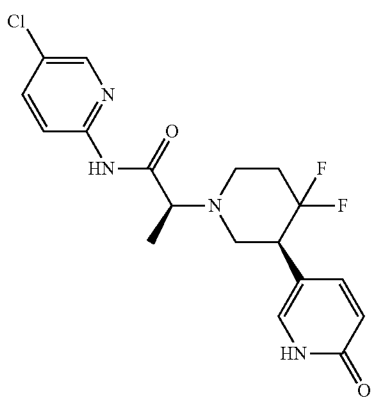 [SMILES: C[C@@H](C(=O)Nc1ccc(Cl)cn1)N1CCC(F)(F)[C@@H](c2ccc(=O)[nH]c2)C1] | ¹H NMR: (400 MHz, DMSO-d₆) δ ppm 11.58 (s, 1H), 10.43 (s, 1H), 8.39-8.38 (m, 1H), 8.15-8.13 (m, 1H), 7.94-7.91 (m, 1H), 7.45-7.38 (m, 1H), 7.31-7.30 (m, 1H), 6.29 (d, J = 9.2 Hz, 1H), 3.70-3.65 (m, 1H), 3.34-3.16 (m, 1H), 2.94-2.79 (m, 3H), 2.53-2.48 (m, 1H), 2.11-1.99 (m, 2H), 1.23-1.20 (m, 3H). | 397; rt 0.936. LC/MS Method 11 | 3 |
| 82 | 2-((S)-4,4-difluoro-3-(6-oxo-1,6-dihydropyridin-3-yl)piperidin-1-yl)-N-(5-isopropylpyridin-2-yl)propanamide | 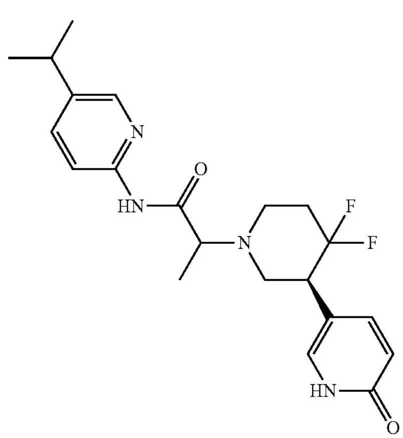 [SMILES: CC(C)c1ccc(NC(=O)C(C)N2CCC(F)(F)[C@@H](c3ccc(=O)[nH]c3)C2)nc1] | ¹H NMR: (400 MHz, CD₃OD) δ ppm 8.18 (d, J = 2.4 Hz, 1H), 8.09 (d, J = 8.4 Hz, 1H), 7.74-7.71 (m, 1H), 7.66-7.61 (m, 1H), 7.43-7.41 (m, 1H), 6.54-6.49 (m, 1H), 3.56-3.49 (m, 1H), 3.41-3.30 (m, 1H), 3.02-2.58 (m, 5H), 2.33-2.16 (m, 2H), 1.34 (d, J = 5.1 Hz, 3H), 1.27 (d, J = 5.1 Hz, 6H). | 405; rt 1.363 and 1.391. LC/MS Method 14 | 5 |

| Ex | Name | Structure | ¹H NMR | LC/MS: (M + H)⁺; retention time (min); LC/MS Method of analysis | Int |
|----|------|-----------|--------|-----|-----|
| 83 | cyclopropyl 6-(2-((S)-4,4-difluoro-3-(6-oxo-1,6-dihydropyridin-3-yl)piperidin-1-yl)propanamido)nicotinate | 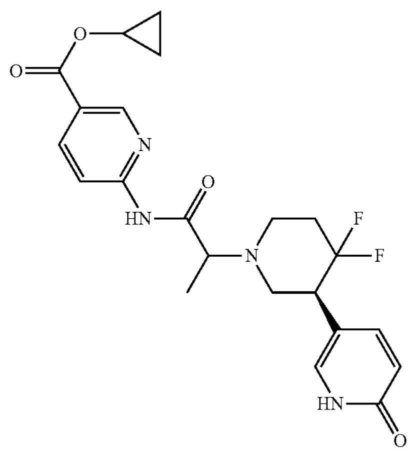 [SMILES: CC(C(=O)Nc1ccc(C(=O)OC2CC2)cn1)N1CCC(F)(F)[C@@H](c2ccc(=O)[nH]c2)C1] | ¹H NMR: (300 MHz, CDCl₃) δ ppm 12.41 (br, 1H), 9.71 (d, J = 5.1 Hz, 1H), 8.87 (s, 1H), 8.31-8.27 (m, 2H), 7.46-7.28 (m, 2H), 6.62-6.52 (m, 1H), 4.46-4.34 (m, 1H), 3.52-3.41 (m, 1H), 3.20-2.64 (m, 5H), 2.34-2.18 (m, 2H), 1.37-1.34 (m, 3H), 0.85 (d, J = 4.8 Hz, 4H). | 447; rt 2.589 and 2.649. LC/MS Method 18 | 67 |
| 84 | (S)-N-(5-(cyclobutylmethyl)pyridin-2-yl)-2-((S)-4,4-difluoro-3-(6-oxo-1,6-dihydropyridin-3-yl)piperidin-1-yl)propanamide | 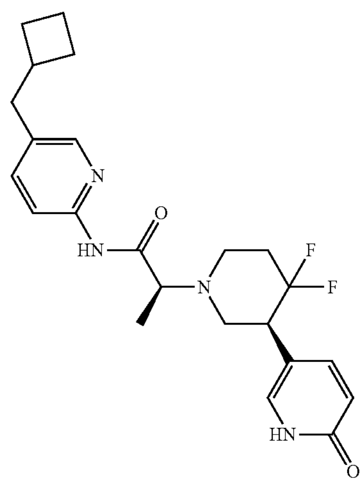 [SMILES: C[C@@H](C(=O)Nc1ccc(CC2CCC2)cn1)N1CCC(F)(F)[C@@H](c2ccc(=O)[nH]c2)C1] | ¹H NMR: (400 MHz, CD₃OD) δ ppm 8.11-8.06 (m, 2H), 7.66-7.61 (m, 2H), 7.41 (d, J = 2.4 Hz, 1H), 6.52 (d, J = 9.2 Hz, 1H), 3.56-3.50 (m, 1H), 3.39-3.30 (m, 1H), 2.99-2.94 (m, 2H), 2.91-2.87 (m, 1H), 2.69 (d, J = 7.2 Hz, 2H), 2.68-2.55 (m, 2H), 2.34-2.11 (m, 2H), 2.04-2.01 (m, 2H), 1.89-1.83 (m, 2H), 1.76-1.72 (m, 2H), 1.33 (d, J = 7.2 Hz, 3H). | 431; rt 1.098. LC/MS Method 19 | 51 |
| 85 | (S)-2-((S)-4,4-difluoro-3-(6-oxo-1,6-dihydropyridin-3-yl)piperidin-1-yl)-N-(5-(2,4-difluorophenoxy)pyrazin-2-yl)propanamide | 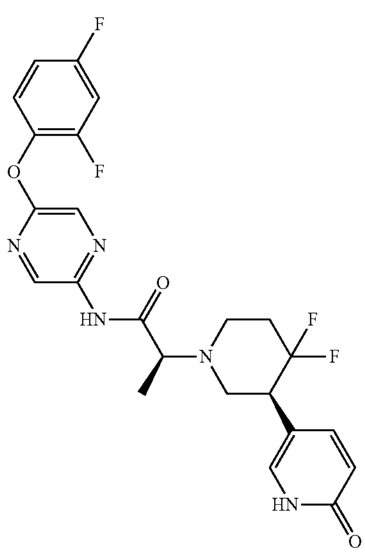 [SMILES: C[C@@H](C(=O)Nc1cnc(Oc2ccc(F)cc2F)cn1)N1CCC(F)(F)[C@@H](c2ccc(=O)[nH]c2)C1] | ¹H NMR (400 MHz, DMSO-d6) δ 11.59 (br s, 1H), 10.55 (s, 1H), 8.82 (d, J = 1.5 Hz, 1H), 8.46 (d, J = 1.5 Hz, 1H), 7.53-7.40 (m, 3H), 7.31 (d, J = 2.0 Hz, 1H), 7.22-7.13 (m, 1H), 6.30 (d, J = 9.8 Hz, 1H), 3.68 (q, J = 7.2 Hz, 1H), 3.28-3.13 (m, 1H), 2.97-2.77 (m, 3H), 2.15-1.94 (m, 2H), 1.22 (d, J = 6.8 Hz, 3H). | 492; rt 0.85. LC/MS Method 2 | 65 |

-continued

| Ex | Name | Structure | ¹H NMR | LC/MS: (M + H)⁺; retention time (min); LC/MS Method of analysis | Int |
|---|---|---|---|---|---|
| 86 | 2-((S)-4,4-difluoro-3-(6-oxo-1,6-dihydropyridin-3-yl)piperidin-1-yl)-N-(3-fluoro-5-(4-fluorophenoxy)pyridin-2-yl)propanamide | 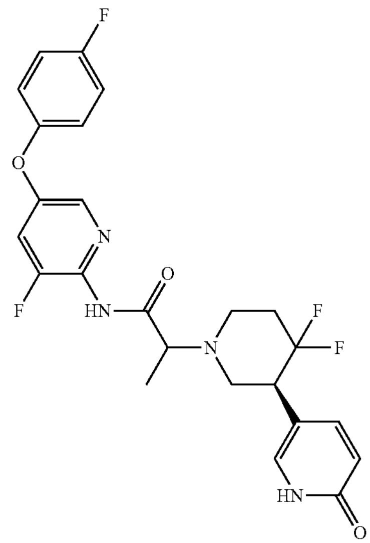 [SMILES: CC(C(=O)Nc1ncc(Oc2ccc(F)cc2)cc1F)N1CCC(F)(F)[C@@H](c2ccc(=O)[nH]c2)C1] | ¹H NMR (400 MHz, METHANOL-d₄) δ 8.01 (d, J = 2.4 Hz, 1H), 7.64 (dt, J = 9.5, 2.8 Hz, 1H), 7.43 (s, 1H), 7.35 (dd, J = 10.3, 2.4 Hz, 1H), 7.24-7.11 (m, 4H), 6.52 (d, J = 9.3 Hz, 1H), 3.61-3.49 (m, 1H), 3.28-3.19 (m, 1H), 3.16-2.86 (m, 3H), 2.84-2.72 (m, 1H), 2.71-2.60 (m, 1H), 2.31-2.11 (m, 2H), 1.36 (dd, J = 7.1, 2.2 Hz, 3H). | 491; rt 0.91. LC/MS Method 3 | 60 |
| 87 | 2-((S)-4,4-difluoro-3-(6-oxo-1,6-dihydropyridin-3-yl)piperidin-1-yl)-N-(5-(2,4-difluorophenoxy)-3-fluoropyridin-2-yl)propanamide | 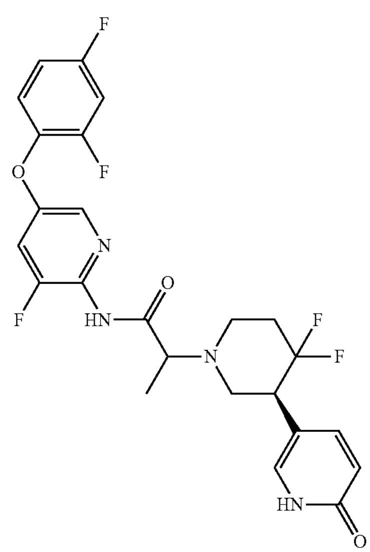 [SMILES: CC(C(=O)Nc1ncc(Oc2ccc(F)cc2F)cc1F)N1CCC(F)(F)[C@@H](c2ccc(=O)[nH]c2)C1] | ¹H NMR (400 MHz, METHANOL-d₄) δ 8.02 (d, J = 2.9 Hz, 1H), 7.64 (dt, J = 9.5, 2.8 Hz, 1H), 7.43 (s, 1H), 7.39-7.29 (m, 2H), 7.22 (ddd, J = 11.1, 8.4, 2.9 Hz, 1H), 7.12-7.02 (m, 1H), 6.53 (d, J = 9.3 Hz, 1H), 3.65-3.46 (m, 1H), 3.29-3.16 (m, 1H), 3.15-2.59 (m, 5H), 2.34-2.12 (m, 2H), 1.36 (dd, J = 7.1, 2.2 Hz, 3H). | 509; rt 0.93. LC/MS Method 3 | 59 |

| Ex | Name | Structure | ¹H NMR | LC/MS: (M + H)⁺; retention time (min); LC/MS Method of analysis | Int |
|---|---|---|---|---|---|
| 88 | (S)-N-(5-((5-chloropyridin-2-yl)oxy)pyridin-2-yl)-2-((S)-4,4-difluoro-3-(6-oxo-1,6-dihydropyridin-3-yl)piperidin-1-yl)propanamide | 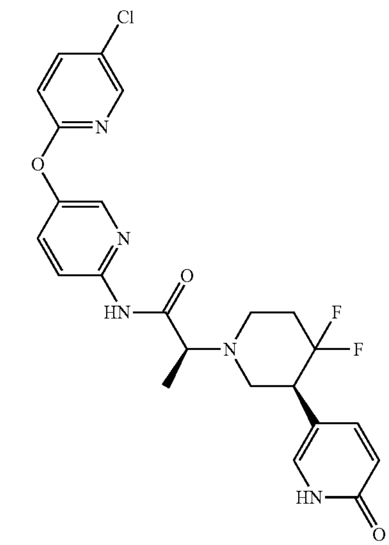 [SMILES: C[C@@H](C(=O)Nc1ccc(Oc2ccc(Cl)cn2)cn1)N1CCC(F)(F)[C@@H](c2ccc(=O)[nH]c2)C1] | ¹H NMR (400 MHz, CDCl₃) δ 12.89-12.64 (m, 1H), 9.75-9.57 (m, 1H), 8.34 (d, J = 8.8 Hz, 1H), 8.21 (d, J = 2.4 Hz, 1H), 8.10 (d, J = 2.0 Hz, 1H), 7.71 (dd, J = 8.8, 2.4 Hz, 1H), 7.57 (dd, J = 9.3, 2.9 Hz, 1H), 7.49 (dd, J = 9.3, 2.4 Hz, 1H), 7.37 (d, J = 2.0 Hz, 1H), 6.98 (d, J = 8.8 Hz, 1H), 6.61 (d, J = 9.3 Hz, 1H), 3.57-3.41 (m, 1H), 3.37-3.15 (m, 1H), 3.05-2.85 (m, 3H), 2.77-2.57 (m, 1H), 2.26 (br d, J = 13.2 Hz, 2H), 1.41 (d, J = 6.8 Hz, 3H). | 490; rt 0.68. LC/MS Method 5 | 102 |
| 89 | (S)-2-((S)-4,4-difluoro-3-(6-oxo-1,6-dihydropyridin-3-yl)piperidin-1-yl)-N-(6-(neopenlyloxy)pyridazin-3-yl)propanamide | 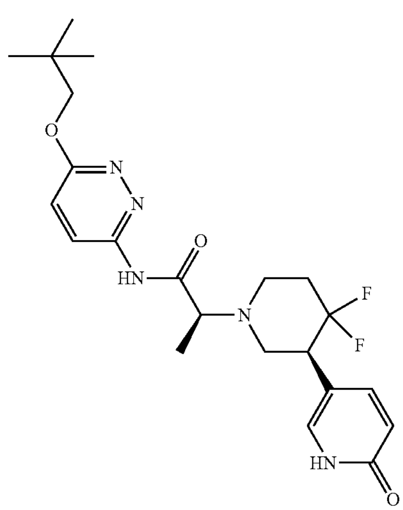 [SMILES: C[C@@H](C(=O)Nc1ccc(OCC(C)(C)C)nn1)N1CCC(F)(F)[C@@H](c2ccc(=O)[nH]c2)C1] | ¹H NMR: (400 MHz, DMSO-d₆) δ 11.51 (s, 1H), 10.06 (s, 1H), 8.01-7.99 (m, 2H), 7.42 (dd, J = 2.8, 8.8 Hz, 1H), 6.62 (s, 2H), 6.52 (s, 1H), 3.86 (d, J = 7.2 Hz, 2H), 3.59-3.54 (m, 1H), 3.05-2.92 (m, 2H), 2.86-2.79 (m, 2H), 2.50-2.47 (m, 1H), 2.25-1.89 (m, 2H), 1.25-1.17 (m, 4H), 0.60-0.55 (m, 2H), 0.34-0.30 (m, 2H). | 450; rt 0.73. LC/MS Method 5 | 21 |

-continued

| Ex | Name | Structure | ¹H NMR | LC/MS: (M + H)⁺; retention time (min); LC/MS Method of analysis | Int |
|---|---|---|---|---|---|
| 90 | N-(5-((3-chloro-5-fluoropyridin-2-yl)oxy)pyridin-2-yl)-2-((S)-4,4-difluoro-3-(6-oxo-1,6-dihydropyridin-3-yl)piperidin-1-yl)propanamide | 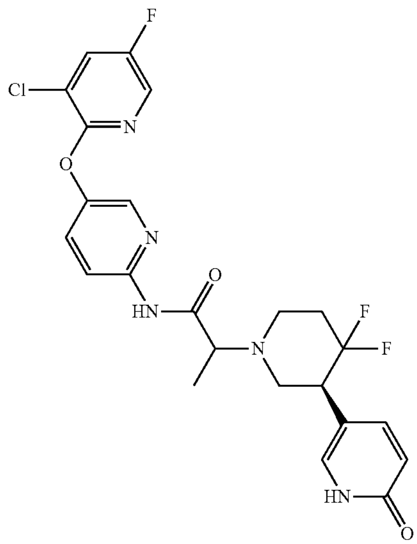 [SMILES: CC(C(=O)Nc1ccc(Oc2ncc(F)cc2Cl)cn1)N1CCC(F)(F)[C@@H](c2ccc(=O)[nH]c2)C1] | ¹H NMR (400 MHz, DMSO-d₆) δ 11.70-11.40 (m, 1H), 10.36 (d, J = 9.3 Hz, 1H), 8.30 (dd, J = 7.6, 3.2 Hz, 1H), 8.26 (t, J = 2.4 Hz, 1H), 8.21-8.10 (m, 2H), 7.75-7.66 (m, 1H), 7.47-7.37 (m, 1H), 7.35-7.27 (m, 1H), 6.34-6.21 (m, 1H), 3.74-3.54 (m, 1H), 3.29-3.11 (m, 1H), 3.04-2.84 (m, 2H), 2.72-2.62 (m, 1H), 2.17-1.98 (m, 2H), 1.23 (dd, J = 6.8, 4.4 Hz, 3H). | 508; rt 0.73. LC/MS Method 5 | 95 |
| 91 | 2-((S)-4,4-difluoro-3-(6-oxo-1,6-dihydropyridin-3-yl)piperidin-1-yl)-N-(3-fluoro-5-((5-fluoropyridin-2-yl)oxy)pyridin-2-yl)propanamide | 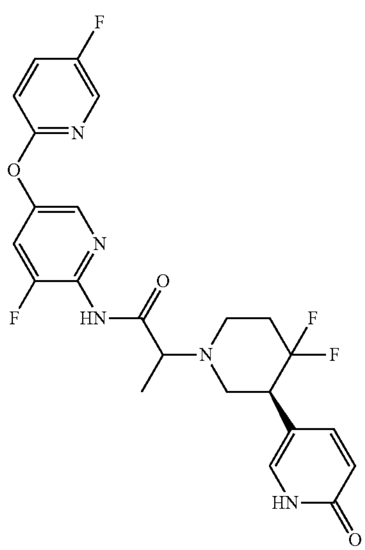 | ¹H NMR (400 MHz, DMSO-d₆) δ 11.67-11.49 (m, 1H), 10.27-10.13 (m, 1H), 8.28-8.15 (m, 2H), 7.97-7.81 (m, 2H), 7.48-7.22 (m, 3H), 6.31 (dd, J = 9.5, 1.7 Hz, 1H), 3.64-3.52 (m, 1H), 3.29-3.11 (m, 1H), 3.04-2.54 (m, 4H), 2.22-1.99 (m, 2H), 1.27-1.20 (m, 3H). | 492; rt 0.56. LC/MS Method 5 | 107 |

| Ex | Name | Structure | ¹H NMR | LC/MS: (M + H)⁺; retention time (min); LC/MS Method of analysis | Int |
|---|---|---|---|---|---|
| 92 | N-(5-((3-cyano-5-fluoropyridin-2-yl)oxy)pyridin-2-yl)-2-((S)-4,4-difluoro-3-(6-oxo-1,6-dihydropyridin-3-yl)piperidin-1-yl)propanamide | 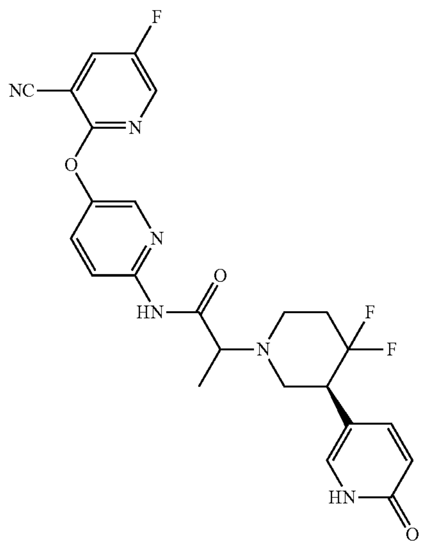 [SMILES: CC(C(=O)Nc1ccc(Oc2ncc(F)cc2C#N)cn1)N1CCC(F)(F)[C@@H](c2ccc(=O)[nH]c2)C1] | ¹H NMR (400 MHz, DMSO-$d_6$) δ 11.68-11.44 (m, 1H), 10.43-10.35 (m, 1H), 8.64-8.58 (m, 1H), 8.46 (dd, J = 2.9, 2.0 Hz, 1H), 8.32 (t, J = 2.7 Hz, 1H), 8.19 (dd, J = 9.0, 1.7 Hz, 1H), 7.78 (dt, J = 9.2, 3.0 Hz, 1H), 7.47-7.38 (m, 1H), 7.32 (br s, 1H), 6.29 (dd, J = 9.3, 7.8 Hz, 1H), 3.72-3.58 (m, 1H), 3.28-3.11 (m, 1H), 3.03-2.79 (m, 3H), 2.66 (br t, J = 11.2 Hz, 1H), 2.18-1.93 (m, 2H), 1.23 (dd, J = 6.8, 4.4 Hz, 3H). | 499; rt 0.69. LC/MS Method 5 | 96 |
| 93 | 2-((S)-4,4-difluoro-3-(6-oxo-1,6-dihydropyridin-3-yl)piperidin-1-yl)-N-(6-(spiro[3.3]heptan-2-yloxy)pyridazin-3-yl)propanamide | 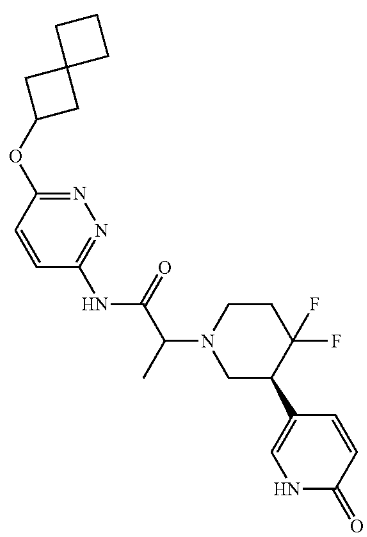 [SMILES: CC(C(=O)Nc1ccc(OC2CC3(CCC3)C2)nn1)N1CCC(F)(F)[C@@H](c2ccc(=O)[nH]c2)C1] | ¹H NMR (400 MHz, METHANOL-$d_4$) δ 8.36 (d, J = 9.54 Hz, 1H), 7.70-7.61 (m, 1H), 7.45 (d, J = 2.20 Hz, 1H), 7.17 (d, J = 9.54 Hz, 1H), 6.53 (d, J = 9.54 Hz, 1H), 5.16 (s, 1H), 3.59 (d, J = 6.85 Hz, 1H), 3.12-2.99 (m, 1H), 2.95-2.69 (m, 3H), 2.64 (d, J = 2.69 Hz, 2H), 2.27-2.01 (m, 7H), 1.92 (d, J = 7.09 Hz, 2H), 1.36 (d, J = 7.09 Hz, 3H). | 473; rt 0.79. LC/MS Method 3 | 17 |
| 94 | N-(5-bromopyridin-2-yl)-2-((S)-4,4-difluoro-3-(6-oxo-1,6-dihydropyridin-3-yl)piperidin-1-yl)propanamide | 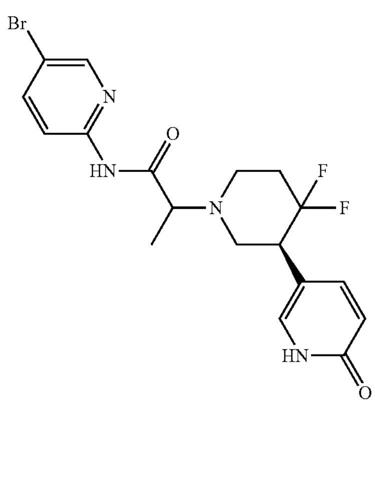 [SMILES: CC(C(=O)Nc1ccc(Br)cn1)N1CCC(F)(F)[C@@H](c2ccc(=O)[nH]c2)C1] | ¹H NMR (400 MHz, METHANOL-$d_4$) δ 8.41 (d, J = 2.45 Hz, 1H), 8.16 (d, J = 9.05 Hz, 1H), 7.96 (dd, J = 8.80, 2.45 Hz, 1H), 7.72-7.61 (m, 1H), 7.49-7.39 (m, 1H), 6.53 (dd, J = 9.41, 5.99 Hz, 1H), 3.56 (dd, J = 14.55, 6.97 Hz, 1H), 3.41-3.35 (m, 1H), 3.11-2.55 (m, 4H), 2.38-2.11 (m, 2H), 1.36 (d, J = 6.85 Hz, 3H). | 441; rt 0.57. LC/MS Method 3 | 4 |

| Ex | Name | Structure | ¹H NMR | LC/MS: (M + H)⁺; retention time (min); LC/MS Method of analysis | Int |
|---|---|---|---|---|---|
| 95 | 2-((S)-4,4-difluoro-3-(6-oxo-1,6-dihydropyridin-3-yl)piperidin-1-yl)-N-(5-((6-methoxypyridin-2-yl)oxy)pyridin-2-yl)propanamide | 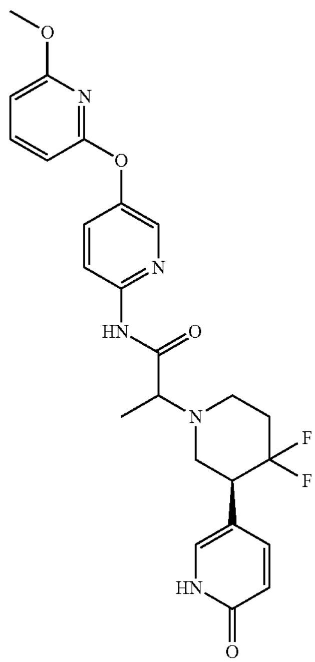 [SMILES: COc1cccc(Oc2ccc(NC(=O)C(C)N3CCC(F)(F)[C@@H](c4ccc(=O)[nH]c4)C3)nc2)n1] | ¹H NMR (400 MHz, METHANOL-d₄) δ 8.29-8.18 (m, 1H), 7.79-7.62 (m, 2H), 7.45 (d, J = 2.20 Hz, 1H), 6.60-6.46 (m, 3H), 3.55 (d, J = 7.09 Hz, 1H), 3.33 (dt, J = 3.24, 1.68 Hz, 5H), 3.12-2.99 (m, 1H), 2.98-2.72 (m, 3H), 2.41-2.15 (m, 2H), 1.38 (d, J = 6.85 Hz, 3H). | 485; rt 0.68. LC/MS Method 5 | 18 |
| 96 | (S)-2-((S)-4,4-difluoro-3-(6-oxo-1,6-dihydropyridin-3-yl)piperidin-1-yl)-N-(5-(2,4,6-trifluorophenoxy)pyridin-2-yl)propanamide | 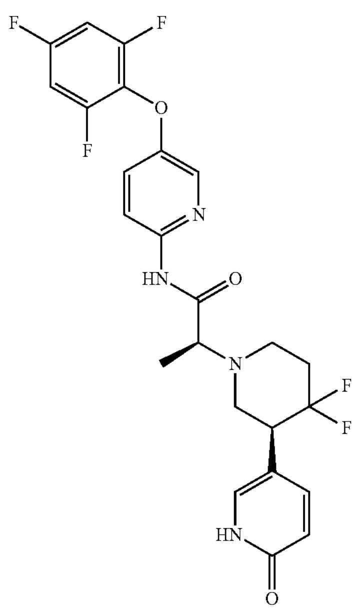 [SMILES: C[C@@H](C(=O)Nc1ccc(Oc2c(F)cc(F)cc2F)cn1)N1CCC(F)(F)[C@@H](c2ccc(=O)[nH]c2)C1] | ¹H NMR (400 MHz, METHANOL-d₄) δ 8.24-8.01 (m, 1H), 7.66 (dd, J = 9.41, 2.08 Hz, 1H), 7.51-7.39 (m, 2H), 7.17-7.03 (m, 2H), 6.54 (d, J = 9.29 Hz, 1H), 3.56 (q, J = 6.85 Hz, 1H), 3.44-3.24 (m, 2H), 3.06-2.85 (m, 3H), 2.71-2.56 (m, 1H), 2.36-2.11 (m, 2H), 1.35 (d, J = 7.09 Hz, 3H). | 508; rt 1.05. LC/MS Method 3 | 77 |

-continued

| Ex | Name | Structure | ¹H NMR | LC/MS: (M + H)⁺; retention time (min); LC/MS Method of analysis | Int |
|---|---|---|---|---|---|
| 97 | (S)-2-((S)-4,4-difluoro-3-(6-oxo-1,6-dihydropyridin-3-yl)piperidin-1-yl)-N-(5-(2,4,5-trifluorophenoxy)pyridin-2-yl)propanamide | 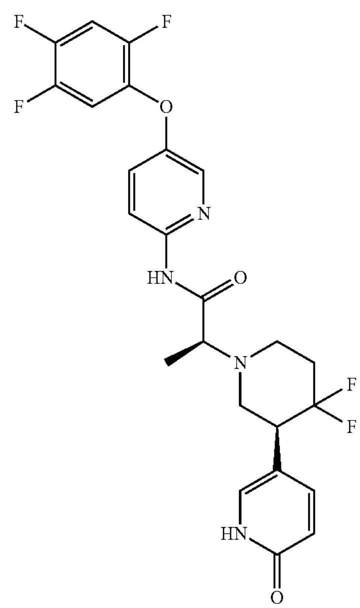 [SMILES: C[C@@H](C(=O)Nc1ccc(Oc2cc(F)c(F)cc2F)cn1)N1CCC(F)(F)[C@@H](c2ccc(=O)[nH]c2)C1] | ¹H NMR (400 MHz, METHANOL-d₄) δ 8.27-8.05 (m, 1H), 7.76-7.61 (m, 1H), 7.55-7.34 (m, 3H), 7.25 (d, J = 10.76 Hz, 1H), 6.54 (d, J = 9.54 Hz, 1H), 3.57 (d, J = 6.85 Hz, 1H), 2.97 (d, J = 11.49 Hz, 3H), 2.70-2.55 (m, 1H), 2.09-2.40 (m, 2H), 1.36 (d, J = 7.09 Hz, 3H). | 508; rt 1.07. LC/MS Method 3 | 78 |
| 98 | (S)-2-((S)-4,4-difluoro-3-(6-oxo-1,6-dihydropyridin-3-yl)piperidin-1-yl)-N-(5-(2-((dimethylamino)methyl)-4-fluorophenoxy)pyridin-2-yl)propanamide | 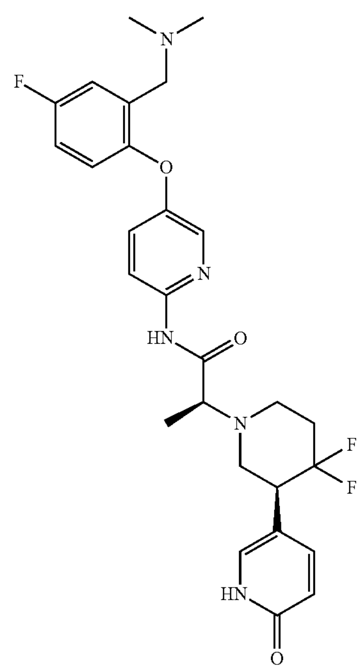 [SMILES: C[C@@H](C(=O)Nc1ccc(Oc2ccc(F)cc2CN(C)C)cn1)N1CCC(F)(F)[C@@H](c2ccc(=O)[nH]c2)C1] | ¹H NMR (400 MHz, METHANOL-d₄) δ 8.17 (d, J = 9.29 Hz, 1H), 8.05 (d, J = 2.45 Hz, 1H), 7.67 (dd, J = 9.41, 2.08 Hz, 1H), 7.43 (td, J = 8.50, 2.57 Hz, 2H), 7.28 (dd, J = 9.17, 3.06 Hz, 1H), 7.15-7.04 (m, 1H), 7.01-6.92 (m, 1H), 6.54 (d, J = 9.54 Hz, 1H), 3.62-3.45 (m, 4H), 3.07-2.86 (m, 3H), 2.73-2.58 (m, 1H), 2.36-2.14 (m, 6H), 1.94-1.80 (m, 1H), 1.73 (d, J = 13.45 Hz, 1H), 1.44-1.33 (m, 2H), 1.17 (br. s., 1H). | 529; rt 1.01. LC/MS Method 3 | 79 |

| Ex | Name | Structure | ¹H NMR | LC/MS: (M + H)⁺; retention time (min); LC/MS Method of analysis | Int |
|---|---|---|---|---|---|
| 99 | (S)-2-((S)-4,4-difluoro-3-(6-oxo-1,6-dihydropyridin-3-yl)piperidin-1-yl)-N-(5-(2-fluoro-4-(2-methylthiazol-4-yl)phenoxy)pyridin-2-yl)propanamide | 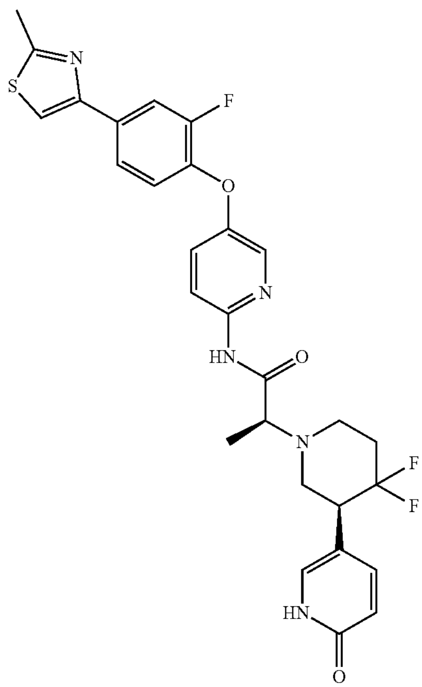 [SMILES: Cc1nc(-c2ccc(Oc3ccc(NC(=O)[C@H](C)N4CCC(F)(F)[C@@H](c5ccc(=O)[nH]c5)C4)nc3)c(F)c2)cs1] | ¹H NMR (METHANOL-d₄) δ: 8.30-8.07 (m, 2H), 7.84 (dd, J = 12.2, 2.0 Hz, 1H), 7.79-7.60 (m, 2H), 7.78-7.59 (m, 1H), 7.58-7.38 (m, 2H), 7.29-7.14 (m, 1H), 6.63-6.45 (m, 1H), 3.65-3.50 (m, 1H). 3.12-2.86 (m, 3H), 2.84-2.55 (m, 4H), 2.34-2.10 (m, 2H), 1.30-1.45 (m, 3H). | 569; rt 1.14. LC/MS Method 9 | 80 |
| 100 | (S)-N-(6-cyclobutoxy-pyridazin-3-yl)-2-((S)-4,4-difluoro-3-(6-oxo-1,6-dihydropyridin-3-yl)piperidin-1-yl)propanamide | 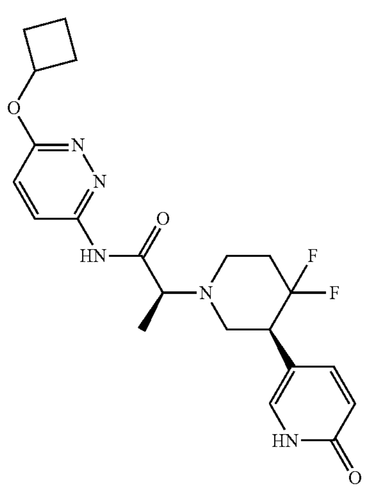 [SMILES: C[C@@H](C(=O)Nc1ccc(OC2CCC2)nn1)N1CCC(F)(F)[C@@H](c2ccc(=O)[nH]c2)C1] | ¹H NMR: (400 MHz, CHLOROFORM-d) δ 13.31 (br. s., 1H), 10.06 (br. s., 1H), 8.41 (d, J = 9.54 Hz, 1H), 7.48 (d, J = 8.80 Hz, 1H), 7.37 (s., 1H), 7.00 (d, J = 9.54 Hz, 1H), 6.59 (d, J = 9.29 Hz, 1H), 5.32 (quin, J = 7.21 Hz, 1H), 3.48 (q, J = 6.68 Hz, 1H), 3.09-3.25 (m, 1H), 2.82-2.99 (m, 3H), 2.50-2.67 (m, 3H), 2.09-2.29 (m, 4H), 1.83-1.95 (m, 1H), 1.64-1.80 (m, 1H), 1.38 (d, J = 6.85 Hz, 3H). | 434; rt 0.88. LC/MS Method 3 | 19 |

| Ex | Name | Structure | $^1$H NMR | LC/MS: (M + H)$^+$; retention time (min); LC/MS Method of analysis | Int |
|---|---|---|---|---|---|
| 101 | (S)-N-(6-(cyclopentyloxy)pyridazin-3-yl)-2-((S)-4,4-difluoro-3-(6-oxo-1,6-dihydropyridin-3-yl)piperidin-1-yl)propanamide | 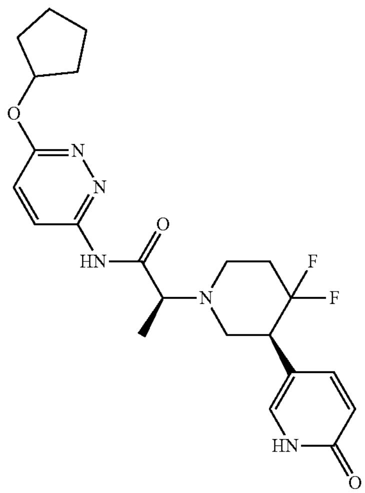 [SMILES: C[C@@H](C(=O)Nc1ccc(OC2CCCC2)nn1)N1CCC(F)(F)[C@@H](c2ccc(=O)[nH]c2)C1] | $^1$H NMR: NMR (400 MHz, CHLOROFORM-d) δ 11.98-13.78 (m, 1H), 9.85-10.48 (m, 1H), 8.41 (d, J = 9.54 Hz, 1H), 7.48 (dd, J = 9.41, 2.32 Hz, 1H) 7.36 (d, J = 2.20 Hz, 1H), 7.01 (d, J = 9.54 Hz, 1H), 6.60 (d, J = 9.54 Hz, 1H), 5.53-5.61 (m, 1H), 3.52 (br. s., 1H), 3.12-3.30 (m, 1H), 2.85-3.02 (m, 3H), 2.65 (br. s., 1H), 2.25 (d, J = 16.87 Hz, 2H), 1.99-2.11 (m, 2H), 1.76-1.91 (m, 4H), 1.61-1.71 (m, 2H), 1.40 (d, J = 7.09 Hz, 3H). | 448; rt 0.96. LC/MS Method 3 | 20 |
| 102 | (S)-N-(5-(difluoro(4-fluorophenyl)methyl)pyridin-2-yl)-2-((S)-4,4-difluoro-3-(6-oxo-1,6-dihydropyridin-3-yl)piperidin-1-yl)propanamide | 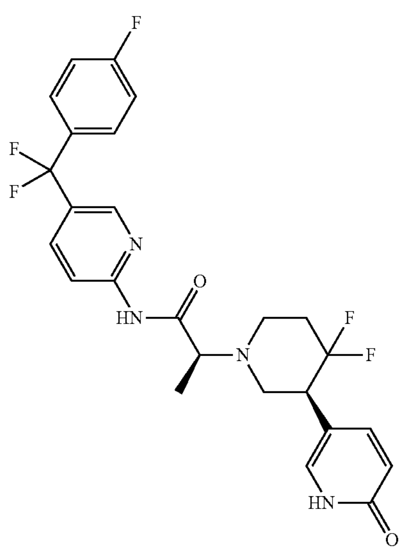 [SMILES: C[C@@H](C(=O)Nc1ccc(C(F)(F)c2ccc(F)cc2)cn1)N1CCC(F)(F)[C@@H](c2ccc(=O)[nH]c2)C1] | $^1$H NMR: NMR (400 MHz, CHLOROFORM-d) δ 12.27-13.49 (m, 1H), 9.72 (br. s., 1H), 8.44 (br. s., 1H), 8.32 (d, J = 8.80 Hz, 1H), 7.81 (dd, J = 8.80, 2.20 Hz, 1H), 7.46-7.57 (m, 3H), 7.37 (d, J = 1.96 Hz, 1H), 7.15 (t, J = 8.56 Hz, 2H), 6.60 (d, J = 9.54 Hz, 1H), 3.49 (br. s., 1H), 3.10-3.33 (m, 1H), 2.80-3.02 (m, 3H), 2.57-2.72 (m, 1H), 2.06-2.33 (m, 2H), 1.39 (d, J = 6.85 Hz, 3H). | 507; rt 1.08. LC/MS Method 3 | 104 |

Example 103

(S)-2-((R)-4,4-difluoro-3-(5-oxo-4-(2,2,2-trifluoroethyl)-4,5-dihydropyrazin-2-yl)piperidin-1-yl)-N-(5-fluoropyridin-2-yl)propanamide

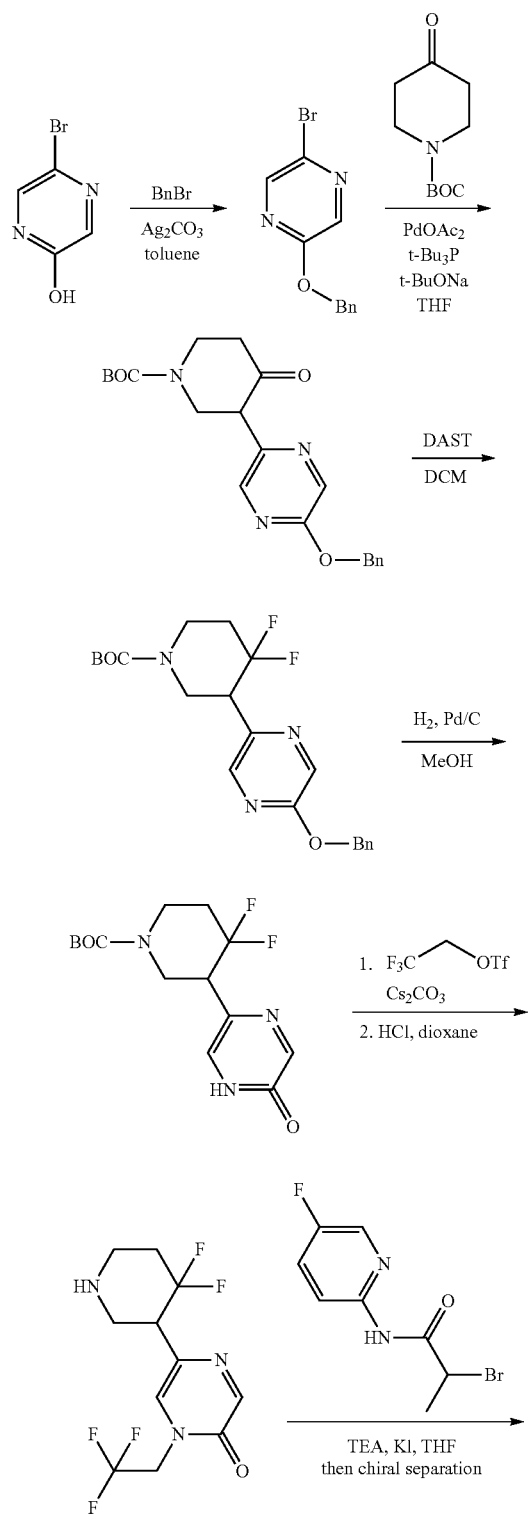

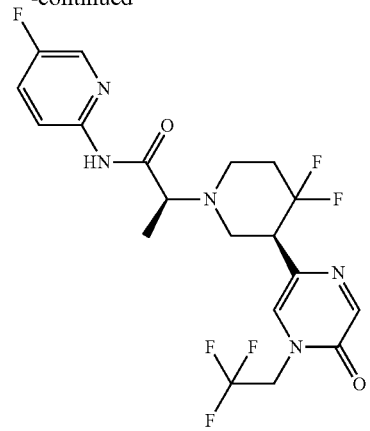

-continued

Step 1

To 5-bromopyrazin-2-ol (5.0 g 28.7 mmol, 1.0 eq) in toluene (200 mL) at 25° C. was added (bromomethyl)benzene (7.4 g, 43.1 mmol, 1.5 eq) and Ag$_2$CO$_3$ (15.7 g, 57.5 mmol, 2.0 eq). After 15 h, the reaction was filtered, diluted with water (100 mL) and extracted with ethyl acetate (100 mL×3). The organic layers were combined, washed with water (300 mL), dried over Na$_2$SO$_4$, concentrated and purified over a silica gel column, eluting with ethyl acetate: petroleum ether (1:20) to give 6.0 g 2-(benzyloxy)-5-bromopyrazine (purity: 80%, yield: 79%) as a yellow solid. LCMS: (ES, m/s) 265 [M+H]$^+$. $^1$H NMR: (300 MHz, CDCl$_3$) δ ppm 8.23 (d, J=1.2 Hz, 1H), 8.09 (d, J=1.6 Hz, 1H), 7.48-7.35 (m, 5H), 5.39 (s, 2H).

Step 2

A mixture of t-BuONa (1.82 g, 18.95 mmol, 2.5 eq) in THF (16 mL) was stirred at 43° C. for 5 min followed by addition of Pd(OAc)$_2$ (170 mg, 0.76 mmol, 0.1 eq) and (t-Bu)$_3$P (153 mg, 0.76 mmol, 0.1 eq, 10% in hexane). After 5 min, 2-(benzyloxy)-5-bromopyrazine (2.0 g, 7.58 mmol, 1.0 eq) and tert-butyl 4-oxopiperidine-1-carboxylate (2.26 g, 11.36 mmol, 1.5 eq) were added, and the mixture was stirred for 15 h at 43° C., quenched with water (200 mL), and extracted with ethyl acetate (200 mL×3). The combined organic extracts were washed with brine (600 mL), dried over sodium sulfate, concentrated and purified over a silica gel column, eluting with ethyl acetate:petroleum ether (1:3) to give 7.8 g crude tert-butyl 3-(5-(benzyloxy)pyrazin-2-yl)-4-oxopiperidine-1-carboxylate 4.8 g as yellow oil. LCMS: (ES, m/s) 384 [M+H]$^+$. $^1$H NMR: (300 MHz, CDCl$_3$) δ ppm 8.25 (d, J=1.2 Hz, 1H), 7.99 (d, J=1.5 Hz, 1H), 7.50-7.35 (m, 5H), 5.39 (s, 2H), 4.25-4.17 (m, 1H), 3.95-3.63 (m, 3H), 3.55-3.45 (m, 1H), 2.65-2.60 (m, 1H), 2.47-2.43 (m, 1H), 1.49 (m, 9H).

Step 3

To tert-butyl 3-(5-(benzyloxy)pyrazin-2-yl)-4-oxopiperidine-1-carboxylate (7.8 g, 20.36 mmol, 1.0 eq) in DCM (20 mL) at 25° C. was added DAST (6.6 g, 40.7 mmol, 2.0 eq), and the mixture was stirred for 12 h, quenched with ice/water (100 mL) and extracted with DCM (100 mL×3). The combined organic phases were dried over Na$_2$SO$_4$, concentrated and purified over a silica gel column, eluting with ethyl acetate:petroleum ether (1:4) to give 3.6 g tert-butyl 3-(5-(benzyloxy)pyrazin-2-yl)-4,4-difluoropiperidine-1-carboxylate (purity: 50%, yield: 44%) as a yellow oil. LCMS (ES, m/s): 406 [M+H]+ $^1$H NMR: (300 MHz, CDCl$_3$) δ ppm 8.25 (d, J=1.5 Hz, 1H), 8.10 (s, 1H), 7.48-7.31 (m, 5H), 5.39

(s, 2H), 4.21-4.15 (m, 1H), 3.73-3.52 (m, 2H), 3.34-3.20 (m, 2H), 2.30-2.20 (m, 1H), 2.10-1.90 (m, 1H), 1.46 (m, 9H).

Step 4

A mixture of tert-butyl 3-(5-(benzyloxy)pyrazin-2-yl)-4,4-difluoropiperidine-1-carboxylate (1.38 g, 3.40 mmol, 1.0 eq) and Pd/C (1.0 g, 10%) in methanol (10 mL) was stirred at 25° C. for 1 h under an atmosphere of hydrogen, filtered, concentrated and purified over a silica gel column, eluting with ethyl acetate in petroleum ether (0-10%) to give tert-butyl 4,4-difluoro-3-(5-oxo-4,5-dihydropyrazin-2-yl)piperidine-1-carboxylate (600 mg, yield: 34%, purity: 60%) as a light yellow oil. LCMS: (ES, m/s): 316[M+H]$^+$, retention time 0.948 min, LCMS Method 32.

Step 5

A mixture of tert-butyl 4,4-difluoro-3-(5-oxo-4,5-dihydropyrazin-2-yl)piperidine-1-carboxylate (600 mg, 1.90 mmol, 1.0 eq), 2,2,2-trifluoroethyl trifluoromethanesulfonate (1.10 g, 4.76 mmol, 2.5 eq) and Cs$_2$CO$_3$ (1.55 g, 4.76 mmol, 2.5 eq) in DMF (8 mL) was stirred for 6 h at 25° C. The reaction was quenched with water (50 mL) and extracted with ethyl acetate (50 mL×2). The organic layers were washed with brine (100 mL×2), dried over sodium sulfate, concentrated and purified over a silica gel column, eluting with ethyl acetate in petroleum ether (0-20%) to give 0.69 g (purity: 90%, yield: 46%) of tert-butyl 4,4-difluoro-3-(5-oxo-4-(2,2,2-trifluoroethyl)-4,5-dihydropyrazin-2-yl)piperidine-1-carboxylate as a light yellow oil. LCMS: (ES, m/z): 398 [M+H]$^+$, retention time 1.278 min, LCMS Method 32. $^1$H NMR (400 MHz, DMSO-d$_6$) δ 8.13 (d, J=1.2 Hz, 1H), 7.66 (s, 1H), 4.05-3.85 (m, 3H), 3.29-3.12 (m, 3H), 2.25-2.15 (m, 1H), 2.05-1.90 (m, 2H), 1.39 (s, 9H).

Step 6

A mixture of tert-butyl 4,4-difluoro-3-(5-oxo-4-(2,2,2-trifluoroethyl)-4,5-dihydropyrazin-2-yl)piperidine-1-carboxylate (280 mg, 0.71 mmol, 1.0 eq) and HCl (5 mL, 4 M in dioxane) was stirred for 2 h at rt. The reaction mixture was concentrated, diluted with NaHCO$_3$ (30 mL, aq., sat.) and extracted with DCM (30 mL×2). The organic layers were combined, dried over Na$_2$SO$_4$ and concentrated. The residue was purified with by prep HPLC (Column: Sun Fire C18 OBD) eluting with 15-20% AcCN in water (0.05% TFA) to give 100 mg 5-(4,4-difluoropiperidin-3-yl)-1-(2,2,2-trifluoroethyl)pyrazin-2 (1H)-one (purity: 90%, yield: 47%) as a light yellow oil. LCMS (ES, m/z): 298 [M+H]$^+$, retention time 0.616, LCMS Method 33.

Step 7

A mixture of 5-(4,4-difluoropiperidin-3-yl)-1-(2,2,2-trifluoroethyl)pyrazin-2 (1H)-one (100 mg, 0.34 mmol, 1.0 eq), 2-bromo-N-(5-fluoropyridin-2-yl)propanamide (Intermediate 1) (83 mg, 0.34 mmol, 1.0 eq), KI (56 mg, 0.34 mmol, 1.0 eq) and TEA (0.38 mL, 2.69 mmol, 8.0 eq) in THF (5 mL) was stirred 12 h at 60° C., filtered, concentrated and purified by prep TLC with 1:3 EtOAc:petroleum ether. The collected product (40 mg) was chirally separated by chiral purification (Chiralpak IG, 20×250 mm, 5 um; Mobile Phase A: Hex [8 mM NH$_3$.MeOH], Mobile Phase B: EtOH; Flow rate: 20 mL/min; 85:15 A:B over 17 min) to give 4 isomers with retention times of: RT1, 13.989 min; RT2, 16.569 min; RT3, 18.549 min; and RT4, 20.702 min. Isomer 3, (RT 18.549 min) was collected to give 4.0 mg (S)-2-((R)-4,4-difluoro-3-(5-oxo-4-(2,2,2-trifluoroethyl)-4,5-dihydropyrazin-2-yl)piperidin-1-yl)-N-(5-fluoropyridin-2-yl)propanamide (purity: 98.7%, yield: 3%) as white solid. LCMS (ES, m/s): 464 [M+H]+ $^1$H NMR: (400 MHz, CD$_3$OD) δ 8.20-8.16 (m, 3H), 7.62-7.57 (m, 2H), 4.82-4.75 (m, 2H), 3.59-3.41 (m, 2H), 3.04-2.88 (m, 3H), 2.75-2.71 (m, 1H), 2.40-2.16 (m, 2H), 1.32 (d, J=6.8 Hz, 3H).

Example 104

(S)-2-((R)-3-(6-amino-5-oxo-4,5-dihydropyrazin-2-yl)-4,4-difluoropiperidin-1-yl)-N-(6-(cyclopropylmethoxy)pyridazin-3-yl)propanamide

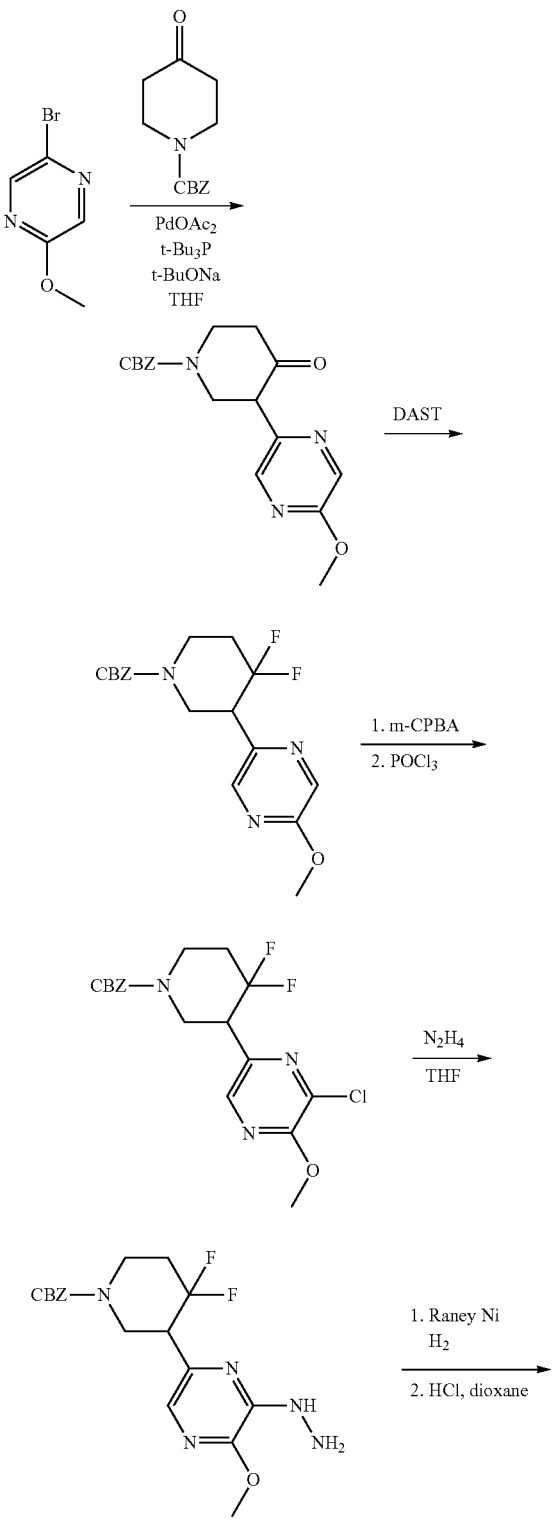

-continued

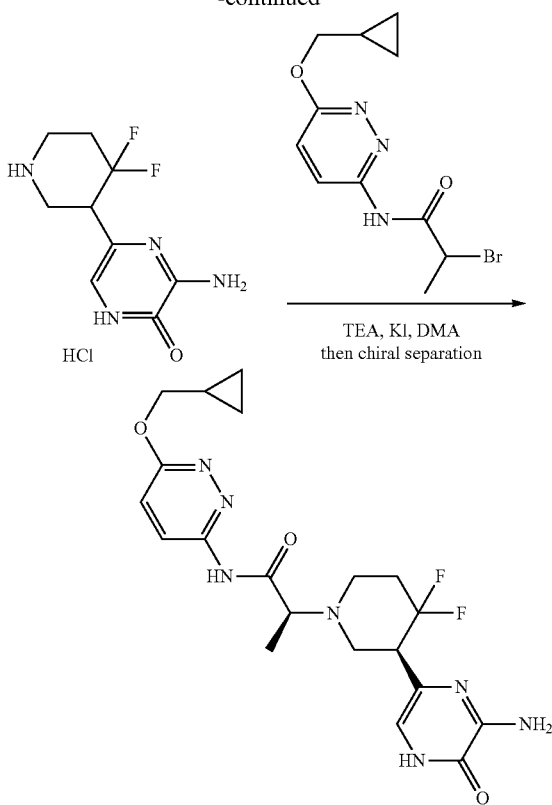

Step 1

To t-BuONa (15.2 g, 159.0 mmol, 3 eq) in THF (80 mL) was added Pd(OAc)$_2$ (1.2 g, 5.3 mmol, 0.1 eq), (t-Bu)$_3$P (21.6 g, 10.7 mmol, 0.2 eq, 10% in hexane), 2-bromo-5-methoxypyrazine (10 g, 52.9 mmol, 1 eq) and benzyl 4-oxopiperidine-1-carboxylate (15.9 g, 68 mmol, 1.3 eq), and the resulting mixture was stirred at 42° C. After 16 h, the reaction was quenched with water (400 mL) and extracted with EA (300 mL×3). The combined organic phases were dried over Na$_2$SO$_4$, concentrated and loaded onto a silica gel column, eluting with ethyl acetate:petroleum ether (1:3) to give 11 g (purity: 71%, yield: 44%) of benzyl 3-(5-methoxypyrazin-2-yl)-4-oxopiperidine-1-carboxylate as a yellow oil. LCMS: (ES, m/s) 342 [M+H]$^+$. $^1$H NMR: (300 MHz, CDCl$_3$) δ ppm 8.17 (s, 1H), 7.97 (s, 1H), 7.48-7.33 (m, 5H), 5.28-5.17 (m, 2H), 4.42-4.26 (m, 1H), 3.97 (s, 3H), 3.88-3.13 (m, 4H), 2.73-2.52 (m, 2H).

Step 2

To benzyl 3-(5-methoxypyrazin-2-yl)-4-oxopiperidine-1-carboxylate (11 g, 32.2 mmol, 1 eq) in DCM (60 ml) at 0° C. was added DAST (10.4 g, 64.4 mmol, 2 eq). The resulting mixture was stirred at 25° C. for 15 h, quenched with ice water (150 mL) and extracted with ethyl acetate (100 mL×3). The combined organic phases were dried over Na$_2$SO$_4$, concentrated and loaded onto a silica gel column, eluting with ethyl acetate:petroleum ether (1:5) to give 4.2 g (purity: 81%, yield: 28.5%) of benzyl 4,4-difluoro-3-(5-methoxypyrazin-2-yl)piperidine-1-carboxylate as a yellow oil. LCMS: (ES, m/s) 364 [M+H]$^+$. $^1$H NMR: (300 MHz, CDCl$_3$) δ ppm 8.19 (s, 1H), 8.09 (s, 1H), 7.45-7.31 (s, 5H), 5.33-4.97 (m, 2H), 4.25-4.10 (m, 1H), 3.99 (s, 3H), 3.90-3.59 (m, 2H), 3.42-3.19 m, 2H), 2.44-1.83 (m, 2H).

Step 3

To benzyl 4,4-difluoro-3-(5-methoxypyrazin-2-yl)piperidine-1-carboxylate (4.2 g, 11.5 mmol, 1 eq) in DCM (60 ml) at 0° C. was added m-CPBA (4.0 g, 23 mmol, 2 eq). The resulting mixture was stirred at 25° C. for 4 h, quenched with Na$_2$S$_2$O$_3$ (100 mL, aq., sat.) and extracted with DCM (100 mL×3). The organic layers were dried over sodium sulfate, concentrated and loaded onto a silica gel column, eluting with ethyl acetate:petroleum ether (1:5) to give 3.0 g (purity: 91%, yield: 62.3%) of 2-(1-((benzyloxy)carbonyl)-4,4-difluoropiperidin-3-yl)-5-methoxypyrazine 1-oxide as a yellow oil. LCMS (ES, m/s): 380 [M+H]+ $^1$H NMR: (300 MHz, CDCl$_3$) δ ppm 8.21 (s, 1H), 7.88 (s, 1H), 7.43-7.31 (m, 5H), 5.30-5.04 (m, 2H), 4.54-4.23 (m, 3H), 4.00 (s, 3H), 3.29-3.08 (m, 2H), 2.33-1.93 (m, 2H).

Step 4

To 2-(1-((benzyloxy)carbonyl)-4,4-difluoropiperidin-3-yl)-5-methoxypyrazine 1-oxide (3.0 g, 7.8 mmol, 1 eq) was added POCl$_3$ (8 mL), and the resulting mixture was stirred at 25° C. for 15 h and poured into ice water (50 mL). The pH was adjusted to 9 with 4M NaOH (aq.) at 0° C., and the reaction was extracted with dichloromethane (100 mL×3). The combined organic layers were dried over sodium sulfate, concentrated and loaded onto a silica gel column, eluting with ethyl acetate:petroleum ether (1:5) to give 2.4 g (purity: 100%, yield: 76%) of benzyl 3-(6-chloro-5-methoxypyrazin-2-yl)-4,4-difluoropiperidine-1-carboxylate as an off-white oil. LCMS: (ES, m/s): 398 [M+H]+ $^1$H NMR: (300 MHz, CDCl$_3$) δ ppm 8.04 (s, 1H), 7.46-7.30 (m, 5H), 5.23-5.11 (m, 2H), 4.37-4.14 (m, 2H), 4.06 (s, 3H), 3.76-3.57 (m, 1H), 3.47-3.16 (m, 2H), 2.38-1.86 (m, 2H).

Step 5

Into a 40 ml sealed tube, benzyl 3-(6-chloro-5-methoxypyrazin-2-yl)-4,4-difluoropiperidine-1-carboxylate (2.4 g, 6 mmol, 1 eq) was stirred in N$_2$H$_4$ (1M in THF, 10 ml). The tube was sealed, and the resulting mixture was stirred at 115° C. for 8 h, then poured into water (100 mL). The resulting solution was extracted with ethyl acetate (100 mL×3). The combined organic layers were dried over sodium sulfate and concentrated to give 2.3 g (purity: 93%, yield: 95%) of benzyl 4,4-difluoro-3-(6-hydrazineyl-5-methoxypyrazin-2-yl)piperidine-1-carboxylate as a yellow oil, which was used without purification. LCMS: (ES, m/z): 394 [M+H]+.

Step 6

Benzyl 4,4-difluoro-3-(6-hydrazineyl-5-methoxypyrazin-2-yl)piperidine-1-carboxylate (2.3 g, 5.8 mmol, 1 eq) and Raney-nickel (3.4 g, 40 mmol, 6.9 eq) in ethanol (8 mL) were stirred under H$_2$ (3 atm) for 15 h. The reaction was filtered, and the filtrate was concentrated to give 1.2 g (purity: 92%, yield: 85%) of 6-(4,4-difluoropiperidin-3-yl)-3-methoxypyrazin-2-amine as a yellow oil, which was used without purification. LCMS (ES, m/z): 245 [M+H]+. $^1$H NMR: (400 MHz, DMSO-d$_6$) δ ppm 7.23 (s, 1H), 6.30 (s, 2H), 3.92-3.90 (m, 1H), 3.86 (s, 3H), 3.12-2.83 (m, 4H), 2.13-1.81 (m, 3H).

Step 7

To a tube of 6-(4,4-difluoropiperidin-3-yl)-3-methoxypyrazin-2-amine (1.2 g, 4.9 mmol, 1 eq) in dioxane (3 mL) was added HCl (3 mL, 6 M in H$_2$O). The tube was sealed, and the resulting mixture was stirred at 80° C. for 15 h. The reaction was concentrated to give 1.2 g (purity: 90%, yield: 92%) of 3-amino-5-(4,4-difluoropiperidin-3-yl)pyrazin-2 (1H)-one hydrochloride as a red solid, which was used without purification. LCMS: (ES, m/z): 231 [M+H]+. $^1$H NMR: (400 MHz, DMSO-d$_6$) δ ppm 12.39 (s, 1H), 8.60 (br, 2H), 6.82 (s, 1H), 3.70-3.62 (m, 1H), 3.52-3.35 (m, 3H), 3.17-2.83 (m, 1H), 2.44-2.28 (m, 2H).

Step 8

A mixture of 3-amino-5-(4,4-difluoropiperidin-3-yl)pyrazin-2(1H)-one hydrochloride (120 mg, 0.521 mmol, 1 eq), 2-bromo-N-(6-(cyclopropylmethoxy)pyridazin-3-yl)propanamide (Intermediate 14) (188 mg, 0.625 mmol, 1.2 eq), KI (87 mg, 0.521 mmol, 1 eq) and TEA (0.218 mL, 1.564 mmol, 3 eq) in N,N-dimethylacetamide (5 mL) was stirred 3 h at 60° C., quenched with water (15 mL) and extracted with ethyl acetate (15 mL×3). The combined organic phases were washed with brine (15 mL), dried over sodium sulfate, concentrated and purified by prep TLC with 1:10 MeOH:DCM. The collected product (125 mg) was chirally separated (XBridge Shield RP18 OBD Column, 30×150 mm, 5 um; Mobile Phase A: water [10 mmol/L NH$_4$HCO$_3$], Mobile Phase B: ACN; Flow rate: 60 mL/min; 22-42% B in A over 10 min) to give products with retention times of 8.18 and 9.25 minutes. The product from the first peak (8.18 min) was chirally separated again (Chiralpak IE, 2×25 cm, 5 um; Mobile Phase A: Hex: DCM (10 mM NH$_3$-MeOH), 3:1; Mobile Phase B: EtOH; Flow rate: 20 mL/min; 7:3 A:B over 10 min), resulting in two peaks with retention times of 5.396 and 7.166 minutes. The second peak (7.166 min) was collected to give 6 mg (purity: 96.0%, 5% yield) of (S)-2-((R)-3-(6-amino-5-oxo-4,5-dihydropyrazin-2-yl)-4,4-difluoropiperidin-1-yl)-N-(6-(cyclopropylmethoxy)pyridazin-3-yl)propanamide as a white solid. LCMS (ES, m/s): 450 [M+H]+ $^1$H NMR: (400 MHz, DMSO-d$_6$) δ 11.54 (s, 1H), 10.68 (s, 1H), 8.24 (d, J=9.2 Hz, 1H), 7.27 (d, J=9.6 Hz, 1H), 6.60 (s, 2H), 6.52 (s, 1H), 4.21 (dd, J=1.6, 7.2 Hz, 2H), 3.70-3.61 (m, 1H), 3.12-2.78 (m, 4H), 2.51-2.40 (m, 1H), 2.20-1.91 (m, 2H), 1.29-1.23 (m, 1H), 1.21 (d, J=6.8 Hz, 3H), 0.59-0.55 (m, 2H), 0.38-0.34 (m, 2H).

Examples 105-108 were synthesized in an analogous manner using the designated Intermediate in Step 8.

| Ex | Name | Structure | $^1$H NMR | LC/MS: (M + H)$^+$; retention time (min); LC/MS Method of analysis | Int |
|---|---|---|---|---|---|
| 105 | (S)-2-((R)-3-(6-amino-5-oxo-4,5-dihydropyrazin-2-yl)-4,4-difluoropiperidin-1-yl)-N-(5-(cyclopropylmethoxy)pyridin-2-yl)propanamide | 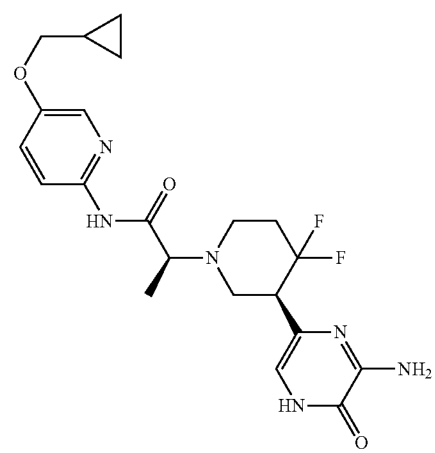 [SMILES: C[C@@H](C(=O)Nc1ccc(OCC2CC2)cn1)N1CCC(F)(F)[C@@H](c2c[nH]c(=O)c(N)n2)C1] | $^1$H NMR: (400 MHz, DMSO-d$_6$) δ ppm 11.51 (s, 1H), 10.06 (s, 1H), 8.01-7.99 (m, 2H), 7.42 (dd, J = 2.8, 8.8 Hz, 1H), 6.62 (s, 2H), 6.52 (s, 1H), 3.86 (d, J = 7.2 Hz, 2H), 3.59-3.54 (m, 1H), 3.05-2.92 (m, 2H), 2.86-2.79 (m, 2H), 2.50-2.47 (m, 1H), 2.25-1.89 (m, 2H), 1.25-1.17 (m, 4H), 0.60-0.55 (m, 2H), 0.34-0.30 (m, 2H). | 449; rt 0.932. LLC/MS Method 13 | 22 |
| 106 | (S)-2-((R)-3-(6-amino-5-oxo-4,5-dihydropyrazin-2-yl)-4,4-difluoropiperidin-1-yl)-N-(5-fluoropyridin-2-yl)propanamide | 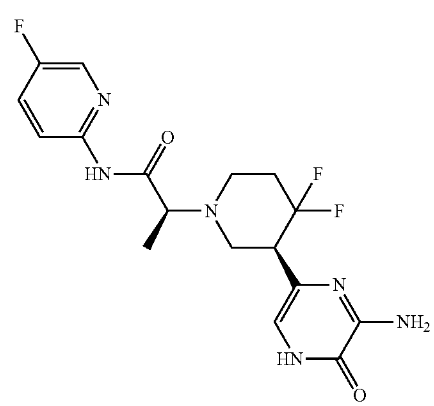 [SMILES: C[C@@H](C(=O)Nc1ccc(F)cn1)N1CCC(F)(F)[C@@H](c2c[nH]c(=O)c(N)n2)C1] | $^1$H NMR: (400 MHz, DMSO-d$_6$) δ ppm 11.52 (s, 1H), 10.31 (s, 1H), 8.31 (d, J = 2.8, 1H), 8.15-8.12 (m, 1H), 7.78-7.73 (m, 1H), 6.60 (s, 2H), 6.52 (s, 1H), 3.62 (d, J = 6.8 Hz, 1H), 3.10-2.80 (m, 4H), 2.51-2.50 (m, 1H), 2.21-2.20 (m, 1H), 2.08-1.96 (m, 1H), 1.19 (d, J = 6.8 Hz, 3H). | 397; rt 0.757. LC/MS Method 13 | 1 |

| Ex | Name | Structure | ¹H NMR | LC/MS: (M + H)+; retention time (min); LC/MS Method of analysis | Int |
|---|---|---|---|---|---|
| 107 | (S)-2-((R)-3-(6-amino-5-oxo-4,5-dihydropyrazin-2-yl)-4,4-difluoropiperidin-1-yl)-N-(5-chloropyridin-2-yl)propanamide | 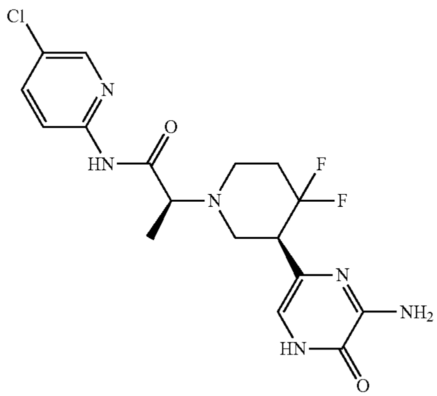 [SMILES: C[C@@H](C(=O)Nc1ccc(Cl)cn1)N1CCC(F)(F)[C@@H](c2c[nH]c(=O)c(N)n2)C1] | ¹H NMR: (400 MHz, DMSO-d₆) δ ppm 11.51 (s, 1H), 10.35 (s, 1H), 8.35 (d, J = 2.4 Hz, 1H), 8.12 (d, J = 9.2 Hz, 1H), 7.92 (dd, J = 2.4, 8.8 Hz, 1H), 6.6 (s, 2H), 6.52 (d, J = 9.2 Hz, 1H), 3.64-3.62 (m, 1H), 2.92-2.82 (m, 4H), 2.51-2.50 (m, 1H), 2.28-1.90 (m, 2H), 1.19 (d, J = 6.8 Hz, 3H). | 413; rt 0.859. LC/MS Method | 3 |
| 108 | (S)-2-((R)-3-(6-amino-5-oxo-4,5-dihydropyrazin-2-yl)-4,4-difluoropiperidin-1-yl)-N-(5-(4-fluorophenoxy)pyridin-2-yl)propanamide | 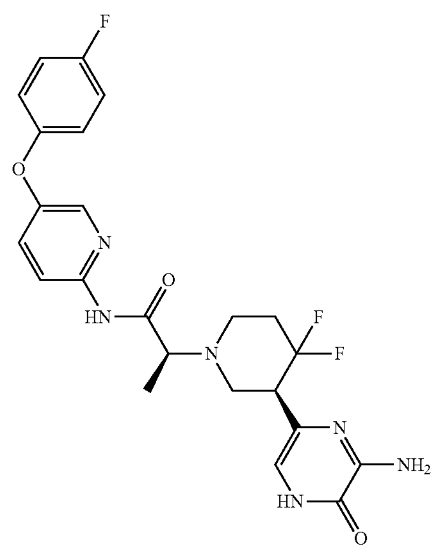 [SMILES: C[C@@H](C(=O)Nc1ccc(Oc2ccc(F)cc2)cn1)N1CCC(F)(F)[C@@H](c2c[nH]c(=O)c(N)n2)C1] | ¹H NMR: (400 MHz, CDCl₃) δ ppm 10.59 (br s, 1H), 10.03-10.23 (m, 1H), 8.31 (br d, J = 8.8 Hz, 1H), 8.04 (d, J = 2.4 Hz, 2H), 7.38 (dd, J = 9.0, 2.7 Hz, 1H), 6.80-7.22 (m, 5H), 6.63 (s, 1H), 3.31-3.44 (m, 1H), 2.98 (br d, J = 7.8 Hz, 1H), 2.77 (br s, 2H), 2.44-2.58 (m, 1H), 2.01-2.15 (m, 1H), 1.62 (br s, 2H), 1.36 (br d, J = 6.8 Hz, 3H). | 489; rt 0.69. LC/MS Method 5 | 70 |

Example 109

4-((S)-1-((S)-1-((6-(cyclopropylmethoxy)pyridazin-3-yl)amino)-1-oxopropan-2-yl)-4,4-difluoropiperidin-3-yl)pyridine 1-oxide

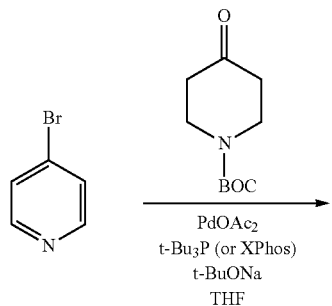

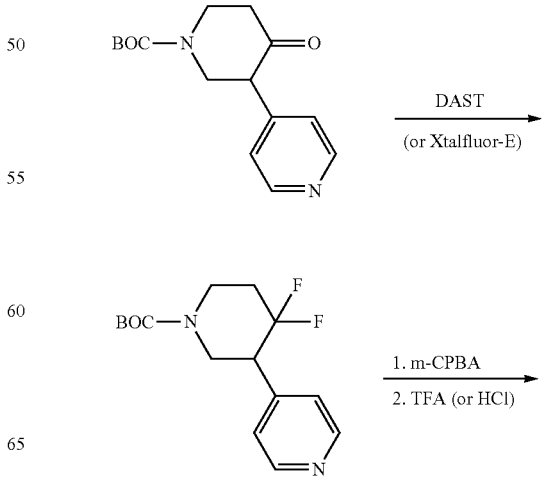

235

-continued

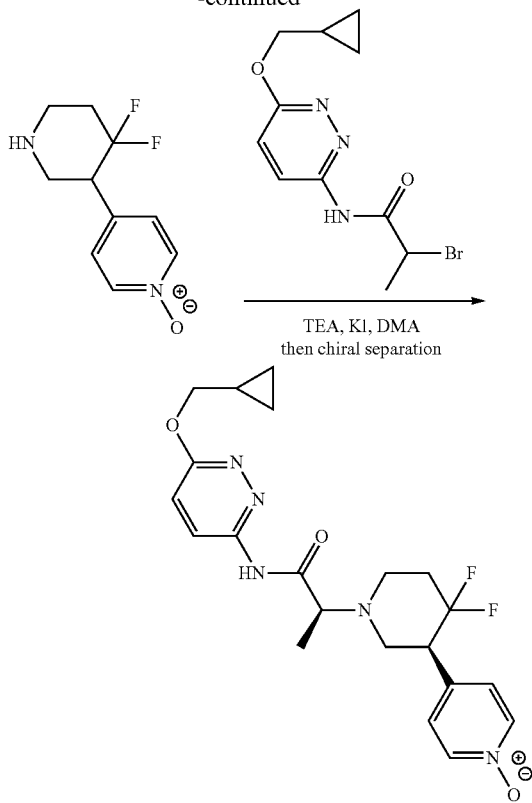

Step 1 t-BuONa (61.10 g, 635.7 mmol, 2.5 eq) in THF (600 mL) was stirred for 10 min, followed by addition of Pd(OAc)$_2$ (5.74 g, 25.64 mmol, 0.1 eq) and (t-Bu)$_3$P (51.79 g, 25.64 mmol, 0.1 equiv, 10% in hexane). After 5 min, 4-bromopyridine (40.00 g, 256.41 mmol, 1.0 eq) and tert-butyl 4-oxopiperidine-1-carboxylate (76.54 g, 384.62 mmol, 1.5 eq) were added, and the resulting mixture was stirred at 43° C. After 16 h, the reaction was dissolved in methanol (500 mL), treated with silica (100-200 mesh, 200 g), concentrated and loaded onto a silica gel column (100-200 mesh, 330+330 g), eluting with ethyl acetate in petroleum ether (0-85%) to give 21.0 g (yield: 30%, purity: 72%) of tert-butyl 4-oxo-3-(pyridin-4-yl)piperidine-1-carboxylate as a yellow oil. LCMS: (ES, m/s) 277 [M+H]+, retention time 0.957 min, LCMS Method 34. $^1$H NMR: (300 MHz, CDCl$_3$) δ ppm 8.60 (d, J=6.0 Hz, 2H), 7.15 (d, J=5.7 Hz, 2H), 4.39-4.17 (m, 2H), 3.76-3.68 (m, 1H), 3.62-3.46 (m, 2H), 2.65-2.40 (m, 2H), 1.52 (s, 9H).

Step 2

To tert-butyl 4-oxo-3-(pyridin-4-yl)piperidine-1-carboxylate (5.00 g, 18.05 mmol 1.0 eq) in DCM (400 ml) at 0° C. was added DAST (5.83 g, 36.10 mmol, 2.0 eq), dropwise. The resulting mixture was stirred at 25° C. for 16 h, quenched with ice water (500 mL) and extracted with DCM (100 mL×3). The combined organic phases were washed with brine (1 L), dried over Na$_2$SO$_4$ and concentrated. The crude product was dissolved in methanol (32 mL) and purified by prep HPLC (column: C18 cirregular 40-60 um 60 A 330 g), eluting with 5-70% AcCN in water (0.1% formic acid) to give 900 mg (yield: 17%, purity: 91%) of tert-butyl 4,4-difluoro-3-(pyridin-4-yl)piperidine-1-carboxylate as yellow oil. LCMS: (ES, m/s) 299 [M+H]$^+$, retention time 1.232, LCMS Method 35. $^1$H NMR: (300 MHz, CDCl$_3$) δ ppm 8.62 (d, J=2.0 Hz, 2H), 7.30 (d, J=3.2 Hz, 2H), 4.42-4.15 (m, 2H), 3.49-3.07 (m, 3H), 2.24-1.95 (m, 2H), 1.50 (s, 9H).

Step 3 To tert-butyl 4,4-difluoro-3-(pyridin-4-yl)piperidine-1-carboxylate (900 mg, 3.02 mmol, 1.0 eq) in DCM (20 ml) at 0° C. was added m-CPBA (1.04 g, 6.03 mmol, 2.0 eq). The resulting mixture was stirred for 2 h, quenched with Na$_2$S$_2$O$_3$ (100 mL, aq., sat.) and extracted with DCM (100 mL×3). The organic layers were washed with brine (200 mL), dried over sodium sulfate and concentrated. The crude product was dissolved in MeOH (4 mL) and purified by prep HPLC (column: C$_{18}$ spherical 20-35 um 100 A 120 g), eluting with 5-50% AcCN in water (10 mM NH$_4$HCO$_3$) to give 550 mg (yield: 58.0%, purity: 100%) of 4-(1-(tert-butoxycarbonyl)-4,4-difluoropiperidin-3-yl)pyridine 1-oxide as a yellow oil. LCMS (ES, m/s): 315 [M+H]+, retention time 1.156 min, LCMS Method 10. $^1$H NMR: (300 MHz, CDCl$_3$) δ ppm 8.20 (d, J=6.9 Hz, 2H), 7.23 (d, J=9.6 Hz, 2H), 4.23-4.21 (m, 2H), 3.23-3.02 (m, 3H), 2.23-2.15 (m, 1H), 1.97-1.92 (m, 1H), 1.49 (s, 9H).

Step 4

To 4-(1-(tert-butoxycarbonyl)-4,4-difluoropiperidin-3-yl)pyridine 1-oxide (550 mg, 1.75 mmol, 1.0 eq) in dichloromethane (25 mL) was added TFA (5 mL). After 14 h, the mixture was concentrated to give 520 mg (yield: 86%, purity: 92%) of 4-(4,4-difluoropiperidin-3-yl)pyridine 1-oxide, TFA salt, as a light yellow oil which was used without purification. In some cases this material was used as a racemic mixture, and in other cases was first separated via chiral chromatography to a single enantiomer (see Example 133, Step 4).

LCMS (ES, m/s): 215 [M+H]$^+$, retention time 0.396 min, LCMS Method 36. $^1$H NMR: (300 MHz, CD$_3$OD-d4) 8 ppm 8.33 (d, J=6.9 Hz, 2H), 7.58 (d, J=6.9 Hz, 2H), 4.31-4.18 (m, 2H), 3.47-3.17 (m, 3H), 2.25-2.10 (m, 2H).

Step 5

A mixture of 4-(4,4-difluoropiperidin-3-yl)pyridine 1-oxide, TFA salt (520 mg, 1.58 mmol, 1.0 eq), 2-bromo-N-(6-(cyclopropylmethoxy)pyridazin-3-yl)propanamide (Intermediate 14) (476 mg, 1.58 mmol, 1.0 eq), KI (263 mg, 1.58 mmol, 1.0 eq) and TEA (160 mg, 15.84 mmol, 10.0 eq) in N,N-dimethylacetamide (5 mL) was stirred 2 h at 60° C., quenched with ice water (100 mL) and extracted with DCM (100 mL×4). The combined organic phases were dried over sodium sulfate and concentrated. The product was chirally separated (XBridge Shield RP18 OBD Column, 30×150 mm, 5 um; Mobile Phase A: water [10 mmol/L NH$_4$HCO$_3$+ 0.1% NH$_3$.H$_2$O], Mobile Phase B: ACN; Flow rate: 60 mL/min; 18-40% B in A over 10 min) to give products with retention times of 8.57 and 9.07 minutes.

The product from the second peak (9.07 min) was chirally separated again (Chiralpak IF, 2×25 cm, 5 um; Mobile Phase A: MTBE [8 mM NH$_3$.MeOH], Mobile Phase B: EtOH; Flow rate: 11 mL/min; 1:1 A:B over 20 min), resulting in two peaks with retention times of 13.564 and 16.488 minutes. The first peak (13.564 min) was collected to give 23.5 mg (yield: 3.36%, purity: 98.1%, ee: 100%) 4-((S)-1-((S)-1-((6-(cyclopropylmethoxy)pyridazin-3-yl)amino)-1-oxopropan-2-yl)-4,4-difluoropiperidin-3-yl)pyridine 1-oxide as yellow solid. LCMS (ES, m/s): 434 [M+H]+ $^1$H NMR: (400 MHz, CDCl$_3$) δ 10.55 (br, 1H), 8.62-8.51 (m, 1H), 8.14-8.10 (m, 2H), 7.38-7.32 (m, 2H), 7.23-7.15 (m, 1H), 4.31-4.29 (m, 2H), 3.69-3.55 (m, 2H), 3.03-2.96 (m, 4H), 2.39-2.26 (m, 2H), 1.41-1.32 (m, 4H), 0.68-0.64 (m, 2H), 0.41-0.36 (m, 2H).

Examples 110-132 were synthesized in an analogous manner using the designated Intermediate in Step 5.

| Ex | Name | Structure | ¹H NMR | LC/MS: (M + H)⁺; retention time (min); LC/MS Method of analysis | Int |
|---|---|---|---|---|---|
| 110 | 4-(4,4-difluoro-1-(1-oxo-1-((5-phenoxypyridin-2-yl)piperidin-3-yl)pyridine 1-oxide | 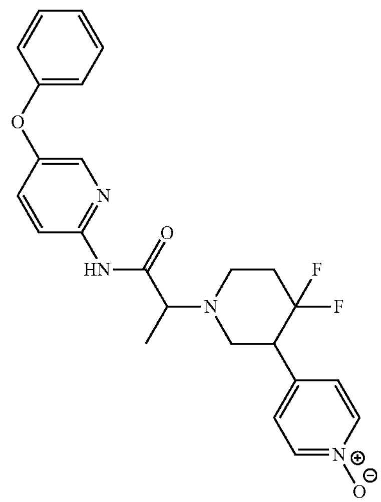 [SMILES: CC(C(=O)Nc1ccc(Oc2ccccc2)cn1)N1CCC(F)(F)C(c2cc[n+]([O-])cc2)C1] | ¹H NMR: (400 MHz, CD₃OD) δ ppm 8.34 (dd, J = 2.4, 6.8 Hz, 2H), 8.14-8.08 (m, 2H), 7.60 (d, J = 6.4 Hz, 2H), 7.50-7.46 (m, 1H), 7.41-7.36 (m, 2H), 7.18-7.16 (m, 1H), 7.03-7.01 (m, 2H), 3.92-3.72 (m, 2H), 3.46-3.42 (m, 3H), 3.26-3.06 (m, 1H), 2.51-2.35 (m, 2H), 1.54 (d, J = 6.8 Hz, 3H). | 455; rt 2.716 and 2.775. LC/MS Method 23 | 72 |
| 111 | 4-((S)-1-((S)-1-((5-(cyclopropyl methoxy)pyridin-2-yl)amino)-1-oxopropan-2-yl)-4,4-difluoropiperidin-3-yl)pyridine 1-oxide | 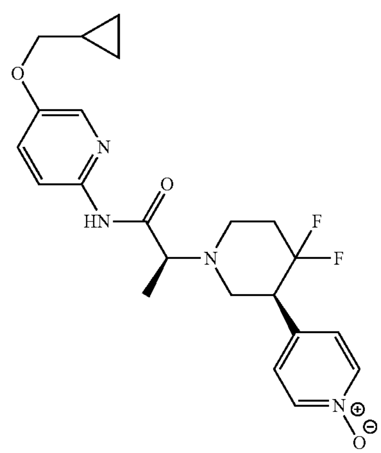 [SMILES: C[C@@H](C(=O)Nc1ccc(OCC2CC2)cn1)N1CCC(F)(F)[C@@H](c2cc[n+]([O-])cc2)C1] | ¹H NMR: (400 MHz, CD₃OD) δ ppm 8.30 (d, J = 6.8 Hz, 2H), 8.05 (d, J = 8.8 Hz, 1H), 8.00-7.98 (m, 1H), 7.60-7.58 (m, 2H), 7.43-7.40 (m, 1H), 3.89-3.88 (m, 2H), 3.72-3.54 (m, 2H), 3.08-3.05 (m, 2H), 2.96-2.93 (m, 1H), 2.68-2.67 (m, 1H), 2.26-2.20 (m, 2H), 1.35 (d, J = 6.8 Hz, 3H), 1.27-1.24 (m, 1H), 0.64-0.58 (m, 2H), 0.38-0.32 (m, 2H). | 433; rt 0.966. LC/MS Method 19 | 22 |
| 112 | 4-((S)-1-((S)-1-((5-chloropyridin-2-yl)amino)-1-oxopropan-2-yl)-4,4-difluoropiperidin-3-yl)pyridine 1-oxide | 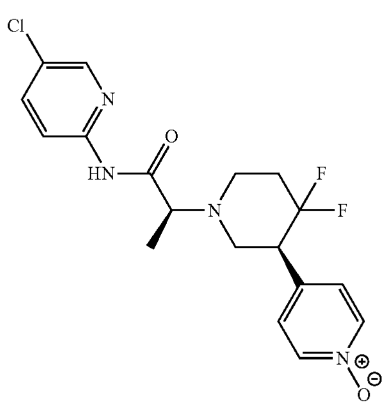 [SMILES: C[C@@H](C(=O)Nc1ccc(Cl)cn1)N1CCC(F)(F)[C@@H](c2cc[n+]([O-])cc2)C1] | ¹H NMR: (400 MHz, CDCl₃) δ ppm 9.58 (br, 1H), 8.26-8.13 (m, 4H), 7.70 (dd, J = 2.7, 9 Hz, 1H), 7.26-7.23 (m, 2H), 3.50-3.38 (m, 2H), 3.08-2.91 (m, 3H), 2.72-2.64 (m, 1H), 2.31-2.17 (m, 2H), 1.40 (d, J = 6.9 Hz, 3H). | 397; rt 1.387. LC/MS Method 27 | 3 |

| Ex | Name | Structure | ¹H NMR | LC/MS: (M + H)⁺; retention time (min); LC/MS Method of analysis | Int |
|---|---|---|---|---|---|
| 113 | 4-((S)-4,4-difluoro-1-((S)-1-((5-fluoropyridin-2-yl)amino)-1-oxopropan-2-yl)piperidin-3-yl)pyridine 1-oxide | 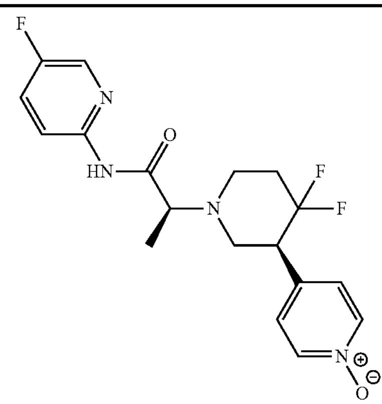 | ¹H NMR: (400 MHz, CD₃OD) δ ppm 8.30-8.26 (m, 2H), 8.22-8.18 (m, 2H), 7.65-7.59 (m, 3H), 3.71-3.56 (m, 2H), 3.13-3.03 (m, 2H), 2.95-2.66 (m, 2H), 2.34-2.22 (m, 2H), 1.35 (d, J = 7.2 Hz, 3H) | 381; rt 0.825. LC/MS Method 19 | 1 |
| 114 | 4-((S)-4,4-difluoro-1-((S)-1-((5-(4-fluorophenoxy)pyridin-2-yl)amino)-1-oxopropan-2-yl)piperidin-3-yl)pyridine 1-oxide | 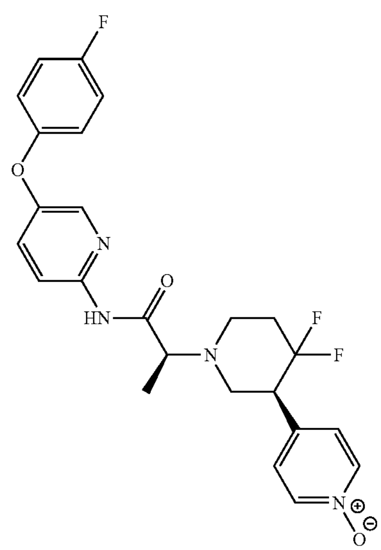 [SMILES: C[C@@H](C(=O)Nc1ccc(Oc2ccc(F)cc2)cn1)N1CCC(F)(F)[C@@H](c2cc[n+]([O-])cc2)C1] | ¹H NMR: (400 MHz, CDCl₃) δ ppm 9.38-9.93 (m, 1H), 8.27 (d, J = 9.05 Hz, 1H), 8.21 (d, J = 7.09 Hz, 2H), 8.08 (d, J = 2.20 Hz, 1H), 7.40 (dd, J = 9.05, 2.93 Hz, 1H), 7.26-7.31 (m, 2H), 7.03-7.14 (m, 2H), 6.89-7.03 (m, 2H), 3.49 (d, J = 6.36 Hz, 2H), 2.81-3.12 (m, 3H), 2.69 (br. s., 1H), 2.13-2.40 (m, 2H), 1.42 (d, J = 6.85 Hz, 3H). | 473; rt 0.97. LC/MS Method 3 | 70 |
| 115 | 4-((S)-4,4-difluoro-1-((S)-(1-((5-((5-fluoropyridin-2-yl)oxy)pyridin-2-yl)amino)-1-oxopropan-2-yl)piperidin-3-yl)pyridine 1-oxide | 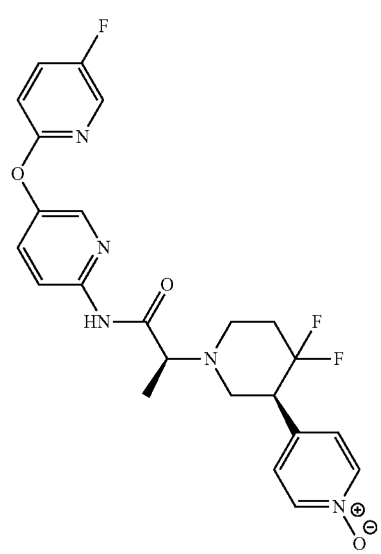 [SMILES: C[C@@H](C(=O)Nc1ccc(Oc2ccc(F)cn2)cn1)N1CCC(F)(F)[C@@H](c2cc[n+]([O-])cc2)C1] | ¹H NMR (400 MHz, CDCl₃) δ ppm 9.62 (br. s., 1H), 8.34 (d, J = 9.05 Hz, 1H), 8.17-8.24 (m, 3H), 7.99 (d, J = 2.93 Hz, 1H), 7.58 (dd, J = 9.05, 2.69 Hz, 1H), 7.51 (ddd, J = 8.99, 7.27, 3.06 Hz, 1H), 7.25-7.33 (m, 2H), 7.01 (dd, J = 8.93, 3.55 Hz, 1H), 3.38-3.60 (m, 2H), 2.86-3.09 (m, 3H), 2.67 (t, J = 11.13 Hz, 1H), 2.19-2.36 (m, 2H), 1.42 (d, J = 6.85 Hz, 3H). | 474; rt 0.85. LC/MS Method 3 | 100 |

| Ex | Name | Structure | ¹H NMR | LC/MS: (M + H)⁺; retention time (min); LC/MS Method of analysis | Int |
|---|---|---|---|---|---|
| 116 | 4-((S)-1-((S)-(1-((5-((3,5-difluoropyridin-2-yl)oxy)pyridin-2-yl)amino)-1-oxopropan-2-yl)-4,4-difluoropiperidin-3-yl)pyridine 1-oxide | 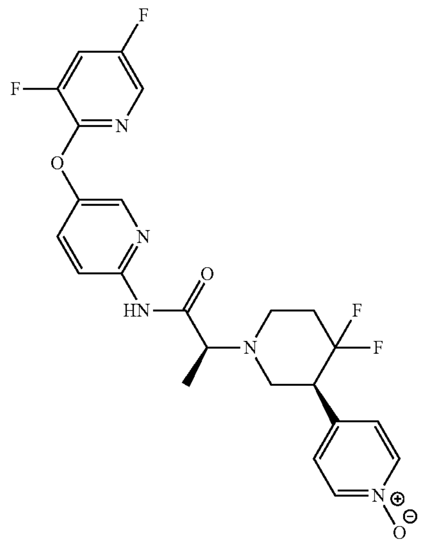 [SMILES: C[C@@H](C(=O)Nc1ccc(Oc2ncc(F)cc2F)cn1)N1CCC(F)(F)[C@@H](c2cc[n+]([O-])cc2)C1] | ¹H NMR (400 MHz, MeOH-d₄) δ ppm 8.30 (d, J = 7.09 Hz, 2H), 8.18-8.26 (m, 2H), 7.86 (d, J = 2.45 Hz, 1H), 7.74 (ddd, J = 9.84, 7.64, 2.57 Hz, 1H), 7.67 (dd, J = 9.05, 2.69 Hz, 1H), 7.60 (d, J = 6.85 Hz, 2H), 3.51-3.76 (m, 2H), 3.09 (d, J = 8.56 Hz, 2H), 2.96 (d, J = 11.74 Hz, 1H), 2.62-2.69 (m, 1H), 2.13-2.36 (m, 2H), 1.37 (d, J = 6.85 Hz, 3H). | 492; rt 0.90. LC/MS Method 3 | 99 |
| 117 | 4-((S)-1-((S)-1-((5-(2,4-difluorophenoxy)pyridin-2-yl)amino)-1-oxopropan-2-yl)-4,4-difluoropiperidin-3-yl)pyridine 1-oxide | 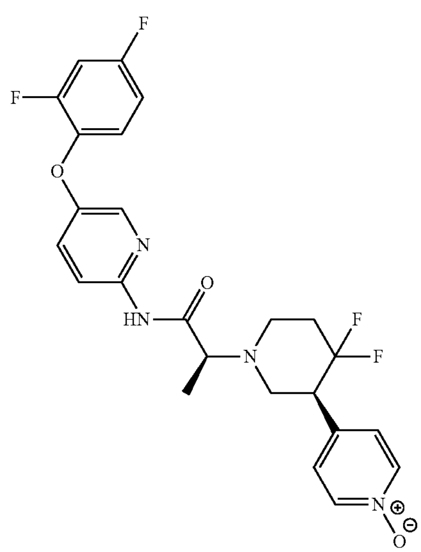 [SMILES: C[C@@H](C(=O)Nc1ccc(Oc2ccc(F)cc2F)cn1)N1CCC(F)(F)[C@@H](c2cc[n+]([O-])cc2)C1] | ¹H NMR (400 MHz, CDCl₃) δ ppm 9.51 (br. s., 1H), 8.18-8.27 (m, 3H), 8.08 (d, J = 2.93 Hz, 1H), 7.32 (dd, J = 9.05, 2.93 Hz, 1H), 7.27 (s, 2H), 7.10 (td, J = 8.93, 5.38 Hz, 1H), 7.00 (ddd, J = 10.70, 8.13, 2.93 Hz, 1H), 6.86-6.94 (m, 1H), 3.35-3.51 (m, 2H), 3.01 (d, J = 8.80 Hz, 2H), 2.92 (d, J = 11.25 Hz, 1H), 2.67 (t, J = 11.74 Hz, 1H), 2.11-2.34 (m, 2H), 1.41 (d, J = 7.09 Hz, 3H). | 491; rt 0.98. LC/MS Method 3 | 71 |

| Ex | Name | Structure | ¹H NMR | LC/MS: (M + H)⁺; retention time (min); LC/MS Method of analysis | Int |
|---|---|---|---|---|---|
| 118 | 4-((S)-4,4-difluoro-1-((S)-1-((5-(4-fluorophenoxy)pyrazin-2-yl)amino)-1-oxopropan-2-yl)piperidin-3-yl)pyridine 1-oxide | 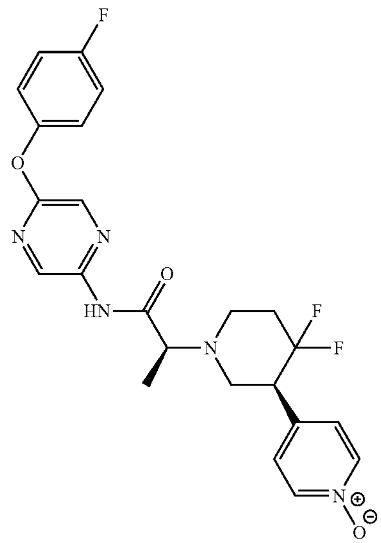 | ¹H NMR (400 MHz, CDCl₃) δ ppm 9.44 (s, 1H), 9.09 (d, J = 1.22 Hz, 1H), 8.21 (d, J = 7.34 Hz, 2H), 8.13 (d, J = 1.47 Hz, 1H), 7.27 (s, 2H), 7.10-7.16 (m, 4H), 3.50 (q, J = 6.85 Hz, 1H), 3.38 (s, 1H), 2.96-3.07 (m, 2H), 2.90 (d, J = 11.74 Hz, 1H), 2.62-2.74 (m, 1H), 2.12-2.40 (m, 2H), 1.41 (d, J = 7.09 Hz, 3H). | 474; rt 0.92. LC/MS Method 3 | 58 |
| 119 | 4-((S)-4,4-difluoro-1-((S)-1-oxo-1-((5-(2,4,6-trifluorophenoxy)pyrazin-2-yl)amino)propan-2-yl)piperidin-3-yl)pyridine 1-oxide | 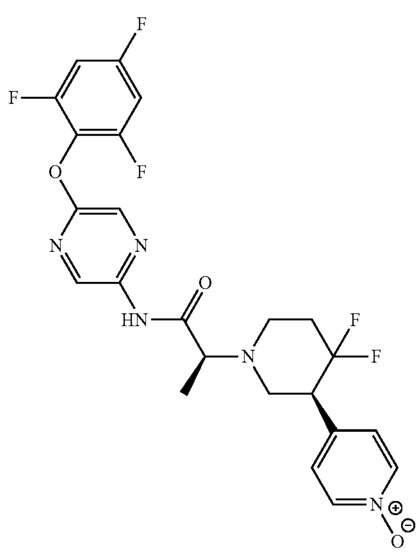 [SMILES: C[C@@H](C(=O)Nc1cnc(Oc2c(F)cc(F)cc2F)cn1)N1CCC(F)(F)[C@@H](c2cc[n+]([O-])cc2)C1] | ¹H NMR (400 MHz, METHANOL-d₄) δ ppm 8.88 (d, J = 1.47 Hz, 1H), 8.39 (d, J = 1.47 Hz, 1H), 8.29-8.35 (m, 2H), 7.62 (d, J = 6.85 Hz, 2H), 7.02-7.13 (m, 2H), 3.61-3.70 (m, 2H), 3.04-3.17 (m, 2H), 2.94-3.02 (m, 1H), 2.64-2.77 (m, 1H), 2.15-2.35 (m, 2H), 1.37 (d, J = 6.85 Hz, 3H). | 510; rt 0.98. LC/MS Method 3 | 63 |

-continued

| Ex | Name | Structure | ¹H NMR | LC/MS: (M + H)⁺; retention time (min); LC/MS Method of analysis | Int |
|---|---|---|---|---|---|
| 120 | 4-((S)-4,4-difluoro-1-((S)-1-oxo-1-((5-(2,4,5-trifluorophenoxy)pyrazin-2-yl)amino)propan-2-yl)piperidin-3-yl)pyridine 1-oxide | 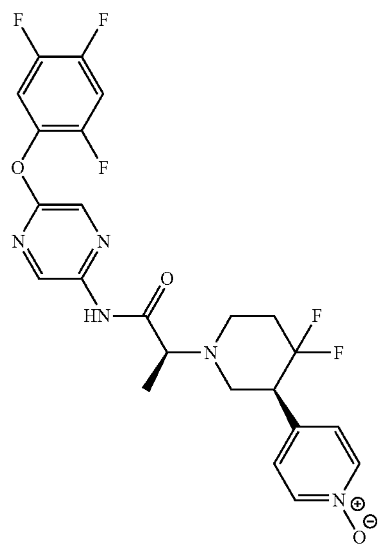 [SMILES: C[C@@H](C(=O)Nc1cnc(Oc2cc(F)c(F)cc2F)cn1)N1CCC(F)(F)[C@@H](c2cc[n+]([O-])cc2)C1] | ¹H NMR (400 MHz, METHANOL-d₄) δ ppm 8.90 (d, J = 0.98 Hz, 1H), 8.29-8.35 (m, 3H), 7.62 (d, J = 7.34 Hz, 2H), 7.33-7.46 (m, 2H), 3.59-3.69 (m, 2H), 3.03-3.18 (m, 2H), 2.94-3.02 (m, 1H), 2.66-2.78 (m, 1H), 2.16-2.34 (m, 2H), 1.37 (d, J = 6.85 Hz, 3H). | 510; rt 0.97. LC/MS Method 3 | 64 |
| 121 | 4-((S)-1-((S)-1-((5-(2,6-difluorophenoxy)pyrazin-2-yl)amino)-1-oxopropan-2-yl)-4,4-difluoropiperidin-3-yl)pyridine 1-oxide | 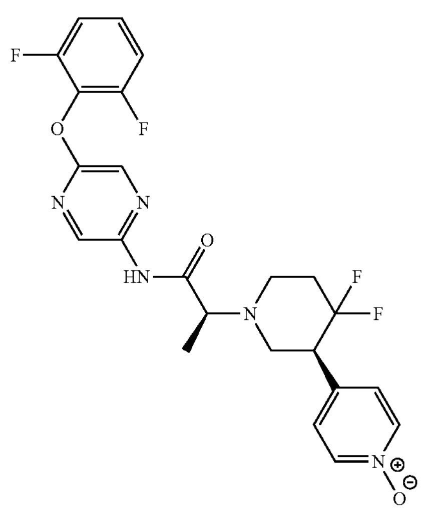 [SMILES: C[C@@H](C(=O)Nc1cnc(Oc2c(F)cccc2F)cn1)N1CCC(F)(F)[C@@H](c2cc[n+]([O-])cc2)C1] | ¹H NMR (400 MHz, METHANOL-d₄) δ ppm 8.88 (d, J = 1.47 Hz, 1H), 8.38 (d, J = 0.98 Hz, 1H), 8.30-8.35 (m, 2H), 7.62 (d, J = 6.85 Hz, 2H), 7.27-7.38 (m, 1H), 7.08-7.20 (m, 2H), 3.59-3.70 (m, 2H), 3.06-3.15 (m, 2H), 2.95-3.03 (m, 1H), 2.67-2.78 (m, 1H), 2.17-2.35 (m, 2H), 1.37 (d, J = 6.85 Hz, 3H). | 492; rt 0.95. LC/MS Method 3 | 61 |

| Ex | Name | Structure | ¹H NMR | LC/MS: (M + H)⁺; retention time (min); LC/MS Method of analysis | Int |
|---|---|---|---|---|---|
| 122 | 4-((S)-4,4-difluoro-1-((S)-1-oxo-1-((5-(2,3,4-trifluorophenoxy)pyrazin-2-yl)amino)propan-2-yl)piperidin-3-yl)pyridine 1-oxide | 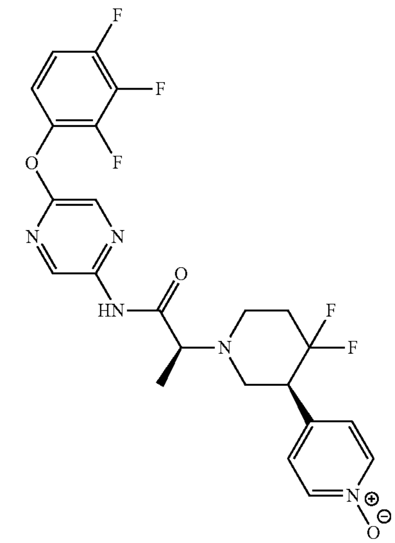 [SMILES: C[C@@H](C(=O)Nc1cnc(Oc2ccc(F)c(F)c2F)cn1)N1CCC(F)(F)[C@@H](c2cc[n+]([O-])cc2)C1] | ¹H NMR (400 MHz, METHANOL-d₄) δ ppm 8.90 (d, J = 1.47 Hz, 1H), 8.29-8.38 (m, 3H), 7.62 (d, J = 6.85 Hz, 2H), 7.12-7.27 (m, 2H), 3.57-3.70 (m, 2H), 3.06-3.14 (m, 2H), 2.93-3.03 (m, 1H), 2.67-2.78 (m, 1H), 2.16-2.34 (m, 2H), 1.37 (d, J = 6.85 Hz, 3H). | 510; rt 1.00. LC/MS Method 3 | 62 |
| 123 | 4-((S)-4,4-difluoro-1-((S)-1-oxo-1-((5-(2,4,6-trifluorophenoxy)pyridin-2-yl)amino)propan-2-yl)piperidin-3-yl)pyridine 1-oxide | 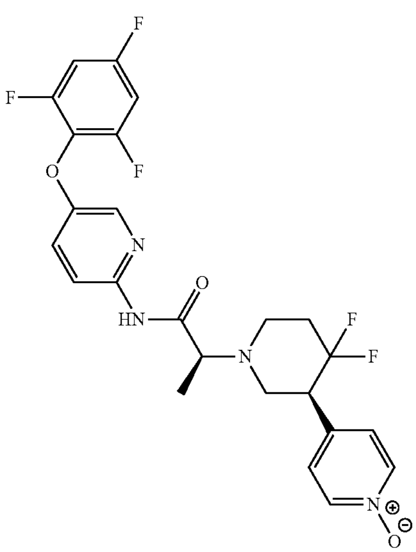 [SMILES: C[C@@H](C(=O)Nc1ccc(Oc2c(F)cc(F)cc2F)cn1)N1CCC(F)(F)[C@@H](c2cc[n+]([O-])cc2)C1] | ¹H NMR (400 MHz, METHANOL-d₄) δ ppm 8.32 (d, J = 7.34 Hz, 2H), 8.16 (d, J = 9.29 Hz, 1H), 8.12 (d, J = 2.93 Hz, 1H), 7.62 (d, J = 6.85 Hz, 2H), 7.44 (dd, J = 9.05, 3.18 Hz, 1H), 7.06-7.17 (m, 2H), 3.55-3.74 (m, 2H), 3.06-3.14 (m, 2H), 2.90-3.01 (m, 1H), 2.70 (td, J = 11.62, 3.67 Hz, 1H), 2.19-2.42 (m, 2H), 1.37 (d, J = 6.85 Hz, 3H). | 509; rt 1.00. LC/MS Method 3 | 77 |

| Ex | Name | Structure | $^1$H NMR | LC/MS: (M + H)$^+$; retention time (min); LC/MS Method of analysis | Int |
|---|---|---|---|---|---|
| 124 | 4-((S)-4,4-difluoro-1-((S)-1-oxo-1-((5-(2,4,5-trifluorophenoxy)pyridin-2-yl)amino)propan-2-yl)piperidin-3-yl)pyridine 1-oxide | 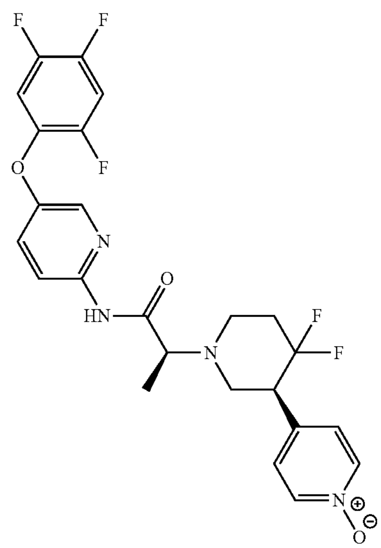 [SMILES: C[C@@H](C(=O)Nc1ccc(Oc2cc(F)c(F)cc2F)cn1)N1CCC(F)(F)[C@@H](c2cc[n+]([O-])cc2)C1] | $^1$H NMR (400 MHz, METHANOL-d$_4$) δ ppm 8.32 (d, J = 7.34 Hz, 2H), 8.20 (d, J = 9.29 Hz, 1H), 8.14 (d, J = 2.45 Hz, 1H), 7.62 (d, J = 6.85 Hz, 2H), 7.50 (dd, J = 9.29, 2.93 Hz, 1H), 7.42 (td, J = 10.27, 7.34 Hz, 1H), 7.26 (dt, J = 10.76, 7.58 Hz, 1H), 3.57-3.73 (m, 2H), 3.06-3.13 (m, 2H), 2.93-3.01 (m, 1H), 2.71 (td, J = 11.49, 3.42 Hz, 1H), 2.21-2.38 (m, 2H), 1.38 (d, J = 6.85 Hz, 3H). | 509; rt 1.00. LC/MS Method 3 | 78 |
| 125 | 4-((S)-4,4-difluoro-1-((S)-1-((5-((3-fluoropyridin-2-yl)oxy)pyridin-2-yl)amino)-1-oxopropan-2-yl)piperidin-3-yl)pyridine 1-oxide | 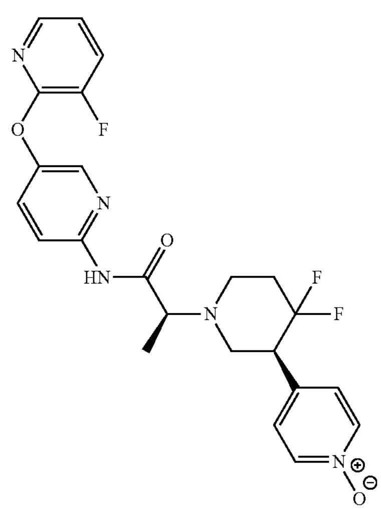 [SMILES: C[C@@H](C(=O)Nc1ccc(Oc2ncccc2F)cn1)N1CCC(F)(F)[C@@H](c2cc[n+]([O-])cc2)C1] | $^1$H NMR: (400 MHz, CHLOROFORM-d) δ ppm 9.55 (br. s., 1H), 8.34 (d, J = 8.80 Hz, 1H), 8.25 (d, J = 2.45 Hz, 1H), 8.20 (d, J = 7.34 Hz, 2H), 7.91 (dd, J = 4.89, 1.47 Hz, 1H), 7.62 (dd, J = 9.05, 2.69 Hz, 1H), 7.52 (ddd, J = 9.78, 8.07, 1.47 Hz, 1H), 7.27 (s, 2H), 7.05 (ddd, J = 7.89, 4.83, 3.18 Hz, 1H), 3.32-3.54 (m, 2H), 3.01 (d, J = 8.56 Hz, 2H), 2.94 (d, J = 11.49 Hz, 1H), 2.57-2.72 (m, 1H), 2.12-2.35 (m, 2H), 1.41 (d, J = 6.85 Hz, 3H). | 474; rt 0.86 LC/MS Method 3 | 98 |

| Ex | Name | Structure | ¹H NMR | LC/MS: (M + H)⁺; retention time (min); LC/MS Method of analysis | Int |
|---|---|---|---|---|---|
| 126 | 4-((S)-4,4-difluoro-1-((S)-1-oxo-1-((5-(pyridin-2-yloxy)pyridin-2-yl)amino)propan-2-yl)piperidin-3-yl)pyridine 1-oxide | 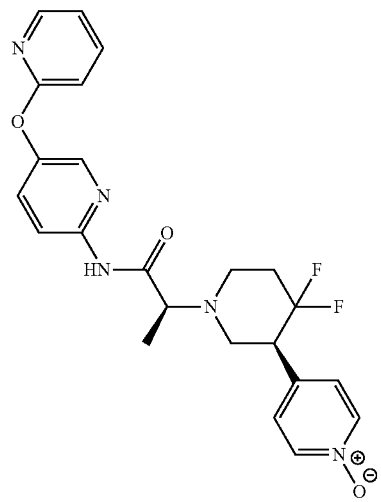 [SMILES: C[C@@H](C(=O)Nc1ccc(Oc2ccccn2)cn1)N1CCC(F)(F)[C@@H](c2cc[n+]([O-])cc2)C1] | ¹H NMR: NMR (400 MHz, CHLOROFORM-d) δ 9.64 (br. s., 1H), 8.34 (d, J = 9.05 Hz, 1H), 8.19-8.24 (m, 3H), 8.16 (dd, J = 4.89, 1.47 Hz, 1H), 7.71-7.80 (m, 1H), 7.60 (dd, J = 9.05, 2.69 Hz, 1H), 7.28 (t, J = 3.42 Hz, 2H), 7.05 (ddd, J = 6.60, 5.62, 0.73 Hz, 1H), 7.01 (d, J = 8.31 Hz, 1H), 3.31-3.63 (m, 2H), 2.89-3.12 (m, 3H), 2.60-2.75 (m, 1H), 2.16-2.37 (m, 2H), 1.42 (d, J = 6.85 Hz, 3H). | 456; rt 0.81 LC/MS Method 3 | 93 |
| 127 | 4-((S)-1-((S)-1-((5-(difluoro(4-fluorophenyl)methyl)pyridin-2-yl)amino)-1-oxopropan-2-yl)-4,4-difluoropiperidin-3-yl)pyridine 1-oxide | 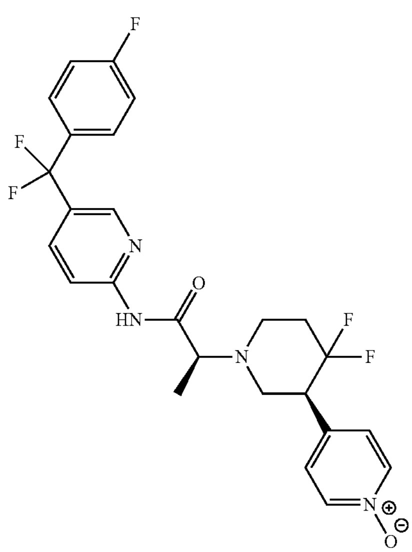 [SMILES: C[C@@H](C(=O)Nc1ccc(C(F)(F)c2ccc(F)cc2)cn1)N1CCC(F)(F)[C@@H](c2cc[n+]([O-])cc2)C1] | ¹H NMR: NMR (400 MHz, CHLOROFORM-d) δ 9.65 (br. s., 1H), 8.43 (s, 1H), 8.31 (d, J = 8.80 Hz, 1H), 8.20 (d, J = 7.09 Hz, 2H), 7.76-7.86 (m, 1H), 7.51 (dd, J = 8.44, 5.26 Hz, 2H), 7.26 (d, 1 H, overlapping with CDCL3), 7.15 (t, J = 8.44 Hz, 2H), 3.35-3.59 (m, 2H), 2.96-3.09 (m, 2H), 2.90 (d, J = 10.03 Hz, 1H), 2.62-2.74 (m, 1H), 2.11-2.36 (m, 2H), 1.42 (s, 3H). | 507; rt 1.06 LC/MS Method 3 | 104 |

| Ex | Name | Structure | ¹H NMR | LC/MS: (M + H)⁺; retention time (min); LC/MS Method of analysis | Int |
|---|---|---|---|---|---|
| 128 | 4-((S)-4,4-difluoro-1-((S)-1-((5-(4-fluorobenzoyl)pyridin-2-yl)amino)-1-oxopropan-2-yl)piperidin-3-yl)pyridine 1-oxide | 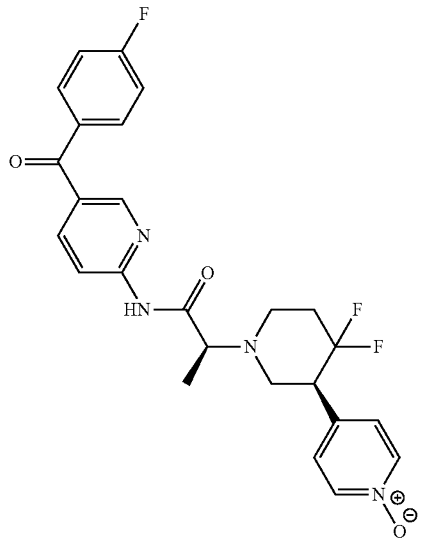 [SMILES: C[C@@H](C(=O)Nc1ccc(C(=O)c2ccc(F)cc2)cn1)N1CCC(F)(F)[C@@H](c2cc[n+]([O-])cc2)C1] | ¹H NMR: 400 MHz, CHLOROFORM-d δ 9.77-9.88 br. s, 1H), 8.75 (d, J = 1.96 Hz, 1H), 8.39 (d, J = 8.80 Hz, 1H), 8.22 (d, J = 7.34 Hz, 2H), 8.19 (dd, J = 8.80, 2.45 Hz, 1H), 7.83-7.90 (m, 2H), 7.30 (s, 2H), 7.23 (t, J = 8.56 Hz, 2H), 3.39-3.67 (m, 2H), 2.86-3.24 (m, 3H), 2.74 (br d, J = 10.76 Hz, 1H), 2.18-2.42 (m, 2H), 1.44 (d, J = 6.85 Hz, 3H). | 485; rt 0.94 LC/MS Method 3 | 105 |
| 129 | 4-((3S)-4,4-difluoro-1-(1-((5-((4-fluorophenyl)(hydroxy)methyl)pyridin-2-yl)amino)-1-oxopropan-2-yl)piperidin-3-yl)pyridine 1-oxide | 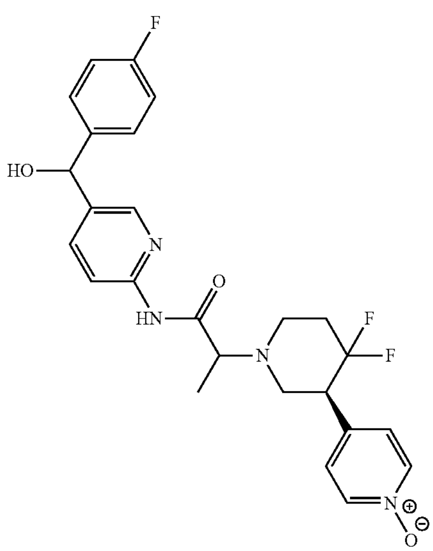 [SMILES: CC(C(=O)Nc1ccc(C(O)c2ccc(F)cc2)cn1)N1CCC(F)(F)[C@@H](c2cc[n+]([O-])cc2)C1] | ¹H NMR (400 MHz, CHLOROFORM-d) δ ppm 9.57 (br s, 1H), 8.10-8.34 (m, 4H), 7.66-7.75 (m, 1H), 7.35 (ddd, J = 8.68, 5.50, 2.93 Hz, 2H), 7.24 (dd, J = 6.11, 4.16 Hz, 2H), 6.99-7.10 (m, 2H), 3.46 (q, J = 6.85 Hz, 2H), 3.24 (br s, 1H), 2.98 (br d, J = 7.83 Hz, 3H), 2.61-2.81 (m, 1H), 2.28 (br dd, J = 8.56, 4.65 Hz, 2H), 1.38 (dd, J = 7.09, 1.22 Hz, 3H). | 487; rt 0.81, 0.83. LC/MS Method 3 | 106 |

| Ex | Name | Structure | ¹H NMR | LC/MS: (M + H)⁺; retention time (min); LC/MS Method of analysis | Int |
|---|---|---|---|---|---|
| 130 | 4-((S)-1-((S)-1-((5-(2,6-difluorophenoxy)pyridin-2-yl)amino)-1-oxopropan-2-yl)-4,4-difluoropiperidin-3-yl)pyridine 1-oxide | 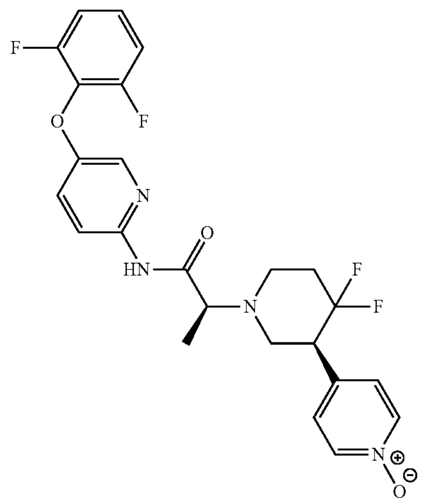 [SMILES: C[C@@H](C(=O)Nc1ccc(Oc2c(F)cccc2F)cn1)N1CCC(F)(F)[C@@H](c2cc[n+]([O-])cc2)C1] | ¹H NMR (400 MHz, METHANOL-d₄) δ 8.32 (d, J = 7.34 Hz, 2H), 8.16 (d, J = 9.29 Hz, 1H), 8.10 (d, J = 2.93 Hz, 1H), 7.62 (d, J = 6.85 Hz, 2H), 7.42 (dd, J = 9.05, 3.18 Hz, 1H), 7.29-7.38 (m, 1H), 7.13-7.23 (m, 2H), 3.56-3.73 (m, 2H), 3.09 (d, J = 8.80 Hz, 2H), 2.97 (br d, J = 11.74 Hz, 1H), 2.70 (td, J = 11.62, 3.67 Hz, 1H), 2.19-2.38 (m, 2H), 1.37 (d, J = 6.85 Hz, 3H). | 491; rt 0.97. LC/MS Method 3 | 81 |
| 131 | 4-((S)-4,4-difluoro-1-((S)-1-oxo-1-((5-(2,3,4-trifluorophenoxy)pyridin-2-yl)amino)propan-2-yl)piperidin-3-yl)pyridine 1-oxide | 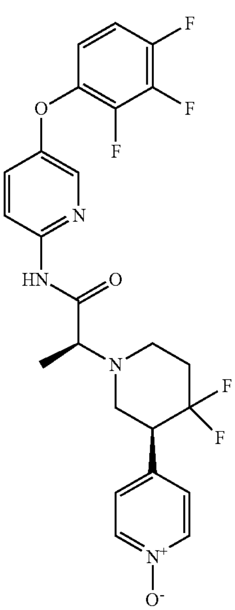 [SMILES: C[C@@H](C(=O)Nc1ccc(Oc2ccc(F)c(F)c2F)cn1)N1CCC(F)(F)[C@@H](c2cc[n+]([O-])cc2)C1] | ¹H NMR (400 MHz, METHANOL-d₄) δ 8.32 (d, J = 7.34 Hz, 2H), 8.20 (d, J = 9.29 Hz, 1H), 8.16 (d, J = 2.93 Hz, 1H), 7.62 (d, J = 6.85 Hz, 2H), 7.52 (dd, J = 8.80, 2.93 Hz, 1H), 7.13-7.23 (m, 1H), 7.01 (dddd, J = 9.41, 8.31, 4.77, 2.45 Hz, 1H), 3.57-3.74 (m, 2H), 3.06-3.13 (m, 2H), 2.97 (br d, J = 11.74 Hz, 1H), 2.71 (td, J = 11.49, 3.42 Hz, 1H), 2.21-2.37 (m, 2H), 1.38 (d, J = 6.85 Hz, 3H). | 509; rt 1.02. LC/MS Method 3 | 82 |

Example 132

4-((S)-1-((S)-1-((5-(2,4-difluorophenoxy)pyrazin-2-yl)amino)-1-oxopropan-2-yl)-4,4-difluoropiperidin-3-yl)pyridine 1-oxide

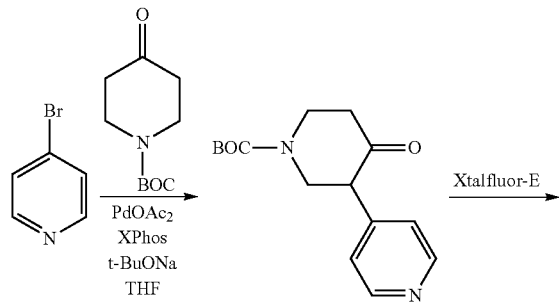

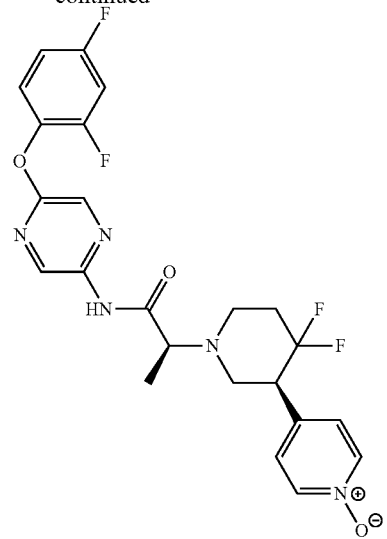

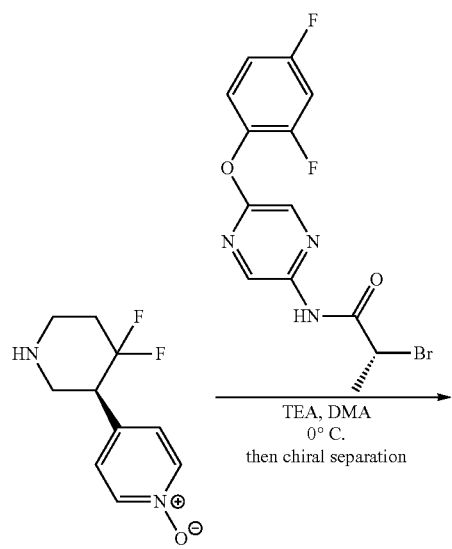

Step 1

To a mixture of sodium tert-butoxide (158.19 g, 1646 mmol) and THF (2 L) was added 4-bromopyridine hydrochloride (80.10 g, 412 mmol) and 2-Me-THF (100 mL). The vessel was evacuated and back-filled with nitrogen (3×), and an exotherm was observed, warming the reaction to about 33° C. After approximately 20 min, tert-butyl 4-oxopiperidine-1-carboxylate (111.40 g, 559 mmol) was added, along with 2-Me-THF (200 mL), and the vessel was evacuated and back-filled with nitrogen (3×). After about 10 minutes, XPhos (39.390 g, 83 mmol) and palladium(II) acetate (9.260 g, 41.2 mmol) were added, along with 2-Me-THF (100 mL), and the vessel was evacuated and back-filled with nitrogen (5×). An exotherm was observed, warming the reaction to 36.8° C. over 30 minutes. A heating mantle was employed to heat the mixture, with a target temperature of 48° C. The temperature rose to approximately 53° C., then stabilized back down to 48° C.

After about 7 h, the reaction was stirred at ambient temperature overnight, diluted with hexanes (1200 mL), cooled on an ice bath, and quenched with the portion-wise addition of saturated NH$_4$Cl (1200 mL), keeping the internal temperature below 20° C. The resulting solids were collected by filtration, and the aqueous and organic layers were separated. The aqueous layer was extracted with Et$_2$O (500 mL), and then with EtOAc (500 mL). The filtered solids were rinsed with Et$_2$O (50 mL), followed by DCM (2×50 mL), and these organic rinses were combined with the organic extracts. The organics were concentrated, diluted with EtOAc (250 mL), warmed to 50° C. and filtered while warm through Celite. The filter pad was rinsed with EtOAc (2×50 mL), and the filtrate was concentrated. The resulting residue was diluted with Et$_2$O (250 mL) and filtered through Celite. The resulting filtrate was stirred, and hexanes (500 mL) were added slowly. The resulting solids were broken up and vigorously stirred to make a suspension. The solids were collected by filtration and rinsed with 2:1 hexanes: Et$_2$O (2×100 mL) to give 90.69 g (328 mmol, 80% yield) tert-butyl 4-oxo-3-(pyridin-4-yl)piperidine-1-carboxylate as a yellow-tan solid. LCMS retention time=0.41 min, Method 2, (ES, m/s): 277.2 [M+H]+. $^1$H NMR (400 MHz, DMSO-d$_6$) δ 8.55-8.49 (m, 2H), 7.26-7.20 (m, 2H), 4.21-3.99 (m, 2H), 3.90 (dd, J=10.8, 5.9 Hz, 1H), 3.70-3.39 (m, 2H), 2.66-2.55 (m, 1H), 2.41 (dt, J=14.9, 4.3 Hz, 1H), 1.43 (br s, 9H).

Step 2

To triethylamine trihydrofluoride (131 g, 814 mmol, 3 eq) in DCM (1.8 L) was added XtalFluor-E (124 g, 543 mmol, 2 eq), slowly over 5 min. The reaction was cooled to about 0° C., and tert-butyl 4-oxo-3-(pyridin-4-yl)piperidine-1-carboxylate (75 g, 271 mmol) was added slowly over 5 min, keeping the temperature at approximately 5° C. After 3.5 h, the reaction was added to water (1.8 L) at 0° C. over 44 min, keeping the temperature in the 2.4-3.6° C. range. The reaction was stirred for approximately 5 min, the layers were separated and the water layer was washed with dichloromethane (300 mL). The combined organic layers were cooled to approximately 0° C. and quenched with saturated sodium bicarbonate (650 mL) over 12 min (reaction temperature stayed in the 3.8-9.1° C. range). After approximately 5 min, the organic layer was isolated, and water (600 mL), Celite 454 (120.44 g) and potassium permanganate (32.22 g, 204 mmol, 0.75 eq) were added. After 1 h, the mixture was cooled in an ice bath and quenched with sat'd sodium metabisulfite (4×100 mL portions, keeping temperature in the 8.9-15° C. range). The reaction was warmed to rt and filtered, washing the filter cake with dichloromethane. The organic layer was isolated, concentrated and purified via silica gel chromatography (330 g gold column), eluting with 0-32.8% (3:1 ethyl acetate: ethanol) in hexanes to yield partially pure product which was triturated with 1:1 ethyl acetate: hexanes to give 31.59 g (39% yield) tert-butyl 4,4-difluoro-3-(pyridin-4-yl)piperidine-1-carboxylate as a cream colored powder. LCMS retention time=0.60 min, Method 2, (ES, m/s): 299.1 [M+H]+. $^1$H NMR (400 MHz, DMSO-d6) δ 8.58-8.51 (m, 2H), 7.36 (d, J=5.4 Hz, 2H), 4.16-3.88 (m, 2H), 3.51-3.27 (m, 2H, water overlap), 3.19-2.98 (m, 1H), 2.22-2.10 (m, 1H), 2.10-1.90 (m, 1H), 1.41 (s, 9H).

Step 3

To tert-butyl 4,4-difluoro-3-(pyridin-4-yl)piperidine-1-carboxylate (24.395 g, 82 mmol) in acetone (400 mL) and water (400 mL) was added $K_2CO_3$ (22.661 g, 164 mmol), and the reaction was cooled in an ice bath. OXONE monopersulfate (37.778 g, 123 mmol) was added portion-wise over approximately 13 minutes (1 small scoop about every 15 seconds), and the temperature rose from 4.6° C. to 5.5° C. over 14 minutes, then decreased. After 2 h, additional OXONE monopersulfate (5.021 g, 16.33 mmol) was added over approximately 3 min, and no exotherm was detected. After an additional 2 h, the reaction was diluted with DCM (1 L), and saturated sodium metabisulfite (500 mL) was added over approximately 1 h 54 min, as the internal temperature rose form 3.8° C. to 8.3° C. After 15 minutes the mixture was transferred to a separatory funnel, and the organic layer was collected, leaving an aqueous layer and an emulsified layer. The emulsion layer was isolated and filtered, rinsing with DCM, and the filtrate was collected. The remaining aqueous layer was extracted with DCM (100 mL), and all the organic extracts and filtrate were combined, dried with $MgSO_4$, filtered over Celite and concentrated to give 26.43 g (84 mmol, quantitative yield) 4-(1-(tert-butoxycarbonyl)-4,4-difluoropiperidin-3-yl)pyridine 1-oxide as a cream-colored foamy solid. LCMS retention time=0.74 min, Method 3, (ES, m/s): 315.1 [M+H]+. $^1$H NMR (400 MHz, DMSO-d$_6$) δ 8.23-8.17 (m, 2H), 7.37 (d, J=6.8 Hz, 2H), 4.14-3.87 (m, 2H), 3.47-3.21 (m, 2H, water overlap), 3.15-2.96 (m, 1H), 2.22-2.12 (m, 1H), 2.07-1.87 (m, 1H), 1.41 (s, 9H).

Step 4

To 4-(1-(tert-butoxycarbonyl)-4,4-difluoropiperidin-3-yl) pyridine 1-oxide (20.5 g, 65.2 mmol) in ethyl acetate (350 mL) and methanol (35 mL) was added HCl (4.0 M in dioxane; 100 mL, 400 mmol) over 30 min. After 16 h, the reaction was concentrated and diluted with diethyl ether (200 mL). After 1 h, the resulting solid was collected by filtration and washed with additional diethyl ether (100 mL) to afford 4-(4,4-difluoropiperidin-3-yl)pyridine 1-oxide, hydrochloride salt (16.3 g, 95% yield). This racemic mixture was purified via chiral chromatography (Agilent 1260 autoprep, Column: Chiralpak IG, 30×250 mm, 5 micron; Mobile phase: 50:50 acetonitrile:methanol; Flow rate: 45 mL/min; 0.5 g sample mixture in 9 mL mobile phase with 0.5 mL $Et_3N$ added to neutralize HCl salt) to give two isomers with retention times of 4.3 and 6.4 min. Collection and concentration of the fractions corresponding to the earlier peak (rt=4.3 min) afforded (S)-4-(4,4-difluoropiperidin-3-yl)pyridine 1-oxide (5.8 g) as an oil (free base). LCMS retention time=0.35 min, Method 3, (ES, m/s): 215.2 [M+H]+. $^1$H NMR (400 MHz, DMSO-d$_6$) δ 8.28-8.06 (m, 2H), 7.34 (d, J=6.8 Hz, 2H), 3.25-3.00 (m, 3H), 2.94-2.81 (m, 1H), 2.69 (td, J=12.7, 2.9 Hz, 2H), 2.11-1.99 (m, 1H), 1.95-1.74 (m, 1H).

Step 5

To (S)-4-(4,4-difluoropiperidin-3-yl)pyridine 1-oxide (4.0 g, 18.67 mmol) and (R)-2-bromo-N-(5-(2,4-difluorophenoxy)pyrazin-2-yl)propanamide (Intermediate 65) (8.03 g, 22.41 mmol) mixed as solids in a vessel cooled to 0° C. was added DMA (16.98 ml). After a solution was formed, TEA (3.12 ml, 22.41 mmol) was added slowly, and the reaction was stirred at 0° C. After 48 h, the reaction was poured into ice (about 150 g), with some stirring. DCM (150 mL) was added with stirring, the layers were separated, and the organic layer was washed with sat'd $NH_4Cl$ (100 ml). The organic layer was dried over magnesium sulfate, filtered through Celite, concentrated and purified via silica gel column, eluting with 7-70% 3:1 EtOAc: (EtOH+2% $NH_4OH$) in heptane to afford a diastereomeric mixture (5.95 g). This material was further purified via Chiral column over a Chiralpak AD 20 u 100×250 mm, 80:20-$CH_3CN$:$CH_3OH$, 400 ml/min, ambient temp and in 300 ml mobile phase. Collected the only major peak to afford 4.1 g (8.18 mmol, 43.8% yield) 4-((S)-1-((S)-1-((5-(2,4-difluorophenoxy) pyrazin-2-yl)amino)-1-oxopropan-2-yl)-4,4-difluoropiperidin-3-yl)pyridine 1-oxide as a yellow glassy solid. LCMS retention time=0.95 min, Method 3, (ES, m/s): 492.3 [M+H]+. $^1$H NMR (400 MHz, DMSO-d$_6$) δ 10.57 (s, 1H), 8.81 (d, J=1.5 Hz, 1H), 8.46 (d, J=1.5 Hz, 1H), 8.22-8.11 (m, 2H), 7.56-7.44 (m, 2H), 7.39 (d, J=6.8 Hz, 2H), 7.23-7.10 (m, 1H), 3.71 (q, J=6.8 Hz, 1H), 3.58-3.45 (m, 1H), 3.05-2.96 (m, 1H), 2.95-2.84 (m, 2H), 2.56 (br d, J=2.9 Hz, 1H), 2.19-1.98 (m, 2H), 1.22 (d, J=6.8 Hz, 3H). Vibration circular dichroism (VCD): Inspection of VCD data in the analysis range indicated that the VCD spectrum for Model fs1ss is a good match with experimentally determined values. Therefore, the absolute configuration of the chiral centers in the sample were confirmed to both be (S). The confidence limit for this assignment was estimated to be >99% based on the current database that includes 88 previous correct assignments for different chiral structures. The IR spectrum of the sample was compared with the IR spectrum calculated for Model fs1ss. Again, the model spectrum is in good qualitative agreement with experimental results, confirming the overall structure of this sample (i.e., its molecular connectivity) and providing additional support for satisfactory coverage of its solution phase conformational space by the computational analysis.

Example 132A 4-((S)-1-((S)-1-((5-(2,4-difluorophenoxy)pyrazin-2-yl)amino)-1-oxopropan-2-yl)-4,4-difluoropiperidin-3-yl)pyridine 1-oxide, Hydrochloride

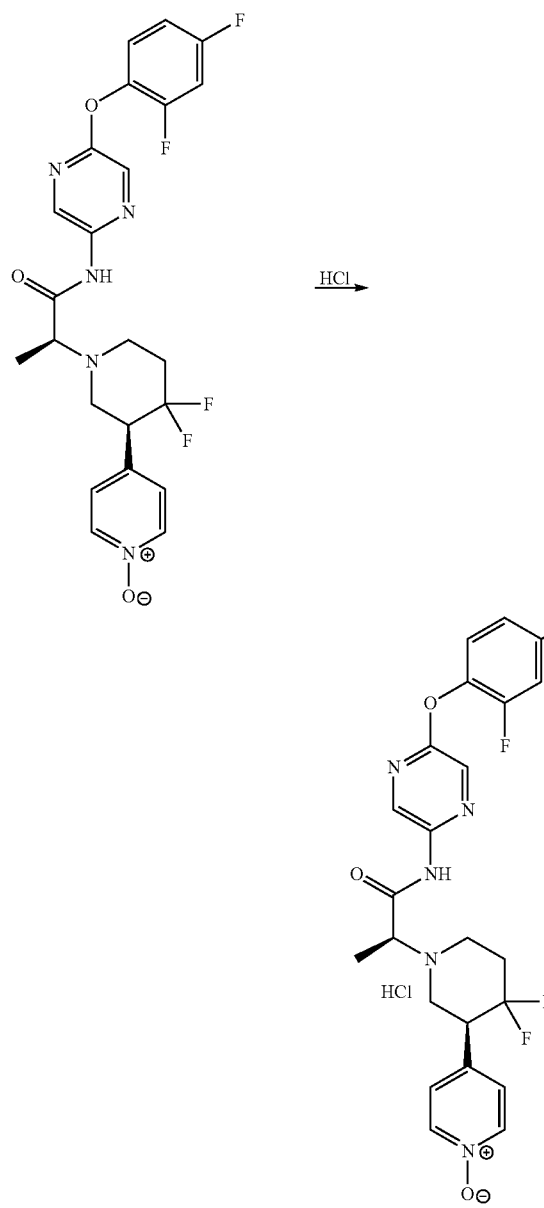

Step 1

To a solution of 4-((S)-1-((S)-1-((5-(2,4-difluorophenoxy)pyrazin-2-yl)amino)-1-oxopropan-2-yl)-4,4-difluoropiperidin-3-yl)pyridine 1-oxide (2.06 g, 4.19 mmol) in ethyl acetate (16 mL) was added dropwise with stirring 4M aqueous HCl (2.096 mL, 8.38 mmol). The pale-yellow solution was gently warmed and sonicated in a water bath for five minutes. The suspension was stirred 18 h at room temperature. The solid product was collected by filtration. The solid was allowed to air dry in a filtration funnel for 2 h and then placed in a vacuum oven at 46° C. for 5.5 h until a constant weight was reached affording 4-((S)-1-((S)-1-((5-(2,4-difluorophenoxy)pyrazin-2-yl)amino)-1-oxopropan-2-yl)-4,4-difluoropiperidin-3-yl)pyridine 1-oxide, Hydrochloride (2.14 g, 4.05 mmol, 97% yield, 100% purity). LCMS (Method 5) (ES, m/z): 492 [M+H]; retention time: 0.75 min. 1H NMR (D$_2$O, 400 MHz) δ 8.42 (s, 1H), 8.1-8.3 (m, 3H), 7.51 (d, 2H, J=7.3 Hz), 7.0-7.3 (m, 2H), 6.9-7.0 (m, 1H), 4.34 (d, 1H, J=6.8 Hz), 3.7-4.1 (m, 4H), 3.4-3.6 (m, 1H), 2.4-2.7 (m, 2H), 1.70 (d, 3H, J=6.8 Hz).

Example 133

(S)—N-(5-(cyclopropylmethoxy)pyridin-2-yl)-2-((R)-4,4-difluoro-3-(5-oxo-4,5-dihydropyrazin-2-yl)piperidin-1-yl)propanamide

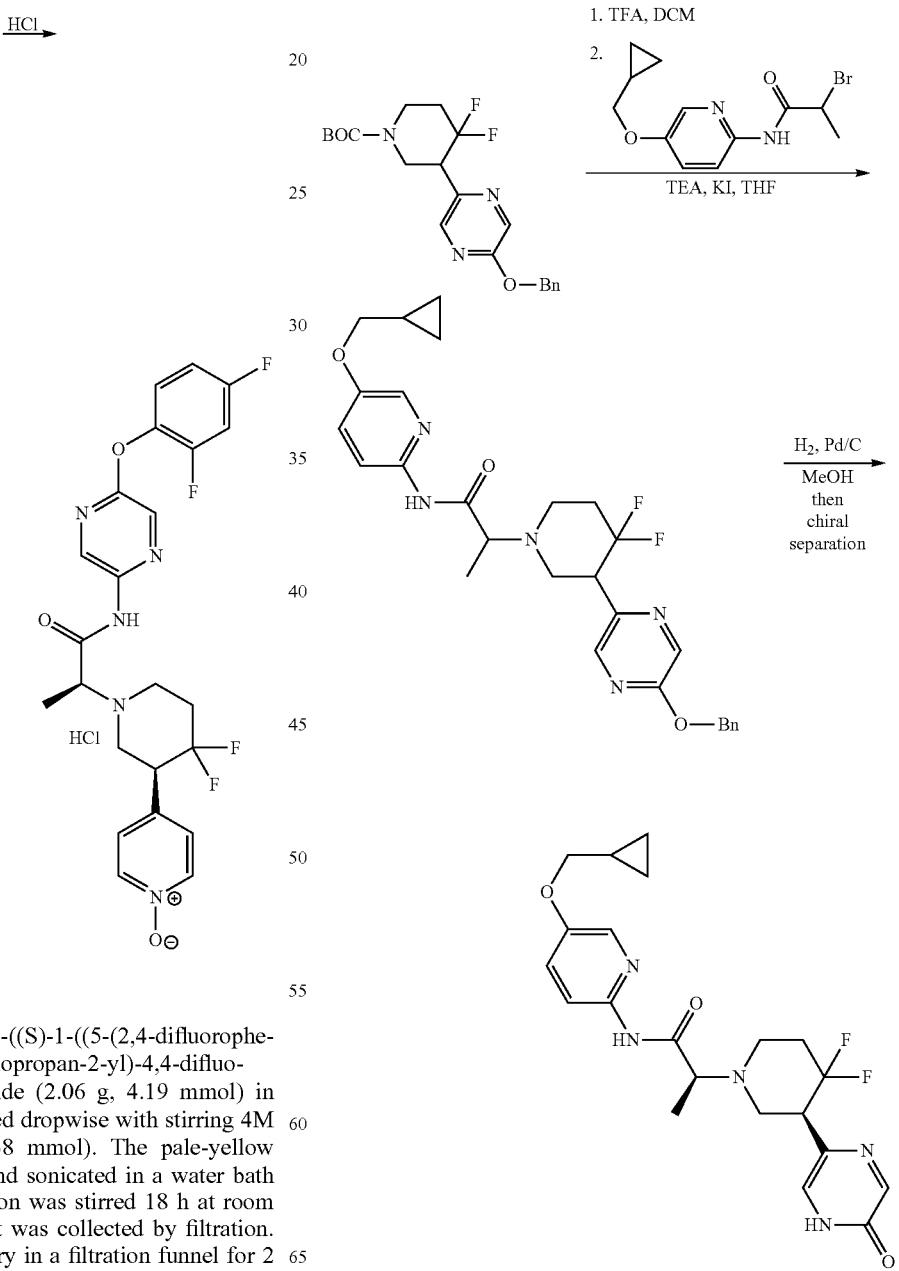

Step 1

To tert-butyl 3-(5-(benzyloxy)pyrazin-2-yl)-4,4-difluoropiperidine-1-carboxylate (Example 103, Step 3) (1.8 g, 4.44 mmol, 1.0 eq) in DCM (20 mL) at 25° C. was added TFA (5 mL). After 1 h, the reaction was concentrated to give 1.4 g (crude) of 2-(benzyloxy)-5-(4,4-difluoropiperidin-3-yl)pyrazine, TFA salt, as a red oil, which was used without purification. LCMS: (ES, m/z): 306 [M+H]+. $^1$H NMR (400 MHz, CD$_3$OD) δ 8.29-8.26 (m, 2H), 7.49-7.32 (m, 5H), 5.46-5.45 (m, 2H), 3.90-3.82 (m, 2H), 3.70-3.64 (m, 1H), 3.53-3.49 (m, 2H), 2.48-2.33 (m, 2H).

Step 2

To 2-(benzyloxy)-5-(4,4-difluoropiperidin-3-yl)pyrazine (as free base) (1.28 g, 4.2 mmol, 1.0 eq) in THF (25 mL) was added 2-bromo-N-(5-(cyclopropylmethoxy)pyridin-2-yl)propanamide (Intermediate 22) (1.25 g, 4.2 mmol, 1.0 eq), TEA (3.4 g, 33.6 mmol, 8.0 eq) and KI (697 mg, 4.2 mmol, 1.0 eq). After 15 h at 60° C., the reaction was quenched with water (100 mL) and extracted with ethyl acetate (100 mL×3). The combined organic phases were dried over Na$_2$SO$_4$, concentrated and applied onto a silica gel column, eluting with ethyl acetate:petroleum ether (1:4), to give 1.25 g (purity: 80%, yield: 57%) of 2-(3-(5-(benzyloxy)pyrazin-2-yl)-4,4-difluoropiperidin-1-yl)-N-(5-(cyclopropylmethoxy)pyridin-2-yl)propanamide as yellow solid. LCMS (ES, m/z): 524 [M+H]+. $^1$H NMR (400 MHz, CD$_3$OD) δ 8.32-8.25 (m, 1H), 8.21-8.17 (m, 1H), 8.10-7.95 (m, 2H), 7.49-7.32 (m, 6H), 5.39 (s, 2H), 3.90-3.93 (m, 2H), 3.75-3.45 (m, 2H), 3.20-2.90 (m, 3H), 2.75-2.60 (m, 1H), 2.40-2.20 (m, 2H), 1.34 (d, J=6.9 Hz, 3H), 1.28-1.23 (m, 1H), 0.65-0.60 (m, 2H), 0.40-0.33 (m, 2H).

Step 3

2-(3-(5-(Benzyloxy)pyrazin-2-yl)-4,4-difluoropiperidin-1-yl)-N-(5-(cyclopropylmethoxy)pyridin-2-yl)propanamide (500 mg, 0.96 mmol, 1.0 eq), MeOH (15 mL) and Pd/C (200 mg, 10%) were stirred for 1.0 h at room temperature under H$_2$. The solid was filtered out, and the filtrate was concentrated and purified by prep HPLC (Sun Five Prep C18 OBD column), eluting with 25-45% AcCN in water (0.1% FA) to give 200 mg of product as a white solid. The material was subject to chiral purification (Column: CHIRALPAK AD-H, 2.0 cm I.D×25 cm L; Mobile Phase A: Hex [8 mM NH$_3$.MeOH], Mobile Phase B: EtOH; Flow rate: 18 mL/min; 1:1 A:B), and peaks with the following retention times were collected: RT1: 7.121 min; RT2-RT3: 10.513-11.433 min; RT4: 17.052 min. The second peak (RT2-RT3: 10.513-11.433) was further purified (CHIRALPAK AD-H, 2.0 cm I.D×25 cm L; Mobile Phase A: Hex [8 mM NH$_3$. MeOH], Mobile Phase B: EtOH; Flow rate: 18 mL/min; 1:1 A:B), and two peaks were collected: RT1: 11.28 min and RT2: 13.927 min. The fractions for the second isomer (RT2: 13.927) were concentrated to give 45 mg (purity: 98.4%, yield: 9%) of (S)—N-(5-(cyclopropylmethoxy)pyridin-2-yl)-2-((R)-4,4-difluoro-3-(5-oxo-4,5-dihydropyrazin-2-yl)piperidin-1-yl)propanamide as an off white solid. LCMS (ES, m/s): 434 [M+H]+ $^1$H NMR: (300 MHz, CD$_3$OD) δ 8.10 (d, J=1.2 Hz, 1H), 8.03 (d, J=9.0 Hz, 1H), 7.99-7.98 (m, 1H), 7.41-7.37 (m, 2H), 3.87 (d, J=6.9 Hz, 2H), 3.55-3.45 (m, 2H), 3.10-3.01 (m, 2H), 2.99-2.83 (m, 1H), 2.72-2.63 (m, 1H), 2.40-2.25 (m, 2H), 1.32 (d, J=6.9 Hz, 3H), 1.28-1.23 (m, 1H), 0.65-0.59 (m, 2H), 0.38-0.33 (m, 2H).

Examples 134-137 were synthesized in an analogous manner using the designated Intermediate in Step 2.

| Ex | Name | Structure | $^1$H NMR | LC/MS: (M + H)+; retention time (min); LC/MS Method of analysis | Int |
|---|---|---|---|---|---|
| 134 | (S)-N-(6-(cyclopropylmethoxy)pyridazin-3-yl)-2-((R)-4,4-difluoro-3-(5-oxo-4,5-dihydropyrazin-2-yl)piperidin-1-yl)propanamide | 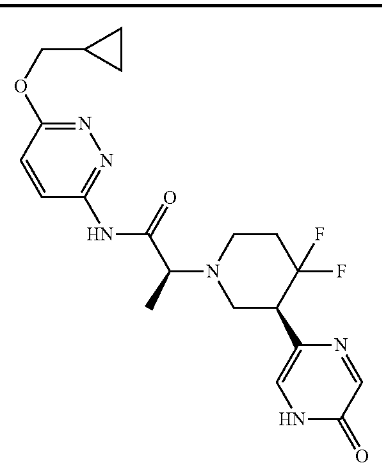 | $^1$H NMR: (400 MHz, CD$_3$OD) δ ppm 8.34 (d, J = 9.6 Hz, 1H), 8.08 (s, 1H), 7.44 (s, 1H), 7.19 (d, J = 9.6 Hz, 1H), 4.25 (d, J = 7.2 Hz, 2H), 3.60-3.56 (m, 1H), 3.51-3.39 (m, 1H), 3.08-3.02 (m, 2H), 2.94-2.91 (m, 1H), 2.70-2.64 (m, 1H), 2.27-2.18 (m, 2H), 1.36-1.29 (m, 4H), 0.64-0.58 (m, 2H), 0.39-0.36 (m, 2H). | 435; rt 1.232 LC/MS Method 14 | 14 |

-continued

| Ex | Name | Structure | ¹H NMR | LC/MS: (M + H)⁺; retention time (min); LC/MS Method of analysis | Int |
|---|---|---|---|---|---|
| 135 | (S)-2-((R)-4,4-difluoro-3-(5-oxo-4,5-dihydropyrazin-2-yl)piperidin-1-yl)-N-(5-fluoropyridin-2-yl)propanamide | 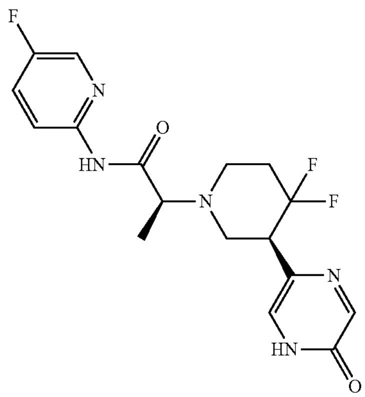 [SMILES: C[C@@H](C(=O)Nc1ccc(F)cn1)N1CCC(F)(F)[C@@H](c2c[nH]c(=O)cn2)C1] | ¹H NMR: (400 MHz, CD₃OD) δ ppm 8.22-8.16 (m, 2H), 8.11 (d, J = 1.2 Hz, 1H), 7.63-7.58 (m, 1H), 7.43 (s, 1H), 3.60-3.47 (m, 2H), 3.19-2.90 (m, 3H), 2.79-2.76 (m, 1H), 2.48-2.12 (m, 2H), 1.40-1.36 (m, 3H). | 382; rt 1.076 LC/MS Method 15 | 1 |
| 136 | (S)-N-(5-chloropyridin-2-yl)-2-((R)-4,4-difluoro-3-(5-oxo-4,5-dihydropyrazin-2-yl)piperidin-1-yl)propanamide | 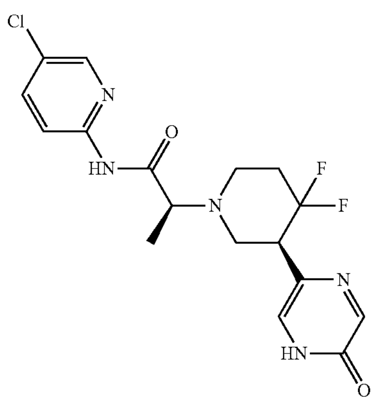 [SMILES: C[C@@H](C(=O)Nc1ccc(Cl)cn1)N1CCC(F)(F)[C@@H](c2c[nH]c(=O)cn2)C1] | ¹H NMR: (400 MHz, CD₃OD) δ ppm 8.32-8.28 (m, 1H), 8.18-8.14 (m, 1H), 8.12 (d, J = 1.2 Hz, 1H), 7.81-7.77 (m, 1H), 7.41 (s, 1H), 3.60-3.52 (m, 1H), 3.50-3.38 (m, 1H), 3.10-2.98 (m, H), 2.94-2.82 (m, 1H), 2.78-2.68 (m, 1H), 2.51-2.30 (m, 1H), 2.29-2.09 (m, 1H), 1.33-1.30 (m, 3H). | 398; rt 1.198 LC/MS Method 15 | 3 |
| 137 | (S)-N-(5-cyclopropylpyridin-2-yl)-2-((R)-4,4-difluoro-3-(5-oxo-4,5-dihydropyrazin-2-yl)piperidin-1-yl)propanamide | 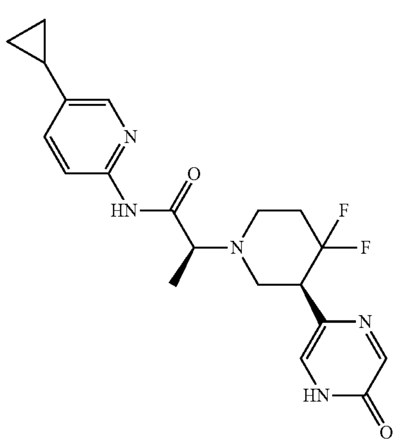 | ¹H NMR: (400 MHz, CD₃OD) δ ppm 8.13-8.10 (m, 2H), 8.02-7.96 (m, 1H), 7.48-7.42 (m, 2H), 3.56-3.47 (m, 2H), 3.38-2.94 (m, 3H), 2.81-2.71 (m, 1H), 2.40-2.23 (m, 2H), 1.96-1.89 (m, 1H), 1.42-1.28 (m, 3H), 1.04-0.98 (m, 2H), 0.73-0.69 (m, 2H). | 404; rt 1.236 LC/MS Method 14 | 2 |

Example 138

(S)-2-((S)-3-(5-amino-6-oxo-1,6-dihydropyridin-3-yl)-4,4-difluoropiperidin-1-yl)-N-(5-(cyclopropylmethoxy)pyridin-2-yl)propanamide

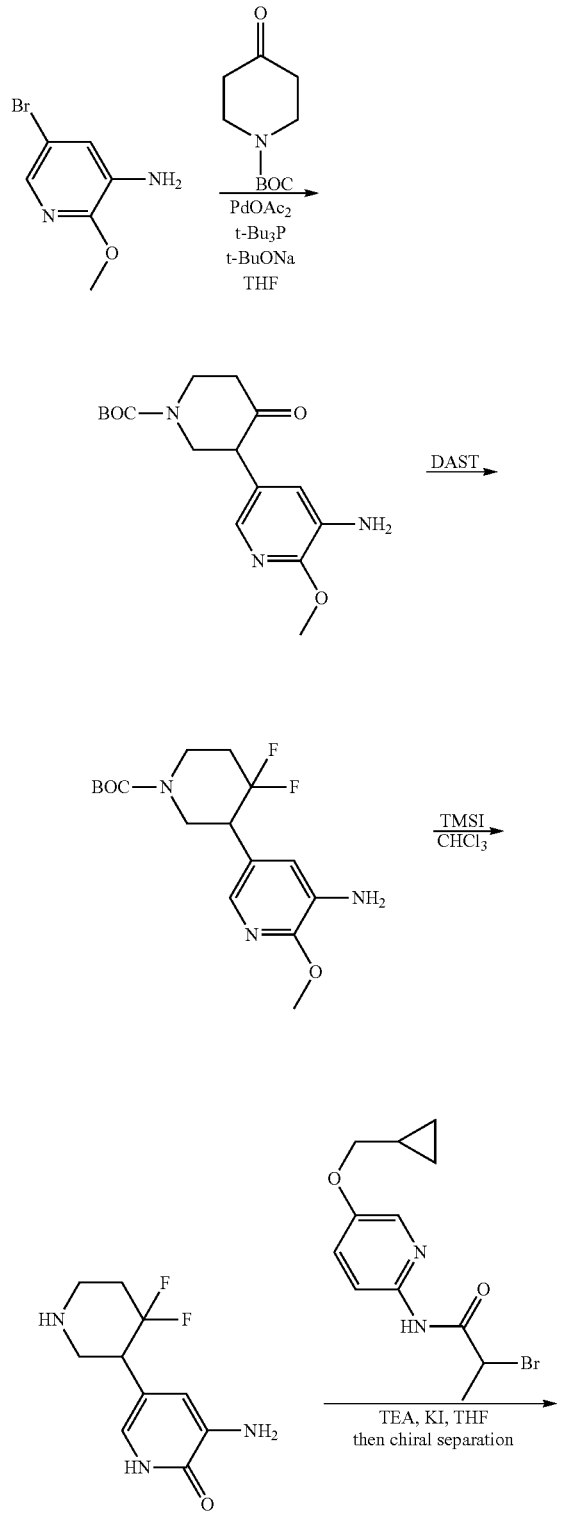

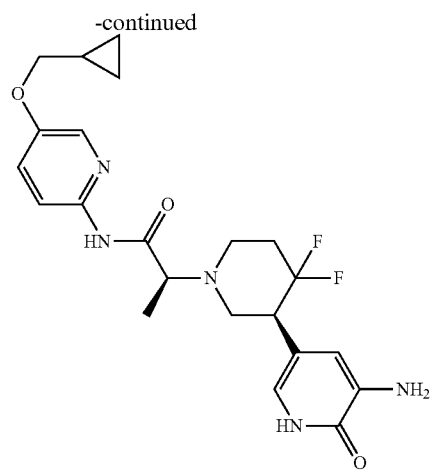

Step 1 t-BuONa (2.38 g, 24.75 mmol, 2.5 eq) in THF (16 mL) at 42° C. was stirred for 10 min, followed by addition of Pd(OAc)$_2$ (0.22 g, 0.99 mmol, 0.1 eq) and (t-Bu)$_3$P (200 mg, 0.99 mmol, 0.1 eq). After 5 min, 5-bromo-2-methoxypyridin-3-amine (2.0 g, 9.9 mmol, 1.0 eq) and tert-butyl 4-oxopiperidine-1-carboxylate (2.96 g, 14.85 mmol, 1.5 eq) were added. After 15 h, the reaction was quenched with water (100 mL) and extracted with ethyl acetate (100 mL×2). The organic phases were combined, dried over Na$_2$SO$_4$, concentrated and purified over a silica gel column, eluting with ethyl acetate:petroleum ether (2:3) to give 4.5 g (purity: 33%) of tert-butyl 3-(5-amino-6-methoxypyridin-3-yl)-4-oxopiperidine-1-carboxylate as yellow solid. LCMS: (ES, m/s) 322 [M+H]+. $^1$H NMR: (300 MHz, CD$_3$OD) δ ppm 7.39-7.20 (m, 1H), 6.84-6.83 (m, 1H), 4.13-4.11 (m, 1H), 3.96 (s, 3H), 3.45-3.40 (m, 2H), 3.15-3.05 (m, 2H), 2.55-2.45 (m, 2H), 1.51 (s, 9H).

Step 2

To tert-butyl 3-(5-amino-6-methoxypyridin-3-yl)-4-oxopiperidine-1-carboxylate (4.2 g, 13.08 mmol, 1.0 eq) in DCM (60 ml) at 0° C. was added DAST (4.21 g, 26.17 mmol, 2.0 eq). The resulting mixture was stirred for 15 h, quenched with ice water (100 mL) and extracted with DCM (100 mL×2). The combined organic phases were dried over Na$_2$SO$_4$, concentrated and purified over a silica gel column, eluting with ethyl acetate:petroleum ether (1:2) to give 1.5 g (purity: 27%) of tert-butyl 3-(5-amino-6-methoxypyridin-3-yl)-4,4-difluoropiperidine-1-carboxylate as gray solid. LCMS: (ES, m/s) 344 [M+H]+.

Step 3

To tert-butyl 3-(5-amino-6-methoxypyridin-3-yl)-4,4-difluoropiperidine-1-carboxylate (3.3 g, 9.6 mmol, 1.0 eq) in CHCl$_3$ (40 mL) was added TMSI (19.2 g, 96.2 mmol, 10.0 eq), and the reaction was stirred at 50° C. After 4 h, MeOH (950 mL) was added, and the mixture was stirred for 0.5 h at 25° C. The solvent was removed, and the residue was dissolved in a solution of Na$_2$S$_2$O$_3$ (15 mL) and NaHCO$_3$ (15 mL). The mixture was concentrated, and the residue was applied onto a silica gel column, eluting with methanol:dichloromethane (1:5) to give 820 mg (purity: 80%, yield: 37%) of 3-amino-5-(4,4-difluoropiperidin-3-yl)pyridin-2 (1H)-one as a brown solid. LCMS (ES, m/s): 230 [M+H]+ $^1$H NMR: (300 MHz, DMSO-d$_6$) δ 11.28 (s, 1H), 6.50-6.47 (m, 1H), 6.42-6.39 (m, 1H), 5.00 (s, 2H), 3.50-3.40 (m, 1H), 3.08-2.90 (m, 3H), 2.78-2.60 (m, 3H), 2.03-1.95 (m, 1H).

Step 4

A mixture of 3-amino-5-(4,4-difluoropiperidin-3-yl)pyridin-2 (1H)-one (820 mg, 3.58 mmol, 1.0 eq), 2-bromo-N-(5-(cyclopropylmethoxy)pyridin-2-yl)propanamide (Intermediate 22) (1.07 g, 3.58 mmol, 1.0 eq), KI (654 mg, 3.94 mmol, 1.1 eq) and TEA (2.89 g, 28.65 mmol, 8.0 eq) in THF (5 mL) was stirred 48 h at 60° C., quenched with water (100 mL) and extracted with EtOAc (100 mL×3). The combined organic phases were dried over sodium sulfate, concentrated and purified by reverse-phase chromatography (C18 silica gel, 330 g, 20-45 μm), eluting with 5-70% AcCN in water (0.05% FA) to produce 340 mg of material which was chirally separated (Column: Lux 5 u Cellulose-4, AXIA Packed, 2.12×25 cm, 5 μm; Mobile Phase 1: 1 [Hex {8 mM NH₃. MeOH}]: [1:1 MeOH: EtOH]; Flow rate: 20 mL/min) to give 4 isomers with retention times of 7.628, 10.531, 12.743 and 21.863 minutes. The second peak (RT 10.531 min) was collected to give 50 mg (purity: 98.8%, yield: 3%) of (S)-2-((S)-3-(5-amino-6-oxo-1,6-dihydropyridin-3-yl)-4,4-difluoropiperidin-1-yl)-N-(5-(cyclopropylmethoxy)pyridin-2-yl)propanamide as an off white solid. LCMS (ES, m/s): 448 [M+H]+ ¹H NMR: (400 MHz, DMSO-d₆) δ 11.30 (br, 1H), 10.12 (s, 1H), 8.03-8.01 (m, 2H), 7.43 (dd, J=9.2, 3.2 Hz, 1H), 6.56 (s, 1H), 6.48 (s, 1H), 5.03 (s, 2H), 3.87 (d, J=7.2 Hz, 2H), 3.64-3.59 (m, 1H), 3.08-2.98 (m, 1H), 2.95-2.84 (m, 2H), 2.78-2.72 (m, 1H), 2.50-2.49 (m, 1H), 2.14-1.90 (m, 2H), 1.22-1.19 (m, 4H), 0.60-0.55 (m, 2H), 0.35-0.31 (m, 2H).

Examples 139-142 were synthesized in an analogous manner using the designated Intermediate in Step 4.

| Ex | Name | Structure | ¹H NMR | LC/MS: (M + H)+; retention time (min); LC/MS Method of analysis | Int |
|---|---|---|---|---|---|
| 139 | 2-(3-(5-amino-6-oxo-1,6-dihydropyridin-3-yl)-4,4-difluoropiperidin-1-yl)-N-(5-phenoxypyridin-2-yl)propanamide | 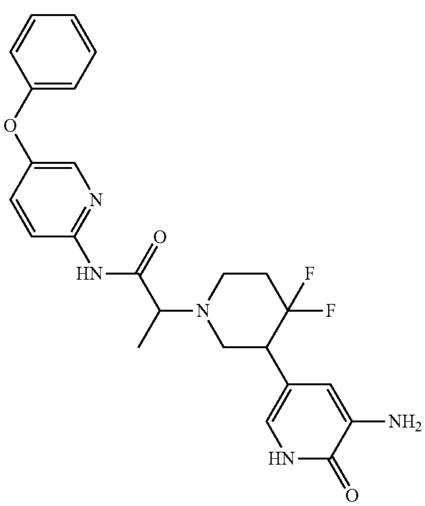 [SMILES: CC(C(=O)Nc1ccc(Oc2ccccc2)cn1)N1CCC(F)(F)C(c2c[nH]c(=O)c(N)c2)C1] | ¹H NMR: (400 MHz, DMSO-d₆) δ ppm 11.29 (br, 1H), 10.35 (br, 1H), 8.16-8.13 (m, 2H), 7.56-7.52 (m, 1H), 7.42-7.37 (m, 2H), 7.17-7.13 (m, 1H), 7.04-7.02 (m, 2H), 6.56 (s, 1H), 6.47 (d, J = 11.4 Hz, 1H), 5.03 (d, J = 7.2 Hz, 2H), 3.67-3.61 (m, 1H), 3.01-2.86 (m, 3H), 2.76-2.59 (m, 2H), 2.09-1.94 (m, 2H), 1.22 (dd, J = 6.2, 6.8 Hz, 3H). | 470; rt 2.760 and 2.813. LC/MS Method 18 | 72 |
| 140 | (S)-2-((S)-3-(5-amino-6-oxo-1,6-dihydropyridin-3-yl)-4,4-difluoropiperidin-1-yl)-N-(6-(cyclopropyl methoxy) pyridazin-3-yl)propanamide | 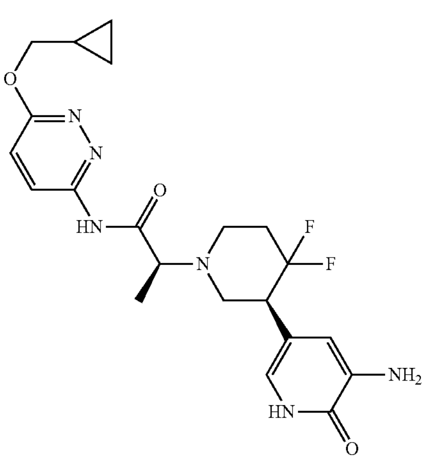 [SMILES: C[C@@H](C(=O)Nc1ccc(OCC2CC2)nn1)N1CCC(F)(F)[C@@H](c2c[nH]c(=O)c(N)c2)C1] | ¹H NMR: (400 MHz, DMSO-d₆) δ ppm 11.31 (s, 1H), 10.71 (s, 1H), 8.25 (d, J = 9.6 Hz, 1H), 7.27 (d, J = 9.6 Hz, 1H), 6.56 (s, 1H), 6.47 (s, 1H), 5.04 (s, 2H), 4.24-4.19 (m, 2H), 3.70-3.65 (m, 1H), 3.08-2.98 (m, 1H), 2.95-2.91 (m, 2H), 2.78-2.73 (m, 1H), 2.50-2.48 (m, 1H), 2.09-2.00 (m, 2H), 1.31-1.26 (m, 1H), 1.21 (d, J = 7.2 Hz, 3H), 0.60-0.55 (m, 2H), 0.38-0.36 (m, 2H). | 449; rt 0.904. LC/MS Method 11 | 14 |

-continued

| Ex | Name | Structure | ¹H NMR | LC/MS: (M + H)⁺; retention time (min); LC/MS Method of analysis | Int |
|---|---|---|---|---|---|
| 141 | (S)-2-((S)-3-(5-amino-6-oxo-1,6-dihydropyridin-3-yl)-4,4-difluoropiperidin-1-yl)-N-(5-chloropyridin-2-yl)propanamide | 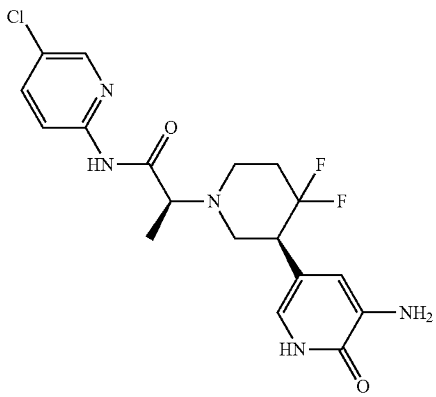 [SMILES: C[C@@H](C(=O)Nc1ccc(Cl)cn1)N1CCC(F)(F)[C@@H](c2c[nH]c(=O)c(N)c2)C1] | ¹H NMR: (400 MHz, DMSO-d₆) δ ppm 8.31-8.29 (m, 1H), 8.18 (d, J = 8.8 Hz, 1H), 7.83-7.80 (m, 1H), 6.80-6.76 (m, 2H), 3.56-3.51 (m, 1H), 3.23-3.13 (m, 1H), 2.97-2.86 (m, 3H), 2.63-2.57 (m, 1H), 2.25-2.03 (m, 2H), 1.37-1.33 (m, 3H). | 412; rt 1.146. LC/MS Method 28 | 3 |
| 142 | (S)-2-((S)-3-(5-amino-6-oxo-1,6-dihydropyridin-3-yl)-4,4-difluoropiperidin-1-yl)-N-(5-fluoropyridin-2-yl)propanamide | 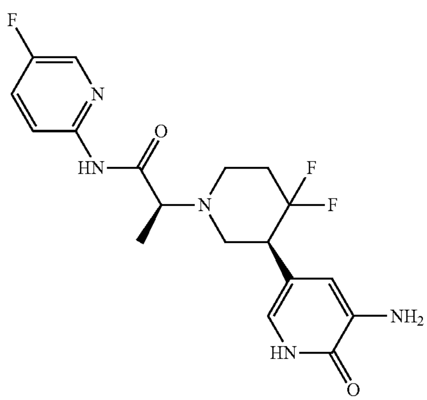 [SMILES: C[C@@H](C(=O)Nc1ccc(F)cn1)N1CCC(F)(F)[C@@H](c2c[nH]c(=O)c(N)c2)C1] | ¹H NMR: (400 MHz, DMSO-d₆) δ ppm 11.37 (br, 1H), 10.40 (s, 1H), 8.35 (d, J = 3 Hz, 1H), 8.17-8.13 (m, 1H), 7.80-7.73 (m, 1H), 6.61 (s, 1H), 6.47 (s, 1H), 5.03 (br, 2H), 3.67-3.63 (m, 1H), 3.10-2.72 (m, 4H), 2.51-2.44 (m, 1H), 2.10-1.95 (m, 2H), 1.21 (d, J = 6.9 Hz, 3H). | 396; rt 0.993. LC/MS Method 28 | 1 |

Example 143

(S)-2-((R)-3-(5-amino-6-oxo-1,6-dihydropyridazin-3-yl)-4,4-difluoropiperidin-1-yl)-N-(5-fluoropyridin-2-yl)propanamide

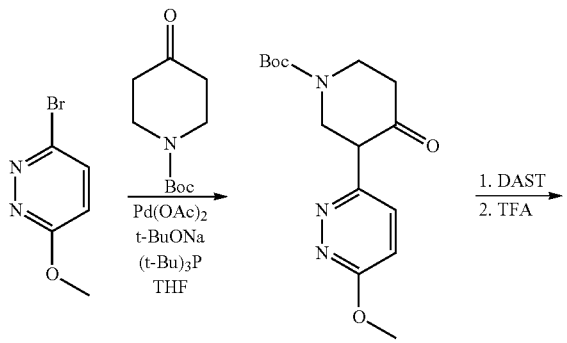

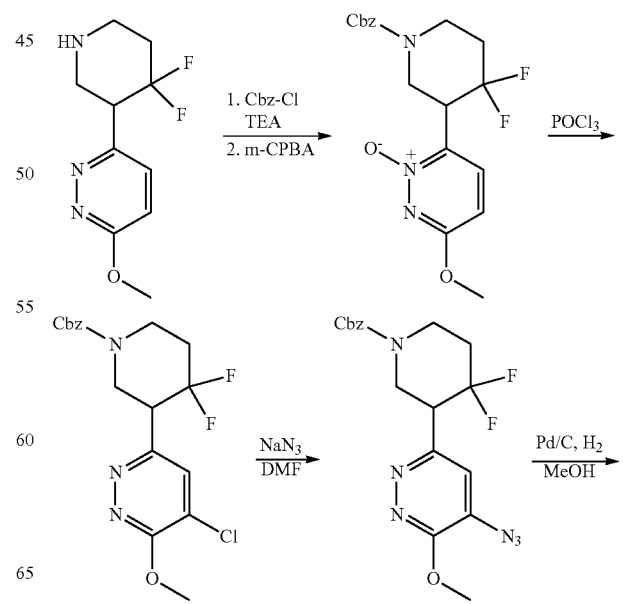

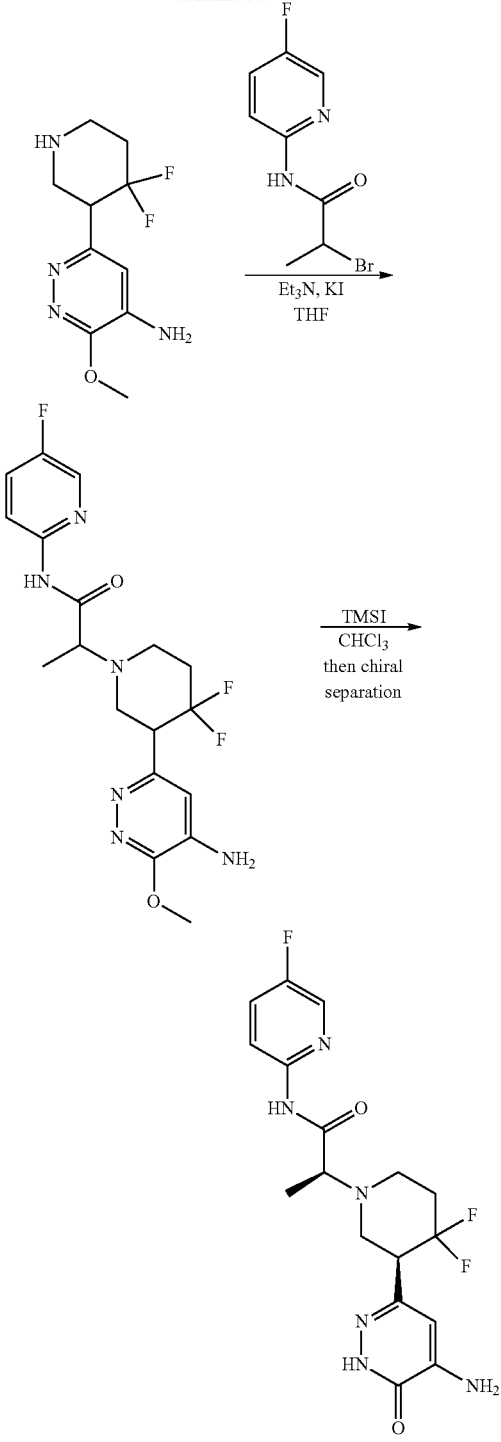

concentrated. The residue was dissolved in DCM (100 ml), treated with silica (100-200 mesh, 70.0 g), concentrated and loaded onto a silica gel column (330 g, 100-200 mesh), eluting with ethyl acetate:petroleum ether (1:1) to give 1.4 g (purity: 82%, yield: 54%) of tert-butyl 3-(6-methoxy-pyridazin-3-yl)-4-oxopiperidine-1-carboxylate as yellow solid. LCMS: (ES, m/s) 308 [M+H]+. $^1$H NMR: (300 MHz, CDCl$_3$) δ ppm 7.05-6.95 (m, 2H), 4.25-4.20 (m, 3H), 4.02-3.98 (m, 2H), 3.70-3.65 (m, 1H), 3.50-3.48 (m, 2H), 2.50-2.44 (m, 2H), 1.51-1.49 (m, 9H).

Step 2

To tert-butyl 3-(6-methoxypyridazin-3-yl)-4-oxopiperidine-1-carboxylate (14.0 g, 45.6 mmol, 1.0 eq) in DCM (150 mL) at 0° C. was added DAST (14.6 g, 91.2 mmol, 2.0 eq). The resulting mixture was stirred 15.0 h at 25° C., poured into 100 mL of water/ice and extracted with DCM (100 mL×3). The combined organic layers were dried over sodium sulfate and concentrated. The residue was dissolved in DCM (40 ml), silica (100-200 mesh, 30.0 g) was added, and the mixture was concentrated and loaded onto a silica gel column (330 g, 100-200 mesh), eluting with ethyl acetate/petroleum ether (3/7) gave 3.6 g (purity: 60%, yield: 24%) of tert-butyl 4,4-difluoro-3-(6-methoxypyridazin-3-yl)piperidine-1-carboxylate as yellow solid.

LCMS: (ES, m/s) 330 [M+H]+. $^1$H NMR: (300 MHz, CDCl$_3$) δ ppm 7.44-7.41 (m, 1H), 6.98 (d, J=9.3 Hz, 1H), 4.16-4.14 (m, 3H), 3.60-3.50 (m, 1H), 3.49-3.40 (m, 1H), 3.19-3.14 (m, 1H), 2.29-2.24 (m, 1H), 2.08-1.99 (m, 2H), 1.75-1.72 (m, 1H), 1.49-1.46 (m, 9H).

Step 3

To tert-butyl 4,4-difluoro-3-(6-methoxypyridazin-3-yl)piperidine-1-carboxylate (3.6 g, 10.94 mmol, 1.0 eq) in DCM (36 mL) at 25° C. was added TFA (12 mL). After 1.5 h, the reaction was concentrated, treated with NaHCO$_{3(aq)}$ (40 mL) and extracted with DCM (40 mL×2). The organic layers were dried over sodium sulfate and concentrated. The residue was dissolved in DCM (10 ml), silica (100-200 mesh, 5.0 g) was added, and the mixture was concentrated and loaded onto a silica gel column (120 g, 100-200 mesh), eluting with MeOH:DCM (1:10) to give 1.99 g (purity: 50%, yield: 40%) of 3-(4,4-difluoropiperidin-3-yl)-6-methoxy-pyridazine as yellow oil. LCMS (ES, m/s): 230 [M+H]+ $^1$H NMR: (300 MHz, CDCl$_3$) δ 7.44-7.41 (m, 1H), 6.98-6.95 (m, 1H), 4.14-4.13 (m, 3H), 3.49 (s, 1H), 3.45-3.20 (m, 3H), 3.21-3.06 (m, 2H), 2.12-1.88 (m, 2H).

Step 4

To 3-(4,4-difluoropiperidin-3-yl)-6-methoxypyridazine (0.75 g, 3.28 mmol, 1.0 eq) and TEA (1.66 g, 16.4 mmol, 5.0 eq) in DCM (10 mL) at 0° C. was added CBZ-Cl (0.557 g, 3.28 mmol, 1.0 eq). After 1.5 h, the mixture was concentrated, dissolved in DCM (10 ml), adsorbed onto silica and loaded onto a silica gel column (80 g, 100-200 mesh), eluting with ethyl acetate:petroleum ether (1:1) to give 1.09 g (purity: 80%, yield: 87%) of benzyl 4,4-difluoro-3-(6-methoxypyridazin-3-yl)piperidine-1-carboxylate as yellow oil. LCMS (ES, m/s): 364 [M+H]+ $^1$H NMR: (300 MHz, DMSO-d$_6$) δ 7.57 (d, J=9.0 Hz, 1H), 7.40-7.20 (m, 6H), 5.19-5.08 (m, 2H), 4.06-3.98 (m, 4H), 3.75-3.60 (m, 2H), 3.32-3.24 (m, 2H), 2.29-2.07 (m, 2H).

Step 5

To benzyl 4,4-difluoro-3-(6-methoxypyridazin-3-yl)piperidine-1-carboxylate (1.09 g, 3.0 mmol, 1.0 eq) in DCM (15 mL) at 0° C. was added m-CPBA (1.03 g, 6.0 mmol, 2.0 eq), in portions. The mixture was stirred for 4.0 h at rt, poured into Na$_2$S$_2$O$_{3(aq)}$ (30 mL) and extracted with DCM (30 mL×3). The organic layers were combined, dried over Na$_2$SO$_4$, filtered, concentrated, adsorbed onto silica and Step 1 t-BuONa (2.56 g, 26.6 mmol, 2.5 eq) in THF (16 mL) at 42° C. was stirred for 30 min, followed by addition of 3-bromo-6-methoxypyridazine (2.00 g, 10.63 mmol, 1.0 eq) and tert-butyl 4-oxopiperidine-1-carboxylate (3.17 g, 15.95 mmol, 1.5 eq). After 5 min, Pd(OAc)$_2$ (0.238 g, 1.06 mmol, 0.1 eq) and (t-Bu)$_3$P (214 mg, 1.06 mmol, 0.1 eq) were added. After 15 h, the reaction was quenched with water (200 mL) and extracted with ethyl acetate (200 mL×2). The organic phases were combined, dried over Na$_2$SO$_4$ and applied onto a silica gel column (100-200 mesh, 80 g), eluting with 0-25% ethyl acetate in petroleum ether to give 0.93 g (purity: 90%, yield: 81%) of 6-(1-(benzyloxycarbonyl)-4,4-difluoropiperidin-3-yl)-3-methoxypyridazine 1-oxide as white solid.

LCMS (ES, m/s): 380 [M+H]+ $^1$H NMR: (300 MHz, DMSO-$d_6$) δ 7.91-7.88 (m, 1H), 7.44-7.29 (m, 5H), 6.92 (d, J=9.0 Hz, 1H), 5.11 (s, 2H), 4.30-4.10 (m, 3H), 3.89 (s, 3H), 3.33-3.13 (m, 2H), 2.25-2.10 (m, 2H).

Step 6

6-(1-(Benzyloxycarbonyl)-4,4-difluoropiperidin-3-yl)-3-methoxypyridazine 1-oxide (0.93 g, 2.45 mmol, 1.0 eq) and POCl$_3$ (10 ml) were stirred at rt 17 h and concentrated at 0° C.

The residue was dissolved in DCM (30 mL) then poured into H$_2$O (30 mL). The pH of the solution was adjusted to 8-9 with K$_2$CO$_3$(aq), and the reaction was extracted with DCM (30 mL×2). The organic layers were combined, dried over Na$_2$SO$_4$, filtered, concentrated, adsorbed onto silica and applied onto a silica gel column (100-200 mesh, 120 g), eluting with 0-25% ethyl acetate in petroleum ether to give 0.75 g (purity: 90%, yield: 77%) of benzyl 3-(5-chloro-6-methoxypyridazin-3-yl)-4,4-difluoropiperidine-1-carboxylate as light-yellow oil. LCMS (ES, m/s): 398 [M+H]+ $^1$H NMR: (300 MHz, DMSO-$d_6$) δ 7.91 (m, 1H), 7.42-7.19 (m, 5H), 5.14-5.04 (s, 2H), 4.15-3.95 (m, 4H), 3.81-3.60 (m, 2H), 3.40-3.20 (m, 2H), 2.35-2.00 (m, 2H).

Step 7

Benzyl 3-(5-chloro-6-methoxypyridazin-3-yl)-4,4-difluoropiperidine-1-carboxylate (1.05 g, 2.64 mmol, 1.0 eq) and sodium azide (0.343 g, 5.28 mmol, 2.0 eq) in DMF (15 mL) were stirred for 13 h at 80° C., cooled to 25° C., poured into water (50 mL) and extracted with ethyl acetate (50 mL×3). The organic layers were combined, washed with brine (100 mL×3), dried over Na$_2$SO$_4$, filtered, concentrated, adsorbed onto silica and applied onto a silica gel column (100-200 mesh, 120 g), eluting with 0-25% ethyl acetate in petroleum ether to give 0.78 g (purity: 90%, yield: 73%) of benzyl 3-(5-azido-6-methoxypyridazin-3-yl)-4,4-difluoropiperidine-1-carboxylate as light yellow oil. LCMS (ES, m/s): 405 [M+H]+ $^1$H NMR: (300 MHz, DMSO-$d_6$) δ 7.45-7.20 (m, 6H), 5.15-4.95 (s, 2H), 4.20-3.95 (m, 4H), 3.85-3.60 (m, 2H), 3.40-3.20 (m, 2H), 2.40-2.05 (m, 2H).

Step 8

A mixture of benzyl 3-(5-azido-6-methoxypyridazin-3-yl)-4,4-difluoropiperidine-1-carboxylate (0.78 g, 1.93 mmol, 1.0 eq), MeOH (15 mL) and Pd/C (0.4 g) was stirred under a hydrogen balloon for 2 h, filtered and concentrated. The residue was adsorbed onto silica and applied onto a silica gel column (100-200 mesh, 120 g), eluting with 0-20% MeOH in DCM to give 0.41 g (purity: 80%, yield: 87%) of 6-(4,4-difluoropiperidin-3-yl)-3-methoxypyridazin-4-amine as light yellow solid. LCMS (ES, m/s): 245 [M+H]+ $^1$H NMR: (300 MHz, DMSO-$d_6$) δ 6.54 (s, 1H), 6.16 (s, 2H), 4.02-3.94 (m, 4H), 3.15-2.92 (m, 3H), 2.81-2.72 (m, 2H), 2.10-1.80 (m, 2H).

Step 9

6-(4,4-Difluoropiperidin-3-yl)-3-methoxypyridazin-4-amine (0.41 g, 1.68 mmol, 1.0 eq), KI (0.279 g, 1.68 mmol, 1.0 eq), TEA (1.7 g, 16.8 mmol, 10.0 eq) and 2-bromo-N-(5-fluoropyridin-2-yl)propanamide (Intermediate 1) (0.413 g, 1.68 mmol, 1.0 eq) in THF (20 mL) were stirred for 15.0 h at 60° C., poured into water (30 mL) and extracted with ethyl acetate (30 mL×3). The combined organic layers were dried over sodium sulfate, concentrated, adsorbed onto silica and applied onto a silica gel column (100-200 mesh, 80 g), eluting with 0-100% ethyl acetate in petroleum ether to give 0.59 g (purity: 90%, yield: 85%) of 2-(3-(5-amino-6-methoxypyridazin-3-yl)-4,4-difluoropiperidin-1-yl)-N-(5-fluoropyridin-2-yl)propanamide as yellow solid. LCMS (ES, m/s): 411 [M+H]+ $^1$H NMR: (300 MHz, DMSO-$d_6$) δ 10.37 (d, J=3.6 Hz, 1H), 8.31 (d, J=3.3 Hz, 1H), 8.15-8.10 (m, 1H), 7.77-7.69 (m, 1H), 6.59-6.56 (m, 1H), 6.12 (s, 2H), 3.95-3.92 (m, 3H), 3.70-3.60 (m, 1H), 3.46-3.35 (m, 1H), 3.05-2.65 (m, 4H), 2.20-2.06 (m, 2H), 1.18-1.12 (m, 3H).

Step 10

2-(3-(5-Amino-6-methoxypyridazin-3-yl)-4,4-difluoropiperidin-1-yl)-N-(5-fluoropyridin-2-yl)propanamide (0.61 g, 1.49 mmol, 1.0 eq)) and TMSI (2.9 g, 14.9 mmol, 10.0 eq) in CHCl$_3$ (15 mL) were stirred for 10.0 h at 50° C. MeOH (20 mL) was added, and the reaction was stirred for 15.0 min at 25° C., concentrated, dissolved in DCM (30 mL) and poured into (Na$_2$S203+NaHCO$_3$, aq) (50 mL). The mixture was extracted with DCM (50 mL×3), and the organic layers were dried over sodium sulfate and concentrated. The crude product was purified by prep-HPLC (XBridge Prep C18 OBD Column), eluting with 20-30% AcCN in water [0.1% FA] to give 370 mg yellow solid. This material was separated by chiral-HPLC (CHIRALPAK IG, 20×250 mm, 5 μm; Mobile Phase A: Hex [8 mM NH$_3$. MeOH)], Mobile Phase B: EtOH; Flow rate: 16 mL/min; 1:1: A:B over 18 mi) to give 4 isomers with retention times of RT1: 9.472 min; RT2: 10.893 min; RT3: 11.789 min; and RT4: 13.674 min. The second isomer (RT2: 10.893 min) was collected to give 40 mg (purity: 99.8%, yield: 7%) of (S)-2-((R)-3-(5-amino-6-oxo-1,6-dihydropyridazin-3-yl)-4,4-difluoropiperidin-1-yl)-N-(5-fluoropyridin-2-yl)propanamide as white solid. LCMS (ES, m/s): 397 [M+H]+ $^1$H NMR: (400 MHz, CD$_3$OD) δ 8.37 (d, J=2.0 Hz, 1H), 8.29 (dd, J=9.2, 4.0 Hz, 1H), 7.67-7.62 (m, 1H), 6.45 (s, 1H), 3.52-3.47 (m, 1H), 3.31-3.23 (m, 1H), 3.09-2.98 (m, 2H), 2.80-2.77 (m, 2H), 2.35-2.21 (m, 1H), 2.09-2.03 (m, 1H), 1.31 (d, J=7.2 Hz, 3H).

Example 144 was synthesized in an analogous manner using the designated Intermediate in Step 9.

| Ex | Name | Structure | ¹H NMR | LC/MS: (M + H)⁺; retention time (min); LC/MS Method of analysis | Int |
|---|---|---|---|---|---|
| 144 | (S)-2-((R)-3-(5-amino-6-oxo-1,6-dihydropyridazin-3-yl)-4,4-difluoropiperidin-1-yl)-N-(6-(cyclopropyl methoxy) pyridazin-3-yl)propanamide | 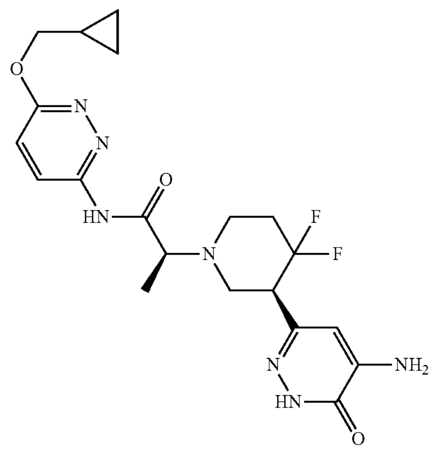 [SMILES: C[C@@H](C(=O)Nc1ccc(OCC2CC2)nn1)N1CCC(F)(F)[C@@H](c2cc(N)c(=O)[nH]n2)C1] | ¹H NMR: (400 MHz, CD₃OD) δ ppm 8.44 (d, J = 9.6 Hz, 1H), 7.19 (d, J = 9.6 Hz, 1H), 6.48 (s, 1H), 4.28 (d, J = 7.2 Hz, 2H), 3.59-3.55 (m, 1H), 3.37-3.31 (m, 1H), 3.00-2.96 (m, 1H), 2.94-2.89 (m, 2H), 2.72-2.68 (m, 1H), 2.24-2.04 (m, 2H), 1.34-1.32 (m, 4H), 0.64-0.60 (m, 2H), 0.40-0.38 (m, 2H). | 450; rt 1.421. LC/MS Method 15 | 14 |

Example 145

(S)—N-(5-(cyclopropylmethoxy)pyridin-2-yl)-2-((R)-4,4-difluoro-3-(6-oxo-1,6-dihydropyridazin-3-yl)piperidin-1-yl)propanamide

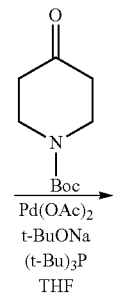

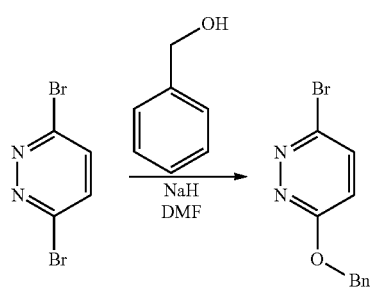

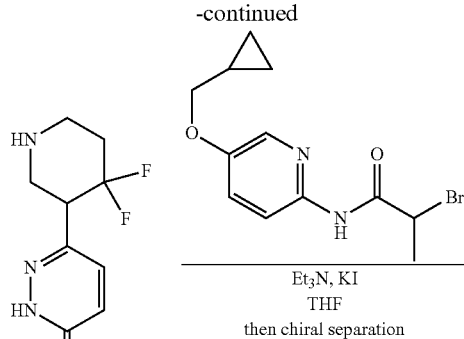

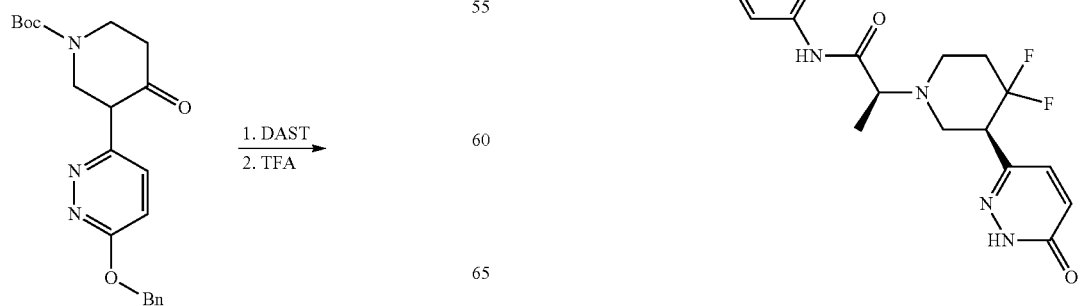

Step 1

To phenylmethanol (4.57 g, 42.31 mmol, 1.0 eq) in DMF (50 mL) at 0° C. was added sodium hydride (2.54 g, 63.47 mmol, 1.5 eq, 60%), in several batches. After 30 min, 3,6-dibromopyridazine (10.00 g, 42.37 mmol, 1.0 eq) was added, and the resulting mixture was stirred 1 h at 80° C., cooled to room temperature, poured into ice water (300 mL), and extracted with ethyl acetate (300 mL×3). The combined organic extracts were washed with brine (800 mL), dried over sodium sulfate, concentrated and applied onto a silica gel column, eluting with ethyl acetate in petroleum ether (0-50%) to give 7.5 g (yield: 57%, purity: 85%) of 3-(benzyloxy)-6-bromopyridazine as a yellow solid. LCMS: (ES, m/s) 265 [M+H]+, retention time 1.326 min, LCMS Method 30. $^1$H NMR: (300 MHz, CDCl$_3$) δ ppm 7.53-7.50 (m, 3H), 7.45-7.37 (m, 3H), 6.92 (d, J=9.0 Hz, 1H), 5.55 (s, 2H).

Step 2 t-BuONa (850 mg, 9.48 mmol, 2.5 eq) in THF (16 mL) was stirred for 10 min, followed by addition of Pd(OAc)$_2$ (84 mg, 0.38 mmol, 0.1 eq) and (t-Bu)$_3$P (765 mg, 0.38 mmol, 0.1 eq, 10% in hexane). After 5 min, 3-(benzyloxy)-6-bromopyridazine (1.00 g, 3.79 mmol, 1.0 eq) and tert-butyl 4-oxopiperidine-1-carboxylate (1.13 g, 5.68 mmol, 1.5 eq) were added, and the mixture was flushed with nitrogen (3×) and heated to 40° C. After 20 h, the reaction was quenched with water (400 mL) and extracted with ethyl acetate (400 mL×3). The organic phases were combined, washed with brine (1 L), dried over Na$_2$SO$_4$ and concentrated. The residue was dissolved in DCM (100 ml), treated with silica (100-200 mesh, 70.0 g), concentrated and loaded onto a silica gel column (330 g, 100-200 mesh), eluting with 0-50% ethyl acetate in petroleum ether to give 3.9 g (crude) of tert-butyl 3-(6-(benzyloxy)pyridazin-3-yl)-4-oxopiperidine-1-carboxylate as a yellow oil. LCMS: (ES, m/s) 384 [M+H]+.

Step 3

To tert-butyl 3-(6-(benzyloxy)pyridazin-3-yl)-4-oxopiperidine-1-carboxylate (3.90 g, 10.2 mmol, 1.0 eq) in DCM (40 mL) at 0° C. was added diethylaminosulfur trifluoride (4.92 g, 30.5 mmol, 3.0 eq), dropwise, and the reaction was warmed to rt. After 18 h, the mixture was poured into ice/water (200 mL) and extracted with dichloromethane (200 mL×3). The combined organic phases were dried over sodium sulfate, concentrated and applied onto a silica gel column, eluting with ethyl acetate in petroleum ether (0-50%) to give 620 mg (yield: 15% (two steps), purity: 91%) tert-butyl 3-(6-(benzyloxy)pyridazin-3-yl)-4,4-difluoropiperidine-1-carboxylate as a yellow oil. LCMS: (ES, m/s) 406 [M+H]+. $^1$H NMR: (300 MHz, CDCl$_3$) δ ppm 7.51-7.28 (m, 6H), 7.01 (d, J=9.0 Hz, 1H), 5.58 (s, 2H), 4.43-4.36 (m, 1H), 4.05-3.90 (m, 1H), 3.62-3.42 (m, 2H), 3.16-3.00 (m, 1H), 2.26-2.16 (m, 2H), 1.47 (s, 9H).

Step 4

To tert-butyl 3-(6-(benzyloxy)pyridazin-3-yl)-4,4-difluoropiperidine-1-carboxylate (620 mg, 1.53 mmol, 1.0 eq) in dichloromethane (10 mL), trifluoroacetic acid (3 mL) was added dropwise. The mixture was stirred for 1 h and concentrated to give 500 mg (crude) 6-(4,4-difluoropiperidin-3-yl)pyridazin-3 (2H)-one as a yellow oil which was used without purification. LCMS (ES, m/s): 216 [M+H]+

Step 5

To 6-(4,4-difluoropiperidin-3-yl)pyridazin-3 (2H)-one (as a free base) (400 mg, 1.85 mmol, 1.0 eq) and 2-bromo-N-(5-(cyclopropylmethoxy)pyridin-2-yl)propanamide (Intermediate 22) (556 mg, 1.85 mmol, 1.0 eq) in THF (15 mL), triethylamine (1.88 g, 18.61 mmol, 10.0 eq) and potassium iodide (308 mg, 1.85 mmol, 1.0 eq) were added, and the reaction was stirred for 16 h at 60° C. The mixture was poured into water (100 mL) and extracted with ethyl acetate (100 mL×3). The combined organic phases were washed with brine (200 mL), dried over sodium sulfate, concentrated and purified by C18 column chromatography, eluting with 5-90% AcCN in water (10 mmom/L NH$_4$HCO$_3$) to give 200 mg of a yellow syrup. This material was separated by chiral-HPLC (CHIRALPAK IA, 2×25 cm, 5 um; Mobile Phase A: Hex [8 mmol/L, NH3MeOH], Mobile Phase B: EtOH; Flow rate: 18 mL/min; 1:1 A:B) to give peaks with retention times of RT1: 9.86 min; RT2: 13.301 min; and RT3: 19.31 min. The third peak (RT3: 19.31 min) was collected and separated by chiral-HPLC (CHIRALPAK IF, 2×25 cm, 5 um; Mobile Phase A: Hex [8 mmol/L, NH3MeOH], Mobile Phase B: EtOH; Flow rate: 14 mL/min; 1:1 A:B) to give peaks with retention times of RT1: 16.432 min and RT2: 21.38 min. The second peak (RT2: 21.38 min) was collected to give 12.4 mg (yield: 6%, purity: 99%, ee %: 100%) of rel-(S)—N-(5-(cyclopropylmethoxy)pyridin-2-yl)-2-((R)-4,4-difluoro-3-(6-oxo-1,6-dihydropyridazin-3-yl)piperidin-1-yl)propanamide as a yellow solid. LCMS (ES, m/s): 434 [M+H]+ $^1$H NMR: (300 MHz, DMSO-d$_6$) δ 13.06 (s, 1H), 10.11 (s, 1H), 8.03-8.00 (m, 2H), 7.44-7.40 (m, 2H), 6.85 (d, J=9.6 Hz, 1H), 3.86 (d, J=6.9 Hz, 2H), 3.64-3.62 (m, 1H), 3.53-3.42 (m, 1H), 3.05-3.02 (m, 1H), 2.94-2.87 (m, 2H), 2.49-2.47 (m, 1H), 2.18-2.07 (m, 2H), 1.21-1.19 (m, 4H), 0.59-0.56 (m, 2H), 0.33-0.32 (m, 2H).

Examples 146-149 were synthesized in an analogous manner using the designated Intermediate in Step 5.

| Ex | Name | Structure | ¹H NMR | LC/MS: (M + H)⁺; retention time (min); LC/MS Method of analysis | Int |
|---|---|---|---|---|---|
| 146 | (S)-N-(6-(cyclopropyl methoxy) pyridazin-3-yl)-2-((R)-4,4-difluoro-3-(6-oxo-1,6-dihydropyridazin-3-yl)piperidin-1-yl)propanamide | 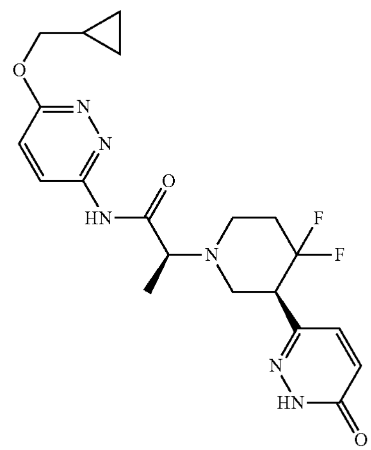 [SMILES: C[C@@H](C(=O)Nc1ccc(OCC2CC2)nn1)N1CCC(F)(F)[C@@H](c2ccc(=O)[nH]n2)C1] | ¹H NMR: (400 MHz, CD₃OD) δ ppm 8.42 (d, J = 9.6 Hz, 1H), 7.56-7.53 (m, 1H), 7.22-7.19 (m, 1H), 6.95 (d, J = 10.0 Hz, 1H), 4.27-4.23 (m, 2H), 3.63-3.53 (m, 2H), 3.30-3.06 (m, 2H), 2.97-2.94 (m, 1H), 2.73-2.66 (m, 1H), 2.28-2.17 (m, 2H), 1.40-1.30 (m, 3H), 1.29-1.28 (m, 1H), 0.65-0.58 (m, 2H), 0.40-0.36 (m, 2H). | 435; rt 1.444. LC/MS Method 15 | 14 |
| 147 | (S)-N-(5-cyclopropyl pyridin-2-yl)-2-((R)-4,4-difluoro-3-(6-oxo-1,6-dihydropyridazin-3-piperidin-1-yl)propanamide | 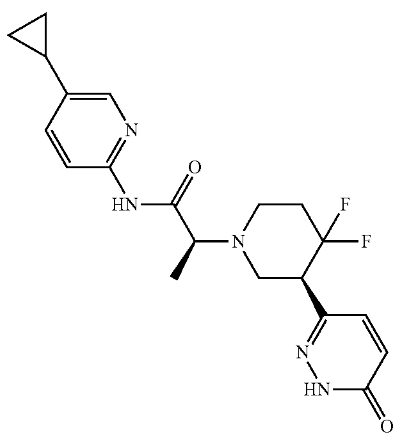 [SMILES: C[C@@H](C(=O)Nc1ccc(C2CC2)cn1)N1CCC(F)(F)[C@@H](c2ccc(=O)[nH]n2)C1] | ¹H NMR: (400 MHz, CD₃OD) δ ppm 8.21 (s, 7.55-7.48 (m, 2H), 6.98-6.94 (m, 1H), 3.59-3.54 (m, 2H), 3.15-3.10 (m, 1H), 3.06-3.03 (m, 1H), 2.97-3.93 (m, 1H), 2.76-2.70 (m, 1H), 2.26-2.20 (m, 2H), 1.97-1.91 (m, 1H), 1.34 (d, J = 6.8 Hz, 3H), 1.04-0.98 (m, 2H), 0.75-0.67 (m, 2H). | 404; rt 1.452. LC/MS Method 14 | 2 |
| 148 | (S)-2-((R)-4,4-difluoro-3-(6-oxo-1,6-dihydropyridazin-3-yl)piperidin-1-yl)-N-(5-fluoropyridin-2-yl)propanamide | 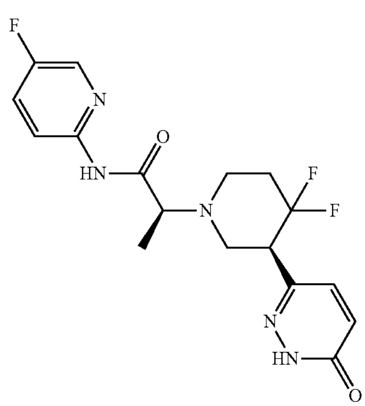 [SMILES: C[C@@H](C(=O)Nc1ccc(F)cn1)N1CCC(F)(F)[C@@H](c2ccc(=O)[nH]n2)C1] | ¹H NMR: (400 MHz, CD₃OD) δ ppm 8.28-8.24 (m, 2H), 7.65-7.60 (m, 1H), 7.53 (d, J = 10.0 Hz, 1H), 6.94 (d, J = 10.0 Hz, 1H), 3.60-3.53 (m, 2H), 3.12-3.02 (m, 2H), 2.94-2.90 (m, 1H), 2.73-2.70 (m, 1H), 2.25-2.21 (m, 2H), 1.33 (d, J = 7.2 Hz, 3H). | 382; rt 1.264. LC/MS Method 14 | 1 |

| Ex | Name | Structure | ¹H NMR | LC/MS: (M + H)⁺; retention time (min); LC/MS Method of analysis | Int |
|---|---|---|---|---|---|
| 149 | (S)-N-(5-chloropyridin-2-yl)-2-((R)-4,4-difluoro-3-(6-oxo-1,6-dihydropyridazin-3-yl)piperidin-1-yl)propanamide | 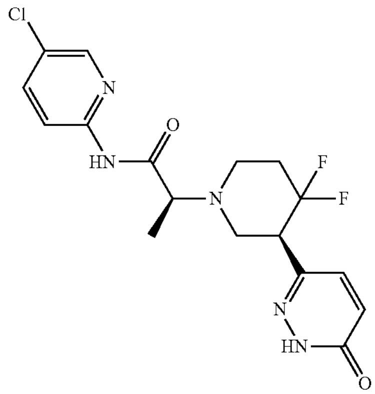 [SMILES: C[C@@H](C(=O)Nc1ccc(Cl)cn1)N1CCC(F)(F)[C@@H](c2ccc(=O)[nH]n2)C1] | ¹H NMR: (400 MHz, CD₃OD) δ ppm 8.37 (d, J = 2.4 Hz, 1H), 8.24 (d, J = 9.0 Hz, 1H), 7.84-7.81 (m, 1H), 7.53 (d, J = 9.9 Hz, 1H), 6.94 (d, J = 9.9 Hz, 1H), 3.62-3.51 (m, 2H), 3.12-2.98 (m, 2H), 2.94-2.89 (m, 1H), 2.77-2.65 (m, 1H), 2.32-2.25 (m, 2H), 1.34-1.32 (m, 3H). | 398; rt 1.416. LC/MS Method 14 | 3 |

Example 150

(S)—N-(5-(cyclopropylmethoxy)pyridin-2-yl)-2-((S)-4,4-difluoro-3-(1-methyl-6-oxo-1,6-dihydro-pyridin-3-yl)piperidin-1-yl)propanamide

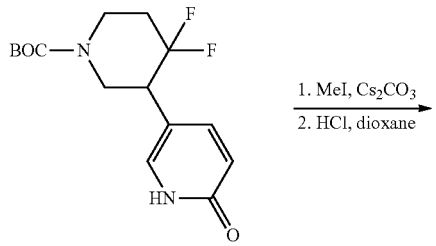

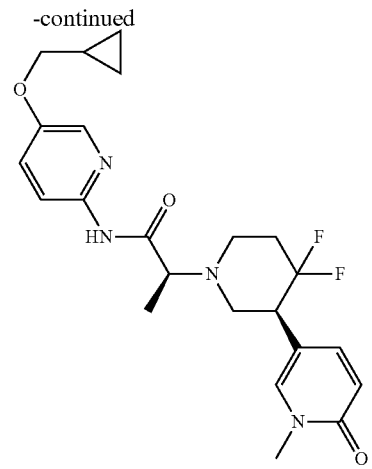

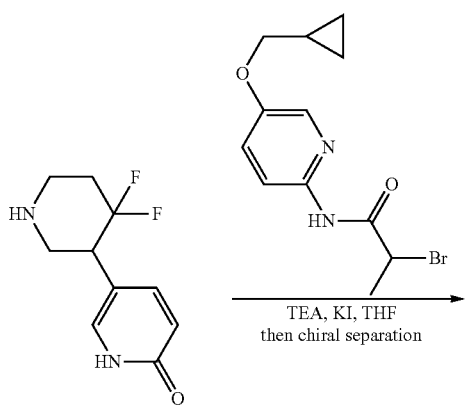

Step 1 tert-Butyl 4,4-difluoro-3-(6-oxo-1,6-dihydropyridin-3-yl) piperidine-1-carboxylate (Example 1, Step 3) (628 mg, 2 mmol, 1.0 eq), CH₃I (852 mg, 6 mmol, 3.0 eq) and Cs₂CO₃ (1.96 g, 6 mmol, 3.0 eq) in DMF (10 mL) were stirred at room temperature for 16 h, diluted with water (100 mL) and extracted with ethyl acetate (100 mL×2). The combined organic layers were washed with brine (100 mL×2), dried over sodium sulfate, concentrated and applied onto a silica gel column, eluting with ethyl acetate:petroleum ether (1:1) to give 650 mg (purity: 95%) of tert-butyl 4,4-difluoro-3-(1-methyl-6-oxo-1,6-dihydropyridin-3-yl) piperidine-1-carboxylate as a colorless oil.

LCMS: (ES, m/z): 329 [M+H]+. ¹H NMR (300 MHz, DMSO-d₆) δ 7.66 (d, J=2.4 Hz, 1H), 7.37 (dd, J=9.6, 2.4 Hz, 1H), 6.35 (d, J=9.6 Hz, 1H), 4.07-3.94 (m, 4H), 3.93 (s, 2H), 3.15-2.91 (m, 2H), 2.18-1.76 (m, 1H), 1.39-1.37 (m, 10H).

Step 2 tert-Butyl 4,4-difluoro-3-(1-methyl-6-oxo-1,6-dihydro-pyridin-3-yl) piperidine-1-carboxylate (650 mg, 2 mmol, 1.0 eq) and HCl (15 mL, 4M in dioxane) were stirred for 2 h and concentrated to give 600 mg of 5-(4,4-difluoropiperidin-3- yl)-1-methylpyridin-2 (1H)-one as a colorless oil which was used without purification. LCMS (ES, m/z): 229 [M+H]+. $^1$H NMR: (300 MHz, DMSO-d$_6$) δ 9.98 (s, 1H), 9.84 (s, 1H), 7.77 (d, J=2.6 Hz, 1H), 7.39 (d, J=9.3 Hz, 1H), 6.38 (d, J=9.3 Hz, 1H), 3.61-3.52 (m, 1H), 3.41-3.29 (m, 4H), 3.30-3.25 (m, 1H), 3.04-2.97 (m, 2H), 2.44-2.31 (m, 2H).

Step 3

A mixture of 5-(4,4-difluoropiperidin-3-yl)-1-methylpyridin-2 (1H)-one hydrochloride (277 mg, 1.05 mmol, 1.5 eq), 2-bromo-N-(5-(cyclopropylmethoxy)pyridin-2-yl)propanamide (Intermediate 22) (210 mg, 0.7 mmol, 1.0 eq), TEA (141 mg, 1.4 mmol, 2.0 eq) and KI (116 mg, 0.7 mmol, 1 eq) in THF (10 mL) was stirred 72 h at 60° C. The reaction was poured into water (100 mL) and extracted with EtOAc (100 mL×2). The organic layers were washed with brine (2×200 mL), dried over sodium sulfate, concentrated and purified over a silica gel column, eluting with methanol:dichloromethane (1:20) to give 0.2 g product as a yellow solid. This material was treated for chiral separation (CHIRAL ART Cellulose-SB, 2×25 cm, 5 um; Mobile phase A: Hex [8 mmol/L NH$_3$-MeOH], Mobile phase B: EtOH, Flow rate: 20 mL/min; 1:1 A:B); which gave peaks with retention times RT1: 5.97 min and RT2: 7.072. The second peak (RT2: 7.027 min) was collected to give 25 mg (8% yield) (S)—N-(5-(cyclopropylmethoxy)pyridin-2-yl)-2-((S)-4,4-difluoro-3-(1-methyl-6-oxo-1,6-dihydropyridin-3-yl)piperidin-1-yl)propanamide as a white solid. LCMS (ES, m/s): 447 [M+H]+ $^1$H NMR: (400 MHz, CD$_3$OD) δ 8.05 (d, J=9.2 Hz, 1H), 7.99-7.98 (m, 1H), 7.67-7.66 (m, 1H), 7.59-7.56 (m, 1H), 7.42-7.39 (m, 1H), 6.52 (d, J=9.2 Hz, 1H), 3.87 (d, J=7.2 Hz, 2H), 3.57 (s, 3H), 3.55-3.48 (m, 1H), 3.35-3.32 (m, 1H), 2.99-2.97 (m, 3H), 2.65-2.59 (m, 1H), 2.28-2.15 (m, 2H), 1.34 (d, J=7.2 Hz, 3H), 1.29-1.22 (m, 1H), 0.65-0.60 (m, 2H), 0.38-0.34 (m, 2H).

Example 151

(S)-2-((S)-4,4-difluoro-3-(6-oxo-5-(2,2,2-trifluoroethyl)-1,6-dihydropyridin-3-yl)piperidin-1-yl)-N-(5-fluoropyridin-2-yl)propanamide

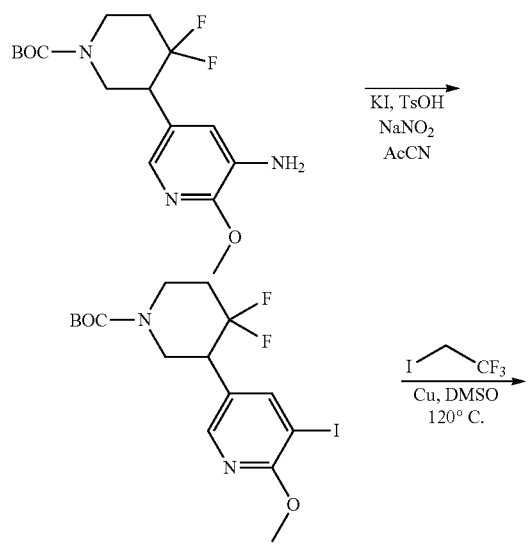

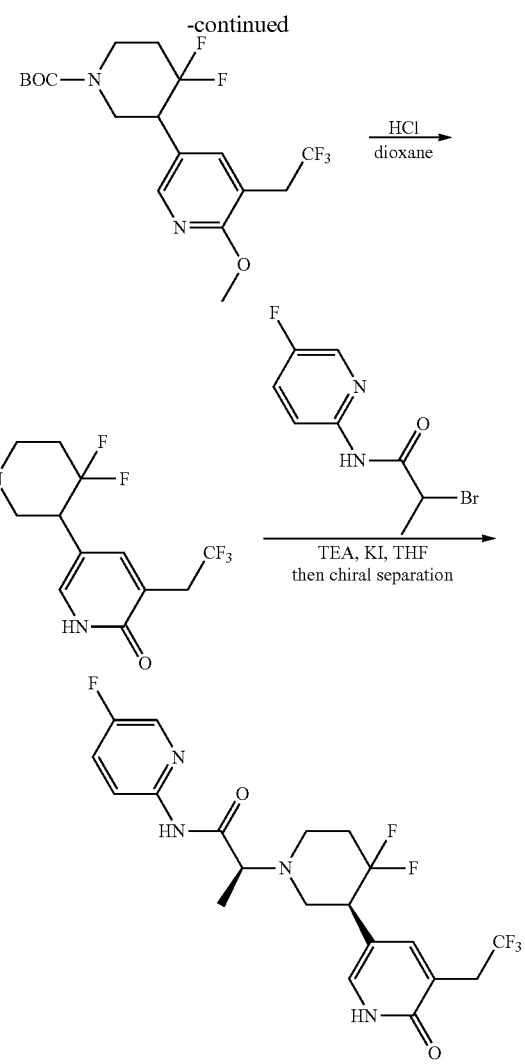

To tert-butyl 3-(5-amino-6-methoxypyridin-3-yl)-4,4-difluoropiperidine-1-carboxylate (Example 138, Step 2) (800 mg, 2.33 mmol, 1 eq) and tosic acid hydrate (1329 mg, 6.99 mmol, 3 eq) in acetone (30 mL) at 0° C. was added, dropwise, a solution of sodium nitrite (321 mg, 4.66 mmol, 2 eq) and potassium iodide (774 mg, 4.66 mmol, 2 eq) in water (10.0 mL) over 5 min. The reaction was stirred at rt for 1 h, quenched NaHSO$_3$ (100 mL, aq., sat.) and extracted with ethyl acetate (100 mL×3). The combined organic layers were washed with NaHCO$_3$ (100 mL, aq., sat.), dried over sodium sulfate, concentrated and applied onto a silica gel column, eluting with ethyl acetate:petroleum ether (1:1) to give 400 mg (purity: 90%, yield: 37.3%) of tert-butyl 4,4-difluoro-3-(5-iodo-6-methoxypyridin-3-yl)piperidine-1-carboxylate as a yellow solid. LCMS: (ES, m/s) 455 [M+H]+. $^1$H NMR: (400 MHz, CDCl$_3$) δ ppm 8.07 (s, 1H), 8.03 (s, 1H), 4.30-4.15 (m, 2H), 4.02 (s, 3H), 3.23-3.14 (m, 2H), 2.21-2.13 (m, 1H), 2.09-2.00 (m, 1H), 1.96-1.73 (m, 1H), 1.50 (s, 9H).

Step 2

To tert-butyl 4,4-difluoro-3-(5-iodo-6-methoxypyridin-3-yl)piperidine-1-carboxylate (800 mg, 1.7 mmol, 1 eq) in dimethyl sulfoxide (4 mL) were added 1,1,1-trifluoro-2-iodoethane (3.5 g, 17 mmol, 10 eq) and copper (2 g, 31 mmol, 18 eq), and the reaction mixture was stirred at 120°

C. for 48 h. The reaction was cooled to room temperature, diluted with water (100 mL) and extracted with ethyl acetate (100 mL×3). The combined organic extracts were washed with brine (50 mL×3), dried over sodium sulfate, concentrated and purified by reverse phase chromatography (C18 column, 80 g, 19×150 mm 5 um), eluting with 5-95% AcCN in water (10 mM TFA) to give 200 mg (purity: 87%, yield: 28%) of tert-butyl 4,4-difluoro-3-(6-methoxy-5-(2,2,2-trifluoroethyl)pyridin-3-yl)piperidine-1-carboxylate as a brown solid. LCMS: (ES, m/s) 411 [M+H]+, retention time 0.861 min, LCMS Method 37. $^1$H NMR: (400 MHz, CD$_3$OD) δ ppm 8.11 (d, J=2.4 Hz, 1H), 7.69 (d, J=2.4 Hz, 1H), 4.24-4.09 (m, 2H), 4.06-3.98 (m, 2H), 3.97 (s, 3H), 3.55-3.51 (m, 2H), 3.37-3.31 (m, 1H), 3.29-3.14 (m, 1H), 2.23-1.93 (m, 1H), 1.49 (s, 9H).

Step 3 tert-Butyl 4,4-difluoro-3-(6-methoxy-5-(2,2,2-trifluoroethyl)pyridin-3-yl)piperidine-1-carboxylate (200 mg, 0.48 mmol, 1.0 eq), dioxane (2 mL) and 6 M HCl (2 mL, aq.) were stirred at 80° C. for 24 h, concentrated, diluted with water (10 mL), and adjusted to pH 6-7 with sodium bicarbonate (aq., sat.). The resulting solution was concentrated and purified by reverse phase chromatography (C18 column, 40 g, Column 19×150 mm 5 um), eluting with 5-95% AcCN in water (10 mM NH$_4$HCO$_3$) to give 100 mg (purity: 95%, yield: 70%) of 5-(4,4-difluoropiperidin-3-yl)-3-(2,2,2-trifluoroethyl)pyridin-2 (1H)-one as a brown solid. LCMS (ES, m/s): 297 [M+H]+ $^1$H NMR: (400 MHz, CD$_3$OD) δ ppm 7.66 (s, 1H), 7.38 (d, J=2.4 Hz, 1H), 3.47-3.37 (m, 3H), 3.37 (s, 1H), 3.13-3.10 (m, 1H), 3.06-2.91 (m, 2H), 2.93-2.82 (m, 1H), 2.15-2.11 (m, 1H), 2.08-1.86 (m, 1H).

Step 4

A mixture of 5-(4,4-difluoropiperidin-3-yl)-3-(2,2,2-trifluoroethyl)pyridin-2 (1H)-one (100 mg, 0.33 mmol, 1.0 eq), 2-bromo-N-(5-fluoropyridin-2-yl)propanamide (Intermediate 1) (95 mg, 0.39 mmol, 1.2 eq), Et$_3$N (168 mg, 1.6 mmol, 5 eq) and KI (55 mg, 0.33 mmol, 1.0 eq) in DMF (8 mL) was stirred 2 h at 60° C., quenched with water (50 mL) and extracted with ethyl acetate (50 mL×3). The combined organic layers were dried over Na$_2$SO$_4$, concentrated and applied onto a silica gel column, eluting with methanol: dichloromethane (1:10) to give 80 mg of an off white solid. The material was chirally separated (CHIRALPAK IA, 2×25 cm, 5 um; Mobile Phase A: Hex [8 mM NH$_3$.MeOH], Mobile Phase B; Flow rate: 20 mL/min; 1:1 A:B) to give peaks with retention times of RT1:11.103 min, RT2:12.453 min and RT3:18.199 min. The second peak (Rt: 12.453 min) was collected and concentrated to give 20 mg (ee %=90%) of product. The product was repurified (CHIRALPAK IC, 2×25 cm, 5 um; Mobile Phase A:Hex [8 mM NH$_3$.MeOH], Mobile Phase B:IPA; Flow rate: 20 mL/min; 1:1 A:B, RT: 16.989 min) to give 8 mg (purity: 98%, yield: 5%) of (S)-2-((S)-4,4-difluoro-3-(6-oxo-5-(2,2,2-trifluoroethyl)-1, 6-dihydropyridin-3-yl)piperidin-1-yl)-N-(5-fluoropyridin-2-yl)propanamide as a white solid. LCMS (ES, m/s): 463 [M+H]+ $^1$H NMR: (400 MHz, CD$_3$OD) δ ppm 8.22-8.18 (m, 2H), 7.70 (s, 1H), 7.65-7.60 (m, 1H), 7.42 (d, J=2.4 Hz, 1H), 3.56-3.53 (m, 1H), 3.50-3.41 (m, 3H), 2.99-2.89 (m, 3H), 2.64-2.60 (m, 1H), 2.21-2.14 (m, 2H), 1.36 (d, J=7.2 Hz, 3H).

Example 152

(S)—N-(5-(cyclopropylmethoxy)pyridin-2-yl)-2-((S)-4,4-difluoro-3-(5-(2-hydroxypropan-2-yl)-6-oxo-1,6-dihydropyridin-3-yl)piperidin-1-yl)propanamide

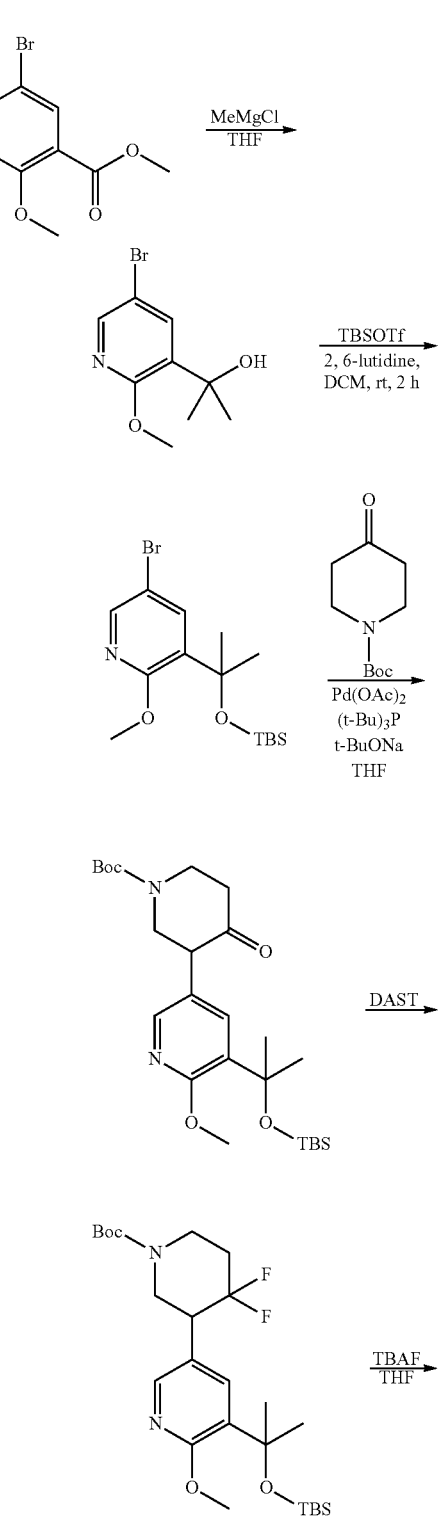

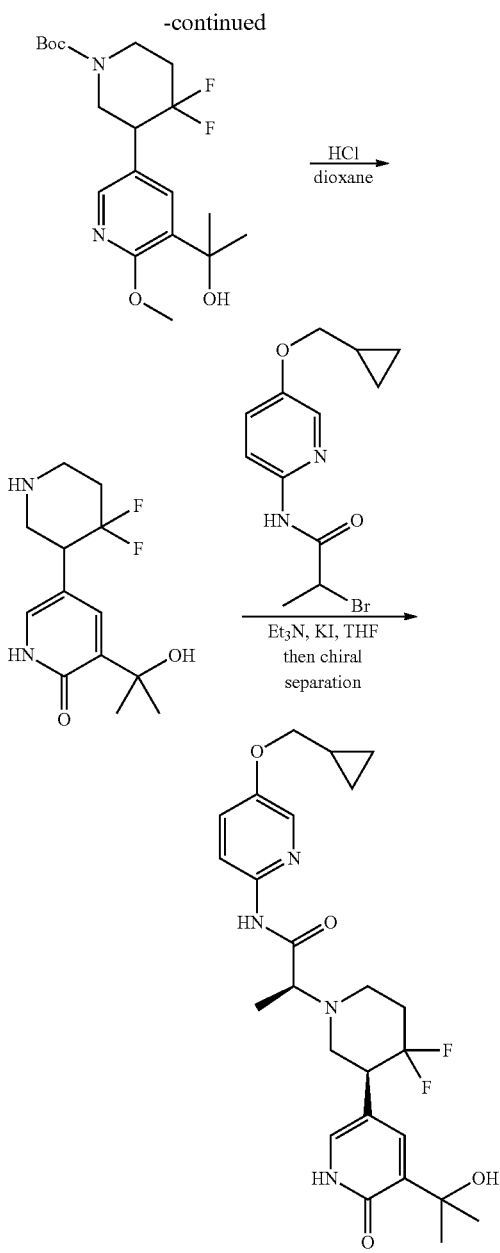

TBSOTf (8.73 g, 33.06 mmol, 1.5 eq), dropwise. After 2 h, the reaction was quenched with water (100 mL) and extracted with ethyl acetate (100 mL×2). The organic phases were combined, dried over $Na_2SO_4$, concentrated and applied onto a silica gel column, eluting with ethyl acetate: petroleum ether (1:20) to give 6.7 g (purity: 73%, yield: 84%) of 5-bromo-3-(2-(tert-butyldimethylsilyloxy)propan-2-yl)-2-methoxypyridine as a light yellow oil. LCMS: (ES, m/s) 360 [M+H]+. $^1$H NMR: (300 MHz, $CD_3OD$-d4) δ 8.16-8.08 (m, 2H), 3.95 (s, 3H), 1.65 (s, 6H), 1.01 (s, 9H), 0.21 (s, 6H).

Step 3 t-BuONa (1.14 g, 11.85 mmol, 2.5 eq) and THF (16 mL) were stirred for 10 min at 43° C., then $Pd(OAc)_2$ (0.11 g, 0.47 mmol, 0.1 eq) and $(t-Bu)_3P$ (96 mg, 0.47 mmol, 0.1 eq) were added. After 5 min, 5-bromo-3-(2-(tert-butyldimethylsilyloxy)propan-2-yl)-2-methoxypyridine (1.7 g, 4.74 mmol, 1.0 eq) and tert-butyl 4-oxopiperidine-1-carboxylate (1.41 g, 7.11 mmol, 1.5 eq) were added. After 15 h, the mixture was quenched with water (200 mL) and extracted with ethyl acetate (200 mL×2). The organic phases were combined, dried over $Na_2SO_4$, concentrated and applied onto a silica gel column, eluting with ethyl acetate:petroleum (1:10) to give 6.3 g (purity: 64%) of tert-butyl 3-(5-(2-(tert-butyldimethylsilyloxy)propan-2-yl)-6-methoxypyridin-3-yl)-4-oxopiperidine-1-carboxylate as a light yellow oil. LCMS: (ES, m/s) 479 [M+H]$^+$. $^1$H NMR: (400 MHz, $CD_3OD$) δ ppm 7.87-7.82 (m, 2H), 4.29-4.25 (m, 1H), 3.96-3.93 (m, 3H), 3.45-3.35 (m, 2H), 2.90-2.65 (m, 2H), 2.55-2.40 (m, 2H), 1.52-1.49 (m, 15H), 1.00-0.95 (m, 9H), 0.20-0.15 (m, 6H).

Step 4

To tert-butyl 3-(5-(2-(tert-butyldimethylsilyloxy)propan-2-yl)-6-methoxypyridin-3-yl)-4-oxopiperidine-1-carboxylate (6.0 g, 12.55 mmol, 1.0 eq) in DCM (50 ml) at 0° C. was added DAST (4.04 g, 25.10 mmol, 2.0 eq). The mixture was stirred at room temperature for 12 h, quenched with ice/water (100 mL) and extracted with DCM (100 mL×2). The organic phases were combined, dried over $Na_2SO_4$, concentrated and applied onto a silica gel column, eluting with ethyl acetate:petroleum (1:10) to give 1.9 g (purity: 72%, yield: 30%) of tert-butyl 3-(5-(2-(tert-butyldimethylsilyloxy)propan-2-yl)-6-methoxypyridin-3-yl)-4,4-difluoropiperidine-1-carboxylate as light yellow oil. LCMS (ES, m/s): 501 [M+H]+ $^1$H NMR (300 MHz, $CD_3OD$) δ ppm 8.05-8.03 (m, 1H), 7.96 (d, J=2.4 Hz, 1H), 4.25-4.22 (m, 1H), 3.97 (s, 3H), 3.75-3.65 (m, 1H), 3.22-3.05 (m, 3H), 2.20-2.05 (m, 2H), 1.67-1.66 (m, 6H), 1.50 (s, 9H), 1.02 (s, 9H), 0.21-0.20 (m, 6H).

Step 5

To tert-butyl 3-(5-(2-(tert-butyldimethylsilyloxy)propan-2-yl)-6-methoxypyridin-3-yl)-4,4-difluoropiperidine-1-carboxylate (1.9 g, 3.8 mmol, 1.0 eq) in THF (30 ml) at 0° C. was added TBAF (1.0 mol/L, 19.0 ml, 19.0 mmol, 5.0 eq), dropwise. The mixture was stirred at room temperature for 12 h, quenched with water (50 mL) and extracted with ethyl acetate (50 mL×2). The organic phases were combined, dried over $Na_2SO_4$, concentrated and applied onto a silica gel column, eluting with ethyl acetate:petroleum (1:4) to give 1.2 g (purity: 83%, yield: 81%) of tert-butyl 4,4-difluoro-3-(5-(2-hydroxypropan-2-yl)-6-methoxypyridin-3-yl)piperidine-1-carboxylate as a light yellow oil. LCMS (ES, m/s): 387 [M+H]+ $^1$H NMR (300 MHz, $CD_3OD$) δ ppm 7.99-7.97 (m, 1H), 7.91-7.88 (m, 1H), 4.27-4.22 (m, 1H), 4.03-3.95 (s, 3H), 3.78-3.65 (m, 1H), 3.28-3.05 (m, 3H), 2.20-1.98 (m, 2H), 1.59 (s, 6H), 1.49 (s, 9H).

Step 1

To methyl 5-bromo-2-methoxynicotinate (6.5 g, 26.53 mmol, 1.0 eq) in THF (10 mL) at 0° C. was added methylmagnesium chloride (3 M, 88.4 ml, 265.3 mmol, 10 eq), dropwise. The reaction mixture was warmed to room temperature naturally, quenched with $NH_4Cl$ (100 mL, aq., sat.) and extracted with ethyl acetate (100 mL×2). The organic phases were combined, dried over $Na_2SO_4$, concentrated and applied onto a silica gel column, eluting with ethyl acetate:petroleum ether (1:10) to give 5.4 g (purity: 97%, yield: 83%) of 2-(5-bromo-2-methoxypyridin-3-yl)propan-2-ol as a white solid. LCMS: (ES, m/s) 246 [M+H]+. $^1$H NMR: (400 MHz, DMSO-$d_6$) δ 8.14 (d, J=2.8 Hz, 1H), 7.99 (d, J=2.8 Hz, 1H), 5.31 (s, 1H), 3.89 (s, 3H), 1.47 (s, 6H).

Step 2

To 2-(5-bromo-2-methoxypyridin-3-yl)propan-2-ol (5.4 g, 22.04 mmol, 1.0 eq) in DCM (30 mL) was added 2,6-lutidine (4.72 g, 44.08 mmol, 2.0 eq) followed by Step 6

To tert-butyl 4,4-difluoro-3-(5-(2-hydroxypropan-2-yl)-6-methoxypyridin-3-yl)piperidine-1-carboxylate (900 mg, 2.33 mmol, 1.0 eq) in dioxane (10 mL) was added HCl (6 mol/L, 10 mL). The mixture was stirred for 12 h at 80° C., concentrated, diluted with water, and adjusted to pH 8 with sodium bicarbonate (aq., sat.). The resulting solution was concentrated and applied onto a silica gel column, eluting with methanol:dichloromethane (1:5) to give 0.28 g (purity: 31%, yield: 44%) of 5-(4,4-difluoropiperidin-3-yl)-3-(2-hydroxypropan-2-yl)pyridin-2 (1H)-one as a light yellow oil. LCMS (ES, m/s): 273 [M+H]+ $^1$H NMR (300 MHz, CD$_3$OD) δ ppm 7.70-7.68 (m, 1H), 7.35-7.32 (m, 1H), 3.96-3.94 (m, 1H), 3.28-3.20 (m, 2H), 3.16-3.09 (m, 2H), 2.35-2.25 (m, 1H), 2.15-2.05 (m, 1H), 1.57 (s, 6H).

Step 7

To 5-(4,4-difluoropiperidin-3-yl)-3-(2-hydroxypropan-2-yl)pyridin-2 (1H)-one (250 mg, 0.92 mmol, 1.0 eq) and 2-bromo-N-(5-(cyclopropylmethoxy)pyridin-2-yl)propanamide (Intermediate 22) (270 mg, 0.92 mmol, 1.0 eq) in THF (10 mL) were added KI (150 mg, 0.92 mmol, 1.0 eq) and TEA (740 mg, 7.36 mmol, 8.0 eq). The mixture was stirred for 12.0 h at 60° C., quenched with water (100 mL) and extracted with ethyl acetate (100 mL×2). The organic phases were combined, dried over Na$_2$SO$_4$, concentrated and purified by prep-HPLC (Column: XBridge Prep C18 OBD), eluting with 20-42% AcCN in water (0.05% TFA) to give 150 mg product as white solid. This material was separated by chiral-HPLC (CHIRAL ART Cellulose-SB, 2×25 cm, 5 um; Mobile Phase A: Hex [8 mM NH$_3$.MeOH], Mobile Phase B: EtOH; Flow rate: 20 mL/min; 1:1 A:B) to give peaks with retention times of RT1: 13.731 min, RT2-RT3: 15.668-16.733 min and RT4: 23.372 min. The second peak (RT2-RT3: 15.668-16.733 min) was collected and separated by chiral-HPLC (CHIRALPAK IG, 2×25 cm, 5 um; Mobile Phase A: Hex:DCM=3:1 [10 mm NH$_3$.MeOH], Mobile Phase B: EtOH; Flow rate: 20 mL/min; 1:1 A:B) to give peaks with retention times of RT1: 7.018 min and RT2: 9.527 min. The first peak (RT1: 7.018 min) was collected to give 14.0 mg (purity: 98.3%, yield: 3%) of (S)—N-(5-(cyclopropylmethoxy)pyridin-2-yl)-2-((S)-4,4-difluoro-3-(5-(2-hydroxypropan-2-yl)-6-oxo-1,6-dihydropyridin-3-yl)piperidin-1-yl)propanamide as white solid. LCMS (ES, m/s): 491 [M+H]+ $^1$H NMR: (400 MHz, CD$_3$OD) δ ppm 8.06 (d, J=8.8 Hz, 1H), 7.99 (d, J=2.8 Hz, 1H), 7.71 (d, J=2.4 Hz, 1H), 7.43-7.40 (m, 1H), 7.33 (d, J=2.4 Hz, 1H), 3.88 (d, J=6.8 Hz, 2H), 3.53-3.48 (m, 1H), 3.39-3.32 (m, 1H), 3.01-2.90 (m, 3H), 2.65-2.60 (m, 1H), 2.32-2.10 (m, 2H), 1.54 (s, 6H), 1.34 (d, J=6.8 Hz, 3H), 1.26-1.22 (m, 1H), 0.65-0.60 (m, 2H), 0.38-0.34 (m, 2H).

Example 153

(S)-2-((S)-4,4-difluoro-3-(5-(hydroxymethyl)-6-oxo-1,6-dihydropyridin-3-yl)piperidin-1-yl)-N-(5-fluoropyridin-2-yl)propanamide

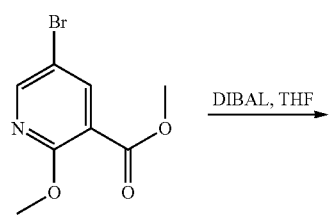

DIBAL, THF

-continued

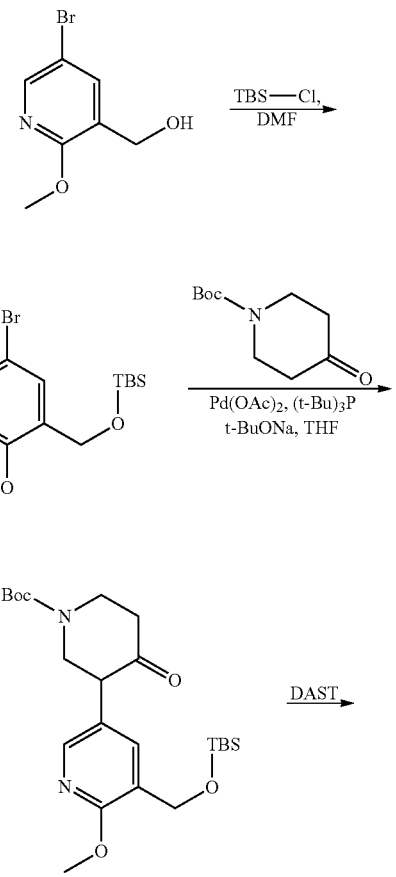

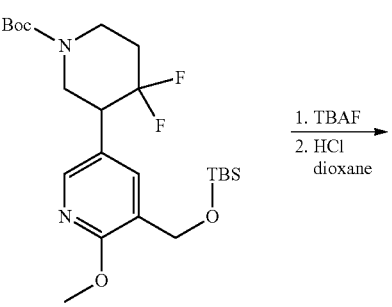

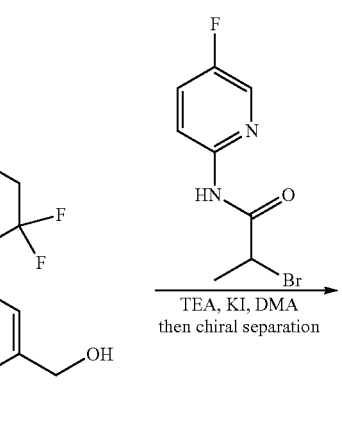

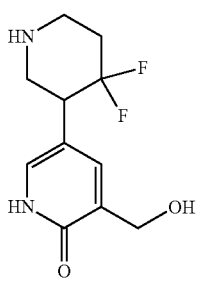

TEA, KI, DMA
then chiral separation

-continued

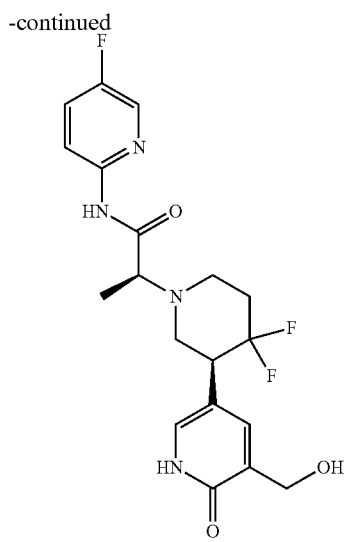

Step 1

To methyl 5-bromo-2-methoxynicotinate (20.0 g, 81.0 mmol, 1.0 eq) in THF (200 mL) at 0° C. was added DIBAL-H (171 mL, 171.0 mmol, 2.1 eq, 1 M in n-hexane). The reaction mixture was stirred at room temperature for 1 h, poured into 10% potassium sodium tartrate tetrahydrate solution (500 mL) at 0° C. and extracted with ethyl acetate (500 mL×2). The organic phases were washed with brine (600 mL), dried over Na$_2$SO$_4$, concentrated and applied to a silica gel column, eluting with 0-25% ethyl acetate in petroleum ether to give 17.0 g (purity: 96%, yield: 92%) of (5-bromo-2-methoxypyridin-3-yl)methanol as a white solid. LCMS: (ES, m/s) 218 [M+H]+, retention time 0.795 min, LCMS Method 33. $^1$H NMR: (400 MHz, DMSO-d$_6$) δ 8.17-8.15 (m, 1H), 7.83-7.81 (m, 1H), 5.38-5.36 (m, 1H), 4.45-4.43 (m, 2H), 3.87 (s, 3H).

Step 2

(5-Bromo-2-methoxypyridin-3-yl)methanol (16.0 g, 73.4 mmol, 1.0 eq), tert-butylchlorodimethylsilane (55.3 g, 367.0 mmol, 5.0 eq), 1H-imidazole (50.0 g, 734.0 mmol, 10.0 eq) and DMAP (0.89 g, 7.34 mmol, 0.1 eq) in DMF (160 mL) were stirred at 60° C. for 2 h, poured into ice/water (200 mL), and extracted with ethyl acetate (200 mL×2). The combined organic phases were washed with brine (400 mL×3), dried over Na$_2$SO$_4$, concentrated and applied onto a silica gel column, eluting with 0-4% ethyl acetate in petroleum ether to give 24.0 g (purity: 80%, yield: 79%) of 5-bromo-3-(((tert-butyldimethylsilyl)oxy)methyl)-2-methoxypyridine as a colorless oil. LCMS: (ES, m/s) 332 [M+H]+. $^1$H NMR: (400 MHz, DMSO-d$_6$) δ 8.21-8.19 (m, 1H), 7.78-7.77 (m, 1H), 4.64-4.63 (m, 2H), 3.88 (s, 3H), 0.92 (s, 9H), 0.11 (s, 6H).

Step 3

Sodium tert-butoxide (1.45 g, 15.0 mmol, 2.5 eq) in THF (16 mL) was stirred at 42° C. for 10 min, followed by addition of tri-t-butylphosphine (1.22 g, 0.60 mmol, 0.1 eq, 10% in hexane) and palladium(II) acetate (0.13 g, 0.6 mmol, 0.1 eq). After 5 min, 5-bromo-3-(((tert-butyldimethylsilyl)oxy)methyl)-2-methoxypyridine (2.0 g, 6 mmol, 1.0 eq) and tert-butyl 4-oxopiperidine-1-carboxylate (1.79 g, 9.0 mmol, 1.5 eq) were added. After 15 h, the mixture was poured into water (300 mL) and extracted with ethyl acetate (300 mL×3). The combined organic phases were washed with brine (500 mL), dried over Na$_2$SO$_4$, and applied onto a silica gel column, eluting with 0-15% ethyl acetate in petroleum ether to give 3.8 g (purity: 32%, yield: 45%) of tert-butyl 3-(5-(((tert-butyldimethylsilyl)oxy)methyl)-6-methoxypyridin-3-yl)-4-oxopiperidine-1-carboxylate as a brown oil. LCMS: (ES, m/s) 451 [M+H]+, retention time 1.469 min, LCMS Method 34. $^1$H NMR: (300 MHz, DMSO-d$_6$) δ 7.89 (d, J=2.4 Hz, 1H), 7.51 (d, J=2.4 Hz, 1H), 5.76 (s, 2H), 4.10-4.07 (m, 1H), 3.87 (s, 3H), 3.64-3.44 (m, 4H), 2.83-2.61 (m, 2H), 1.43 (s, 9H), 0.91 (s, 9H), 0.09 (s, 6H).

Step 4

To tert-butyl 3-(5-(((tert-butyldimethylsilyl)oxy)methyl)-6-methoxypyridin-3-yl)-4-oxopiperidine-1-carboxylate (3.8 g, 8.43 mmol, 1.0 eq) in DCM (40 mL) was added a solution of DAST (2.3 mL, 16.86 mmol, 2.0 eq) in DCM (4 mL), dropwise. After 15 h, the mixture was poured into ice water (100 mL) and extracted with DCM (100 mL×3). The combined organic phases were washed with brine (200 mL), dried over Na$_2$SO$_4$, concentrated and purified via silica gel column, eluting with 0-10% ethyl acetate in petroleum ether to give 0.44 g (purity: 49%, yield: 11%) of tert-butyl 3-(5-(((tert-butyldimethylsilyl)oxy)methyl)-6-methoxypyridin-3-yl)-4,4-difluoropiperidine-1-carboxylate as a yellow oil. LCMS (ES, m/s): 473 [M+H]+, retention time 1.588 min, LCMS Method 36. $^1$H NMR (400 MHz, DMSO-d$_6$) δ ppm 8.02 (d, J=2.4 Hz, 1H), 7.69-7.67 (m, 1H), 4.65 (s, 2H), 4.15-4.05 (m, 1H), 4.04-3.94 (m, 1H), 3.88 (s, 3H), 3.30-3.20 (m, 2H), 3.10-3.00 (m, 1H), 2.20-1.95 (m, 2H), 1.41 (s, 9H), 0.91 (s, 9H), 0.09 (s, 6H).

Step 5

To tert-butyl 3-(5-(((tert-butyldimethylsilyl)oxy)methyl)-6-methoxypyridin-3-yl)-4,4-difluoropiperidine-1-carboxylate (440 mg, 0.93 mmol, 1.0 eq) in THF (4 mL) was added TBAF (4.6 mL, 4.60 mmol, 5.0 eq, 1 M in THF), dropwise. After 2 h, the mixture was poured into water (50 mL) and extracted with ethyl acetate (50 mL×2). The combined organic phases were washed with brine (100 mL), dried over Na$_2$SO$_4$, concentrated and purified via silica gel column, eluting with 0-30% ethyl acetate in petroleum ether to give 270 mg (purity: 78%, yield: 63%) of tert-butyl 4,4-difluoro-3-(5-(hydroxymethyl)-6-methoxypyridin-3-yl)piperidine-1-carboxylate as a colorless oil. LCMS (ES, m/s): 359 [M+H]+, retention time 1.098 min, LCMS Method 34. $^1$H NMR (400 MHz, DMSO-d$_6$) δ ppm 7.99 (d, J=2.0 Hz, 1H), 7.71-7.69 (m, 1H), 5.27-5.24 (m, 1H), 4.46 (d, J=5.2 Hz, 2H), 4.16-4.06 (m, 1H), 3.99-3.90 (m, 1H), 3.87 (s, 3H), 3.30-3.20 (m, 2H), 3.15-3.00 (m, 1H), 2.20-2.02 (m, 2H), 1.42 (s, 9H).

Step 6

To tert-butyl 4,4-difluoro-3-(5-(hydroxymethyl)-6-methoxypyridin-3-yl)piperidine-1-carboxylate (270 mg, 0.75 mmol, 1.0 eq) in dioxane (15 mL) was added HCl (7.5 mL, 6 M in H$_2$O). The reaction was stirred at 80° C. for 2 h and concentrated to give 250 mg (crude) 5-(4,4-difluoropiperidin-3-yl)-3-(hydroxymethyl)pyridin-2 (1H)-one, HCl salt, as a colorless oil, which was used without purification. LCMS (ES, m/s): 245 [M+H]+, retention time 0.438 min, LCMS Method 10. $^1$H NMR (400 MHz, DMSO-d$_6$) δ 11.60 (br, 1H), 9.68-9.57 (m, 1H), 7.44-7.12 (m, 1H), 5.64 (s, 2H), 4.29 (s, 1H), 3.60-3.35 (m, 2H), 3.20-3.00 (m, 1H), 2.79 (s, 2H), 2.45-2.30 (m, 1H), 1.96 (s, 2H).

Step 7

A mixture of 5-(4,4-difluoropiperidin-3-yl)-3-(hydroxymethyl)pyridin-2 (1H)-one (free base) (210 mg, 0.86 mmol, 1.0 eq), 2-bromo-N-(5-fluoropyridin-2-yl)propanamide (Intermediate 1) (212 mg, 0.86 mmol, 1.0 eq), TEA (0.6 mL, 4.30 mmol, 5.0 eq) and KI (143 mg, 0.86 mmol, 1.0 eq) in DMA (5 mL) was stirred at 60° C. for 2 h, poured into water (50 mL) and extracted with ethyl acetate (50 mL×2). The combined organic phases were washed with brine (100 mL), dried over Na₂SO₄, concentrated and purified via a silica gel column, eluting with 0-5% MeOH in dichloromethane to give 110 mg product as a light yellow solid. This material was separated by chiral-HPLC (CHIRAL PAK IE, 2×25 cm, 5 um; Mobile Phase A: Hex [8 mM NH₃·MeOH], Mobile Phase B: EtOH; Flow rate: 20 mL/min; 1:1 A:B) to give peaks with retention times of RT1-RT2: 11.787-12.836 min, RT3: 15.892 min, and RT4: 18.73 4 min. The first peak (RT1-RT2: 11.787-12.836 min) was collected and separated by chiral-HPLC (CHIRAL ART Cellulose-SB S-5 um, 2×25 cm, 5 um; Mobile Phase A: MTBE [10 mm NH₃-MeOH], Mobile Phase B: EtOH; Flow rate: 20 mL/min; 1:1 A:B) to give peaks with retention times of RT1: 15.290 min and RT2: 22.223 min. The second peak (RT2: 22.223 min) was collected to give 7.0 mg (purity: 97.5%, yield: 2%) of (S)-2-((S)-4,4-difluoro-3-(5-(hydroxymethyl)-6-oxo-1,6-dihydropyridin-3-yl)piperidin-1-yl)-N-(5-fluoropyridin-2-yl)propanamide as a white solid. LCMS (ES, m/s): 411 [M+H]+ ¹H NMR: (400 MHz, CD₃OD) δ ppm 8.22-8.19 (m, 2H), 7.71-7.70 (m, 1H), 7.65-7.60 (m, 1H), 7.34 (d, J=2.4 Hz, 1H), 4.49 (s, 2H), 3.57-3.52 (m, 1H), 3.39-3.31 (m, 1H), 3.01-2.89 (m, 3H), 2.67-2.61 (m, 1H), 2.29-2.15 (m, 2H), 1.34 (d, J=6.8 Hz, 3H).

Examples 154-157 were synthesized in an analogous manner using the designated Intermediate in Step 7.

| Ex | Name | Structure | ¹H NMR | LC/MS: (M + H)⁺; retention time (min); LC/MS Method of analysis | Int |
|---|---|---|---|---|---|
| 154 | (S)-N-(6-(cyclopropyl methoxy) pyridazin-3-yl)-2-(4,4-difluoro-3-(5-(hydroxymethyl)-6-oxo-1,6-dihydropyridin-3-yl)piperidin-1-yl)propanamide | 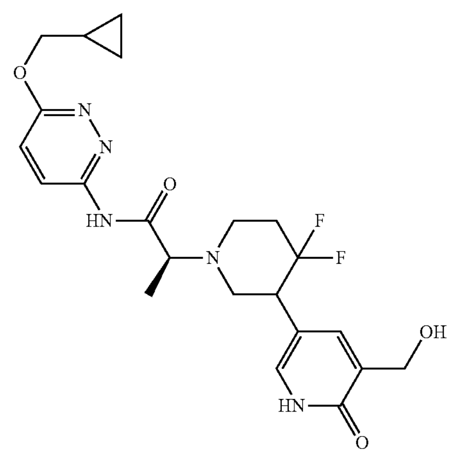 [SMILES: C[C@@H](C(=O)Nc1ccc(OCC2CC2)nn1)N1CCC(F)(F)C(c2c[nH]c(=O)c(CO)c2)C1] | ¹H NMR (400 MHz, CDCl₃) δ ppm 11.76-12.21 (m, 1H), 9.91 (br d, J = 18.58 Hz, 1H), 8.40 (d, J = 10.27 Hz, 1H), 7.51 (br d, J = 8.80 Hz, 1H), 7.29 (d, J = 1.96 Hz, 1H), 7.05 (d, J = 9.29 Hz, 1H), 4.60 (br d, J = 6.36 Hz, 2H), 4.30 (dd, J = 7.09, 1.71 Hz, 2H), 3.54-3.77 (m, 1H), 3.40-3.52 (m, 1H), 3.03-3.29 (m, 1H), 2.80-2.99 (m, 3H), 2.59-2.76 (m, 1H), 2.11-2.36 (m, 2H), 1.36-1.40 (m, 3H), 1.29-1.35 (m, 1H), 0.59-0.71 (m, 2H), 0.39 (q, J = 5.22 Hz, 2H). | 464; rt 0.56. LC/MS Method 5 | 14 |
| 155 | N-(5-chloropyridin-2-yl)-2-(4,4-difluoro-3-(5-(hydroxymethyl)-6-oxo-1,6-dihydropyridin-3-yl)piperidin-1-yl)propanamide | 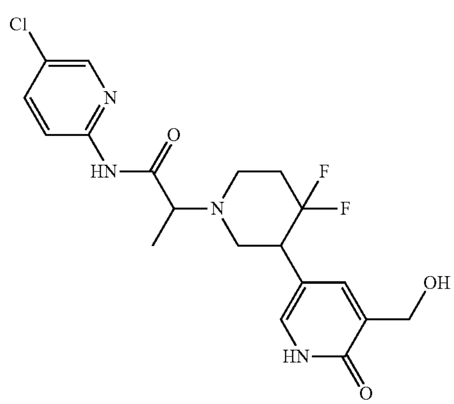 [SMILES: CC(C(=O)Nc1ccc(Cl)cn1)N1CCC(F)(F)C(c2c[nH]c(=O)c(CO)c2)C1] | ¹H NMR (400 MHz, CDCl₃) δ ppm 12.68 (br s, 1H), 9.54 (br d, J = 9.78 Hz, 1H), 8.19-8.28 (m, 2H), 7.69 (dt, J = 9.05, 1.83 Hz, 1H), 7.53 (br s, 1H), 7.30 (t, J = 2.93 Hz, 1H), 4.61 (br s, 2H), 3.73 (br s, 1H), 3.36-3.48 (m, 1H), 3.03-3.26 (m, 1H), 2.78-2.95 (m, 3H), 2.58-2.75 (m, 1H), 2.11-2.33 (m, 2H), 1.37 (d, J = 6.85 Hz, 3H). | 427; rt 0.51. LC/MS Method 5 | 3 |

| Ex | Name | Structure | ¹H NMR | LC/MS: (M + H)⁺; retention time (min); LC/MS Method of analysis | Int |
|---|---|---|---|---|---|
| 156 | (S)-2-((S)-(4,4-difluoro-3-(5-(hydroxymethyl)-6-oxo-1,6-dihydropyridin-3-yl)piperidin-1-yl)-N-(5-(4-fluorophenoxy)pyridin-2-yl)propanamide | 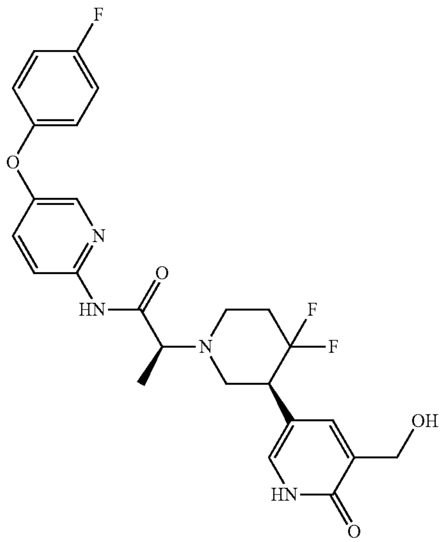 [SMILES: C[C@@H](C(=O)Nc1ccc(Oc2ccc(F)cc2)cn1)N1CCC(F)(F)[C@@H](c2c[nH]c(=O)c(CO)c2)C1] | ¹H NMR (400 MHz, CDCl₃) δ ppm 11.91 (br s, 1H), 9.47 (s, 1H), 8.23 (d, J = 9.29 Hz, 1H), 8.07 (d, J = 2.93 Hz, 1H), 7.56 (br s, 1H), 7.35 (dd, J = 9.05, 2.69 Hz, 1H), 7.29 (br d, J = 1.96 Hz, 1H), 7.02-7.12 (m, 2H), 6.93-7.01 (m, 2H), 4.61 (br s, 2H), 3.71 (br s, 1H), 3.38-3.51 (m, 1H), 3.09-3.27 (m, 1H), 2.82-3.01 (m, 3H), 2.60-2.75 (m, 1H), 2.05-2.37 (m, 2H), 1.38 (br d, J = 6.85 Hz, 3H). | 503; rt 0.67. LC/MS Method 5 | 70 |
| 157 | (S)-2-((S)-4,4-difluoro-3-(5-(hydroxymethyl)-6-oxo-1,6-dihydropyridin-3-yl)piperidin-1-yl)-N-(5-((5-fluoropyridin-2-yl)oxy)pyridin-2-yl)propanamide | 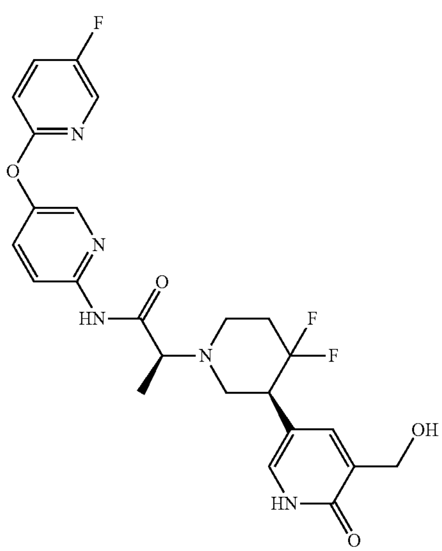 [SMILES: C[C@@H](C(=O)Nc1ccc(Oc2ccc(F)cn2)cn1)N1CCC(F)(F)[C@@H](c2c[nH]c(=O)c(CO)c2)C1] | ¹H NMR (400 MHz, CHLOROFORM-d) δ 12.43 (br. s., 1H), 9.57 (br. s., 1H), 8.33 (d, J = 9.05 Hz, 1H), 8.19 (d, J = 2.69 Hz, 1H), 7.99 (d, J = 3.18 Hz, 1H), 7.57 (dd, J = 8.93, 2.81 Hz, 2H), 7.50 (ddd, J = 8.93, 7.34, 3.06 Hz, 1H), 7.32 (d, J = 2.20 Hz, 1H), 7.00 (dd, J = 8.80, 3.42 Hz, 1H), 4.64 (s, 2H), 3.67-4.11 (m, 1H), 3.41-3.53 (m, 1H), 3.11-3.30 (m, 1H), 2.95 (br. s., 3H), 2.68 (br. s., 1H), 2.06-2.37 (m, 2H), 1.40 (d, J = 6.60 Hz, 3H). | 504; rt 0.83. LC/MS Method 3 | 100 |

Example 158

(S)—N-(5-chloropyridin-2-yl)-2-((S)-3-(6-oxo-1,6-dihydropyridin-3-yl)piperidin-1-yl)propanamide

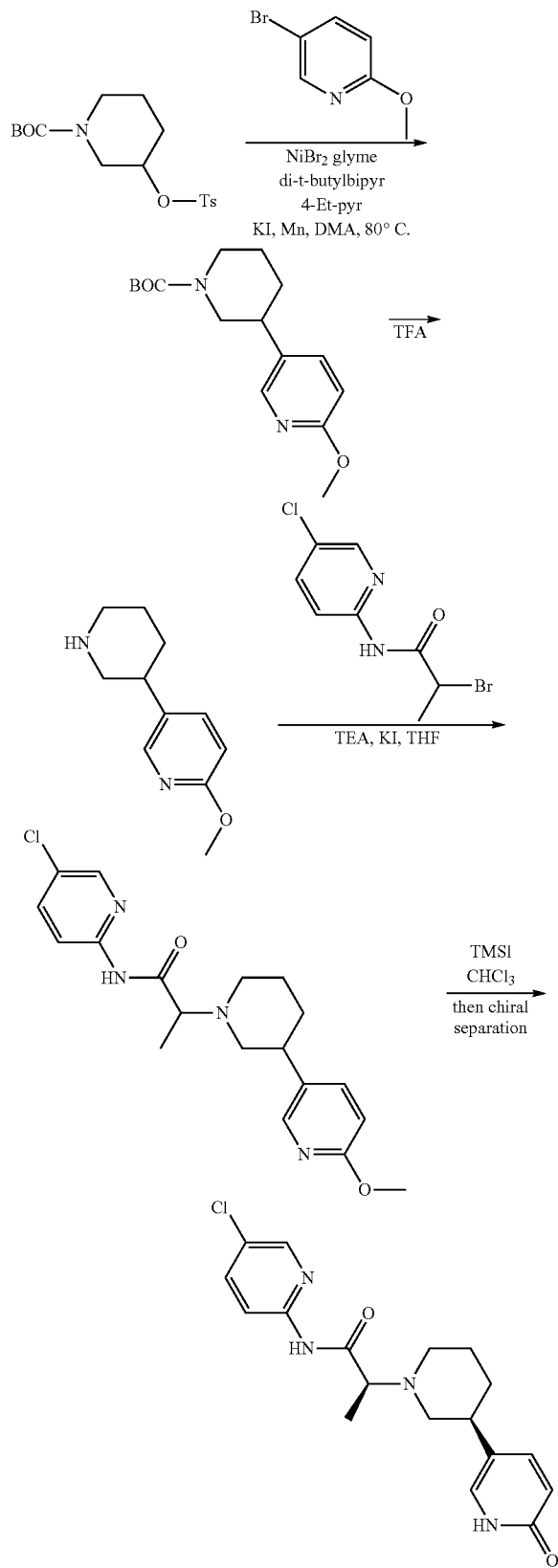

Step 1

A mixture of tert-butyl 3-(tosyloxy)piperidine-1-carboxylate (3.0 g, 8.45 mmol, 1.0 eq), 5-bromo-2-methoxypyridine (1.6 g, 8.45 mmol, 1.0 eq), NiBr$_2$ (298 mg, 0.84 mmol, 0.1 eq), glyme, di-tert-butylbipyridine (226 mg, 0.84 mmol, 0.1 eq), 4-ethylpyridine (904 mg, 8.45 mmol, 1.0 eq), KI (1.4 g, 8.45 mmol, 1.0 eq) and Mn (930 mg, 16.9 mmol, 2.0 eq) in DMA (20 mL) was stirred at 80° C. for 12 h, then diluted with ethyl acetate (200 mL). The resulting mixture was stirred at 25° C. for 1 h, filtered, washed with water (200 mL), dried over Na$_2$SO$_4$, concentrated and purified via silica gel column, eluting with ethyl acetate/petroleum ether (1:5) to give 380 mg (purity: 90%, yield: 15%) of tert-butyl 3-(6-methoxypyridin-3-yl)piperidine-1-carboxylate as a colorless solid.

LCMS: (ES, m/s) 293 [M+H]+.

Step 2

A mixture of tert-butyl 3-(6-methoxypyridin-3-yl)piperidine-1-carboxylate (1.0 g, 3.43 mmol, 1.0 eq), DCM (12.0 mL) and TFA (4.0 mL) was stirred for 1 h at 30° C. and concentrated to give 1.03 g (crude) of 2-methoxy-5-(piperidin-3-yl)pyridine, TFA salt, as a red oil which was used without purification. LCMS: (ES, m/s) 192 [M+H]+.

Step 3

A mixture of 2-methoxy-5-(piperidin-3-yl)pyridine (as the free base) (660 mg, 3.44 mmol, 1.0 eq), 2-bromo-N-(5-chloropyridin-2-yl)propanamide (Intermediate 3) (1.35 g, 5.16 mmol, 1.5 eq), KI (571 mg, 3.44 mmol, 1.0 eq) and TEA (1.74 g, 17.2 mmol, 5.0 eq) in THF (15 mL) was stirred for 15 h at 60° C., poured into H$_2$O (40 mL) and extracted with ethyl acetate (40 mL×3). The organic layers were combined, dried over sodium sulfate, concentrated and purified via silica gel column, eluting with ethyl acetate: petroleum ether (1:5) to give 516 mg (purity: 90%, yield: 40%) of N-(5-chloropyridin-2-yl)-2-(3-(6-methoxypyridin-3-yl)piperidin-1-yl)propanamide as a yellow oil.

LCMS (ES, m/s): 375 [M+H]+

Step 4

A mixture of N-(5-chloropyridin-2-yl)-2-(3-(6-methoxypyridin-3-yl)piperidin-1-yl)propanamide (486 mg, 1.3 mmol, 1.0 eq) and iodotrimethylsilane (2.6 g, 13.0 mmol, 10.0 eq) in CHCl$_3$ (10 mL) was stirred for 3 h at 50° C. and diluted with MeOH (10.0 mL) at 0° C. The resulting solution was stirred for 0.5 h at 25° C., concentrated and purified by reversed phase column (C18 silica gel, 80 g, 20-45 um, 100 A), eluting with 5-95% AcCN in water (with 10 mM NH$_4$HCO$_3$) to give 310 mg product as a yellow solid. The material was chirally separated (CHIRAL ART Cellulose-SB, 2×25 cm, 5 um; Mobile Phase A: [Hex:DCM=5:1], Mobile Phase B: EtOH; Flow rate: 20 mL/min; 1:1 A:B) to give peaks with retention times of RT1: 8.048 min, RT2: 9.550 min, RT3: 10.848 min and RT4:12.848 min. The second peak (RT: 9.550 min) was repurified (CHIRAL ART Cellulose-SB S-5 um, 2×25 cm, 5 um; Mobile Phase A: Hex:DCM=5:1, Mobile Phase B: EtOH; Flow rate: 20 mL/min; 1:1 A:B) to give 40 mg (purity: 98.5%, yield: 9%) of (S)—N-(5-chloropyridin-2-yl)-2-((S)-3-(6-oxo-1,6-dihydropyridin-3-yl)piperidin-1-yl)propanamide as a white solid. LCMS (ES, m/s): 361 [M+H]+ $^1$H NMR: (300 MHz, CD$_3$OD) δ ppm 8.29-8.28 (m, 1H), 8.20-8.17 (m, 1H), 7.84-7.80 (m, 1H), 7.64-7.60 (m, 1H), 7.31 (d, J=2.4 Hz, 1H), 6.52 (d, J=9.3 Hz, 1H), 3.45-3.38 (m, 1H), 2.94-2.77 (m, 3H), 2.48-2.41 (m, 1H), 2.32-2.25 (m, 1H), 1.92-1.75 (m, 3H), 1.46-1.41 (m, 1H), 1.30 (d, J=7.2 Hz, 3H).

Example 159 was synthesized in an analogous manner using the designated Intermediate in Step 3.

| Ex | Name | Structure | ¹H NMR | LC/MS: (M + H)⁺; retention time (min); LC/MS Method of analysis | Int |
|---|---|---|---|---|---|
| 159 | (S)-N-(5-(cyclopropyl methoxy) pyridin-2-yl)-2-((S)-3-(6-oxo-1,6-dihydropyridin-3-yl)piperidin-1-yl)propanamide | 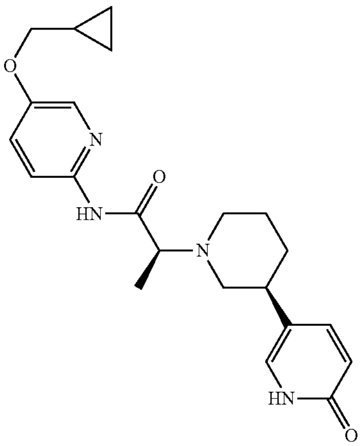 [SMILES: C[C@@H](C(=O)Nc1ccc(OCC2CC2)cn1)N1CCC[C@@H](c2ccc(=O)[nH]c2)C1] | ¹H NMR: (300 MHz, DMSO-d₆) δ ppm 11.40 (s, 1H), 9.94 (s, 1H), 8.04-8.01 (m, 2H), 7.45-7.41 (m, 2H), 7.19 (d, J = 5.1 Hz, 1H), 6.28 (d, J = 9.6 Hz, 1H), 3.87 (d, J = 6.9 Hz, 2H), 3.48-3.46 (m, 1H), 2.86 (d, J = 9.3 Hz, 1H), 2.74-2.55 (m, 2H), 2.38-2.24 (m, 1H), 2.22-2.13 (m, 1H), 1.74 (s, 2H), 1.58-1.50 (m, 1H), 1.44-0.98 (m, 5H), 0.60-0.56 (m, 2H), 0.35-0.32 (m, 2H). | 397; rt 0.844. LC/MS Method 11 | 22 |

Example 160a,b

Ex. 160a: (S)—N-(5-(cyclopropylmethoxy)pyridin-2-yl)-2-((3S,4R)-4-fluoro-3-(6-oxo-1,6-dihydropyridin-3-yl)piperidin-1-yl)propanamide or Ex. 160b: (S)—N-(5-(cyclopropylmethoxy)pyridin-2-yl)-2-((3S,4S)-4-fluoro-3-(6-oxo-1,6-dihydropyridin-3-yl)piperidin-1-yl)propanamide

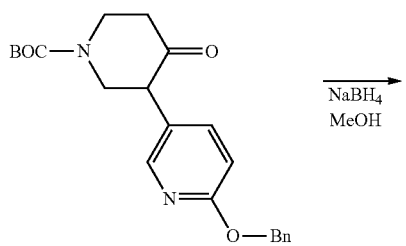

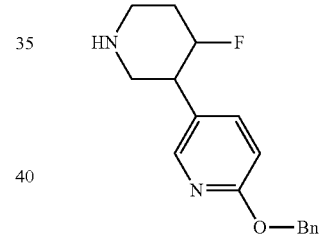

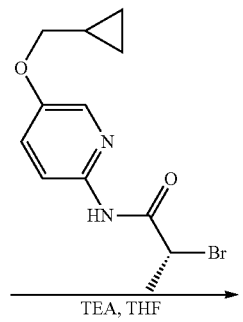

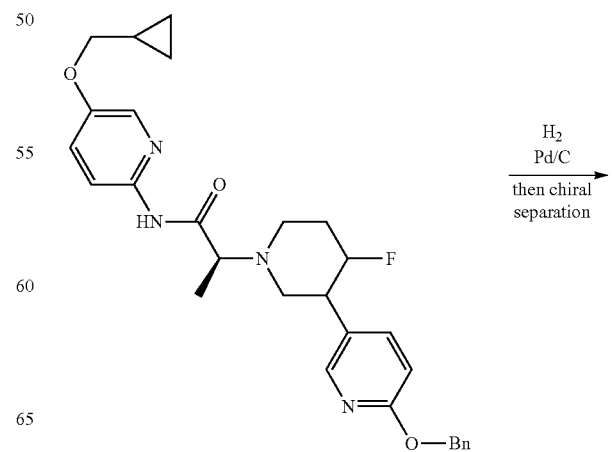

-continued

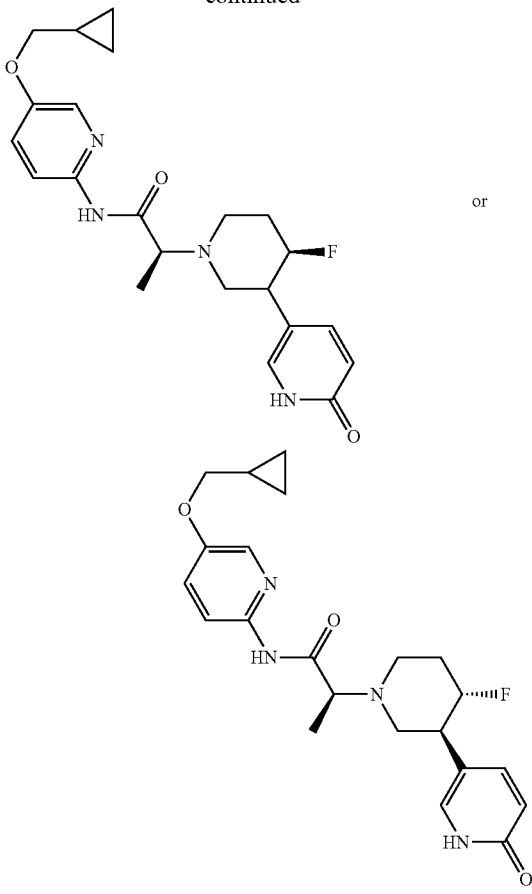

Step 1

To tert-butyl 3-(6-(benzyloxy)pyridin-3-yl)-4-oxopiperidine-1-carboxylate (Example 1, Step 1) (2.5 g, 6.54 mmol, 1.0 eq) in methanol (100 mL) at 0° C. was added NaBH$_4$ (497 mg, 13.09 mmol, 2.0 eq), in portions. The reaction was stirred at room temperature for 3 h, quenched with water (10 mL) and concentrated. The residue was diluted with water (200 mL) and extracted with ethyl acetate (200 mL×3). The combined organic layers were dried over sodium sulfate and concentrated to give 1.8 g (yield: 42%, purity: 59%) of tert-butyl 3-(6-(benzyloxy)pyridin-3-yl)-4-hydroxypiperidine-1-carboxylate as a black oil, which was used without purification. LCMS: (ES, m/s) 385 [M+H]+, retention time 1.264 min, LCMS Method 32. $^1$H NMR (300 MHz, CD$_3$OD) δ ppm 8.08-8.04 (m, 1H), 7.70-7.60 (m, 1H), 7.44-7.26 (m, 5H), 6.86-6.53 (m, 1H), 5.33-5.32 (m, 2H), 4.16-4.03 (m, 3H), 3.86-3.74 (m, 1H), 2.92-2.79 (m, 2H), 2.54-2.45 (m, 1H), 1.81-1.71 (m, 1H), 1.49 (s, 9H).

Step 2

To tert-butyl 3-(6-(benzyloxy)pyridin-3-yl)-4-hydroxypiperidine-1-carboxylate (2.00 g, 5.21 mmol, 1.0 eq) in dichloromethane (100 mL) at 0° C., DAST (1.68 g, 10.42 mmol, 2.0 eq) was added, dropwise. The reaction was stirred at room temperature for 18 h, quenched with cold water (400 mL) and extracted with dichloromethane (300 mL×3). The combined organic extracts were washed with brine (500 mL×2), dried over sodium sulfate and concentrated to give 1.8 g (yield: 75%, purity: 84%) of tert-butyl 3-(6-(benzyloxy)pyridin-3-yl)-4-fluoropiperidine-1-carboxylate as a black oil, which was used without further purification. LCMS: (ES, m/s) 387 [M+H]+, retention time 1.408 min, LCMS Method 36. $^1$H NMR: (300 MHz, CDCl$_3$) δ ppm 8.27-7.88 (m, 2H), 7.33-7.27 (m, 2H), 7.22-7.08 (m, 3H), 6.69-6.57 (m, 1H), 5.21-5.19 (m, 2H), 4.51-4.41 (m, 1H), 4.01-3.98 (m, 1H), 3.62-3.11 (m, 4H), 2.86-2.67 (m, 2H), 1.29 (s, 9H).

Step 3

To tert-butyl 3-(6-(benzyloxy)pyridin-3-yl)-4-fluoropiperidine-1-carboxylate (1.50 g, 3.89 mmol, 1.0 eq) in dichloromethane (30 mL), TFA (15 mL) was added. The reaction was stirred at rt for 3 h and concentrated to give 310 mg (yield, 28%, purity: 100%) 2-(benzyloxy)-5-(4-fluoropiperidin-3-yl)pyridine as a yellow solid, which was used without purification. LCMS (ES, m/s): 287 [M+H]+, retention time 0.830 minutes, LCMS Method 36. $^1$HNMR: (300 MHz, CD$_3$OD) δ ppm 8.11-8.04 (m, 1H), 7.75-7.64 (m, 1H), 7.45-7.41 (m, 2H), 7.38-7.26 (m, 3H), 6.89-6.83 (m, 1H), 5.35 (s, 2H), 3.46-3.53 (m, 1H), 3.20-3.01 (m, 2H), 2.81-2.62 (m, 2H), 2.23-2.15 (m, 1H), 1.74-1.65 (m, 1H), 1.38-1.29 (m, 1H).

Step 4

To 2-(benzyloxy)-5-(4-fluoropiperidin-3-yl)pyridine (as free base) (310 mg, 1.08 mmol, 1.0 eq) and (R)-2-bromo-N-(5-(cyclopropylmethoxy)pyridin-2-yl)propanamide (Intermediate 22) (323 mg, 1.08 mmol, 1.0 eq) in THF (30 mL) was added triethylamine (547 mg, 5.40 mmol, 5.0 eq). The mixture was stirred at 45° C. for 2 days, quenched with water (100 mL) and extracted with ethyl acetate (100 mL×3). The organic phases were washed with brine (200 mL), dried over sodium sulfate, concentrated and purified by preparative TLC (ethyl acetate:petroleum ether=1:2) to give 270 mg (yield, 50%, purity: 87%) of (2S)-2-(3-(6-(benzyloxy)pyridin-3-yl)-4-fluoropiperidin-1-yl)-N-(5-(cyclopropyl methoxy)pyridin-2-yl)propanamide as a yellow oil. LCMS (ES, m/s): 505 [M+H]+, retention time 1.641 min, LCMS Method 38. $^1$HNMR: (300 MHz, CDCl$_3$) δ ppm 9.56 (br, 1H), 8.18-8.10 (m, 2H), 8.03-7.99 (m, 1H), 7.50-7.45 (m, 3H), 7.42-7.35 (m, 3H), 7.31-7.29 (m, 1H), 6.83-6.79 (m, 1H), 5.39-5.37 (m, 2H), 4.69-4.49 (m, 1H), 3.87 (d, J=6.9 Hz, 2H), 3.41-3.36 (m, 1H), 3.21-2.95 (m, 3H), 2.69-2.61 (m, 1H), 2.49-2.23 (m, 2H), 2.10-2.02 (m, 2H), 1.37-1.29 (m, 3H), 0.72-0.63 (m, 2H), 0.41-0.36 (m, 2H).

Step 5

A mixture of (2S)-2-(3-(6-(benzyloxy)pyridin-3-yl)-4-fluoropiperidin-1-yl)-N-(5-(cyclopropylmethoxy)pyridin-2-yl)propanamide (270 mg, 0.53 mmol, 1.0 eq), methanol (20 mL) and Pd/C (300 mg, 10%) was evacuated and flushed three times with nitrogen, followed by flushing with hydrogen. The mixture was stirred 2 h at room temperature under an atmosphere of hydrogen, filtered and concentrated to give 200 mg (yield: 82%, purity: 91%) of the crude product. A portion (50 mg, 0.12 mmol) was dissolved in methanol (2 mL) and purified by prep HPLC (XBridge Shield RP18 OBD Column, 30×150 mm, 5 um), eluting with 30-40% AcCN in water (10 mM NH$_4$HCO$_3$+0.1% NH$_3$.H$_2$O) to give 13 mg product. This material was chirally separated (CHIRALPAK IA, 2×25 cm, 5 um; Mobile Phase A: Hex [8 mmol/L NH$_3$. MeOH], Mobile Phase B: EtOH; Flow rate: 18 mL/min; 1:1 A:B) to give peaks with retention times of RT1: 12.067 min, RT2: 17.441 min and RT3: 20.296 min.

The third peak (RT: 20.296 min) was repurified (CHIRAL ART Cellulose-SB, 2×25 cm, 5 um; Mobile Phase A: Hex [8 mmol/L NH$_3$, MeOH], Mobile Phase B: IPA; Flow rate: 20 mL/min; 1:1 A:B) to give 12.0 mg (yield: 12%, purity: 99%, ee %: 100%) of (S)—N-(5-(cyclopropylmethoxy)pyridin-2-yl)-2-((3S,4R)-(4-fluoro-3-(6-oxo-1,6-dihydropyridin-3-yl)piperidin-1-yl)propanamide or (S)—N-(5-(cyclopropylmethoxy)pyridin-2-yl)-2-((3S,4S)-(4-fluoro-3-(6-oxo-1,6-dihydropyridin-3-yl)piperidin-1-yl)propanamide as white solid. LCMS (ES, m/s): 415 [M+H]+ $^1$H NMR: (300 MHz, CD$_3$OD) δ ppm 8.05 (d, J=9.3 Hz, 1H), 7.99 (d, J=2.4 Hz, 1H), 7.65 (dd, J=2.7, 9.3 Hz, 1H), 7.40 (dd, J=3.0, 9.0 Hz, 2H), 6.54 (d, J=9.3 Hz, 1H), 4.65-4.47 (m, 1H), 3.87 (d, J=6.9 Hz, 2H), 3.46-3.39 (m, 1H), 3.01-2.87 (m, 3H), 2.65-2.57 (m, 1H), 2.49-2.41 (m, 1H), 2.22-2.18 (m, 1H), 1.99-1.91 (m, 1H), 1.31-1.21 (m, 4H), 0.65-0.59 (m, 2H), 0.38-0.33 (m, 2H).

Example 161 was synthesized in an analogous manner using the designated Intermediate in Step 4.

Example 162

(S)—N-(5-fluoropyridin-2-yl)-2-((3S,5R)-3-methyl-5-(6-oxo-1,6-dihydropyridazin-3-yl)piperidin-1-yl)propanamide

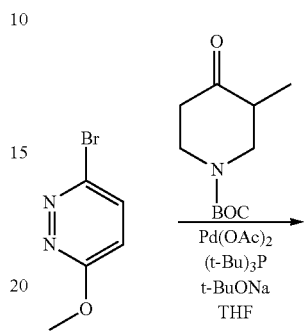

| Ex | Name | Structure | $^1$H NMR | LC/MS: (M + H)$^+$; retention time (min); LC/MS Method of analysis | Int |
|---|---|---|---|---|---|
| 161a,b | Ex. 161a: (S)-2-((3S,4R)-4-fluoro-3-(6-oxo-1,6-dihydropyridin-3-yl)piperidin-1-yl)-N-(5-fluoropyridin-2-yl)propanamide or Ex. 161b: (S)-2-((3S,4S)-4-fluoro-3-(6-oxo-1,6-dihydropyridin-3-yl)piperidin-1-yl)-N-(5-fluoropyridin-2-yl)propanamide | | $^1$H NMR: (400 MHz, CD$_3$OD) δ ppm 8.20-8.17 (m, 2H), 7.66-7.57 (m, 2H), 7.40 (d, J = 2.0 Hz, 1H), 6.55 (d, J = 10.0 Hz, 1H), 4.64-4.47 (m, 1H), 3.48-3.44 (m, 1H), 2.96-2.86 (m, 3H), 2.64-2.59 (m, 1H), 2.48-2.42 (m, 1H), 2.19-2.18 (m, 1H), 1.97-1.86 (m, 1H), 1.31-1.29 (m, 3H). | 363; rt 0.710. LC/MS Method 19 | 14 |

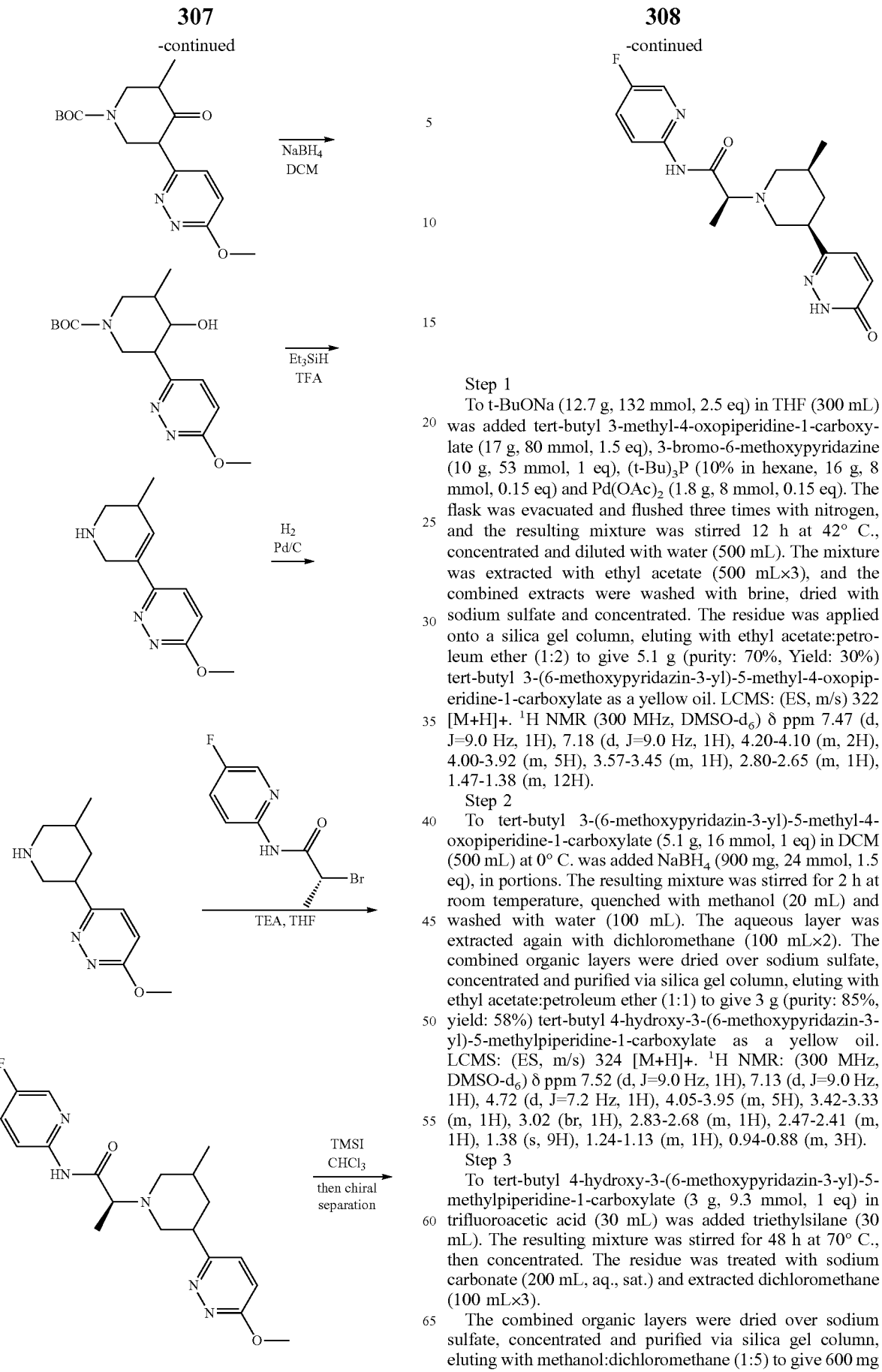

Step 1

To t-BuONa (12.7 g, 132 mmol, 2.5 eq) in THF (300 mL) was added tert-butyl 3-methyl-4-oxopiperidine-1-carboxylate (17 g, 80 mmol, 1.5 eq), 3-bromo-6-methoxypyridazine (10 g, 53 mmol, 1 eq), (t-Bu)$_3$P (10% in hexane, 16 g, 8 mmol, 0.15 eq) and Pd(OAc)$_2$ (1.8 g, 8 mmol, 0.15 eq). The flask was evacuated and flushed three times with nitrogen, and the resulting mixture was stirred 12 h at 42° C., concentrated and diluted with water (500 mL). The mixture was extracted with ethyl acetate (500 mL×3), and the combined extracts were washed with brine, dried with sodium sulfate and concentrated. The residue was applied onto a silica gel column, eluting with ethyl acetate:petroleum ether (1:2) to give 5.1 g (purity: 70%, Yield: 30%) tert-butyl 3-(6-methoxypyridazin-3-yl)-5-methyl-4-oxopiperidine-1-carboxylate as a yellow oil. LCMS: (ES, m/s) 322 [M+H]+. $^1$H NMR (300 MHz, DMSO-d$_6$) δ ppm 7.47 (d, J=9.0 Hz, 1H), 7.18 (d, J=9.0 Hz, 1H), 4.20-4.10 (m, 2H), 4.00-3.92 (m, 5H), 3.57-3.45 (m, 1H), 2.80-2.65 (m, 1H), 1.47-1.38 (m, 12H).

Step 2

To tert-butyl 3-(6-methoxypyridazin-3-yl)-5-methyl-4-oxopiperidine-1-carboxylate (5.1 g, 16 mmol, 1 eq) in DCM (500 mL) at 0° C. was added NaBH$_4$ (900 mg, 24 mmol, 1.5 eq), in portions. The resulting mixture was stirred for 2 h at room temperature, quenched with methanol (20 mL) and washed with water (100 mL). The aqueous layer was extracted again with dichloromethane (100 mL×2). The combined organic layers were dried over sodium sulfate, concentrated and purified via silica gel column, eluting with ethyl acetate:petroleum ether (1:1) to give 3 g (purity: 85%, yield: 58%) tert-butyl 4-hydroxy-3-(6-methoxypyridazin-3-yl)-5-methylpiperidine-1-carboxylate as a yellow oil. LCMS: (ES, m/s) 324 [M+H]+. $^1$H NMR: (300 MHz, DMSO-d$_6$) δ ppm 7.52 (d, J=9.0 Hz, 1H), 7.13 (d, J=9.0 Hz, 1H), 4.72 (d, J=7.2 Hz, 1H), 4.05-3.95 (m, 5H), 3.42-3.33 (m, 1H), 3.02 (br, 1H), 2.83-2.68 (m, 1H), 2.47-2.41 (m, 1H), 1.38 (s, 9H), 1.24-1.13 (m, 1H), 0.94-0.88 (m, 3H).

Step 3

To tert-butyl 4-hydroxy-3-(6-methoxypyridazin-3-yl)-5-methylpiperidine-1-carboxylate (3 g, 9.3 mmol, 1 eq) in trifluoroacetic acid (30 mL) was added triethylsilane (30 mL). The resulting mixture was stirred for 48 h at 70° C., then concentrated. The residue was treated with sodium carbonate (200 mL, aq., sat.) and extracted dichloromethane (100 mL×3).

The combined organic layers were dried over sodium sulfate, concentrated and purified via silica gel column, eluting with methanol:dichloromethane (1:5) to give 600 mg (purity: 90%, yield: 31%) of 3-methoxy-6-(5-methyl-1,2,5,6-tetrahydropyridin-3-yl)pyridazine as a yellow oil. LCMS (ES, m/s): 206 [M+H]+ $^1$HNMR: (300 MHz, DMSO-d$_6$) δ ppm 7.90 (d, J=9.3 Hz, 1H), 7.16 (d, J=9.3 Hz, 1H), 6.55-6.54 (m, 1H), 4.00 (s, 3H), 3.87-3.67 (m, 2H), 3.15-3.03 (m, 2H), 2.48-2.39 (m, 2H), 1.02 (d, J=6.6 Hz, 3H).

Step 4

A mixture of 3-methoxy-6-(5-methyl-1,2,5,6-tetrahydropyridin-3-yl)pyridazine (600 mg, 2.9 mmol, 1 eq), methanol (20 mL), and Pd/C (600 mg, 10%) was stirred under H$_2$ (3 atm) for 2 h, filtered and concentrated to give 300 mg (purity: 75%, yield: 50%) of 3-methoxy-6-(5-methylpiperidin-3-yl)pyridazine as red oil, which was used without purification. LCMS (ES, m/s): 208 [M+H]+ $^1$HNMR: (300 MHz, CD$_3$OD) δ ppm 7.69 (d, J=9.3 Hz, 1H), 7.22 (d, J=9.3 Hz, 1H), 4.07 (s, 3H), 3.70-3.63 (m, 1H), 3.50-3.34 (m, 2H), 3.27-3.23 (m, 1H), 2.87-2.63 (m, 1H), 2.24-2.01 (m, 2H), 1.58-1.40 (m, 1H), 1.06 (d, J=6.6 Hz, 3H).

Step 5

To 3-methoxy-6-(5-methylpiperidin-3-yl)pyridazine (280 mg, 1.2 mmol, 1 eq) in THF (10 mL) was added (R)-2-bromo-N-(5-fluoropyridin-2-yl)propanamide (Intermediate 1) (350 mg, 1.4 mmol, 1.25 eq) and triethylamine (364 mg, 3.6 mmol, 3 eq). The resulting mixture was stirred for 16 h at 40° C., concentrated and purified via silica gel column, eluting with ethyl acetate:petroleum ether (1:1) to give 180 mg (purity: 90%, yield: 40%) of (2S)—N-(5-fluoropyridin-2-yl)-2-(3-(6-methoxypyridazin-3-yl)-5-methylpiperidin-1-yl) propanamide as a yellow oil. LCMS (ES, m/s): 374 [M+H]+ $^1$HNMR: (300 MHz, CD$_3$OD) δ ppm 8.23-8.18 (m, 2H), 7.65-7.52 (m, 2H), 7.14-7.09 (m, 1H), 4.04 (d, J=4.5 Hz, 3H), 3.50-3.34 (m, 1H), 3.28-3.21 (m, 1H), 3.08-2.92 (m, 2H), 2.81-2.79 (m, 1H), 2.65-2.58 (m, 1H), 2.43-2.34 (m, 1H), 2.17-1.90 (m, 2H), 1.33-1.28 (m, 3H), 0.98 (m, 3H).

Step 6

To (2S)—N-(5-fluoropyridin-2-yl)-2-(3-(6-methoxypyridazin-3-yl)-5-methylpiperidin-1-yl) propanamide (180 mg, 0.48 mmol) in chloroform (5 mL) was added TMSI (482 mg, 2.4 mmol). The resulting mixture was stirred for 2 h at 50° C., quenched with methanol (2 mL), diluted with sodium carbonate (50 mL, aq., sat.) and extracted with dichloromethane (50 mL×3). The combined organic layers were dried over sodium sulfate, concentrated and purified via silica gel column, eluting with methanol:dichloromethane (1:10) to give two peaks: 80 mg of the isomeric mixture 1 and 40 mg of another, isomeric mixture 2. The mixture 1 (80 mg) was separated by prep-chiral HPLC (column: CHIRAL ART Cellulose-SB, 2×25 cm, 5 um; Mobile Phase A: Hex[8 mM NH$_3$.MeOH], Mobile Phase B: EtOH; Flow rate: 20 mL/min; 1:1 A:B) to give peaks with retention times of RT1:6.085 min and RT2: 6.631 min. The first eluting isomer (RT=6.085 min) was collected to give 25 mg (purity: 99%, yield: 14%) of (S)—N-(5-fluoropyridin-2-yl)-2-((3S,5R)-3-methyl-5-(6-oxo-1,6-dihydropyridazin-3-yl)piperidin-1-yl) propanamide as a white solid. LCMS (ES, m/s): 359 [M+H]+ $^1$H NMR: (300 MHz, CD$_3$OD) δ ppm 8.23-8.20 (m, 2H), 7.64-7.59 (m, 1H), 7.50 (d, J=9.6 Hz, 1H), 6.93 (d, J=9.6 Hz, 1H), 3.48-3.32 (m, 1H), 3.08-3.01 (m, 2H), 2.81-2.74 (m, 1H), 2.52-2.47 (m, 1H), 2.04-2.00 (m, 1H), 1.93-1.85 (m, 2H), 1.31 (d, J=7.2 Hz, 3H), 1.18-1.09 (m, 1H), 0.97 (d, J=8.4 Hz, 3H).

Example 163

(S)—N-(5-(cyclopropylmethoxy)pyridin-2-yl)-2-((S)-4,4-difluoro-3-methyl-3-(6-oxo-1,6-dihydropyridin-3-yl)piperidin-1-yl)propanamide

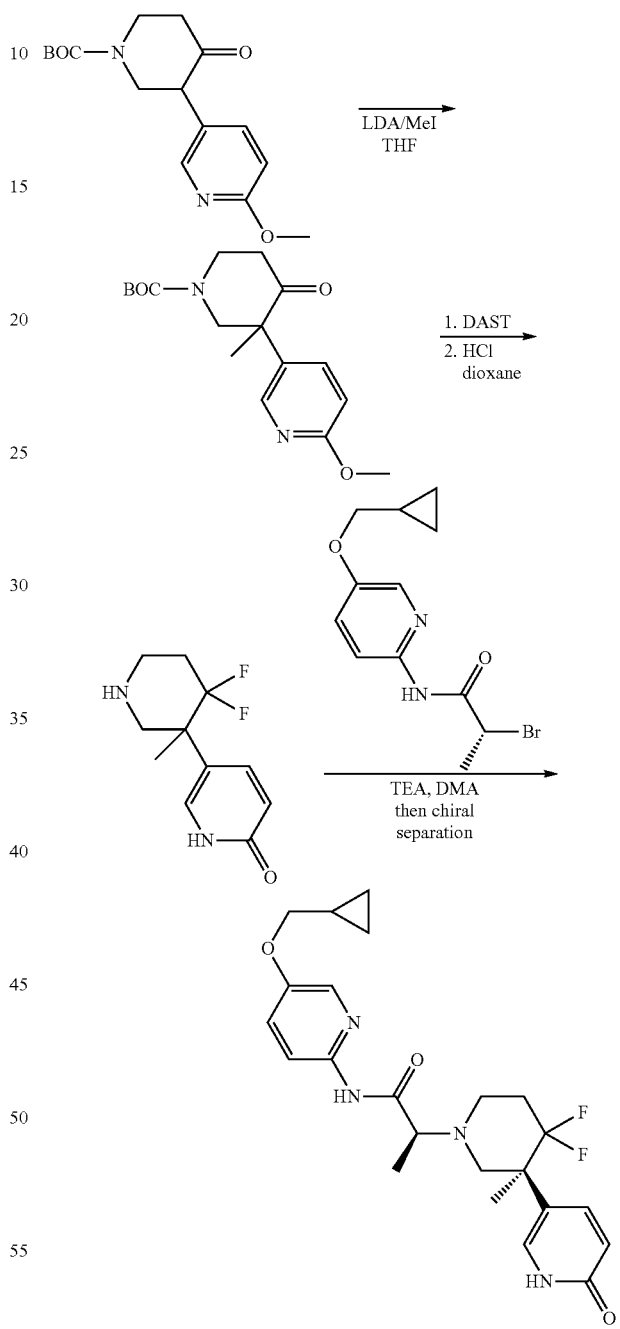

Step 1

To tert-butyl 3-(6-methoxypyridin-3-yl)-4-oxopiperidine-1-carboxylate (Example 4, Step 1) (10.2 g, 33.3 mmol, 1.0 eq) in THF (100 ml) at −30° C. was added LDA (27 ml, 49.5 mmol, 1.5 eq), dropwise. After 1 h CH$_3$I (4.7 g, 33.3 mmol, 1.0 eq) was added, and the mixture was allowed to warm to rt. After 2 h, the reaction was quenched with water (200 mL) and extracted with EtOAc (200 mL×3). The combined organic phases were dried over Na₂SO₄, concentrated and purified via silica gel column with ethyl acetate:petroleum ether (1:5) to give 3.2 g (purity: 85%, yield: 30%) of tert-butyl 3-(6-methoxypyridin-3-yl)-3-methyl-4-oxopiperidine-1-carboxylate as a yellow solid.

LCMS: (ES, m/s) 321 [M+H]⁺. ¹H NMR (300 MHz, CDCl₃) δ 8.07 (s, 1H), 7.69-7.44 (m, 1H), 6.74 (d, J=8.7 Hz, 1H), 4.86-4.50 (m, 1H), 4.25-4.00 (m, 1H), 3.94 (s, 3H), 3.49-3.01 (m, 2H), 2.69-2.21 (m, 2H), 1.41 (s, 9H), 1.34 (s, 3H).

Step 2

To tert-butyl 3-(6-methoxypyridin-3-yl)-3-methyl-4-oxopiperidine-1-carboxylate (3.2 g, 10.0 mmol, 1.0 eq) in dioxane (60 ml), DAST (4.4 g, 20 mmol, 2.0 eq) was added, and the resulting mixture was stirred at 100° C. After 3 h, the reaction was quenched with ice water (80 mL) and extracted with EtOAc (100 mL×3). The combined organic phases were dried over Na₂SO₄, concentrated and purified via silica gel column, eluting with acetate:petroleum ether (1:4) to give 320 mg (purity: 92%, yield: 9%) of tert-butyl 4,4-difluoro-3-(6-methoxypyridin-3-yl)-3-methylpiperidine-1-carboxylate as a yellow oil. LCMS: (ES, m/s) 343 [M+H]+. ¹H NMR: (300 MHz, CDCl₃) δ ppm 8.28 (s, 1H), 7.85-7.66 (m, 1H), 6.75 (d, J=8.9 Hz, 1H), 4.14-3.98 (m, 1H), 3.95 (s, 3H), 3.89-3.71 (m, 2H), 3.48-3.21 (m, 1H), 2.24-1.87 (m, 2H), 1.50 (s, 9H), 1.43 (s, 3H).

Step 3

In a sealed tube, a mixture of tert-butyl 4,4-difluoro-3-(6-methoxypyridin-3-yl)-3-methylpiperidine-1-carboxylate (300 mg, 0.87 mmol, 1.0 eq) in HCl (6M in H₂O)/dioxane=1/1 (4 mL) was stirred at 80° C. for 15 h, concentrated and purified over a C18 column (120 g), eluting with 10-60% AcCN in water to give 110 mg (purity: 95%, yield: 47%) of 5-(4,4-difluoro-3-methylpiperidin-3-yl)pyridin-2 (1H)-one as a yellow oil. LCMS (ES, m/s): 229 [M+H]+ ¹HNMR: (300 MHz, DMSO-d₆) δ ppm 11.52 (s, 1H), 7.63-7.54 (m, 1H), 7.38 (d, J=2.9 Hz, 1H), 6.29 (d, J=9.7 Hz, 1H), 3.08 (d, J=12.7 Hz, 1H), 3.01-2.86 (m, 1H), 2.80-2.63 (m, 2H), 2.09-1.65 (m, 2H), 1.32 (s, 3H).

Step 4

A mixture of 5-(4,4-difluoro-3-methylpiperidin-3-yl)pyridin-2 (1H)-one (as free base) (100 mg, 0.44 mmol, 1.0 eq), (R)-2-bromo-N-(5-(cyclopropylmethoxy)pyridin-2-yl)propanamide (Intermediate 22) (131 mg, 0.44 mmol, 1.0 eq) and TEA (133 mg, 1.3 mmol, 3 eq) in THF (5 mL) was stirred 12 h at 60° C., quenched with water (15 ml) and extracted with ethyl acetate (15 ml×3). The combined organic phases were washed with brine (15 ml), dried over Na₂SO₄, concentrated and purified by prep-TLC with DCM/MeOH=10/1 to give N-(5-(cyclopropylmethoxy)pyridin-2-yl)-2-(4,4-difluoro-3-methyl-3-(6-oxo-1,6-dihydropyridin-3-yl)piperidin-1-yl)propanamide (110 mg, purity: 89%, yield: 56%) as a yellow solid. This material was separated by prep-chiral HPLC (Column: Chiralpak ID-2, 2*25 cm, 5 um; Mobile Phase A: Hex:DCM=3:1 [10 mM NH3-MeOH], Mobile Phase B: EtOH; Flow rate: 15 mL/min; 1:1 A:B) to give peaks with retention times of RT1: 8.361 min and RT2: 12.644 min. The second-eluting isomer (RT 12.644 min) was collected to give (S)—N-(5-(cyclopropylmethoxy)pyridin-2-yl)-2-((S)-4,4-difluoro-3-methyl-3-(6-oxo-1,6-dihydropyridin-3-yl)piperidin-1-yl)propanamide (25 mg, 0.055 mmol, 12.51% yield) as white solid. LCMS (ES, m/s): 447 [M+H]+ ¹H NMR: (300 MHz, CD₃OD) δ ppm 8.02 (d, J=9.2, 1H), 7.97 (d, J=2.8, 1H), 7.84-7.81 (m, 1H), 7.67 (s, 1H), 7.38 (dd, J=2.8, 9.2 Hz, 1H), 6.50 (d, J=10.0 Hz, 1H), 3.86 (d, J=7.2 Hz, 2H), 3.53-3.48 (m, 1H), 3.03-3.00 (m, 1H), 2.82-2.75 (m, 2H), 2.72-2.65 (m, 1H), 2.30-1.99 (m, 2H), 1.49 (s, 3H), 1.38-1.19 (m, 4H), 0.64-0.57 (m, 2H), 0.37-0.33 (m, 2H).

Example 164

N-(5-(cyclopropylmethoxy)pyridin-2-yl)-2-(3,3-difluoro-4-(6-oxo-1,6-dihydropyridin-3-yl)pyrrolidin-1-yl)propanamide

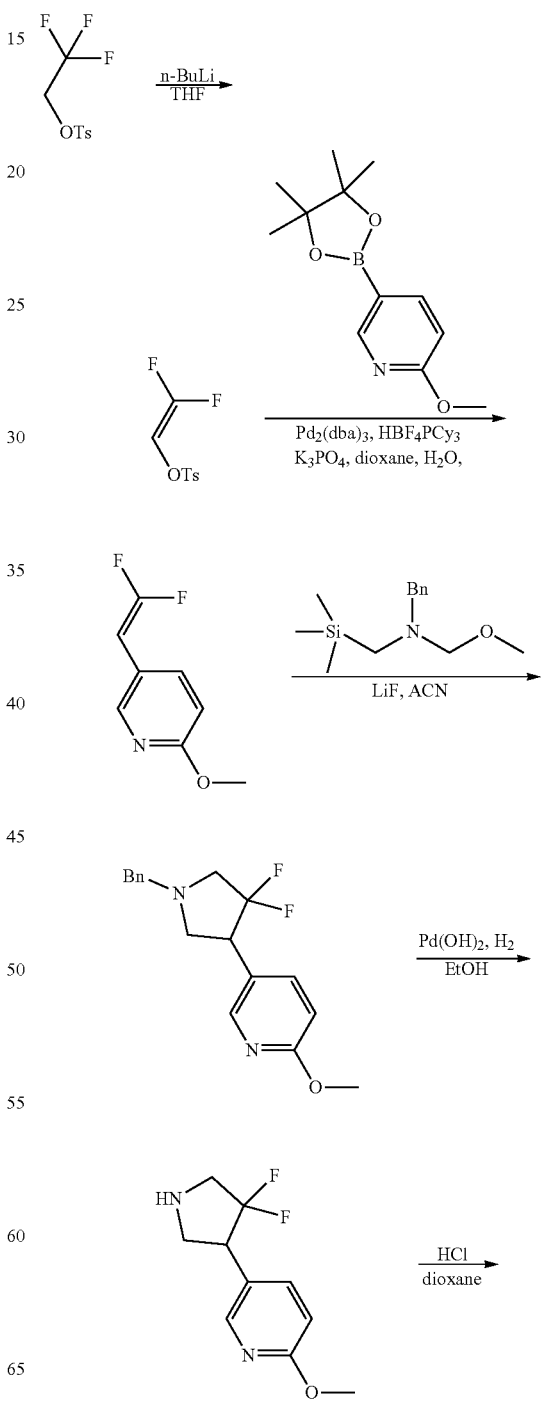

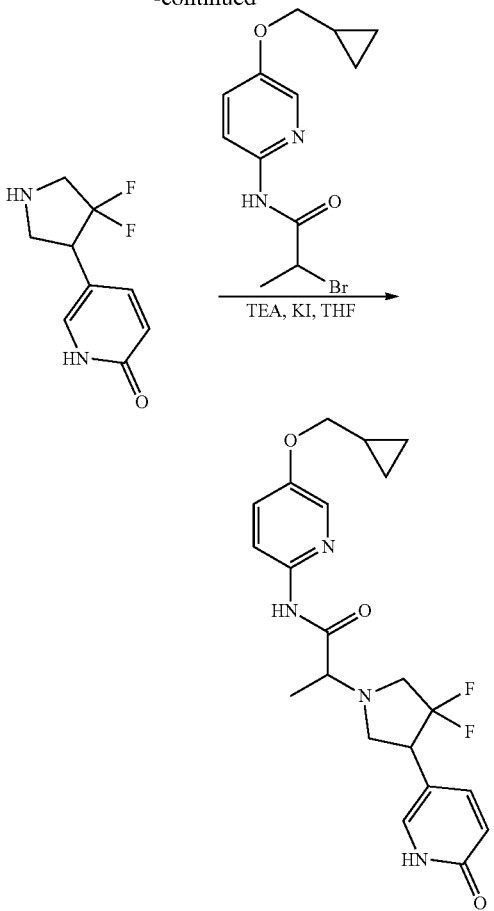

Step 1

A mixture of 2,2,2-trifluoroethyl 4-methylbenzenesulfonate (5.0 g, 19.7 mmol, 1.0 eq) in tetrahydrofuran (120 mL) was evacuated and flushed three times with nitrogen and cooled to −78° C. n-BuLi (15.7 mL, 39.4 mmol, 2.0 eq, 2.5 M in tetrahydrofuran) was added, dropwise. After 1 h, the reaction was quenched with water (200 mL) and extracted with ethyl acetate (200 mL×3). The organic layers were combined, washed with brine, concentrated and purified via a silica gel column, eluting with ethyl acetate: petroleum ether (1:2) to give 4 g (purity: 95%, yield: 86%) of 2,2-difluorovinyl 4-methylbenzenesulfonate as colorless oil. $^1$H NMR (400 MHz, DMSO-$d_6$) δ ppm 7.87 (d, J=8.0 Hz, 2H), 7.55 (d, J=8.0 Hz, 2H), 6.87 (dd, J=16.0, 4.0 Hz, 1H), 2.45 (s, 3H).

Step 2

To 2,2-difluorovinyl 4-methylbenzenesulfonate (3.5 g, 15 mmol, 1.0 eq) and 2-methoxy-5-(4,4,5,5-tetramethyl-1,3,2-dioxaborolan-2-yl)pyridine (7 g, 30 mmol, 2.0 eq) in dioxane (70 mL) and H$_2$O (15 mL) were added Pd$_2$(dba)$_3$ CHCl$_3$ (310 mg, 0.3 mmol, 0.02 eq), HBF$_4$PCy$_3$ (221 mg, 0.6 mmol, 0.04 eq) and K$_3$PO$_4$ (6.4 g, 30 mmol, 2 eq). The reaction was evacuated and flushed three times with nitrogen and stirred at 85° C. After 16 h, the mixture was cooled to rt, filtered, concentrated and purified via silica gel column, eluting with ethyl acetate:petroleum ether (1:2) to give 850 mg (purity: 90%, yield: 33%) of 5-(2,2-difluorovinyl)-2-methoxypyridine as a yellow oil. LCMS: (ES, m/s) 172 [M+H]+. $^1$H NMR: (300 MHz, CDCl$_3$) δ ppm 8.07 (d, J=2.4 Hz, 1H), 7.61 (dd, J=8.7, 2.4 Hz, 1H), 6.74 (d, J=8.7 Hz, 1H), 5.26-5.16 (m, 1H), 3.93 (s, 3H).

Step 3

To 5-(2,2-difluorovinyl)-2-methoxypyridine (1.0 g, 5.8 mmol, 1.0 eq) and N-benzyl-1-methoxy-N-((trimethylsilyl)methyl)methanamine (8.2 g, 35 mmol, 6 eq) in acetonitrile (40 mL) was added LiF (1.2 g, 46.4 mmol, 8 eq), and the mixture was stirred at 60° C. After 16 h, the reaction was cooled to room temperature, concentrated and purified via a silica gel column, eluting with ethyl acetate:petroleum ether (1:1) to give 1.5 g (purity: 85%, yield: 85%) of 5-(1-benzyl-4,4-difluoropyrrolidin-3-yl)-2-methoxypyridine as a colorless oil. LCMS (ES, m/s): 305 [M+H]+ $^1$HNMR: (300 MHz, CDCl$_3$) δ ppm 8.06 (d, J=2.4 Hz, 1H), 7.59-7.55 (m, 1H), 7.42-7.28 (m, 5H), 6.75-6.72 (m, 1H), 3.93 (s, 3H), 3.64 (s, 2H), 3.37-3.21 (m, 1H), 3.20-3.06 (m, 1H), 3.05-3.03 (m, 1H), 3.01-2.89 (m, 1H), 2.84-2.77 (m, 1H).

Step 4

A mixture of 5-(1-benzyl-4,4-difluoropyrrolidin-3-yl)-2-methoxypyridine (1.4 g, 4.6 mmol, 1.0 eq) and Pd(OH)$_2$/C (420 mg, 20%) in ethanol (30 mL) was stirred 16 h at 25° C. under an atmosphere of hydrogen, filtered and concentrated to give 800 mg (purity: 85%, yield: 81%) of 5-(4,4-difluoropyrrolidin-3-yl)-2-methoxypyridine as colorless oil, which was used without purification. LCMS (ES, m/s): 215 [M+H]+ $^1$HNMR: (300 MHz, DMSO-$d_6$) δ ppm 8.06 (s, 1H), 7.64 (d, J=8.7 Hz, 1H), 6.80 (d, J=8.7 Hz, 1H), 3.82 (s, 3H), 3.57-3.24 (m, 4H), 3.22-3.07 (m, 1H), 3.04-3.00 (m, 1H).

Step 5

5-(4,4-Difluoropyrrolidin-3-yl)-2-methoxypyridine (800 mg, 3.7 mmol, 1.0 eq), 6 M HCl (10 mL, aq.) and dioxane (10 mL) were stirred at 80° C. for 16 h and concentrated to give 600 mg (crude product) of 5-(4,4-difluoropyrrolidin-3-yl)pyridin-2 (1H)-one as a brown solid which was used without purification. LCMS (ES, m/s): 201 [M+H]+ $^1$HNMR: (300 MHz, DMSO-$d_6$) δ ppm 10.52 (s, 1H), 7.54-7.50 (m, 1H), 7.33-7.29 (m, 1H), 6.44-6.42 (m, 1H), 3.54-3.37 (m, 4H), 2.88-2.77 (m, 1H).

Step 6

A mixture of 5-(4,4-difluoropyrrolidin-3-yl)pyridin-2 (1H)-one (free base) (100 mg, 0.50 mmol, 1.0 eq), 2-bromo-N-(5-(cyclopropylmethoxy)pyridin-2-yl)propanamide (Intermediate 22) (150 mg, 0.50 mmol, 1.0 eq), triethylamine (253 mg, 2.5 mmol, 5.0 eq) and potassium iodide (83 mg, 0.50 mmol, 1.0 eq). in tetrahydrofuran (8 mL) was stirred 16 h at 60° C., quenched with water (30 mL) and extracted with ethyl acetate (30 mL×3). The combined organic layers were dried over Na$_2$SO$_4$, concentrated and purified by prep-HPLC (XBridge Prep OBD C18 Column, 30×150 mm 5 um), eluting with 25-45% AcCN in water (10 mM NH$_4$HCO$_3$), flow rate 60 mL/min, collecting a peak with an 8.80 min retention time to give 15 mg (purity: 99.8%, yield: 7%) of N-(5-(cyclopropylmethoxy)pyridin-2-yl)-2-(3,3-difluoro-4-(6-oxo-1,6-dihydropyridin-3-yl)pyrrolidin-1-yl) propanamide as a white solid. LCMS (ES, m/s): 419 [M+H]+ $^1$H NMR: (400 MHz, DMSO-$d_6$) δ ppm 11.60 (s, 1H), 10.16 (d, J=8.4 Hz, 1H), 8.03-8.00 (m, 2H), 7.43 (dd, J=9.2, 2.8 Hz, 2H), 7.32 (t, J=3.4 Hz, 1H), 6.32 (d, J=9.6 Hz, 1H), 3.86 (d, J=7.2 Hz, 2H), 3.60-3.40 (m, 2H), 3.30-3.02 (m, 3H), 2.95-2.76 (m, 1H), 1.37-1.02 (m, 4H), 0.58-0.55 (m, 2H), 0.34-0.30 (m, 2H).

Example 165 was synthesized in an analogous manner using the designated Intermediate in Step 6.

| Ex | Name | Structure | ¹H NMR | LC/MS: (M + H)⁺; retention time (min); LC/MS Method of analysis | Int |
|---|---|---|---|---|---|
| 165 | 2-(3,3-difluoro-4-(6-oxo-1,6-dihydropyridin-3-yl)pyrrolidin-1-yl)-N-(5-fluoropyridin-2-yl)propanamide | 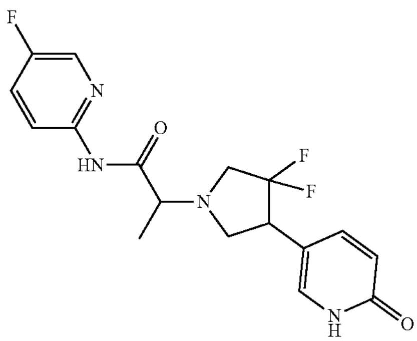 [SMILES: CC(C(=O)Nc1ccc(F)cn1)N1CC(c2ccc(=O)[nH]c2)C(F)(F)C1] | ¹H NMR: (400 MHz, CD₃OD) δ ppm 8.18-8.22 (m, 1H), 7.61-7.65 (m, 2H), 7.39-7.42 (m, 1H), 6.53-6.57 (m, 2H), 3.35-3.43 (m, 4H), 3.31-3.32 (m, 1H), 2.92-2.98 (m, 1H), 1.41 (dd, J = 6.9, 3.6 Hz, 3H). | 367; rt 1.124. LC/MS Method 15 | 1 |
Example 166
(S)—N-(5-chloropyridin-2-yl)-2-((R)-(3-(5-oxo-4,5-dihydropyrazin-2-yl)piperidin-1-yl)propanamide
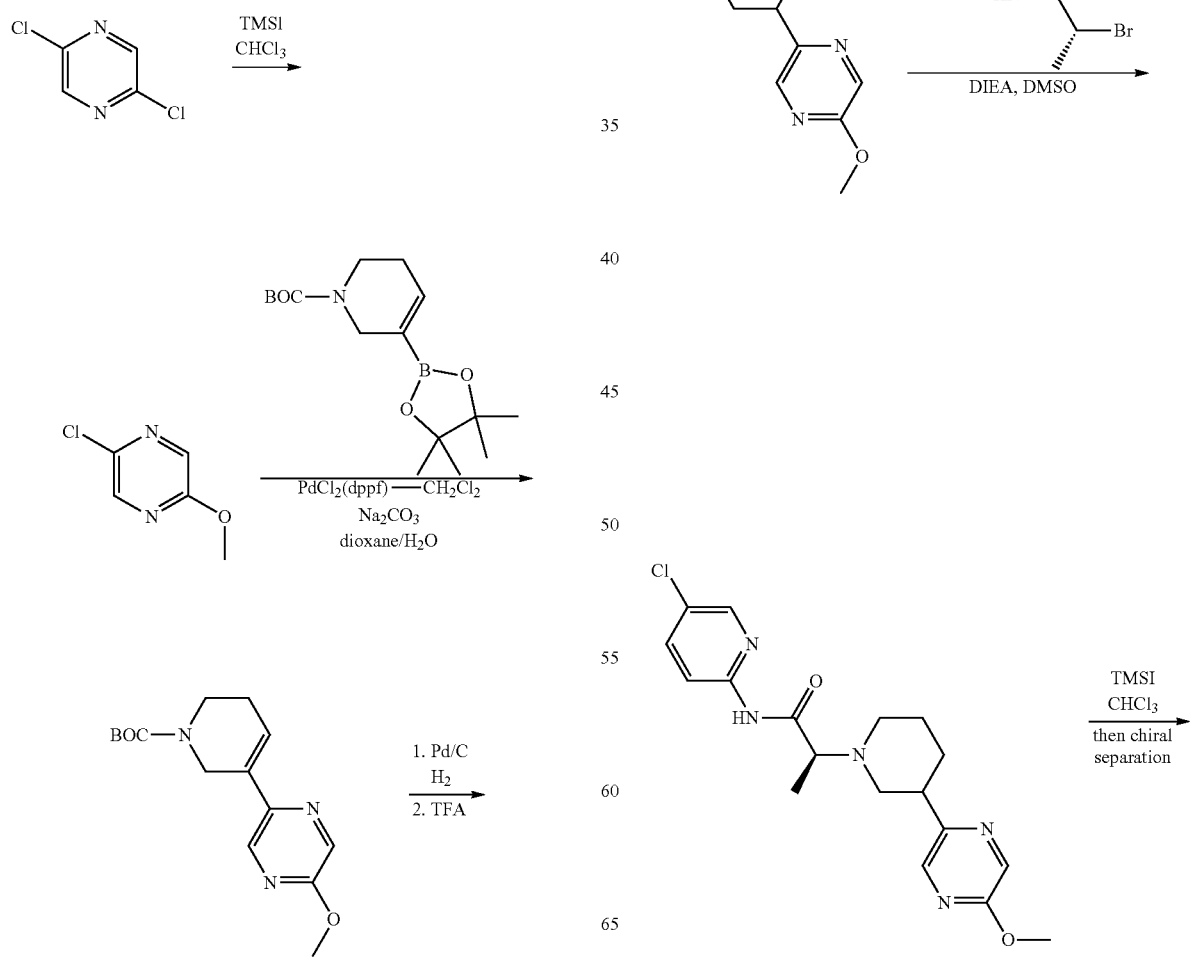

-continued

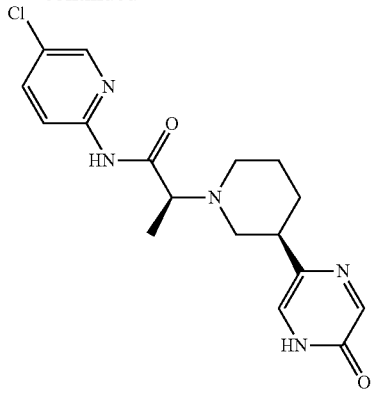 [SMILES: C[C@@H](C(=O)Nc1ccc(Cl)cn1)N1CCC[C@@H](c2c[nH]c(=O)cn2)C1]

Step 2

A mixture of 2,5-dichloropyrazine (5.00 g, 33.6 mmol) and K$_2$CO$_3$ (9.28 g, 67.1 mmol) in methanol (80 mL) was stirred at 60° C. overnight, cooled to RT, filtered and concentrated.

The residue was diluted with water and extracted with DCM (3×). The combined organic extracts were washed with brine (2×), dried over Na$_2$SO$_4$, filtered and concentrated to afford 2-chloro-5-methoxypyrazine (4.90 g, 33.9 mmol, quantitative yield) as a colorless oil, which was used without further purification. LCMS: (ES, m/s) 145 [M+H]$^+$, retention time 0.63 min, LCMS Method 5. $^1$H NMR (400 MHz, DMSO-d$_6$) δ ppm: 8.37 (d, J=1.3 Hz, 1H), 8.20 (d, J=1.3 Hz, 1H), 3.92 (s, 3H) Step 2 To 2-chloro-5-methoxypyrazine (1.00 g, 6.92 mmol), Na$_2$CO$_3$ (1.466 g, 13.84 mmol) and tert-butyl 5-(4,4,5,5-tetramethyl-1,3,2-dioxaborolan-2-yl)-3,6-dihydropyridine-1 (2H)-carboxylate (2.353 g, 7.61 mmol) in water (10.00 mL) and dioxane (30.0 mL) was added PdCl$_2$(dppf)-CH$_2$Cl$_2$-adduct (0.565 g, 0.692 mmol). The resulting mixture was heated to 95° C. for 3 hours, cooled to RT, diluted with water and extracted with EtOAc (3×). The combined organic layers were washed with brine (2×), dried over Na$_2$SO$_4$, filtered and concentrated. The residue was purified via normal phase chromatography (Combiflash Rf, 80 g silica column, 60 mL/min, EtOAc in hexanes 0-40%) to afford tert-butyl 5-(5-methoxypyrazin-2-yl)-3,6-dihydropyridine-1 (2H)-carboxylate (2.02 g, 6.93 mmol, 100% yield) as an off-white solid. LCMS: (ES, m/s) 292 [M+H]$^+$, retention time 1.12 min, LCMS Method 5. $^1$H NMR (400 MHz, DMSO-d$_6$) δ ppm: 8.44 (s, 1H), 8.27 (s, 1H), 6.70 (br s, 1H), 4.28 (br s, 2H), 3.91 (s, 3H), 3.47 (br t, J=5.4 Hz, 2H), 2.28 (br d, J=3.5 Hz, 2H), 1.42 (s, 9H) Step 3 To a solution of tert-butyl 5-(5-methoxypyrazin-2-yl)-3,6-dihydropyridine-1 (2H)-carboxylate (2.02 g, 6.93 mmol) in ethanol (30 mL) under N$_2$ was added Pd/C, 10% (0.074 g, 0.693 mmol). The mixture was hydrogenated under H$_2$ balloon overnight, then filtered through Celite and washed with EtOH. The filtrate was concentrated and purified via normal phase chromatography (Combiflash Rf, 80 g silica column, 60 mL/min, EtOAc in hexanes 0-40%) to afford tert-butyl 3-(5-methoxypyrazin-2-yl)piperidine-1-carboxylate (1.67 g, 5.69 mmol, 82% yield) as a colorless wax LCMS (ES, m/s): 294 [M+H]+, retention time 1.08 min, LCMS Method 5. $^1$H NMR (400 MHz, DMSO-d$_6$) δ ppm: 8.25 (s, 1H), 8.16 (s, 1H), 3.90-4.13 (m, 2H), 3.88 (s, 3H), 2.65-3.07 (m, 3H), 1.92 (br d, J=10.0 Hz, 1H), 1.63-1.77 (m, 2H), 1.43-1.51 (m, 1H), 1.39 (s, 9H)

Step 4

To tert-butyl 3-(5-methoxypyrazin-2-yl)piperidine-1-carboxylate (580 mg, 1.977 mmol) was added TFA (3.0 mL, 38.9 mmol), and the mixture was stirred for 1 hour, then concentrated to afford 2-methoxy-5-(piperidin-3-yl)pyrazine, trifluoroacetic acid salt (607 mg, 1.975 mmol, 100% yield) as a colorless wax, which was used without purification. LCMS (ES, m/s): 194 [M+H]+, retention time 0.34 min, LCMS Method 5.

Step 5

To 2-methoxy-5-(piperidin-3-yl)pyrazine, trifluoroacetic acid salt (607 mg, 1.975 mmol) and (R)-2-bromo-N-(5-chloropyridin-2-yl)propanamide (Intermediate 3) (521 mg, 1.975 mmol) in DMSO (10.0 mL) was added DIEA (1.380 mL, 7.90 mmol). The mixture was stirred overnight, diluted with water and extracted with EtOAc (3×). The combined organic layers were washed with brine (2×), dried over Na$_2$SO$_4$, filtered and concentrated. The residue was purified via normal phase chromatography (Combiflash Rf, 40 g silica column, 40 mL/min, EtOAc in hexanes 20-70%) to afford (2S)—N-(5-chloropyridin-2-yl)-2-(3-(5-methoxypyrazin-2-yl)piperidin-1-yl)propanamide (605 mg, 1.610 mmol, 81% yield) as an off white solid. LCMS (ES, m/s): 389 [M+H]$^+$, retention time 0.63 min, LCMS Method 5. $^1$H NMR (400 MHz, DMSO-d$_6$) δ ppm: 10.29 (br d, J=5.8 Hz, 1H), 8.37 (s, 1H), 8.22 (d, J=6.3 Hz, 1H), 8.10-8.18 (m, 2H), 7.92 (dt, J=9.0, 2.5 Hz, 1H), 3.87 (d, J=5.8 Hz, 3H), 3.45-3.59 (m, 1H), 2.70-3.05 (m, 3H), 2.51-2.59 (m, 1H), 2.31-2.43 (m, 1H), 1.81-1.92 (m, 1H), 1.71-1.80 (m, 1H), 1.49-1.67 (m, 2H), 1.17 (br d, J=6.8 Hz, 3H).

Step 6

To (2S)—N-(5-chloropyridin-2-yl)-2-(3-(5-methoxypyrazin-2-yl)piperidin-1-yl)propanamide (600 mg, 1.596 mmol) and sodium iodide (1196 mg, 7.98 mmol) in acetonitrile (4 mL) was added TMS-Cl (1.020 mL, 7.98 mmol), dropwise. The mixture was stirred overnight, diluted with water and extracted with EtOAc (3×). The combined organic layers were washed with brine (2×), dried over Na$_2$SO$_4$, filtered and concentrated. The residue was purified via normal phase chromatography (Combiflash Rf, 80 g silica column, 65 mL/min, MeOH in DCM 0-10%) to afford 500 mg of product as a mixture of diastereomers. The mixture was purified via SFC chiral separation (Column: Chiralpak IA 20×250 mm, 5 u, 50 g/mL, Co-solvent: 30% MeOH), and fractions from the second peak were collected and concentrated to afford (S)—N-(5-chloropyridin-2-yl)-2-((R)-(3-(5-oxo-4,5-dihydropyrazin-2-yl)piperidin-1-yl)propanamide (142 mg, 0.373 mmol, 23.35% yield) as a light yellow solid. LCMS (ES, m/s): 262 [M+H]+, retention time 0.63 min, LCMS Method 5. $^1$H NMR (400 MHz, DMSO-d$_6$) δ ppm: 11.93-12.15 (m, 1H), 10.24 (s, 1H), 8.36 (dd, J=2.8, 0.8 Hz, 1H), 8.14 (dd, J=9.0, 0.8 Hz, 1H), 7.95 (d, J=1.3 Hz, 1H), 7.92 (dd, J=8.9, 2.6 Hz, 1H), 7.34 (s, 1H), 3.52 (q, J=6.9 Hz, 1H), 2.90-2.99 (m, 1H), 2.68-2.83 (m, 2H), 2.44 (t, J=10.7 Hz, 1H), 2.14-2.24 (m, 1H), 1.70-1.83 (m, 2H), 1.39-1.61 (m, 2H), 1.16 (d, J=7.0 Hz, 3H).

Example 167

(S)—N-(5-chloropyridin-2-yl)-2-((S)-3-(6-oxo-1-(2,2,2-trifluoroethyl)-1,6-dihydropyridin-3-yl)piperidin-1-yl)propanamide

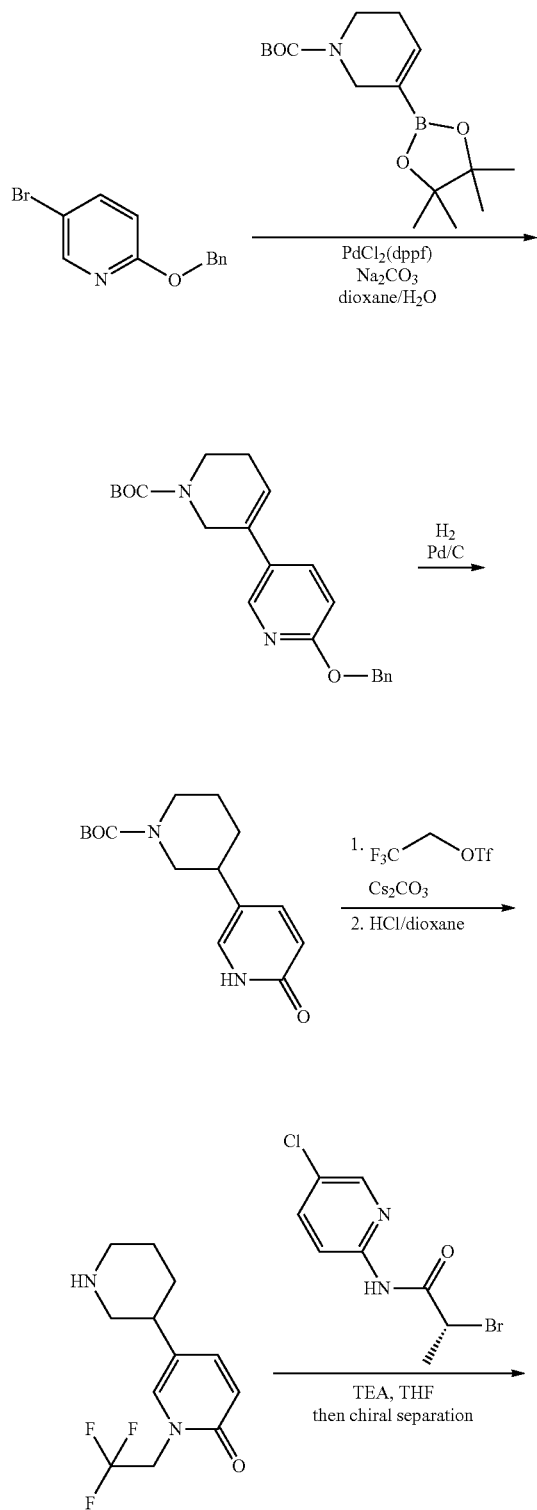

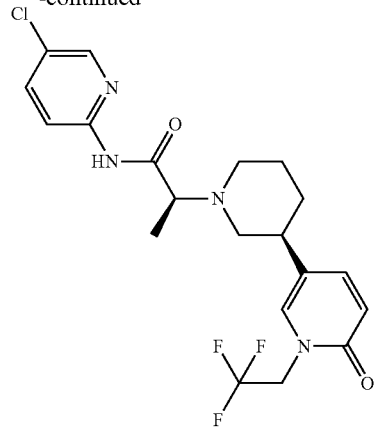

Step 1

A mixture of methyl 2-(benzyloxy)-5-bromopyridine (2.64 g, 10 mmol, 1.0 eq), tert-butyl 5-(4,4,5,5-tetramethyl-1,3,2-dioxaborolan-2-yl)-3,6-dihydropyridine-1 (2H)-carboxylate (4.64 g, 15 mmol, 1.5 eq), Pd(dppf)Cl$_2$ (732 mg, 1 mmol, 0.1 eq), Na$_2$CO$_3$ (2.12 g, 20 mmol, 2.0 eq) in dioxane (40 mL) and water (10 mL) was flushed with nitrogen and stirred at 90° C. After 12 h, the mixture was filtered, concentrated, diluted with water (100 mL) and extracted with ethyl acetate (100 mL×3). The combined organic extracts were dried over sodium sulfate, concentrated and purified via silica gel column, eluting with ethyl acetate: petroleum ether (1:10) to give 3.5 g (purity: 99%, yield: 96%) of tert-butyl 6'-(benzyloxy)-5,6-dihydro-[3,3'-bipyridine]-1 (2H)-carboxylate as a yellow solid. LCMS: (ES, m/s) 367 [M+H]+. $^1$H NMR (300 MHz, DMSO-d$_6$) δ ppm 8.18 (d, J=2.4 Hz, 1H), 7.79 (dd, J=8.7, 2.7 Hz, 1H), 7.47-7.31 (m, 5H), 6.86 (d, J=8.4 Hz, 1H), 6.25-6.22 (m, 1H), 5.33 (s, 2H), 4.17-4.16 (m, 2H), 3.46-3.32 (m, 1H), 3.33 (d, J=6.8 Hz, 1H), 2.23-2.22 (m, 2H), 1.41 (s, 9H).

Step 2

A mixture of tert-butyl 6'-(benzyloxy)-5,6-dihydro-[3,3'-bipyridine]-1 (2H)-carboxylate (1.8 g, 4.9 mmol, 1.0 eq) and Pd/C (180 mg, 10%) in dioxane (30 mL) was evacuated and flushed three times with hydrogen, stirred 12 h at room temperature under an atmosphere of hydrogen, filtered, concentrated and purified via a silica gel column, eluting with methanol:dichloromethane (1:10) to give 1.4 g (purity: 74%, yield: 74%) of tert-butyl 3-(6-oxo-1,6-dihydropyridin-3-yl)piperidine-1-carboxylate as a yellow oil. LCMS: (ES, m/s) 279 [M+H]+. $^1$H NMR: (300 MHz, DMSO-d$_6$) δ ppm 11.45 (s, 1H), 7.39 (dd, J=9.3, 2.7 Hz, 1H), 7.18 (d, J=2.7 Hz, 1H), 6.28 (d, J=9.3 Hz, 1H), 3.90-3.80 (m, 2H), 2.81-2.62 (m, 2H), 2.40-2.33 (m, 1H), 1.78-1.74 (m, 1H), 1.67-1.62 (m, 1H), 1.59-1.37 (m, 2H), 1.38 (s, 9H).

Step 3

A mixture of tert-butyl 3-(6-oxo-1,6-dihydropyridin-3-yl)piperidine-1-carboxylate (500 mg, 1.8 mmol, 1.0 eq), 2,2,2-trifluoroethyl trifluoromethanesulfonate (1.04 g, 4.5 mmol, 2.5 eq) and Cs$_2$CO$_3$ (1.47 g, 4.5 mmol, 2.5 eq) in DMF (10 mL) was stirred 16 h at 28° C., quenched with water (100 mL) and extracted with ethyl acetate (100 mL×3). The combined organic phases were dried over Na$_2$SO$_4$, concentrated and purified via silica gel column, eluting with ethyl acetate:petroleum ether (1:1) to give 200 mg (purity: 75%, yield: 31%) of tert-butyl 3-(6-oxo-1-(2,2,2-trifluoroethyl)-1,6-dihydropyridin-3-yl)piperidine-1-carboxylate as off white solid. LCMS (ES, m/s): 361 [M+H]+

¹H NMR: (400 MHz, DMSO-d₆) δ ppm 7.56-7.49 (m, 2H), 6.47 (d, J=9.2 Hz, 1H), 4.84-4.77 (m, 2H), 3.93-3.89 (m, 4H), 2.44-2.40 (m, 1H), 1.84-1.81 (m, 1H), 1.71-1.69 (m, 1H), 1.57-1.40 (m, 2H), 1.40 (s, 9H).

Step 4 tert-Butyl 3-(6-oxo-1-(2,2,2-trifluoroethyl)-1,6-dihydropyridin-3-yl)piperidine-1-carboxylate (195 mg, 0.54 mmol, 1.0 eq) and HCl (5 mL, 4M in dioxane) were stirred 2 h at 28° C. and concentrated. THF (10 mL), (R)-2-bromo-N-(5-chloropyridin-2-yl)propanamide (Intermediate 3) (142 mg, 0.54 mmol, 1.0 eq) and TEA (164 mg, 1.63 mmol, 3.0 eq) were added, and the mixture was stirred at 40° C. After 2 days, the reaction was quenched with water (100 mL) and extracted with ethyl acetate (100 mL×3). The combined organic phases were dried over Na₂SO₄, concentrated and purified via silica gel column, eluting with ethyl acetate: petroleum ether (1:1) to give 80 mg of (2R)—N-(5-chloropyridin-2-yl)-2-(3-(6-oxo-1-(2,2,2-trifluoroethyl)-1,6-dihydropyridin-3-yl)piperidin-1-yl)propanamide as a yellow solid. The material was chirally separated ([R,R]-WHELK-O1-Kromasil[02], 5 cm×25 cm[5 um]; Mobile Phase A: Hex [0.1% DEA], Mobile Phase B: Ethanol; Flow rate: 14 mL/min; 1:1 A:B) to give peaks with retention times of RT1:8.04 min and RT2:13.26 min. The second peak (RT: 13.26 min) was collected and concentrated to give 21 mg (purity: 99%, yield: 8%) of (S)—N-(5-chloropyridin-2-yl)-2-((S)-3-(6-oxo-1-(2,2,2-trifluoroethyl)-1,6-dihydropyridin-3-yl)piperidin-1-yl)propanamide as white solid. LCMS (ES, m/s): 443 [M+H]+ ¹H NMR: (400 MHz, DMSO-d₆) δ ppm 10.26 (s, 1H), 8.37 (d, J=2.8 Hz, 1H), 8.14 (d, J=9.2 Hz, 1H), 7.92 (dd, J=9.2, 2.8 Hz, 1H), 7.55-7.49 (m, 2H), 6.43 (d, J=9.2 Hz, 1H), 4.84-4.77 (m, 2H), 3.57-3.52 (m, 1H), 2.90-2.88 (m, 1H), 2.72-2.59 (m, 2H), 2.35 (t, J=10.8 Hz, 1H), 2.20 (t, J=11.6 Hz, 1H), 1.79-1.73 (m, 2H), 1.57-1.50 (m, 1H), 1.36-1.30 (m, 1H), 1.17 (d, J=6.8 Hz, 3H).

Example 168

(S)-2-((S)-3-(1-benzyl-6-oxo-1,6-dihydropyridin-3-yl)piperidin-1-yl)-N-(5-chloropyridin-2-yl)propanamide

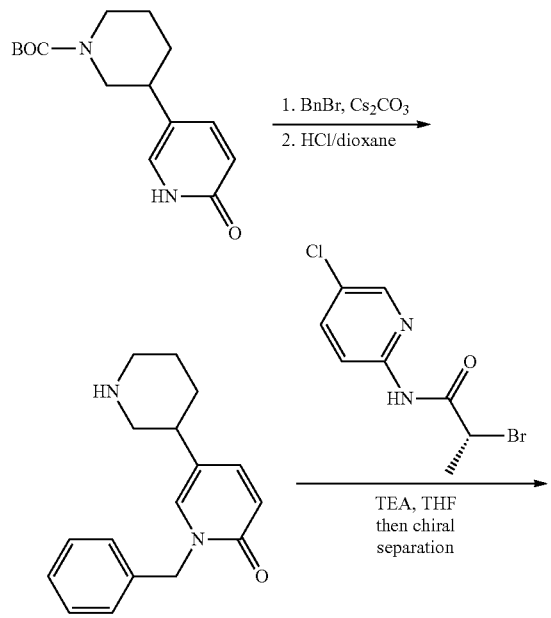

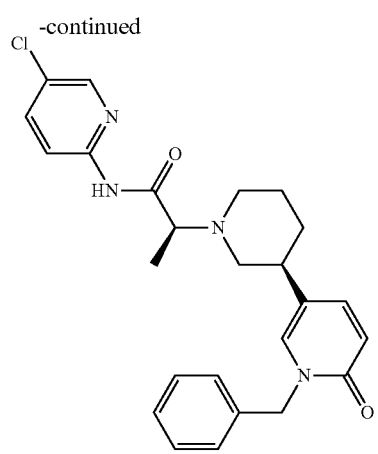

Step 1

A mixture of tert-butyl 3-(6-oxo-1,6-dihydropyridin-3-yl)piperidine-1-carboxylate (Example 167, Step 2) (500 mg, 1.8 mmol, 1.0 eq), BnBr (770 mg, 4.5 mmol, 2.5 eq) and Cs₂CO₃ (1.47 g, 4.5 mmol, 2.5 eq) in DMF (10 mL) was stirred 16 h at 28° C., quenched with water (100 mL) and extracted with ethyl acetate (100 mL×3). The combined organic phases were dried over Na₂SO₄, concentrated and purified via silica gel column, eluting with ethyl acetate: petroleum ether (1:1) to give 500 mg (purity: 71%, yield: 75%) of tert-butyl 3-(1-benzyl-6-oxo-1,6-dihydropyridin-3-yl)piperidine-1-carboxylate as colorless oil. LCMS (ES, m/s): 369 [M+H]+ ¹H NMR: (400 MHz, DMSO-d₆) δ ppm 7.70 (d, J=2.4 Hz, 1H), 7.43 (dd, J=9.2, 2.4 Hz, 1H), 7.39-7.30 (m, 2H), 7.29-7.19 (m, 3H), 6.41 (d, J=9.2 Hz, 1H), 5.07 (s, 2H), 3.96-3.87 (m, 2H), 3.30-3.10 (m, 2H), 2.43-2.24 (m, 1H), 1.82-1.78 (m, 1H), 1.69-1.63 (m, 1H), 1.57-1.50 (m, 2H), 1.39 (s, 9H).

Step 2 tert-Butyl 3-(1-benzyl-6-oxo-1,6-dihydropyridin-3-yl)piperidine-1-carboxylate (200 mg, 0.54 mmol, 1.0 eq) and HCl (5 mL, 4 M in dioxane) were stirred 2 h at 28° C. and concentrated. THF (10 mL), (R)-2-bromo-N-(5-chloropyridin-2-yl)propanamide (Intermediate 3) (142 mg, 0.54 mmol, 1.0 eq) and TEA (164 mg, 1.63 mmol, 3.0 eq) were added, and the mixture was stirred at 40° C. After 3 days, the reaction was quenched with water (100 mL) and extracted with ethyl acetate (100 mL×3). The combined organic phases were dried over Na₂SO₄, concentrated and purified via prep TLC, eluting with MeOH:DCM (1:10) to give 100 mg (purity: 92%, yield: 41%) of (2S)-2-(3-(1-benzyl-6-oxo-1,6-dihydropyridin-3-yl)piperidin-1-yl)-N-(5-chloropyridin-2-yl)propanamide as white solid. The material was chirally separated (Chiralpak ID-2, 2×25 cm, 5 um; Mobile Phase A:Hex [8 mM NH₃.MeOH], Mobile Phase B: EtOH; Flow rate: 18 mL/min; 1:1 A:B) to give peaks with retention times of RT1: 14.519 min and RT2: 22.752 min. The second peak (RT: 22.752 min) was collected and concentrated to give 21 mg (purity: 99.1%, yield: 21%) of the pure product (S)-2-((S)-3-(1-benzyl-6-oxo-1,6-dihydropyridin-3-yl)piperidin-1-yl)-N-(5-chloropyridin-2-yl)propanamide as white solid. LCMS (ES, m/s): 451 [M+H]+ ¹H NMR: (400 MHz, DMSO-d₆) δ ppm 10.25 (s, 1H), 8.37-8.36 (m, 1H), 8.15-8.12 (m, 1H), 7.93-7.91 (m, 1H), 7.69 (d, J=2.4 Hz, 1H), 7.45-7.42 (m, 1H), 7.35-7.25 (m, 5H), 6.38 (d, J=9.2 Hz, 1H), 5.10-5.02 (m, 2H), 3.55-3.50 (m, 1H), 2.88-2.85 (m, 1H), 2.70-2.58 (m, 2H), 2.37-2.32 (m, 1H), 2.21-2.16 (m, 1H), 1.77-1.71 (m, 2H), 1.54-1.51 (m, 1H), 1.35-1.31 (m, 1H), 1.16 (d, J=6.8 Hz, 3H).

Example 169

(S)—N-(5-(cyclopropylmethoxy)pyridin-2-yl)-2-((S)-3-(6-oxo-4-(trifluoromethyl)-1,6-dihydropyridin-3-yl)piperidin-1-yl)propanamide

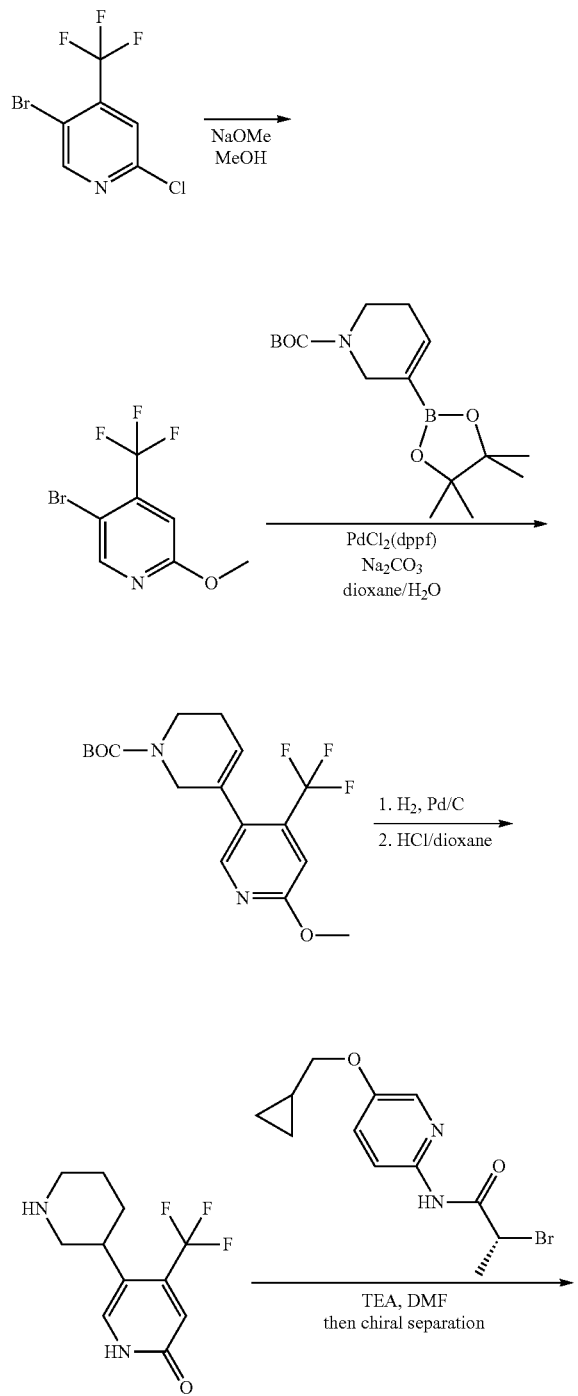

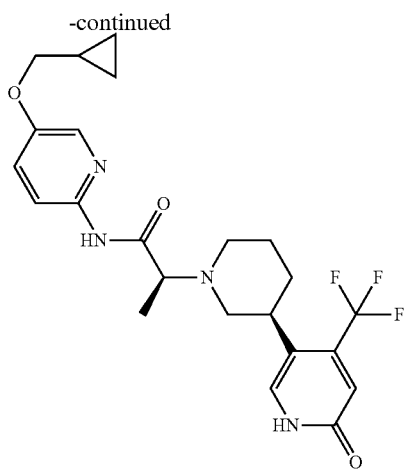

Step 1

A mixture of 5-bromo-2-chloro-4-(trifluoromethyl)pyridine (3 g, 11.54 mmol, 1.0 eq), methanol (30 mL) and NaOMe (1.25 g, 23.08 mmol, 2.0 eq) was stirred at 70° C. for 2 h, concentrated, diluted with water (100 mL) and extracted with ethyl acetate (100 mL×3). The combined organic extracts were dried over sodium sulfate, concentrated and purified via silica gel column, eluting with ethyl acetate:petroleum ether (1:20) to give 2 g (purity: 99%, yield: 68%) of 5-bromo-2-methoxy-4-(trifluoromethyl)pyridine as a white solid. LCMS: (ES, m/s) 256 [M+H]+. $^1$H NMR (300 MHz, DMSO-d$_6$) δ ppm 8.61 (s, 1H), 7.34 (s, 1H), 3.92 (s, 3H).

Step 2

A mixture of 5-bromo-2-methoxy-4-(trifluoromethyl)pyridine (2 g, 7.81 mmol, 1.0 eq), Pd(dppf)Cl$_2$ (571 mg, 0.78 mmol, 0.1 eq), tert-butyl 5-(4,4,5,5-tetramethyl-1,3,2-dioxaborolan-2-yl)-3,6-dihydropyridine-1 (2H)-carboxylate (3.6 g, 11.7 mmol, 1.5 eq) and Na$_2$CO$_3$ (1.65 g, 15.6 mmol, 2.0 eq) in dioxane (48 mL) and water (12 mL) was stirred at 90° C. for 12 h, filtered, concentrated, diluted with water (100 mL) and extracted with ethyl acetate (100 mL×3). The combined organic extracts were dried over sodium sulfate, concentrated and purified via silica gel column, eluting with ethyl acetate:petroleum ether (1:5) to give 2.8 g (purity: 90%, yield: quantitative) of tert-butyl 6'-methoxy-4'-(trifluoromethyl)-5,6-dihydro-[3,3'-bipyridine]-1 (2H)-carboxylate as a colorless oil. LCMS: (ES, m/s) 359 [M+H]+. $^1$H NMR: (300 MHz, DMSO-d$_6$) δ ppm 8.22 (s, 1H), 7.15 (s, 1H), 5.77 (s, 1H), 3.94-3.91 (m, 2H), 3.90 (s, 3H), 3.46-3.40 (m, 2H), 2.20-2.16 (m, 2H), 1.38 (s, 9H).

Step 3

A mixture of tert-butyl 6'-methoxy-4'-(trifluoromethyl)-5,6-dihydro-[3,3'-bipyridine]-1 (2H)-carboxylate (2.8 g, 7.82 mmol, 1.0 eq) and Pd/C (0.28 g, 10%) in methanol (40 mL) was stirred 1 h under an atmosphere of hydrogen, filtered, concentrated and purified via silica gel column, eluting with ethyl acetate:petroleum ether (1:10) to give 1.5 g (purity: 98%, yield: 53%) of tert-butyl 3-(6-methoxy-4-(trifluoromethyl)pyridin-3-yl)piperidine-1-carboxylate as a colorless oil.

LCMS (ES, m/s): 361 [M+H]+ $^1$H NMR: (300 MHz, DMSO-d$_6$) δ ppm 8.52 (s, 1H), 7.12 (s, 1H), 3.91 (s, 3H), 3.33-3.32 (m, 1H), 2.52-2.50 (m, 2H), 2.96-2.75 (m, 2H), 1.87-1.80 (m, 2H), 1.76-1.71 (m, 1H), 1.45-1.38 (m, 10H).

Step 4

A mixture of tert-butyl 3-(6-methoxy-4-(trifluoromethyl) pyridin-3-yl)piperidine-1-carboxylate (720 mg, 2 mmol, 1.0 eq), dioxane (15 mL) and 6 M HCl (aq.) was stirred at 80° C. for 12 h and concentrated to give 750 mg of 5-(piperidin-3-yl)-4-(trifluoromethyl)pyridin-2 (1H)-one hydrochloride as a yellow oil, which was used without purification. LCMS (ES, m/s): 247 [M+H]+ $^1$H NMR: (400 MHz, DMSO-$d_6$) δ ppm 9.51 (br, 1H), 9.14 (br, 1H), 7.78 (s, 1H), 6.70 (s, 1H), 3.75-3.63 (m, 1H), 3.51-3.48 (m, 1H), 3.24-3.21 (m, 1H), 3.13-3.04 (m, 2H), 3.01-2.94 (m, 1H), 1.85-1.64 (m, 4H).

Step 5

A mixture of 5-(piperidin-3-yl)-4-(trifluoromethyl)pyridin-2 (1H)-one hydrochloride (282 mg, 1 mmol, 2.0 eq), (R)-2-bromo-N-(5-(cyclopropylmethoxy) pyridin-2-yl)propanamide (Intermediate 22) (150 mg, 0.5 mmol, 1.0 eq) and TEA (101 mg, 1 mmol, 2.0 eq) in DMF (10 mL) was stirred at 40° C. for 72 h, poured into water (100 mL) and extracted with ethyl acetate (100 mL×2). The combined extracts were washed with brine (200 mL×3), dried over sodium sulfate, concentrated and purified via silica gel column, eluting with methanol:dichloromethane (1:5) give 140 mg (crude product) as a yellow oil. The material was chirally separated (CHIRAL PAK IG, 2×25 cm, 5 um; Mobile phase A: Hex:DCM=5:1 [10 mmol/L NH$_3$-MeOH], Mobile phase B: EtOH, Flow rate: 20 mL/min; 1:1 A:B) to give peaks with retention times of RT1: 6.057 min and RT2: 7.407 min. The first peak (RT: 6.057 min) was collected and concentrated to give 20 mg (purity: 96%, yield: 8.6%) of (S)—N-(5-(cyclopropylmethoxy)pyridin-2-yl)-2-((S)-3-(6-oxo-4-(trifluoromethyl)-1,6-dihydropyridin-3-yl)piperidin-1-yl)propanamide as a white solid. LCMS (ES, m/s): 465 [M+H]+ $^1$H NMR: (400 MHz, CD$_3$OD) δ ppm 8.06 (d, J=9.2 Hz, 1H), 7.98-7.96 (m, 1H), 7.61 (s, 1H), 7.42-7.39 (m, 1H), 6.80 (s, 1H), 3.88 (d, J=6.8 Hz, 2H), 3.36-3.33 (m, 1H), 3.03-3.00 (m, 1H), 2.95-2.91 (m, 1H), 2.87-2.84 (m, 1H), 2.43-2.40 (m, 1H), 2.33-2.27 (m, 1H), 1.94-1.91 (m, 1H), 1.87-1.82 (m, 1H), 1.80-1.76 (m, 1H), 1.48-1.43 (m, 1H), 1.30 (d, J=7.2 Hz, 3H), 1.28-1.24 (m, 1H), 0.65-0.60 (m, 2H), 0.38-0.34 (m, 2H).

Example 170

((S)-2-((S)-3-(5-amino-6-oxo-1,6-dihydropyridin-3-yl)piperidin-1-yl)-N-(5-chloropyridin-2-yl)propanamide

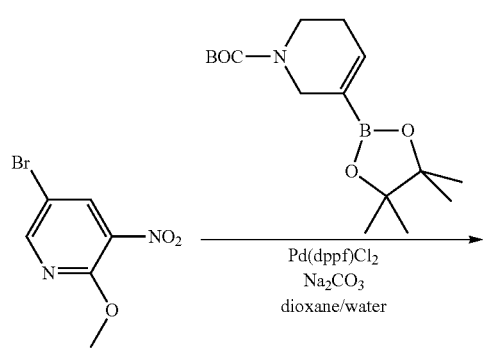

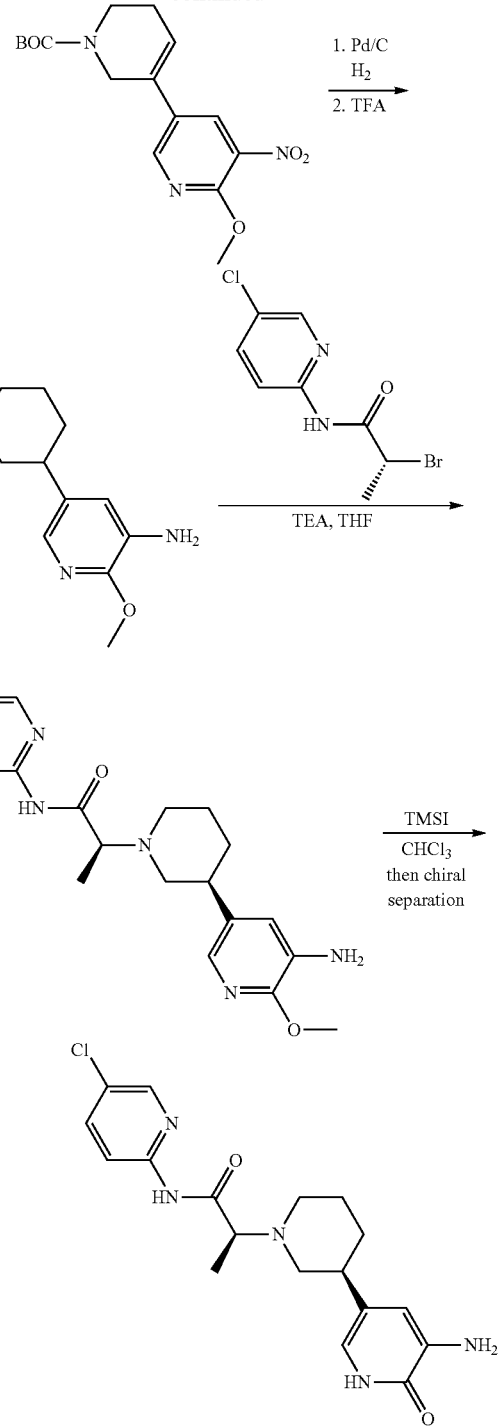

Step 1

To 5-bromo-2-methoxy-3-nitropyridine (1.5 g, 6.4 mmol, 1.0 eq) in dioxane (15 mL) was added tert-butyl 5-(4,4,5,5-tetramethyl-1,3,2-dioxaborolan-2-yl)-3,6-dihydropyridine-1 (2H)-carboxylate (3.0 g, 9.7 mmol, 1.5 eq), Pd(dppf)Cl$_2$ (1 g, 1.3 mmol, 0.2 eq), Na$_2$CO$_3$ (2 g, 19.0 mmol, 3.0 eq) and H$_2$O (5 mL). The reaction was evacuated and flushed with nitrogen three times, stirred 1.5 h at 90° C., cooled to room temperature, quenched with water (200 mL) and extracted with ethyl acetate (200 mL×3). The combined organic phases were dried over Na$_2$SO$_4$, concentrated and purified via silica gel column, eluting with ethyl acetate: petroleum (1:1) to give 1.7 g (purity: 88%) of tert-butyl 6'-methoxy-5'-nitro-5,6-dihydro-[3,3'-bipyridine]-1 (2H)-carboxylate as a brown solid. $^1$H NMR: (300 MHz, CD$_3$OD) δ ppm 8.47 (d, J=2.1 Hz, 1H), 8.35 (d, J=2.4 Hz, 1H), 6.39-6.35 (m, 1H), 4.10 (s, 3H), 4.30-4.26 (m, 2H), 3.61-3.57 (m, 2H), 2.39-2.31 (m, 2H), 1.52 (s, 9H).

Step 2

A mixture of tert-butyl 6'-methoxy-5'-nitro-5,6-dihydro-[3,3'-bipyridine]-1 (2H)-carboxylate (1.7 g, 5.1 mmol, 1.0 eq) and Pd/C (500 mg, 10%) in MeOH (30 mL) was stirred for 15 h under an atmosphere of H$_2$, filtered and concentrated to give 1.8 g crude tert-butyl 3-(5-amino-6-methoxypyridin-3-yl)piperidine-1-carboxylate as an off white solid, which was used without purification. LCMS: (ES, m/s) 308 [M+H]+.

Step 3

To tert-butyl 3-(5-amino-6-methoxypyridin-3-yl)piperidine-1-carboxylate (1.6 g, 5.21 mmol, 1.0 eq) in DCM (15 mL) was added TFA (10 mL). The reaction was stirred for 1 h at room temperature and concentrated to give 1.05 g crude 2-methoxy-5-(piperidin-3-yl)pyridin-3-amine, TFA salt, as a yellow solid, which was used without purification. LCMS (ES, m/s): 208 [M+H]+

Step 4

A mixture of 2-methoxy-5-(piperidin-3-yl)pyridin-3-amine (as free base) (1.05 g, 5.1 mmol, 1.2 eq), (R)-2-bromo-N-(5-chloropyridin-2-yl)propanamide (Intermediate 3) (1.11 g, 4.2 mmol, 1.0 eq) and TEA (2.56 g, 25.4 mmol, 6.0 eq) in THF (20 mL) was stirred for 15 h at 40° C., quenched with water (200 mL) and extracted with ethyl acetate (200 mL×3). The combined organic phases were dried over Na$_2$SO$_4$, concentrated and purified via silica gel column, eluting with ethyl acetate:petroleum (1:1) to give 0.93 g (purity: 94%, yield: 57%) of (2S)-2-(3-(5-amino-6-methoxypyridin-3-yl)piperidin-1-yl)-N-(5-chloropyridin-2-yl)propanamide as a white solid.

LCMS (ES, m/s): 390 [M+H]+

Step 5

To (2S)-2-(3-(5-amino-6-methoxypyridin-3-yl)piperidin-1-yl)-N-(5-chloropyridin-2-yl)propanamide (500 mg, 1.29 mmol, 1.0 eq) in CHCl$_3$ (10 mL) was added TMSI (2.57 g, 12.9 mmol, 10.0 eq), and the reaction was stirred at 50° C. After 4 h, the mixture was diluted with MeOH (15 mL), and the resulting solution was stirred for 0.5 h at 25° C. The solvent was removed, and the residue was purified by reversed phase chromatography (C18 silica gel column, 40 g, 20-45 um, 100 A), eluting with 5-95% AcCN in water (10 mM NH$_4$HCO$_3$) to give 170 mg of the product as an off white solid. This material was chirally separated (CHIRALPAK IF, 2×25 cm, 5 um; Mobile Phase A: Hex [8 mM NH$_3$.MeOH], Mobile Phase B: EtOH; Flow rate: 15 mL/min, 1:1 A:B) to give peaks with retention times of 16.462, 19.514 and 25.304 minutes. The third peak (25.304 min) was collected to give 28 mg (purity: 97.1%, yield: 6%) of ((S)-2-((S)-3-(5-amino-6-oxo-1,6-dihydropyridin-3-yl)piperidin-1-yl)-N-(5-chloropyridin-2-yl)propanamide as a white solid. LCMS (ES, m/s): 376 [M+H]+ $^1$H NMR: (300 MHz, DMSO-d$_6$) δ ppm 11.15 (br, 1H), 10.26 (s, 1H), 8.38-8.37 (m, 1H), 8.16-8.13 (m, 1H), 7.92 (dd, J=8.7, 2.7 Hz, 1H), 6.44-6.41 (m 2H), 4.96 (s, 2H), 3.52-3.50 (m, 1H), 2.87-2.84 (m, 1H), 2.73-2.70 (m, 1H), 2.50-2.49 (m, 1H), 2.31-2.24 (m, 1H), 2.14-2.08 (m, 1H), 1.78-1.64 (m, 2H), 1.60-1.40 (m, 1H), 1.27-1.24 (m, 1H), 1.16 (d, J=6.9 Hz, 3H).

Example 171

(S)—N-(5-(cyclopropylmethoxy)pyridin-2-yl)-2-((R)-3-hydroxy-3-(6-oxo-1,6-dihydropyridin-3-yl) piperidin-1-yl)propanamide

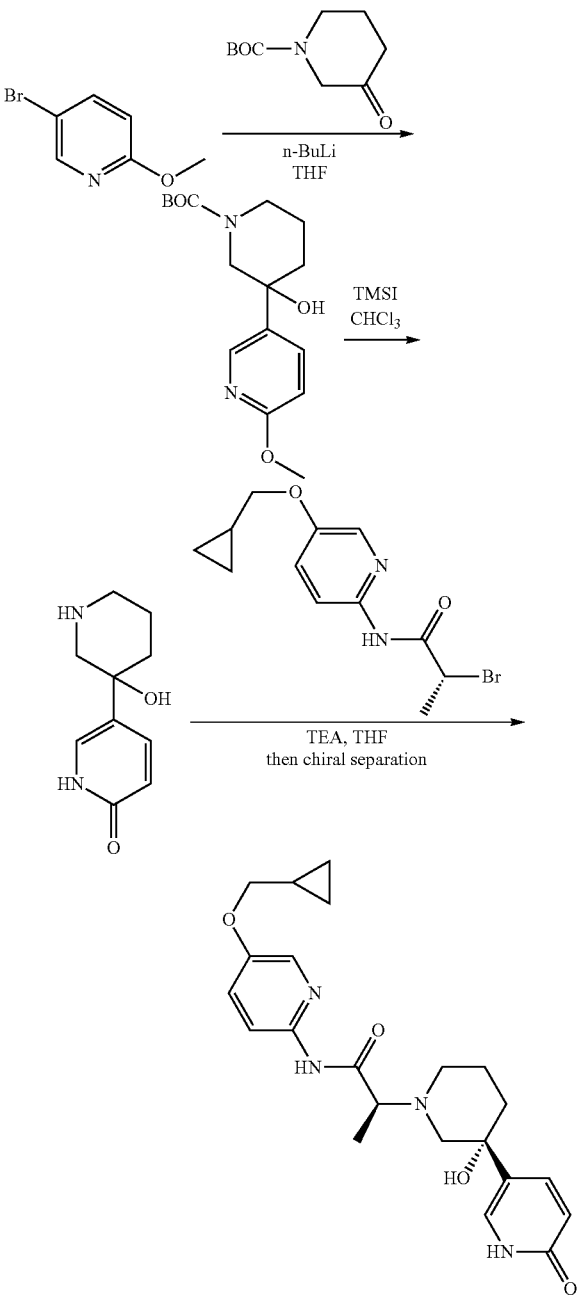

Step 1

To 5-bromo-2-methoxypyridine (2.42 g, 12.9 mmol 3.0 eq) in (tetrahydrofuran:diethyl ether, 1:2) (54 mL) at −78° C. was added n-BuLi (4.44 mL, 11.1 mmol 2.6 eq, 2.5 M in hexane). After 10 min, a solution of tert-butyl 3-oxopiperidine-1-carboxylate (856 mg, 4.30 mmol 1.0 eq) in tetrahydrofuran (3 mL) was added slowly. After 3 h, the reaction was poured into saturated ammonium chloride solution and extracted with ethyl acetate (200 mL×3). The organic layers were combined, washed with brine, dried, concentrated and purified via silica gel column, eluting with ethyl acetate: petroleum ether (1:2) to give 600 mg (purity: 76%, yield=45%) of tert-butyl 3-hydroxy-3-(6-methoxypyridin-3-yl)piperidine-1-carboxylate as a yellow oil. LCMS: (ES, m/s) 309 [M+H]+. $^1$H NMR (300 MHz, DMSO-$d_6$) δ ppm 8.27 (d, J=2.4 Hz, 1H), 7.81 (dd, J=8.8, 2.4 Hz, 1H), 6.78 (d, J=8.8 Hz, 1H), 5.07 (s, 1H), 3.84 (s, 3H), 3.75-3.70 (m, 1H), 3.60-3.57 (m, 1H), 3.21-3.12 (m, 1H), 3.05-2.98 (m, 1H), 1.99-1.95 (m, 1H), 1.88-1.71 (m, 3H), 1.40 (s, 9H).

Step 2

To tert-butyl 3-hydroxy-3-(6-methoxypyridin-3-yl)piperidine-1-carboxylate (600 mg, 1.95 mmol, 1.0 eq) in CHCl$_3$ (25 mL) was added TMSI (1.95 g, 9.74 mmol, 5.0 eq), and the mixture was stirred at 50° C. After 3 h, the reaction was quenched with saturated sodium thiosulfate solution (20 mL) and saturated sodium bicarbonate solution (20 mL). This mixture was concentrated, dissolved in dichloromethane (20 mL) and methanol (5 mL), and filtered. The filtrate was concentrated to give 150 mg crude 5-(3-hydroxypiperidin-3-yl)pyridin-2 (1H)-one as a brown solid, which was used without purification. LCMS: (ES, m/s) 195 [M+H]+. $^1$H NMR: (300 MHz, DMSO-$d_6$) δ ppm 7.80-7.77 (m, 1H), 7.40-7.34 (m, 1H), 6.34-6.31 (m, 1H), 5.02 (s, 1H), 3.60 (br, 1H), 3.21-3.12 (m, 1H), 3.02-2.90 (m, 2H), 2.81-2.65 (m, 2H), 1.83-1.62 (m, 4H).

Step 3

A mixture of 5-(3-hydroxypiperidin-3-yl)pyridin-2 (1H)-one (150 mg, 0.77 mmol, 1.0 eq), (R)-2-bromo-N-(5-(cyclopropylmethoxy) pyridin-2-yl)propanamide (Intermediate 22) (231 mg, 0.77 mmol, 1.0 eq) and TEA (390 mg, 3.87 mmol, 5 eq) in THF (8 mL) was stirred at 40° C. for 16 h, poured into water (100 mL) and extracted with ethyl acetate (100 mL×2). The combined extracts were dried over sodium sulfate, concentrated and purified via silica gel column, eluting with methanol:dichloromethane (1:10) give 50 mg material as a yellow oil. The material was chirally separated (CHIRALPAK IA, 2×25 cm, 5 um; Mobile Phase A: Hex [0.1% DEA], Mobile Phase B: ethanol; Flow rate: 20 mL/min; 1:1 A:B) to give peaks with retention times of RT1: 12.339 min and RT2: 15.935 min. The first peak (RT: 12.339 min) was collected and concentrated to give 17 mg (purity: 95%, yield: 5%) of the pure (S)—N-(5-(cyclopropylmethoxy)pyridin-2-yl)-2-((R)-3-hydroxy-3-(6-oxo-1,6-dihydropyridin-3-yl)piperidin-1-yl)propanamide as white solid. LCMS (ES, m/s): 413 [M+H]+ $^1$H NMR (300 MHz, DMSO-$d_6$) δ ppm 11.41 (br, 1H), 10.27 (s, 1H), 8.04-7.98 (m, 2H), 7.61-7.57 (m, 1H), 7.44-7.36 (m, 2H), 6.27 (d, J=9.6 Hz, 1H), 5.19 (s, 1H), 3.87 (d, J=7.2 Hz, 2H), 3.43-3.40 (m, 1H), 2.75-2.55 (m, 3H), 2.29-2.27 (m, 1H), 1.89-1.82 (m, 1H), 1.76-1.59 (m, 1H), 1.57-1.43 (m, 2H), 1.31-1.19 (m, 1H), 1.14 (d, J=6.9 Hz, 3H), 0.63-0.51 (m, 2H), 0.40-0.26 (m, 2H).

Example 172

(S)—N-(5-chloropyridin-2-yl)-2-((3S,5S)-(3-methyl-5-(6-oxo-1,6-dihydropyridin-3-yl)piperidin-1-yl)propanamide

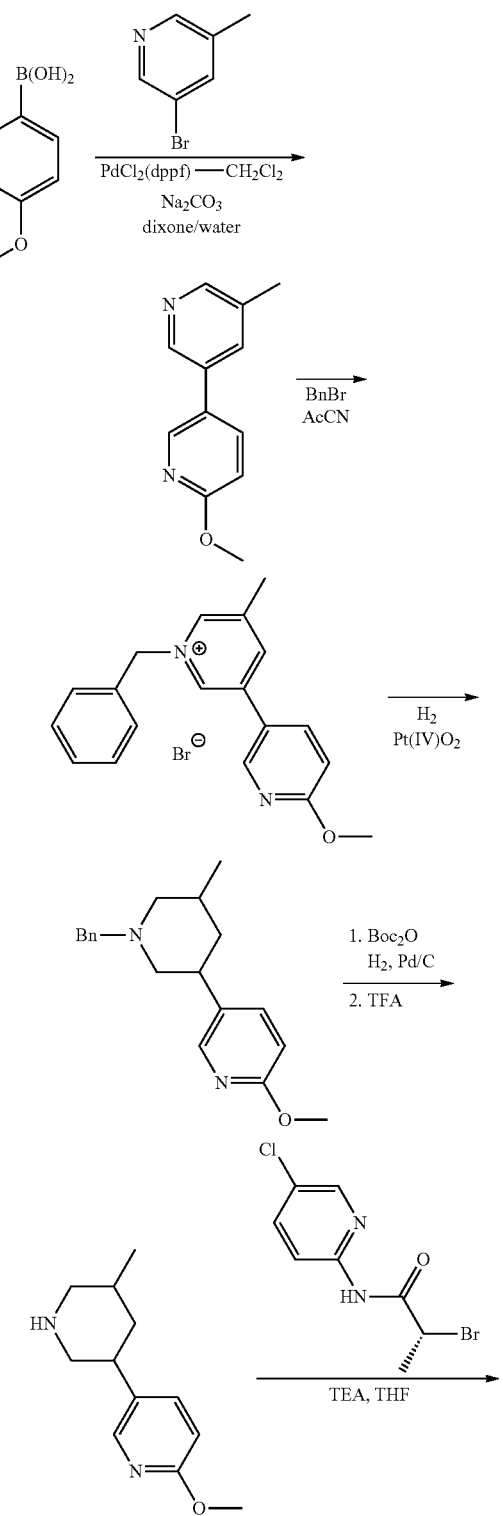

-continued

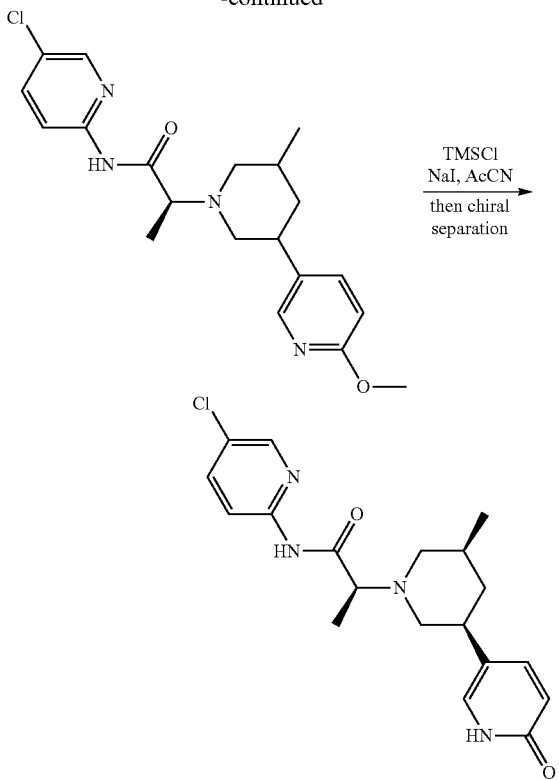

TMSCl
NaI, AcCN
then chiral
separation

Step 1

To (6-methoxypyridin-3-yl)boronic acid (4.00 g, 26.2 mmol), Na$_2$CO$_3$ (5.54 g, 52.3 mmol) and 3-bromo-5-methylpyridine (4.95 g, 28.8 mmol) in water (20.00 mL) and dioxane (60.0 mL) was added PdCl$_2$(dppf)-CH$_2$Cl$_2$ adduct (2.136 g, 2.62 mmol). The mixture was heated to 95° C. for 3 hours, cooled to RT, diluted with water and extracted with EtOAc (3×). The combined organic layers were washed with brine (2×), dried over Na$_2$SO$_4$, filtered and concentrated. The residue was purified via normal phase chromatography (Combiflash Rf, 80 g silica column, 60 mL/min, EtOAc in hexanes 0-50%) to afford 6'-methoxy-5-methyl-3,3'-bipyridine (4.95 g, 24.72 mmol, 95% yield) as an off white solid. LCMS: (ES, m/s) 201 [M+H]+. $^1$H NMR (400 MHz, DMSO-d$_6$) δ ppm: 8.69 (d, J=2.0 Hz, 1H), 8.53 (dd, J=2.4, 0.7 Hz, 1H), 8.41 (dd, J=2.0, 0.7 Hz, 1H), 8.07 (dd, J=8.6, 2.7 Hz, 1H), 7.90 (td, J=2.1, 0.7 Hz, 1H), 6.94 (dd, J=8.7, 0.9 Hz, 1H), 3.90 (s, 3H), 2.36 (d, J=0.7 Hz, 3H)

Step 2

To a suspension of 6'-methoxy-5-methyl-3,3'-bipyridine (3.26 g, 16.28 mmol) in acetonitrile (50.0 mL) was added benzyl bromide (1.936 mL, 16.28 mmol). The reaction was stirred at 70° C. overnight, then cooled to RT. The mixture was concentrated to 1/5 initial volume, and the resulting solid was collected by filtration and air dried to afford 1-benzyl-6'-methoxy-5-methyl-[3,3'-bipyridin]-1-ium bromide (4.68 g, 12.61 mmol, 77% yield) as an off white solid, which was used without purification. LCMS: (ES, m/s) 291 [M+H]+. $^1$H NMR (400 MHz, DMSO-d$_6$) δ ppm: 9.57 (s, 1H), 9.06 (s, 1H), 8.84 (s, 1H), 8.74 (dd, J=2.7, 0.7 Hz, 1H), 8.24 (dd, J=8.8, 2.7 Hz, 1H), 7.57-7.72 (m, 2H), 7.37-7.49 (m, 3H), 7.08 (dd, J=8.8, 0.7 Hz, 1H), 5.83 (s, 2H), 3.95 (s, 3H), 2.54 (s, 3H).

Step 3

To a solution of 1-benzyl-6'-methoxy-5-methyl-[3,3'-bipyridin]-1-ium bromide (5.63 g, 15.16 mmol) in methanol (60 mL) was added platinum(IV) oxide (0.344 g, 1.516 mmol). The mixture was vacuumed and back filled with H$_2$ twice, and the reaction was hydrogenated under an H$_2$ balloon overnight. The mixture was filtered, washed with MeOH and concentrated. The residue was diluted with EtOAc/sat. NaHCO$_3$ and extracted with EtOAc (3×). The combined organic extracts were washed with brine (2×), dried over Na$_2$SO$_4$, filtered and concentrated. The residue was purified via normal phase chromatography (Combiflash Rf, 120 g silica column, 80 mL/min, EtOAc in hexanes 0-80%) to afford 2 isomers. Isomer 2: cis-5-(1-benzyl-5-methylpiperidin-3-yl)-2-methoxypyridine (2.64 g, 8.91 mmol, 58.7% yield) as a light yellow oil. Structure was confirmed by NMR analysis: ROESY showed both H10/H14 and methyl H23 had correlation to H5 axial proton. NMR data indicated both pyridine ring and methyl were at equatorial position as cis-isomer. LCMS (ES, m/s): 297 [M+H]+, retention time 0.54 minutes, LCMS Method 5. $^1$H NMR (400 MHz, DMSO-d$_6$) δ ppm: 8.01 (d, J=2.3 Hz, 1H), 7.57 (dd, J=8.5, 2.4 Hz, 1H), 7.27-7.34 (m, 4H), 7.19-7.26 (m, 1H), 6.72 (d, J=8.6 Hz, 1H), 3.79 (s, 3H), 3.41-3.56 (m, 2H), 2.72-2.84 (m, 3H), 1.84-1.92 (m, 1H), 1.66-1.80 (m, 2H), 1.52-1.62 (m, 1H), 0.99-1.20 (m, 1H), 0.85 (d, J=6.3 Hz, 3H).

Step 4

To cis-5-(1-benzyl-5-methylpiperidin-3-yl)-2-methoxypyridine (500 mg, 1.687 mmol) and Boc-anhydride (0.431 mL, 1.856 mmol) in ethanol (10 mL) under N$_2$ was added palladium on carbon (17.95 mg, 0.169 mmol). The mixture was vacuumed and back filled with H$_2$ twice, stirred under an H$_2$ balloon overnight, filtered, washed with MeOH and concentrated. The residue was purified via normal phase chromatography (Combiflash Rf, 40 g silica column, 40 mL/min, EtOAc in hexanes 0-40%) to afford cis-tert-butyl 3-(6-methoxypyridin-3-yl)-5-methylpiperidine-1-carboxylate (460 mg, 1.501 mmol, 89% yield) as a colorless wax. LCMS (ES, m/s): 307 [M+H]+, retention time 1.00 minutes, LCMS Method 5. $^1$H NMR (400 MHz, DMSO-d$_6$) δ ppm: 8.06 (d, J=2.3 Hz, 1H), 7.62 (dd, J=8.5, 2.5 Hz, 1H), 6.77 (d, J=8.5 Hz, 1H), 3.86-4.02 (m, 2H), 3.81 (s, 3H), 2.57-2.70 (m, 1H), 2.55-2.72 (m, 1H), 1.82 (br d, J=12.5 Hz, 1H), 1.52-1.62 (m, 1H), 1.40 (s, 9H), 1.22-1.34 (m, 2H), 0.88 (d, J=6.5 Hz, 3H).

Step 5 cis-tert-Butyl 3-(6-methoxypyridin-3-yl)-5-methylpiperidine-1-carboxylate (460 mg, 1.501 mmol) in TFA (3.0 mL, 38.9 mmol) was stirred for 1 h and concentrated to afford cis-2-methoxy-5-(5-methylpiperidin-3-yl)pyridine, trifluoroacetic acid salt (481 mg, 1.502 mmol, 100% yield) as a colorless wax. To this material and (R)-2-bromo-N-(5-chloropyridin-2-yl)propanamide (Intermediate 3) (396 mg, 1.502 mmol) in DMSO (10.0 mL) was added DIEA (1.049 mL, 6.01 mmol). The mixture was stirred overnight, diluted with water and extracted with EtOAc (3×). The combined organic layers were washed with brine (2×), dried over Na$_2$SO$_4$, filtered and concentrated. The residue was purified via normal phase chromatography (Combiflash Rf, 40 g silica column, 40 mL/min, EtOAc in hexanes 20-70%) to afford cis-(2S)—N-(5-chloropyridin-2-yl)-2-(3-(6-methoxypyridin-3-yl)-5-methylpiperidin-1-yl)propanamide (525 mg, 1.350 mmol, 90% yield) as a light colored wax. LCMS (ES, m/s): 389 [M+H]+, retention time 0.63 minutes, LCMS Method 5. $^1$H NMR (400 MHz, DMSO-d$_6$) δ ppm: 10.29 (s, 1H), 8.37 (dd, J=6.3, 2.5 Hz, 1H), 8.14 (dd, J=9.0, 3.4 Hz, 1H), 8.04 (dd, J=17.9, 2.4 Hz, 1H), 7.92 (ddd, J=8.6, 5.4, 2.7 Hz, 1H), 7.60 (ddd, J=17.5, 8.6, 2.5 Hz, 1H), 6.74 (dd, J=11.3, 8.5 Hz, 1H), 3.80 (d, J=7.6 Hz, 3H), 3.45-3.62 (m, 1H), 2.64-2.94 (m, 3H), 2.29-2.48 (m, 1H), 1.94-2.19 (m, 1H), 1.64-1.92 (m, 3H), 1.17 (dd, J=6.8, 4.8 Hz, 3H), 0.84-0.91 (m, 3H).

Step 6

To cis-(2S)—N-(5-chloropyridin-2-yl)-2-(3-(6-methoxypyridin-3-yl)-5-methylpiperidin-1-yl)propanamide (520 mg, 1.337 mmol) and sodium iodide (601 mg, 4.01 mmol) in acetonitrile (4 mL) was added TMS-Cl (0.513 mL, 4.01 mmol), dropwise. The mixture was stirred overnight, diluted with water and extracted with EtOAc (3×). The combined organic layers were washed with brine (2×), dried over Na$_2$SO$_4$, filtered, concentrated and purified via normal phase chromatography (Combiflash Rf, 80 g silica column, 65 mL/min, MeOH in DCM 0-10%) to afford 430 mg of product as a mixture of diastereomers. Four isomers were detected by chiral analysis, which suggested epimerization. The mixture was separated by prep-chiral HPLC (Column: CC4 30×250 mm 5 mic; 40:60 Ethanol:Heptane-ramping to 60:40 Ethanol:Heptane after the elution of the 3rd peak [Modifier: 0.1% IPA]). The 2$^{nd}$ peak was collected and concentrated to afford (S)—N-(5-chloropyridin-2-yl)-2-((3S,5S)-(3-methyl-5-(6-oxo-1,6-dihydropyridin-3-yl)piperidin-1-yl)propanamide (112.8 mg, 0.286 mmol, 21.38% yield) as an off white solid. LCMS (ES, m/s): 375 [M+H]+, retention time 0.48 minutes, LCMS Method 5. $^1$H NMR (400 MHz, DMSO-d$_6$) δ ppm: 11.35-11.49 (m, 1H), 10.26 (s, 1H), 8.33-8.42 (m, 1H), 8.14 (d, J=9.5 Hz, 1H), 7.92 (dd, J=8.9, 2.6 Hz, 1H), 7.41 (dd, J=9.4, 2.6 Hz, 1H), 7.17 (d, J=2.5 Hz, 1H), 6.28 (d, J=9.3 Hz, 1H), 3.55 (q, J=6.8 Hz, 1H), 3.33 (s, 3H), 2.82-2.92 (m, 1H), 2.58-2.70 (m, 2H), 2.19-2.35 (m, 1H), 1.62-1.87 (m, 3H), 1.16 (d, J=7.0 Hz, 3H), 0.93-1.05 (m, 1H), 0.85 (d, J=6.5 Hz, 3H).

Example 173

(S)—N-(5-chloropyridin-2-yl)-2-((3R,5S)-(3-methyl-5-(6-oxo-1,6-dihydropyridin-3-yl)piperidin-1-yl)propanamide

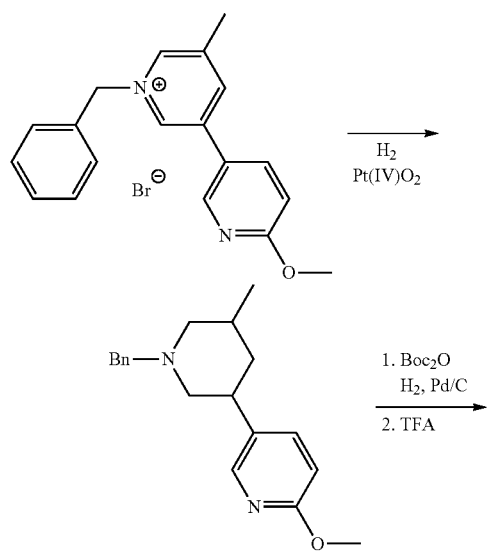

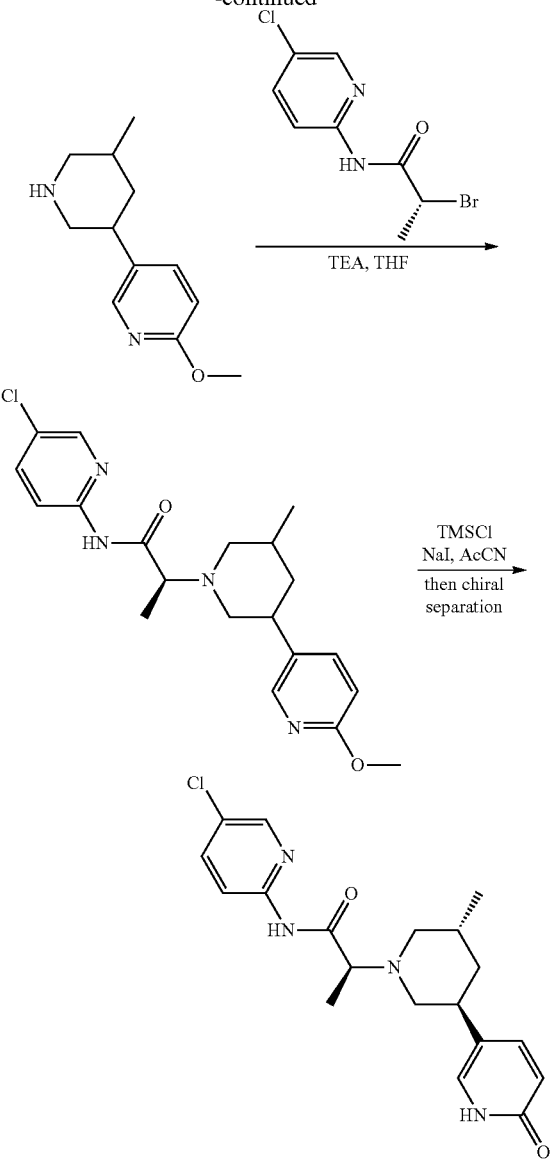

Step 1

To a solution of 1-benzyl-6'-methoxy-5-methyl-[3,3'-bipyridin]-1-ium bromide (5.63 g, 15.16 mmol) (Example 172, Step 2) in methanol (60 mL) was added platinum(IV) oxide (0.344 g, 1.516 mmol). The mixture was vacuumed and back filled with H$_2$ twice, and the reaction was hydrogenated under an H$_2$ balloon overnight. The mixture was filtered, washed with MeOH and concentrated. The residue was diluted with EtOAc/sat. NaHCO$_3$ and extracted with EtOAc (3×). The combined organic extracts were washed with brine (2×), dried over Na$_2$SO$_4$, filtered and concentrated. The residue was purified via normal phase chromatography (Combiflash Rf, 120 g silica column, 80 mL/min, EtOAc in hexanes 0-80%) to afford 2 isomers. Isomer 2 elucidated in Example 173, Step 3 above; Isomer 1: trans-5-(1-benzyl-5-methylpiperidin-3-yl)-2-methoxypyridine (0.54 g, 1.822 mmol, 12.01% yield) as a light yellow oil. LCMS (ES, m/s): 297 [M+H]$^+$, retention time 0.52 minutes, LCMS Method 5. $^1$H NMR (400 MHz, DMSO-d$_6$) δ ppm: 8.14 (d, J=2.0 Hz, 1H), 7.73 (dd, J=8.4, 2.1 Hz, 1H), 7.28-7.37 (m, 4H), 7.20-7.26 (m, 1H), 6.72 (d, J=8.5 Hz, 1H), 3.80 (s, 3H), 3.40-3.51 (m, 2H), 2.96-3.03 (m, 1H), 2.57 (br d, J=8.5 Hz, 1H), 2.34-2.47 (m, 2H), 2.09-2.20 (m, 1H), 1.81 (br s, 1H), 1.61-1.76 (m, 1H), 1.42-1.52 (m, 1H), 0.97 (br d, J=6.5 Hz, 3H).

Step 2

To trans-5-(1-benzyl-5-methylpiperidin-3-yl)-2-methoxypyridine (540 mg, 1.822 mmol) and Boc-anhydride (0.465 mL, 2.004 mmol) in ethanol (10 mL) under $N_2$ was added palladium on carbon (19.39 mg, 0.182 mmol). The mixture was vacuumed and back filled with $H_2$ twice, stirred under an $H_2$ balloon overnight, filtered, washed with MeOH and concentrated. The residue was purified via normal phase chromatography (Combiflash Rf, 40 g silica column, 40 mL/min, EtOAc in hexanes 0-40%) to afford trans-tert-butyl 3-(6-methoxypyridin-3-yl)-5-methylpiperidine-1-carboxylate (460 mg, 1.501 mmol, 89% yield) as a colorless wax. LCMS (ES, m/s): 307 [M+H]$^+$, retention time 0.93 minutes, LCMS Method 5. $^1$H NMR (400 MHz, DMSO-d$_6$) δ ppm: 8.07 (d, J=2.2 Hz, 1H), 7.63 (dd, J=8.5, 2.6 Hz, 1H), 6.76 (d, J=8.5 Hz, 1H), 3.81 (s, 3H), 2.95-3.80 (m, 4H), 2.90 (br s, 1H), 1.81-1.93 (m, 2H), 1.53-1.65 (m, 1H), 1.38 (br s, 9H), 0.95 (br d, J=2.6 Hz, 3H).

Step 3 trans-tert-Butyl 3-(6-methoxypyridin-3-yl)-5-methylpiperidine-1-carboxylate (480 mg, 1.567 mmol) in TFA (3.0 mL, 38.9 mmol) was stirred for 1 hour and concentrated to afford trans-2-methoxy-5-(5-methylpiperidin-3-yl)pyridine, trifluoroacetic acid salt (502 mg, 1.567 mmol, 100% yield) as a colorless wax. To this material and (R)-2-bromo-N-(5-chloropyridin-2-yl)propanamide (Intermediate 3) (413 mg, 1.567 mmol) in DMSO (5.0 mL) was added DIEA (1.095 mL, 6.27 mmol). The mixture was stirred overnight, diluted with water and extracted with EtOAc (3×). The combined organic layers were washed with brine (2×), dried over Na$_2$SO$_4$, filtered and concentrated. The residue was purified via normal phase chromatography (Combiflash Rf, 40 g silica column, 40 mL/min, EtOAc in hexanes 20-70%) to afford trans-(2S)—N-(5-chloropyridin-2-yl)-2-(3-(6-methoxypyridin-3-yl)-5-methylpiperidin-1-yl)propanamide (525 mg, 1.350 mmol, 86% yield) as a light colored wax. LCMS (ES, m/s): 389 [M+H]$^+$, retention time 0.61, 0.62 minutes, LCMS Method 5. $^1$H NMR (400 MHz, DMSO-d$_6$) δ ppm: 10.21 (d, J=13.1 Hz, 1H), 8.37 (d, J=2.5 Hz, 1H), 8.08-8.18 (m, 2H), 7.92 (dd, J=8.9, 2.6 Hz, 1H), 7.71 (br d, J=8.8 Hz, 1H), 6.71 (t, J=8.3 Hz, 1H), 3.80 (s, 3H), 3.40-3.58 (m, 1H), 2.94-3.15 (m, 1H), 2.73-2.84 (m, 1H), 2.52-2.69 (m, 2H), 2.25-2.40 (m, 1H), 1.82-2.00 (m, 1H), 1.65-1.80 (m, 1H), 1.44-1.55 (m, 1H), 1.17 (dd, J=12.9, 6.9 Hz, 3H), 1.07 (dd, J=17.6, 6.8 Hz, 3H).

Step 4

To trans-(2S)—N-(5-chloropyridin-2-yl)-2-(3-(6-methoxypyridin-3-yl)-5-methylpiperidin-1-yl)propanamide (520 mg, 1.337 mmol) and sodium iodide (1002 mg, 6.69 mmol) in acetonitrile (4 mL) was added TMS-Cl (0.854 mL, 6.69 mmol), dropwise. The mixture was stirred overnight, diluted with water and extracted with EtOAc (3×). The combined organic layers were washed with brine (2×), dried over Na$_2$SO$_4$, filtered, concentrated and purified via normal phase chromatography (Combiflash Rf, 80 g silica column, 65 mL/min, MeOH in DCM 0-10%) to afford 430 mg of product as a mixture of diastereomers. Four isomers were detected by chiral analysis, which suggested epimerization. The mixture was separated by prep-chiral HPLC (Column: Lux Amylose 30×250 mm 5 mic; 70:30 Ethanol:Heptane [Modifier: 0.1% IPA]). The 2$^{nd}$ peak was collected and concentrated to afford (S)—N-(5-chloropyridin-2-yl)-2-((3R,5S)-(3-methyl-5-(6-oxo-1,6-dihydropyridin-3-yl)piperidin-1-yl)propanamide (57.2 mg, 0.145 mmol, 10.84% yield) as an off white solid. LCMS (ES, m/s): 375 [M+H]$^+$, retention time 0.50 minutes, LCMS Method 5. $^1$H NMR (400 MHz, DMSO-d$_6$) δ ppm: 11.18-11.50 (m, 1H), 10.17 (s, 1H), 8.27-8.43 (m, 1H), 8.07-8.19 (m, 1H), 7.91 (dd, J=8.9, 2.6 Hz, 1H), 7.45 (dd, J=9.5, 2.8 Hz, 1H), 7.25 (d, J=2.5 Hz, 1H), 6.22 (d, J=9.5 Hz, 1H), 3.52 (q, J=6.9 Hz, 1H), 2.87 (dt, J=8.5, 4.4 Hz, 1H), 2.67-2.78 (m, 1H), 2.51-2.58 (m, 2H), 2.19-2.31 (m, 1H), 1.85-1.99 (m, 1H), 1.62 (ddd, J=13.2, 9.2, 4.5 Hz, 1H), 1.43 (dt, J=13.0, 4.8 Hz, 1H), 1.14 (d, J=7.0 Hz, 3H), 1.00-1.10 (m, 3H).

Example 174

(S)-2-((R)-3-(6-amino-5-oxo-4,5-dihydropyrazin-2-yl)piperidin-1-yl)-N-(5-chloropyridin-2-yl)propanamide

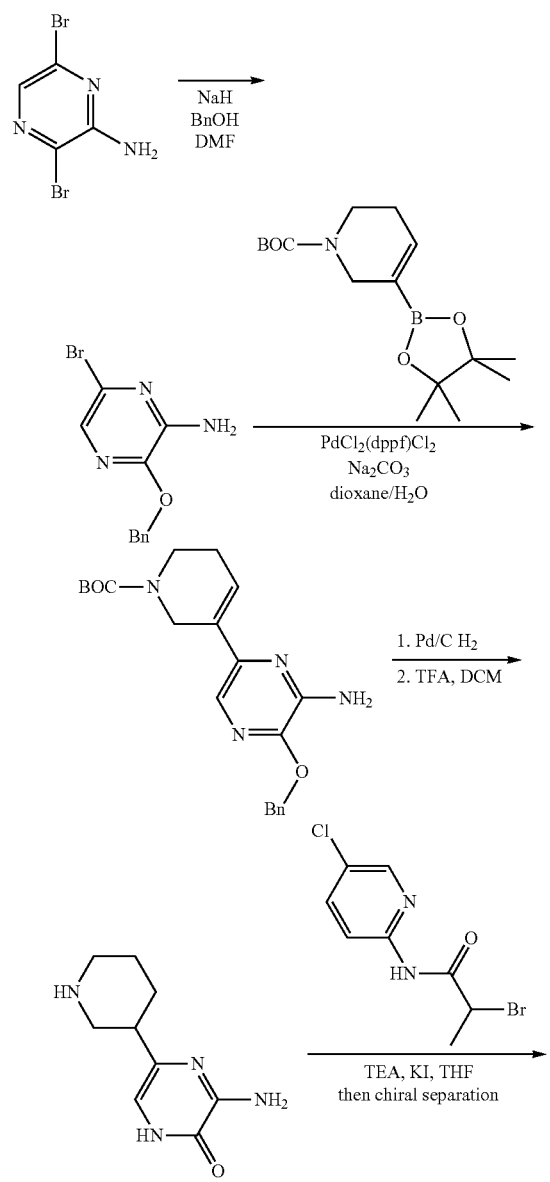

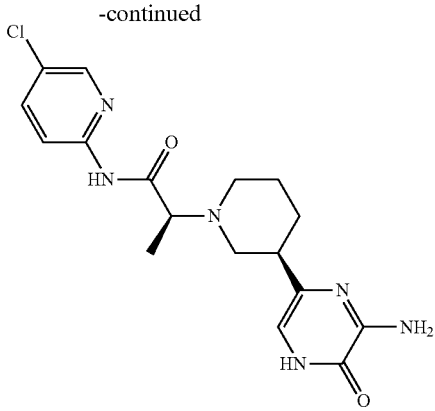

Step 1

To benzyl alcohol (4.30 g, 39.84 mmol, 1.0 eq) in DMF (50 mL) at 0° C., sodium hydride (60%, 2.39 g, 59.76 mmol, 1.5 eq) was added in batches. After 20 min, 3,6-dibromopyrazin-2-amine (10.00 g, 39.84 mmol, 1.0 eq) was added, and the reaction was stirred at 80° C. After 2 h, the reaction was quenched with saturated aqueous $NH_4Cl$ (10 mL), poured into water (800 mL) and extracted with ethyl acetate (500 mL×3). The combined organic phases were dried over sodium sulfate, concentrated and purified via silica gel column, eluting with ethyl acetate in petroleum ether (0-30%) to give 9.6 g crude 3-(benzyloxy)-6-bromopyrazin-2-amine as a green solid. LCMS: (ES, m/s) 280 [M+H]+. $^1$H NMR: (400 MHz, DMSO-$d_6$) δ ppm 7.47-7.45 (m, 2H), 7.41-7.32 (m, 3H), 7.25 (s, 1H), 6.71 (s, 2H), 5.27 (s, 2H).

Step 2

To 3-(benzyloxy)-6-bromopyrazin-2-amine (2.00 g, 7.17 mmol, 1.0 eq) in dioxane (60 mL) and water (30 mL) were added tert-butyl 5-(4,4,5,5-tetramethyl-1,3,2-dioxaborolan-2-yl)-3,6-dihydropyridine-1 (2H)-carboxylate (3.32 g, 10.76 mmol, 1.5 eq), sodium carbonate (2.97 g, 21.5 mmol, 3 eq) and Pd(dppf)$Cl_2$ (525 mg, 0.72 mmol, 0.1 eq). The reaction was evacuated and flushed with nitrogen three times, stirred 2 h at 95° C., cooled to room temperature, poured into water (300 mL) and extracted with ethyl acetate (200 mL×3). The combined organic extracts were dried over sodium sulfate, concentrated and purified via silica gel column, eluting with ethyl acetate in petroleum ether (0-20%, over 30 min) to give 1.48 g (yield: 54%, purity: 99%) of tert-butyl 5-(6-amino-5-(benzyloxy)pyrazin-2-yl)-3,6-dihydropyridine-1 (2H)-carboxylate as a yellow oil. LCMS: (ES, m/s) 384 [M+H]+. $^1$H NMR: (300 MHz, $CD_3OD$) δ ppm 7.49-7.46 (m, 2H), 7.42-7.32 (m, 4H), 6.57-6.53 (m, 1H), 5.42 (s, 2H), 4.29-4.28 (m, 2H), 3.58-3.53 (m, 2H), 2.33-2.28 (m, 2H), 1.51 (s, 9H).

Step 3

A mixture of tert-butyl 5-(6-amino-5-(benzyloxy)pyrazin-2-yl)-3,6-dihydropyridine-1 (2H)-carboxylate (1.38 g, 3.61 mmol, 1.0 eq) and Pd/C (433 mg, 10%) in methanol (70 mL) was evacuated and flushed three times with nitrogen, followed by flushing with hydrogen. The mixture was stirred 18 h under an atmosphere of hydrogen (balloon), filtered, concentrated and purified via silica gel column, eluting with ethyl acetate:petroleum ether (0-30%, in 30 min) to give 300 mg (yield: 30%, purity: 90%) of tert-butyl 3-(6-amino-5-hydroxypyrazin-2-yl)piperidine-1-carboxylate as a white solid. LCMS (ES, m/s): 259 [M+H]+ $^1$H NMR: (400 MHz, $CD_3OD$) δ ppm 6.49 (s, 1H), 4.13-3.99 (m, 2H), 2.99-2.81 (m, 2H), 2.45-2.38 (m, 1H), 1.95-1.90 (m, 1H), 1.77-1.65 (m, 2H), 1.57-1.49 (m, 1H), 1.51 (s, 9H).

Step 4

A mixture of tert-butyl 3-(6-amino-5-hydroxypyrazin-2-yl)piperidine-1-carboxylate (300 mg, 1.02 mmol, 1.0 eq), dichloromethane (13 mL) and trifluoroacetic acid (13 mL) was stirred 2 h and concentrated to give 634 mg crude 3-amino-5-(piperidin-3-yl)pyrazin-2-ol, TFA salt, as a yellow oil, which was used without purification. LCMS: (ES, m/s): 195

Step 5

To 3-amino-5-(piperidin-3-yl)pyrazin-2-ol (as a free base) (634 mg, 3.27 mmol, 1.0 eq) and 2-bromo-N-(5-chloropyridin-2-yl)propanamide (Intermediate 3) (856 mg, 3.27 mmol, 1.0 eq) in THF (30 mL) were added potassium iodide (543 mg, 3.27 mmol, 1.0 eq) and triethylamine (1.95 g, 13 mmol, 4.0 eq). The reaction was stirred 24 h at 60° C., concentrated and purified via a silica gel column, eluting with ethyl acetate:petroleum ether (0-50%, in 30 min) to give a racemic product (130 mg) as a white solid. This material was chirally separated (CHIRALPAK IF-2, 2×25 cm, 5 um; Mobile Phase A: Hex [8 mmol/L $NH_3$.MeOH] Mobile Phase B: EtOH; Flow rate: 16 mL/min; 1:1 A:B), resulting in four peaks with retention times of 10.782, 12.385, 15.323 and 16.819 minutes. The third peak (15.323 min) was collected to give 30 mg (yield: 2%, purity: 98%, ee %: 99%) of (S)-2-((R)-3-(6-amino-5-oxo-4,5-dihydropyrazin-2-yl)piperidin-1-yl)-N-(5-chloropyridin-2-yl)propanamide as a white solid. LCMS (ES, m/s): 377 [M+H]+ $^1$H NMR: (400 MHz, DMSO-$d_6$) δ 11.38 (s, 1H), 10.23 (s, 1H), 8.36 (d, J=2.0 Hz, 1H), 8.13 (d, J=9.2 Hz, 1H), 7.92 (dd, J=2.0, 9.2 Hz, 1H), 6.53-6.49 (m, 2H), 6.38 (s, 1H), 3.49 (d, J=6.8 Hz, 1H), 2.93-2.90 (m, 1H), 2.72-2.70 (m, 1H), 2.50-2.46 (m, 1H), 2.40-2.35 (m, 1H), 2.17-2.11 (m, 1H), 1.74-1.72 (m, 2H), 1.53-1.50 (m, 1H), 1.43-1.38 (m, 1H), 1.16 (d, J=6.4 Hz, 3H).

Example 175

(S)-2-((S)-3-(5-(aminomethyl)-6-oxo-1,6-dihydropyridin-3-yl)piperidin-1-yl)-N-(5-chloropyridin-2-yl)propanamide

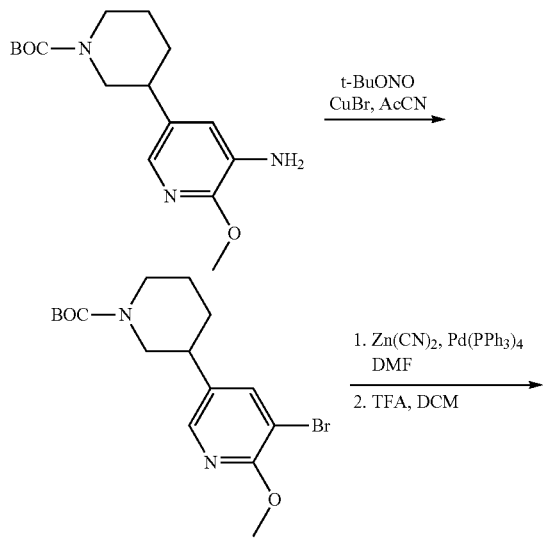

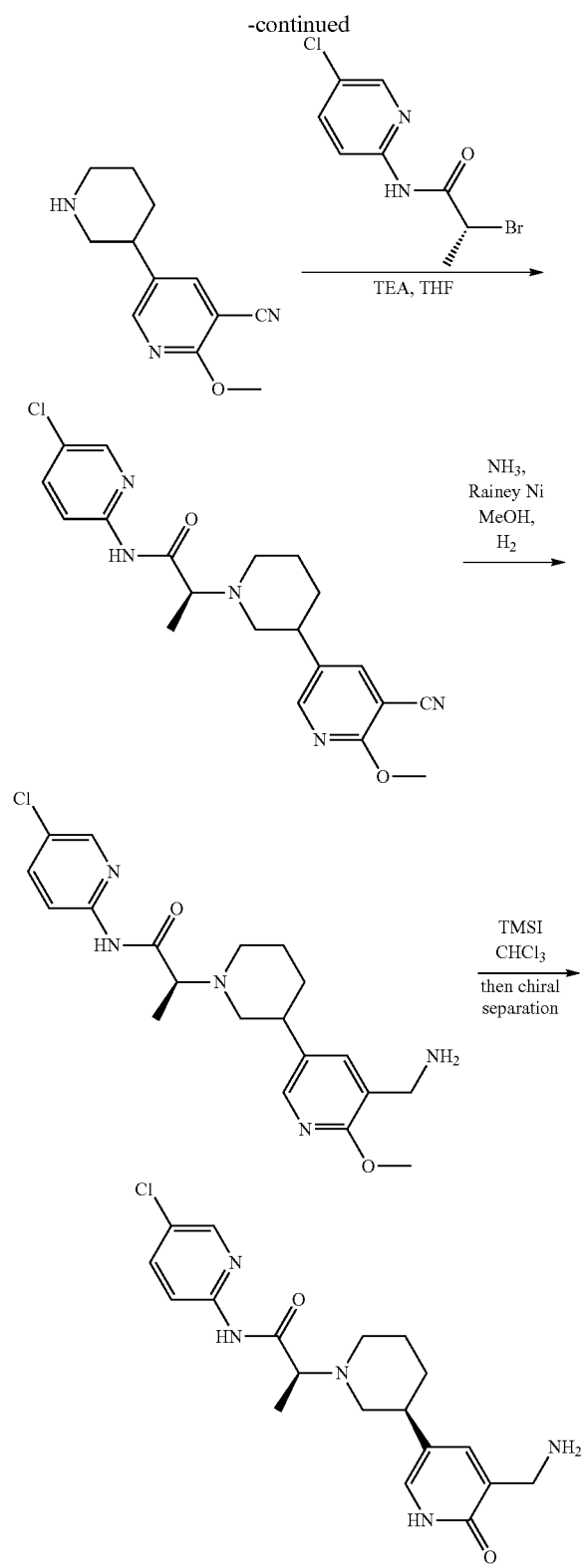

Step 1

To tert-butyl 3-(5-amino-6-methoxypyridin-3-yl)piperidine-1-carboxylate (Example 170, Step 2) (10.50 g, 34.09 mmol, 1.0 eq) in acetonitrile (150 mL) was added cuprous bromide (24.82 g, 174.76 mmol, 5.0 eq) and t-BuONO (7.20 g, 69.90 mmol, 2.0 eq). The mixture was stirred 1 h at 85° C., quenched with water (300 mL) and extracted with ethyl acetate (300 mL×3). The combined organic phases were dried over sodium sulfate, concentrated and purified via silica gel column, eluting with ethyl acetate in petroleum ether (0-50%, 30 min) to give 5.8 g (yield: 45%, purity: 83%) tert-butyl 3-(5-bromo-6-methoxypyridin-3-yl)piperidine-1-carboxylate as an off white solid. LCMS: (ES, m/s) 371 [M+H]+. $^1$H NMR: (400 MHz, DMSO-$d_6$) δ ppm 8.11-8.05 (m, 1H), 7.99-7.96 (m, 1H), 3.96-3.81 (m, 4H), 2.95-2.72 (m, 2H), 2.65-2.57 (m, 1H), 1.90-1.77 (m, 1H), 1.70-1.54 (m, 2H), 1.48-1.44 (m, 11H).

Step 2

To tert-butyl 3-(5-bromo-6-methoxypyridin-3-yl)piperidine-1-carboxylate (1.00 g, 2.70 mmol, 1.0 eq) in DMF (10 mL) was added dicyanozinc (172 mg, 1.48 mmol, 0.5 eq) and tetrakis(triphenylphosphine)palladium(0) (312 mg, 0.27 mmol, 0.1 eq). The reaction was evacuated and flushed three times with nitrogen, stirred at 120° C. for 3 h, cooled to room temperature, poured into water (100 mL) and extracted with ethyl acetate (100 mL×3). The combined organic phases were washed with brine (200 mL), dried over sodium sulfate, concentrated and purified via silica gel column, eluting with ethyl acetate in petroleum ether (0% to 35%) to give 500 mg (yield: 58%, purity: 98%) of tert-butyl 3-(5-cyano-6-methoxypyridin-3-yl)piperidine-1-carboxylate as a colorless oil. LCMS: (ES, m/s) 318 [M+H]+. $^1$H NMR: (300 MHz, CDCl$_3$) δ ppm 8.25 (d, J=2.4 Hz, 1H), 7.76 (d, J=2.4 Hz, 1H), 4.18-4.11 (m, 1H), 4.06 (s, 3H), 2.84-2.69 (m, 3H), 2.04-1.97 (m, 1H), 1.84-1.76 (m, 1H), 1.65-1.58 (m, 3H), 1.49 (s, 9H).

Step 3

A mixture of 3-(5-cyano-6-methoxypyridin-3-yl)piperidine-1-carboxylate (481 mg, 1.51 mmol, 1.0 eq) and TFA (2 mL) in dichloromethane (10 mL) was stirred for 2 h and concentrated to give 300 mg (yield: 60%, purity: 83%) of (2-methoxy-5-(piperidin-3-yl)nicotinonitrile) TFA salt, as a yellow oil, which was used without purification. LCMS (ES, m/s): 218 [M+H]+ $^1$H NMR: (400 MHz, CD$_3$OD) δ ppm 8.37 (d, J=2.4 Hz, 1H), 8.09 (d, J=2.8 Hz, 1H), 4.06 (s, 3H), 3.48-3.45 (m, 2H), 3.15-3.30 (m, 3H), 2.22-2.03 (m, 2H), 1.93-1.86 (m, 2H).

Step 4

A mixture of 2-methoxy-5-(piperidin-3-yl)nicotinonitrile (free base) (130 mg, 0.38 mmol, 1.0 eq), triethylamine (198 mg, 1.96 mmol, 5.0 eq) and (R)-2-bromo-N-(5-chloropyridin-2-yl)propanamide (Intermediate 3) (100 mg, 0.38 mmol, 1.0 eq) in THF (8 mL) was stirred at 40° C. for 3 days, concentrated and purified via silica gel column, eluting with ethyl acetate:petroleum (1:2) to give 120 mg (yield: 77%, purity: 95%) of (2S)—N-(5-chloropyridin-2-yl)-2-(3-(5-cyano-6-hydroxypyridin-3-yl)piperidin-1-yl)propanamide as a colorless oil. LCMS: (ES, m/s): 400. $^1$H NMR: (400 MHz, CDCl$_3$) δ ppm 9.79 (br, 1H), 8.28-8.24 (m, 3H), 7.77-7.68 (m, 2H), 4.05 (d, J=8.4 Hz, 3H), 3.37-3.32 (m, 1H), 3.04-2.80 (m, 3H), 2.53-2.45 (m, 1H), 2.32-2.20 (m, 1H), 2.02-1.77 (m, 3H), 1.48-1.45 (m, 1H), 1.35-1.27 (m, 3H).

Step 5

A mixture of (2S)—N-(5-chloropyridin-2-yl)-2-(3-(5-cyano-6-hydroxypyridin-3-yl)piperidin-1-yl)propanamide (90 mg, 0.23 mmol, 1 eq) and Raney-Ni (50 mg) in NH$_3$ (3 mL, 7 M in methanol) was evacuated and flushed with nitrogen three times, followed by replacement with hydrogen. The mixture was stirred 45 min under an atmosphere of hydrogen (balloon), filtered, concentrated and purified via silica gel column, eluting with methanol:dichloromethane (1:5) to give 65 mg (yield: 70%, purity: 99%) (2S)-2-(3-(5-(aminomethyl)-6-methoxypyridin-3-yl)piperidin-1-yl)-N-(5-chloropyridin-2-yl)propanamide as a colorless oil. LCMS: (ES, m/s): 404. ¹H NMR: (400 MHz, CDCl₃) δ ppm 9.89 (br, 1H), 8.28-8.23 (m, 2H), 7.96 (dd, J=2.4, 9.2 Hz, 1H), 7.70-7.66 (m, 1H), 7.45 (dd, J=1.6, 10.4 Hz, 1H), 3.97 (d, J=5.2 Hz, 3H), 3.86-3.85 (m, 2H), 3.36-3.30 (m, 1H), 3.00-2.76 (m, 3H), 2.53-2.45 (m, 1H), 2.30-2.08 (m, 2H), 1.99-1.95 (m, 1H), 1.83-1.77 (m, 1H), 1.53-1.46 (m, 1H), 1.34-1.28 (m, 3H).

Step 6 To (2S)-2-(3-(5-(aminomethyl)-6-methoxypyridin-3-yl)piperidin-1-yl)-N-(5-chloropyridin-2-yl)propanamide (280 mg, 0.70 mmol, 1.0 eq) in chloroform (3 mL) was added TMSI (1.39 g, 6.95 mmol, 10 eq). The mixture was stirred at 50° C. for 2 h, quenched with methanol (10 mL), filtered, concentrated and purified by Prep-HPLC (Column: XBridge Prep OBD C₁₈), eluting with 25-45% AcCN in water (10 mM NH₄HCO₃). The resulting material was chirally separated (phenomenex LUX 5 u cellulose-4, AXIA packed, 2.12×25 cm, 5 um; Mobile Phase A: Hex [8 mmol/L NH₃.MeOH], Mobile Phase B: MeOH/EtOH 1/1; Flow rate: 20 mL/min; 1:1 A:B), resulting in two peaks with retention times of 10.056 and 17.077 minutes. The first peak (10.056 min) was collected to give 30 mg (yield: 11.0%, purity: 98.4%, ee %: 99.9%) of (S)-2-((S)-3-(5-(aminomethyl)-6-oxo-1,6-dihydropyridin-3-yl)piperidin-1-yl)-N-(5-chloropyridin-2-yl)propanamide as a white solid. LCMS (ES, m/s): 390 [M+H]+ ¹H NMR: (400 MHz, CD₃OD) δ ppm 8.29-8.28 (m, 1H), 8.18 (d, J=8.8 Hz, 1H), 7.81 (dd, J=2.4, 8.8 Hz, 1H), 7.59 (d, J=2.4 Hz, 1H), 7.26 (d, J=2.4 Hz, 1H), 3.71 (s, 2H), 3.48-3.38 (m, 1H), 2.97-2.93 (m, 1H), 2.83-2.77 (m, 2H), 2.47-2.44 (m, 1H), 2.32-2.25 (m, 1H), 1.92-1.72 (m, 3H), 1.51-1.48 (m, 1H), 1.30 (d, J=6.8 Hz, 3H).

Example 176

(S)—N-(5-chloropyridin-2-yl)-2-((S)-3-(1-methyl-6-oxo-1,6-dihydropyridin-3-yl)piperidin-1-yl)propanamide

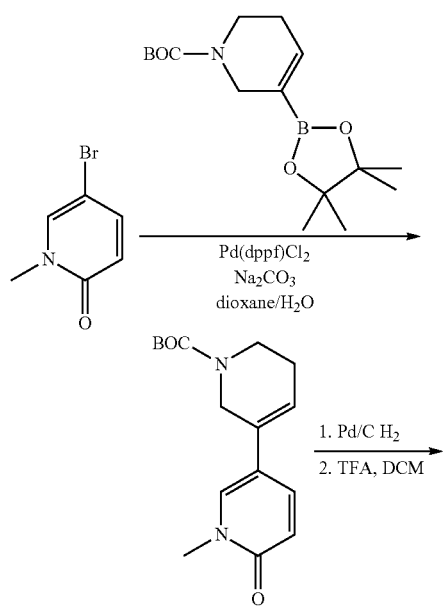

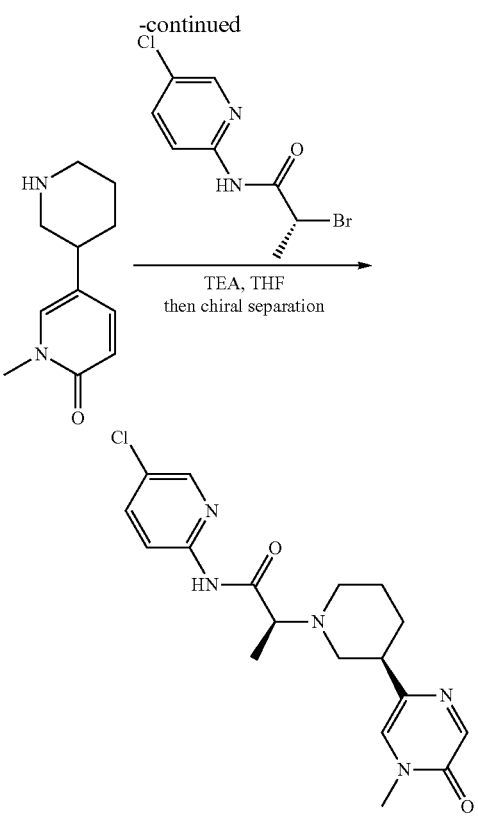

Step 1
A mixture of 5-bromo-1-methylpyridin-2 (1H)-one (1.0 g, 5 mmol, 1.0 eq), tert-butyl 5-(4,4,5,5-tetramethyl-1,3,2-dioxaborolan-2-yl)-3,6-dihydropyridine-1 (2H)-carboxylate (2.5 g, 8.0 mmol, 1.5 eq), Pd(dppf)Cl₂ (813 mg, 1.1 mmol, 0.2 eq), and Na₂CO₃ (1.7 g, 16.0 mmol, 3.0 eq) in dioxane (10 mL) and H₂O (3 mL) was evacuated and flushed three times with nitrogen, stirred 1.5 h at 100° C., cooled to room temperature, quenched with water (200 mL) and extracted with ethyl acetate (200 mL×3). The combined organic phases were dried over Na₂SO₄, concentrated and purified via a silica gel column, eluting with methanol dichloromethane (1:10) to give 1.2 g (purity: 92%, yield: 80%) of tert-butyl 1'-methyl-6'-oxo-1',5,6,6'-tetrahydro-[3,3'-bipyridine]-1 (2H)-carboxylate as a brown solid. LCMS: (ES, m/s) 291 [M+H]+.

Step 2
A mixture of tert-butyl 1'-methyl-6'-oxo-1',5,6,6'-tetrahydro-[3,3'-bipyridine]-1 (2H)-carboxylate (1.0 g, 3.45 mmol, 1.0 eq) and Pd/C (500 mg, 10%) in MeOH (30 mL) was stirred under an atmosphere of hydrogen for 15 h, filtered and concentrated to give 1.0 g crude tert-butyl 3-(1-methyl-6-oxo-1,6-dihydropyridin-3-yl)piperidine-1-carboxylate as a brown oil, which was used without purification. LCMS: (ES, m/s) 293 [M+H]+.

Step 3
A mixture of tert-butyl 3-(1-methyl-6-oxo-1,6-dihydropyridin-3-yl)piperidine-1-carboxylate (1.0 g, 3 mmol, 1.0 eq) and TFA (10 mL) in DCM (10 mL) was stirred for 1 h and concentrated to give 1.0 g crude 1-methyl-5-(piperidin-3-yl)pyridin-2 (1H)-one, TFA salt, as a yellow solid, which was used without purification. LCMS (ES, m/s): 193 [M+H Step 4
A mixture of 1-methyl-5-(piperidin-3-yl)pyridin-2 (1H)-one (as free base) (572 mg, 2.98 mmol, 1.2 eq), (R)-2- bromo-N-(5-chloropyridin-2-yl)propanamide (Intermediate 3) (650 mg, 2.48 mmol, 1.0 eq) and TEA (1.75 g, 17.37 mmol, 7.0 eq) in THF (10 mL) was stirred for 15 h at 40° C., quenched with water (200 mL) and extracted with ethyl acetate (200 mL×3). The combined organic phases were dried over Na₂SO₄, concentrated and purified via a silica gel column, eluting with ethyl acetate:petroleum ether (1:3) to give 500 mg product as an off white solid. This material was chirally separated (CHIRAL ART Cellulose-SB, 2×25 cm, 5 um; Mobile Phase A: Hex, Mobile Phase B: EtOH; Flow rate: 20 mL/min; 1:1 A:B), resulting in four peaks with retention times of 7.772, 9.363, 11.078 and 12.301 minutes. The second peak (9.363 min) was collected to give 47.4 mg (purity: 99.6%, yield: 5%) of (S)—N-(5-chloropyridin-2-yl)-2-((S)-3-(1-methyl-6-oxo-1,6-dihydropyridin-3-yl)piperidin-1-yl)propanamide as a white solid. LCMS (ES, m/s): 375 [M+H]+ ¹H NMR: (400 MHz, CD₃OD) δ 8.29-8.28 (m, 1H), 8.19-8.16 (m, 1H), 7.81 (dd, J=9.3, 2.7 Hz, 1H), 7.54-7.51 (m 2H), 6.53-6.49 (m, 1H), 3.55 (s, 3H), 3.43-3.40 (m, 1H), 2.95-2.92 (m, 1H), 2.84-2.76 (m, 2H), 2.50-2.46 (m, 1H), 2.34-2.26 (m, 1H), 1.93-1.69 (m, 3H), 1.52-1.42 (m, 1H), 1.31 (d, J=6.9 Hz, 3H).

Example 177

(S)—N-(5-chloropyridin-2-yl)-2-((S)-3-(5-(hydroxymethyl)-6-oxo-1,6-dihydropyridin-3-yl)piperidin-1-yl)propanamide

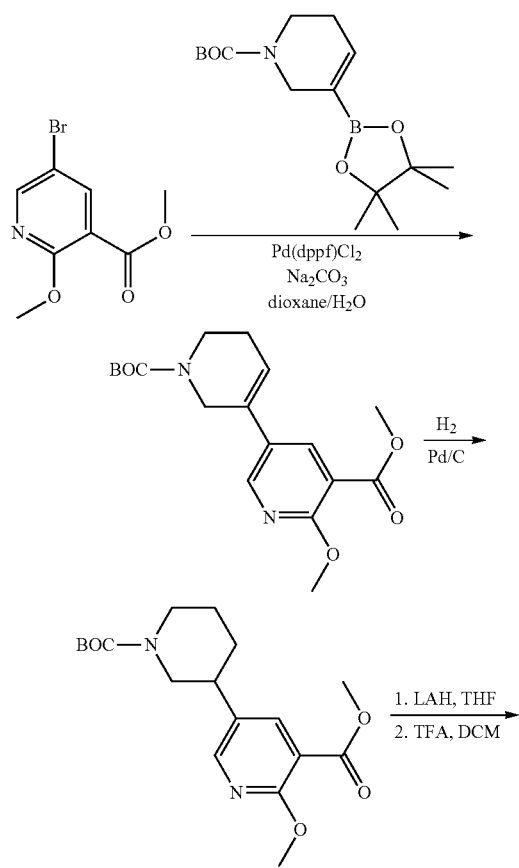

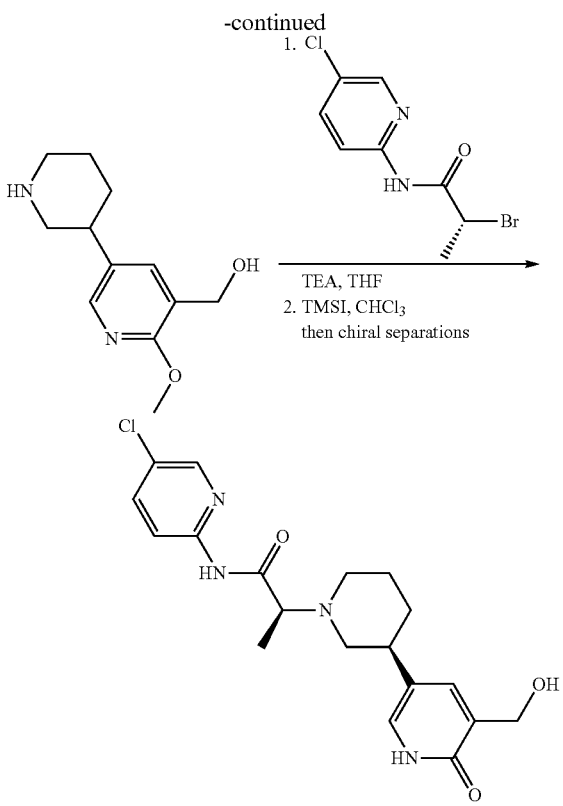

Step 1

A mixture of methyl 5-bromo-2-methoxynicotinate (1.0 g, 4.1 mmol, 1.0 eq), tert-butyl 3-(4,4,5,5-tetramethyl-1,3,2-dioxaborolan-2-yl)-5,6-dihydropyridine-1 (2H)-carboxylate (1.89 g, 6.1 mmol, 1.5 eq), Pd(dppf)Cl₂ (0.6 g, 0.8 mmol, 0.2 eq) and Na₂CO₃ (1.3 g, 12.3 mmol, 3.0 eq). in dioxane (40 mL) and H₂O (10 mL) was evacuated and flushed with nitrogen three times, stirred for 1.0 h at 100° C., concentrated and purified via silica gel column, eluting with ethyl acetate:petroleum ether (1:3) to give 2.0 g (purity: 98%, yield: quantitative) of methyl 5-(1-(tert-butoxycarbonyl)-1,2,5,6-tetrahydropyridin-3-yl)-2-methoxynicotinate as a yellow oil. LCMS: (ES, m/s) 349 [M+H]+.

Step 2

A mixture of methyl 5-(1-(tert-butoxycarbonyl)-1,2,5,6-tetrahydropyridin-3-yl)-2-methoxynicotinate (2.0 g, 5.7 mmol, 1.0 eq) and Pd/C (0.4 g, 10%) in MeOH (20 mL) was flushed three times with nitrogen, flushed with hydrogen, stirred for 15 h under an atmosphere of hydrogen (balloon), filtered and concentrated to give 2.0 g (purity: 70%, yield: 99%) methyl 5-(1-(tert-butoxycarbonyl)piperidin-3-yl)-2-methoxynicotinate as a yellow oil, which was used without purification. LCMS: (ES, m/s) 351 [M+H]+.

Step 3

To methyl 5-(1-(tert-butoxycarbonyl)piperidin-3-yl)-2-methoxynicotinate (2.0 g, 5.7 mmol, 1.0 eq) in THF (20 mL) at 0° C. was added LiAlH₄ (0.26 g, 6.85 mmol, 1.2 eq). The mixture was stirred for 1 h at room temperature, poured into NH₄Cl (aq., sat., 40 mL) and extracted with ethyl acetate (40 mL×3). The combined organic layers were washed with brine (120 mL×3), dried over sodium sulfate, concentrated and purified via a silica gel column, eluting with methanol:dichloromethane (1:30) to give 0.92 g (purity: 90%, yield: 50%) of tert-butyl 3-(5-(hydroxymethyl)-6-methoxypyridin-3-yl)piperidine-1-carboxylate as a yellow oil. LCMS: (ES, m/s) 323 [M+H]+.

Step 4

A mixture of tert-butyl 3-(5-(hydroxymethyl)-6-methoxypyridin-3-yl)piperidine-1-carboxylate (0.92 g, 2.86 mmol, 1.0 eq), DCM (6 mL) and TFA (2 mL) was stirred for 1 h and concentrated to give 1.0 g crude (2-methoxy-5-(piperidin-3-yl)pyridin-3-yl)methanol, TFA salt, as a red oil which was used without purification. LCMS (ES, m/s): 223

Step 5

A mixture of (2-methoxy-5-(piperidin-3-yl)pyridin-3-yl)methanol (as free base) (0.635 g, 2.86 mmol, 1.0 eq), (R)-2-bromo-N-(5-chloropyridin-2-yl)propanamide (Intermediate 3) (0.749 g, 2.86 mmol, 1.0 eq) and TEA (2.89 g, 28.6 mmol, 10.0 eq) in THF (10 mL) was stirred for 15 h at 43° C., poured into water (50 mL) and extracted with ethyl acetate (50 mL×3). The combined organic layers were dried over sodium sulfate, concentrated and purified via a silica gel column, eluting with ethyl acetate:hexane (1:1) to give 0.640 g (purity: 90%, yield: 56%) of (2S)—N-(5-chloropyridin-2-yl)-2-(3-(5-(hydroxymethyl)-6-methoxypyridin-3-yl)piperidin-1-yl)propanamide as a white solid. LCMS (ES, m/s): 405 [M+H]+

Step 6

A mixture of (2S)—N-(5-chloropyridin-2-yl)-2-(3-(5-(hydroxymethyl)-6-methoxypyridin-3-yl)piperidin-1-yl)propanamide (0.64 g, 1.58 mmol, 1.0 eq) and TMSI (3.16 g, 15.8 mmol, 10.0 eq) in CHCl₃ (10 mL) was stirred for 5 h at 50° C., diluted with MeOH (15 mL), stirred for 0.5 h at 25° C., concentrated and purified by reversed phase column (C18 silica gel, 120 g, 20-45 um, 100 A), eluting with 5-70% AcCN in water (10 mM NH₄HCO₃) to give 0.31 g product as a yellow solid. This material was separated by chiral-HPLC (CHIRAL PAK IG, 20×250 mm, 5 um; Mobile Phase A: Hex:DCM=3:1 [with 10 mm NH₃.MeOH], Mobile Phase B: EtOH; Flow rate: 20 mL/min; 1:1 A:B) to give three peaks with retention times of 7.495, 8.067 and 11.799 min. The third peak (11.799 min) was collected to give 66.0 mg (purity: 99.4%, yield: 11%) of (S)—N-(5-chloropyridin-2-yl)-2-((S)-3-(5-(hydroxymethyl)-6-oxo-1,6-dihydropyridin-3-yl)piperidin-1-yl)propanamide as a white solid. LCMS (ES, m/s): 391 [M+H]+ ¹H NMR: (400 MHz, CD₃OD) δ ppm 8.29-8.28 (m, 1H), 8.18 (d, J=9.0 Hz, 1H), 7.83-7.79 (m, 1H), 7.65-7.64 (m, 1H), 7.21 (d, J=2.1 Hz, 1H), 4.48 (s, 2H), 3.43-3.32 (m, 1H), 2.95-2.78 (m, 3H), 2.49-2.42 (m, 1H), 2.33-2.24 (m, 1H), 1.93-1.75 (m, 3H), 1.48-1.44 (m, 1H), 1.30 (d, J=7.2 Hz, 3H).

Example 178

(S)—N-(5-chloropyridin-2-yl)-2-((S)-3-(6-oxo-5-phenyl-1,6-dihydropyridin-3-yl)piperidin-1-yl)propanamide

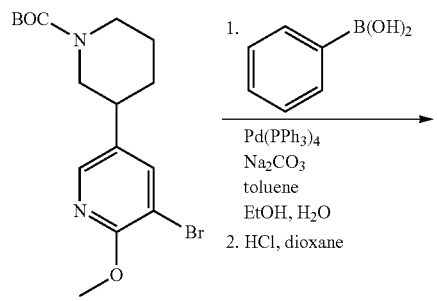

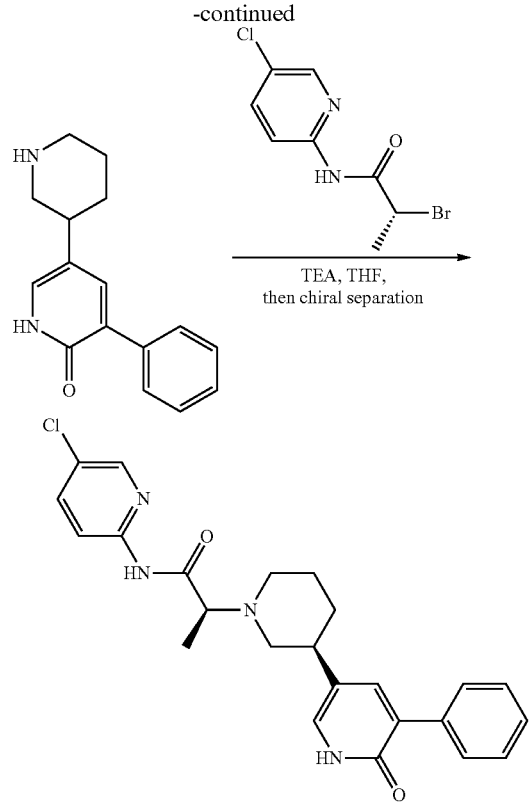

Step 1

To tert-butyl 3-(5-bromo-6-methoxypyridin-3-yl)piperidine-1-carboxylate (Example 175, Step 1) (1.00 g, 2.7 mmol, 1.0 eq) in toluene (4 ml) was added Pd(PPh₃)₄ (375 mg, 0.324 mmol, 0.12 eq), followed by a solution of phenylboronic acid (0.99 g, 8.11 mmol, 3.0 eq) in ethanol (6 mL), then sodium carbonate (2.31 g, 21.79 mmol, 8 eq) in water (12 mL). The reaction was evacuated and flushed three times with nitrogen, stirred at reflux for 2 h, cooled to room temperature, poured into water (100 mL) and extracted with ethyl acetate (100 mL×3). The combined organic extracts were washed with brine (200 mL), dried over sodium sulfate, concentrated and purified via a silica gel column, eluting with ethyl acetate in petroleum ether (0-30%, in 30 min) to give 0.8 g (yield: 82%, purity: 90%) of tert-butyl 3-(6-methoxy-5-phenylpyridin-3-yl)piperidine-1-carboxylate as a colorless oil. LCMS: (ES, m/s) 369 [M+H]+. ¹H NMR: (400 MHz, CDCl₃) δ ppm 8.07-8.06 (m, 1H), 7.57-7.58 (m, 3H), 7.47-7.43 (m, 2H), 7.40-7.36 (m, 1H), 4.34-4.09 (m, 2H), 4.01 (s, 3H), 2.86-2.84 (m, 3H), 2.07-2.01 (m, 1H), 1.82-1.78 (m, 1H), 1.70-1.57 (m, 2H), 1.49 (s, 9H).

Step 2

A mixture of tert-butyl 3-(6-methoxy-5-phenylpyridin-3-yl)piperidine-1-carboxylate (800 mg, 2 mmol, 1.0 eq) and hydrochloric acid (10 ml, 6 M in H₂O) in dioxane (10 mL) was stirred at 80° C. for 7 h and concentrated to give 500 mg (purity: 95%) of (3-phenyl-5-(piperidin-3-yl)pyridin-2 (1H)-one), HCl salt, as a yellow oil, which was used without purification. LCMS: (ES, m/s) 255 [M+H]+. ¹H NMR: (300 MHz, CD₃OD) δ ppm 8.08 (s, 1H), 7.85 (s, 1H), 7.66-7.64 (m, 2H), 7.52-7.43 (m, 3H), 3.52-3.44 (m, 2H), 3.28-3.03 (m, 3H), 2.11-2.08 (m, 2H), 2.00-1.85 (m, 2H).

Step 3

A mixture of 3-phenyl-5-(piperidin-3-yl)pyridin-2 (1H)-one (free base) (127 mg, 0.50 mmol, 1.0 eq), triethylamine (183 mg, 1.81 mmol, 3.6 eq) and (R)-2-bromo-N-(5-chloropyridin-2-yl)propanamide (Intermediate 3) (130 mg, 0.50 mmol, 1.0 eq) in THF (2 mL) was stirred at 40° C. for 4 days, diluted with methanol (5 mL) and purified by Prep-HPLC (XBridge Prep C18 OBD Column 19×150 mm 5 μm), eluting with 47-53% AcCN in water (with 10 mM NH$_4$HCO$_3$). This material was chirally separated (CHIRALPAK IF, 2×25 cm, 5 um; Mobile Phase A: Hex [8 mmol/L NH$_3$.MeOH], Mobile Phase B: EtOH; Flow rate: 15 mL/min; 1:1 A:B), resulting in two peaks with retention times of 10.93 and 11.61 minutes. The second peak (11.61 min) was collected to give 32 mg (yield: 14.6%, purity: 99.5%, ee %: 99.7%) of (S)—N-(5-chloropyridin-2-yl)-2-((S)-3-(6-oxo-5-phenyl-1,6-dihydropyridin-3-yl)piperidin-1-yl)propanamide as a white solid. LCMS (ES, m/s): 437 [M+H]+. $^1$H NMR: (400 MHz, CD$_3$OD) δ ppm 8.28-8.27 (m, 1H), 8.18 (d, J=8.8 Hz, 1H), 7.80 (dd, J=2.8, 8.8 Hz, 1H), 7.67 (d, J=2.4 Hz, 1H), 7.62-7.60 (m, 2H), 7.40-7.30 (m, 4H), 3.44-3.42 (m, 1H), 3.00-2.97 (m, 1H), 2.89-2.78 (m, 2H), 2.53-2.48 (m, 1H), 2.32-2.31 (m, 1H), 1.98-1.94 (m, 1H), 1.91-1.74 (m, 2H), 1.52-1.48 (m, 1H), 1.30 (d, J=6.8 Hz, 3H).

Example 179

(S)—N-(5-chloropyridin-2-yl)-2-((S)-3-(5-cyclopropyl-6-oxo-1,6-dihydropyridin-3-yl)piperidin-1-yl)propanamide

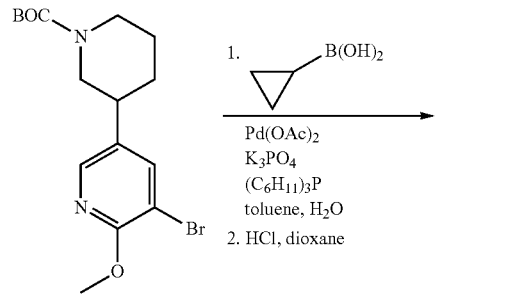

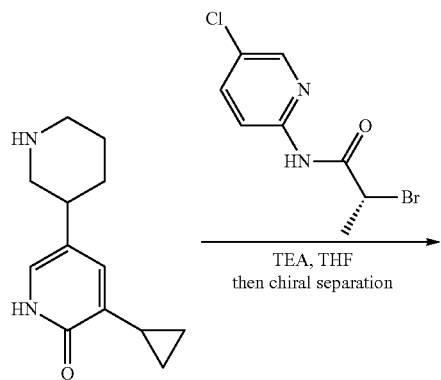

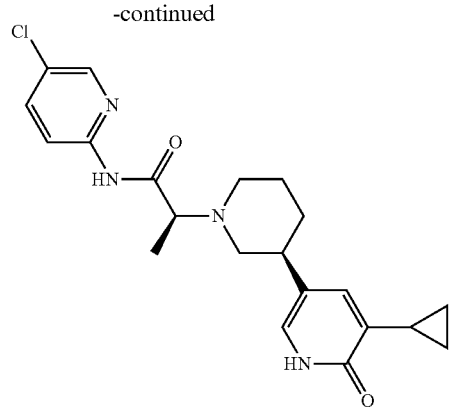

Step 1

To tert-butyl 3-(5-bromo-6-methoxypyridin-3-yl)piperidine-1-carboxylate (Example 175, Step 1) (1.00 g, 2.7 mmol, 1.0 eq) in toluene (10 mL) and water (0.5 mL) were added cyclopropylboronic acid (303 mg, 3.50 mmol, 1.3 eq), Pd(OAc)$_2$ (31 mg, 0.14 mmol, 0.05 eq), K$_3$PO$_4$ (2.01 g, 9.46 mmol, 3.5 eq) and (C$_6$H$_{11}$)$_3$P (76 mg, 0.27 mmol, 0.1 eq). The reaction was evacuated and flushed three times with nitrogen, stirred at 100° C. for 2 h, quenched with water (50 mL) and extracted with ethyl acetate (50 mL×3). The combined organic phases were dried over sodium sulfate, concentrated and purified via a silica gel column, eluting with ethyl acetate in petroleum ether (0-50%) to give 650 mg (yield: 72%, purity: 96%) tert-butyl 3-(5-cyclopropyl-6-methoxypyridin-3-yl)piperidine-1-carboxylate as a yellow oil. LCMS: (ES, m/s) 333 [M+H]+. $^1$H NMR: (300 MHz, DMSO-d$_6$) δ ppm 7.82 (d, J=1.8 Hz, 1H), 7.13 (d, J=1.5 Hz, 1H), 3.98-3.78 (m, 5H), 2.88-2.70 (m, 2H), 2.04-1.89 (m, 1H), 1.84-1.76 (m, 1H), 1.69-1.54 (m, 2H), 1.48-1.44 (m, 1H), 1.38 (m, 9H), 1.12-0.98 (m, 1H), 0.92-0.85 (m, 2H), 0.86-0.66 (m, 2H).

Step 2

A mixture of tert-butyl 3-(6-methoxy-5-nitropyridin-3-yl)-5,6-dihydropyridine-1 (2H)-carboxylate (600 mg, 1.81 mmol, 1.0 eq) and HCl (3 mL, 6 M in H$_2$O) in dioxane (3 mL) was stirred 16 h at 80° C. and concentrated to give 340 mg (yield: 74%, purity: 83%) 3-cyclopropyl-5-(piperidin-3-yl)pyridin-2 (1H)-one, HCl salt, as a yellow oil, which was used without purification. LCMS: (ES, m/s) 219 [M+H]+. $^1$H NMR: (400 MHz, CD$_3$OD) δ ppm 7.90 (s, 2H), 3.47-3.45 (m, 2H), 3.20-3.03 (m, 3H), 2.10-1.82 (m, 5H), 1.15-1.10 (m, 2H), 0.91-0.87 (m, 2H).

Step 3

A mixture of 3-cyclopropyl-5-(piperidin-3-yl)pyridin-2 (1H)-one (as free base) (242 mg, 1.11 mmol, 1.0 eq), (R)-2-bromo-N-(5-chloropyridin-2-yl)propanamide (Intermediate 3) (291 mg, 1.1 mmol, 1.0 eq) and triethylamine (561 mg, 5.55 mmol, 5.0 eq) in THF (8 mL) was stirred 3 days at 40° C., concentrated, dissolved in DMF (5 mL) and purified by Prep-HPLC (XBridge Prep Phenyl OBD Column), eluting with 15-50% AcCN in water (0.1% FA). The resulting material was chirally separated (CHIRALPAK IE, 2×25 cm, 5 um; Mobile Phase A: Hex [8 mmol/L NH$_3$.MeOH], Mobile Phase B: EtOH; Flow rate: 20 mL/min; 1:1 A:B), resulting in two peaks with retention times of 14.584 and 16.377 minutes. The first peak (14.584 min) was collected to give 70 mg (yield: 16%, purity: 99%, ee %: 100%) of (S)—N-(5-chloropyridin-2-yl)-2-((S)-3-(5-cyclopropyl-6-oxo-1,6-dihydropyridin-3-yl)piperidin-1-yl)

propanamide as a white solid. LCMS (ES, m/s): 401 [M+H]+ ¹H NMR: (400 MHz, CD₃OD) δ ppm 8.28 (d, J=2.4 Hz, 1H), 8.18 (d, J=8.8 Hz, 1H), 7.81 (dd, J=2.4, 8.8 Hz, 1H), 7.11 (s, 2H), 3.43-3.38 (m, 1H), 2.92-2.87 (m, 1H), 2.79-2.72 (m, 2H), 2.43-2.38 (m, 1H), 2.31-2.25 (m, 1H), 2.00-1.94 (m, 1H), 1.88-1.73 (m, 3H), 1.44-1.40 (m, 1H), 1.29 (d, J=6.8 Hz, 3H), 0.93-0.87 (m, 2H), 0.65-0.59 (m, 2H).

Example 180

4-((S)-1-((S)-1-((5-chloropyridin-2-yl)amino)-1-oxopropan-2-yl)piperidin-3-yl)pyridine 1-oxide

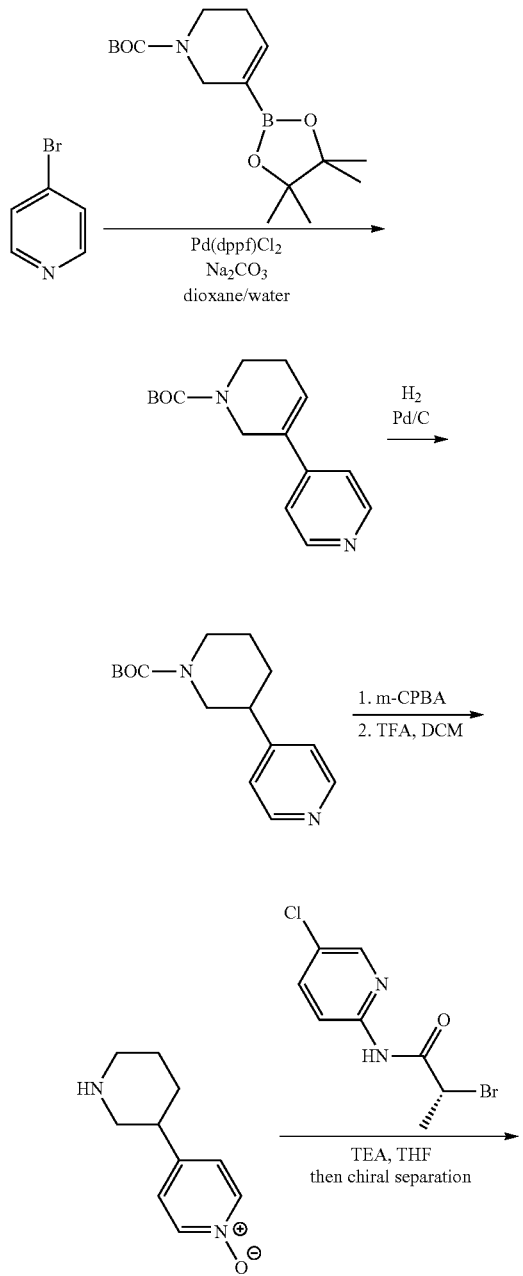

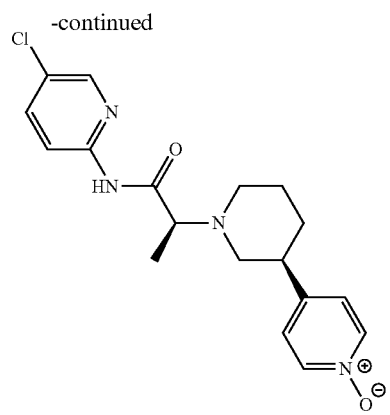

Step 1

A mixture of 4-bromopyridine (200 mg, 1.27 mmol, 1.0 eq), tert-butyl 5-(4,4,5,5-tetramethyl-1,3,2-dioxaborolan-2-yl)-3,6-dihydropyridine-1 (2H)-carboxylate (590 mg, 1.91 mmol, 1.5 eq), Na₂CO₃ (405 mg, 3.82 mmol, 3.0 eq) and Pd(dppf)Cl₂ (187 mg, 0.26 mmol, 0.2 eq) in dioxane (6 mL) was evacuated and flushed with nitrogen three times, stirred for 1 h at 90° C., quenched with water (50 mL) and extracted with ethyl acetate (50 mL×3). The combined organic phases were dried over Na₂SO₄, concentrated and purified via a silica gel column, eluting with ethyl acetate:petroleum (1:3) to give 310 mg (purity: 97%, yield: 94%) of tert-butyl 5,6-dihydro-[3,4'-bipyridine]-1 (2H)-carboxylate as a brown oil. LCMS: (ES, m/s) 261 [M+H]+. ¹H NMR: (300 MHz, CD₃OD) δ ppm 8.51-8.49 (m, 2H), 7.48-7.47 (m, 2H), 6.67-6.64 (m, 1H), 4.34-4.30 (m, 2H), 3.62-3.56 (m, 2H), 2.46-2.36 (m, 2H), 1.52 (s, 9H).

Step 2

A mixture of tert-butyl 5,6-dihydro-[3,4'-bipyridine]-1 (2H)-carboxylate (300 mg, 1.15 mmol, 1.0 eq) and Pd/C (100 mg, 10%) in MeOH was stirred for 2 h under an H₂ atmosphere, filtered and concentrated to give 300 mg crude tert-butyl 3-(pyridin-4-yl)piperidine-1-carboxylate as a yellow oil, which was used without purification. LCMS: (ES, m/s) 263 [M+H]+. ¹H NMR: (300 MHz, CD₃OD) δ ppm 8.48-8.46 (m, 2H), 7.39-7.37 (m, 2H), 4.16-4.04 (m, 2H), 3.00-2.80 (m, 2H), 2.76-2.70 (m, 1H), 2.08-1.99 (m, 1H), 1.82-1.74 (m, 2H), 1.66-1.55 (m, 1H), 1.48 (s, 9H).

Step 3

To tert-butyl 3-(pyridin-4-yl)piperidine-1-carboxylate (250 mg, 0.95 mmol, 1.0 eq) in DCM (5 mL) was added m-CPBA (246 mg, 1.43 mmol, 1.5 eq). The reaction was stirred for 1.5 h, quenched with water (50 mL) and extracted with DCM (50 mL×3). The combined organic phases were dried over Na₂SO₄, concentrated and purified via a silica gel column, eluting with methanol:dichloromethane (1:10) to give 220 mg (purity: 78%, yield: 83%) of 4-(1-(tert-butoxycarbonyl)piperidin-3-yl)pyridine 1-oxide as a yellow oil. LCMS (ES, m/s): 279 [M+H]+ ¹H NMR: (400 MHz, CD₃OD) δ ppm 8.31-8.28 (m, 2H), 7.54-7.49 (m, 2H), 4.14-4.05 (m, 2H), 3.00-2.85 (m, 2H), 2.83-2.76 (m, 1H), 2.07-2.01 (m, 1H), 1.82-1.74 (m, 2H), 1.66-1.55 (m, 1H), 1.48 (s, 9H).

Step 4

A mixture of 4-(1-(tert-butoxycarbonyl)piperidin-3-yl)pyridine 1-oxide (220 mg 0.79 mmol, 1.0 eq) and TFA (2 mL) in DCM (6 mL) was stirred for 1 h and concentrated to give 141 mg crude 4-(piperidin-3-yl)pyridine 1-oxide, TFA salt, as a yellow oil, which was used without purification. LCMS (ES, m/s): 179 [M+H]+ ¹H NMR: (300 MHz, CD₃OD-d₄) δ ppm 8.38-8.35 (m, 2H), 7.58-7.54 (m, 2H), 3.52-3.43 (m, 2H), 3.19-2.99 (m, 3H), 2.11-2.07 (m, 2H), 1.98-1.76 (m, 2H).

Step 5

A mixture of 4-(piperidin-3-yl)pyridine 1-oxide (as free base) (141 mg, 0.79 mmol, 1.0 eq), (R)-2-bromo-N-(5-chloropyridin-2-yl)propanamide (Intermediate 3) (207 mg, 0.79 mmol, 1.0 eq) and TEA (639 mg, 6.33 mmol, 8.0 eq) in THF (5 mL) was stirred for 15 h at 40° C., quenched with water (50 mL) and extracted with ethyl acetate (50 mL×3). The combined organic phases were dried over Na₂SO₄, concentrated and purified via a silica gel column, eluting with ethyl acetate:petroleum ether (1:1) to give 120 mg product as a yellow solid. The collected product was chirally separated (CHIRAL ART Cellulose-SB, 2×25 cm, 5 um; Mobile Phase A: Hex [8 mM NH₃. MeOH], Mobile Phase B: EtOH; Flow rate: 20 mL/min; 1:1 A:B), resulting in four peaks with retention times of 8.239, 9.636, 11.061 and 15.444 minutes. The second peak (9.636 min) was collected to give 30 mg (purity: 99.4%, yield: 10%) of 4-((S)-1-((S)-1-((5-chloropyridin-2-yl)amino)-1-oxopropan-2-yl)piperidin-3-yl)pyridine 1-oxide as an off white solid. LCMS (ES, m/s): 361 [M+H]+ ¹H NMR: (300 MHz, CD₃OD) δ ppm 8.30-8.29 (m, 1H), 8.26-8.16 (m, 3H), 7.81 (dd, J=9.0, 2.7 Hz, 1H), 7.51 (d, J=6.9 Hz, 2H), 3.49-3.42 (m, 1H), 3.13-2.99 (m, 2H), 2.84-2.80 (m, 1H), 2.61-2.54 (m, 1H), 2.40-2.31 (m, 1H), 2.01-1.74 (m, 3H), 1.61-1.47 (m, 1H), 1.31 (d, J=7.2 Hz, 3H).

Examples 181-182 were prepared in an analogous manner using the designated Intermediate in Step 5.

| Ex | Name | Structure | ¹H NMR | LC/MS: (M + H)⁺; retention time (min); LC/MS Method of analysis | Int |
|---|---|---|---|---|---|
| 181 | 4-((S)-1-((S)-1-((5-(2,4-difluorophenoxy)pyrazin-2-yl)amino)-1-oxopropan-2-yl)piperidin-3-yl)pyridine 1-oxide | 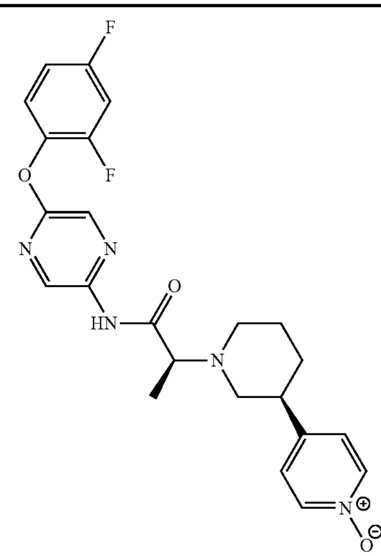 | ¹H NMR (400 MHz, CHLOROFORM-d) δ ppm 9.61-9.83 (m, 1 H,) 9.05 (br. s., 1H), 8.13-8.28 (m, 3H), 7.23 (td, J = 8.80, 5.38 Hz, 1H), 7.18 (d, J = 6.60 Hz, 2H), 6.91-7.02 (m, 2H), 3.29-3.47 (m, 1H), 2.71-3.11 (m, 3H), 2.44-2.60 (m, 1H), 2.21-2.36 (m, 1H), 1.89-2.12 (m, 2H), 1.71-1.87 (m, 1H), 1.42-1.54 (m, 1H), 1.34 (br. s., 3H). | 456; rt 0.95. LC/MS Method 3 | 65 |
| 182 | 4-((S)-1-((S)-1-((5-(2,4-difluorophenoxy)pyridin-2-yl)amino)-1-oxopropan-2-yl)piperidin-3-yl)pyridine 1-oxide | 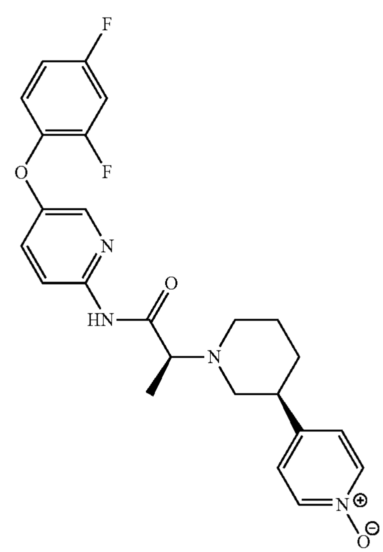 [SMILES: C[C@@H](C(=O)Nc1ccc(Oc2ccc(F)cc2F)cn1)N1CCC[C@@H](c2cc[n+]([O-])cc2)C1] | ¹H NMR (400 MHz, CHLOROFORM-d) δ ppm 9.72 (br. s., 1H), 8.24 (d, J = 9.05 Hz, 1H), 8.17 (d, J = 6.36 Hz, 2H), 8.10 (br. s., 1H), 7.31 (dd, J = 9.17, 2.81 Hz, 1H), 7.16 (d, J = 6.85 Hz, 2H), 7.08 (td, J = 8.99, 5.50 Hz, 1H), 6.95-7.03 (m, 1H), 6.89 (d, J = 8.31 Hz, 1 H,) 3.34 (d, J = 6.60 Hz, 1H), 2.90-3.09 (m, 2H), 2.83 (d, J = 10.76 Hz, 1H), 2.49 (t, J = 10.76 Hz, 1H), 2.18-2.34 (m, 1H), 1.99-2.06 (m, 1H), 1.89-1.97 (m, 1H), 1.80 (d, J = 12.47 Hz, 1H), 1.45 (d, J = 8.80 Hz, 1H), 1.34 (d, J = 6.85 Hz, 3H). | 455; rt 0.99. LC/MS Method 3 | 71 |

Example 183

(S)—N-(5-(cyclopropylmethoxy)pyridin-2-yl)-2-(4,4-difluoro-3-(6-oxo-1,6-dihydropyridin-3-yl)piperidin-1-yl)-2-methylpropanamide

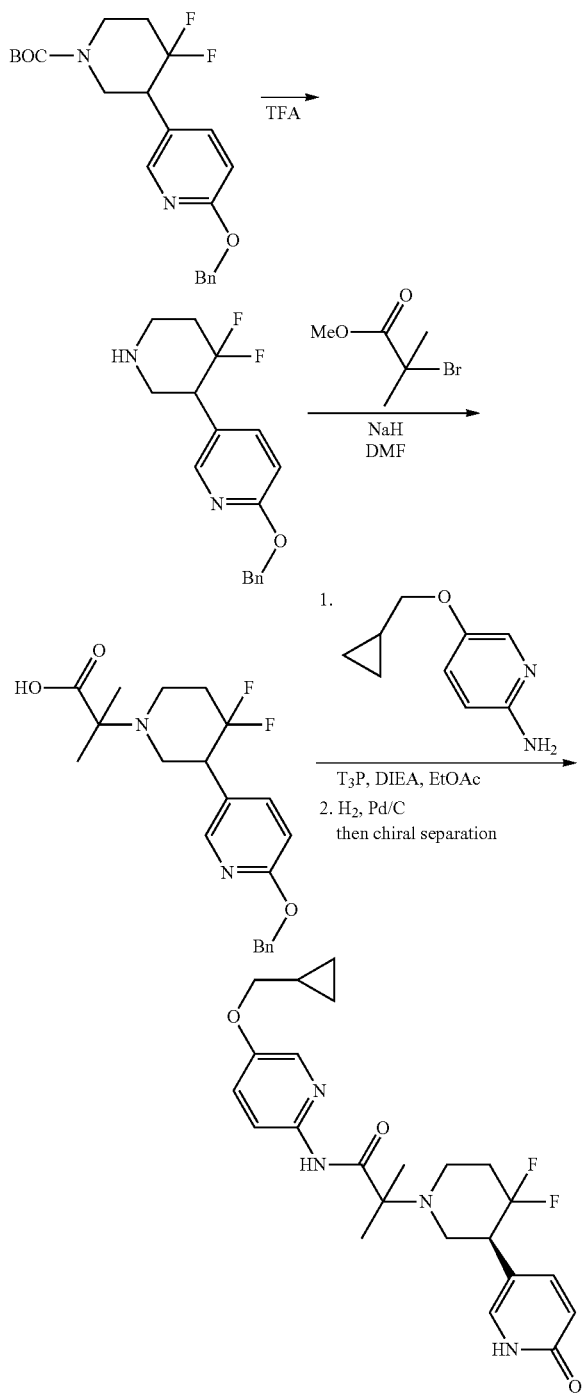

Step 1

To tert-butyl 3-(6-(benzyloxy)pyridin-3-yl)-4,4-difluoropiperidine-1-carboxylate (Example 1, Step 2) (500 mg, 1.25 mmol, 1.0 eq) in DCM (4 mL) was added TFA (1 mL). The mixture was stirred for 1 h at 25° C. and concentrated to give 370 mg crude 2-(benzyloxy)-5-(4,4-difluoropiperidin-3-yl)pyridine as a light yellow solid, which was used without purification. LCMS: (ES, m/s) 305 [M+H]+.

Step 2

To 2-(benzyloxy)-5-(4,4-difluoropiperidin-3-yl)pyridine (as free base) (0.38 g, 1.24 mmol, 1.0 eq) in DMF (4.0 mL) at 0° C. was added NaH (0.50 g, 12.4 mmol, 10.0 eq), in portions. The mixture was stirred for 1.0 h at 25° C., was recooled to 0° C., and methyl 2-bromo-2-methylpropanoate (2.23 g, 12.4 mmol, 10.0 eq) was added, dropwise. The reaction was stirred for 12.0 h at 25° C. and purified by reversed phase column directly (C18 silica gel, 120 g, 20-45 um, 100 A), eluting with 5-70% AcCN in water (with 10 mM NH$_4$HCO$_3$) to give 110 mg (purity: 90%, yield: 23%) of 2-(3-(6-(benzyloxy)pyridin-3-yl)-4,4-difluoropiperidin-1-yl)-2-methylpropanoic acid as white solid. LCMS: (ES, m/s) 391 [M+H]+. $^1$H NMR: (400 MHz, CD$_3$OD) δ 8.13 (d, J=2.4 Hz, 1H), 7.79-7.75 (m, 1H), 7.47-7.44 (m, 2H), 7.39-7.35 (m, 3H), 6.93-6.89 (m, 1H), 5.37 (s, 2H), 4.02-4.00 (m, 1H), 3.29-3.20 (m, 2H), 3.05-2.95 (m, 2H), 2.42-2.30 (m, 2H), 1.47-1.45 (m, 6H).

Step 3

A mixture of 2-(3-(6-(benzyloxy)pyridin-3-yl)-4,4-difluoropiperidin-1-yl)-2-methylpropanoic acid (0.18 g, 0.46 mmol, 1.0 eq), ethyl acetate (4.0 mL), 5-(cyclopropylmethoxy)pyridin-2-amine (Intermediate 22, Step 2) (0.076 g, 0.46 mmol, 1.0 eq), T$_3$P (1.17 g, 1.84 mmol, 4.0 eq) and DIEA (0.297 g, 2.3 mmol, 5.0 eq) was stirred for 15.0 h at 25° C., poured into H$_2$O (30 mL) and extracted with ethyl acetate (30 mL×3).

The combined organic phases were dried over sodium sulfate, concentrated and purified via a silica gel column, eluting with ethyl acetate/petroleum ether (1/1) to give 51 mg (purity: 90%, yield: 21%) of 2-(3-(6-(benzyloxy)pyridin-3-yl)-4,4-difluoropiperidin-1-yl)-N-(5-(cyclopropylmethoxy)pyridin-2-yl)-2-methylpropanamide as yellow oil. LCMS (ES, m/s): 537 [M+H]+ $^1$H NMR: (300 MHz, CD$_3$OD) δ 8.09-8.04 (m, 2H), 7.75-7.70 (m, 2H), 7.46-7.36 (m, 6H), 6.86-6.83 (m, 1H), 5.35 (s, 2H), 3.92-3.89 (m, 3H), 2.80-2.60 (m, 2H), 2.44-2.30 (m, 2H), 1.80-1.67 (m, 2H), 1.50-1.22 (m, 6H), 0.90-0.85 (m, 1H), 0.66-0.64 (m, 2H), 0.39-0.37 (m, 2H).

Step 4

A mixture of 2-(3-(6-(benzyloxy)pyridin-3-yl)-4,4-difluoropiperidin-1-yl)-N-(5-(cyclopropylmethoxy)pyridin-2-yl)-2-methylpropanamide (0.1 g, 0.187 mmol, 1.0 eq) and Pd/C (0.03 g, 10%) in MeOH (5.0 mL) was evacuated and flushed three times with nitrogen, flushed with hydrogen, stirred under an atmosphere of hydrogen (balloon) for 1.0 h at 25° C., filtered, concentrated and purified by reversed phase column (C$_{18}$ silica gel, 80 g, 20-45 um, 100 A), eluting with 5-70% AcCN in water (0.05% FA) to give 0.06 g product as a light yellow solid.

The collected product was chirally separated (CHIRAL ART Cellulose-SB S-5 um, 2×25 cm, 5 μm; Mobile Phase A: Hex [8 mM NH$_3$. MeOH], Mobile Phase B: EtOH; Flow rate: 20 mL/min; 1:1 A:B), resulting in two peaks with retention times of 8.001 and 12.335 minutes. The first peak (8.001 min) was collected to give 10.0 mg (purity: 98.6%, yield: 12%) of (S)—N-(5-(cyclopropylmethoxy)pyridin-2-yl)-2-(4,4-difluoro-3-(6-oxo-1,6-dihydropyridin-3-yl)piperidin-1-yl)-2-methylpropanamide as white solid. LCMS (ES, m/s): 447 [M+H]+ $^1$H NMR: (300 MHz, CD$_3$OD) δ 8.07-8.00 (m, 2H), 7.65-7.62 (m, 1H), 7.46-7.40 (m, 2H), 6.53 (d, J=9.3 Hz, 1H), 3.89 (d, J=6.9 Hz, 2H), 3.41-3.31 (m, 1H), 2.98-2.92 (m, 2H), 2.76-2.61 (m, 2H), 2.25-2.19 (m, 2H), 1.35-1.27 (m, 7H), 0.67-0.61 (m, 2H), 0.40-0.36 (m, 2H).

Example 184

(S)—N-(5-chloropyridin-2-yl)-2-((S)-3-(5-methyl-6-oxo-1,6-dihydropyridin-3-yl)piperidin-1-yl)propanamide

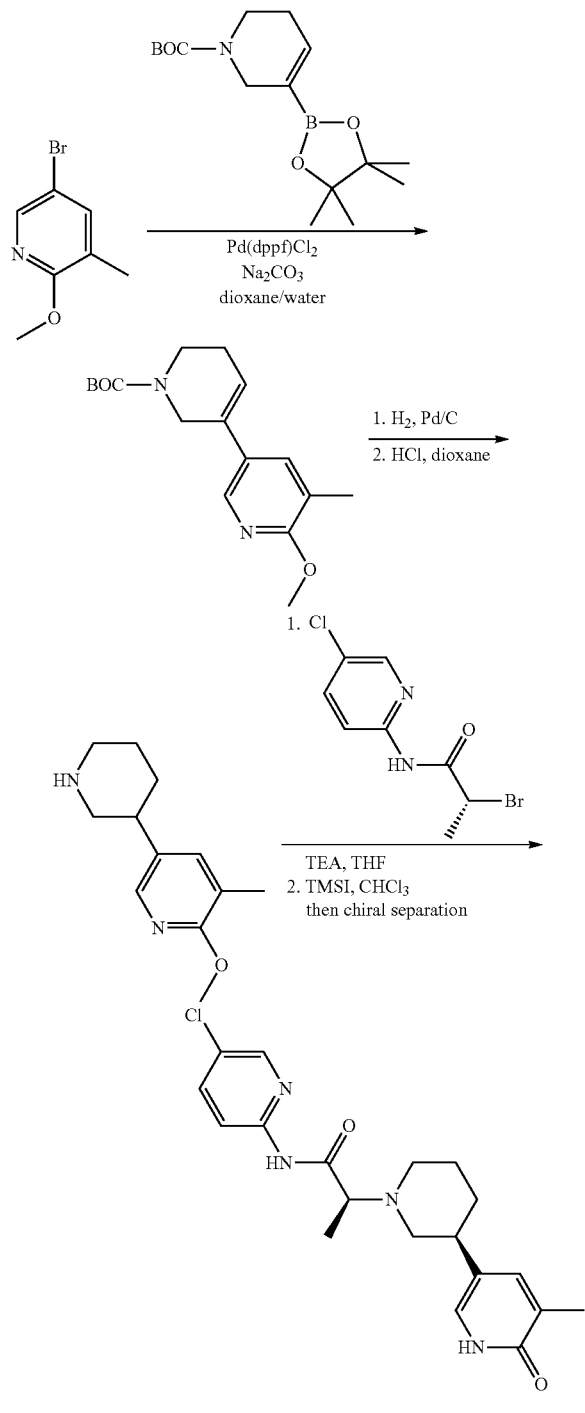

Step 1

A mixture 5-bromo-2-methoxy-3-methylpyridine (2.00 g, 9.95 mmol, 1.0 eq), tert-butyl 5-(4,4,5,5-tetramethyl-1,3,2-dioxaborolan-2-yl)-3,6-dihydropyridine-1 (2H)-carboxylate (3.69 g, 11.94 mmol, 1.2 eq), Pd(dppf)Cl$_2$ (1.62 g, 1.99 mmol, 0.2 eq) and sodium carbonate (4.12 g, 38.9 mmol, 3.9 eq) in dioxane/water (50 mL, 4/1) was flushed with nitrogen three times, stirred for 3 h at 60° C., cooled to room temperature, quenched with water (100 mL) and extracted with ethyl acetate (100 mL×3). The combined organic phases were dried over Na$_2$SO$_4$, concentrated and purified via silica gel column, eluting with ethyl acetate:petroleum ether (0:100-1:1) to give tert-butyl 6'-methoxy-5'-methyl-5,6-dihydro-[3,3'-bipyridine]-1 (2H)-carboxylate (1.76 g, yield: 58%, purity: 100%) as yellow syrup. LCMS: (ES, m/s) 305 [M+H]+.

Step 2

A mixture of tert-butyl 6'-methoxy-5'-methyl-5,6-dihydro-[3,3'-bipyridine]-1 (2H)-carboxylate (1.20 g, 3.95 mmol, 1.0 eq) and Pd/C (500 mg, 10%) in methanol (40 mL) was evacuated and flushed three times with nitrogen, flushed with hydrogen, stirred under hydrogen for 2 h, filtered and concentrated to give tert-butyl 3-(6-methoxy-5-methylpyridin-3-yl)piperidine-1-carboxylate (970 mg, yield: 81%, purity: 99%) as a yellow syrup, which was used without purification. LCMS: (ES, m/s) 307 [M+H]+.

Step 3

To tert-butyl 3-(6-methoxy-5-methylpyridin-3-yl)piperidine-1-carboxylate (970 mg, 3.16 mmol, 1.0 eq) in dioxane (4 mL) was added HCl (4M in dioxane, 4.0 mL, 16.00 mmol). The reaction was stirred for 16 h and concentrated to give 2-methoxy-3-methyl-5-(piperidin-3-yl)pyridine (600 mg, yield: 78%, purity: 99%) as a purple solid. LCMS: (ES, m/s) 207 [M+H]+.

Step 4

A mixture of 2-methoxy-3-methyl-5-(piperidin-3-yl)pyridine (as free base) (300 mg, 1.45 mmol, 1.0 eq), (R)-2-bromo-N-(5-chloropyridin-2-yl)propanamide (Intermediate 3) (382 mg, 1.45 mmol, 1.0 eq) and TEA (1.47 g, 14.55 mmol, 10.0 eq) in THF (15 mL) was stirred for 16 h at 43° C., quenched with water (50 mL) and extracted with ethyl acetate (50 mL×3). The organic phases were washed with water (100 mL) and brine (100 mL), dried over sodium sulfate, concentrated and purified via preparative TLC developed with ethyl acetate/petroleum ether (1/5) to give (2S)—N-(5-chloropyridin-2-yl)-2-(3-(6-methoxy-5-methylpyridin-3-yl)piperidin-1-yl)propanamide (450 mg, yield: 80%, purity: 94%) as a yellow solid. LCMS (ES, m/s): 389 [M+H]+.

Step 5

A mixture of (2S)—N-(5-chloropyridin-2-yl)-2-(3-(6-methoxy-5-methylpyridin-3-yl)piperidin-1-yl)propanamide (450 mg, 1.16 mmol, 1.0 eq) and TMSI (2.32 g, 11.57 mmol, 10.0 eq) in chloroform (15 mL) was stirred for 16 h at 50° C., cooled to 0° C., quenched with MeOH (50 mL), concentrated and purified by C18 column chromatography, eluting with 30-80% AcCN in water (0.1% FA) to give 200 mg of a yellow solid. This material was separated by chiral-HPLC (CHIRALPAK IG, 20×250 mm, 5 um; Mobile Phase A: Hex, Mobile Phase B: EtOH; Flow rate: 20 mL/min; 1:1 A:B) to give two peaks with retention times of 28.915 and 34.297 min. The second peak (34.297 min) was collected to give (S)—N-(5-chloropyridin-2-yl)-2-(3-(5-methyl-6-oxo-1,6-dihydropyridin-3-yl)piperidin-1-yl)propanamide as a white solid (34.6 mg, yield: 17%, purity: 95%, ee %: 94%). LCMS (ES, m/s): 375 [M+H]+ $^1$H NMR: (300 MHz, DMSO-d$_6$) δ ppm 11.33 (s, 1H), 10.26 (s, 1H), 8.37 (d, J=2.1 Hz, 1H), 8.14 (d, J=9.0 Hz, 1H), 7.92 (dd, J=2.7, 9.0 Hz, 1H), 7.31-7.27 (m, 1H), 7.04-7.01 (m, 1H), 3.54-3.51 (m, 1H), 2.86-2.83 (m, 1H), 2.71-2.67 (m, 1H), 2.60-2.57 (m, 1H), 2.37-2.30 (m, 1H), 2.18-2.13 (m, 1H), 1.94 (s, 3H), 1.75-1.71 (m, 2H), 1.59-1.53 (m, 1H), 1.34-1.28 (m, 1H), 1.16 (d, J=7.2 Hz, 3H).

Example 185

(S)—N-(5-(cyclopropylmethoxy)pyridin-2-yl)-2-((R)-3-(6-oxo-1,6-dihydropyridazin-3-yl)piperidin-1-yl)propanamide

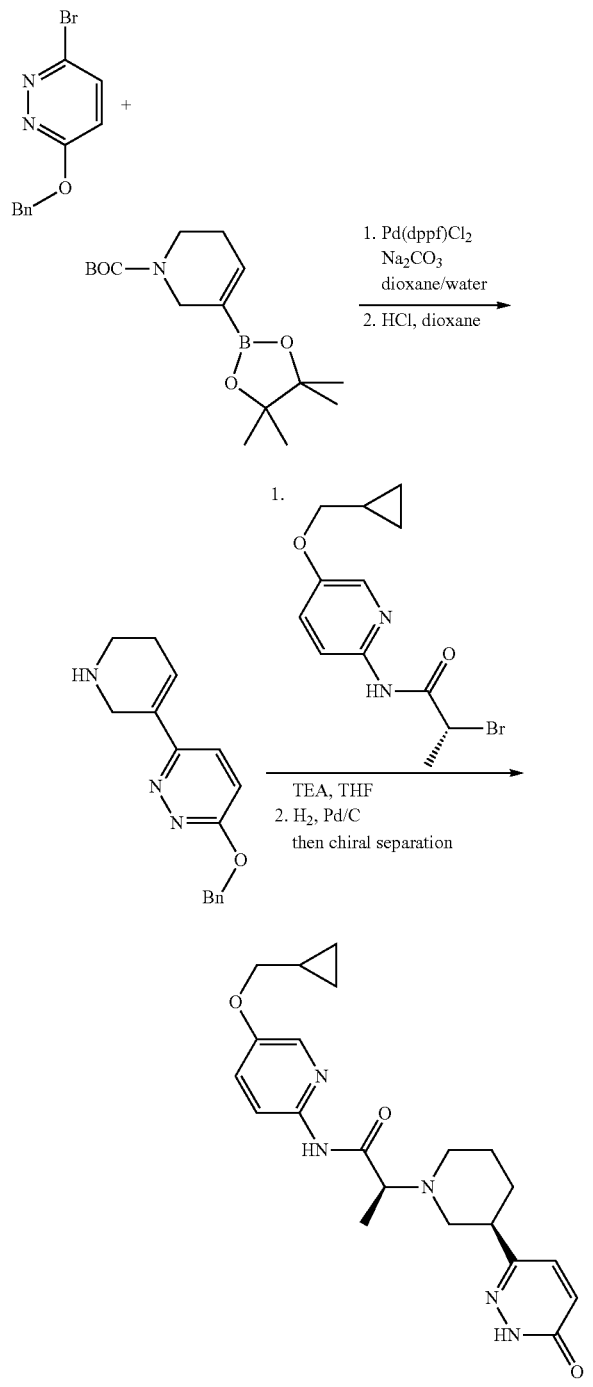

Step 1

A mixture of 3-(benzyloxy)-6-bromopyridazine (1.00 g, 3.79 mmol, 1.0 eq). tert-butyl 5-(4,4,5,5-tetramethyl-1,3,2-dioxaborolan-2-yl)-3,6-dihydropyridine-1 (2H)-carboxylate (1.17 g, 3.79 mmol, 1.0 eq), Pd(dppf)Cl$_2$ (540 mg, 0.74 mmol, 0.2 eq) and sodium carbonate (1.50 g, 10.87 mmol, 3.0 eq, in 10 mL water) in dioxane (10 mL) was evacuated and flushed with nitrogen three times, stirred for 2 hours at 90° C., cooled to room temperature, poured into water (200 mL) and extracted with ethyl acetate (200 mL×3). The organic layers were dried over sodium sulfate, concentrated and purified by silica gel chromatography, eluting with ethyl acetate:petroleum ether (1:3) to give 1.3 g (yield: 92%, purity: 98%) of tert-butyl 5-(6-(benzyloxy)pyridazin-3-yl)-3,6-dihydropyridine-1 (2H)-carboxylate as a white solid. LCMS: (ES, m/s) 368 [M+H]+.

Step 2

A mixture of tert-butyl 5-(6-(benzyloxy)pyridazin-3-yl)-3,6-dihydropyridine-1 (2H)-carboxylate (200 mg, 0.54 mmol, 1.0 eq) and HCl (4 mL, 4 M in dioxane) was stirred for 16 h and concentrated to give 100 mg crude 3-(benzyloxy)-6-(1,2,5,6-tetrahydropyridin-3-yl)pyridazine, HCl salt, as a yellow solid, which was used without purification. LCMS: (ES, m/s) 268 [M+H]+.

Step 3

A mixture of 3-(benzyloxy)-6-(1,2,5,6-tetrahydropyridin-3-yl)pyridazine (free base) (100 mg, 0.37 mmol, 1.0 eq), (R)-2-bromo-N-(5-(cyclopropylmethoxy)pyridin-2-yl)propanamide (Intermediate 22) (100 mg, 0.33 mmol, 1.0 eq) and triethylamine (200 mg, 1.98 mmol, 5 eq) in THF (2 mL) was stirred at 40° C. for 18 h, concentrated and purified via silica gel column, eluting with ethyl acetate:petroleum ether (1:1) to give 70 mg (yield: 43%, purity: 95%) of (S)-2-(5-(6-(benzyloxy)pyridazin-3-yl)-3,6-dihydropyridin-1 (2H)-yl)-N-(5-(cyclopropylmethoxy)pyridin-2-yl)propanamide as a yellow oil. LCMS: (ES, m/s) 486 [M+H]+.

Step 4

A mixture of (S)-2-(5-(6-(benzyloxy)pyridazin-3-yl)-3,6-dihydropyridin-1 (2H)-yl)-N-(5-(cyclopropylmethoxy) pyridine-2-yl)propanamide (70 mg, 0.14 mmol, 1.0 eq) and Pd/C (100 mg, 10%) in methanol (5 mL) was evacuated and flushed three times with nitrogen, flushed with hydrogen, stirred under an atmosphere of hydrogen for 16 h, filtered, concentrated and purified via silica gel column, eluting with ethyl acetate:petroleum ether (1:1) to give 50 mg product. This material was separated by chiral-HPLC (CHIRALART Cellulose-SB, 2×25 cm, 5 um; Mobile phase A: Hex [8 mM NH$_3$/MeOH], Mobile phase B: EtOH; Flow rate: 18 mL/min; 1:1 A:B) to give two peaks with retention times of 9.328 and 12.838 min. The first peak (9.328 min) was collected to give 1.7 mg (yield: 3%, purity: 96.2%, ee %: 99.9%) of (S)—N-(5-(cyclopropylmethoxy)pyridin-2-yl)-2-((R)-3-(6-oxo-1,6-dihydropyridazin-3-yl)piperidin-1-yl) propanamide as a colorless oil. LCMS (ES, m/s): 398 [M+H]+ $^1$H NMR: (400 MHz, CDCl$_3$) 13.01 (br, 1H), 11.41 (br, 1H), 8.44 (d, J=9.2 Hz, 1H), 8.15 (d, J=2.8 Hz, 1H), 7.34-7.31 (m, 1H), 7.22-7.17 (m, 1H), 7.00-6.99 (m, 1H), 3.86 (d, J=6.8 Hz, 2H), 3.44-3.43 (m, 1H), 3.20-3.15 (m, 1H), 2.99 (s, 1H), 2.75-2.62 (m, 3H), 1.95-1.90 (m, 1H), 1.85-1.75 (m, 1H), 1.70-1.60 (m, 2H), 1.34 (d, J=7.2 Hz, 3H), 1.27-1.23 (m, 1H), 0.68-0.63 (m, 2H), 0.38-0.34 (m, 2H).

Example 186 was synthesized in an analogous manner using the designated Intermediate in Step 3.

| Ex | Name | Structure | ¹H NMR | LC/MS: (M + H)⁺; retention time (min); LC/MS Method of analysis | Int |
|---|---|---|---|---|---|
| 186 | (S)-N-(5-chloropyridin-2-yl)-2-((R)-3-(6-oxo-1,6-dihydropyridazin-3-yl)piperidin-1-yl)propanamide | 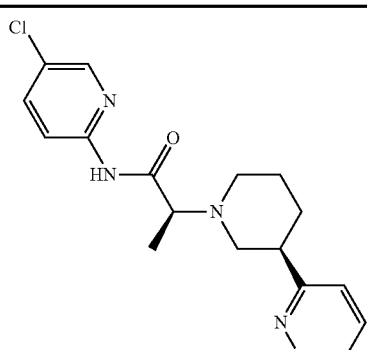 | ¹H NMR: (300 MHz, DMSO-d₆) δ ppm 12.80 (s, 1H), 10.26 (s, 1H), 8.36 (d, J = 3.3 Hz, 1H), 8.14 (d, J = 9.0 Hz, 1H), 7.94-7.90 (m, 1H), 7.43 (d, J = 9.9 Hz, 1H), 6.81 (d, J = 9.6 Hz, 1H), 3.55-3.52 (m, 1H), 3.02-2.96 (m, 1H), 2.85-2.82 (m, 1H), 2.74-2.70 (m, 1H), 2.45-2.41 (m, 1H), 2.30-2.21 (m, 1H), 1.89-1.85 (m, 1H), 1.78-1.74 (m, 1H), 1.57-1.44 (m, 1H), 1.41-1.37 (m, 1H), 1.17 (d, J = 6.9 Hz, 3H). | 362; rt 1.383. LC/MS Method 14 | 3 |

Example 187

(2S)-2-(3-(5-amino-6-oxo-1-(2,2,2-trifluoroethyl)-1,6-dihydropyridin-3-yl)-4,4-difluoropiperidin-1-yl)-N-(5-fluoropyridin-2-yl)propanamide

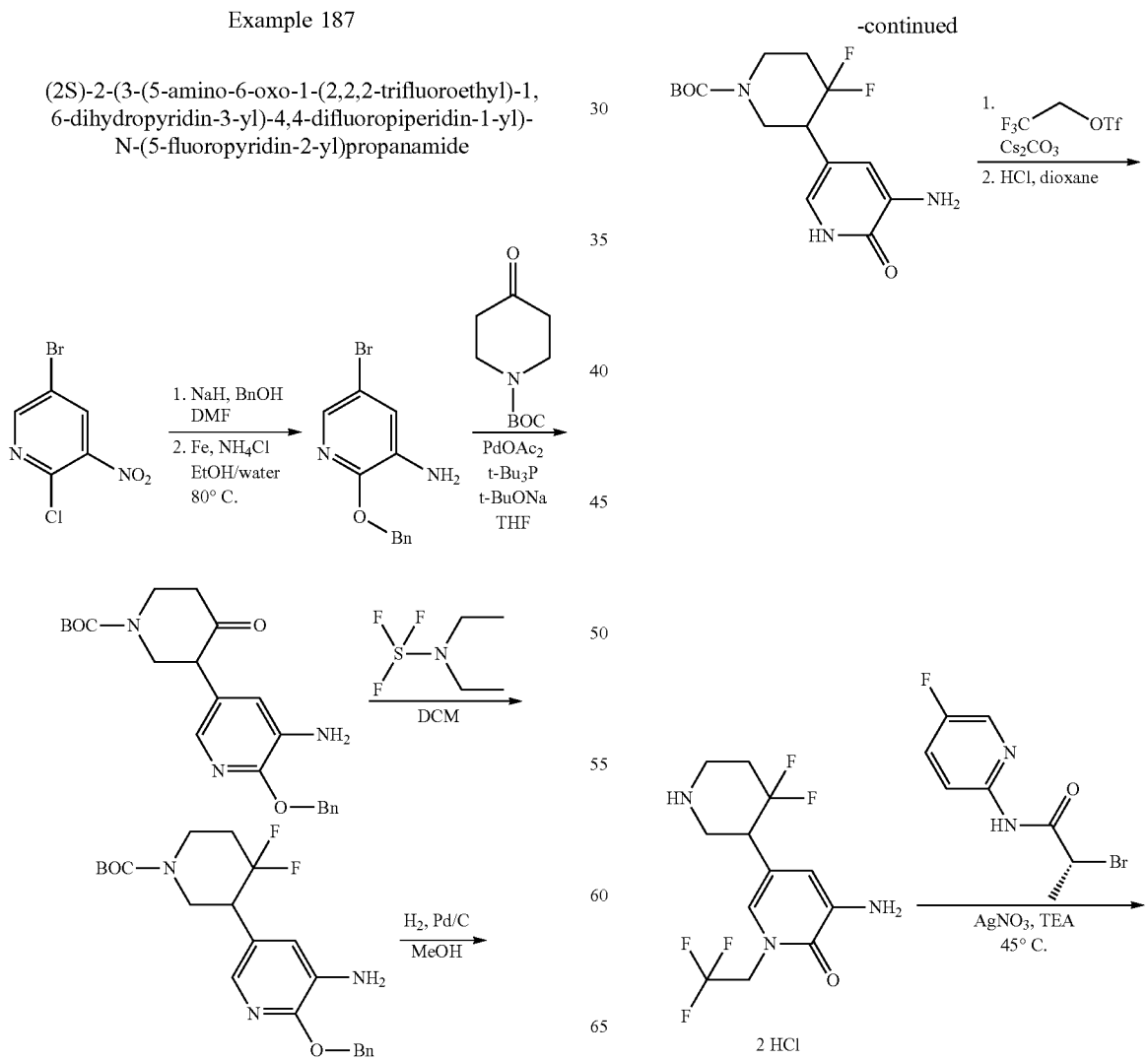

-continued

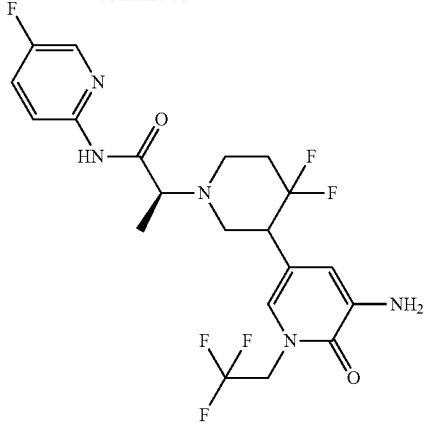

Step 1

To a solution of 5-bromo-2-chloro-3-nitropyridine (50 g, 211 mmol) and phenylmethanol (26.2 mL, 253 mmol) in DMF (400 mL) at 0° C. was added solid sodium hydride (10.95 g, 274 mmol) portion wise, over 5 minutes. After 30 minutes, the reaction was allowed to stir at rt for 16 hours. The mixture was poured over crushed ice (200 g) and diluted with water (2 L). The resulting solid was collected by filtration to give the crude product 2-(benzyloxy)-5-bromo-3-nitropyridine (60 g, 140 mmol, purity 72%, recovery 66%) as a brown solid, which was used without purification. LCMS (m/z) no exact mass, retention time: 1.313 min, LC/MS Method 29.

Step 2

To a solution of 2-(benzyloxy)-5-bromo-3-nitropyridine (60 g, 140 mmol) and ammonium chloride (37.4 g, 699 mmol) in ethanol (500 mL) and water (125 mL) stirred in air at 80° C. was added a suspension of iron (78 g, 1.398 mol), portion wise, over 15 min. The reaction mixture was stirred at 80° C. for 2 h, filtered, and concentrated. The residue was diluted with water (1 L), then extracted with ethyl acetate (1000 mL×2). The organic phase was dried over sodium sulfate and concentrated to give the crude product as a brown oil. The sample was adsorbed onto silica and purified over a silica gel column (330 g) eluting with 0-15% ethyl acetate in petroleum ether to afford 2-(benzyloxy)-5-bromopyridin-3-amine (22.5 g, 81 mmol, purity: 100%, recovery: 58%) as an orange oil. LCMS (m/z) 279 (M+H)$^+$, retention time: 1.252 min, LC/MS Method 30.

Step 3

In two batches, to a solution of sodium 2-methylpropan-2-olate (4.30 g, 44.8 mmol and 15.06 g, 157 mmol), tri-tert-butylphosphane (5.44 g, 2.69 mmol and 19.03 g, 9.40 mmol) and diacetoxypalladium (0.603 g, 2.69 mmol 2.11 g, 9.40 mmol) in THF (60 mL and 60 mL) stirred in air were added 2-(benzyloxy)-5-bromopyridin-3-amine (5 g, 17.91 mmol and 17.5 g, 62.7 mmol) and tert-butyl 4-oxopiperidine-1-carboxylate (5.35 g, 26.9 mmol and 18.74 g, 94 mmol). The reactions were stirred at 42° C. for 16 h, combined, diluted with water (1000 mL), then extracted with ethyl acetate (1000 mL×2). The combined organic phases were washed with brine (1000 mL×2), dried over sodium sulfate and concentrated to give the crude product as a brown oil. The sample was preabsorbed on silica and purified over a silica gel column (330 g), eluting with 0-30% ethyl acetate in petroleum ether to provide crude tert-butyl 3-(5-amino-6-(benzyloxy)pyridin-3-yl)-4-oxopiperidine-1-carboxylate (5 g, 3.14 mmol, purity: 25%, recovery: 4%) as a brown solid. LCMS (m/z) 398 (M+H)$^+$, retention time: 1.194 min, LC/MS Method 29.

Step 4

To a solution of tert-butyl 3-(5-amino-6-(benzyloxy)pyridin-3-yl)-4-oxopiperidine-1-carboxylate (5 g, 3.14 mmol) in DCM (50 mL) at 0° C. was added a solution of N,N-diethyl-1,1,1-trifluoro-14-sulfanamine (1.246 mL, 9.43 mmol) in DCM (2 mL), dropwise, over 5 mins. The reaction was allowed to warm to rt and after 3 h was poured into crushed ice (10 g) and water (100 mL), and extracted with dichloromethane (100 mL). The organic phase was washed with brine (100 mL), dried over sodium sulfate and concentrated to give the crude product as a black oil. The sample was adsorbed on silica and purified over a silica gel column (330 g), eluting with 0-30% ethyl acetate in petroleum ether to provide tert-butyl 3-(5-amino-6-(benzyloxy)pyridin-3-yl)-4,4-difluoropiperidine-1-carboxylate (310 mg, 0.576 mmol, purity: 78%, recovery: 18%) as a yellow oil. LCMS (m/z) 420 (M+H)$^+$, retention time: 1.311 min, LC/MS Method 29.

Step 5

A flask of tert-butyl 3-(5-amino-6-(benzyloxy)pyridin-3-yl)-4,4-difluoropiperidine-1-carboxylate (310 mg, 0.576 mmol) and Pd/C (153 mg, 1.441 mmol) in methanol (5 mL) was evacuated and flushed three times with hydrogen. The reaction was stirred for 2 h under an atmosphere of hydrogen (balloon), filtered, concentrated and purified on a silica gel column (40 g), eluting with 0-7% methanol in dichloromethane to provide tert-butyl 3-(5-amino-6-oxo-1,6-dihydropyridin-3-yl)-4,4-difluoropiperidine-1-carboxylate (160 mg, 0.481 mmol, purity: 99%, recovery: 83%) as a white solid. LCMS (m/z) 330 (M+H)$^+$, retention time: 0.910 min, LC/MS Method 29.

Step 6

A mixture of 2,2,2-trifluoroethyl trifluoromethanesulfonate (282 mg, 1.215 mmol), Cs$_2$CO$_3$ (396 mg, 1.215 mmol) and tert-butyl 3-(5-amino-6-oxo-1,6-dihydropyridin-3-yl)-4,4-difluoropiperidine-1-carboxylate (160 mg, 0.486 mmol) in DMF (3 mL) was stirred for 16 h, diluted with water (50 mL) and extracted with ethyl acetate (50 mL×2). The organic phase was washed with brine (100 mL), dried over sodium sulfate and concentrated to give the crude product as a yellow oil. The sample was adsorbed on silica and purified over a silica gel column (40 g), eluting with 0-50% ethyl acetate in pet ether to provide tert-butyl 3-(5-amino-6-oxo-1-(2,2,2-trifluoroethyl)-1,6-dihydropyridin-3-yl)-4,4-difluoropiperidine-1-carboxylate (60 mg, 0.140 mmol, purity: 96%, recovery: 29%) as a white solid. LCMS (m/z) 412 (M+H)$^+$, retention time: 1.563 min, LC/MS Method 29.

Step 7

To tert-butyl 3-(5-amino-6-oxo-1-(2,2,2-trifluoroethyl)-1,6-dihydropyridin-3-yl)-4,4-difluoropiperidine-1-carboxylate (0.06 g, 0.146 mmol) in dioxane (0.5 ml) was added HCl (4M in dioxane) (0.1 ml, 0.400 mmol). After 1 h, additional HCl (4M in dioxane) (0.3 ml, 1.200 mmol) was added. After stirring for 1 h, the reaction was concentrated to provide crude 3-amino-5-(4,4-difluoropiperidin-3-yl)-1-(2,2,2-trifluoroethyl)pyridin-2(1H)-one dihydrochloride (58 mg, 0.151 mmol, purity: 96%, recovery: 104%) as a rose-colored solid, which was used without purification. LCMS (m/z) 312 (M+H)$^+$, retention time: 0.36 min, LC/MS Method 5.

Step 8

To 3-amino-5-(4,4-difluoropiperidin-3-yl)-1-(2,2,2-trifluoroethyl)pyridin-2(1H)-one dihydrochloride (0.05 g, 0.130 mmol), TEA (0.054 ml, 0.390 mmol) and silver nitrate (0.022 g, 0.130 mmol) in DMA (0.7 ml) was added (R)-2-bromo-N-(5-fluoropyridin-2-yl)propanamide (Intermediate 1) (0.035 g, 0.143 mmol). The reaction was heated 45° C. for 30 min, and additional silver nitrate (0.08 g, 0.471 mmol) was added. After an additional hour, the reaction was diluted with water and extracted with ethyl acetate (2×). The combined organics were dried over sodium sulfate, filtered, concentrated and purified over silica via ISCO Combiflash, eluting with 20-70% 3:1 EtOAc:EtOH in heptanes to yield partially pure product, which was further purified by HPLC (Waters MDAP), eluting with 30-85% AcCN in 10 mM ammonium bicarbonate in water (adjusted to pH 10 with ammonia) to afford (2S)-2-(3-(5-amino-6-oxo-1-(2,2,2-trifluoroethyl)-1,6-dihydropyridin-3-yl)-4,4-difluoropiperidin-1-yl)-N-(5-fluoropyridin-2-yl)propanamide (7.4 mg, 0.015 mmol, purity: 98%, recovery: 12%) as a rose-colored solid. LCMS (m/z) 478 (M+H)+, retention time: 0.61 min, LC/MS Method 5. $^1$H NMR (400 MHz, MeOH-d$_4$) δ ppm 8.17-8.24 (m, 2H), 7.62 (ddd, J=9.17, 7.95, 2.93 Hz, 1H), 6.97 (s, 1H), 6.73 (d, J=6.85 Hz, 1H), 4.73-4.83 (m, 2H), 3.46-3.58 (m, 1H), 3.10-3.24 (m, 1H), 2.58-3.03 (m, 4H), 2.10-2.33 (m, 2H), 1.34 (d, J=6.85 Hz, 3H).

Example 188

(2S)-2-(3-(1-ethyl-6-oxo-1,6-dihydropyridin-3-yl)-4,4-difluoropiperidin-1-yl)-N-(5-fluoropyridin-2-yl)propanamide

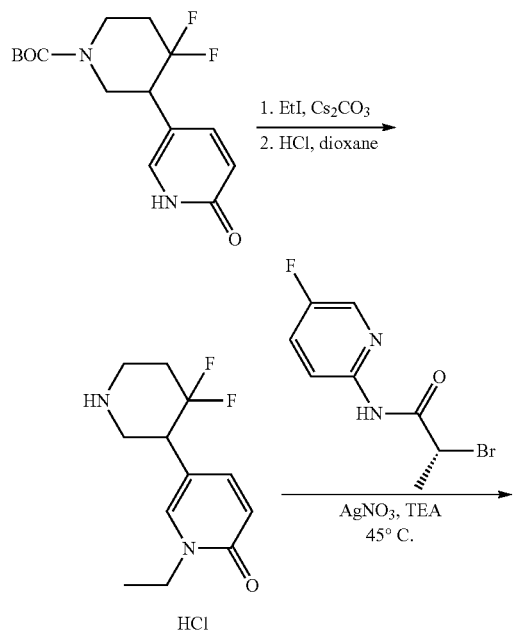

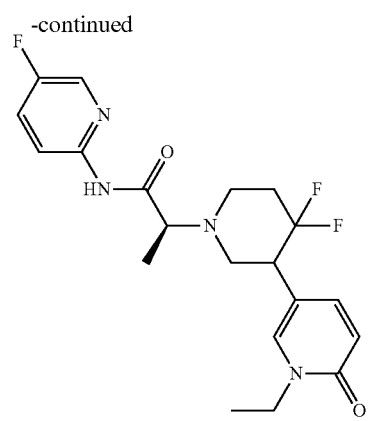

Step 1

To tert-butyl 4,4-difluoro-3-(6-oxo-1,6-dihydropyridin-3-yl)piperidine-1-carboxylate (Example 1, Step 3) (0.5 g, 1.591 mmol) and cesium carbonate (1.555 g, 4.77 mmol) in DMF (5.0 ml) was added iodoethane (0.2 ml, 2.475 mmol). After stirring overnight, the reaction was diluted with water and extracted with ethyl acetate (2×). The combined organics were washed with brine, dried over sodium sulfate, filtered, concentrated and purified by silica gel chromatography, eluting with 20-100% ethyl acetate in heptane to provide tert-butyl 3-(1-ethyl-6-oxo-1,6-dihydropyridin-3-yl)-4,4-difluoropiperidine-1-carboxylate (309 mg, 0.902 mmol, purity: 100%, recovery: 57%) as a colorless oil. LCMS (m/z) 343 (M+H)+, retention time: 0.87 min, LC/MS Method 5.

Step 2

To tert-butyl 3-(1-ethyl-6-oxo-1,6-dihydropyridin-3-yl)-4,4-difluoropiperidine-1-carboxylate (0.3 g, 0.876 mmol) in dioxane (4 ml) was added HCl (4 M in dioxane) (0.5 ml, 2.00 mmol). After 1 h, additional HCl (4M in dioxane) (0.5 ml, 2.00 mmol) was added. After additional stirring and addition of HCl (4M in dioxane) (0.25 ml, 1.00 mmol), the reaction was concentrated to provide crude 3-amino-5-(4,4-difluoropiperidin-3-yl)-1-(2,2,2-trifluoroethyl)pyridin-2 (1H)-one (372 mg, 1.058 mmol, purity: 96%, recovery: quantitative) as a white solid, which was used without purification. LCMS (m/z) 243 (M+H)+, retention time: 0.30 min, LC/MS Method: 5.

Step 3

To 5-(4,4-difluoropiperidin-3-yl)-1-ethylpyridin-2 (1H)-one hydrochloride (0.20 g, 0.717 mmol), TEA (0.26 ml, 1.865 mmol), and silver nitrate (0.108 g, 0.635 mmol) in DMA (1.3 ml) was added (R)-2-bromo-N-(5-fluoropyridin-2-yl)propanamide (Intermediate 1) (0.172 g, 0.698 mmol). The reaction was heated at 45° C. for 30 min, and additional silver nitrate (0.15 g, 0.883 mmol) was added. After an additional hour, the reaction was diluted with water and extracted with ethyl acetate (2×). The combined organics were dried over sodium sulfate, filtered, concentrated and purified over silica via ISCO Combiflash, eluting with 20-70% 3:1 EtOAc:EtOH in heptanes to afford (2S)-2-(3-(1-ethyl-6-oxo-1,6-dihydropyridin-3-yl)-4,4-difluoropiperidin-1-yl)-N-(5-fluoropyridin-2-yl)propanamide (55 mg, 0.128 mmol, purity: 96%, recovery: 18%) as a tan solid. LCMS (m/z) 409 (M+H)+, retention time: 0.55 min, LC/MS Method 5. $^1$H NMR (400 MHz, DMSO-d$_6$) δ ppm 10.37 (d, J=4.40 Hz, 1H), 8.34 (t, J=2.69 Hz, 1H), 8.14 (dd, J=9.29, 3.91 Hz, 1H), 7.75 (tt, J=8.68, 3.06 Hz, 1H), 7.69 (t, J=2.69 Hz, 1H), 7.35-7.43 (m, 1H), 6.32 (dd, J=9.29, 7.34 Hz, 1H), 3.82-3.95 (m, 2H), 3.58-3.70 (m, 1H), 3.06-3.25 (m, 1H), 2.80-3.01 (m, 3H), 2.64-2.74 (m, 1H), 2.05-2.16 (m, 1H), 1.93-2.03 (m, 1H), 1.15-1.24 (m, 6H).

Example 189 was synthesized in an analogous manner using the designated Intermediate in Step 3.

| Ex | Name | Structure | ¹H NMR | LC/MS: (M + H)⁺; retention time (min); LC/MS Method of analysis | Int |
|---|---|---|---|---|---|
| 189 | (S)-N-(6-(cyclopropyl-methoxy)pyri-dazin-3-yl)-2-((S)-(3-(1-ethyl-6-oxo-1,6-dihydropyridin-3-yl)-4,4-difluoropiper-idin-1-yl)propanamide | 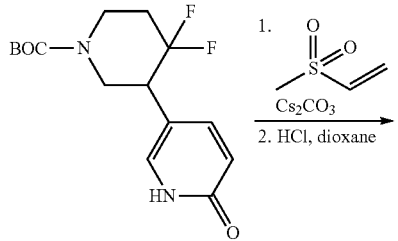 | ¹H NMR (400 MHz, CDCl₃) δ ppm 9.96 (br d, J = 0.98 Hz, 1H), 8.42 (d, J = 9.78 Hz, 1H), 7.31 (dd, J = 9.54, 1.71 Hz, 1H), 7.24 (d, J = 2.45 Hz, 1H), 7.07 (d, J = 8.80 Hz, 1H), 6.55 (d, J = 9.29 Hz, 1H), 4.30 (d, J = 7.34 Hz, 2H), 3.92-4.06 (m, 2H), 3.38-3.51 (m, 1H), 3.06-3.21 (m, 1H), 2.78-3.02 (m, 3H), 2.55-2.68 (m, 1H), 2.05-2.31 (m, 2H), 1.18-1.43 (m, 7H), 0.60-0.70 (m, 2H), 0.35-0.43 (m, 2H). | 4.362; rt 0.66. LC/MS Method 5 | 14 |

Example 190

(2S)-2-(4,4-difluoro-3-(1-(2-(methylsulfonyl)ethyl)-6-oxo-1,6-dihydropyridin-3-yl)piperidin-1-yl)-N-(5-fluoropyridin-2-yl)propanamide

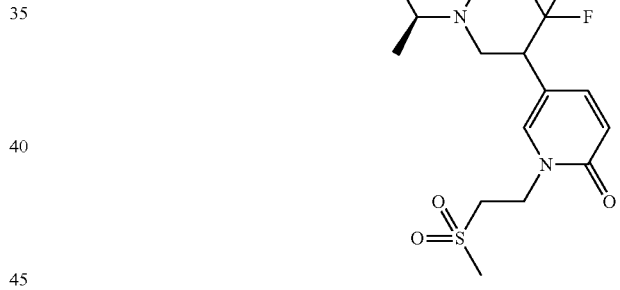

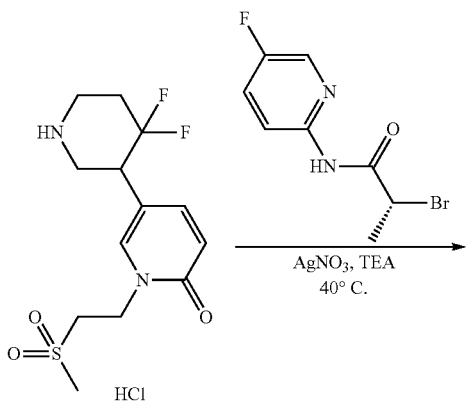

Step 1

To tert-butyl 4,4-difluoro-3-(6-oxo-1,6-dihydropyridin-3-yl)piperidine-1-carboxylate (Example 1, Step 3) (0.150 g, 0.477 mmol) and cesium carbonate (1.555 g, 4.77 mmol) in DMF (5.0 ml) was added (methylsulfonyl)ethene (0.084 mL, 0.954 mmol). After 30 min, the reaction was diluted with EtOAc and washed with water, 1N HCl and brine, then dried over sodium sulfate, filtered and concentrated. The resulting solid was purified by silica gel chromatography (12 g ISCO column), eluting with 10-70% 3:1 EtOAc: EtOH in heptane to provide tert-butyl 4,4-difluoro-3-(1-(2-(methyl-sulfonyl)ethyl)-6-oxo-1,6-dihydropyridin-3-yl)piperidine-1-carboxylate (164 mg, 0.371 mmol, purity: 95%, recovery: 78%) as a colorless gum. LCMS (m/z) 421 (M+H)⁺, retention time 0.79 min, LCMS Method 5. ¹H NMR (400 MHz, CDCl$_3$) δ ppm 7.31-7.41 (m, 2H), 6.55 (d, J=9.29 Hz, 1H), 4.29-4.42 (m, 2H), 4.07-4.28 (m, 2H), 3.49-3.62 (m, 2H), 3.02-3.24 (m, 2H), 2.75-2.90 (m, 1H), 2.80 (s, 3H), 2.07-2.20 (m, 1H), 1.80-2.00 (m, 1H), 1.46 (s, 9H).

Step 2

To tert-butyl 4,4-difluoro-3-(1-(2-(methylsulfonyl)ethyl)-6-oxo-1,6-dihydropyridin-3-yl)piperidine-1-carboxylate (270 mg, 0.642 mmol) in dioxane (5 ml) was added HCl (4M in dioxane) (6 ml, 24 mmol). After stirring overnight, the reaction was concentrated and azeotroped with methylene chloride to provide crude 5-(4,4-difluoropiperidin-3-yl)-1-(2-(methylsulfonyl)ethyl)pyridin-2 (1H)-one dihydrochloride (267 mg, 0.673 mmol, purity: 90%, recovery: quantitative) as a white solid, which was used without purification. LCMS (m/z) 321 (M+H)$^+$, retention time 0.28 min, LCMS Method 5. $^1$H NMR (400 MHz, MeOH-d$_4$) δ ppm 7.81 (d, J=2.45 Hz, 1H), 7.58-7.66 (m, 1H), 6.61 (d, J=9.29 Hz, 1H), 4.49 (t, J=6.85 Hz, 2H), 3.68-3.80 (m, 1H), 3.65 (t, J=6.36 Hz, 2H), 3.34-3.63 (m, 4H), 3.03 (s, 3H), 2.29-2.60 (m, 2H).

Step 3

To a sealed tube of (R)-2-bromo-N-(5-fluoropyridin-2-yl)propanamide (Intermediate 1) (100 mg, 0.364 mmol) in DMA (1 ml) was added a solution of 5-(4,4-difluoropiperidin-3-yl)-1-(2-(methylsulfonyl)ethyl)pyridin-2 (1H)-one hydrochloride (162 mg, 0.455 mmol) in DMA (2 ml), followed by Et$_3$N (0.063 mL, 0.455 mmol) and silver nitrate (61.9 mg, 0.364 mmol). The tube was capped and heated to 40° C. After 18 h, additional Et$_3$N (0.076 mL, 0.546 mmol) was added. After 15 h, the reaction was filtered, diluted with EtOAc and washed with water and a mix of sat'd K$_2$CO$_3$ and brine. The combined aqueous phases were back-extracted with EtOAc. This EtOAc phase was washed with water and with brine. The EtOAc phases were combined, dried over Na$_2$SO$_4$, filtered and concentrated to give a yellow liquid which was purified by silica gel chromatography (12 g ISCO column), eluting with 10-70% 3:1 EtOAc: EtOH in heptane to provide (2S)-2-(4,4-difluoro-3-(1-(2-(methylsulfonyl)ethyl)-6-oxo-1,6-dihydropyridin-3-yl)piperidin-1-yl)-N-(5-fluoropyridin-2-yl)propanamide (123 mg, 0.128 mmol, purity: 95%, recovery: 69%) as a light yellow foam. LCMS (m/z) 487 (M+H)$^+$, retention time: 0.50 min, LC/MS Method 5. $^1$H NMR (400 MHz, CDCl$_3$) δ ppm 9.48 (br d, J=12.72 Hz, 1H), 8.25 (dt, J=9.41, 3.85 Hz, 1H), 8.16 (dd, J=2.93, 1.47 Hz, 1H), 7.41-7.51 (m, 2H), 7.33-7.41 (m, 1H), 6.56 (dd, J=9.78, 5.87 Hz, 1H), 4.29-4.46 (m, 2H), 3.51-3.64 (m, 2H), 3.43 (qd, J=7.01, 2.45 Hz, 1H), 3.00-3.25 (m, 1H), 2.78-2.99 (m, 6H), 2.57-2.75 (m, 1H), 2.08-2.35 (m, 2H), 1.38 (dd, J=7.09, 2.69 Hz, 3H).

Examples 191 and 192 were synthesized in an analogous manner using the designated Intermediate in Step 3.

| Ex | Name | Structure | $^1$H NMR | LC/MS: (M + H)$^+$; retention time (min); LC/MS Method of analysis | Int |
|---|---|---|---|---|---|
| 191 | (2S)-N-(6-(cyclopropylmethoxy)pyridazin-3-yl)-2-(4,4-difluoro-3-(1-(2-(methylsulfonyl)ethyl)-6-oxo-1,6-dihydropyridin-3-yl)piperidin-1-yl)propanamide | 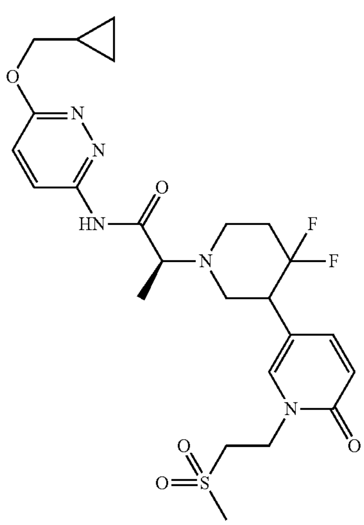 [SMILES: C[C@@H](C(=O)Nc1ccc(OCC2CC2)nn1)N1CCC(F)(F)C(c2ccc(=O)n(CCS(C)(=O)=O)c2)C1] | $^1$H NMR (400 MHz, CDCl$_3$) δ ppm 9.86 (br d, J = 6.85 Hz, 1H), 8.39 (dd, J = 9.54, 1.71 Hz, 1H), 7.32-7.48 (m, 2H), 7.05 (dd, J = 9.54, 1.71 Hz, 1H), 6.55 (dd, J = 9.05, 8.07 Hz, 1H), 4.32-4.44 (m, 2H), 4.29 (dd, J = 7.34, 0.98 Hz, 2H), 3.51-3.62 (m, 2H), 3.41-3.50 (m, 1H), 3.04-3.24 (m, 1H), 2.85-3.00 (m, 3H), 2.84 (d, J = 3.42 Hz, 3H), 2.57-2.75 (m, 1H), 2.10-2.31 (m, 2H), 1.38 (dd, J = 6.85, 2.93 Hz, 3H), 1.29-1.36 (m, 1H), 0.59-0.71 (m, 2H). | 540; rt 0.62. LC/MS Method 5 | 14 |

| Ex | Name | Structure | ¹H NMR | LC/MS: (M + H)⁺; retention time (min); LC/MS Method of analysis | Int |
|---|---|---|---|---|---|
| 192 | 2-(4,4-difluoro-3-(1-(2-(methylsulfonyl)ethyl)-6-oxo-1,6-dihydropyridin-3-yl)piperidin-1-yl)-N-(5-(4-fluorophenoxy)pyridin-2-yl)propanamide | 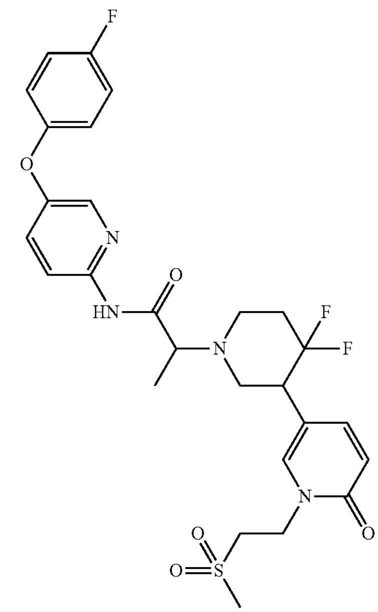 [SMILES: CC(C(=O)Nc1ccc(Oc2ccc(F)cc2)cn1)N1CCC(F)(F)C(c2ccc(=O)n(CCS(C)(=O)=O)c2)C1] | ¹H NMR (400 MHz, CDCl₃) δ ppm 9.47 (br d, J = 13.69 Hz, 1H), 8.21 (dd, J = 9.05, 3.18 Hz, 1H), 8.07 (d, J = 2.93 Hz, 1H), 7.41-7.48 (m, 1H), 7.32-7.41 (m, 2H), 7.01-7.10 (m, 2H), 6.92-7.00 (m, 2H), 6.56 (dd, J = 9.29, 5.87 Hz, 1H), 4.29-4.45 (m, 2H), 3.49-3.63 (m, 2H), 3.43 (qd, J = 7.01, 2.45 Hz, 1H), 3.03-3.27 (m, 1H), 2.84-3.00 (m, 3H), 2.82 (d, J = 3.42 Hz, 3H), 2.57-2.74 (m, 1H), 2.07-2.32 (m, 2H), 1.38 (dd, J = 6.85, 2.45 Hz, 3H). | 579; rt 0.75. LC/MS Method 5 | 70 |

Example 193

(S)-2-((S)-(3-(1-(2,2-difluoroethyl)-6-oxo-1,6-dihydropyridin-3-yl)-4,4-difluoropiperidin-1-yl)-N-(5-fluoropyridin-2-yl)propanamide

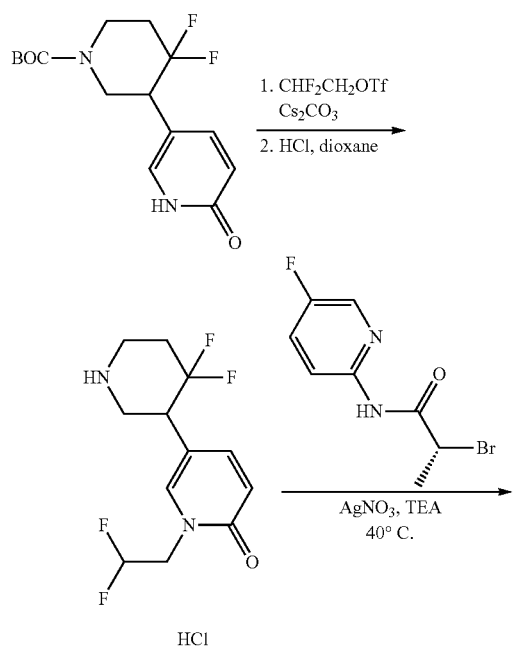

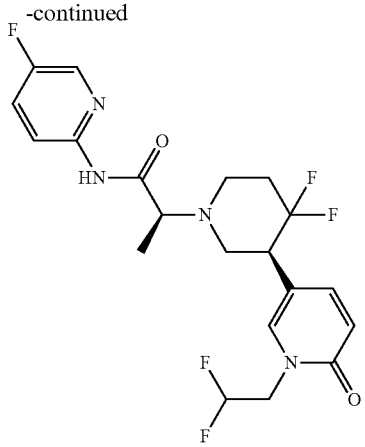

Step 1

To a solution of tert-butyl 4,4-difluoro-3-(6-oxo-1,6-dihydropyridin-3-yl)piperidine-1-carboxylate (Example 1, Step 3) (500 mg, 1.591 mmol) in DMF (8 mL) was added 2,2-difluoroethyl trifluoromethanesulfonate (681 mg, 3.18 mmol) and Cs₂CO₃ (1037 mg, 3.18 mmol). After 4 h, the reaction was quenched with water and extracted with EtOAc (3×50 ml). The combined extracts were washed with brine, dried over sodium sulfate, concentrated and purified over silica gel, eluting with 0 to 100% EtOAc in heptanes to provide tert-butyl 3-(1-(2,2-difluoroethyl)-6-oxo-1,6-dihydropyridin-3-yl)-4,4-difluoropiperidine-1-carboxylate (171 mg, 0.452 mmol, purity: 100%, recovery: 28%) as a colorless gum. LCMS (m/z) 378 (M+H)⁺, retention time: 0.94 min, LC/MS Method 3.

Step 2

To tert-butyl 3-(1-(2,2-difluoroethyl)-6-oxo-1,6-dihydropyridin-3-yl)-4,4-difluoropiperidine-1-carboxylate (171 mg, 0.452 mmol) in dioxane (3 ml) was added HCl (4M) (3 ml, 12 mmol). After 4 h, more HCl (4M) (3 mL, 12 mmol) was added, and after 2 h the reaction was concentrated and azeotroped with methylene chloride to provide crude 1-(2,2-difluoroethyl)-5-(4,4-difluoropiperidin-3-yl)pyridin-2(1H)-one dihydrochloride (168 mg, 0.534 mmol, purity: 100%, recovery: quantitative) as a white solid, which was used without purification. LCMS (m/z) 278 (M+H)$^+$, retention time: 0.51 min, LC/MS Method 3.

Step 3

To a sealed tube of (R)-2-bromo-N-(5-fluoropyridin-2-yl)propanamide (Intermediate 1) (140 mg, 0.510 mmol) in DMA (1.5 ml) was added a solution of 1-(2,2-difluoroethyl)-5-(4,4-difluoropiperidin-3-yl)pyridin-2 (1H)-one hydrochloride (141 mg, 0.448 mmol) in DMA (2.5 ml), followed by Et$_3$N (0.185 mL, 1.326 mmol) and silver nitrate (87 mg, 0.510 mmol). The tube was capped and heated to 40° C. After 17 h, the reaction was filtered, diluted with EtOAc and washed with water and a mix of sat'd K$_2$CO$_3$ and brine. The combined aqueous phases were back-extracted with EtOAc, and this EtOAc phase was washed with water and with brine. The EtOAc phases were combined, dried over Na$_2$SO$_4$, filtered, concentrated and purified by silica gel chromatography (40 g ISCO column), eluting with 0-70% 3:1 EtOAc: EtOH in heptane. A small amount of the resulting purified material (15 mg) was purified by MDAP (HPH condition, XSELECT CSH C18 column), eluting with 30-99% AcCN in 10 mM ammonium bicarbonate in water (adjusted to pH 10 with ammonia) to provide (S)-2-((S)-(3-(1-(2,2-difluoroethyl)-6-oxo-1,6-dihydropyridin-3-yl)-4,4-difluoropiperidin-1-yl)-N-(5-fluoropyridin-2-yl)propanamide, (1.5 mg, 3.38 μmol, purity: 100%, recovery: 0.7%) as a pale yellow foam. LCMS (m/z) 444 (M+H)$^+$, retention time: 0.93 min, LC/MS Method 3. $^1$H NMR (400 MHz, CDCl$_3$) δ ppm 9.51 (s, 1H), 8.28 (dd, J=9.17, 4.03 Hz, 1H), 8.17 (d, J=2.93 Hz, 1H), 7.48 (ddd, J=9.11, 7.76, 2.93 Hz, 1H), 7.40 (dd, J=9.54, 1.71 Hz, 1H), 7.25 (d, J=1.96 Hz, 1H), 6.60 (d, J=9.29 Hz, 1H), 5.93-6.32 (m, 1H), 4.18-4.36 (m, 2H), 3.45 (d, J=7.09 Hz, 1H), 3.07-3.25 (m, 1H), 2.84-3.00 (m, 3H), 2.64 (d, J=2.45 Hz, 1H), 2.06-2.35 (m, 2H), 1.40 (d, J=7.09 Hz, 3H).

Example 194

(2S)-2-(4,4-difluoro-3-(1-isopropyl-6-oxo-1,6-dihydropyridin-3-yl)piperidin-1-yl)-N-(5-fluoropyridin-2-yl)propanamide

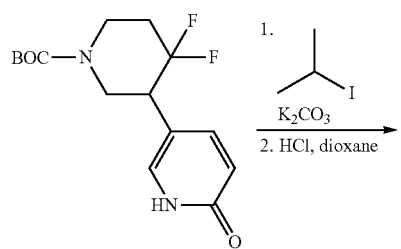

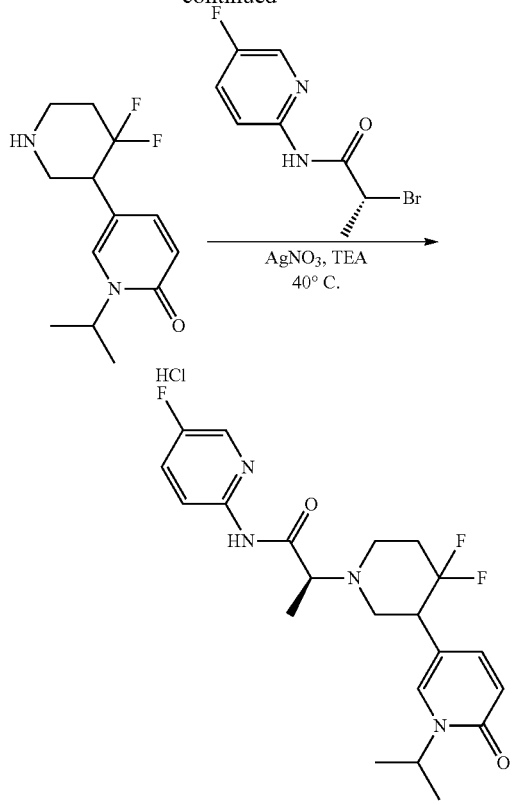

Step 1

In two batches, to tert-butyl 4,4-difluoro-3-(6-oxo-1,6-dihydropyridin-3-yl)piperidine-1-carboxylate (Example 1, Step 3) (100 mg, 0.318 mmol and 400 mg, 1.273 mmol) in DMF (1.5 and 3 ml) was added K$_2$CO$_3$ (132 mg, 0.954 mmol and 528 mg, 3.82 mmol), followed by 2-iodopropane (0.064 mL, 0.636 mmol and 0.382 mL, 3.82 mmol). After heating at 80° C. for 2 h, additional K$_2$CO$_3$ (44.0 mg, 0.318 mmol and 352 mg, 2.55 mmol) and 2-iodopropane (0.032 mL, 0.318 mmol and 0.254 mL, 2.55 mmol) were added. After 30 min, the reactions were diluted with EtOAc, washed with water and brine, dried over sodium sulfate, filtered, concentrated and purified by silica gel chromatography (12 g ISCO column), eluting with 10-100% EtOAc in heptane to provide tert-butyl 4,4-difluoro-3-(1-isopropyl-6-oxo-1,6-dihydropyridin-3-yl)piperidine-1-carboxylate (150 mg, 0.371 mmol, purity: 95%, recovery: 25%). LCMS (m/z) 357 (M+H)$^+$, retention time 0.60 minutes, LCMS Method 5. $^1$H NMR (400 MHz, CDCl$_3$) δ ppm 7.24-7.30 (m, 2H), 6.57 (J=10.27, 1H), 5.29 (spt, J=6.85 Hz, 1H), 4.07-4.37 (m, 2H), 3.06-3.27 (m, 2H), 2.76-2.95 (m, 1H), 2.09-2.22 (m, 1H), 1.84-2.05 (m, 1H), 1.50 (s, 9H), 1.37 (d, J=6.85 Hz, 6H).

Step 2

To tert-butyl 4,4-difluoro-3-(1-isopropyl-6-oxo-1,6-dihydropyridin-3-yl)piperidine-1-carboxylate (150 mg, 0.421 mmol) in dioxane (3 ml) was added HCl (4M in dioxane) (3 ml, 12 mmol). After 2 h, the reaction was stored in the freezer over the weekend. The reaction was concentrated and azeotroped with methylene chloride to provide crude 5-(4,4-difluoropiperidin-3-yl)-1-isopropylpyridin-2 (1H)-one hydrochloride (143 mg, 0.673 mmol, purity: 70%, recovery: quantitative), which was used without purification. LCMS (m/z) 257 (M+H)$^+$, retention time 0.38 minutes, LCMS Method 5. $^1$H NMR (400 MHz, MeOH-d$_4$) δ ppm 8.03 (d, J=1.96 Hz, 1H), 7.81 (br d, J=9.29 Hz, 1H), 6.93 (d, J=9.29 Hz, 1H), 5.19 (spt, J=6.77 Hz, 1H), 3.81-4.00 (m, 1H), 3.44-3.61 (m, 3H), 3.21-3.29 (m, 1H), 2.49-2.72 (m, 1H), 2.29-2.45 (m, 1H), 1.45 (d, J=6.85 Hz, 6H).

Step 3

To a sealed tube of (R)-2-bromo-N-(5-fluoropyridin-2-yl) propanamide (Intermediate 1) (100 mg, 0.364 mmol) in DMA (1 ml) was added a solution of 5-(4,4-difluoropiperidin-3-yl)-1-isopropylpyridin-2(1H)-one hydrochloride (133 mg, 0.455 mmol) in DMA (2 ml), followed by Et₃N (0.063 mL, 0.455 mmol) and silver nitrate (61.9 mg, 0.364 mmol). The tube was capped and heated to 40° C. After 18 h, additional Et₃N (0.076 mL, 0.546 mmol) was added. After 15 h, the reaction was filtered, diluted with EtOAc and washed with water and a mix of sat'd K₂CO₃ and brine. The combined aqueous phases were back-extracted with EtOAc, and this EtOAc phase was washed with water and with brine. The EtOAc phases were combined, dried over Na₂SO₄, filtered, concentrated and purified by silica gel chromatography (12 g ISCO column), eluting with 0-60% 3:1 EtOAc: EtOH in heptane to provide (2S)-2-(4,4-difluoro-3-(1-(2-(methylsulfonyl)ethyl)-6-oxo-1,6-dihydropyridin-3-yl)piperidin-1-yl)-N-(5-fluoropyridin-2-yl)propanamide contaminated with DMA. To remove the DMA, the material was dissolved in EtOAc, washed with water (3×) and brine, dried over Na₂SO₄, filtered and concentrated to give a colorless oil. The compound was then dissolved in 2 ml of DCM, transferred into a vial, concentrated under a nitrogen stream and dried under high vacuum overnight to give the desired product as a white foam (85 mg, 0.128 mmol, purity: 100%, recovery: 53%). LCMS (m/z) 423 (M+H)⁺, retention time 0.60 minutes, LCMS Method 5. ¹H NMR (400 MHz, CDCl₃) δ ppm 9.54 (br d, J=18.58 Hz, 1H), 8.21-8.30 (m, 1H), 8.16 (d, J=2.93 Hz, 1H), 7.41-7.51 (m, 1H), 7.27-7.31 (m, 1H), 7.23-7.27 (m, 1H), 6.49-6.58 (m, 1H), 5.22-5.30 (m, 1H), 3.36-3.49 (m, 1H), 2.77-3.26 (m, 4H), 2.56-2.73 (m, 1H), 2.07-2.33 (m, 2H), 1.32-1.47 (m, 9H).

Example 195

(S)-2-((S)-(3-(1-benzyl-6-oxo-1,6-dihydropyridin-3-yl)-4,4-difluoropiperidin-1-yl)-N-(5-fluoropyridin-2-yl)propanamide

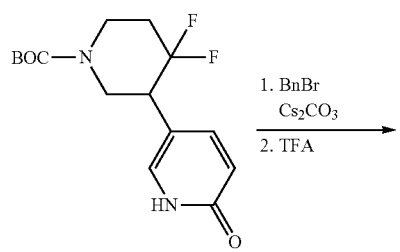

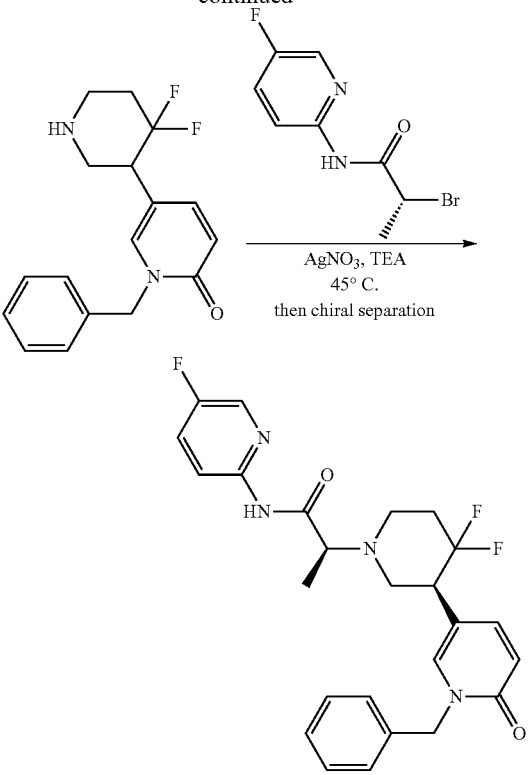

Step 1

To tert-butyl 4,4-difluoro-3-(6-oxo-1,6-dihydropyridin-3-yl)piperidine-1-carboxylate (Example 1, Step 3) (0.5 g, 1.591 mmol) and Cs₂CO₃ (1.555 g, 4.77 mmol) in DMF (5 ml) was added benzyl bromide (0.25 ml, 2.102 mmol). After stirring overnight, the reaction was diluted with water and extracted with EtOAc (2×). The combined organic layers were washed with brine, dried over sodium sulfate, filtered, concentrated and purified by silica gel chromatography, eluting with 20-100% EtOAc in heptane to provide tert-butyl 3-(1-benzyl-6-oxo-1,6-dihydropyridin-3-yl)-4,4-difluoropiperidine-1-carboxylate (452 mg, 1.118 mmol, purity: 95%, recovery: 70%). LCMS (m/z) 405 (M+H)⁺, retention time: 1.04 min, LC/MS Method 5.

Step 2

To tert-butyl 3-(1-benzyl-6-oxo-1,6-dihydropyridin-3-yl)-4,4-difluoropiperidine-1-carboxylate (0.200 g, 0.494 mmol) in DCM (1.5 ml) was added TFA (0.1 ml, 1.298 mmol). After 2 h, additional TFA (0.2 ml, 2.60 mmol) was added. After another hour, the reaction was concentrated, taken up into EtOAc, washed with sat'd aq NaHCO₃ and brine, dried over sodium sulfate, filtered and concentrated to provide crude 1-benzyl-5-(4,4-difluoropiperidin-3-yl)pyridin-2(1H)-one (138 mg, 0.453 mmol, purity: 100%, recovery: 92%) as a colorless oil, which was used without purification. LCMS (m/z) 305 (M+H)⁺, retention time: 0.46 min, LC/MS Method 5.

Step 3

To 1-benzyl-5-(4,4-difluoropiperidin-3-yl)pyridin-2 (1H)-one (0.12 g, 0.394 mmol), TEA (0.110 ml, 0.789 mmol), and silver nitrate (0.067 g, 0.394 mmol) in DMA (1.0 ml) was added (R)-2-bromo-N-(5-fluoropyridin-2-yl) propanamide (Intermediate 1) (0.107 g, 0.434 mmol), followed by heating at 45° C. for 2 hours. The reaction was diluted with water and extracted with EtOAc (2×). The combined organics were dried over sodium sulfate, filtered, concentrated and purified by silica gel chromatography (ISCO column), eluting with 20-70% 3:1 EtOAc: EtOH in heptane to provide (2S)-2-(3-(1-benzyl-6-oxo-1,6-dihydro-pyridin-3-yl)-4,4-difluoropiperidin-1-yl)-N-(5-fluoropyridin-2-yl)propanamide (114 mg, 0.218 mmol, purity: 92%, recovery: 53%) as a tan solid. LCMS (m/z) 471 (M+H)⁺, retention time: 0.72 min, LC/MS Method 5. ¹H NMR (400 MHz, DMSO-d) S ppm 10.38 (d, J=10.76 Hz, 1H), 8.34 (t, J=2.93 Hz, 1H), 8.14 (dd, J=9.29, 4.40 Hz, 1H), 7.83 (t, J=2.45 Hz, 1H), 7.70-7.80 (m, 1H), 7.44 (ddd, J=12.47, 9.54, 2.45 Hz, 1H), 7.22-7.37 (m, 5H), 6.39 (t, J=8.80 Hz, 1H), 5.02-5.16 (m, 2H), 3.58-3.71 (m, 1H), 3.07-3.27 (m, 1H), 2.82-3.01 (m, 2H), 2.64-2.73 (m, 1H), 2.04-2.17 (m, 1H), 1.15-1.32 (m, 5H). The diastereomers were separated on a Chiralpak IG 250 mm×20 mm 5 u dp, eluting with 75:25 heptane:EtOH. Diastereomer 1 (first-eluting) was further purified on the Chiralpak IG twice, eluting first with 65:35 heptane:EtOH, then purified a second time with 20-60% EtOH (0.1% isopropylamine modifier) in heptane. Final purification on a Chiralpak IF, eluting with 20-60% EtOH (0.1% isopropylamine modifier) in heptane gave (S)-2-((S)-(3-(1-benzyl-6-oxo-1,6-dihydropyridin-3-yl)-4,4-difluoropiperidin-1-yl)-N-(5-fluoropyridin-2-yl)propanamide (14.3 mg, 0.030 mmol, purity: 100%, recovery: 8%).

Example 196

2-(4,4-difluoro-3-(6-oxo-1-(pyridin-2-ylmethyl)-1,6-dihydropyridin-3-yl)piperidin-1-yl)-N-(5-fluoropyridin-2-yl)propanamide

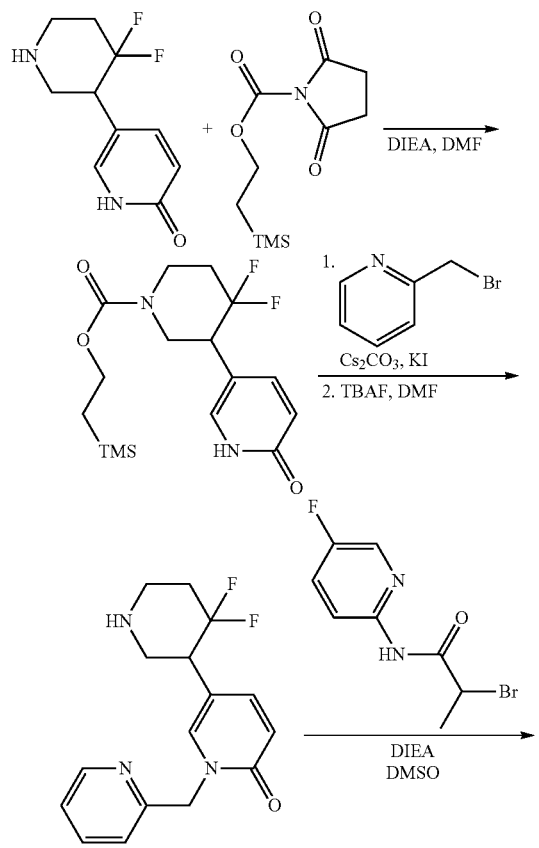

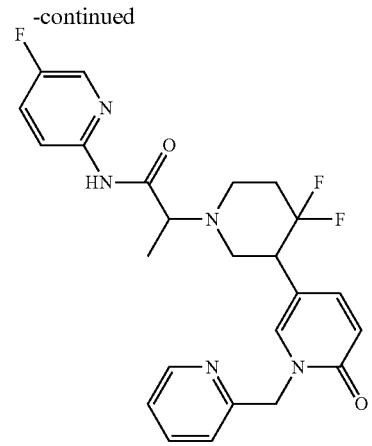

Step 1

To 5-(4,4-difluoropiperidin-3-yl)pyridin-2 (1H)-one (hydrochloride salt) (Example 4, Step 3) (0.5 g, 1.741 mmol) and diisopropylethylamine (0.912 mL, 5.22 mmol) in DMF (4 mL) was added 2,5-dioxopyrrolidin-1-yl (2-(trimethylsilyl)ethyl) carbonate (0.452 g, 1.741 mmol). After 2 h, the reaction was diluted with water (150 mL) and extracted with EtOAc (2×). The organic phases were dried over sodium sulfate, concentrated and purified over silica (80 g ISCO Gold column), eluting with 50-100% ethyl acetate in heptane, then 15% MeOH in DCM to provide 2-(trimethylsilyl)ethyl 4,4-difluoro-3-(6-oxo-1,6-dihydropyridin-3-yl)piperidine-1-carboxylate (478 mg, 1.333 mmol, purity: 78%, recovery: 29%) as a colorless foam. LCMS (m/z) 359 (M+H)⁺, retention time: 1.01 min, LC/MS Method 3.

Step 2

To cesium carbonate (364 mg, 1.116 mmol) and 2-(bromomethyl)pyridine hydrobromide (85 mg, 0.335 mmol) was added a solution of 2-(trimethylsilyl)ethyl 4,4-difluoro-3-(6-oxo-1,6-dihydropyridin-3-yl)piperidine-1-carboxylate (100 mg, 0.279 mmol) in DMF (1 mL). After 3 h, the mixture was partitioned between ethyl acetate and water, the organic layer was isolated, and the aqueous was extracted again with EtOAc. The combined organics were then dried over sodium sulfate, filtered, concentrated and purified via MDAP (Method C, extended), eluting with 30-85% MeCN in water [10 mM ammonium bicarbonate+0.075% aqueous ammonium hydroxide to pH10]) to provide 2-(trimethylsilyl)ethyl 4,4-difluoro-3-(6-oxo-1-(pyridin-2-ylmethyl)-1,6-dihydropyridin-3-yl)piperidine-1-carboxylate (93 mg, 0.207 mmol, purity: 86%, recovery: 74%) as a colorless foam. LCMS (m/z) 450 (M+H)⁺, retention time: 1.12 min, LC/MS Method 3.

Step 3

To tetrabutylammonium fluoride trihydrate (208 mg, 0.661 mmol) was added a solution of 2-(trimethylsilyl)ethyl 4,4-difluoro-3-(6-oxo-1-(pyridin-2-ylmethyl)-1,6-dihydropyridin-3-yl)piperidine-1-carboxylate (99 mg, 0.220 mmol) in DMF (2 mL). The reaction was stirred over the weekend and purified directly by MDAP (Darwin HPH flex method), eluting with 5-50% MeCN in water [10 mM ammonium carbonate+0.075% aqueous ammonium hydroxide solution to pH 10]) to afford 5-(4,4-difluoropiperidin-3-yl)-1-(pyridin-2-ylmethyl)pyridin-2 (1H)-one (25 mg, 0.078 mmol, purity: 84%, recovery: 35%) as a gum. LCMS (m/z) 306 (M+H)⁺, retention time: 0.52 min, LC/MS Method 3.

Step 4

To 2-bromo-N-(5-fluoropyridin-2-yl)propanamide (Intermediate 1) (23.26 mg, 0.094 mmol) was added a solution of 5-(4,4-difluoropiperidin-3-yl)-1-(pyridin-2-ylmethyl)pyridin-2 (1H)-one (25 mg, 0.082 mmol) and diisopropylethylamine (0.043 mL, 0.246 mmol) in DMSO (1 mL). The reaction was stirred overnight and purified directly by MDAP (Darwin Method B, extended, HPH), eluting with 15-55% MeCN in aqueous (0.1% ammonium carbonate+ 0.075 mM NH4OH to pH 10). Fractions containing product were concentrated to remove AcCN, treated with sat'd sodium bicarbonate solution and extracted with EtOAc (2×). The organic extracts were dried over sodium sulfate and concentrated to afford 2-(4,4-difluoro-3-(6-oxo-1-(pyridin-4-ylmethyl)-1,6-dihydropyridin-3-yl)piperidin-1-yl)-N-(5-fluoropyridin-2-yl)propanamide (27 mg, 0.054 mmol, purity: 100%, recovery: 66%) as a light tan solid. LCMS (m/z) 474 (M+H)$^+$, retention time 0.87-0.88 min, LC/MS Method 3. $^1$H NMR (400 MHz, Dichloromethane-d$_2$) δ ppm 9.54 (br d, J=5.87 Hz, 1H), 8.45-8.57 (m, 1H), 8.22 (dt, J=9.29, 4.65 Hz, 1H), 8.13 (t, J=2.93 Hz, 1H), 7.61-7.71 (m, 1H), 7.41-7.53 (m, 2H), 7.25-7.39 (m, 2H), 7.16-7.23 (m, 1H), 6.47 (dd, 5 J=9.78, 7.83 Hz, 1H), 5.09-5.25 (m, 2H), 3.37-3.46 (m, 1H), 3.00-3.24 (m, 1H), 2.76-2.98 (m, 3H), 2.54-2.71 (m, 1H), 2.04-2.31 (m, 2H), 1.32 (dd, J=7.09, 3.18 Hz, 3H).

Examples 197 and 198 were synthesized in an analogous manner using the designated alkyl halide in Step 2.

| Ex | Name | Structure | $^1$H NMR | LC/MS: (M + H)$^+$; retention time (min); LC/MS Method of analysis | Alkyl halide |
|---|---|---|---|---|---|
| 197 | 2-(4,4-difluoro-3-(6-oxo-1-(pyridin-4-ylmethyl)-1,6-dihydropyridin-3-yl)piperidin-1-yl)-N-(5-fluoropyridin-2-yl)propanamide | 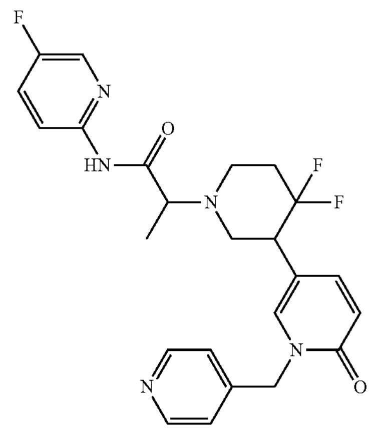 [SMILES: CC(C(=O)Nc1ccc(F)cn1)N1CCC(F)(F)C(c2ccc(=O)n(Cc3ccncc3)c2)C1] | $^1$H NMR (400 MHz, Dichloromethane-d$_2$) δ ppm 9.50 (br d, J = 12.72 Hz, 1H), 8.46-8.60 (m, 2H), 8.22 (dt, J = 9.17, 4.46 Hz, 1H), 8.12 (t, J = 3.18 Hz, 1H), 7.46 (dddd, J = 9.17, 7.70, 2.93, 1.71 Hz, 1H), 7.32-7.41 (m, 1H), 7.27 (d, J = 1.96 Hz, 1H), 7.07-7.16 (m, 2H), 6.47-6.58 (m, 1H), 5.00-5.19 (m, 2H), 3.41 (qd, J = 7.01, 2.45 Hz, 1H), 2.99-3.23 (m, 1H), 2.74-2.97 (m, 3H), 2.53-2.69 (m, 1H), 2.03-2.30 (m, 2H), 1.32 (dd, J = 7.09, 2.20 Hz, 3H). | 472; rt 0.82-0.84. LC/MS Method 3 | 4-(bromomethyl)pyridine |
| 198 | 2-(4,4-difluoro-3-(1-(oxazol-2-ylmethyl)-6-oxo-1,6-dihydropyridin-3-yl)piperidin-1-yl)-N-(5-fluoropyridin-2-yl)propanamide | 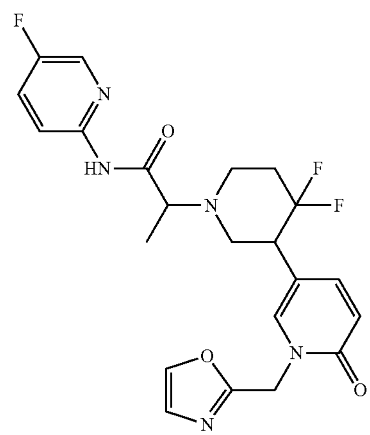 [SMILES: CC(C(=O)Nc1ccc(F)cn1)N1CCC(F)(F)C(c2ccc(=O)n(Cc3ncco3)c2)C1] | $^1$H NMR (400 MHz, Dichloromethane-d$_2$) δ ppm 9.54 (br d, J = 10.76 Hz, 1H), 8.22 (dt, J = 9.05, 4.77 Hz, 1H), 8.07-8.15 (m, 1H), 7.60-7.69 (m, 1H), 7.42 (s, 2H), 7.35 (td, J = 9.54, 1.47 Hz, 1H), 7.01-7.09 (m, 1H), 6.48 (dd, J = 9.29, 7.83 Hz, 1H), 5.12-5.27 (m, 2H), 3.43 (q, J = 6.85 Hz, 1H), 3.01-3.23 (m, 1H), 2.75-2.98 (m, 3H), 2.53-2.71 (m, 1H), 2.03-2.31 (m, 2H), (dd, J = 6.85, 1.96 Hz, 3H). | 462; rt 0.82-0.84. LC/MS Method 3 | 2-(chloromethyl)oxazole |

Examples 199 and 200
(2S)-2-(4,4-difluoro-3-(5-(hydroxymethyl)-6-oxo-1-(2,2,2-trifluoroethyl)-1,6-dihydropyridin-3-yl)piperidin-1-yl)-N-(5-fluoropyridin-2-yl)propanamide and (2S)-2-(4,4-difluoro-3-(5-methyl-6-oxo-1-(2,2,2-trifluoroethyl)-1,6-dihydropyridin-3-yl)piperidin-1-yl)-N-(5-fluoropyridin-2-yl)propanamide
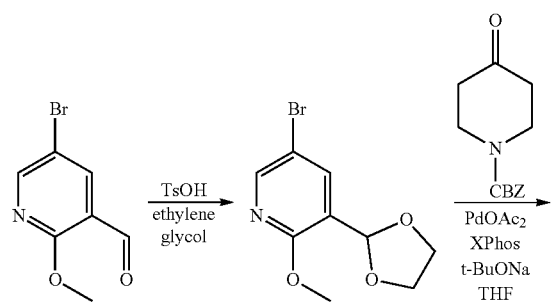
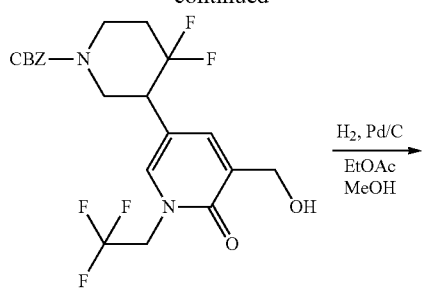
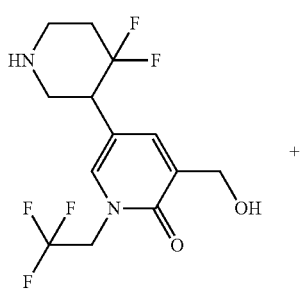
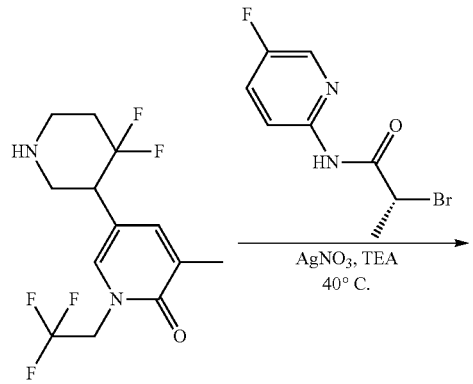
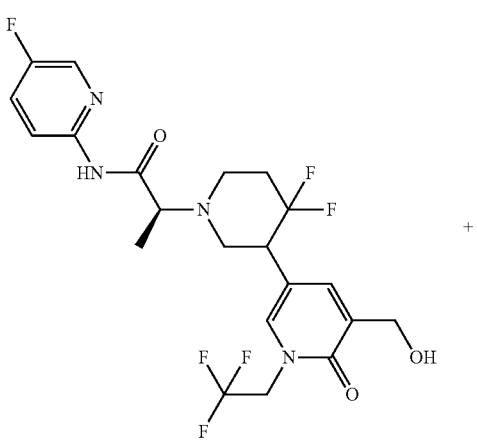

-continued

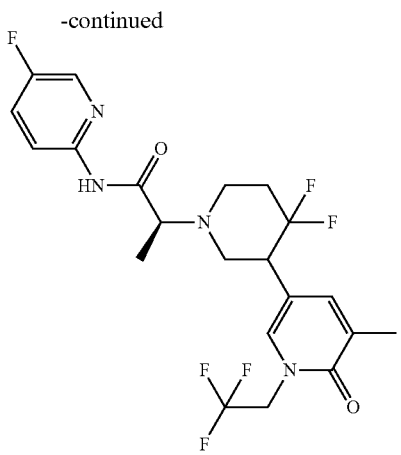

Step 1

Under a Dean-Stark condenser, 5-bromo-2-methoxynico-tinaldehyde (10 g, 46.3 mmol), 4-methylbenzenesulfonic acid (1.196 g, 6.94 mmol) and ethylene glycol (38.7 ml, 694 mmol) in toluene (231 ml) were heated to reflux for 3 h, poured into 5% aqueous NaHCO$_3$ and extracted with toluene. The organic extracts were dried with Na$_2$SO$_4$ and concentrated to afford crude product 5-bromo-3-(1,3-dioxolan-2-yl)-2-methoxypyridine (8.02 g, 30.8 mmol, recovery 67%), which was used without purification.

Step 2

A 25 ml reaction tube, under N$_2$, was charged with sodium tert-butoxide (2M in THF) (17.30 mL, 34.6 mmol), then benzyl 4-oxopiperidine-1-carboxylate (4.04 g, 17.30 mmol), followed by 5-bromo-3-(1,3-dioxolan-2-yl)-2-methoxypyridine (3 g, 11.53 mmol). After 2 minutes, PdOAc$_2$ (0.129 g, 0.577 mmol) and XPhos (0.550 g, 1.153 mmol) were added. The reaction was evacuated and back-filled with N$_2$ three times and heated at 45° C. for approximately 15 h. The mixture was partitioned between EtOAc and water, and the organic phase was isolated and washed with brine. The combined aqueous phases were back-extracted with EtOAc, and this EtOAc phase was washed with brine. The organic phases were combined, dried over Na$_2$SO$_4$, filtered and concentrated. The crude mixture was purified by silica gel chromatography (120 g Isco gold column), eluting with 0-70% EtOAc in heptane, to afford benzyl 3-(5-(1,3-dioxolan-2-yl)-6-methoxypyridin-3-yl)-4-oxopiperidine-1-carboxylate (927 mg, 2.135 mmol, purity: 98%, recovery: 19%) as a yellow foam. LCMS (m/z) 413 (M+H)$^+$, retention time 0.93 min, LC/MS Method 5. $^1$H NMR (400 MHz, CHLOROFORM-d) δ ppm 7.96 (br s, 1H), 7.61 (d, J=1.96 Hz, 1H), 7.32-7.45 (m, 5H), 6.02 (s, 1H), 5.21 (s, 2H), 4.29-4.55 (m, 2H), 4.07-4.15 (m, 2H), 4.01-4.07 (m, 2H), 4.00 (s, 3H), 3.62-3.78 (m, 1H), 3.38-3.57 (m, 2H), 2.48-2.72 (m, 2H).

Step 3

To benzyl 3-(5-(1,3-dioxolan-2-yl)-6-methoxypyridin-3-yl)-4-oxopiperidine-1-carboxylate (0.925 g, 2.243 mmol) in DCM (8 ml), in an ice bath, was added DAST (0.593 mL, 4.49 mmol), dropwise. The mixture was allowed to warm to rt slowly, then was stirred overnight and poured slowly into sat'd. NaHCO$_3$ solution (about 30 ml). The mixture was extracted with DCM (2×), and the organic extracts were combined, washed with brine, dried over Na$_2$SO$_4$, filtered and concentrated. The material was purified by silica gel chromatography (24 g Isco Gold column), eluting with 0-70% EtOAc in heptane to provide benzyl 3-(5-(1,3-dioxolan-2-yl)-6-methoxypyridin-3-yl)-4,4-difluoropiperidine-1-carboxylate (748 mg, 1.550 mmol, purity: 90%, recovery: 69%) as a light yellow gummy foam. LCMS (m/z) 435 (M+H)$^+$, retention time 0.87-1.09 min, LC/MS Method 5. $^1$H NMR (400 MHz, CHLOROFORM-d) δ ppm 8.09 (d, J=0.98 Hz, 1H), 7.75 (s, 1H), 7.31-7.42 (m, 5H), 6.03 (s, 1H), 5.13-5.22 (m, 2H), 4.21-4.45 (m, 2H), 4.08-4.15 (m, 2H), 4.02-4.08 (m, 2H), 4.01 (s, 3H), 3.27-3.45 (m, 1H), 3.14-3.26 (m, 1H), 2.96-3.13 (m, 1H), 2.11-2.26 (m, 1H), 1.87-2.09 (m, 1H).

Step 4

To benzyl 3-(5-(1,3-dioxolan-2-yl)-6-methoxypyridin-3-yl)-4,4-difluoropiperidine-1-carboxylate (670 mg, 1.388 mmol) in THF (10 ml) was added 1N HCl (10 mL, 10.00 mmol), followed by heating at 40° C. for approximately 2 h. The reaction was partitioned between EtOAc and dilute brine, and the organic phase was separated and washed with sat'd brine. The combined aqueous phases were back-extracted with EtOAc, and this EtOAc phase was washed with brine. The organic phases were combined, dried over Na$_2$SO$_4$, filtered, concentrated and purified over silica (24 g ISCO Gold column), eluting with 0-40% ethyl acetate in heptane to provide benzyl 4,4-difluoro-3-(5-formyl-6-methoxypyridin-3-yl)piperidine-1-carboxylate (572 mg, 1.319 mmol, purity: 90%, recovery: 95%) as a colorless gum. LCMS (m/z) 391 (M+H)$^+$, retention time 1.11 min, LC/MS Method 5. $^1$H NMR (400 MHz, CHLOROFORM-d) δ ppm 10.37 (s, 1H), 8.30 (d, J=2.45 Hz, 1H), 8.06 (br s, 1H), 7.30-7.44 (m, 5H), 5.13-5.22 (m, 2H), 4.19-4.50 (m, 2H), 4.06-4.11 (m, 3H), 2.99-3.47 (m, 3H), 2.13-2.28 (m, 1H), 1.90-2.12 (m, 1H).

Step 5

To benzyl 4,4-difluoro-3-(5-formyl-6-methoxypyridin-3-yl)piperidine-1-carboxylate (570 mg, 1.314 mmol) in MeCN (5 ml) was added sodium iodide (591 mg, 3.94 mmol) followed by chlorotrimethylsilane (0.500 mL, 3.94 mmol). After 1 h, additional sodium iodide (394 mg, 2.63 mmol) was added, followed by chlorotrimethylsilane (0.334 mL, 2.63 mmol), then 30 min later additional sodium iodide (394 mg, 2.63 mmol) was added, followed by chlorotrimethylsilane (0.334 mL, 2.63 mmol). After 10 min, the reaction was concentrated and partitioned between EtOAc and aq. NaHCO$_3$ solution. The organic phase was washed with brine, and the combined aqueous washes were extracted with EtOAc. This EtOAc phase was washed with brine, and the organic phases were combined, dried over Na$_2$SO$_4$, filtered, concentrated and purified over silica (24 g ISCO Gold column), eluting with 10-75% 3:1 (EtOAc: EtOH) in heptane to provide benzyl 4,4-difluoro-3-(5-formyl-6-oxo-1,6-dihydropyridin-3-yl)piperidine-1-carboxylate (481 mg, 1.022 mmol, purity: 80%, recovery: 78%) as a white solid. LCMS (m/z) 377 (M+H)$^+$, retention time 0.83 min, LC/MS Method 5. $^1$H NMR (400 MHz, CHLOROFORM-d) δ ppm 13.26-13.59 (m, 1H), 10.29 (s, 1H), 8.09 (br s, 1H), 7.68 (d, J=2.45 Hz, 1H), 7.32-7.43 (m, 5H), 5.09-5.24 (m, 2H), 4.19-4.50 (m, 2H), 3.07-3.36 (m, 2H), 2.82-3.04 (m, 1H), 2.12-2.30 (m, 1H), 1.86-2.05 (m, 1H).

Step 6

To a solution of benzyl 4,4-difluoro-3-(5-formyl-6-oxo-1,6-dihydropyridin-3-yl)piperidine-1-carboxylate (176 mg, 0.421 mmol) in DMF (3 ml) was added potassium carbonate (175 mg, 1.263 mmol), followed by dropwise addition of 2,2,2-trifluoroethyl trifluoromethanesulfonate (0.121 mL, 0.842 mmol). After 90 min, the reaction was diluted with EtOAc, washed with water and brine, dried over Na$_2$SO$_4$, filtered, concentrated and purified over silica (12 g ISCO Gold column), eluting with 0-70% EtOAc in heptane to provide benzyl 4,4-difluoro-3-(5-formyl-6-oxo-1-(2,2,2-trifluoroethyl)-1,6-dihydropyridin-3-yl)piperidine-1-carboxylate (121 mg, 0.256 mmol, purity: 94%, recovery: 59%). LCMS (m/z) 459 (M+H)+, retention time 1.04 min, LC/MS Method 5. $^1$H NMR (400 MHz, CHLOROFORM-d) δ ppm 10.31 (s, 1H), 8.02 (br s, 1H), 7.52 (br s, 1H), 7.32-7.43 (m, 5H), 5.08-5.25 (m, 2H), 4.57-4.77 (m, 2H), 4.17-4.44 (m, 2H), 3.07-3.33 (m, 2H), 2.78-3.03 (m, 1H), 2.12-2.27 (m, 1H), 1.84-2.04 (m, 1H).

Step 7

In two batches, to benzyl 4,4-difluoro-3-(5-formyl-6-oxo-1-(2,2,2-trifluoroethyl)-1,6-dihydropyridin-3-yl)piperidine-1-carboxylate (17 mg, 0.033 mmol and 121 mg, 0.238 mmol) in MeOH (3 mL, 5 ml) was added sodium borohydride (12.63 mg, 0.334 mmol and 90 mg, 2.376 mmol). After 2 h and after 40 min, respectively, the reactions were concentrated and partitioned between EtOAc and dilute aq. HCl. The organic phase was separated, washed with brine, and the combined aqueous phases were back-extracted with EtOAc. This EtOAc phase was washed with brine, and the organic phases were combined, dried over Na$_2$SO$_4$, filtered, concentrated and purified over silica (12 g ISCO Gold column), eluting with 10-90% EtOAc in heptane to provide benzyl 4,4-difluoro-3-(5-(hydroxymethyl)-6-oxo-1-(2,2,2-trifluoroethyl)-1,6-dihydropyridin-3-yl)piperidine-1-carboxylate (90 mg, 0.186 mmol, purity: 95%, recovery: 73%). LCMS (m/z) 461 (M+H), retention time 0.94 min, LC/MS Method 5. $^1$H NMR (400 MHz, CHLOROFORM-d) δ ppm 7.32-7.40 (m, 6H), 7.18 (br s, 1H), 5.10-5.23 (m, 2H), 4.51-4.70 (m, 4H), 4.17-4.44 (m, 2H), 3.09-3.32 (m, 3H), 2.73-2.97 (m, 1H), 2.10-2.27 (m, 1H), 1.82-2.04 (m, 1H).

Step 8

A flask containing benzyl 4,4-difluoro-3-(5-(hydroxymethyl)-6-oxo-1-(2,2,2-trifluoroethyl)-1,6-dihydropyridin-3-yl)piperidine-1-carboxylate (90 mg, 0.195 mmol) in EtOAc (5 ml) was evacuated and back-filled twice with N$_2$ followed by the addition of Pd/C (10%, Degussa type) (90 mg, 0.195 mmol). The flask was evacuated and back-filled three times with H$_2$, and stirred under an H$_2$ balloon. After 30 min, additional Pd/C (10%, Degussa type) (90 mg, 0.195 mmol) was added, followed by methanol (2 ml), and the mixture was reset under H$_2$. After 30 min, the reaction was filtered through a PTFE filter and the catalyst was washed with MeOH. The filtrate was concentrated to give 68 mg of a crude mix of approximately 15% 5-(4,4-difluoropiperidin-3-yl)-3-(hydroxymethyl)-1-(2,2,2-trifluoroethyl)pyridin-2 (1H)-one (M+H 327) and approximately 85% 5-(4,4-difluoropiperidin-3-yl)-3-methyl-1-(2,2,2-trifluoroethyl)pyridin-2 (1H)-one (M+H 311), which was taken on to the next step without purification.

Step 9

To (R)-2-bromo-N-(5-fluoropyridin-2-yl)propanamide (Intermediate 1) (10.04 mg, 0.041 mmol) in DMA (2 ml) was added a solution of a crude mixture of 5-(4,4-difluoropiperidin-3-yl)-3-(hydroxymethyl)-1-(2,2,2-trifluoroethyl)pyridin-2 (1H)-one (15%, 68 mg, 0.031 mmol) and 5-(4,4-difluoropiperidin-3-yl)-3-methyl-1-(2,2,2-trifluoroethyl)pyridin-2 (1H)-one (85%, 68 mg, 0.186 mmol) in DMF (2 ml), followed by silver nitrate (5.84 mg, 0.034 mmol) and TEA (4.79 µl, 0.034 mmol). The mixture was heated at 40° C. for 15 h, followed by heating at 50° C. for 3 h. The reaction was filtered, diluted with EtOAc and washed with dilute aq. K$_2$CO$_3$ and with a mixture of sat'd K$_2$CO$_3$ solution and brine. The combined aqueous phases were back-extracted with EtOAc (2×), and these EtOAc phases were washed with brine plus satd. K$_2$CO$_3$ solution. The EtOAc phases were combined, dried over Na$_2$SO$_4$, filtered, concentrated and purified over silica (12 g ISCO Gold column), eluting with 0-80% 3:1 (EtOAc: EtOH) in heptane to provide:

Example 199 (2S)-2-(4,4-difluoro-3-(5-(hydroxymethyl)-6-oxo-1-(2,2,2-trifluoroethyl)-1,6-dihydropyridin-3-yl)piperidin-1-yl)-N-(5-fluoropyridin-2-yl)propanamide carboxylate (7 mg, 0.014 mmol, purity: 95%, recovery: 43%). LCMS (m/z) 493 (M+H), retention time 0.62 min, LC/MS Method 5. $^1$H NMR (400 MHz, CHLOROFORM-d) δ ppm 9.45 (br d, J=19.56 Hz, 1H), 8.24-8.30 (m, 1H), 8.14 (d, J=2.93 Hz, 1H), 7.44-7.53 (m, 2H), 7.23 (s, 1H), 4.55-4.73 (m, 4H), 3.35-3.50 (m, 2H), 3.02-3.23 (m, 1H), 2.80-2.99 (m, 3H), 2.61-2.77 (m, 1H), 2.09-2.40 (m, 2H), 1.38 (d, J=7.34 Hz, 3H), and Example 200 (2S)-2-(4,4-difluoro-3-(5-methyl-6-oxo-1-(2,2,2-trifluoroethyl)-1,6-dihydropyridin-3-yl)piperidin-1-yl)-N-(5-fluoropyridin-2-yl)propanamide carboxylate (42 mg, 0.082 mmol, purity: 93%, recovery: 26%). LCMS (m/z) 477 (M+H), retention time 0.72 min, LC/MS Method 5. $^1$H NMR (400 MHz, CHLOROFORM-d) δ ppm 9.51 (br d, J=16.14 Hz, 1H), 8.22-8.32 (m, 1H), 8.15 (d, J=2.93 Hz, 1H), 7.41-7.51 (m, 1H), 7.19-7.25 (m, 1H), 7.14 (s, 1H), 4.54-4.74 (m, 2H), 3.43 (qd, J=7.01, 5.38 Hz, 1H), 2.76-3.19 (m, 4H), 2.56-2.72 (m, 1H), 2.18-2.30 (m, 2H), 2.16 (d, J=4.40 Hz, 3H), 1.38 (dd, J=7.09, 1.22 Hz, 3H).

Example 201

(S)-2-((S)-3-(5-(aminomethyl)-6-oxo-1,6-dihydropyridin-3-yl)-4,4-difluoropiperidin-1-yl)-N-(5-fluoropyridin-2-yl)propanamide

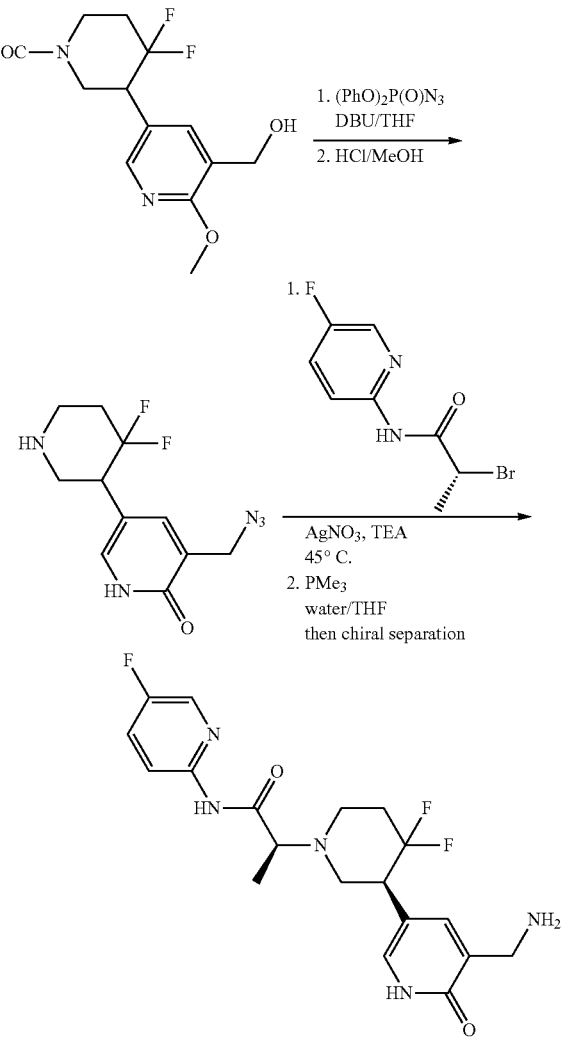

Step 1

To tert-butyl 4,4-difluoro-3-(5-(hydroxymethyl)-6-methoxypyridin-3-yl)piperidine-1-carboxylate (Example 153, Step 5) (195 mg, 0.544 mmol) and diphenyl phosphorazidate (0.141 mL, 0.653 mmol) in THF (2 mL) was added DBU (0.098 mL, 0.653 mmol). After stirring overnight, the reaction was concentrated and purified over silica (Combiflash, 24 g Gold column), eluting with 0-20% EtOAc in heptane to provide tert-butyl 3-(5-(azidomethyl)-6-methoxypyridin-3-yl)-4,4-difluoropiperidine-1-carboxylate (215 mg, 0.544 mmol, purity: 97%, recovery: quantitative) as a colorless oil. LCMS (m/z) 384 (M+H)$^+$, retention time 1.24 min, LC/MS Method 3. $^1$H NMR (400 MHz, CHLOROFORM-d) δ ppm 8.08 (d, J=2.20 Hz, 1H), 7.54 (s, 1H), 4.38 (s, 2H), 4.11-4.33 (m, 2H), 4.02 (s, 3H), 2.98-3.34 (m, 3H), 2.12-2.26 (m, 1H), 1.90-2.09 (m, 1H), 1.50 (s, 9H).

Step 2

Hydrogen chloride (4 N, 1.116 mL, 4.47 mmol) was added to tert-butyl 3-(5-(azidomethyl)-6-methoxypyridin-3-yl)-4,4-difluoropiperidine-1-carboxylate (107 mg, 0.279 mmol) in MeOH (2 mL), and the reaction was heated to 50° C. After 40 h, the mixture was concentrated to provide crude 3-(azidomethyl)-5-(4,4-difluoropiperidin-3-yl)pyridin-2 (1H)-one hydrochloride (85 mg, 0.278 mmol, purity: 97%, recovery: quantitative) as a yellow, sticky oil, which was used without purification. LCMS (m/z) 270 (M+H)$^+$, retention time: 0.50 min, LC/MS Method 2.

Step 3

Silver nitrate (47.2 mg, 0.278 mmol) was added to 3-(azidomethyl)-5-(4,4-difluoropiperidin-3-yl)pyridin-2 (1H)-one hydrochloride (85 mg, 0.278 mmol), (R)-2-bromo-N-(5-fluoropyridin-2-yl)propanamide (Intermediate 1) (68.7 mg, 0.278 mmol) and Et$_3$N (0.078 mL, 0.556 mmol) in DMA (2 mL). The reaction was stirred at 40° C. overnight and partitioned between EtOAc and water. The aqueous phase was extracted with EtOAc (3×), and the combined organic phases were washed with 5% LiCl and brine, dried over Na$_2$SO$_4$, filtered, concentrated and purified by silica gel chromatography (Combiflash, 24 g Gold column), eluting with 0-9% MeOH in DCM to provide (2S)-2-(3-(5-(azidomethyl)-6-oxo-1,6-dihydropyridin-3-yl)-4,4-difluoropiperidin-1-yl)-N-(5-fluoropyridin-2-yl)propanamide (92 mg, 0.211 mmol, purity: 100%, recovery: 76%) as a yellow solid. LCMS (m/z) 436 (M+H)+, retention time: 0.86-0.88 min, LC/MS Method 2.

Step 4

Trimethylphosphane (0.395 mL, 0.395 mmol) was added to (2S)-2-(3-(5-(azidomethyl)-6-oxo-1,6-dihydropyridin-3-yl)-4,4-difluoropiperidin-1-yl)-N-(5-fluoropyridin-2-yl)propanamide (86 mg, 0.198 mmol) and water (0.018 mL, 0.988 mmol) in THF (1.8 mL). After 30 min, the reaction was concentrated and purified by MDAP (XSelect CSH Prep C18 5 um OBD column), eluting with 15-55% AcCN in water (10 mM ammonium bicarb and 0.075% ammonium hydroxide) to provide 66 mg product. This material was chirally separated (Agilent 1100 Lux Cell-2 5 u 30×250 mm, eluting with 60:40 heptane: EtOH, flow rate 45 ml/min) to provide two peaks with retention times of 14.3 and 24.3 min. The first peak (14.3 min) was collected to give 9.3 mg (S)-2-((S)-3-(5-(aminomethyl)-6-oxo-1,6-dihydropyridin-3-yl)-4,4-difluoropiperidin-1-yl)-N-(5-fluoropyridin-2-yl)propanamide as a white, fluffy solid. LCMS (m/z) 410 (M+H)$^+$, retention time: 0.68 min, LC/MS Method 2. $^1$H NMR (400 MHz, MeOH-d$_4$) δ ppm 8.20-8.26 (m, 2H), 7.60-7.69 (m, 2H), 7.37 (d, J=2.20 Hz, 1H), 3.68 (s, 2H), 3.56 (d, J=6.85 Hz, 1H), 3.25-3.32 (m, 1H), 2.89-3.04 (m, 3H), 2.65 (br. s., 1H), 2.20 (dd, J=6.85, 3.42 Hz, 2H), 1.37 (d, J=7.09 Hz, 3H).

Examples 202-208 were synthesized in an analogous manner using the designated Intermediate in Step 3.

| Ex | Name | Structure | $^1$H NMR | LC/MS: (M + H)$^+$; retention time (min); LC/MS Method of analysis | Int |
|---|---|---|---|---|---|
| 202 | 2-(3-(5-(aminomethyl)-6-oxo-1,6-dihydropyridin-3-yl)-4,4-difluoropiperidin-1-yl)-N-(5-phenoxypyridin-2-yl)propanamide | 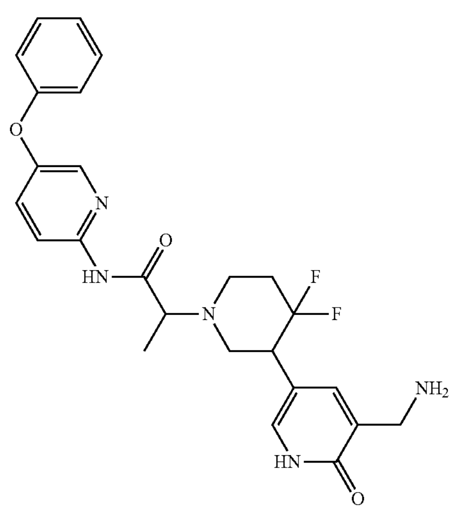 [SMILES: CC(C(=O)Nc1ccc(Oc2ccccc2)cn1)N1CCC(F)(F)C(c2c[nH]c(=O)c(CN)c2)C1] | $^1$H NMR (400 MHz, MeOH-d$_4$) δ ppm 8.19 (d, J = 9.05 Hz, 1H), 8.09 (d, J = 2.93 Hz, 1H), 7.61-7.67 (m, 1H), 7.47-7.53 (m, 1H), 7.36-7.44 (m, 3H), 7.17 (s, 1H), 7.01-7.07 (m, 2H), 3.71 (d, J = 3.18 Hz, 2H), 3.52-3.60 (m, 1H), 3.34-3.42 (m, 1H), 2.61-3.08 (m, 44H), 2.14-2.38 (m, 2H), 1.37 (dd, J = 6.97, 2.32 Hz, 3H). | 484; rt 0.89-091. LC/MS Method 3 | 72 |

| Ex | Name | Structure | ¹H NMR | LC/MS: (M + H)⁺; retention time (min); LC/MS Method of analysis | Int |
|---|---|---|---|---|---|
| 203 | (S)-2-((S)-3-(5-(aminomethyl)-6-oxo-1,6-dihydropyridin-3-yl)-4,4-difluoropiperidin-1-yl)-N-(6-(cyclopropylmethoxy)pyridazin-3-yl)propanamide | 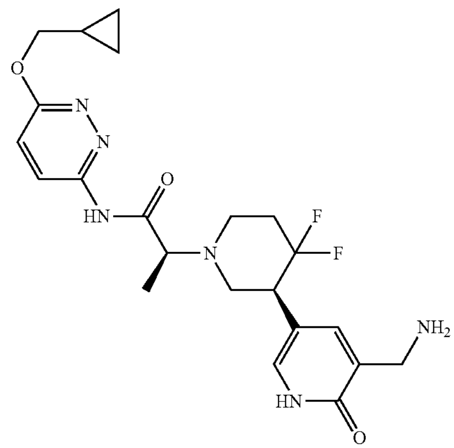 [SMILES: C[C@@H](C(=O)Nc1ccc(OCC2CC2)nn1)N1CCC(F)(F)[C@@H](c2c[nH]c(=O)c(CN)c2)C1] | ¹H NMR (400 MHz, MeOH-d₄) δ ppm 8.38 (d, J = 9.54 Hz, 1H), 7.77-7.82 (m, 1H), 7.51 (s, 1H), 7.23 (d, J = 9.54 Hz, 1H), 4.27 (d, J = 7.34 Hz, 2H), 3.96 (s, 2H), 3.58 (s, 1H), 3.34-3.44 (m, 1H), 2.96 (s, 3H), 2.62-2.72 (m, 1H), 2.15-2.36 (m, 2H), 1.34-1.40 (m, 4H), 0.65 (dd, J = 8.19, 1.34 Hz, 2H), 0.40 (dd, J = 4.77, 1.10 Hz, 2H). | 463; rt 0.79. LC/MS Method 3 | 14 |
| 204 | (S)-2-((S)-3-(5-(aminomethyl)-6-oxo-1,6-dihydropyridin-3-yl)-4,4-difluoropiperidin-1-yl)-N-(5-(4-fluorophenoxy)pyridin-2-yl)propanamide | 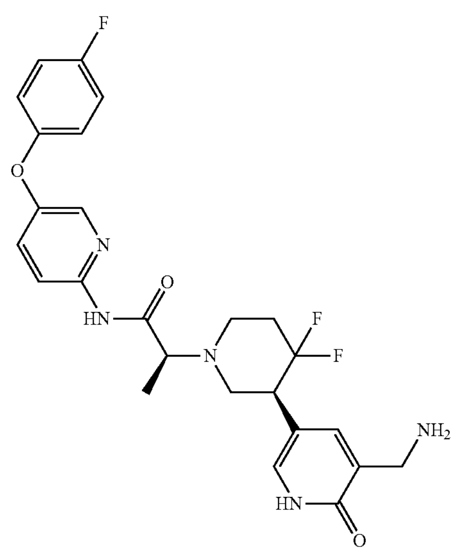 [SMILES: C[C@@H](C(=O)Nc1ccc(Oc2ccc(F)cc2)cn1)N1CCC(F)(F)[C@@H](c2c[nH]c(=O)c(CN)c2)C1] | ¹H NMR (400 MHz, MeOH-d₄) δ ppm 8.18 (d, J = 9.05 Hz, 1H), 8.08 (d, J = 2.69 Hz, 1H), 7.62 (s, 1H), 7.47 (dd, J = 9.05, 2.93 Hz, 1H), 7.37 (d, J = 2.20 Hz, 1H), 7.11-7.18 (m, 2H), 7.03-7.10 (m, 2H), 3.67 (s, 2H), 3.55 (q, J = 6.93 Hz, 1H), 3.34-3.42 (m, 1H), 2.89-3.05 (m, 3H), 2.60-2.70 (m, 1H), 2.14-2.34 (m, 2H), 1.37 (d, J = 6.85 Hz, 3H). | 502; rt 0.93. LC/MS Method 3 | 70 |

| Ex | Name | Structure | ¹H NMR | LC/MS: (M + H)⁺; retention time (min); LC/MS Method of analysis | Int |
|---|---|---|---|---|---|
| 205 | (S)-2-((S)-3-(5-(aminomethyl)-6-oxo-1,6-dihydropyridin-3-yl)-4,4-difluoropiperidin-1-yl)-N-(5-(2,4-difluorophenoxy)pyridin-2-yl)propanamide | 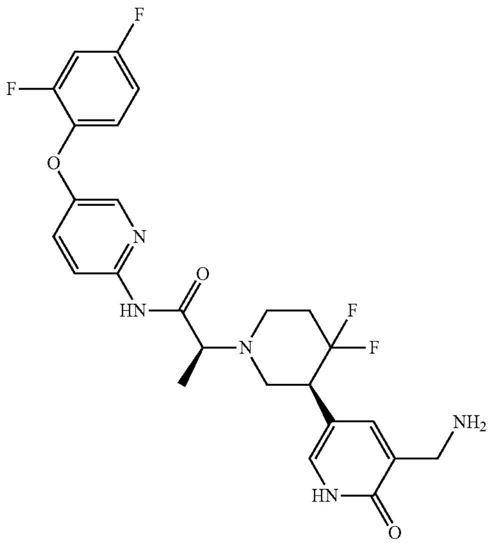 [SMILES: C[C@@H](C(=O)Nc1ccc(Oc2ccc(F)cc2F)cn1)N1CCC(F)(F)[C@@H](c2c[nH]c(=O)c(CN)c2)C1] | ¹H NMR (400 MHz, MeOH-d₄) δ ppm 8.17 (d, J = 9.29 Hz, 1H), 8.08 (d, J = 2.93 Hz, 1H), 7.65 (s, 1H), 7.44 (dd, J = 9.05, 2.93 Hz, 1H), 7.40 (d, J = 2.20 Hz, 1H), 7.15-7.29 (m, 2H), 6.97-7.07 (m, 1H), 3.74 (s, 2H), 3.55 (d, J = 7.09 Hz, 1H), 3.34-3.41 (m, 1H), 2.88-3.04 (m, 3H), 2.60-2.71 (m, 1H), 2.19 (m, 2H), 1.37 (d, J = 6.85 Hz, 3H). | 520; rt 0.94. LC/MS Method 3 | 71 |
| 206 | (S)-2-((S)-3-(5-(aminomethyl)-6-oxo-1,6-dihydropyridin-3-yl)-4,4-difluoropiperidin-1-yl)-N-(5-(4-fluorophenoxy)pyrazin-2-yl)propanamide | 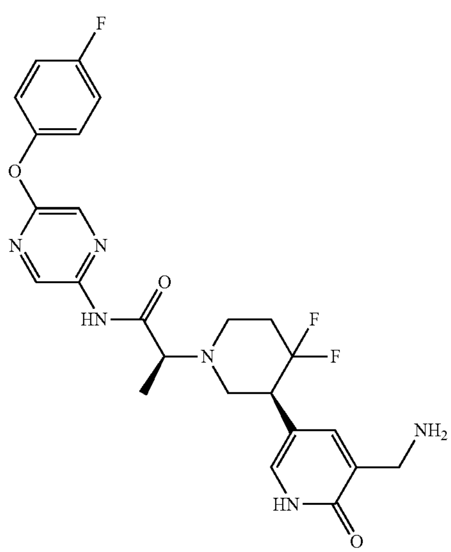 [SMILES: C[C@@H](C(=O)Nc1cnc(Oc2ccc(F)cc2)cn1)N1CCC(F)(F)[C@@H](c2c[nH]c(=O)c(CN)c2)C1] | ¹H NMR (400 MHz, MeOH-d₄) δ ppm 8.92 (d, J = 1.22 Hz, 1H), 8.53 (br. s., 1H), 8.21 (d, J = 1.22 Hz, 1H), 7.79 (s, 1H), 7.54 (d, J = 2.20 Hz, 1H), 7.13-7.22 (m, 4H), 4.01 (s, 2H), 3.59 (q, J = 7.01 Hz, 1H), 3.26 (br. s., 1H), 2.91-3.07 (m, 3H), 2.62-2.71 (m, 1H), 2.13-2.30 (m, 2H), 1.38 (d, J = 7.09 Hz, 3H). | 503; rt 0.89. LC/MS Method 3 | 58 |

-continued

| Ex | Name | Structure | ¹H NMR | LC/MS: (M + H)⁺; retention time (min); LC/MS Method of analysis | Int |
|---|---|---|---|---|---|
| 207 | (S)-2-((S)-3-(5-(aminomethyl)-6-oxo-1,6-dihydropyridin-3-yl)-4,4-difluoropiperidin-1-yl)-N-(5-phenoxypyrazin-2-yl)propanamide | 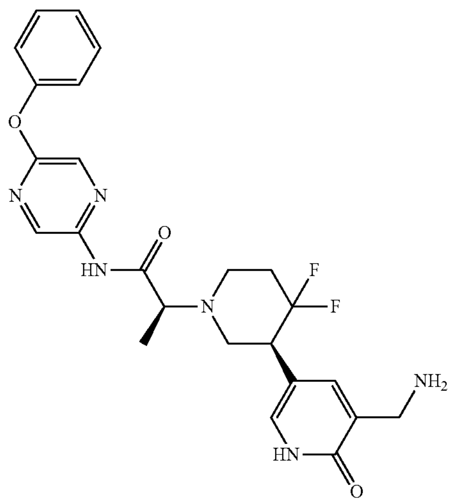 [SMILES: C[C@@H](C(=O)Nc1cnc(Oc2ccccc2)cn1)N1CCC(F)(F)[C@@H](c2c[nH]c(=O)c(CN)c2)C1] | ¹H NMR (400 MHz, MeOH-d₄) δ ppm 8.94 (d, J = 1.47 Hz, 1H), 8.18 (d, J = 1.22 Hz, 1H), 7.65 (s, 1H), 7.37-7.47 (m, 3H), 7.22-7.28 (m, 1H), 7.13-7.19 (m, 2H), 3.73 (s, 2H), 3.56-3.62 (m, 1H), 3.22-3.31 (m, 1H), 2.91-3.06 (m, 3H), 2.61-2.71 (m, 1H), 2.20 (d, J = 15.89 Hz, 2H), 1.37 (d, J = 7.09 Hz, 3H). | 485; rt 0.86. LC/MS Method 3 | 56 |
| 208 | (S)-2-((S)-3-(5-(aminomethyl)-6-oxo-1,6-dihydropyridin-3-yl)-4,4-difluoropiperidin-1-yl)-N-(5-((5-fluoropyridin-2-yl)oxy)pyridin-2-yl)propanamide | 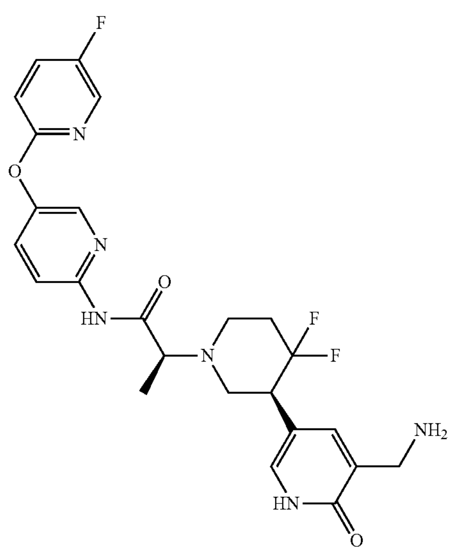 [SMILES: C[C@@H](C(=O)Nc1ccc(Oc2ccc(F)cn2)cn1)N1CCC(F)(F)[C@@H](c2c[nH]c(=O)c(CN)c2)C1] | ¹H NMR (400 MHz, CHLOROFORM-d) ☐ ppm 9.62 (s, 1H), 8.32 (d, J = 9.05 Hz, 1H), 8.19 (d, J = 2.69 Hz, 1H), 7.98 (d, J = 2.93 Hz, 1H), 7.55 (dd, J = 9.05, 2.93 Hz, 1H), 7.45-7.52 (m, 2H), 7.30 (s, 1H), 6.99 (dd, J = 8.93, 3.55 Hz, 1H), 3.82 (s, 2H), 3.44 (q, J = 6.77 Hz, 1H), 3.11-3.25 (m, 1H), 2.80-2.97 (m, 3H), 2.60 (t, J = 10.88 Hz, 1H), 2.14-2.30 (m, 2H), 1.38 (d, J = 6.85 Hz, 3H), 1.25-1.29 (m, 3H). | 503; rt 0.82. LC/MS Method 3 | 100 |

Example 209a,b

Ex. 209a: (S)-2-((S)-4,4-difluoro-3-(6-oxo-5-((S)-2,2,2-trifluoro-1-hydroxyethyl)-1,6-dihydropyridin-3-yl)piperidin-1-yl)-N-(5-fluoropyridin-2-yl)propanamide or Ex. 209b: (S)-2-((S)-4,4-difluoro-3-(6-oxo-5-((R)-2,2,2-trifluoro-1-hydroxyethyl)-1,6-dihydropyridin-3-yl)piperidin-1-yl)-N-(5-fluoropyridin-2-yl)propanamide

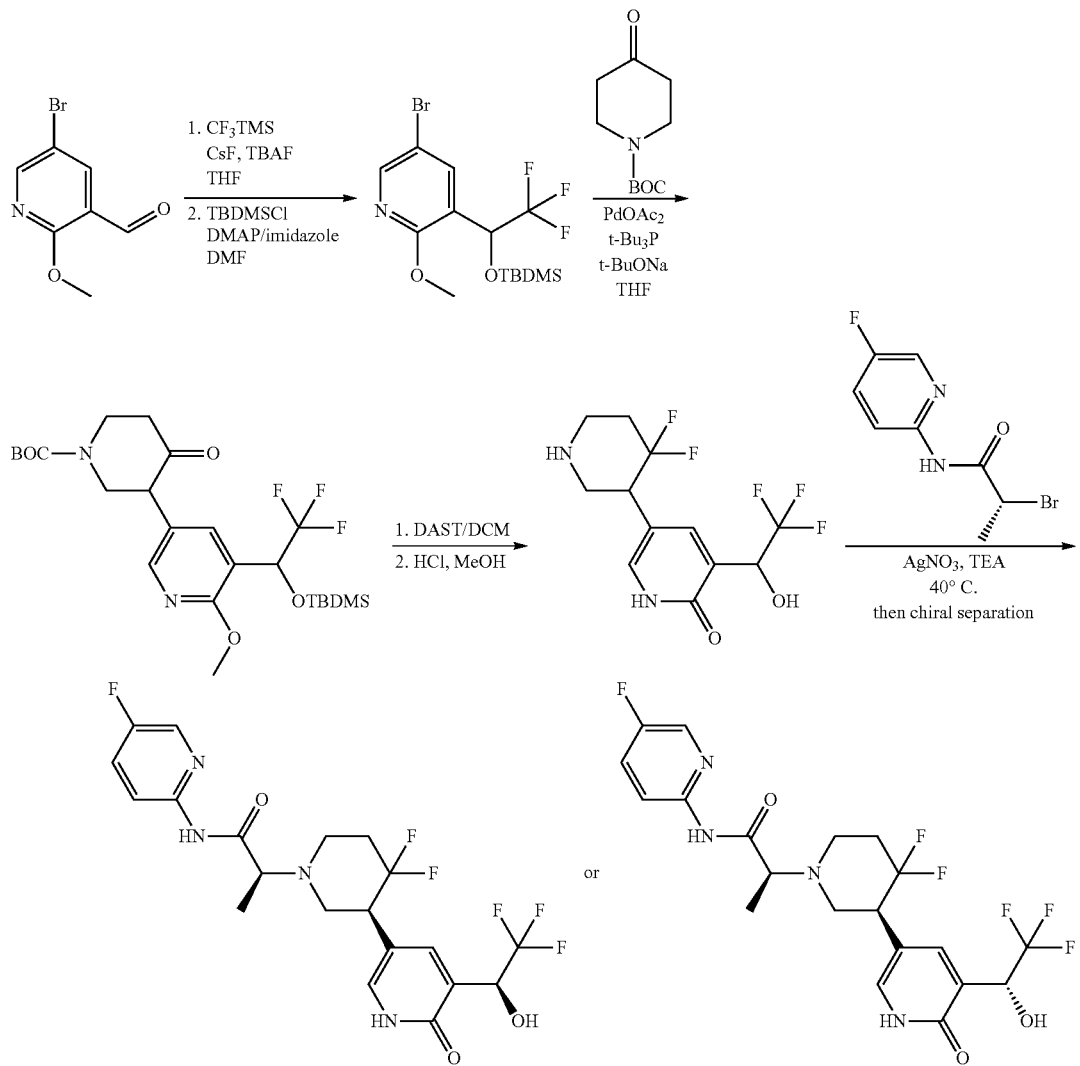

Step 1

CsF (7.03 g, 46.3 mmol) was added to 5-bromo-2-methoxynicotinaldehyde (10 g, 46.3 mmol) in THF (50 mL), and the mixture was cooled to 0° C.

Trimethyl(trifluoromethyl)silane (7.90 g, 55.5 mmol) was added dropwise, and the reaction was stirred at rt for 4 h. TBAF (1M, 23.14 mL, 23.14 mmol) was added dropwise, and after 5 h sat'd aqueous $NH_4Cl$ (20 mL) was added. The mixture was extracted with EtOAc (3×50 mL), and the combined organics were washed with brine, dried over sodium sulfate, concentrated and purified by silica gel chromatography (330 g column), eluting with 0-20% EtOAc in hexane to provide 1-(5-bromo-2-methoxypyridin-3-yl)-2,2,2-trifluoroethan-1-ol (12 g, 40 mmol, purity 95%, recovery 86%) as a light yellow solid. LCMS (m/z) 286 $(M+H)^+$, retention time: 0.998 min, LC/MS Method 4.

Step 2

To 1-(5-bromo-2-methoxypyridin-3-yl)-2,2,2-trifluoroethan-1-ol (12 g, 42.0 mmol), tert-butylchlorodimethylsilane (31.6 g, 210 mmol) and 1H-imidazole (28.6 g, 420 mmol) in DMF (5 mL) at 25° C. was added DMAP (0.513 g, 4.20 mmol). After 18 hr, the reaction was poured into water (100 mL) and extracted with ethyl acetate (100 mL×3). The combined organic phases were washed with brine (100 mL), dried over $Na_2SO_4$, concentrated and purified by silica gel chromatography (330 g column), eluting with 0-8% EtOAc in pet ether to provide 5-bromo-3-(1-((tert-butyldimethylsilyl)oxy)-2,2,2-trifluoroethyl)-2-methoxypyridine (19 g, 18.99 mmol, purity: 100%, recovery: 45%) as a yellow oil. LCMS (m/z) 400 $(M+H)^+$, retention time: 1.480 min, LC/MS Method 4.

Step 3

Sodium tert-butoxide (11.40 g, 119 mmol) (1.14 g×10 batches) was dissolved in THF (16 mL) (16 mL×10 batches) and stirred for 10 min at 42° C. Palladium(II) acetate (1.066 g, 4.75 mmol) (1.066 g×10 batches) and tri-t-butylphosphine (9.60 g, 4.75 mmol) (0.96 g×10 batches) were added and stirred for 5 min, followed by 5-bromo-3-(1-((tert-butyldimethylsilyl)oxy)-2,2,2-trifluoroethyl)-2-methoxypyridine (19 g, 47.5 mmol) (1.9 g×10 batches) and tert-butyl 4-oxopiperidine-1-carboxylate (14.19 g, 71.2 mmol) (1.418 g×10 batches). After 12 h, the reactions were combined, quenched with water (100 mL) and extracted with ethyl acetate (100 mL×2). The combined organic phases were dried over $Na_2SO_4$, concentrated and purified by silica gel chromatography (330 g column), eluting with 0-15% EtOAc in hexane to provide tert-butyl 3-(5-(1-((tert-butyldimethylsilyl)oxy)-2,2,2-trifluoroethyl)-6-methoxypyridin-3-yl)-4-oxopiperidine-1-carboxylate (5.4 g, 7.29 mmol, purity: 70%, recovery: 15%) as a light yellow oil. LCMS (m/z) 519 (M+H)$^+$, retention time: 1.380 min, LC/MS Method 4.

Step 4

To a solution of tert-butyl 3-(5-(1-((tert-butyldimethylsilyl)oxy)-2,2,2-trifluoroethyl)-6-methoxypyridin-3-yl)-4-oxopiperidine-1-carboxylate (5.4 g, 10.41 mmol) in DCM (4 mL) at 0° C. was added DAST (1.376 mL, 10.41 mmol). When complete, the reaction was quenched with water (100 mL) and extracted with DCM (100 mL×2). The combined organic phases were dried over $Na_2SO_4$, concentrated and purified by silica gel chromatography (220 g column), eluting with 0-20% EtOAc in hexane to provide tert-butyl 3-(5-(1-((tert-butyldimethylsilyl)oxy)-2,2,2-trifluoroethyl)-6-methoxypyridin-3-yl)-4,4-difluoropiperidine-1-carboxylate (2.5 g, 2.77 mmol, purity: 83%, recovery: 27%) as a light yellow oil. LCMS (m/z) 541 (M+H)$^+$, retention time: 1.497 min, LC/MS Method 4.

Step 5

Hydrogen chloride (4 N, 2.59 mL, 10.36 mmol) was added to tert-butyl 3-(5-(1-((tert-butyldimethylsilyl)oxy)-2,2,2-trifluoroethyl)-6-methoxypyridin-3-yl)-4,4-difluoropiperidine-1-carboxylate (500 mg, 0.647 mmol) in MeOH (8 mL) at 0° C. The mixture was warmed to rt, stirred overnight and concentrated to provide crude 5-(4,4-difluoropiperidin-3-yl)-3-(2,2,2-trifluoro-1-hydroxyethyl)pyridin-2-ol dihydrochloride (contaminated with 3-(1-((tert-butyldimethylsilyl)oxy)-2,2,2-trifluoroethyl)-5-(4,4-difluoropiperidin-3-yl)-2-methoxypyridine dihydrochloride), which was used without purification. LCMS (m/z) 441 (M+H)$^+$, retention time: 1.41-1.42 min, LC/MS Method 4.

Step 6

Silver nitrate (64.6 mg, 0.380 mmol) was added to crude 5-(4,4-difluoropiperidin-3-yl)-3-(2,2,2-trifluoro-1-hydroxyethyl)pyridin-2-ol diydrochloride (157 mg, 0.19 mmol), (R)-2-bromo-N-(5-fluoropyridin-2-yl)propanamide (Intermediate 1) (94 mg, 0.380 mmol) and $Et_3N$ (0.106 mL, 0.760 mmol) in DMA (2 mL), and the reaction was stirred at 40° C. overnight. The mixture was partitioned between EtOAc and water. The organic phase was separated, and the aqueous phase was extracted with EtOAc (3×). The combined organic phases were washed with 5% LiCl and brine, dried over $Na_2SO_4$, filtered, concentrated and purified by silica gel chromatography (Combiflash, 24 g Gold column), eluting with 0-9% MeOH in DCM to provide 89 mg of a light brown solid. This material was chirally separated (column: CC4, 20×250 mm, 5 micron; flow rate: 20 mL/min, solvents: 85:15 Heptane:EtOH, then @ 9 min, 80:20, modifier: 50 mM $NH_4OAc$ in the EtOH) to provide four peaks with retention times of 19, 22, 26 and 34 min. The second peak (22 min) was collected to give 18.8 mg, (0.039 mmol, purity: 100%, recovery: 10%) (S)-2-((S)-4,4-difluoro-3-(6-oxo-5-((S)-2,2,2-trifluoro-1-hydroxyethyl)-1,6-dihydropyridin-3-yl)piperidin-1-yl)-N-(5-fluoropyridin-2-yl)propanamide or: (S)-2-((S)-4,4-difluoro-3-(6-oxo-5-((R)-2,2,2-trifluoro-1-hydroxyethyl)-1,6-dihydropyridin-3-yl)piperidin-1-yl)-N-(5-fluoropyridin-2-yl)propanamide as a fluffy white solid. LCMS (m/z) 479 (M+H)$^+$, retention time: 0.87 min, LC/MS Method 4. $^1$H NMR (400 MHz, MeOH-$d_4$) δ ppm 8.24 (m, 2H), 7.88-7.92 (m, 1H), 7.61-7.69 (m, 1H), 7.48 (d, J=2.45 Hz, 1H), 5.30-5.38 (m, 1H), 3.54-3.62 (m, 1H), 3.35-3.45 (m, 1H), 2.89-3.07 (m, 3H), 2.62-2.71 (m, 1H), 2.16-2.34 (m, 2H), 1.37 (d, J=7.09 Hz, 3H).

Example 210 was synthesized in an analogous manner using the designated Intermediate in Step 6.

| Ex | Name | Structure | $^1$H NMR | LC/MS: (M + H)$^+$; retention time (min); LC/MS Method of analysis | Int |
|---|---|---|---|---|---|
| 210a, b | Ex. 210a: (S)-N-(6-(cyclopropylmethoxy)pyridazin-3-yl)-2-((S)-4,4-difluoro-3-(6-oxo-5-((S)-2,2,2-trifluoro-1-hydroxyethyl)-1,6-dihydropyridin-3-yl)piperidin-1-yl)propanamide or | 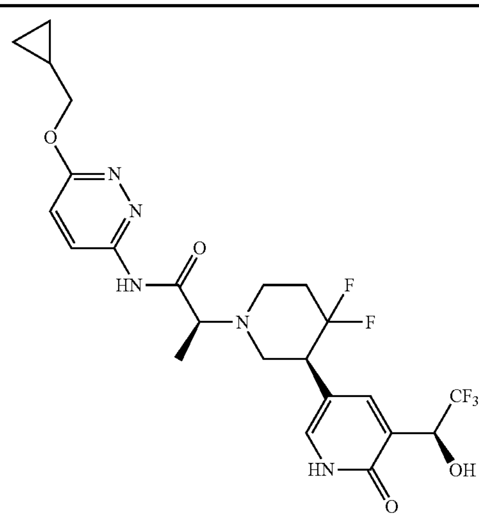 | $^1$H NMR (400 MHz, MeOH-$d_4$) δ ppm 8.38 (d, J = 9.54 Hz, 1H), 7.90 (d, J = 1.47 Hz, 1H), 7.48 (d, J = 2.20 Hz, 1H), 7.22 (d, J = 9.54 Hz, 1H), 5.34 (d, J = 6.60 Hz, 1H), 4.28 (d, J = 7.09 Hz, 2H), 3.61 (d, J = 6.85 Hz, 1H), 3.35-3.47 (m, 1H), 2.90-3.09 (m, 3H), 2.68 (d, J = 3.18 Hz, 1H), 2.20 (dd, J = 10.03, 5.62 Hz, 2H), 1.30-1.41 (m, 5H), 0.61-0.69 (m, 2H), 0.37-0.44 (m, 2H). | 532; rt 0.96. LC/MS Method 3 | 14 |

| Ex | Name | Structure | ¹H NMR | LC/MS: (M + H)⁺; retention time (min); LC/MS Method of analysis | Int |
|---|---|---|---|---|---|
| Ex. 210b | (S)-N-(6-(cyclopropylmethoxy(pyridazin-3-yl)-2-((S)-4,4-difluoro-3-(6-oxo-5-((R)-2,2,2-trifluoro-1-hydroxyethyl)-1,6-dihydropyridin-3-yl)piperidin-1-yl)propanamide | | | | |
| 211 | (2S)-2-(4,4-difluoro-3-(6-oxo-5-(2,2,2-trifluoro-1-hydroxyethyl)-1,6-dihydropyridin-3-yl)piperidin-10-yl)-N-(5-(4-fluorophenoxy)pyridin-2-yl)propanamide | 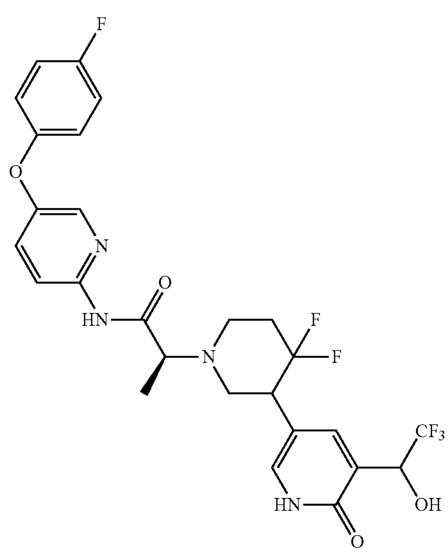 [SMILES: C[C@@H](C(=O)Nc1ccc(Oc2ccc(F)cc2)cn1)N1CCC(F)(F)C(c2c[nH]c(=O)c(C(O)C(F)(F)F)c2)C1] | ¹H NMR (400 MHz, METHANOL-d₄) δ ppm 8.18 (dd, J = 9.05, 2.20 Hz, 1H), 8.09 (d, J = 2.93 Hz, 1H), 7.84-7.92 (m, 1H), 7.44-7.51 (m, 2H), 7.11-7.19 (m, 2H), 7.03-1.11 (m, 2H), 5.34 (dt, J = 6.66, 3.39 Hz, 1H), 3.50-3.63 (m, 1H), 3.35-3.47 (m, 1H), 2.61-3.08 (m, 4H), 2.21 (m, 2H), 1.37 (d, J = 7.09 Hz, 3H). | 571; rt 1.09. LC/MS Method 3 | 70 |

| Ex | Name | Structure | ¹H NMR | LC/MS: (M + H)⁺; retention time (min); LC/MS Method of analysis | Int |
|---|---|---|---|---|---|
| 212 | (2S)-2-(4,4-difluoro-3-(6-oxo-5-(2,2,2-trifluoro-1-hydroxyethyl)-1,6-dihydropyridin-3-yl)piperidin-1-yl)-N-(5-(2,4-difluorophenoxy)pyridin-2-yl)propanamide | 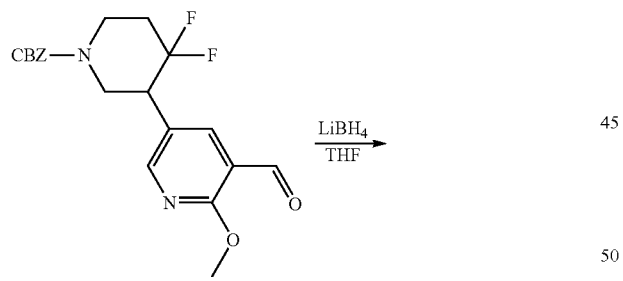 | ¹H NMR (400 MHz, METHANOL-$d_4$) δ ppm 8.17 (dd, J = 9.05, 2.45 Hz, 1H), 8.08 (d, J = 3.18 Hz, 1H), 7.89 (d, J = 9.05 Hz, 1H), 7.45 (td, J = 9.17, 2.69 Hz, 2H), 7.15-7.28 (m, 2H), 7.03 (t, J = 8.44 Hz, 1H), 5.28-5.39 (m, 1H), 3.50-3.61 (m, 1H), 3.40 (td, J = 10.39, 5.38 Hz, 1H), 2.61-3.07 (m, 4H), 2.15-2.38 (m, 2H), 1.37 (d, J = 6.85 Hz, 3H). | 589; rt 1.10. LC/MS Method 3 | 71 |

Example 213

2-(4,4-difluoro-3-(5-((methylsulfonyl)methyl)-6-oxo-1,6-dihydropyridin-3-yl)piperidin-1-yl)-N-(5-fluoropyridin-2-yl)propanamide

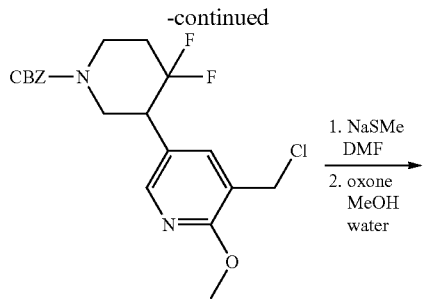

1. NaSMe DMF
2. oxone MeOH water

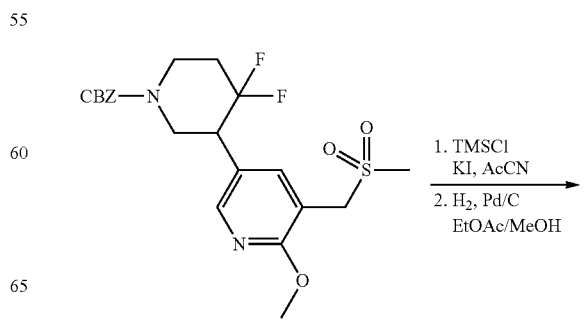

1. TMSCl KI, AcCN
2. H₂, Pd/C EtOAc/MeOH

-continued

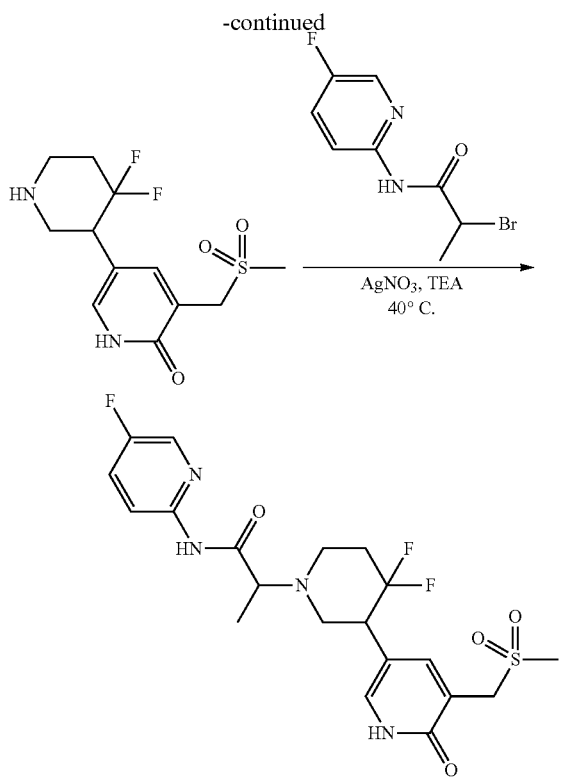

Step 1

To benzyl 4,4-difluoro-3-(5-formyl-6-methoxypyridin-3-yl)piperidine-1-carboxylate (Example 199, Step 4) (700 mg, 1.618 mmol) in THF (8 ml) at 0° C. was added LiBH$_4$ (2M in THF) (2.427 mL, 4.85 mmol), dropwise. After about 1 h, EtOAc (15 ml) was added, and the mixture was concentrated. The residue was partitioned between EtOAc and 0.5 N HCl, and the organic phase was washed with brine. The combined aqueous phases were back-extracted with EtOAc, and this EtOAc phase was washed with brine. The organic phases were combined, dried over Na$_2$SO$_4$, filtered and concentrated to afford crude product benzyl 4,4-difluoro-3-(5-(hydroxymethyl)-6-methoxypyridin-3-yl)piperidine-1-carboxylate (625 mg, 1.433 mmol, purity 90%, recovery 67%). LCMS (m/z) 393 (M+H)$^+$, retention time: 0.87 min, LC/MS Method 5.

Step 2

To benzyl 4,4-difluoro-3-(5-(hydroxymethyl)-6-methoxypyridin-3-yl)piperidine-1-carboxylate (625 mg, 1.433 mmol) in CH$_2$Cl$_2$ (4 ml) was added DIEA (0.325 mL, 1.864 mmol), followed by dropwise addition of methanesulfonyl chloride (0.134 mL, 1.720 mmol). After 90 min, additional DIEA (0.325 mL, 1.864 mmol) and methanesulfonyl chloride (0.134 mL, 1.720 mmol) were added, and after 20 min, the reaction mixture was concentrated. The residue was partitioned between EtOAc and 0.5 N HCl, and the organic phase was washed with brine. The combined aqueous phases were back-extracted with EtOAc, and this EtOAc phase was washed with brine. The organic phases were combined, dried over Na$_2$SO$_4$, filtered, concentrated and purified by silica gel chromatography (24 g Isco Gold column), eluting with 0-70% EtOAc in heptane, to afford benzyl 3-(5-(chloromethyl)-6-methoxypyridin-3-yl)-4,4-difluoropiperidine-1-carboxylate (612 mg, 1.341 mmol, purity: 90%, recovery: 94%). LCMS (m/z) 411 (M+H)$^+$. retention time: 1.20 min, LC/MS Method 5.

Step 3

To benzyl 3-(5-(chloromethyl)-6-methoxypyridin-3-yl)-4,4-difluoropiperidine-1-carboxylate (610 mg, 1.485 mmol) in DMF (5 mL) was added sodium thiomethoxide (125 mg, 1.782 mmol). After 2 h, the reaction was diluted with EtOAc, washed with water (2×) and brine, dried over Na$_2$SO$_4$, filtered, concentrated and purified by silica gel chromatography (12 g Isco Gold column), eluting with 0-50% EtOAc in heptane, to afford 5 benzyl 4,4-difluoro-3-(6-methoxy-5-((methylthio)methyl)pyridin-3-yl)piperidine-1-carboxylate (551 mg, 1.174 mmol, purity: 90%, recovery: 79%). LCMS (m/z) 423 (M+H)$^+$. retention time: 1.27 min, LC/MS Method 5.

Step 4

To a solution of benzyl 4,4-difluoro-3-(6-methoxy-5-((methylthio)methyl)pyridin-3-yl)piperidine-1-carboxylate (300 mg, 0.639 mmol) in MeOH (about 7 ml) was added a solution of oxone (1179 mg, 1.917 mmol) in water (about 7 ml). Immediately upon addition, a white solid precipitated out. After about 2 h, the reaction mixture was partially concentrated, and the residue was partitioned between EtOAc and water. The organic phase was washed with water and brine, dried over Na$_2$SO$_4$, filtered and concentrated to provide crude benzyl 4,4-difluoro-3-(6-methoxy-5-((methylsulfonyl)methyl)pyridin-3-yl)piperidine-1-carboxylate (411 mg, 0.633 mmol, purity: 70%, recovery: 90%) as a colorless gum, which was used without further purification. LCMS (m/z) 455 (M+H)$^+$. retention time: 1.01 min, LC/MS Method 5.

Step 5

To benzyl 4,4-difluoro-3-(6-methoxy-5-((methylsulfonyl)methyl)pyridin-3-yl)piperidine-1-carboxylate (320 mg, 0.633 mmol) in MeCN (7 ml) was added sodium iodide (285 mg, 1.899 mmol), followed by chlorotrimethylsilane (0.241 mL, 1.899 mmol). After 60 h, the light-orange heterogeneous reaction mixture was partially concentrated, diluted with EtOAc and washed with a mixture of sat'd aq. NaHCO$_3$ and aq Na$_2$S$_2$O$_3$. The organic phase was washed with aq Na$_2$S$_2$O$_3$ and brine, then dried over Na$_2$SO$_4$, filtered, concentrated and purified by silica gel chromatography (24 g Isco Gold column), eluting with 5-80% (3:1 EtOAc: MeOH) in heptane, to afford benzyl 4,4-difluoro-3-(5-((methylsulfonyl)methyl)-6-oxo-1,6-dihydropyridin-3-yl)piperidine-1-carboxylate (250 mg, 0.528 mmol, purity: 93%, recovery: 80%) as a white foam. LCMS (m/z) 441 (M+H)$^+$. retention time: 0.80 min, LC/MS Method 5.

Step 6

To benzyl 4,4-difluoro-3-(5-((methylsulfonyl)methyl)-6-oxo-1,6-dihydropyridin-3-yl)piperidine-1-carboxylate (250 mg, 0.528 mmol) in EtOAc (5 ml) and MeOH (5 ml) was under N$_2$ was added 10% Pd/C (Degussa type) (110 mg, 1.137 mmol). The reaction flask was evacuated and back-filled with H$_2$ (3×), and then the reaction mixture was stirred under an H$_2$ balloon. After 45 min, additional 10% Pd/C (Degussa type) (110 mg, 1.137 mmol) was added, followed after 1 h by more 10% Pd/C (Degussa type) (110 mg, 1.137 mmol). After stirring overnight, the reaction was filtered and washed with MeOH (pdt is poorly soluble), and the filtrate concentrated to give 5-(4,4-difluoropiperidin-3-yl)-3-((methylsulfonyl)methyl)pyridin-2 (1H)-one (165 mg, 0.485 mmol, purity: 90%, recovery: 43%) as a white solid, which was used without purification. LCMS (m/z) 307 (M+H)$^+$, retention time: 0.27 min, LC/MS Method 5.

Step 7

To a solution of 5-(4,4-difluoropiperidin-3-yl)-3-((methylsulfonyl)methyl)pyridin-2 (1H)-one (60 mg, 0.196 mmol) in DMF (2 ml) was added TEA (0.068 mL, 0.490 mmol), followed by 2-bromo-N-(5-fluoropyridin-2-yl)propanamide (Intermediate 1) (58.1 mg, 0.235 mmol) and silver nitrate (36.6 mg, 0.215 mmol). The mixture was heated at 40° C. for approximately 15 h, filtered to remove silver salts, and the solids were washed with EtOAc. The filtrate was washed with dil. aq. KHCO$_3$, water (2×) and brine. The combined aqueous phases were back-extracted with EtOAc, and this EtOAc phase was washed with water (2×) and brine. The organic phases were combined, dried over Na$_2$SO$_4$, filtered, concentrated and purified by silica gel chromatography (12 g Isco Gold column), eluting with 5-80% (3:1 EtOAc: MeOH) in heptane, to afford 2-(4,4-difluoro-3-(5-((methylsulfonyl)methyl)-6-oxo-1,6-dihydropyridin-3-yl)piperidin-1-yl)-N-(5-fluoropyridin-2-yl)propanamide (60 mg, 0.121 mmol, purity: 95%, recovery: 62%) as a white solid. LCMS (m/z) 473 (M+H)$^+$, retention time: 0.49 min, LC/MS Method 5. $^1$H NMR (400 MHz, CHLOROFORM-d) δ ppm 12.91 (br s, 1H), 9.51 (d, J=13.69 Hz, 1H), 8.25 (dt, J=8.80, 4.40 Hz, 1H), 8.14-8.18 (m, 1H), 7.74 (br s, 1H), 7.43-7.50 (m, 1H), 7.40 (dd, J=7.82, 2.45 Hz, 1H), 4.29 (d, J=2.93 Hz, 2H), 3.44 (q, J=6.85 Hz, 1H), 3.06-3.30 (m, 1H), 2.78-3.02 (m, 6H), 2.55-2.77 (m, 1H), 2.08-2.37 (m, 2H), 1.38 (dd, J=7.09, 1.22 Hz, 3H).

Examples 214-216 were synthesized in an analogous manner using the designated Intermediate in Step 7.

| Ex | Name | Structure | $^1$H NMR | LC/MS: (M + H)$^+$; retention time (min); LC/MS Method of analysis | Int |
|---|---|---|---|---|---|
| 214 | (S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyridin-2-yl)propanamide | 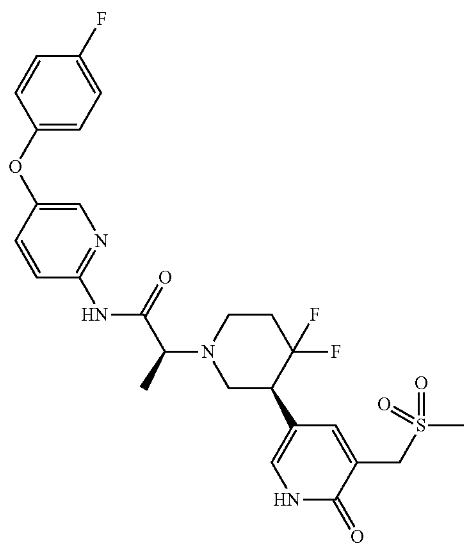 [SMILES: C[C@@H](C(=O)Nc1ccc(Oc2ccc(F)cc2)cn1)N1CCC(F)(F)[C@@H](c2c[nH]c(=O)c(CS(C)(=O)=O)c2)C1] | $^1$H NMR (400 MHz, CDCl$_3$) δ ppm 12.32-12.48 (m, 1H), 9.47 (br d, J = 8.80 Hz, 1H), 8.22 (dd, J = 8.80, 4.40 Hz, 1H), 8.08 (d, J = 2.93 Hz, 1H), 7.71-7.75 (m, 1H), 7.31-7.42 (m, 2H), 7.02-7.11 (m, 2H), 6.93-7.01 (m, 2H), 4.28 (d, J = 1.96 Hz, 2H), 3.38-3.50 (m, 1H), 3.08-3.32 (m, 1H), 2.77-3.05 (m, 6H), 2.56-2.75 (m, 1H), 2.08-2.35 (m, 2H), 1.38 (dd, J = 6.85, 1.96 Hz, 3H). | 565; rt 0.74. LC/MS Method 3 | 70 |
| 215 | (S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyrazin-2-yl)propanamide | 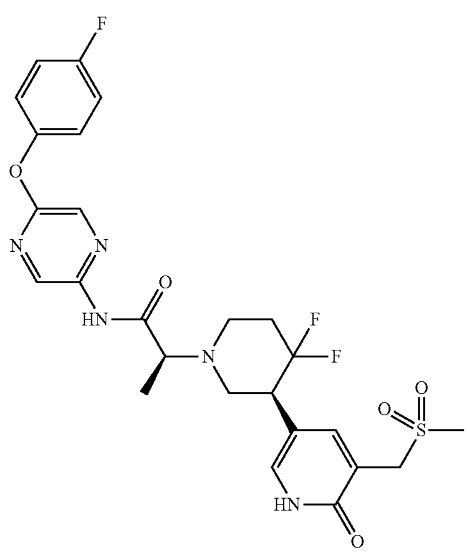 [SMILES: C[C@@H](C(=O)Nc1cnc(Oc2ccc(F)cc2)cn1)N1CCC(F)(F)[C@@H](c2c[nH]c(=O)c(CS(C)(=O)=O)c2)C1] | $^1$H NMR (400 MHz, METHANOL-d$_4$) δ ppm 8.92 (d, J = 1.47 Hz, 1H), 8.19 (d, J = 1.47 Hz, 1H), 7.91-7.79 (m, 1H), 7.58-7.41 (m, 1H), 7.29-7.04 (m, 4H), 4.36 (s, 2H), 3.59 (d, J = 6.85 Hz, 1H), 3.37 (s, 6H), 3.15-2.84 (m, 6H), 2.76-2.54 (m, 1H), 2.39-2.00 (m, 2H), 1.36 (d, J = 6.85 Hz, 3H). | 566.3; rt 0.94. LC/MS Method 3 | 58 |

| Ex | Name | Structure | ¹H NMR | LC/MS: (M + H)⁺; retention time (min); LC/MS Method of analysis | Int |
|---|---|---|---|---|---|
| 216 | (S)-2-((S)-4,4-difluoro-3-(5-((methylsulfonyl)methyl)-6-oxo-1,6-dihydropyridin-3-yl)piperidin-1-yl)-N-(5-(2,4-difluorophenoxy)pyridin-2-yl)propanamide | 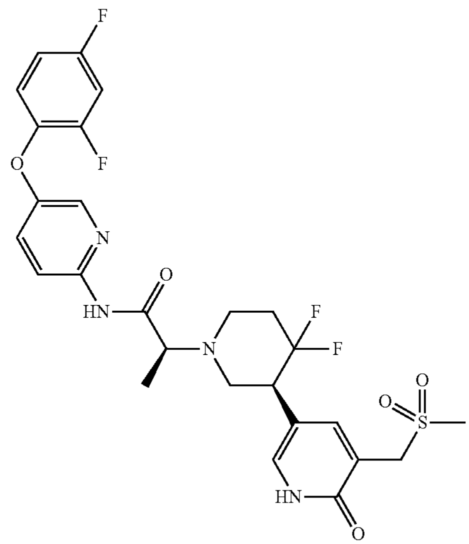 [SMILES: C[C@@H](C(=O)Nc1ccc(Oc2ccc(F)cc2F)cn1)N1CCC(F)(F)[C@@H](c2c[nH]c(=O)c(CS(C)(=O)=O)c2)C1] | ¹H NMR (400 MHz, METHANOL-d₄) δ ppm 8.28-8.02 (m, 2H), 7.85 (d, J = 2.45 Hz, 1H), 7.59-7.38 (m, 2H), 7.32-6.93 (m, 3H), 4.36 (s, 2H), 3.49-3.36 (m, 1H), 3.11-2.86 (m, 6H), 2.66 (br d, J = 3.42 Hz, 1H), 2.33-2.12 (m, 2H), 1.36 (d, J = 6.85 Hz, 3H). | 583.3; rt 1.00. LC/MS Method 3 | 71 |

Example 217

4-(4,4-difluoro-1l-((S)-1-((5-fluoropyridin-2-yl)amino)-1-oxopropan-2-yl)piperidin-3-yl)-2-methylpyridine 1-oxide

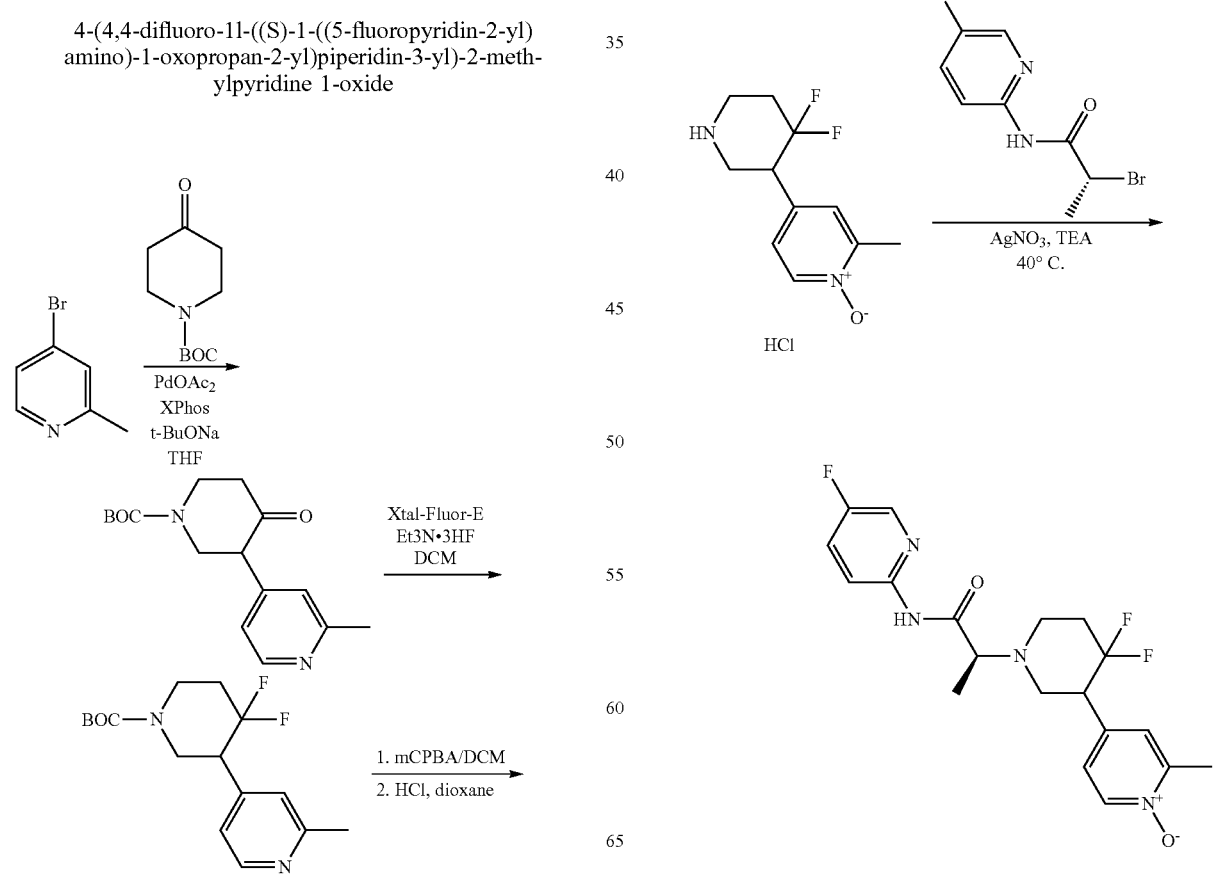

Step 1

To sodium tert-butoxide (2 M in THF) (13.08 mL, 26.2 mmol) was added tert-butyl 4-oxopiperidine-1-carboxylate (2.78 g, 13.95 mmol), followed after 5 min by 4-bromo-2-methylpyridine (1.034 mL, 8.72 mmol), then after 5 more min by XPhos (0.416 g, 0.872 mmol) and PdOAc$_2$ (0.098 g, 0.436 mmol). The mixture was evacuated and back-filled with N$_2$ three times and heated at 45° C. for 15 h. The reaction was partitioned between EtOAc and water, and the organic phase was washed with satd. brine. The combined aqueous phases were back-extracted with EtOAc, and this EtOAc phase was washed with brine. The organic phases were combined, dried over Na$_2$SO$_4$, filtered, concentrated and purified by silica gel chromatography (80 g column), eluting with 0-60% (3:1 EtOAc:MeOH) in heptane to provide tert-butyl 3-(2-methylpyridin-4-yl)-4-oxopiperidine-1-carboxylate (2.63 g, 8.33 mmol, purity 92%, recovery 96%) as an orange gum. LCMS (m/z) 291 (M+H)$^+$, retention time: 0.53 min, Method 5.

Step 2

In two batches, to a suspension of XtalFluor-E (2.177 g, 9.51 mmol and 1.18 g, 5.15 mmol) in DCM (2×10 ml) at 0° C. was added triethylamine trihydrofluoride (1.548 mL, 9.51 mmol and 0.838 mL, 5.15 mmol), dropwise. After 15 min, a solution of tert-butyl 3-(2-methylpyridin-4-yl)-4-oxopiperidine-1-carboxylate (1.38 g, 4.75 mmol and 0.50 g, 1.722 mmol) in DCM (8 ml and 5 ml) was added dropwise, and the reaction was stirred at rt 3 days. The reaction mixtures were cooled in an ice bath, and satd. K$_2$CO$_3$ solution (15 ml) was added slowly. The mixtures were diluted with DCM and washed with water. The aqueous phases were washed with DCM (2×), and the combined organic phases were washed with brine, dried over Na$_2$SO$_4$, filtered, concentrated, combined and purified by silica gel chromatography (80 g column), eluting with 0-60% EtOAc in heptane to provide tert-butyl 4,4-difluoro-3-(2-methylpyridin-4-yl)piperidine-1-carboxylate (636 mg, 1.934 mmol, purity: 95%, recovery: 31%). LCMS (m/z) 313 (M+H)$^+$, retention time: 0.63 min, Method 5.

Step 3

To tert-butyl 4,4-difluoro-3-(2-methylpyridin-4-yl)piperidine-1-carboxylate (630 mg, 2.017 mmol) in DCM (10 ml) at 0° C. was added m-CPBA (994 mg, 4.03 mmol), in portions. The reaction was warmed to rt, and after 45 min was diluted with more DCM and washed with sat'd K$_2$CO$_3$ solution (3×) and brine. The combined aqueous phases were back-extracted with DCM, and this DCM phase was washed with a mixture of satd. K$_2$CO$_3$ and brine. The DCM phases were combined, dried over Na$_2$SO$_4$, filtered, concentrated and purified by silica gel chromatography (24 g column), eluting with 0-100% (3:1 EtOAc: MeOH) in heptane to provide 4-(1-(tert-butoxycarbonyl)-4,4-difluoropiperidin-3-yl)-2-methylpyridine 1-oxide (605 mg, 1.75 mmol, purity: 95%, recovery: 87%) as a white foam. LCMS (m/z) 329 (M+H)$^+$, retention time: 0.77 min, LC/MS Method 5.

Step 4

To 4-(1-(tert-butoxycarbonyl)-4,4-difluoropiperidin-3-yl)-2-methylpyridine 1-oxide (605 mg, 1.842 mmol) in dioxane (5 ml) was added 4 M HCl in dioxane (15 mL, 60.0 mmol). After 2 h, additional 4 M HCl in dioxane (5 mL, 20.00 mmol) was added. After 4 h, the reaction was azeotroped with DCM to provide crude 4-(4,4-difluoropiperidin-3-yl)-2-methylpyridine 1-oxide hydrochloride (627 mg, 2.250 mmol, purity: 95%, recovery: quantitative) as an off-white solid, which was used without purification. LCMS (m/z) 229 (M+H)$^+$, retention time: 0.27 min, LC/MS Method 5.

Step 5

To (R)-2-bromo-N-(5-fluoropyridin-2-yl)propanamide (Intermediate 1) (202 mg, 0.816 mmol) in DMF (3 ml) was added 4-(4,4-difluoropiperidin-3-yl)-2-methylpyridine 1-oxide hydrochloride (200 mg, 0.680 mmol), followed by TEA (0.379 mL, 2.72 mmol) and silver nitrate (127 mg, 0.748 mmol), and the mixture was stirred at 40° C. over the weekend. The reaction was filtered to remove the silver salts, diluted with EtOAc and washed with dilute aq. K$_2$CO$_3$ and a mixture of sat'd K$_2$CO$_3$ solution and brine. The combined aqueous phases were back-extracted with EtOAc (2×), and these EtOAc phases were washed with brine and sat'd K$_2$CO$_3$ solution. The EtOAc phases were combined, dried over Na$_2$SO$_4$, filtered, concentrated and purified by silica gel chromatography (24 g column), eluting with 10-100% (3:1 EtOAc: MeOH) in heptane to provide 4-(4,4-difluoro-1-((S)-1-((5-fluoropyridin-2-yl)amino)-1-oxopropan-2-yl)piperidin-3-yl)-2-methylpyridine 1-oxide (139 mg, 0.335 mmol, purity: 95%, recovery: 49%) as an off-white foam. LCMS (m/z) 395 (M+H)$^+$, retention time: 0.51-0.52 min, LC/MS Method 5. $^1$H NMR (400 MHz, Chloroform-d) δ ppm 9.50 (br d, J=8.31 Hz, 1H), 8.19-8.28 (m, 2H), 8.15 (d, J=2.45 Hz, 1H), 7.42-7.50 (m, 1H), 7.22 (dd, J=6.36, 2.45 Hz, 1H), 7.11 (td, J=6.85, 2.45 Hz, 1H), 3.41-3.49 (m, 1H), 3.21-3.41 (m, 1H), 2.83-3.05 (m, 3H), 2.60-2.82 (m, 1H), 2.52 (d, J=5.38 Hz, 3H), 2.10-2.37 (m, 2H), 1.39 (dd, J=7.09, 3.18 Hz, 3H).

Example 218 was synthesized in an analogous manner using the designated Intermediate in Step 5.

| Ex | Name | Structure | ¹H NMR | LC/MS: (M + H)⁺; retention time (min); LC/MS Method of analysis | Int |
|---|---|---|---|---|---|
| 218 | 1:1 mixture of: 4-((R)-4,4-difluoro-1-((R)-1-((5-(4-fluorophenoxy)pyridin-2-yl)amino)-1-oxopropan-2-yl)piperidin-3-yl)-2-methylpyridine 1-oxide and | 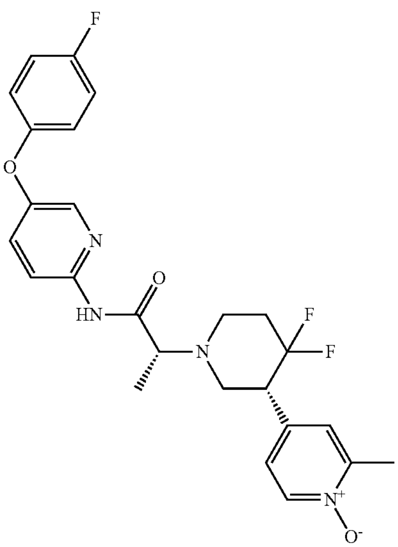 [SMILES: Cc1cc([C@H]2CN([C@@H](C)C(=O)Nc3ccc(Oc4ccc(F)cc4)cn3)CCC2(F)F)cc[n+]1[O-]] | ¹H NMR (400 MHz, CHLOROFORM-d) δ ppm 9.49 (s, 1H), 8.23 (s, 1H), 8.20-8.22 (m, 1H), 8.06-8.09 (m, 1H), 7.35 (dd, J = 8.93, 2.81 Hz, 1H), 7.23 (d, J = 2.20 Hz, 1H), 7.12 (dd, J = 6.85, 2.45 Hz, 1H), 7.01-7.09 (m, 2H), 6.94-7.00 (m, 2H), 3.45 (q, J = 7.09 Hz, 1H), 3.29-3.41 (m, 1H), 2.95-3.04 (m, 2H), 2.86-2.95 (m, 1H), 2.59-2.71 (m, 1H), 2.52 (s, 3H), 2.10-2.34 (m, 2H), 1.39 (d, J = 7.09 Hz, 3H). | 487; rt 1.02. LC/MS Method 3 | 70 |
| | 4-((S)-4,4-difluoro-1-((S)-1-((5-(4-fluorophenoxy)pyridin-2-yl)amino)-1-oxopropan-2-yl)piperidin-3-yl)-2-methylpyridine 1-oxide | | | | |

Example 219

4-(S)-4,4-difluoro-1-((S)-1-((5-fluoropyridin-2-yl)amino)-1-oxopropan-2-yl)piperidin-3-yl)-2-(2,2,2-trifluoroethyl)pyridine 1-oxide

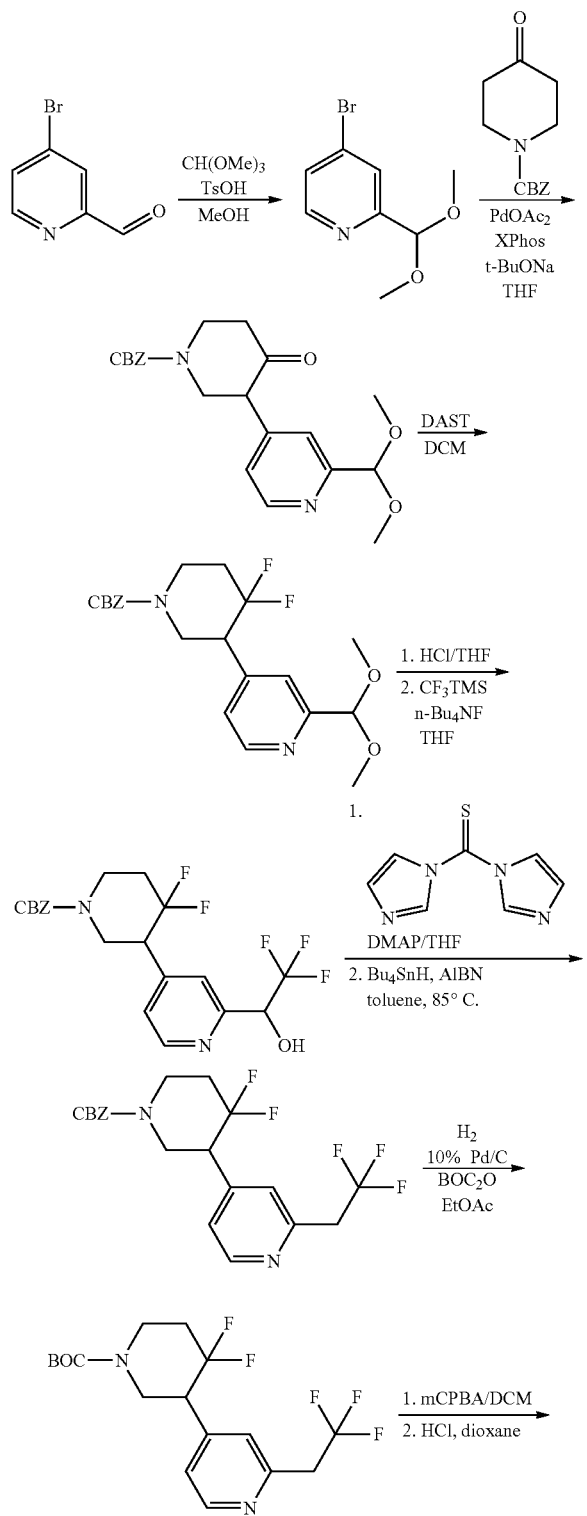

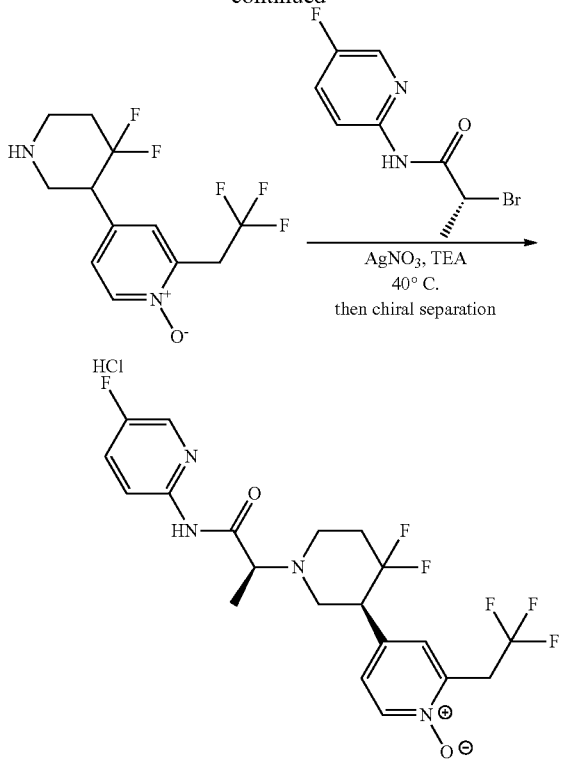

To 4-bromopicolinaldehyde (1 g, 5.38 mmol) in MeOH (5 ml) was added trimethyl orthoformate (2.5 mL, 22.62 mmol) and tosic acid (0.020 g, 0.108 mmol). The mixture was heated at 80° C. for 15 h, concentrated, dissolved in EtOAc, washed with sat'd NaHCO$_3$ solution and brine, dried over Na$_2$SO$_4$, filtered, concentrated and purified by silica gel chromatography (24 g column), eluting with 0-50% EtOAc in heptane to provide 4-bromo-2-(dimethoxymethyl)pyridine (1.13 g, 4.63 mmol, purity 96%, recovery 86%) as a colorless oil. LCMS (m/z) 2321234 (M+H)$^+$, retention time: 0.56 min, LCMS Method 5.

Step 2

A reaction tube was charged with sodium tert-butoxide (2 M in THF) (3.23 ML, 6.46 mmol) diluted with THF (3 ml). Benzyl 4-oxopiperidine-1-carboxylate (754 mg, 3.23 mmol) was added, followed by a solution of 4-bromo-2-(dimethoxymethyl)pyridine (500 mg, 2.154 mmol) in THF (4 ml). After 2 minutes, PdOAc$_2$ (24.18 mg, 0.108 mmol) and XPhos (103 mg, 0.215 mmol) were added, and the reaction was evacuated and back-filled with N$_2$ (3×), followed by stirring at 45° C. for 15 h and at rt for 40 h. Water (3 ml) was added, and the mixture was partitioned between EtOAc and dilute brine. The organic phase was washed with brine, and the combined aqueous phases were back-extracted with EtOAc. This EtOAc phase was washed with brine, and the organic phases were combined, dried over Na$_2$SO$_4$, filtered, concentrated, combined and purified by silica gel chromatography (24 g column), eluting with 0-50% 3:1 (EtOAc:MeOH) in heptane to provide benzyl 3-(2-(dimethoxymethyl)pyridin-4-yl)-4-oxopiperidine-1-carboxylate (680 mg, 1.592 mmol, purity: 90%, recovery: 74%) as a yellow oil. LCMS (m/z) 385 (M+H)$^+$, retention time: 0.83 min, LCMS Method 5.

Step 3

To benzyl 3-(2-(dimethoxymethyl)pyridin-4-yl)-4-oxopiperidine-1-carboxylate (672 mg, 1.573 mmol) in DCM (8 ml) at 0° C. was added DAST (0.416 mL, 3.15 mmol), dropwise. The reaction was allowed to warm to rt slowly, and then stirred overnight. The mixture was poured slowly into sat't NaHCO$_3$ solution (20 ml) and diluted with DCM (30 ml). The aqueous phase was separated and extracted with DCM, and the organic phases were combined, washed with brine, dried over Na$_2$SO$_4$, filtered, concentrated and purified by silica gel chromatography (24 g column), eluting with 0-60% EtOA in heptane to provide benzyl 3-(2-(dimethoxymethyl)pyridin-4-yl)-4,4-difluoropiperidine-1-carboxylate (335 mg, 0.684 mmol, purity: 83%, recovery: 44%) as a colorless oil. LCMS (m/z) 407 (M+H)$^+$, retention time: 0.80 min, LCMS Method 5.

Step 4

To benzyl 3-(2-(dimethoxymethyl)pyridin-4-yl)-4,4-difluoropiperidine-1-carboxylate (285 mg, 0.645 mmol) in THF (6 ml) was added 3 N HCl (3 ml), and the reaction was heated to 60° C. After 15 h, the mixture was poured slowly into sat'd NaHCO$_3$ solution and extracted with EtOAc. The EtOAc phase was washed with brine, and the combined aqueous phases were back-extracted with EtOAc. This EtOAc phase was washed with brine, and the organic phases were combined, dried over Na$_2$SO$_4$, filtered, concentrated and purified by silica gel chromatography (12 g column), eluting with 0-70% EtOA in heptane to provide benzyl 4,4-difluoro-3-(2-formylpyridin-4-yl)piperidine-1-carboxylate (174 mg, 0.449 mmol, purity: 93%, recovery: 70%). $^1$H NMR (400 MHz, Chloroform-d) δ ppm 10.09 (s, 1H), 8.76 (d, J=5.38 Hz, 1H), 7.91 (br s, 1H), 7.46 (d, J=4.89 Hz, 1H), 7.36 (m, 5H), 5.08-5.25 (m, 2H), 4.18-4.51 (m, 2H), 3.39 (m, 1H), 3.22 (m, 2H), 2.20 (m, J=6.85 Hz, 1H), 1.88-2.12 (m, 1H).

Step 5

In two batches, to benzyl 4,4-difluoro-3-(2-formylpyridin-4-yl)piperidine-1-carboxylate (170 mg, 0.472 mmol and 35 mg, 0.097 mmol) in THF (5 ml and 4 ml) at 0° C. was added trifluoromethyltrimethylsilane (0.091 mL, 0.613 mmol and 0.019 mL, 0.126 mmol), followed by dropwise addition of tetrabutylammonium fluoride (1M in THF) (0.1 mL, 0.100 mmol and 0.019 mL, 0.019 mmol). After 5-10 min, additional tetrabutylammonium fluoride (1M in THF) (0.6 mL, 0.472 mmol and 0.107 mL, 0.107 mmol) was added. After 1 h, water (10 ml) was slowly added, and the mixtures were extracted with EtOAc. The organic phases were washed with brine, dried over Na$_2$SO$_4$, filtered, concentrated, combined and purified by silica gel chromatography (12 g column), eluting with 0-60% EtOAc in heptane to provide benzyl 4,4-difluoro-3-(2-(2,2,2-trifluoro-1-hydroxyethyl)pyridin-4-yl)piperidine-1-carboxylate (200 mg, 0.418 mmol, purity: 90%, recovery: 80%). LCMS (m/z) 431 (M+H)$^+$, retention time: 0.97 min, LCMS Method 5.

Step 6

To benzyl 4,4-difluoro-3-(2-(2,2,2-trifluoro-1-hydroxyethyl)pyridin-4-yl)piperidine-1-carboxylate (150 mg, 0.314 mmol) in THF (6 ml) was added di(1H-imidazol-1-yl)methanethione (84 mg, 0.471 mmol), followed by DMAP (3.83 mg, 0.031 mmol). The mixture was then heated at 60° C. for 2.5 h, and additional di(1H-imidazol-1-yl)methanethione (25 mg, 0.140 mmol) and DMAP (5 mg, 0.041 mmol) were added. After 20 min, the reaction was partitioned between with EtOAc and dilute brine. The organic phase was separated, washed with brine, dried over Na$_2$SO$_4$, filtered, concentrated and purified by silica gel chromatography (12 g column), eluting with 0-70% EtOA in heptane to provide benzyl 3-(2-(1-((1H-imidazole-1-carbonothioyl)oxy)-2,2,2-trifluoroethyl)pyridin-4-yl)-4,4-difluoropiperidine-1-carboxylate (152 mg, 0.253 mmol, purity: 90%, recovery: 81%) as a colorless oil. $^1$H NMR (400 MHz, Chloroform-d) δ ppm 8.65 (d, J=4.89 Hz, 1H), 8.43 (s, 1H), 7.71 (s, 1H), 7.29-7.47 (m, 7H), 7.10 (d, J=0.98 Hz, 1H), 6.79-6.90 (m, 1H), 5.08-5.24 (m, 2H), 4.20-4.49 (m, 2H), 3.37 (br t, J=12.23 Hz, 1H), 3.03-3.29 (m, 2H), 2.12-2.30 (m, 1H), 1.87-2.10 (m, 1H).

Step 7

To benzyl 3-(2-(1-((1H-imidazole-1-carbonothioyl)oxy)-2,2,2-trifluoroethyl)pyridin-4-yl)-4,4-difluoropiperidine-1-carboxylate (186 mg, 0.310 mmol) in toluene (4 ml) was added tributyltin hydride (0.125 mL, 0.465 mmol), followed by a catalytic amount of AIBN. The mixture was heated at 85° C., and additional AIBN was added at intervals, in small portions (total of 10 mg). After 25 min, the reaction was concentrated and purified by silica gel chromatography (12 g column), eluting with 0-60% EtOAc in heptane to provide benzyl 4,4-difluoro-3-(2-(2,2,2-trifluoroethyl)pyridin-4-yl)piperidine-1-carboxylate (98 mg, 0.213 mmol, purity: 90%, recovery: 69%). LCMS (m/z) 415 (M+H)$^+$, retention time: 1.01 min, LCMS Method 5.

Step 8

A solution of benzyl 4,4-difluoro-3-(2-(2,2,2-trifluoroethyl)pyridin-4-yl)piperidine-1-carboxylate (98 mg, 0.213 mmol) and di-tert-butyl dicarbonate (0.062 mL, 0.266 mmol) in EtOAc (6 ml) was purged with N$_2$, and 10% Pd/C (Degussa type) (10 mg, 0.213 mmol) was added. The reaction mixture was purged with H$_2$ and then stirred under an H$_2$ balloon for 1 h. Additional 10% Pd/C (Degussa type) (20 mg, 0.213 mmol) was added, and the reaction mixture was reset under H$_2$. After 45 min, the reaction was filtered, concentrated and purified by silica gel chromatography (4 g column), eluting with 0-60% EtOAc in heptane to provide benzyl 4,4-difluoro-3-(2-(2,2,2-trifluoroethyl)pyridin-4-yl)piperidine-1-carboxylate (72 mg, 0.180 mmol, purity: 95%, recovery: 84%) as a colorless oil. LCMS (m/z) 381 (M+H)$^+$, retention time: 0.97 min, LCMS Method 5.

Step 9

To tert-butyl 4,4-difluoro-3-(2-(2,2,2-trifluoroethyl)pyridin-4-yl)piperidine-1-carboxylate (72 mg, 0.189 mmol) in DCM (5 ml) was added m-CPBA (77% purity) (65 mg, 0.290 mmol), and after 90 min, additional m-CPBA (77% purity) (45 mg, 0.201 mmol) was added. After 25 min the reaction was diluted with more DCM and washed with sat'd K$_2$CO$_3$ solution (3×) and brine. The combined aqueous phases were back-extracted with DCM, and this DCM phase was washed with a mixture of satd. K$_2$CO$_3$ and brine. The DCM phases were combined, dried over Na$_2$SO$_4$, filtered, concentrated and purified by silica gel chromatography (4 g column), eluting with 0-60% (3:1 EtOAc: MeOH) in heptane to provide 4-(1-(tert-butoxycarbonyl)-4,4-difluoropiperidin-3-yl)-2-methylpyridine 1-oxide (68 mg, 0.163 mmol, purity: 95%, recovery: 86%). LCMS (m/z) 397 (M+H)$^+$, retention time: 0.91 min, LCMS Method 5.

Step 10

To 4-(1-(tert-butoxycarbonyl)-4,4-difluoropiperidin-3-yl)-2-(2,2,2-trifluoroethyl)pyridine 1-oxide (68 mg, 0.172 mmol) in dioxane (3 ml) was added 4 M HCl in dioxane (4 mL, 16.00 mmol). After 1 h, additional 4 M HCl in dioxane (4 mL, 16.00 mmol) was added. After another h, the reaction was azeotroped with DCM to provide crude 4-(4,4-difluoropiperidin-3-yl)-2-(2,2,2-trifluoroethyl)pyridine 1-oxide hydrochloride (81 mg, 0.231 mmol, purity: 95%, recovery: quantitative) as an off-white solid, which was used without purification. LCMS (m/z) 297 (M+H)$^+$, retention time: 0.37 min, LCMS Method 5.

Step 11

To (R)-2-bromo-N-(5-fluoropyridin-2-yl)propanamide (Intermediate 1) (25.5 mg, 0.103 mmol) in DMA (1 ml) was added a solution of 4-(4,4-difluoropiperidin-3-yl)-2-(2,2,2-trifluoroethyl)pyridine 1-oxide hydrochloride (28.6 mg, 0.086 mmol) in DMA (2 ml), followed by TEA (0.048 mL, 0.344 mmol) and silver nitrate (16.07 mg, 0.095 mmol), and the mixture was stirred overnight. Additional TEA (0.048 mL, 0.344 mmol) and (R)-2-bromo-N-(5-fluoropyridin-2-yl)propanamide (14 mg, 0.057 mmol) were added, and the mixture was stirred at for 2 h, then heated at 40° C. After 15 h, the reaction was filtered to remove the silver salts, and the filtrate was diluted with EtOAc and washed with dilute aq. $K_2CO_3$ and a mixture of sat'd $K_2CO_3$ solution and brine. The combined aqueous phases were back-extracted with EtOAc (2×), and these EtOAc phases were washed with brine and sat'd $K_2CO_3$ solution. The EtOAc phases were combined, dried over $Na_2SO_4$, filtered, concentrated and purified by silica gel chromatography (4 g Gold column), eluting with 0-70% (3:1 EtOAc: MeOH) in heptane to give product contaminated with DMA. This material was dissolved in EtOAc, washed with water (2×) and brine, dried over $Na_2SO_4$, filtered and concentrated to give pure product (28 mg, 0.058 mmol, recovery: 67%). This material was chirally separated (column: Lux Cell 2, 5 micron, 30×250 mm, flow rate: 45 mL/min, solvent: AcCN with 0.1% isopropylamine modifier) to provide three peaks with retention times of 7.5, 9.19 and 11.5 min. The third peak (11.5 min) was collected to give 4-((S)-4,4-difluoro-1-((S)-1-((5-fluoropyridin-2-yl)amino)-1-oxopropan-2-yl)piperidin-3-yl)-2-(2,2,2-trifluoroethyl)pyridine 1-oxide (8.98 mg, 0.039 mmol, purity: 95% by chiral analysis, recovery: 21%). LCMS (m/z) 463 (M+H)+, retention time: 0.65 min, LCMS Method 5. $^1$H NMR (400 MHz, CDCl$_3$) δ ppm 9.50 (s, 1H), 8.22-8.31 (m, 2H), 8.16 (d, J=2.93 Hz, 1H), 7.47 (ddd, J=9.05, 7.83, 2.93 Hz, 1H), 7.41 (d, J=1.71 Hz, 1H), 7.25 (dd, J=6.97, 2.57 Hz, 1H), 3.85-4.05 (m, 2H), 3.34-3.51 (m, 2H), 2.95-3.03 (m, 2H), 2.90 (br dd, J=10.03, 1.96 Hz, 1H), 2.67 (td, J=11.98, 3.18 Hz, 1H), 2.10-2.39 (m, 2H), 1.40 (d, J=6.85 Hz, 3H).

Example 220 was synthesized in an analogous manner using the designated Intermediate in Step 11.

| Ex Name | Structure | $^1$H NMR | LC/MS: (M + H)+; retention time (min); LC/MS Method of analysis | Int |
|---|---|---|---|---|
| 220 4-((S)-1-((S)-1-((6-(cyclopropyl-methoxy)pyridazin-3-yl)amino)-1-oxopropan-2-yl)-4,4-difluoropiperidin-3-yl)-2-(2,2,2-trifluoroethyl)pyridine 1-oxide | | $^1$H NMR (400 MHz, CDCl$_3$) δ ppm 9.85 (s, 1H), 8.04 (d, J = 9.78 Hz, 1H), 8.27 (d, J = 6.36 Hz, 1H), 7.40 (d, J = 1.47 Hz, 1H), 7.25 (dd, J = 6.85, 2.45 Hz, 1H), 7.06 (d, J = 9.78 Hz, 1H), 4.31 (d, J = 7.34 Hz, 2H), 3.84-4.03 (m, 2H), 3.48 (q, J = 6.85 Hz, 1H), 3.30-3.45 (m, 1H), 2.97-3.04 (m, 2H), 2.91 (br d, J = 11.25 Hz, 1H), 2.61-2.74 (m, 1H), 2.11-2.37 (m, 2H), 1.41 (d, J = 6.85 Hz, 3H), 1.31-1.37 (m, 1H), 0.61-0.70 (m, 2H), 0.35-0.43 (m, 2H). | 516; rt 0.76. LC/MS Method 5 | 14 |

Example 221

(2S)-2-(3-(5-bromo-6-oxo-1,6-dihydropyridin-3-yl)-4,4-difluoropiperidin-1-yl)-N-(6-(cyclopropyl-methoxy)pyridazin-3-yl)propanamide

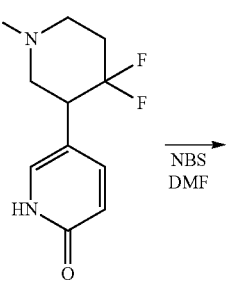

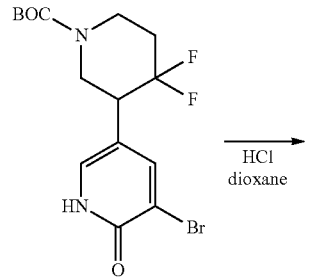

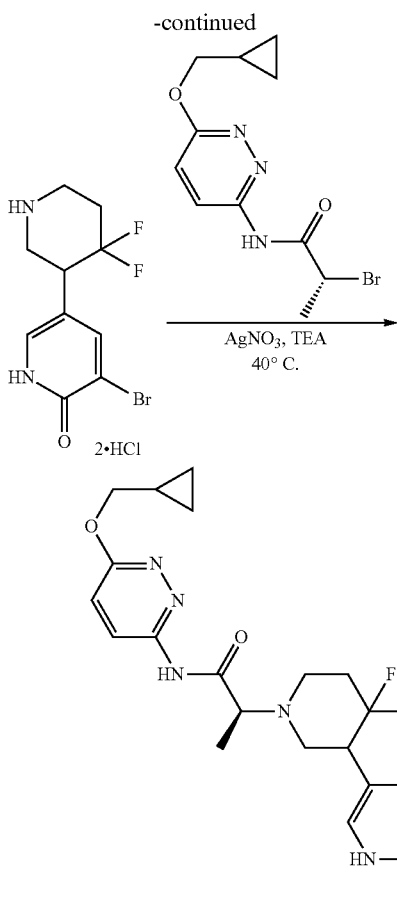

Step 1

To tert-butyl 4,4-difluoro-3-(6-oxo-1,6-dihydropyridin-3-yl)piperidine-1-carboxylate (Example 1, Step 3) (0.370 g, 1.177 mmol) in DMF (5 ml) was added NBS (0.230 g, 1.295 mmol). After stirring overnight, the reaction was quenched with sat'd aq $Na_2S_2O_3$ and extracted with EtOAc (2×). The combined organics were washed with water and brine, dried over $Na_2SO_4$, filtered, concentrated and purified over silica, eluting with 20-70% (3:1 EtOAc: EtOH) in heptane to give tert-butyl 3-(5-bromo-6-oxo-1,6-dihydropyridin-3-yl)-4,4-difluoropiperidine-1-carboxylate (349 mg, 0.888 mmol, purity: 100%, recovery: 75%). LCMS (m/z) 395 (M+H)+ retention time: 0.90 min, LC/MS Method 5. $^1$H NMR (400 MHz, DMSO-$d_6$) δ ppm 12.22 (br s, 1H), 7.91 (d, J=1.47 Hz, 1H), 7.42 (d, J=1.96 Hz, 1H), 3.98-4.07 (m, 1H), 3.85-3.97 (m, 1H), 2.93-3.29 (m, 3H), 2.06-2.21 (m, 1H), 1.78-1.98 (m, 1H), 1.41 (s, 9H).

Step 2

To tert-butyl 3-(5-bromo-6-oxo-1,6-dihydropyridin-3-yl)-4,4-difluoropiperidine-1-carboxylate (0.12 g, 0.305 mmol) in dioxane (0.5 ml) was added HCl in dioxane (4 M, 1 ml, 4.00 mmol), followed after 20 min by another portion of HCl (4 M in dioxane, 1 mL, 4.00 mmol). After 1 h, the reaction was concentrated and triturated with toluene to provide crude 3-bromo-5-(4,4-difluoropiperidin-3-yl)pyridin-2(1H)-one dihydrochloride (120 mg, 0.328 mmol, recovery: quantitative) as a yellow solid, which was used without further purification. LCMS (m/z) 295 (M+H)+, retention time: 0.31 min, LC/MS LC/MS Method 5.

Step 3

To crude 3-bromo-5-(4,4-difluoropiperidin-3-yl)pyridin-2(1H)-one dihydrochloride (0.115 g, 0.314 mmol) in DMF (1 mL) were added (R)-2-bromo-N-(6-(cyclopropylmethoxy)pyridazin-3-yl)propanamide (Intermediate 14) (0.125 g, 0.416 mmol), silver nitrate (0.053 g, 0.314 mmol), and TEA (0.15 ml, 1.076 mmol). The reaction was heated to 40° C. overnight, quenched with water and extracted with ethyl acetate (3×). The combined organic extracts were washed with brine, dried over sodium sulfate, filtered, concentrated and purified by silica gel chromatography, eluting with 10-70% (3:1 EtOAc:EtOH) in heptanes to give (2S)-2-(3-(5-bromo-6-oxo-1,6-dihydropyridin-3-yl)-4,4-difluoropiperidin-1-yl)-N-(6-(cyclopropylmethoxy)pyridazin-3-yl)propanamide (76 mg, 0.147 mmol, 46.7% yield). LCMS (m/z) 514 (M+H)+, retention time: 0.70 min, LCMS Method 5. $^1$H NMR (400 MHz, DMSO-$d_6$) δ ppm 12.16 (br s, 1H), 10.66 (d, J=4.40 Hz, 1H), 8.24 (dd, J=9.54, 2.69 Hz, 1H), 7.90 (dd, J=4.89, 1.96 Hz, 1H), 7.42 (br s, 1H), 7.26 (dd, J=9.54, 2.20 Hz, 1H), 4.16-4.25 (m, 2H), 3.60-3.72 (m, 1H), 2.82-3.02 (m, 2H), 2.65-2.72 (m, 1H), 2.05-2.16 (m, 1H), 1.90-2.03 (m, 1H), 1.17-1.31 (m, 5H), 0.81-0.91 (m, 1H), 0.52-0.62 (m, 2H), 0.32-0.39 (m, 2H). 11.80-11.53 (m, 2H),

Example 222

(2S)-2-(3-(5-(1-aminoethyl)-6-oxo-1,6-dihydropyridin-3-yl)-4,4-difluoropiperidin-1-yl)-N-(6-(cyclopropylmethoxy)pyridazin-3-yl)propanamide

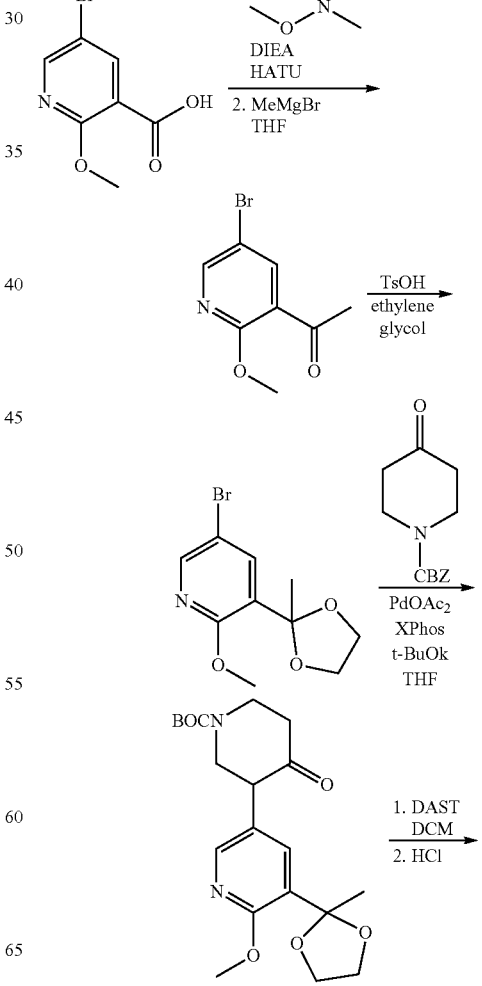

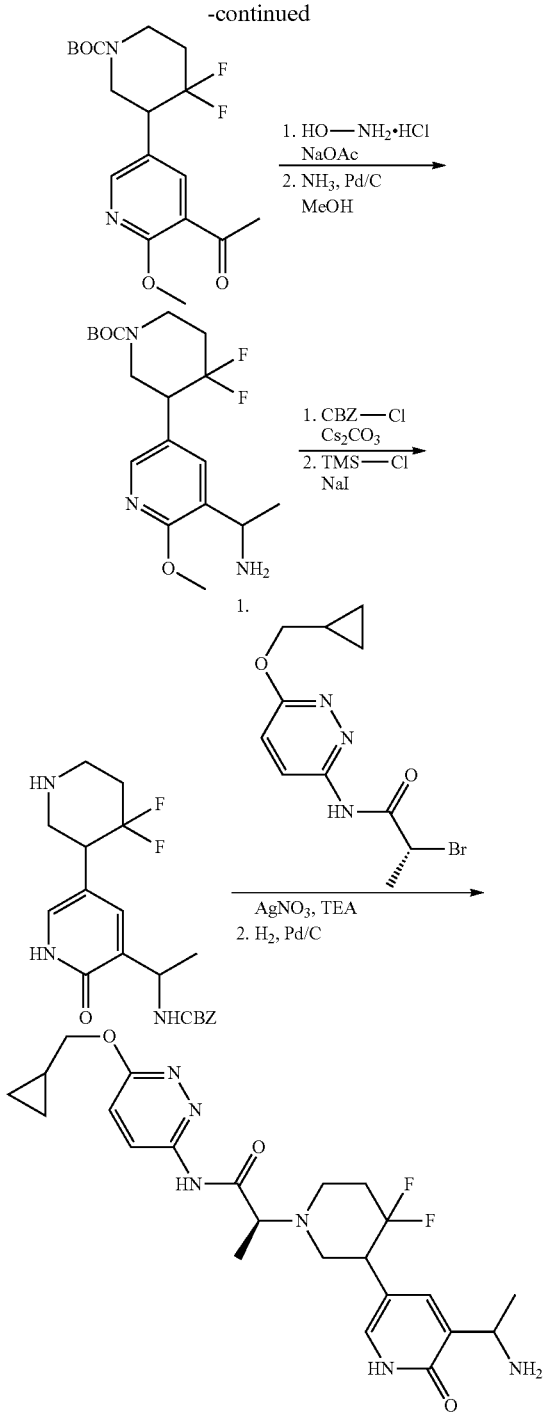

Step 1

5-Bromo-2-methoxynicotinic acid (4.5 g, 19.39 mmol), DIEA (6.77 mL, 38.8 mmol), HATU (9.22 g, 24.24 mmol) and N,O-dimethylhydroxylamine (1.303 g, 21.33 mmol) in THF (25 mL) were stirred at 20° C. for 1.5 h. The reaction was diluted with water and extracted with ethyl acetate (20 ml×2). The combined organic phases were washed with 0.5 M HCl (2×10 ml) and brine (2×10 ml), dried over MgSO$_4$, and concentrated to give crude 5-bromo-N,2-dimethoxy-N-methylnicotinamide (8.02 g, 30.8 mmol, purity: 90%, recovery: 67%), which was used without further purification. $^1$H NMR (400 MHz, CDCl$_3$) δ ppm 8.24 (d, J=1.2 Hz, 1H), 7.69 (s, 1H), 3.96 (s, 3H), 3.54 (br s, 3H), 3.33 (br s, 3H).

Step 2

To 5-bromo-N,2-dimethoxy-N-methylnicotinamide (2.85 g, 10.36 mmol) in THF (50 ml) at 0° C. was slowly added methylmagnesium bromide in diethyl ether (3M, 6.91 ml, 20.72 mmol). After 5 min, the reaction was warmed to rt for 15 min, then re-cooled to ° C. Additional methylmagnesium bromide in diethyl ether (3M, 1.55 ml, 4.65 mmol) was slowly added, and after 10 min the reaction was quenched with sat. aq. ammonium chloride, diluted with water, and extracted with EtOAc (2×). The organic phases were combined, washed with brine, dried over Na$_2$SO$_4$, filtered and concentrated to afford 1-(5-bromo-2-methoxypyridin-3-yl) ethan-1-one (2.22 g, 9.65 mmol, purity: 100%, recovery: 93%) as a tan solid, which was used without further purification. LCMS (m/z) 230, 232 (M+H)$^+$, retention time: 0.87 min, LC/MS Method 5.

Step 3

Under a Dean-Stark condenser, 1-(5-bromo-2-methoxypyridin-3-yl)ethan-1-one (1 g, 4.35 mmol), 4-methylbenzenesulfonic acid (41 mg, 0.217 mmol) and ethylene glycol (0.727 ml, 13.04 mmol) in toluene (10 ml) were stirred at 130° C. for 2 h, then rt overnight. The reaction was concentrated and purified by silica gel chromatography, eluting with 10-70% EtOAc in heptane to provide 5-bromo-2-methoxy-3-(2-methyl-1,3-dioxolan-2-yl)pyridine (739 mg, 2.70 mmol, purity: 100%, recovery: 62%) as a colorless oil. LCMS (m/z) 276 (M+H)$^+$, retention time: 0.90 min, LC/MS Method 5. $^1$H NMR (400 MHz, CDCl$_3$) δ ppm 8.15 (d, J=2.45 Hz, 1H), 7.85-7.87 (m, 1H), 4.05-4.10 (m, 2H), 4.00 (s, 3H), 3.83-3.88 (m, 2H), 1.74 (s, 3H).

Step 4 tert-Butyl 4-oxopiperidine-1-carboxylate (0.644 g, 3.23 mmol) and potassium tert-butoxide (0.755 g, 6.73 mmol) in THF (10 ml) were stirred under nitrogen for 3 min, followed by addition of 5-bromo-2-methoxy-3-(2-methyl-1,3-dioxolan-2-yl)pyridine (0.738 g, 2.69 mmol), and then PdOAc$_2$ (0.060 g, 0.269 mmol) and Xphos (0.257 g, 0.538 mmol) combined in one portion. The vessel was evacuated and purged with nitrogen (3×) and heated to 45° C. overnight. The reaction was poured into ice-water and extracted with ethyl acetate (3×). The combined organics were washed with brine, dried over Na$_2$SO$_4$, filtered, concentrated and purified over silica, eluting with 10-70% (3:1 ethyl acetate: ethanol) in heptane to provide tert-butyl 3-(6-methoxy-5-(2-methyl-1,3-dioxolan-2-yl)pyridin-3-yl)-4-oxopiperidine-1-carboxylate (365 mg, 0.930 mmol, purity: 90%, recovery: 35%). LCMS (m/z) 393 (M+H)$^+$ retention time: 0.89 min, LC/MS Method 5. $^1$H NMR (400 MHz, CDCl$_3$) δ ppm 7.91 (d, J=2.45 Hz, 1H), 7.56 (d, J=2.45 Hz, 1H), 4.34 (br d, J=6.85 Hz, 1H), 4.03-4.12 (m, 3H), 4.02 (s, 3H), 3.80-3.93 (m, 2H), 3.64-3.76 (m, 1H), 3.27-3.44 (m, 2H), 2.59-2.68 (m, 1H), 2.51-2.58 (m, 1H), 1.76 (s, 3H), 1.51 (s, 9H).

Step 5

To tert-butyl 3-(6-methoxy-5-(2-methyl-1,3-dioxolan-2-yl)pyridin-3-yl)-4-oxopiperidine-1-carboxylate (0.365 g, 0.930 mmol) in DCM (4.5 ml) cooled in an ice-bath was added DAST (0.25 ml, 1.892 mmol), dropwise. The reaction was warmed to rt and stirred overnight. Additional DAST (0.1 ml, 0.757 mmol) was added, and the mixture was stirred over the weekend, diluted with DCM, and then added slowly to a flask of ice/sat'd NaHCO$_3$ solution. The mixture was extracted with DCM (2×), and the combined organics were washed with brine, dried over Na$_2$SO$_4$, filtered, concentrated and purified over silica, eluting with 10-50% (3:1 EtOAc: EtOH) in heptane to provide tert-butyl 4,4-difluoro-3-(6- methoxy-5-(2-methyl-1,3-dioxolan-2-yl)pyridin-3-yl)piperidine-1-carboxylate (161 mg, 0.388 mmol, purity: 80%, recovery: 42%) as a colorless oil. LCMS (m/z) 415 (M+H)$^+$ retention time: 1.09 min, LC/MS Method 5. $^1$H NMR (400 MHz, CHLOROFORM-d) δ ppm 8.04 (d, J=2.45 Hz, 1H), 7.72 (s, 1H), 4.15-4.31 (m, 2H), 4.05-4.12 (m, 2H), 4.03 (s, 3H), 3.79-3.90 (m, 2H), 2.93-3.33 (m, 3H), 2.11-2.24 (m, 1H), 1.87-2.08 (m, 1H), 1.77 (s, 3H), 1.48-1.52 (m, 9H).

Step 6 tert-Butyl 4,4-difluoro-3-(6-methoxy-5-(2-methyl-1,3-dioxolan-2-yl)pyridin-3-yl)piperidine-1-carboxylate (0.19 g, 0.458 mmol) was stirred in aq. HCl (1 M, 1.4 ml, 1.400 mmol) overnight, and the reaction was diluted with water and ethyl acetate. The organic layer was separated, and the aqueous layer was extracted with EtOAc. The combined organics were washed with sat'd aq. NaHCO$_3$ and brine, dried over Na$_2$SO$_4$, filtered, concentrated and purified over silica, eluting with 20-70% EtOAc in heptane to provide tert-butyl 3-(5-acetyl-6-methoxypyridin-3-yl)-4,4-difluoropiperidine-1-carboxylate (133 mg, 0.358 mmol, purity: 80%, recovery: 78%). LCMS (m/z) 371 (M+H)$^+$ retention time: 1.13 min, LC/MS Method 5. $^1$H NMR (400 MHz, CDCl$_3$) δ ppm 8.25 (d, J=1.96 Hz, 1H), 8.07 (d, J=1.47 Hz, 1H), 4.12-4.37 (m, 2H), 4.07 (s, 3H), 3.21-3.36 (m, 1H), 2.98-3.17 (m, 2H), 2.65 (s, 3H), 2.11-2.22 (m, 1H), 1.88-2.07 (m, 1H), 1.48 (s, 9H).

Step 7

To tert-butyl 3-(5-acetyl-6-methoxypyridin-3-yl)-4,4-difluoropiperidine-1-carboxylate (0.13 g, 0.351 mmol) in EtOH (1.8 ml) was added hydroxylamine hydrochloride (73 mg, 1.053 mmol) and sodium acetate (72 mg, 0.877 mmol). The reaction was heated to 70° C. overnight, concentrated and partitioned between water and EtOAc. The organic layer was separated, and the aqueous layer was extracted with EtOAc. The combined organics were washed with brine, dried over Na$_2$SO$_4$, filtered, concentrated and purified over silica, eluting with 10-70% (3:1 EtOAc: EtOH) in heptane to give tert-butyl 4,4-difluoro-3-(5-(1-(hydroxyimino)ethyl)-6-methoxypyridin-3-yl)piperidine-1-carboxylate (127 mg, 0.330 mmol, purity: 84%, recovery: 94%) as a white solid. LCMS (m/z) 386 (M+H)$^+$ retention time: 1.03 min, LC/MS Method 5. $^1$H NMR (400 MHz, CDCl$_3$) δ ppm 8.11 (d, J=1.96 Hz, 1H), 7.60 (d, J=1.47 Hz, 1H), 4.13-4.34 (m, 2H), 4.00 (s, 3H), 3.18-3.32 (m, 1H), 2.97-3.17 (m, 2H), 2.25 (s, 3H), 2.11-2.21 (m, 1H), 1.88-2.06 (m, 1H), 1.48 (s, 9H).

Step 8

A mixture of tert-butyl 4,4-difluoro-3-(5-(1-(hydroxyimino)ethyl)-6-methoxypyridin-3-yl)piperidine-1-carboxylate (0.127 g, 0.330 mmol), ammonia in MeOH (7 M, 1 ml) and 10% Pd/C (0.035 g, 0.033 mmol) under a hydrogen balloon was stirred overnight, then filtered through Celite, washing with EtOAc. The filtrate was concentrated and purified by reverse-phase chromatography, eluting with 15-100% AcCN in water (with 0.1% NH$_4$OH) to give tert-butyl 3-(5-(1-aminoethyl)-6-methoxypyridin-3-yl)-4,4-difluoropiperidine-1-carboxylate (49 mg, 0.132 mmol, purity: 92%, recovery: 40%) as a colorless oil. LCMS (m/z) 372 (M+H)$^+$ retention time: 0.67 min, LC/MS Method 5. $^1$H NMR (400 MHz, CDCl$_3$) δ ppm 7.95 (d, J=1.96 Hz, 1H), 7.55 (br s, 1H), 4.08-4.30 (m, 3H), 3.96 (s, 3H), 3.23 (br s, 1H), 2.92-3.17 (m, 2H), 2.08-2.25 (m, 1H), 1.87-2.05 (m, 1H), 1.46 (s, 9H), 1.37 (dd, J=6.85, 1.47 Hz, 3H).

Step 9

To tert-butyl 3-(5-(1-aminoethyl)-6-methoxypyridin-3-yl)-4,4-difluoropiperidine-1-carboxylate (49 mg, 0.132 mmol) and cesium carbonate (64 mg, 0.198 mmol) in THF (0.300 ml) and water (0.3 ml) at 0° C. was added benzyl chloroformate (0.023 ml, 0.158 mmol). The reaction was warmed to rt, stirred overnight, diluted with water and extracted with ethyl acetate (2×). The combined organics were washed with brine, dried over Na$_2$SO$_4$, filtered, concentrated and purified over silica, eluting with 10-50% EtOAc in heptane to give tert-butyl 3-(5-(1-(((benzyloxy)carbonyl)amino)ethyl)-6-methoxypyridin-3-yl)-4,4-difluoropiperidine-1-carboxylate (51 mg, 0.101 mmol, purity: 84%, recovery: 76%) as a colorless oil. LCMS (m/z) 506 (M+H)$^+$ retention time: 1.03 min, LC/MS Method 5. $^1$H NMR (400 MHz, CDCl$_3$) δ ppm 7.99 (d, J=1.96 Hz, 1H), 7.40-7.47 (m, 1H), 7.30-7.40 (m, 5H), 5.50-5.60 (m, 1H), 5.03-5.15 (m, 2H), 4.87-4.99 (m, 1H), 4.07-4.37 (m, 2H), 3.98 (s, 3H), 2.93-3.27 (m, 3H), 2.11-2.21 (m, 1H), 1.87-2.08 (m, 1H), 1.43-1.51 (m, 12H).

Step 10

To tert-butyl 3-(5-(1-(((benzyloxy)carbonyl)amino)ethyl)-6-methoxypyridin-3-yl)-4,4-difluoropiperidine-1-carboxylate (20 mg, 0.040 mmol) in AcCN (1.0 ml) was added sodium iodide (18 mg, 0.119 mmol), followed by TMS-Cl (0.015 ml, 0.119 mmol). The reaction was stirred overnight and concentrated. The residue was taken up in EtOAc, washed with sat'd NaHCO$_3$ solution, dried over Na$_2$SO$_4$, filtered and concentrated to give benzyl (1-(5-(4,4-difluoropiperidin-3-yl)-2-oxo-1,2-dihydropyridin-3-yl)ethyl)carbamate (17 mg, 0.043 mmol, purity: 82%, recovery: quantitative), which was used without further purification. LCMS (m/z) 392 (M+H)$^+$ retention time: 0.53 min, LC/MS Method 5.

Step 11

To crude benzyl (1-(5-(4,4-difluoropiperidin-3-yl)-2-oxo-1,2-dihydropyridin-3-yl)ethyl)carbamate (35 mg, 0.089 mmol) in DMA (1 ml) were added (R)-2-bromo-N-(6-(cyclopropylmethoxy)pyridazin-3-yl)propanamide (Intermediate 14) (44 mg, 0.147 mmol), silver nitrate (17 mg, 0.100 mmol) and TEA (0.05 ml, 0.359 mmol), and the reaction was heated to 40° C. After stirring overnight, the mixture was quenched with water and extracted with EtOAc (3×). The combined organics were washed with brine, dried over Na$_2$SO$_4$, filtered, concentrated and purified over silica, eluting with 10-70% (3:1 EtOAc: EtOH) in heptane to give benzyl (1-(5-(1-(1-((6-(cyclopropylmethoxy)pyridazin-3-yl)amino)-1-oxopropan-2-yl)-4,4-difluoropiperidin-3-yl)-2-oxo-1,2-dihydropyridin-3-yl)ethyl)carbamate (22.6 mg, 0.035 mmol, purity: 84%, recovery: 39%) as a colorless oil. LCMS (m/z) 611 (M+H)$^+$ retention time: 0.82-0.83 min, LC/MS Method 5. $^1$H NMR (400 MHz, CDCl$_3$) δ ppm 12.79-12.97 (m, 1H), 10.02 (br s, 1H), 8.40 (ddd, J=9.42, 4.28, 2.45 Hz, 1H), 7.28-7.35 (m, 6H), 7.01-7.07 (m, 1H), 6.37-6.48 (m, 1H), 5.02-5.13 (m, 2H), 4.74-4.82 (m, 1H), 4.25-4.31 (m, 2H), 3.46 (br d, J=6.85 Hz, 1H), 2.62 (br d, J=12.23 Hz, 1H), 2.11-2.26 (m, 2H), 2.08 (s, 5H), 1.47 (br t, J=7.34 Hz, 3H), 1.28-1.38 (m, 4H), 0.61-0.67 (m, 2H), 0.35-0.40 (m, 2H).

Step 12

A mixture of benzyl (1-(5-(1-((S)-1-((6-(cyclopropylmethoxy)pyridazin-3-yl)amino)-1-oxopropan-2-yl)-4,4-difluoropiperidin-3-yl)-2-oxo-1,2-dihydropyridin-3-yl)ethyl)carbamate (20 mg, 0.033 mmol), EtOH (0.5 mL) and 10% Pd/C (3.49 mg, 3.28 μmol) under an H$_2$ balloon was stirred overnight. Additional 10% Pd/C (3.49 mg, 3.28 μmol) was added, the H$_2$ atmosphere was restored, and after 6 h the reaction was filtered through Celite, rinsing with EtOAc. The filtrate was concentrated, and the reside was purified by reverse-phase chromatography, eluting with 10-85% AcCN in water (with 0.1% NH$_4$OH) to provide (2S)-2-(3-(5-(1-aminoethyl)-6-oxo-1,6-dihydropyridin-3-yl)-4,4-difluoropiperidin-1-yl)-N-(6-(cyclopropylmethoxy)pyridazin-3-yl)propanamide (7.7 mg, 0.016 mmol, purity: 99%, recovery: 49%). LCMS (m/z) 477 (M+H)$^+$ retention time: 0.82-0.83 min, LC/MS Method 5. $^1$H NMR (400 MHz, CDCl$_3$) δ ppm 10.01 (br s, 1H), 8.39 (dd, J=9.54, 1.71 Hz, 1H), 7.44 (br d, J=11.25 Hz, 1H), 7.28 (br d, J=1.47 Hz, 1H), 7.04 (dd, J=9.54, 1.71 Hz, 1H), 4.28 (dd, J=7.34, 1.96 Hz, 2H), 4.19 (dq, J=12.17, 6.38 Hz, 1H), 3.42-3.52 (m, 1H), 3.02-3.23 (m, 1H), 2.76-3.00 (m, 5H), 2.54-2.72 (m, 1H), 2.05-2.31 (m, 2H), 1.40-1.46 (m, 3H), 1.28-1.38 (m, 4H), 0.59-0.67 (m, 2H), 0.33-0.41 (m, 2H).

Example 223

(2S)-2-(3-(5-cyano-6-oxo-1,6-dihydropyridin-3-yl)-4,4-difluoropiperidin-1-yl)-N-(6-(cyclopropylmethoxy)pyridazin-3-yl)propanamide

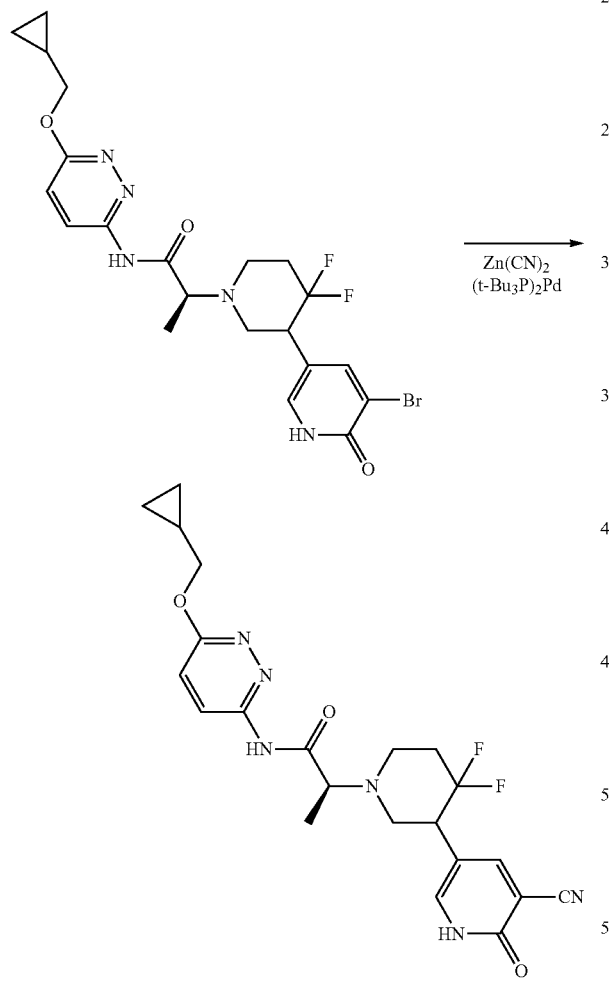

To (2S)-2-(3-(5-bromo-6-oxo-1,6-dihydropyridin-3-yl)-4,4-difluoropiperidin-1-yl)-N-(6-(cyclopropylmethoxy)pyridazin-3-yl)propanamide (Example 221) (0.07 g, 0.137 mmol) and dicyanozine (0.021 g, 0.178 mmol) in DMF (1.2 ml) and one drop of water was added bis(tri-t-butylphosphino)Pd (0) (0.077 g, 0.150 mmol). The reaction was purged with nitrogen (3×) and heated to 100° C. After 2 h the reaction was filtered through Celite, concentrated and purified over silica, eluting with 2-10% MeOH in DCM to yield a colorless oil that was triturated with heptanes to give a white solid. This material was further purified over reverse-phase MDAP HPLC, eluting with 15-85%, acetonitrile in water (with 10 mM ammonium bicarbonate and ammonia to adjust to pH 10) to provide (2S)-2-(3-(5-cyano-6-oxo-1,6-dihydropyridin-3-yl)-4,4-difluoropiperidin-1-yl)-N-(6-(cyclopropylmethoxy)pyridazin-3-yl)propanamide (18 mg, 0.039 mmol, purity: 99%, recovery: 28%) as a white solid. LCMS (m/z) 459 (M+H)$^+$, retention time: 0.68 min, LC/MS Method 5. $^1$H NMR (400 MHz, CDCl$_3$) δ ppm 13.18-13.42 (m, 1H), 9.99-10.27 (m, 1H), 8.44 (dd, J=9.78, 4.40 Hz, 1H), 7.94 (dd, J=11.25, 2.45 Hz, 1H), 7.77 (br s, 1H), 7.05-7.14 (m, 1H), 4.23-4.35 (m, 2H), 3.48-3.61 (m, 1H), 3.15-3.41 (m, 1H), 2.82-3.05 (m, 4H), 2.30-2.31 (m, 1H), 2.14-2.34 (m, 1H), 1.37-1.41 (m, 3H), 1.34 (td, J=7.70, 4.65 Hz, 1H), 0.60-0.70 (i, 2H), 0.36-0.44 (m 2H).

Example 224

(2S)—N-(6-(cyclopropylmethoxy)pyridazin-3-yl)-2-(4,4-difluoro-3-(pyridin-4-yl)piperidin-1-yl)propanamide

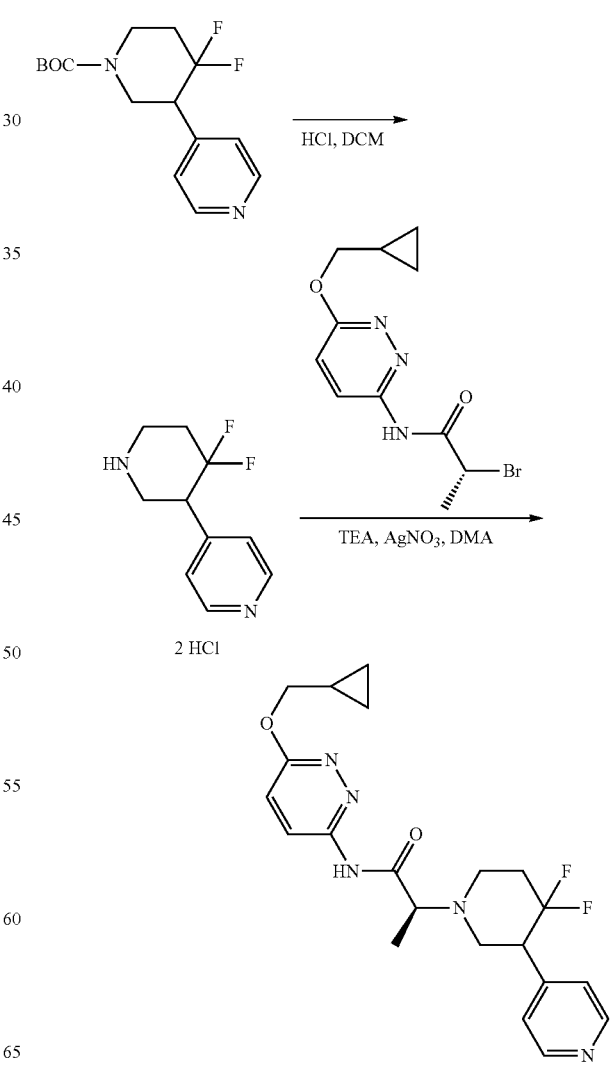

Step 1

To tert-butyl 4,4-difluoro-3-(pyridin-4-yl)piperidine-1-carboxylate (Example 109, Step 2) (170 mg, 0.570 mmol) in DCM (2 mL) was added HCl (4 M, 2 mL, 8.00 mmol). After 3.5 h, the reaction was concentrated, azeotroped with toluene, then azeotroped with ether to afford 4-(4,4-difluoropiperidin-3-yl)pyridine diydrochloride (148 mg, 0.546 mmol, 96% yield) as a white solid, which was used without further purification. LCMS: (ES, m/s) 199 [M+H]+, retention time 0.50 min, LCMS Method 3. $^1$H NMR: (400 MHz, CD$_3$OD) δ ppm 8.97 (d, J=6.85 Hz, 2H), 8.23 (d, J=6.36 Hz, 2H), 4.11-4.29 (m, 1H), 3.80-3.97 (m, 2H), 3.70-3.79 (m, 1H), 3.38-3.54 (m, 1H), 2.48-2.69 (m, 2H).

Step 2

To 4-(4,4-difluoropiperidin-3-yl)pyridine diydrochloride (148 mg, 0.546 mmol) in DMF (3 mL) was added Et$_3$N (0.228 mL, 1.638 mmol), (R)-2-bromo-N-(6-(cyclopropylmethoxy)pyridazin-3-yl)propanamide (Intermediate 14) (180 mg, 0.600 mmol), then silver nitrate (278 mg, 1.638 mmol). The reaction was heated in a sealed tube at 45° C. over the weekend and filtered. The filtrate was diluted with EtOAc, then washed with water and a mixture of sat'd NaHCO3 and brine. The combined aqueous phases were back-extracted with EtOAc (2x), and this EtOAc phase was washed with water and brine. The EtOAc phases were combined, dried over Na$_2$SO$_4$, filtered and concentrated. The residue was dissolved in DCM and loaded onto ISCO (24 g) column, eluting with 0 to 100% (3:1 EtOAc: EtOH) in heptane to give (2S)—N-(6-(cyclopropylmethoxy)pyridazin-3-yl)-2-(4,4-difluoro-3-(pyridin-4-yl)piperidin-1-yl)propanamide (158.3 mg, 0.379 mmol, 69.5% yield). LCMS: (ES, m/s) 418 [M+H]+, retention time 0.99 min, LCMS Method 3. $^1$H NMR: (400 MHz, CDCl$_3$) δ ppm 9.94 (br d, J=8.3 Hz, 1H), 8.55-8.63 (m, 2H), 8.41 (dd, J=9.3, 4.4 Hz, 1H), 7.24-7.29 (m, 2H), 7.06 (dd, J=9.3, 4.4 Hz, 1H), 4.31 (dd, J=7.1, 1.2 Hz, 2H), 3.50 (qd, J=7.0, 4.9 Hz, 1H), 3.25-3.45 (m, 1H), 3.05-3.16 (m, 1H), 2.97-3.05 (m, 1H), 2.87-2.96 (m, 2H), 2.21-2.37 (m, 2H), 1.40 (dd, J=7.1, 5.1 Hz, 3H), 1.32-1.38 (m, 1H), 0.63-0.70 (m, 2H), 0.37-0.43 (m, 2H).

Example 225

(S)—N-(6-(cyclopropylmethoxy)pyridazin-3-yl)-2-((S)-4,4-difluoro-3-(5-(morpholinomethyl)-6-oxo-1,6-dihydropyridin-3-yl)piperidin-1-yl)propanamide

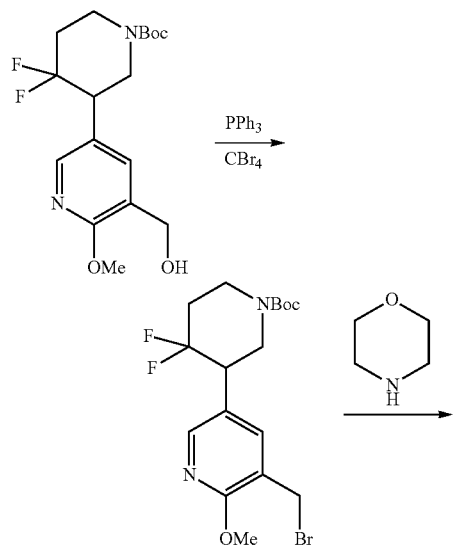

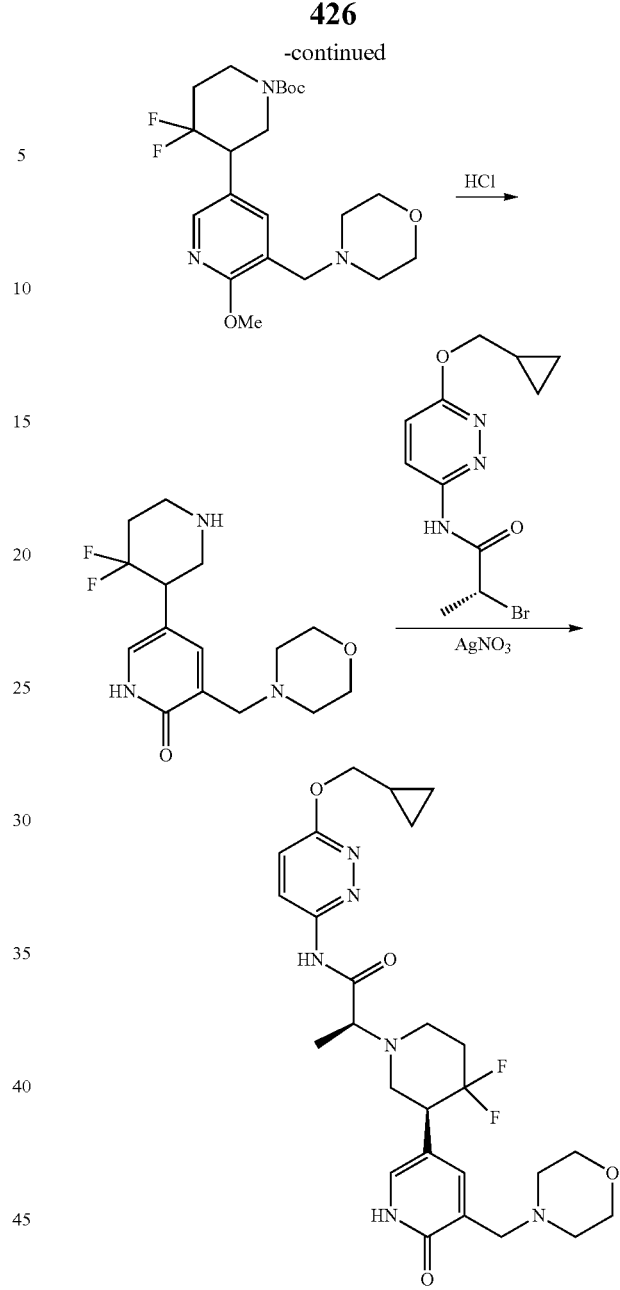

Step 1

Triphenylphosphane (167 mg, 0.638 mmol) was added to a mixture of tert-butyl 4,4-difluoro-3-(5-(hydroxymethyl)-6-methoxypyridin-3-yl)piperidine-1-carboxylate (Example 153, Step 5) (208 mg, 0.580 mmol) and perbromomethane (212 mg, 0.638 mmol) in dichloromethane (5 mL) at 0° C. After 20 min, the reaction was warmed to rt, stirred for 2 h, concentrated and purified by column chromatography (Combiflash, 40 g golden column, 40 ml/min), eluting with 0-20% EtOAc in heptane to afford 178 mg (0.423 mmol, 72.8%) tert-butyl 3-(5-(bromomethyl)-6-methoxypyridin-3-yl)-4,4-difluoropiperidine-1-carboxylate as a white solid. LCMS (ES, m/z): 421 [M+H]+. $^1$H NMR (400 MHz, CHLOROFORM-d) δ ppm 8.07 (d, J=2.20 Hz, 1H), 7.61 (s, 1H), 4.50 (d, J=2.20 Hz, 2H), 4.14-4.35 (m, 2H), 4.05 (s, 3H), 2.96-3.32 (m, 3H), 2.12-2.24 (m, 1H), 1.90-2.09 (m, 1H), 1.50 (s, 9H).

Step 2

Morpholine (0.028 mL, 0.320 mmol) was added to a solution of tert-butyl 3-(5-(bromomethyl)-6-methoxypyridin-3-yl)-4,4-difluoropiperidine-1-carboxylate (54 mg, 0.128 mmol) in acetonitrile (1 mL). After 2 h, the reaction was concentrated and purified by column chromatography (Combiflash, 12 g golden column, 30 ml/min), eluting with 0-10% MeOH in DCM to afford 57 mg (0.127 mmol, 99%) tert-butyl 4,4-difluoro-3-(6-methoxy-5-(morpholinomethyl)pyridin-3-yl)piperidine-1-carboxylate as a colorless sticky oil. LCMS (ES, m/z): 428 [M+H]$^+$. $^1$H NMR (400 MHz, CHLOROFORM-d) δ ppm 8.00 (d, J=1.71 Hz, 1H), 7.64 (br. s., 1H), 4.26 (br. s., 2H), 3.97 (s, 3H), 3.76 (t, J=4.40 Hz, 4H), 3.51 (s, 2H), 3.09 (m, 3H), 2.51 (br. s., 4H), 2.17 (m, 2H), 1.50 (s, 9H).

Step 3

Hydrogen chloride (0.515 mL, 2.059 mmol, 1 M in dioxane) was added to a solution of tert-butyl 4,4-difluoro-3-(6-methoxy-5-(morpholinomethyl)pyridin-3-yl)piperidine-1-carboxylate (55 mg, 0.129 mmol) in dioxane (1 mL). The mixture was heated to 40° C., and after 20 h was concentrated to give 5-(4,4-difluoropiperidin-3-yl)-3-(morpholinomethyl)pyridin-2-ol dihydrochloride as a white solid which was used in the next step without purification. Assumed quantitative yield. LCMS (ES, m/z): 314 [M+H]$^+$.

Step 4

Silver nitrate (21.55 mg, 0.127 mmol) was added to a mixture of 5-(4,4-difluoropiperidin-3-yl)-3-(morpholinomethyl)pyridin-2-ol dihydrochloride (49 mg, 0.127 mmol), (R)-2-bromo-N-(6-(cyclopropylmethoxy)pyridazin-3-yl)propanamide (Intermediate 14) (40.0 mg, 0.133 mmol) and Et$_3$N (0.053 mL, 0.381 mmol) in DMA (1 mL). The mixture was stirred at 40° C. overnight, cooled, filtered by syringe filter (0.2 uM) and purified by MDAP (XSelect CSH Prep C18 5 um OBD column, 30-85%, acetonitrile/water with 10 mM ammonium bicarb and 0.075% ammonium hydroxide, 40 mL/min flow rate, 27 min run time) to give two diastereomers. The later-eluting peak was collected as (S)—N-(6-(cyclopropylmethoxy)pyridazin-3-yl)-2-((S)-4,4-difluoro-3-(5-(morpholinomethyl)-6-oxo-1,6-dihydropyridin-3-yl)piperidin-1-yl)propanamide, an off-white, fluffy solid, 21.1 mg. LCMS (ES, m/z): 533 [M+H]$^+$, rt=0.88 min, method 3. $^1$H NMR (400 MHz, METHANOL-d$_4$) δ ppm 8.39 (d, J=9.54 Hz, 1H), 7.72-7.79 (m, 1H), 7.41-7.47 (m, 1H), 7.23 (d, J=9.54 Hz, 1H), 4.27 (d, J=7.09 Hz, 2H), 3.77 (br. s., 4H), 3.54-3.70 (m, 3H), 3.35-3.45 (m, 1H), 2.92-3.08 (m, 3H), 2.61-2.83 (m, 5H), 2.14-2.37 (m, 2H), 1.38 (m, 4H), 0.65 (dd, J=8.07, 1.47 Hz, 2H), 0.37-0.43 (m, 2H).

Examples 226-231 were synthesized in an analogous manner using the appropriate amine in Step 3 and the designated Intermediate in Step 4.

| Ex | Name | Structure | $^1$H NMR | LC/MS: (M + H)$^+$; retention time (min); LC/MS Method of analysis | Int |
|---|---|---|---|---|---|
| 226 | 2-(4,4-difluoro-3-(5-(morpholinomethyl)-6-oxo-1,6-dihydropyridin-3-yl)piperidin-1-yl)-N-(5-(4-fluorophenoxy)pyridin-2-yl)propanamide | 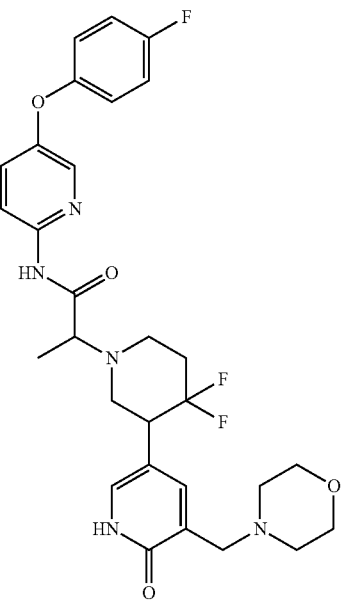 [SMILES: CC(C(=O)Nc1ccc(Oc2ccc(F)cc2)cn1)N1CCC(F)(F)C(c2c[nH]c(=O)c(CN3CCOCC3)c2)C1] | $^1$H NMR (400 MHz, METHANOL-d$_4$) δ ppm 8.19 (d, J = 9.05 Hz, 1H), 8.09 (d, J = 2.20 Hz, 1H), 7.69 (d, J = 4.16 Hz, 1H), 7.48 (dd, J = 9.05, 2.93 Hz, 1H), 7.38 (br. s., 1H), 7.11-7.18 (m, 2H), 7.03-7.10 (m, 2H), 3.70 (dt, J = 9.84, 4.74 Hz, 4H), 3.56 (dd, J = 6.97, 2.32 Hz, 1H), 3.44 (d, J = 4.89 Hz, 2H), 3.35-3.41 (m, 1H), 2.95 (m, 4H), 2.47-2.56 (m, 4H), 2.18-2.36 (m, 2H), 1.37 (dd, J = 6.97, 2.81 Hz, 3H). | 572; rt 101. LC/MS Method 3 | 70 |

-continued

| Ex | Name | Structure | ¹H NMR | LC/MS: (M + H)⁺; retention time (min); LC/MS Method of analysis | Int |
|---|---|---|---|---|---|
| 227 | (S)-2-((S)-4,4-difluoro-3-(5-(morpholino-methyl)-6-oxo-1,6-dihydropyridin-3-yl)piperidin-1-yl)-N-(5-(2,4-difluorophe-noxy)pyridin-2-yl)propanamide | 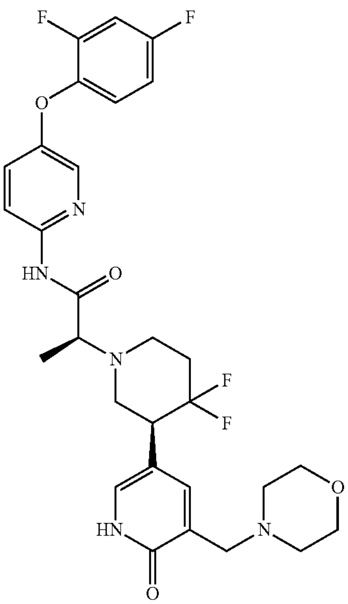 [SMILES: C[C@@H](C(=O)Nc1ccc(Oc2ccc(F)cc2F)cn1)N1CCC(F)(F)[C@@H](c2c[nH]c(=O)c(CN3CCOCC3)c2)C1] | ¹H NMR (400 MHz, METHANOL-d₄) δ ppm 8.17 (d, J = 9.29 Hz, 1H), 8.09 (d, J = 2.93 Hz, 1H), 7.70 (s, 1H), 7.44 (dd, J = 9.05, 2.93 Hz, 1H), 7.38 (d, J = 2.45 Hz, 1H), 7.15-7.29 (m, 2H), 6.99-7.06 (m, 1H), 3.68-3.73 (m, 4H), 3.55 (q, J = 7.09 Hz, 1H), 3.44 (s, 2H), 3.38 (dd, J = 11.86, 8.44 Hz, 1H), 2.91-3.05 (m, 3H), 2.61-2.70 (m, 1H), 2.47-2.56 (m, 4H), 2.13-2.34 (m, 2H), 1.37 (d, J = 6.85 Hz, 3H). | 590; rt 1.02, LC/MS Method 3 | 71 |
| 228 | (S)-2-((S)-4,4-difluoro-3-(5-(morpholino-methyl)-6-oxo-1,6-dihydropyridin-3-yl)piperidin-1-yl)-N-(5-((3,5-difluoropyridin-2-yl)oxy)pyridin-2-yl)propanamide | 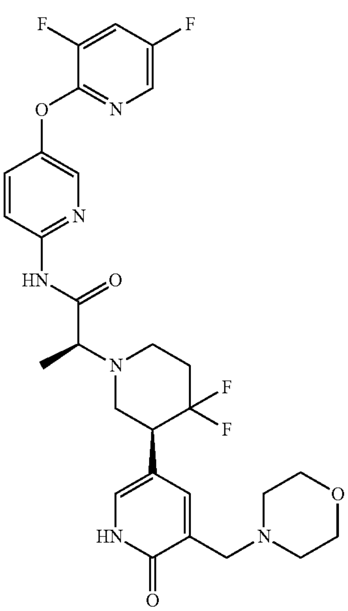 [SMILES: C[C@@H](C(=O)Nc1ccc(Oc2ncc(F)cc2F)cn1)N1CCC(F)(F)[C@@H](c2c[nH]c(=O)c(CN3CCOCC3)c2)C1] | ¹H NMR (400 MHz, METHANOL-d₄) δ ppm 8.23-8.29 (m, 2H), 7.88 (d, J = 2.45 Hz, 1H), 7.76 (ddd, J = 9.90, 7.70, 2.69 Hz, 1H), 7.67-7.73 (m, 2H), 7.39 (d, J = 2.20 Hz, 1H), 3.69-3.74 (m, 4H), 3.59 (q, J = 7.01 Hz, 1H), 3.45 (s, 2H), 3.35-3.43 (m, 1H), 2.92-3.07 (m, 3H), 2.62-2.71 (m, 1H), 2.48-2.56 (m, 4H), 2.17-2.34 (m, 2H), 1.39 (d, J = 6.85 Hz, 3H). | 591; rt 0.95, LC/MS Method 3 | 99 |

| Ex | Name | Structure | ¹H NMR | LC/MS: (M + H)⁺; retention time (min); LC/MS Method of analysis | Int |
|---|---|---|---|---|---|
| 229 | (S)-2-((S)-4,4-difluoro-3-(5-(morpholino-methyl)-6-oxo-1,6-dihydropyridin-3-yl)piperidin-1-yl)-N-(5-(2,4-difluorophe-noxy)pyrazin-2-yl)propanamide | 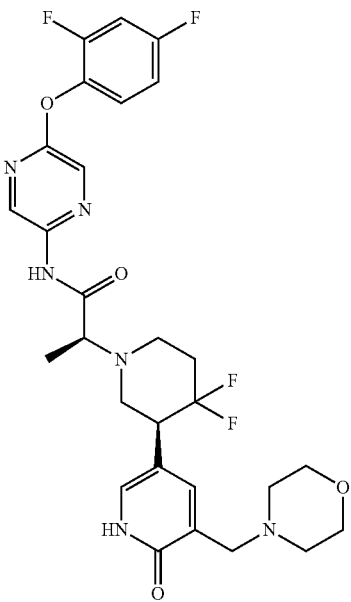 [SMILES: C[C@@H](C(=O)Nc1cnc(Oc2ccc(F)cc2F)cn1)N1CCC(F)(F)[C@@H](c2c[nH]c(=O)c(CN3CCOCC3)c2)C1] | ¹H NMR (400 MHz, METHANOL-d₄) δ ppm 8.88 (d, J = 1.47 Hz, 1H), 8.29 (d, J = 1.22 Hz, 1H), 7.70 (s, 1H), 7.29-7.41 (m, 2H), 7.15 (ddd, J = 10.88, 8.44, 2.93 Hz, 1H), 6.99-7.08 (m, 1H), 3.68-3.75 (m, 4H), 3.59 (q, J = 7.01 Hz, 1H), 3.44 (s, 2H), 3.22-3.31 (m, 1H), 2.90-3.07 (m, 3H), 2.61-2.71 (m, 1H), 2.47-2.56 (m, 4H), 2.11-2.28 (m, 2H), 1.37 (d, J = 6.85 Hz, 3H). | 591; rt 1.01. LC/MS Method 3 | 65 |
| 230 | 2-(3-(5-((dimethyla-mino)methyl)-6-oxo-1,6-dihydropyridin-3-yl)-4,4-difluoropiper-idin-1-yl)-N-(5-(4-fluorophenoxy)pyridin-2-yl)propanamide | 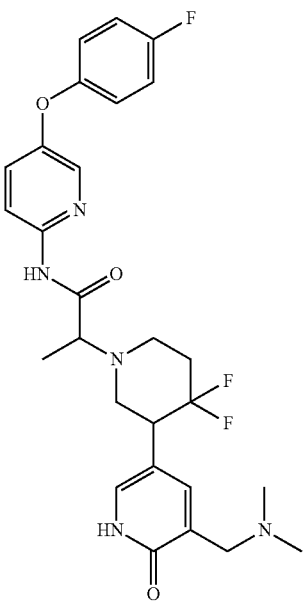 [SMILES: CC(C(=O)Nc1ccc(Oc2ccc(F)cc2)cn1)N1CCC(F)(F)C(c2c[nH]c(=O)c(CN(C)C)c2)C1] | ¹H NMR (400 MHz, METHANOL-d₄) δ ppm 1.03. 8.18 (d, J = 9.05 Hz, 1H), 8.06-8.10 (m, 1H), 7.65 (d, J = 7.58 Hz, 1H), 7.47 (dd, J = 9.05, 2.93 Hz, 1H), 7.36-7.42 (m, 1H), 7.11-7.18 (m, 2H), 7.03-7.10 (m, 2H), 3.51-3.60 (m, 1H), 3.41 (d, J = 3.91 Hz, 2H), 3.37 (m, 1H), 3.00 (m, 4H), 2.29 (d, J = 5.38 Hz, 6H), 2.14-2.25 (m, 2H), 1.37 (d, J = 7.09 Hz, 3H). | 530; rt 1.01, 1.03. LC/MS Method 3 | 70 |

| Ex | Name | Structure | $^1$H NMR | LC/MS: (M + H)$^+$; retention time (min); LC/MS Method of analysis | Int |
|---|---|---|---|---|---|
| 231 | (S)-N-(6-(cyclopropyl-methoxy(pyri-dazin-3-yl)-2-((S)-3-(5-((dimethyla-mino)methyl)-6-oxo-1,6-dihydropyridin-3-yl)-4,4-difluoropiper-idin-1-yl)propanamide | 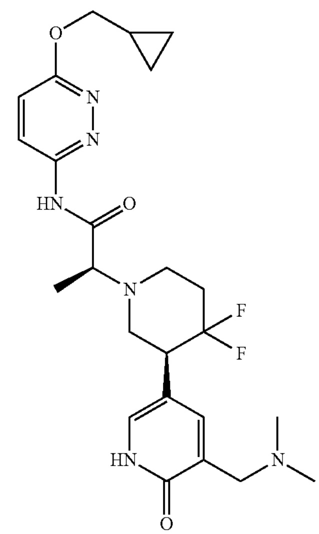 [SMILES: C[C@@H](C(=O)Nc1ccc(OCC2CC2)nn1)N1CCC(F)(F)[C@@H](c2c[nH]c(=O)c(CN(C)C)c2)C1] | $^1$H NMR (400 MHz, METHANOL-d$_4$) δ ppm 8.38 (d, J = 9.54 Hz, 1H), 7.77 (br. s., 1H), 7.51 (br. s., 1H), 7.23 (d, J = 9.54 Hz, 1H), 4.24-4.31 (m, 2H), 3.84 (br. s., 2H), 3.59 (q, J = 6.85 Hz, 1H), 3.41 (d, J = 11.49 Hz, 1H), 2.92-3.09 (m, 3H), 2.49-2.73 (m, 7H), 2.14-2.35 (m, 2H), 1.30-1.42 (m, 4H), 0.61-0.69 (m, 2H), 0.37-0.44 (m, 2H). | 491; rt 0.89. LC/MS Method 3 | 14 |

Example 232

(2S)-2-(3-(5-(1-amino-2,2-trifluoroethyl)-6-oxo-1,6-dihydropyridin-3-yl)-4,4-difluoropiperidin-1-yl)-N-(5-fluoropyridin-2-yl)propanamide

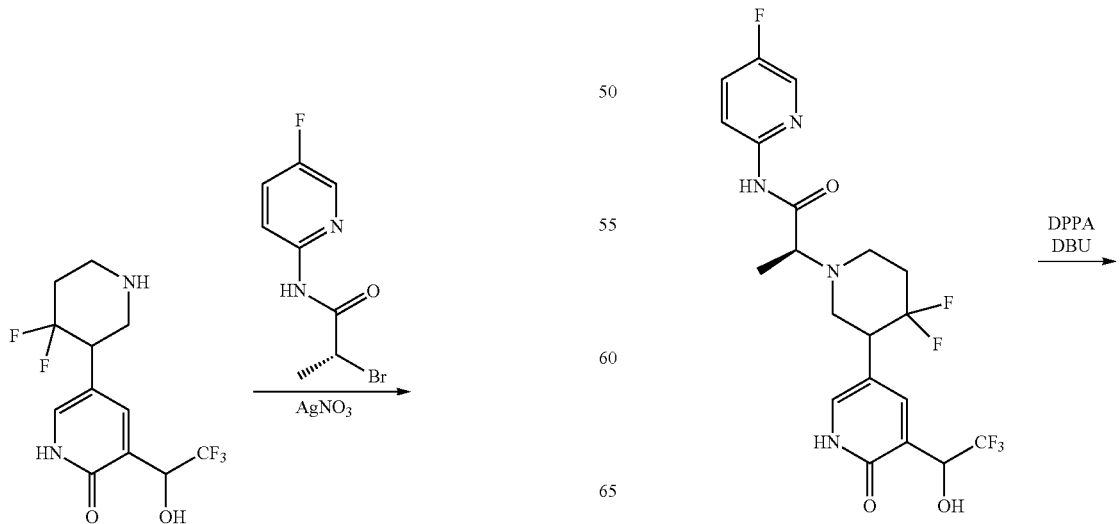

-continued

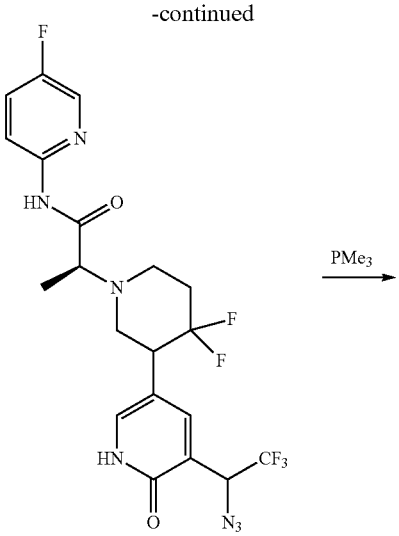

Step 1

Silver nitrate (0.054 g, 0.320 mmol) was added to a mixture of 5-(4,4-difluoropiperidin-3-yl)-3-(2,2,2-trifluoro-1-hydroxyethyl)pyridin-2-ol hydrochloride (Example 209, Step 5) (0.124 g, 0.320 mmol), (R)-2-bromo-N-(5-fluoropyridin-2-yl)propanamide (Intermediate 1) (0.079 g, 0.320 mmol) and Et$_3$N (0.134 mL, 0.960 mmol) in DMA (2 mL). The reaction was stirred at 40° C. overnight, cooled to rt and partitioned between EtOAc and water. The organic phase was separated, and the aqueous phase was extracted with EtOAc (3×). The combined organic phases were washed with 5% LiCl and brine, dried over Na$_2$SO$_4$, filtered, concentrated and purified by column chromatography (Combiflash, 24 g golden column, 35 ml/min), eluting with 0-9% MeOH in DCM to afford 78 mg (0.163 mmol, 50.9%) (2S)-2-(4,4-difluoro-3-(6-hydroxy-5-(2,2,2-trifluoro-1-hydroxyethyl)pyridin-3-yl)piperidin-1-yl)-N-(5-fluoropyridin-2-yl)propanamide as a light-yellow solid. LCMS (ES, m/z): 479 [M+H]$^+$. $^1$H NMR (400 MHz, CHLOROFORM-d) δ ppm 12.83-13.08 (m, 1H), 9.43-9.59 (m, 1H), 8.24-8.33 (m, 1H), 8.13-8.20 (m, 1H), 7.40-7.53 (m, 2H), 6.40-6.64 (m, 1H), 5.02 (br s, 1H), 338-3.56 (m, 1H), 3.09-3.32 (m, 1H), 2.79-3.03 (m, 3H), 2.59-2.77 (m, 1H), 2.13-2.37 (m, 2H), 1.70 (br s, 1H), 1.40 (br d, J=5.87 Hz, 3H).

Step 2

To (2S)-2-(4,4-difluoro-3-(6-hydroxy-5-(2,2,2-trifluoro-1-hydroxyethyl)pyridin-3-yl)piperidin-1-yl)-N-(5-fluoropyridin-2-yl)propanamide (68 mg, 0.142 mmol) and diphenyl phosphorazidate (0.037 mL, 0.171 mmol) in tetrahydrofuran (1 mL) was added DBU (0.026 mL, 0.171 mmol). The resulting mixture was stirred overnight, concentrated and purified by column chromatography (Combiflash, 12 g golden column, 30 ml/min), eluting with 0-8% MeOH in DCM to afford 30 mg (0.060 mmol, 41.9%) (2S)-2-(3-(5-(1-azido-2,2,2-trifluoroethyl)-6-hydroxypyridin-3-yl)-4,4-difluoropiperidin-1-yl)-N-(5-fluoropyridin-2-yl)propanamide as a light-yellow foam. LCMS (ES, m/z): 504 [M+H]$^+$. $^1$H NMR (400 MHz, CHLOROFORM-d) δ ppm 13.30 (br s, 1H), 9.46-9.61 (m, 1H), 8.23-8.31 (m, 1H), 8.17 (d, J=2.93 Hz, 1H), 7.65-7.73 (m, 1H), 7.42-7.50 (m, 2H), 5.55 (quin, J=6.24 Hz, 1H), 3.41-3.53 (m, 1H), 3.10-3.32 (m, 1H), 2.81-3.03 (m, 3H), 2.61-2.77 (m, 1H), 2.15-2.35 (m, 2H), 1.37-1.45 (m, 3H).

Step 3

Trimethylphosphane (0.135 mL, 0.135 mmol) was added to (2S)-2-(3-(5-(1-azido-2,2,2-trifluoroethyl)-6-hydroxypyridin-3-yl)-4,4-difluoropiperidin-1-yl)-N-(5-fluoropyridin-2-yl)propanamide (34 mg, 0.068 mmol) and water (6.08 µl, 0.338 mmol) in tetrahydrofuran (1 mL). After 30 min, the reaction was concentrated and purified by MDAP (XSelect CSH Prep C18 5 um OBD column, 15-55%, acetonitrile in water with 10 mM ammonium bicarb and 0.075% ammonium hydroxide, 40 mL/min flow rate, 17 min run time) to afford 21.7 mg (0.045 mmol, 67.3%) (2S)-2-(3-(5-(1-amino-2,2,2-trifluoroethyl)-6-hydroxypyridin-3-yl)-4,4-difluoropiperidin-1-yl)-N-(5-fluoropyridin-2-yl)propanamide as a white, fluffy solid. LCMS (ES, m/z): 478 [M+H]$^+$, rt=0.80 min, 0.82 min, method 3. $^1$H NMR (400 MHz, METHANOL-d$_4$) δ ppm 8.24 (d, J=2.93 Hz, 2H), 7.82-7.91 (m, 1H), 7.60-7.69 (m, 1H), 7.42-7.49 (m, 1H), 4.68-4.80 (m, 1H), 3.48-3.63 (m, 1H), 2.60-3.09 (m, 5H), 2.12-2.36 (m, 2H), 1.37 (d, J=6.85 Hz, 3H).

Examples 233-236 were synthesized in an analogous manner using the designated Intermediate.

| Ex | Name | Structure | ¹H NMR | LC/MS: (M + H)⁺; retention time (min); LC/MS Method of analysis | Int |
|---|---|---|---|---|---|
| 233, 234 | Ex. 233: (S)-2-((S)-3-(5-((S)-1-amino-2,2,2-trifluoroethyl)-6-oxo-1,6-dihydropyridin-3-yl)-4,4-difluoropiper-idin-1-yl)-N-(5-(4-fluorophenoxy)pyridin-2-yl)propanamide and | 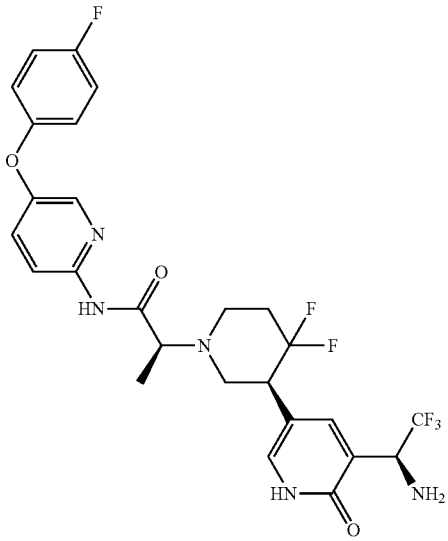 [SMILES: C[C@@H](C(=O)Nc1ccc(Oc2ccc(F)cc2)cn1)N1CCC(F)(F)[C@@H](c2c[nH]c(=O)c([C@@H](N)C(F)(F)F)c2)C1] and | Isomer 1 ¹H NMR (400 MHz, METHANOL-d₄) δ ppm 8.18 (d, J = 9.05 Hz, 1H), 8.08 (d, J = 2.69 Hz, 1H), 7.88 (s, 1H), 7.44-7.50 (m, 2H), 7.11-71.8 (m, 2H), 7.03-7.10 (m, 2H), 4.76 (q, J = 7.74 Hz, 1H), 3.56 (q, J = 7.01 Hz, 1H), 3.35-3.45 (m, 1H), 3.01 (d, J = 8.31 Hz, 2H), 2.94 (d, J = 11.49 Hz, 1H), 2.60-2.72 (m, 1H), 2.15-2.36 (m, 2H), 1.37 (d, J = 7.09 Hz, 3H). | Isomer 1 570; rt 1.05. LC/MS Method 3 | 70 |
| | Ex. 234: (S)-2-((S)-3-(5-((R)-1-amino-2,2,2-trifluoroethyl)-6-oxo-1,6-dihydropyridin-3-yl)-4,4-difluoropiper-idin-1-yl)-N-(5-(4-fluorophenoxy)pyridin-2-yl)propanamide | 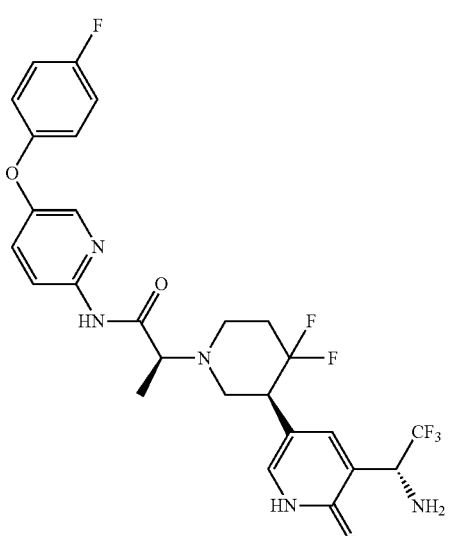 | Isomer 2 ¹H NMR (400 MHz, METHANOL-d₄) δ ppm 8.19 (d, J = 9.05 Hz, 1H), 8.08 (d, J = 2.69 Hz, 1H), 7.87 (d, J = 1.71 Hz, 1H), 7.45-7.50 (m, 2H), 7.11-7.18 (m, 2H), 7.04-7.10 (m, 2H), 4.74 (q, J = 7.74 Hz, 1H), 3.57 (q, J = 6.85 Hz, 1H), 3.34-3.45 (m, 1H), 2.89-3.07 (m, 3H), 2.61-2.71 (m, 1H), 2.16-2.34 (m, 2H), 1.37 (d, J = 7.09 Hz, 3H). | Isomer 2 570; rt 1.04. LC/MS Method 3 | |

-continued

| Ex | Name | Structure | ¹H NMR | LC/MS: (M + H)⁺; retention time (min); LC/MS Method of analysis | Int |
|---|---|---|---|---|---|
| 235, 236 | Ex. 235: (S)-2-((S)-3-(5-((S)-1-amino-2,2,2-trifluoroethyl)-6-oxo-1,6-dihydropyridin-3-yl)-4,4-difluoropiper-idin-1-yl)-N-(5-(2,4-difluorophe-noxy)pyridin-2-yl)propanamide and | 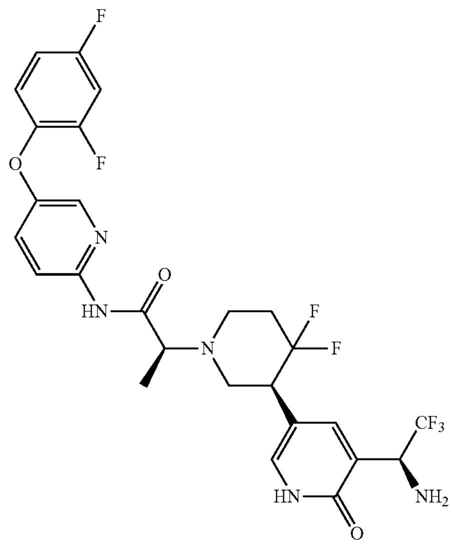 [SMILES: C[C@@H](C(=O)Nc1ccc(Oc2ccc(F)cc2F)cn1)N1CCC(F)(F)[C@@H](c2c[nH]c(=O)c([C@@H](N)C(F)(F)F)c2)C1] | Isomer 1<br>¹H NMR (400 MHz, METHANOL-d₄) δ ppm 8.17 (d, J = 9.05 Hz, 1H), 8.08 (d, J = 2.69 Hz, 1H), 7.88 (s, 1H), 7.41-7.47 (m, 2H), 7.14-7.28 (m, 2H), 7.02 (dddd, J = 9.26, 7.86, 2.93, 1.71 Hz, 1H), 4.76 (q, J = 7.82 Hz, 1H), 3.56 (q, J = 6.85 Hz, 1H), 3.40 (m, 1H), 3.01 (d, J = 8.56 Hz, 2H), 2.93 (d, J = 11.49 Hz, 1H), 2.60-2.70 (m, 1H), 2.15-2.34 (m, 2H), 1.37 (d, J = 6.85 Hz, 3H). | Isomer 1<br>588; rt 1.06.<br>LC/MS Method | 71 |
| | Ex. 236: (S)-2-((S)-3-(5-((R)-1-amino-2,2,2-trifluoroethyl)-6-oxo-1,6-dihydropyridin-3-yl)-4,4-difluoropiper-idin-1-yl)-N-(5-(2,4-difluorophe-noxy)pyridin-2-yl)propanamide | | Isomer 2<br>¹H NMR (400 MHz, METHANOL-d₄) δ ppm 8.17 (d, J = 9.05 Hz, 1H), 8.08 (d, J = 2.93 Hz, 1H), 7.87 (d, J = 1.71 Hz, 1H), 7.46 (d, J = 2.20 Hz, 1H), 7.44 (dd, J = 9.05, 2.93 Hz, 1H), 7.15-7.28 (m, 2H), 7.02 (dddd, J = 9.17, 7.70, 2.93, 1.71 Hz, 1H), 4.74 (q, J = 7.82 Hz, 1H), 3.56 (q, J = 7.09 Hz, 1H), 3.39 (m, 1H), 2.88-3.04 (m, 3H), 2.66 (td, J = 11.62, 3.18 Hz, 1H), 2.15-2.33 (m, 2H), 1.37 (d, J = 7.09 Hz, 3H). | Isomer 2<br>588; rt 1.06,<br>LC/MS Method 3 | |

Example 237
2-(4,4-difluoro-3-(5-((methylamino)methyl)-6-oxo-1,6-dihydropyridin-3-yl)piperidin-1-yl)-N-(5-(4-fluorophenoxy)pyridin-2-yl)propanamide
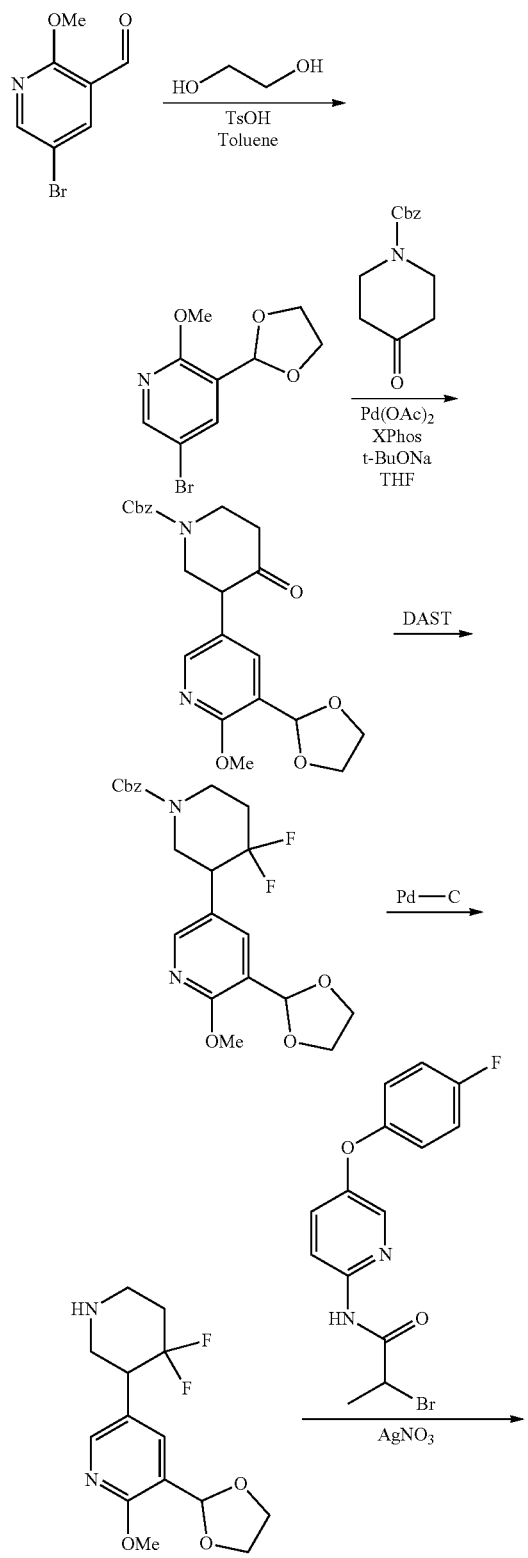

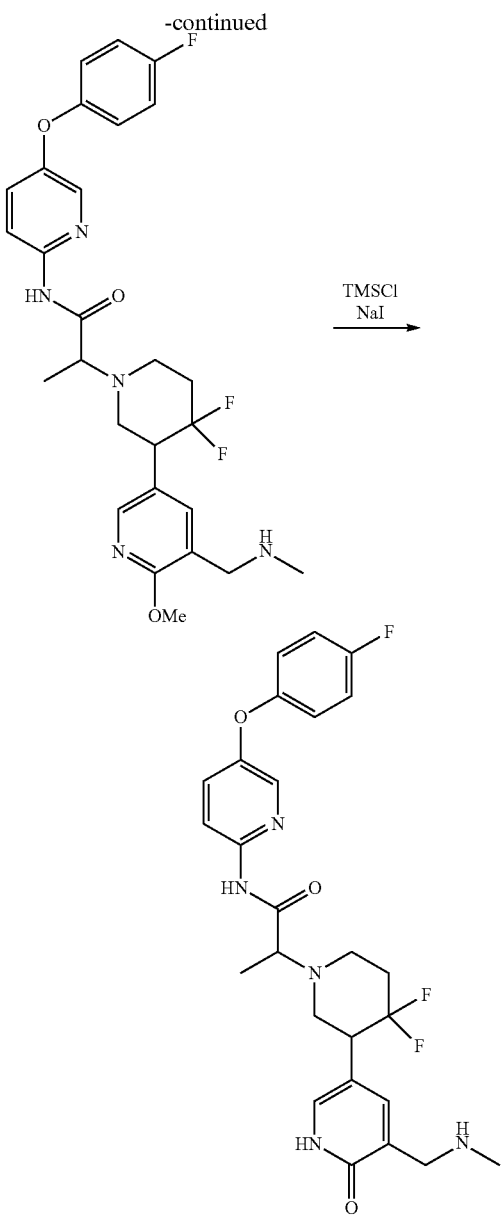

Step 1

To a suspension of 5-bromo-2-methoxynicotinaldehyde (5 g, 23.14 mmol) in toluene (50 mL) was added ethane-1,2-diol (3.87 mL, 69.4 mmol) and tosic acid (0.220 g, 1.157 mmol). The mixture was heated at 165° C. under a Dean Stark trap for 16 h, cooled to rt, and diluted with EtOAc (100 ml), sat'd NaHCO₃ and water. The organic layer was separated, and the aqueous phase was extracted with EtOAc (2×). the combined organics were washed with brine, dried over Na₂SO₄, filtered, concentrated and purified by column chromatography (Combiflash, 80 g golden column, 60 ml/min), eluting with 0-25% EtOAc in heptane to afford 5.38 g (89%) 5-bromo-3-(1,3-dioxolan-2-yl)-2-methoxypyridine as a yellow oil. LCMS (ES, m/z): 260 [M+H]⁺. ¹H NMR (400 MHz, CHLOROFORM-d) δ ppm 8.22 (d, J=2.45 Hz, 1H), 7.92 (d, J=2.69 Hz, 1H), 6.02 (s, 1H), 4.11-4.17 (m, 2H), 4.04-4.11 (m, 2H), 4.01 (s, 3H).

Step 2

To sodium tert-butoxide (3.88 g, 40.4 mmol) was added THF (70 mL), in one portion. After 5 min, benzyl 4-oxopiperidine-1-carboxylate (4.71 g, 20.19 mmol) was added, followed by 5-bromo-3-(1,3-dioxolan-2-yl)-2-methoxypyridine (3.5 g, 13.46 mmol). The resulting mixture was stirred, evacuated and back-filled with N₂ (3×). After 5 min, Pd(OAc)₂ (0.227 g, 1.009 mmol) and XPhos (0.962 g, 2.019 mmol) were added, and the mixture was evacuated and back-filled with N₂ (3×). The reaction was heated to 40° C. for 16 h, cooled to RT, diluted with cold water (about 50 ml) and partitioned between EtOAc and dilute brine. The organic phase was separated, and the aqueous phase was extracted with EtOAc (2×). The combined organic phases were washed with brine, dried over Na₂SO₄, filtered, concentrated and purified by silica gel chromatography (120 g Isco gold column; 85 mL/Min), eluting with 0-60% EtOAc in heptane to give 2.53 g (6.13 mmol, 45.6%) benzyl 3-(5-(1,3-dioxolan-2-yl)-6-methoxypyridin-3-yl)-4-oxopiperidine-1-carboxylate as a yellow foam. LCMS (ES, m/z): 413 [M+H]⁺. ¹H NMR (400 MHz, CHLOROFORM-d) δ ppm 7.98 (br. s., 1H), 7.64 (d, J=2.20 Hz, 1H), 7.33-7.45 (m, 5H), 6.04 (s, 1H), 5.23 (s, 2H), 4.42 (br. s., 2H), 4.09-4.15 (m, 2H), 4.04-4.09 (m, 2H), 4.03 (s, 3H), 3.72 (br. s., 1H), 3.47 (m, 2H), 2.61 (m, 2H).

Step 3

To benzyl 3-(5-(1,3-dioxolan-2-yl)-6-methoxypyridin-3-yl)-4-oxopiperidine-1-carboxylate (2.53 g, 6.13 mmol) in DCM (40 ml) at 0° C. was added DAST (1.621 mL, 12.27 mmol), dropwise. The reaction was warmed to RT overnight and poured slowly and carefully into saturated NaHCO₃ solution (about 50 ml). The phases were separated, and the aqueous phase was extracted with CH₂Cl₂ (2×). The combined CH₂Cl₂ phases were washed with brine, dried over Na₂SO₄, filtered, concentrated and purified by silica gel chromatography (80 g Isco gold column; 60 mL/Min), eluting with 0-50% EtOAc in heptane to give the product as a light-yellow foam (2.1 g) which was 83% pure, with 15% of fluoro-olefin by-product. This material was further purified by reverse phase chromatography (275 g C18Aq gold column; 125 mL/Min, 0-100%, acetonitrile/water with 10 mM ammonium bicarb and 0.075% ammonium hydroxide) to afford 1.69 g (3.89 mmol, 63.4%) benzyl 3-(5-(1,3-dioxolan-2-yl)-6-methoxypyridin-3-yl)-4,4-difluoropiperidine-1-carboxylate as a white foam. LCMS (ES, m/z): 435 [M+H]⁺. ¹H NMR (400 MHz, CHLOROFORM-d) δ ppm 8.10 (br. s., 1H), 7.77 (s, 1H), 7.38 (br. s., 5H), 6.04 (s, 1H), 5.18 (s, 2H), 4.22-4.46 (m, 2H), 4.04-4.16 (m, 4H), 4.03 (s, 3H), 2.98-3.42 (m, 3H), 1.89-2.28 (m, 2H).

Step 4

A mixture of benzyl 3-(5-(1,3-dioxolan-2-yl)-6-methoxypyridin-3-yl)-4,4-difluoropiperidine-1-carboxylate (218 mg, 0.502 mmol), ethyl acetate (2 mL) and Pd—C (53.4 mg, 0.050 mmol) was stirred under H₂ (balloon) overnight, filtered and washed with EtOAc (3×). The filtrate was concentrated to afford 150 mg (0.499 mmol, 100%) 5-(4,4-difluoropiperidin-3-yl)-3-(1,3-dioxolan-2-yl)-2-methoxypyridine as a colorless sticky oil. LCMS (ES, m/z): 301 [M+H]⁺. ¹H NMR (400 MHz, CHLOROFORM-d) δ ppm 8.11 (d, J=2.20 Hz, 1H), 7.80 (s, 1H), 6.05 (s, 1H), 4.12-4.19 (m, 2H), 4.04-4.09 (m, 2H), 4.02 (s, 3H), 2.94-3.26 (m, 5H), 2.20 (m, 1H), 1.90 (m, 2H).

Step 5

Silver nitrate (103 mg, 0.609 mmol) was added to 5-(4,4-difluoropiperidin-3-yl)-3-(1,3-dioxolan-2-yl)-2-methoxypyridine (182.8 mg, 0.609 mmol), 2-bromo-N-(5-(4-fluorophenoxy)pyridin-2-yl)propanamide (Intermediate 70) (206 mg, 0.609 mmol) and Et₃N (0.127 mL, 0.913 mmol) in DMA (5 mL). The reaction was stirred at 40° C. overnight, cooled to RT, and partitioned between EtOAc and water. The organic phase was separated, and the aqueous phase was extracted with EtOAc (3×). The combined organic phases were washed with 5% LiCl and brine, dried over Na$_2$SO$_4$, filtered, concentrated and purified by column chromatography (Combiflash, 40 g golden column, 40 ml/min), eluting with 0-25% EtOAc in DCM to afford 175 mg (0.313 mmol, 51.5%) 2-(3-(5-(1,3-dioxolan-2-yl)-6-methoxypyridin-3-yl)-4,4-difluoropiperidin-1-yl)-N-(5-(4-fluorophenoxy) pyridin-2-yl)propanamide as a white foam. LCMS (ES, m/z): 559 [M+H]$^+$. $^1$H NMR (400 MHz, CHLOROFORM-d) δ ppm 9.62 (br. s., 1H), 8.24 (dd, J=9.05, 4.65 Hz, 1H), 8.13 (dd, J=6.11, 2.20 Hz, 1H), 8.10 (d, J=2.20 Hz, 1H), 7.80 (d, J=6.85 Hz, 1H), 7.37 (dt, J=9.05, 2.32 Hz, 1H), 7.03-7.11 (m, 2H), 6.96-7.02 (m, 2H), 6.04 (d, J=5.38 Hz, 1H), 4.12-4.19 (m, 2H), 4.05-4.10 (m, 2H), 4.02 (d, J=4.65 Hz, 3H), 3.45 (br. s., 2H), 2.89 (m, 3H), 2.26 (m, 2H), 1.41 (t, J=6.60 Hz, 3H).

Step 6

To 2-(3-(5-(1,3-dioxolan-2-yl)-6-methoxypyridin-3-yl)-4,4-difluoropiperidin-1-yl)-N-(5-(4-fluorophenoxy)pyridin-2-yl)propanamide (175 mg, 0.313 mmol) in tetrahydrofuran (2.5 mL) was added HCl (2.506 mL, 2.506 mmol). The mixture was stirred for 2 h, cooled to 0° C., neutralized with saturated NaHCO$_3$ and diluted with EtOAc. The organic phase was separated, and the aqueous phase was extracted with EtOAc (3×). The combined organic layers were washed with brine, dried over Na$_2$SO$_4$, filtered and concentrated to afford 160 mg (0.311 mmol, 99%) 2-(4,4-difluoro-3-(5-formyl-6-methoxypyridin-3-yl)piperidin-1-yl)-N-(5-(4-fluorophenoxy)pyridin-2-yl)propanamide as a white foam, which was used without further purification. LCMS (ES, m/z): 515 [M+H]$^+$. $^1$H NMR (400 MHz, CHLOROFORM-d) δ ppm 10.38 (d, J=5.14 Hz, 1H), 9.50-9.74 (m, 1H), 8.36 (dd, J=6.11, 2.69 Hz, 1H), 8.25 (dd, J=8.93, 6.24 Hz, 1H), 8.06-8.14 (m, 2H), 7.38 (dt, J=9.05, 3.18 Hz, 1H), 7.03-7.12 (m, 2H), 6.96-7.03 (m, 2H), 4.10 (d, J=5.38 Hz, 3H), 3.48 (br. s., 2H), 2.88 (m, 4H), 2.29 (br. s., 2H), 1.42 (t, J=6.36 Hz, 3H).

Step 7

To 2-(4,4-difluoro-3-(5-formyl-6-methoxypyridin-3-yl)piperidin-1-yl)-N-(5-(4-fluorophenoxy)pyridin-2-yl)propanamide (25 mg, 0.049 mmol) in methanol (0.5 mL) at 0° C. in a microwave vial was added methanamine (0.437 mL, 0.875 mmol, 2 M in THF), followed by acetic acid (0.050 mL, 0.875 mmol). The mixture was stirred at rt overnight, cooled to 0° C. and treated with sodium triacetoxyborohydride (25.7 mg, 0.121 mmol). The reaction was stirred at rt for 2 h, quenched with ice and partitioned between EtOAc and water. The organic phase was separated, and the aqueous phase was extracted with EtOAc (3×). The combined organic phases were washed with brine, dried over Na$_2$SO$_4$, filtered and concentrated to afford the crude product 2-(4,4-difluoro-3-(6-methoxy-5-((methylamino)methyl)pyridin-3-yl)piperidin-1-yl)-N-(5-(4-fluorophenoxy)pyridin-2-yl) propanamide as a white solid (purity, 94% based on LCMS), which was used without further purification. LCMS (ES, m/z): 530 [M+H]$^+$. $^1$H NMR (400 MHz, METHANOL-d$_4$) δ ppm 8.18 (dd, J=9.54, 1.22 Hz, 1H), 8.09 (d, J=2.93 Hz, 1H), 8.05 (dd, J=6.85, 2.45 Hz, 1H), 7.69 (br d, J=3.91 Hz, 1H), 7.47 (ddd, J=9.29, 2.93, 1.47 Hz, 1H), 7.12-7.18 (m, 2H), 7.05-7.10 (m, 2H), 3.98 (d, J=3.42 Hz, 3H), 3.74 (d, J=3.42 Hz, 2H), 3.41-3.62 (m, 3H), 2.83-3.12 (m, 4H), 2.41 (d, J=3.42 Hz, 3H), 2.18-2.27 (m, 1H), 1.37 (dd, J=7.09, 3.18 Hz, 3H).

Step 8

To 2-(4,4-difluoro-3-(6-methoxy-5-((methylamino) methyl)pyridin-3-yl)piperidin-1-yl)-N-(5-(4-fluorophenoxy)pyridin-2-yl)propanamide (25 mg, 0.047 mmol) in acetonitrile (0.5 mL) was added sodium iodide (35.4 mg, 0.236 mmol), followed by TMSCl (0.030 mL, 0.236 mmol). After 1 h, additional sodium iodide (21.23 mg, 0.142 mmol) was added, followed by TMSCl (0.018 mL, 0.142 mmol). After 1 h, the reaction was concentrated and partitioned between EtOAc and aq. NaHCO$_3$ solution. The organic phase was separated, and the aqueous layer was extracted with EtOAc (3×). The combined organic extracts were washed with brine, dried over Na$_2$SO$_4$, filtered, concentrated and purified by MDAP (XSelect CSH Prep C18 5 um OBD column, 30-85%, acetonitrile/water with 10 mM ammonium bicarb and 0.075% ammonium hydroxide, 40 mL/min flow rate, 27 min run time) to afford 19.6 mg (0.038 mmol, 81%) 2-(4,4-difluoro-3-(5-((methylamino)methyl)-6-oxo-1,6-dihydropyridin-3-yl)piperidin-1-yl)-N-(5-(4-fluorophenoxy) pyridin-2-yl)propanamide as a white, fluffy solid. LCMS (ES, m/z): 516 [M+H]$^+$, rt=0.96 min, 0.98 min, Method 3. $^1$H NMR (400 MHz, METHANOL-d$_4$) δ ppm 8.18 (d, J=9.05 Hz, 1H), 8.08 (d, J=2.69 Hz, 1H), 7.62 (m, 1H), 7.48 (dd, J=9.05, 2.93 Hz, 1H), 7.37-7.41 (m, 1H), 7.11-7.19 (m, 2H), 7.03-7.10 (m, 2H), 3.62 (d, J=3.42 Hz, 2H), 3.52-3.59 (m, 1H), 3.35-3.42 (m, 1H), 2.66-3.08 (m, 4H), 2.40 (d, J=3.42 Hz, 3H), 2.14-2.36 (m, 2H), 1.37 (dd, J=7.09, 1.47 Hz, 3H).

Examples 238-244 were synthesized in an analogous manner using the appropriate amine in Step 7 and the designated Intermediate in Step 5. In some cases the treatment with HCl in Step 6 results in complete deprotection to the pyridinone, after which reductive amination with the appropriate amine gives the final target.

| Ex | Name | Structure | ¹H NMR | LC/MS: (M + H)+; retention time (min); LC/MS Method of analysis | Int |
|---|---|---|---|---|---|
| 238 | 2-(4,4-difluoro-3-(5-(((2-hydroxyethyl)amino)methyl)-6-oxo-1,6-dihydropyridin-3-yl)piperidin-1-yl)-N-(5-(4-fluorophenoxy)pyridin-2-yl)propanamide | 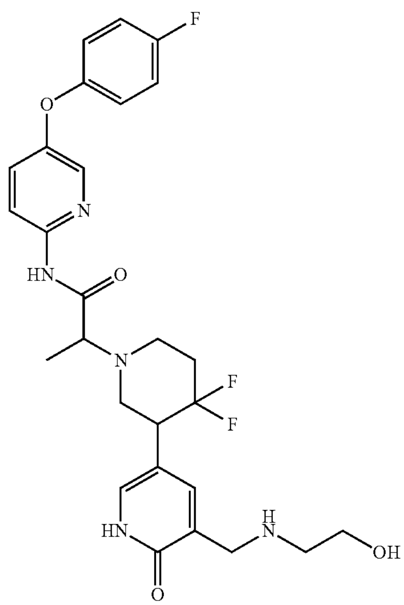 [SMILES: CC(C(=O)Nc1ccc(Oc2ccc(F)cc2)cn1)N1CCC(F)(F)C(c2c[nH]c(=O)c(CNCCO)c2)C1] | ¹H NMR (400 MHz, METHANOL-d₄) δ ppm 8.18 (d, J = 9.05 Hz, 1H), 8.09 (d, J = 2.93 Hz, 1H), 7.65 (d, J = 3.67 Hz, 1H), 7.48 (dd, J = 9.17, 3.06 Hz, 1H), 7.39 (s, 1H), 7.11-71.8 (m, 2H), 7.04-7.10 (m, 2H), 3.65-3.72 (m, 4H), 3.55 (qd, J = 6.93, 2.93 Hz, 1H), 3.35-3.42 (m, 1H), 2.61-3.08 (m, 6H), 2.14-2.36 (m, 2H), 1.37 (dd, J = 6.97, 1.59 Hz, 3H). | 546; rt 0.92, 0.94. LC/MS Method 3 | 70 |
| 239 | 2-(4,4-difluoro-3-(5-(((2-methoxyethyl)amino)methyl)-6-oxo-1,6-dihydropyridin-3-yl)piperidin-1-yl)-N-(5-(4-fluorophenoxy)pyridin-2-yl)propanamide | 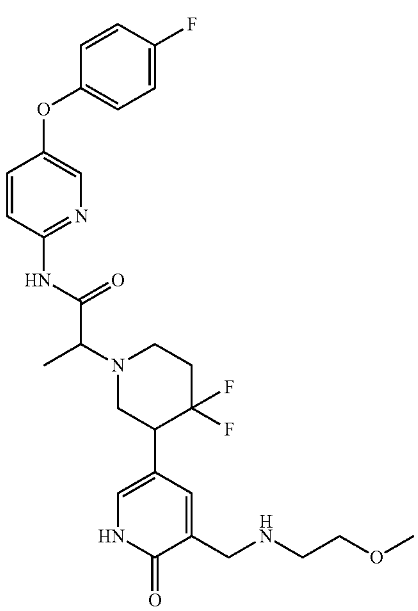 [SMILES: COCCNCc1cc(C2CN(C(C)C(=O)Nc3ccc(Oc4ccc(F)cc4)cn3)CCC2(F)F)c[nH]c1=O] | ¹H NMR (400 MHz, METHANOL-d₄) δ ppm 8.18 (d, J = 9.05 Hz, 1H), 8.08 (d, J = 2.69 Hz, 1H), 7.63 (d, J = 3.42 Hz, 1H), 7.47 (dd, J = 9.05, 2.93 Hz, 1H), 7.39 (t, J = 2.57 Hz, 1H), 7.11-7.19 (m, 2H), 7.03-7.10 (m, 2H), 3.67 (s, 2H), 3.48-3.59 (m, 3H), 3.34-3.41 (m, 3H), 2.63-3.08 (m, 6H), 2.13-2.39 (m, 2H), 1.37 (dd, J = 6.97, 1.59 Hz, 3H). | 560; rt 0.99, 1.01. LC/MS Method 3 | 70 |

| Ex | Name | Structure | ¹H NMR | LC/MS: (M + H)⁺; retention time (min); LC/MS Method of analysis | Int |
|---|---|---|---|---|---|
| 240 | (S)-N-(5-(2,4-difluorophe-noxy)pyridin-2-yl)-2-((S)-3-(5-((4,4-difluoropiper-idin-1-yl)methyl)-6-oxo-1,6-dihydropyridin-3-yl)-4,4-difluoropiper-idin-1-yl)propanamide | 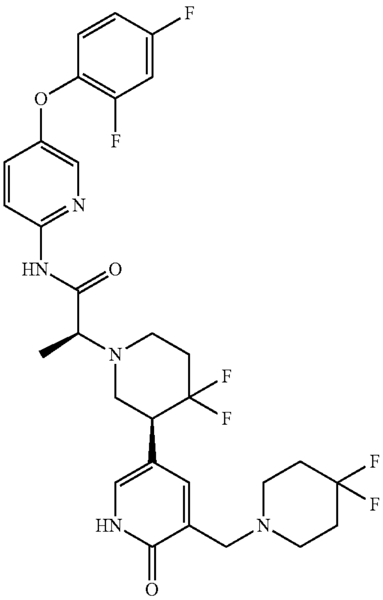 [SMILES: C[C@@H](C(=O)Nc1ccc(Oc2ccc(F)cc2F)cn1)N1CCC(F)(F)[C@@H](c2c[nH]c(=O)c(CN3CCC(F)(F)CC3)c2)C1] | ¹H NMR (400 MHz, METHANOL-d₄) δ ppm 8.17 (d, J = 9.05 Hz, 1H), 8.08 (d, J = 2.93 Hz, 1H), 7.70 (s, 1H), 7.44 (dd, J = 9.05, 3.18 Hz, 1H), 7.38 (d, J = 2.20 Hz, 1H), 7.15-7.29 (m, 2H), 6.98-7.08 (m, 1H), 3.55 (q, J = 6.93 Hz, 1H), 3.49 (s, 2H), 3.39 (m, 1H), 2.90-3.06 (m, 3H), 2.56-2.70 (m, 5H), 2.15-2.35 (m, 2H), 1.93-2.07 (m, 4H), 1.37 (d, J = 7.09 Hz, 3H). | 624; rt 1.16. LC/MS Method 3 | 71 |
| 241 | (S)-2-((S)-3-(5-(((3,3-difluorocyclo-butyl)amino)methyl)-6-oxo-1,6-dihydropyridin-3-yl)-4,4-difluoropiper-idin-1-yl)-N-(5-(2,4-difluorophe-noxy)pyridin-2-yl)propanamide | 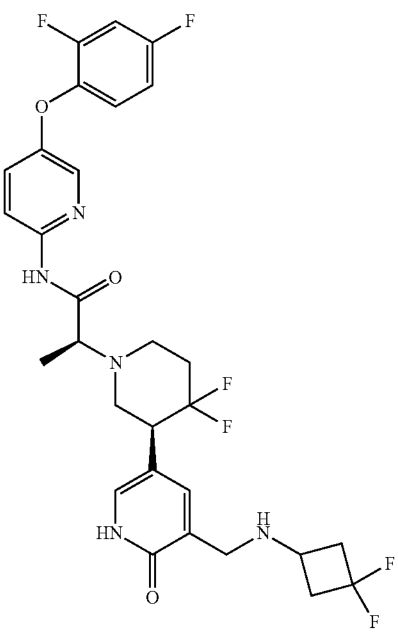 [SMILES: C[C@@H](C(=O)Nc1ccc(Oc2ccc(F)cc2F)cn1)N1CCC(F)(F)[C@@H](c2c[nH]c(=O)c(CNC3CC(F)(F)C3)c2)C1] | ¹H NMR (400 MHz, METHANOL-d₄) δ ppm 8.17 (d, J = 9.05 Hz, 1H), 8.08 (d, J = 2.93 Hz, 1H), 7.65 (s, 1H), 7.44 (dd, J = 9.05, 2.93 Hz, 1H), 7.39 (d, J = 2.20 Hz, 1H), 7.15-7.29 (m, 2H), 6.99-7.06 (m, 1H), 1H), 3.60 (s, 2H), 3.55 (q, J = 6.85 Hz, 1H), 3.38 (m, 1H), 3.18-3.26 (m, 1H), 2.91-3.03 (m, 3H), 2.60-2.82 (m, 3H), 2.17-2.44 (m, 4H), 1.37 (d, J = 6.85 Hz, 3H). | 610; rt 1.12. LC/MS Method 3 | 71 |

| Ex | Name | Structure | ¹H NMR | LC/MS: (M + H)⁺; retention time (min); LC/MS Method of analysis | Int |
|---|---|---|---|---|---|
| 242 | (S)-2-((S)-4,4-difluoro-3-(6-oxo-5-(((2,2,2-trifluoroethyl)amino)methyl)-1,6-dihydropyridin-3-yl)piperidin-1-yl)-N-(5-(2,4-difluorophenoxy)pyridin-2-yl)propanamide | 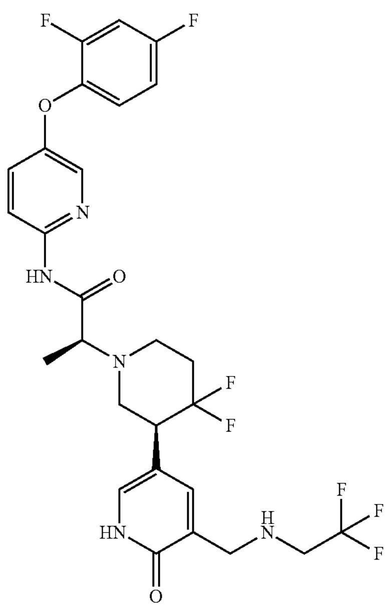 [SMILES: C[C@@H](C(=O)Nc1ccc(Oc2ccc(F)cc2F)cn1)N1CCC(F)(F)[C@@H](c2c[nH]c(=O)c(CNCC(F)(F)F)c2)C1] | ¹H NMR (400 MHz, METHANOL-d₄) δ ppm 8.17 (d, J = 9.05 Hz, 1H), 8.08 (d, J = 2.93 Hz, 1H), 7.68 (s, 1H), 7.44 (dd, J = 9.05, 2.93 Hz, 1H), 7.38 (d, J = 2.45 Hz, 1H), 7.15-7.29 (m, 2H), 7.03 (dddd, J = 9.23, 7.76, 2.93, 1.83 Hz, 1H), 3.74 (s, 2H), 3.56 (q, J = 6.85 Hz, 1H), 3.37 (m, 1H), 3.22 (q, J = 9.78 Hz, 2H), 2.90-3.05 (m, 3H), 2.65 (td, J = 11.68, 3.55 Hz, 1H), 2.15-2.34 (m, 2H), 1.37 (d, J = 6.85 Hz, 3H). | 602; rt 1.14. LC/MS Method 3 | 71 |
| 243 | (S)-2-((S)-4,4-difluoro-3-(5-((methylamino)methyl)-6-oxo-1,6-dihydropyridin-3-yl)piperidin-1-yl)-N-(5-(2,4-difluorophenoxy)pyridin-2-yl)propanamide | 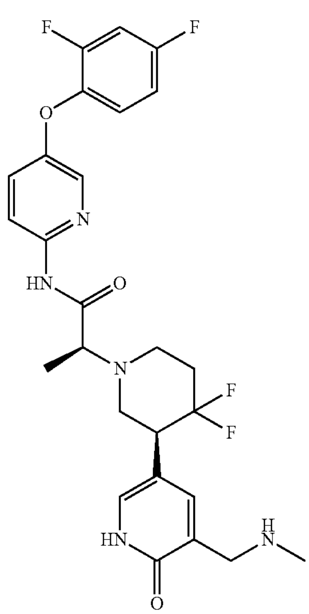 [SMILES: CNCc1cc([C@H]2CN([C@@H](C)C(=O)Nc3ccc(Oc4ccc(F)cc4F)cn3)CCC2(F)F)c[nH]c1=O] | ¹H NMR (400 MHz, METHANOL-d₄) δ ppm 8.17 (d, J = 9.29 Hz, 1H), 8.08 (d, J = 2.93 Hz, 1H), 7.55-7.78 (m, 1H), 7.44 (dd, J = 9.05, 3.18 Hz, 1H), 7.40 (d, J = 2.45 Hz, 1H), 7.13-7.34 (m, 2H), 7.03 (tdd, 1H), 3.65 (s, 2H), 3.55 (q, J = 6.85 Hz, 1H), 3.35-3.45 (m, 1H), 2.83-3.08 (m, 3H), 2.53-2.81 (m, 1H), 2.41 (s, 3H), 2.10-2.32 (m, 2H), 1.37 (d, J = 6.85 Hz, 3H). | 534; rt 0.96. LC/MS Method 3 | 71 |

| Ex | Name | Structure | ¹H NMR | LC/MS: (M + H)⁺; retention time (min); LC/MS Method of analysis | Int |
|---|---|---|---|---|---|
| 244 | (S)-2-((S)-4,4-difluoro-3-(5-((methylamino)methyl)-6-oxo-1,6-dihydropyridin-3-yl)piperidin-1-yl)-N-(5-(2,4-difluorophenoxy)pyrazin-2-yl)propanamide | 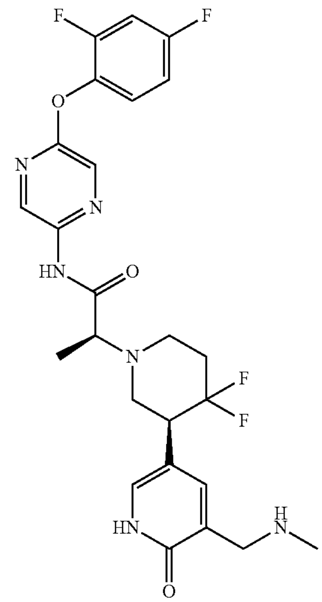 [SMILES: CNCc1cc([C@H]2CN([C@@H](C)C(=O)Nc3cnc(Oc4ccc(F)cc4F)cn3)CCC2(F)F)c[nH]c1=O] | ¹H NMR (400 MHz, METHANOL-d₄) δ ppm 8.88 (d, J = 1.47 Hz, 1H), 8.30 (d, J = 1.47 Hz, 1H), 7.64 (d, J = 1.47 Hz, 1H), 7.41 (d, J = 2.45 Hz, 1H), 7.34 (td, J = 8.93, 5.62 Hz, 1H), 7.16 (ddd, J = 10.76, 8.31, 2.93 Hz, 1H), 7.00-7.08 (m, 1H), 3.65 (s, 2H), 3.59 (q, J = 6.85 Hz, 1H), 3.22-3.31 (m, 1H), 2.92-3.07 (m, 3H), 2.66 (dt, J = 15.53, 5.69 Hz, 1H), 2.42 (s, 3H), 2.13-2.29 (m, 2H), 1.37 (d, J = 7.34 Hz, 3H). | 535; rt 0.93. LC/MS Method 3 | 65 |

Example 245

(S)-2-((S)-3-(5-(acetamidomethyl)-6-oxo-1,6-dihydropyridin-3-yl)-4,4-difluoropiperidin-1-yl)-N-(5-(4-fluorophenoxy)pyridin-2-yl)propanamide

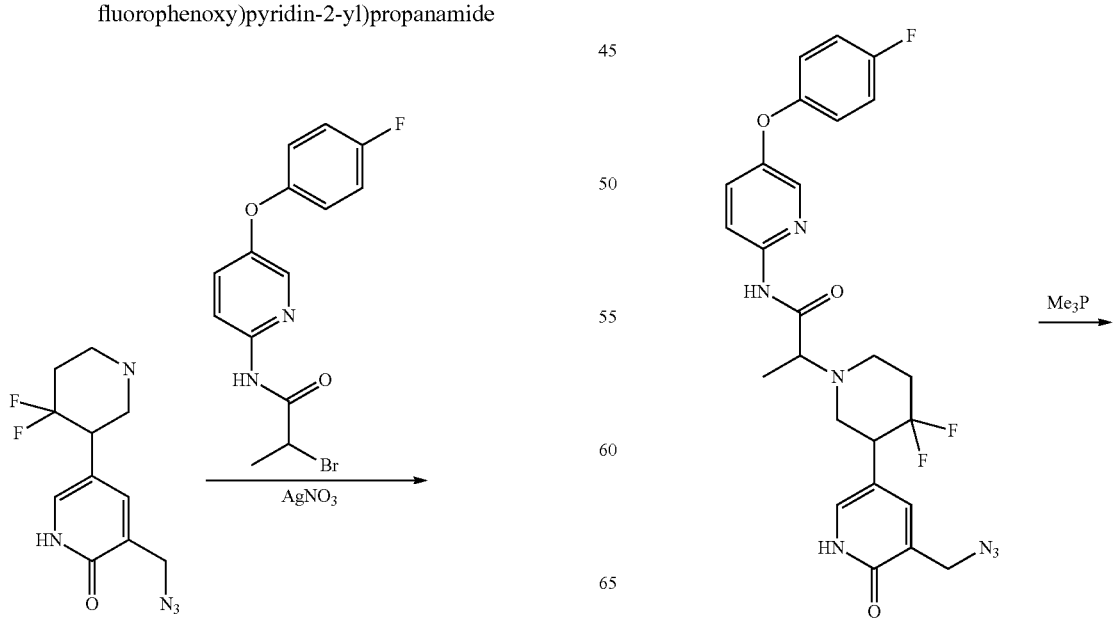

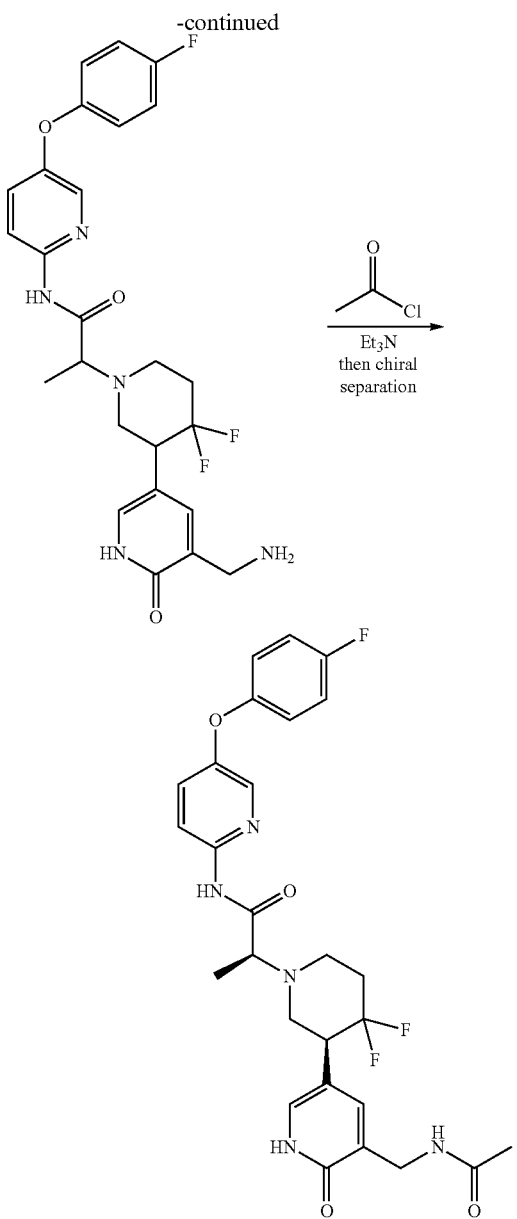

Step 1

Silver nitrate (44.5 mg, 0.262 mmol) was added to a mixture of 3-(azidomethyl)-5-(4,4-difluoropiperidin-3-yl)pyridin-2(1H)-one hydrochloride (Example 201, Step 2) (80 mg, 0.262 mmol), 2-bromo-N-(5-(4-fluorophenoxy)pyridin-2-yl)propanamide (Intermediate 70) (89 mg, 0.262 mmol) and Et₃N (0.073 mL, 0.523 mmol) in DMA (1.5 mL). The mixture was stirred at 40° C. overnight and partitioned between EtOAc and water. The organic phase was separated, and the aqueous phase was extracted with EtOAc (3×). The combined organic phases were washed with 5% LiCl and brine, dried over Na₂SO₄, filtered, concentrated and purified by normal phase chromatography (Combiflash, 24 g golden column, 35 ml/min), eluting with 0-8% MeOH in DCM to afford 94.8 mg (0.180 mmol, 68.7%) 2-(3-(5-(azidomethyl)-6-oxo-1,6-dihydropyridin-3-yl)-4,4-difluoropiperidin-1-yl)-N-(5-(4-fluorophenoxy)pyridin-2-yl)propanamide as a light-yellow foam. LCMS (ES, m/z): 528 [M+H]⁺. ¹H NMR (400 MHz, CHLOROFORM-d) δ ppm 12.30 (br.s., 1H), 9.55 (br.s., 1H), 8.24 (dd, J=9.05, 3.42 Hz, 1H), 8.09 (d, J=2.93 Hz, 1H), 7.50 (d, J=6.11 Hz, 1H), 7.33-7.41 (m, 2H), 7.04-7.11 (m, 2H), 6.96-7.03 (m, 2H), 4.35 (d, J=4.65 Hz, 2H), 3.42-3.55 (m, 1H), 3.09-3.32 (m, 1H), 2.97 (s, 3H), 2.60-2.76 (m, 1H), 2.15-2.37 (m, 2H), 1.41 (d, J=6.60 Hz, 3H).

Step 2

Trimethylphosphane (0.356 mL, 0.356 mmol) was added to 2-(3-(5-(azidomethyl)-6-oxo-1,6-dihydropyridin-3-yl)-4,4-difluoropiperidin-1-yl)-N-(5-(4-fluorophenoxy)pyridin-2-yl)propanamide (94 mg, 0.178 mmol) and water (0.016 mL, 0.891 mmol) in tetrahydrofuran (2 mL). After 30 min, the reaction was concentrated and purified by MDAP (XSelect CSH Prep C18 5 um OBD column, 30-85%, acetonitrile/water with 10 mM ammonium bicarb and 0.075% ammonium hydroxide, 40 mL/min flow rate, 17 min run time) to afford 77.6 mg (0.155 mmol, 87%) 2-(3-(5-(aminomethyl)-6-oxo-1,6-dihydropyridin-3-yl)-4,4-difluoropiperidin-1-yl)-N-(5-(4-fluorophenoxy)pyridin-2-yl)propanamide as a white, fluffy solid. LCMS (ES, m/z): 502 [M+H]⁺. ¹H NMR (400 MHz, METHANOL-d₄) δ ppm 8.18 (d, J=9.05 Hz, 1H), 8.09 (d, J=2.93 Hz, 1H), 7.61 (d, J=3.91 Hz, 1H), 7.48 (dd, J=9.05, 2.93 Hz, 1H), 7.37 (t, J=2.32 Hz, 1H), 7.11-7.19 (m, 2H), 7.04-7.10 (m, 2H), 3.67 (d, J=3.18 Hz, 2H), 3.51-3.59 (m, 1H), 3.21-3.31 (m, 1H), 2.74-3.07 (m, 4H), 2.14-2.37 (m, 2H), 1.37 (dd, J=6.97, 1.59 Hz, 3H).

Step 3

Acetyl chloride (9.22 µl, 0.130 mmol) was added to 2-(3-(5-(aminomethyl)-6-oxo-1,6-dihydropyridin-3-yl)-4,4-difluoropiperidin-1-yl)-N-(5-(4-fluorophenoxy)pyridin-2-yl)propanamide (65 mg, 0.130 mmol) and Et₃N (0.036 mL, 0.259 mmol) in dichloromethane (1.5 mL) at 0° C. The reaction was stirred for 30 min at 0° C., stirred at rt for 1 h, concentrated and purified by MDAP (XSelect CSH Prep C18 5 um OBD column, 30-85%, acetonitrile/water with 10 mM ammonium bicarb and 0.075% ammonium hydroxide, 40 mL/min flow rate, 17 min run time) to afford 66 mg (0.121 mmol, 94%) (S)-2-((S)-3-(5-(acetamidomethyl)-6-oxo-1,6-dihydropyridin-3-yl)-4,4-difluoropiperidin-1-yl)-N-(5-(4-fluorophenoxy)pyridin-2-yl)propanamide as a white, fluffy solid as a mixture of diastereomers. This material was separated by a chiral SFC 80 instrument: Column: Chiralpak CCC, 30×250 mm, 5 µm; Co-solvent: 20% MeOH; Flow rate: 65 g/min; giving peaks with retention times of RT1: 15.1-17.6; RT2: 18.8-20.3; RT3: 20.9-23.2; and RT4: 23.8-28.0. The third peak (RT3-RT3: 20.9-23.2), was concentrated to give 13.1 mg (S)-2-((S)-3-(5-(acetamidomethyl)-6-oxo-1,6-dihydropyridin-3-yl)-4,4-difluoropiperidin-1-yl)-N-(5-(4-fluorophenoxy)pyridin-2-yl)propanamide. LCMS (ES, m/z): 544 [M+H]⁺, rt=0.94 min, Method 3. ¹H NMR (400 MHz, METHANOL-d₄) δ ppm 8.18 (d, J=9.05 Hz, 1H), 8.09 (d, J=2.69 Hz, 1H), 7.54 (s, 1H), 7.48 (dd, J=9.05, 2.93 Hz, 1H), 7.37 (d, J=2.20 Hz, 1H), 7.11-7.18 (m, 2H), 7.04-7.10 (m, 2H), 4.22 (d, J=2.20 Hz, 2H), 3.55 (q, J=7.09 Hz, 1H), 3.37 (m, 1H), 2.89-3.04 (m, 3H), 2.65 (m, 1H), 2.15-2.33 (m, 2H), 2.01 (s, 3H), 1.37 (d, J=7.09 Hz, 3H).

Example 246

(S)—N-(5-(4-fluorophenoxy)pyridin-2-yl)-2-((S)-3-(5-(methylsulfonyl)-6-oxo-1,6-dihydropyridin-3-yl)piperidin-1-yl)propanamide and (R)—N-(5-(4-fluorophenoxy)pyridin-2-yl)-2-((R)-3-(5-(methylsulfonyl)-6-oxo-1,6-dihydropyridin-3-yl)piperidin-1-yl)propanamide (1:1 Mixture)

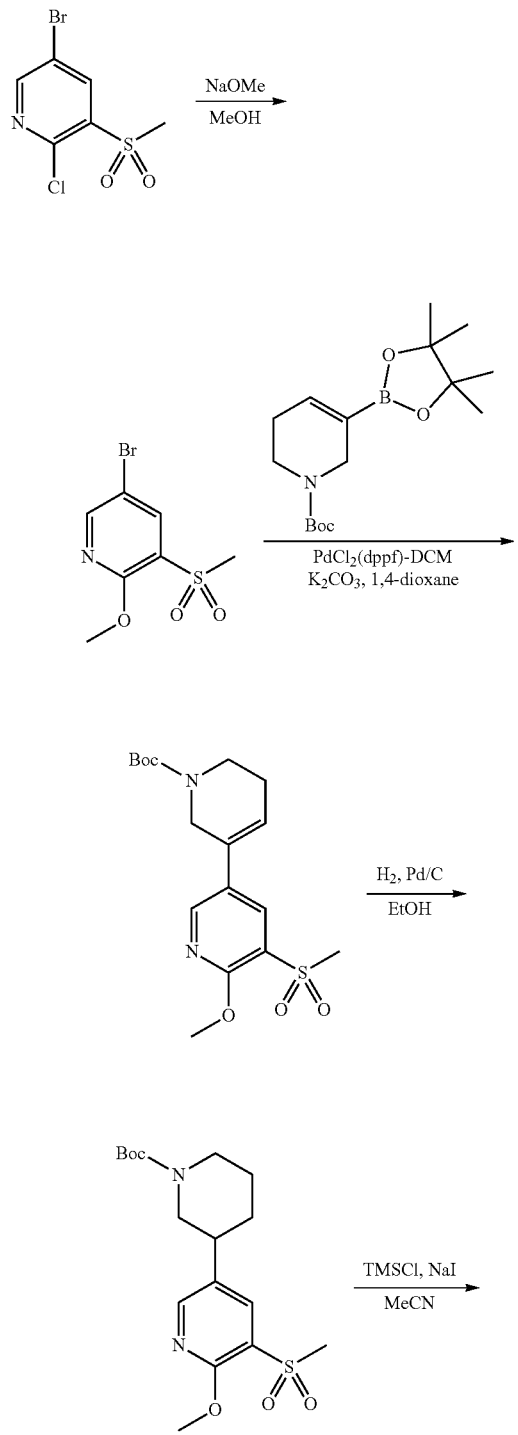
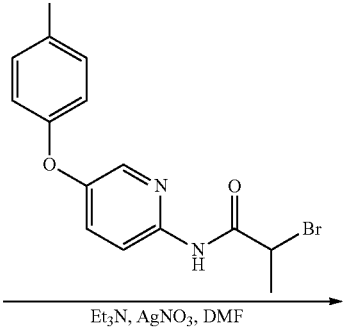

Step 1

To 5-bromo-2-chloro-3-(methylsulfonyl)pyridine (0.2 g, 0.739 mmol) in methanol (2.5 ml) was added sodium methoxide (25 wt % in MeOH, 0.2 ml, 0.875 mmol). After 90 min, additional sodium methoxide (25 wt % in MeOH, 0.2 ml, 0.875 mmol) was added. After 1 h, the reaction was concentrated, diluted with ethyl acetate, washed with 1 N aq. HCl and brine, dried over sodium sulfate, filtered, concentrated and purified by silica gel chromatography (ISCO Combiflash), eluting with 10-70% ethyl acetate in heptanes to give 105 mg (yield: 50.2%) 5-bromo-2-methoxy-3-(methylsulfonyl)pyridine as a white solid. LCMS: (ES, m/s) 266 [M+H]+, rt=0.64 min, Method 5. $^1$H NMR (400 MHz, CHLOROFORM-d) δ ppm 8.44 (d, J=2.45 Hz, 1H), 8.36 (d, J=2.45 Hz, 1H), 4.13 (s, 3H), 3.24 (s, 3H).

Step 2

5-Bromo-2-methoxy-3-(methylsulfonyl)pyridine (0.1 g, 0.376 mmol), tert-butyl 5-(4,4,5,5-tetramethyl-1,3,2-dioxaborolan-2-yl)-3,6-dihydropyridine-1(2H)-carboxylate (0.110 g, 0.356 mmol), K$_2$CO$_3$ (0.12 g, 0.868 mmol), and PdCl$_2$(dppf)-CH$_2$Cl$_2$ adduct (10 mg, 0.012 mmol) in a sealed vessel were purged with nitrogen (2×). Dioxane (1.2 ml) and water (0.120 ml) were added. The vessel was purged again with nitrogen (3×), heated to 100° C. overnight, quenched with water and extracted with ethyl acetate (2×). The combined organics were washed with brine, dried over sodium sulfate, filtered, concentrated and purified by silica gel chromatography (ISCO Combiflash), eluting with 10-70% 3:1 EtOAc: EtOH in heptanes to give 126 mg (yield: 89%) tert-butyl 6'-methoxy-5'-(methylsulfonyl)-5,6-dihydro-[3,3'-bipyridine]-1 (2H)-carboxylate. LCMS: (ES, m/s) $^1$H NMR (400 MHz, CHLOROFORM-d) δ ppm 8.36 (d, J=2.45 Hz, 1H), 8.26 (d, J=2.45 Hz, 1H), 6.24 (tt, J=4.10, 2.02 Hz, 1H), 4.24 (br s, 2H), 4.14 (s, 3H), 3.56 (t, J=5.62 Hz, 2H), 3.25 (s, 3H), 2.34 (br d, J=4.40 Hz, 2H), 1.51 (s, 9H), Step 3

A mixture of tert-butyl 6'-methoxy-5'-(methylsulfonyl)-5,6-dihydro-[3,3'-bipyridine]-1 (2H)-carboxylate (0.12 g, 0.326 mmol) and 10 wt % degussa of Pd—C (0.035 g, 0.033 mmol) in ethanol (3.26 ml) was evacuated and flushed with hydrogen via balloon (3×) before stirring under a hydrogen balloon over the weekend. The reaction was filtered through Celite (rinsing with ethyl acetate) and concentrated to give 124 mg (yield: 89%) tert-butyl 3-(6-methoxy-5-(methylsulfonyl)pyridin-3-yl)piperidine-1-carboxylate as a golden oil, which was used without further purification. LCMS (ES, m/s): [M+H]+ $^1$H NMR (400 MHz, CHLOROFORM-d) δ=8.28 (d, J=2.4 Hz, 1H), 8.12 (d, J=2.4 Hz, 1H), 4.12 (s, 3H), 3.24 (s, 3H), 2.75 (br d, J=7.3 Hz, 3H), 2.03-1.97 (m, 1H), 1.83-1.73 (m, 1H), 1.66-1.56 (m, 3H), 1.48 (s, 10H)

Step 4

To tert-butyl 3-(6-methoxy-5-(methylsulfonyl)pyridin-3-yl)piperidine-1-carboxylate (0.12 g, 0.324 mmol) in acetonitrile (1.0 ml) was added sodium iodide (0.097 g, 0.648 mmol), followed by TMS-Cl (0.083 ml, 0.648 mmol). After 30 min the reaction was concentrated and purified by reverse phase C$_{18}$ chromatography (ISCO Combiflash), eluting with 10% AcCN in H$_2$O with 0.1% NH$_4$OH to give 87 mg (yield: 94%) 3-(methylsulfonyl)-5-(piperidin-3-yl)pyridin-2 (1H)-one as a white solid. LCMS: (ES, m/s): 257 [M+H]$^+$, rt=0.31 min, Method 3. $^1$H NMR (400 MHz, DMSO-d$_6$) δ ppm 8.06 (d, J=2.45 Hz, 1H), 7.71 (d, J=2.93 Hz, 1H), 3.24 (s, 3H), 3.14 (br t, J=10.52 Hz, 2H), 2.80-2.90 (m, 1H), 2.69-2.79 (m, 2H), 1.76-1.83 (m, 2H), 1.54-1.67 (m, 2H).

Step 5

To crude 3-(methylsulfonyl)-5-(piperidin-3-yl)pyridin-2 (1H)-one (0.066 g, 0.257 mmol) in DMF (1.200 ml) was added 2-bromo-N-(5-(4-fluorophenoxy)pyridin-2-yl)propanamide (Intermediate 70) (0.096 g, 0.283 mmol), silver nitrate (0.044 g, 0.257 mmol) and TEA (0.072 ml, 0.515 mmol). The reaction was heated to 40° C. overnight, cooled to rt, quenched with water and extracted with ethyl acetate (3×). The combined organics were washed with brine, dried over sodium sulfate, filtered, concentrated and purified by reverse phase HPLC using a Waters MDAP, eluting with 15-85% AcCN in H$_2$O with 0.1% TFA to give 10.2 mg (0.015 mmol, 5.99% yield) of a 1:1 racemic mixture of (S)—N-(5-(4-fluorophenoxy)pyridin-2-yl)-2-((S)-3-(5-(methylsulfonyl)-6-oxo-1,6-dihydropyridin-3-yl)piperidin-1-yl)propanamide and (R)—N-(5-(4-fluorophenoxy)pyridin-2-yl)-2-((R)-3-(5-(methylsulfonyl)-6-oxo-1,6-dihydropyridin-3-yl)piperidin-1-yl)propanamide as the trifluoroacetic acid salt. LCMS: (ES, m/z): 515 [M+H]+, rt=0.67 min, Method 5. $^1$H NMR (400 MHz, CHLOROFORM-d) δ ppm 8.31 (br d, J=9.29 Hz, 1H), 8.20 (s, 1H), 7.95 (d, J=2.45 Hz, 1H), 7.85 (br s, 1H), 7.69 (dd, J=9.29, 2.45 Hz, 1H), 7.09-7.15 (m, 2H), 7.00-7.05 (m, 2H), 4.33-4.42 (m, 1H), 3.85-3.95 (m, 1H), 3.64 (br d, J=10.27 Hz, 1H), 3.34-3.44 (m, 1H), 3.23 (s, 4H), 2.99-3.10 (m, 1H), 2.07-2.24 (m, 2H), 2.03 (br d, J=12.72 Hz, 1H), 1.66-1.83 (m, 4H).

Example 247

(S)—N-(5-(4-fluorophenoxy)pyridin-2-yl)-2-((S)-3-(5-(N-methylsulfamoyl)-6-oxo-1,6-dihydropyridin-3-yl)piperidin-1-yl)propanamide and (R)—N-(5-(4-fluorophenoxy)pyridin-2-yl)-2-((R)-3-(5-(N-methylsulfamoyl)-6-oxo-1,6-dihydropyridin-3-yl)piperidin-1-yl)propanamide (1:1 Mixture)

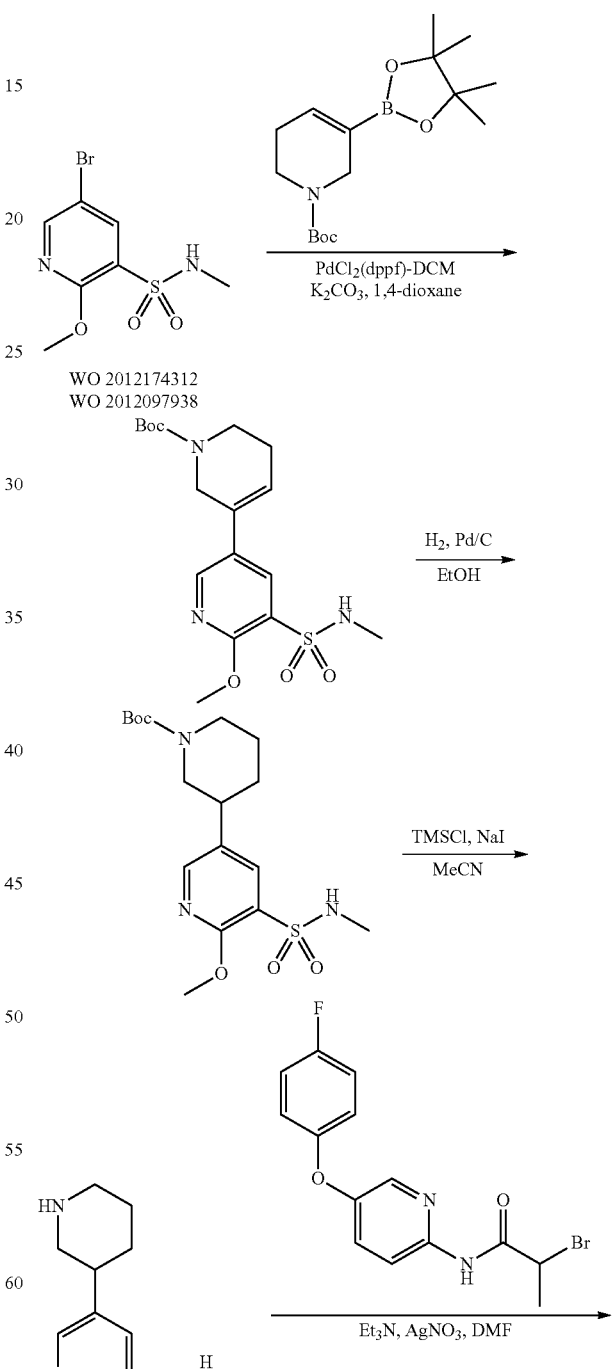

WO 2012174312
WO 2012097938

461

-continued

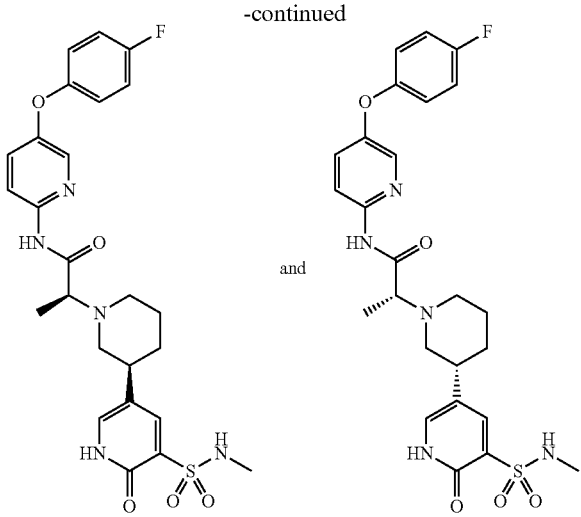

Step 1

A mixture of 5-bromo-2-methoxy-N-methylpyridine-3-sulfonamide (0.118 g, 0.420 mmol), tert-butyl 5-(4,4,5,5-tetramethyl-1,3,2-dioxaborolan-2-yl)-3,6-dihydropyridine-1 (2H)-carboxylate (0.169 g, 0.546 mmol), $K_2CO_3$ (0.174 g, 1.259 mmol), and $PdCl_2(dppf)\cdot CH_2Cl_2$ adduct (3.43 mg, 4.20 μmol) in a sealed vessel were purged with nitrogen (2×). Dioxane (2 ml) and water (0.200 ml) were added, and the vessel was purged again with nitrogen (3×), heated to 100° C. overnight, quenched with water, then extracted with ethyl acetate (3×). The combined organics were washed with brine, dried over sodium sulfate, filtered, concentrated and purified by silica gel chromatography (ISCO Combiflash), eluting with 10-70% EtOAc in heptanes to give 71 mg (yield: 44.1%) tert-butyl 6'-methoxy-5'-(N-methylsulfamoyl)-5,6-dihydro-[3,3'-bipyridine]-1 (2H)-carboxylate as a white solid. LCMS (ES, m/z): [M+H]+. $^1$H NMR (400 MHz, CHLOROFORM-d) δ ppm 8.32 (d, J=2.45 Hz, 1H), 8.20 (d, J=2.45 Hz, 1H), 6.24 (dt, J=4.04, 2.14 Hz, 1H), 4.85 (q, J=5.05 Hz, 1H), 4.25 (br s, 2H), 4.12 (s, 3H), 3.57 (t, J=5.62 Hz, 2H), 2.65 (d, J=5.38 Hz, 3H), 2.34 (br d, J=3.42 Hz, 2H), 1.51 (s, 9H).

Step 2

A mixture of tert-butyl 6'-methoxy-5'-(N-methylsulfamoyl)-5,6-dihydro-[3,3'-bipyridine]-1 (2H)-carboxylate (0.07 g, 0.183 mmol) and 10 wt % degussa of Pd—C (0.019 g, 0.018 mmol) in ethanol (2 ml) was evacuated and flushed with hydrogen via balloon (3×). The reaction was stirred under a hydrogen balloon overnight, filtered through Celite (rinsing with EtOAc) and concentrated to give 72 mg (yield: 92%) tert-butyl 3-(6-methoxy-5-(N-methylsulfamoyl)pyridin-3-yl)piperidine-1-carboxylate as a colorless oil, which was used without further purification. LCMS (ES, m/z): [M+H]+. $^1$H NMR (400 MHz, CHLOROFORM-d) δ ppm 8.21 (t, J=1.96 Hz, 1H), 8.04 (d, J=2.45 Hz, 1H), 4.97 (br s, 1H), 4.09-4.15 (m, 2H), 4.08 (d, J=1.47 Hz, 3H), 2.73 (br s, 3H), 2.58-2.64 (m, 3H), 1.97-2.02 (m, 1H), 1.77 (br d, J=9.78 Hz, 1H), 1.54-1.69 (m, 2H), 1.46 (d, J=1.47 Hz, 9H).

Step 3

To tert-butyl 3-(6-methoxy-5-(N-methylsulfamoyl)pyridin-3-yl)piperidine-1-carboxylate (0.07 g, 0.182 mmol) in acetonitrile (1.0 ml) was added sodium iodide (0.066 g, 0.440 mmol), followed by TMS-Cl (0.05 ml, 0.391 mmol). The reaction was stirred overnight, concentrated, diluted with EtOAc, washed with sat. $NHCO_3$, dried over sodium sulfate, filtered, concentrated and purified by C-18 silica gel chromatography (ISCO Combiflash), eluting with 10% AcCN in $H_2O$ with 0.1% $NH_4OH$ to give 28 mg (0.103 mmol, 56.8% yield) N-methyl-2-oxo-5-(piperidin-3-yl)-1,2-dihydropyridine-3-sulfonamide as a white solid. LCMS (ES, m/z): 272 [M+H]+.

Step 4

To crude N-methyl-2-oxo-5-(piperidin-3-yl)-1,2-dihydropyridine-3-sulfonamide (0.028 g, 0.103 mmol) in DMF (0.7 mL) was added 2-bromo-N-(5-(4-fluorophenoxy)pyridin-2-yl)propanamide (Intermediate 70) (0.042 g, 0.124 mmol), silver nitrate (0.018 g, 0.103 mmol), and TEA (0.03 mL, 0.215 mmol). The reaction was heated to 40° C. overnight, cooled to rt, quenched with water and extracted with ethyl acetate (3×). The combined organics were washed with brine, dried over sodium sulfate, filtered, concentrated and purified by silica gel chromatography (ISCO Combiflash), eluting with 2-10% DCM in MeOH to give partially pure product. This material was further purified by reverse phase C18 Waters MDAP, eluting with 15-85% AcCN in $H_2O$ with 0.1% TFA to give 6.8 mg (10.46 μmol, 10.14% yield) of a 1:1 racemic mixture of (S)—N-(5-(4-fluorophenoxy)pyridin-2-yl)-2-((S)-3-(5-(N-methylsulfamoyl)-6-oxo-1,6-dihydropyridin-3-yl)piperidin-1-yl)propanamide and (R)—N-(5-(4-fluorophenoxy)pyridin-2-yl)-2-((R)-3-(5-(N-methylsulfamoyl)-6-oxo-1,6-dihydropyridin-3-yl)piperidin-1-yl)propanamide as the TFA salt. LCMS (ES, m/z): 530 [M+H]+, rt=0.69 min Method 5. $^1$H NMR (400 MHz, CHLOROFORM-d) δ ppm 8.26 (br d, J=8.80 Hz, 1H), 8.18 (br s, 1H), 8.03 (d, J=2.45 Hz, 1H), 7.71 (br s, 1H), 7.48 (dd, J=9.05, 2.69 Hz, 1H), 7.05-7.12 (m, 2H), 6.95-7.04 (m, 2H), 4.68 (br dd, J=5.14, 2.20 Hz, 1H), 3.89 (br d, J=7.83 Hz, 1H), 3.58-3.70 (m, 1H), 3.27-3.44 (m, 3H), 3.01-3.09 (m, 1H), 2.14-2.25 (m, 1H), 2.62 (s, 3H), 2.03-2.11 (m, 2H), 1.69 (br d, J=6.36 Hz, 3H).

Example 248

(S)-2-((S)-3,3-difluoro-5-(6-oxo-1,6-dihydropyridin-3-yl)piperidin-1-yl)-N-(5-fluoropyridin-2-yl)propanamide and (R)-2-((R)-3,3-difluoro-5-(6-oxo-1,6-dihydropyridin-3-yl)piperidin-1-yl)-N-(5-fluoropyridin-2-yl)propanamide

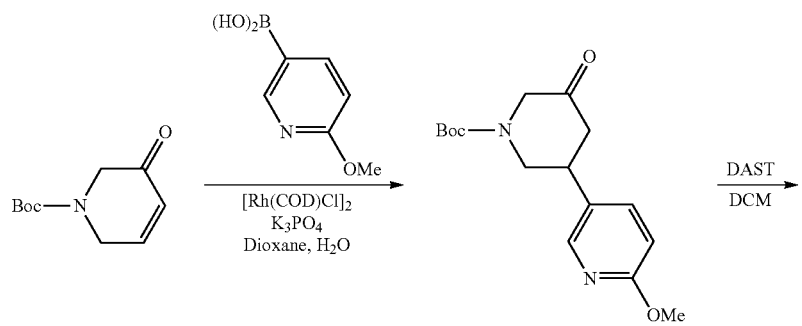

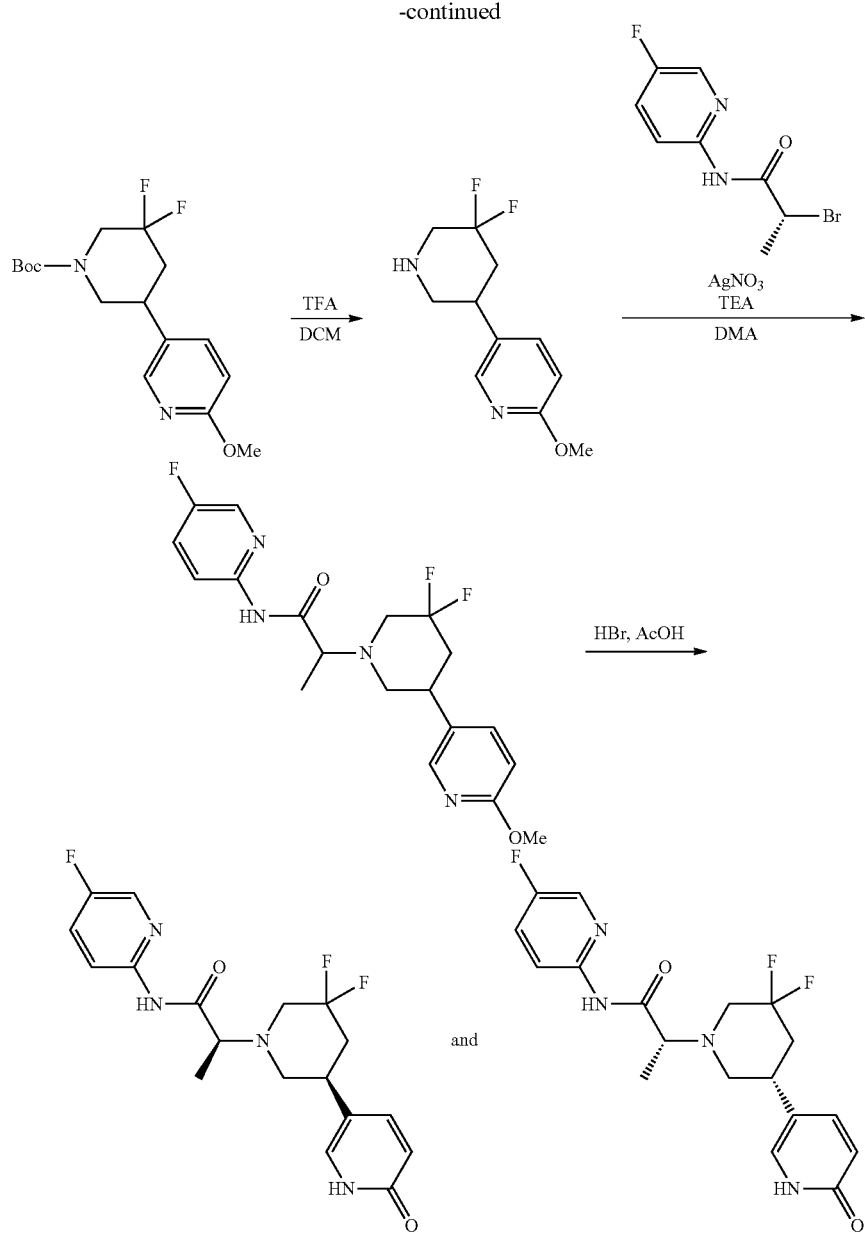

Step 1

A mixture of tert-butyl 3-oxo-3,6-dihydropyridine-1(2H)-carboxylate (1.00 g, 5.09 mmol, 1.00 eq), (6-methoxypyridin-3-yl)boronic acid (1.56 g, 10.2 mmol, 2.00 eq), and chloro(1,5-cyclooctadiene)rhodium(I) dimer (0.0696 g, 0.141 mmol, 0.0277 eq) in dioxane (27 mL) was degassed with nitrogen for 20 minutes, then treated with a degassed solution of $K_3PO_4$ (4.46 g, 21.0 mmol, 4.12 eq) in water (31 mL). The resulting mixture was stirred at 60° C. for 15 h, concentrated, redissolved in DCM and filtered. The filtrate was concentrated and loaded onto a silica gel column, eluting with 0-50% EtOAc in heptane to give 0.743 g (purity: 99%, yield: 47.7%) of tert-butyl 3-(6-methoxypyridin-3-yl)-5-oxopiperidine-1-carboxylate as a yellow solid. LCMS: (ES, m/z) 307 [M+H]+. $^1$H NMR: (400 MHz, DMSO-$d_6$) δ 8.06 (br s, 1H), 7.74-7.55 (m, 1H), 6.82 (d, J=8.3 Hz, 1H), 4.09-3.92 (m, 2H), 3.83 (s, 3H), 3.60-3.43 (m, 1H), 3.31 (s, 1H), 2.90-2.71 (m, 1H), 2.71-2.62 (m, 1H), 2.37-2.30 (m, 1H), 1.34 (br d, J=2.0 Hz, 9H).

Step 2

A solution of tert-butyl 3-(6-methoxypyridin-3-yl)-5-oxopiperidine-1-carboxylate (0.742 g, 2.43 mmol, 1.00 eq) in DCM (25 ml) at 0° C. was treated with DAST (0.96 mL, 7.3 mmol, 3.0 eq), and the resulting mixture was stirred for 30 min, quenched with sat'd. aqueous $NaHCO_3$ (40 mL) at 0° C. and extracted with ethyl acetate (3×30 mL). The combined organic layers were washed with brine (30 mL), dried over $MgSO_4$, filtered, concentrated, and loaded onto a silica gel column, eluting with 0-50% ethyl acetate in heptane to give 0.633 g (purity: 91%, yield: 72.3%) of tert-butyl 3,3-difluoro-5-(6-methoxypyridin-3-yl)piperidine-1-carboxylate as a white solid. LCMS: (ES, m/z) 329 [M+H]+. $^1$H NMR: (400 MHz, DMSO-$d_6$) δ 8.15 (d, J=2.0 Hz, 1H), 7.73 (dd, J=8.8, 2.4 Hz, 1H), 6.82 (d, J=8.3 Hz, 1H), 4.30-4.08 (br m, 1H), 4.05-3.87 (br m, 1H), 3.84 (s, 3H), 3.49-3.15 (br s, 1H), 2.93 (br s, 2H), 2.40-2.21 (m, 2H), 1.42 (s, 9H).

Step 3

A solution of tert-butyl 3,3-difluoro-5-(6-methoxypyridin-3-yl)piperidine-1-carboxylate (0.619 g, 1.89 mmol, 1.00 eq) in DCM (8 ml) was treated with TFA (2 mL, 26 mmol, 13.8 eq), and the resulting mixture was stirred at 25° C. for 2 h and concentrated. The crude residue, 5-(5,5-difluoropiperidin-3-yl)-2-methoxypyridine, was taken onto the next step without further purification. LCMS (ES, m/z): 229 [M+H]$^+$.

Step 4

Crude 5-(5,5-difluoropiperidin-3-yl)-2-methoxypyridine (1.89 mmol, 1.00 eq) in DMA (3 mL) was treated with silver nitrate (321 mg, 1.89 mmol, 1.00 eq), (R)-2-bromo-N-(5-fluoropyridin-2-yl)propanamide (Intermediate 1) (469 mg, 1.90 mmol, 1.01 eq) and triethylamine (1.0 mL, 7.2 mmol, 3.8 eq). The resulting mixture was stirred at 60° C. for 15 h. Additional reagents, (R)-2-bromo-N-(5-fluoropyridin-2-yl)propanamide (468 mg, 1.23 mmol) and triethylamine (1.5 mL, 3.6 mmol), were added portionwise over the next 7 h, and the mixture was stirred at 60° C. for 26 h. The reaction was purified by reverse phase HPLC (Column XSelect CSH Prep OBD C18 30×150 mm, 5 μm OBD); Mobile Phase A: water (0.1% TFA), Mobile Phase B: MeCN (0.1% TFA); Flow Rate 40 mL/min; Gradient 30% B to 99% B over 17 min). Two diastereomers with retention times 8.81 and 9.46 minutes were separated and concentrated. The second peak (9.46 min) was collected to give 254 mg (purity: 98%, 34% yield) of (2S)-2-(3,3-difluoro-5-(6-methoxypyridin-3-yl)piperidin-1-yl)-N-(5-fluoropyridin-2-yl)propanamide as a brown oil. LCMS (ES, m/s): 395 [M+H]$^+$. $^1$H NMR: (400 MHz, DMSO-d$_6$) δ 10.36 (s, 1H), 8.36 (d, J=2.9 Hz, 1H), 8.24-8.14 (m, 2H), 7.86-7.70 (m, 2H), 6.81 (d, J=8.8 Hz, 1H), 3.83 (s, 3H), 3.75 (br d, J=6.8 Hz, 1H), 3.12 (td, J=7.3, 4.9 Hz, 2H), 3.00 (br d, J=11.2 Hz, 1H), 2.86-2.70 (m, 1H), 2.70-2.60 (m, 1H), 2.30-2.11 (m, 2H), 1.25 (d, J=6.8 Hz, 3H).

Step 5

A solution of (2S)-2-(3,3-difluoro-5-(6-methoxypyridin-3-yl)piperidin-1-yl)-N-(5-fluoropyridin-2-yl)propanamide (200 mg, 0.321 mmol, 1.00 eq) and 33% HBr in acetic acid (4 mL) was stirred at 90° C. for 5 h. The mixture was quenched with water (20 mL) and satd. aqueous NaHCO$_3$ solution (50 mL), then extracted with DCM (3×50 mL). The combined organic phases were dried over MgSO$_4$, filtered, concentrated and loaded onto a silica gel column, eluting with 0-20% MeOH in DCM to give 112 mg (purity: 96%, yield: 92%) of an enantiomeric mixture of (S)-2-((S)-3,3-difluoro-5-(6-oxo-1,6-dihydropyridin-3-yl)piperidin-1-yl)-N-(5-fluoropyridin-2-yl)propanamide and (R)-2-((R)-3,3-difluoro-5-(6-oxo-1,6-dihydropyridin-3-yl)piperidin-1-yl)-N-(5-fluoropyridin-2-yl)propanamide as a white solid. LCMS: (ES, m/z) 381 [M+H]$^+$, rt=0.68, Method 5. Analytical Chiral HPLC (Column: CCO-F4, 4.6×150 mm, 5 μm; Mobile Phase: 60:40:0.1 Heptane:Ethanol:Isopropylamine; Flow Rate: 1.5 mL/min): 4.0 min and 4.67 min. $^1$H NMR: (400 MHz, CDCl$_3$) δ 9.74 (br s, 1H), 8.29 (dd, J=9.3, 3.9 Hz, 1H), 8.21 (d, J=2.9 Hz, 1H), 7.54-7.47 (m, 2H), 7.37 (d, J=1.5 Hz, 1H), 6.73 (d, J=9.8 Hz, 1H), 3.60-3.52 (m, 1H), 3.24 (br t, J=11.2 Hz, 1H), 3.13-2.95 (m, 1H), 2.66-2.53 (m, 2H), 2.49-2.39 (m, 1H), 1.95-1.77 (m, 2H), 1.37 (d, J=6.8 Hz, 3H).

Example 249

2-(3-(5-cyano-6-oxo-1,6-dihydropyridin-3-yl)-4,4-difluoropiperidin-1-yl)-N-(5-fluoropyridin-2-yl)propanamide

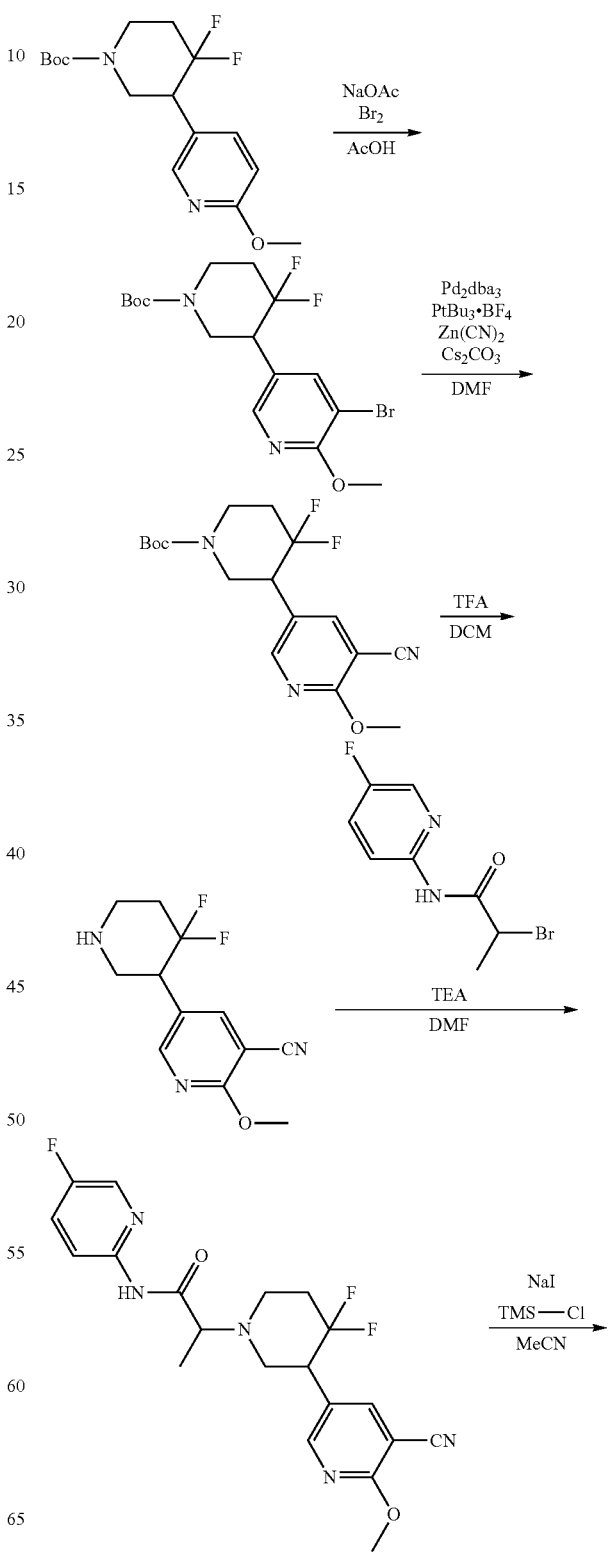

-continued

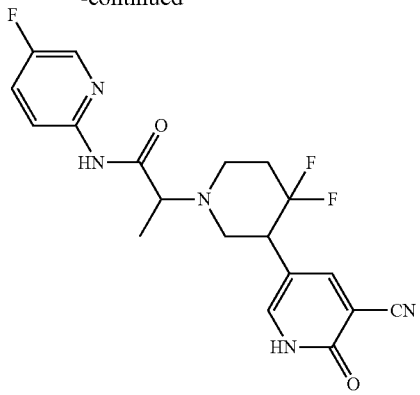

Step 1

To tert-butyl 4,4-difluoro-3-(6-methoxypyridin-3-yl)piperidine-1-carboxylate (Example 4, Step 2) (374 mg, 1.14 mmol) and sodium acetate (280 mg, 3.42 mmol) in acetic acid (5 ml), bromine (0.12 ml, 2.28 mmol) was added, and the reaction was stirred overnight. An additional equivalent of bromine was added, and after 6 h the mixture was partitioned between ethyl acetate and water. The organic layer was isolated, washed with 2M aq. sodium carbonate and 10% $Na_2S_2O_3$, dried over sodium sulfate, filtered, concentrated and purified by flash chromatography (24 g Isco Gold), eluting with 0-60% EtOAc in heptane to give 410 mg (0.96 mmol, 84% yield) tert-butyl 3-(5-bromo-6-methoxypyridin-3-yl)-4,4-difluoropiperidine-1-carboxylate as a white solid. LCMS (ES, m/s): 407.2, 409.2 [M+H]$^+$. $^1$H NMR (400 MHz, METHANOL-$d_4$) δ 8.06 (d, J=2.0 Hz, 1H), 7.92 (d, J=1.0 Hz, 1H), 4.33-4.06 (m, 2H), 3.98 (s, 3H), 3.27-3.05 (m, 2H), 2.28-1.89 (m, 2H), 1.47 (s, 9H).

Step 2

To cesium carbonate (164 mg, 0.50 mmol), $Pd_2(dba)_3$ (92 mg, 0.10 mmol), tri-tert-butylphosphonium tetrafluoroborate (117 mg, 0.40 mmol) and dicyanozinc (142 mg, 1.21 mmol) in a microwave vial was added tert-butyl 3-(5-bromo-6-methoxypyridin-3-yl)-4,4-difluoropiperidine-1-carboxylate (410 mg, 1.01 mmol) in DMF (10 mL). The reaction vessel was sealed, evacuated, purged with nitrogen (5×), heated to 100° C. for 1 h, then stirred at rt overnight. The reaction was filtered through Celite (rinsing with EtOAc), concentrated and purified by reverse phase flash chromatography (100 g C18 Gold, 60 mL/min, 45 to 80% MeCN in water with 10 mM ammonium bicarbonate adjusted to pH 10 with ammonia) to give 344 mg (0.83 mmol, 82% yield) tert-butyl 3-(5-cyano-6-methoxypyridin-3-yl)-4,4-difluoropiperidine-1-carboxylate as a yellow solid. LCMS (ES, m/s): 354.2 [M+H]$^+$. $^1$H NMR (400 MHz, DICHLOROMETHANE-$d_2$) δ 8.28 (d, J=2.4 Hz, 1H), 7.87 (d, J=1.5 Hz, 1H), 4.34-4.12 (m, 2H), 4.05 (s, 3H), 3.33-3.00 (m, 4H), 2.24-1.88 (m, 2H), 1.70-1.53 (m, 1H), 1.51-1.41 (m, 9H).

Step 3

To tert-butyl 3-(5-cyano-6-methoxypyridin-3-yl)-4,4-difluoropiperidine-1-carboxylate (100 mg, 0.28 mmol) in DCM (1 mL) was added TFA (1 mL). After 30 min, the reaction was azeotroped with toluene to give 111 mg (0.24 mmol, 85% yield) 5-(4,4-difluoropiperidin-3-yl)-2-methoxynicotinonitrile, trifluoroacetic acid salt as an off white solid. LCMS (ES, m/s): 254.1 [M+H]$^+$. $^1$H NMR (400 MHz, METHANOL-$d_4$) δ 8.40 (d, J=2.4 Hz, 1H), 8.15 (dd, J=2.4, 1.0 Hz, 1H), 4.08 (s, 3H), 3.79-3.55 (m, 5H), 3.43-3.34 (m, 1H), 2.65-2.26 (m, 2H).

Step 4

To 5-(4,4-difluoropiperidin-3-yl)-2-methoxynicotinonitrile, TFA salt (104 mg, 0.28 mmol) and 2-bromo-N-(5-fluoropyridin-2-yl)propanamide (Intermediate 1) (77 mg, 0.31 mmol) in DMF (2 mL) was added TEA (0.08 mL, 0.57 mmol). The reaction was stirred overnight, heated to 50° C. for 4 h, cooled, filtered through a 0.2 micron syringe filter and purified by MDAP (Xselect CSH C18 column 150 mm×30 mm, 5 micron, 17 minute run, 30 to 85% MeCN in water with 10 mM ammonium bicarbonate adjusted to pH 10 with ammonia) to give 84 mg (0.19 mmol, 66% yield) 2-(3-(5-cyano-6-methoxypyridin-3-yl)-4,4-difluoropiperidin-1-yl)-N-(5-fluoropyridin-2-yl)propanamide as a white solid. LCMS (ES, m/s): 420.3 [M+H]$^+$. $^1$H NMR (400 MHz, METHANOL-$d_4$) δ 8.35 (dd, J=7.8, 2.4 Hz, 1H), 8.24-8.15 (m, 2H), 8.10-8.04 (m, 1H), 7.59 (dddd, J=9.3, 7.8, 3.2, 1.7 Hz, 1H), 4.02 (d, J=5.4 Hz, 3H), 3.64-3.46 (m, 2H), 3.11-2.79 (m, 4H), 2.72-2.59 (m, 1H), 2.41-2.14 (m, 2H), 1.34 (d, J=6.8 Hz, 3H).

Step 5

To 2-(3-(5-cyano-6-methoxypyridin-3-yl)-4,4-difluoropiperidin-1-yl)-N-(5-fluoropyridin-2-yl)propanamide (84 mg, 0.20 mmol) in MeCN (1.5 mL) was added sodium iodide (90 mg, 0.60 mmol), followed by TMS-Cl (0.08 mL, 0.60 mmol). The reaction was heated to 50° C. overnight, quenched with water (0.5 mL), filtered through a 0.45 micron syringe filter and purified by MDAP (Xselect CSH C18 column 150 mm×30 mm, 5 micron, 17 minute run, 15 to 55% MeCN in water with 10 mM ammonium bicarbonate adjusted to pH 10 with ammonia) to give 50 mg (0.12 mmol, 59% yield) 2-(3-(5-cyano-6-oxo-1,6-dihydropyridin-3-yl)-4,4-difluoropiperidin-1-yl)-N-(5-fluoropyridin-2-yl)propanamide as a white solid. LCMS (ES, m/s): 406.3 [M+H]$^+$ ·rt=0.67 min, Method 3. $^1$H NMR (400 MHz, METHANOL-$d_4$) δ 8.26-8.17 (m, 2H), 8.14 (dd, J=6.4, 2.4 Hz, 1H), 7.75 (d, J=2.4 Hz, 1H), 7.62 (ddd, J=9.2, 7.9, 2.9 Hz, 1H), 3.61-3.47 (m, 1H), 3.40 (dt, J=11.2, 3.9 Hz, 1H), 3.05-2.60 (m, 4H), 2.34-2.14 (m, 2H), 1.34 (d, J=6.8 Hz, 3H).

Examples 250-251 were synthesized in an analogous manner using the designated Intermediate in Step 4.

| Ex | Name | Structure | ¹H NMR | LC/MS: (M + H)⁺; retention time (min); LC/MS Method of analysis | Int |
|---|---|---|---|---|---|
| 250 | 2-(3-(5-cyano-6-oxo-1,6-dihydropyridin-3-yl)-4,4-difluoropiperidin-1-yl)-N-(5-(4-fluorophenoxy)pyrazin-2-yl)propanamide | 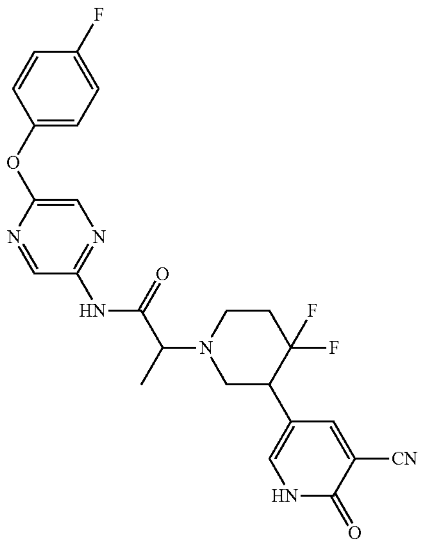 | ¹H NMR (400 MHz, METHANOL-d₄) δ 8.88 (dd, J = 2.9, 1.5 Hz, 1H), 8.22-8.08 (m, 2H), 7.76 (t, J = 2.4 Hz, 1H), 7.23-7.10 (m, 4H), 3.61-3.48 (m, 1H), 3.07-2.58 (m, 4H), 2.29-2.02 (m, 2H), 1.34 (dd, J = 7.1, 1.7 Hz, 3H). | 449; rt 0.85. LC/MS Method 3 | 58 |
| 251 | (S)-2-((S)-3-(5-cyano-6-oxo-1,6-dihydropyridin-3-yl)-4,4-difluoropiperidin-1-yl)-N-(5-(4-fluorophenoxy)pyridin-2-yl)propanamide | 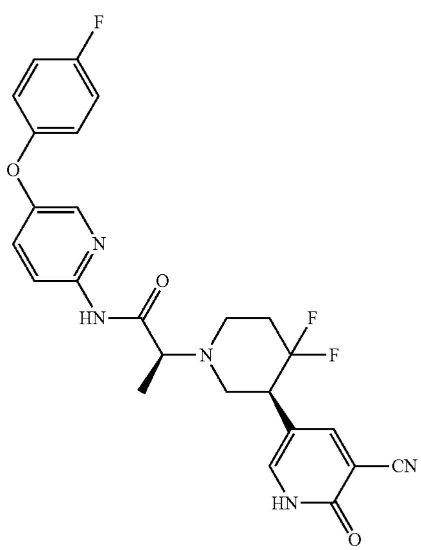 [SMILES: C[C@@H](C(=O)Nc1ccc(Oc2ccc(F)cc2)cn1)N1CCC(F)(F)[C@@H](c2c[nH]c(=O)c(C#N)c2)C1] | ¹H NMR (400 MHz, DMSO-d₆) δ 12.81-12.47 (m, 1H), 10.28 (s, 1H), 8.20 (d, J = 2.4 Hz, 1H), 8.16-8.11 (m, 2H), 7.79 (d, J = 2.4 Hz, 1H), 7.51 (dd, J = 9.0, 3.2 Hz, 1H), 7.28-7.20 (m, 2H), 7.14-7.05 (m, 2H), 3.66 (q, J = 6.8 Hz, 1H), 3.50-3.35 (m, 1H), 2.98-2.83 (m, 3H), 2.23-1.90 (m, 3H), 1.23 (d, J = 7.3 Hz, 3H). | 498; rt 0.98. LC/MS Method 2 | 70 |

Example 252

5-((S)-4,4-difluoro-1-((S)-1-((5-(4-fluorophenoxy)pyridin-2-yl)amino)-1-oxopropan-2-yl)piperidin-3-yl)-2-oxo-1,2-dihydropyridine-3-carboxamide

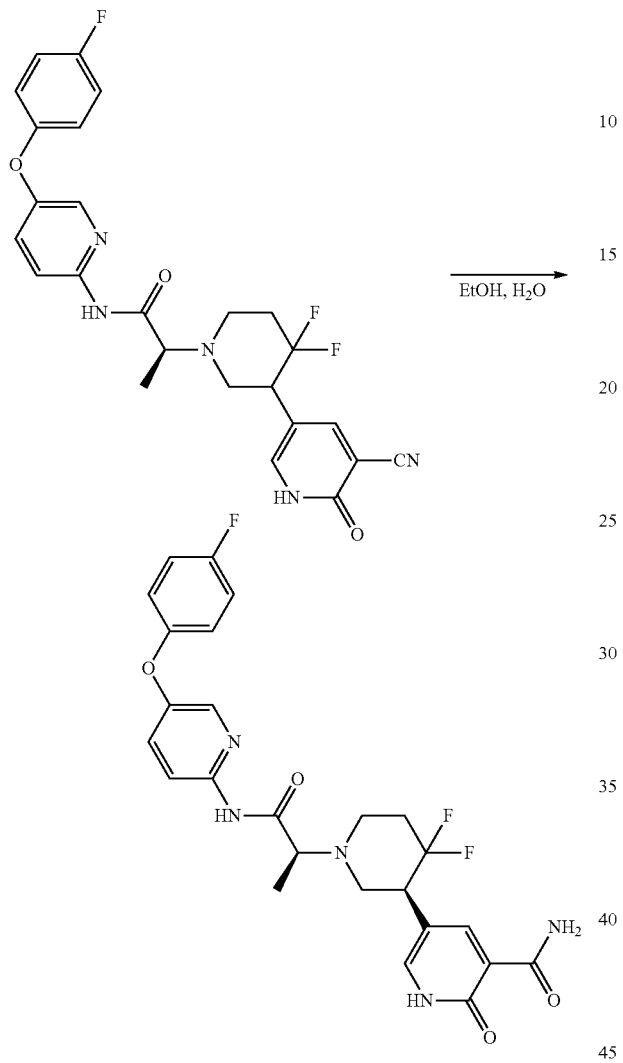

Step 1

A mixture of (2S)-2-(3-(5-cyano-6-oxo-1,6-dihydropyridin-3-yl)-4,4-difluoropiperidin-1-yl)-N-(5-(4-fluorophenoxy)pyridin-2-yl)propanamide (Example 251, prior to separation) (70 mg, 0.14 mmol) and hydrido(dimethylphosphinous acid-kP)[hydrogen bis(dimethylphosphinito-kP)]platinum(II) (3 mg, 7.04 μmol) in EtOH (1 mL) and water (0.250 mL) was degassed with nitrogen for 5 minutes, heated to 80° C. for 16 h, cooled to rt, concentrated and purified by reverse phase chromatography (MDAP, Formic acid column [XSelect CSH Prep C18 5 um OBD], 30-85% gradient, acetonitrile with 0.1% formic acid in water with 0.1% Formic acid, 40 mL/min flow rate, 17 min overall run time) to give 20 mg (0.04 mmol, 27% yield) 5-((S)-4,4-difluoro-1-((S)-1-((5-(4-fluorophenoxy)pyridin-2-yl)amino)-1-oxopropan-2-yl)piperidin-3-yl)-2-oxo-1,2-dihydropyridine-3-carboxamide as a white solid. LCMS (ES, m/s): 516.3 [M+H]$^+$, rt=0.86 min, Method 2. $^1$H NMR (400 MHz, METHANOL-d$_4$) δ 8.55 (d, J=2.4 Hz, 1H), 8.17 (d, J=9.3 Hz, 1H), 8.08 (d, J=2.9 Hz, 1H), 7.71 (d, J=2.4 Hz, 1H), 7.46 (dd, J=8.8, 2.9 Hz, 1H), 7.18-7.11 (m, 2H), 7.10-7.03 (m, 2H), 3.57 (q, J=6.8 Hz, 1H), 3.52-3.38 (m, 1H), 3.09-2.90 (m, 3H), 2.72-2.61 (m, 1H), 2.38-2.15 (m, 2H), 1.37 (d, J=6.8 Hz, 3H).

Example 253 was synthesized in an analogous manner starting with the appropriate nitrile.

| Ex | Name | Structure | $^1$H NMR | LC/MS: (M + H)$^+$; retention time (min); LC/MS Method of analysis | Nitrile |
|---|---|---|---|---|---|
| 253 | 5-(4,4-difluoro-1-(1-((5-fluoro-pyridin-2-yl)-amino)-1-oxo-propan-2-yl)-piperidin-3-yl)-2-oxo-1,2-dihydro-pyridine-3-carbox-amide | 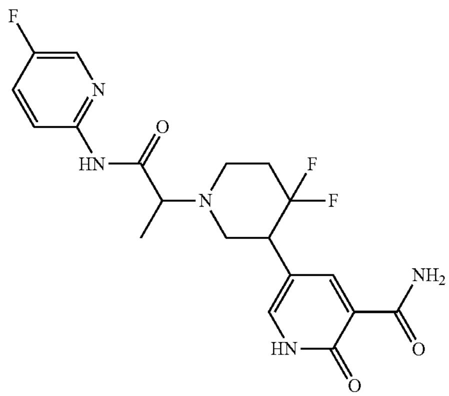 [SMILES: CC(C(=O)Nc1ccc(F)cn1)N1CCC(F)(F)C(c2c[nH]c(=O)c(C(N)=O)c2)C1] | $^1$H NMR (400 MHz, DMSO-d$_6$) δ 10.39 (s, 1H), 9.16-9.01 (m, 1H), 8.40-8.24 (m, 2H), 8.22-8.06 (m, 1H), 7.81-7.54 (m, 3H), 3.75-3.56 (m, 2H), 3.30 (s, 1H), 3.11-2.61 (m, 6H), 2.38-2.31 (m, 1H), 2.19-2.03 (m, 2H), 1.23 (dd, J = 6.8, 3.9 Hz, 3H). | 424; rt 0.68. LC/MS Method 3 | Ex. 249 |

Example 254

4-((S)-4,4-difluoro-1-((S)-1-((5-(4-fluorophenoxy)pyridin-2-yl)amino)-1-oxopropan-2-yl)piperidin-3-yl)-2-(hydroxymethyl)pyridine 1-oxide

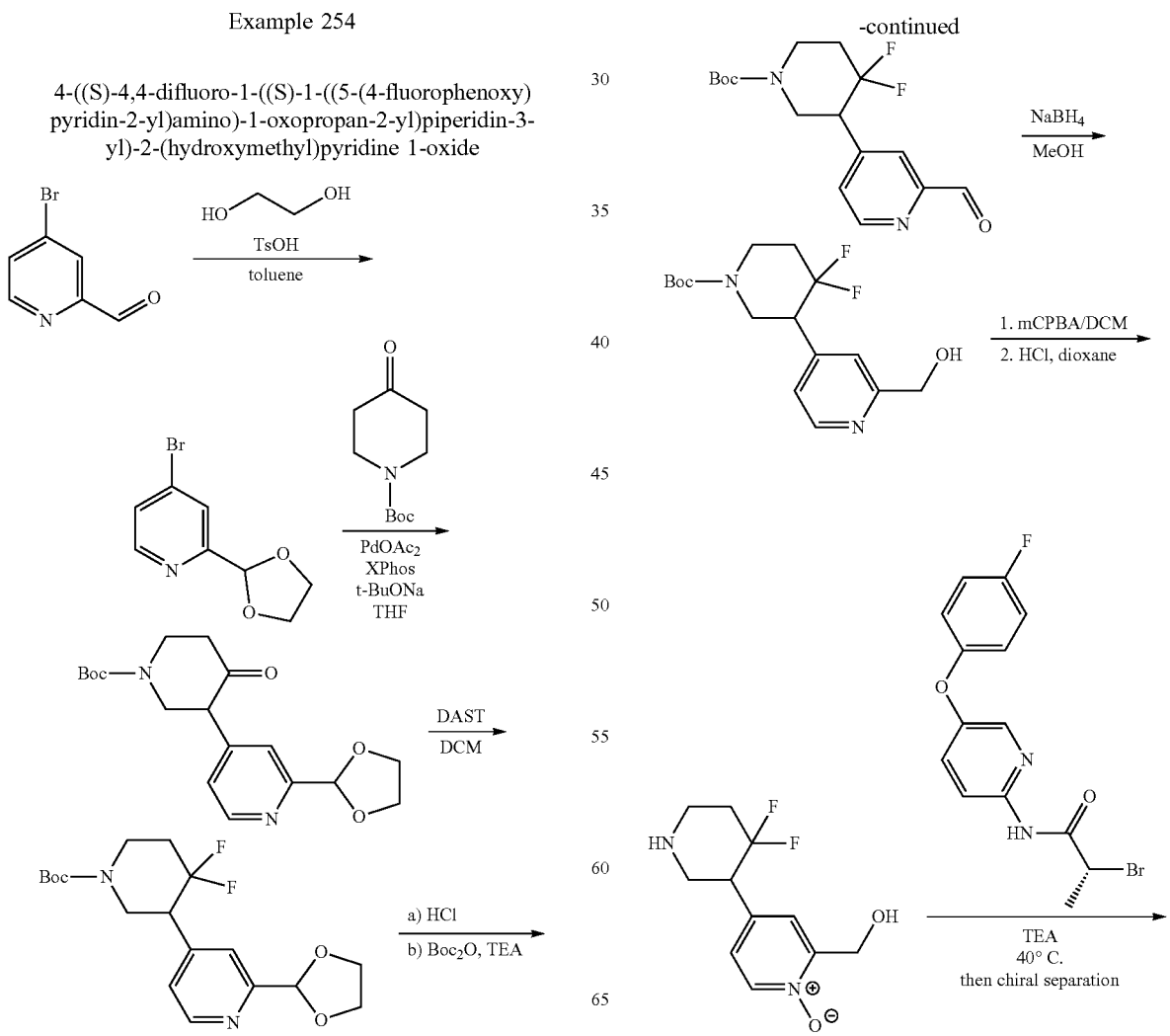

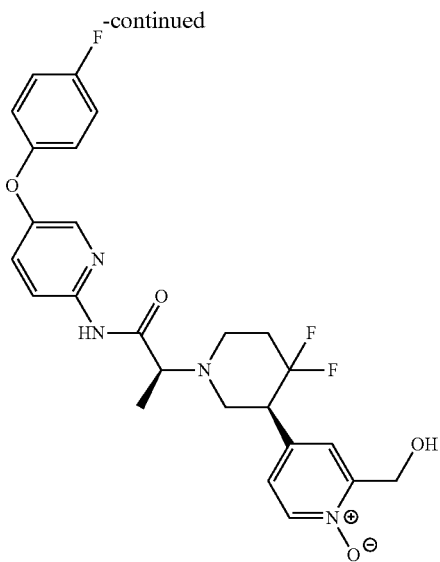

Step 1

To 4-bromopicolinaldehyde (2.5 g, 13.44 mmol) in toluene (10 ml) was added ethane-1,2-diol (2.249 mL, 40.3 mmol) and tosic acid (0.128 g, 0.672 mmol), and the mixture was heated at an external temperature of 130° C. under a Dean Stark trap overnight. The reaction was poured into EtOAc (100 ml) with stirring, then NaHCO$_3$ (sat) and water were added. After 20 min, the layers were separated, and the aqueous layer was back extracted with EtOAc. The combined organics were dried over magnesium sulfate, filtered, concentrated and purified via silica gel column, eluting with 3-40% EtOAc in heptane to a afford 2.6 g (10.74 mmol, 80% yield) 4-bromo-2-(1,3-dioxolan-2-yl)pyridine. LCMS (ES, m/s): 230.2 [M+H]$^+$. $^1$H NMR (400 MHz, DMSO-d6) δ 8.52-8.37 (m, 1H), 7.78-7.65 (m, 2H), 5.80-5.67 (m, 1H), 4.16-4.06 (m, 2H), 4.03-3.93 (m, 2H).

Step 2

To sodium tert-butoxide (3.26 g, 33.9 mmol) in THF (60 mL) was added tert-butyl 4-oxopiperidine-1-carboxylate (3.15 g, 15.82 mmol) and 4-bromo-2-(1,3-dioxolan-2-yl) pyridine (2.6 g, 11.30 mmol), then the mixture was degassed with N$_2$ for 15 min. XPhos (1.078 g, 2.260 mmol) was added, the reaction was degassed for 2 min, and PdOAc$_2$ (0.254 g, 1.130 mmol) was added. The mixture was degassed for 1 min, heated at 45° C. overnight and poured into water/brine (200 ml), with stirring. After 5 min, the mixture was extracted with EtOAc (2×, 200 mL, then 100 mL). The combined organics were dried over magnesium sulfate, filtered, concentrated and purified via silica gel column, eluting with 15-100% EtOAc in heptane to afford 3.50 g (9.54 mmol, 84% yield) tert-butyl 3-(2-(1,3-dioxolan-2-yl)pyridin-4-yl)-4-oxopiperidine-1-carboxylate as a foam. LCMS (ES, m/s): 349.3 [M+H]+. $^1$H NMR (400 MHz, DMSO-d$_6$) δ 8.53-8.45 (m, 1H), 7.38 (s, 1H), 7.25 (dd, J=5.1, 1.7 Hz, 1H), 5.75-5.65 (m, 1H), 4.15-4.05 (m, 4H), 4.01-3.93 (m, 3H), 3.68-3.42 (m, 2H), 2.66-2.55 (m, 1H), 2.46-2.34 (m, 1H), 1.49-1.41 (m, 9H).

Step 3

To tert-butyl 3-(2-(1,3-dioxolan-2-yl)pyridin-4-yl)-4-oxopiperidine-1-carboxylate (3.5 g, 10.05 mmol) in DCM (100 mL) at 0° C. was added DAST (2.65 mL, 20.09 mmol) in DCM (8 mL) over 30 mins. After stirring at rt overnight, the reaction was poured slowly into ice/NaHCO$_3$ (sat) (400 mL) with stirring, rinsing with DCM (100 ml). After 30 min the layers were separated, and the aqueous layer was extracted with DCM. The combined organics were dried over magnesium sulfate, filtered, concentrated and purified via silica gel column, eluting with 15-85% EtOAc in heptane to a afford the product 2.2 g, (4.45 mmol, 44.3% yield) tert-butyl 3-(2-(1,3-dioxolan-2-yl)pyridin-4-yl)-4,4-difluoropiperidine-1-carboxylate. LCMS (ES, m/s): 371.3 [M+H]+. $^1$H NMR (400 MHz, DMSO-d$_6$) δ 8.60-8.44 (m, 1H), 7.55-7.46 (m, 1H), 7.43-7.35 (m, 1H), 5.76-5.66 (m, 1H), 4.14-4.04 (m, 3H), 4.03-3.90 (m, 3H), 3.52-3.38 (m, 1H), 3.19-2.97 (m, 1H), 2.23-2.10 (m, 1H), 2.09-1.89 (m, 1H), 1.48-1.30 (m, 9H).

Step 4

To tert-butyl 3-(2-(1,3-dioxolan-2-yl)pyridin-4-yl)-4,4-difluoropiperidine-1-carboxylate (1.80 g, 4.86 mmol) in THF (25 mL) was added HCl (3 M, 24.30 mL, 72.9 mmol). The reaction was stirred 10 min at rt, then overnight at 60° C. The mixture was concentrated, and the residue was stirred with acetonitrile (30.00 mL) and TEA (3.39 mL, 24.30 mmol). Boc-anhydride (1.354 mL, 5.83 mmol) was added, and after about 1 h the reaction was partitioned between NH$_4$Cl (sat, 100 ml) and EtOAc (200 ml) and stirred for 10 mins. The aqueous layer was isolated and extracted with EtOAc (100 ml). The combined organics were dried over magnesium sulfate, filtered, concentrated and purified via silica gel column, eluting with 5-65% EtOAc in heptane to afford 1.20 g (3.49 mmol, 71.9% yield) tert-butyl 4,4-difluoro-3-(2-formylpyridin-4-yl)piperidine-1-carboxylate. LCMS (ES, m/s): 327.3 [M+H]+. $^1$H NMR (400 MHz, DMSO-d$_6$) δ 10.04-9.95 (m, 1H), 8.86-8.77 (m, 1H), 7.95-7.85 (m, 1H), 7.73-7.66 (m, 1H), 4.16-3.91 (m, 2H), 3.67-3.36 (m, 3H), 3.22-2.98 (m, 1H), 2.24-1.90 (m, 2H), 1.47-1.37 (m, 9H).

Step 5

To tert-butyl 4,4-difluoro-3-(2-formylpyridin-4-yl)piperidine-1-carboxylate (510 mg, 1.563 mmol) in methanol (15 mL) in an ice bath was added NaBH$_4$ (10-40 mesh, 118 mg, 3.13 mmol). After 1 h, the reaction was warmed to rt. After 1 h 15 min, the mixture was re-cooled in an ice bath, and HCl (1 N, 4 ml) in water (25 mL) was added over about 2 min. After 10 min, EtOAc (120 ml) was added, the layers were separated, and the aqueous layer was back extracted with EtOAc (50 ml). The pH of the aqueous layer was adjusted to about pH 7, then extracted with DCM (50 ml, 2×). The combined organics were dried over magnesium sulfate, filtered, concentrated and purified via silica gel column, eluting with 10-75% 3:1 EtOAc: EtOH (+2% NH$_4$OH) in heptane to afford 398 mg (1.091 mmol, 69.8% yield) tert-butyl 4,4-difluoro-3-(2-(hydroxymethyl)pyridin-4-yl)piperidine-1-carboxylate. LCMS (ES, m/s): 329.3 [M+H]+. $^1$H NMR (400 MHz, DMSO-d$_6$) δ 8.49-8.36 (m, 1H), 7.50-7.39 (m, 1H), 7.28-7.14 (m, 1H), 5.44 (br t, J=5.4 Hz, 1H), 4.66-4.45 (m, 2H), 4.13-3.95 (m, 2H), 3.50-3.38 (m, 1H), 3.10 (br dd, J=4.4, 3.4 Hz, 1H), 2.21-1.98 (m, 2H), 1.41 (br s, 11H).

Step 6

To tert-butyl 4,4-difluoro-3-(2-(hydroxymethyl)pyridin-4-yl)piperidine-1-carboxylate (390 mg, 1.188 mmol) in DCM (12 mL), cooled in an ice bath, was added m-CPBA (77% purity, 319 mg, 1.425 mmol). After 90 min, the reaction was partitioned between DCM (25 ml) and NaHCO$_3$ (sat, 25 ml), and the layers were separated. The aqueous layer was back extracted with DCM, and the combined organics were dried over magnesium sulfate, filtered, concentrated and purified via silica gel column, eluting with 8-65% 3:1 EtOAc: EtOH (+2% NH$_4$OH) in heptane to afford 310 mg (0.855 mmol, 72.0% yield) 4-(1-

(tert-butoxycarbonyl)-4,4-difluoropiperidin-3-yl)-2-(hydroxymethyl)pyridine 1-oxide. LCMS (ES, m/s): 345.3 [M+H]+. $^1$H NMR (400 MHz, DMSO-$d_6$) δ 8.30-8.18 (m, 1H), 7.51 (d, J=2.4 Hz, 1H), 7.30 (dd, J=6.4, 2.4 Hz, 1H), 5.72-5.55 (m, 1H), 4.57 (d, J=5.9 Hz, 2H), 4.14-3.95 (m, 2H), 3.53-3.37 (m, 1H), 3.17-3.00 (m, 1H), 2.20-2.10 (m, 1H), 2.08-1.89 (m, 1H), 1.50-1.28 (m, 9H).

Step 7

To 4-(1-(tert-butoxycarbonyl)-4,4-difluoropiperidin-3-yl)-2-(hydroxymethyl)pyridine 1-oxide (308 mg, 0.894 mmol) in ethyl acetate (10 mL) and methanol (1 mL) was added HCl (4 M in dioxane, 3.35 mL, 13.42 mmol). After stirring overnight, the reaction was concentrated to afford 256 mg (0.821 mmol, 92% yield) 4-(4,4-difluoropiperidin-3-yl)-2-(hydroxymethyl)pyridine 1-oxide hydrochloride, which was used without further purification. LCMS (ES, m/s): 245.2 [M+H]+. $^1$H NMR (400 MHz, DMSO-$d_6$) δ 9.99-9.49 (m, 2H), 8.34-8.27 (m, 1H), 7.50 (d, J=2.0 Hz, 1H), 7.36 (dd, J=6.4, 2.4 Hz, 1H), 5.70-5.53 (m, 3H), 4.63-4.53 (m, 2H), 3.93-3.76 (m, 1H), 3.59-3.54 (m, 2H), 3.22-3.09 (m, 1H), 2.46-2.40 (m, 1H).

Step 8

To 2-bromo-N-(5-(4-fluorophenoxy)pyridin-2-yl)propanamide (Intermediate 70) (1.600 mL, 0.472 mmol) in DMF (6 mL) was added 4-(4,4-difluoropiperidin-3-yl)-2-(hydroxymethyl)pyridine 1-oxide hydrochloride (126 mg, 0.448 mmol) and TEA (0.263 mL, 1.887 mmol). The reaction was heated to 35° C. overnight, then treated with sodium bromide (485 mg, 4.72 mmol). The reaction was stirred at 40° C. overnight and partitioned between NH$_4$Cl (sat, 60 ml) and DCM (20 ml). The layers were separated, and the aqueous layer was back extracted with DCM (20 ml). The combined organics were dried over magnesium sulfate, filtered, concentrated and purified via silica gel column, eluting with 5-65% 3:1 EtOAc: EtOH (+2% NH$_4$OH) in heptane to afford the product as a mixture of isomers (130 mg, 0.243 mmol, 51.6% yield). Chiral purification of the mixture (Column: Chiralpak IC, 5 micron; 21×250 mm; 95:5 acetonitrile:methanol; Flow rate: 20 mL/min) gave 4 isomer peaks at retention times of 15.4, 17.4, 17.9, and 19.1 min. The fractions corresponding to the peak at 17.4 min retention time were concentrated to give 21 mg, (17% yield) 4-((S)-4,4-difluoro-1-((S)-1-((5-(4-fluorophenoxy)pyridin-2-yl)amino)-1-oxopropan-2-yl)piperidin-3-yl)-2-(hydroxymethyl)pyridine 1-oxide. LCMS (ES, m/s): 503.3 [M+H]+, rt=0.73, Method 5. $^1$H NMR (400 MHz, DMSO-$d_6$) δ 10.40-10.32 (m, 1H), 8.23-8.18 (m, 1H), 8.16-8.10 (m, 2H), 7.55-7.47 (m, 2H), 7.32 (dd, J=6.6, 2.7 Hz, 1H), 7.28-7.20 (m, 2H), 7.14-7.05 (m, 2H), 5.69-5.62 (m, 1H), 4.61-4.51 (m, 2H), 3.74-3.65 (m, 1H), 3.61-3.47 (m, 1H), 3.07-3.01 (m, 1H), 2.98-2.88 (m, 2H), 2.63-2.53 (m, 1H), 2.21-2.04 (m, 2H), 1.23 (d, J=6.8 Hz, 3H).

Example 255 was prepared in an analogous manner using the designated intermediate in Step 8.

| Ex | Name | Structure | $^1$H NMR | LC/MS: (M + H)+; retention time (min); LC/MS Method of analysis | Intermediate |
|---|---|---|---|---|---|
| 255 | 4-((S)-1-((S)-1-((5-(2,4-difluorophenoxy)-pyridin-2-yl)amino)-1-oxopropan-2-yl)-4,4-difluoropiperidin-3-yl)-2-(hydroxymethyl)-pyridine 1-oxide | 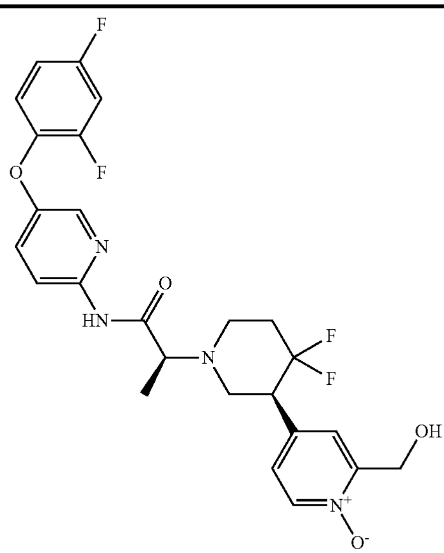 | $^1$H NMR (400 MHz, DMSO-$d_6$ δ 10.36 (s, 1H), 8.24-8.07 (m, 3H), 7.56-7.46 (m, 3H), 7.37-7.25 (m, 2H), 7.18-7.09 (m, 1H), 5.69-5.61 (m, 1H), 4.56 (d, J = 5.4 Hz, 2H), 3.74-3.64 (m, 1H), 3.61-3.46 (m, 1H), 3.07-3.00 (m, 1H), 2.93 (br t, J = 11.0 Hz, 2H), 2.63-2.53 (m, 1H), 2.21-2.02 (m, 2H), 1.22 (d, J = 6.8 Hz, 3H). | 521; rt 0.74. LC/MS Method 5 | 71 |

Example 256

4-(4,4-difluoro-1-(1-((5-fluoropyridin-2-yl)amino)-1-oxopropan-2-yl)piperidin-3-yl)-2-(2,2,2-trifluoro-1-hydroxyethyl)pyridine 1-oxide

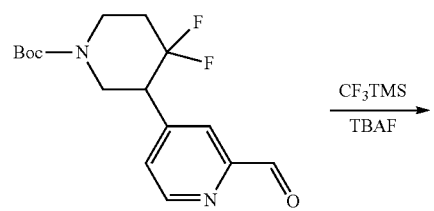

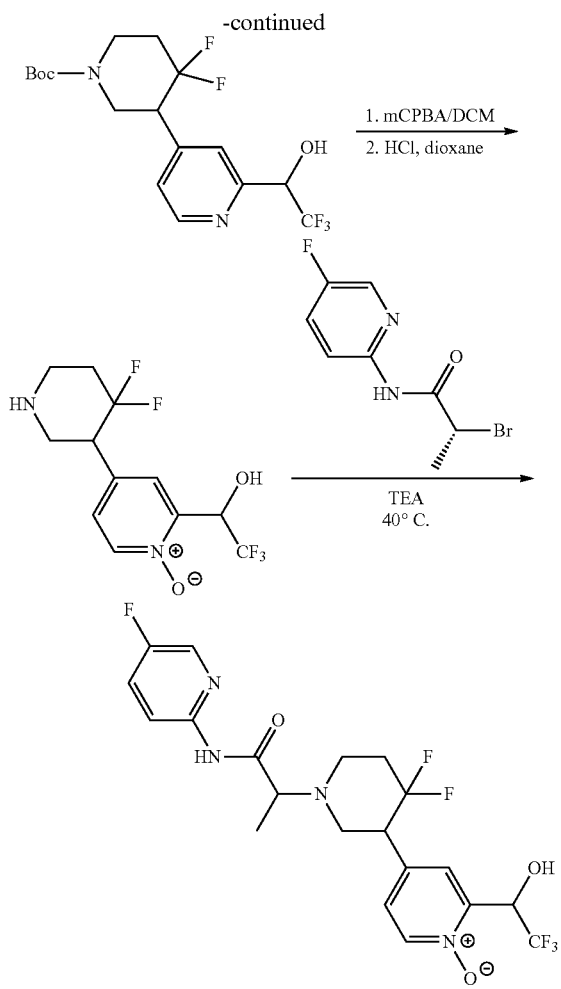

Step 1

To tert-butyl 4,4-difluoro-3-(2-formylpyridin-4-yl)piperidine-1-carboxylate (Example 254, Step 4) (327 mg, 1.002 mmol) in THF (10 mL) at 0° C. was added trifluoromethyltrimethylsilane (0.222 mL, 1.503 mmol) followed by TBAF (1.303 mL, 1.303 mmol), dropwise over 10 min. After 1 h, the reaction was quenched with water (5 mL) and partitioned between ethyl acetate and NaHCO$_3$ (sat). The layers were separated, and the aqueous layer was back extracted with ethyl acetate. The combined organics were dried over magnesium sulfate, filtered, concentrated and purified via silica gel column, eluting with 5-50% 3:1 EtOAc: EtOH (+2% NH$_4$OH) in heptane to afford 280 mg (0.530 mmol, 52.9% yield) tert-butyl 4,4-difluoro-3-(2-(2,2,2-trifluoro-1-hydroxyethyl)pyridin-4-yl)piperidine-1-carboxylate. LCMS (ES, m/s): 397.3 [M+H]$^+$. $^1$H NMR (400 MHz, DMSO-d$_6$) δ 8.62-8.51 (m, 1H), 7.66-7.55 (m, 1H), 7.41 (br d, J=4.4 Hz, 1H), 7.15-7.01 (m, 1H), 5.19-5.07 (m, 1H), 4.14-3.90 (m, 2H), 3.67-3.39 (m, 2H), 3.19-3.08 (m, 1H), 2.19-1.90 (m, 2H), 1.51-1.34 (m, 9H).

Step 2 To tert-butyl 4,4-difluoro-3-(2-(2,2,2-trifluoro-1-hydroxyethyl)pyridin-4-yl)piperidine-1-carboxylate (280 mg, 0.706 mmol) in DCM (10 mL) at 0° C. was added m-CPBA (77% purity) (222 mg, 0.989 mmol). After 90 min the reaction was partitioned between DCM (20 mL) and NaHCO$_3$ (sat, 20 mL). The layers were separated, and the aqueous layer was back extracted with DCM (15 mL). The combined organics were dried over magnesium sulfate, filtered, concentrated and purified via silica gel column, eluting with 0-65% 3:1 EtOAc: EtOH (+2% NH$_{40}$H) in heptane to afford 212 mg (0.463 mmol, 65.5% yield) 4-(1-(tert-butoxycarbonyl)-4,4-difluoropiperidin-3-yl)-2-(2,2,2-trifluoro-1-hydroxyethyl)pyridine 1-oxide. LCMS (ES, m/s): 413.2 [M+H]+. $^1$H NMR (400 MHz, DMSO-d$_6$) δ 8.34 (d, J=6.8 Hz, 1H), 7.65-7.56 (m, 1H), 7.49-7.32 (m, 2H), 5.98-5.88 (m, 1H), 4.15-3.92 (m, 2H), 3.58-3.46 (m, 1H), 3.16-3.00 (m, 1H), 2.22-2.08 (m, 1H), 2.07-1.92 (m, 1H), 1.47-1.37 (m, 9H).

Step 3

To 4-(1-(tert-butoxycarbonyl)-4,4-difluoropiperidin-3-yl)-2-(2,2,2-trifluoro-1-hydroxyethyl)pyridine 1-oxide (208 mg, 0.504 mmol) in EtOAc (5 mL) and methanol (5 mL) was added HCl (4M in dioxane, 1.892 mL, 7.57 mmol). The reaction was stirred overnight and concentrated to yield 197 mg (0.480 mmol, 95% yield) 4-(4,4-difluoropiperidin-3-yl)-2-(2,2,2-trifluoro-1-hydroxyethyl)pyridine 1-oxide hydrochloride, which was used without further purification. LCMS (ES, m/s): 313.2 [M+H]$^+$. $^1$H NMR (400 MHz, DMSO-d$_6$) δ 9.75-9.37 (m, 2H), 8.39 (d, J=6.8 Hz, 1H), 7.63-7.56 (m, 1H), 7.52-7.42 (m, 1H), 5.93 (q, J=6.4 Hz, 1H), 4.02-3.93 (m, 4H), 3.64-3.57 (m, 1H), 3.54-3.44 (m, 1H), 3.26-3.03 (m, 1H), 2.46-2.38 (m, 1H).

Step 4

To (R)-2-bromo-N-(5-fluoropyridin-2-yl)propanamide (Intermediate 1) (70 mg, 0.283 mmol), 4-(4,4-difluoropiperidin-3-yl)-2-(2,2,2-trifluoro-1-hydroxyethyl)pyridine 1-oxide hydrochloride (99 mg, 0.283 mmol) and sodium bromide (292 mg, 2.83 mmol) in DMF (4 mL) was added TEA (0.158 mL, 1.133 mmol). The reaction was heated to 45° C. for 4 h, then to 40° C. overnight. The mixture was partitioned between NH$_4$Cl (sat, 25 mL) and DCM (20 mL), the layers were separated and the aqueous phase was back extracted with DCM. The combined organics were dried over magnesium sulfate, filtered, concentrated and purified via silica gel column, eluting with 5-65% 3:1 EtOAc: EtOH (+2% NH$_4$OH) in heptane to afford 85 mg (0.169 mmol, 59.6% yield) 4-(4,4-difluoro-1-(1-((5-fluoropyridin-2-yl)amino)-1-oxopropan-2-yl)piperidin-3-yl)-2-(2,2,2-trifluoro-1-hydroxyethyl)pyridine 1-oxide. LCMS (ES, m/s): 479.3 [M+H]+, rt=0.65, Method 5. $^1$H NMR (400 MHz, DMSO-d$_6$) δ 10.46-10.34 (m, 1H), 8.36-8.27 (m, 2H), 8.18-8.11 (m, 1H), 7.75 (tt, J=8.7, 2.8 Hz, 1H), 7.65-7.59 (m, 1H), 7.47 (br dd, J=6.4, 2.4 Hz, 1H), 7.41-7.32 (m, 1H), 5.98-5.86 (m, 1H), 3.75-3.51 (m, 2H), 3.06-2.89 (m, 2H), 2.80-2.69 (m, 1H), 2.62-2.52 (m, 1H), 2.20-1.99 (m, 2H), 1.26-1.18 (m, 3H).

Example 257 was prepared in an analogous manner using the designated intermediate in Step 4.

| Ex | Name | Structure | ¹H NMR | LC/MS: (M + H)⁺; retention time (min); LC/MS Method of analysis | Intermediate |
|---|---|---|---|---|---|
| 257 | 4-(4,4-difluoro-1-(1-((5-(4-fluoro-phenoxy)-pyridin-2-yl)amino)-1-oxo-propan-2-yl)piperidin-3-yl)-2-(2,2,2-trifluoro-1-hydroxy-ethyl)pyridine 1-oxide | 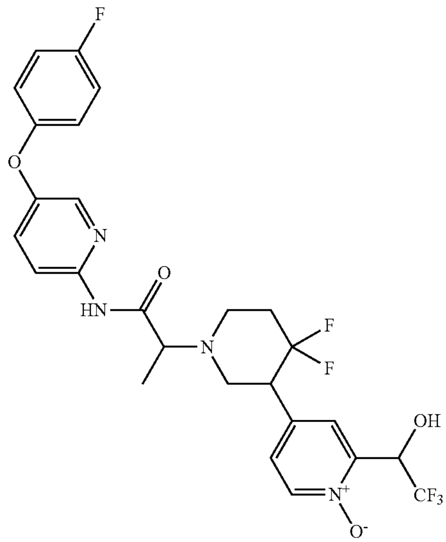 [SMILES: CC(C(=O)Nc1ccc(Oc2ccc(F)cc2)cn1)N1CCC(F)(F)C(c2cc[n+]([O-])c(C(O)C(F)(F)F)c2)C1] | ¹H NMR (400 MHz, DMSO-d₆) δ 10.40-10.31 (m, 1H), 8.35-8.27 (m, 1H), 8.18-8.07 (m, 2H), 7.66-7.60 (m, 1H), 7.55-7.44 (m, 2H), 7.41-7.33 (m, 1H), 7.27-7.19 (m, 2H), 7.13-7.05 (m, 2H), 5.97-5.87 (m, 1H), 3.76-3.53 (m, 2H), 3.06-2.89 (m, 2H), 2.82-2.69 (m, 1H), 2.63-2.53 (m, 1H), 2.20-1.99 (m, 2H), 1.29-1.20 (m, 3H). | 571; rt 0.88. LC/MS Method 5 | 70 |

Example 258

2-carbamoyl-4-((S)-1-((S)-1-((5-(2,4-difluorophe-noxy)pyridin-2-yl)amino)-1-oxopropan-2-yl)-4,4-difluoropiperidin-3-yl)pyridine 1-oxide

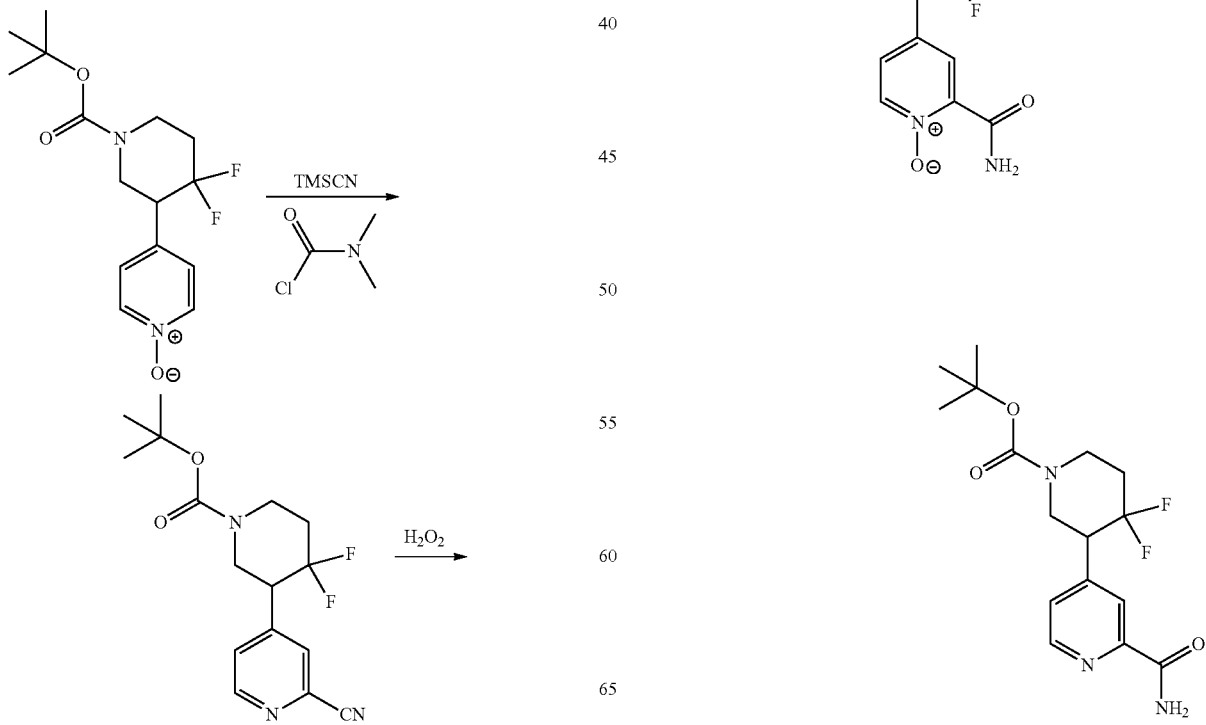

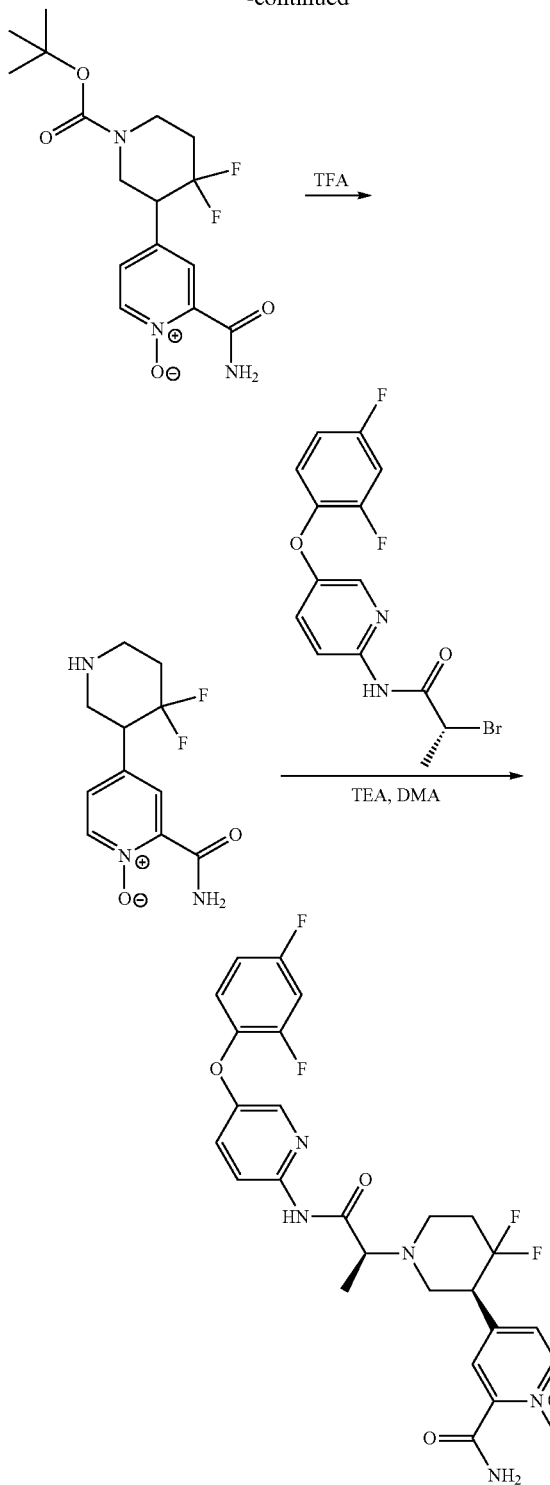

Step 1

TMS-CN (0.377 mL, 2.81 mmol) was added to 4-(1-(tert-butoxycarbonyl)-4,4-difluoropiperidin-3-yl)pyridine 1-oxide (Example 109, Step 3) (632 mg, 2.01 mmol) in DCM (9 mL), followed by dimethylcarbamoyl chloride (0.259 mL, 2.81 mmol). After 72 h, the reaction was partitioned between DCM (60 mL) and saturated $K_2CO_3$ solution (10 mL) and water (10 mL). The layers were separated, and the organic layer was washed with water (20 mL) and brine (20 mL), then dried over $Na_2SO_4$. Organic solvents were removed in vacuo, and the residue was purified by column chromatography (ISCO 24 g), eluting with 0-50% EtOAc in heptane to give 602 mg (1.862 mmol, 93% yield) tert-butyl 3-(2-cyanopyridin-4-yl)-4,4-difluoropiperidine-1-carboxylate. LCMS: (ES, m/z): 324.2 [M+H]⁺.

Step 2

To tert-butyl 3-(2-cyanopyridin-4-yl)-4,4-difluoropiperidine-1-carboxylate (196 mg, 0.606 mmol) in methanol (3 mL) was added pH 7.4 buffer (2 mL) and hydrogen peroxide (0.310 mL, 3.03 mmol). The reaction was stirred overnight, treated with saturated $NaHCO_3$ solution (20 mL) and extracted with DCM (3×25 mL). The combined organic layers were washed with brine, dried over $Na_2SO_4$, concentrated and purified by silica gel chromatography (ISCO 12 g column), eluting with 30-100% EtOAc in heptane to give 56 mg (0.157 mmol, 25.9% yield) 4-(1-(tert-butoxycarbonyl)-4,4-difluoropiperidin-3-yl)-2-carbamoylpyridine 1-oxide and 140 mg (0.410 mmol, 67.7% yield) tert-butyl 3-(2-carbamoylpyridin-4-yl)-4,4-difluoropiperidine-1-carboxylate.

4-(1-(tert-butoxycarbonyl)-4,4-difluoropiperidin-3-yl)-2-carbamoylpyridine 1-oxide: LCMS: (ES, m/z): 358.3 [M+H]⁺. ¹H NMR (400 MHz, CHLOROFORM-d) δ ppm 10.80 (br s, 1H), 8.36 (d, J=2.93 Hz, 1H), 8.25 (d, J=6.85 Hz, 1H), 7.35-7.41 (m, 1H), 6.06 (br s, 1H), 4.27 (br s, 2H), 3.28 (br s, 1H), 3.08-3.23 (m, 2H), 2.14-2.26 (m, 1H), 1.93-2.08 (m, 1H), 1.49 (s, 9H).

tert-butyl 3-(2-carbamoylpyridin-4-yl)-4,4-difluoropiperidine-1-carboxylate: LCMS: (ES, m/z): 342.3 [M+H]⁺. ¹H NMR (400 MHz, CHLOROFORM-d) δ ppm 8.56 (d, J=5.38 Hz, 1H), 8.19 (s, 1H), 7.92 (br s, 1H), 7.44 (br d, J=4.89 Hz, 1H), 5.64 (br s, 1H), 4.26 (br s, 2H), 3.35 (br s, 1H), 3.06-3.24 (m, 2H), 2.13-2.25 (m, 1H), 1.91-2.10 (m, 1H), 1.48 (s, 9H).

Step 3

To 4-(1-(tert-butoxycarbonyl)-4,4-difluoropiperidin-3-yl)-2-carbamoylpyridine 1-oxide (56 mg, 0.157 mmol) in DCM (2 mL) was added TFA (0.2 mL, 2.60 mmol). After 2 h the reaction was concentrated to give 58.2 mg (0.157 mmol, 100% yield) 2-carbamoyl-4-(4,4-difluoropiperidin-3-yl)pyridine 1-oxide trifluoroacetic acid salt, which was used without purification. LCMS: (ES, m/z): 258.2 [M+H]⁺.

Step 4

To (R)-2-bromo-N-(5-(2,4-difluorophenoxy)pyridin-2-yl)propanamide (Intermediate 71) (110 mg, 0.308 mmol) in DMA (2 ml) was added 2-carbamoyl-4-(4,4-difluoropiperidin-3-yl)pyridine 1-oxide, trifluoroacetic acid salt (114 mg, 0.308 mmol), followed by TEA (0.215 mL, 1.54 mmol). The mixture was stirred at rt for 16 h, at 50° C. for 3 h, diluted with EtOAc, washed with satd. $K_2CO_3$ solution and 1:1 sat'd. $K_2CO_3$ solution: brine, dried over $Na_2SO_4$, filtered, concentrated and purified by reverse phase Xselect CSH Prep C18 5 uM OBD (Gradient 30% to 85% B over 17 min, flow rate 40 mL/min, A: Water with 10 mM Ammonium Bicarb and 0.075% Ammonium Hydroxide/B: Acetonitrile) to give 77.3 mg (0.143 mmol, 46.6% yield) 2-carbamoyl-4-(1-(1-((5-(2,4-difluorophenoxy)pyridin-2-yl)amino)-1-oxopropan-2-yl)-4,4-difluoropiperidin-3-yl)pyridine 1-oxide (mixture of 4 diasteromers). LCMS (ES, m/s): 534.1 [M+H]⁺, rt=1.01 min, Method 3. The mixture was further separated by chiral chromatography (Column: LuxCellulose-2, 5 micron, 20 mm×250 mm); Flow Rate: 45 mL/min; Mobile Phase: 75:25 Acetonitrile: Methanol, modifier: 0.1% isopropylamine). Peak 4 (retention time of 18.6 min) was collected to give 25.3 mg (0.046 mmol, 34.9% yield) 2-carbamoyl-4-((S)-1-((S)-1-((5-(2,4-difluorophenoxy)

pyridin-2-yl)amino)-1-oxopropan-2-yl)-4,4-difluoropiperidin-3-yl)pyridine 1-oxide. LCMS (ES, m/s): 534.0 [M+H]⁺. ¹H NMR (400 MHz, DMSO-d$_6$) δ ppm 10.35 (s, 1H), 10.31 (d, J=3.91 Hz, 1H), 8.39 (d, J=6.85 Hz, 1H), 8.31 (d, J=4.40 Hz, 1H), 8.19 (d, J=2.93 Hz, 1H), 8.09-8.17 (m, 2H), 7.61 (dd, J=6.85, 2.45 Hz, 1H), 7.45-7.54 (m, 2H), 7.30 (td, J=9.29, 5.38 Hz, 1H), 7.09-7.19 (m, 1H), 3.56-3.78 (m, 2H), 3.03-3.12 (m, 1H), 2.95 (br t, J=11.49 Hz, 2H), 2.52-2.62 (m, 1H), 2.01-2.22 (m, 2H), 1.23 (d, J=6.85 Hz, 3H).

Examples 259 and 260 were synthesized in an analogous manner, using the designated Intermediate in Step 4.

| Ex | Name | Structure | ¹H NMR | Analytical LC/MS: (M + H)⁺; retention time (min); LC/MS Method of analysis | Int |
|---|---|---|---|---|---|
| 259 | 2-carbamoyl-4-((S)-4,4-difluoro-1-((S)-1-((5-fluoropyridin-2-yl)amino)-1-oxopropan-2-yl)piperidin-3-yl)-pyridine 1-oxide | 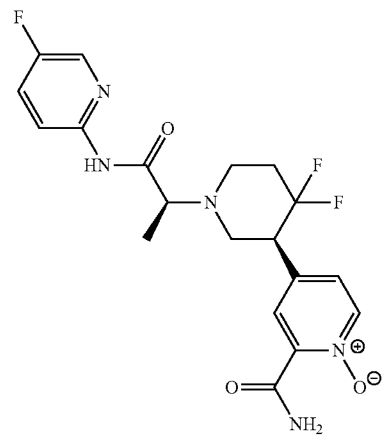 [SMILES: C[C@@H](C(=O)Nc1ccc(F)cn1)N1CCC(F)(F)[C@@H](c2cc[n+]([O-])c(C(N)=O)c2)C1] | ¹H NMR (400 MHz, DMSO-d$_6$) δ 10.40 (s, 1H), 10.31 (br d, J = 4.40 Hz, 1H), 8.39 (d, J = 6.85 Hz, 1H), 8.25-8.37 (m, 2H), 8.07-8.24 (m, 2H), 7.75 (td, J = 8.68, 3.18 Hz, 1H), 7.61 (dd, J = 6.85, 2.93 Hz, 1H), 3.59-3.79 (m, 2H), 3.07 (br d, J = 11.25 Hz, 1H), 2.81-3.02 (m, 2H), 2.58 (br t, J = 11.00 Hz, 1H), 2.00-2.23 (m, 2H), 1.23 (d, J = 6.85 Hz, 3H). | 424.1; rt 0.75. LC/MS Method 3 | 1 |
| 260 | 2-carbamoyl-4-(1-(1-((5-(2,4-difluorophenoxy)-pyrazin-2-yl)amino)-1-oxopropan-2-yl)-4,4-difluoro-piperidin-3-yl)pyridine 1-oxide | 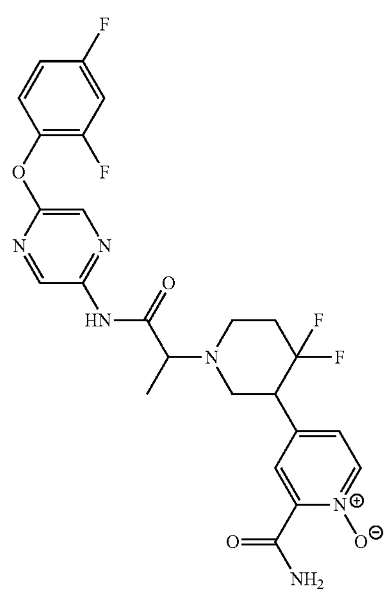 [SMILES: CC(C(=O)Nc1cnc(Oc2ccc(F)cc2F)cn1)N1CCC(F)(F)C(c2cc[n+]([O-])c(C(N)=O)c2)C1] | ¹H NMR (400 MHz, DMSO-d$_6$) δ 10.58 (d, J = 3.91 Hz, 1H), 10.25-10.33 (m, 1H), 8.78-8.84 (m, 1H), 8.45 (s, 1H), 8.36-8.41 (m, 1H), 8.26-8.32 (m, 1H), 8.19 (s, 1H), 7.60 (dd, J = 6.85, 2.45 Hz, 1H), 7.40-7.53 (m, 2H), 7.11-7.21 (m, 1H), 3.55-3.76 (m, 2H), 2.91-3.09 (m, 2H), 2.54-2.87 (m, 2H), 2.01-2.20 (m, 2H), 1.15-1.35 (m, 3H). | 535.0; rt 0.94-0.98. LC/MS Method 3 | 65 |

Example 261

4-(1-((S)-1-((5-(2,4-difluorophenoxy)pyridin-2-yl)amino)-1-oxopropan-2-yl)-4,4-difluoropiperidin-3-yl)picolinamide

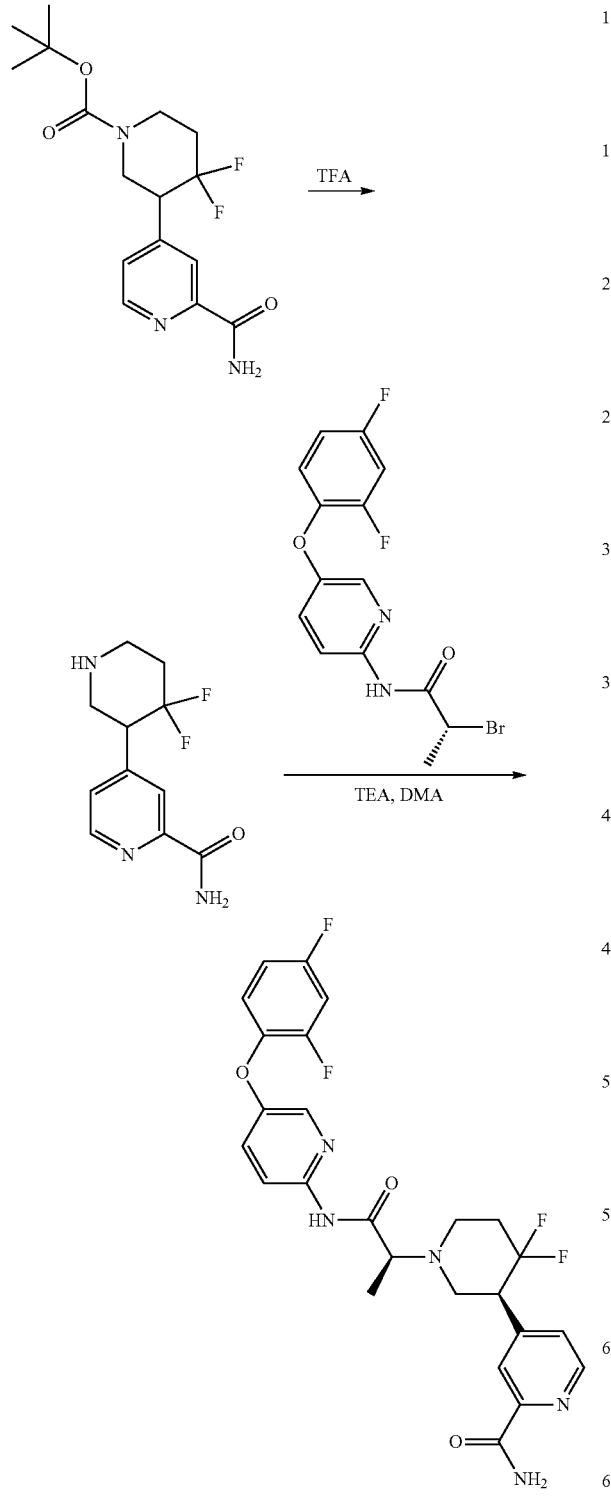

Step 1
To tert-butyl 3-(2-carbamoylpyridin-4-yl)-4,4-difluoropiperidine-1-carboxylate (Example 258, Step 2) (135 mg, 0.395 mmol) in DCM (3 mL) was added TFA (0.3 mL, 3.89 mmol). After 2 h, the reaction was concentrated to give 141 mg (0.395 mmol, 100% yield) 4-(4,4-difluoropiperidin-3-yl)picolinamide, trifluoroacetic acid salt, which was used without further purification. LCMS: (ES, m/z): 242.2 [M+H]$^+$.

Step 2
To (R)-2-bromo-N-(5-(2,4-difluorophenoxy)pyridin-2-yl)propanamide (Intermediate 71) (141 mg, 0.395 mmol) in DMA (2 ml) was added 4-(4,4-difluoropiperidin-3-yl)picolinamide trifluoroacetic acid salt (140 mg, 0.395 mmol), followed by TEA (0.275 mL, 1.975 mmol). The mixture was stirred overnight, diluted with EtOAc, washed with sat'd K$_2$CO$_3$ solution and 1:1 sat'd K$_2$CO$_3$ solution: brine, dried over Na$_2$SO$_4$, filtered, concentrated and purified by reverse phase Xselect CSH Prep C18 5 uM OBD (Gradient 45% to 75% B over 17 min, flow rate 60 mL/min, A: Water with 10 mM Ammonium Bicarb and 0.075% Ammonium Hydroxide/B: Acetonitrile) to give 73.6 mg (0.138 mmol, 34.9% yield) 4-(1-((S)-1-((5-(2,4-difluorophenoxy)pyridin-2-yl)amino)-1-oxopropan-2-yl)-4,4-difluoropiperidin-3-yl)picolinamide (Mixture of 2 diastereomers). LCMS (ES, m/s): 518.1 [M+H]$^+$, rt=1.08-1.13 min, Method 3. $^1$H NMR (400 MHz, DMSO-d$_6$) δ ppm 10.37 (d, J=7.34 Hz, 1H), 8.58 (t, J=5.14 Hz, 1H), 8.09-8.19 (m, 3H), 8.02 (d, J=3.91 Hz, 1H), 7.68 (br d, J=4.89 Hz, 1H), 7.58 (t, J=4.65 Hz, 1H), 7.46-7.54 (m, 2H), 7.30 (tdd, 1H), 7.09-7.17 (m, 1H), 3.53-3.74 (m, 2H), 2.91-3.07 (m, 2H), 2.53-2.89 (m, 2H), 2.09-2.22 (m, 2H), 1.24 (t, J=7.09 Hz, 3H).

Example 262

2-(acetamidomethyl)-4-(1-(1-((5-(2,4-difluorophenoxy)pyridin-2-yl)amino)-1-oxopropan-2-yl)-4,4-difluoropiperidin-3-yl)pyridine 1-oxide

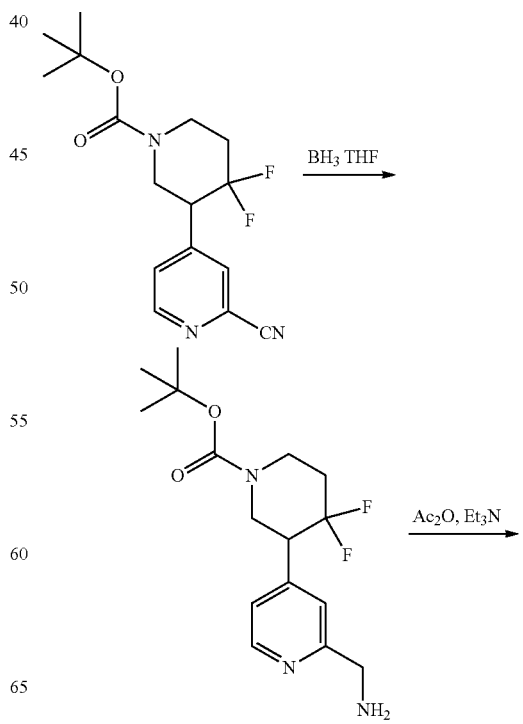

489
-continued

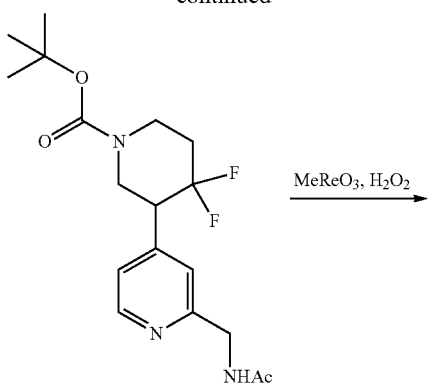

MeReO₃, H₂O₂ →

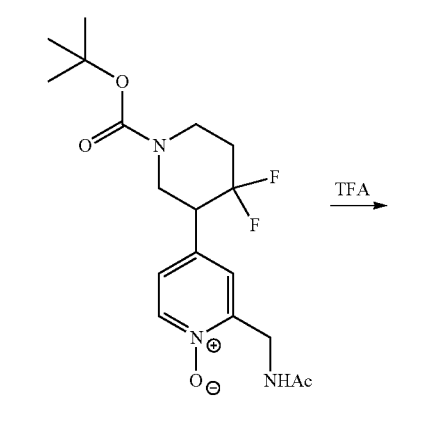

TFA →

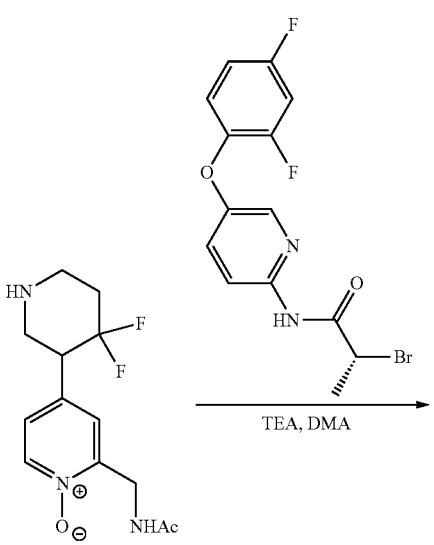

TEA, DMA →

490
-continued

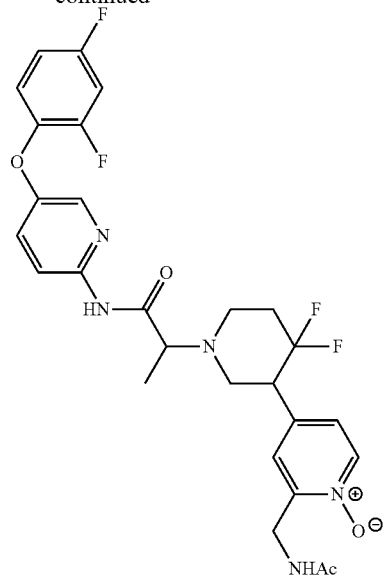

Step 1

To tert-butyl 3-(2-cyanopyridin-4-yl)-4,4-difluoropiperidine-1-carboxylate (Example 258, Step 1) (500 mg, 1.546 mmol) in THF (7 mL) was added BH₃.THF (4.64 mL, 4.64 mmol). The reaction was stirred overnight, and MeOH (5 mL) and AcOH (0.885 mL, 15.46 mmol) were added, dropwise. After 2 h, saturated Na₂CO₃ solution (20 mL) was added to adjust the pH to approximately 11. The mixture was extracted with DCM (3×25 mL), and the combined organic layers were washed with brine, dried over Na₂SO₄ and concentrated to give 613 mg (1.498 mmol, 97% yield) tert-butyl 3-(2-(aminomethyl)pyridin-4-yl)-4,4-difluoropiperidine-1-carboxylate, which was used without further purification. LCMS: (ES, m/z): 328.3 [M+H]⁺.

Step 2

To tert-butyl 3-(2-(aminomethyl)pyridin-4-yl)-4,4-difluoropiperidine-1-carboxylate (408 mg, 1.022 mmol) in DCM (10 mL) was added triethylamine (0.285 mL, 2.044 mmol) and acetic anhydride (0.116 mL, 1.23 mmol). The reaction was stirred overnight and partitioned between saturated NaHCO₃ solution (20 mL) and DCM (20 mL). After layer separation, the aqueous layer was extracted with DCM (2×25 mL). The combined organics were dried over Na₂SO₄, concentrated and purified over silica column (ISCO 24 g), eluting with 0-60% 3:1 EtOAc: EtOH in heptane to give 220 mg (0.596 mmol, 58.3% yield) tert-butyl 3-(2-(acetamidomethyl)pyridin-4-yl)-4,4-difluoropiperidine-1-carboxylate. LCMS: (ES, m/z): 370.3 [M+H]⁺. ¹H NMR (400 MHz, CHLOROFORM-d) δ ppm 8.51 (d, J=4.89 Hz, 1H), 7.20 (s, 1H), 7.17 (d, J=5.38 Hz, 1H), 6.71 (br s, 1H), 4.57 (d, J=4.89 Hz, 2H), 4.15-4.39 (m, 2H), 3.27 (br s, 1H), 2.98-3.20 (m, 2H), 2.12-2.23 (m, 1H), 2.09 (s, 3H), 1.88-2.03 (m, 1H), 1.48 (s, 9H).

Step 3

To tert-butyl 3-(2-(acetamidomethyl)pyridin-4-yl)-4,4-difluoropiperidine-1-carboxylate (220 mg, 0.596 mmol) in DCM (8 mL) was added methyltrioxorhenium(VII) (9.90 mg, 0.030 mmol), followed by dropwise addition of hydrogen peroxide (0.122 mL, 1.191 mmol). After 20 h, excess hydrogen peroxide was destroyed by catalytic decomposition induced by addition of manganese dioxide (2.59 mg, 0.030 mmol), and the reaction was stirred unstoppered until gas evolution subsided (approximately 30 min). The mixture was partitioned between DCM (20 mL) and saturated NaHCO₃ (10 mL), the organic layer was separated, and the aqueous layer was re-extracted with DCM (20 mL). The combined organics were dried over Na₂SO₄, filtered, and concentrated to afford 218 mg (0.566 mmol, 95% yield) crude 2-(acetamidomethyl)-4-(1-(tert-butoxycarbonyl)-4,4-difluoropiperidin-3-yl)pyridine 1-oxide, which was used without further purification. LCMS: (ES, m/z): 386.3 [M+H]⁺. ¹H NMR (400 MHz, CHLOROFORM-d) δ ppm 8.20 (d, J=6.85 Hz, 1H), 7.39 (d, J=2.45 Hz, 1H), 7.21 (br dd, J=6.85, 2.45 Hz, 1H), 7.01 (br d, J=5.87 Hz, 1H), 4.60 (d, J=6.36 Hz, 2H), 4.24 (br s, 2H), 2.99-3.29 (m, 3H), 2.11-2.25 (m, 1H), 1.88-2.07 (m, 4H), 1.49 (s, 9H).

Step 4

To 2-(acetamidomethyl)-4-(1-(tert-butoxycarbonyl)-4,4-difluoropiperidin-3-yl)pyridine 1-oxide (213 mg, 0.553 mmol) in DCM (5 mL) was added TFA (1 mL, 12.98 mmol). After 2 h, the reaction was concentrated to give 221 mg (0.553 mmol, 100% yield) 2-(acetamidomethyl)-4-(4,4-difluoropiperidin-3-yl)pyridine 1-oxide, trifluoroacetic acid salt, which was used without further purification. LCMS: (ES, m/z): 286.2 [M+H]⁺.

Step 5

To (R)-2-bromo-N-(5-(2,4-difluorophenoxy)pyridin-2-yl)propanamide (Intermediate 71) (99 mg, 0.276 mmol) in DMA (2 ml) was added 2-(acetamidomethyl)-4-(4,4-difluoropiperidin-3-yl)pyridine 1-oxide trifluoroacetic acid salt (110 mg, 0.276 mmol), followed by TEA (0.192 mL, 1.380 mmol). The reaction was stirred at rt 16 h, heated to 50° C. for 3 h, diluted with EtOAc, washed with sat'd. K₂CO₃ solution and with a mix of sat'd. K₂CO₃ solution and brine, dried over Na₂SO₄, filtered, concentrated and purified over normal phase silica column (4 g), eluting with 0-100% 3:1 EtOAc: EtOH in heptane to give 30.2 mg (0.053 mmol, 19.10% yield) 2-(acetamidomethyl)-4-(1-(1-((5-(2,4-difluorophenoxy)pyridin-2-yl)amino)-1-oxopropan-2-yl)-4,4-difluoropiperidin-3-yl)pyridine 1-oxide (mixture of 4 isomers). LCMS (ES, m/s): 562.1 [M+H]⁺, rt=0.92-0.96 min, Method 3. ¹H NMR (400 MHz, DMSO-d₆) δ ppm 10.37 (d, J=15.16 Hz, 1H), 8.39-8.47 (m, 1H), 8.24 (t, J=6.60 Hz, 1H), 8.08-8.18 (m, 2H), 7.46-7.55 (m, 2H), 7.26-7.36 (m, 3H), 7.13 (br t, J=8.56 Hz, 1H), 4.24-4.39 (m, 2H), 3.61-3.72 (m, 1H), 3.43-3.58 (m, 1H), 2.87-3.02 (m, 2H), 2.69-2.79 (m, 1H), 2.53-2.63 (m, 1H), 2.01-2.21 (m, 2H), 1.83-1.96 (m, 3H), 1.22 (t, J=6.36 Hz, 3H).

Example 263 was synthesized in an analogous manner, using the designated Intermediate in Step 5.

| Ex | Name | Structure | ¹H NMR | Analytical LC/MS: (M + H)⁺; retention time (min); LC/MS Method of analysis | Int |
|---|---|---|---|---|---|
| 263 | 2-(acetamidomethyl)-4-(4,4-difluoro-1-(1-((5-fluoropyridin-2-yl)amino)-1-oxopropan-2-yl)piperidin-3-yl)-pyridine 1-oxide | 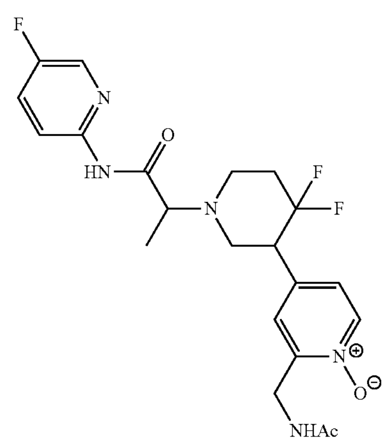 [SMILES: CC(=O)NCc1cc(C2CN(C(C)C(=O)Nc3ccc(F)cn3)CCC2(F)F)cc[n+]1[O-]] | ¹H NMR (400 MHz, DMSO-d₆) δ 10.41 (d, J = 15.65 Hz, 1H), 8.38-8.51 (m, 1H), 8.34 (t, J = 3.42 Hz, 1H), 8.24 (t, J = 6.79 Hz, 1H), 8.15 (dd, J = 9.29, 3.91 Hz, 1H), 7.75 (tt, J = 8.68, 3.30 Hz, 1H), 7.26-7.38 (m, 2H), 4.24-4.39 (m, 2H), 3.61-3.72 (m, 1H), 3.44-3.61 (m, 1H), 2.86-3.04 (m, 2H), 2.53-2.83 (m, 2H), 2.01-2.18 (m, 2H), 1.85-1.96 (m, 3H), 1.23 (t, J = 6.36 Hz, 3H). | 452.4; rt 0.57-0.62. LC/MS Method 2 | 1 |

Example 264

2-(3-(2-(aminomethyl)pyridin-4-yl)-4,4-difluoropiperidin-1-yl)-N-(5-(2,4-difluorophenoxy)pyridin-2-yl)propanamide

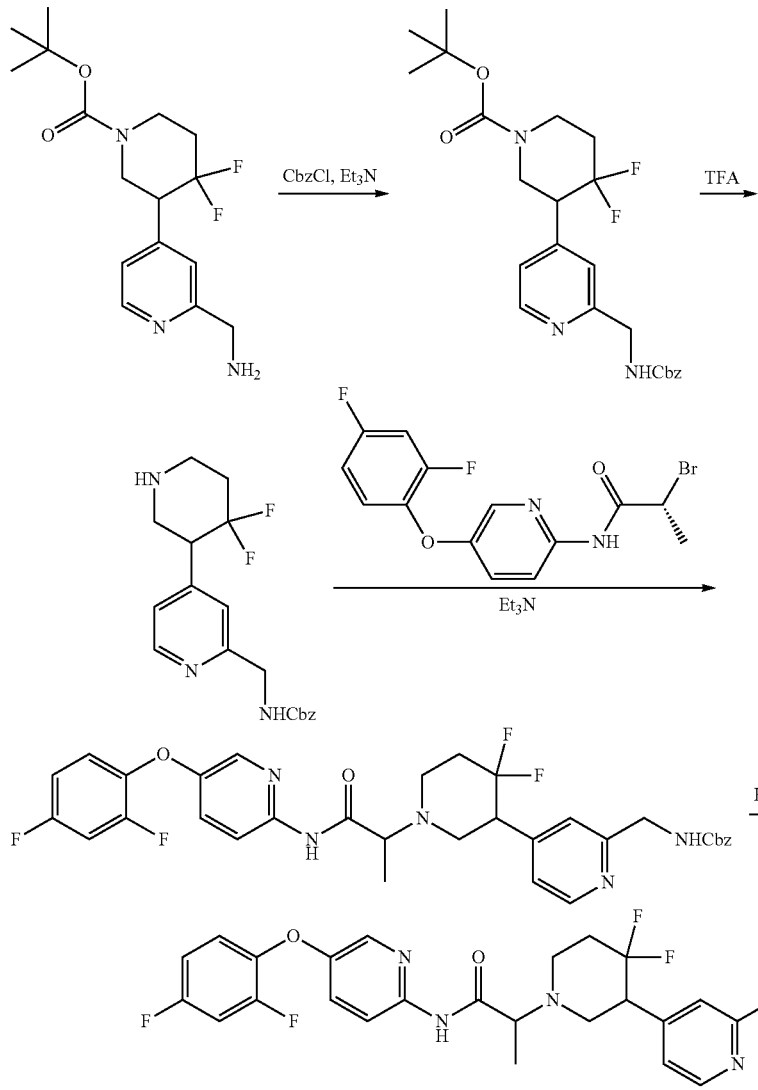

Step 1

To tert-butyl 3-(2-(aminomethyl)pyridin-4-yl)-4,4-difluoropiperidine-1-carboxylate (Example 262, Step 1) (204 mg, 0.499 mmol) in DCM (5 mL) was added triethylamine (0.139 mL, 0.997 mmol) and Cbz-Cl (0.085 mL, 0.598 mmol). The reaction was stirred for 2 h, then partitioned between saturated NaHCO$_3$ solution (15 mL) and DCM (15 mL). After layer separation, the aqueous layer was extracted with DCM (2×20 mL), and the combined organics were dried over Na$_2$SO$_4$, concentrated and purified over a silica column (ISCO, 12 g), eluting with 0-70% EtOAc in heptane to give 138 mg (0.299 mmol, 60.0% yield) tert-butyl 3-(2-((((benzyloxy)carbonyl)amino)methyl)pyridin-4-yl)-4,4-difluoropiperidine-1-carboxylate. LCMS: (ES, m/z): 462.4 [M+H]$^+$. $^1$H NMR (400 MHz, CHLOROFORM-d) δ ppm 8.51 (d, J=4.89 Hz, 1H), 7.28-7.45 (m, 5H), 7.21 (s, 1H), 7.15 (br d, J=4.89 Hz, 1H), 5.82 (br s, 1H), 5.16 (s, 2H), 4.54 (d, J=5.38 Hz, 2H), 4.23 (br s, 2H), 2.98-3.30 (m, 3H), 2.11-2.24 (m, 1H), 1.88-2.03 (m, 1H), 1.48 (s, 9H).

Step 2

To tert-butyl 3-(2-((((benzyloxy)carbonyl)amino)methyl)pyridin-4-yl)-4,4-difluoropiperidine-1-carboxylate (135 mg, 0.293 mmol) in DCM (2 mL) was added TFA (0.3 mL, 3.89 mmol). After 2 h, the reaction was concentrated to give 139 mg (0.293 mmol, 100% yield) benzyl ((4-(4,4-difluoropiperidin-3-yl)pyridin-2-yl)methyl)carbamate, trifluoroacetic acid salt, which was used without further purification. LCMS: (ES, m/z): 362.1 [M+H]$^+$.

Step 3

To (R)-2-bromo-N-(5-(2,4-difluorophenoxy)pyridin-2-yl)propanamide (Intermediate 71) (105 mg, 0.293 mmol) in DMA (2 ml) was added benzyl ((4-(4,4-difluoropiperidin-3-yl)pyridin-2-yl)methyl)carbamate, trifluoroacetic acid salt (139 mg, 0.293 mmol), followed by TEA (0.204 mL, 1.465 mmol). The mixture was stirred at rt for 16 h, heated to 50° C. for 3 h, filtered, washed with a mix of sat'd K$_2$CO$_3$ solution and brine, dried over Na$_2$SO$_4$, filtered, concentrated and purified by silica column (ISCO 12 g), eluting with 0-50% 3:1 EtOAc:EtOH in heptane to give 107 mg (0.168 mmol, 57.3% yield) benzyl ((4-(1-(1-((5-(2,4-difluorophenoxy)pyridin-2-yl)amino)-1-oxopropan-2-yl)-4,4-difluoropiperidin-3-yl)pyridin-2-yl)methyl)carbamate (mixture of 4 isomers). LCMS: (ES, m/z): 638.3 [M+H]+. 1H NMR (400 MHz, CHLOROFORM-d) δ ppm 9.48 (br d, J=17.12 Hz, 1H), 8.50 (t, J=5.14 Hz, 1H), 8.20 (dd, J=9.05, 5.13 Hz, 1H), 8.07 (d, J=2.93 Hz, 1H), 7.28-7.41 (m, 5H), 7.22-7.26 (m, 1H), 7.17 (br t, J=6.11 Hz, 1H), 7.02-7.12 (m, 1H), 6.94-7.02 (m, 1H), 6.83-6.92 (m, 1H), 5.88 (br s, 1H), 5.15 (d, J=5.38 Hz, 2H), 4.53 (br t, J=4.40 Hz, 2H), 3.24-3.47 (m, 2H), 2.59-3.10 (m, 5H), 2.26 (br d, J=14.18 Hz, 2H), 1.38 (t, J=6.60 Hz, 3H).

Step 4

A mixture of benzyl ((4-(1-(1-(((5-(2,4-difluorophenoxy)pyridin-2-yl)amino)-1-oxopropan-2-yl)-4,4-difluoropiperidin-3-yl)pyridin-2-yl)methyl)carbamate (107 mg, 0.168 mmol) and Pd—C (17.86 mg, 0.017 mmol) in methanol (3 mL) was stirred under hydrogen for 4 h, filtered, concentrated and purified by reverse phase Xselect CSH Prep C18 5 uM OBD (Gradient 30% to 85% B over 19 min, flow rate 40 mL/min, A: Water with 10 mM Ammonium Bicarb and 0.075% Ammonium Hydroxide/B: Acetonitrile) to give 48.6 mg (0.092 mmol, 54.6% yield) 2-(3-(2-(aminomethyl)pyridin-4-yl)-4,4-difluoropiperidin-1-yl)-N-(5-(2,4-difluorophenoxy)pyridin-2-yl)propanamide (Mixture of 4 isomers). LCMS (ES, m/z): 504.2 [M+H]+, rt=1.02-1.09 min, Method 3. 1H NMR (400 MHz, DMSO-d6) δ ppm 10.34 (br d, J=9.78 Hz, 1H), 8.41 (t, J=5.14 Hz, 1H), 8.07-8.19 (m, 2H), 7.39-7.55 (m, 3H), 7.07-7.37 (m, 4H), 3.77 (d, J=5.87 Hz, 2H), 3.60-3.71 (m, 1H), 3.45 (br s, 1H), 2.89-3.08 (m, 3H), 2.81 (br t, J=11.25 Hz, 1H), 2.61-2.75 (m, 1H), 2.16 (br s, 2H), 1.23 (t, J=6.85 Hz, 3H).

Example 265

(2S)-2-(4,4-difluoro-3-(5-(2,2,2-trifluoro-1-hydroxyethyl)pyridin-3-yl)piperidin-1-yl)-N-(5-(2,4-difluorophenoxy)pyridin-2-yl)propanamide

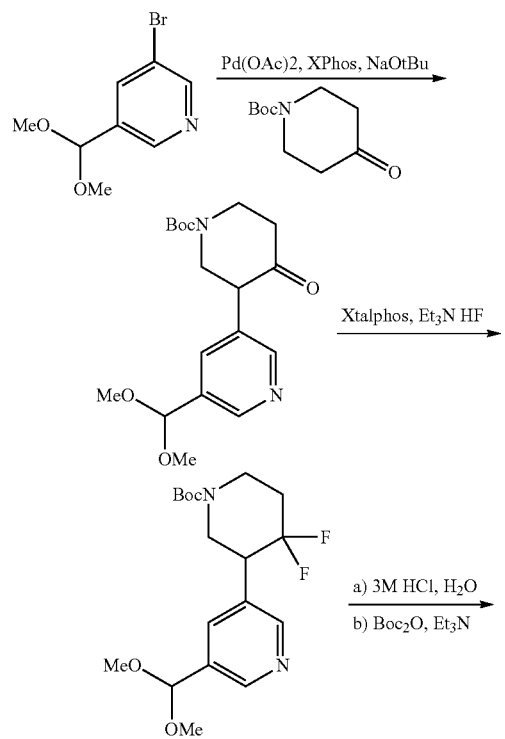

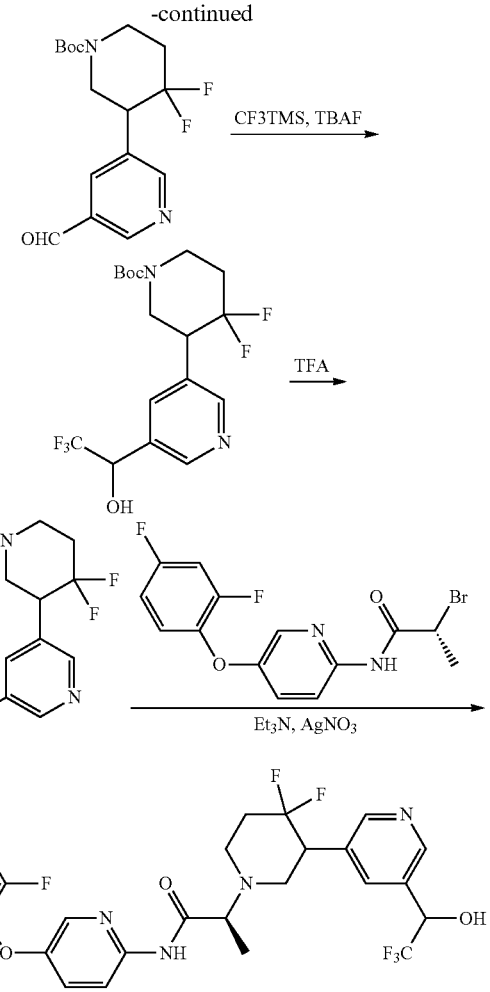

Step 1

A degassed solution of tert-butyl 4-oxopiperidine-1-carboxylate (3477 mg, 17.45 mmol) and sodium tert-butoxide (3354 mg, 34.9 mmol) in THF (27 ml) was treated with 3-bromo-5-(dimethoxymethyl)pyridine (2700 mg, 11.63 mmol), followed by XPhos (1109 mg, 2.327 mmol) and palladium(II) acetate (261 mg, 1.163 mmol). The reaction was heated at 50° C. overnight, diluted with water and extracted with EtOAc (3×100 mL). The combined organic extracts were washed with brine, dried over sodium sulfate, concentrated and purified by silica column (ISCO 80 g), eluting with 0-100% EtOAc in heptane to give 190 mg (0.542 mmol, 41.9% yield) tert-butyl 3-(5-(dimethoxymethyl)pyridin-3-yl)-4-oxopiperidine-1-carboxylate). LCMS: (ES, m/z): 351.2 [M+H]+. 1H NMR (400 MHz, CHLOROFORM-d) δ ppm 8.62 (d, J=1.96 Hz, 1H), 8.40 (d, J=1.96 Hz, 1H), 7.61 (t, J=1.96 Hz, 1H), 5.47 (s, 1H), 4.33 (br d, J=9.78 Hz, 2H), 3.77 (br dd, J=10.76, 5.87 Hz, 1H), 3.42 (ddd, J=13.45, 10.51, 4.40 Hz, 2H), 3.34 (s, 6H), 2.60-2.71 (m, 1H), 2.52-2.60 (m, 1H), 1.51 (s, 9H).

Step 2

To XtalFluor-E (1307 mg, 5.71 mmol) in DCM (6 mL) cooled in an ice bath was added triethylamine trihydrofluoride (0.929 mL, 5.71 mmol) in DCM (3 mL). After 20 min, tert-butyl 3-(5-(dimethoxymethyl)pyridin-3-yl)-4-oxopiperidine-1-carboxylate (1000 mg, 2.85 mmol) in DCM (3 mL) was slowly added. After 30 min, the reaction was stirred at rt. After 3 h, the mixture was re-chilled in an ice bath, and sat'd. NaHCO₃ solution (10 mL) was slowly added, followed by DCM (10 mL). The layers were separated, and aqueous layer was extracted with DCM (2×25 mL). The combined organic layers were washed with brine, dried over Na₂SO₄, filtered, concentrated and purified by silica column (ISCO 40 g), eluting with 10-100% EtOAc in heptane to give 500 mg (1.208 mmol, 42.3% yield) tert-butyl 3-(5-(dimethoxymethyl)pyridin-3-yl)-4,4-difluoropiperidine-1-carboxylate. LCMS: (ES, m/z): 373.3 [M+H]⁺. ¹H NMR (400 MHz, CHLOROFORM-d) δ ppm 8.65 (d, J=1.47 Hz, 1H), 8.53 (d, J=1.96 Hz, 1H), 7.75 (s, 1H), 5.48 (s, 1H), 4.26 (br s, 2H), 3.35 (s, 7H), 3.03-3.20 (m, 2H), 2.13-2.23 (m, 1H), 1.90-2.09 (m, 1H), 1.44-1.50 (m, 9H).

Step 3

To tert-butyl 3-(5-(dimethoxymethyl)pyridin-3-yl)-4,4-difluoropiperidine-1-carboxylate (480 mg, 1.160 mmol) in THF (12 mL) was added HCl (5.80 mL, 17.40 mmol), and the reaction was heated to 60° C. After 1 h, the mixture was concentrated to give crude 5-(4,4-difluoropiperidin-3-yl)nicotinaldehyde (262 mg, 1.16 mmol). This material was stirred in DCM (6 mL), and triethylamine (0.808 mL, 5.80 mmol) and Boc-anhydride (0.323 mL, 1.392 mmol) were added. After 3 h, the reaction was partitioned between DCM (40 mL) and water (30 mL). After layer separation, the aqueous layer was extracted with DCM (2×mL). The combined organic layers were washed with brine (20 mL), dried over Na₂SO₄, filtered, concentrated and purified by silica column (ISCO 24 g), eluting with 0-50% EtOAc in heptane to give 267 mg (0.818 mmol, 70.5% yield) tert-butyl 4,4-difluoro-3-(5-formylpyridin-3-yl)piperidine-1-carboxylate. LCMS: (ES, m/z): 327.1 [M+H]⁺.

Step 4

To tert-butyl 4,4-difluoro-3-(5-formylpyridin-3-yl)piperidine-1-carboxylate (267 mg, 0.818 mmol) in THF (8 mL) at 0° C. was slowly added trifluoromethyltrimehtylthylsilane (0.181 mL, 1.227 mmol), followed by TBAF (1.064 mL, 1.064 mmol), dropwise over 10 min. After 1 h, the reaction was quenched with water (5 mL) and partitioned between EtOAc and NaHCO₃ (sat). The layers were separated, and the aqueous layer was back extracted with EtOAc. The combined organics were dried over magnesium sulfate, filtered through Celite, concentrated and purified by silica column (ISCO 12 g), eluting with 30-100% EtOAc in heptane to give 240 mg (0.606 mmol, 74.0% yield) tert-butyl 4,4-difluoro-3-(5-(2,2,2-trifluoro-1-hydroxyethyl)pyridin-3-yl)piperidine-1-carboxylate LCMS: (ES, m/z): 397.3 [M+H]⁺. ¹H NMR (400 MHz, CHLOROFORM-d) δ ppm 8.60-8.65 (m, 1H), 8.56 (d, J=1.47 Hz, 1H), 7.87 (br d, J=6.36 Hz, 1H), 5.13 (q, J=6.85 Hz, 1H), 4.24 (br d, J=6.36 Hz, 2H), 3.24-3.38 (m, 1H), 3.08-3.22 (m, 2H), 2.13-2.26 (m, 1H), 1.91-2.04 (m, 1H), 1.46-1.50 (m, 9H).

Step 5

To tert-butyl 4,4-difluoro-3-(5-(2,2,2-trifluoro-1-hydroxyethyl)pyridin-3-yl)piperidine-1-carboxylate (80 mg, 0.202 mmol) in DCM (3 mL) was added TFA (0.3 mL, 3.89 mmol). After 3 h. the reaction was concentrated to give 83 mg (0.202 mmol, 100% yield) 1-(5-(4,4-difluoropiperidin-3-yl)pyridin-3-yl)-2,2,2-trifluoroethan-1-ol, trifluoroacetic acid salt, which was used without further purification. LCMS: (ES, m/z): 297.2 [M+H]⁺.

Step 6

To (R)-2-bromo-N-(5-(2,4-difluorophenoxy)pyridin-2-yl)propanamide (Intermediate 71) (72.1 mg, 0.202 mmol) in DMA (1.5 mL) was added 1-(5-(4,4-difluoropiperidin-3-yl)pyridin-3-yl)-2,2,2-trifluoroethan-1-ol, trifluoroacetic acid salt (83 mg, 0.202 mmol), followed by TEA (0.169 mL, 1.212 mmol). The reaction was stirred overnight, diluted with EtOAc, washed with satd. K₂CO₃ solution and a mix of satd. K₂CO₃ solution and brine, dried over Na₂SO₄, filtered, concentrated and purified by reverse phase Xselect CSH Prep C18 5 uM OBD (Gradient 50% to 99% B over 19 min, flow rate 40 mL/min, A: Water with 10 mM Ammonium Bicarb and 0.075% Ammonium Hydroxide/B: Acetonitrile) to give 11.5 mg (0.020 mmol, 9.85% yield) (2S)-2-(4,4-difluoro-3-(5-(2,2,2-trifluoro-1-hydroxyethyl)pyridin-3-yl)piperidin-1-yl)-N-(5-(2,4-difluorophenoxy)pyridin-2-yl)propanamide (Mixture of 4 isomers). LCMS (ES, m/z): 573.2 [M+H]+: rt=1.15-1.22 min, Method 3. ¹H NMR (400 MHz, DMSO-d₆) δ ppm 10.32-10.41 (m, 1H), 8.60 (br d, J=4.89 Hz, 1H), 8.56 (br d, J=4.89 Hz, 1H), 8.06-8.19 (m, 2H), 7.90 (br s, 1H), 7.42-7.58 (m, 2H), 7.30 (tdd, 1H), 7.02-7.18 (m, 2H), 5.33 (br d, J=2.93 Hz, 1H), 3.48-3.74 (m, 2H), 2.91-3.06 (m, 2H), 2.54-2.86 (m, 2H), 2.16 (br s, 2H), 1.23 (dd, J=6.60, 5.14 Hz, 3H).

Example 266

3-(1-(1-((5-(2,4-difluorophenoxy)pyridin-2-yl)amino)-1-oxopropan-2-yl)-4,4-difluoropiperidin-3-yl)-5-(2,2,2-trifluoro-1-hydroxyethyl)pyridine 1-oxide

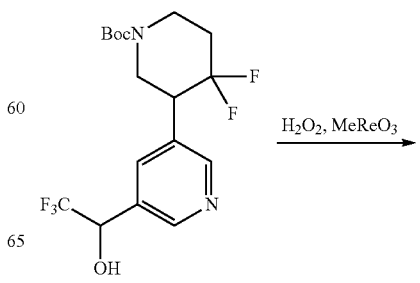

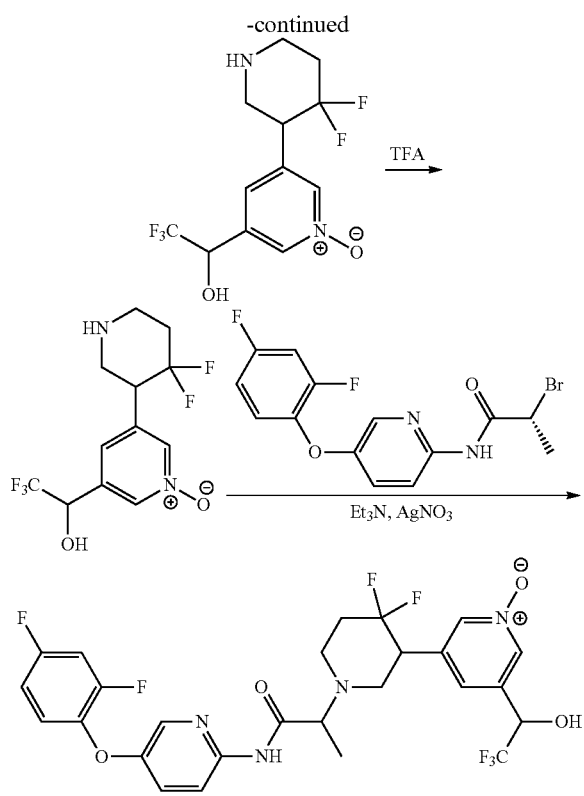

Step 1

To tert-butyl 4,4-difluoro-3-(5-(2,2,2-trifluoro-1-hydroxyethyl)pyridin-3-yl)piperidine-1-carboxylate (Example 265, Step 4) (160 mg, 0.404 mmol) in DCM (3 mL) was added methyltrioxorhenium(VII) (10.06 mg, 0.040 mmol), followed by dropwise addition of hydrogen peroxide (0.025 mL, 0.807 mmol). After 20 h, the excess hydrogen peroxide was destroyed by catalytic decomposition induced by addition of manganese dioxide (1.755 mg, 0.020 mmol), and the mixture was stirred until gas evolution subsided (30 min). The mixture was partitioned between DCM (20 mL) and saturated NaHCO$_3$ (10 mL). The organic layer was separated, and the aqueous layer was re-extracted with DCM (20 mL). The combined organic extracts were dried over Na$_2$SO$_4$, filtered, and concentrated to afford oxide 156 mg (0.378 mmol, 94% yield) crude 3-(1-(tert-butoxycarbonyl)-4,4-difluoropiperidin-3-yl)-5-(2,2,2-trifluoro-1-hydroxyethyl)pyridine 1-oxide. LCMS: (ES, m/z): 413.3 [M+H]$^+$.

Step 2

To 3-(1-(tert-butoxycarbonyl)-4,4-difluoropiperidin-3-yl)-5-(2,2,2-trifluoro-1-hydroxyethyl)pyridine 1-oxide (156 mg, 0.378 mmol) in DCM (3 mL) was added TFA (0.3 mL, 3.89 mmol). After 2 h, the reaction was concentrated to give 161 mg (0.378 mmol, 100% yield) 3-(4,4-difluoropiperidin-3-yl)-5-(2,2,2-trifluoro-1-hydroxyethyl)pyridine 1-oxide, trifluoroacetic acid salt, which was used without further purification. LCMS: (ES, m/z): 313.3 [M+H]$^+$.

Step 3

To (R)-2-bromo-N-(5-(2,4-difluorophenoxy)pyridin-2-yl)propanamide (Intermediate 71) (66.1 mg, 0.185 mmol) in DMA (2 ml) was added 3-(4,4-difluoropiperidin-3-yl)-5-(2,2,2-trifluoro-1-hydroxyethyl)pyridine 1-oxide, trifluoroacetic acid salt (79 mg, 0.185 mmol), followed by TEA (0.155 mL, 1.110 mmol). The mixture was stirred at rt for 16 h, heated to 50° C. for 3 h, diluted with EtOAc, washed with sat'd. K$_2$CO$_3$ solution and a mix of sa'd. K$_2$CO$_3$ solution and brine, dried over Na$_2$SO$_4$, filtered, concentrated and purified by reverse phase Xselect CSH Prep C18 5 uM OBD (Gradient 30% to 85% B over 19 min, flow rate 40 mL/min, A: Water with 10 mM Ammonium Bicarb and 0.075% Ammonium Hydroxide/B: Acetonitrile) to give 46.1 mg (0.077 mmol, 41.5% yield) 3-(1-(1-((5-(2,4-difluorophenoxy)pyridin-2-yl)amino)-1-oxopropan-2-yl)-4,4-difluoropiperidin-3-yl)-5-(2,2,2-trifluoro-1-hydroxyethyl)pyridine 1-oxide (Mixture of 4 isomers). LCMS: (ES, m/z): 589.2 [M+H]+ rt=1.03-1.08 min, Method 3. $^1$H NMR (400 MHz, DMSO-d$_6$) δ ppm 10.24-10.41 (m, 1H), 8.23-8.32 (m, 2H), 8.06-8.18 (m, 2H), 7.44-7.55 (m, 3H), 7.22-7.34 (m, 2H), 7.09-7.17 (m, 1H), 5.28-5.39 (m, 1H), 3.67 (dq, J=19.68, 6.81 Hz, 1H), 3.48-3.60 (m, 1H), 2.66-3.11 (m, 4H), 1.97-2.19 (m, 2H), 1.17-1.29 (m, 3H).

Example 267

2-((S)-4,4-difluoro-3-(6-oxo-1,6-dihydropyridin-3-yl)piperidin-1-yl)-N-(5-((6-oxo-1,6-dihydropyridin-2-yl)oxy)pyridin-2-yl)propanamide

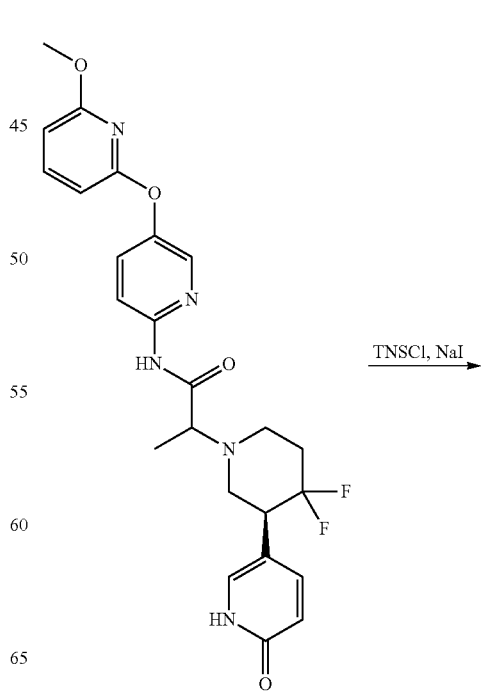

501
-continued

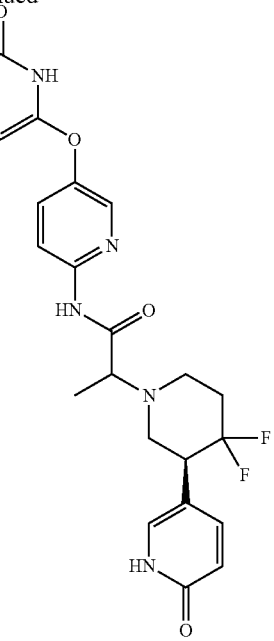

Step 1

To 2-((S)-4,4-difluoro-3-(6-oxo-1,6-dihydropyridin-3-yl)piperidin-1-yl)-N-(5-(((6-methoxypyridin-2-yl)oxy)pyridin-2-yl)propanamide (Example 95) (90 mg, 0.185 mmol) in acetonitrile (5 mL) was added sodium iodide (167 mg, 1.112 mmol)ed by TMSCl (0.142 mL, 1.112 mmol). The resulting mixture was heated at 50° C. overnight, concentrated and purified by reverse phase HPLC (XSELECT CSH C18 column, 15-85%, acetonitrile/water with 0.1% TFA, 40 mL/min flow rate, 27 min run time) to yield 28 mg, (0.047 mmol, 25.3% yield) 2-((S)-4,4-difluoro-3-(6-oxo-1,6-dihydropyridin-3-yl)piperidin-1-yl)-N-(5-((6-oxo-1,6-dihydropyridin-2-yl)oxy)pyridin-2-yl)propanamide, trifluoroacetic acid salt as a white solid. LCMS (ES, m/s): 471 [M+H]+, rt=0.51 min, Method 5; ¹H NMR (400 MHz, METHANOL-$d_4$) δ 8.29-8.13 (m, 1H), 7.74-7.61 (m, 2H), 7.58-7.49 (m, 1H), 6.67-6.55 (m, 1H), 6.38 (s, 2H), 4.23-4.10 (m, 1H), 3.85-3.65 (m, 2H), 3.65-3.40 (m, 3H), 2.59-2.34 (m, 2H), 1.71 (dd, J=6.85, 5.14 Hz, 3H).

502

Example 268

(S)-2-((S)-4,4-difluoro-3-(6-oxo-1,6-dihydropyridin-3-yl)piperidin-1-yl)-N-(5-(3,4-difluorophenoxy)pyridin-2-yl)propanamide

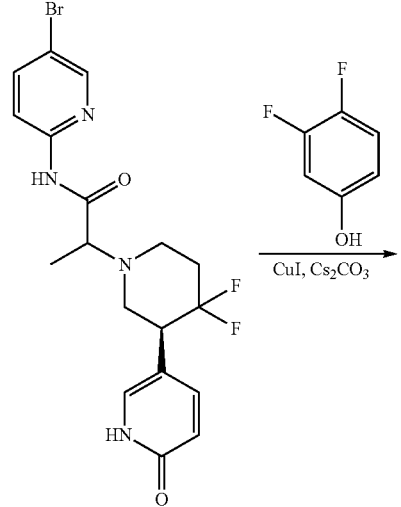

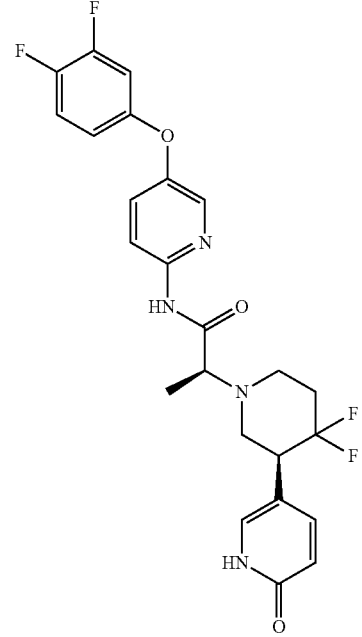

Step 1

A mixture of 3,4-difluorophenol (64.3 mg, 0.494 mmol), cesium carbonate (241 mg, 0.741 mmol), copper(I) iodide (9.41 mg, 0.049 mmol), dimethylglycine (5.09 mg, 0.049 mmol) and N-(5-bromopyridin-2-yl)-2-((S)-4,4-difluoro-3-(6-oxo-1,6-dihydropyridin-3-yl)piperidin-1-yl)propanamide (Example 94) (109 mg, 0.247 mmol) in dioxane (10 mL) in a microwave vial was purged with nitrogen. The mixture was stirred at 110° C. overnight and partitioned between EtOAc and water. The layers were separated, and the aqueous layer was extracted with EtOAc (2×). The combined organics were washed with brine, concentrated and purified by reverse phase HPLC (XSelect CSH Prep C18 5 um OBD column, 30-85%, acetonitrile/water with 10 mM ammonium bicarb and 0.075% ammonium hydroxide, 40 mL/min flow rate, 27 min run time) to yield 8 mg (0.015 mmol, 5.94% yield) (S)-2-((S)-4,4-difluoro-3-(6-oxo-1,6-dihydropyridin-3-yl)piperidin-1-yl)-N-(5-(3,4-difluorophenoxy)pyridin-2-yl)propanamide as a white solid. LCMS (ES, m/s): 490 [M+H]⁺, rt=1.05 min, Method 3. ¹H NMR (400 MHz, METHANOL-d4) δ 8.28-8.18 (m, 1H), 8.18-8.08 (m, 1H), 7.73-7.64 (m, 1H), 7.58-7.50 (m, 1H), 7.50-7.40 (m, 1H), 7.37-7.24 (m, 1H), 7.12-6.96 (m, 1H), 6.89-6.80 (m, 1H), 6.59-6.49 (m, 1H), 3.62-3.51 (m, 1H), 3.07-2.86 (m, 3H), 2.76-2.53 (m, 1H), 2.38-2.11 (m, 2H), 1.37 (d, J=7.09 Hz, 3H).

Example 269 was prepared in an analogous manner using the designated phenol in Step 1.

| Ex | Name | Structure | ¹H NMR | LC/MS: (M + H)⁺; retention time (min); LC/MS Method of analysis | Phenol |
|---|---|---|---|---|---|
| 269 | (S)-2-((S)-4,4-difluoro-3-(6-oxo-1,6-dihydro-pyridin-3-yl)-piperidin-1-yl)-N-(5-(4-fluoro-2-methoxyphen-oxy)pyridin-2-yl)propan-amide | 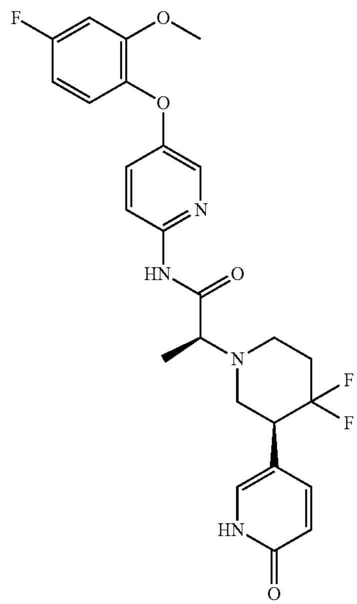 [SMILES: COc1cc(F)ccc1Oc1ccc(NC(=O)[C@H](C)N2CCC(F)(F)[C@@H](c3ccc(=O)[nH]c3)C2)nc1] | ¹H NMR (400 MHz, METHANOL-d₄) δ 8.13-8.04 (m, 1H), 8.01-7.92 (m, 1H), 7.72-7.63 (m, 1H), 7.49-7.40 (m, 1H), 7.34-7.22 (m, 1H), 7.19-7.07 (m, 1H), 7.03-6.94 (m, 1H), 6.81-6.69 (m, 1H), 6.59-6.48 (m, 1H), 3.80 (s, 3H), 3.61-3.48 (m, 1H), 3.06-2.86 (m, 3H), 2.68 (s, 1H), 2.38-2.09 (m, 2H), 1.36 (d, J = 6.85 Hz, 3H). | 502; rt 1.00. LC/MS Method 3 | 4-fluoro-2-meth-oxyphenol |

Example 270

(2S)-2-(3-(2-((3,3-difluoroazetidin-1-yl)methyl)pyridin-4-yl)-4,4-difluoropiperidin-1-yl)-N-(5-(2,4-difluorophenoxy)pyridin-2-yl)propanamide

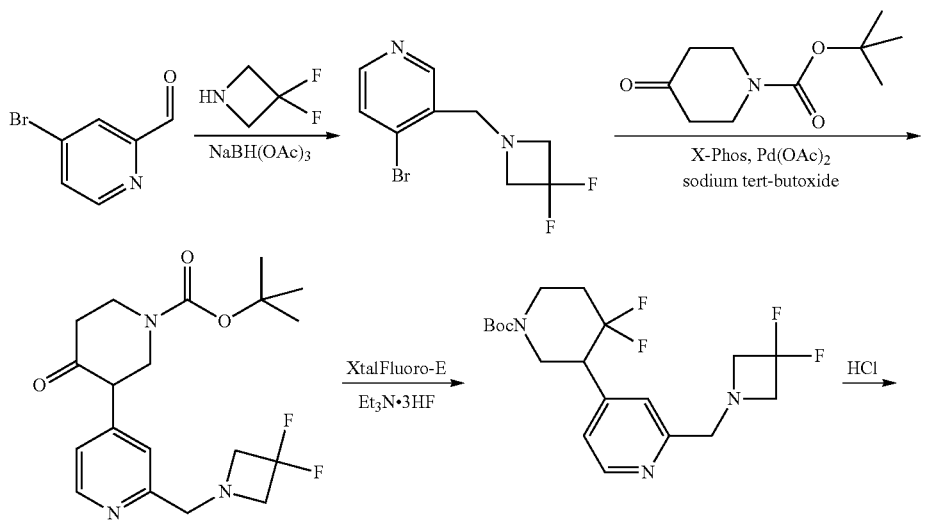

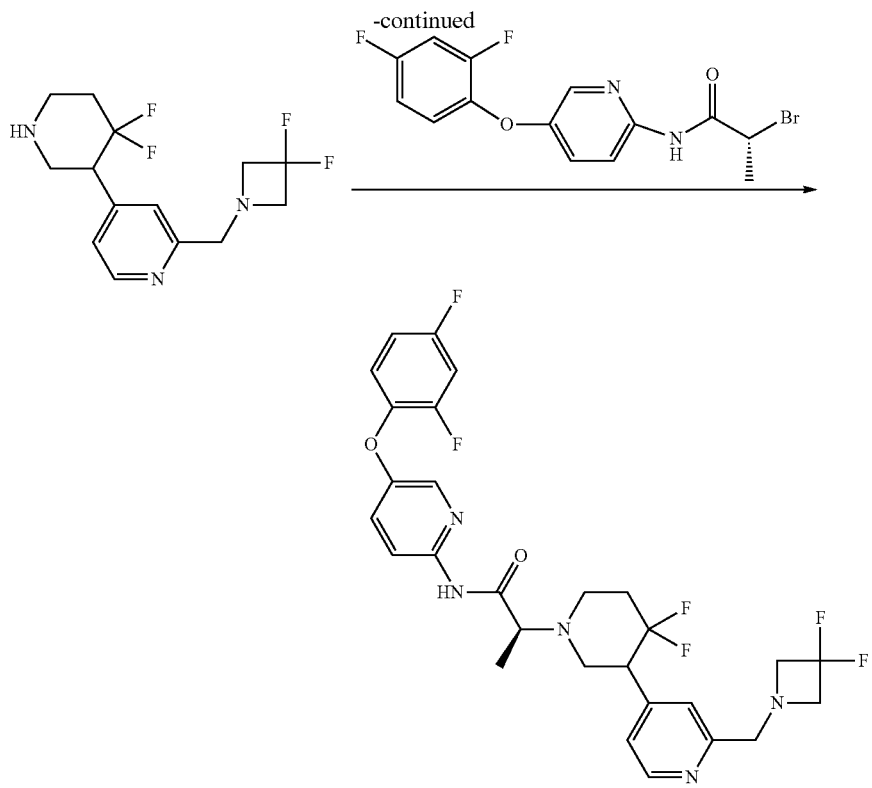

Step 1

To 4-bromopicolinaldehyde (500 mg, 2.69 mmol) in 1,2-dichloroethane (10 mL) was added 3,3-difluoroazetidine hydrochloride (453 mg, 3.49 mmol). After 30 min, sodium triacetoxyborohydride (1139 mg, 5.38 mmol) was added. After stirring overnight, Hunig's base (0.435 mL, 2.49 mmol) and more sodium triacetoxyborohydride (1139 mg, 5.38 mmol) were added, followed, after stirring another night, by more sodium triacetoxyborohydride (300 mg, 1.42 mmol). After another 2 h, the reaction was quenched with water (30 mL) then extracted with DCM. Sat'd NaHCO$_3$ solution was added to make the remaining aqueous slightly basic, after which it was extracted with DCM again. The combined organics were washed with 1:1 sat'd NaHCO$_3$: brine, dried over MgSO$_4$, filtered and concentrated to afford 710 mg (2.70 mmol, 100% yield) 4-bromo-2-((3,3-difluoroazetidin-1-yl)methyl)pyridine an amber colored oil, which was used without further purification. LCMS: (ES, m/s): 263, 265 [M+H]$^+$, rt=0.82 min, Method 3. $^1$H NMR (400 MHz, CHLOROFORM-d) δ ppm 8.38 (d, J=5.38 Hz, 1H), 7.58 (d, J=1.96 Hz, 1H), 7.39 (dd, J=5.38, 1.96 Hz, 1H), 3.90 (s, 2H), 3.74 (t, J=12.23 Hz, 4H).

Step 2

To tert-butyl 4-oxopiperidine-1-carboxylate (716 mg, 3.59 mmol) and 4-bromo-3-((3,3-difluoroazetidin-1-yl)methyl)pyridine (700 mg, 2.66 mmol) in THF (8 mL) was added sodium tert-butoxide (3.99 mL, 7.98 mmol) followed after 30 minutes by XPhos (254 mg, 0.532 mmol) and PdOAc2 (59.7 mg, 0.266 mmol). The reaction mixture was degassed under N$_2$, heated at 48° C. overnight, quenched with cold water and brine, and extracted with EtOAc. The organics were washed with brine, dried over sodium sulfate, filtered, concentrated and purified over silica, eluting with 0-80% 3:1 EtOAc: EtOH in heptane to afford 252 mg (0.661 mmol, 24.83% yield) tert-butyl 3-(2-((3,3-difluoroazetidin-1-yl)methyl)pyridin-4-yl)-4-oxopiperidine-1-carboxylate as a yellowish oil. LCMS: (ES, m/s): 382 [M+H]$^+$, rt=0.94 min, Method 3. $^1$H NMR (400 MHz, CHLOROFORM-d) δ ppm 8.54 (d, J=4.89 Hz, 1H), 7.21 (s, 1H), 7.04 (dd, J=5.14, 1.71 Hz, 1H), 4.19-4.46 (m, 2H), 3.91 (s, 2H), 3.72 (t, J=12.23 Hz, 5H), 3.41-3.60 (m, 2H), 2.50-2.72 (m, 2H), 1.53 (s, 9H).

Step 3

To triethylamine trihydrofluoride (0.534 mL, 3.28 mmol) in DCM (1.5 mL) was added XtalFluoro-E (450 mg, 1.966 mmol). The mixture was cooled to −20° C., and tert-butyl 3-(2-((3,3-difluoroazetidin-1-yl)methyl)pyridin-4-yl)-4-oxopiperidine-1-carboxylate (250 mg, 0.655 mmol) in DCM (2 mL) was added over about 20 minutes. After 45 minutes, the reaction was warmed to 0° C. over 1 hour, then stirred at 0° C. overnight. The mixture was poured to an ice cold mixture of sat'd NaHCO₃ and brine, then diluted with DCM. After partitioning of the layers, the aqueous layer was extracted with DCM. The combined organics were washed with brine, dried over Na₂SO₄, filtered, concentrated and purified over silica, eluting with 0-100% 3:1 EtOAc:EtOH in heptane to afford 98 mg, (0.243 mmol, 37.1% yield) tert-butyl 3-(2-((3,3-difluoroazetidin-1-yl)methyl)pyridin-4-yl)-4,4-difluoropiperidine-1-carboxylate a yellowish oil. LCMS: (ES, m/s): 404 [M+H]⁺, rt=0.71 min, Method 5. ¹H NMR (400 MHz, CHLOROFORM-d) δ ppm 8.54 (d, J=5.38 Hz, 1H), 7.33 (s, 1H), 7.17 (d, J=4.89 Hz, 1H), 4.18-4.45 (m, 2H), 3.93 (s, 2H), 3.73 (t, J=12.23 Hz, 4H), 3.02-3.39 (m, 3H), 2.13-2.28 (m, 1H), 1.88-2.06 (m, 1H), 1.50 (s, 9H).

Step 4

To tert-butyl 3-(2-((3,3-difluoroazetidin-1-yl)methyl)pyridin-4-yl)-4,4-difluoropiperidine-1-carboxylate (45 mg, 0.112 mmol) in DCM (1 mL) was added HCl (1 mL, 4.00 mmol). After 2 h, the mixture was concentrated to give a mixture (52 mg) of 2-((3,3-difluoroazetidin-1-yl)methyl)-4-(4,4-difluoropiperidin-3-yl)pyridine dihydrochloride and 3-chloro-N-((4-(4,4-difluoropiperidin-3-yl)pyridin-2-yl)methyl)-2,2-difluoropropan-1-amine dihydrochloride which was used without further purification. LCMS: (ES, m/s): 304 [M+H]⁺ rt=0.64, Method 3, min for 2-((3,3-difluoroazetidin-1-yl)methyl)-4-(4,4-5 difluoropiperidin-3-yl)pyridine and 340 [M+H]⁺, rt=0.74 min, Method, for 3-chloro-N-((4-(4,4-difluoropiperidin-3-yl)pyridin-2-yl)methyl)-2,2-difluoropropan-1-amine.

Step 5

To a mixture of 2-((3,3-difluoroazetidin-1-yl)methyl)-4-(4,4-difluoropiperidin-3-yl)pyridine (44 mg, 0.145 mmol) and 3-chloro-N-((4-(4,4-difluoropiperidin-3-yl)pyridin-2-yl)methyl)-2,2-difluoropropan-1-amine (side product brought from previous reaction) in DMF (1 mL) was added (R)-2-bromo-N-(5-(2,4-difluorophenoxy)pyridin-2-yl)propanamide (Intermediate 71) (104 mg, 0.290 mmol), followed by Et₃N (0.101 mL, 0.725 mmol) and silver nitrate (99 mg, 0.580 mmol). The mixture was heated to 35° C. for 4 h, filtered through Celite, diluted with MeOH, re-filtered and loaded onto MDAP for purification (Column: Xselect CSH Prep OBD C18 Column 30×150 mm, 5 mm; Mobile Phase A: water (10 mM Ammonium Bicarbonate in H2O adjusted to pH 10 with Ammonia. Mobile Phase B: MeCN; Flow rate: 40 mL/min; Gradient: 50% B to 99% B over 27 min; Rt: 11.3 min). The desired product was then dissolved in DCM, washed with sat'd NaHCO₃ solution and concentrated to afford 5.1 mg (8.80 μmol, 6.07% yield) (2S)-2-(3-(2-((3,3-difluoroazetidin-1-yl)methyl)pyridin-4-yl)-4,4-difluoropiperidin-1-yl)-N-(5-(2,4-difluorophenoxy)pyridin-2-yl)propanamide), a diastereomeric mixture as a white fluffy solid. LCMS: (ES, m/s): 580 [M+H]⁺, rt=1.23 min and 1.24 min, Method 3. ¹H NMR (400 MHz, CHLOROFORM-d) δ ppm 8.62 (dd, J=10.76, 5.38 Hz, 1H), 8.51 (dd, J=13.94, 9.54 Hz, 1H), 7.98 (d, J=2.45 Hz, 1H), 7.52-7.68 (m, 2H), 7.45 (m, 1H), 7.10-7.23 (m, 2H), 7.00-7.07 (m, 1H), 6.97 (m, 1H), 4.38-4.54 (m, 4H), 3.47-3.83 (m, 3H), 2.88-3.25 (m, 4H), 2.68-2.83 (m, 1H), 2.21-2.48 (m, 2H), 1.43 (dd, J=6.85, 3.42 Hz, 3H).

Example 271

(S)-2-((S)-4,4-difluoro-3-(6-oxo-1,6-dihydropyridin-3-yl)piperidin-1-yl)-N-(5-(4-fluoro-2-(hydroxymethyl)phenoxy)pyridin-2-yl)propanamide

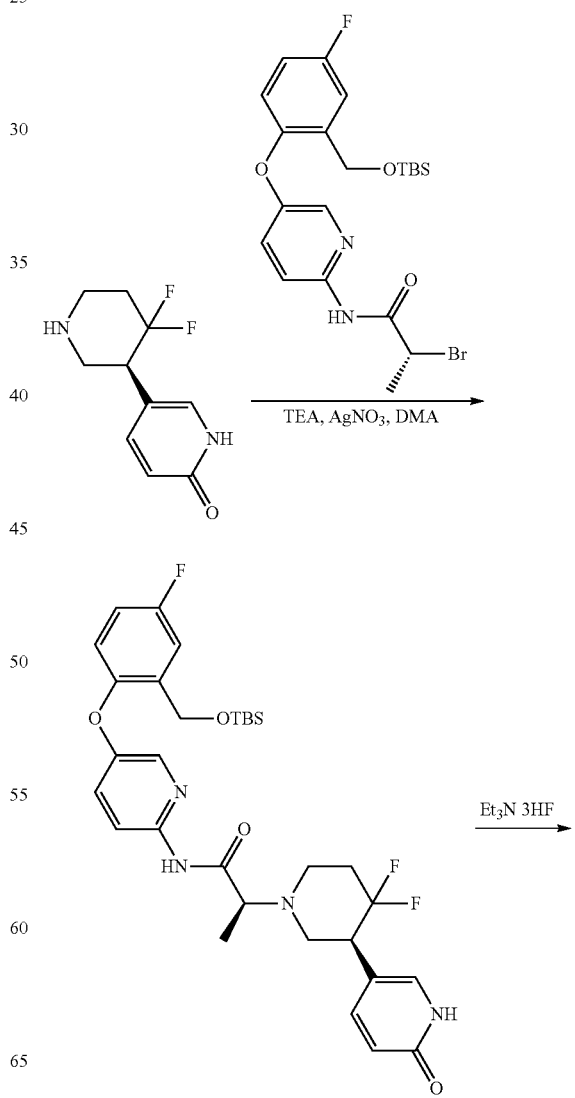

-continued

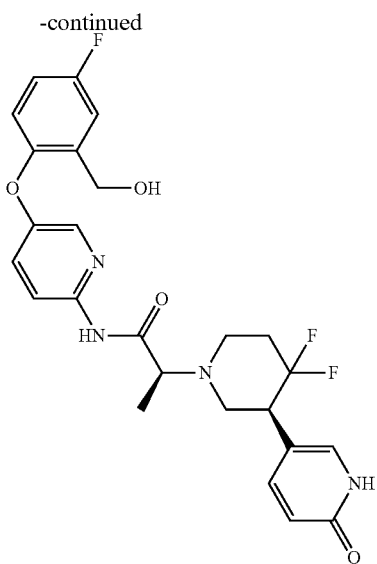

Step 1

To a solution of (R)-2-bromo-N-(5-(2-(((tert-butyldimethylsilyl)oxy)methyl)-4-fluorophenoxy)pyridin-2-yl)propanamide (Intermediate 108) (210 mg, 0.434 mmol) in DMA (2 ml) was added (S)-5-(4,4-difluoropiperidin-3-yl)pyridin-2(1H)-one (Example 4, Step 3) (93 mg, 0.434 mmol), followed by TEA (0.182 mL, 1.303 mmol) and silver nitrate (73.8 mg, 0.434 mmol). The mixture was stirred at rt overnight, diluted with EtOAc (10 mL), filtered, concentrated to approximately a 2 mL solution in DMA, and purified over silica column (ISCO 24 g), eluting with 0-50% EtOAc in heptane to give 193 mg (0.313 mmol, 72.0% yield) N-(5-(2-(((tert-butyldimethylsilyl)oxy)methyl)-4-fluorophenoxy)pyridin-2-yl)-2-((S)-4,4-difluoro-3-(6-oxo-1,6-dihydropyridin-3-yl)piperidin-1-yl)propanamide (d.r.>9:1). LCMS (ES, m/s): 617.3 [M+H]$^+$.

Step 2

To N-(5-(2-(((tert-butyldimethylsilyl)oxy)methyl)-4-fluorophenoxy)pyridin-2-yl)-2-((S)-4,4-difluoro-3-(6-oxo-1,6-dihydropyridin-3-yl)piperidin-1-yl)propanamide (193 mg, 0.313 mmol) in THF (2 mL) was added triethylamine trihydrofluoride (0.102 mL, 0.626 mmol). After 3 h, the reaction was concentrated and purified by reverse phase Xselect CSH Prep C18 5 uM OBD (Gradient 30% to 85% B over 9 min, flow rate 40 mL/min, A: Water with 10 mM Ammonium Bicarb and 0.075% Ammonium Hydroxide/B: Acetonitrile) to give 72.4 mg (0.141 mmol, 45.1% yield) 2-((S)-4,4-difluoro-3-(6-oxo-1,6-dihydropyridin-3-yl)piperidin-1-yl)-N-(5-(4-fluoro-2-(hydroxymethyl)phenoxy)pyridin-2-yl)propanamide (as a mixture of 2 diasteromers). The diasteromers were separated via chiral column (column: CCC, 5 micron, 30×250 mm, flow rate: 45 mL/min, solvents: 60:40 Heptane: EtOH, modifier: none, length of run: 15 min). Peak at 11.0-14.3 min was collected to give (31 mg, 0.060 mmol, 55.2% yield) (S)-2-((S)-4,4-difluoro-3-(6-oxo-1,6-dihydropyridin-3-yl)piperidin-1-yl)-N-(5-(4-fluoro-2-(hydroxymethyl)phenoxy)pyridin-2-yl)propanamide. LCMS (ES, m/s): 503.3 [M+H]$^+$, rt=0.88 min, Method 3. $^1$H NMR (400 MHz, METHANOL-d$_4$) δ ppm 8.14 (d, J=9.29 Hz, 1H), 8.03 (d, J=2.93 Hz, 1H), 7.65 (dd, J=9.29, 1.96 Hz, 1H), 7.37-7.44 (m, 2H), 7.31 (dd, J=9.29, 2.93 Hz, 1H), 7.02 (td, J=8.44, 3.18 Hz, 1H), 6.92 (dd, J=9.05, 4.65 Hz, 1H), 6.52 (d, J=9.78 Hz, 1H), 4.64 (s, 2H), 3.54 (q, J=6.85 Hz, 1H), 3.33 (br d, J=1.47 Hz, 1H), 2.87-3.04 (m, 3H), 2.57-2.69 (m, 1H), 2.14-2.30 (m, 2H), 1.34 (d, J=7.34 Hz, 3H).

Example 272 was synthesized in an analogous manner, using the designated Intermediate in Step 1.

| Ex | Name | Structure | $^1$H NMR | Analytical LC/MS: (M + H)$^+$; retention time (min); LC/MS Method of analysis | Int |
|---|---|---|---|---|---|
| 272 | (S)-2-((S)-4,4-difluoro-3-(6-oxo-1,6-dihydropyridin-3-yl)-piperidin-1-yl)-N-(5-(4-fluoro-2-(hydroxymethyl)phenoxy)pyrazin-2-yl)propanamide | 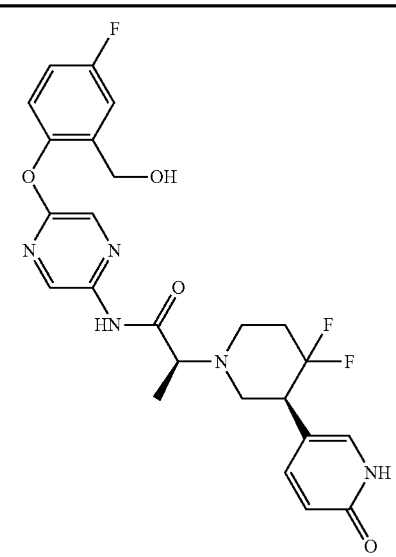 | $^1$H NMR (400 MHz, METHANOL-d$_4$) δ 8.87 (d, J = 0.98 Hz, 1H), 8.20 (d, J = 1.47 Hz, 1H), 7.65 (dd, J = 9.54, 2.20 Hz, 1H), 7.43 (d, J = 2.45 Hz, 1H), 7.30 (dd, J = 9.29, 2.93 Hz, 1H), 7.01-7.12 (m, 2H), 6.52 (d, J = 9.78 Hz, 1H), 4.56 (s, 2H), 3.57 (q, J = 6.85 Hz, 1H), 3.20-3.30 (m, 1H), 2.87-3.05 (m, 3H), 2.64 (td, J = 11.00, 4.89 Hz, 1H), 2.08-2.28 (m, 2H), 1.34 (d, J = 6.85 Hz, 3H). | 504.3; rt 0.81. LC/MS Method 3 | 109 |

Example 273

4-((S)-4,4-difluoro-1-((S)-1-((5-(4-fluoro-2-(hydroxymethyl)phenoxy)pyridin-2-yl)amino)-1-oxopropan-2-yl)piperidin-3-yl)pyridine 1-oxide

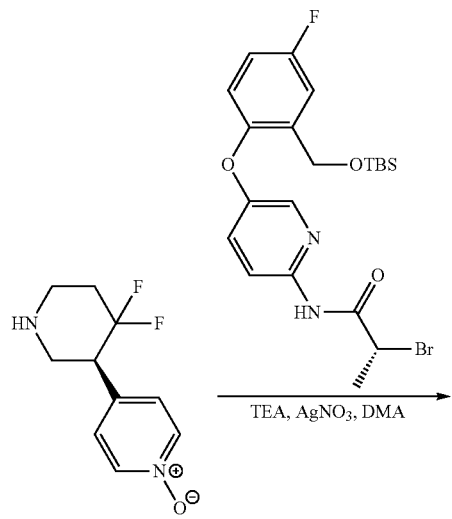

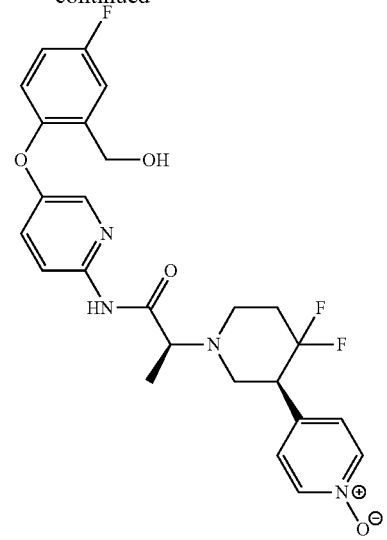

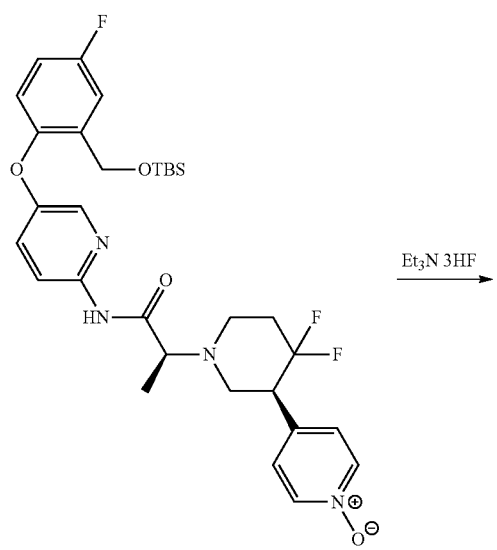

Step 1

To (R)-2-bromo-N-(5-(2-(((tert-butyldimethylsilyl)oxy)methyl)-4-fluorophenoxy)pyridin-2-yl)propanamide (Intermediate 108) (113 mg, 0.233 mmol) in dimethylacetamide (1 mL) was added (S)-4-(4,4-difluoropiperidin-3-yl)pyridine 1-oxide (Example 132, Step 4) (50 mg, 0.233 mmol), followed by TEA (0.098 mL, 0.700 mmol). The mixture was stirred overnight, heated to 50° C. for 3 h, diluted with EtOAc (10 mL), filtered and concentrated to about 1 mL solution (DMA). The crude product was used directly in next step without further purification. The yield was assumed as 100%. LCMS (ES, m/s): 617.3 [M+H]$^+$.

Step 2

To a solution of 4-((3S)-1-(1-((5-(2-(((tert-butyldimethylsilyl)oxy)methyl)-4-fluorophenoxy)pyridin-2-yl)amino)-1-oxopropan-2-yl)-4,4-difluoropiperidin-3-yl)pyridine 1-oxide (144 mg, 0.233 mmol) in DMA (1 mL) was added triethylamine trihydrofluoride (0.076 mL, 0.467 mmol). The mixture was stirred overnight, diluted with EtOAc (8 mL), filtered, concentrated to about 2 mL solution (DMA), and purified by reverse phase Xselect CSH Prep C18 5 uM OBD (Gradient 35% to 85% B over 19 min, flow rate 40 mL/min, A: Water with 10 mM Ammonium Bicarb and 0.075% Ammonium Hydroxide/B: Acetonitrile) to give the desired product (48 mg, 0.094 mmol, 40.1% yield) as a mixture of 2 diasteromers. The diasteromers were separated via chiral column (column: CC4, 5 micron, 20×250 mm, flow rate: 20 mL/min, solvents: 40:60 Heptane:EtOH, modifier: 0.1% isopropylamine, length of run: 30 min). The peak at 18-24 min was collected to give 25 mg (0.049 mmol, 44.5% yield) 4-((S)-4,4-difluoro-1-((S)-1-((5-(4-fluoro-2-(hydroxymethyl)phenoxy)pyridin-2-yl)amino)-1-oxopropan-2-yl)piperidin-3-yl)pyridine 1-oxide. LCMS (ES, m/s): 503.3 [M+H]$^+$, rt=0.82 min, Method 3. $^1$H NMR (400 MHz, METHANOL-d$_4$) δ ppm 8.22-8.37 (m, 2H), 8.13 (d, J=9.29 Hz, 1H), 8.04 (d, J=2.93 Hz, 1H), 7.59 (d, J=6.85 Hz, 2H), 7.35-7.42 (m, 1H), 7.31 (dd, J=9.05, 3.18 Hz, 1H), 6.97-7.06 (m, 1H), 6.89-6.96 (m, 1H), 4.64 (s, 2H), 3.54-3.71 (m, 2H), 3.03-3.12 (m, 2H), 2.95 (br d, J=11.74 Hz, 1H), 2.63-2.75 (m, 1H), 2.16-2.39 (m, 2H), 1.35 (d, J=7.34 Hz, 3H).

Example 274 was synthesized in an analogous manner, using the designated Intermediate in Step 1.

| Ex | Name | Structure | ¹H NMR | Analytical LC/MS: (M + H)⁺; retention time (min); LC/MS Method of analysis | Int |
|---|---|---|---|---|---|
| 274 | 4-((3S)-4,4-difluoro-1-(1-((5-(4-fluoro-2-(hydroxymethyl)phenoxy)pyrazin-2-yl)amino)-1-oxopropan-2-yl)piperidin-3-yl)-pyridine 1-oxide | 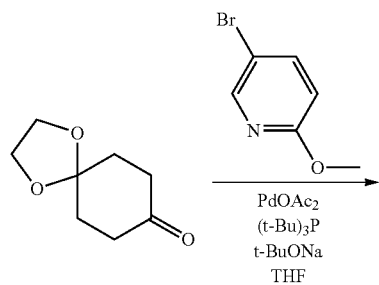 | ¹H NMR (400 MHz, DMSO-d₆) δ 10.48-10.55 (m, 1H), 8.78-8.83 (m, 1H), 8.31 (dd, J = 4.40, 1.47 Hz, 1H), 8.12-8.20 (m, 2H), 7.38 (dd, J = 7.09, 2.69 Hz, 2H), 7.30 (dd, J = 9.54, 2.69 Hz, 1H), 7.09-7.18 (m, 2H), 5.31 (br t, J = 5.62 Hz, 1H), 4.42 (d, J = 5.38 Hz, 2H), 3.68 (dq, J = 14.49, 7.07 Hz, 1H), 3.42-3.56 (m, 1H), 3.01 (br d, J = 9.78 Hz, 1H), 2.85-2.97 (m, 2H), 2.66-2.80 (m, 1H), 2.52-2.62 (m, 1H), 2.13 (br s, 1H), 1.19-1.27 (m, 3H). | 504.2; rt 0.75-0.80. LC/MS Method 3 | 109 |

Example 275

(R)—N-(5-(cyclopropylmethoxy)pyridin-2-yl)-2-((1S,3R)-4,4-difluoro-3-(6-oxo-1,6-dihydropyridin-3-yl)cyclohexyl)propanamide

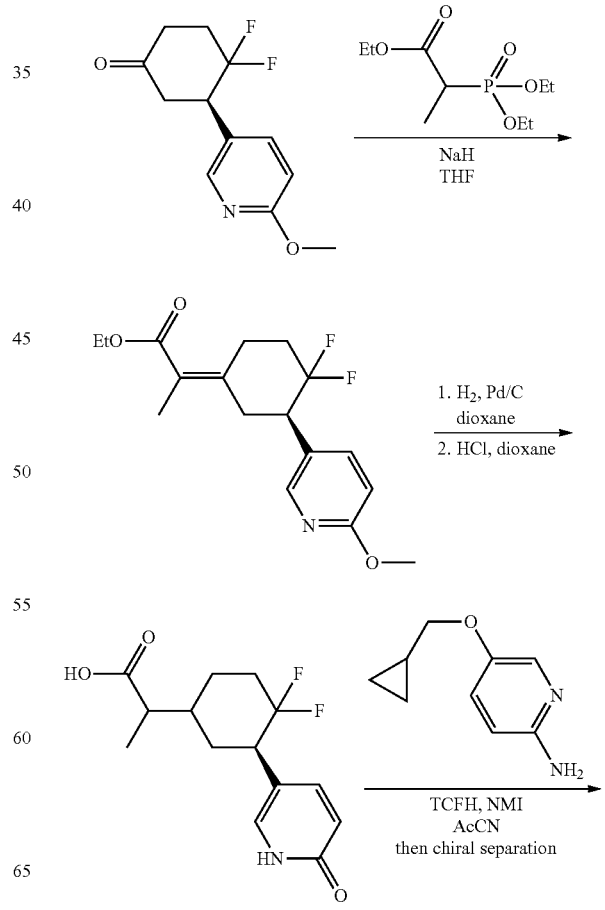

-continued

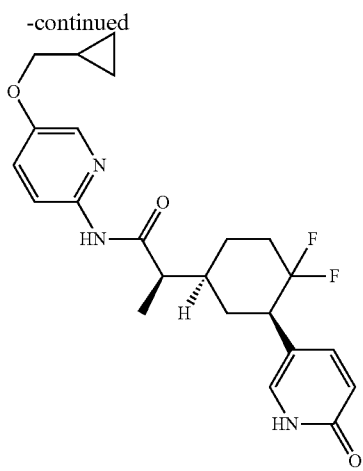

Step 1

To t-BuONa (3.08 g, 32.1 mmol, 2.5 eq) in tetrahydrofuran (30 mL) was added 1,4-dioxaspiro[4.5]decan-8-one (2.0 g, 12.8 mmol, 1.0 q) and 5-bromo-2-methoxypyridine (2.41 g, 12.8 mmol, 1.0 eq). After 5 min, (t-Bu)$_3$P (2.58 g, 1.28 mmol, 0.1 eq, 10% in hexane) and Pd(OAc)$_2$ (287 mg, 1.28 mmol, 0.1 eq) were added, the reaction was evacuated and flushed three times with nitrogen and the mixture was stirred 16 h at 42° C. The reaction was concentrated, diluted with water (500 mL) and extracted with ethyl acetate (500 mL×3). The combined organic layers were washed with brine (500 mL), dried over sodium sulfate, concentrated and purified via a silica gel column, eluting with ethyl acetate:petroleum ether (1:2) to give 9.0 g (purity: 70%) of 7-(6-methoxypyridin-3-yl)-1,4-dioxaspiro[4.5]decan-8-one as a yellow oil. LCMS: (ES, m/s) 264 [M+H]$^+$. $^1$H NMR: (300 MHz, DMSO-d$_6$) δ ppm 7.93 (d, J=2.4 Hz, 1H), 7.53 (dd, J=8.4, 2.4 Hz, 1H), 6.76 (d, J=8.4 Hz, 1H), 4.37-3.99 (m, 4H), 3.83 (s, 3H), 3.32-3.10 (m, 1H), 2.79-2.67 (m, 1H), 2.43-2.25 (m, 2H), 2.25-2.03 (m, 2H), 2.08-1.82 (m, 1H).

Step 2

To 7-(6-methoxypyridin-3-yl)-1,4-dioxaspiro[4.5]decan-8-one (22 g, 83.6 mmol, 1.0 eq) in dichloromethane (300 mL) at 0° C. was added DAST (26.9 g, 167.2 mmol, 2.0 eq), dropwise. The resulting mixture was stirred for 16 h at room temperature, poured into crushed ice (300 g) and extracted with ethyl acetate (500 mL×3). The combined organic extracts were dried over sodium sulfate, concentrated and purified via a silica gel column, eluting with ethyl acetate:petroleum ether (1:2) to give 18 g (purity: 80%) of 5-(8,8-difluoro-1,4-dioxaspiro[4.5]decan-7-yl)-2-methoxypyridine as a brown oil. LCMS: (ES, m/s) 286 [M+H]$^+$. $^1$H NMR: (300 MHz, DMSO-d$_6$) δ ppm 8.10 (d, J=2.4 Hz, 1H), 7.78-7.63 (m, 1H), 6.79 (d, J=8.4 Hz, 1H), 4.02-3.87 (m, 4H), 3.93-3.85 (m, 1H), 3.84 (s, 3H), 2.27-2.14 (m, 2H), 2.12-2.08 (s, 1H), 2.07-1.80 (m, 3H).

Step 3

A mixture of 5-(8,8-difluoro-1,4-dioxaspiro[4.5]decan-7-yl)-2-methoxypyridine (13 g, 45.6 mmol, 1.0 eq) and 1M HCl (91.2 mL, aq.) in THF (90 mL) was stirred at 50° C. for 16 h, concentrated and diluted with water (300 mL). The pH was adjusted to 6-7 with sodium bicarbonate (sat., aq.), and extracted with dichloromethane (500 mL×2). The combined organic extracts were dried over sodium sulfate, concentrated and purified via a silica gel column, eluting with ethyl acetate:petroleum ether (1:1) to give 4 g (mixture of two compounds) of 4,4-difluoro-3-(6-methoxypyridin-3-yl)cyclohexan-1-one as a brown oil. The product was chirally separated (CHIRALPAK AD-H-TC001 SFC, 2×25 cm, 5 um; Mobile Phase A: CO$_2$; Mobile Phase B: Acetonitrile; Flow rate: 50 mL/min; 7:3 A:B), resulting in two peaks with retention times of 2.72 and 4.27 minutes. The first peak (2.72 min) was collected to give 1.6 g (purity: 95%, yield: 28%) of rel-(R)-4,4-difluoro-3-(6-methoxypyridin-3-yl)cyclohexan-1-one as yellow oil. LCMS (ES, m/s): 242 [M+H]+ $^1$H NMR: (300 MHz, DMSO-d$_6$) δ ppm 8.09 (d, J=2.5 Hz, 1H), 7.74-7.62 (m, 1H), 6.89-6.75 (m, 1H), 3.95-3.83 (m, 1H), 3.85 (s, 3H), 3.22-3.15 (m, 2H), 2.79-2.62 (m, 1H), 2.48-2.32 (m, 2H), 1.99 (s, 1H).

Step 4

To NaH (398 mg, 9.96 mmol, 1.5 eq, 60%) in THF (20 mL) at 0° C. was added ethyl 2-(diethoxyphosphoryl)propanoate (2.37 g, 9.96 mmol, 1.5 eq), dropwise. After 30 min, a solution of (R)-4,4-difluoro-3-(6-methoxypyridin-3-yl)cyclohexan-1-one (1.6 g, 6.64 mmol, 1.0 eq) in THF (5 mL) was added dropwise. After 3 h, the reaction was poured into crushed ice and water (100 mL), and extracted with ethyl acetate (100 mL×3). The organic extracts were dried over sodium sulfate, concentrated and purified via a silica gel column, eluting with ethyl acetate:petroleum ether (1:5) to give 1.6 g (purity: 95%, yield: 74%) of (R)-2-(4,4-difluoro-3-(6-methoxypyridin-3-yl)cyclohexylidene) propanoate as a yellow solid. LCMS (ES, m/s): 326 [M+H]+ $^1$H NMR: (300 MHz, DMSO-d$_6$) δ ppm 8.07 (dd, J=10.2, 2.4 Hz, 1H), 7.78-7.66 (m, 1H), 6.81 (dd, J=8.7, 3.6 Hz, 1H), 4.27-4.13 (m, 2H), 3.92 (d, J=1.1 Hz, 3H), 3.26-3.07 (m, 2H), 2.69-2.52 (m, 2H), 2.41-2.26 (m, 2H), 1.97-1.91 (m, 4H), 1.38-1.23 (m, 3H).

Step 5

A mixture of ethyl (R)-2-(4,4-difluoro-3-(6-methoxypyridin-3-yl)cyclohexylidene) propanoate (1.6 g, 4.92 mmol, 1.0 eq) and Pd/C (600 mg, 10%) in dioxane (30 mL) was evacuated and flushed three times with hydrogen, stirred for 3 h under an atmosphere of hydrogen (balloon), filtered and concentrated to give 1.6 g (purity: 95%, yield: 99%) of ethyl 2-((3R)-4,4-difluoro-3-(6-methoxypyridin-3-yl)cyclohexyl) propanoate as a yellow oil, which was used without further purification. LCMS (ES, m/s): 328 [M+H]+ $^1$H NMR: (300 MHz, DMSO-d6) δ ppm 8.05 (d, J=2.8 Hz, 1H), 7.62 (d, J=8.8 Hz, 1H), 6.80 (dd, J=8.8, 2.8 Hz, 1H), 4.17-4.00 (m, 2H), 3.84 (s, 3H), 3.33-3.30 (m, 2H), 3.30-3.15 (m, 1H), 2.42-2.34 (m, 1H), 1.86-1.63 (m, 4H), 1.45-1.31 (m, 1H), 1.24-1.09 (m, 6H).

Step 6

A mixture of ethyl 2-((3R)-4,4-difluoro-3-(6-methoxypyridin-3-yl)cyclohexyl) propanoate (400 mg, 1.22 mmol, 1.0 eq), dioxane (10 mL) and 6M HCl (10 mL, aq.) was stirred at 80° C. for 16 h, concentrated, dissolved in methanol (10 mL) and purified by reverse phase chromatograpghy (C18 spherical column, 20-35 um, 100 A), eluting with 5-30% AcCN in water (0.05% TFA) to give 1 g (purity: 96%) of 2-((3R)-4,4-difluoro-3-(6-oxo-1,6-dihydropyridin-3-yl)cyclohexyl)propanoic acid as a yellow solid. LCMS (ES, m/s): 286 [M+H]+ $^1$H NMR: (300 MHz, DMSO-d6) δ ppm 11.38 (s, 1H), 7.73 (s, 1H), 7.48-7.37 (m, 1H), 7.31-7.20 (m, 1H), 6.33 (d, J=9.2 Hz, 1H), 3.80-3.36 (m, 2H), 3.23-2.60 (m, 2H), 2.26-2.21 (m, 1H), 2.19-1.43 (m, 3H), 1.13-1.00 (m, 4H).

Step 7

A mixture of 2-((3R)-4,4-difluoro-3-(6-oxo-1,6-dihydropyridin-3-yl) propanoic acid (500 mg, 1.75 mmol, 1.0 eq), 5-(cyclopropylmethoxy)pyridin-2-amine (Intermediate 22, Step 2) (346 mg, 2.11 mmol, 1.2 eq), 1-methylimidazole (430 mg, 5.25 mmol, 3.0 eq) and N-(chloro (dimethylamino) methylene)-N-methylmethanaminium hexafluorophosphate(V) (591 mg, 2.11 mmol, 1.2 eq) in acetonitrile (10 mL) was stirred for 12 h, concentrated, diluted with water (100 mL) and extracted with ethyl acetate (100 mL×2). The combined organic layers were washed with brine (100 mL×2), dried over sodium sulphate, concentrated, dissolved in DMF (5 mL) and purified by reverse phase chromatography (C18 spherical column, 20-35 um, 100 A), eluting with 0-40% AcCN in water (10 mM NH$_4$HCO$_3$). The collected product was chirally separated (CHIRALPAK IE, 2×25 cm, 5 um; Mobile Phase A: Hex [8 mM NH$_3$ in methanol], Mobile Phase B: ethanol; Flow rate: 15 mL/min; 1:1 A:B), resulting in two peaks with retention times of 11.8 and 15 minutes. The first peak (11.8 min) was collected to give 30 mg (purity: 99%) of the pure product (R)—N-(5-(cyclopropylmethoxy)pyridin-2-yl)-2-((1S,3R)-4,4-difluoro-3-(6-oxo-1,6-dihydropyridin-3-yl)cyclohexyl) propanamide as a white solid. LCMS (ES, m/s): 432 [M+H]+ $^1$H NMR: (300 MHz, DMSO-d$_6$) δ ppm 11.50 (br, 1H), 10.29 (s, 1H), 8.02-7.93 (m, 2H), 7.39-7.32 (m, 2H), 7.17 (d, J=2.4 Hz, 1H), 6.28 (d, J=9.3 Hz, 1H), 3.84 (d, J=7.2 Hz, 2H), 3.11-2.99 (m, 1H), 2.50-2.47 (m, 1H), 2.13-2.08 (m, 1H), 2.15-1.70 (m, 3H), 1.69-1.58 (m, 2H), 1.31-0.98 (m, 5H), 0.60-0.50 (m, 2H), 0.36-0.28 (m, 2H).

Examples 276-281 were synthesized in an analogous manner using the designated Intermediate in Step 7.

| Ex | Name | Structure | $^1$H NMR | LC/MS: (M + H)+; retention time (min); LC/MS Method of analysis | Int |
|---|---|---|---|---|---|
| 276 | (R)-N-(6-(cyclopropyl methoxy)-pyridazin-3-yl)-2-((1S,3R)-4,4-difluoro-3-(6-oxo-1,6-dihydro-pyridin-3-yl)-cyclohexyl)-propanamide | 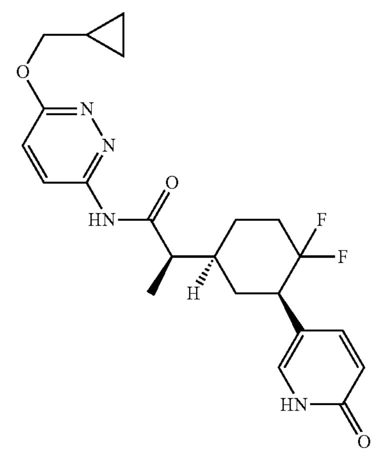 [SMILES: C[C@@H](C(=O)Nc1ccc(OCC2CC2)nn1)[C@H]1CCC(F)(F)[C@@H](c2ccc(=O)[nH]c2)C1] | $^1$H NMR: (400 MHz, DMSO-d$_6$) δ ppm 11.52 (s, 1H), 10.90 (s, 1H), 8.26 (d, J = 9.6 Hz, 1H), 7.40-7.37 (m, 1H), 7.26-7.21 (m, 2H), 6.30 (d, J = 9.6 Hz, 1H), 4.21 (d, J = 7.2 Hz, 2H), 3.13-2.29 (m, 1H), 2.64-2.55 (m, 1H), 2.14-2.03 (m, 1H), 1.98-1.67 (m, 4H), 1.58-1.32 (m, 2H), 1.31-1.21 (m, 1H), 1.07 (d, J = 6.9 Hz, 3H), 0.64-0.52 (m, 2H), 0.42-0.31 (m, 2H). | 433; rt 1.272. LC/MS Method 25 | 14, Step 1 |
| 277 | (R)-2-((1S,3R)-4,4-difluoro-3-(6-oxo-1,6-dihydro-pyridin-3-yl)-cyclohexyl)-N-(5-fluoro-pyridin-2-yl)-propanamide | 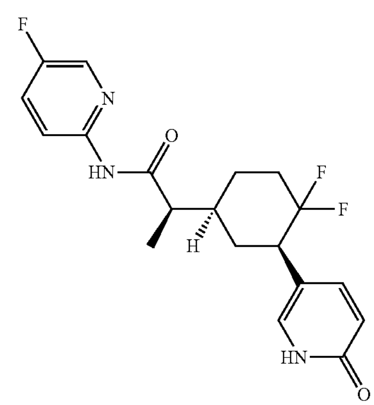 [SMILES: C[C@@H](C(=O)Nc1ccc(F)cn1)[C@H]1CCC(F)(F)[C@@H](c2ccc(=O)[nH]c2)C1] | $^1$H NMR: (400 MHz, CD$_3$OD) δ ppm 8.20 (d, J = 3.0 Hz, 1H), 8.16-8.12 (m, 1H), 7.65-7.51 (m, 2H), 7.32 (d, J = 2.7 Hz, 1H), 6.53-6.49 (m, 1H), 3.10-2.92 (m, 1H), 2.51-2.42 (m, 1H), 2.27-2.18 (m, 1H), 2.12-1.85 (m, 3H), 1.83-1.69 (m, 1H), 1.51-1.31 (m, 2H), 1.26 (d, J = 6.9 Hz, 3H). | 380; rt 1.316. LC/MS Method 11 | 5-fluoro-pyridin-2-amine |

| Ex | Name | Structure | $^1$H NMR | LC/MS: (M + H)$^+$; retention time (min); LC/MS Method of analysis | Int |
|---|---|---|---|---|---|
| 278 | 2-(4,4-difluoro-3-(6-oxo-1,6-dihydropyridin-3-yl)-cyclohexyl)-N-(5-(4-fluorophenoxy)pyridin-2-yl)propanamide | 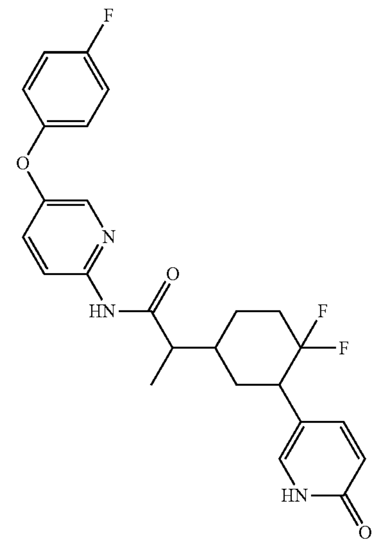 [SMILES: CC(C(=O)Nc1ccc(Oc2ccc(F)cc2)cn1)C1CCC(F)(F)C(c2ccc(=O)[nH]c2)C1] | $^1$H NMR: (400 MHz, DMSO-d$_6$) δ ppm 11.54 (br. s, 1H), 10.56 and 10.52 (2 x s, 1H), 8.10-8.17 (m, 2H), 7.45-7.52 (m, 1H), 7.33-7.41 (m, 1H), 7.17-7.27 (m, 3H), 7.06-7.12 (m, 2H), 6.29 (dd, J = 6.4, 9.1 Hz, 1H), 2.93-3.12 (m, 1H), 2.05-2.18 (m, 1H), 1.59-1.99 (m, 5H), 1.37-1.54 (m, 1H), 1.20-1.26 (m, 1H), 1.11 (t, J = 7.1 Hz, 3H). | 472; rt 0.90-0.94. LC/MS Method 5 | 70, Step 2 |
| 279 | (R)-2-((1S,3R)-4,4-difluoro-3-(6-oxo-1,6-dihydro-pyridin-3-yl)-cyclohexyl)-N-(5-((5-fluoropyridin-2-yl)oxy)-pyridin-2-yl)-propanamide | 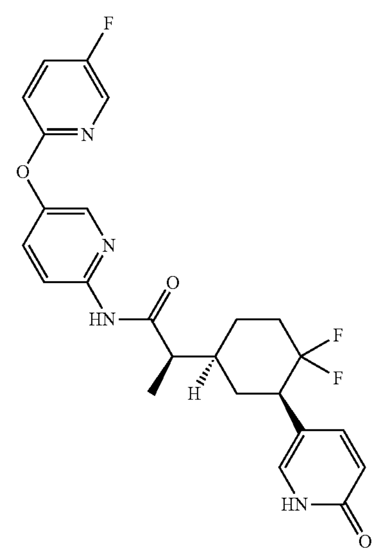 [SMILES: C[C@@H](C(=O)Nc1ccc(Oc2ccc(F)cn2)cn1)[C@H]1CCC(F)(F)[C@@H](c2ccc(=O)[nH]c2)C1] | $^1$H NMR (DMSO-d$_6$) δ 11.52 (br. s., 1H), 10.54 (s, 1H), 8.19 (d, J = 2.7 Hz, 1H), 8.11-8.16 (m, 2H), 7.85 (ddd, J = 9.0, 8.1, 3.2 Hz, 1H), 7.61 (dd, J = 8.9, 2.8 Hz, 1H), 7.35 (d, J = 12.2 Hz, 1H), 7.19 (dd, J = 9.0, 3.7 Hz, 2H), 6.29 (d, J = 9.3 Hz, 1H), 2.92-3.10 (m, 1H), 2.55-2.59 (m, 1H), 2.07-2.21 (m, 1H), 1.74-2.02 (m, 3H), 1.59-1.71 (m, 2H), 1.17-1.30 (m, 1H), 1.12 (d, J = 6.8 Hz, 3H). | 473.3; rt. 0.80. LC/MS Method 5 | 100, Step 1 |

| Ex | Name | Structure | ¹H NMR | LC/MS: (M + H)⁺; retention time (min); LC/MS Method of analysis | Int |
|----|------|-----------|--------|--------|-----|
| 280 | (R)-2-((1S,3R)-4,4-difluoro-3-(6-oxo-1,6-dihydropyridin-3-yl)cyclohexyl)-N-(5-(2,4-difluorophenoxy)pyridin-2-yl)propanamide | 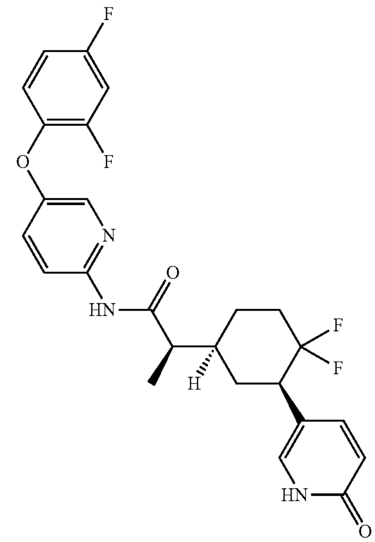 [SMILES: C[C@@H](C(=O)Nc1ccc(Oc2ccc(F)cc2F)cn1)[C@H]1CCC(F)(F)[C@@H](c2ccc(=O)[nH]c2)C1] | ¹H NMR(DMSO-d₆) δ 11.52 (br. s., 1H), 10.52 (s, 1H), 8.06-8.17 (m, 2H), 7.48-7.57 (m, 1H), 7.42-7.48 (m, 1H), 7.35 (d, J = 11.0 Hz, 1H), 7.28 (td, J = 9.2, 5.5 Hz, 1H), 7.18 (br. s., 1H), 7.07-7.15 (m, 1H), 6.28 (d, J = 9.5 Hz, 1H), 2.90-3.08 (m, 1H), 2.53-2.58 (m, 1H), 2.06-2.20 (m, 1H), 1.73-2.02 (m, 3H), 1.63 (t, J = 9.3 Hz, 2H), 1.16-1.31 (m, 1H), 1.11 (d, J = 6.8 Hz, 3H). | 490.3; rt. 0.93. LC/MS Method 5 | 71, Step 2 |
| 281 | (R)-2-((1S,3R)-4,4-difluoro-3-(6-oxo-1,6-dihydropyridin-3-yl)cyclohexyl)-N-(5-((3,5-difluoropyridin-2-yl)oxy)pyridin-2-yl)propanamide | 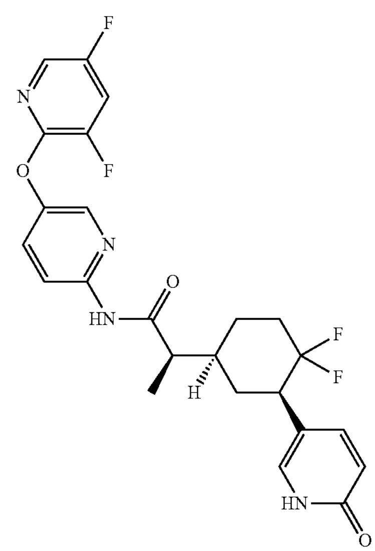 [SMILES: C[C@@H](C(=O)Nc1ccc(Oc2ncc(F)cc2F)cn1)[C@H]1CCC(F)(F)[C@@H](c2ccc(=O)[nH]c2)C1] | ¹H NMR (DMSO-d₆) δ 11.52 (br. s., 1H), 10.57 (s, 1H), 8.25 (d, J = 2.7 Hz, 1H), 8.13-8.20 (m, 2H), 8.03 (d, J = 2.4 Hz, 1H), 7.68 (dd, J = 9.0, 2.9 Hz, 1H), 7.33-7.39 (m, J = 1.0, 1.0 Hz, 1H), 7.18 (s, 1H), 6.29 (d, J = 9.5 Hz, 1H), 2.88-3.12 (m, 1H), 2.55 (t, J = 7.3 Hz, 1H), 2.07-2.22 (m, 1H), 1.91-1.98 (m, 1H), 1.73-1.88 (m, 2H), 1.65 (t, J = 8.8 Hz, 2H), 1.23 (d, J = 11.2 Hz, 1H), 1.12 (d, J = 6.6 Hz, 3H) | 491.3; rt. 0.86. LC/MS Method 5 | 99, Step 1 |

Example 282
(R)—N-(5-(2,4-difluorophenoxy)pyridin-2-yl)-2-((1S,3R)-3-(6-oxo-1,6-dihydropyridin-3-yl)cyclohexyl)propanamide
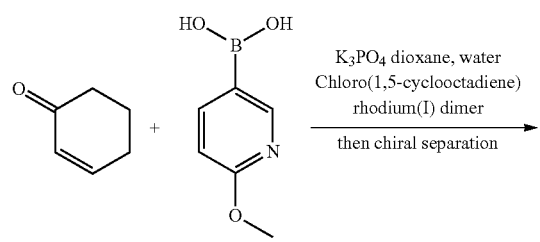
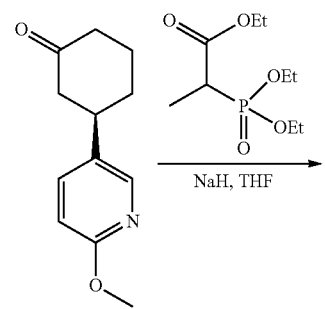
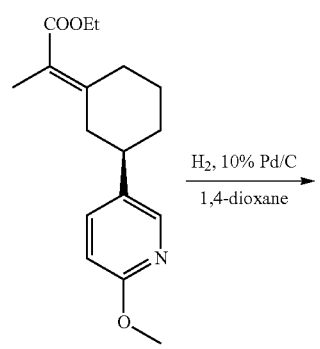
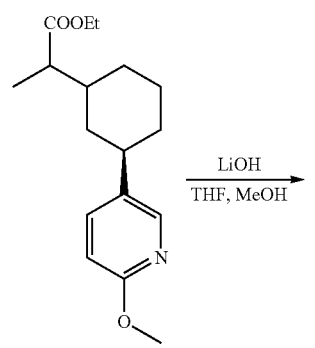
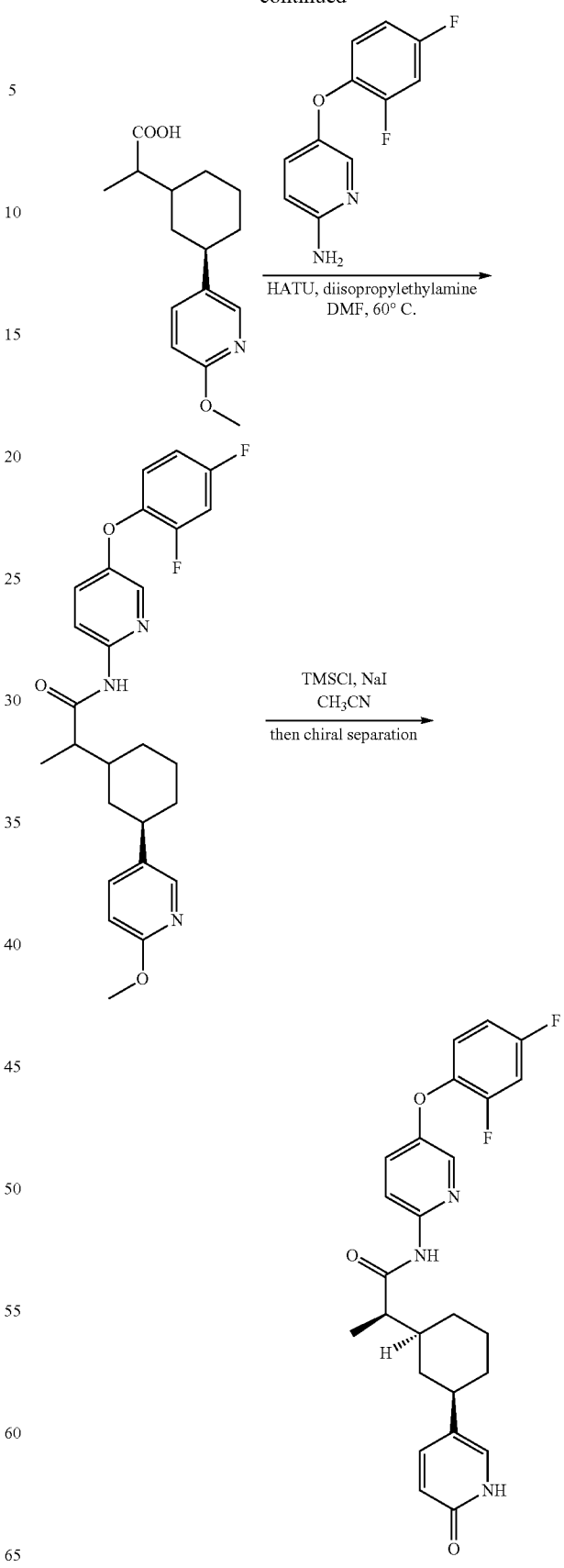

Step 1

To cyclohex-2-en-1-one (2.4 g, 24.97 mmol), (6-methoxypyridin-3-yl)boronic acid (7.64 g, 49.9 mmol), and chloro(1,5-cyclooctadiene)rhodium(I) dimer (CAS: 12092-47-6) (0.311 ml, 0.624 mmol) in dioxane (50 ml) was added potassium phosphate (21.20 g, 100 mmol) in water (75 mL). The reaction was stirred overnight at 60° C., treated with brine and extracted with dichloromethane (AX). The combined organics were dried over MgSO$_4$, filtered, concentrated and purified via silica gel chromatography, eluting with 2% MeOH in DCM to afford 2.76 g (12.51 mmol, 50.1% yield, 96% purity) 3-(6-methoxypyridin-3-yl) cyclohexan-1-one as a yellow oil. LCMS (Method 5) (ES, m/z): 206 [M+H]. $^1$H NMR (400 MHz, DMSO-d$_6$) δ 8.07 (d, J=2.4 Hz, 1H), 7.68 (dd, J=8.6, 2.7 Hz, 1H), 6.79 (d, J=8.8 Hz, 1H), 3.83 (s, 3H), 3.08-2.86 (m, 1H), 2.76-2.58 (m, 2H), 2.48-2.13 (m, 3H), 2.10-1.59 (m, 3H). The product was resolved via chiral chromatography Agilent 1200 Series using column: Chiral Technologies Chiralpak IG (5 microns-4.6 mm×150 mm); Mobile Phase: 100:0.1% Acetonitrile: isopropylamine (isocratic). Wavelength: 280 nm. Temperature: Ambient. Flow: 1.0 ml/min. Two stereoisomers were separated with retention times of 4.51 minutes and 6.96 minutes. The desired enantiomer eluted in the first peak (retention time 4.51 min) giving (R)-3-(6-methoxypyridin-3-yl)cyclohexan-1-one. $^1$H NMR (400 MHz, CHLOROFORM-d) δ 8.05 (d, J=2.0 Hz, 1H), 7.48 (dt, J=8.8, 2.0 Hz, 1H), 6.75 (d, J=8.3 Hz, 1H), 3.95 (d, J=1.0 Hz, 3H), 3.00 (ddt, J=11.9, 7.9, 3.8 Hz, 1H), 2.67-2.32 (m, 4H), 2.26-2.05 (m, 2H), 1.94-1.71 (m, 2H).

Step 2

To a stirred, cooled (0° C.) suspension of sodium hydride (0.537 g, 13.42 mmol) in THF (14 mL) was added ethyl 2-(diethoxyphosphoryl)propanoate (2.88 mL, 13.42 mmol), dropwise. The mixture was stirred for 20 minutes, and a solution of (R)-3-(6-methoxypyridin-3-yl)cyclohexan-1-one (1.836 g, 8.94 mmol) in THF (5 mL) was added, dropwise. The resulting mixture was allowed to warm to ambient temperature and stirred for 2 h. The mixture was quenched with water and extracted with EtOAc (3×). The combined organic layers were washed with brine, dried over Na$_2$SO$_4$, filtered, concentrated and purified using silica gel column chromatography, eluting with 25% EtOAc in heptane to give 2.027 g (7.00 mmol, 78% yield, 100% purity) ethyl (R,E)-2-(3-(6-methoxypyridin-3-yl)cyclohexylidene)propanoate as an oil. LCMS (ES, m/z): 290 [M+H]. $^1$H NMR (400 MHz, CHLOROFORM-d) δ 8.01 (dd, J=4.9, 2.4 Hz, 1H), 7.45 (ddd, J=8.4, 5.7, 2.9 Hz, 1H), 6.69 (t, J=8.8 Hz, 1H), 4.23-4.08 (m, 2H), 3.91 (d, J=3.9 Hz, 3H), 3.16-3.02 (m, 1H), 2.78-2.56 (m, 2H), 2.06-1.82 (m, 6H), 1.64-1.39 (m, 2H), 1.35-1.22 (m, 3H).

Step 3

A mixture of ethyl (R,E)-2-(3-(6-methoxypyridin-3-yl) cyclohexylidene)propanoate (2.02 g, 6.98 mmol) and Degusa type Pd—C 10% (0.4 g, 3.76 mmol) in dioxane (20 mL) was evacuated and purged with nitrogen three times and then placed under hydrogen. After stirring overnight, the reaction was filtered through Celite, rinsing with EtOAc/ methanol. The solvents were removed, and the product purified by normal phase silica gel column chromatography, eluting with 50-60% EtOAc in heptane to give 1.91 g (6.55 mmol, 94% yield, 94% purity) ethyl 2-((3R)-3-(6-methoxypyridin-3-yl)cyclohexyl)propanoate as a colorless oil. LCMS (ES, m/z): 292 [M+H]. $^1$H NMR (400 MHz, CHLOROFORM-d) δ 8.02-7.96 (m, 1H), 7.46-7.38 (m, 1H), 6.69-6.65 (m, 1H), 4.19-4.07 (m, 2H), 3.92-3.87 (m, 3H), 2.54-2.45 (m, 1H), 2.27 (quind, J=7.0, 2.0 Hz, 1H), 1.48-1.19 (m, 6H), 1.16-0.93 (m, 5H).

Step 4

To ethyl 2-((3R)-3-(6-methoxypyridin-3-yl)cyclohexyl) propanoate (0.98 g, 3.36 mmol) in THF (16 mL) and methanol (8.00 mL) was added aqueous LiOH (1 M, 10.09 mL, 10.09 mmol). The reaction was stirred for 2 h, heated to 50° C. overnight, concentrated, diluted with water (4 mL) and brought to pH 7 by the addition of 1 N HCl. The resulting suspension was extracted with EtOAc (2×). The aqueous solution pH was adjusted to 3 with addition of 1 N HCl and extracted with EtOAc (2×). The organic layers were washed with brine, dried over Na$_2$SO$_4$ and concentrated to give 0.807 g (3.06 mmol, 91% yield, 96% purity) 2-((3R)- 3-(6-methoxypyridin-3-yl)cyclohexyl)propanoic acid a colorless glass, which was used without further purification. LCMS (ES, m/z): 264 [M+H]. $^1$H NMR (400 MHz, METHANOL-d$_4$) δ 7.94 (d, J=5.2 Hz, 1H), 7.62-7.50 (m, 1H), 6.73 (d, J=8.5 Hz, 1H), 3.87-3.84 (m, 3H), 2.54 (tt, J=12.0, 3.1 Hz, 1H), 2.32-2.06 (m, 1H), 1.95-1.67 (m, 5H), 1.51-1.33 (m, 2H), 1.29-1.01 (m, 5H).

Step 5

To 2-((3R)-3-(6-methoxypyridin-3-yl)cyclohexyl)propanoic acid (129 mg, 0.490 mmol) in DMF (1.5 mL) was added HATU (186 mg, 0.490 mmol). After 15 minutes, 5-(2,4-difluorophenoxy)pyridin-2-amine (Intermediate 71, Step 2) (174 mg, 0.784 mmol) and diisopropylethylamine (0.086 mL, 0.490 mmol) were added, and the reaction was heated to 60° C. After 11 h, the mixture was diluted with EtOAc, washed with phosphate buffer (pH 4) (2×) and brine, dried over Na$_2$SO$_4$, concentrated and purified by silica gel column chromatography, eluting with 25% 3:1 EtOH: EtOAc in heptane to give 198 mg (0.424 mmol, 86% yield, 97% purity) N-(5-(2,4-difluorophenoxy)pyridin-2-yl)-2- ((3R)-3-(6-methoxypyridin-3-yl)cyclohexyl)propanamide as a colorless glass. LCMS (ES, m/z): 468 [M+H]. $^1$H NMR (400 MHz, CHLOROFORM-d) δ 8.48-8.31 (m, 1H), 8.25 (dd, J=12.5, 9.0 Hz, 1H), 8.07-7.93 (m, 2H), 7.41 (ddd, J=14.4, 8.6, 2.9 Hz, 1H), 7.35-7.23 (m, 1H), 7.12-7.01 (m, 1H), 7.01-6.92 (m, 1H), 6.92-6.85 (m, 1H), 6.68 (dd, J=13.7, 8.3 Hz, 1H), 3.91 (d, J=10.3 Hz, 3H), 2.51 (br t, J=12.2 Hz, 1H), 2.27-2.12 (m, 1H), 2.04-1.71 (m, 5H), 1.57-1.16 (m, 5H), 1.14-1.01 (m, 1H), 0.94-0.83 (m, 2H).

Step 6

To N-(5-(2,4-difluorophenoxy)pyridin-2-yl)-2-((3R)-3- (6-methoxypyridin-3-yl)cyclohexyl)propanamide (196 mg, 0.419 mmol) in acetonitrile (6 mL) was added sodium iodide (189 mg, 1.258 mmol), followed by TMS-chloride (0.161 mL, 1.258 mmol). The resulting yellow suspension was stirred at 50° C. for 18 h, heated to 58° C. for 2.5 h, concentrated and partitioned between EtOAc and saturated aqueous NaHCO$_3$. The organic layer was separated, washed with aqueous Na$_2$S$_2$O$_3$ and brine, dried over Na$_2$SO$_4$, filtered, concentrated and purified over a silica gel column, eluting with 0-10% MeOH in dichloromethane to give product. This material was further purified using chiral chromatography via Gilson preparative HPLC. Column: ChromegaChiral™ CC4 3 Micron Chiral Column, 5 micron, 20×250 mm; flow rate: 20 mL/min; solvents: 80:20 Heptane: EtOH; wavelength: 254 nm, giving two peaks eluting with retention times of 15.8 min and 20.5 min. The desired enantiomer (retention time 15.8 min) was obtained as a white solid, 32 mg (17% yield, 100% chiral purity, 98% purity by LCMS) (R)—N-(5-(2,4-difluorophenoxy)pyridin- 2-yl)-2-((1S,3R)-3-(6-oxo-1,6-dihydropyridin-3-yl)cyclohexyl)propanamide. LCMS (ES, m/z): 454 [M+H], rt=0.97 min, Method 5. $^1$H NMR (400 MHz, CHLOROFORM-d) δ 12.83 (br s, 1H), 9.18 (s, 1H), 8.23 (d, J=9.3 Hz, 1H), 7.99 (d, J=2.9 Hz, 1H), 7.32 (d, J=9.3 Hz, 1H), 7.29-7.25 (m, 1H), 7.07-6.92 (m, 3H), 6.88-6.82 (m, 1H), 6.50 (d, J=9.3 Hz, 1H), 2.32-2.22 (m, 2H), 1.89 (br d, J=11.2 Hz, 2H), 1.82 (br s, 1H), 1.79-1.75 (m, 1H), 1.71-1.67 (m, 1H), 1.41-1.14 (m, 6H), 1.10-0.82 (m, 2H).

Examples 283-286 were prepared in an analogous manner using the designated intermediate.

| Ex | Name | Structure | ¹H NMR | LC/MS: (M + H)⁺; retention time (min); LC/MS Method of analysis | Int |
|---|---|---|---|---|---|
| 283 | (R)-N-(5((5-fluoropyridin-2-yl)oxy)pyridin-2-yl)-2-((1S,3R)-3-(6-oxo-1,6-dihydropyridin-3-yl)-cyclohexyl)-propanamide | 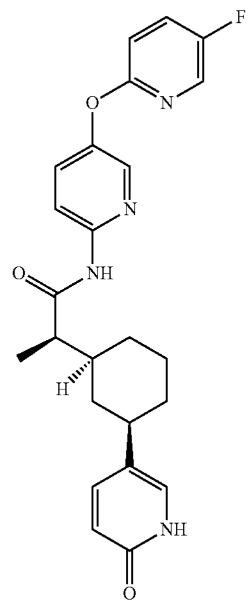 [SMILES: C[C@@H](C(=O)Nc1ccc(Oc2ccc(F)cn2)cn1)[C@H]1CCC[C@@H](c2ccc(=O)[nH]c2)C1] | ¹H NMR (400 MHz, CHLOROFORM-d) δ 12.88 (br s, 1H), 9.46 (s, 1H), 8.36 (d, J = 9.3 Hz, 1H), 8.13 (d, J = 2.0 Hz, 1H), 7.95 (d, J = 2.9 Hz, 1H), 7.56-7.45 (m, 2H), 7.36 (dd, J = 9.3, 2.4 Hz, 1H), 7.04 (d, J = 2.4 Hz, 1H), 6.97 (dd, J = 8.8, 3.4 Hz, 1H), 6.53 (d, J = 9.3 Hz, 1H), 2.38-2.24 (m, 2H), 1.91 (br d, J = 11.2 Hz, 3H), 1.80-1.74 (m, 1H), 1.44-1.19 (m, 6H), 1.09 (q, J = 12.4 Hz, 1H), 1.01-0.85 (m, 1H). | 437; rt 0.84. LC/MS Method 5 | 100, Step 1 |
| 284 | N-(5-(4-fluorophenoxy)pyrazin-2-yl)-2-((3R)-3-(6-oxo-1,6-dihydropyridin-3-yl)cyclohexyl)propanamide | 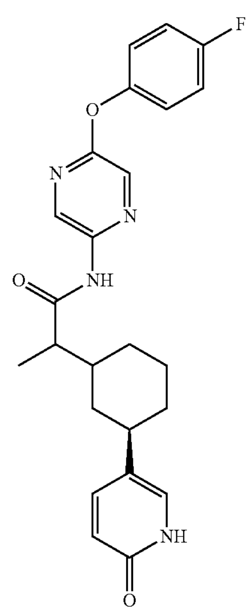 [SMILES: CC(C(=O)Nc1cnc(Oc2ccc(F)cc2)cn1)C1CCC[C@@H](c2ccc(=O)[nH]c2)C1] | ¹H NMR (400 MHz, CHLOROFORM-d) δ 9.11 (d, J = 4.4 Hz, 1H), 8.19 (s, 1H), 8.12-8.03 (m, 1H), 7.44-7.30 (m, 1H), 7.16-7.08 (m, 3H), 6.57 (br d, J = 9.3 Hz, 1H), 6.54 (br d, J = 9.8 Hz, 1H), 2.43-2.19 (m, 2H), 2.13-1.89 (m, 2H), 1.88-1.75 (m, 3H), 1.48-1.21 (m, 6H), 1.14-0.96 (m, 1H), 0.93-0.83 (m, 1H) | 437; rt 0.97. LC/MS Method 5 | 58, Step 1 |

| Ex | Name | Structure | ¹H NMR | LC/MS: (M + H)⁺; retention time (min); LC/MS Method of analysis | Int |
|---|---|---|---|---|---|
| 285 | (R)-N-(5-((3,5-difluoro-pyridin-2-yl)-oxy)pyridin-2-yl)-2-((1S,3R)-3-(6-oxo-1,6-dihydropyri-din-3-yl)cyclo-hexyl)propan-amide | 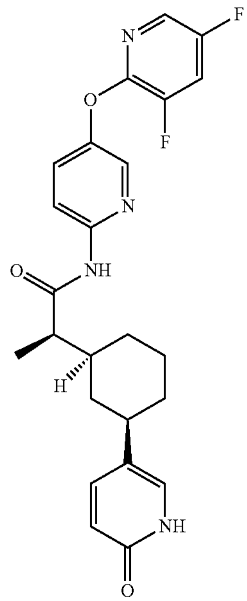 [SMILES: C[C@@H](C(=O)Nc1ccc(Oc2ncc(F)cc2F)cn1)[C@H]1CCC[C@@H](c2ccc(=O)[nH]c2)C1] | ¹H NMR (400 MHz, CHLOROFORM-d) δ 12.74 (br s, 1H), 9.38 (s, 1H), 8.38 (d, J = 9.3 Hz, 1H), 8.18 (d, J = 2.4 Hz, 1H), 7.79 (d, J = 2.9 Hz, 1H), 7.59-7.55 (m, 1H), 7.40-7.33 (m, 2H), 7.04 (d, J = 2.4 Hz, 1H), 6.53 (d, J = 9.3 Hz, 1H), 3.74 (q, J = 7.0 Hz, 1H), 2.38-2.25 (m, 2H), 1.92 (br d, J = 11.2 Hz, 2H), 1.85-1.61 (m, 3H), 1.37 (br s, 1H), 1.33-1.18 (m, 8H), 1.10 (br d, J = 12.7 Hz, 1H), 0.96 (br d, J = 9.8 Hz, 1H). | 455; rt 0.88. LC/MS Method 5 | 99, Step 1 |
| 286 | (R)-N-(5-(2,4-difluorophen-oxy)pyrazin-2-yl)-2-((1S,3R)-3-(6-oxo-1,6-dihydropyri-din-3-yl)cyclo-hexyl)propan-amide | 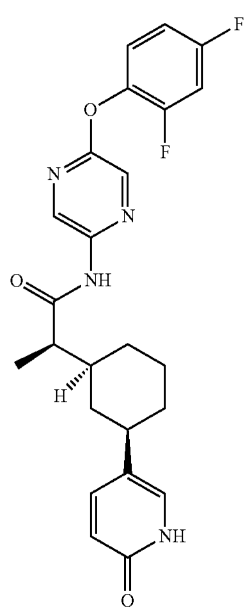 [SMILES: C[C@@H](C(=O)Nc1cnc(Oc2ccc(F)cc2F)cn1)[C@H]1CCC[C@@H](c2ccc(=O)[nH]c2)C1] | ¹H NMR (400 MHz, METHANOL-d₄) δ 8.84 (d, J = 1.5 Hz, 1H), 8.26-8.24 (m, 1H), 7.58 (d, J = 9.2 Hz, 1H), 7.36-7.27 (m, 1H), 7.22-7.11 (m, 2H), 7.05-6.99 (m, 1H), 6.51 (d, J = 9.3 Hz, 1H), 2.47-2.38 (m, 2H), 2.00-1.90 (m, 2H), 1.88-1.70 (m, 3H), 1.53-1.41 (m, 1H), 1.37-1.13 (m, 6H), 1.10-0.86 (m, 1H). | 455; rt 0.98. LC/MS Method 5 | 65, Step 1 |

Example 287

4-((1R,3S)-3-((R)-1-((5-((5-fluoropyridin-2-yl)oxy)pyridin-2-yl)amino)-1-oxopropan-2-yl)cyclohexyl)pyridine 1-oxide

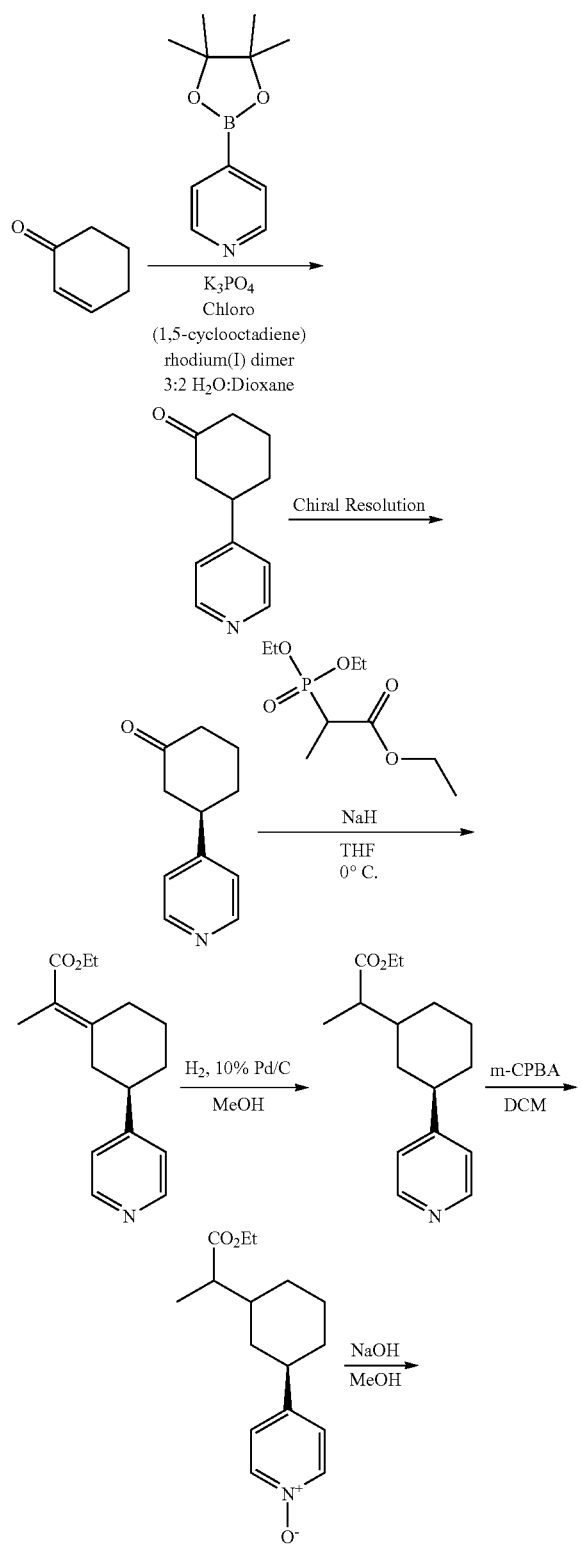

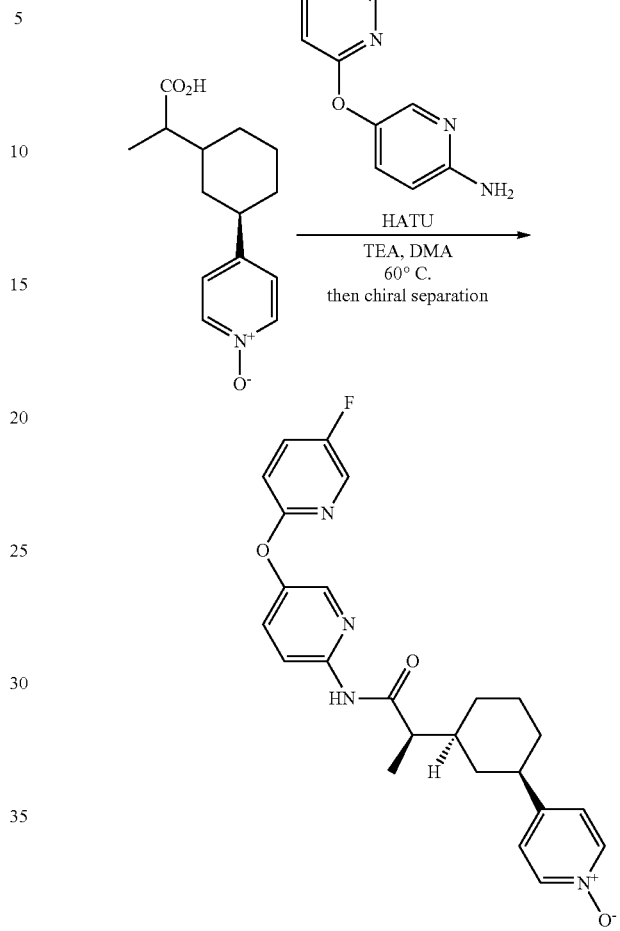

Step 1

A solution of chloro (1,5-cyclooctadiene) rhodium(I) dimer (0.385 g, 0.780 mmol), cyclohex-2-en-1-one (3.0 g, 31.2 mmol), and 4-(4,4,5,5-tetramethyl-1,3,2-dioxaborolan-2-yl)pyridine (12.80 g, 62.4 mmol) in dioxane (62.4 ml) was degassed with $N_2$. A separate solution of potassium phosphate (26.5 g, 125 mmol) in water (94 ml) was degassed with $N_2$. The aqueous solution was added via syringe to the stirring mixture of organics. The resulting mixture was stirred for 16 h at 60° C. Brine was added to the cooled mixture, and the reaction was extracted with DCM (3×). The combined organics were washed with brine, dried over $MgSO_4$, filtered, concentrated and loaded onto a silica gel column, eluting with 0-20% MeOH in DCM to give 6.7 g (purity: 80%, yield 98%) of 3-(pyridin-4-yl)cyclohexan-1-one) as a colorless oil. LCMS: (ES, m/z) 176.2 [M+H]+.

Step 2

Enantiomers of 3-(pyridin-4-yl)cyclohexan-1-one (6.7 g in 56 ml of MeOH, 30.6 mmol, 80% pure) were separated using the following conditions: (Instrument: SFC 80; Column: Chiralpak AD 30×250 mm, 5 u; Co-solvent: 15% MeOH; Flow rate: 65 g/min; UV wavelength: 250 nm; Temperature: 30° C.; Injection vol: 1 ml; Stacking injection: 7.9 min. Desired fractions, enantiomer 1 (8-9.5 min) and enantiomer 2 (10.2-15 min) were collected. Both sample were re-prepped with the same method, except MeOH with 0.3% of isopropylamine was used as the co-solvent for re-prep of enantiomer 2, to give 800 mg (purity: 99%, yield 15%) of enantiomer 1 as a colorless oil; LCMS (ES) m/z 176.2 [M+H]+; and 800 mg (purity: 99%, yield 15%) of enantiomer 2 as a colorless oil; LCMS (ES) m/z 176.2 [M+H]$^+$. Inspection of VCD data in the analysis range indicates that the calculated VCD spectrum for Enantiomer 1 Model is a close match with the experimental of enantiomer 1, but opposite to the VCD features of enantiomer 2. These findings are consistent with enantiomer 1 being assigned with (R)-absolute configuration, and enantiomer 2 with (S)-absolute configuration.

Step 3

Ethyl 2-(diethoxyphosphoryl)propanoate (1.431 ml, 6.85 mmol) was added dropwise to a stirring 0° C. solution of NaH (0.274 g, 6.85 mmol) in THF (10 ml). After 15 min, (R)-3-(pyridin-4-yl)cyclohexan-1-one (0.800 g, 4.57 mmol) in THF (5 ml) was added dropwise. The resulting mixture was allowed to come to RT over 16 h. Saturated NaHCO$_3$ was added, and the organic layer was extracted with EtOAc (3×). The combined organics were washed with brine, dried over MgSO4, filtered, concentrated and loaded onto a silica gel column, eluting with 0-50% EtOAC in heptane to give 1.009 g (purity: 96%, yield 82%) of ethyl (R,E)-2-(3-(pyridin-4-yl)cyclohexylidene)propanoate as a colorless oil. LCMS: (ES, m/z) 260.3 [M+H]+.

Step 4

A mixture of ethyl (R,E)-2-(3-(pyridin-4-yl)cyclohexylidene)propanoate (1.009 g, 3.89 mmol) and Pd—C in ethanol was degassed and backfilled with N$_2$ (3×). The mixture was then degassed and backfilled with H2. The resulting mixture was hydrogenated for 3.5 h. The mixture was filtered, washing with EtOH, and the filtrate concentrated to give 0.93 g (purity: 99%, yield 92%) of ethyl 2-((3R)-3-(pyridin-4-yl)cyclohexyl)propanoate as a colorless oil, which was used without further purification. LCMS: (ES, m/z) 262.3 [M+H]$^+$.

Step 5 m-CPBA (1.549 g, 6.91 mmol) was added to ethyl 2-((3R)-3-(pyridin-4-yl)cyclohexyl)propanoate (0.903 g, 3.45 mmol) in DCM (11.52 ml). After 16 h, the mixture was loaded onto a silica gel column, eluting with 0-10% MeOH in EtOAC to give 1.405 g (purity: 68%, yield 99%) of 4-((1R)-3-(1-ethoxy-1-oxopropan-2-yl)cyclohexyl)pyridine 1-oxide as a colorless solid. LCMS: (ES, m/z) 278.3 [M+H]$^+$.

Step 6

NaOH (5 M) (2.067 ml, 10.33 mmol) was added to 4-((1R)-3-(1-ethoxy-1-oxopropan-2-yl)cyclohexyl)pyridine 1-oxide (1.405 g, 3.44 mmol) in ethanol (11.48 ml). The resulting mixture was stirred for 16 h. HCl (6 M) (1.722 ml, 10.33 mmol) was added, and the resulting mixture was concentrated to give 2.185 g crude (purity: 68%, yield 99%) of 4-((1R)-3-(1-carboxyethyl)cyclohexyl)pyridine 1-oxide, with 3 eq. of NaCl, as a colorless solid, which was used without further purification. LCMS: (ES, m/z) 250.3 [M+H]$^+$.

Step 7

DIEA (492 μl, 2.83 mmol) was added to a mixture of 5-((5-fluoropyridin-2-yl)oxy)pyridin-2-amine (Intermediate 100, Step 1) (242 mg, 1.177 mmol), 4-((1R)-3-(1-carboxyethyl)cyclohexyl)pyridine 1-oxide with 3 eq. of NaCl (400 mg, 0.942 mmol) and HATU (537 mg, 1.413 mmol) in DMF (2355 μl). The mixture was stirred for 16 h at 60° C., diluted with DCM, washed with brine (3×), dried over MgSO$_4$, filtered, concentrated and loaded onto a silica gel column, eluting with 0-100% (3:1 EtOAc: EtOH) in EtOAc to give product. This diastereomeric mixture was purified on chiralpak ic using isocratic 80:20 acetonitrile: methanol. Two peaks were identified with the desired mass at retention times of 6.44 min and 7.36 min. The diastereomer with the retention time of 7.36 min was concentrated to give 59.2 mg (purity: 99% ee, yield 14%, rt=7.36 min, Optical Rotation αDEI=−92.4 (C=0.10, MeOH)) of 4-((1R,3S)-3-((R)-1-((5-((5-fluoropyridin-2-yl)oxy)pyridin-2-yl)amino)-1-oxopropan-2-yl)cyclohexyl)pyridine 1-oxide as a light yellow solid. LCMS: (ES, m/z) 437.4 [M+H]$^+$. $^1$H NMR (DMSO-d$_6$) δ 10.49 (s, 1H), 8.06-8.20 (m, 5H), 7.81-7.89 (m, 1H), 7.60 (dd, J=9.0, 2.9 Hz, 1H), 7.25 (d, J=7.1 Hz, 2H), 7.19 (dd, J=9.0, 3.7 Hz, 1H), 3.17 (d, J=5.1 Hz, 1H), 2.57 (m, 1H), 1.86 (d, J=11.5 Hz, 2H), 1.66-1.80 (m, 3H), 1.30-1.44 (m, 2H), 1.16-1.27 (m, 1H), 1.10 (d, J=6.8 Hz, 3H), 0.85-1.04 (m, 1H). VCD analysis identified diastereomer 1 as 4-((1R,3S)-3-((S)-1-((5-((5-fluoropyridin-2-yl)oxy)pyridin-2-yl)amino)-1-oxopropan-2-yl)cyclohexyl)pyridine 1-oxide and diastereomer 2 as 4-((1R,3S)-3-((R)-1-((5-((5-fluoropyridin-2-yl)oxy)pyridin-2-yl)amino)-1-oxopropan-2-yl)cyclohexyl)pyridine 1-oxide.

Examples 288-290 were prepared in an analogous manner using the designated intermediate.

| Ex | Name | Structure | ¹H NMR | LC/MS: (M + H)⁺; retention time (min); LC/MS Method of analysis | Int |
|---|---|---|---|---|---|
| 288 | 4-((1R,3S)-3-((R)-1-((5-((5-fluoro-pyridin-2-yl)-oxy)pyridin-2-yl)amino)-1-oxopropan-2-yl)cyclohexyl)pyridine 1-oxide | 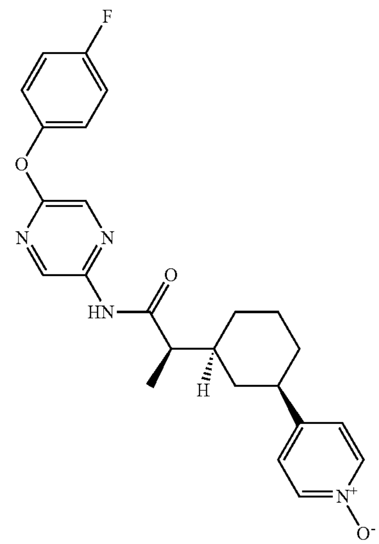 [SMILES: C[C@@H](C(=O)Nc1cnc(Oc2ccc(F)cc2)cn1)[C@H]1CCC[C@@H](c2cc[n+]([O-])cc2)C1] | ¹H NMR (DMSO-d₆) δ 10.68 (s, 1H), 8.87 (d, J = 1.2 Hz, 1H), 8.27 (d, J = 1.2 Hz, 1H), 8.09 (d, J = 7.1 Hz, 2H), 7.17-7.29 (m, 6H), 2.53-2.64 (m, 2H), 1.86 (d, J = 10.8 Hz, 2H), 1.60-1.78 (m, 3H), 1.28-1.45 (m, 2H), 1.14-1.27 (m, 1H), 1.10 (d, J = 6.8 Hz, 3H), 0.85-1.00 (m, 1H). | 437.4; rt. 0.89; LC/MS Method 5 | 58, Step 1 |
| 289 | 4-((1R,3S)-3-((R)-1-((5-(2,4-difluorophen-oxy)pyridin-2-yl)amino)-1-oxopropan-2-yl)cyclohexyl)-pyridine 1-oxide | 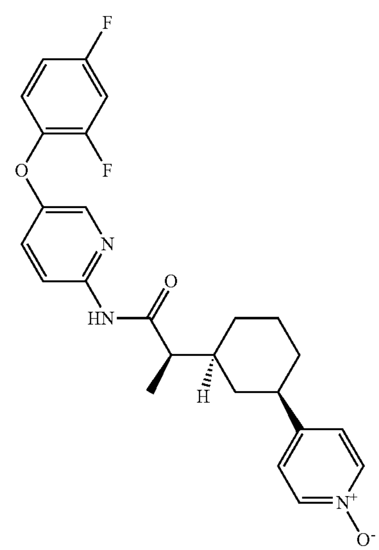 [SMILES: C[C@@H](C(=O)Nc1ccc(Oc2ccc(F)cc2F)cn1)[C@H]1CCC[C@@H](c2cc[n+]([O-])cc2)C1] | ¹H NMR (DMSO-d₆) δ 10.47 (s, 1H), 8.06-8.14 (m, 4H), 7.42-7.54 (m, 2H), 7.22-7.32 (m, 3H), 7.08-7.15 (m, 1H), 3.17 (d, J = 5.1 Hz, 1H), 2.54-2.59 (m, 1H), 1.85 (d, J = 9.8 Hz, 2H), 1.64-1.78 (m, 3H), 1.28-1.40 (m, 2H), 1.13-1.24 (m, 1H), 1.08 (d, J = 6.8 Hz, 3H), 0.85-0.98 (m, 1H). | 454.4; rt. 0.90; LC/MS Method 5 | 71, Step 2 |

| Ex | Name | Structure | $^1$H NMR | LC/MS: (M + H)$^+$; retention time (min); LC/MS Method of analysis | Int |
|---|---|---|---|---|---|
| 290 | 4-((1R,3S)-3-((R)-1-((5-((3,5-difluoro-pyridin-2-yl)-oxy)pyridin-2-yl)amino)-1-oxopropan-2-yl)cyclohexyl)-pyridine 1-oxide | 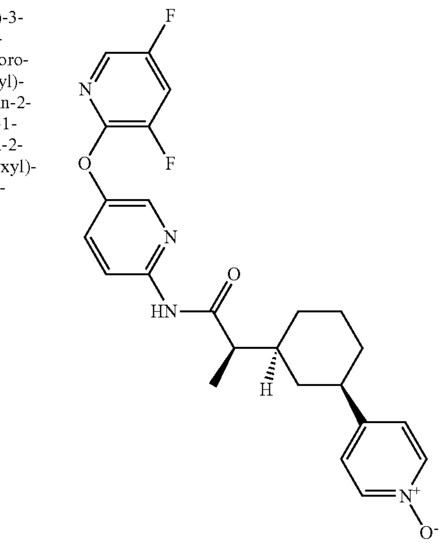 | $^1$H NMR (DMSO-d$_6$) δ 10.56 (s, 1H), 8.26 (d, J = 2.4 Hz, 1H), 8.14-8.22 (m, 2H), 8.11 (d, J = 7.1 Hz, 2H), 8.04 (d, J = 2.7 Hz, 1H), 7.69 (dd, J = 9.0, 2.9 Hz, 1H), 7.30 (d, J = 6.8 Hz, 2H), 2.56-2.65 (m, 1H), 1.90 (d, J = 12.7 Hz, 1H), 1.72-1.86 (m, 2H), 1.61-1.72 (m, 2H), 1.26-1.38 (m, 2H), 1.02-1.10 (m, 6H). | 455.4; rt. 0.83; LC/MS Method 5 | 99, Step 1 |

Example 291

4-((1R,5S)-5-((R)-1-((5-(2,4-difluorophenoxy)pyridin-2-yl)amino)-1-oxopropan-2-yl)-2,2-difluorocyclohexyl)pyridine 1-oxide

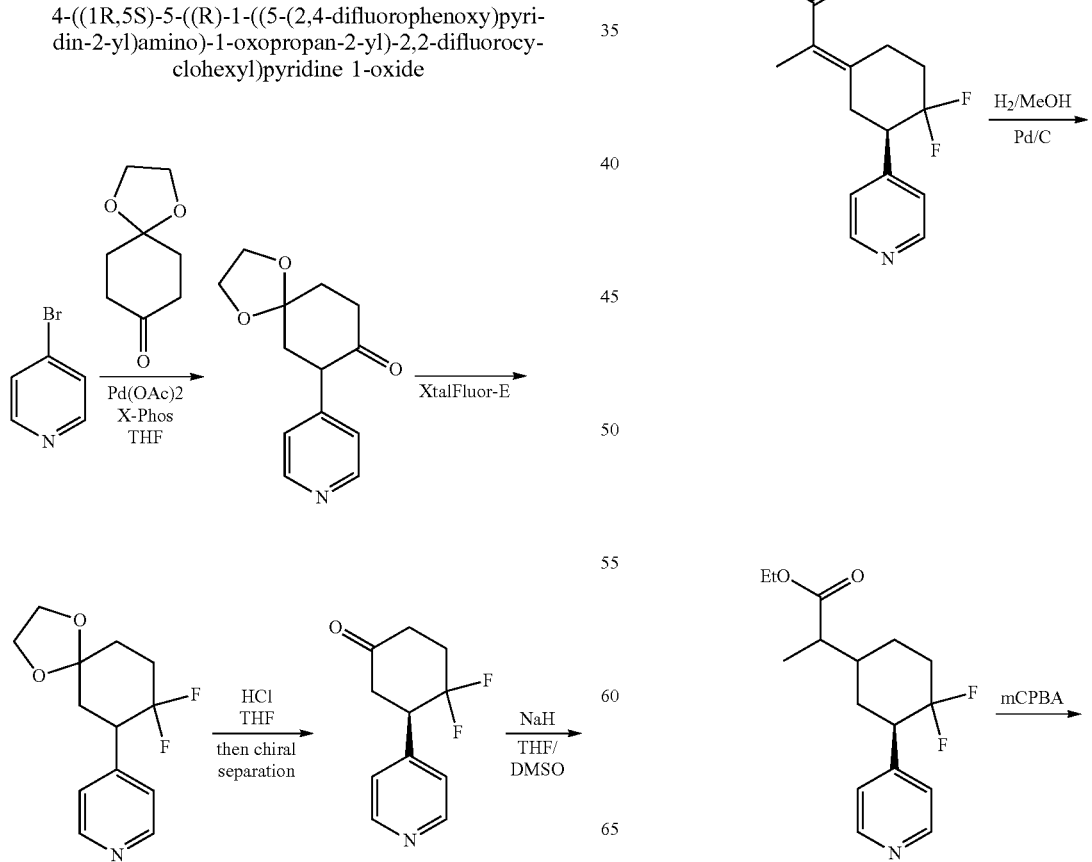

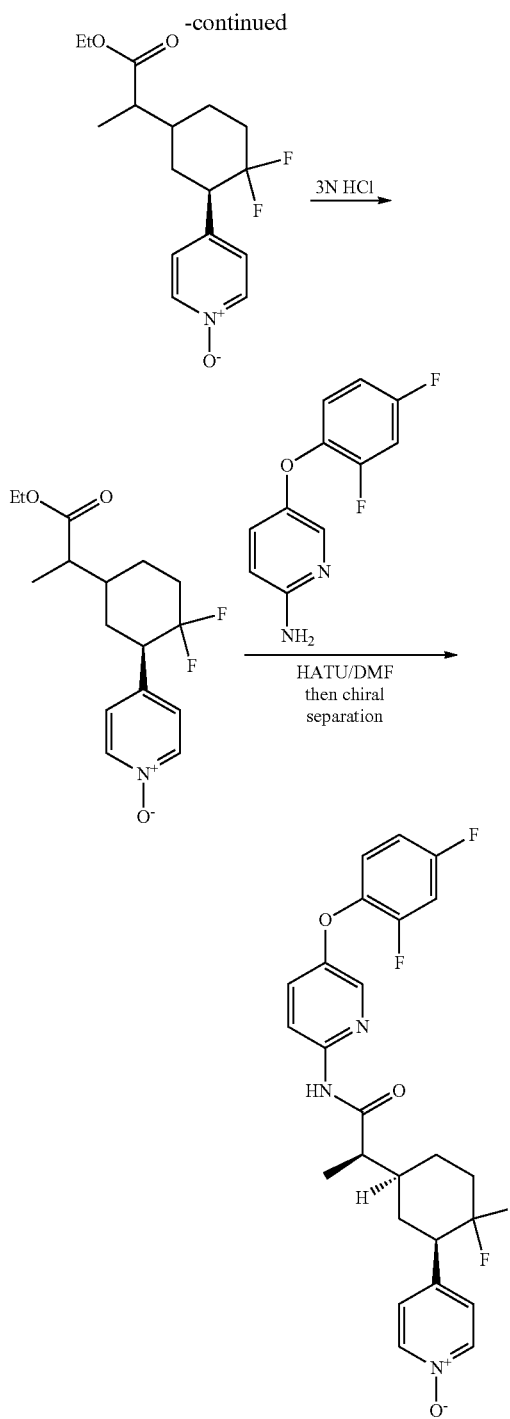

Step 1

To sodium tert-butoxide (21.54 g, 224 mmol) in THF (150 mL) was added 1,4-dioxaspiro[4.5]decan-8-one (10 g, 64.0 mmol) followed by 4-bromopyridine hydrochloride (13.07 g, 67.2 mmol). After 5 min, XPhos (3.05 g, 6.40 mmol) was added, followed by palladium(II) acetate (1.437 g, 6.40 mmol). The reaction vessel was evacuated and purged with nitrogen three times, then heated at 45° C. overnight. The mixture was concentrated and partitioned between EtOAc and water. The aqueous layer was isolated and extracted with EtOAc (2×). (The organic phase and aqueous phase were hard to separate; the mixture was filtered through Celite). The combined organic layers were washed with brine, dried over $Na_2SO_4$, filtered, concentrated and chromatographed on silica gel (120 g column), eluting with 0-100% 3:1 EtOAc: EtOH in heptane to give partially pure material which was recrystallized with DMSO to give 4.52 g (17.44 mmol, yield 27.2%) of 7-(pyridin-4-yl)-1,4-dioxaspiro[4.5]decan-8-one as a yellow solid. LCMS: (ES, m/z) 234.2 (M+H)+. $^1$H NMR (DMSO-$d_6$) δ 8.42-8.57 (m, 2H), 7.11-7.31 (m, 2H), 3.89-4.14 (m, 5H), 2.75 (td, J=13.9, 6.7 Hz, 1H), 2.24-2.44 (m, 2H), 1.89-2.19 (m, 3H).

Step 2

To a stirred, cooled (0° C.) suspension of XtalFluor-E (8.84 g, 38.6 mmol) in DCM (50 mL) was added triethylamine trihydrofluoride (6.28 mL, 38.6 mmol), dropwise. After 20 min, a solution of 7-(pyridin-4-yl)-1,4-dioxaspiro[4.5]decan-8-one (4.5 g, 19.29 mmol) in DCM (50 mL) was added dropwise via a dropping funnel. Upon complete addition, the funnel was rinsed with dichloromethane (5 mL), and the mixture was allowed to warm slowly to rt overnight. The mixture was cooled in an ice bath and carefully quenched with the dropwise addition of saturated aqueous $NaHCO_3$ (50 mL). The reaction was poured into water and extracted with dichlormethane (2×). The combined organic layers were washed with brine, dried over $Na_2SO_4$, and filtered. ISOLUTE was added to the mixture, solvent was removed under reduced pressure and the remaining powder was chromatographed on silica gel (120 g Redi Sep Gold silica cartridge), eluting with 5-50% 3:1 EtOAc: EtOH in heptane to give 2.5 g (8.81 mmol, 45.7% yield) 4-(8,8-difluoro-1,4-dioxaspiro[4.5]decan-7-yl)pyridine as a yellow solid. LCMS: (ES, m/z) 256.1 (M+H)+. $^1$H NMR (CHLOROFORM-d) δ 8.59 (d, J=6.1 Hz, 2H), 7.15-7.35 (m, 2H), 3.95-4.18 (m, 4H), 3.22-3.50 (m, 1H), 1.69-2.42 (m, 6H).

Step 3

To 4-(8,8-difluoro-1,4-dioxaspiro[4.5]decan-7-yl)pyridine (2500 mg, 9.79 mmol) in THF (3 mL) in a microwave tube was added hydrogen chloride (4 M, 3.67 mL, 14.69 mmol).

The mixture was microwaved at 100° C. for 20 minutes and concentrated. The remaining aqueous mixture was adjusted to pH=7 with saturated aqueous $NaHCO_3$ at a rate that controlled vigorous gas evolution, and then was extracted with dichlormethane (2×). During the extraction, the product crashed out of solution. The material was filtered to afford 4,4-difluoro-3-(pyridin-4-yl)cyclohexan-1-one. LCMS: (ES, m/z) 212.2 (M+H)$^+$ and 230.2 (M+ water). $^1$H NMR (METHANOL-d4) δ 8.43-8.54 (m, 2H), 7.37-7.47 (m, 2H), 3.39-3.58 (m, 1H), 1.88-2.41 (m, 6H). Enantiomers were separated using the following conditions: (Instrument: Agilent Semi-Prep 1200 series; Column: IG, 5 micron-20 mm×250 mm; Mobile Phase: 100:0.25% Acetonitrile: FA (isocratic); Flow rate: 45 g/min; UV wavelength: 254 nm; Temperature: Amibient; A single prep injection was made of 60 mg in 5 mL; enantiomer 1 was observed at ~5.01 minutes and the second enantiomer 2 was observed at ~7.21 minutes. Further injections were made with a max injection concentration of 60 mg per 5 mL. Desired fractions of enantiomer 1 and enantiomer 2 were collected and combined respectively. The pH of the solution was adjusted to 7 using 3M potassium carbonate aqueous solution. The resulting solution was filtered, and the filtrate was dried in vacuo to give 620 mg (purity: 94%, yield 28.2%) of enantiomer 1 as a white solid; LCMS (ES) m/z 212.1 [M+H]+. Inspection of VCD data in the analysis range indicates that the calculated VCD spectrum for Enantiomer 1 Model is a close match with the experimental of enantiomer 1, and opposite to the VCD features of enantiomer 2. These findings are consistent with enantiomer 1 being assigned with (R)-absolute configuration, and enantiomer 2 with (S)-absolute configuration.

Step 4

To a cooled (0° C.) suspension of a 60% mineral oil dispersion of sodium hydride (185 mg, 4.62 mmol) in THF (6.00 mL) was added ethyl 2-(diethoxyphosphoryl)propanoate (0.991 mL, 4.62 mmol), dropwise. After 30 min, this mixture was added to (R)-4,4-difluoro-3-(pyridin-4-yl)cyclohexan-1-one (650 mg, 3.08 mmol) in DMSO (6 mL), dropwise. After 3 h, the reaction was quenched with water and extracted with EtOAc (3×). The combined organic layers were washed with brine, dried over $Na_2SO_4$, filtered, concentrated and chromatographed on silica gel (220 g Redi Sep Gold silica cartridge), eluting with 5-80% EtOAc in heptane to give 620 mg (1.994 mmol, 64.8% yield) ethyl (R,E)-2-(4,4-difluoro-3-(pyridin-4-yl)cyclohexylidene)propanoate, as a colorless oil. LCMS and NMR analysis confirmed it as mixture of (E) and (Z) isomers. LCMS: (ES, m/z) 296.3 (M+H)+. $^1H$ NMR (METHANOL-$d_4$) δ 8.46-8.58 (m, 2H), 7.45 (dd, J=13.4, 5.6 Hz, 2H), 4.05-4.29 (m, 2H), 3.11-3.40 (m, 2H), 2.80-2.97 (m, 1H), 2.58-2.75 (m, 1H), 2.23-2.45 (m, 2H), 1.83-2.11 (m, 4H), 1.13-1.45 (m, 5H).

Step 5

A mixture of ethyl (E)-2-(4,4-difluoro-3-(pyridin-4-yl) cyclohexylidene)propanoate (620 mg, 2.099 mmol) and 10% palladium on carbon (35 mg, 0.033 mmol) in ethanol (20 mL) was fitted with a hydrogen filled balloon and stirred overnight. The mixture was filtered through Celite, rinsing with methanol, and concentrated to give 580 mg (1.892 mmol, 90% yield) ethyl 2-(4,4-difluoro-3-(pyridin-4-yl)cyclohexyl)propanoate as a colorless oil, which was used without further purification. LCMS: (ES, m/z) 298.3 (M+H)+.

Step 6

To a cold (0° C.) solution of ethyl 2-((3R)-4,4-difluoro-3-(pyridin-4-yl)cyclohexyl)propanoate (580 mg, 1.951 mmol) in DCM (10 mL) was added a solution of m-CPBA (673 mg, 3.90 mmol) in DCM (10 mL). The solution was stirred for 1 h, then a stream of air was used to blow off some of the DCM. Do not concentrate. The mixture was loaded onto silica gel column, eluting with 20% MeOH in DCM to give 600 mg (1.915 mmol, 98% yield) 4-((1R)-5-(1-ethoxy-1-oxopropan-2-yl)-2,2-difluorocyclohexyl) pyridine 1-oxide as a colorless glass. LCMS: (ES, m/z) 314.2 (M+H)+. $^1H$ NMR (CHLOROFORM-d) δ 8.14-8.26 (m, 2H), 7.18-7.35 (m, 2H), 4.04-4.25 (m, 2H), 2.94-3.14 (m, 1H), 1.39-2.44 (m, 9H), 1.10-1.32 (m, 5H).

Step 7

To 4-((1R)-5-(1-ethoxy-1-oxopropan-2-yl)-2,2-difluorocyclohexyl)pyridine 1-oxide (600 mg, 1.915 mmol) in water (2 mL) was added HCl(aq) (6.38 mL, 38.3 mmol). The mixture was stirred at 60° C. overnight and concentrated to give 550 mg (1.831 mmol, 96% yield) 4-((1R)-5-(1-carboxyethyl)-2,2-difluorocyclohexyl)pyridine 1-oxide as colorless film, which was used without further purification. LCMS (ES, m/z): 286 [M+H]+. $^1H$ NMR (400 MHz, DMSO-$d_6$) δ 7.98-8.24 (m, 2H), 7.98-8.24 (m, 2H), 2.71-3.06 (m, 1H), 1.18 (br d, J=3.42 Hz, 7H), 0.41 (br t, J=7.34 Hz, 5H).

Step 8

N-Ethyl-N-isopropylpropan-2-amine (0.183 ml, 1.052 mmol) was added to a mixture of 5-(2,4-difluorophenoxy) pyridin-2-amine (Intermediate 71, Step 2) (117 mg, 0.526 mmol), 4-((1R)-5-(1-carboxyethyl)-2,2-difluorocyclohexyl) pyridine 1-oxide (100 mg, 0.351 mmol) and 2-(3H-[1,2,3] triazolo[4,5-b]pyridin-3-yl)-1,1,3,3-tetramethylisouronium hexafluorophosphate(V) (200 mg, 0.526 mmol) in DMF (3 ml). The mixture was stirred at 60° C. for 18 h, diluted with DCM, washed with brine (3×), dried over $Na_2SO_4$, filtered, concentrated and purified by MDAP, using HpH column (XSelect CSH Prep C18 5 um OBD), 30-85% gradient, Acetonitrile/Water with 10 mM Ammonium Bicarb and 0.075% Ammonium Hydroxide to afford 47 mg (0.091 mmol, 26.0% yield) 4-((1R,5S)-5-((R)-1-((5-(2,4-difluorophenoxy)pyridin-2-yl)amino)-1-oxopropan-2-yl)-2,2-difluorocyclohexyl)pyridine 1-oxide as a white solid. LCMS (ES, m/z): 490.3 [M+H]+, rt=0.97 min, Method 3. $^1H$ NMR (400 MHz, METHANOL-$d_4$) δ 8.20-8.39 (m, 2H), 7.98-δ 8.11 (m, 2H), 7.52 (d, J=6.85 Hz, 2H), 6.91-7.43 (m, 5H), 2.43-2.57 (m, 1H), 1.80-2.36 (m, 6H), 1.35-1.59 (m, 1H), 1.21-1.33 (m, 3H).

Examples 292-295 were synthesized in an analogous manner using the designated Intermediate in Step 8.

| Ex | Name | Structure | ¹H NMR | LC/MS: (M + H)⁺; retention time (min); LC/MS Method of analysis | Int |
|---|---|---|---|---|---|
| 292 | 4-((1R,5S)-2,2-difluoro-5-((R)-1-((5-(4-fluoro-phenoxy)-pyrazin-2-yl)-amino)-1-oxo-propan-2-yl)-cyclohexyl)-pyridine 1-oxide | 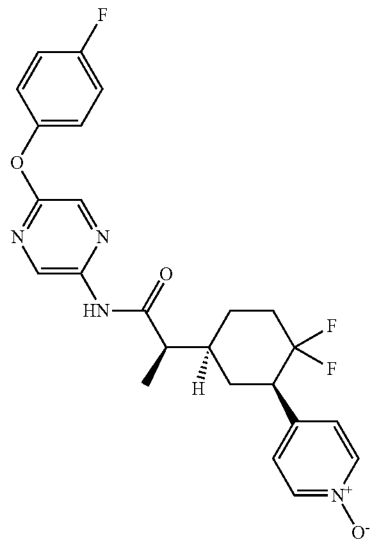 [SMILES: C[C@@H](C(=O)Nc1cnc(Oc2ccc(F)cc2)cn1)[C@H]1CCC(F)(F)[C@@H](c2cc[n+]([O-])cc2)C1] | ¹H NMR (400 MHz, METHANOL-d₄) δ ppm 8.88 (d, J = 1.47 Hz, 1H), 8.38-8.09 (m, 3H), 7.51 (d, J = 6.85 Hz, 2H), 7.24-7.10 (m, 4H), 3.37 (s, 3H), 2.82-1.74 (m, 8H), 1.31-1.21 (m, 3H). | 473.2; rt 0.91. LC/MS Method 3 | 58, Step 1 |
| 293 | 4-((1R,5S)-5-((R)-1-((5-((3,5-difluoro-pyridin-2-yl)-oxy)pyridin-2-yl)amino)-1-oxopropan-2-yl)-2,2-difluorocyclo-hexyl)pyridine 1-oxide | 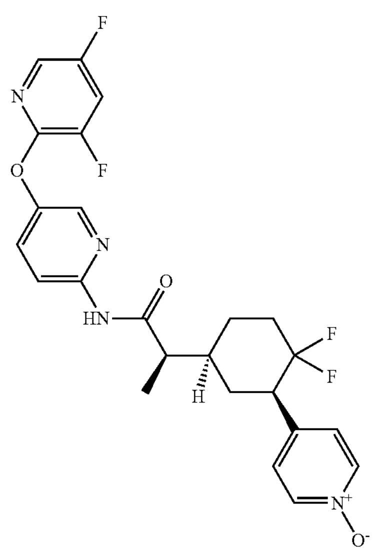 [SMILES: C[C@@H](C(=O)Nc1ccc(Oc2ncc(F)cc2F)cn1)[C@H]1CCC(F)(F)[C@@H](c2cc[n+]([O-])cc2)C1] | ¹H NMR (400 MHz, METHANOL-d₄) δ ppm 8.09-8.36 (m, 4H), 7.81-7.93 (m, 1H), 7.42-7.77 (m, 4H), 3.37 (s, 4H), 2.38-2.62 (m, 1H), 1.54-2.36 (m, 7H), 1.27 (dd, J = 11.74, 6.85 Hz, 3H). | 491.1; rt 0.88. LC/MS Method 3 | 99, Step 1 |

| Ex | Name | Structure | ¹H NMR | LC/MS: (M + H)⁺; retention time (min); LC/MS Method of analysis | Int |
|---|---|---|---|---|---|
| 294 | 4-((1R,5S)-2,2-difluoro-5-((R)-1-((5-((5-fluoro-pyridin-2-yl)-oxy)pyridin-2-yl)amino)-1-oxopropan-2-yl)cyclo-hexyl)pyridine 1-oxide | 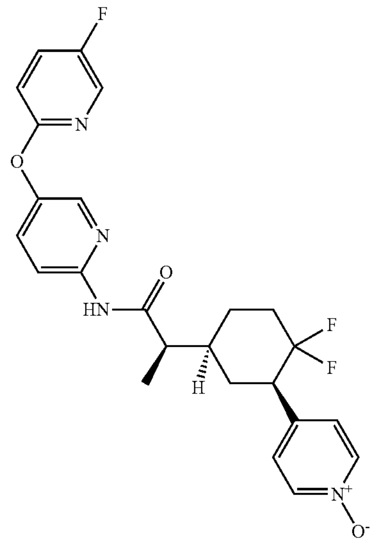 [SMILES: C[C@@H](C(=O)Nc1ccc(Oc2ccc(F)cn2)cn1)[C@H]1CCC(F)(F)[C@@H](c2cc[n+]([O-])cc2)C1] | ¹H NMR (400 MHz, METHANOL-d₄) δ ppm 1.28 (d, J = 6.85 Hz, 3H), 1.38-1.54 (m, 1H), 1.88 (br d, J = 11.74 Hz, 5H), 2.20-2.31 (m, 1H), 2.45-2.59 (m, 1H), 3.33 (s, 1H), 7.01-7.14 (m, 1H), 7.44-7.59 (m, 3H), 7.62-7.71 (m, 1H), 7.94-8.00 (m, 1H), 8.14 (s, 2H), 8.28 (d, J = 6.85 Hz, 2H). | 473.1; rt 0.85. LC/MS Method 3 | 100, Step 1 |
| 295 | 4-((1R,5S)-5-((R)-1-((5-(2,4-difluoro-phenoxy)-pyrazin-2-yl)-amino)-1-oxo-propan-2-yl)-2,2-difluoro-cyclohexyl)-pyridine 1-oxide | 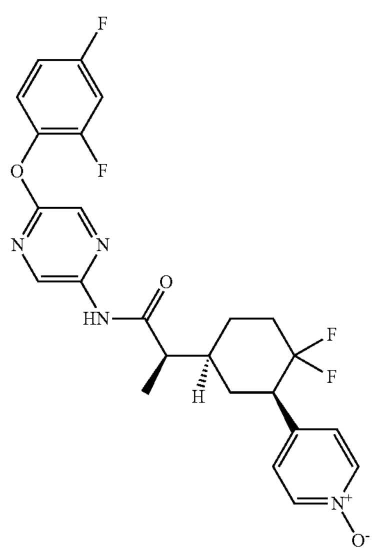 [SMILES: C[C@@H](C(=O)Nc1cnc(Oc2ccc(F)cc2F)cn1)[C@H]1CCC(F)(F)[C@@H](c2cc[n+]([O-])cc2)C1] | ¹H NMR (400 MHz, METHANOL-d₄) δ 8.84 (d, J = 1.5 Hz, 1H), 8.32-8.26 (m, 2H), 8.25 (d, J = 1.5 Hz, 1H), 7.52 (d, J = 7.3 Hz, 2H), 7.31 (td, J = 8.8, 5.4 Hz, 1H), 7.19-7.10 (m, 1H), 7.06-6.97 (m, 1H), 3.37 (s, 2H), 2.57-2.46 (m, 1H), 2.33-2.20 (m, 1H), 2.07 (br s, 1H), 2.03-1.82 (m, 3H), 1.53-1.39 (m, 1H), 1.28 (d, J = 6.8 Hz, 3H). | 491; rt 0.93. LC/MS Method 5 | 65, Step 1 |

Example 296 was synthesized in an analogous manner to Example 275, using Intermediate 65, Step 1 in the final coupling.

| Ex | Name | Structure | ¹H NMR | LC/MS: (M + H)⁺; retention time (min); LC/MS Method of analysis | Int |
|----|------|-----------|--------|---|---|
| 296 | (R)-2-((1S,3R)-4,4-difluoro-3-(6-oxo-1,6-dihydropyridin-3-yl)cyclohexyl)-N-(5-(2,4-difluorophenoxy)-pyrazin-2-yl)-propanamide | 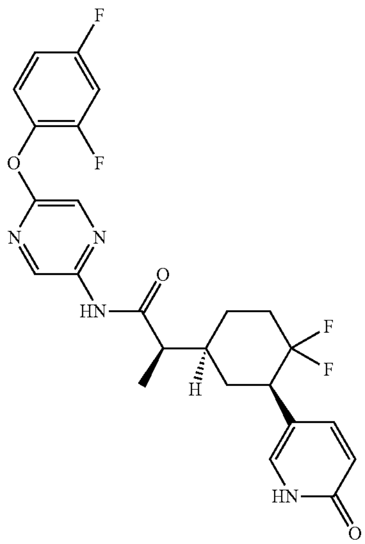 [SMILES: C[C@@H](C(=O)Nc1cnc(Oc2ccc(F)cc2F)cn1)[C@H]1CCC(F)(F)[C@@H](c2ccc(=O)[nH]c2)C1] | 1H NMR (400 MHz, METHANOL-d4) δ 8.84 (d, J = 1.5 Hz, 1H), 8.25 (d, J = 1.5 Hz, 1H), 7.65-7.56 (m, 1H), 7.37-7.25 (m, 2H), 7.18-7.09 (m, 1H), 7.07-6.92 (m, 1H), 6.51 (d, J = 9.8 Hz, 1H), 3.09-2.89 (m, 1H), 2.50 (s, 1H), 2.33-2.13 (m, 1H), 2.12-1.66 (m, 5H), 1.48-1.33 (m, 1H), 1.26 (d, J = 6.8 Hz, 3H). | 491; rt 0.98 LC/MS Method 3 | 65, Step 1 |

Example 297

(S)-2-((S)-4,4-difluoro-3-(pyridin-4-yl)piperidin-1-yl)-N-(5-(2,4-difluorophenoxy)pyrazin-2-yl)-propanamide

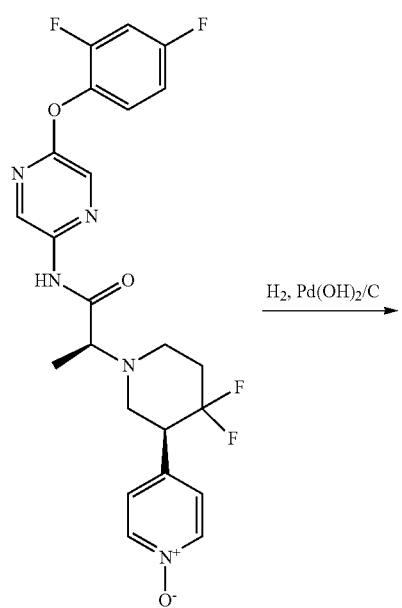

$\xrightarrow{\text{H}_2,\ \text{Pd(OH)}_2/\text{C}}$

-continued

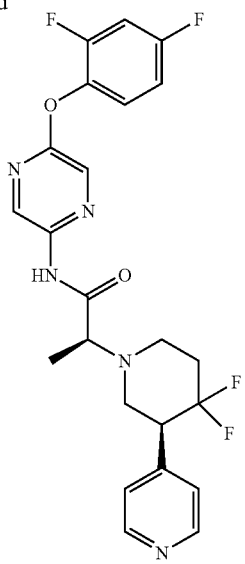

Step 1

To a solution of 4-((S)-1-((S)-1-((5-(2,4-difluorophenoxy)pyrazin-2-yl)amino)-1-oxopropan-2-yl)-4,4-difluoropiperidin-3-yl)pyridine 1-oxide (100 mg, 0.203 mmol) in methanol (2 mL) was added palladium hydroxide on carbon (143 mg, 0.203 mmol). The mixture was degassed under H₂ balloon (3×) and then stirred under H2 for 29 h. The catalyst was filtered and the filtration cake was washed with MeOH. The filtrate was concentrated and the residue was dissolved in MeOH and purified by HPLC (XSelect CSH Prep C18 5 um OBD column, 30-85%, acetonitrile/water with 10 mM ammonium bicarbonate and 0.075% ammonium hydroxide, 40 mL/min flow rate, 27 min run time) affording (S)-2-((S)-4,4-difluoro-3-(pyridin-4-yl)piperidin-1-yl)-N-(5-(2,4-difluorophenoxy)pyrazin-2-yl)propanamide (43.8 mg, 0.092 mmol, 45.3% yield) as a white foam. LCMS rt: 1.14 min (LC/MS Method 3, ES): m/z 476 [M+H]+. $^1$H NMR (400 MHz, CHLOROFORM-d) δ ppm 9.52 (s, 1H) 9.05 (d, J=1.47 Hz, 1H) 8.62 (br d, J=5.38 Hz, 2H) 8.21 (d, J=1.47 Hz, 1H) 7.30 (d, J=5.38 Hz, 2H) 7.23 (td, J=8.80, 5.38 Hz, 1H) 6.92-7.03 (m, 2H) 3.33-3.56 (m, 2H) 3.06-3.16 (m, 1H) 2.96-3.05 (m, 1H) 2.86-2.95 (m, 1H) 2.70 (td, J=11.98, 2.93 Hz, 1H) 2.13-2.39 (m, 2H) 1.41 (d, J=6.85 Hz, 3H).

Example 298

4-((S)-1-((S)-1-((5-(2,4-difluoro-6-(hydroxymethyl)phenoxy)pyrazin-2-yl)amino)-1-oxopropan-2-yl)-4,4-difluoropiperidin-3-yl)pyridine 1-oxide

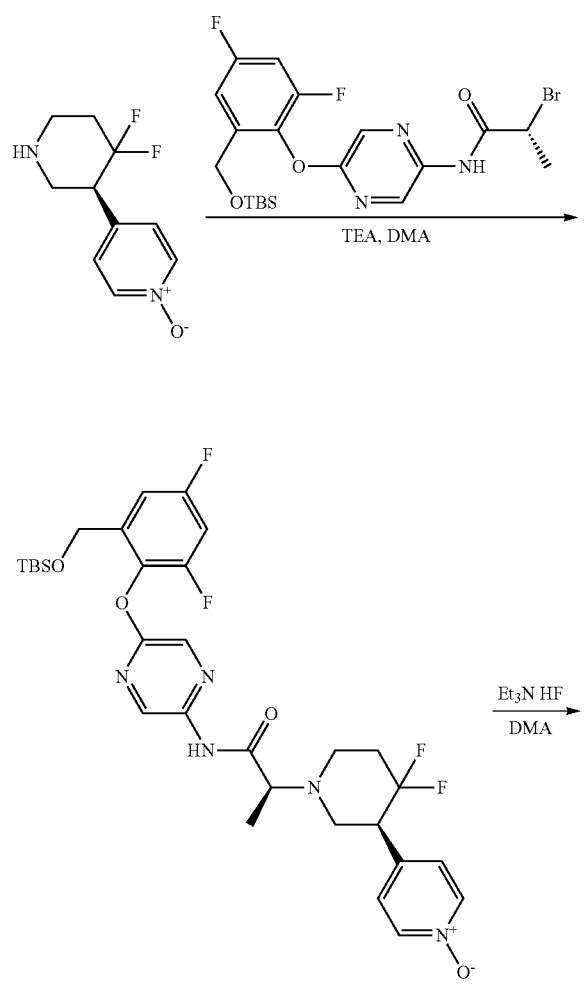

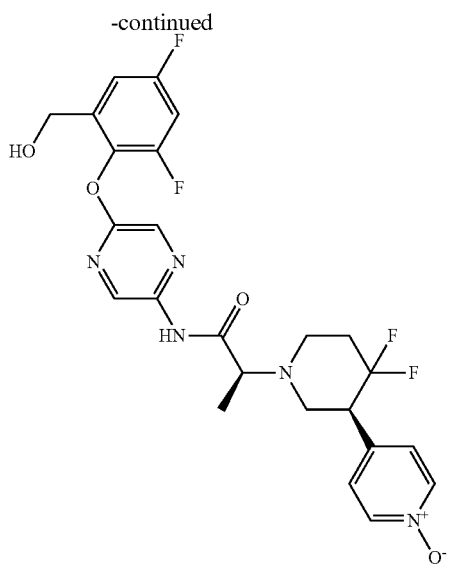

Step 1

A solution of (R)-2-bromo-N-(5-(2-(((tert-butyldimethylsilyl)oxy)methyl)-4,6-difluorophenoxy)pyrazin-2-yl)propanamide (Intermediate 110) (280 mg, 0.56 mmol) in DMA (0.5 ml) at 0° C. was treated with (S)-4-(4,4-difluoropiperidin-3-yl)pyridine 1-oxide (100 mg, 0.47 mmol) and triethylamine (0.091 ml, 0.65 mmol) and the resulting mixture was stirred at 0° C. for 69 hours. The reaction mixture was diluted with water and extracted with EtOAc (2×15 mL). The combined organic layers were washed with water (×3), washed with brine, dried over MgSO$_4$, concentrated and applied onto a silica column, eluting with 0-30% MeOH in EtOAc to give 130 mg (purity: 80%, yield 44%) of 4-((S)-1-((S)-1-((5-(2-(((tert-butyldimethylsilyl)oxy)methyl)-4,6-difluorophenoxy)pyrazin-2-yl)amino)-1-oxopropan-2-yl)-4,4-difluoropiperidin-3-yl)pyridine 1-oxide as an off-white solid. LCMS (ES, m/z): 636 [M+H]+. $^1$H NMR (400 MHz, DMSO-d$_6$) δ 10.57 (s, 1H), 8.80 (d, J=1.5 Hz, 1H), 8.46 (d, J=1.5 Hz, 1H), 8.18 (d, J=7.3 Hz, 2H), 7.47-7.36 (m, 3H), 7.22-7.14 (m, 1H), 4.67 (s, 2H), 3.77-3.66 (m, 1H), 3.60-3.41 (m, 2H), 3.01 (br d, J=10.3 Hz, 1H), 2.92 (br d, J=10.8 Hz, 2H), 2.23-2.04 (m, 2H), 1.23 (d, J=6.8 Hz, 3H), Step 2

A solution of 4-((S)-1-((S)-1-((5-(2-(((tert-butyldimethylsilyl)oxy)methyl)-4,6-difluorophenoxy)pyrazin-2-yl)amino)-1-oxopropan-2-yl)-4,4-difluoropiperidin-3-yl)pyridine 1-oxide (130 mg, 0.21 mmol) in DMA (1 ml) at 23° C. was treated with triethylamine trihydrofluoride (0.067 ml, 0.41 mmol) and the resulting mixture was stirred at 23° C. for 2.5 hours. The reaction mixture was diluted with saturated aqueous sodium bicarbonate solution and extracted with EtOAc (2×15 mL). The combined organic layers were washed with water (×3), washed with brine, dried over MgSO$_4$, concentrated and purified by Prep HPLC (Column: Xselect CSH Prep C18 Column 30×150 mm, 5 μm; Mobile Phase A: water (10 mmol/L NH$_4$HCO$_3$ adjusted to pH=10 with NH$_4$OH), Mobile Phase B: MeCN; Flow rate: 40 mL/min; Gradient: 15% B to 55% B in 19 min; Minor diastereomer impurity: Rt=16.68 min; Desired Product: Rt=16.98 min) to give 50 mg (purity: 99%, yield 46%) of 4-((S)-1-((S)-1-((5-(2,4-difluoro-6-(hydroxymethyl)phenoxy)pyrazin-2-yl)amino)-1-oxopropan-2-yl)-4,4-difluoropiperidin-3-yl)pyridine 1-oxide as a white solid. LCMS (ES, m/z): 522 [M+H]+; rt (min): 0.64; LCMS Method 5. $^1$H NMR (400 MHz, DMSO-d6) δ 10.57 (s, 1H), 8.79 (d, J=1.5 Hz, 1H), 8.47 (d, J=1.5 Hz, 1H), 8.24-8.11 (m, 2H), 7.44-7.31 (m, 3H), 7.20 (br dd, J=9.3, 1.5 Hz, 1H), 5.45 (t, J=5.9 Hz, 1H), 4.46 (d, J=5.9 Hz, 2H), 3.71 (q, J=6.8 Hz, 1H), 3.58-3.41 (m, 1H), 3.10-2.86 (m, 3H), 2.63-2.53 (m, 1H), 2.23-1.98 (m, 2H), 1.23 (d, J=6.8 Hz, 3H).

Example 299 was synthesized in an analogous manner using the designated Intermediate in Step 1.

| Ex | Name | Structure | ¹H NMR | LC/MS: (M + H)⁺; retention time (min); LC/MS Method of analysis | Int |
|---|---|---|---|---|---|
| 299 | 4-((S)-1-((S)-1-((5-(2,4-difluoro-6-(hydroxymethyl)phenoxy)pyridin-2-yl)amino)-1-oxopropan-2-yl)-4,4-difluoropiperidin-3-yl)pyridine 1-oxide | 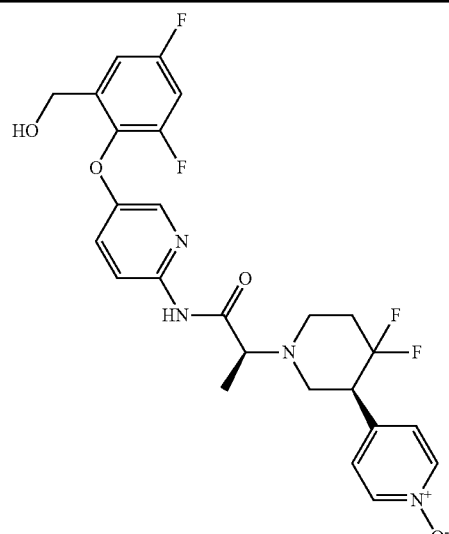 | ¹H NMR: (400 MHz, DMSO-d₆) δ 10.31 (s, 1H), 8.29-8.15 (m, 2H), 8.11-8.00 (m, 2H), 7.51-7.31 (m, 4H), 7.27-7.15 (m, 1H), 5.49 (t, J = 5.6 Hz, 1H), 4.49 (d, J = 5.4 Hz, 2H), 3.68 (q, J = 6.8 Hz, 1H), 3.59-3.40 (m, 1H), 3.09-2.86 (m, 3H), 2.62-2.53 (m, 1H), 2.21-1.97 (m, 2H), 1.22 (d, J = 6.8 Hz, 3H). | 521; rt 0.66 LC/MS Method 5 | 111 |

Examples 300-301 were synthesized in an analogous manner to Example 271 using the designated intermediate in Step 1.

| Ex | Name | Structure | ¹H NMR | LC/MS: (M + H)⁺; retention time (min); LC/MS Method of analysis | Int |
|---|---|---|---|---|---|
| 300 | (S)-2-((S)-4,4-difluoro-3-(6-oxo-1,6-dihydropyridin-3-yl)piperidin-1-yl)-N-(5-(2,4-difluoro-6-(hydroxymethyl)phenoxy)pyrazin-2-yl)propanamide | 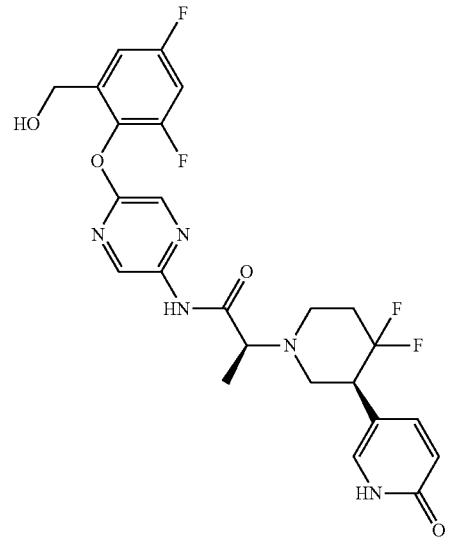 [SMILES: C[C@@H](C(=O)Nc1cnc(Oc2c(F)cc(F)cc2CO)cn1)N1CCC(F)(F)[C@@H](c2ccc(=O)[nH]c2)C1] | ¹H NMR: (400 MHz, DMSO-d₆) δ 11.57 (br, d, J = 2.0 Hz, 1H), 10.54 (s, 1H), 8.79 (d, J = 1.5 Hz, 1H), 8.46 (d, J = 1.5 Hz, 1H), 7.43 (dd, J = 9.5, 2.2 Hz, 1H), 7.39-7.27 (m, 2H), 7.22-7.16 (m, 1H), 6.30 (d, J = 9.8 Hz, 1H), 5.45 (br t, J = 5.6 Hz, 1H), 4.46 (d, J = 4.9 Hz, 2H), 3.68 (q, J = 6.8 Hz, 1H), 3.29-3.12 (m, 1H), 3.01-2.75 (m, 3H), 2.59-2.53 (m, 1H), 2.19-1.92 (m, 2H), 1.22 (d, J = 6.8 Hz, 3H). | 522; rt 0.62 LC/MS Method 5 | 110 |

-continued

| Ex | Name | Structure | $^1$H NMR | LC/MS: $(M + H)^+$; retention time (min); LC/MS Method of analysis | Int |
|---|---|---|---|---|---|
| 301 | (S)-2-((S)-4,4-difluoro-3-(6-oxo-1,6-dihydro-pyridin-3-yl)piperidin-1-yl)-N-(5-(2,4-difluoro-6-(hydroxy-methyl)phen-oxy)pyridin-2-yl)propan-amide | 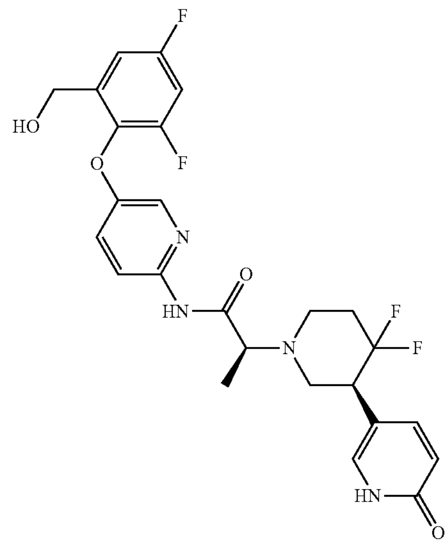 [SMILES: C[C@@H](C(=O)Nc1ccc(Oc2c(F)cc(F)cc2CO)cn1)N1CCC(F)(F)[C@@H](c2ccc(=O)[nH]c2)C1] | $^1$H NMR: (400 MHz, DMSO-$d_6$) δ 10.27 (s, 1H), 8.11-8.01 (m, 2H), 7.48-7.29 (m, 4H), 7.26-7.19 (m, 1H), 6.30 (d, J = 9.8 Hz, 1H), 5.49 (t, J = 5.6 Hz, 1H), 4.49 (d, J = 5.4 Hz, 2H), 3.65 (q, J = 6.8 Hz, 1H), 3.28-3.10 (m, 1H), 2.99-2.77 (m, 3H), 2.59-2.52 (m, 1H), 2.20-1.91 (m, 3H), 1.21 (d, J = 6.8 Hz, 3H). | 521; rt 0.632 LC/MS Method 5 | 111 |

Assay Protocol

A Ca$^{2+}$ mobilization assay was used to assess the activity of the compounds of this invention. A HEK293 cell line with stably expressing human MRGPRX2 and mouse Galpha15 genes was used in the assay. Briefly, cells were seeded into black clear-bottomed 384-well plates at 1.5×10$^4$ cells/well and culture at 37° C. for 24 hours prior to assay. On the day of assay, cells were loaded with Ca$^{2+}$ indicator dye in 20 μL Hank's buffered saline solution containing 25 mmol/L HEPES, pH 7.2 (assay buffer) supplemented with 2 μmol/L Fluo-4 dye (Molecular Probes), 2.5 mmol/L probenecid (Sigma) & 0.5 mmol/L Brilliant Black (MP Biomedicals). Activation of human MRGPRX2 by a peptide agonist, Cortistatin-14 (PCKNFFWKTFSSCK, Disulfide Bridge: 2-13, TFA salt, GeneScript), was measured on FLIPR$^{TETRA}$ (Molecular Devices) instrument as increased fluorescence intensity (488 nm excitation/530 nm emission) upon receptor binding, leading to G-protein activation and Ca$^{2+}$ mobilization. An activation dose response curve was produced for Cortistatin-14 to determine the EC50 value of the agonist on the day of assay. Compounds of this invention were prepared as 1 mM or 10 mM solution in DMSO. Serial dilutions of 11 concentrations at 3-folds were made in DMSO for each compound and then diluted in assay buffer prior to addition onto the dye-loaded cells (final testing concentration range of 100 μmol/L-100 μmol/L for compounds with final 1% DMSO in assay buffer). After 30 min incubation at 37° C., agonist Cortistatin-14 was added to the cell culture at 4×EC50 final concentration. Fluorescence intensity was measured on FLIPR$^{TETRA}$ for compounds' ability to inhibit agonist mediated MRGPRX2 activation. Dose dependent inhibition curves were fitted in ActivityBase (IDBS) data analysis platform to report a pIC50 value for each individual compound dilution series.

The pIC50s for each compound of this invention were averaged to determine a mean value, for a minimum of 2 experiments. For instance, the compounds of Examples 1-304 inhibited MRGPRX2 activation in the above method with a pIC50 value between approximately 9.5 and 4.5.

Biological Data

The exemplified compounds were tested according to the FLIPR$^{TETRA}$ assay described above and were found to be MrgX2 antagonists with pIC50>4.5.

As determined using the above method, the compounds of Examples 1-304 exhibited a pIC$_{50}$ between approximately 9.6-4.5.

The compounds of Examples 1-7, 66, 69, 85, 87, 90, 96, 97, 103, 104, 108, 110, 114, 117, 119-124, 130-133, 156, 182, 193, 195, 202, 204, 205, 208, 210-212, 214, 216, 220, 227, 229, 233-245, 251, 252, 254, 255, 258, 260-262, 264, 265, 268, 269, 275, 278-283, 285, 286, 289, 291, and 293-295 exhibited a pIC$_{50}$≥8.0.

The compounds of Examples 8-10, 12, 13-16, 21, 60, 61, 65, 67, 68, 72, 75, 76, 79, 80, 84, 86, 88, 92, 95, 99, 101, 102, 105, 106, 111, 115, 116, 125-127, 134, 135, 138-140, 143-146, 150-152, 157, 181, 189, 192, 196-198, 203, 206, 207, 209, 215, 218, 219, 221-223, 226, 228, 230, 246, 247, 256-258, 266, 267, 270-273, 276, 277, 284, 287, 288, 290, and 292 exhibited 8.0>pIC$_{50}$≥7.0.

The compounds of Examples 11, 17-20, 22, 23-28, 30-42, 46-52, 54, 57-59, 63, 64, 70, 71, 73, 74, 77, 78, 81-83, 89, 91, 93, 94, 98, 100, 107, 109, 112, 113, 128, 136, 137, 141, 142, 147-149, 153-155, 158-170, 172, 174, 178, 179, 183, 185, 186, 188, 190, 191, 194, 199, 201, 213, 217, 224, 225, 231, 232, 249, 250, 253, 263, and 274 exhibited 7.0>pIC$_{50}$≥5.5.

The compound of Example 132 exhibited a pIC$_{50}$ of 8.6.

The compounds of Examples 43-45, 53, 55, 56, 62, 129, 171, 173, 175-177, 180, 184, 187, 200, and 248 exhibited 5.5>pIC$_{50}$>4.5.

The invention claimed is:
1. A compound according to Formula (I)

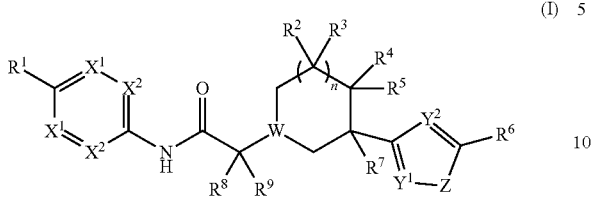

or a pharmaceutically acceptable salt thereof,
wherein:
W is N or CH;
each $X^1$ is independently N or $CR^{10}$;
each $X^2$ is independently N or $CR^{11}$;
$Y^1$ is N or $CR^{12}$;
$Y^2$ is N $CR^{12}$;
Z is

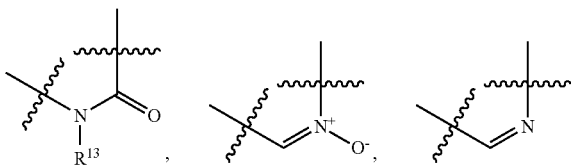

n is 0 or 1;
$R^1$ is hydrogen, halogen, $(C_1-C_6)$alkyl, -$(C_1-C_6)$alkyl-$NH_2$, -$(C_1-C_6)$alkyl-NH$((C_1-C_6)$alkyl$)$, -$(C_1-C_6)$alkyl-N$((C_1-C_6)$alkyl$)((C_1-C_6)$alkyl$)$, -$(C_1-C_6)$alkyl-$(C_3-C_8)$cycloalkyl, -$(C_1-C_6)$alkyl-aryl, 5- or 6-membered heteroaryl$(C_1-C_4)$alkyl-, $(C_3-C_8)$cycloalkyl, $(C_2-C_6)$alkenyl, -$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-aryl, —O—$(C_1-C_6)$alkyl-5-6 membered heteroaryl, —O—$(C_2-C_6)$alkenyl, —O—$(C_3-C_8)$cycloalkyl, —O-aryl, —O-heteroaryl, —C(O)-aryl, -$CO_2$H, -$CO_2(C_1-C_6)$alkyl, -$CO_2(C_3-C_8)$cycloalkyl, -$CO_2C(C_1-C_6)$alkyl, -$O_2C(C_3-C_8)$cycloalkyl, -$NH_2$, —NH$(C_1-C_6)$alkyl, -N$((C_1-C_6)$alkyl$)((C_1-C_6)$alkyl$)$, aryl, or 5-6 membered heteroaryl, wherein any said $(C_1-C_6)$alkyl, -$(C_1-C_6)$alkyl-$(C_3-C_8)$cycloalkyl, -$(C_1-C_6)$alkyl-aryl, $(C_1-C_4)$alkoxy, -0-$(C_1-C_6)$alkyl-$(C_3-C_8)$cycloalkyl, —O—$(C_3-C_8)$cycloalkyl, —O-aryl, —O—5-6-membered heteroaryl, —C(O)-aryl, aryl, or 5-6 membered heteroaryl is optionally substituted one, two, or three times by $R^{14}$;
$R^2$ is hydrogen, halogen, $(C_1-C_6)$alkyl, or —OH, wherein any said $(C_1-C_6)$alkyl is optionally substituted one, two, or three times by halogen;
$R^3$ is hydrogen, halogen, $(C_1-C_6)$alkyl, or —OH, wherein any said $(C_1-C_6)$alkyl is optionally substituted one, two, or three times by halogen;
$R^4$ is hydrogen, halogen, or $(C_1-C_6)$alkyl;
$R^5$ is hydrogen, halogen, or $(C_1-C_6)$alkyl;
$R^6$ is hydrogen, halogen, $(C_1-C_6)$alkyl, $(C_3-C_8)$cycloalkyl, $(C_1-C_4)$alkoxy, -$(C_1-C_6)$alkyl-OH, -$(C_1-C_6)$alkyl-O—$(C_1-C_6)$alkyl, -$(C_1-C_6)$alkyl-$NH_2$, -$(C_1-C_6)$alkyl-NH$((C_1-C_6)$alkyl$)$, -$(C_1-C_6)$alkyl-N-$((C_1-C_6)$alkyl$)((C_1-C_6)$alkyl$)$, -$(C_1-C_6)$alkyl-NH$((C_1-C_6)$alkyl$)$-OH, -$(C_1-C_6)$alkyl-NH$((C_1-C_6)$alkyl$)$-O—$(C_1-C_6)$alkyl$)$, -$(C_1-C_6)$alkyl-N-$((C_1-C_6)$alkyl$)((C_1-C_6)$alkyl$)$-OH, -$(C_1-C_6)$alkyl-N-$((C_1-C_6)$alkyl$)((C_1-C_6)$alkyl$)$-O—$(C_1-C_6)$alkyl$)$, -$(C_1-C_6)$alkyl-NH-$(C_3-C_8)$cycloalkyl, -$(C_1-C_6)$alkyl-NH-4- to 6-membered heterocycloalkyl, -$(C_1-C_6)$alkyl-4- to 6-membered heterocycloalkyl, -$(C_1-C_6)$alkyl-NHC(O)-$((C_1-C_6)$alkyl$)$, -$(C_1-C_6)$alkyl-$SO_2$-$(C_1-C_6)$alkyl, -$(C_1-C_6)$alkyl-$SO_2$—NH-$(C_1-C_6)$alkyl, —CN, —C(O)$NH_2$, -C(O)NH$(C_1-C_6)$alkyl, —C(O)N$(C_1-C_6)$alkyl$)$ $(C_1-C_6)$alkyl$)$, —$NH_2$, —NH$(C_1-C_6)$alkyl, -N$((C_1-C_6)$alkyl$)((C_1-C_6)$alkyl$)$, -$SO_2$ $((C_1-C_6)$alkyl$)$, -$SO_2$—NH$((C_1-C_6)$alkyl$)$, or aryl, wherein any said $(C_1-C_6)$alkyl, $(C_3-C_8)$cycloalkyl, -$(C_1-C_6)$alkyl-OH, -$(C_1-C_6)$alkyl-$NH_2$, -$(C_1-C_6)$alkyl-NH$((C_1-C_6)$alkyl$)$, -$(C_1-C_6)$alkyl-NH-$(C_3-C_8)$cycloalkyl, -$(C_1-C_6)$alkyl-NH-4- to 6-membered heterocycloalkyl, or -$(C_1-C_6)$alkyl-4- to 6-membered heterocycloalkyl is optionally substituted one, two, or three times by halogen;
$R^7$ is hydrogen, $(C_1-C_6)$alkyl, or —OH;
$R^8$ is hydrogen, $(C_1-C_6)$alkyl, or $(C_1-C_4)$alkoxy;
$R^9$ is hydrogen, $(C_1-C_6)$alkyl, or $(C_1-C_4)$alkoxy;
each $R^{10}$ is independently hydrogen, halogen, $(C_1-C_6)$alkyl, $(C_2-C_6)$alkenyl, -$(C_1-C_6)$alkyl-$NH_2$, -$(C_1-C_6)$alkyl-NH$((C_1-C_6)$alkyl$)$, -$(C_1-C_6)$alkyl-N$((C_1-C_6)$alkyl$)$ $((C_1-C_6)$alkyl$)$, $(C_2-C_6)$alkenyl, —O—$(C_1-C_6)$alkyl, —$NH_2$, —NH$((C_1-C_6)$alkyl$)$, -N$((C_1-C_6)$alkyl$)((C_1-C_6)$alkyl$)$, -$NCH_2$, or —CHNH;
or $R^1$ and any $R^{10}$ taken together with the atoms to which they are attached, form a 5-, 6-, or 7-membered ring optionally containing one, two, or three heteroatoms independently selected from oxygen, nitrogen, and sulfur, wherein said ring is optionally substituted by one or two substituents independently selected from halogen, $(C_1-C_6)$alkyl, -$(C_1-C_6)$alkyl-$(C_3-C_8)$cycloalkyl, halo$(C_1-C_6)$alkyl, and $(C_3-C_8)$cycloalkyl;
each $R^{11}$ is independently hydrogen, halogen, $(C_1-C_6)$alkyl, or $(C_2-C_6)$alkenyl;
or any $R^{10}$ and any $R^{11}$ taken together with the atoms to which they are attached, form a 5-, 6-, or 7-membered ring optionally containing one, two, or three heteroatoms independently selected from oxygen, nitrogen, and sulfur; wherein said ring is optionally substituted by one or two substituents independently selected from halogen, $(C_1-C_6)$alkyl, halo$(C_1-C_6)$alkyl, and $(C_3-C_8)$cycloalkyl;
$R^{12}$ is hydrogen, halogen, or $(C_1-C_6)$alkyl, wherein said $(C_1-C_6)$alkyl is optionally substituted one, two, or three times by halogen;
$R^{13}$ is hydrogen, $(C_1-C_6)$alkyl, -$(C_1-C_6)$alkyl-$SO_2$-$(C_1-C_6)$alkyl, -$(C_1-C_6)$alkyl-aryl, or -$(C_1-C_6)$alkyl-5-6-membered heteroaryl, wherein said $(C_1-C_6)$alkyl, -$(C_1-C_6)$alkyl-$SO_2$-$(C_1-C_6)$alkyl, -$(C_1-C_6)$alkyl-aryl, or -$(C_1-C_6)$alkyl-5-6-membered heteroaryl is optionally substituted one, two, or three times by halogen;
each $R^{14}$ is independently halogen, $(C_1-C_6)$alkyl, $(C_3-C_8)$cycloalkyl, —CN, —$(C_1-C_6)$—OH, —$(C_1-C_6)$alkyl-$NH_2$, —$(C_1-C_6)$alkyl-NH$((C_1-C_6)$alkyl$)$, —$(C_1-C_6)$alkyl-N$((C_1-C_6)$alkyl$)((C_1-C_6)$alkyl$)$, —OH, $(C_1-C_4)$alkoxy, -O—$(C_3-C_8)$cycloalkyl, -aryl, 5-6 membered heteroaryl, wherein $(C_1-C_6)$alkyl, $(C_3-C_8)$cycloalkyl, aryl, or 5-6 membered heteroaryl is further optionally substituted by one, two, or three substituents independently selected from halogen, $(C_1-C_6)$alkyl, —$(C_1-C_6)$alkyl-OH, —$(C_1-C_6)$alkyl-O—$(C_1-C_6)$alkyl, or $(C_1-C_4)$alkoxy.

2. The compound or pharmaceutically acceptable salt thereof according to claim 1 wherein W is N.

3. The compound or pharmaceutically acceptable salt thereof according to claim 1, wherein $Y^1$ is $CR^{12}$ and $R^{12}$ is hydrogen or $(C_1-C_6)$alkyl optionally substituted one, two, or three times by halogen.

4. The compound or pharmaceutically acceptable salt thereof according to claim 1, wherein $Y^2$ is N.

5. The compound or pharmaceutically acceptable salt thereof according to claim 1, wherein $Y^2$ is $CR^{12}$ and $R^{12}$ is hydrogen.

6. The compound or pharmaceutically acceptable salt thereof according to claim 1, wherein Z is

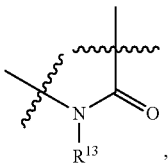

and
$R^{13}$ is hydrogen, $(C_1-C_6)$alkyl, —$(C_1-C_6)$alkyl-$SO_2$—$(C_1-C_6)$alkyl, —$(C_1-C_6)$alkyl-aryl, or -$(C_1-C_6)$alkyl-5-6-membered heteroaryl, wherein said $(C_1-C_6)$alkyl is optionally substituted one, two, or three times by halogen.

7. The compound or pharmaceutically acceptable salt thereof according to claim 1, wherein Z is

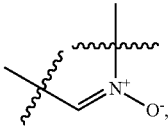

and
$R^6$ is hydrogen, $(C_1-C_6)$alkyl, —$(C_1-C_6)$alkyl-OH, —$(C_1-C_6)$alkyl-NHC(O)—$((C_1-C_6)$alkyl), or —C(O)$NH_2$, wherein any said $(C_1-C_6)$alkyl or —$(C_1-C_6)$alkyl-OH is optionally substituted one, two, or three times by halogen.

8. The compound or pharmaceutically acceptable salt thereof according to claim 1, wherein Z is

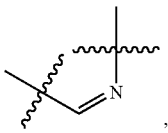 [SMILES: */C=N\*]

and
$R^6$ is hydrogen, —$(C_1-C_6)$alkyl-$NH_2$, —$(C_1-C_6)$alkyl-4- to 6-membered heterocycloalkyl, -C(O)$NH_2$, wherein any said —$(C_1-C_6)$alkyl-4- to 6-membered heterocycloalkyl is optionally substituted one, two, or three times by halogen.

9. The compound or pharmaceutically acceptable salt thereof according to claim 1, wherein n is 1.

10. The compound or pharmaceutically acceptable salt thereof according to claim 1, wherein
$R^1$ is halogen, $(C_1-C_6)$alkyl, —$(C_1-C_6)$alkyl-$NH_2$, —$(C_1-C_6)$alkyl-$(C_3-C_8)$cycloalkyl, -$(C_1-C_6)$alkyl-aryl, 5- or 6-membered heteroaryl$(C_1-C_4)$alkyl-, $(C_3-C_8)$cycloalkyl, $(C_2-C_6)$alkenyl, —$(C_2-C_6)$alkenyl-$(C_3-C_8)$cycloalkyl, —OH, $(C_1-C_4)$alkoxy, —O—$(C_1-C_6)$alkyl-$(C_3-C_8)$cycloalkyl, —O—$(C_1-C_6)$alkyl-5-6 membered heteroaryl, —O—$(C_3-C_8)$cycloalkyl, —O-aryl, —O-heteroaryl, —C(O)-aryl, -$CO_2(C_3-C_8)$cycloalkyl, —$NH_2$, aryl, or 5-6 membered heteroaryl, wherein any said $(C_1-C_6)$alkyl, —$(C_1-C_6)$alkyl-$(C_3-C_8)$cycloalkyl, —$(C_1-C_6)$alkyl-aryl, $(C_1-C_4)$alkoxy, —O—$(C_1-C_6)$alkyl-$(C_3-C_8)$cycloalkyl, —O—$(C_3-C_8)$cycloalkyl, —O-aryl, —O—5-6-membered heteroaryl, —C(O)-aryl, aryl, or 5-6 membered heteroaryl is optionally substituted one, two, or three times by $R^{14}$; and
each $R^{14}$ is independently halogen, $(C_1-C_6)$alkyl, $(C_3-C_8)$cycloalkyl, —CN, —$(C_1-C_6)$—OH, —$(C_1-C_6)$alkyl-N$((C_1-C_6)$alkyl)$((C_1-C_6)$alkyl), —OH, $(C_1-C_4)$alkoxy, 5-6 membered heteroaryl, wherein $(C_1-C_6)$alkyl, $(C_3-C_8)$cycloalkyl, aryl, or 5-6 membered heteroaryl is further optionally substituted by one, two, or three substituents independently selected from halogen, $(C_1-C_6)$alkyl, —$(C_1-C_6)$alkyl-OH, —$(C_1-C_6)$alkyl-O—$(C_1-C_6)$alkyl, or $(C_1-C_4)$alkoxy.

11. The compound or pharmaceutically acceptable salt thereof according to claim 1, wherein $R^2$ is hydrogen, halogen, or $(C_1-C_6)$alkyl; and/or $R^3$ is hydrogen, halogen, or $(C_1-C_6)$alkyl.

12. The compound or pharmaceutically acceptable salt thereof according to claim 1, wherein $R^4$ is hydrogen or halogen; and/or $R^5$ is hydrogen or halogen.

13. The compound or pharmaceutically acceptable salt thereof according to claim 1, wherein $R^6$ is hydrogen, $(C_1-C_6)$alkyl, $(C_3-C_8)$cycloalkyl, —$(C_1-C_6)$alkyl-OH, $(C_1-C_6)$alkyl-$NH_2$, —$(C_1-C_6)$alkyl-NH$((C_1-C_6)$alkyl), —$(C_1-C_6)$alkyl-N4$C_1-C_6)$alkyl*$C_1-C_6)$alkyl), —$(C_1-C_6)$alkyl-NH$((C_1-C_6)$alkyl)-OH, —$(C_1-C_6)$alkyl-NH$((C_1-C_6)$alkyl)-O—$(C_1-C_6)$alkyl), —$(C_1-C_6)$alkyl-NH-$(C_3-C_8)$cycloalkyl, —$(C_1-C_6)$alkyl-NH-4- to 6-membered heterocycloalkyl, —$(C_1-C_6)$alkyl-4- to 6-membered heterocycloalkyl, —$(C_1-C_6)$alkyl-NHC(O)—$((C_1-C_6)$alkyl), —$(C_1-C_6)$alkyl-$SO_2$—$(C_1-C_6)$alkyl, —$(C_1-C_6)$alkyl-$SO_2$—$NH_4C_1-C_6)$alkyl, —CN, —C(O)$NH_2$, —$NH_2$, -$SO_2((C_1-C_6)$alkyl), -$SO_2$—NH$((C_1-C_6)$alkyl), or aryl, wherein any said $(C_1-C_6)$alkyl, $(C_1-C_6)$alkyl-OH, —$(C_1-C_6)$alkyl-$NH_2$, —$(C_1-C_6)$alkyl-NH$((C_1-C_6)$alkyl), —$(C_1-C_6)$alkyl-NH-$(C_3-C_8)$cycloalkyl, —$(C_1-C_6)$alkyl-NH-4- to 6-membered heterocycloalkyl, or —$(C_1-C_6)$alkyl-4- to 6-membered heterocycloalkyl is optionally substituted one, two, or three times by halogen.

14. The compound or pharmaceutically acceptable salt thereof according to claim 1, wherein $R^7$ is hydrogen; and/or $R^8$ is $(C_1-C_6)$alkyl and $R^9$ is hydrogen.

15. The compound according to claim 1 which is:
(S)-N-(6-(cyclopropylmethoxy)pyridazin-3-yl)-2-((S)-4,4-difluoro-3-(6-oxo-1-(2,2,2-trifluoroethyl)-1,6-dihydropyridin-3-yl)piperidin-1-yl)propanamide;
(S)-N-(5-(cyclopropylmethoxy)pyridin-2-yl)-24(S)-4,4-difluoro-3-(6-oxo-1-(2,2,2-trifluoroethyl)-1,6-dihydropyridin-3-yl)piperidin-1-yl)propanamide;
(S)-2-((S)-4,4-difluoro-3-(6-oxo-1-(2,2,2-trifluoroethyl)-1,6-dihydropyridin-3-yl)piperidin-1-yl)-N-(5-fluoropyridin-2-yl)propanamide;
(S)-2-((S)-4,4-difluoro-3-(6-oxo-1,6-dihydropyridin-3-yl)piperidin-1-yl)-N-(5-(2,4-difluorophenoxy)pyridin-2-yl)propanamide;
(S)-2-((S)-4,4-difluoro-3-(6-oxo-1,6-dihydropyridin-3-yl)piperidin-1-yl)-N-(5-(4-fluorophenoxy)pyridin-2-yl)propanamide;

(S)-24(S)-4,4-difluoro-3-(6-oxo-1,6-dihydropyridin-3-yl)piperidin-1-yl)-N-(5-phenoxypyridin-2-yl)propanamide;
(S)-N-(5-benzylpyridin-2-yl)-2-((S)-4,4-difluoro-3-(6-oxo-1,6-dihydropyridin-3-yl)piperidin-1-yl)propanamide;
N-(6-(cyclopropylmethoxy)pyridazin-3-yl)-2-((S)-4,4-difluoro-3-(6-oxo-1,6-dihydropyridin-3-yl)piperidin-1-yl)propanamide;
(S)-N-(5-(cyclopentyloxy)pyridin-2-yl)-2-((S)-4,4-difluoro-3-(6-oxo-1,6-dihydropyridin-3-yl)piperidin-1-yl)propanamide;
(S)-N-(54(E)-2-cyclopropylvinyl)pyridin-2-yl)-24(S)-4,4-difluoro-3-(6-oxo-1,6-dihydropyridin-3-yl)piperidin-1-yl)propanamide;
(S)-N-(6-benzylpyridazin-3-yl)-2-((S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(5-(pyridin-4-ylmethyl)pyridin-2-yl)propanamide;
(S)-N-(5-cyclopentylpyridin-2-yl)-2-((S)-4,4-difluoro-3-(6-oxo-1,6-dihydropyridin-3-yl)piperidin-1-yl)propanamide;
(S)-N-(5-cyclopropylpyridin-2-yl)-24(S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(5-(m-tolyl)pyridin-2-yl)propanamide;
(S)-N-(2-cyclopropyloxazolo[4,5-b]pyridin-5-yl)-2-((S)-4,4-difluoro-3-(6-oxo-1,6-dihydropyridin-3-yl)piperidin-1-yl)propanamide;
(S)-N-(5-cyclobutylpyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(6-phenoxypyridazin-3-yl)propanamide;
(S)-2-((S)-4,4-difluoro-3-(6-oxo-1,6-dihydropyridin-3-yl)piperidin-1-yl)-N-(6-(o-tolyloxy)pyridazin-3-yl)propanamide;
N-(5-(2-cyclopropylethyl)pyridin-2-yl)-2-((S)-4,4-difluoro-3-(6-oxo-1,6-dihydropyridin-3-yl)piperidin-1-yl)propanamide;
(S)-N-(5-(benzyloxy)pyridin-2-yl)-24(S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(5-phenylpyridin-2-yl)propanamide;
N-(5-(cyclohexyloxy)pyridin-2-yl)-2-((S)-4,4-difluoro-3-(6-oxo-1,6-dihydropyridin-3-yl)piperidin-1-yl)propanamide;
(S)-N-(6-cyclopropylquinolin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-isopropoxypyridin-2-yl)propanamide;
N-(5-(cyclohexylmethyl)pyridin-2-yl)-24(S)-4,4-difluoro-3-(6-oxo-1,6-dihydropyridin-3-yl)piperidin-1-yl)propanamide;
(S)-N-(5-(cyclopropylmethoxy)-3-fluoropyridin-2-yl)-24(S)-4,4-difluoro-3-(6-oxo-1,6-dihydropyridin-3-yl)piperidin-1-yl)propanamide;
(S)-N-(5-(cyclopropylmethoxy)pyrazin-2-yl)-2-((S)-4,4-difluoro-3-(6-oxo-1,6-dihydropyridin-3-yl)piperidin-1-yl)propanamide;
N-(5-(cyclobutylmethoxy)pyridin-2-yl)-2-((S)-4,4-difluoro-3-(6-oxo-1,6-dihydropyridin-3-yl)piperidin-1-yl)propanamide;
N-(5-(1-cyclopropylethoxy)pyridin-2-yl)-24(S)-4,4-difluoro-3-(6-oxo-1,6-dihydropyridin-3-yl)piperidin-1-yl)propanamide;
(S)-N-(6-cyclopropyl-6,7-dihydro-5H-pyrrolo[3,4-b]pyridin-2-yl)-24(S)-4,4-difluoro-3-(6-oxo-1,6-dihydropyridin-3-yl)piperidin-1-yl)propanamide;
N-(5-(cyclopentylmethyl)pyridin-2-yl)-2-((S)-4,4-difluoro-3-(6-oxo-1,6-dihydropyridin-3-yl)piperidin-1-yl)propanamide;
(S)-2-((S)-4,4-difluoro-3-(6-oxo-1,6-dihydropyridin-3-yl)piperidin-1-yl)-N-(isoquinolin-3-yl)propanamide;
(S)-N-(5-(cyclopropylmethoxy)pyrimidin-2-yl)-24(S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-((2,2-difluorocyclopropyl)methoxy)pyridin-2-yl)propanamide;
cyclobutyl 6-((S)-2-((S)-4,4-difluoro-3-(6-oxo-1,6-dihydropyridin-3-yl)piperidin-1-yl)propanamido)nicotinate;
(S)-24(S)-4,4-difluoro-3-(6-oxo-1,6-dihydropyridin-3-yl)piperidin-1-yl)-N-(5-(oxazol-2-ylmethoxy)pyridin-2-yl)propanamide;
2-((S)-4,4-difluoro-3-(6-oxo-1,6-dihydropyridin-3-yl)piperidin-1-yl)-N-(4,5-difluoropyridin-2-yl)propanamide;
N-(1-(cyclopropylmethyl)-1H-pyrazolo[3,4-c]pyridin-5-yl)-24(S)-4,4-difluoro-3-(6-oxo-1,6-dihydropyridin-3-yl)piperidin-1-yl)propanamide;
N-(5-(cyclopropylmethyl)pyridin-2-yl)-2-((S)-4,4-difluoro-3-(6-oxo-1,6-dihydropyridin-3-yl)piperidin-1-yl)propanamide;
N-(5-cyclohexylpyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(6-methoxypyridazin-3-yl)propanamide;
2-((S)-4,4-difluoro-3-(6-oxo-1,6-dihydropyridin-3-yl)piperidin-1-yl)-N-(5-methoxypyridin-2-yl)propanamide;
2-((S)-4,4-difluoro-3-(6-oxo-1,6-dihydropyridin-3-yl)piperidin-1-yl)-N-(5-(pyridin-3-ylmethyl)pyridin-2-yl)propanamide;
cyclopentyl 6-((S)-2-((S)-4,4-difluoro-3-(6-oxo-1,6-dihydropyridin-3-yl)piperidin-1-yl)propanamido)nicotinate;
N-(5-(cyclopentylmethoxy)pyridin-2-yl)-2-((S)-4,4-difluoro-3-(6-oxo-1,6-dihydropyridin-3-yl)piperidin-1-yl)propanamide;
N-(5-(cyclopropoxymethyl)pyridin-2-yl)-2-((S)-4,4-difluoro-3-(6-oxo-1,6-dihydropyridin-3-yl)piperidin-1-yl)propanamide;
2-((S)-4,4-difluoro-3-(6-oxo-1,6-dihydropyridin-3-yl)piperidin-1-yl)-N-(5-(2,2-difluoroethoxy)pyridin-2-yl)propanamide;
2-((S)-4,4-difluoro-3-(6-oxo-1,6-dihydropyridin-3-yl)piperidin-1-yl)-N-(5-(thiophen-2-yl)pyridin-2-yl)propanamide;
N-(1-(cyclopropylmethyl)-1H-pyrrolo[2,3-c]pyridin-5-yl)-24(S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(5-(thiazol-2-ylmethyl)pyridin-2-yl)propanamide;

2((S)-4,4-difluoro-3-(6-oxo-1,6-dihydropyridin-3-yl)piperidin-1-yl)-N-(5-(oxazol-2-ylmethyl)pyridin-2-yl)propanamide;

(S)-2-((S)-4,4-difluoro-3-(6-oxo-1,6-dihydropyridin-3-yl)piperidin-1-yl)-N-(quinolin-2-yl)propanamide;

24(S)-4,4-difluoro-3-(6-oxo-1,6-dihydropyridin-3-yl)piperidin-1-yl)-N-(5-(1-methyl-1H-pyrazol-3-yl)pyridin-2-yl)propanamide;

24(S)-4,4-difluoro-3-(6-oxo-1,6-dihydropyridin-3-yl)piperidin-1-yl)-N-(5-(isoxazol-3-yl)pyridin-2-yl)propanamide;

2-((S)-4,4-difluoro-3-(6-oxo-1,6-dihydropyridin-3-yl)piperidin-1-yl)-N-(5-(pyridin-2-ylmethyl)pyridin-2-yl)propanamide hydrochloride;

(S)-2-((S)-4,4-difluoro-3-(6-oxo-1,6-dihydropyridin-3-yl)piperidin-1-yl)-N-(5-(pyridin-3-yloxy)pyridin-2-yl)propanamide;

(S)-2-((S)-4,4-difluoro-3-(6-oxo-1,6-dihydropyridin-3-yl)piperidin-1-yl)-N-(5-phenoxypyrazin-2-yl)propanamide;

(S)-2-((S)-4,4-difluoro-3-(6-oxo-1,6-dihydropyridin-3-yl)piperidin-1-yl)-N-(5-(pyridin-2-yloxy)pyridin-2-yl)propanamide;

N-(6-(2-cyanophenoxy)pyridazin-3-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(6-(4-fluorophenoxy)pyridazin-3-yl)propanamide;

2-((S)-4,4-difluoro-3-(6-oxo-1,6-dihydropyridin-3-yl)piperidin-1-yl)-N-(5-(pyridin-4-yloxy)pyridin-2-yl)propanamide;

(S)-24(S)-4,4-difluoro-3-(6-oxo-1,6-dihydropyridin-3-yl)piperidin-1-yl)-N-(5-(3-fluoropyridin-2-yl)oxy)pyridin-2-yl)propanamide;

(S)-2-((S)-4,4-difluoro-3-(6-oxo-1,6-dihydropyridin-3-yl)piperidin-1-yl)-N-(5-((3,5-difluoropyridin-2-yl)oxy)pyridin-2-yl)propanamide;

24(S)-4,4-difluoro-3-(6-oxo-1,6-dihydropyridin-3-yl)piperidin-1-yl)-N-(5-(5-fluoropyridin-3-yl)oxy)pyridin-2-yl)propanamide;

(S)-2-((S)-4,4-difluoro-3-(6-oxo-1,6-dihydropyridin-3-yl)piperidin-1-yl)-N-(5-(4-fluorophenoxy)pyrazin-2-yl)propanamide;

(S)-2-((S)-4,4-difluoro-3-(6-oxo-1,6-dihydropyridin-3-yl)piperidin-1-yl)-N-(5-((5-fluoropyridin-2-yl)oxy)pyridin-2-yl)propanamide;

(S) -N-(5-cyclopropylpyridin-2-yl)-2-((S)-4,4-difluoro-3-(6-oxo-1,6-dihydropyridin-3-yl)piperidin-1-yl)propanamide;

(S)-N-(6-(cyclobutylmethoxy)pyridazin-3-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(5-((2-oxo-1,2-dihydropyridin-3-yl)oxy)pyridin-2-yl)propanamide;

2-((S)-4,4-difluoro-3-(6-oxo-1,6-dihydropyridin-3-yl)piperidin-1-yl)-N-(5-(spiro[3.3]heptan-2-yloxy)pyridin-2-yl)propanamide;

(S)-2-((S)-4,4-difluoro-3-(6-oxo-1,6-dihydropyridin-3-yl)piperidin-1-yl)-N-(5-(pyrimidin-4-yloxy)pyridin-2-yl)propanamide;

(S)-N-(5-(cyclopropylmethoxy)pyridin-2-yl)-24(S)-4,4-difluoro-3-(6-oxo-1,6-dihydropyridin-3-yl)piperidin-1-yl)propanamide;

(S)-N-(5-(cyclopropylmethoxy)-4-fluoropyridin-2-yl)-2-((S)-4,4-difluoro-3-(6-oxo-1,6-dihydropyridin-3-yl)piperidin-1-yl)propanamide;

N-(6-cyclopropyl-1,8-naphthyridin-2-yl)-2-((S)-4,4-difluoro-3-(6-oxo-1,6-dihydropyridin-3-yl)piperidin-1-yl)propanamide;

N-(5-cyclobutoxypyridin-2-yl)-2-((S)-4,4-difluoro-3-(6-oxo-1,6-dihydropyridin-3-yl)piperidin-1-yl)propanamide;

(S)-24(S)-4,4-difluoro-3-(6-oxo-1,6-dihydropyridin-3-yl)piperidin-1-yl)-N-(5-fluoropyridin-2-yl)propanamide;

(S)-N-(5-((Z)-2-cyclopropylvinyl)pyridin-2-yl)-2-((S)-4,4-difluoro-3-(6-oxo-1,6-dihydropyridin-3-yl)piperidin-1-yl)propanamide;

(S)-N-(5-chloropyridin-2-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(5-isopropylpyridin-2-yl)propanamide;

cyclopropyl 6-(2-((S)-4,4-difluoro-3-(6-oxo-1,6-dihydropyridin-3-yl)piperidin-1-yl)propanamido)nicotinate;

(S)-N-(5-(cyclobutylmethyl)pyridin-2-yl)-24(S)-4,4-difluoro-3-(6-oxo-1,6-dihydropyridin-3-yl)piperidin-1-yl)propanamide;

(S)-24(S)-4,4-difluoro-3-(6-oxo-1,6-dihydropyridin-3-yl)piperidin-1-yl)-N-(5-(2,4-difluorophenoxy)pyrazin-2-yl)propanamide;

2-((S)-4,4-difluoro-3-(6-oxo-1,6-dihydropyridin-3-yl)piperidin-1-yl)-N-(3-fluoro-5-(4-fluorophenoxy)pyridin-2-yl)propanamide;

2-((S)-4,4-difluoro-3-(6-oxo-1,6-dihydropyridin-3-yl)piperidin-1-yl)-N-(5-(2,4-difluorophenoxy)-3-fluoropyridin-2-yl)propanamide;

(S)-2-((S)-4,4-difluoro-3-(6-oxo-1,6-dihydropyridin-3-yl)piperidin-1-yl)-N-(6-(neopentyloxy)pyridazin-3-yl)propanamide;

N-(5-((3-chloro-5-fluoropyridin-2-yl)oxy)pyridin-2-yl)-24(S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(3-fluoro-5-((5-fluoropyridin-2-yl)oxy)pyridin-2-yl)propanamide;

N-(5-((3-cyano-5-fluoropyridin-2-yl)oxy)pyridin-2-yl)-2-((S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(6-(spiro[3.3]heptan-2-yloxy)pyridazin-3-yl)propanamide;

N-(5-bromopyridin-2-yl)-24(S)-4,4-difluoro-3-(6-oxo-1,6-dihydropyridin-3-yl)piperidin-1-yl)propanamide;

2-((S)-4,4-difluoro-3-(6-oxo-1,6-dihydropyridin-3-yl)piperidin-1-yl)-N-(5-((6-methoxypyridin-2-yl)oxy)pyridin-2-yl)propanamide;

(S)-2-((S)-4,4-difluoro-3-(6-oxo-1,6-dihydropyridin-3-yl)piperidin-1-yl)-N-(5-(2,4,6-trifluorophenoxy)pyridin-2-yl)propanamide;

(S)-2-((S)-4,4-difluoro-3-(6-oxo-1,6-dihydropyridin-3-yl)piperidin-1-yl)-N-(5-(2,4,5-trifluorophenoxy)pyridin-2-yl)propanamide;

(S)-2-((S)-4,4-difluoro-3-(6-oxo-1,6-dihydropyridin-3-yl)piperidin-1-yl)-N-(5-(2-((dimethylamino)methyl)-4-fluorophenoxy)pyridin-2-yl)propanamide;

(S)-2-((S)-4,4-difluoro-3-(6-oxo-1,6-dihydropyridin-3-yl)piperidin-1-yl)-N-(5-(2-fluoro-4-(2-methylthiazol-4-yl)phenoxy)pyridin-2-yl)propanamide;

(S)-N-(6-cyclobutoxy pyridazin-3-yl)-24(S)-4,4-difluoro-3-(6-oxo-1,6-dihydropyridin-3-yl)piperidin-1-yl)propanamide;

(S)-N-(6-(cyclopentyloxy)pyridazin-3-yl)-2-((S)-4,4-difluoro-3-(6-oxo-1,6-dihydropyridin-3-yl)piperidin-1-yl)propanamide;

(S)-N-(5-(difluoro(4-fluorophenyl)methyl)pyridin-2-yl)-2-((S)-4,4-difluoro-3-(6-oxo-1,6-dihydropyridin-3-yl)piperidin-1-yl)propanamide;

(S)-2-((R)-4,4-difluoro-3-(5-oxo-4-(2,2,2-trifluoroethyl)-4, 5-dihydropyrazin-2-yl)piperidin-1-yl)-N-(5-fluoropyridin-2-yl)propanamide;

(S)-24(R)-3-(6-amino-5-oxo-4,5-dihydropyrazin-2-yl)-4,4-difluoropiperidin-1-yl)-N-(6-(cyclopropylmethoxy)pyridazin-3-yl)propanamide;

(S)-2-((R)-3-(6-amino-5-oxo-4,5-dihydropyrazin-2-yl)-4,4-difluoropiperidin-1-yl)-N-(5-(cyclopropylmethoxy)pyridin-2-yl)propanamide;

(S)-24(R)-3-(6-amino-5-oxo-4,5-dihydropyrazin-2-yl)-4,4-difluoropiperidin-1-yl)-N-(5-fluoropyridin-2-yl)propanamide;

(S)-2-((R)-3-(6-amino-5-oxo-4,5-dihydropyrazin-2-yl)-4,4-difluoropiperidin-1-yl)-N-(5-chloropyridin-2-yl)propanamide;

(S)-2-((R)-3-(6-amino-5-oxo-4,5-dihydropyrazin-2-yl)-4,4-difluoropiperidin-1-yl)-N-(5-(4-fluorophenoxy)pyridin-2-yl)propanamide;

4-((S)-1-((S)-1-((6-(cyclopropylmethoxy)pyridazin-3-yl)amino)-1-oxopropan-2-yl)-4,4-difluoropiperidin-3-yl)pyridine 1-oxide;

4-(4,4-difluoro-1-(1-oxo-1-((5-phenoxypyridin-2-yl)amino)propan-2-yl)piperidin-3-yl)pyridine 1-oxide;

4-((S)-1-((S)-1-((5-(cyclopropylmethoxy)pyridin-2-yl)amino)-1-oxopropan-2-yl)-4,4-difluoropiperidin-3-yl)pyridine 1-oxide;

4-((S)-1-((S)-1-((5-chloropyridin-2-yl)amino)-1-oxopropan-2-yl)-4,4-difluoropiperidin-3-yl)pyridine 1-oxide;

4-((S)-4,4-difluoro-1-((S)-1-((5-fluoropyridin-2-yl)amino)-1-oxopropan-2-yl)piperidin-3-yl)pyridine 1-oxide;

4-((S)-4,4-difluoro-1-((S)-1-((5-(4-fluorophenoxy)pyridin-2-yl)amino)-1-oxopropan-2-yl)piperidin-3-yl)pyridine 1-oxide;

44(S)-4,4-difluoro-1-((S)-(1-((5-((5-fluoropyridin-2-yl)oxy)pyridin-2-yl)amino)-1-oxopropan-2-yl)piperidin-3-yl)pyridine 1-oxide;

4-((S)-1-((S)-(1-((5-((3,5-difluoropyridin-2-yl)oxy)pyridin-2-yl)amino)-1-oxopropan-2-yl)-4,4-difluoropiperidin-3-yl)pyridine 1-oxide;

4-((S)-1-((S)-1-((5-(2,4-difluorophenoxy)pyridin-2-yl)amino)-1-oxopropan-2-yl)-4,4-difluoropiperidin-3-yl)pyridine 1-oxide;

4-((S)-4,4-difluoro-1-((S)-1-((5-(4-fluorophenoxy)pyrazin-2-yl)amino)-1-oxopropan-2-yl)piperidin-3-yl)pyridine 1-oxide;

4-((S)-4,4-difluoro-1-((S)-1-oxo-1-((5-(2,4,6-trifluorophenoxy)pyrazin-2-yl)amino)propan-2-yl)piperidin-3-yl)pyridine 1-oxide;

4-((S)-4,4-difluoro-1-((S)-1-oxo-1-((5-(2,4,5-trifluorophenoxy)pyrazin-2-yl)amino)propan-2-yl)piperidin-3-yl)pyridine 1-oxide;

4-((S)-1-((S)-1-((5-(2,6-difluorophenoxy)pyrazin-2-yl)amino)-1-oxopropan-2-yl)-4,4-difluoropiperidin-3-yl)pyridine 1-oxide;

4-((S)-4,4-difluoro-1-((S)-1-oxo-1-((5-(2,3,4-trifluorophenoxy)pyrazin-2-yl)amino)propan-2-yl)piperidin-3-yl)pyridine 1-oxide;

4-((S)-4,4-difluoro-1-((S)-1-oxo-1-((5-(2,4,6-trifluorophenoxy)pyridin-2-yl)amino)propan-2-yl)piperidin-3-yl)pyridine 1-oxide;

4-((S)-4,4-difluoro-1-((S)-1-oxo-1-((5-(2,4,5-trifluorophenoxy)pyridin-2-yl)amino)propan-2-yl)piperidin-3-yl)pyridine 1-oxide;

4-((S)-4,4-difluoro-1-((S)-1-((5-((3-fluoropyridin-2-yl)oxy)pyridin-2-yl)amino)-1-oxopropan-2-yl)piperidin-3-yl)pyridine 1-oxide;

4-((S)-4,4-difluoro-1-((S)-1-oxo-1-((5-(pyridin-2-yloxy)pyridin-2-yl)amino)propan-2-yl)piperidin-3-yl)pyridine 1-oxide;

4-((S)-1-((S)-1-((5-(difluoro(4-fluorophenyl)methyl)pyridin-2-yl)amino)-1-oxopropan-2-yl)-4,4-difluoropiperidin-3-yl)pyridine 1-oxide;

4-((S)-4,4-difluoro-1-((S)-145-(4-fluorobenzoyl)pyridin-2-yl)amino)-1-oxopropan-2-yl)piperidin-3-yl)pyridine 1-oxide;

443S)-4,4-difluoro-1-(145-(4-fluorophenyl)(hydroxy)methyl)pyridin-2-yl)amino)-1-oxopropan-2-yl)piperidin-3-yl)pyridine 1-oxide;

4-((S)-1-((S)-1-((5-(2,6-difluorophenoxy)pyridin-2-yl)amino)-1-oxopropan-2-yl)-4,4-difluoropiperidin-3-yl)pyridine 1-oxide;

4-((S)-4,4-difluoro-1-((S)-1-oxo-1-((5-(2,3,4-trifluorophenoxy)pyridin-2-yl)amino)propan-2-yl)piperidin-3-yl)pyridine 1-oxide;

4-((S)-1-((S)-1-((5-(2,4-difluorophenoxy)pyrazin-2-yl)amino)-1-oxopropan-2-yl)-4,4-difluoropiperidin-3-yl)pyridine 1-oxide;

(S)-N- (5-(cyclopropylmethoxy)pyridin-2-yl)-24(R)-4,4-difluoro-3-(5-oxo-4,5-dihydropyrazin-2-yl)piperidin-1-yl)propanamide;

(S)-N-(6-(cyclopropylmethoxy)pyridazin-3-yl)-2-((R)-4,4-difluoro-3-(5-oxo-4,5-dihydropyrazin-2-yl)piperidin-1-yl)propanamide;

(S)-2-((R)-4,4-difluoro-3-(5-oxo-4,5-dihydropyrazin-2-yl)piperidin-1-yl)-N-(5-fluoropyridin-2-yl)propanamide;

(S)-N-(5-chloropyridin-2-yl)-2-((R)-4,4-difluoro-3-(5-oxo-4,5-dihydropyrazin-2-yl)piperidin-1-yl)propanamide;

(S)-N- (5-cyclopropylpyridin-2-yl)-2-((R)-4,4-difluoro-3-(5-oxo-4, 5-dihydropyrazin-2-yl)piperidin-1-yl)propanamide;

(S)-24(S)-3-(5-amino-6-oxo-1,6-dihydropyridin-3-yl)-4,4-difluoropiperidin-1-yl)-N-(5-(cyclopropylmethoxy)pyridin-2-yl)propanamide;

2-(3-(5-amino-6-oxo-1,6-dihydropyridin-3-yl)-4,4-difluoropiperidin-1-yl)-N-(5-phenoxypyridin-2-yl)propanamide;

(S)-24(S)-3-(5-amino-6-oxo-1,6-dihydropyridin-3-yl)-4,4-difluoropiperidin-1-yl)-N-(6-(cyclopropylmethoxy)pyridazin-3-yl)propanamide;

(S)-24(S)-3-(5-amino-6-oxo-1,6-dihydropyridin-3-yl)-4,4-difluoropiperidin-1-yl)-N-(5-chloropyridin-2-yl)propanamide;

(S)-24(S)-3-(5-amino-6-oxo-1,6-dihydropyridin-3-yl)-4,4-difluoropiperidin-1-yl)-N-(5-fluoropyridin-2-yl)propanamide;

(S)-2-((R)-3-(5-amino-6-oxo-1,6-dihydropyridazin-3-yl)-4,4-difluoropiperidin-1-yl)-N-(5-fluoropyridin-2-yl)propanamide;

(S)-2-((R)-3-(5-amino-6-oxo-1,6-dihydropyridazin-3-yl)-4,4-difluoropiperidin-1-yl)-N-(6-(cyclopropylmethoxy)pyridazin-3-yl)propanamide;

(S)-N- (5-(cyclopropylmethoxy)pyridin-2-yl)-2-((R)-4,4-difluoro-3-(6-oxo-1,6-dihydropyridazin-3-yl)piperidin-1-yl)propanamide;

(S)-N-(6-(cyclopropylmethoxy)pyridazin-3-yl)-2-((R)-4,4-difluoro-3-(6-oxo-1,6-dihydropyridazin-3-yl)piperidin-1-yl)propanamide;

(S)-N-(5-cyclopropylpyridin-2-yl)-24(R)-4,4-difluoro-3-(6-oxo-1,6-dihydropyridazin-3-yl)piperidin-1-yl)propanamide;

(S)-2-((R)-4,4-difluoro-3-(6-oxo-1,6-dihydropyridazin-3-yl)piperidin-1-yl)-N-(5-fluoropyridin-2-yl)propanamide;

(S)-N- (5-(cyclopropylmethoxy)pyridin-2-yl)-24(S)-4,4-difluoro-3-(1-methyl -6-oxo-1, 6-dihydropyridin-3-yl)piperidin-1-yl)propanamide;

(S)-2-((S)-4,4-difluoro-3-(6-oxo-5-(2,2,2-trifluoroethyl)-1,6-dihydropyridin-3-yl)piperidin-1-yl)-N-(5-fluoropyridin-2-yl)propanamide;

(S)-N - (5-(cyclopropylmethoxy)pyridin-2-yl)-2-((S)-4,4-difluoro-3-(5-(2-hydroxypropan-2-yl)-6-oxo-1,6-dihydropyridin-3-yl)piperidin-1-yl)propanamide;

(S)-2-((S)-4,4-difluoro-3-(5-(hydroxymethyl)-6-oxo-1,6-dihydropyridin-3-yl)piperidin-1-yl)-N-(5-fluoropyridin-2-yl)propanamide;

(S)-N-(6-(cyclopropylmethoxy)pyridazin-3-yl)-2-(4,4-difluoro-3-(5-(hydroxymethyl)-6-oxo-1,6-dihydropyridin-3-yl)piperidin-1-yl)propanamide;

N-(5-chloropyridin-2-yl)-2-(4,4-difluoro-3-(5-(hydroxymethyl)-6-oxo-1,6-dihydropyridin-3-yl)piperidin-1-yl)propanamide;

(S)-24(S)-(4,4-difluoro-3-(5-(hydroxymethyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-(hydroxymethyl)-6-oxo-1,6-dihydropyridin-3-yl)piperidin-1-yl)-N-(5-((5-fluoropyridin-2-yl)oxy)pyridin-2-yl)propanamide;

(S)-N-(5-chloropyridin-2-yl)-24(S)-3-(6-oxo-1,6-dihydropyridin-3-yl)piperidin-1-yl)propanamide;

(S)-N-(5-(cyclopropylmethoxy)pyridin-2-yl)-2-((S)-3-(6-oxo-1,6-dihydropyridin-3-yl)piperidin-1-yl)propanamide;

(S)-N-(5-(cyclopropylmethoxy)pyridin-2-yl)-2-((3S,4R)-(4-fluoro-3-(6-oxo-1,6-dihydropyridin-3-yl)piperidin-1-yl)propanamide;

(S)-N-(5-(cyclopropylmethoxy)pyridin-2-yl)-2-((3S,4S)-(4-fluoro-3-(6-oxo-1,6-dihydropyridin-3-yl)piperidin-1-yl)propanamide;

(S)-2-((3S,4R)-4-fluoro-3-(6-oxo-1,6-dihydropyridin-3-yl)piperidin-1-yl)-N-(5-fluoropyridin-2-yl)propanamide;

(S)-243S,4S)-4-fluoro-3-(6-oxo-1,6-dihydropyridin-3-yl)piperidin-1-yl)-N-(5-fluoropyridin-2-yl)propanamide;

(S)-N-(5-fluoropyridin-2-yl)-2-((3S,5R)-3-methyl-5-(6-oxo-1,6-dihydropyridazin-3-yl)piperidin-1-yl)propanamide;

(S)-N-(5-(cyclopropylmethoxy)pyridin-2-yl)-24(S)-4,4-difluoro-3-methyl-3-(6-oxo-1,6-dihydropyridin-3-yl)piperidin-1-yl)propanamide;

N-(5-(cyclopropylmethoxy)pyridin-2-yl)-2-(3,3-difluoro-4-(6-oxo-1,6-dihydropyridin-3-yl)pyrrolidin-1-yl)propanamide;

2-(3,3-difluoro-4-(6-oxo-1,6-dihydropyridin-3-yl)pyrrolidin-1-yl)-N-(5-fluoropyridin-2-yl)propanamide;

(S)-N-(5-chloropyridin-2-yl)-2-((R)-(3-(5-oxo-4,5-dihydropyrazin-2-yl)piperidin-1-yl)propanamide;

(S)-N-(5-chloropyridin-2-yl)-2-((S)-3-(6-oxo-1-(2,2,2-trifluoroethyl)-1,6-dihydropyridin-3-yl)piperidin-1-yl)propanamide;

(S)-2-((S)-3-(1-benzyl-6-oxo-1,6-dihydropyridin-3-yl)piperidin-1-yl)-N-(5-chloropyridin-2-yl)propanamide;

(S)-N- (5-(cyclopropylmethoxy)pyridin-2-yl)-24(S)-3-(6-oxo-4-(trifluoromethyl)-1,6-dihydropyridin-3-yl)piperidin-1-yl)propanamide;

((S)-2-((S)-3-(5-amino-6-oxo-1,6-dihydropyridin-3-yl)piperidin-1-yl)-N-(5-chloropyridin-2-yl)propanamide;

(S)-N- (5-(cyclopropylmethoxy)pyridin-2-yl)-2-((R)-3-hydroxy-3-(6-oxo-1,6-dihydropyridin-3-yl)piperidin-1-yl)propanamide;

(S)-N-(5-chloropyridin-2-yl)-2-((3S,5S)-(3-methyl-5-(6-oxo-1,6-dihydropyridin-3-yl)piperidin-1-yl)propanamide;

(S)-N-(5-chloropyridin-2-yl)-2-((3R,5S)-(3-methyl-5-(6-oxo-1,6-dihydropyridin-3-yl)piperidin-1-yl)propanamide;

(S)-2-((R)-3-(6-amino-5-oxo-4,5-dihydropyrazin-2-yl)piperidin-1-yl)-N-(5-chloropyridin-2-yl)propanamide;

(S)-24(S)-3-(5-(aminomethyl)-6-oxo-1,6-dihydropyridin-3-yl)piperidin-1-yl)-N-(5-chloropyridin-2-yl)propanamide;

(S)-N- (5-chloropyridin-2-yl)-2-((S)-3-(1-methyl-6-oxo-1,6-dihydropyridin-3-yl)piperidin-1-yl)propanamide;

(S)-N- (5-chloropyridin-2-yl)-2-((S)-3-(5-(hydroxymethyl)-6-oxo-1,6-dihydropyridin-3-yl)piperidin-1-yl)propanamide;

(S)-N- (5-chloropyridin-2-yl)-2-((S)-3-(6-oxo-5-phenyl-1,6-dihydropyridin-3-yl)piperidin-1-yl)propanamide;

(S)-N-(5-chloropyridin-2-yl)-2-((S)-3-(5-cyclopropyl-6-oxo-1,6-dihydropyridin-3-yl)piperidin-1-yl)propanamide;

4-((S)-1-((S)-1-((5-chloropyridin-2-yl)amino)-1-oxopropan-2-yl)piperidin-3-yl)pyridine 1-oxide;

4-((S)-1-((S)-1-((5-(2,4-difluorophenoxy)pyrazin-2-yl)amino)-1-oxopropan-2-yl)piperidin-3-yl)pyridine 1-oxide;

4-((S)-1-((S)-1-((5-(2,4-difluorophenoxy)pyridin-2-yl)amino)-1-oxopropan-2-yl)piperidin-3-yl)pyridine 1-oxide;

(S)-N-(5-(cyclopropylmethoxy)pyridin-2-yl)-2-(4,4-difluoro-3-(6-oxo-1,6-dihydropyridin-3-yl)piperidin-1-yl)-2-methylpropanamide;

(S)-N-(5-chloropyridin-2-yl)-2-((S)-3-(5-methyl-6-oxo-1,6-dihydropyridin-3-yl)piperidin-1-yl)propanamide;

(S)-N-(5-(cyclopropylmethoxy)pyridin-2-yl)-2-((R)-3-(6-oxo-1,6-dihydropyridazin-3-yl)piperidin-1-yl)propanamide;

(S)-N-(5-chloropyridin-2-yl)-24(R)-3-(6-oxo-1,6-dihydropyridazin-3-yl)piperidin-1-yl)propanamide;

(2S)-2-(3-(5-amino-6-oxo-1-(2,2,2-trifluoroethyl)-1,6-dihydropyridin-3-yl)-4,4-difluoropiperidin-1-yl)-N-(5-fluoropyridin-2-yl)propanamide;

(2S)-2-(3-(1-ethyl-6-oxo-1,6-dihydropyridin-3-yl)-4,4-difluoropiperidin-1-yl)-N-(5-fluoropyridin-2-yl)propanamide;

(S)-N-(6-(cyclopropylmethoxy)pyridazin-3-yl)-2-((S)-(3-(1-ethyl-6-oxo-1,6-dihydropyridin-3-yl)-4,4-difluoropiperidin-1-yl)propanamide;

(2S)-2-(4,4-difluoro-3-(1-(2-(methylsulfonyl)ethyl)-6-oxo-1,6-dihydropyridin-3-yl)piperidin-1-yl)-N-(5-fluoropyridin-2-yl)propanamide;

(2 S)-N-(6-(cyclopropylmethoxy)pyridazin-3-yl)-2-(4,4-difluoro-3-(1-(2-(methylsulfonyl)ethyl)-6-oxo-1,6-dihydropyridin-3-yl)piperidin-1-yl)propanamide;

2-(4,4-difluoro-3-(1-(2-(methylsulfonyl)ethyl)-6-oxo-1,6-dihydropyridin-3-yl)piperidin-1-yl)-N-(5-(4-fluorophenoxy)pyridin-2-yl)propanamide;

(S)-24(S)-(3-(1-(2,2-difluoroethyl)-6-oxo-1,6-dihydropyridin-3-yl)-4,4-difluoropiperidin-1-yl)-N-(5-fluoropyridin-2-yl)propanamide;

(2S)-2-(4,4-difluoro-3-(1-isopropyl-6-oxo-1,6-dihydropyridin-3-yl)piperidin-1-yl)-N-(5-fluoropyridin-2-yl)propanamide;

(5)-24(S)-(3-(1-benzyl-6-oxo-1,6-dihydropyridin-3-yl)-4,4-difluoropiperidin-1-yl)-N-(5-fluoropyridin-2-yl)propanamide;

2-(4,4-difluoro-3-(6-oxo-1-(pyridin-2-ylmethyl)-1,6-dihydropyridin-3-yl)piperidin-1-yl)-N-(5-fluoropyridin-2-yl)propanamide;

2-(4,4-difluoro-3-(6-oxo-1-(pyridin-4-ylmethyl)-1,6-dihydropyridin-3-yl)piperidin-1-yl)-N-(5-fluoropyridin-2-yl)propanamide;

2-(4,4-difluoro-3-(1-(oxazol-2-ylmethyl)-6-oxo-1,6-dihydropyridin-3-yl)piperidin-1-yl)-N-(5-fluoropyridin-2-yl)propanamide;

(2S)-2-(4,4-difluoro-3-(5-(hydroxymethyl)-6-oxo-1-(2,2,2-trifluoroethyl)-1,6-dihydropyridin-3-yl)piperidin-1-yl)-N-(5-fluoropyridin-2-yl)propanamide;

(2S)-2-(4,4-difluoro-3-(5-methyl-6-oxo-1-(2,2,2-trifluoroethyl)-1,6-dihydropyridin-3-yl)piperidin-1-yl)-N-(5-fluoropyridin-2-yl)propanamide;

(S)-24(S)-3-(5-(aminomethyl)-6-oxo-1,6-dihydropyridin-3-yl)-4,4-difluoropiperidin-1-yl)-N-(5-fluoropyridin-2-yl)propanamide;

2-(3-(5-(aminomethyl)-6-oxo-1,6-dihydropyridin-3-yl)-4,4-difluoropiperidin-1-yl)-N-(5-phenoxypyridin-2-yl)propanamide;

(S)-24(S)-3-(5-(aminomethyl)-6-oxo-1,6-dihydropyridin-3-yl)-4,4-difluoropiperidin-1-yl)-N-(6-(cyclopropylmethoxy)pyridazin-3-yl)propanamide;

(S)-24(S)-3-(5-(aminomethyl)-6-oxo-1,6-dihydropyridin-3-yl)-4,4-difluoropiperidin-1-yl)-N-(5-(4-fluorophenoxy)pyridin-2-yl)propanamide;

(S)-24(S)-3-(5-(aminomethyl)-6-oxo-1,6-dihydropyridin-3-yl)-4,4-difluoropiperidin-1-yl)-N-(5-(2,4-difluorophenoxy)pyridin-2-yl)propanamide;

(S)-24(S)-3-(5-(aminomethyl)-6-oxo-1,6-dihydropyridin-3-yl)-4,4-difluoropiperidin-1-yl)-N-(5-(4-fluorophenoxy)pyrazin-2-yl)propanamide;

(S)-24(S)-3-(5-(aminomethyl)-6-oxo-1,6-dihydropyridin-3-yl)-4,4-difluoropiperidin-1-yl)-N-(5-phenoxypyrazin-2-yl)propanamide;

(S)-24(S)-3-(5-(aminomethyl)-6-oxo-1,6-dihydropyridin-3-yl)-4,4-difluoropiperidin-1-yl)-N-(5-((5-fluoropyridin-2-yl)oxy)pyridin-2-yl)propanamide;

(S)-2-((S)-4,4-difluoro-3-(6-oxo-54(S)-2,2,2-trifluoro-1-hydroxyethyl)-1,6-dihydropyridin-3-yl)piperidin-1-yl)-N-(5-fluoropyridin-2-yl)propanamide;

(S)-2-((S)-4,4-difluoro-3-(6-oxo-5-((R)-2,2,2-trifluoro-1-hydroxyethyl)-1,6-dihydropyridin-3-yl)piperidin-1-yl)-N-(5-fluoropyridin-2-yl)propanamide;

(S)-N-(6-(cyclopropylmethoxy)pyridazin-3-yl)-24(S)-4,4-difluoro-3-(6-oxo-5-((S)-2,2,2-trifluoro-1-hydroxyethyl)-1,6-dihydropyridin-3-yl)piperidin-1-yl)propanamide;

(S)-N-(6-(cyclopropylmethoxy)pyridazin-3-yl)-2-((S)-4,4-difluoro-3-(6-oxo-5-((R)-2,2,2-trifluoro-1-hydroxyethyl)-1,6-dihydropyridin-3-yl)piperidin-1-yl)propanamide;

(2S)-2-(4,4-difluoro-3-(6-oxo-5-(2,2,2-trifluoro-1-hydroxyethyl)-1,6-dihydropyridin-3-yl)piperidin-1-yl)-N-(5-(4-fluorophenoxy)pyridin-2-yl)propanamide;

(2S)-2-(4,4-difluoro-3-(6-oxo-5-(2,2,2-trifluoro-1-hydroxyethyl)-1,6-dihydropyridin-3-yl)piperidin-1-yl)-N-(5-(2,4-difluorophenoxy)pyridin-2-yl)propanamide;

2-(4,4-difluoro-3-(5-((methylsulfonyl)methyl)-6-oxo-1,6-dihydropyridin-3-yl)piperidin-1-yl)-N-(5-fluoropyridin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(4-fluorophenoxy)pyrazin-2-yl)propanamide;

(S)-2-((S)-4,4-difluoro-3-(5-((methylsulfonyl)methyl)-6-oxo-1,6-dihydropyridin-3-yl)piperidin-1-yl)-N-(5-(2,4-difluorophenoxy)pyridin-2-yl)propanamide;

4-(4,4-difluoro-14(S)-1-(5-fluoropyridin-2-yl)amino)-1-oxopropan-2-yl)piperidin-3-yl)-2-methylpyridine 1-oxide;

44(R)-4,4-difluoro-1-((R)-1-((5-(4-fluorophenoxy)pyridin-2-yl)amino)-1-oxopropan-2-yl)piperidin-3-yl)-2-methylpyridine 1-oxide;

4-((S)-4,4-difluoro-1-((S)-1-((5-(4-fluorophenoxy)pyridin-2-yl)amino)-1-oxopropan-2-yl)piperidin-3-yl)-2-methylpyridine 1-oxide;

4-((S)-4,4-difluoro-14(S)-1-(5-fluoropyridin-2-yl)amino)-1-oxopropan-2-yl)piperidin-3-yl)-2-(2,2,2-trifluoroethyl)pyridine 1-oxide;

4-((S)-14(S)-146-(cyclopropylmethoxy)pyridazin-3-yl)amino)-1-oxopropan-2-yl)-4,4-difluoropiperidin-3-yl)-2-(2,2,2-trifluoroethyl)pyridine 1-oxide;

(2S)-2-(3-(5-bromo-6-oxo-1,6-dihydropyridin-3-yl)-4,4-difluoropiperidin-1-yl)-N-(6-(cyclopropylmethoxy)pyridazin-3-yl)propanamide;

(2S)-2-(3-(5-(1-aminoethyl)-6-oxo-1,6-dihydropyridin-3-yl)-4,4-difluoropiperidin-1-yl)-N-(6-(cyclopropylmethoxy)pyridazin-3-yl)propanamide;

(2S)-2-(3-(5-cyano-6-oxo-1,6-dihydropyridin-3-yl)-4,4-difluoropiperidin-1-yl)-N-(6-(cyclopropylmethoxy)pyridazin-3-yl)propanamide;

(2S)-N-(6-(cyclopropylmethoxy)pyridazin-3-yl)-2-(4,4-difluoro-3-(pyridin-4-yl)piperidin-1-yl)propanamide;

(S)-N-(6-(cyclopropylmethoxy)pyridazin-3-yl)-2-((S)-4,4-difluoro-3-(5-(morpholinomethyl)-6-oxo-1,6-dihydropyridin-3-yl)piperidin-1-yl)propanamide;

2-(4,4-difluoro-3-(5-(morpholinomethyl)-6-oxo-1,6-dihydropyridin-3-yl)piperidin-1-yl)-N-(5-(4-fluorophenoxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-(2,4-difluorophenoxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-((3,5-difluoropyridin-2-yl)oxy)pyridin-2-yl)propanamide;

(S)-2-((S)-4,4-difluoro-3-(5-(morpholinomethyl)-6-oxo-1,6-dihydropyridin-3-yl)piperidin-1-yl)-N-(5-(2,4-difluorophenoxy)pyrazin-2-yl)propanamide;

2-(3-(5-((dimethylamino)methyl)-6-oxo-1,6-dihydropyridin-3-yl)-4,4-difluoropiperidin-1-yl)-N-(5-(4-fluorophenoxy)pyridin-2-yl)propanamide;

(S)-N-(6-(cyclopropylmethoxy)pyridazin-3-yl)-2-((S)-3-(5-((dimethylamino)methyl)-6-oxo-1,6-dihydropyridin-3-yl)-4,4-difluoropiperidin-1-yl)propanamide;

(2S)-2-(3-(5-(1-amino-2,2,2-trifluoroethyl)-6-oxo-1,6-dihydropyridin-3-yl)-4,4-difluoropiperidin-1-yl)-N-(5-fluoropyridin-2-yl)propanamide;

(S)-2-((S)-3-(5-((S)-1-amino-2,2,2-trifluoroethyl)-6-oxo-1,6-dihydropyridin-3-yl)-4,4-difluoropiperidin-1-yl)-N-(5-(4-fluorophenoxy)pyridin-2-yl)propanamide;

(S)-2-(S)-3-(5-((R)-1-amino-2,2,2-trifluoroethyl)-6-oxo-1,6-dihydropyridin-3-yl)-4,4-difluoropiperidin-1-yl)-N-(5-(4-fluorophenoxy)pyridin-2-yl)propanamide;

(S)-2-((S)-3-(5-((S)-1-amino-2,2,2-trifluoroethyl)-6-oxo-1,6-dihydropyridin-3-yl)-4,4-difluoropiperidin-1-yl)-N-(5-(2,4-difluorophenoxy)pyridin-2-yl)propanamide;

(S)-24(S)-3-(5-((R)-1-amino-2,2,2-trifluoroethyl)-6-oxo-1,6-dihydropyridin-3-yl)-4,4-difluoropiperidin-1-yl)-N-(5-(2,4-difluorophenoxy)pyridin-2-yl)propanamide;

2-(4,4-difluoro-3-(5-((methylamino)methyl)-6-oxo-1,6-dihydropyridin-3-yl)piperidin-1-yl)-N-(5-(4-fluorophenoxy)pyridin-2-yl)propanamide;

2-(4,4-difluoro-3-(5-(((2-hydroxyethyl)amino)methyl)-6-oxo-1,6-dihydropyridin-3-yl)piperidin-1-yl)-N-(5-(4-fluorophenoxy)pyridin-2-yl)propanamide;

2-(4,4-difluoro-3-(5-(((2-methoxyethyl)amino)methyl)-6-oxo-1,6-dihydropyridin-3-yl)piperidin-1-yl)-N-(5-(4-fluorophenoxy)pyridin-2-yl)propanamide;

(S)-N - (5-(2,4-difluorophenoxy)pyridin-2-yl)-2-((S)-3-(5,4,4-difluoropiperidin-1-yl)methyl)-6-oxo-1,6-dihydropyridin-3-yl)-4,4-difluoropiperidin-1-yl)propanamide;

(S)-24(S)-3-(5-4(3,3-difluorocyclobutyl)amino)methyl)-6-oxo-1,6-dihydropyridin-3-yl)-4,4-difluoropiperidin-1-yl)-N-(5-(2,4-difluorophenoxy)pyridin-2-yl)propanamide;

(S)-2-((S)-4,4-difluoro-3-(6-oxo-54(2,2,2-trifluoroethyl)amino)methyl)-1,6-dihydropyridin-3-yl)piperidin-1-yl)-N-(5-(2,4-difluorophenoxy)pyridin-2-yl)propanamide;

(S)-2-((S)-4,4-difluoro-3-(5-((methylamino)methyl)-6-oxo-1,6-dihydropyridin-3-yl)piperidin-1-yl)-N-(5-(2,4-difluorophenoxy)pyridin-2-yl)propanamide;

S)-2-((S)-4,4-difluoro-3-(5-((methylamino)methyl)-6-oxo-1,6-dihydropyridin-3-yl)piperidin-1-yl)-N-(5-(2,4-difluorophenoxy)pyrazin-2-yl)propanamide;

(S)-24(S)-3-(5-(acetamidomethyl)-6-oxo-1,6-dihydropyridin-3-yl)-4,4-difluoropiperidin-1-yl)-N-(5-(4-fluorophenoxy)pyridin-2-yl)propanamide;

(S)-N-(5-(4-fluorophenoxy)pyridin-2-yl)-24(S)-3-(5-(methylsulfonyl)-6-oxo-1,6-dihydropyridin-3-yl)piperidin-1-yl)propanamide (R)-N -(5-(4-fluorophenoxy)pyridin-2-yl)-24(R)-3-(5-(methylsulfonyl)-6-oxo-1,6-dihydropyridin-3-yl)piperidin-1-yl)propanamide;

(S)-N-(5-(4-fluorophenoxy)pyridin-2-yl)-2-((S)-3-(5-(N-methylsulfamoyl)-6-oxo-1,6-dihydropyridin-3-yl)piperidin-1-yl)propanamide;

(R)-N -(5-(4-fluorophenoxy)pyridin-2-yl)-2-((R)-3-(5-(N-methylsulfamoyl)-6-oxo-1,6-dihydropyridin-3-yl)piperidin-1-yl)propanamide;

(S)-2-((S)-3,3-difluoro-5-(6-oxo-1,6-dihydropyridin-3-yl)piperidin-1-yl)-N-(5-fluoropyridin-2-yl)propanamide;

(R)-24(R)-3,3-difluoro-5-(6-oxo-1,6-dihydropyridin-3-yl)piperidin-1-yl)-N-(5-fluoropyridin-2-yl)propanamide;

2-(3-(5-cyano-6-oxo-1,6-dihydropyridin-3-yl)-4,4-difluoropiperidin-1-yl)-N-(5-fluoropyridin-2-yl)propanamide;

2-(3-(5-cyano-6-oxo-1,6-dihydropyridin-3-yl)-4,4-difluoropiperidin-1-yl)-N-(5-(4-fluorophenoxy)pyrazin-2-yl)propanamide;

(S)-2-((S)-3-(5-cyano-6-oxo-1,6-dihydropyridin-3-yl)-4,4-difluoropiperidin-1-yl)-N-(5-(4-fluorophenoxy)pyridin-2-yl)propanamide;

5-((S)-4,4-difluoro-1-((S)-1-(5-(4-fluorophenoxy)pyridin-2-yl)amino)-1-oxopropan-2-yl)piperidin-3-yl)-2-oxo-1,2-dihydropyridine-3-carboxamide;

5-(4,4-difluoro-1-(1-(5-fluoropyridin-2-yl)amino)-1-oxopropan-2-yl)piperidin-3-yl)-2-oxo-1,2-dihydropyridine-3-carboxamide;

4-((S)-4,4-difluoro-1-((S)-145-(4-fluorophenoxy)pyridin-2-yl)amino)-1-oxopropan-2-yl)piperidin-3-yl)-2-(hydroxymethyl)pyridine 1-oxide;

4-((S)-1-((S)-1-((5-(2,4-difluorophenoxy)pyridin-2-yl)amino)-1-oxopropan-2-yl)-4,4-difluoropiperidin-3-yl)-2-(hydroxymethyl)pyridine 1-oxide;

4-(4,4-difluoro-1-(1-((5-fluoropyridin-2-yl)amino)-1-oxopropan-2-yl)piperidin-3-yl)-2-(2,2,2-trifluoro-1-hydroxyethyl)pyridine 1-oxide;

4-(4,4-difluoro-1-(1-((5-(4-fluorophenoxy)pyridin-2-yl)amino)-1-oxopropan-2-yl)piperidin-3-yl)-2-(2,2,2-trifluoro-1-hydroxyethyl)pyridine 1-oxide;

2-carbamoyl-4-((S)-1-((S)-1-((5-(2,4-difluorophenoxy)pyridin-2-yl)amino)-1-oxopropan-2-yl)-4,4-difluoropiperidin-3-yl)pyridine 1-oxide;

2-carbamoyl-44(S)-4,4-difluoro-1-((S)-1-((5-fluoropyridin-2-yl)amino)-1-oxopropan-2-yl)piperidin-3-yl)pyridine 1-oxide;

2-carbamoyl-4-(1-(1-((5-(2,4-difluorophenoxy)pyrazin-2-yl)amino)-1-oxopropan-2-yl)-4,4-difluoropiperidin-3-yl)pyridine 1-oxide;

4-(1-((S)-1-((5-(2,4-difluorophenoxy)pyridin-2-yl)amino)-1-oxopropan-2-yl)-4,4-difluoropiperidin-3-yl)picolinamide;

2-(acetamidomethyl)-4-(1-(1-((5-(2,4-difluorophenoxy)pyridin-2-yl)amino)-1-oxopropan-2-yl)-4,4-difluoropiperidin-3-yl)pyridine 1-oxide;

2-(acetamidomethyl)-4-(4,4-difluoro-1-(1-((5-fluoropyridin-2-yl)amino)-1-oxopropan-2-yl)piperidin-3-yl)pyridine 1-oxide;

2-(3-(2-(aminomethyl)pyridin-4-yl)-4,4-difluoropiperidin-1-yl)-N-(5-(2,4-difluorophenoxy)pyridin-2-yl)propanamide;

(2S)-2-(4,4-difluoro-3-(5-(2,2,2-trifluoro-1-hydroxyethyl)pyri din-3-yl)piperidin-1-yl)-N-(5-(2,4-difluorophenoxy)pyridin-2-yl)propanamide;

3-(1-(1-45-(2,4-difluorophenoxy)pyridin-2-yl)amino)-1-oxopropan-2-yl)-4,4-difluoropiperidin-3-yl)-5-(2,2,2-trifluoro-1-hydroxyethyl)pyridine 1-oxide;

2-((S)-4,4-difluoro-3-(6-oxo-1,6-dihydropyridin-3-yl)piperidin-1-yl)-N-(5-((6-oxo-1,6-dihydropyridin-2-yl)oxy)pyridin-2-yl)propanamide;

(S)-2-((S)-4,4-difluoro-3-(6-oxo-1,6-dihydropyridin-3-yl)piperidin-1-yl)-N-(5-(3,4-difluorophenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-methoxyphenoxy)pyridin-2-yl)propanamide;

(2S)-2-(3-(2-((3,3-difluoroazetidin-1-yl)methyl)pyridin-4-yl)-4,4-difluoropiperidin-1-yl)-N-(5-(2,4-difluorophenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-(hydroxymethyl)phenoxy)pyridin-2-yl)propanamide;

(S)-2-((S)-4,4-difluoro-3-(6-oxo-1,6-dihydropyridin-3-yl)piperidin-1-yl)-N-(5-(4-fluoro-2-(hydroxymethyl)phenoxy)pyrazin-2-yl)propanamide;

4-((S)-4,4-difluoro-1-((S)-1-(5-(4-fluoro-2-(hydroxymethyl)phenoxy)pyridin-2-yl)amino)-1-oxopropan-2-yl)piperidin-3-yl)pyridine 1-oxide;

4-((3S)-4,4-difluoro-1-(1-45-(4-fluoro-2-(hydroxymethyl)phenoxy)pyrazin-2-yl)amino)-1-oxopropan-2-yl)piperidin-3-yl)pyridine 1-oxide;

(R)-N -(5-(cyclopropylmethoxy)pyridin-2-yl)-241S,3R)-4,4-difluoro-3-(6-oxo-1,6-dihydropyridin-3-yl)cyclohexyl)propanamide;

(R)-N-(6-(cyclopropylmethoxy)pyridazin-3-yl)-24/S,3R)-4,4-difluoro-3-(6-oxo-1,6-dihydropyridin-3-yl)cyclohexyl)propanamide;

(R)-2-((1S,3R)-4,4-difluoro-3-(6-oxo-1,6-dihydropyridin-3-yl)cyclohexyl)-N-(5-fluoropyridin-2-yl)propanamide;

2-(4,4-difluoro-3-(6-oxo-1,6-dihydropyridin-3-yl)cyclohexyl)-N-(5-(4-fluorophenoxy)pyridin-2-yl)propanamide;

(R)-2-((1S,3R)-4,4-difluoro-3-(6-oxo-1,6-dihydropyridin-3-yl)cyclohexyl)-N-(5-((5-fluoropyridin-2-yl)oxy)pyridin-2-yl)propanamide;

(R)-2-((1S,3R)-4,4-difluoro-3-(6-oxo-1,6-dihydropyridin-3-yl)cyclohexyl)-N-(5-(2,4-difluorophenoxy)pyridin-2-yl)propanamide;

(R)-2-((1S,3R)-4,4-difluoro-3-(6-oxo-1,6-dihydropyridin-3-yl)cyclohexyl)-N-(5-((3,5-difluoropyridin-2-yl)oxy)pyridin-2-yl)propanamide;

(R)-N-(5-(2,4-difluorophenoxy)pyridin-2-yl)-241S,3R)-3-(6-oxo-1,6-dihydropyridin-3-yl)cyclohexyl)propanamide;

(R)-N-(5((5fluoropyridin-2yl)oxy)pyridin-2-yl)-241S,3R)-3-(6-oxo-1,6-dihydropyridin-3yl)cyclohexyl)propanamide;

N-(5-(4-fluorophenoxy)pyrazin-2-yl)-2-((3R)-3-(6-oxo-1,6dihydropyridin-3-yl)cyclohexyl)propanamide;

(R)-N -(5-(3,5-difluoropyridin-2-yl)oxy)pyridin-2-yl)-2-41S,3R)-3-(6-oxo-1,6-dihydropyridin-3-yl)cyclohexyl)propanamide;

(R)-N -(5-(2,4-difluorophenoxy)pyrazin-2-yl)-2-41S,3R)-3-(6-oxo-1,6-dihydropyridin-3-yl)cyclohexyl)propanamide;

4-(1R,3S)-3-(R)-1-((5-((5-fluoropyridin-2-yl)oxy)pyridin-2-yl)amino)-1-oxopropan-2-yl)cyclohexyl)pyridine 1-oxide;

4-((1R,3S)-3-((R)-1-((5-((5-fluoropyridin-2-yl)oxy)pyridin-2-yl)amino)-1-oxopropan-2-yl)cyclohexyl)pyridine 1-oxide;

4-(1R,35)-3-((R)-1-((5-(2,4-difluorophenoxy)pyridin-2-yl)amino)-1-oxopropan-2-yl)cyclohexyl)pyridine 1-oxide;

4-(1R,3S)-3-((S)-1-45-((3,5-difluoropyridin-2-yl)oxy)pyridin-2-yl)amino)-1-oxopropan-2-yl)cyclohexyl)pyridine 1-oxide;

4-((1R,5S)-5-((R)-1-((5-(2,4-difluorophenoxy)pyridin-2-yl)amino)-1-oxopropan-2-yl)-2,2-difluorocyclohexyl)pyridine 1-oxide;

4-((1R,5S)-2,2-difluoro-5-((R)-1-((5-(4-fluorophenoxy)pyrazin-2-yl)amino)-1-oxopropan-2-yl)cyclohexyl)pyridine 1-oxide;

4-((1R,5S)-5-((R)-1-((5-((3,5-difluoropyridin-2-yl)oxy)pyridin-2-yl)amino)-1-oxopropan-2-yl)-2,2-difluorocyclohexyl)pyridine 1-oxide;

4-((1R,5S)-2,2-difluoro-5-((R)-1-(5-((5-fluoropyridin-2-yl)oxy)pyridin-2-yl)amino)-1-oxopropan-2-yl)cyclohexyl)pyridine 1-oxide; and 4-((1R,5S)-5-((R)-1-((5-(2,4-difluorophenoxy)pyrazin-2-yl)amino)-1-oxopropan-2-yl)-2,2-difluorocyclohexyl)pyridine 1-oxide;

(R)-2-((1S,3R)-4,4-difluoro-3-(6-oxo-1,6-dihydropyridin-3-yl)cyclohexyl)-N-(5-(2,4-difluorophenoxy)pyrazin-2-yl)propenamide;

(S)-2-((S)-4,4-difluoro-3-(pyridin-4-yl)piperidin-1-yl)-N-(5-(2,4-difluorophenoxy)pyrazin-2-yl)propanamide;

4-((S)-1-((S)-1-45-(2,4-difluoro-6-(hydroxymethyl)phenoxy)pyrazin-2-yl)amino)-1-oxopropan-2-yl)-4,4-difluoropiperidin-3-yl)pyridine 1-oxide 4-((S)-1-((S)-1-((5-(2,4-difluoro-6-(hydroxymethyl)phenoxy)pyridin-2-yl)amino)-1-oxopropan-2-yl)-4,4-difluoropiperidin-3-yl)pyridine 1-oxide (S)-2-((S)-4,4-difluoro-3-(6-oxo-1,6-dihydropyridin-3-yl)piperidin-1-yl)-N-(5-(2,4-difluoro-6-(hydroxymethyl)phenoxy)pyrazin-2-yl)propanamide;

(S)-2-((S)-4,4-difluoro-3-(6-oxo-1,6-dihydropyridin-3-yl)piperidin-1-yl)-N-(5-(2,4-difluoro-6-(hydroxymethyl)phenoxy)pyridin-2-yl)propanamide;

or pharmaceutically acceptable salts thereof.

16. The compound according to claim 1 which is 4-((S)-1-((S)-1-((5-(2,4-difluorophenoxy)pyrazin-2-yl)amino)-1-oxopropan-2-yl)-4,4-difluoropiperidin-3-yl)pyridine 1-oxide as represented by the below formula

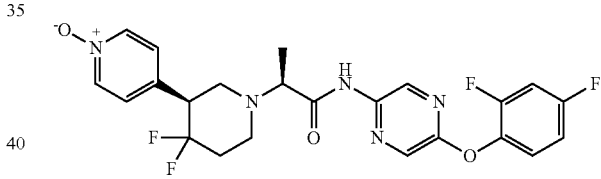

or a pharmaceutically acceptable salt thereof.

17. The compound according to claim 16, wherein the compound is a hydrochloride salt of 4-((S)-14(S)-1-45-(2,4-difluorophenoxy)pyrazin-2-yl)amino)-1-oxopropan-2-yl)-4,4-difluoropiperidin-3-yl)pyridine 1-oxide.

18. A pharmaceutical composition comprising the compound or pharmaceutically acceptable salt thereof according to claim 1 and a pharmaceutically acceptable excipient.

19. A method of treating an MrgX2-mediated disease or disorder in a human in need thereof comprising administering to the human a therapeutically effective amount of the compound or pharmaceutically acceptable salt thereof according to claim 1, wherein the MrgX2-mediated disease or disorder is selected from the group consisting of chronic spontaneous urticaria, cold urticaria, atopic dermatitis, ulcerative colitis, inflammatory pain, asthma, chronic inducible urticaria, pseudo anaphylaxis, and contact urticaria.

20. The method according to claim 19, wherein the MrgX2-mediated disease or disorder is chronic spontaneous urticaria.

* * * * *